US006535820B1

(12) United States Patent
Strickland et al.

(10) Patent No.: US 6,535,820 B1
(45) Date of Patent: Mar. 18, 2003

(54) CRYSTALLINE FARNESYL PROTEIN TRANSFERASE COMPOSITIONS AND METHODS FOR USE

(75) Inventors: Corey Strickland, North Plainfield, NJ (US); Patricia C. Weber, Yardley, PA (US)

(73) Assignee: Schering Corporation, Kenilworth, NJ (US)

(*) Notice: Subject to any disclaimer, the term of this patent is extended or adjusted under 35 U.S.C. 154(b) by 0 days.

(21) Appl. No.: 09/383,364

(22) Filed: Aug. 26, 1999

Related U.S. Application Data

(60) Provisional application No. 60/098,331, filed on Aug. 28, 1998.

(51) Int. Cl.[7] ........................ G01N 33/48; G01N 23/20

(52) U.S. Cl. ........................ 702/19; 435/193; 424/94.5; 530/350; 514/2; 514/12

(58) Field of Search ........................ 530/350; 435/69.1, 435/320.1, 325, 193; 424/94.5; 514/2, 12; 702/19

(56) References Cited

U.S. PATENT DOCUMENTS 5,420,245 A 5/1995 Brown et al. ............... 530/328
5,525,479 A 6/1996 Anthony et al.

FOREIGN PATENT DOCUMENTS

WO WO 94/04561 3/1994 ............ C07K/5/10
WO WO-97/23478 * 7/1997

OTHER PUBLICATIONS

Pompliano, et al., (1992) Biochemistry 31:3800–3807.

Strickland, et al., Proceedings of the American Association for Cancer Research Annual Meeting, (Mar., 1998) 39:270. Meeting information: 89$^{th}$ annual meeting of the American Association for Cancer Research New Orleans, Louisiana, USA on Mar. 28–Apr. 1, 1998; abstract# 1844.

Gilliland, et al., (1996) Current Opinions in Structural Biology 6(5): 595–603.

Wu, et al., (1999) Protein Engineering 12(4): 341–348.

Dunten et al., 1998, *Biochemistry*, 37(22):7907–12.

Strickland et al., 1998, Biochemistry 37(47)16601–16611.

Wu et al., 1999, Biochemistry 38(35):11234–49.

Dunten et al., 1998, *Biochemistry*, 37:22.

Long et al., 19989, *Biochemistry*, 37:9612–9618.

Park et al., 1997, *Current Opinion in Structural Biology*, 7:873–880.

Park et al., 1997, *Science*, 275:1800–1804.

* cited by examiner

*Primary Examiner*—Marianne P. Allen
(74) *Attorney, Agent, or Firm*—Thomas Triolo

(57) ABSTRACT

The present invention relates to crystalline compositions comprising farnesyl protein transferase-like polypeptides in complex with substrates and inhibitors. Also disclosed are crystallization conditions for these compositions and their use for structural determination of FPT:FPP/FPP analog: peptide/inhibitor complexes.

12 Claims, 3 Drawing Sheets

SEQUENCE LISTING

```
<160> NUMBER OF SEQ ID NOS: 6

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Peptide
<220> FEATURE:
<221> NAME/KEY: MOD_RES
<222> LOCATION: (4)
<223> OTHER INFORMATION: Xaa is methionine OR selenomethionine
      (methionine residue with selenium in place of sulfur)

<400> SEQUENCE: 1

Cys Val Ile Xaa
  1


<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence:
      Peptide
<220> FEATURE:
<221> NAME/KEY: MOD_RES
<222> LOCATION: (1)
<223> OTHER INFORMATION: ACETYLATION

<400> SEQUENCE: 2

Cys Val Leu Ser
  1


<210> SEQ ID NO 3
<211> LENGTH: 4
<212> TYPE: PRT
<213> ORGANISM: Artificial Sequence
<220> FEATURE:
<221> NAME/KEY: MOD_RES
<222> LOCATION: (1)
<223> OTHER INFORMATION: ACETYLATION
<220> FEATURE:
<223> OTHER INFORMATION: Description of Artificial Sequence:
      Peptide

<400> SEQUENCE: 3

Cys Val Phe Met
  1


<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Ca1a2X
      Peptide
<220> FEATURE:
<221> NAME/KEY: variant
<222> LOCATION: 2
<223> OTHER INFORMATION: any amino acid
<220> FEATURE:
<221> NAME/KEY: variant
<222> LOCATION: 3
<223> OTHER INFORMATION: small apolar or aromatic amino acid
<220> FEATURE:
<221> NAME/KEY: variant
<222> LOCATION: 4
<223> OTHER INFORMATION: Ser, Met, Cys, Ala or Gln
```

-continued

<400> SEQUENCE: 4

Cys Xaa Xaa Xaa

<210> SEQ ID NO 5
<211> LENGTH: 1134
<212> TYPE: DNA
<213> ORGANISM: Rattus norvegicus

<400> SEQUENCE: 5
atggcggcca ctgagggggt cggggaatct gcgccaggcg gtgagccggg acagccagag 60
cagccgccgc ccccgcctcc tccgccgcca gcacagcagc cgcaggaaga agagatggcg 120
gccgaggccg gggaagcagc ggcgtcccct atggacgacg ggtttctgag cctggactcg 180
cccacctatg tcttgtacag ggacagggca gagtgggctg acatagaccc agtgccccag 240
aatgatggcc ccagtccagt ggtccagatc atctacagtg aaaagtttag agacgtctat 300
gattacttcc gagctgttct gcagcgcgat gaaagaagcg aacgagcctt taagctcact 360
cgagatgcta ttgagttaaa cgcagccaac tatacggtgt ggcattttcg gagagttctc 420
ttgaggtcgc ttcagaagga tctgcaagaa gaaatgaact acatcatcgc aataattgag 480
gaacagccca aaaactatca agtttggcac cataggagag tattagtgga gtggctgaaa 540
gatccttctc aagagctcga gttcatcgcc gatatcctta atcaggatgc aaagaattac 600
catgcctggc agcatcgaca gtgggtcatt caggagtttc gactttggga taatgagctg 660
cagtatgtgg accagcttct caaagaggat gtgagaaata actctgtgtg gaaccaaaga 720
cacttcgtca tttctaatac cactggctac agtgatcgcg ctgtgttgga gagagaagtc 780
caatatactc tggaaatgat caaattagtg ccacacaatg agagtgcgtg gaactacttg 840
aaagggattt tgcaggaccg tggtctttcc agatacccta atctattaaa ccagttgctt 900
gatttacaac caagtcacag ctccccctac ctaattgcct ttcttgtgga tatctatgaa 960
gacatgctgg aaaaccagtg tgacaacaag gaggacattc ttaataaagc actagagtta 1020
tgtgagattc tagctaaaga aaaggacact ataagaaagg aatattggag atatattgga 1080
cggtccctcc agagtaaaca cagcagagaa agtgacatac cggcgagtgt atag 1134

<210> SEQ ID NO 6
<211> LENGTH: 1314
<212> TYPE: DNA
<213> ORGANISM: Rattus norvegicus

<400> SEQUENCE: 6
atggcttctt cgagttcctt cacctattat tgtcctccat cttcttcccc tgtttggtca 60
gaaccgctgt atagtctgag acctgagcac gcgcgggagc ggttgcaaga cgactcagtg 120
gaaacagtca cgtccataga acaggccaaa gtagaagaaa agatccagga ggtcttcagt 180
tcttacaagt ttaaccacct cgtaccaagg ctcgttctgc agagggagaa gcacttccat 240
tatctgaaaa gaggccttcg acaactgaca gatgcctatg agtgtctgga tgccagccgc 300
ccctggctct gctactggat cctgcacagc ttggagctcc tcgacgaacc catccccccaa 360 atagtggcta cagatgtgtg tcagttcttg gagctgtgtc agagtccaga cggtggcttt 420
ggagggggcc ctggtcagta cccacacctc gctcccacgt atgcagctgt caacgcgcta 480
tgcatcattg gcacggagga agcctacaac gtcattaaca gagagaagct ccttcagtac 540
ttgtactccc taaagcaacc ggatggctct ttttctcatgc acgtcggagg agaggtggat 600
gtaagaagtg cgtactgtgc tgcctcagta gcctctctca ccaacatcat cactcctgac 660

-continued

| | |
|---|---|
| ctcttcgaag gcactgctga atggatagca aggtgccaga actgggaagg cggcattggc | 720 |
| ggggtgccag ggatggaagc ccacggtggc tacaccttct gtggcttggc tgcgctggtg | 780 |
| atcctcaaga aggaacgttc tttgaacctg aagagcttgc tacaatgggt gacaagccgg | 840 |
| cagatgcggt tcgaaggagg atttcagggc cgctgcaaca agctggtgga cggctgctac | 900 |
| tccttctggc aggcaggact tctgcccctg ttgcaccggg cactccacgc tcaaggtgac | 960 |
| cctgccctca gcatgagcca ctggatgttc catcagcagg cgctgcagga gtacatcctc | 1020 |
| atgtgctgcc agtgtccggc tgggggtctc ctggacaaac ctggcaagtc acgtgacttc | 1080 |
| taccatactt gctactgcct gagcggcctg tccattgccc agcattttgg aagtggagcc | 1140 |
| atgctgcacg atgtggtcat gggtgtgcct gaaaatgttc tgcagcccac tcaccctgtg | 1200 |
| tacaacatcg gacctgataa ggtgatccag gccaccacac actttctgca gaagccggtc | 1260 |
| ccaggctttg aggaatgcga agatgcggtg acctcagatc ctgccactga ctag | 1314 |

CRYSTALLINE FARNESYL PROTEIN TRANSFERASE COMPOSITIONS AND METHODS FOR USE

This application claims priority from U.S. Provisional Application Serial No. 60/098,331, filed Aug. 28, 1998, which is incorporated entirely herein.

TECHNICAL FIELD OF INVENTION

The present invention relates to crystalline farnesyl protein transferase (FPT) and FPT in complex with substrates or inhibitors. This invention also relates to methods of using the structure coordinates of FPT to solve the structure of similar or homologous proteins or protein substrate or inhibitor complexes.

BACKGROUND OF THE INVENTION

The biological significance of the Ras oncogene, and the role of both Ras and the enzyme known as farnesyl protein transferase ("FPT") in the conversion of normal cells to cancer cells, are described in PCT International Publication Nos. WO95/00497 and WO95/10516. To undergo transforming potential, the precursor of the Ras oncoprotein must undergo farnesylation of the cysteine residue located in a carboxyl-terminal tetrapeptide. Farnesyl protein transferase catalyzes this modification. Inhibitors of this enzyme have therefore been suggested as anticancer agents for tumors in which RAS contributes to transformation.

Drug discovery efforts directed toward FPT inhibitors have been hampered by the lack of adequate structural information about FPT and its complex with substrates and inhibitors. The structure of FPT was first determined at Duke University using a crystalline form where the active site was blocked by the carboxy terminus of an adjacent molecule in the crystalline lattice. Beese et al., 1997, *Science* 275:1800–1804. These crystals are not suited for drug discovery because, as reported therein, the active site is blocked by part of the crystal lattice. Another crystalline form of FPT was also reported in Dunten et al., 1998, *Biochemistry* 37(22):7907–7912. These crystals grow at pH 4.4 and are reported to only diffract to 2.8 Å resolution. However, the authors point out that there are no substrates or peptide inhibitors bound due to the low pH of the crystallization. Thus these crystals are not suitable for structure-based drug design.

Structural information from FPT crystalline complexes would provide valuable information in discovery of FPT inhibitors. This information could be used to design more potent, selective and metabolically stable FPT inhibitors for use as drugs against cancer.

SUMMARY OF THE INVENTION

Applicants have solved this problem by providing crystalline compositions comprising a farnesyl protein transferase (FPT) complexed with its natural substrates and with molecules that mimic its natural substrates. The invention also provides the structure coordinates of these complexes. Further provided are methods for soaking these crystalline complexes in the presence of an inhibitor, thereby efficiently forming new crystalline enzyme: inhibitor complexes.

The invention also provides a method for determining at least a portion of the three-dimensional structure of molecules or molecular complexes which contain at least some structurally similar features to an FPT: substrate or FPT: inhibitor complex.

DETAILED DESCRIPTION OF THE INVENTION

Figure 1:
FIG. 1 depicts stereo ribbon diagrams of an FPT:αHFP:Ac-CVIM-COOH complex. The view is into the active site cavity of the enzyme.

FPT-mediated prenylation of Ras involves formation of a ternary complex comprising farnesyl protein transferase (FPT), farnesyl diphosphate (FPP) and Ras (FPT:FPP:Ras), followed by transfer of the 15-carbon isoprenoid from FPP to a cysteine sidechain of Ras. The cysteine residue is part of a conserved carboxyl terminal $Ca_1a_2X$ (SEQ ID No: 4) sequence where X is a serine residue in H-Ras and methionine in N-Ras, K-Ras 4a, and K-Ras 4b isoforms.

Applicants have discovered crystalline forms of farnesyl protein transferase (FPT) suited for structure-based drug design. Provided herein are two basic crystal forms—wherein an FPT-like polypeptide is complexed with FPP and an inhibitor, and wherein an FPT-like polypeptide is complexed with molecules that mimic the natural substrates. (These complexes are referred to throughout as FPT:FPP/FPP analog:Peptide/Inhibitor complexes.)

The FPT-like polypeptide portion of the complex is any polypeptide that has the activity of naturally occurring FPT (Reiss et al, 1990, *Cell* 62:81–88), particularly the ability to cause farnesylation of the cysteine residue located in a carboxyl-terminal tetrapeptide of the precursor of the Ras oncoprotein. The terms "FPT" and "FPT-like polypeptide" are used interchangeably herein and include FPT and polypeptides that differ from FPT by having amino acid deletions, substitutions, and additions, but which retain the activity of FPT.

In one embodiment, FPT is complexed with farnesyl diphosphate (FPP) and an inhibitor. These crystals diffract to at least 2.2 Å resolution. At this resolution, most atoms of the FPT:FPP:inhibitor complex can be visualized using x-ray crystallographic methods.

In another embodiment, the pre-formed crystals of FPT are grown by first complexing FPT with molecules that mimic the natural substrates. FPT is complexed with an FPP analog and a tetrapeptide substrate based on the carboxy terminus of Ras referred to herein as a $Ca_1a_2X$ (SEQ ID No: 4) peptide. Preferably, the FPP analog used is α-hydroxyphosphonic acid (αHFP) (Calbiochem-Novabiochem Corp.), and the $Ca_1a_2X$ (SEQ ID No: 4) peptide is N-acetyl-Cys-Val-Ile-Met-COOH (CVIM) (SEQ ID No: 1) (SynPep Inc.). These crystals diffract to 2.4 Å resolution. At this resolution, most atoms of the complex can be visualized using x-ray crystallographic methods.

Those skilled in the art will understand, of course, that other FPP analogs and other $Ca_1a_2X$ (SEQ ID No: 4) peptides may be used in these complexes. For example, methylene-farnesyl diphosphate [Davisson et al, 1986, *J. Org. Chem.* 51:4768–4779] can also be used in place of αHFP as an FPP analog, however any analog of FPP could be used. Likewise, many other $Ca_1a_2X$ (SEQ ID No: 4) peptides may be used. In preferred embodiments, X is serine, methionine, cysteine, alanine or glutamine. See Reiss et al, 1991, PNAS 88:732–36. A variety of both natural and unnatural amino acids can be accommodated at the $a_1$ position without loss of activity. Peptides having small apolar residues at $a_2$ are also good substrates, while those with aromatic sidechains at this position competitively inhibit binding of peptide substrates. Goldstein et al., *J. Biol Chem* 266:15575–15578. In more preferred embodiments, the $Ca_1a_2X$ (SEQ ID No: 4).

The pre-formed FPT:FPP analog: peptide crystals of this invention can be soaked in the presence of an inhibitor, thereby forming new protein/compound complexes and obviating the need to crystallize each individual protein/compound complex. Crystalline complexes of FPT with FPP and an inhibitor can also be soaked in the presence of another inhibitor so that the original inhibitor is displaced and a new crystalline FPT:FPP:inhibitor complex is formed. The ability to form FPT:FPP:inhibitor complexes in the crystalline state allows very rapid turnaround of structural information.

According to one embodiment of the invention, an FPT:αHFP:CVIM complex is crystallized from a well-defined solution. A solution for stabilizing the crystals (artificial mother liquor) has been discovered. To obtain the structure of FPT inhibitors complexed with FPT, the crystals of FPT:αHFP:CVIM are soaked in solutions of artificial mother liquor containing inhibitor and farnesyl diphosphate (FPP). The crystalline nature of FPT is retained during this procedure, only the molecules bound to the active site are altered.

The present invention provides the three-dimensional structure of (1) an FPT:αHFP:CVIM peptide complex at 2.4 Å resolution, (2) an FPT:FPP:SCH66381 complex at 2.2 Å resolution, (3) an FPT:FPP:SCH66701 complex at 2.9 Å resolution, and (4) an FPT:FPP:SCH69132 complex at 2.5 Å resolution. Importantly, the crystalline structures of the present invention provide information about the shape and structure of the FPT active site containing both an isoprenoid and a peptide or inhibitor.

The three-dimensional structures of three FPT complexes of this invention are defined by a set of structure coordinates as set forth in FIGS. 2–5. The term "structure coordinates" refers to Cartesian coordinates derived from mathematical equations related to the patterns obtained on diffraction of a monochromatic beam of X-rays by the atoms (scattering centers) of FPT:FPP/FPP analog:Peptide/Inhibitor complexes in crystal form. The diffraction data are used to calculate an electron density map of the repeating unit of the crystal. The electron density maps are then used to establish the positions of the individual atoms of the FPT:FPP/FPP analog: Peptide/Inhibitor complexes.

Those of skill in the art will understand that a set of structure coordinates for an enzyme or an enzyme-complex or a portion thereof, is a relative set of points that define a shape in three dimensions. Thus, it is possible that an entirely different set of coordinates could define a similar or identical shape. Moreover, slight variations in the individual coordinates will have little effect on overall shape.

The variations in coordinates discussed above may be generated because of mathematical manipulations of the structure coordinates. For example, the structure coordinates set forth in Tables 2–5 could be manipulated by crystallographic permutations of the structure coordinates, fractionalization of the structure coordinates, rotation of the structure coordinates, integer additions or subtractions to sets of the structure coordinates, inversion of the structure coordinates or any combination of the above.

Alternatively, modifications in the crystal structure due to mutations, additions, substitutions, and/or deletions of amino acids, or other changes in any of the components that make up the crystal could also account for variations in structure coordinates. If such variations are within an acceptable standard error as compared to the original coordinates, the resulting three-dimensional shape is considered to be the same.

Various computational analyses are therefore necessary to determine whether a molecule or molecular complex or a portion thereof is sufficiently similar to all or parts of the FPT enzyme or enzyme complex as described above as to be considered the same. Such analyses may be performed using automated or manual tools in current software applications, such as those sold by Molecular Simulations Incorporated, and referred to as INSIGHT or QUANTA.

The Molecular Similarity application,(Molecular Simulations Incorporated) permits comparisons between different structures, different conformations of the same structure, and different parts of the same structure. The procedure used in Molecular Similarity to compare structures is divided into four steps: 1) load the structures to be compared; 2) define the atom equivalencies in these structures; 3) perform a fitting operation; and 4) analyze the results.

Each structure is identified by a name. One structure is identified as the target (i.e., the fixed structure); all remaining structures are working structures (i.e., moving structures). Since atom equivalency within QUANTA is defined by user input, for the purpose of this invention we will define equivalent atoms as protein backbone atoms (N, Ca, C and O) for all conserved residues between the two structures being compared.

When a rigid fitting method is used, the working structure is translated and rotated to obtain an optimum fit with the target structure. The fitting operation uses an algorithm that computes the optimum translation and rotation to be applied to the moving structure, such that the root mean square difference of the fit over the specified pairs of equivalent atom is an absolute minimum. This number, given in angstroms, is reported by QUANTA.

For the purpose of this invention, any molecule or molecular complex that has a root mean square deviation of conserved residue backbone atoms (N, Ca, C, O) of less than 3 Å when superimposed on the relevant backbone atoms described by structure coordinates listed in any one of Tables 2–5 are considered identical. More preferably, the root mean square deviation is less than 1.0 Å.

The term "root mean square deviation" means the square root of the arithmetic mean of the squares of the deviations from the mean. It is a way to express the deviation or variation from a trend or object. For purposes of this invention, the "root mean square deviation" defines the variation in the backbone of a protein or protein complex from the relevant portion of the backbone of the FPT-like polypeptide portion of the complex as defined by the structure coordinates described herein.

Once the structure coordinates of a protein crystal have been determined they are useful in solving the structures of other crystals.

Thus, in accordance with the present invention, the structure coordinates of an FPT:FPP/FPP analog: peptide/Inhibitor complex and portions thereof are stored in a machine-readable storage medium. Such data may be used for a variety of purposes, such as drug discovery and X-ray crystallographic analysis of protein crystals.

Accordingly, in one embodiment of this invention is provided a machine-readable data storage medium comprising a data storage material encoded with the structure coordinates set forth in Table 2, 3, 4 or 5.

Figure 2:
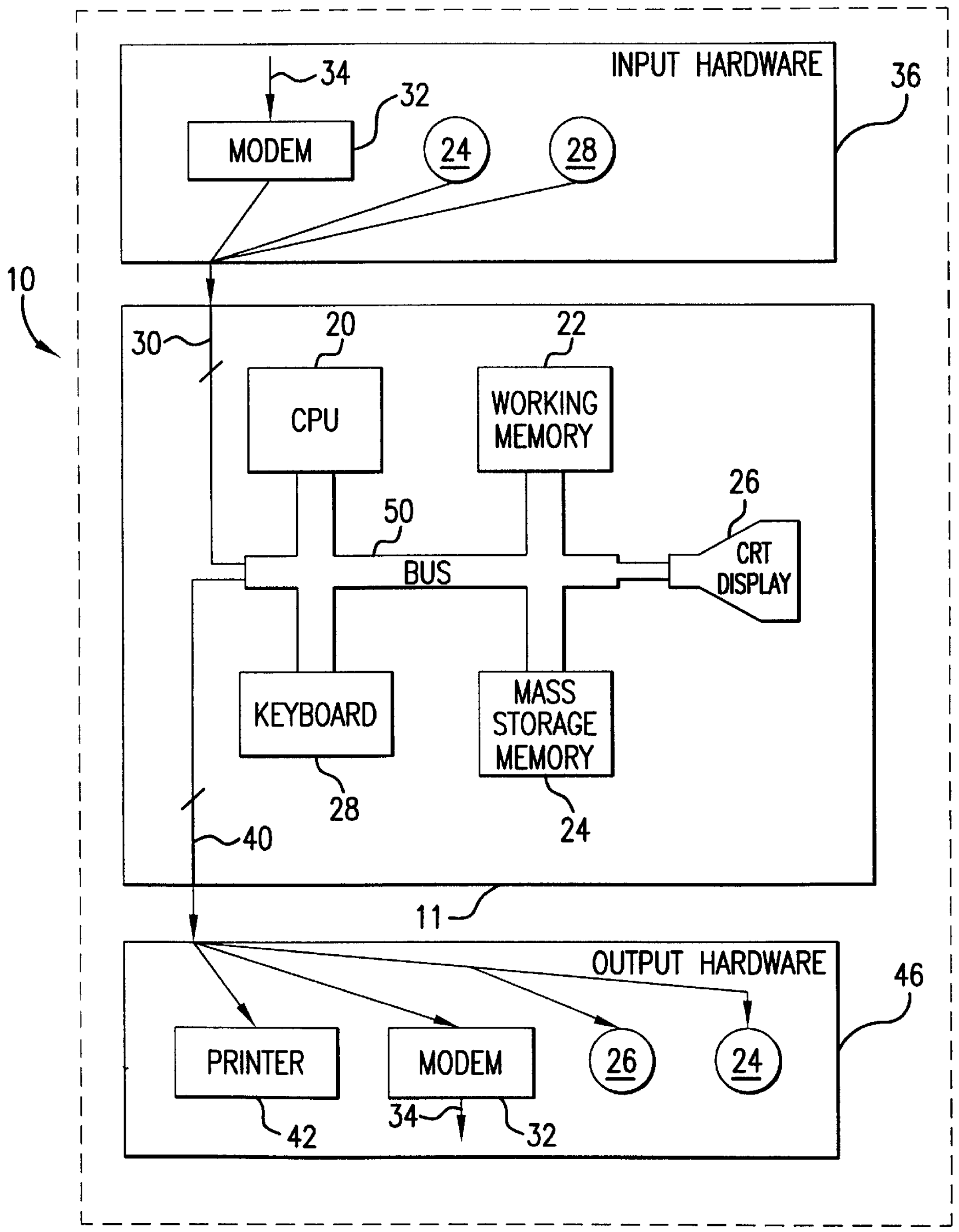
FIG. 2 shows a diagram of a system used to carry out the instructions encoded by the storage medium of FIGS. 3 and 4.

FIG. 2 demonstrates one version of these embodiments. System 10 includes a computer 11 comprising a central processing unit ("CPU") 20, a working memory 22 which may be, e.g. RAM (random-access memory) or "core" memory, mass storage memory 24 (such as one or more disk drives or CD-ROM drives), one or more cathode-ray tube ("CRT") display terminals 26, one or more keyboards 28, one or more input lines 30, and one or more output lines 40, all of which are interconnected by a conventional bi-directional system bus 50.

Input hardware 36, coupled to computer 11 by input lines 30, may be implemented in a variety of ways. Machine-readable data of this invention may be inputted via the use of a modem or modems 32 connected by a telephone line or dedicated data line 34. Alternatively or additionally, the input hardware 36 may comprise CD-ROM drives or disk drives 24. In conjunction with display terminal 26, keyboard 28 may also be used as an input device.

Output hardware 46, coupled to computer 11 by output lines 40, may similarly be implemented by conventional devices. By way of example, output hardware 46 may include CRT display terminal 26 for displaying a graphical representation of a binding pocket of this invention using a program such as INSIGHT as described herein. Output hardware might also include a printer 42, so that hard copy output may be produced, or a disk drive 24, to store system output for later use.

In operation, CPU 20 coordinates the use of the various input and output devices 36, 46, coordinates data accesses from mass storage 24 and accesses to and from working memory 22, and determines the sequence of data processing steps. A number of programs may be used to process the machine-readable data of this invention. Such programs are discussed in reference to the computational methods of drug discovery as described herein. Specific references to components of hardware system 10 are included as appropriate throughout the following description of the data storage medium.

Figure 3:
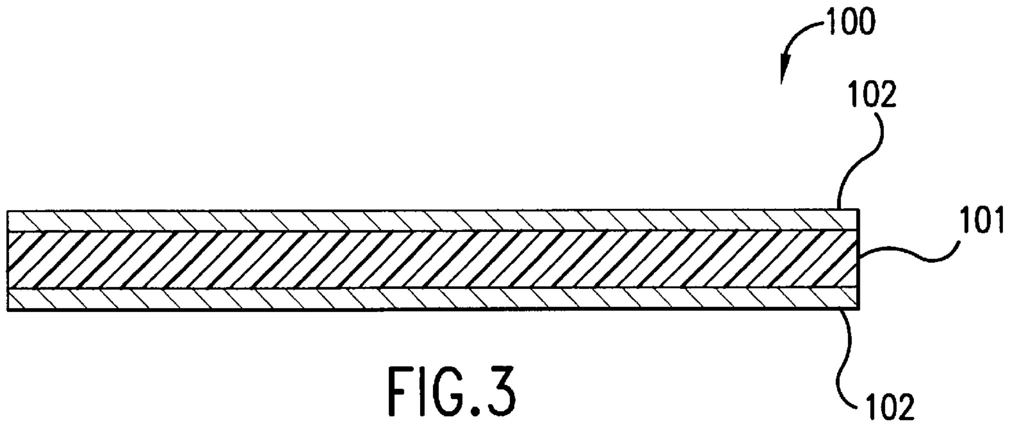
FIG. 3 shows a cross section of a magnetic storage medium.

FIG. 3 shows a cross section of a magnetic data storage medium 100 which can be encoded with a machine-readable data that can be carried out by a system such as system 10 of FIG. 2. Medium 100 can be a conventional floppy diskette or hard disk, having a suitable substrate 101, which may be conventional, and a suitable coating 102, which may be conventional, on one or both sides, containing magnetic domains (not visible) whose polarity or orientation can be altered magnetically. Medium 100 may also have an opening (not shown) for receiving the spindle of a disk drive or other data storage device 24.

The magnetic domains of coating 102 of medium 100 are polarized or oriented so as to encode in manner which may be conventional, machine readable data such as that described herein, for execution by a system such as system 10 of FIG. 2.

Figure 4:
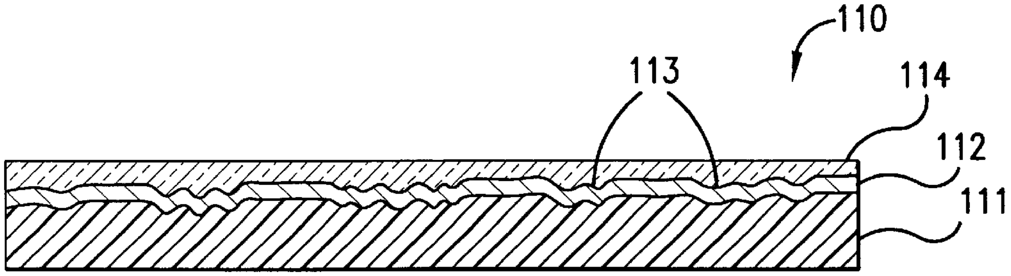
FIG. 4 shows a cross section of a optically-readable data storage medium.

FIG. 4 shows a cross section of an optically-readable data storage medium 110 which also can be encoded with such a machine-readable data, or set of instructions, which can be carried out by a system such as system 10 of FIG. 2. Medium 110 can be a conventional compact disk read only memory (CD-ROM) or a rewritable medium such as a magneto-optical disk which is optically readable and magneto-optically writable. Medium 100 preferably has a suitable coating 112, which may be conventional, usually of one side of substrate 111.

In the case of CD-ROM, as is well known, coating 112 is reflective and is impressed with a plurality of pits 113 to encode the machine-readable data. The arrangement of pits is read by reflecting laser light off the surface of coating 112. A protective coating 114, which preferably is substantially transparent, is provided on top of coating 112.

In the case of a magneto-optical disk, as is well known, coating 112 has no pits 113, but has a plurality of magnetic domains whose polarity or orientation can be changed magnetically when heated above a certain temperature, as by a laser (not shown). The orientation of the domains can be read by measuring the polarization of laser light reflected from coating 112. The arrangement of the domains encodes the data as described above.

The present invention permits the use of structure-based or rational drug design techniques to design, select, and synthesize chemical entities, including inhibitory compounds that are capable of binding to the active site of FPT, or any portion thereof.

One particularly useful drug design technique enabled by this invention is iterative drug design. Iterative drug design is a method for optimizing associations between a protein and a compound by determining and evaluating the three-dimensional structures of successive sets of FPT:FPP or FPP analog:Peptide or Inhibitor complexes.

Those of skill in the art will realize that association of natural ligands or substrates with the binding pockets of their corresponding receptors or enzymes is the basis of many biological mechanisms of action. The term "binding pocket," as used herein, refers to a region of a molecule or molecular complex, that, as a result of its shape, favorably associates with another chemical entity or compound. Similarly, many drugs exert their biological effects through association with the binding pockets of receptors and enzymes. Such associations may occur with all or any parts of the binding pockets. An understanding of such associations will help lead to the design of drugs having more favorable associations with their target receptor or enzyme, and thus, improved biological effects. Therefore, this information is valuable in designing potential ligands or inhibitors of receptors or enzymes, such as inhibitors of FPT.

The term "associating with" refers to a condition of proximity between chemical entities or compounds, or portions thereof. The association may be non-covalent—wherein the juxtaposition is energetically favored by exclusively or a combination of hydrogen bonding or van der Waals and/or electrostatic interactions—or it may be covalent.

In iterative drug design, crystals of a series of protein/compound complexes are obtained and then the three-dimensional structure of each complex is solved. Such an approach provides insight into the association between the proteins and compounds of each complex. This is accomplished by selecting compounds with inhibitory activity, obtaining crystals of this new protein/compound complex, solving the three-dimensional structure of the complex, and comparing the associations between the new protein/compound complex and previously solved protein/compound complexes. By observing how changes in the compound affected the protein/compound associations, these associations may be optimized.

In some cases, iterative drug design is carried out by forming successive protein-compound complexes and then crystallizing each new complex. Alternatively, a pre-formed protein crystal is soaked in the presence of an inhibitor, thereby forming a protein/compound complex and obviating the need to crystallize each individual protein/compound complex. Advantageously, the FPT:FPP/FPP analog:Peptide/Inhibitor complex crystals, and in particular the FPT:αHFP:CVIM crystals, provided by this invention may be soaked in the presence of a compound or compounds, to provide FPT:FPP:inhibitor crystal complexes.

As used herein, the term "soaked" refers to a process in which the crystal is transferred to a solution containing the compound of interest.

The structure coordinates set forth in Tables 2–5 can also be used to aid in obtaining structural information about another crystallized molecule or molecular complex. This may be achieved by any of a number of well-known techniques, including molecular replacement.

The structure coordinates set forth in Tables 2–5 can also be used for determining at least a portion of the three-dimensional structure of molecules or molecular complexes which contain at least some structurally similar features to FPT. In particular, structural information about another crystallized molecule or molecular complex may be obtained. This may be achieved by any of a number of well-known techniques, including molecular replacement.

Therefore, in another embodiment this invention provides a method of utilizing molecular replacement to obtain structural information about a crystallized molecule or molecular complex whose structure is unknown comprising the steps of:

a) generating an X-ray diffraction pattern from said crystallized molecule or molecular complex; and b) applying at least a portion of the structure coordinates set forth in any one of Tables 2–5 to the X-ray diffraction pattern to generate a three-dimensional electron density map of the molecule or molecular complex whose structure is unknown.

By using molecular replacement, all or part of the structure coordinates of the FPT:FPP/FPP analog:Peptide/Inhibitor complexes provided by this invention (and set forth in Tables) can be used to determine the structure of a crystallized molecule or molecular complex whose structure is unknown more quickly and efficiently than attempting to determine such information ab initio or by isomorphous replacement methods.

Molecular replacement provides an accurate estimation of the phases for an unknown structure. Phases are a factor in equations used to solve crystal structures that can not be determined directly. Obtaining accurate values for the phases, by methods other than molecular replacement, is a time-consuming process that involves iterative cycles of approximations and refinements and greatly slows the solution of crystal structures. However, when the crystal structure of a protein containing at least a homologous portion has been solved, the phases from the known structure provide a satisfactory estimate of the phases for the unknown structure.

Thus, this method involves generating a preliminary model of a molecule or molecular complex whose structure coordinates are unknown, by orienting and positioning the relevant portion of the complex according to any one of Tables 2–5 within the unit cell of the crystal of the unknown molecule or molecular complex so as best to account for the observed X-ray diffraction pattern of the crystal of the molecule or molecular complex whose structure is unknown. Phases can then be calculated from this model and combined with the observed X-ray diffraction pattern amplitudes to generate an electron density map of the structure whose coordinates are unknown. This, in turn, can be subjected to any well-known model building and structure refinement techniques to provide a final, accurate structure of the unknown crystallized molecule or molecular complex (E. Lattman, "Use of the Rotation and Translation Functions," in *Meth. Enzymol.,* 115, pp. 55–77 (1985); M. G. Rossmann, ed., "The Molecular Replacement Method," *Int. Sci. Rev. Ser.,* No. 13, Gordon & Breach, New York (1972).

The structure of any portion of any crystallized molecule or molecular complex that is sufficiently homologous to any portion of the FPT:FPP/FPP analog:Peptide/Inhibitor complex can be solved by this method.

In a preferred embodiment, the method of molecular replacement is utilized to obtain structural information about a molecule or molecular complex, wherein the complex comprises an FPT:FPP/FPP analog:Peptide/Inhibitor complex.

The structure coordinates provided by this invention are particularly useful to solve the structure of crystals of FPT:FPP/FPP analog:Peptide/Inhibitor complexes, particularly FPT:FPP, co-complexed with a variety of chemical entities. This approach enables the determination of the optimal sites for interaction between chemical entities, including interaction of candidate FPT inhibitors with FPT or the FPT:FPP complex. For example, high resolution X-ray diffraction data collected from crystals exposed to different types of solvent allows the determination of where each type of solvent molecule resides. Small molecules that bind tightly to those sites can then be designed and synthesized and tested for their FPT inhibition activity.

All of the complexes referred to above may be studied using well-known X-ray diffraction techniques and may be refined versus 1.5–3 Å resolution X-ray data to an R value of about 0.25 or less using computer software, such as XPLOR [Yale University, ©1992; see, e.g., Blundell & Johnson, supra; *Meth. Enzymol.,* vol. 114 and 115, H. W. Wyckoff et al., eds., Academic Press (1985)]. This information may thus be used to optimize known FPT inhibitors, and more importantly, to design new FPT inhibitors.

In order that this invention be more fully understood, the following examples are set forth. These examples are for the illustrative purposes only and are not to be construed as limiting the scope of this invention in any way.

EXAMPLE 1

Expression and Purification of FPT in Sf9 Cells For Analog Complexes

Preparation of Expression Constructs

Rat FPT α and β subunit cDNAs in pUC13 were obtained from ATCC (ATCC clone numbers 63134 and 63127 respectively). The rat α subunit cDNA was excised from pUC13 with Eco RI (5') and Hind III (3') and ligated downstream of the polyhedron promoter in p2Bac (Invitrogen) cut with Eco RI and Hind III to produce pRatA-2B. The ATG start codon in the Nco I site upstream of the rat α subunit in pRatA-2B was removed by cutting with Nco I, removing the single stranded ends with mung bean nuclease, and religating the blunt ends together to produce pRatAN-2B. The rat β subunit was excised from pUC13 with Xma I (5') and Nhe I (3') and ligated downstream of the P10 promoter in pRatAN-2B cut with Xma I (5') and Xba I (3') to produce pRABN-Bac.

pRABN-Bac was co-transfected with Baculovirus Gold DNA (Pharmingen) into Sf9 cells following the manufacturer's protocol. Recombinant baculoviruses were plaque purified and individual clones were tested for expression of FPT activity by SPA (Amersham) and for protein expression by Western blot (Santa Cruz anti-rat FPT antibodies). The highest expressing virus was amplified to high titre (>$10^9$/ml) in Sf9 cells (infecting at MOI <0.1 to retard amplification of defective viruses).

Expression and Purification of Rat FPT from Sf9 Cells

Protein purification was conducted at 4° C. At each stage of the purification eluted proteins were detected by absorbance at 280 nm and active enzyme fractions were assayed by the SPA assay as described below. Western blotting during protein purification was carried out according to a standard protocol using a BCIP/NBT kit (Kirkegaard & Perry Laboratories, Gaitherburg, Md.) with an anti-α subunit polyclonal antibody raised against two peptide sequences of FPT α subunit and an anti-β subunit polyclonal antibody obtained from Santa Cruz Biotechnology (Santa Cruz, Calif.). The molecular weight of FPT was determined by MALDI mass spectroscopy with sinapinic acid as the matrix on a Voyager DE TOF mass spectrometer (PerSeptive Biosystem, Framingham, Mass.). FPT concentrations were determined either by the method of Bradford using a Bio-Rad assay kit with bovine serum albumin (BSA) as a standard or using UV absorption at 280 nm with a molar extinction coefficient of $1.53\times10^5$ $M^{-1}$ $cm^{-1}$.

Ten liters of Sf9 cells were grown at 27° C. to a cell density of $4.0\times10^6$ cells/ml in SF 900II Media (GibcoBRL). Bacculovirus construct RABN-Bac containing the rat FPT gene was added at a multiplicity of infection (MOI) of 2:1. This culture was incubated until the cell viability reached 60–70% (approximately 3 days). Cells were harvested by centrifugation for 20 min at 4° C. and produced ~100 g of a wet cell pellet. The cell pellet was resuspended in 300 ml homogenization buffer containing 50 mM Tris-HCl, pH 7.5, 1 μg/ml E-64, 2 μg/ml aprotinin, 0.7 μg/ml pepstatin, 0.1 mM leupeptin, 1 mM Pefabloc® SC, 1 mM EDTA, 1 mM EGTA and 1 mM DTT (inhibitors from Boehringer Mannheim, DTT from Calbiochem). The resuspended cells were disrupted by pressure using a microfluidizer (Microfluidics Corporation, Newton, Mass.). Cell debris was removed by ultracentrifugation at 100,000 g for 1 hr. The supernatant, containing 1–3% FPT, was adjusted to 2 mM DTT and pH 7.7 then loaded onto a Fast Flow Q-Sepharose column (5×10 cm, Pharmacia) equilibrated in 20 mM Tris, 0.15 M NaCl, 10 μM $ZnCl_2$, 2 mM DTT, pH 7.7. The column was washed with the equilibration buffer, followed by a salt gradient of 0.15 M to 0.5 M NaCl. FPT activity eluted at about 300 mM NaCl and was ~10% pure. The active fractions were adjusted to 0.75 M NaCl using a 5 M NaCl stock solution. This sample was loaded onto a Phenyl Sepharose CL-4B column (Pharmacia), washed with the same starting buffer and the protein was eluted using a 0.75 M–0 M NaCl gradient. The protein eluted at the end of the gradient ~0 M NaCl and was ~50–70% pure. The pooled rat FPT fractions were adjusted to 0.1 M NaCl and loaded onto a Mono Q HR10/10 column (Pharmacia), washed with the same buffer and eluted with a gradient of 0.1–0.5 M NaCl. The active fractions eluted ~0.3 M NaCl and were 60–80% pure. The active fractions were pooled and the buffer was adjusted to 0.75 M NaCl, 20 mM Tris, 10 μM $ZnCl_2$, 1 mM DTT, pH 7.7. This sample was loaded onto a Phenyl Superose HR 10/10 column (Pharmacia), washed with the starting buffer and sample eluted using a 0.75–0 M NaCl gradient. FPT fractions (eluting ~0 M NaCl) that were >95% pure were pooled and dialyzed into a storage buffer consisting of 20 mM Tris-HCl, 20 mM KCl, 10 μM $ZnCl_2$, 1 mM DTT, pH 7.7. The resulting protein solution was stored at −80° C. until use.

FPT Activity Assay. FPT fractions were assayed using the Amersham Scintillation Proximity Assay (SPA) kit. Assays were performed at 23° C. in 200 μL with biotinylated human K-Ras-4B C-terminal peptide KKSKTKCVIM (100 nM) and [1-$^3$H]-FPP (90 nM) as substrates in a buffer of 50 mM Tris, pH 7.7, 5 mM $MgCl_2$, 5 μM $ZnCl_2$, 0.01% Triton X-100, 0.2 mg/ml BSA and 2 mM DTT. Reactions were initiated by adding FPT fractions (25 to 250 ng) to the substrate mixture. The reaction mixture was incubated for 30 min before it was terminated by 3 reaction volumes of a quench solution containing 5 mg/mL scintillation beads, 500 mM EDTA, pH 8.0, and 0.5% BSA. After rocking the quenched solution at room temperature for 30 min, the radioactivity incorporated into the product was directly counted in a 96-well plate format with a Wallac 1204 Betaplate BS liquid scintillation counter.

EXAMPLE 2

Co-Crystallization of FPT:αHFP:Peptide Complexes

Purified rat FPT was dialyzed against 20 mM Tris pH 7.7, 1 mM DTT, 20 mM KCl, 10 μM $ZnCl_2$ and concentrated to 0.27 mM (25 mg/mL) and stored at −30° C. prior to crystallization. The Ac-Cys-Val-Ile-selenoMet-COOH:αHFP: FPT(CVIM:αHFP:FPT) ternary complex was prepared by incubating 108 μM FPT (10 mg/ml) with 300 μM αHFP (Calbiochem-Novabiochem Corporation) for about 2 hours prior to adding 300 μM Ac-Cys-Val-Ile-Met (Se)-COOH (AnaSpec Inc.). αHFP was added from a 23.6 mM solution in ethanol, yielding 0.6% (v/v) ethanol in the final solution. The peptide was added from a 50 mM solution in DMSO, resulting in a 0.3% (v/v) final DMSO concentration. The ternary mixture was incubated at 4° C. for approximately 4 hours. Vapor diffusion crystallization experiments were conducted using the hanging drop method. Potential crystallization conditions were screened by sparse matrix sampling (Jancarik et al., 1991, *J. Appl. Cryst.* 24:409–411) and systematic grid screens (Cox et al, 1998, *J. Cryst. Growth* 90:318–324) using standard solutions (Hampton Research Inc.). Crystals formed when the reservoir contained polyethylene glycol (PEG) and sodium acetate. Crystals most suitable for structure determination grew when the droplet contained 4 μl of the αHFP:CVIM-:FPT complex, 4 μl of the reservoir solution (7% PEG 4000, 0.1 M sodium acetate, pH 5.7) and 1 μl of 200 mM DTT. Crystallization trays were incubated at 22° C. and after 2–3 weeks, hexagonal rods (0.1 mm×0.3 mm) appeared. Crystals can also be grown with other combinations of FPP analogs and $Ca_1a_2X$ (SEQ ID No: 4) peptides such as the following:

| FPP or FPP Analog | $Ca_1a_2X$ (SEQ ID No: 4) Peptide |
|---|---|
| HFP | Ac-CVIM-COOH (SEQ ID NO: 1) |
| FPP | Ac-CVFM-COOH (SEQ ID NO: 3) |

EXAMPLE 3

Co-crystallization of FPT:FPP:Inhibitor Complexes

Cocrystals of FPT:FPP:Inhibitor complexes were grown as described above by substituting FPP at 150 μM. for αHFP and the inhibitor at 150 μM for the CVIM (SEQ ID No: 1) peptide. The following are examples of inhibitors that have been used to form FPT:FPP:Inhibitor co-crystals:

SCH66381 WO 97/23478

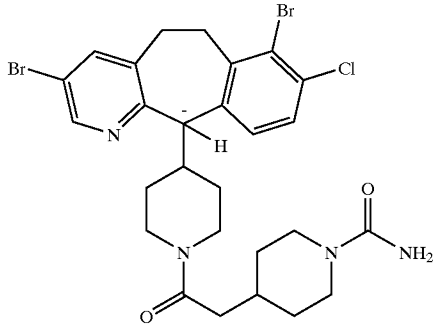

SCH66701 WO 97/23478

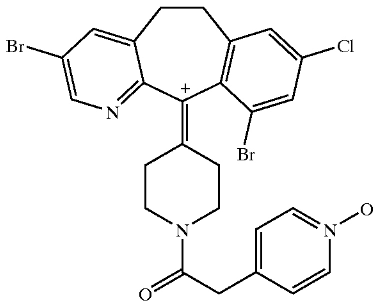

SCH69132 WO 97/23478

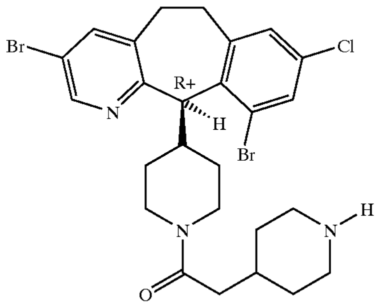

Many FPT inhibitors that are not listed will also be able to be used to form crystals.

EXAMPLE 4

Formation of FPT:FPP:Inhibitor Complexes by Soaking Preformed Co-Crystals

The cocrystals of FPT with αHFP and the CVIM peptide or with FPP and an inhibitor as described above in Examples 2 and 3 can be used to soak FPT inhibitors. Crystals are harvested into the reservoir solution at 4° C. For each new inhibitor, crystals are transferred into reservoir solution supplemented with 10 μM $ZnCl_2$, 2 mM DTT, 100 μM FPP and 100 μM inhibitor. The complex is allowed to form for about 24 hours at 4° C. In the presence of FPP and inhibitors, the FPP analog and peptide or original inhibitor are displaced, allowing structure determination of the new inhibitor:FPP:FPT complex.

EXAMPLE 5

Data Collection

X-ray diffraction data were collected on FPT complexes formed by co-crystallization. Prior to data collection, crystals were taken from the crystallization droplet and flash frozen in liquid propane using a cryoprotectant consisting of the reservoir solution supplemented with 25% (v/v) glycerol. Crystals belong to space group $P6_1$. The unit cell parameters vary less than 2% between crystals and are approximately a=b=174.13 Å, c=69.71 Å, α=β=90°, γ=120°.

Data were acquired by oscillation photography on a Rigaku R-AXIS IIC phosphor imaging area detector mounted on a Rigaku RU200 rotating anode generator (Molecular Structure Corp.), operating at 50 kV and 100 mA. Measured intensities were integrated, scaled and merged using the HKL software package (Z. Otwinowski and W. Minor). Statistics from four selected crystals are shown in Table 1, below:

TABLE 1

Data and Refinement Statistics

| Crystallization Method | Example 2 (αHFP + CVIM) | Example 3 (FPP + SCH66381) | Example 3 (FPP + SCH66701) | Example 3 (FPP + SCH69132) |
|---|---|---|---|---|
| Max Resolution (Å) | 2.4 | 2.2 | 2.9 | 2.5 |
| Linear R-factor (%) | 6.1 | 5.5 | 9.6 | 5.9 |

TABLE 1-continued

| Crystallization Method | Example 2 (αHFP + CVIM) | Example 3 (FPP + SCH66381) | Example 3 (FPP + SCH66701) | Example 3 (FPP + SCH69132) |
|---|---|---|---|---|
| Data and Refinement Statistics | | | | |
| Percent Complete | 90.4 | 90.5 | 97.9 | 59.9 |
| Structure Determination Method | Example 7 | Example 8 | Example 9 | Example 10 |
| Structure Coordinates | Table 2 | Table 3 | Table 4 | Table 5 |
| Refinement R-Factor (%) | 21.5 | 22.3 | 19.5 | 21.0 |

TABLE 2

The following table lists the atomic structure coordinates for FPT in complex with αHFP and CVIM as derived by X-ray diffraction from crystals of that complex. The following abbreviations are used in the table: "RES" refers to the amino acid, FPP, FPP analog, peptide or inhibitor that the atom belongs to. "Atom" refers to the element whose coordinates have been determined. Elements are defined by the first letter in the column except for zinc which is defined by the letters "ZIN", bromine which is defined by the letters "BR" and chlorine which is defined by the letters "CL". "#" is a number to identify the amino acid, FPP, FPP analog, peptide or inhibitor. "X, Y, Z" is the crystallographically determined atomic position determined for each atom. "B" is a thermal factor that measures movement of the atom around its atomic center. "C" refers to the part of the complex the atom belongs to. A = alpha subunit of FPT. B = beta subunit of FPT. Z = zinc atom. F = FPP, H = αHFP, I = FPT inhibitor; W = ordered solvent molecules, P = CVIM peptide.

| RES | ATOM | # | X | Y | Z | B | C |
|---|---|---|---|---|---|---|---|
| PHE | CB | 55 | 192.7 | 152.2 | 10.1 | 88 | A |
| PHE | CG | 55 | 192.8 | 153.3 | 9.1 | 90 | A |
| PHE | CD1 | 55 | 193.7 | 153.3 | 8.1 | 91 | A |
| PHE | CD2 | 55 | 191.8 | 154.4 | 9.2 | 91 | A |
| PHE | CE1 | 55 | 193.8 | 154.4 | 7.2 | 92 | A |
| PHE | CE2 | 55 | 191.9 | 155.4 | 8.3 | 92 | A |
| PHE | CZ | 55 | 192.9 | 155.4 | 7.2 | 92 | A |
| PHE | C | 55 | 194.1 | 153.1 | 12.0 | 83 | A |
| PHE | O | 55 | 194.8 | 154.1 | 11.7 | 83 | A |
| PHE | N | 55 | 194.0 | 150.7 | 11.6 | 85 | A |
| PHE | CA | 55 | 194.0 | 152.0 | 10.9 | 85 | A |
| LEU | N | 56 | 193.4 | 152.9 | 13.1 | 80 | A |
| LEU | CA | 56 | 193.5 | 153.9 | 14.2 | 77 | A |
| LEU | CB | 56 | 192.2 | 154.8 | 14.1 | 77 | A |
| LEU | CG | 56 | 192.4 | 156.3 | 14.5 | 76 | A |
| LEU | CD1 | 56 | 191.2 | 157.1 | 14.1 | 75 | A |
| LEU | CD2 | 56 | 192.7 | 156.5 | 16.0 | 75 | A |
| LEU | C | 56 | 193.5 | 153.1 | 15.5 | 75 | A |
| LEU | O | 56 | 192.5 | 152.4 | 15.9 | 74 | A |
| SER | N | 57 | 194.6 | 153.2 | 16.2 | 72 | A |
| SER | CA | 57 | 194.8 | 152.5 | 17.5 | 69 | A |
| SER | CB | 57 | 196.2 | 152.8 | 18.1 | 70 | A |
| SER | OG | 57 | 197.2 | 152.7 | 17.1 | 73 | A |
| SER | C | 57 | 193.8 | 152.7 | 18.6 | 67 | A |
| SER | O | 57 | 193.3 | 153.9 | 18.8 | 67 | A |
| LEU | N | 58 | 193.5 | 151.7 | 19.4 | 63 | A |
| LEU | CA | 58 | 192.6 | 151.8 | 20.5 | 60 | A |
| LEU | CB | 58 | 192.2 | 150.4 | 21.1 | 58 | A |
| LEU | CG | 58 | 191.0 | 149.7 | 20.6 | 56 | A |
| LEU | CD1 | 58 | 191.0 | 148.4 | 21.3 | 56 | A |
| LEU | CD2 | 58 | 189.8 | 150.4 | 20.9 | 55 | A |
| LEU | C | 58 | 193.3 | 152.6 | 21.6 | 60 | A |
| LEU | O | 58 | 192.7 | 153.2 | 22.4 | 59 | A |
| ASP | N | 59 | 194.7 | 152.6 | 21.5 | 60 | A |
| ASP | CA | 59 | 195.5 | 153.3 | 22.4 | 59 | A |
| ASP | CB | 59 | 196.7 | 152.4 | 22.7 | 62 | A |
| ASP | CG | 59 | 196.3 | 151.0 | 23.2 | 65 | A |
| ASP | OD1 | 59 | 196.6 | 150.1 | 22.4 | 66 | A |
| ASP | OD2 | 59 | 195.6 | 150.9 | 24.2 | 67 | A |
| ASP | C | 59 | 196.0 | 154.7 | 22.0 | 56 | A |

TABLE 2-continued

| | | | | | | | |
|---|---|---|---|---|---|---|---|
| ASP | O | 59 | 196.7 | 155.4 | 22.8 | 56 | A |
| SER | N | 60 | 195.7 | 155.1 | 20.7 | 52 | A |
| SER | CA | 60 | 196.1 | 156.4 | 20.2 | 49 | A |
| SER | CB | 60 | 195.7 | 156.5 | 18.8 | 49 | A |
| SER | OG | 60 | 195.9 | 157.8 | 18.3 | 48 | A |
| SER | C | 60 | 195.5 | 157.5 | 21.1 | 47 | A |
| SER | O | 60 | 194.3 | 157.4 | 21.4 | 47 | A |
| PRO | N | 61 | 196.3 | 158.5 | 21.3 | 45 | A |
| PRO | CD | 61 | 197.6 | 158.8 | 20.8 | 44 | A |
| PRO | CA | 61 | 195.8 | 159.7 | 22.1 | 43 | A |
| PRO | CB | 61 | 197.0 | 160.6 | 22.2 | 43 | A |
| PRO | CG | 61 | 197.7 | 160.3 | 20.9 | 44 | A |
| PRO | C | 61 | 194.6 | 160.4 | 21.4 | 42 | A |
| PRO | O | 61 | 193.8 | 161.1 | 22.0 | 40 | A |
| THR | N | 62 | 194.6 | 160.2 | 20.1 | 41 | A |
| THR | CA | 62 | 193.6 | 160.8 | 19.2 | 42 | A |
| THR | CB | 62 | 194.2 | 161.6 | 18.1 | 41 | A |
| THR | OG1 | 62 | 195.0 | 160.8 | 17.2 | 41 | A |
| THR | CG2 | 62 | 195.1 | 162.7 | 18.7 | 40 | A |
| THR | C | 62 | 192.6 | 159.7 | 18.7 | 42 | A |
| THR | O | 62 | 192.2 | 159.8 | 17.5 | 43 | A |
| TYR | N | 63 | 192.3 | 158.8 | 19.5 | 41 | A |
| TYR | CA | 63 | 191.3 | 157.7 | 19.1 | 39 | A |
| TYR | CB | 63 | 191.5 | 156.5 | 20.1 | 37 | A |
| TYR | CG | 63 | 190.4 | 155.5 | 19.9 | 35 | A |
| TYR | CD1 | 63 | 190.5 | 154.5 | 18.9 | 35 | A |
| TYR | CE1 | 63 | 189.5 | 153.5 | 18.7 | 35 | A |
| TYR | CD2 | 63 | 189.2 | 155.5 | 20.7 | 35 | A |
| TYR | CE2 | 63 | 188.2 | 154.5 | 20.5 | 35 | A |
| TYR | CZ | 63 | 188.4 | 153.6 | 19.5 | 34 | A |
| TYR | OH | 63 | 187.4 | 152.6 | 19.3 | 34 | A |
| TYR | C | 63 | 189.9 | 158.3 | 19.3 | 40 | A |
| TYR | O | 63 | 189.6 | 158.9 | 20.3 | 40 | A |
| VAL | N | 64 | 189.1 | 158.1 | 18.3 | 40 | A |
| VAL | CA | 64 | 187.7 | 158.5 | 18.4 | 40 | A |
| VAL | CB | 64 | 187.4 | 159.5 | 17.3 | 40 | A |
| VAL | CG1 | 64 | 188.1 | 160.8 | 17.5 | 40 | A |
| VAL | CG2 | 64 | 187.7 | 159.0 | 15.9 | 39 | A |
| VAL | C | 64 | 186.7 | 157.4 | 18.3 | 40 | A |
| VAL | O | 64 | 186.9 | 156.4 | 17.5 | 40 | A |
| LEU | N | 65 | 185.6 | 157.4 | 19.1 | 40 | A |
| LEU | CA | 65 | 184.6 | 156.4 | 19.1 | 39 | A |
| LEU | CB | 65 | 183.4 | 156.8 | 20.0 | 36 | A |
| LEU | CG | 65 | 183.9 | 157.1 | 21.5 | 36 | A |
| LEU | CD1 | 65 | 182.7 | 157.5 | 22.3 | 36 | A |
| LEU | CD2 | 65 | 184.6 | 156.0 | 22.1 | 34 | A |
| LEU | C | 65 | 184.0 | 156.3 | 17.7 | 42 | A |
| LEU | O | 65 | 183.9 | 157.2 | 16.9 | 43 | A |
| TYR | N | 66 | 183.6 | 155.0 | 17.4 | 44 | A |
| TYR | CA | 66 | 183.0 | 154.7 | 16.1 | 43 | A |
| TYR | CB | 66 | 182.6 | 153.2 | 16.0 | 41 | A |
| TYR | CG | 66 | 183.8 | 152.4 | 15.7 | 40 | A |
| TYR | CD1 | 66 | 184.7 | 152.1 | 16.7 | 40 | A |
| TYR | CE1 | 66 | 185.8 | 151.4 | 16.4 | 40 | A |
| TYR | CD2 | 66 | 184.0 | 151.9 | 14.5 | 39 | A |
| TYR | CE2 | 66 | 185.1 | 151.1 | 14.2 | 39 | A |
| TYR | CZ | 66 | 186.0 | 150.9 | 15.2 | 40 | A |
| TYR | OH | 66 | 187.1 | 150.1 | 14.9 | 40 | A |
| TYR | C | 66 | 181.7 | 155.6 | 15.9 | 43 | A |
| TYR | O | 66 | 181.5 | 156.0 | 14.7 | 44 | A |
| ARG | N | 67 | 181.0 | 155.9 | 16.9 | 44 | A |
| ARG | CA | 67 | 179.8 | 156.1 | 16.8 | 46 | A |
| ARG | CB | 67 | 179.0 | 156.8 | 18.1 | 46 | A |
| ARG | CG | 67 | 179.7 | 157.5 | 19.3 | 47 | A |
| ARG | CD | 67 | 178.7 | 157.7 | 20.4 | 48 | A |
| ARG | NE | 67 | 179.2 | 158.1 | 21.6 | 49 | A |
| ARG | CZ | 67 | 179.3 | 157.4 | 22.7 | 50 | A |
| ARG | NH1 | 67 | 179.0 | 156.1 | 22.7 | 52 | A |
| ARG | NH2 | 67 | 179.8 | 157.9 | 23.8 | 51 | A |
| ARG | C | 67 | 180.2 | 158.1 | 16.4 | 46 | A |
| ARG | O | 67 | 179.5 | 158.7 | 15.6 | 49 | A |
| ASP | N | 68 | 181.4 | 158.6 | 16.8 | 46 | A |
| ASP | CA | 68 | 181.9 | 159.9 | 16.3 | 45 | A |
| ASP | CB | 68 | 182.8 | 160.5 | 17.4 | 45 | A |
| ASP | CG | 68 | 182.1 | 160.9 | 18.6 | 46 | A |
| ASP | OD1 | 68 | 180.8 | 161.1 | 18.6 | 47 | A |
| ASP | OD2 | 68 | 182.7 | 161.1 | 19.7 | 47 | A |
| ASP | C | 68 | 182.6 | 159.8 | 15.0 | 45 | A |
| ASP | O | 68 | 183.2 | 160.8 | 14.6 | 47 | A |

TABLE 2-continued

| | | | | | | | |
|---|---|---|---|---|---|---|---|
| ARG | N | 69 | 182.5 | 158.7 | 14.3 | 45 | A |
| ARG | CA | 69 | 183.2 | 158.5 | 13.0 | 46 | A |
| ARG | CB | 69 | 183.9 | 157.2 | 12.9 | 46 | A |
| ARG | CG | 69 | 185.0 | 157.0 | 14.0 | 44 | A |
| ARG | CD | 69 | 185.9 | 155.8 | 13.8 | 41 | A |
| ARG | NE | 69 | 186.6 | 155.5 | 15.0 | 38 | A |
| ARG | CZ | 69 | 187.6 | 154.6 | 15.1 | 35 | A |
| ARG | NH1 | 69 | 188.0 | 154.0 | 14.0 | 34 | A |
| ARG | NH2 | 69 | 188.1 | 154.4 | 16.3 | 34 | A |
| ARG | C | 69 | 182.4 | 158.8 | 11.8 | 48 | A |
| ARG | O | 69 | 181.3 | 158.2 | 11.6 | 49 | A |
| ALA | N | 70 | 183.0 | 159.6 | 10.9 | 50 | A |
| ALA | CA | 70 | 182.4 | 160.0 | 9.6 | 52 | A |
| ALA | CB | 70 | 183.2 | 161.1 | 9.0 | 52 | A |
| ALA | C | 70 | 182.2 | 158.8 | 8.7 | 53 | A |
| ALA | O | 70 | 181.2 | 158.9 | 7.9 | 54 | A |
| GLU | N | 71 | 183.1 | 157.9 | 8.7 | 56 | A |
| GLU | CA | 71 | 183.0 | 156.7 | 7.7 | 58 | A |
| GLU | CB | 71 | 184.4 | 156.2 | 7.3 | 59 | A |
| GLU | CG | 71 | 185.3 | 155.7 | 8.5 | 62 | A |
| GLU | CD | 71 | 185.9 | 156.7 | 9.4 | 62 | A |
| GLU | OE1 | 71 | 186.1 | 156.4 | 10.6 | 63 | A |
| GLU | OE2 | 71 | 186.2 | 157.9 | 9.0 | 63 | A |
| GLU | C | 71 | 182.1 | 155.6 | 8.3 | 58 | A |
| GLU | O | 71 | 182.0 | 154.5 | 7.7 | 58 | A |
| TRP | N | 72 | 181.6 | 155.9 | 9.5 | 59 | A |
| TRP | CA | 72 | 180.7 | 154.9 | 10.3 | 61 | A |
| TRP | CB | 72 | 181.5 | 154.4 | 11.5 | 60 | A |
| TRP | CG | 72 | 182.5 | 153.3 | 11.2 | 58 | A |
| TRP | CD2 | 72 | 182.2 | 151.9 | 11.1 | 57 | A |
| TRP | CE2 | 72 | 183.4 | 151.3 | 10.8 | 58 | A |
| TRP | CE3 | 72 | 181.0 | 151.2 | 11.1 | 57 | A |
| TRP | CD1 | 72 | 183.8 | 153.5 | 11.0 | 58 | A |
| TRP | NE1 | 72 | 184.4 | 152.2 | 10.7 | 58 | A |
| TRP | CZ2 | 72 | 183.5 | 149.9 | 10.6 | 57 | A |
| TRP | CZ3 | 72 | 181.1 | 149.8 | 10.9 | 56 | A |
| TRP | CH2 | 72 | 182.3 | 149.2 | 10.7 | 56 | A |
| TRP | C | 72 | 179.4 | 155.6 | 10.7 | 62 | A |
| TRP | O | 72 | 179.1 | 155.6 | 11.9 | 62 | A |
| ALA | N | 73 | 178.7 | 156.3 | 9.8 | 64 | A |
| ALA | CA | 73 | 177.5 | 157.0 | 10.1 | 65 | A |
| ALA | CB | 73 | 177.7 | 158.5 | 9.8 | 66 | A |
| ALA | C | 73 | 176.3 | 156.4 | 9.4 | 64 | A |
| ALA | O | 73 | 175.1 | 156.6 | 9.8 | 64 | A |
| ASP | N | 74 | 176.6 | 155.7 | 8.3 | 64 | A |
| ASP | CA | 74 | 175.5 | 155.1 | 7.5 | 63 | A |
| ASP | CB | 74 | 176.1 | 154.7 | 6.1 | 63 | A |
| ASP | CG | 74 | 177.3 | 153.8 | 6.2 | 62 | A |
| ASP | OD1 | 74 | 177.1 | 152.5 | 6.0 | 62 | A |
| ASP | OD2 | 74 | 178.4 | 154.2 | 6.4 | 62 | A |
| ASP | C | 74 | 175.0 | 153.9 | 8.3 | 63 | A |
| ASP | O | 74 | 173.9 | 153.4 | 8.0 | 64 | A |
| ILE | N | 75 | 175.8 | 153.4 | 9.3 | 62 | A |
| ILE | CA | 75 | 175.4 | 152.2 | 10.1 | 61 | A |
| ILE | CB | 75 | 176.6 | 151.3 | 10.3 | 61 | A |
| ILE | CG2 | 75 | 176.1 | 150.0 | 11.0 | 61 | A |
| ILE | CG1 | 75 | 177.2 | 150.9 | 9.0 | 60 | A |
| ILE | CD1 | 75 | 178.4 | 150.1 | 9.1 | 61 | A |
| ILE | C | 75 | 174.8 | 152.6 | 11.4 | 61 | A |
| ILE | O | 75 | 175.3 | 153.7 | 12.0 | 61 | A |
| ASP | N | 76 | 173.9 | 151.8 | 11.9 | 61 | A |
| ASP | CA | 76 | 173.3 | 152.1 | 13.3 | 60 | A |
| ASP | CB | 76 | 171.8 | 151.9 | 13.2 | 63 | A |
| ASP | CG | 76 | 171.1 | 153.1 | 12.4 | 65 | A |
| ASP | OD1 | 76 | 170.6 | 152.9 | 11.3 | 65 | A |
| ASP | OD2 | 76 | 171.0 | 154.2 | 13.0 | 65 | A |
| ASP | C | 76 | 173.9 | 151.0 | 14.2 | 59 | A |
| ASP | O | 76 | 173.9 | 149.8 | 13.9 | 59 | A |
| PRO | N | 77 | 174.5 | 151.4 | 15.3 | 57 | A |
| PRO | CD | 77 | 174.8 | 152.8 | 15.6 | 56 | A |
| PRO | CA | 77 | 175.1 | 150.5 | 16.3 | 55 | A |
| PRO | CB | 77 | 175.8 | 151.5 | 17.2 | 56 | A |
| PRO | CG | 77 | 175.0 | 152.7 | 17.1 | 56 | A |
| PRO | C | 77 | 174.1 | 149.7 | 17.0 | 55 | A |
| PRO | O | 77 | 173.2 | 150.2 | 17.7 | 55 | A |
| VAL | N | 78 | 174.2 | 148.4 | 16.8 | 53 | A |
| VAL | CA | 78 | 173.2 | 147.4 | 17.4 | 51 | A |
| VAL | CB | 78 | 173.2 | 146.1 | 16.6 | 52 | A |
| VAL | CG1 | 78 | 172.2 | 145.1 | 17.2 | 51 | A |

TABLE 2-continued

| | | | | | | | |
|---|---|---|---|---|---|---|---|
| VAL | CG2 | 78 | 172.8 | 146.4 | 15.2 | 51 | A |
| VAL | C | 78 | 173.8 | 147.1 | 18.8 | 52 | A |
| VAL | O | 78 | 174.9 | 146.5 | 18.9 | 52 | A |
| PRO | N | 79 | 173.1 | 147.5 | 19.8 | 52 | A |
| PRO | CD | 79 | 171.9 | 148.4 | 19.7 | 51 | A |
| PRO | CA | 79 | 173.4 | 147.3 | 21.2 | 52 | A |
| PRO | CB | 79 | 172.5 | 148.3 | 21.9 | 52 | A |
| PRO | CG | 79 | 171.3 | 148.2 | 21.1 | 52 | A |
| PRO | C | 79 | 173.2 | 145.9 | 21.7 | 53 | A |
| PRO | O | 79 | 172.3 | 145.2 | 21.1 | 54 | A |
| GLN | N | 80 | 173.8 | 145.5 | 22.8 | 54 | A |
| GLN | CA | 80 | 173.6 | 144.2 | 23.3 | 54 | A |
| GLN | CB | 80 | 174.7 | 143.8 | 24.3 | 53 | A |
| GLN | CG | 80 | 174.8 | 142.3 | 24.5 | 53 | A |
| GLN | CD | 80 | 176.0 | 141.9 | 25.3 | 54 | A |
| GLN | OE1 | 80 | 176.3 | 142.3 | 26.4 | 55 | A |
| GLN | NE2 | 80 | 176.8 | 141.1 | 24.6 | 55 | A |
| GLN | C | 80 | 172.3 | 144.1 | 24.0 | 55 | A |
| GLN | O | 80 | 171.8 | 145.0 | 24.6 | 57 | A |
| ASN | N | 81 | 171.6 | 142.9 | 23.8 | 56 | A |
| ASN | CA | 81 | 170.3 | 142.6 | 24.3 | 56 | A |
| ASN | CB | 81 | 169.4 | 142.1 | 23.2 | 58 | A |
| ASN | CG | 81 | 168.0 | 141.8 | 23.8 | 60 | A |
| ASN | OD1 | 81 | 167.5 | 142.3 | 24.8 | 59 | A |
| ASN | ND2 | 81 | 167.3 | 140.9 | 23.1 | 61 | A |
| ASN | C | 81 | 170.5 | 141.6 | 25.4 | 55 | A |
| ASN | O | 81 | 170.4 | 140.4 | 25.2 | 54 | A |
| ASP | N | 82 | 170.7 | 142.1 | 26.7 | 54 | A |
| ASP | CA | 82 | 170.8 | 141.2 | 27.9 | 54 | A |
| ASP | CB | 82 | 171.7 | 141.9 | 28.9 | 53 | A |
| ASP | CG | 82 | 173.2 | 141.8 | 28.4 | 53 | A |
| ASP | OD1 | 82 | 173.5 | 141.4 | 27.3 | 52 | A |
| ASP | OD2 | 82 | 174.0 | 142.3 | 29.3 | 53 | A |
| ASP | C | 82 | 169.5 | 140.9 | 28.5 | 55 | A |
| ASP | O | 82 | 169.4 | 140.3 | 29.6 | 54 | A |
| GLY | N | 83 | 168.4 | 141.4 | 28.0 | 56 | A |
| GLY | CA | 83 | 167.1 | 141.2 | 28.5 | 57 | A |
| GLY | C | 83 | 166.7 | 142.2 | 29.6 | 57 | A |
| GLY | O | 83 | 167.6 | 142.7 | 30.4 | 58 | A |
| PRO | N | 84 | 165.4 | 142.6 | 29.7 | 57 | A |
| PRO | CD | 84 | 164.4 | 141.9 | 28.9 | 56 | A |
| PRO | CA | 84 | 164.9 | 143.5 | 30.6 | 56 | A |
| PRO | CB | 84 | 163.4 | 143.3 | 30.4 | 57 | A |
| PRO | CG | 84 | 163.2 | 141.9 | 29.9 | 57 | A |
| PRO | C | 84 | 165.3 | 143.4 | 32.1 | 56 | A |
| PRO | O | 84 | 165.2 | 144.3 | 32.9 | 57 | A |
| SER | N | 85 | 165.8 | 142.2 | 32.4 | 56 | A |
| SER | CA | 85 | 166.3 | 142.0 | 33.8 | 56 | A |
| SER | CB | 85 | 165.2 | 141.2 | 34.5 | 57 | A |
| SER | OG | 85 | 163.9 | 141.6 | 34.2 | 60 | A |
| SER | C | 85 | 167.6 | 141.2 | 33.7 | 55 | A |
| SER | O | 85 | 167.6 | 140.0 | 33.6 | 55 | A |
| PRO | N | 86 | 168.7 | 141.9 | 33.6 | 54 | A |
| PRO | CD | 86 | 168.7 | 143.4 | 33.4 | 54 | A |
| PRO | CA | 86 | 170.1 | 141.4 | 33.5 | 52 | A |
| PRO | CB | 86 | 170.9 | 142.6 | 33.2 | 53 | A |
| PRO | CG | 86 | 169.9 | 143.6 | 32.5 | 53 | A |
| PRO | C | 86 | 170.6 | 140.6 | 34.6 | 49 | A |
| PRO | O | 86 | 170.2 | 140.8 | 35.8 | 49 | A |
| VAL | N | 87 | 171.6 | 139.7 | 34.3 | 46 | A |
| VAL | CA | 87 | 172.3 | 138.9 | 35.3 | 43 | A |
| VAL | CB | 87 | 171.7 | 137.4 | 35.4 | 44 | A |
| VAL | CG1 | 87 | 170.5 | 137.4 | 36.3 | 44 | A |
| VAL | CG2 | 87 | 171.3 | 136.9 | 34.0 | 43 | A |
| VAL | C | 87 | 173.7 | 138.9 | 34.8 | 42 | A |
| VAL | O | 87 | 173.9 | 139.1 | 33.6 | 42 | A |
| VAL | N | 88 | 174.7 | 138.6 | 35.7 | 41 | A |
| VAL | CA | 88 | 176.1 | 138.7 | 35.5 | 39 | A |
| VAL | CB | 88 | 176.7 | 137.3 | 35.1 | 38 | A |
| VAL | CG1 | 88 | 176.8 | 136.5 | 36.4 | 37 | A |
| VAL | CG2 | 88 | 176.0 | 136.6 | 34.0 | 37 | A |
| VAL | C | 88 | 176.3 | 139.6 | 34.3 | 41 | A |
| VAL | O | 88 | 176.8 | 139.3 | 33.2 | 42 | A |
| GLN | N | 89 | 175.8 | 140.9 | 34.5 | 41 | A |
| GLN | CA | 89 | 175.9 | 141.9 | 33.5 | 42 | A |
| GLN | CB | 89 | 174.7 | 142.8 | 33.7 | 42 | A |
| GLN | CG | 89 | 174.7 | 144.1 | 33.2 | 44 | A |
| GLN | CD | 89 | 173.6 | 144.9 | 33.8 | 46 | A |
| GLN | OE1 | 89 | 173.4 | 144.9 | 35.0 | 46 | A |

TABLE 2-continued

| | | | | | | | |
|---|---|---|---|---|---|---|---|
| GLN | NE2 | 89 | 172.8 | 145.6 | 33.0 | 46 | A |
| GLN | C | 89 | 177.2 | 142.8 | 33.7 | 42 | A |
| GLN | O | 89 | 177.4 | 143.4 | 34.8 | 43 | A |
| ILE | N | 90 | 178.0 | 142.8 | 32.7 | 42 | A |
| ILE | CA | 90 | 179.3 | 143.6 | 32.8 | 42 | A |
| ILE | CB | 90 | 180.3 | 143.0 | 31.8 | 40 | A |
| ILE | CG2 | 90 | 181.7 | 143.5 | 32.1 | 40 | A |
| ILE | CG1 | 90 | 180.3 | 141.4 | 31.9 | 39 | A |
| ILE | CD1 | 90 | 180.9 | 140.7 | 30.8 | 37 | A |
| ILE | C | 90 | 179.1 | 145.1 | 32.4 | 44 | A |
| ILE | O | 90 | 178.3 | 145.4 | 31.5 | 45 | A |
| ILE | N | 91 | 179.7 | 146.0 | 33.2 | 46 | A |
| ILE | CA | 91 | 179.6 | 147.4 | 33.0 | 45 | A |
| ILE | CB | 91 | 179.6 | 148.2 | 34.3 | 46 | A |
| ILE | CG2 | 91 | 179.6 | 149.7 | 34.0 | 46 | A |
| ILE | CG1 | 91 | 178.5 | 147.9 | 35.3 | 46 | A |
| ILE | CD1 | 91 | 177.1 | 148.1 | 34.6 | 47 | A |
| ILE | C | 91 | 180.7 | 147.7 | 32.1 | 44 | A |
| ILE | O | 91 | 181.8 | 148.0 | 32.6 | 42 | A |
| TYR | N | 92 | 180.5 | 147.7 | 30.8 | 44 | A |
| TYR | CA | 92 | 181.5 | 147.9 | 29.8 | 43 | A |
| TYR | CB | 92 | 181.1 | 147.5 | 28.4 | 42 | A |
| TYR | CG | 92 | 180.5 | 146.2 | 28.3 | 42 | A |
| TYR | CD1 | 92 | 179.2 | 146.0 | 27.8 | 42 | A |
| TYR | CE1 | 92 | 178.5 | 144.8 | 27.7 | 41 | A |
| TYR | CD2 | 92 | 181.1 | 145.0 | 28.7 | 41 | A |
| TYR | CE2 | 92 | 180.5 | 143.7 | 28.6 | 41 | A |
| TYR | CZ | 92 | 179.2 | 143.6 | 28.1 | 40 | A |
| TYR | OH | 92 | 178.6 | 142.4 | 28.0 | 39 | A |
| TYR | C | 92 | 181.8 | 149.4 | 29.8 | 43 | A |
| TYR | O | 92 | 181.0 | 150.2 | 30.3 | 44 | A |
| SER | N | 93 | 183.0 | 149.7 | 29.4 | 44 | A |
| SER | CA | 93 | 183.5 | 151.1 | 29.3 | 45 | A |
| SER | CB | 93 | 185.0 | 151.1 | 29.1 | 45 | A |
| SER | OG | 93 | 185.4 | 150.1 | 28.2 | 46 | A |
| SER | C | 93 | 182.8 | 151.6 | 28.0 | 45 | A |
| SER | O | 93 | 182.3 | 150.9 | 27.2 | 46 | A |
| GLU | N | 94 | 182.8 | 152.9 | 27.9 | 45 | A |
| GLU | CA | 94 | 182.1 | 153.5 | 26.7 | 47 | A |
| GLU | CB | 94 | 182.2 | 155.1 | 26.8 | 49 | A |
| GLU | CG | 94 | 181.1 | 155.8 | 26.0 | 52 | A |
| GLU | CD | 94 | 179.8 | 155.8 | 26.7 | 54 | A |
| GLU | OE1 | 94 | 178.7 | 155.7 | 26.0 | 54 | A |
| GLU | OE2 | 94 | 179.7 | 155.9 | 28.0 | 54 | A |
| GLU | C | 94 | 182.8 | 153.1 | 25.5 | 46 | A |
| GLU | O | 94 | 182.2 | 152.9 | 24.4 | 46 | A |
| LYS | N | 95 | 184.1 | 152.8 | 25.6 | 45 | A |
| LYS | CA | 95 | 184.9 | 152.4 | 24.5 | 43 | A |
| LYS | CB | 95 | 186.4 | 152.6 | 24.7 | 43 | A |
| LYS | CG | 95 | 187.2 | 152.8 | 23.5 | 43 | A |
| LYS | CD | 95 | 188.5 | 153.4 | 23.7 | 43 | A |
| LYS | CE | 95 | 189.5 | 152.3 | 24.2 | 43 | A |
| LYS | NZ | 95 | 190.8 | 152.9 | 24.0 | 43 | A |
| LYS | C | 95 | 184.7 | 150.9 | 24.1 | 42 | A |
| LYS | O | 95 | 184.6 | 150.6 | 22.9 | 42 | A |
| PHE | N | 96 | 184.5 | 150.0 | 25.1 | 41 | A |
| PHE | CA | 96 | 184.2 | 148.6 | 24.8 | 39 | A |
| PHE | CB | 96 | 184.3 | 147.8 | 26.1 | 36 | A |
| PHE | CG | 96 | 184.3 | 146.3 | 26.0 | 35 | A |
| PHE | CD1 | 96 | 185.4 | 145.6 | 26.1 | 35 | A |
| PHE | CD2 | 96 | 183.1 | 145.7 | 25.7 | 35 | A |
| PHE | CE1 | 96 | 185.4 | 144.2 | 25.9 | 33 | A |
| PHE | CE2 | 96 | 183.0 | 144.3 | 25.6 | 34 | A |
| PHE | CZ | 96 | 184.2 | 143.6 | 25.7 | 34 | A |
| PHE | C | 96 | 182.9 | 148.5 | 24.2 | 39 | A |
| PHE | O | 96 | 182.7 | 147.8 | 23.2 | 39 | A |
| ARG | N | 97 | 181.9 | 149.1 | 24.8 | 39 | A |
| ARG | CA | 97 | 180.5 | 149.1 | 24.3 | 40 | A |
| ARG | CB | 97 | 179.6 | 150.0 | 25.2 | 43 | A |
| ARG | CG | 97 | 178.6 | 149.2 | 26.0 | 48 | A |
| ARG | CD | 97 | 177.6 | 150.1 | 26.7 | 52 | A |
| ARG | NE | 97 | 178.3 | 151.0 | 27.6 | 56 | A |
| ARG | CZ | 97 | 178.7 | 152.3 | 27.3 | 57 | A |
| ARG | NH1 | 97 | 178.4 | 152.8 | 26.1 | 58 | A |
| ARG | NH2 | 97 | 179.3 | 153.0 | 28.2 | 58 | A |
| ARG | C | 97 | 180.4 | 149.7 | 22.9 | 39 | A |
| ARG | O | 97 | 179.7 | 149.2 | 22.1 | 39 | A |
| ASP | N | 98 | 181.2 | 150.8 | 22.7 | 38 | A |
| ASP | CA | 98 | 181.1 | 151.4 | 21.3 | 37 | A |

TABLE 2-continued

| | | | | | | | |
|---|---|---|---|---|---|---|---|
| ASP | CB | 98 | 181.9 | 152.7 | 21.4 | 37 | A |
| ASP | CG | 98 | 182.1 | 153.3 | 20.0 | 38 | A |
| ASP | OD1 | 98 | 181.2 | 153.8 | 19.4 | 39 | A |
| ASP | OD2 | 98 | 183.3 | 153.3 | 19.5 | 39 | A |
| ASP | C | 98 | 181.5 | 150.5 | 20.2 | 36 | A |
| ASP | O | 98 | 180.7 | 150.2 | 19.3 | 36 | A |
| VAL | N | 99 | 182.7 | 149.9 | 20.3 | 34 | A |
| VAL | CA | 99 | 183.3 | 149.0 | 19.3 | 32 | A |
| VAL | CB | 99 | 184.7 | 148.4 | 19.6 | 31 | A |
| VAL | CG1 | 99 | 185.0 | 147.2 | 18.8 | 30 | A |
| VAL | CG2 | 99 | 185.8 | 149.5 | 19.4 | 29 | A |
| VAL | C | 99 | 182.3 | 147.8 | 19.1 | 33 | A |
| VAL | O | 99 | 181.9 | 147.4 | 17.9 | 34 | A |
| TYR | N | 100 | 181.8 | 147.2 | 20.2 | 33 | A |
| TYR | CA | 100 | 180.9 | 146.1 | 20.1 | 35 | A |
| TYR | CB | 100 | 180.9 | 145.3 | 21.4 | 33 | A |
| TYR | CG | 100 | 182.0 | 144.3 | 21.5 | 32 | A |
| TYR | CD1 | 100 | 183.2 | 144.7 | 22.1 | 31 | A |
| TYR | CE1 | 100 | 184.3 | 143.8 | 22.1 | 30 | A |
| TYR | CD2 | 100 | 181.9 | 143.0 | 20.9 | 31 | A |
| TYR | CE2 | 100 | 183.0 | 142.2 | 21.0 | 31 | A |
| TYR | CZ | 100 | 184.2 | 142.5 | 21.5 | 30 | A |
| TYR | OH | 100 | 185.2 | 141.7 | 21.5 | 29 | A |
| TYR | C | 100 | 179.5 | 146.3 | 19.5 | 37 | A |
| TYR | O | 100 | 179.0 | 145.4 | 18.9 | 39 | A |
| ASP | N | 101 | 179.0 | 147.5 | 19.8 | 38 | A |
| ASP | CA | 101 | 177.7 | 147.9 | 19.3 | 37 | A |
| ASP | CB | 101 | 177.2 | 149.3 | 19.8 | 39 | A |
| ASP | CG | 101 | 176.5 | 149.2 | 21.2 | 40 | A |
| ASP | OD1 | 101 | 176.5 | 148.2 | 21.9 | 41 | A |
| ASP | OD2 | 101 | 176.0 | 150.3 | 21.6 | 42 | A |
| ASP | C | 101 | 177.8 | 147.9 | 17.8 | 37 | A |
| ASP | O | 101 | 176.9 | 147.5 | 17.0 | 35 | A |
| TYR | N | 102 | 179.0 | 148.3 | 17.3 | 36 | A |
| TYR | CA | 102 | 179.3 | 148.4 | 15.9 | 36 | A |
| TYR | CB | 102 | 180.4 | 149.3 | 15.6 | 39 | A |
| TYR | CG | 102 | 179.9 | 150.7 | 15.5 | 40 | A |
| TYR | CD1 | 102 | 179.4 | 151.2 | 14.2 | 41 | A |
| TYR | CE1 | 102 | 178.8 | 152.4 | 14.1 | 42 | A |
| TYR | CD2 | 102 | 179.7 | 151.6 | 16.6 | 41 | A |
| TYR | CE2 | 102 | 179.0 | 152.8 | 16.5 | 41 | A |
| TYR | CZ | 102 | 178.6 | 153.2 | 15.3 | 42 | A |
| TYR | OH | 102 | 177.9 | 154.4 | 15.1 | 43 | A |
| TYR | C | 102 | 179.6 | 147.0 | 15.4 | 36 | A |
| TYR | O | 102 | 179.3 | 146.7 | 14.2 | 37 | A |
| PHE | N | 103 | 180.1 | 146.1 | 16.2 | 36 | A |
| PHE | CA | 103 | 180.4 | 144.8 | 15.8 | 36 | A |
| PHE | CB | 103 | 181.3 | 144.0 | 16.7 | 34 | A |
| PHE | CG | 103 | 181.6 | 142.6 | 16.2 | 34 | A |
| PHE | CD1 | 103 | 182.6 | 142.4 | 15.3 | 34 | A |
| PHE | CD2 | 103 | 180.8 | 141.5 | 16.6 | 34 | A |
| PHE | CE1 | 103 | 182.9 | 141.1 | 14.8 | 33 | A |
| PHE | CE2 | 103 | 181.1 | 140.2 | 16.1 | 33 | A |
| PHE | CZ | 103 | 182.1 | 140.0 | 15.2 | 33 | A |
| PHE | C | 103 | 179.1 | 144.0 | 15.5 | 38 | A |
| PHE | O | 103 | 178.9 | 143.3 | 14.5 | 37 | A |
| ARG | N | 104 | 178.2 | 144.1 | 16.5 | 40 | A |
| ARG | CA | 104 | 176.9 | 143.5 | 16.4 | 42 | A |
| ARG | CB | 104 | 176.0 | 143.9 | 17.6 | 43 | A |
| ARG | CG | 104 | 176.5 | 143.4 | 18.9 | 45 | A |
| ARG | CD | 104 | 176.0 | 144.1 | 20.1 | 46 | A |
| ARG | NE | 104 | 176.7 | 143.6 | 21.3 | 49 | A |
| ARG | CZ | 104 | 177.1 | 144.4 | 22.3 | 51 | A |
| ARG | NH1 | 104 | 177.0 | 145.7 | 22.3 | 51 | A |
| ARG | NH2 | 104 | 177.8 | 143.7 | 23.3 | 52 | A |
| ARG | C | 104 | 176.1 | 143.8 | 15.1 | 42 | A |
| ARG | O | 104 | 175.4 | 143.0 | 14.5 | 45 | A |
| ALA | N | 105 | 176.4 | 145.1 | 14.6 | 42 | A |
| ALA | CA | 105 | 175.7 | 145.6 | 13.4 | 42 | A |
| ALA | CB | 105 | 175.7 | 147.1 | 13.4 | 42 | A |
| ALA | C | 105 | 176.3 | 145.1 | 12.1 | 42 | A |
| ALA | O | 105 | 175.6 | 144.7 | 11.2 | 43 | A |
| VAL | N | 106 | 177.7 | 145.2 | 12.0 | 42 | A |
| VAL | CA | 106 | 178.4 | 144.7 | 10.9 | 42 | A |
| VAL | CB | 106 | 179.9 | 145.1 | 11.0 | 42 | A |
| VAL | CG1 | 106 | 180.9 | 143.9 | 10.7 | 41 | A |
| VAL | CG2 | 106 | 180.3 | 146.2 | 10.1 | 41 | A |
| VAL | C | 106 | 178.2 | 143.2 | 10.7 | 42 | A |
| VAL | O | 106 | 178.0 | 142.7 | 9.6 | 40 | A |

TABLE 2-continued

| | | | | | | | |
|---|---|---|---|---|---|---|---|
| LEU | N | 107 | 178.2 | 142.5 | 11.8 | 43 | A |
| LEU | CA | 107 | 178.0 | 141.1 | 11.8 | 44 | A |
| LEU | CB | 107 | 178.3 | 140.5 | 13.2 | 42 | A |
| LEU | CG | 107 | 178.0 | 139.0 | 13.5 | 40 | A |
| LEU | CD1 | 107 | 178.8 | 138.2 | 12.6 | 40 | A |
| LEU | CD2 | 107 | 178.2 | 138.6 | 14.9 | 39 | A |
| LEU | C | 107 | 176.6 | 140.8 | 11.4 | 48 | A |
| LEU | O | 107 | 176.3 | 140.0 | 10.5 | 48 | A |
| GLN | N | 108 | 175.7 | 141.5 | 12.1 | 51 | A |
| GLN | CA | 108 | 174.2 | 141.3 | 11.9 | 54 | A |
| GLN | CB | 108 | 173.5 | 142.3 | 12.7 | 57 | A |
| GLN | CG | 108 | 172.0 | 141.9 | 13.0 | 60 | A |
| GLN | CD | 108 | 171.2 | 143.1 | 13.4 | 62 | A |
| GLN | OE1 | 108 | 170.8 | 143.3 | 14.5 | 64 | A |
| GLN | NE2 | 108 | 170.9 | 143.9 | 12.3 | 63 | A |
| GLN | C | 108 | 173.9 | 141.5 | 10.4 | 55 | A |
| GLN | O | 108 | 173.1 | 140.8 | 9.8 | 56 | A |
| ARG | N | 109 | 174.6 | 142.5 | 9.8 | 54 | A |
| ARG | CA | 109 | 174.4 | 142.8 | 8.4 | 55 | A |
| ARG | CB | 109 | 175.0 | 144.1 | 8.0 | 57 | A |
| ARG | CG | 109 | 174.4 | 145.4 | 8.6 | 61 | A |
| ARG | CD | 109 | 175.2 | 146.5 | 8.0 | 64 | A |
| ARG | NE | 109 | 174.5 | 147.8 | 8.2 | 66 | A |
| ARG | CZ | 109 | 173.3 | 148.2 | 7.7 | 67 | A |
| ARG | NH1 | 109 | 172.6 | 147.3 | 7.0 | 68 | A |
| ARG | NH2 | 109 | 172.9 | 149.4 | 7.9 | 69 | A |
| ARG | C | 109 | 175.2 | 141.8 | 7.6 | 53 | A |
| ARG | O | 109 | 175.0 | 141.6 | 6.4 | 55 | A |
| ASP | N | 110 | 176.2 | 141.2 | 8.2 | 52 | A |
| ASP | CA | 110 | 177.1 | 140.2 | 7.5 | 50 | A |
| ASP | CB | 110 | 176.4 | 139.0 | 6.9 | 50 | A |
| ASP | CG | 110 | 177.4 | 137.9 | 6.5 | 50 | A |
| ASP | OD1 | 110 | 178.6 | 138.0 | 6.7 | 50 | A |
| ASP | OD2 | 110 | 176.9 | 136.9 | 5.9 | 52 | A |
| ASP | C | 110 | 177.9 | 141.1 | 6.5 | 50 | A |
| ASP | O | 110 | 178.1 | 140.7 | 5.3 | 50 | A |
| GLU | N | 111 | 178.2 | 142.3 | 6.9 | 49 | A |
| GLU | CA | 111 | 178.9 | 143.2 | 6.1 | 49 | A |
| GLU | CB | 111 | 178.8 | 144.6 | 6.7 | 48 | A |
| GLU | CG | 111 | 179.3 | 145.7 | 5.7 | 49 | A |
| GLU | CD | 111 | 179.6 | 147.0 | 6.3 | 50 | A |
| GLU | OE1 | 111 | 180.8 | 147.2 | 6.5 | 49 | A |
| GLU | OE2 | 111 | 178.7 | 147.8 | 6.5 | 50 | A |
| GLU | C | 111 | 180.3 | 142.7 | 6.0 | 48 | A |
| GLU | O | 111 | 181.0 | 142.7 | 7.0 | 50 | A |
| ARG | N | 112 | 180.7 | 142.1 | 4.9 | 47 | A |
| ARG | CA | 112 | 182.0 | 141.6 | 4.7 | 46 | A |
| ARG | CB | 112 | 182.0 | 140.3 | 3.9 | 45 | A |
| ARG | CG | 112 | 181.1 | 139.3 | 4.6 | 45 | A |
| ARG | CD | 112 | 181.1 | 138.0 | 3.8 | 46 | A |
| ARG | NE | 112 | 180.3 | 137.0 | 4.5 | 46 | A |
| ARG | CZ | 112 | 180.0 | 135.8 | 4.0 | 46 | A |
| ARG | NH1 | 112 | 180.5 | 135.4 | 2.8 | 46 | A |
| ARG | NH2 | 112 | 179.2 | 134.9 | 4.7 | 47 | A |
| ARG | C | 112 | 182.9 | 142.6 | 4.0 | 47 | A |
| ARG | O | 112 | 183.3 | 142.4 | 2.9 | 46 | A |
| SER | N | 113 | 183.2 | 143.7 | 4.8 | 48 | A |
| SER | CA | 113 | 183.9 | 144.8 | 4.2 | 48 | A |
| SER | CB | 113 | 183.1 | 146.1 | 4.4 | 48 | A |
| SER | OG | 113 | 183.1 | 146.4 | 5.8 | 48 | A |
| SER | C | 113 | 185.2 | 145.0 | 4.9 | 47 | A |
| SER | O | 113 | 185.4 | 144.6 | 6.1 | 47 | A |
| GLU | N | 114 | 186.1 | 145.8 | 4.3 | 47 | A |
| GLU | CA | 114 | 187.4 | 146.2 | 4.8 | 47 | A |
| GLU | CB | 114 | 188.1 | 147.0 | 3.8 | 48 | A |
| GLU | CG | 114 | 189.5 | 147.3 | 4.2 | 49 | A |
| GLU | CD | 114 | 190.3 | 146.2 | 4.7 | 50 | A |
| GLU | OE1 | 114 | 190.9 | 146.2 | 5.8 | 50 | A |
| GLU | OE2 | 114 | 190.4 | 145.2 | 3.9 | 51 | A |
| GLU | C | 114 | 187.3 | 146.9 | 6.1 | 46 | A |
| GLU | O | 114 | 188.1 | 146.8 | 7.0 | 47 | A |
| ARG | N | 115 | 186.2 | 147.8 | 6.3 | 44 | A |
| ARG | CA | 115 | 186.1 | 148.5 | 7.5 | 44 | A |
| ARG | CB | 115 | 185.1 | 149.6 | 7.4 | 45 | A |
| ARG | CG | 115 | 183.7 | 149.2 | 6.9 | 47 | A |
| ARG | CD | 115 | 182.7 | 150.2 | 7.3 | 48 | A |
| ARG | NE | 115 | 181.4 | 150.0 | 6.6 | 50 | A |
| ARG | CZ | 115 | 180.4 | 150.8 | 6.6 | 51 | A |
| ARG | NH1 | 115 | 179.3 | 150.4 | 6.0 | 52 | A |

TABLE 2-continued

| | | | | | | | |
|---|---|---|---|---|---|---|---|
| ARG | NH2 | 115 | 180.4 | 151.9 | 7.3 | 51 | A |
| ARG | C | 115 | 185.7 | 147.5 | 8.6 | 43 | A |
| ARG | O | 115 | 186.0 | 147.7 | 9.8 | 44 | A |
| ALA | N | 116 | 184.9 | 146.5 | 8.2 | 42 | A |
| ALA | CA | 116 | 184.4 | 145.5 | 9.2 | 41 | A |
| ALA | CB | 116 | 183.5 | 144.6 | 8.5 | 41 | A |
| ALA | C | 116 | 185.7 | 144.8 | 9.7 | 40 | A |
| ALA | O | 116 | 185.8 | 144.5 | 10.9 | 40 | A |
| PHE | N | 117 | 186.6 | 144.5 | 8.8 | 38 | A |
| PHE | CA | 117 | 187.8 | 143.8 | 9.0 | 37 | A |
| PHE | CB | 117 | 188.6 | 143.7 | 7.7 | 35 | A |
| PHE | CG | 117 | 189.9 | 142.9 | 7.8 | 33 | A |
| PHE | CD1 | 117 | 189.9 | 141.5 | 8.1 | 32 | A |
| PHE | CD2 | 117 | 191.1 | 143.5 | 7.7 | 33 | A |
| PHE | CE1 | 117 | 191.0 | 140.8 | 8.2 | 31 | A |
| PHE | CE2 | 117 | 192.3 | 142.8 | 7.8 | 31 | A |
| PHE | CZ | 117 | 192.3 | 141.5 | 8.0 | 31 | A |
| PHE | C | 117 | 188.6 | 144.6 | 10.1 | 36 | A |
| PHE | O | 117 | 189.0 | 144.0 | 11.1 | 37 | A |
| LYS | N | 118 | 188.9 | 145.8 | 9.8 | 35 | A |
| LYS | CA | 118 | 189.7 | 146.7 | 10.7 | 35 | A |
| LYS | CB | 118 | 189.8 | 148.1 | 10.1 | 37 | A |
| LYS | CG | 118 | 190.7 | 148.1 | 8.8 | 40 | A |
| LYS | CD | 118 | 191.0 | 149.5 | 8.2 | 43 | A |
| LYS | CE | 118 | 191.9 | 149.3 | 7.0 | 45 | A |
| LYS | NZ | 118 | 192.2 | 150.6 | 6.3 | 47 | A |
| LYS | C | 118 | 189.0 | 146.8 | 12.0 | 33 | A |
| LYS | O | 118 | 189.7 | 147.0 | 13.0 | 33 | A |
| LEU | N | 119 | 187.7 | 146.6 | 12.1 | 32 | A |
| LEU | CA | 119 | 187.0 | 146.7 | 13.4 | 31 | A |
| LEU | CB | 119 | 185.5 | 147.0 | 13.2 | 30 | A |
| LEU | CG | 119 | 184.5 | 146.9 | 14.3 | 29 | A |
| LEU | CD1 | 119 | 184.7 | 147.8 | 15.5 | 28 | A |
| LEU | CD2 | 119 | 183.1 | 147.2 | 13.7 | 30 | A |
| LEU | C | 119 | 187.1 | 145.4 | 14.3 | 30 | A |
| LEU | O | 119 | 187.0 | 145.5 | 15.5 | 31 | A |
| THR | N | 120 | 187.1 | 144.2 | 13.6 | 29 | A |
| THR | CA | 120 | 187.2 | 143.0 | 14.4 | 28 | A |
| THR | CB | 120 | 187.3 | 141.8 | 13.5 | 26 | A |
| THR | OG1 | 120 | 188.3 | 141.9 | 12.5 | 26 | A |
| THR | CG2 | 120 | 185.9 | 141.5 | 12.8 | 24 | A |
| THR | C | 120 | 188.5 | 143.1 | 15.2 | 30 | A |
| THR | O | 120 | 188.6 | 142.6 | 16.3 | 30 | A |
| ARG | N | 121 | 189.5 | 143.8 | 14.6 | 31 | A |
| ARG | CA | 121 | 190.8 | 144.0 | 15.2 | 32 | A |
| ARG | CB | 121 | 191.6 | 144.8 | 14.2 | 36 | A |
| ARG | CG | 121 | 193.1 | 144.5 | 14.2 | 41 | A |
| ARG | CD | 121 | 193.7 | 145.4 | 15.2 | 46 | A |
| ARG | NE | 121 | 194.8 | 146.1 | 14.5 | 52 | A |
| ARG | CZ | 121 | 195.3 | 147.3 | 14.9 | 56 | A |
| ARG | NH1 | 121 | 196.3 | 147.9 | 14.3 | 59 | A |
| ARG | NH2 | 121 | 194.8 | 147.9 | 16.0 | 57 | A |
| ARG | C | 121 | 190.7 | 144.7 | 16.5 | 32 | A |
| ARG | O | 121 | 191.4 | 144.3 | 17.4 | 33 | A |
| ASP | N | 122 | 189.8 | 145.7 | 16.5 | 31 | A |
| ASP | CA | 122 | 189.7 | 146.4 | 17.8 | 29 | A |
| ASP | CB | 122 | 189.0 | 147.8 | 17.5 | 29 | A |
| ASP | CG | 122 | 189.9 | 148.8 | 16.9 | 27 | A |
| ASP | OD1 | 122 | 191.1 | 148.8 | 17.2 | 27 | A |
| ASP | OD2 | 122 | 189.4 | 149.7 | 16.3 | 28 | A |
| ASP | C | 122 | 188.8 | 145.6 | 18.7 | 30 | A |
| ASP | O | 122 | 189.1 | 145.6 | 19.9 | 30 | A |
| ALA | N | 123 | 187.8 | 144.9 | 18.2 | 29 | A |
| ALA | CA | 123 | 187.0 | 144.0 | 19.0 | 28 | A |
| ALA | CB | 123 | 185.9 | 143.4 | 18.1 | 28 | A |
| ALA | C | 123 | 187.8 | 142.9 | 19.6 | 29 | A |
| ALA | O | 123 | 187.5 | 142.5 | 20.8 | 31 | A |
| ILE | N | 124 | 188.8 | 142.4 | 18.9 | 29 | A |
| ILE | CA | 124 | 189.6 | 141.3 | 19.4 | 28 | A |
| ILE | CB | 124 | 190.5 | 140.8 | 18.2 | 26 | A |
| ILE | CG2 | 124 | 191.8 | 140.1 | 18.8 | 24 | A |
| ILE | CG1 | 124 | 189.7 | 139.8 | 17.4 | 23 | A |
| ILE | CD1 | 124 | 190.4 | 139.5 | 16.1 | 23 | A |
| ILE | C | 124 | 190.6 | 141.9 | 20.5 | 30 | A |
| ILE | O | 124 | 190.9 | 141.2 | 21.4 | 31 | A |
| GLU | N | 125 | 191.0 | 143.1 | 20.3 | 32 | A |
| GLU | CA | 125 | 191.9 | 143.7 | 21.3 | 34 | A |
| GLU | CB | 125 | 192.6 | 144.9 | 20.8 | 38 | A |
| GLU | CG | 125 | 193.6 | 145.4 | 21.8 | 44 | A |

TABLE 2-continued

| | | | | | | | |
|---|---|---|---|---|---|---|---|
| GLU | CD | 125 | 194.1 | 146.8 | 21.5 | 48 | A |
| GLU | OE1 | 125 | 194.1 | 147.7 | 22.5 | 50 | A |
| GLU | OE2 | 125 | 194.4 | 147.1 | 20.3 | 50 | A |
| GLU | C | 125 | 191.1 | 144.0 | 22.6 | 33 | A |
| GLU | O | 125 | 191.8 | 144.0 | 23.7 | 34 | A |
| LEU | N | 126 | 189.9 | 144.3 | 22.5 | 30 | A |
| LEU | CA | 126 | 189.0 | 144.6 | 23.7 | 26 | A |
| LEU | CB | 126 | 187.8 | 145.3 | 23.3 | 26 | A |
| LEU | CG | 126 | 188.1 | 146.8 | 22.9 | 25 | A |
| LEU | CD1 | 126 | 186.8 | 147.4 | 22.3 | 24 | A |
| LEU | CD2 | 126 | 188.6 | 147.6 | 24.1 | 24 | A |
| LEU | C | 126 | 188.7 | 143.3 | 24.4 | 26 | A |
| LEU | O | 126 | 188.6 | 143.3 | 25.6 | 28 | A |
| ASN | N | 127 | 188.6 | 142.2 | 23.7 | 25 | A |
| ASN | CA | 127 | 188.3 | 140.8 | 24.3 | 24 | A |
| ASN | CB | 127 | 186.9 | 140.6 | 24.6 | 23 | A |
| ASN | CG | 127 | 186.7 | 139.2 | 25.3 | 24 | A |
| ASN | OD1 | 127 | 187.7 | 138.6 | 25.7 | 24 | A |
| ASN | ND2 | 127 | 185.4 | 138.8 | 25.4 | 22 | A |
| ASN | C | 127 | 188.8 | 139.8 | 23.3 | 24 | A |
| ASN | O | 127 | 188.1 | 139.2 | 22.5 | 23 | A |
| ALA | N | 128 | 190.1 | 139.4 | 23.4 | 24 | A |
| ALA | CA | 128 | 190.7 | 138.5 | 22.5 | 22 | A |
| ALA | CB | 128 | 192.2 | 138.4 | 22.8 | 22 | A |
| ALA | C | 128 | 190.1 | 137.1 | 22.6 | 23 | A |
| ALA | O | 128 | 190.2 | 136.3 | 21.7 | 23 | A |
| ALA | N | 129 | 189.4 | 136.8 | 23.7 | 23 | A |
| ALA | CA | 129 | 188.8 | 135.6 | 24.0 | 22 | A |
| ALA | CB | 129 | 188.6 | 135.3 | 25.5 | 21 | A |
| ALA | C | 129 | 187.4 | 135.5 | 23.3 | 23 | A |
| ALA | O | 129 | 186.6 | 134.5 | 23.5 | 23 | A |
| ASN | N | 130 | 187.0 | 136.5 | 22.5 | 23 | A |
| ASN | CA | 130 | 185.7 | 136.5 | 21.9 | 23 | A |
| ASN | CB | 130 | 185.2 | 137.9 | 21.5 | 23 | A |
| ASN | CG | 130 | 183.8 | 137.9 | 21.1 | 25 | A |
| ASN | OD1 | 130 | 183.5 | 137.3 | 20.0 | 27 | A |
| ASN | ND2 | 130 | 182.9 | 138.5 | 21.8 | 24 | A |
| ASN | C | 130 | 185.9 | 135.7 | 20.6 | 24 | A |
| ASN | O | 130 | 186.3 | 136.2 | 19.5 | 24 | A |
| TYR | N | 131 | 185.5 | 134.4 | 20.7 | 23 | A |
| TYR | CA | 131 | 185.6 | 133.4 | 19.6 | 22 | A |
| TYR | CB | 131 | 185.4 | 132.0 | 20.1 | 20 | A |
| TYR | CG | 131 | 184.0 | 131.8 | 20.7 | 19 | A |
| TYR | CD1 | 131 | 183.0 | 131.3 | 20.0 | 18 | A |
| TYR | CE1 | 131 | 181.7 | 131.2 | 20.5 | 17 | A |
| TYR | CD2 | 131 | 183.8 | 132.1 | 22.0 | 19 | A |
| TYR | CE2 | 131 | 182.5 | 132.0 | 22.6 | 17 | A |
| TYR | CZ | 131 | 181.5 | 131.5 | 21.8 | 17 | A |
| TYR | OH | 131 | 180.3 | 131.4 | 22.4 | 17 | A |
| TYR | C | 131 | 184.7 | 133.7 | 18.3 | 24 | A |
| TYR | O | 131 | 185.0 | 133.3 | 17.2 | 26 | A |
| THR | N | 132 | 183.6 | 134.4 | 18.6 | 23 | A |
| THR | CA | 132 | 182.6 | 134.8 | 17.5 | 21 | A |
| THR | CB | 132 | 181.3 | 135.4 | 18.1 | 22 | A |
| THR | OG1 | 132 | 180.7 | 134.5 | 19.0 | 22 | A |
| THR | CG2 | 132 | 180.4 | 135.8 | 17.0 | 22 | A |
| THR | C | 132 | 183.3 | 135.8 | 16.6 | 21 | A |
| THR | O | 132 | 183.2 | 135.6 | 15.3 | 21 | A |
| VAL | N | 133 | 183.9 | 136.8 | 17.2 | 20 | A |
| VAL | CA | 133 | 184.6 | 137.8 | 16.4 | 19 | A |
| VAL | CB | 133 | 185.2 | 138.9 | 17.3 | 20 | A |
| VAL | CG1 | 133 | 186.0 | 139.9 | 16.4 | 18 | A |
| VAL | CG2 | 133 | 184.1 | 139.7 | 18.0 | 20 | A |
| VAL | C | 133 | 185.8 | 137.1 | 15.6 | 20 | A |
| VAL | O | 133 | 186.0 | 137.5 | 14.5 | 24 | A |
| TRP | N | 134 | 186.5 | 136.2 | 16.3 | 20 | A |
| TRP | CA | 134 | 187.6 | 135.5 | 15.6 | 20 | A |
| TRP | CB | 134 | 188.3 | 134.6 | 16.6 | 18 | A |
| TRP | CG | 134 | 189.3 | 135.2 | 17.4 | 17 | A |
| TRP | CD2 | 134 | 190.6 | 135.7 | 16.9 | 17 | A |
| TRP | CE2 | 134 | 191.3 | 136.3 | 17.9 | 17 | A |
| TRP | CE3 | 134 | 191.2 | 135.8 | 15.6 | 18 | A |
| TRP | CD1 | 134 | 189.3 | 135.5 | 18.7 | 17 | A |
| TRP | NE1 | 134 | 190.5 | 136.1 | 19.0 | 16 | A |
| TRP | CZ2 | 134 | 192.5 | 136.9 | 17.8 | 17 | A |
| TRP | CZ3 | 134 | 192.4 | 136.4 | 15.4 | 17 | A |
| TRP | CH2 | 134 | 193.1 | 136.9 | 16.5 | 18 | A |
| TRP | C | 134 | 187.1 | 134.7 | 14.4 | 24 | A |
| TRP | O | 134 | 187.8 | 134.6 | 13.4 | 26 | A |

TABLE 2-continued

| | | | | | | | |
|---|---|---|---|---|---|---|---|
| HIS | N | 135 | 185.8 | 134.2 | 14.5 | 28 | A |
| HIS | CA | 135 | 185.2 | 133.5 | 13.4 | 30 | A |
| HIS | CB | 135 | 184.0 | 132.8 | 13.9 | 33 | A |
| HIS | CG | 135 | 183.4 | 131.8 | 12.9 | 35 | A |
| HIS | CD2 | 135 | 183.7 | 130.5 | 12.8 | 35 | A |
| HIS | ND1 | 135 | 182.5 | 132.1 | 11.9 | 35 | A |
| HIS | CE1 | 135 | 182.2 | 131.0 | 11.2 | 35 | A |
| HIS | NE2 | 135 | 182.9 | 130.0 | 11.7 | 36 | A |
| HIS | C | 135 | 184.9 | 134.4 | 12.2 | 31 | A |
| HIS | O | 135 | 185.4 | 134.2 | 11.1 | 32 | A |
| PHE | N | 136 | 184.2 | 135.5 | 12.5 | 30 | A |
| PHE | CA | 136 | 183.8 | 136.5 | 11.5 | 29 | A |
| PHE | CB | 136 | 183.0 | 137.6 | 12.1 | 31 | A |
| PHE | CG | 136 | 182.5 | 138.6 | 11.0 | 33 | A |
| PHE | CD1 | 136 | 181.5 | 138.2 | 10.1 | 33 | A |
| PHE | CD2 | 136 | 182.9 | 139.9 | 11.0 | 34 | A |
| PHE | CE1 | 136 | 181.0 | 139.2 | 9.2 | 32 | A |
| PHE | CE2 | 136 | 182.4 | 140.9 | 10.1 | 34 | A |
| PHE | CZ | 136 | 181.4 | 140.5 | 9.2 | 32 | A |
| PHE | C | 136 | 185.1 | 137.0 | 10.8 | 29 | A |
| PHE | O | 136 | 185.1 | 137.3 | 9.6 | 32 | A |
| ARG | N | 137 | 186.2 | 137.1 | 11.6 | 28 | A |
| ARG | CA | 137 | 187.4 | 137.6 | 11.0 | 25 | A |
| ARG | CB | 137 | 188.5 | 137.9 | 12.0 | 24 | A |
| ARG | CG | 137 | 189.8 | 138.4 | 11.5 | 22 | A |
| ARG | CD | 137 | 190.8 | 138.8 | 12.5 | 23 | A |
| ARG | NE | 137 | 192.0 | 139.3 | 12.0 | 22 | A |
| ARG | CZ | 137 | 192.3 | 140.6 | 11.9 | 22 | A |
| ARG | NH1 | 137 | 191.5 | 141.5 | 12.3 | 23 | A |
| ARG | NH2 | 137 | 193.5 | 141.0 | 11.3 | 21 | A |
| ARG | C | 137 | 188.0 | 136.6 | 10.0 | 26 | A |
| ARG | O | 137 | 188.6 | 137.0 | 9.0 | 28 | A |
| ARG | N | 138 | 187.9 | 135.3 | 10.2 | 26 | A |
| ARG | CA | 138 | 188.4 | 134.3 | 9.3 | 26 | A |
| ARG | CB | 138 | 188.5 | 132.9 | 9.9 | 25 | A |
| ARG | CG | 138 | 189.7 | 132.8 | 10.8 | 24 | A |
| ARG | CD | 138 | 190.0 | 131.4 | 11.2 | 22 | A |
| ARG | NE | 138 | 189.1 | 130.9 | 12.2 | 21 | A |
| ARG | CZ | 138 | 189.2 | 131.1 | 13.5 | 21 | A |
| ARG | NH1 | 138 | 190.2 | 131.8 | 14.0 | 23 | A |
| ARG | NH2 | 138 | 188.4 | 130.5 | 14.3 | 21 | A |
| ARG | C | 138 | 187.6 | 134.4 | 8.0 | 27 | A |
| ARG | O | 138 | 188.1 | 134.2 | 6.9 | 28 | A |
| VAL | N | 139 | 186.3 | 134.6 | 8.2 | 29 | A |
| VAL | CA | 139 | 185.4 | 134.7 | 7.0 | 29 | A |
| VAL | CB | 139 | 183.9 | 135.0 | 7.5 | 29 | A |
| VAL | CG1 | 139 | 183.0 | 135.2 | 6.3 | 28 | A |
| VAL | CG2 | 139 | 183.4 | 133.9 | 8.4 | 27 | A |
| VAL | C | 139 | 185.9 | 135.9 | 6.2 | 30 | A |
| VAL | O | 139 | 186.0 | 135.8 | 4.9 | 29 | A |
| LEU | N | 140 | 186.1 | 137.0 | 6.8 | 29 | A |
| LEU | CA | 140 | 186.6 | 138.2 | 6.1 | 29 | A |
| LEU | CB | 140 | 186.7 | 139.4 | 7.0 | 28 | A |
| LEU | CG | 140 | 185.4 | 139.8 | 7.6 | 28 | A |
| LEU | CD1 | 140 | 185.4 | 141.2 | 8.3 | 27 | A |
| LEU | CD2 | 140 | 184.4 | 139.9 | 6.5 | 28 | A |
| LEU | C | 140 | 188.0 | 137.9 | 5.5 | 29 | A |
| LEU | O | 140 | 188.2 | 138.4 | 4.4 | 31 | A |
| LEU | N | 141 | 188.8 | 137.1 | 6.1 | 31 | A |
| LEU | CA | 141 | 190.1 | 136.7 | 5.5 | 32 | A |
| LEU | CB | 141 | 190.9 | 135.8 | 6.5 | 31 | A |
| LEU | CG | 141 | 191.6 | 136.5 | 7.6 | 29 | A |
| LEU | CD1 | 141 | 192.3 | 135.4 | 8.4 | 29 | A |
| LEU | CD2 | 141 | 192.6 | 137.5 | 7.1 | 28 | A |
| LEU | C | 141 | 189.9 | 136.1 | 4.2 | 34 | A |
| LEU | O | 141 | 190.6 | 136.3 | 3.2 | 33 | A |
| ARG | N | 142 | 188.9 | 135.2 | 4.1 | 37 | A |
| ARG | CA | 142 | 188.6 | 134.4 | 2.9 | 40 | A |
| ARG | CB | 142 | 187.8 | 133.2 | 3.2 | 44 | A |
| ARG | CG | 142 | 188.5 | 132.2 | 4.1 | 49 | A |
| ARG | CD | 142 | 187.6 | 131.1 | 4.7 | 53 | A |
| ARG | NE | 142 | 186.9 | 131.6 | 5.9 | 55 | A |
| ARG | CZ | 142 | 186.5 | 130.7 | 6.9 | 56 | A |
| ARG | NH1 | 142 | 186.7 | 129.4 | 6.8 | 56 | A |
| ARG | NH2 | 142 | 185.8 | 131.2 | 7.9 | 56 | A |
| ARG | C | 142 | 187.9 | 135.3 | 1.8 | 39 | A |
| ARG | O | 142 | 188.4 | 135.5 | 0.7 | 39 | A |
| SER | N | 143 | 186.8 | 135.9 | 2.3 | 38 | A |
| SER | CA | 143 | 186.0 | 136.8 | 1.4 | 36 | A |

TABLE 2-continued

| | | | | | | | |
|---|---|---|---|---|---|---|---|
| SER | CB | 143 | 184.9 | 137.3 | 2.2 | 34 | A |
| SER | OG | 143 | 184.2 | 138.3 | 1.4 | 36 | A |
| SER | C | 143 | 186.8 | 137.9 | 0.8 | 36 | A |
| SER | O | 143 | 187.1 | 138.0 | −0.4 | 37 | A |
| LEU | N | 144 | 187.3 | 138.8 | 1.7 | 36 | A |
| LEU | CA | 144 | 188.1 | 140.0 | 1.2 | 35 | A |
| LEU | CB | 144 | 188.4 | 140.9 | 2.3 | 34 | A |
| LEU | CG | 144 | 187.3 | 141.4 | 3.3 | 35 | A |
| LEU | CD1 | 144 | 187.9 | 142.4 | 4.3 | 36 | A |
| LEU | CD2 | 144 | 186.2 | 141.9 | 2.6 | 36 | A |
| LEU | C | 144 | 189.4 | 139.5 | 0.6 | 36 | A |
| LEU | O | 144 | 190.2 | 140.3 | 0.1 | 38 | A |
| GLN | N | 145 | 189.7 | 138.2 | 0.6 | 36 | A |
| GLN | CA | 145 | 190.9 | 137.7 | 0.1 | 38 | A |
| GLN | CB | 145 | 190.9 | 137.8 | −1.5 | 40 | A |
| GLN | CG | 145 | 190.0 | 136.8 | −2.2 | 44 | A |
| GLN | CD | 145 | 190.8 | 135.9 | −3.1 | 46 | A |
| GLN | OE1 | 145 | 191.2 | 136.2 | −4.2 | 48 | A |
| GLN | NE2 | 145 | 191.1 | 134.6 | −2.6 | 47 | A |
| GLN | C | 145 | 192.1 | 138.5 | 0.6 | 37 | A |
| GLN | O | 145 | 192.7 | 139.3 | −0.1 | 38 | A |
| LYS | N | 146 | 192.3 | 138.3 | 1.9 | 36 | A |
| LYS | CA | 146 | 193.4 | 139.0 | 2.6 | 34 | A |
| LYS | CB | 146 | 193.1 | 139.3 | 4.0 | 34 | A |
| LYS | CG | 146 | 191.8 | 140.0 | 4.3 | 34 | A |
| LYS | CD | 146 | 191.8 | 141.4 | 3.7 | 35 | A |
| LYS | CE | 146 | 192.9 | 142.3 | 4.3 | 34 | A |
| LYS | NZ | 146 | 193.0 | 143.6 | 3.7 | 34 | A |
| LYS | C | 146 | 194.8 | 138.3 | 2.5 | 34 | A |
| LYS | O | 146 | 194.8 | 137.1 | 2.3 | 33 | A |
| ASP | N | 147 | 195.8 | 139.1 | 2.6 | 35 | A |
| ASP | CA | 147 | 197.2 | 138.5 | 2.5 | 35 | A |
| ASP | CB | 147 | 198.3 | 139.6 | 2.4 | 37 | A |
| ASP | CG | 147 | 199.7 | 139.0 | 2.3 | 39 | A |
| ASP | OD1 | 147 | 200.0 | 138.1 | 3.0 | 41 | A |
| ASP | OD2 | 147 | 200.5 | 139.5 | 1.5 | 41 | A |
| ASP | C | 147 | 197.3 | 137.8 | 3.9 | 36 | A |
| ASP | O | 147 | 197.4 | 138.4 | 4.9 | 36 | A |
| LEU | N | 148 | 197.4 | 136.5 | 3.8 | 34 | A |
| LEU | CA | 148 | 197.5 | 135.7 | 5.0 | 32 | A |
| LEU | CB | 148 | 197.1 | 134.2 | 4.7 | 29 | A |
| LEU | CG | 148 | 195.7 | 134.1 | 4.2 | 28 | A |
| LEU | CD1 | 148 | 195.5 | 132.7 | 3.8 | 28 | A |
| LEU | CD2 | 148 | 194.7 | 134.5 | 5.3 | 28 | A |
| LEU | C | 148 | 198.8 | 135.8 | 5.7 | 32 | A |
| LEU | O | 148 | 198.8 | 135.7 | 6.9 | 35 | A |
| GLN | N | 149 | 199.9 | 136.0 | 5.0 | 34 | A |
| GLN | CA | 149 | 201.2 | 136.1 | 5.6 | 35 | A |
| GLN | CB | 149 | 202.3 | 136.1 | 4.6 | 35 | A |
| GLN | CG | 149 | 203.6 | 135.6 | 5.1 | 39 | A |
| GLN | CD | 149 | 203.5 | 134.2 | 5.8 | 41 | A |
| GLN | OE1 | 149 | 203.2 | 133.2 | 5.2 | 41 | A |
| GLN | NE2 | 149 | 203.7 | 134.3 | 7.1 | 42 | A |
| GLN | C | 149 | 201.3 | 137.3 | 6.5 | 35 | A |
| GLN | O | 149 | 201.9 | 137.4 | 7.5 | 36 | A |
| GLU | N | 150 | 200.5 | 138.3 | 6.0 | 35 | A |
| GLU | CA | 150 | 200.4 | 139.6 | 6.7 | 35 | A |
| GLU | CB | 150 | 199.7 | 140.5 | 5.8 | 38 | A |
| GLU | CG | 150 | 199.8 | 142.0 | 6.2 | 45 | A |
| GLU | CD | 150 | 198.6 | 142.8 | 5.6 | 49 | A |
| GLU | OE1 | 150 | 197.9 | 142.3 | 4.7 | 51 | A |
| GLU | OE2 | 150 | 198.4 | 143.9 | 6.1 | 52 | A |
| GLU | C | 150 | 199.6 | 139.3 | 8.0 | 33 | A |
| GLU | O | 150 | 199.9 | 139.9 | 9.0 | 31 | A |
| GLU | N | 151 | 198.7 | 138.4 | 7.9 | 31 | A |
| GLU | CA | 151 | 197.8 | 138.0 | 9.0 | 31 | A |
| GLU | CB | 151 | 196.5 | 137.3 | 8.5 | 29 | A |
| GLU | CG | 151 | 195.7 | 136.8 | 9.7 | 27 | A |
| GLU | CD | 151 | 194.8 | 137.8 | 10.4 | 27 | A |
| GLU | OE1 | 151 | 194.9 | 139.0 | 10.0 | 27 | A |
| GLU | OE2 | 151 | 194.0 | 137.4 | 11.2 | 27 | A |
| GLU | C | 151 | 198.6 | 137.1 | 10.0 | 31 | A |
| GLU | O | 151 | 198.4 | 137.1 | 11.2 | 30 | A |
| MET | N | 152 | 199.6 | 136.4 | 9.4 | 29 | A |
| MET | CA | 152 | 200.4 | 135.5 | 10.3 | 29 | A |
| MET | CB | 152 | 201.4 | 134.7 | 9.4 | 28 | A |
| MET | CG | 152 | 201.0 | 133.4 | 9.0 | 30 | A |
| MET | SD | 152 | 200.9 | 132.1 | 10.3 | 29 | A |
| MET | CE | 152 | 202.6 | 132.3 | 10.9 | 30 | A |

TABLE 2-continued

| | | | | | | | |
|---|---|---|---|---|---|---|---|
| MET | C | 152 | 201.2 | 136.4 | 11.2 | 30 | A |
| MET | O | 152 | 201.3 | 136.1 | 12.4 | 31 | A |
| ASN | N | 153 | 201.6 | 137.6 | 10.7 | 30 | A |
| ASN | CA | 153 | 202.3 | 138.5 | 11.6 | 31 | A |
| ASN | CB | 153 | 202.8 | 139.7 | 10.7 | 33 | A |
| ASN | CG | 153 | 203.8 | 139.2 | 9.6 | 36 | A |
| ASN | OD1 | 153 | 204.5 | 138.3 | 9.8 | 36 | A |
| ASN | ND2 | 153 | 203.7 | 139.9 | 8.5 | 38 | A |
| ASN | C | 153 | 201.5 | 139.1 | 12.7 | 29 | A |
| ASN | O | 153 | 201.9 | 139.3 | 13.8 | 30 | A |
| TYR | N | 154 | 200.2 | 139.4 | 12.3 | 28 | A |
| TYR | CA | 154 | 199.2 | 139.9 | 13.3 | 25 | A |
| TYR | CB | 154 | 197.9 | 140.1 | 12.5 | 25 | A |
| TYR | CG | 154 | 196.7 | 140.3 | 13.5 | 26 | A |
| TYR | CD1 | 154 | 196.5 | 141.5 | 14.1 | 26 | A |
| TYR | CE1 | 154 | 195.5 | 141.7 | 15.0 | 26 | A |
| TYR | CD2 | 154 | 195.8 | 139.3 | 13.7 | 27 | A |
| TYR | CE2 | 154 | 194.8 | 139.4 | 14.6 | 27 | A |
| TYR | CZ | 154 | 194.6 | 140.7 | 15.2 | 27 | A |
| TYR | OH | 154 | 193.6 | 140.8 | 16.1 | 30 | A |
| TYR | C | 154 | 199.1 | 138.9 | 14.4 | 25 | A |
| TYR | O | 154 | 199.4 | 139.2 | 15.5 | 25 | A |
| ILE | N | 155 | 198.6 | 137.7 | 14.1 | 24 | A |
| ILE | CA | 155 | 198.4 | 136.6 | 15.1 | 23 | A |
| ILE | CB | 155 | 197.9 | 135.3 | 14.4 | 22 | A |
| ILE | CG2 | 155 | 199.0 | 134.5 | 13.8 | 20 | A |
| ILE | CG1 | 155 | 197.1 | 134.5 | 15.5 | 20 | A |
| ILE | CD1 | 155 | 196.0 | 135.3 | 16.1 | 21 | A |
| ILE | C | 155 | 199.7 | 136.3 | 15.9 | 24 | A |
| ILE | O | 155 | 199.7 | 136.0 | 17.0 | 25 | A |
| THR | N | 156 | 200.9 | 136.6 | 15.2 | 22 | A |
| THR | CA | 156 | 202.2 | 136.3 | 15.9 | 20 | A |
| THR | CB | 156 | 203.3 | 136.6 | 15.0 | 19 | A |
| THR | OG1 | 156 | 203.3 | 135.6 | 13.9 | 19 | A |
| THR | CG2 | 156 | 204.6 | 136.6 | 15.7 | 18 | A |
| THR | C | 156 | 202.3 | 137.3 | 17.1 | 22 | A |
| THR | O | 156 | 202.7 | 136.9 | 18.1 | 23 | A |
| ALA | N | 157 | 202.0 | 138.6 | 16.8 | 23 | A |
| ALA | CA | 157 | 202.0 | 139.6 | 17.8 | 23 | A |
| ALA | CB | 157 | 201.9 | 141.0 | 17.2 | 22 | A |
| ALA | C | 157 | 201.0 | 139.4 | 18.9 | 24 | A |
| ALA | O | 157 | 201.3 | 139.6 | 20.1 | 26 | A |
| ILE | N | 158 | 199.8 | 139.1 | 18.5 | 24 | A |
| ILE | CA | 158 | 198.7 | 138.8 | 19.5 | 22 | A |
| ILE | CB | 158 | 197.3 | 138.5 | 18.7 | 22 | A |
| ILE | CG2 | 158 | 196.2 | 138.3 | 19.7 | 22 | A |
| ILE | CG1 | 158 | 196.9 | 139.7 | 17.9 | 22 | A |
| ILE | CD1 | 158 | 196.4 | 140.9 | 18.7 | 23 | A |
| ILE | C | 158 | 199.0 | 137.7 | 20.4 | 22 | A |
| ILE | O | 158 | 198.6 | 137.8 | 21.6 | 24 | A |
| ILE | N | 159 | 199.6 | 136.6 | 19.9 | 21 | A |
| ILE | CA | 159 | 199.9 | 135.5 | 20.7 | 20 | A |
| ILE | CB | 159 | 200.4 | 134.3 | 19.9 | 20 | A |
| ILE | CG2 | 159 | 200.9 | 133.1 | 20.8 | 20 | A |
| ILE | CG1 | 159 | 199.3 | 133.7 | 19.0 | 18 | A |
| ILE | CD1 | 159 | 199.8 | 132.7 | 18.0 | 16 | A |
| ILE | C | 159 | 201.0 | 135.8 | 21.7 | 22 | A |
| ILE | O | 159 | 201.0 | 135.4 | 22.8 | 22 | A |
| GLU | N | 160 | 201.9 | 136.7 | 21.3 | 24 | A |
| GLU | CA | 160 | 203.0 | 137.1 | 22.2 | 24 | A |
| GLU | CB | 160 | 204.0 | 138.1 | 21.5 | 24 | A |
| GLU | CG | 160 | 204.9 | 137.5 | 20.4 | 26 | A |
| GLU | CD | 160 | 206.1 | 136.7 | 20.8 | 27 | A |
| GLU | OE1 | 160 | 206.4 | 136.6 | 22.0 | 29 | A |
| GLU | OE2 | 160 | 206.7 | 136.0 | 20.0 | 27 | A |
| GLU | C | 160 | 202.4 | 137.8 | 23.3 | 23 | A |
| GLU | O | 160 | 202.8 | 137.7 | 24.5 | 23 | A |
| GLU | N | 161 | 201.2 | 138.4 | 23.1 | 24 | A |
| GLU | CA | 161 | 200.5 | 139.2 | 24.1 | 25 | A |
| GLU | CB | 161 | 199.7 | 140.3 | 23.4 | 25 | A |
| GLU | CG | 161 | 200.6 | 141.4 | 22.9 | 27 | A |
| GLU | CD | 161 | 199.8 | 142.3 | 22.0 | 29 | A |
| GLU | OE1 | 161 | 200.5 | 143.2 | 21.4 | 30 | A |
| GLU | OE2 | 161 | 198.6 | 142.2 | 21.9 | 29 | A |
| GLU | C | 161 | 199.6 | 138.3 | 25.0 | 25 | A |
| GLU | O | 161 | 199.6 | 138.6 | 26.2 | 27 | A |
| GLN | N | 162 | 199.0 | 137.3 | 24.5 | 26 | A |
| GLN | CA | 162 | 198.1 | 136.4 | 25.2 | 25 | A |
| GLN | CB | 162 | 196.6 | 136.7 | 24.7 | 27 | A |

TABLE 2-continued

| | | | | | | | |
|---|---|---|---|---|---|---|---|
| GLN | CG | 162 | 196.5 | 138.1 | 24.3 | 30 | A |
| GLN | CD | 162 | 195.5 | 138.8 | 25.1 | 34 | A |
| GLN | OE1 | 162 | 195.1 | 138.3 | 26.2 | 35 | A |
| GLN | NE2 | 162 | 195.1 | 140.0 | 24.7 | 36 | A |
| GLN | C | 162 | 198.4 | 135.0 | 24.8 | 24 | A |
| GLN | O | 162 | 197.6 | 134.3 | 24.1 | 24 | A |
| PRO | N | 163 | 199.5 | 134.5 | 25.2 | 23 | A |
| PRO | CD | 163 | 200.5 | 135.1 | 26.1 | 22 | A |
| PRO | CA | 163 | 200.0 | 133.1 | 24.8 | 22 | A |
| PRO | CB | 163 | 201.4 | 133.1 | 25.3 | 22 | A |
| PRO | CG | 163 | 201.4 | 133.9 | 26.5 | 21 | A |
| PRO | C | 163 | 199.2 | 132.0 | 25.5 | 23 | A |
| PRO | O | 163 | 199.5 | 130.8 | 25.3 | 24 | A |
| LYS | N | 164 | 198.2 | 132.3 | 26.3 | 23 | A |
| LYS | CA | 164 | 197.3 | 131.4 | 27.0 | 23 | A |
| LYS | CB | 164 | 197.5 | 131.5 | 28.5 | 26 | A |
| LYS | CG | 164 | 198.8 | 131.0 | 29.0 | 30 | A |
| LYS | CD | 164 | 198.6 | 130.9 | 30.5 | 33 | A |
| LYS | CE | 164 | 199.8 | 130.2 | 31.1 | 36 | A |
| LYS | NZ | 164 | 199.5 | 130.0 | 32.5 | 39 | A |
| LYS | C | 164 | 195.9 | 131.4 | 26.5 | 22 | A |
| LYS | O | 164 | 195.0 | 130.9 | 27.2 | 22 | A |
| ASN | N | 165 | 195.7 | 132.1 | 25.4 | 21 | A |
| ASN | CA | 165 | 194.4 | 132.3 | 24.9 | 18 | A |
| ASN | CB | 165 | 194.3 | 133.7 | 24.2 | 17 | A |
| ASN | CG | 165 | 193.1 | 133.9 | 23.3 | 18 | A |
| ASN | OD1 | 165 | 192.9 | 133.2 | 22.3 | 19 | A |
| ASN | ND2 | 165 | 192.3 | 134.8 | 23.7 | 18 | A |
| ASN | C | 165 | 194.2 | 131.1 | 23.9 | 17 | A |
| ASN | O | 165 | 195.1 | 130.8 | 23.2 | 17 | A |
| TYR | N | 166 | 193.0 | 130.5 | 23.9 | 16 | A |
| TYR | CA | 166 | 192.7 | 129.4 | 23.1 | 15 | A |
| TYR | CB | 166 | 191.5 | 128.7 | 23.6 | 14 | A |
| TYR | CG | 166 | 191.7 | 127.7 | 24.7 | 15 | A |
| TYR | CD1 | 166 | 191.7 | 128.1 | 26.0 | 14 | A |
| TYR | CE1 | 166 | 191.9 | 127.2 | 27.0 | 14 | A |
| TYR | CD2 | 166 | 191.7 | 126.3 | 24.4 | 15 | A |
| TYR | CE2 | 166 | 191.9 | 125.4 | 25.4 | 15 | A |
| TYR | CZ | 166 | 191.9 | 125.8 | 26.7 | 15 | A |
| TYR | OH | 166 | 192.1 | 124.9 | 27.8 | 15 | A |
| TYR | C | 166 | 192.5 | 129.8 | 21.6 | 16 | A |
| TYR | O | 166 | 192.8 | 129.0 | 20.7 | 16 | A |
| GLN | N | 167 | 191.8 | 130.9 | 21.4 | 17 | A |
| GLN | CA | 167 | 191.5 | 131.3 | 20.0 | 17 | A |
| GLN | CB | 167 | 190.5 | 132.5 | 20.1 | 18 | A |
| GLN | CG | 167 | 189.1 | 132.1 | 20.6 | 21 | A |
| GLN | CD | 167 | 189.1 | 131.8 | 22.0 | 23 | A |
| GLN | OE1 | 167 | 189.7 | 132.5 | 22.8 | 26 | A |
| GLN | NE2 | 167 | 188.5 | 130.7 | 22.4 | 24 | A |
| GLN | C | 167 | 192.6 | 131.7 | 19.1 | 17 | A |
| GLN | O | 167 | 192.6 | 131.5 | 17.9 | 17 | A |
| VAL | N | 168 | 193.6 | 132.4 | 19.7 | 18 | A |
| VAL | CA | 168 | 194.8 | 132.9 | 19.0 | 17 | A |
| VAL | CB | 168 | 195.6 | 133.8 | 19.9 | 17 | A |
| VAL | CG1 | 168 | 194.9 | 135.1 | 20.2 | 15 | A |
| VAL | CG2 | 168 | 196.0 | 133.2 | 21.2 | 15 | A |
| VAL | C | 168 | 195.6 | 131.7 | 18.5 | 21 | A |
| VAL | O | 168 | 196.1 | 131.8 | 17.3 | 24 | A |
| TRP | N | 169 | 195.8 | 130.7 | 19.2 | 21 | A |
| TRP | CA | 169 | 196.6 | 129.5 | 18.8 | 20 | A |
| TRP | CB | 169 | 196.9 | 128.6 | 19.9 | 20 | A |
| TRP | CG | 169 | 197.9 | 129.1 | 20.8 | 19 | A |
| TRP | CD2 | 169 | 199.3 | 129.0 | 20.5 | 18 | A |
| TRP | CE2 | 169 | 200.0 | 129.6 | 21.7 | 18 | A |
| TRP | CE3 | 169 | 200.1 | 128.6 | 19.5 | 16 | A |
| TRP | CD1 | 169 | 197.8 | 129.6 | 22.0 | 18 | A |
| TRP | NE1 | 169 | 199.0 | 130.0 | 22.5 | 19 | A |
| TRP | CZ2 | 169 | 201.4 | 129.7 | 21.7 | 17 | A |
| TRP | CZ3 | 169 | 201.5 | 128.7 | 19.6 | 16 | A |
| TRP | CH2 | 169 | 202.1 | 129.2 | 20.7 | 16 | A |
| TRP | C | 169 | 195.8 | 128.8 | 17.7 | 22 | A |
| TRP | O | 169 | 196.4 | 128.4 | 16.7 | 23 | A |
| HIS | N | 170 | 194.5 | 128.6 | 17.9 | 23 | A |
| HIS | CA | 170 | 193.7 | 128.0 | 16.9 | 24 | A |
| HIS | CB | 170 | 192.3 | 127.8 | 17.3 | 24 | A |
| HIS | CG | 170 | 191.5 | 127.1 | 16.3 | 24 | A |
| HIS | CD2 | 170 | 190.4 | 127.5 | 15.6 | 25 | A |
| HIS | ND1 | 170 | 191.8 | 125.8 | 15.8 | 25 | A |
| HIS | CE1 | 170 | 190.9 | 125.5 | 14.9 | 25 | A |
| HIS | NE2 | 170 | 190.1 | 126.5 | 14.7 | 25 | A |
| HIS | C | 170 | 193.7 | 128.8 | 15.6 | 26 | A |
| HIS | O | 170 | 193.6 | 128.2 | 14.5 | 28 | A |
| HIS | N | 171 | 193.6 | 130.1 | 15.7 | 24 | A |
| HIS | CA | 171 | 193.6 | 130.9 | 14.5 | 22 | A |
| HIS | CB | 171 | 193.4 | 132.4 | 14.9 | 22 | A |
| HIS | CG | 171 | 193.3 | 133.3 | 13.8 | 22 | A |
| HIS | CD2 | 171 | 194.3 | 134.1 | 13.2 | 22 | A |
| HIS | ND1 | 171 | 192.1 | 133.6 | 13.2 | 21 | A |
| HIS | CE1 | 171 | 192.3 | 134.6 | 12.2 | 20 | A |
| HIS | NE2 | 171 | 193.6 | 134.9 | 12.2 | 21 | A |
| HIS | C | 171 | 194.9 | 130.8 | 13.7 | 23 | A |
| HIS | O | 171 | 194.9 | 130.7 | 12.5 | 24 | A |
| ARG | N | 172 | 196.0 | 130.7 | 14.4 | 23 | A |
| ARG | CA | 172 | 197.3 | 130.5 | 13.8 | 22 | A |
| ARG | CB | 172 | 198.4 | 130.6 | 14.9 | 21 | A |
| ARG | CG | 172 | 199.8 | 130.3 | 14.3 | 20 | A |
| ARG | CD | 172 | 200.9 | 130.7 | 15.2 | 19 | A |
| ARG | NE | 172 | 202.2 | 130.6 | 14.6 | 19 | A |
| ARG | CZ | 172 | 202.9 | 131.7 | 14.3 | 20 | A |
| ARG | NH1 | 172 | 202.6 | 132.9 | 14.6 | 20 | A |
| ARG | NH2 | 172 | 204.1 | 131.5 | 13.7 | 20 | A |
| ARG | C | 172 | 197.4 | 129.2 | 13.1 | 25 | A |
| ARG | O | 172 | 198.0 | 129.1 | 12.0 | 25 | A |
| ARG | N | 173 | 196.8 | 128.1 | 13.7 | 26 | A |
| ARG | CA | 173 | 196.8 | 126.8 | 13.2 | 26 | A |
| ARG | CB | 173 | 196.3 | 125.8 | 14.2 | 27 | A |
| ARG | CG | 173 | 195.6 | 124.6 | 13.6 | 28 | A |
| ARG | CD | 173 | 195.8 | 123.4 | 14.4 | 30 | A |
| ARG | NE | 173 | 195.1 | 122.3 | 13.8 | 35 | A |
| ARG | CZ | 173 | 194.9 | 121.1 | 14.2 | 36 | A |
| ARG | NH1 | 173 | 195.4 | 120.7 | 15.4 | 37 | A |
| ARG | NH2 | 173 | 194.2 | 120.2 | 13.5 | 36 | A |
| ARG | C | 173 | 196.1 | 126.8 | 11.9 | 26 | A |
| ARG | O | 173 | 196.4 | 126.1 | 10.9 | 28 | A |
| VAL | N | 174 | 195.0 | 127.5 | 11.8 | 25 | A |
| VAL | CA | 174 | 194.1 | 127.6 | 10.6 | 24 | A |
| VAL | CB | 174 | 192.8 | 128.4 | 10.9 | 22 | A |
| VAL | CG1 | 174 | 192.1 | 128.7 | 9.6 | 22 | A |
| VAL | CG2 | 174 | 191.9 | 127.5 | 11.7 | 20 | A |
| VAL | C | 174 | 194.9 | 128.3 | 9.5 | 25 | A |
| VAL | O | 174 | 194.9 | 127.8 | 8.4 | 28 | A |
| LEU | N | 175 | 195.5 | 129.4 | 9.8 | 26 | A |
| LEU | CA | 175 | 196.3 | 130.1 | 8.7 | 27 | A |
| LEU | CB | 175 | 197.0 | 131.3 | 9.3 | 27 | A |
| LEU | CG | 175 | 196.1 | 132.5 | 9.9 | 25 | A |
| LEU | CD1 | 175 | 197.0 | 133.6 | 10.4 | 24 | A |
| LEU | CD2 | 175 | 195.2 | 133.0 | 8.8 | 24 | A |
| LEU | C | 175 | 197.4 | 129.2 | 8.2 | 27 | A |
| LEU | O | 175 | 197.6 | 129.2 | 6.9 | 30 | A |
| VAL | N | 176 | 198.2 | 128.5 | 9.0 | 27 | A |
| VAL | CA | 176 | 199.2 | 127.6 | 8.6 | 26 | A |
| VAL | CB | 176 | 200.0 | 127.0 | 9.8 | 24 | A |
| VAL | CG1 | 176 | 201.0 | 126.0 | 9.4 | 24 | A |
| VAL | CG2 | 176 | 200.6 | 128.1 | 10.6 | 23 | A |
| VAL | C | 176 | 198.7 | 126.5 | 7.7 | 27 | A |
| VAL | O | 176 | 199.3 | 126.0 | 6.8 | 28 | A |
| GLU | N | 177 | 197.4 | 126.1 | 8.0 | 28 | A |
| GLU | CA | 177 | 196.8 | 125.0 | 7.2 | 30 | A |
| GLU | CB | 177 | 195.6 | 124.5 | 7.9 | 30 | A |
| GLU | CG | 177 | 195.9 | 123.6 | 9.2 | 31 | A |
| GLU | CD | 177 | 194.6 | 123.2 | 9.9 | 32 | A |
| GLU | OE1 | 177 | 194.6 | 122.2 | 10.5 | 34 | A |
| GLU | OE2 | 177 | 193.6 | 124.0 | 9.8 | 33 | A |
| GLU | C | 177 | 196.5 | 125.6 | 5.8 | 31 | A |
| GLU | O | 177 | 196.8 | 125.1 | 4.8 | 33 | A |
| TRP | N | 178 | 195.9 | 126.8 | 5.8 | 30 | A |
| TRP | CA | 178 | 195.5 | 127.5 | 4.6 | 29 | A |
| TRP | CB | 178 | 194.9 | 128.9 | 4.9 | 27 | A |
| TRP | CG | 178 | 193.5 | 128.9 | 5.4 | 25 | A |
| TRP | CD2 | 178 | 192.8 | 130.1 | 6.0 | 24 | A |
| TRP | CE2 | 178 | 191.5 | 129.7 | 6.3 | 24 | A |
| TRP | CE3 | 178 | 193.2 | 131.4 | 6.2 | 24 | A |
| TRP | CD1 | 178 | 192.5 | 127.9 | 5.4 | 24 | A |
| TRP | NE1 | 178 | 191.3 | 128.3 | 5.9 | 24 | A |
| TRP | CZ2 | 178 | 190.5 | 130.6 | 6.8 | 24 | A |
| TRP | CZ3 | 178 | 192.2 | 132.3 | 6.8 | 24 | A |
| TRP | CH2 | 178 | 190.9 | 131.8 | 7.1 | 24 | A |
| TRP | C | 178 | 196.7 | 127.6 | 3.7 | 31 | A |

TABLE 2-continued

| | | | | | | | |
|---|---|---|---|---|---|---|---|
| TRP | O | 178 | 196.6 | 127.3 | 2.5 | 33 | A |
| LEU | N | 179 | 197.8 | 128.1 | 4.3 | 32 | A |
| LEU | CA | 179 | 199.0 | 128.3 | 3.6 | 33 | A |
| LEU | CB | 179 | 199.9 | 129.3 | 4.3 | 31 | A |
| LEU | CG | 179 | 199.3 | 130.7 | 4.5 | 32 | A |
| LEU | CD1 | 179 | 200.1 | 131.4 | 5.6 | 32 | A |
| LEU | CD2 | 179 | 199.5 | 131.5 | 3.2 | 32 | A |
| LEU | C | 179 | 199.8 | 127.0 | 3.4 | 35 | A |
| LEU | O | 179 | 200.7 | 127.0 | 2.4 | 36 | A |
| LYS | N | 180 | 199.6 | 126.0 | 4.2 | 37 | A |
| LYS | CA | 180 | 200.4 | 124.8 | 4.1 | 39 | A |
| LYS | CB | 180 | 200.2 | 124.1 | 2.7 | 40 | A |
| LYS | CG | 180 | 198.9 | 123.4 | 2.4 | 43 | A |
| LYS | CD | 180 | 198.0 | 124.4 | 1.6 | 46 | A |
| LYS | CE | 180 | 196.6 | 123.8 | 1.4 | 48 | A |
| LYS | NZ | 180 | 195.6 | 124.8 | 0.9 | 50 | A |
| LYS | C | 180 | 201.9 | 125.1 | 4.2 | 38 | A |
| LYS | O | 180 | 202.8 | 124.6 | 3.6 | 40 | A |
| ASP | N | 181 | 202.2 | 126.1 | 5.2 | 36 | A |
| ASP | CA | 181 | 203.5 | 126.6 | 5.4 | 34 | A |
| ASP | CB | 181 | 203.6 | 128.0 | 5.0 | 34 | A |
| ASP | CG | 181 | 204.9 | 128.6 | 5.0 | 35 | A |
| ASP | OD1 | 181 | 205.9 | 127.9 | 5.2 | 35 | A |
| ASP | OD2 | 181 | 205.1 | 129.9 | 4.9 | 36 | A |
| ASP | C | 181 | 203.9 | 126.5 | 6.9 | 35 | A |
| ASP | O | 181 | 203.4 | 127.3 | 7.7 | 37 | A |
| PRO | N | 182 | 204.7 | 125.5 | 7.3 | 35 | A |
| PRO | CD | 182 | 205.0 | 124.3 | 6.5 | 34 | A |
| PRO | CA | 182 | 205.1 | 125.3 | 8.7 | 35 | A |
| PRO | CB | 182 | 205.1 | 123.8 | 8.8 | 35 | A |
| PRO | CG | 182 | 205.8 | 123.5 | 7.5 | 35 | A |
| PRO | C | 182 | 206.4 | 125.9 | 8.9 | 35 | A |
| PRO | O | 182 | 207.0 | 125.6 | 10.0 | 34 | A |
| SER | N | 183 | 206.9 | 126.7 | 8.0 | 35 | A |
| SER | CA | 183 | 208.3 | 127.2 | 8.0 | 36 | A |
| SER | CB | 183 | 208.7 | 127.8 | 6.7 | 36 | A |
| SER | OG | 183 | 207.9 | 129.0 | 6.4 | 39 | A |
| SER | C | 183 | 208.7 | 128.2 | 9.1 | 35 | A |
| SER | O | 183 | 209.8 | 128.4 | 9.4 | 37 | A |
| GLN | N | 184 | 207.7 | 128.9 | 9.7 | 35 | A |
| GLN | CA | 184 | 208.0 | 129.9 | 10.8 | 34 | A |
| GLN | CB | 184 | 207.1 | 131.1 | 10.5 | 36 | A |
| GLN | CG | 184 | 207.3 | 131.8 | 9.2 | 40 | A |
| GLN | CD | 184 | 206.0 | 132.5 | 8.7 | 42 | A |
| GLN | OE1 | 184 | 205.7 | 133.6 | 9.2 | 42 | A |
| GLN | NE2 | 184 | 205.2 | 131.9 | 7.8 | 42 | A |
| GLN | C | 184 | 207.6 | 129.3 | 12.2 | 31 | A |
| GLN | O | 184 | 208.1 | 129.9 | 13.2 | 29 | A |
| GLU | N | 185 | 206.9 | 128.2 | 12.2 | 28 | A |
| GLU | CA | 185 | 206.5 | 127.6 | 13.4 | 27 | A |
| GLU | CB | 185 | 205.6 | 126.4 | 13.1 | 28 | A |
| GLU | CG | 185 | 204.4 | 126.7 | 12.2 | 28 | A |
| GLU | CD | 185 | 203.7 | 128.0 | 12.6 | 29 | A |
| GLU | OE1 | 185 | 202.7 | 127.9 | 13.5 | 31 | A |
| GLU | OE2 | 185 | 204.0 | 129.1 | 12.1 | 30 | A |
| GLU | C | 185 | 207.4 | 127.2 | 14.6 | 27 | A |
| GLU | O | 185 | 207.2 | 127.7 | 15.6 | 27 | A |
| LEU | N | 186 | 208.3 | 126.3 | 14.3 | 27 | A |
| LEU | CA | 186 | 209.2 | 125.9 | 15.4 | 28 | A |
| LEU | CB | 186 | 210.2 | 124.8 | 14.9 | 27 | A |
| LEU | CG | 186 | 209.4 | 123.5 | 14.4 | 26 | A |
| LEU | CD1 | 186 | 210.4 | 122.4 | 14.1 | 27 | A |
| LEU | CD2 | 186 | 208.4 | 123.1 | 15.4 | 26 | A |
| LEU | C | 186 | 210.0 | 127.1 | 16.0 | 29 | A |
| LEU | O | 186 | 210.3 | 127.1 | 17.2 | 29 | A |
| GLU | N | 187 | 210.3 | 128.1 | 15.2 | 31 | A |
| GLU | CA | 187 | 211.0 | 129.3 | 15.6 | 32 | A |
| GLU | CB | 187 | 211.6 | 130.0 | 14.4 | 36 | A |
| GLU | CG | 187 | 212.5 | 131.2 | 14.7 | 41 | A |
| GLU | CD | 187 | 213.0 | 132.0 | 13.4 | 45 | A |
| GLU | OE1 | 187 | 213.1 | 131.3 | 12.3 | 46 | A |
| GLU | OE2 | 187 | 213.3 | 133.2 | 13.5 | 47 | A |
| GLU | C | 187 | 210.1 | 130.2 | 16.4 | 30 | A |
| GLU | O | 187 | 210.6 | 130.9 | 17.3 | 31 | A |
| PHE | N | 188 | 208.9 | 130.3 | 16.0 | 27 | A |
| PHE | CA | 188 | 207.9 | 131.2 | 16.7 | 24 | A |
| PHE | CB | 188 | 206.6 | 131.3 | 16.0 | 23 | A |
| PHE | CG | 188 | 205.6 | 131.9 | 16.8 | 23 | A |
| PHE | CD1 | 188 | 205.7 | 133.1 | 17.4 | 23 | A |
| PHE | CD2 | 188 | 204.4 | 131.2 | 17.1 | 23 | A |
| PHE | CE1 | 188 | 204.7 | 133.7 | 18.2 | 24 | A |
| PHE | CE2 | 188 | 203.4 | 131.7 | 17.9 | 23 | A |
| PHE | CZ | 188 | 203.6 | 133.0 | 18.5 | 24 | A |
| PHE | C | 188 | 207.7 | 130.6 | 18.1 | 24 | A |
| PHE | O | 188 | 207.8 | 131.2 | 19.1 | 24 | A |
| ILE | N | 189 | 207.3 | 129.3 | 18.1 | 23 | A |
| ILE | CA | 189 | 207.0 | 128.5 | 19.3 | 21 | A |
| ILE | CB | 189 | 206.8 | 127.0 | 19.0 | 19 | A |
| ILE | CG2 | 189 | 206.5 | 126.3 | 20.2 | 20 | A |
| ILE | CG1 | 189 | 205.6 | 126.9 | 18.1 | 17 | A |
| ILE | CD1 | 189 | 205.4 | 125.5 | 17.6 | 19 | A |
| ILE | C | 189 | 208.2 | 128.6 | 20.3 | 22 | A |
| ILE | O | 189 | 208.0 | 129.1 | 21.4 | 22 | A |
| ALA | N | 190 | 209.4 | 128.3 | 19.8 | 21 | A |
| ALA | CA | 190 | 210.6 | 128.4 | 20.7 | 20 | A |
| ALA | CB | 190 | 211.8 | 128.0 | 19.9 | 18 | A |
| ALA | C | 190 | 210.7 | 129.8 | 21.3 | 21 | A |
| ALA | O | 190 | 211.3 | 129.9 | 22.4 | 24 | A |
| ASP | N | 191 | 210.2 | 130.8 | 20.6 | 23 | A |
| ASP | CA | 191 | 210.3 | 132.2 | 21.2 | 24 | A |
| ASP | CB | 191 | 210.1 | 133.3 | 20.2 | 25 | A |
| ASP | CG | 191 | 210.1 | 134.6 | 20.9 | 28 | A |
| ASP | OD1 | 191 | 211.2 | 135.0 | 21.3 | 29 | A |
| ASP | OD2 | 191 | 209.0 | 135.3 | 21.0 | 30 | A |
| ASP | C | 191 | 209.3 | 132.3 | 22.3 | 24 | A |
| ASP | O | 191 | 209.5 | 133.0 | 23.4 | 23 | A |
| ILE | N | 192 | 208.1 | 131.7 | 22.2 | 23 | A |
| ILE | CA | 192 | 207.1 | 131.7 | 23.2 | 22 | A |
| ILE | CB | 192 | 205.7 | 131.2 | 22.7 | 20 | A |
| ILE | CG2 | 192 | 204.7 | 131.1 | 23.8 | 20 | A |
| ILE | CG1 | 192 | 205.2 | 132.1 | 21.6 | 19 | A |
| ILE | CD1 | 192 | 204.8 | 133.5 | 22.1 | 18 | A |
| ILE | C | 192 | 207.6 | 130.8 | 24.4 | 23 | A |
| ILE | O | 192 | 207.5 | 131.2 | 25.5 | 24 | A |
| LEU | N | 193 | 208.1 | 129.7 | 24.1 | 24 | A |
| LEU | CA | 193 | 208.6 | 128.8 | 25.1 | 25 | A |
| LEU | CB | 193 | 209.0 | 127.4 | 24.5 | 24 | A |
| LEU | CG | 193 | 207.8 | 126.6 | 24.0 | 23 | A |
| LEU | CD1 | 193 | 208.3 | 125.3 | 23.4 | 22 | A |
| LEU | CD2 | 193 | 206.9 | 126.2 | 25.1 | 24 | A |
| LEU | C | 193 | 209.9 | 129.4 | 25.8 | 27 | A |
| LEU | O | 193 | 210.4 | 128.8 | 26.7 | 28 | A |
| ASN | N | 194 | 210.4 | 130.5 | 25.2 | 30 | A |
| ASN | CA | 194 | 211.6 | 131.1 | 25.8 | 31 | A |
| ASN | CB | 194 | 212.3 | 131.9 | 24.7 | 34 | A |
| ASN | CG | 194 | 213.7 | 132.4 | 25.2 | 37 | A |
| ASN | OD1 | 194 | 213.9 | 133.6 | 25.1 | 38 | A |
| ASN | ND2 | 194 | 214.5 | 131.4 | 25.7 | 37 | A |
| ASN | C | 194 | 211.1 | 132.1 | 26.9 | 31 | A |
| ASN | O | 194 | 211.8 | 132.4 | 27.8 | 30 | A |
| GLN | N | 195 | 209.8 | 132.5 | 26.8 | 29 | A |
| GLN | CA | 195 | 209.2 | 133.4 | 27.7 | 27 | A |
| GLN | CB | 195 | 208.2 | 134.3 | 27.0 | 28 | A |
| GLN | CG | 195 | 208.9 | 135.3 | 26.1 | 29 | A |
| GLN | CD | 195 | 208.1 | 135.8 | 25.0 | 29 | A |
| GLN | OE1 | 195 | 207.2 | 136.6 | 25.1 | 31 | A |
| GLN | NE2 | 195 | 208.4 | 135.3 | 23.8 | 30 | A |
| GLN | C | 195 | 208.5 | 132.5 | 28.8 | 26 | A |
| GLN | O | 195 | 208.4 | 133.0 | 30.0 | 28 | A |
| ASP | N | 196 | 208.1 | 131.3 | 28.5 | 24 | A |
| ASP | CA | 196 | 207.4 | 130.5 | 29.4 | 22 | A |
| ASP | CB | 196 | 205.9 | 130.8 | 29.4 | 22 | A |
| ASP | CG | 196 | 205.1 | 129.9 | 30.3 | 23 | A |
| ASP | OD1 | 196 | 205.6 | 129.0 | 30.9 | 25 | A |
| ASP | OD2 | 196 | 203.9 | 130.2 | 30.5 | 23 | A |
| ASP | C | 196 | 207.6 | 129.0 | 28.9 | 21 | A |
| ASP | O | 196 | 206.8 | 128.5 | 28.1 | 21 | A |
| ALA | N | 197 | 208.6 | 128.4 | 29.4 | 20 | A |
| ALA | CA | 197 | 209.0 | 127.1 | 29.0 | 21 | A |
| ALA | CB | 197 | 210.3 | 126.7 | 29.6 | 21 | A |
| ALA | C | 197 | 208.0 | 125.9 | 29.1 | 21 | A |
| ALA | O | 197 | 208.2 | 124.8 | 28.8 | 23 | A |
| LYS | N | 198 | 206.8 | 126.3 | 29.6 | 21 | A |
| LYS | CA | 198 | 205.8 | 125.3 | 29.8 | 19 | A |
| LYS | CB | 198 | 205.6 | 125.0 | 31.3 | 20 | A |
| LYS | CG | 198 | 206.9 | 124.6 | 32.0 | 19 | A |
| LYS | CD | 198 | 206.8 | 124.4 | 33.5 | 19 | A |
| LYS | CE | 198 | 208.2 | 124.1 | 34.1 | 20 | A |

TABLE 2-continued

| | | | | | | | |
|---|---|---|---|---|---|---|---|
| LYS | NZ | 198 | 208.1 | 123.6 | 35.5 | 21 | A |
| LYS | C | 198 | 204.4 | 125.7 | 29.3 | 19 | A |
| LYS | O | 198 | 203.4 | 125.2 | 29.8 | 21 | A |
| ASN | N | 199 | 204.3 | 126.7 | 28.4 | 17 | A |
| ASN | CA | 199 | 203.1 | 127.1 | 27.9 | 17 | A |
| ASN | CB | 199 | 203.2 | 128.2 | 26.8 | 17 | A |
| ASN | CG | 199 | 201.9 | 128.8 | 26.4 | 18 | A |
| ASN | OD1 | 199 | 201.1 | 128.2 | 25.6 | 18 | A |
| ASN | ND2 | 199 | 201.5 | 130.0 | 26.9 | 17 | A |
| ASN | C | 199 | 202.5 | 125.8 | 27.2 | 18 | A |
| ASN | O | 199 | 203.1 | 125.2 | 26.4 | 22 | A |
| TYR | N | 200 | 201.3 | 125.3 | 27.8 | 19 | A |
| TYR | CA | 200 | 200.6 | 124.1 | 27.2 | 19 | A |
| TYR | CB | 200 | 199.4 | 123.8 | 28.1 | 19 | A |
| TYR | CG | 200 | 199.0 | 122.4 | 28.0 | 17 | A |
| TYR | CD1 | 200 | 199.6 | 121.4 | 28.9 | 18 | A |
| TYR | CE1 | 200 | 199.2 | 120.1 | 28.8 | 18 | A |
| TYR | CD2 | 200 | 198.0 | 122.0 | 27.2 | 17 | A |
| TYR | CE2 | 200 | 197.6 | 120.6 | 27.1 | 18 | A |
| TYR | CZ | 200 | 198.2 | 119.7 | 27.9 | 18 | A |
| TYR | OH | 200 | 197.7 | 118.4 | 27.9 | 17 | A |
| TYR | C | 200 | 200.2 | 124.3 | 25.8 | 20 | A |
| TYR | O | 200 | 200.4 | 123.4 | 25.0 | 21 | A |
| HIS | N | 201 | 199.7 | 125.4 | 25.5 | 21 | A |
| HIS | CA | 201 | 199.2 | 125.7 | 24.1 | 21 | A |
| HIS | CB | 201 | 198.5 | 127.1 | 24.1 | 21 | A |
| HIS | CG | 201 | 197.3 | 127.1 | 24.9 | 22 | A |
| HIS | CD2 | 201 | 197.0 | 127.5 | 26.2 | 21 | A |
| HIS | ND1 | 201 | 196.1 | 126.6 | 24.4 | 21 | A |
| HIS | CE1 | 201 | 195.1 | 126.7 | 25.4 | 22 | A |
| HIS | NE2 | 201 | 195.7 | 127.2 | 26.5 | 22 | A |
| HIS | C | 201 | 200.4 | 125.7 | 23.1 | 21 | A |
| HIS | O | 201 | 200.3 | 125.2 | 22.0 | 23 | A |
| ALA | N | 202 | 201.6 | 126.3 | 23.5 | 19 | A |
| ALA | CA | 202 | 202.8 | 126.3 | 22.7 | 19 | A |
| ALA | CB | 202 | 203.9 | 127.1 | 23.4 | 18 | A |
| ALA | C | 202 | 203.3 | 124.9 | 22.4 | 20 | A |
| ALA | O | 202 | 203.6 | 124.6 | 21.3 | 21 | A |
| TRP | N | 203 | 203.3 | 124.1 | 23.5 | 21 | A |
| TRP | CA | 203 | 203.8 | 122.7 | 23.3 | 22 | A |
| TRP | CB | 203 | 204.0 | 122.0 | 24.6 | 21 | A |
| TRP | CG | 203 | 205.2 | 122.3 | 25.2 | 20 | A |
| TRP | CD2 | 203 | 206.5 | 122.0 | 24.8 | 19 | A |
| TRP | CE2 | 203 | 207.5 | 122.6 | 25.7 | 19 | A |
| TRP | CE3 | 203 | 207.0 | 121.3 | 23.7 | 19 | A |
| TRP | CD1 | 203 | 205.4 | 123.1 | 26.4 | 20 | A |
| TRP | NE1 | 203 | 206.7 | 123.2 | 26.6 | 20 | A |
| TRP | CZ2 | 203 | 208.8 | 122.4 | 25.5 | 18 | A |
| TRP | CZ3 | 203 | 208.4 | 121.1 | 23.5 | 18 | A |
| TRP | CH2 | 203 | 209.3 | 121.7 | 24.4 | 18 | A |
| TRP | C | 203 | 202.8 | 121.8 | 22.4 | 23 | A |
| TRP | O | 203 | 203.3 | 121.0 | 21.6 | 22 | A |
| GLN | N | 204 | 201.5 | 122.1 | 22.6 | 22 | A |
| GLN | CA | 204 | 200.5 | 121.4 | 21.8 | 22 | A |
| GLN | CB | 204 | 199.1 | 121.7 | 22.4 | 22 | A |
| GLN | CG | 204 | 198.0 | 121.0 | 21.7 | 23 | A |
| GLN | CD | 204 | 196.7 | 121.2 | 22.3 | 24 | A |
| GLN | OE1 | 204 | 195.7 | 121.3 | 21.7 | 25 | A |
| GLN | NE2 | 204 | 196.7 | 121.2 | 23.7 | 24 | A |
| GLN | C | 204 | 200.6 | 121.8 | 20.4 | 23 | A |
| GLN | O | 204 | 200.4 | 120.9 | 19.5 | 23 | A |
| HIS | N | 205 | 200.7 | 123.1 | 20.1 | 23 | A |
| HIS | CA | 205 | 200.8 | 123.6 | 18.8 | 23 | A |
| HIS | CB | 205 | 200.8 | 125.1 | 18.8 | 22 | A |
| HIS | CG | 205 | 200.8 | 125.7 | 17.4 | 22 | A |
| HIS | CD2 | 205 | 201.7 | 126.1 | 16.5 | 22 | A |
| HIS | ND1 | 205 | 199.6 | 125.9 | 16.7 | 22 | A |
| HIS | CE1 | 205 | 199.8 | 126.4 | 15.5 | 21 | A |
| HIS | NE2 | 205 | 201.1 | 126.6 | 15.4 | 21 | A |
| HIS | C | 205 | 202.0 | 123.0 | 18.1 | 23 | A |
| HIS | O | 205 | 202.0 | 122.5 | 17.0 | 25 | A |
| ARG | N | 206 | 203.1 | 123.0 | 18.9 | 24 | A |
| ARG | CA | 206 | 204.4 | 122.4 | 18.4 | 24 | A |
| ARG | CB | 206 | 205.5 | 122.6 | 19.5 | 22 | A |
| ARG | CG | 206 | 206.8 | 122.6 | 19.0 | 22 | A |
| ARG | CD | 206 | 207.9 | 122.8 | 20.1 | 22 | A |
| ARG | NE | 206 | 209.2 | 122.6 | 19.6 | 22 | A |
| ARG | CZ | 206 | 210.0 | 123.6 | 19.0 | 24 | A |
| ARG | NH1 | 206 | 209.5 | 124.8 | 18.9 | 24 | A |

TABLE 2-continued

| | | | | | | | |
|---|---|---|---|---|---|---|---|
| ARG | NH2 | 206 | 211.2 | 123.3 | 18.5 | 24 | A |
| ARG | C | 206 | 204.3 | 121.0 | 18.0 | 25 | A |
| ARG | O | 206 | 204.7 | 120.7 | 16.9 | 25 | A |
| GLN | N | 207 | 203.6 | 120.2 | 18.8 | 24 | A |
| GLN | CA | 207 | 203.4 | 118.7 | 18.5 | 23 | A |
| GLN | CB | 207 | 202.8 | 118.0 | 19.6 | 20 | A |
| GLN | CG | 207 | 203.7 | 117.8 | 20.8 | 18 | A |
| GLN | CD | 207 | 203.1 | 116.9 | 21.8 | 18 | A |
| GLN | OE1 | 207 | 201.9 | 116.4 | 21.7 | 16 | A |
| GLN | NE2 | 207 | 203.8 | 116.5 | 22.8 | 16 | A |
| GLN | C | 207 | 202.6 | 118.6 | 17.2 | 23 | A |
| GLN | O | 207 | 202.8 | 117.6 | 16.5 | 25 | A |
| TRP | N | 208 | 201.7 | 119.5 | 16.9 | 24 | A |
| TRP | CA | 208 | 200.9 | 119.5 | 15.7 | 24 | A |
| TRP | CB | 208 | 199.7 | 120.4 | 15.8 | 22 | A |
| TRP | CG | 208 | 198.9 | 120.5 | 14.6 | 22 | A |
| TRP | CD2 | 208 | 199.0 | 121.6 | 13.6 | 21 | A |
| TRP | CE2 | 208 | 198.2 | 121.2 | 12.5 | 21 | A |
| TRP | CE3 | 208 | 199.7 | 122.8 | 13.6 | 22 | A |
| TRP | CD1 | 208 | 198.1 | 119.6 | 14.0 | 21 | A |
| TRP | NE1 | 208 | 197.6 | 120.0 | 12.8 | 21 | A |
| TRP | CZ2 | 208 | 198.0 | 122.0 | 11.4 | 21 | A |
| TRP | CZ3 | 208 | 199.5 | 123.6 | 12.4 | 21 | A |
| TRP | CH2 | 208 | 198.7 | 123.2 | 11.4 | 22 | A |
| TRP | C | 208 | 201.8 | 119.8 | 14.5 | 26 | A |
| TRP | O | 208 | 201.7 | 119.1 | 13.5 | 29 | A |
| VAL | N | 209 | 202.6 | 120.8 | 14.6 | 26 | A |
| VAL | CA | 209 | 203.4 | 121.2 | 13.5 | 25 | A |
| VAL | CB | 209 | 204.2 | 122.5 | 13.7 | 25 | A |
| VAL | CG1 | 209 | 205.0 | 122.9 | 12.5 | 24 | A |
| VAL | CG2 | 209 | 203.3 | 123.6 | 14.1 | 25 | A |
| VAL | C | 209 | 204.4 | 120.1 | 13.1 | 27 | A |
| VAL | O | 209 | 204.6 | 119.8 | 11.9 | 28 | A |
| ILE | N | 210 | 205.0 | 119.5 | 14.1 | 28 | A |
| ILE | CA | 210 | 205.9 | 118.4 | 13.9 | 28 | A |
| ILE | CB | 210 | 206.6 | 118.0 | 15.3 | 25 | A |
| ILE | CG2 | 210 | 207.3 | 116.7 | 15.2 | 25 | A |
| ILE | CG1 | 210 | 207.6 | 119.0 | 15.7 | 23 | A |
| ILE | CD1 | 210 | 208.1 | 118.8 | 17.1 | 21 | A |
| ILE | C | 210 | 205.2 | 117.1 | 13.4 | 30 | A |
| ILE | O | 210 | 205.7 | 116.5 | 12.4 | 31 | A |
| GLN | N | 211 | 204.1 | 116.8 | 14.0 | 33 | A |
| GLN | CA | 211 | 203.4 | 115.6 | 13.5 | 37 | A |
| GLN | CB | 211 | 202.2 | 115.3 | 14.4 | 41 | A |
| GLN | CG | 211 | 202.0 | 113.9 | 14.8 | 47 | A |
| GLN | CD | 211 | 201.3 | 113.7 | 16.2 | 50 | A |
| GLN | OE1 | 211 | 200.9 | 114.6 | 16.8 | 52 | A |
| GLN | NE2 | 211 | 201.1 | 112.4 | 16.5 | 52 | A |
| GLN | C | 211 | 202.9 | 115.8 | 12.0 | 37 | A |
| GLN | O | 211 | 203.3 | 115.0 | 11.2 | 39 | A |
| GLU | N | 212 | 202.1 | 116.8 | 11.8 | 38 | A |
| GLU | CA | 212 | 201.5 | 117.0 | 10.5 | 39 | A |
| GLU | CB | 212 | 200.7 | 118.3 | 10.5 | 42 | A |
| GLU | CG | 212 | 199.4 | 118.2 | 11.2 | 48 | A |
| GLU | CD | 212 | 198.5 | 117.2 | 10.5 | 51 | A |
| GLU | OE1 | 212 | 198.0 | 117.5 | 9.4 | 53 | A |
| GLU | OE2 | 212 | 198.4 | 116.0 | 11.1 | 53 | A |
| GLU | C | 212 | 202.5 | 117.2 | 9.4 | 38 | A |
| GLU | O | 212 | 202.4 | 116.6 | 8.3 | 38 | A |
| PHE | N | 213 | 203.5 | 118.1 | 9.6 | 37 | A |
| PHE | CA | 213 | 204.5 | 118.4 | 8.6 | 36 | A |
| PHE | CB | 213 | 204.9 | 119.8 | 8.6 | 35 | A |
| PHE | CG | 213 | 203.8 | 120.7 | 8.3 | 36 | A |
| PHE | CD1 | 213 | 202.9 | 121.1 | 9.2 | 37 | A |
| PHE | CD2 | 213 | 203.6 | 121.1 | 7.0 | 36 | A |
| PHE | CE1 | 213 | 201.8 | 121.9 | 8.9 | 37 | A |
| PHE | CE2 | 213 | 202.5 | 121.9 | 6.6 | 37 | A |
| PHE | CZ | 213 | 201.6 | 122.3 | 7.6 | 37 | A |
| PHE | C | 213 | 205.7 | 117.5 | 8.7 | 37 | A |
| PHE | O | 213 | 206.7 | 117.7 | 7.9 | 37 | A |
| ARG | N | 214 | 205.7 | 116.5 | 9.6 | 38 | A |
| ARG | CA | 214 | 206.7 | 115.5 | 9.7 | 40 | A |
| ARG | CB | 214 | 206.8 | 114.6 | 8.5 | 43 | A |
| ARG | CG | 214 | 205.8 | 113.4 | 8.6 | 47 | A |
| ARG | CD | 214 | 205.0 | 113.1 | 7.3 | 51 | A |
| ARG | NE | 214 | 203.7 | 113.7 | 7.2 | 56 | A |
| ARG | CZ | 214 | 202.5 | 113.4 | 7.8 | 57 | A |
| ARG | NH1 | 214 | 201.4 | 114.1 | 7.6 | 58 | A |
| ARG | NH2 | 214 | 202.4 | 112.4 | 8.7 | 58 | A |

TABLE 2-continued

| | | | | | | | |
|---|---|---|---|---|---|---|---|
| ARG | C | 214 | 208.1 | 116.2 | 9.9 | 39 | A |
| ARG | O | 214 | 209.1 | 115.9 | 9.2 | 40 | A |
| LEU | N | 215 | 208.2 | 117.2 | 10.9 | 38 | A |
| LEU | CA | 215 | 209.4 | 117.9 | 11.2 | 37 | A |
| LEU | CB | 215 | 209.1 | 119.4 | 11.3 | 37 | A |
| LEU | CG | 215 | 208.2 | 120.1 | 10.3 | 36 | A |
| LEU | CD1 | 215 | 208.0 | 121.5 | 10.6 | 36 | A |
| LEU | CD2 | 215 | 208.7 | 120.0 | 8.9 | 37 | A |
| LEU | C | 215 | 210.1 | 117.4 | 12.4 | 38 | A |
| LEU | O | 215 | 210.5 | 118.2 | 13.3 | 38 | A |
| TRP | N | 216 | 210.4 | 116.1 | 12.4 | 37 | A |
| TRP | CA | 216 | 211.1 | 115.5 | 13.6 | 37 | A |
| TRP | CB | 216 | 210.7 | 114.0 | 13.6 | 33 | A |
| TRP | CG | 216 | 209.3 | 113.7 | 13.4 | 30 | A |
| TRP | CD2 | 216 | 208.4 | 113.5 | 14.5 | 28 | A |
| TRP | CE2 | 216 | 207.1 | 113.2 | 13.9 | 28 | A |
| TRP | CE3 | 216 | 208.4 | 113.6 | 15.9 | 27 | A |
| TRP | CD1 | 216 | 208.6 | 113.4 | 12.3 | 29 | A |
| TRP | NE1 | 216 | 207.3 | 113.1 | 12.5 | 27 | A |
| TRP | CZ2 | 216 | 206.0 | 113.0 | 14.7 | 27 | A |
| TRP | CZ3 | 216 | 207.3 | 113.4 | 16.6 | 26 | A |
| TRP | CH2 | 216 | 206.1 | 113.1 | 16.0 | 26 | A |
| TRP | C | 216 | 212.6 | 115.5 | 13.8 | 39 | A |
| TRP | O | 216 | 213.1 | 115.4 | 14.9 | 39 | A |
| ASP | N | 217 | 213.3 | 115.7 | 12.7 | 42 | A |
| ASP | CA | 217 | 214.8 | 115.7 | 12.8 | 45 | A |
| ASP | CB | 217 | 215.4 | 116.0 | 11.4 | 47 | A |
| ASP | CG | 217 | 214.8 | 115.0 | 10.3 | 50 | A |
| ASP | OD1 | 217 | 214.7 | 115.4 | 9.2 | 51 | A |
| ASP | OD2 | 217 | 214.5 | 113.8 | 10.7 | 51 | A |
| ASP | C | 217 | 215.6 | 116.4 | 13.8 | 45 | A |
| ASP | O | 217 | 216.5 | 115.8 | 14.4 | 47 | A |
| ASN | N | 218 | 215.2 | 117.6 | 14.2 | 45 | A |
| ASN | CA | 218 | 216.0 | 118.4 | 15.1 | 44 | A |
| ASN | CB | 218 | 216.5 | 119.7 | 14.6 | 47 | A |
| ASN | CG | 218 | 217.2 | 119.5 | 13.3 | 48 | A |
| ASN | OD1 | 218 | 216.6 | 119.7 | 12.2 | 49 | A |
| ASN | ND2 | 218 | 218.5 | 119.3 | 13.3 | 49 | A |
| ASN | C | 218 | 215.3 | 118.6 | 16.5 | 43 | A |
| ASN | O | 218 | 215.8 | 119.4 | 17.3 | 43 | A |
| GLU | N | 219 | 214.2 | 118.0 | 16.7 | 41 | A |
| GLU | CA | 219 | 213.4 | 118.2 | 18.0 | 40 | A |
| GLU | CB | 219 | 212.0 | 117.7 | 17.8 | 39 | A |
| GLU | CG | 219 | 211.1 | 118.1 | 19.0 | 37 | A |
| GLU | CD | 219 | 211.0 | 119.6 | 19.3 | 37 | A |
| GLU | OE1 | 219 | 211.6 | 120.4 | 18.6 | 37 | A |
| GLU | OE2 | 219 | 210.3 | 119.9 | 20.3 | 37 | A |
| GLU | C | 219 | 214.1 | 117.5 | 19.2 | 40 | A |
| GLU | O | 219 | 213.9 | 118.1 | 20.3 | 40 | A |
| LEU | N | 220 | 214.7 | 116.4 | 19.1 | 38 | A |
| LEU | CA | 220 | 215.3 | 115.8 | 20.2 | 36 | A |
| LEU | CB | 220 | 215.8 | 114.4 | 19.9 | 35 | A |
| LEU | CG | 220 | 216.2 | 113.7 | 21.2 | 35 | A |
| LEU | CD1 | 220 | 215.2 | 113.8 | 22.3 | 34 | A |
| LEU | CD2 | 220 | 216.6 | 112.3 | 20.9 | 36 | A |
| LEU | C | 220 | 216.5 | 116.7 | 20.7 | 37 | A |
| LEU | O | 220 | 216.8 | 116.7 | 21.9 | 36 | A |
| GLN | N | 221 | 217.1 | 117.3 | 19.7 | 39 | A |
| GLN | CA | 221 | 218.3 | 118.2 | 20.1 | 41 | A |
| GLN | CB | 221 | 219.0 | 118.7 | 18.8 | 46 | A |
| GLN | CG | 221 | 219.8 | 117.7 | 18.0 | 51 | A |
| GLN | CD | 221 | 219.2 | 117.1 | 16.7 | 55 | A |
| GLN | OE1 | 221 | 219.6 | 117.4 | 15.6 | 55 | A |
| GLN | NE2 | 221 | 218.1 | 116.3 | 16.9 | 55 | A |
| GLN | C | 221 | 217.7 | 119.4 | 20.8 | 40 | A |
| GLN | O | 221 | 218.5 | 120.0 | 21.7 | 41 | A |
| TYR | N | 222 | 216.5 | 119.8 | 20.5 | 38 | A |
| TYR | CA | 222 | 215.8 | 121.0 | 21.2 | 35 | A |
| TYR | CB | 222 | 214.6 | 121.3 | 20.4 | 33 | A |
| TYR | CG | 222 | 213.8 | 122.5 | 21.0 | 32 | A |
| TYR | CD1 | 222 | 214.4 | 123.7 | 21.1 | 30 | A |
| TYR | CE1 | 222 | 213.7 | 124.8 | 21.6 | 31 | A |
| TYR | CD2 | 222 | 212.5 | 122.3 | 21.4 | 31 | A |
| TYR | CE2 | 222 | 211.8 | 123.4 | 21.8 | 31 | A |
| TYR | CZ | 222 | 212.4 | 124.7 | 21.9 | 31 | A |
| TYR | OH | 222 | 211.7 | 125.8 | 22.4 | 32 | A |
| TYR | C | 222 | 215.5 | 120.6 | 22.6 | 36 | A |
| TYR | O | 222 | 215.6 | 121.4 | 23.5 | 35 | A |
| VAL | N | 223 | 214.9 | 119.4 | 22.7 | 36 | A |

TABLE 2-continued

| | | | | | | | |
|---|---|---|---|---|---|---|---|
| VAL | CA | 223 | 214.5 | 118.8 | 24.0 | 35 | A |
| VAL | CB | 223 | 213.9 | 117.4 | 23.8 | 34 | A |
| VAL | CG1 | 223 | 213.8 | 116.7 | 25.1 | 34 | A |
| VAL | CG2 | 223 | 212.5 | 117.5 | 23.2 | 34 | A |
| VAL | C | 223 | 215.7 | 118.8 | 24.9 | 36 | A |
| VAL | O | 223 | 215.6 | 119.2 | 26.1 | 37 | A |
| ASP | N | 224 | 216.8 | 118.3 | 24.4 | 37 | A |
| ASP | CA | 224 | 218.0 | 118.2 | 25.2 | 38 | A |
| ASP | CB | 224 | 219.1 | 117.5 | 24.4 | 39 | A |
| ASP | CG | 224 | 219.0 | 116.0 | 24.3 | 40 | A |
| ASP | OD1 | 224 | 218.7 | 115.4 | 25.3 | 42 | A |
| ASP | OD2 | 224 | 219.2 | 115.5 | 23.2 | 41 | A |
| ASP | C | 224 | 218.4 | 119.6 | 25.7 | 39 | A |
| ASP | O | 224 | 218.9 | 119.8 | 26.8 | 40 | A |
| GLN | N | 225 | 218.3 | 120.6 | 24.8 | 38 | A |
| GLN | CA | 225 | 218.7 | 122.0 | 25.1 | 37 | A |
| GLN | CB | 225 | 218.4 | 122.8 | 23.9 | 39 | A |
| GLN | CG | 225 | 218.7 | 124.3 | 24.1 | 44 | A |
| GLN | CD | 225 | 218.2 | 125.2 | 22.9 | 47 | A |
| GLN | OE1 | 225 | 218.2 | 124.8 | 21.7 | 50 | A |
| GLN | NE2 | 225 | 217.8 | 126.5 | 23.2 | 48 | A |
| GLN | C | 225 | 217.8 | 122.5 | 26.3 | 35 | A |
| GLN | O | 225 | 218.4 | 122.9 | 27.3 | 34 | A |
| LEU | N | 226 | 216.5 | 122.3 | 26.2 | 32 | A |
| LEU | CA | 226 | 215.6 | 122.8 | 27.2 | 30 | A |
| LEU | CB | 226 | 214.2 | 122.7 | 26.8 | 28 | A |
| LEU | CG | 226 | 213.7 | 123.6 | 25.6 | 27 | A |
| LEU | CD1 | 226 | 212.3 | 123.7 | 25.7 | 27 | A |
| LEU | CD2 | 226 | 214.4 | 124.9 | 25.7 | 26 | A |
| LEU | C | 226 | 215.8 | 122.0 | 28.5 | 30 | A |
| LEU | O | 226 | 215.6 | 122.5 | 29.6 | 31 | A |
| LEU | N | 227 | 216.1 | 120.7 | 28.4 | 32 | A |
| LEU | CA | 227 | 216.4 | 119.9 | 29.6 | 34 | A |
| LEU | CB | 227 | 216.4 | 118.4 | 29.3 | 33 | A |
| LEU | CG | 227 | 215.0 | 117.7 | 29.3 | 34 | A |
| LEU | CD1 | 227 | 215.1 | 116.3 | 28.8 | 34 | A |
| LEU | CD2 | 227 | 214.4 | 117.8 | 30.6 | 33 | A |
| LEU | C | 227 | 217.6 | 120.3 | 30.3 | 36 | A |
| LEU | O | 227 | 217.8 | 120.1 | 31.5 | 35 | A |
| LYS | N | 228 | 218.5 | 121.0 | 29.6 | 38 | A |
| LYS | CA | 228 | 219.7 | 121.5 | 30.1 | 39 | A |
| LYS | CB | 228 | 220.7 | 121.9 | 29.0 | 41 | A |
| LYS | CG | 228 | 222.2 | 121.5 | 29.5 | 46 | A |
| LYS | CD | 228 | 223.1 | 122.8 | 29.4 | 49 | A |
| LYS | CE | 228 | 224.5 | 122.5 | 29.9 | 51 | A |
| LYS | NZ | 228 | 225.5 | 123.5 | 29.7 | 52 | A |
| LYS | C | 228 | 219.4 | 122.8 | 30.9 | 39 | A |
| LYS | O | 228 | 219.9 | 123.1 | 32.0 | 39 | A |
| GLU | N | 229 | 218.4 | 123.5 | 30.4 | 37 | A |
| GLU | CA | 229 | 218.0 | 124.8 | 31.1 | 36 | A |
| GLU | CB | 229 | 217.2 | 125.6 | 30.1 | 36 | A |
| GLU | CG | 229 | 218.0 | 126.1 | 28.9 | 35 | A |
| GLU | CD | 229 | 217.3 | 126.8 | 27.8 | 36 | A |
| GLU | OE1 | 229 | 216.0 | 126.9 | 27.9 | 38 | A |
| GLU | OE2 | 229 | 217.9 | 127.2 | 26.8 | 37 | A |
| GLU | C | 229 | 217.1 | 124.5 | 32.4 | 35 | A |
| GLU | O | 229 | 217.3 | 125.2 | 33.3 | 35 | A |
| ASP | N | 230 | 216.3 | 123.5 | 32.4 | 34 | A |
| ASP | CA | 230 | 215.5 | 123.2 | 33.5 | 32 | A |
| ASP | CB | 230 | 214.2 | 124.0 | 33.6 | 31 | A |
| ASP | CG | 230 | 213.5 | 123.9 | 34.9 | 31 | A |
| ASP | OD1 | 230 | 213.8 | 123.0 | 35.7 | 30 | A |
| ASP | OD2 | 230 | 212.7 | 124.8 | 35.2 | 31 | A |
| ASP | C | 230 | 215.2 | 121.7 | 33.4 | 32 | A |
| ASP | O | 230 | 214.2 | 121.3 | 32.8 | 32 | A |
| VAL | N | 231 | 216.0 | 120.9 | 34.1 | 31 | A |
| VAL | CA | 231 | 215.8 | 119.4 | 34.1 | 31 | A |
| VAL | CB | 231 | 217.0 | 118.7 | 34.7 | 32 | A |
| VAL | CG1 | 231 | 217.0 | 118.9 | 36.2 | 33 | A |
| VAL | CG2 | 231 | 216.9 | 117.2 | 34.4 | 32 | A |
| VAL | C | 231 | 214.5 | 119.0 | 34.7 | 30 | A |
| VAL | O | 231 | 214.1 | 117.9 | 34.6 | 31 | A |
| ARG | N | 232 | 213.9 | 120.0 | 35.4 | 30 | A |
| ARG | CA | 232 | 212.6 | 119.7 | 36.1 | 29 | A |
| ARG | CB | 232 | 212.5 | 120.4 | 37.4 | 30 | A |
| ARG | CG | 232 | 213.5 | 120.1 | 38.4 | 31 | A |
| ARG | CD | 232 | 213.2 | 120.9 | 39.7 | 32 | A |
| ARG | NE | 232 | 214.1 | 120.7 | 40.8 | 32 | A |
| ARG | CZ | 232 | 215.3 | 121.1 | 40.9 | 33 | A |

TABLE 2-continued

| | | | | | | | |
|---|---|---|---|---|---|---|---|
| ARG | NH1 | 232 | 215.9 | 121.9 | 39.9 | 33 | A |
| ARG | NH2 | 232 | 216.1 | 120.8 | 41.9 | 34 | A |
| ARG | C | 232 | 211.4 | 120.1 | 35.1 | 28 | A |
| ARG | O | 232 | 210.3 | 120.1 | 35.6 | 27 | A |
| ASN | N | 233 | 211.7 | 120.4 | 33.9 | 28 | A |
| ASN | CA | 233 | 210.7 | 120.8 | 33.0 | 27 | A |
| ASN | CB | 233 | 211.2 | 121.6 | 31.8 | 26 | A |
| ASN | CG | 233 | 210.1 | 122.4 | 31.1 | 26 | A |
| ASN | OD1 | 233 | 208.9 | 121.9 | 31.0 | 26 | A |
| ASN | ND2 | 233 | 210.4 | 123.5 | 30.4 | 24 | A |
| ASN | C | 233 | 209.9 | 119.6 | 32.4 | 27 | A |
| ASN | O | 233 | 210.3 | 119.1 | 31.3 | 29 | A |
| ASN | N | 234 | 208.8 | 119.2 | 33.1 | 27 | A |
| ASN | CA | 234 | 208.0 | 118.1 | 32.7 | 26 | A |
| ASN | CB | 234 | 206.8 | 117.9 | 33.7 | 26 | A |
| ASN | CG | 234 | 206.3 | 116.5 | 33.7 | 27 | A |
| ASN | OD1 | 234 | 207.0 | 115.6 | 34.1 | 27 | A |
| ASN | ND2 | 234 | 205.0 | 116.3 | 33.3 | 24 | A |
| ASN | C | 234 | 207.5 | 118.1 | 31.2 | 26 | A |
| ASN | O | 234 | 207.2 | 117.1 | 30.6 | 26 | A |
| SER | N | 235 | 207.3 | 119.3 | 30.7 | 26 | A |
| SER | CA | 235 | 206.8 | 119.5 | 29.3 | 26 | A |
| SER | CB | 235 | 206.5 | 121.0 | 29.1 | 24 | A |
| SER | OG | 235 | 205.4 | 121.4 | 29.9 | 22 | A |
| SER | C | 235 | 207.9 | 119.0 | 28.3 | 26 | A |
| SER | O | 235 | 207.5 | 118.5 | 27.3 | 27 | A |
| VAL | N | 236 | 209.1 | 119.1 | 28.7 | 26 | A |
| VAL | CA | 236 | 210.2 | 118.7 | 27.9 | 25 | A |
| VAL | CB | 236 | 211.5 | 119.4 | 28.3 | 25 | A |
| VAL | CG1 | 236 | 212.6 | 119.1 | 27.3 | 26 | A |
| VAL | CG2 | 236 | 211.2 | 120.9 | 28.3 | 24 | A |
| VAL | C | 236 | 210.4 | 117.2 | 28.1 | 25 | A |
| VAL | O | 236 | 210.7 | 116.5 | 27.1 | 25 | A |
| TRP | N | 237 | 210.2 | 116.6 | 29.3 | 25 | A |
| TRP | CA | 237 | 210.3 | 115.2 | 29.5 | 26 | A |
| TRP | CB | 237 | 210.2 | 114.8 | 30.9 | 27 | A |
| TRP | CG | 237 | 211.5 | 115.0 | 31.7 | 28 | A |
| TRP | CD2 | 237 | 212.6 | 114.2 | 31.6 | 28 | A |
| TRP | CE2 | 237 | 213.6 | 114.7 | 32.5 | 29 | A |
| TRP | CE3 | 237 | 213.0 | 113.0 | 30.9 | 28 | A |
| TRP | CD1 | 237 | 211.8 | 116.0 | 32.6 | 28 | A |
| TRP | NE1 | 237 | 213.0 | 115.8 | 33.1 | 29 | A |
| TRP | CZ2 | 237 | 214.9 | 114.2 | 32.7 | 27 | A |
| TRP | CZ3 | 237 | 214.2 | 112.4 | 31.1 | 26 | A |
| TRP | CH2 | 237 | 215.2 | 113.0 | 32.0 | 26 | A |
| TRP | C | 237 | 209.3 | 114.5 | 28.6 | 26 | A |
| TRP | O | 237 | 209.5 | 113.6 | 27.9 | 26 | A |
| ASN | N | 238 | 208.1 | 115.1 | 28.6 | 27 | A |
| ASN | CA | 238 | 207.0 | 114.6 | 27.9 | 28 | A |
| ASN | CB | 238 | 205.7 | 115.4 | 28.1 | 29 | A |
| ASN | CG | 238 | 204.5 | 114.9 | 27.3 | 31 | A |
| ASN | OD1 | 238 | 203.9 | 113.8 | 27.7 | 31 | A |
| ASN | ND2 | 238 | 204.1 | 115.5 | 26.2 | 30 | A |
| ASN | C | 238 | 207.3 | 114.7 | 26.4 | 28 | A |
| ASN | O | 238 | 207.1 | 113.8 | 25.6 | 28 | A |
| GLN | N | 239 | 207.9 | 115.8 | 25.9 | 28 | A |
| GLN | CA | 239 | 208.3 | 116.1 | 24.5 | 29 | A |
| GLN | CB | 239 | 208.8 | 117.5 | 24.3 | 28 | A |
| GLN | CG | 239 | 209.0 | 117.8 | 22.9 | 28 | A |
| GLN | CD | 239 | 207.7 | 118.1 | 22.1 | 28 | A |
| GLN | OE1 | 239 | 206.6 | 117.8 | 22.6 | 30 | A |
| GLN | NE2 | 239 | 207.8 | 118.5 | 20.9 | 28 | A |
| GLN | C | 239 | 209.3 | 115.1 | 24.0 | 29 | A |
| GLN | O | 239 | 209.3 | 114.7 | 22.9 | 29 | A |
| ARG | N | 240 | 210.2 | 114.7 | 24.9 | 29 | A |
| ARG | CA | 240 | 211.3 | 113.7 | 24.6 | 28 | A |
| ARG | CB | 240 | 212.2 | 113.7 | 25.8 | 28 | A |
| ARG | CG | 240 | 213.3 | 112.7 | 25.7 | 28 | A |
| ARG | CD | 240 | 214.2 | 112.5 | 27.0 | 26 | A |
| ARG | NE | 240 | 215.4 | 111.9 | 26.5 | 27 | A |
| ARG | CZ | 240 | 216.4 | 112.5 | 26.0 | 29 | A |
| ARG | NH1 | 240 | 216.4 | 113.9 | 25.8 | 29 | A |
| ARG | NH2 | 240 | 217.4 | 111.8 | 25.4 | 30 | A |
| ARG | C | 240 | 210.6 | 112.4 | 24.4 | 29 | A |
| ARG | O | 240 | 211.1 | 111.6 | 23.6 | 31 | A |
| HIS | N | 241 | 209.5 | 112.1 | 25.1 | 29 | A |
| HIS | CA | 241 | 208.9 | 110.8 | 24.9 | 27 | A |
| HIS | CB | 241 | 207.9 | 110.6 | 26.1 | 28 | A |
| HIS | CG | 241 | 207.3 | 109.2 | 26.1 | 30 | A |

TABLE 2-continued

| | | | | | | | |
|---|---|---|---|---|---|---|---|
| HIS | CD2 | 241 | 207.5 | 108.2 | 27.0 | 30 | A |
| HIS | ND1 | 241 | 206.5 | 108.7 | 25.1 | 30 | A |
| HIS | CE1 | 241 | 206.2 | 107.4 | 25.4 | 30 | A |
| HIS | NE2 | 241 | 206.9 | 107.1 | 26.5 | 30 | A |
| HIS | C | 241 | 208.1 | 110.9 | 23.6 | 28 | A |
| HIS | O | 241 | 208.1 | 109.9 | 22.8 | 29 | A |
| PHE | N | 242 | 207.4 | 112.0 | 23.4 | 28 | A |
| PHE | CA | 242 | 206.7 | 112.2 | 22.1 | 27 | A |
| PHE | CB | 242 | 206.1 | 113.6 | 22.1 | 24 | A |
| PHE | CG | 242 | 205.5 | 114.1 | 20.8 | 23 | A |
| PHE | CD1 | 242 | 204.2 | 113.7 | 20.4 | 22 | A |
| PHE | CD2 | 242 | 206.2 | 114.9 | 19.9 | 23 | A |
| PHE | CE1 | 242 | 203.6 | 114.2 | 19.3 | 21 | A |
| PHE | CE2 | 242 | 205.6 | 115.4 | 18.8 | 22 | A |
| PHE | CZ | 242 | 204.3 | 115.0 | 18.4 | 21 | A |
| PHE | C | 242 | 207.5 | 112.0 | 20.9 | 28 | A |
| PHE | O | 242 | 207.2 | 111.2 | 20.0 | 30 | A |
| VAL | N | 243 | 208.7 | 112.6 | 21.0 | 29 | A |
| VAL | CA | 243 | 209.7 | 112.5 | 19.9 | 31 | A |
| VAL | CB | 243 | 210.8 | 113.5 | 20.1 | 30 | A |
| VAL | CG1 | 243 | 211.8 | 113.3 | 19.0 | 31 | A |
| VAL | CG2 | 243 | 210.2 | 114.9 | 20.1 | 30 | A |
| VAL | C | 243 | 210.2 | 111.1 | 19.7 | 31 | A |
| VAL | O | 243 | 210.1 | 110.5 | 18.6 | 33 | A |
| ILE | N | 244 | 210.9 | 110.5 | 20.7 | 31 | A |
| ILE | CA | 244 | 211.5 | 109.2 | 20.6 | 31 | A |
| ILE | CB | 244 | 212.2 | 108.8 | 21.8 | 29 | A |
| ILE | CG2 | 244 | 212.6 | 107.3 | 21.7 | 30 | A |
| ILE | CG1 | 244 | 213.4 | 109.6 | 22.1 | 28 | A |
| ILE | CD1 | 244 | 213.9 | 109.5 | 23.5 | 25 | A |
| ILE | C | 244 | 210.4 | 108.2 | 20.2 | 32 | A |
| ILE | O | 244 | 210.6 | 107.4 | 19.2 | 33 | A |
| SER | N | 245 | 209.3 | 108.1 | 20.9 | 33 | A |
| SER | CA | 245 | 208.3 | 107.2 | 20.6 | 34 | A |
| SER | CB | 245 | 207.2 | 107.1 | 21.7 | 34 | A |
| SER | OG | 245 | 206.3 | 108.2 | 21.5 | 35 | A |
| SER | C | 245 | 207.7 | 107.3 | 19.2 | 36 | A |
| SER | O | 245 | 207.1 | 106.3 | 18.8 | 39 | A |
| ASN | N | 246 | 207.8 | 108.4 | 18.6 | 37 | A |
| ASN | CA | 246 | 207.3 | 108.6 | 17.2 | 38 | A |
| ASN | CB | 246 | 206.5 | 109.9 | 17.1 | 36 | A |
| ASN | CG | 246 | 205.1 | 109.8 | 17.6 | 37 | A |
| ASN | OD1 | 246 | 204.9 | 110.3 | 18.7 | 37 | A |
| ASN | ND2 | 246 | 204.3 | 109.2 | 16.9 | 37 | A |
| ASN | C | 246 | 208.3 | 108.5 | 16.1 | 39 | A |
| ASN | O | 246 | 208.0 | 108.4 | 14.9 | 38 | A |
| THR | N | 247 | 209.6 | 108.5 | 16.5 | 40 | A |
| THR | CA | 247 | 210.6 | 108.3 | 15.5 | 41 | A |
| THR | CB | 247 | 211.7 | 109.4 | 15.8 | 40 | A |
| THR | OG1 | 247 | 212.2 | 109.4 | 17.1 | 40 | A |
| THR | CG2 | 247 | 211.1 | 110.8 | 15.5 | 39 | A |
| THR | C | 247 | 211.3 | 106.9 | 15.6 | 42 | A |
| THR | O | 247 | 211.1 | 106.2 | 14.7 | 43 | A |
| THR | N | 248 | 212.0 | 106.6 | 16.7 | 41 | A |
| THR | CA | 248 | 212.6 | 105.3 | 16.8 | 39 | A |
| THR | CB | 248 | 214.0 | 105.4 | 17.3 | 39 | A |
| THR | OG1 | 248 | 214.0 | 105.7 | 18.7 | 39 | A |
| THR | CG2 | 248 | 214.8 | 106.5 | 16.6 | 39 | A |
| THR | C | 248 | 211.9 | 104.3 | 17.6 | 40 | A |
| THR | O | 248 | 211.9 | 103.1 | 17.4 | 43 | A |
| GLY | N | 249 | 211.3 | 104.8 | 18.7 | 41 | A |
| GLY | CA | 249 | 210.6 | 103.9 | 19.6 | 40 | A |
| GLY | C | 249 | 211.6 | 103.5 | 20.7 | 41 | A |
| GLY | O | 249 | 212.8 | 103.8 | 20.5 | 40 | A |
| TYR | N | 250 | 211.1 | 102.9 | 21.7 | 42 | A |
| TYR | CA | 250 | 212.0 | 102.4 | 22.8 | 43 | A |
| TYR | CB | 250 | 211.3 | 102.8 | 24.2 | 41 | A |
| TYR | CG | 250 | 211.2 | 104.2 | 24.5 | 40 | A |
| TYR | CD1 | 250 | 210.1 | 105.0 | 24.1 | 38 | A |
| TYR | CE1 | 250 | 210.0 | 106.3 | 24.3 | 37 | A |
| TYR | CD2 | 250 | 212.2 | 104.9 | 25.2 | 39 | A |
| TYR | CE2 | 250 | 212.2 | 106.2 | 25.4 | 39 | A |
| TYR | CZ | 250 | 211.0 | 106.9 | 25.0 | 38 | A |
| TYR | OH | 250 | 211.0 | 108.3 | 25.3 | 38 | A |
| TYR | C | 250 | 212.2 | 100.9 | 22.8 | 46 | A |
| TYR | O | 250 | 212.8 | 100.4 | 23.8 | 47 | A |
| SER | N | 251 | 211.8 | 100.3 | 21.7 | 49 | A |
| SER | CA | 251 | 212.1 | 98.9 | 21.6 | 51 | A |
| SER | CB | 251 | 211.1 | 98.3 | 20.6 | 52 | A |

TABLE 2-continued

| | | | | | | | |
|---|---|---|---|---|---|---|---|
| SER | OG | 251 | 211.0 | 99.1 | 19.4 | 54 | A |
| SER | C | 251 | 213.5 | 98.6 | 21.2 | 52 | A |
| SER | O | 251 | 214.0 | 97.6 | 21.5 | 54 | A |
| ASP | N | 252 | 214.2 | 99.6 | 20.6 | 54 | A |
| ASP | CA | 252 | 215.6 | 99.5 | 20.2 | 54 | A |
| ASP | CB | 252 | 216.0 | 100.6 | 19.2 | 57 | A |
| ASP | CG | 252 | 217.4 | 100.4 | 18.6 | 59 | A |
| ASP | OD1 | 252 | 218.2 | 99.6 | 19.2 | 60 | A |
| ASP | OD2 | 252 | 217.6 | 101.0 | 17.5 | 61 | A |
| ASP | C | 252 | 216.5 | 99.5 | 21.4 | 54 | A |
| ASP | O | 252 | 216.6 | 100.5 | 22.1 | 53 | A |
| ARG | N | 253 | 217.1 | 98.3 | 21.7 | 54 | A |
| ARG | CA | 253 | 218.0 | 98.1 | 22.9 | 54 | A |
| ARG | CB | 253 | 218.8 | 96.8 | 22.7 | 56 | A |
| ARG | CG | 253 | 218.2 | 95.6 | 23.3 | 58 | A |
| ARG | CD | 253 | 219.0 | 94.3 | 23.0 | 60 | A |
| ARG | NE | 253 | 218.4 | 93.2 | 23.7 | 62 | A |
| ARG | CZ | 253 | 218.2 | 92.0 | 23.2 | 62 | A |
| ARG | NH1 | 253 | 218.5 | 91.8 | 21.9 | 62 | A |
| ARG | NH2 | 253 | 217.6 | 91.1 | 23.9 | 62 | A |
| ARG | C | 253 | 219.0 | 99.2 | 23.1 | 53 | A |
| ARG | O | 253 | 219.2 | 99.6 | 24.3 | 53 | A |
| ALA | N | 254 | 219.6 | 99.7 | 22.1 | 51 | A |
| ALA | CA | 254 | 220.6 | 100.8 | 22.2 | 49 | A |
| ALA | CB | 254 | 221.3 | 101.0 | 20.9 | 50 | A |
| ALA | C | 254 | 219.9 | 102.0 | 22.7 | 49 | A |
| ALA | O | 254 | 220.4 | 102.7 | 23.5 | 49 | A |
| VAL | N | 255 | 218.7 | 102.3 | 22.1 | 48 | A |
| VAL | CA | 255 | 217.9 | 103.5 | 22.4 | 46 | A |
| VAL | CB | 255 | 216.7 | 103.6 | 21.5 | 47 | A |
| VAL | CG1 | 255 | 215.9 | 104.9 | 21.8 | 47 | A |
| VAL | CG2 | 255 | 217.2 | 103.8 | 20.0 | 46 | A |
| VAL | C | 255 | 217.4 | 103.4 | 23.8 | 45 | A |
| VAL | O | 255 | 217.6 | 104.3 | 24.6 | 46 | A |
| LEU | N | 256 | 216.8 | 102.2 | 24.2 | 44 | A |
| LEU | CA | 256 | 216.3 | 102.0 | 25.5 | 44 | A |
| LEU | CB | 256 | 215.8 | 100.6 | 25.6 | 42 | A |
| LEU | CG | 256 | 215.2 | 100.1 | 27.0 | 41 | A |
| LEU | CD1 | 256 | 214.2 | 101.1 | 27.5 | 41 | A |
| LEU | CD2 | 256 | 214.5 | 98.8 | 26.7 | 42 | A |
| LEU | C | 256 | 217.5 | 102.3 | 26.5 | 46 | A |
| LEU | O | 256 | 217.4 | 103.1 | 27.4 | 46 | A |
| GLU | N | 257 | 218.6 | 101.6 | 26.3 | 48 | A |
| GLU | CA | 257 | 219.8 | 101.7 | 27.2 | 49 | A |
| GLU | CB | 257 | 220.9 | 100.9 | 26.6 | 51 | A |
| GLU | CG | 257 | 222.3 | 101.3 | 27.1 | 56 | A |
| GLU | CD | 257 | 222.6 | 101.0 | 28.5 | 59 | A |
| GLU | OE1 | 257 | 221.8 | 100.3 | 29.2 | 60 | A |
| GLU | OE2 | 257 | 223.6 | 101.5 | 29.1 | 59 | A |
| GLU | C | 257 | 220.2 | 103.2 | 27.3 | 48 | A |
| GLU | O | 257 | 220.5 | 103.7 | 28.4 | 48 | A |
| ARG | N | 258 | 220.4 | 103.9 | 26.2 | 48 | A |
| ARG | CA | 258 | 220.8 | 105.3 | 26.1 | 48 | A |
| ARG | CB | 258 | 220.8 | 105.8 | 24.7 | 47 | A |
| ARG | CG | 258 | 221.1 | 107.3 | 24.6 | 46 | A |
| ARG | CD | 258 | 220.6 | 107.9 | 23.3 | 46 | A |
| ARG | NE | 258 | 219.2 | 108.0 | 23.2 | 47 | A |
| ARG | CZ | 258 | 218.4 | 108.0 | 22.1 | 46 | A |
| ARG | NH1 | 258 | 219.0 | 108.1 | 20.9 | 47 | A |
| ARG | NH2 | 258 | 217.1 | 108.0 | 22.1 | 47 | A |
| ARG | C | 258 | 219.9 | 106.1 | 27.0 | 48 | A |
| ARG | O | 258 | 220.3 | 106.9 | 27.8 | 50 | A |
| GLU | N | 259 | 218.6 | 105.8 | 26.9 | 47 | A |
| GLU | CA | 259 | 217.6 | 106.5 | 27.7 | 45 | A |
| GLU | CB | 259 | 216.1 | 106.2 | 27.1 | 44 | A |
| GLU | CG | 259 | 215.8 | 106.8 | 25.8 | 43 | A |
| GLU | CD | 259 | 216.0 | 108.3 | 25.8 | 43 | A |
| GLU | OE1 | 259 | 215.5 | 109.0 | 26.6 | 43 | A |
| GLU | OE2 | 259 | 216.7 | 108.8 | 24.9 | 41 | A |
| GLU | C | 259 | 217.6 | 106.3 | 29.2 | 44 | A |
| GLU | O | 259 | 217.7 | 107.2 | 29.9 | 44 | A |
| VAL | N | 260 | 217.6 | 105.0 | 29.6 | 44 | A |
| VAL | CA | 260 | 217.7 | 104.7 | 31.0 | 43 | A |
| VAL | CB | 260 | 247.6 | 103.1 | 31.2 | 42 | A |
| VAL | CG1 | 260 | 217.8 | 102.8 | 32.7 | 40 | A |
| VAL | CG2 | 260 | 216.2 | 102.6 | 30.7 | 41 | A |
| VAL | C | 260 | 219.0 | 105.2 | 31.6 | 44 | A |
| VAL | O | 260 | 218.9 | 105.6 | 32.8 | 44 | A |
| GLN | N | 261 | 220.0 | 105.2 | 30.9 | 45 | A |

TABLE 2-continued

| | | | | | | | |
|---|---|---|---|---|---|---|---|
| GLN | CA | 261 | 221.3 | 105.6 | 31.3 | 47 | A |
| GLN | CB | 261 | 222.4 | 105.4 | 30.3 | 49 | A |
| GLN | CG | 261 | 223.8 | 105.3 | 30.8 | 54 | A |
| GLN | CD | 261 | 223.9 | 104.2 | 31.9 | 56 | A |
| GLN | OE1 | 261 | 223.8 | 103.1 | 31.5 | 58 | A |
| GLN | NE2 | 261 | 224.0 | 104.6 | 33.1 | 57 | A |
| GLN | C | 261 | 221.3 | 107.1 | 31.6 | 47 | A |
| GLN | O | 261 | 221.6 | 107.6 | 32.7 | 48 | A |
| TYR | N | 262 | 220.8 | 107.9 | 30.6 | 46 | A |
| TYR | CA | 262 | 220.6 | 109.3 | 30.7 | 44 | A |
| TYR | CB | 262 | 220.0 | 109.8 | 29.4 | 42 | A |
| TYR | CG | 262 | 219.5 | 111.3 | 29.5 | 41 | A |
| TYR | CD1 | 262 | 220.4 | 112.3 | 29.5 | 41 | A |
| TYR | CE1 | 262 | 220.0 | 113.6 | 29.7 | 41 | A |
| TYR | CD2 | 262 | 218.2 | 111.5 | 29.6 | 40 | A |
| TYR | CE2 | 262 | 217.7 | 112.8 | 29.8 | 39 | A |
| TYR | CZ | 262 | 218.6 | 113.8 | 29.8 | 40 | A |
| TYR | OH | 262 | 218.2 | 115.1 | 30.0 | 41 | A |
| TYR | C | 262 | 219.7 | 109.7 | 31.9 | 45 | A |
| TYR | O | 262 | 220.0 | 110.6 | 32.6 | 45 | A |
| THR | N | 263 | 218.6 | 108.9 | 32.0 | 44 | A |
| THR | CA | 263 | 217.6 | 109.2 | 33.0 | 44 | A |
| THR | CB | 263 | 216.3 | 108.5 | 32.7 | 43 | A |
| THR | OG1 | 263 | 215.9 | 108.8 | 31.4 | 44 | A |
| THR | CG2 | 263 | 215.2 | 109.1 | 33.6 | 42 | A |
| THR | C | 263 | 218.2 | 108.8 | 34.4 | 45 | A |
| THR | O | 263 | 217.9 | 109.5 | 35.4 | 45 | A |
| LEU | N | 264 | 218.9 | 107.8 | 34.5 | 46 | A |
| LEU | CA | 264 | 219.5 | 107.4 | 35.7 | 47 | A |
| LEU | CB | 264 | 220.1 | 106.0 | 35.7 | 45 | A |
| LEU | CG | 264 | 219.0 | 104.9 | 35.9 | 45 | A |
| LEU | CD1 | 264 | 219.6 | 103.5 | 35.6 | 45 | A |
| LEU | CD2 | 264 | 218.4 | 105.0 | 37.3 | 44 | A |
| LEU | C | 264 | 220.5 | 108.4 | 36.1 | 48 | A |
| LEU | O | 264 | 220.7 | 108.7 | 37.3 | 49 | A |
| GLU | N | 265 | 221.1 | 109.1 | 35.1 | 50 | A |
| GLU | CA | 265 | 222.0 | 110.2 | 35.4 | 53 | A |
| GLU | CB | 265 | 222.6 | 110.7 | 34.1 | 56 | A |
| GLU | CG | 265 | 224.1 | 110.3 | 33.9 | 61 | A |
| GLU | CD | 265 | 224.3 | 108.9 | 33.6 | 64 | A |
| GLU | OE1 | 265 | 224.2 | 108.6 | 32.3 | 66 | A |
| GLU | OE2 | 265 | 224.6 | 108.0 | 34.5 | 66 | A |
| GLU | C | 265 | 221.3 | 111.4 | 36.0 | 52 | A |
| GLU | O | 265 | 221.6 | 111.8 | 37.1 | 52 | A |
| MET | N | 266 | 220.2 | 111.9 | 35.3 | 51 | A |
| MET | CA | 266 | 219.4 | 113.0 | 35.8 | 50 | A |
| MET | CB | 266 | 218.3 | 113.4 | 34.9 | 50 | A |
| MET | CG | 266 | 218.7 | 113.7 | 33.4 | 50 | A |
| MET | SD | 266 | 220.3 | 114.5 | 33.3 | 52 | A |
| MET | CE | 266 | 220.0 | 116.1 | 34.0 | 52 | A |
| MET | C | 266 | 218.9 | 112.8 | 37.2 | 49 | A |
| MET | O | 266 | 218.5 | 113.7 | 37.9 | 49 | A |
| ILE | N | 267 | 218.7 | 111.5 | 37.5 | 50 | A |
| ILE | CA | 267 | 218.2 | 111.1 | 38.8 | 51 | A |
| ILE | CB | 267 | 217.7 | 109.6 | 38.8 | 50 | A |
| ILE | CG2 | 267 | 217.5 | 109.1 | 40.2 | 49 | A |
| ILE | CG1 | 267 | 216.3 | 109.6 | 38.1 | 49 | A |
| ILE | CD1 | 267 | 215.7 | 108.2 | 38.0 | 48 | A |
| ILE | C | 267 | 219.4 | 111.1 | 39.8 | 54 | A |
| ILE | O | 267 | 219.2 | 111.7 | 40.9 | 55 | A |
| LYS | N | 268 | 220.5 | 110.6 | 39.4 | 55 | A |
| LYS | CA | 268 | 221.7 | 110.6 | 40.3 | 56 | A |
| LYS | CB | 268 | 222.6 | 109.4 | 39.9 | 59 | A |
| LYS | CG | 268 | 221.9 | 108.0 | 40.0 | 61 | A |
| LYS | CD | 268 | 222.8 | 106.9 | 39.4 | 63 | A |
| LYS | CE | 268 | 222.0 | 105.5 | 39.4 | 64 | A |
| LYS | NZ | 268 | 222.9 | 104.3 | 39.0 | 65 | A |
| LYS | C | 268 | 222.4 | 111.9 | 40.0 | 55 | A |
| LYS | O | 268 | 223.6 | 111.9 | 39.7 | 57 | A |
| LEU | N | 269 | 221.6 | 113.0 | 40.1 | 52 | A |
| LEU | CA | 269 | 222.1 | 114.4 | 39.9 | 50 | A |
| LEU | CB | 269 | 222.2 | 114.7 | 38.4 | 50 | A |
| LEU | CG | 269 | 222.9 | 115.9 | 37.8 | 51 | A |
| LEU | CD1 | 269 | 221.9 | 116.9 | 37.2 | 51 | A |
| LEU | CD2 | 269 | 223.7 | 116.6 | 38.9 | 52 | A |
| LEU | C | 269 | 221.1 | 115.3 | 40.6 | 48 | A |
| LEU | O | 269 | 221.5 | 116.3 | 41.2 | 49 | A |
| VAL | N | 270 | 219.8 | 115.0 | 40.4 | 46 | A |
| VAL | CA | 270 | 218.7 | 115.8 | 41.1 | 44 | A |

TABLE 2-continued

| | | | | | | | |
|---|---|---|---|---|---|---|---|
| VAL | CB | 270 | 218.0 | 116.8 | 40.1 | 41 | A |
| VAL | CG1 | 270 | 217.1 | 117.7 | 40.9 | 39 | A |
| VAL | CG2 | 270 | 219.1 | 117.6 | 39.4 | 40 | A |
| VAL | C | 270 | 217.7 | 114.7 | 41.6 | 45 | A |
| VAL | O | 270 | 216.5 | 114.8 | 41.2 | 45 | A |
| PRO | N | 271 | 218.1 | 113.8 | 42.5 | 43 | A |
| PRO | CD | 271 | 219.4 | 113.8 | 43.2 | 43 | A |
| PRO | CA | 271 | 217.3 | 112.7 | 43.0 | 42 | A |
| PRO | CB | 271 | 218.2 | 112.2 | 44.2 | 42 | A |
| PRO | CG | 271 | 219.1 | 113.3 | 44.5 | 42 | A |
| PRO | C | 271 | 215.9 | 113.1 | 43.5 | 41 | A |
| PRO | O | 271 | 215.1 | 112.2 | 43.5 | 42 | A |
| HIS | N | 272 | 215.6 | 114.3 | 43.8 | 40 | A |
| HIS | CA | 272 | 214.3 | 114.7 | 44.2 | 41 | A |
| HIS | CB | 272 | 214.3 | 115.6 | 45.4 | 42 | A |
| HIS | CG | 272 | 214.6 | 114.8 | 46.7 | 42 | A |
| HIS | CD2 | 272 | 213.7 | 114.2 | 47.6 | 42 | A |
| HIS | ND1 | 272 | 215.9 | 114.6 | 47.1 | 41 | A |
| HIS | CE1 | 272 | 215.8 | 113.9 | 48.2 | 42 | A |
| HIS | NE2 | 272 | 214.5 | 113.7 | 48.5 | 42 | A |
| HIS | C | 272 | 213.4 | 115.3 | 43.1 | 41 | A |
| HIS | O | 272 | 212.3 | 115.8 | 43.3 | 43 | A |
| ASN | N | 273 | 213.9 | 115.3 | 41.8 | 39 | A |
| ASN | CA | 273 | 213.2 | 115.8 | 40.7 | 36 | A |
| ASN | CB | 273 | 214.2 | 116.1 | 39.6 | 34 | A |
| ASN | CG | 273 | 213.6 | 116.4 | 38.2 | 33 | A |
| ASN | OD1 | 273 | 212.4 | 116.7 | 38.2 | 32 | A |
| ASN | ND2 | 273 | 214.4 | 116.2 | 37.2 | 33 | A |
| ASN | C | 273 | 212.3 | 114.6 | 40.2 | 36 | A |
| ASN | O | 273 | 212.8 | 113.6 | 39.7 | 36 | A |
| GLU | N | 274 | 211.0 | 114.8 | 40.4 | 35 | A |
| GLU | CA | 274 | 210.1 | 113.8 | 40.0 | 34 | A |
| GLU | CB | 274 | 208.7 | 114.2 | 40.5 | 34 | A |
| GLU | CG | 274 | 207.7 | 113.1 | 40.3 | 37 | A |
| GLU | CD | 274 | 206.4 | 113.5 | 40.8 | 38 | A |
| GLU | OE1 | 274 | 205.4 | 113.1 | 40.2 | 39 | A |
| GLU | OE2 | 274 | 206.4 | 114.4 | 41.7 | 41 | A |
| GLU | C | 274 | 210.0 | 113.4 | 38.6 | 35 | A |
| GLU | O | 274 | 209.8 | 112.2 | 38.3 | 36 | A |
| SER | N | 275 | 210.1 | 114.3 | 37.6 | 35 | A |
| SER | CA | 275 | 209.9 | 114.0 | 36.2 | 34 | A |
| SER | CB | 275 | 210.2 | 115.3 | 35.4 | 34 | A |
| SER | OG | 275 | 209.2 | 116.3 | 35.7 | 35 | A |
| SER | C | 275 | 210.8 | 112.9 | 35.7 | 34 | A |
| SER | O | 275 | 210.3 | 112.0 | 35.0 | 33 | A |
| ALA | N | 276 | 212.1 | 113.0 | 36.0 | 33 | A |
| ALA | CA | 276 | 213.1 | 111.9 | 35.6 | 33 | A |
| ALA | CB | 276 | 214.5 | 112.3 | 36.1 | 31 | A |
| ALA | C | 276 | 212.7 | 110.6 | 36.1 | 34 | A |
| ALA | O | 276 | 212.8 | 109.6 | 35.4 | 35 | A |
| TRP | N | 277 | 212.1 | 110.5 | 37.2 | 35 | A |
| TRP | CA | 277 | 211.6 | 109.3 | 37.8 | 35 | A |
| TRP | CB | 277 | 211.2 | 109.5 | 39.3 | 37 | A |
| TRP | CG | 277 | 212.4 | 109.4 | 40.2 | 39 | A |
| TRP | CD2 | 277 | 213.1 | 108.2 | 40.5 | 40 | A |
| TRP | CE2 | 277 | 214.2 | 108.6 | 41.3 | 40 | A |
| TRP | CE3 | 277 | 213.0 | 106.9 | 40.2 | 40 | A |
| TRP | CD1 | 277 | 213.0 | 110.4 | 40.8 | 40 | A |
| TRP | NE1 | 277 | 214.1 | 109.9 | 41.5 | 41 | A |
| TRP | CZ2 | 277 | 215.1 | 107.7 | 41.8 | 40 | A |
| TRP | CZ3 | 277 | 213.9 | 105.9 | 40.7 | 39 | A |
| TRP | CH2 | 277 | 214.9 | 106.3 | 41.5 | 39 | A |
| TRP | C | 277 | 210.4 | 108.7 | 37.1 | 35 | A |
| TRP | O | 277 | 210.3 | 107.5 | 36.8 | 34 | A |
| ASN | N | 278 | 209.4 | 109.6 | 36.8 | 35 | A |
| ASN | CA | 278 | 208.2 | 109.2 | 36.1 | 35 | A |
| ASN | CB | 278 | 207.1 | 110.4 | 36.1 | 37 | A |
| ASN | CG | 278 | 206.8 | 110.8 | 37.6 | 37 | A |
| ASN | OD1 | 278 | 207.2 | 110.1 | 38.5 | 38 | A |
| ASN | ND2 | 278 | 206.0 | 111.8 | 37.7 | 35 | A |
| ASN | C | 278 | 208.5 | 108.9 | 34.6 | 34 | A |
| ASN | O | 278 | 207.8 | 108.2 | 34.0 | 33 | A |
| TYR | N | 279 | 209.6 | 109.4 | 34.1 | 34 | A |
| TYR | CA | 279 | 210.1 | 109.1 | 32.8 | 35 | A |
| TYR | CB | 279 | 211.1 | 110.2 | 32.3 | 33 | A |
| TYR | CG | 279 | 211.5 | 109.9 | 30.9 | 31 | A |
| TYR | CD1 | 279 | 210.8 | 110.2 | 29.8 | 30 | A |
| TYR | CE1 | 279 | 211.2 | 109.9 | 28.5 | 30 | A |
| TYR | CD2 | 279 | 212.8 | 109.3 | 30.6 | 31 | A |

TABLE 2-continued

| | | | | | | | |
|---|---|---|---|---|---|---|---|
| TYR | CE2 | 279 | 213.2 | 109.0 | 29.3 | 30 | A |
| TYR | CZ | 279 | 212.4 | 109.3 | 28.3 | 30 | A |
| TYR | OH | 279 | 212.9 | 109.1 | 27.0 | 29 | A |
| TYR | C | 279 | 210.7 | 107.7 | 32.7 | 37 | A |
| TYR | O | 279 | 210.3 | 106.9 | 32.0 | 38 | A |
| LEU | N | 280 | 211.7 | 107.5 | 33.6 | 38 | A |
| LEU | CA | 280 | 212.4 | 106.2 | 33.7 | 38 | A |
| LEU | CB | 280 | 213.4 | 106.2 | 34.9 | 38 | A |
| LEU | CG | 280 | 213.9 | 104.8 | 35.2 | 36 | A |
| LEU | CD1 | 280 | 215.0 | 104.5 | 34.2 | 36 | A |
| LEU | CD2 | 280 | 214.5 | 104.9 | 36.6 | 37 | A |
| LEU | C | 280 | 211.4 | 105.0 | 33.9 | 39 | A |
| LEU | O | 280 | 211.5 | 104.0 | 33.4 | 38 | A |
| LYS | N | 281 | 210.4 | 105.3 | 34.8 | 40 | A |
| LYS | CA | 281 | 209.4 | 104.4 | 35.1 | 41 | A |
| LYS | CB | 281 | 208.5 | 104.9 | 36.2 | 41 | A |
| LYS | CG | 281 | 207.2 | 104.1 | 36.4 | 42 | A |
| LYS | CD | 281 | 206.7 | 104.2 | 37.8 | 45 | A |
| LYS | CE | 281 | 205.3 | 104.7 | 38.0 | 47 | A |
| LYS | NZ | 281 | 205.3 | 106.2 | 37.8 | 49 | A |
| LYS | C | 281 | 208.5 | 104.2 | 33.9 | 42 | A |
| LYS | O | 281 | 208.2 | 103.0 | 33.5 | 41 | A |
| GLY | N | 282 | 208.2 | 105.3 | 33.2 | 42 | A |
| GLY | CA | 282 | 207.4 | 105.2 | 32.0 | 42 | A |
| GLY | C | 282 | 208.0 | 104.5 | 30.9 | 43 | A |
| GLY | O | 282 | 207.2 | 103.8 | 30.2 | 45 | A |
| ILE | N | 283 | 209.3 | 104.6 | 30.6 | 44 | A |
| ILE | CA | 283 | 209.9 | 103.9 | 29.5 | 45 | A |
| ILE | CB | 283 | 211.2 | 104.7 | 29.0 | 44 | A |
| ILE | CG2 | 283 | 210.9 | 106.1 | 28.7 | 45 | A |
| ILE | CG1 | 283 | 212.2 | 104.6 | 30.1 | 43 | A |
| ILE | CD1 | 283 | 213.6 | 105.1 | 29.7 | 42 | A |
| ILE | C | 283 | 210.1 | 102.5 | 29.7 | 48 | A |
| ILE | O | 283 | 210.3 | 101.7 | 28.7 | 49 | A |
| LEU | N | 284 | 210.2 | 102.0 | 31.0 | 50 | A |
| LEU | CA | 284 | 210.5 | 100.6 | 31.3 | 52 | A |
| LEU | CB | 284 | 211.5 | 100.5 | 32.5 | 50 | A |
| LEU | CG | 284 | 212.9 | 101.0 | 32.4 | 50 | A |
| LEU | CD1 | 284 | 213.6 | 100.7 | 33.7 | 50 | A |
| LEU | CD2 | 284 | 213.6 | 100.3 | 31.2 | 50 | A |
| LEU | C | 284 | 209.2 | 99.8 | 31.7 | 54 | A |
| LEU | O | 284 | 209.1 | 98.7 | 31.2 | 53 | A |
| GLN | N | 285 | 208.4 | 100.5 | 32.5 | 58 | A |
| GLN | CA | 285 | 207.1 | 99.9 | 32.9 | 62 | A |
| GLN | CB | 285 | 206.3 | 100.8 | 33.8 | 64 | A |
| GLN | CG | 285 | 205.4 | 101.8 | 33.1 | 67 | A |
| GLN | CD | 285 | 204.5 | 102.7 | 34.0 | 68 | A |
| GLN | OE1 | 285 | 203.8 | 103.6 | 33.5 | 70 | A |
| GLN | NE2 | 285 | 204.6 | 102.5 | 35.3 | 69 | A |
| GLN | C | 285 | 206.2 | 99.3 | 31.8 | 64 | A |
| GLN | O | 285 | 205.2 | 98.7 | 32.0 | 65 | A |
| ASP | N | 286 | 206.6 | 99.6 | 30.6 | 66 | A |
| ASP | CA | 286 | 205.9 | 99.1 | 29.4 | 68 | A |
| ASP | CB | 286 | 205.6 | 100.2 | 28.4 | 70 | A |
| ASP | CG | 286 | 204.3 | 100.0 | 27.7 | 72 | A |
| ASP | OD1 | 286 | 203.3 | 100.0 | 28.3 | 73 | A |
| ASP | OD2 | 286 | 204.4 | 99.7 | 26.4 | 73 | A |
| ASP | C | 286 | 206.7 | 98.0 | 28.8 | 68 | A |
| ASP | O | 286 | 207.1 | 98.1 | 27.6 | 69 | A |
| ARG | N | 287 | 207.0 | 97.0 | 29.7 | 67 | A |
| ARG | CA | 287 | 207.8 | 95.8 | 29.3 | 66 | A |
| ARG | CB | 287 | 209.1 | 96.1 | 28.5 | 68 | A |
| ARG | CG | 287 | 209.6 | 95.0 | 27.7 | 70 | A |
| ARG | CD | 287 | 210.6 | 94.1 | 28.5 | 72 | A |
| ARG | NE | 287 | 211.1 | 93.0 | 27.7 | 74 | A |
| ARG | CZ | 287 | 212.4 | 92.6 | 27.7 | 75 | A |
| ARG | NH1 | 287 | 213.2 | 93.2 | 28.5 | 76 | A |
| ARG | NH2 | 287 | 212.7 | 91.5 | 27.0 | 74 | A |
| ARG | C | 287 | 208.1 | 95.0 | 30.5 | 63 | A |
| ARG | O | 287 | 208.4 | 93.8 | 30.4 | 63 | A |
| GLY | N | 288 | 207.8 | 95.6 | 31.7 | 61 | A |
| GLY | CA | 288 | 208.0 | 94.9 | 32.9 | 59 | A |
| GLY | C | 288 | 209.3 | 95.3 | 33.6 | 58 | A |
| GLY | O | 288 | 210.4 | 95.1 | 33.0 | 59 | A |
| LEU | N | 289 | 209.2 | 96.0 | 34.7 | 56 | A |
| LEU | CA | 289 | 210.4 | 96.4 | 35.4 | 55 | A |
| LEU | CB | 289 | 210.0 | 97.2 | 36.7 | 52 | A |
| LEU | CG | 289 | 210.0 | 98.8 | 36.6 | 50 | A |
| LEU | CD1 | 289 | 210.0 | 99.3 | 35.2 | 50 | A |

TABLE 2-continued

| | | | | | | | |
|---|---|---|---|---|---|---|---|
| LEU | CD2 | 289 | 208.7 | 99.3 | 37.3 | 50 | A |
| LEU | C | 289 | 211.2 | 95.2 | 35.8 | 55 | A |
| LEU | O | 289 | 212.4 | 95.2 | 35.9 | 55 | A |
| SER | N | 290 | 210.5 | 94.1 | 36.1 | 55 | A |
| SER | CA | 290 | 211.1 | 92.9 | 36.5 | 56 | A |
| SER | CB | 290 | 210.1 | 91.9 | 37.2 | 56 | A |
| SER | OG | 290 | 209.2 | 91.5 | 36.3 | 58 | A |
| SER | C | 290 | 211.9 | 92.1 | 35.4 | 57 | A |
| SER | O | 290 | 212.6 | 91.2 | 35.7 | 57 | A |
| ARG | N | 291 | 211.8 | 92.6 | 34.2 | 57 | A |
| ARG | CA | 291 | 212.5 | 92.0 | 33.1 | 57 | A |
| ARG | CB | 291 | 211.8 | 92.1 | 31.7 | 59 | A |
| ARG | CG | 291 | 210.5 | 91.4 | 31.7 | 63 | A |
| ARG | CD | 291 | 209.8 | 91.4 | 30.3 | 66 | A |
| ARG | NE | 291 | 210.4 | 90.3 | 29.4 | 69 | A |
| ARG | CZ | 291 | 209.9 | 89.9 | 28.2 | 71 | A |
| ARG | NH1 | 291 | 210.5 | 89.0 | 27.5 | 72 | A |
| ARG | NH2 | 291 | 208.8 | 90.5 | 27.8 | 73 | A |
| ARG | C | 291 | 213.9 | 92.6 | 33.0 | 55 | A |
| ARG | O | 291 | 214.7 | 92.3 | 32.1 | 55 | A |
| TYR | N | 292 | 214.2 | 93.4 | 34.0 | 53 | A |
| TYR | CA | 292 | 215.4 | 94.2 | 34.2 | 51 | A |
| TYR | CB | 292 | 215.2 | 95.7 | 33.9 | 48 | A |
| TYR | CG | 292 | 214.6 | 95.9 | 32.6 | 45 | A |
| TYR | CD1 | 292 | 213.3 | 96.3 | 32.4 | 44 | A |
| TYR | CE1 | 292 | 212.7 | 96.5 | 31.2 | 44 | A |
| TYR | CD2 | 292 | 215.3 | 95.7 | 31.5 | 44 | A |
| TYR | CE2 | 292 | 214.8 | 95.8 | 30.2 | 45 | A |
| TYR | CZ | 292 | 213.5 | 96.2 | 30.0 | 45 | A |
| TYR | OH | 292 | 213.0 | 96.4 | 28.8 | 45 | A |
| TYR | C | 292 | 216.0 | 93.9 | 35.6 | 53 | A |
| TYR | O | 292 | 215.7 | 94.7 | 36.5 | 52 | A |
| PRO | N | 293 | 216.7 | 92.8 | 35.7 | 55 | A |
| PRO | CD | 293 | 217.2 | 92.0 | 34.6 | 55 | A |
| PRO | CA | 293 | 217.4 | 92.3 | 37.0 | 55 | A |
| PRO | CB | 293 | 218.1 | 91.1 | 36.5 | 55 | A |
| PRO | CG | 293 | 218.5 | 91.4 | 35.1 | 55 | A |
| PRO | C | 293 | 218.3 | 93.4 | 37.6 | 56 | A |
| PRO | O | 293 | 218.1 | 93.6 | 38.8 | 56 | A |
| ASN | N | 294 | 219.2 | 93.9 | 36.8 | 58 | A |
| ASN | CA | 294 | 220.1 | 94.9 | 37.3 | 60 | A |
| ASN | CB | 294 | 221.0 | 95.4 | 36.2 | 61 | A |
| ASN | CG | 294 | 221.8 | 94.3 | 35.5 | 61 | A |
| ASN | OD1 | 294 | 221.3 | 93.7 | 34.5 | 62 | A |
| ASN | ND2 | 294 | 223.0 | 94.0 | 35.9 | 61 | A |
| ASN | C | 294 | 219.4 | 96.1 | 37.9 | 61 | A |
| ASN | O | 294 | 219.9 | 96.7 | 38.9 | 61 | A |
| LEU | N | 295 | 218.2 | 96.4 | 37.4 | 63 | A |
| LEU | CA | 295 | 217.4 | 97.6 | 37.9 | 63 | A |
| LEU | CB | 295 | 216.0 | 97.5 | 37.3 | 63 | A |
| LEU | CG | 295 | 215.3 | 98.9 | 37.3 | 62 | A |
| LEU | CD1 | 295 | 216.0 | 99.8 | 36.4 | 62 | A |
| LEU | CD2 | 295 | 213.9 | 98.6 | 36.8 | 63 | A |
| LEU | C | 295 | 217.4 | 97.6 | 39.4 | 63 | A |
| LEU | O | 295 | 218.0 | 98.5 | 40.0 | 63 | A |
| LEU | N | 296 | 216.7 | 96.7 | 40.1 | 63 | A |
| LEU | CA | 296 | 216.5 | 96.7 | 41.5 | 64 | A |
| LEU | CB | 296 | 216.0 | 95.3 | 42.0 | 62 | A |
| LEU | CG | 296 | 215.8 | 95.2 | 43.5 | 61 | A |
| LEU | CD1 | 296 | 214.8 | 96.3 | 44.0 | 60 | A |
| LEU | CD2 | 296 | 215.3 | 93.8 | 43.9 | 61 | A |
| LEU | C | 296 | 217.9 | 97.0 | 42.3 | 65 | A |
| LEU | O | 296 | 217.9 | 97.6 | 43.3 | 65 | A |
| ASN | N | 297 | 219.0 | 96.5 | 41.7 | 67 | A |
| ASN | CA | 297 | 220.3 | 96.7 | 42.3 | 70 | A |
| ASN | CB | 297 | 221.3 | 95.8 | 41.7 | 72 | A |
| ASN | CG | 297 | 221.0 | 94.4 | 42.0 | 74 | A |
| ASN | OD1 | 297 | 220.6 | 94.1 | 43.2 | 76 | A |
| ASN | ND2 | 297 | 221.3 | 93.4 | 41.1 | 75 | A |
| ASN | C | 297 | 220.7 | 98.2 | 42.2 | 70 | A |
| ASN | O | 297 | 220.9 | 98.8 | 43.2 | 70 | A |
| GLN | N | 298 | 221.0 | 98.7 | 41.0 | 69 | A |
| GLN | CA | 298 | 221.4 | 100.0 | 40.8 | 69 | A |
| GLN | CB | 298 | 221.3 | 100.4 | 39.3 | 69 | A |
| GLN | CG | 298 | 221.3 | 99.3 | 38.3 | 70 | A |
| GLN | CD | 298 | 222.7 | 99.0 | 37.7 | 70 | A |
| GLN | OE1 | 298 | 223.3 | 98.0 | 38.0 | 70 | A |
| GLN | NE2 | 298 | 223.1 | 99.8 | 36.7 | 70 | A |
| GLN | C | 298 | 220.6 | 101.0 | 41.6 | 69 | A |

TABLE 2-continued

| | | | | | | | |
|---|---|---|---|---|---|---|---|
| GLN | O | 298 | 221.1 | 101.9 | 42.3 | 69 | A |
| LEU | N | 299 | 219.3 | 100.8 | 41.7 | 70 | A |
| LEU | CA | 299 | 218.4 | 101.6 | 42.4 | 72 | A |
| LEU | CB | 299 | 216.9 | 101.4 | 42.1 | 70 | A |
| LEU | CG | 299 | 216.4 | 101.7 | 40.7 | 69 | A |
| LEU | CD1 | 299 | 214.9 | 101.8 | 40.8 | 68 | A |
| LEU | CD2 | 299 | 216.9 | 103.0 | 40.2 | 69 | A |
| LEU | C | 299 | 218.6 | 101.5 | 43.9 | 73 | A |
| LEU | O | 299 | 218.5 | 102.4 | 44.7 | 74 | A |
| LEU | N | 300 | 218.9 | 100.2 | 44.3 | 75 | A |
| LEU | CA | 300 | 219.1 | 99.9 | 45.7 | 77 | A |
| LEU | CB | 300 | 219.2 | 98.4 | 45.9 | 76 | A |
| LEU | CG | 300 | 218.3 | 97.8 | 47.0 | 77 | A |
| LEU | CD1 | 300 | 217.0 | 98.6 | 47.3 | 77 | A |
| LEU | CD2 | 300 | 217.9 | 96.4 | 46.7 | 77 | A |
| LEU | C | 300 | 220.4 | 100.6 | 46.2 | 78 | A |
| LEU | O | 300 | 220.5 | 100.9 | 47.4 | 78 | A |
| ASP | N | 301 | 221.3 | 100.8 | 45.2 | 80 | A |
| ASP | CA | 301 | 222.6 | 101.4 | 45.5 | 83 | A |
| ASP | CB | 301 | 223.5 | 101.3 | 44.3 | 84 | A |
| ASP | CG | 301 | 223.9 | 99.8 | 44.0 | 86 | A |
| ASP | OD1 | 301 | 223.7 | 98.9 | 44.9 | 87 | A |
| ASP | OD2 | 301 | 224.5 | 99.5 | 42.9 | 86 | A |
| ASP | C | 301 | 222.4 | 102.9 | 45.9 | 84 | A |
| ASP | O | 301 | 223.1 | 103.4 | 46.7 | 85 | A |
| LEU | N | 302 | 221.4 | 103.5 | 45.3 | 84 | A |
| LEU | CA | 302 | 221.1 | 104.9 | 45.5 | 84 | A |
| LEU | CB | 302 | 220.2 | 105.4 | 44.4 | 85 | A |
| LEU | CG | 302 | 220.8 | 105.4 | 43.0 | 84 | A |
| LEU | CD1 | 302 | 219.9 | 106.2 | 42.1 | 85 | A |
| LEU | CD2 | 302 | 222.2 | 105.9 | 43.0 | 85 | A |
| LEU | C | 302 | 220.4 | 105.2 | 46.8 | 84 | A |
| LEU | O | 302 | 220.1 | 106.3 | 47.2 | 84 | A |
| GLN | N | 303 | 220.0 | 104.1 | 47.6 | 84 | A |
| GLN | CA | 303 | 219.3 | 104.2 | 48.9 | 85 | A |
| GLN | CB | 303 | 219.2 | 102.8 | 49.5 | 85 | A |
| GLN | CG | 303 | 217.9 | 102.1 | 49.1 | 86 | A |
| GLN | CD | 303 | 216.7 | 102.7 | 49.7 | 86 | A |
| GLN | OE1 | 303 | 216.6 | 103.9 | 49.9 | 85 | A |
| GLN | NE2 | 303 | 215.7 | 101.8 | 49.9 | 86 | A |
| GLN | C | 303 | 219.9 | 105.2 | 49.8 | 85 | A |
| GLN | O | 303 | 219.1 | 105.9 | 50.5 | 85 | A |
| PRO | N | 304 | 221.2 | 105.3 | 50.0 | 84 | A |
| PRO | CD | 304 | 222.2 | 104.2 | 49.7 | 84 | A |
| PRO | CA | 304 | 221.8 | 106.3 | 50.9 | 83 | A |
| PRO | CB | 304 | 222.8 | 105.4 | 51.7 | 83 | A |
| PRO | CG | 304 | 223.4 | 104.6 | 50.6 | 84 | A |
| PRO | C | 304 | 222.4 | 107.5 | 50.2 | 83 | A |
| PRO | O | 304 | 222.5 | 108.5 | 50.8 | 82 | A |
| SER | N | 305 | 222.8 | 107.3 | 49.0 | 83 | A |
| SER | CA | 305 | 223.5 | 108.4 | 48.2 | 82 | A |
| SER | CB | 305 | 224.5 | 107.8 | 47.3 | 83 | A |
| SER | OG | 305 | 225.7 | 107.3 | 48.0 | 83 | A |
| SER | C | 305 | 222.6 | 109.3 | 47.4 | 81 | A |
| SER | O | 305 | 222.9 | 110.4 | 47.0 | 81 | A |
| HIS | N | 306 | 221.4 | 108.8 | 47.0 | 79 | A |
| HIS | CA | 306 | 220.4 | 109.6 | 46.2 | 77 | A |
| HIS | CB | 306 | 220.7 | 109.4 | 44.7 | 78 | A |
| HIS | CG | 306 | 222.1 | 109.6 | 44.3 | 79 | A |
| HIS | CD2 | 306 | 223.2 | 108.8 | 44.2 | 79 | A |
| HIS | ND1 | 306 | 222.6 | 110.8 | 43.9 | 80 | A |
| HIS | CE1 | 306 | 223.9 | 110.7 | 43.6 | 80 | A |
| HIS | NE2 | 306 | 224.2 | 109.5 | 43.8 | 80 | A |
| HIS | C | 306 | 219.0 | 109.2 | 46.5 | 75 | A |
| HIS | O | 306 | 218.2 | 109.0 | 45.6 | 75 | A |
| SER | N | 307 | 218.6 | 109.2 | 47.8 | 72 | A |
| SER | CA | 307 | 217.2 | 108.8 | 48.2 | 69 | A |
| SER | CB | 307 | 217.3 | 107.9 | 49.4 | 70 | A |
| SER | OG | 307 | 216.1 | 107.1 | 49.6 | 70 | A |
| SER | C | 307 | 216.2 | 109.8 | 48.4 | 67 | A |
| SER | O | 307 | 216.4 | 110.9 | 48.9 | 66 | A |
| SER | N | 308 | 215.0 | 109.4 | 48.1 | 64 | A |
| SER | CA | 308 | 213.7 | 110.2 | 48.2 | 61 | A |
| SER | CB | 308 | 213.6 | 111.1 | 46.9 | 61 | A |
| SER | OG | 308 | 213.8 | 110.3 | 45.7 | 61 | A |
| SER | C | 308 | 212.6 | 109.2 | 48.2 | 59 | A |
| SER | O | 308 | 212.8 | 108.0 | 47.9 | 58 | A |
| PRO | N | 309 | 211.4 | 109.6 | 48.4 | 56 | A |
| PRO | CD | 309 | 210.9 | 111.0 | 48.9 | 56 | A |

TABLE 2-continued

| | | | | | | | |
|---|---|---|---|---|---|---|---|
| PRO | CA | 309 | 210.3 | 108.7 | 48.4 | 56 | A |
| PRO | CB | 309 | 209.1 | 109.5 | 49.0 | 57 | A |
| PRO | CG | 309 | 209.5 | 110.9 | 48.6 | 57 | A |
| PRO | C | 309 | 210.0 | 108.1 | 47.0 | 56 | A |
| PRO | O | 309 | 209.1 | 107.3 | 46.8 | 55 | A |
| TYR | N | 310 | 210.8 | 108.6 | 46.0 | 56 | A |
| TYR | CA | 310 | 210.7 | 108.2 | 44.6 | 55 | A |
| TYR | CB | 310 | 211.2 | 109.3 | 43.7 | 54 | A |
| TYR | CG | 310 | 210.7 | 110.6 | 43.9 | 53 | A |
| TYR | CD1 | 310 | 211.5 | 111.7 | 44.2 | 53 | A |
| TYR | CE1 | 310 | 210.9 | 113.0 | 44.5 | 53 | A |
| TYR | CD2 | 310 | 209.3 | 110.8 | 43.8 | 53 | A |
| TYR | CE2 | 310 | 208.7 | 112.1 | 44.1 | 53 | A |
| TYR | CZ | 310 | 209.6 | 113.1 | 44.4 | 53 | A |
| TYR | OH | 310 | 209.0 | 114.3 | 44.7 | 55 | A |
| TYR | C | 310 | 211.4 | 106.9 | 44.5 | 55 | A |
| TYR | O | 310 | 211.0 | 106.0 | 43.7 | 57 | A |
| LEU | N | 311 | 212.6 | 106.8 | 45.1 | 54 | A |
| LEU | CA | 311 | 213.4 | 105.6 | 45.1 | 53 | A |
| LEU | CB | 311 | 214.7 | 105.7 | 45.9 | 53 | A |
| LEU | CG | 311 | 215.8 | 104.7 | 45.8 | 54 | A |
| LEU | CD1 | 311 | 216.2 | 104.5 | 44.3 | 55 | A |
| LEU | CD2 | 311 | 217.0 | 105.0 | 46.6 | 54 | A |
| LEU | C | 311 | 212.6 | 104.5 | 45.7 | 51 | A |
| LEU | O | 311 | 212.4 | 103.4 | 45.1 | 51 | A |
| ILE | N | 312 | 212.0 | 104.8 | 46.9 | 51 | A |
| ILE | CA | 312 | 211.2 | 103.8 | 47.6 | 50 | A |
| ILE | CB | 312 | 210.7 | 104.4 | 49.0 | 50 | A |
| ILE | CG2 | 312 | 209.9 | 103.5 | 49.8 | 50 | A |
| ILE | CG1 | 312 | 212.0 | 104.9 | 49.8 | 51 | A |
| ILE | CD1 | 312 | 211.6 | 105.6 | 51.1 | 52 | A |
| ILE | C | 312 | 209.9 | 103.5 | 46.8 | 49 | A |
| ILE | O | 312 | 209.4 | 102.3 | 46.9 | 48 | A |
| ALA | N | 313 | 209.3 | 104.5 | 46.2 | 46 | A |
| ALA | CA | 313 | 208.1 | 104.2 | 45.4 | 44 | A |
| ALA | CB | 313 | 207.4 | 105.5 | 45.0 | 45 | A |
| ALA | C | 313 | 208.4 | 103.4 | 44.1 | 43 | A |
| ALA | O | 313 | 207.6 | 102.5 | 43.7 | 42 | A |
| PHE | N | 314 | 209.6 | 103.6 | 43.6 | 42 | A |
| PHE | CA | 314 | 210.0 | 102.8 | 42.4 | 43 | A |
| PHE | CB | 314 | 211.3 | 103.4 | 41.7 | 43 | A |
| PHE | CG | 314 | 211.4 | 103.0 | 40.3 | 44 | A |
| PHE | CD1 | 314 | 211.3 | 103.9 | 39.3 | 45 | A |
| PHE | CD2 | 314 | 211.8 | 101.7 | 39.9 | 44 | A |
| PHE | CE1 | 314 | 211.4 | 103.6 | 37.9 | 44 | A |
| PHE | CE2 | 314 | 212.0 | 101.4 | 38.6 | 44 | A |
| PHE | CZ | 314 | 211.8 | 102.3 | 37.6 | 44 | A |
| PHE | C | 314 | 210.2 | 101.4 | 42.8 | 43 | A |
| PHE | O | 314 | 209.8 | 100.5 | 42.1 | 44 | A |
| LEU | N | 315 | 210.9 | 101.2 | 43.9 | 44 | A |
| LEU | CA | 315 | 211.2 | 99.9 | 44.4 | 42 | A |
| LEU | CB | 315 | 212.1 | 99.9 | 45.7 | 41 | A |
| LEU | CG | 315 | 213.5 | 100.6 | 45.6 | 40 | A |
| LEU | CD1 | 315 | 214.1 | 100.7 | 47.0 | 39 | A |
| LEU | CD2 | 315 | 214.4 | 99.8 | 44.7 | 40 | A |
| LEU | C | 315 | 209.9 | 99.2 | 44.6 | 42 | A |
| LEU | O | 315 | 209.7 | 98.0 | 44.3 | 42 | A |
| VAL | N | 316 | 208.9 | 99.9 | 45.2 | 42 | A |
| VAL | CA | 316 | 207.6 | 99.3 | 45.5 | 43 | A |
| VAL | CB | 316 | 206.7 | 100.2 | 46.2 | 43 | A |
| VAL | CG1 | 316 | 205.4 | 99.5 | 46.5 | 42 | A |
| VAL | CG2 | 316 | 207.3 | 100.6 | 47.5 | 44 | A |
| VAL | C | 316 | 207.0 | 98.9 | 44.2 | 45 | A |
| VAL | O | 316 | 206.2 | 98.0 | 44.1 | 45 | A |
| ASP | N | 317 | 207.4 | 99.5 | 43.1 | 47 | A |
| ASP | CA | 317 | 206.8 | 99.2 | 41.7 | 49 | A |
| ASP | CB | 317 | 206.9 | 100.4 | 40.8 | 51 | A |
| ASP | CG | 317 | 205.9 | 101.5 | 41.2 | 53 | A |
| ASP | OD1 | 317 | 204.8 | 101.2 | 41.6 | 53 | A |
| ASP | OD2 | 317 | 206.2 | 102.7 | 41.1 | 54 | A |
| ASP | C | 317 | 207.6 | 98.0 | 41.1 | 49 | A |
| ASP | O | 317 | 207.0 | 97.3 | 40.3 | 49 | A |
| ILE | N | 318 | 208.9 | 97.9 | 41.4 | 49 | A |
| ILE | CA | 318 | 209.6 | 96.8 | 40.8 | 49 | A |
| ILE | CB | 318 | 211.1 | 96.8 | 41.2 | 49 | A |
| ILE | CG2 | 318 | 211.7 | 95.5 | 40.8 | 49 | A |
| ILE | CG1 | 318 | 211.7 | 98.0 | 40.4 | 49 | A |
| ILE | CD1 | 318 | 213.2 | 98.0 | 40.6 | 49 | A |
| ILE | C | 318 | 209.0 | 95.6 | 41.5 | 51 | A |

TABLE 2-continued

| | | | | | | | |
|---|---|---|---|---|---|---|---|
| ILE | O | 318 | 208.5 | 94.7 | 40.9 | 52 | A |
| TYR | N | 319 | 209.1 | 95.6 | 42.9 | 52 | A |
| TYR | CA | 319 | 208.6 | 94.5 | 43.7 | 54 | A |
| TYR | CB | 319 | 208.5 | 94.9 | 45.2 | 53 | A |
| TYR | CG | 319 | 209.9 | 95.0 | 45.8 | 52 | A |
| TYR | CD1 | 319 | 210.1 | 95.9 | 46.9 | 52 | A |
| TYR | CE1 | 319 | 211.4 | 96.0 | 47.5 | 51 | A |
| TYR | CD2 | 319 | 211.0 | 94.3 | 45.3 | 51 | A |
| TYR | CE2 | 319 | 212.3 | 94.5 | 45.9 | 51 | A |
| TYR | CZ | 319 | 212.4 | 95.4 | 46.9 | 51 | A |
| TYR | OH | 319 | 213.7 | 95.5 | 47.4 | 51 | A |
| TYR | C | 319 | 207.2 | 94.0 | 43.2 | 56 | A |
| TYR | O | 319 | 206.9 | 92.8 | 43.1 | 57 | A |
| GLU | N | 320 | 206.3 | 94.9 | 42.9 | 59 | A |
| GLU | CA | 320 | 204.9 | 94.6 | 42.4 | 62 | A |
| GLU | CB | 320 | 204.1 | 95.9 | 42.0 | 65 | A |
| GLU | CG | 320 | 203.7 | 96.7 | 43.2 | 68 | A |
| GLU | CD | 320 | 203.5 | 98.2 | 42.9 | 70 | A |
| GLU | OE1 | 320 | 203.3 | 99.0 | 43.8 | 72 | A |
| GLU | OE2 | 320 | 203.4 | 98.5 | 41.7 | 71 | A |
| GLU | C | 320 | 205.0 | 93.7 | 41.2 | 63 | A |
| GLU | O | 320 | 204.2 | 92.8 | 41.0 | 63 | A |
| ASP | N | 321 | 205.9 | 94.0 | 40.3 | 63 | A |
| ASP | CA | 321 | 206.1 | 93.3 | 39.0 | 64 | A |
| ASP | CB | 321 | 206.7 | 94.2 | 38.0 | 63 | A |
| ASP | CG | 321 | 206.6 | 93.6 | 36.6 | 63 | A |
| ASP | OD1 | 321 | 205.5 | 93.1 | 36.2 | 64 | A |
| ASP | OD2 | 321 | 207.6 | 93.5 | 35.8 | 63 | A |
| ASP | C | 321 | 206.8 | 92.0 | 39.2 | 65 | A |
| ASP | O | 321 | 206.7 | 91.1 | 38.3 | 65 | A |
| MET | N | 322 | 207.7 | 91.9 | 40.2 | 66 | A |
| MET | CA | 322 | 208.4 | 90.6 | 40.4 | 69 | A |
| MET | CB | 322 | 209.6 | 90.8 | 41.3 | 68 | A |
| MET | CG | 322 | 210.6 | 91.8 | 40.8 | 68 | A |
| MET | SD | 322 | 212.1 | 91.6 | 41.8 | 69 | A |
| MET | CE | 322 | 211.5 | 91.8 | 43.4 | 68 | A |
| MET | C | 322 | 207.4 | 89.7 | 41.0 | 71 | A |
| MET | O | 322 | 207.7 | 88.5 | 41.1 | 73 | A |
| LEU | N | 323 | 206.3 | 90.2 | 41.5 | 74 | A |
| LEU | CA | 323 | 205.3 | 89.4 | 42.1 | 76 | A |
| LEU | CB | 323 | 204.6 | 90.2 | 43.3 | 75 | A |
| LEU | CG | 323 | 205.1 | 90.0 | 44.7 | 73 | A |
| LEU | CD1 | 323 | 206.6 | 89.6 | 44.7 | 72 | A |
| LEU | CD2 | 323 | 204.8 | 91.2 | 45.5 | 73 | A |
| LEU | C | 323 | 204.2 | 89.0 | 41.1 | 78 | A |
| LEU | O | 323 | 203.8 | 87.9 | 41.0 | 79 | A |
| GLU | N | 324 | 203.8 | 89.9 | 40.2 | 82 | A |
| GLU | CA | 324 | 202.9 | 89.7 | 39.1 | 85 | A |
| GLU | CB | 324 | 202.7 | 90.8 | 38.2 | 86 | A |
| GLU | CG | 324 | 202.1 | 92.1 | 38.7 | 87 | A |
| GLU | CD | 324 | 202.1 | 93.3 | 37.6 | 88 | A |
| GLU | OE1 | 324 | 201.6 | 93.1 | 36.6 | 88 | A |
| GLU | OE2 | 324 | 202.7 | 94.3 | 37.9 | 88 | A |
| GLU | C | 324 | 203.4 | 88.5 | 38.3 | 86 | A |
| GLU | O | 324 | 202.7 | 87.6 | 37.9 | 87 | A |
| ASN | N | 325 | 204.7 | 88.5 | 38.1 | 88 | A |
| ASN | CA | 325 | 205.4 | 87.5 | 37.4 | 91 | A |
| ASN | CB | 325 | 206.6 | 88.1 | 36.6 | 90 | A |
| ASN | CG | 325 | 206.1 | 89.0 | 35.4 | 90 | A |
| ASN | OD1 | 325 | 207.0 | 89.6 | 34.7 | 90 | A |
| ASN | ND2 | 325 | 204.8 | 89.1 | 35.3 | 89 | A |
| ASN | C | 325 | 205.9 | 86.3 | 38.2 | 93 | A |
| ASN | O | 325 | 206.5 | 85.3 | 37.6 | 94 | A |
| GLN | N | 326 | 205.7 | 86.3 | 39.5 | 95 | A |
| GLN | CA | 326 | 206.1 | 85.2 | 40.4 | 98 | A |
| GLN | CB | 326 | 205.4 | 83.9 | 40.0 | 98 | A |
| GLN | CG | 326 | 204.1 | 83.7 | 40.7 | 98 | A |
| GLN | CD | 326 | 203.2 | 84.9 | 40.7 | 98 | A |
| GLN | OE1 | 326 | 202.8 | 85.5 | 39.7 | 97 | A |
| GLN | NE2 | 326 | 202.8 | 85.4 | 41.9 | 98 | A |
| GLN | C | 326 | 207.6 | 85.0 | 40.5 | 99 | A |
| GLN | O | 326 | 208.3 | 84.8 | 39.4 | 0 | |
| CYS | N | 327 | 208.2 | 85.1 | 41.7 | 0 | |
| CYS | CA | 327 | 209.6 | 85.0 | 41.8 | 0 | |
| CYS | CB | 327 | 210.3 | 86.3 | 41.7 | 0 | |
| CYS | SG | 327 | 212.1 | 86.2 | 41.7 | 0 | |
| CYS | C | 327 | 210.0 | 84.3 | 43.1 | 0 | |
| CYS | O | 327 | 209.2 | 84.5 | 44.1 | 0 | |
| ASP | N | 328 | 211.1 | 83.5 | 43.2 | 0 | |

TABLE 2-continued

| | | | | | | | |
|---|---|---|---|---|---|---|---|
| ASP | CA | 328 | 211.5 | 82.9 | 44.4 | 0 | |
| ASP | CB | 328 | 212.7 | 82.0 | 44.2 | 0 | |
| ASP | CG | 328 | 212.8 | 80.8 | 45.2 | 0 | |
| ASP | OD1 | 328 | 212.2 | 80.8 | 46.3 | 0 | |
| ASP | OD2 | 328 | 213.6 | 79.8 | 44.9 | 0 | |
| ASP | C | 328 | 211.8 | 84.0 | 45.4 | 0 | |
| ASP | O | 328 | 212.2 | 85.1 | 45.0 | 0 | |
| ASN | N | 329 | 211.6 | 83.7 | 46.7 | 0 | |
| ASN | CA | 329 | 211.8 | 84.6 | 47.8 | 0 | |
| ASN | CB | 329 | 213.1 | 85.4 | 47.6 | 0 | |
| ASN | CG | 329 | 214.3 | 84.5 | 47.4 | 0 | |
| ASN | OD1 | 329 | 214.8 | 83.9 | 48.4 | 0 | |
| ASN | ND2 | 329 | 214.7 | 84.3 | 46.2 | 0 | |
| ASN | C | 329 | 210.6 | 85.6 | 47.8 | 0 | |
| ASN | O | 329 | 210.6 | 86.5 | 48.5 | 0 | |
| LYS | N | 330 | 209.6 | 85.3 | 46.9 | 0 | |
| LYS | CA | 330 | 208.4 | 86.2 | 46.8 | 0 | |
| LYS | CB | 330 | 207.3 | 85.6 | 45.9 | 0 | |
| LYS | CG | 330 | 206.5 | 84.5 | 46.5 | 0 | |
| LYS | CD | 330 | 205.0 | 84.7 | 46.3 | 0 | |
| LYS | CE | 330 | 204.7 | 85.1 | 44.9 | 0 | |
| LYS | NZ | 330 | 205.0 | 84.1 | 43.8 | 0 | |
| LYS | C | 330 | 207.8 | 86.6 | 48.2 | 0 | |
| LYS | O | 330 | 207.3 | 87.7 | 48.3 | 0 | |
| GLU | N | 331 | 207.9 | 85.7 | 49.1 | 0 | |
| GLU | CA | 331 | 207.4 | 86.0 | 50.4 | 0 | |
| GLU | CB | 331 | 207.4 | 84.8 | 51.4 | 0 | |
| GLU | CG | 331 | 206.6 | 85.0 | 52.7 | 0 | |
| GLU | CD | 331 | 205.3 | 85.8 | 52.4 | 0 | |
| GLU | OE1 | 331 | 204.5 | 85.3 | 51.7 | 0 | |
| GLU | OE2 | 331 | 205.2 | 86.9 | 53.1 | 0 | |
| GLU | C | 331 | 208.1 | 87.2 | 51.1 | 0 | |
| GLU | O | 331 | 207.5 | 88.1 | 51.6 | 0 | |
| ASP | N | 332 | 209.5 | 87.1 | 51.0 | 99 | A |
| ASP | CA | 332 | 210.3 | 88.2 | 51.6 | 97 | A |
| ASP | CB | 332 | 211.8 | 87.8 | 51.5 | 99 | A |
| ASP | CG | 332 | 212.7 | 88.8 | 52.2 | 0 | |
| ASP | OD1 | 332 | 213.7 | 89.2 | 51.5 | 0 | |
| ASP | OD2 | 332 | 212.5 | 89.2 | 53.3 | 0 | |
| ASP | C | 332 | 210.1 | 89.4 | 50.7 | 95 | A |
| ASP | O | 332 | 209.9 | 90.5 | 51.3 | 95 | A |
| ILE | N | 333 | 210.1 | 89.3 | 49.4 | 91 | A |
| ILE | CA | 333 | 209.8 | 90.4 | 48.5 | 87 | A |
| ILE | CB | 333 | 209.7 | 89.9 | 47.0 | 87 | A |
| ILE | CG2 | 333 | 209.1 | 90.9 | 46.2 | 87 | A |
| ILE | CG1 | 333 | 211.1 | 89.6 | 46.5 | 87 | A |
| ILE | CD1 | 333 | 211.2 | 89.0 | 45.1 | 87 | A |
| ILE | C | 333 | 208.6 | 91.1 | 48.9 | 85 | A |
| ILE | O | 333 | 208.6 | 92.3 | 49.1 | 84 | A |
| LEU | N | 334 | 207.5 | 90.4 | 49.2 | 83 | A |
| LEU | CA | 334 | 206.3 | 91.0 | 49.6 | 82 | A |
| LEU | CB | 334 | 205.2 | 89.9 | 49.7 | 81 | A |
| LEU | CG | 334 | 203.8 | 90.4 | 50.2 | 81 | A |
| LEU | CD1 | 334 | 203.3 | 91.5 | 49.3 | 80 | A |
| LEU | CD2 | 334 | 202.8 | 89.2 | 50.2 | 81 | A |
| LEU | C | 334 | 206.4 | 91.7 | 51.0 | 82 | A |
| LEU | O | 334 | 205.7 | 92.7 | 51.2 | 83 | A |
| ASN | N | 335 | 207.3 | 91.1 | 51.8 | 82 | A |
| ASN | CA | 335 | 207.5 | 91.7 | 53.2 | 81 | A |
| ASN | CB | 335 | 208.2 | 90.7 | 54.1 | 81 | A |
| ASN | CG | 335 | 207.5 | 89.4 | 54.3 | 81 | A |
| ASN | OD1 | 335 | 206.2 | 89.4 | 54.4 | 81 | A |
| ASN | ND2 | 335 | 208.2 | 88.4 | 54.5 | 81 | A |
| ASN | C | 335 | 208.2 | 93.0 | 53.0 | 80 | A |
| ASN | O | 335 | 207.8 | 94.0 | 53.6 | 79 | A |
| LYS | N | 336 | 209.3 | 93.0 | 52.2 | 78 | A |
| LYS | CA | 336 | 210.1 | 94.2 | 52.0 | 77 | A |
| LYS | CB | 336 | 211.2 | 93.9 | 51.0 | 78 | A |
| LYS | CG | 336 | 212.1 | 95.1 | 50.6 | 79 | A |
| LYS | CD | 336 | 212.5 | 95.9 | 51.7 | 80 | A |
| LYS | CE | 336 | 213.3 | 97.2 | 51.2 | 81 | A |
| LYS | NZ | 336 | 213.6 | 98.1 | 52.4 | 81 | A |
| LYS | C | 336 | 209.2 | 95.3 | 51.4 | 75 | A |
| LYS | O | 336 | 209.2 | 96.5 | 51.8 | 74 | A |
| ALA | N | 337 | 208.4 | 94.9 | 50.4 | 72 | A |
| ALA | CA | 337 | 207.5 | 95.9 | 49.7 | 70 | A |
| ALA | CB | 337 | 206.9 | 95.2 | 48.5 | 69 | A |
| ALA | C | 337 | 206.4 | 96.5 | 50.6 | 68 | A |
| ALA | O | 337 | 206.0 | 97.6 | 50.4 | 69 | A |

TABLE 2-continued

| | | | | | | | |
|---|---|---|---|---|---|---|---|
| LEU | N | 338 | 205.9 | 95.7 | 51.5 | 66 | A |
| LEU | CA | 338 | 204.8 | 96.2 | 52.4 | 64 | A |
| LEU | CB | 338 | 204.1 | 95.0 | 53.0 | 64 | A |
| LEU | CG | 338 | 203.3 | 94.1 | 52.0 | 63 | A |
| LEU | CD1 | 338 | 203.0 | 92.8 | 52.7 | 63 | A |
| LEU | CD2 | 338 | 202.0 | 94.9 | 51.6 | 63 | A |
| LEU | C | 338 | 205.4 | 97.1 | 53.5 | 63 | A |
| LEU | O | 338 | 204.7 | 98.0 | 54.0 | 61 | A |
| GLU | N | 339 | 206.6 | 96.9 | 53.8 | 62 | A |
| GLU | CA | 339 | 207.4 | 97.6 | 54.8 | 62 | A |
| GLU | CB | 339 | 208.7 | 96.9 | 55.2 | 64 | A |
| GLU | CG | 339 | 209.6 | 97.7 | 56.0 | 67 | A |
| GLU | CD | 339 | 211.0 | 97.7 | 55.5 | 69 | A |
| GLU | OE1 | 339 | 211.8 | 98.5 | 55.8 | 70 | A |
| GLU | OE2 | 339 | 211.3 | 96.8 | 54.6 | 70 | A |
| GLU | C | 339 | 207.6 | 99.0 | 54.2 | 59 | A |
| GLU | O | 339 | 207.5 | 100.0 | 54.9 | 58 | A |
| LEU | N | 340 | 208.0 | 99.0 | 52.9 | 56 | A |
| LEU | CA | 340 | 208.3 | 100.2 | 52.2 | 54 | A |
| LEU | CB | 340 | 208.8 | 99.9 | 50.8 | 51 | A |
| LEU | CG | 340 | 210.2 | 99.2 | 50.7 | 50 | A |
| LEU | CD1 | 340 | 210.5 | 99.1 | 49.2 | 49 | A |
| LEU | CD2 | 340 | 211.2 | 100.1 | 51.4 | 49 | A |
| LEU | C | 340 | 206.9 | 101.0 | 52.1 | 55 | A |
| LEU | O | 340 | 206.9 | 102.2 | 52.2 | 56 | A |
| CYS | N | 341 | 205.8 | 100.2 | 51.9 | 54 | A |
| CYS | CA | 341 | 204.5 | 100.9 | 51.8 | 55 | A |
| CYS | CB | 341 | 203.4 | 99.9 | 51.4 | 55 | A |
| CYS | SG | 341 | 203.3 | 99.5 | 49.7 | 54 | A |
| CYS | C | 341 | 204.1 | 101.5 | 53.1 | 56 | A |
| CYS | O | 341 | 203.4 | 102.6 | 53.1 | 55 | A |
| GLU | N | 342 | 204.6 | 101.0 | 54.3 | 58 | A |
| GLU | CA | 342 | 204.3 | 101.6 | 55.6 | 59 | A |
| GLU | CB | 342 | 204.4 | 100.5 | 56.7 | 61 | A |
| GLU | CG | 342 | 203.0 | 99.9 | 57.0 | 65 | A |
| GLU | CD | 342 | 201.9 | 100.8 | 56.8 | 67 | A |
| GLU | OE1 | 342 | 201.6 | 101.7 | 57.7 | 68 | A |
| GLU | OE2 | 342 | 201.2 | 100.8 | 55.7 | 68 | A |
| GLU | C | 342 | 205.2 | 102.7 | 55.9 | 59 | A |
| GLU | O | 342 | 204.8 | 103.7 | 56.6 | 59 | A |
| ILE | N | 343 | 206.5 | 102.7 | 55.5 | 59 | A |
| ILE | CA | 343 | 207.4 | 103.8 | 55.6 | 58 | A |
| ILE | CB | 343 | 208.8 | 103.4 | 55.1 | 57 | A |
| ILE | CG2 | 343 | 209.7 | 104.6 | 55.2 | 57 | A |
| ILE | CG1 | 343 | 209.3 | 102.2 | 55.8 | 58 | A |
| ILE | CD1 | 343 | 210.5 | 101.5 | 55.2 | 60 | A |
| ILE | C | 343 | 206.9 | 105.0 | 54.9 | 58 | A |
| ILE | O | 343 | 206.8 | 106.1 | 55.4 | 58 | A |
| LEU | N | 344 | 206.6 | 104.8 | 53.6 | 57 | A |
| LEU | CA | 344 | 206.0 | 105.8 | 52.8 | 57 | A |
| LEU | CB | 344 | 205.8 | 105.3 | 51.3 | 56 | A |
| LEU | CG | 344 | 207.0 | 105.0 | 50.5 | 55 | A |
| LEU | CD1 | 344 | 206.7 | 104.3 | 49.2 | 55 | A |
| LEU | CD2 | 344 | 207.7 | 106.3 | 50.2 | 55 | A |
| LEU | C | 344 | 204.7 | 106.3 | 53.4 | 57 | A |
| LEU | O | 344 | 204.5 | 107.5 | 53.5 | 57 | A |
| ALA | N | 345 | 203.8 | 105.4 | 53.8 | 58 | A |
| ALA | CA | 345 | 202.5 | 105.8 | 54.4 | 59 | A |
| ALA | CB | 345 | 201.6 | 104.6 | 54.4 | 58 | A |
| ALA | C | 345 | 202.6 | 106.5 | 55.8 | 60 | A |
| ALA | O | 345 | 201.8 | 107.4 | 56.0 | 59 | A |
| LYS | N | 346 | 203.5 | 106.0 | 56.6 | 62 | A |
| LYS | CA | 346 | 203.7 | 106.5 | 58.0 | 63 | A |
| LYS | CB | 346 | 204.0 | 105.4 | 58.9 | 66 | A |
| LYS | CG | 346 | 202.9 | 104.4 | 59.2 | 68 | A |
| LYS | CD | 346 | 203.5 | 103.2 | 60.0 | 70 | A |
| LYS | CE | 346 | 202.4 | 102.1 | 60.4 | 71 | A |
| LYS | NZ | 346 | 203.0 | 100.8 | 60.8 | 71 | A |
| LYS | C | 346 | 204.7 | 107.6 | 58.1 | 63 | A |
| LYS | O | 346 | 204.6 | 108.5 | 58.9 | 64 | A |
| GLU | N | 347 | 205.9 | 107.4 | 57.4 | 63 | A |
| GLU | CA | 347 | 207.0 | 108.4 | 57.5 | 63 | A |
| GLU | CB | 347 | 208.2 | 107.6 | 58.1 | 65 | A |
| GLU | CG | 347 | 209.5 | 108.4 | 58.0 | 69 | A |
| GLU | CD | 347 | 210.7 | 107.7 | 58.7 | 72 | A |
| GLU | OE1 | 347 | 210.7 | 107.6 | 60.0 | 74 | A |
| GLU | OE2 | 347 | 211.6 | 107.2 | 58.0 | 73 | A |
| GLU | C | 347 | 207.4 | 109.1 | 56.3 | 61 | A |
| GLU | O | 347 | 207.4 | 110.3 | 56.2 | 60 | A |

TABLE 2-continued

| | | | | | | | |
|---|---|---|---|---|---|---|---|
| LYS | N | 348 | 207.9 | 108.4 | 55.3 | 59 | A |
| LYS | CA | 348 | 208.4 | 108.9 | 54.1 | 58 | A |
| LYS | CB | 348 | 209.1 | 107.8 | 53.3 | 60 | A |
| LYS | CG | 348 | 210.5 | 108.1 | 52.8 | 62 | A |
| LYS | CD | 348 | 211.6 | 107.7 | 53.9 | 64 | A |
| LYS | CE | 348 | 211.6 | 108.7 | 55.1 | 64 | A |
| LYS | NZ | 348 | 212.8 | 108.4 | 56.0 | 65 | A |
| LYS | C | 348 | 207.6 | 109.7 | 53.1 | 56 | A |
| LYS | O | 348 | 208.1 | 110.6 | 52.4 | 57 | A |
| ASP | N | 349 | 206.3 | 109.5 | 53.1 | 54 | A |
| ASP | CA | 349 | 205.4 | 110.3 | 52.1 | 51 | A |
| ASP | CB | 349 | 205.6 | 109.8 | 50.7 | 51 | A |
| ASP | CG | 349 | 204.8 | 110.6 | 49.7 | 51 | A |
| ASP | OD1 | 349 | 204.9 | 111.8 | 49.7 | 51 | A |
| ASP | OD2 | 349 | 204.1 | 109.9 | 48.9 | 51 | A |
| ASP | C | 349 | 203.9 | 110.2 | 52.5 | 50 | A |
| ASP | O | 349 | 203.1 | 109.7 | 51.8 | 50 | A |
| THR | N | 350 | 203.6 | 110.8 | 53.7 | 49 | A |
| THR | CA | 350 | 202.3 | 110.7 | 54.3 | 47 | A |
| THR | CB | 350 | 202.3 | 111.1 | 55.7 | 48 | A |
| THR | OG1 | 350 | 202.2 | 112.5 | 55.9 | 50 | A |
| THR | CG2 | 350 | 203.6 | 110.6 | 56.4 | 49 | A |
| THR | C | 350 | 201.2 | 111.5 | 53.6 | 46 | A |
| THR | O | 350 | 200.0 | 111.4 | 54.0 | 46 | A |
| ILE | N | 351 | 201.5 | 112.4 | 52.7 | 46 | A |
| ILE | CA | 351 | 200.4 | 113.2 | 52.1 | 44 | A |
| ILE | CB | 351 | 200.9 | 114.3 | 51.1 | 43 | A |
| ILE | CG2 | 351 | 201.4 | 113.7 | 49.8 | 41 | A |
| ILE | CG1 | 351 | 199.8 | 115.3 | 50.9 | 43 | A |
| ILE | CD1 | 351 | 199.3 | 116.0 | 52.1 | 42 | A |
| ILE | C | 351 | 199.4 | 112.2 | 51.4 | 45 | A |
| ILE | O | 351 | 198.2 | 112.4 | 51.4 | 45 | A |
| ARG | N | 352 | 200.0 | 111.1 | 50.9 | 46 | A |
| ARG | CA | 352 | 199.2 | 110.1 | 50.2 | 48 | A |
| ARG | CB | 352 | 199.7 | 109.8 | 48.8 | 48 | A |
| ARG | CG | 352 | 201.1 | 109.9 | 48.5 | 47 | A |
| ARG | CD | 352 | 201.4 | 110.5 | 47.1 | 47 | A |
| ARG | NE | 352 | 202.6 | 111.4 | 47.1 | 48 | A |
| ARG | CZ | 352 | 202.6 | 112.7 | 46.9 | 48 | A |
| ARG | NH1 | 352 | 201.5 | 113.4 | 46.7 | 48 | A |
| ARG | NH2 | 352 | 203.7 | 113.4 | 47.1 | 48 | A |
| ARG | C | 352 | 199.3 | 108.8 | 51.0 | 51 | A |
| ARG | O | 352 | 199.9 | 107.8 | 50.6 | 52 | A |
| LYS | N | 353 | 198.8 | 108.8 | 52.3 | 53 | A |
| LYS | CA | 353 | 198.8 | 107.7 | 53.2 | 53 | A |
| LYS | CB | 353 | 198.7 | 108.2 | 54.6 | 53 | A |
| LYS | CG | 353 | 197.5 | 108.9 | 55.0 | 55 | A |
| LYS | CD | 353 | 197.5 | 109.7 | 56.3 | 55 | A |
| LYS | CE | 353 | 196.2 | 110.4 | 56.6 | 55 | A |
| LYS | NZ | 353 | 196.3 | 111.4 | 57.7 | 55 | A |
| LYS | C | 353 | 197.7 | 106.8 | 52.8 | 53 | A |
| LYS | O | 353 | 197.7 | 105.6 | 53.1 | 53 | A |
| GLU | N | 354 | 196.6 | 107.4 | 52.2 | 53 | A |
| GLU | CA | 354 | 195.4 | 106.7 | 51.8 | 53 | A |
| GLU | CB | 354 | 194.4 | 107.7 | 51.3 | 56 | A |
| GLU | CG | 354 | 193.7 | 108.4 | 52.4 | 59 | A |
| GLU | CD | 354 | 193.1 | 107.4 | 53.5 | 61 | A |
| GLU | OE1 | 354 | 193.6 | 107.3 | 54.6 | 63 | A |
| GLU | OE2 | 354 | 192.1 | 106.7 | 53.1 | 63 | A |
| GLU | C | 354 | 195.8 | 105.8 | 50.6 | 53 | A |
| GLU | O | 354 | 195.3 | 104.7 | 50.5 | 54 | A |
| TYR | N | 355 | 196.7 | 106.3 | 49.7 | 50 | A |
| TYR | CA | 355 | 197.1 | 105.6 | 48.6 | 49 | A |
| TYR | CB | 355 | 197.7 | 106.5 | 47.5 | 45 | A |
| TYR | CG | 355 | 198.4 | 105.8 | 46.4 | 41 | A |
| TYR | CD1 | 355 | 197.7 | 105.3 | 45.3 | 39 | A |
| TYR | CE1 | 355 | 198.3 | 104.7 | 44.3 | 38 | A |
| TYR | CD2 | 355 | 199.8 | 105.6 | 46.4 | 39 | A |
| TYR | CE2 | 355 | 200.4 | 105.0 | 45.4 | 38 | A |
| TYR | CZ | 355 | 199.7 | 104.5 | 44.3 | 38 | A |
| TYR | OH | 355 | 200.3 | 103.9 | 43.3 | 41 | A |
| TYR | C | 355 | 198.1 | 104.5 | 48.9 | 51 | A |
| TYR | O | 355 | 197.9 | 103.3 | 48.5 | 52 | A |
| TRP | N | 356 | 199.1 | 104.9 | 49.7 | 53 | A |
| TRP | CA | 356 | 200.2 | 104.0 | 50.1 | 55 | A |
| TRP | CB | 356 | 201.2 | 104.7 | 50.9 | 55 | A |
| TRP | CG | 356 | 202.1 | 105.4 | 49.9 | 55 | A |
| TRP | CD2 | 3S6 | 202.7 | 104.8 | 48.8 | 54 | A |
| TRP | CE2 | 356 | 203.5 | 105.8 | 48.2 | 55 | A |

TABLE 2-continued

| | | | | | | | |
|---|---|---|---|---|---|---|---|
| TRP | CE3 | 356 | 202.7 | 103.6 | 48.2 | 55 | A |
| TRP | CD1 | 356 | 202.6 | 106.7 | 50.0 | 54 | A |
| TRP | NE1 | 356 | 203.4 | 107.0 | 48.9 | 55 | A |
| TRP | CZ2 | 356 | 204.3 | 105.6 | 47.0 | 55 | A |
| TRP | CZ3 | 356 | 203.4 | 103.3 | 47.0 | 55 | A |
| TRP | CH2 | 356 | 204.2 | 104.3 | 46.5 | 55 | A |
| TRP | C | 356 | 199.7 | 102.7 | 51.0 | 56 | A |
| TRP | O | 356 | 200.4 | 101.7 | 51.0 | 56 | A |
| ARG | N | 357 | 198.7 | 102.9 | 51.8 | 58 | A |
| ARG | CA | 357 | 198.2 | 101.8 | 52.6 | 60 | A |
| ARG | CB | 357 | 197.4 | 102.3 | 53.8 | 60 | A |
| ARG | CG | 357 | 198.3 | 102.9 | 54.9 | 62 | A |
| ARG | CD | 357 | 197.6 | 103.1 | 56.2 | 64 | A |
| ARG | NE | 357 | 196.4 | 103.8 | 56.1 | 65 | A |
| ARG | CZ | 357 | 196.3 | 105.1 | 56.4 | 65 | A |
| ARG | NH1 | 357 | 195.1 | 105.7 | 56.2 | 65 | A |
| ARG | NH2 | 357 | 197.3 | 105.8 | 56.8 | 66 | A |
| ARG | C | 357 | 197.3 | 101.0 | 51.7 | 59 | A |
| ARG | O | 357 | 197.2 | 99.8 | 51.8 | 61 | A |
| TYR | N | 358 | 196.7 | 101.6 | 50.7 | 57 | A |
| TYR | CA | 358 | 195.8 | 100.9 | 49.7 | 55 | A |
| TYR | CB | 358 | 195.0 | 101.9 | 48.9 | 55 | A |
| TYR | CG | 358 | 194.6 | 101.3 | 47.6 | 54 | A |
| TYR | CD1 | 358 | 193.3 | 100.7 | 47.5 | 54 | A |
| TYR | CE1 | 358 | 192.9 | 100.1 | 46.3 | 54 | A |
| TYR | CD2 | 358 | 195.4 | 101.2 | 46.5 | 54 | A |
| TYR | CE2 | 358 | 195.0 | 100.6 | 45.3 | 54 | A |
| TYR | CZ | 358 | 193.8 | 100.0 | 45.2 | 54 | A |
| TYR | OH | 358 | 193.4 | 99.4 | 44.0 | 52 | A |
| TYR | C | 358 | 196.7 | 100.0 | 48.9 | 55 | A |
| TYR | O | 358 | 196.2 | 99.0 | 48.4 | 55 | A |
| ILE | N | 359 | 197.9 | 100.5 | 48.6 | 56 | A |
| ILE | CA | 359 | 198.8 | 99.6 | 47.8 | 57 | A |
| ILE | CB | 359 | 200.0 | 100.5 | 47.3 | 57 | A |
| ILE | CG2 | 359 | 201.1 | 99.6 | 46.5 | 55 | A |
| ILE | CG1 | 359 | 199.5 | 101.5 | 46.3 | 56 | A |
| ILE | CD1 | 359 | 198.8 | 101.0 | 45.1 | 56 | A |
| ILE | C | 359 | 199.4 | 98.5 | 48.7 | 59 | A |
| ILE | O | 359 | 199.9 | 97.5 | 48.2 | 59 | A |
| GLY | N | 360 | 199.2 | 98.7 | 50.0 | 60 | A |
| GLY | CA | 360 | 199.6 | 97.6 | 50.9 | 60 | A |
| GLY | C | 360 | 198.6 | 96.5 | 50.9 | 60 | A |
| GLY | O | 360 | 198.9 | 95.4 | 50.9 | 60 | A |
| ARG | N | 361 | 197.3 | 97.0 | 50.9 | 61 | A |
| ARG | CA | 361 | 196.2 | 96.1 | 50.9 | 62 | A |
| ARG | CB | 361 | 194.9 | 96.8 | 51.3 | 62 | A |
| ARG | CG | 361 | 194.9 | 97.4 | 52.7 | 63 | A |
| ARG | CD | 361 | 193.6 | 97.9 | 53.2 | 64 | A |
| ARG | NE | 361 | 193.0 | 98.9 | 52.3 | 67 | A |
| ARG | CZ | 361 | 193.4 | 100.2 | 52.4 | 68 | A |
| ARG | NH1 | 361 | 192.8 | 101.1 | 51.6 | 69 | A |
| ARG | NH2 | 361 | 194.4 | 100.6 | 53.2 | 69 | A |
| ARG | C | 361 | 196.0 | 95.3 | 49.6 | 63 | A |
| ARG | O | 361 | 195.5 | 94.2 | 49.6 | 65 | A |
| SER | N | 362 | 196.3 | 96.0 | 48.5 | 63 | A |
| SER | CA | 362 | 196.1 | 95.3 | 47.2 | 64 | A |
| SER | CB | 362 | 196.1 | 96.3 | 46.1 | 63 | A |
| SER | OG | 362 | 194.9 | 97.1 | 46.1 | 64 | A |
| SER | C | 362 | 197.2 | 94.3 | 47.0 | 65 | A |
| SER | O | 362 | 197.1 | 93.3 | 46.5 | 65 | A |
| LEU | N | 363 | 198.4 | 94.7 | 47.6 | 66 | A |
| LEU | CA | 363 | 199.6 | 93.8 | 47.6 | 67 | A |
| LEU | CB | 363 | 200.8 | 94.6 | 48.1 | 66 | A |
| LEU | CG | 363 | 202.1 | 94.6 | 47.3 | 66 | A |
| LEU | CD1 | 363 | 201.8 | 94.6 | 45.8 | 65 | A |
| LEU | CD2 | 363 | 202.9 | 95.9 | 47.7 | 65 | A |
| LEU | C | 363 | 199.3 | 92.5 | 48.4 | 69 | A |
| LEU | O | 363 | 200.1 | 91.6 | 48.4 | 68 | A |
| GLN | N | 364 | 198.2 | 92.5 | 49.2 | 72 | A |
| GLN | CA | 364 | 197.8 | 91.4 | 50.0 | 75 | A |
| GLN | CB | 364 | 196.9 | 91.8 | 51.1 | 76 | A |
| GLN | CG | 364 | 197.6 | 92.7 | 52.1 | 77 | A |
| GLN | CD | 364 | 199.0 | 92.2 | 52.5 | 78 | A |
| GLN | OE1 | 364 | 199.2 | 91.6 | 53.5 | 79 | A |
| GLN | NE2 | 364 | 200.0 | 92.5 | 51.6 | 78 | A |
| GLN | C | 364 | 197.1 | 90.4 | 49.1 | 78 | A |
| GLN | O | 364 | 197.5 | 89.3 | 48.9 | 79 | A |
| SER | N | 365 | 196.0 | 90.9 | 48.5 | 80 | A |
| SER | CA | 365 | 195.2 | 90.1 | 47.6 | 83 | A |

TABLE 2-continued

| | | | | | | | |
|---|---|---|---|---|---|---|---|
| SER | CB | 365 | 194.0 | 90.9 | 47.1 | 83 | A |
| SER | OG | 365 | 193.2 | 91.4 | 48.2 | 83 | A |
| SER | C | 365 | 196.0 | 89.7 | 46.4 | 86 | A |
| SER | O | 365 | 196.2 | 88.5 | 46.2 | 86 | A |
| LYS | N | 366 | 196.6 | 90.6 | 45.7 | 89 | A |
| LYS | CA | 366 | 197.4 | 90.3 | 44.5 | 92 | A |
| LYS | CB | 366 | 196.6 | 90.7 | 43.2 | 93 | A |
| LYS | CG | 366 | 195.9 | 92.1 | 43.2 | 94 | A |
| LYS | CD | 366 | 194.6 | 92.2 | 44.0 | 94 | A |
| LYS | CE | 366 | 194.1 | 93.6 | 44.2 | 94 | A |
| LYS | NZ | 366 | 192.9 | 93.6 | 45.1 | 94 | A |
| LYS | C | 366 | 198.8 | 90.9 | 44.4 | 93 | A |
| LYS | OT1 | 366 | 199.8 | 90.1 | 44.5 | 93 | A |
| LYS | OT2 | 366 | 199.0 | 92.2 | 44.3 | 93 | A |
| LEU | CB | 523 | 196.2 | 122.2 | 61.7 | 47 | B |
| LEU | CG | 523 | 194.9 | 123.0 | 62.1 | 48 | B |
| LEU | CD1 | 523 | 195.1 | 124.4 | 61.7 | 48 | B |
| LEU | CD2 | 523 | 193.7 | 122.4 | 61.4 | 48 | B |
| LEU | C | 523 | 197.5 | 120.0 | 61.6 | 48 | B |
| LEU | O | 523 | 198.6 | 120.2 | 62.0 | 49 | B |
| LEU | N | 523 | 196.5 | 120.8 | 63.7 | 49 | B |
| LEU | CA | 523 | 196.3 | 120.7 | 62.2 | 48 | B |
| TYR | N | 524 | 197.2 | 119.1 | 60.6 | 47 | B |
| TYR | CA | 524 | 198.2 | 118.4 | 59.9 | 47 | B |
| TYR | CB | 524 | 197.5 | 117.6 | 58.8 | 46 | B |
| TYR | CG | 524 | 198.5 | 116.9 | 57.9 | 46 | B |
| TYR | CD1 | 524 | 199.3 | 115.8 | 58.4 | 47 | B |
| TYR | CE1 | 524 | 200.2 | 115.1 | 57.7 | 47 | B |
| TYR | CD2 | 524 | 198.7 | 117.2 | 56.6 | 47 | B |
| TYR | CE2 | 524 | 199.6 | 116.5 | 55.8 | 47 | B |
| TYR | CZ | 524 | 200.4 | 115.4 | 56.3 | 47 | B |
| TYR | OH | 524 | 201.2 | 114.8 | 55.5 | 47 | B |
| TYR | C | 524 | 199.3 | 119.3 | 59.5 | 47 | B |
| TYR | O | 524 | 200.5 | 119.0 | 59.7 | 45 | B |
| SER | N | 525 | 198.9 | 120.5 | 58.9 | 48 | B |
| SER | CA | 525 | 199.8 | 121.5 | 58.4 | 49 | B |
| SER | CB | 525 | 199.0 | 122.5 | 57.6 | 48 | B |
| SER | OG | 525 | 198.3 | 121.9 | 56.5 | 49 | B |
| SER | C | 525 | 200.7 | 122.2 | 59.4 | 51 | B |
| SER | O | 525 | 201.9 | 122.5 | 59.1 | 51 | B |
| LEU | N | 526 | 200.1 | 122.7 | 60.5 | 52 | B |
| LEU | CA | 526 | 200.8 | 123.5 | 61.5 | 52 | B |
| LEU | CB | 526 | 199.8 | 124.3 | 62.3 | 52 | B |
| LEU | CG | 526 | 198.7 | 125.1 | 61.7 | 52 | B |
| LEU | CD1 | 526 | 198.0 | 126.0 | 62.7 | 52 | B |
| LEU | CD2 | 526 | 199.2 | 126.0 | 60.5 | 51 | B |
| LEU | C | 526 | 201.7 | 122.6 | 62.4 | 53 | B |
| LEU | O | 526 | 202.4 | 123.1 | 63.3 | 53 | B |
| ARG | N | 527 | 201.7 | 121.3 | 62.1 | 53 | B |
| ARG | CA | 527 | 202.5 | 120.4 | 62.9 | 55 | B |
| ARG | CB | 527 | 202.2 | 118.9 | 62.7 | 54 | B |
| ARG | CG | 527 | 200.8 | 118.5 | 63.2 | 54 | B |
| ARG | CD | 527 | 200.4 | 117.1 | 62.9 | 53 | B |
| ARG | NE | 527 | 199.0 | 117.0 | 63.1 | 54 | B |
| ARG | CZ | 527 | 198.3 | 116.0 | 62.5 | 54 | B |
| ARG | NH1 | 527 | 198.9 | 115.1 | 61.7 | 55 | B |
| ARG | NH2 | 527 | 197.0 | 116.0 | 62.6 | 54 | B |
| ARG | C | 527 | 204.0 | 120.6 | 62.6 | 57 | B |
| ARG | O | 527 | 204.3 | 121.3 | 61.6 | 58 | B |
| PRO | N | 528 | 204.9 | 120.2 | 63.5 | 59 | B |
| PRO | CD | 528 | 204.5 | 120.0 | 65.0 | 60 | B |
| PRO | CA | 528 | 206.3 | 120.4 | 63.4 | 61 | B |
| PRO | CB | 528 | 206.8 | 120.2 | 64.9 | 60 | B |
| PRO | CG | 528 | 205.7 | 120.7 | 65.7 | 60 | B |
| PRO | C | 528 | 207.1 | 119.4 | 62.5 | 62 | B |
| PRO | O | 528 | 208.1 | 119.8 | 62.0 | 63 | B |
| GLU | N | 529 | 206.5 | 118.2 | 62.3 | 63 | B |
| GLU | CA | 529 | 207.2 | 117.3 | 61.4 | 64 | B |
| GLU | CB | 529 | 206.8 | 115.8 | 61.8 | 66 | B |
| GLU | CG | 529 | 205.3 | 115.5 | 62.1 | 68 | B |
| GLU | CD | 529 | 204.9 | 115.7 | 63.5 | 69 | B |
| GLU | OE1 | 529 | 203.7 | 116.1 | 63.8 | 69 | B |
| GLU | OE2 | 529 | 205.7 | 115.5 | 64.4 | 70 | B |
| GLU | C | 529 | 206.8 | 117.6 | 59.9 | 64 | B |
| GLU | O | 529 | 207.6 | 117.2 | 59.0 | 65 | B |
| HIS | N | 530 | 205.7 | 118.2 | 59.7 | 64 | B |
| HIS | CA | 530 | 205.2 | 118.6 | 58.4 | 64 | B |
| HIS | CB | 530 | 203.9 | 119.3 | 58.5 | 64 | B |
| HIS | CG | 530 | 203.4 | 120.0 | 57.2 | 63 | B |

TABLE 2-continued

| | | | | | | | |
|---|---|---|---|---|---|---|---|
| HIS | CD2 | 530 | 202.7 | 119.6 | 56.2 | 62 | B |
| HIS | ND1 | 530 | 203.8 | 121.3 | 56.9 | 63 | B |
| HIS | CE1 | 530 | 203.2 | 121.7 | 55.7 | 62 | B |
| HIS | NE2 | 530 | 202.6 | 120.6 | 55.3 | 62 | B |
| HIS | C | 530 | 206.2 | 119.6 | 57.7 | 63 | B |
| HIS | O | 530 | 206.3 | 119.7 | 56.5 | 64 | B |
| ALA | N | 531 | 207.0 | 120.2 | 58.5 | 63 | B |
| ALA | CA | 531 | 208.0 | 121.1 | 58.0 | 63 | B |
| ALA | CB | 531 | 208.6 | 121.9 | 59.1 | 64 | B |
| ALA | C | 531 | 209.2 | 120.4 | 57.3 | 63 | B |
| ALA | O | 531 | 210.0 | 121.0 | 56.6 | 63 | B |
| ARG | N | 532 | 209.2 | 119.1 | 57.4 | 63 | B |
| ARG | CA | 532 | 210.2 | 118.3 | 56.7 | 64 | B |
| ARG | CB | 532 | 210.3 | 116.9 | 57.5 | 69 | B |
| ARG | CG | 532 | 210.8 | 117.1 | 58.9 | 74 | B |
| ARG | CD | 532 | 210.5 | 115.9 | 59.8 | 79 | B |
| ARG | NE | 532 | 211.3 | 116.0 | 61.0 | 84 | B |
| ARG | CZ | 532 | 211.6 | 114.9 | 61.7 | 86 | B |
| ARG | NH1 | 532 | 212.4 | 115.1 | 62.8 | 88 | B |
| ARG | NH2 | 532 | 211.3 | 113.7 | 61.3 | 87 | B |
| ARG | C | 532 | 209.7 | 118.0 | 55.3 | 62 | B |
| ARG | O | 532 | 210.4 | 117.4 | 54.5 | 62 | B |
| GLU | N | 533 | 208.4 | 118.4 | 55.1 | 58 | B |
| GLU | CA | 533 | 207.8 | 118.2 | 53.7 | 57 | B |
| GLU | CB | 533 | 206.3 | 118.1 | 53.8 | 56 | B |
| GLU | CG | 533 | 205.9 | 116.8 | 54.6 | 56 | B |
| GLU | CD | 533 | 206.2 | 115.5 | 53.9 | 56 | B |
| GLU | OE1 | 533 | 205.2 | 114.8 | 53.6 | 57 | B |
| GLU | OE2 | 533 | 207.3 | 115.2 | 53.7 | 56 | B |
| GLU | C | 533 | 208.3 | 119.3 | 52.8 | 55 | B |
| GLU | O | 533 | 207.8 | 119.3 | 51.7 | 56 | B |
| ARG | N | 534 | 209.2 | 120.1 | 53.3 | 53 | B |
| ARG | CA | 534 | 209.7 | 121.3 | 52.5 | 50 | B |
| ARG | CB | 534 | 210.6 | 122.1 | 53.4 | 51 | B |
| ARG | CG | 534 | 210.7 | 123.5 | 53.1 | 52 | B |
| ARG | CD | 534 | 209.4 | 124.3 | 53.4 | 52 | B |
| ARG | NE | 534 | 209.5 | 125.6 | 52.8 | 54 | B |
| ARG | CZ | 534 | 209.6 | 126.8 | 53.4 | 54 | B |
| ARG | NH1 | 534 | 209.5 | 126.8 | 54.8 | 55 | B |
| ARG | NH2 | 534 | 209.7 | 127.9 | 52.8 | 54 | B |
| ARG | C | 534 | 210.5 | 120.7 | 51.3 | 48 | B |
| ARG | O | 534 | 210.9 | 119.6 | 51.3 | 46 | B |
| LEU | N | 535 | 210.7 | 121.6 | 50.3 | 46 | B |
| LEU | CA | 535 | 211.4 | 121.2 | 49.0 | 44 | B |
| LEU | CB | 535 | 211.2 | 122.3 | 48.0 | 40 | B |
| LEU | CG | 535 | 212.0 | 122.2 | 46.7 | 38 | B |
| LEU | CD1 | 535 | 211.7 | 121.0 | 45.9 | 36 | B |
| LEU | CD2 | 535 | 211.9 | 123.4 | 45.8 | 37 | B |
| LEU | C | 535 | 212.8 | 120.9 | 49.2 | 45 | B |
| LEU | O | 535 | 213.6 | 121.6 | 49.7 | 45 | B |
| GLN | N | 536 | 213.2 | 119.7 | 48.6 | 47 | B |
| GLN | CA | 536 | 214.6 | 119.2 | 48.6 | 50 | B |
| GLN | CB | 536 | 214.6 | 117.7 | 48.6 | 52 | B |
| GLN | CG | 536 | 213.7 | 117.1 | 49.6 | 54 | B |
| GLN | CD | 536 | 214.2 | 117.0 | 51.0 | 56 | B |
| GLN | OE1 | 536 | 215.3 | 116.4 | 51.2 | 56 | B |
| GLN | NE2 | 536 | 213.6 | 117.7 | 51.9 | 56 | B |
| GLN | C | 536 | 215.1 | 119.7 | 47.2 | 51 | B |
| GLN | O | 536 | 214.7 | 119.0 | 46.2 | 51 | B |
| ASP | N | 537 | 215.8 | 120.8 | 47.2 | 52 | B |
| ASP | CA | 537 | 216.3 | 121.4 | 46.0 | 53 | B |
| ASP | CB | 537 | 216.8 | 122.8 | 46.3 | 55 | B |
| ASP | CG | 537 | 217.7 | 123.4 | 45.2 | 58 | B |
| ASP | OD1 | 537 | 218.7 | 124.1 | 45.6 | 60 | B |
| ASP | OD2 | 537 | 217.4 | 123.2 | 44.1 | 60 | B |
| ASP | C | 537 | 217.4 | 120.6 | 45.3 | 52 | B |
| ASP | O | 537 | 217.7 | 120.7 | 44.1 | 50 | B |
| ASP | N | 538 | 218.1 | 119.7 | 46.0 | 52 | B |
| ASP | CA | 538 | 219.3 | 118.9 | 45.5 | 52 | B |
| ASP | CB | 538 | 218.9 | 118.1 | 44.3 | 53 | B |
| ASP | CG | 538 | 217.8 | 117.0 | 44.5 | 54 | B |
| ASP | OD1 | 538 | 217.9 | 116.3 | 45.6 | 54 | B |
| ASP | OD2 | 538 | 216.9 | 116.9 | 43.7 | 55 | B |
| ASP | C | 538 | 220.5 | 119.8 | 45.2 | 51 | B |
| ASP | O | 538 | 221.5 | 119.3 | 44.7 | 49 | B |
| SER | N | 539 | 220.4 | 121.0 | 45.6 | 51 | B |
| SER | CA | 539 | 221.4 | 122.1 | 45.4 | 52 | B |
| SER | CB | 539 | 222.7 | 121.6 | 45.9 | 53 | B |
| SER | OG | 539 | 222.7 | 121.3 | 47.3 | 55 | B |

TABLE 2-continued

| | | | | | | | |
|---|---|---|---|---|---|---|---|
| SER | C | 539 | 221.5 | 122.4 | 43.9 | 52 | B |
| SER | O | 539 | 222.3 | 123.2 | 43.5 | 54 | B |
| VAL | N | 540 | 220.6 | 121.7 | 43.1 | 50 | B |
| VAL | CA | 540 | 220.6 | 121.9 | 41.7 | 48 | B |
| VAL | CB | 540 | 220.5 | 120.6 | 41.0 | 47 | B |
| VAL | CG1 | 540 | 220.6 | 120.8 | 39.5 | 46 | B |
| VAL | CG2 | 540 | 221.7 | 119.7 | 41.4 | 46 | B |
| VAL | C | 540 | 219.3 | 122.7 | 41.5 | 47 | B |
| VAL | O | 540 | 218.3 | 122.2 | 41.2 | 49 | B |
| GLU | N | 541 | 219.4 | 124.0 | 41.6 | 47 | B |
| GLU | CA | 541 | 218.3 | 124.9 | 41.5 | 47 | B |
| GLU | CB | 541 | 218.4 | 126.1 | 42.4 | 49 | B |
| GLU | CG | 541 | 219.7 | 126.9 | 42.1 | 53 | B |
| GLU | CD | 541 | 220.0 | 127.9 | 43.2 | 55 | B |
| GLU | OE1 | 541 | 221.0 | 127.7 | 44.0 | 57 | B |
| GLU | OE2 | 541 | 219.2 | 128.9 | 43.3 | 55 | B |
| GLU | C | 541 | 218.0 | 125.3 | 40.1 | 45 | B |
| GLU | O | 541 | 218.9 | 125.8 | 39.3 | 46 | B |
| THR | N | 542 | 216.7 | 125.2 | 39.7 | 41 | B |
| THR | CA | 542 | 216.3 | 125.5 | 38.3 | 38 | B |
| THR | CB | 542 | 215.8 | 124.4 | 37.5 | 38 | B |
| THR | OG1 | 542 | 214.6 | 123.8 | 38.1 | 38 | B |
| THR | CG2 | 542 | 216.9 | 123.3 | 37.4 | 37 | B |
| THR | C | 542 | 215.1 | 126.5 | 38.5 | 37 | B |
| THR | O | 542 | 214.6 | 126.6 | 39.6 | 37 | B |
| VAL | N | 543 | 214.7 | 127.0 | 37.4 | 35 | B |
| VAL | CA | 543 | 213.5 | 127.9 | 37.4 | 34 | B |
| VAL | CB | 543 | 213.1 | 128.3 | 36.0 | 35 | B |
| VAL | CG1 | 543 | 212.0 | 129.3 | 36.0 | 34 | B |
| VAL | CG2 | 543 | 214.2 | 128.8 | 35.2 | 35 | B |
| VAL | C | 543 | 212.3 | 127.3 | 38.1 | 34 | B |
| VAL | O | 543 | 211.5 | 128.0 | 38.7 | 35 | B |
| THR | N | 544 | 212.3 | 126.0 | 38.1 | 34 | B |
| THR | CA | 544 | 211.2 | 125.3 | 38.8 | 34 | B |
| THR | CB | 544 | 211.0 | 123.9 | 38.3 | 35 | B |
| THR | OG1 | 544 | 211.0 | 123.8 | 36.9 | 35 | B |
| THR | CG2 | 544 | 209.6 | 123.3 | 38.8 | 34 | B |
| THR | C | 544 | 211.3 | 125.3 | 40.4 | 34 | B |
| THR | O | 544 | 210.3 | 125.5 | 41.1 | 35 | B |
| SER | N | 545 | 212.5 | 125.0 | 40.8 | 34 | B |
| SER | CA | 545 | 212.8 | 124.9 | 42.3 | 33 | B |
| SER | CB | 545 | 214.3 | 124.6 | 42.5 | 33 | B |
| SER | OG | 545 | 214.9 | 123.8 | 41.5 | 35 | B |
| SER | C | 545 | 212.5 | 126.2 | 42.9 | 33 | B |
| SER | O | 545 | 211.8 | 126.3 | 43.8 | 34 | B |
| ILE | N | 546 | 213.1 | 127.3 | 42.3 | 33 | B |
| ILE | CA | 546 | 213.0 | 128.6 | 42.7 | 32 | B |
| ILE | CB | 546 | 213.6 | 129.6 | 41.6 | 31 | B |
| ILE | CG2 | 546 | 213.3 | 131.0 | 41.9 | 30 | B |
| ILE | CG1 | 546 | 215.1 | 129.3 | 41.5 | 31 | B |
| ILE | CD1 | 546 | 215.7 | 130.0 | 40.3 | 32 | B |
| ILE | C | 546 | 211.5 | 129.0 | 42.9 | 34 | B |
| ILE | O | 546 | 211.2 | 129.5 | 44.0 | 35 | B |
| GLU | N | 547 | 210.7 | 128.8 | 41.9 | 33 | B |
| GLU | CA | 547 | 209.3 | 129.2 | 42.0 | 34 | B |
| GLU | CB | 547 | 208.6 | 129.0 | 40.6 | 35 | B |
| GLU | CG | 547 | 209.1 | 130.0 | 39.6 | 35 | B |
| GLU | CD | 547 | 209.1 | 131.4 | 40.1 | 37 | B |
| GLU | OE1 | 547 | 208.1 | 132.0 | 40.5 | 38 | B |
| GLU | OE2 | 547 | 210.2 | 132.0 | 40.1 | 39 | B |
| GLU | C | 547 | 208.6 | 128.4 | 43.0 | 32 | B |
| GLU | O | 547 | 207.8 | 129.0 | 43.8 | 33 | B |
| GLN | N | 548 | 208.8 | 127.1 | 43.1 | 32 | B |
| GLN | CA | 548 | 208.2 | 126.2 | 44.1 | 31 | B |
| GLN | CB | 548 | 208.6 | 124.8 | 43.9 | 29 | B |
| GLN | CG | 548 | 208.0 | 123.8 | 44.9 | 26 | B |
| GLN | CD | 548 | 206.5 | 123.8 | 44.9 | 25 | B |
| GLN | OE1 | 548 | 205.9 | 123.5 | 45.9 | 26 | B |
| GLN | NE2 | 548 | 205.9 | 124.2 | 43.8 | 25 | B |
| GLN | C | 548 | 208.5 | 126.7 | 45.5 | 33 | B |
| GLN | O | 548 | 207.7 | 127.0 | 46.3 | 34 | B |
| ALA | N | 549 | 209.8 | 126.9 | 45.7 | 34 | B |
| ALA | CA | 549 | 210.3 | 127.4 | 47.0 | 35 | B |
| ALA | CB | 549 | 211.8 | 127.5 | 46.9 | 35 | B |
| ALA | C | 549 | 209.7 | 128.8 | 47.3 | 36 | B |
| ALA | O | 549 | 209.5 | 129.0 | 48.5 | 39 | B |
| LYS | N | 550 | 209.3 | 129.6 | 46.3 | 36 | B |
| LYS | CA | 550 | 208.7 | 130.8 | 46.6 | 38 | B |
| LYS | CB | 550 | 208.6 | 131.7 | 45.4 | 38 | B |

TABLE 2-continued

| | | | | | | | |
|---|---|---|---|---|---|---|---|
| LYS | CG | 550 | 209.9 | 132.2 | 44.9 | 40 | B |
| LYS | CD | 550 | 209.7 | 133.1 | 43.7 | 42 | B |
| LYS | CE | 550 | 211.0 | 133.5 | 43.0 | 43 | B |
| LYS | NZ | 550 | 210.7 | 134.2 | 41.8 | 46 | B |
| LYS | C | 550 | 207.3 | 130.6 | 47.2 | 39 | B |
| LYS | O | 550 | 206.9 | 131.3 | 48.2 | 40 | B |
| VAL | N | 551 | 206.6 | 129.8 | 46.6 | 40 | B |
| VAL | CA | 551 | 205.2 | 129.5 | 47.0 | 41 | B |
| VAL | CB | 551 | 204.4 | 128.6 | 46.1 | 40 | B |
| VAL | CG1 | 551 | 203.0 | 128.4 | 46.6 | 40 | B |
| VAL | CG2 | 551 | 204.4 | 129.2 | 44.7 | 40 | B |
| VAL | C | 551 | 205.3 | 128.9 | 48.4 | 42 | B |
| VAL | O | 551 | 204.6 | 129.4 | 49.3 | 42 | B |
| GLU | N | 552 | 206.2 | 128.0 | 48.7 | 42 | B |
| GLU | CA | 552 | 206.3 | 127.4 | 50.0 | 43 | B |
| GLU | CB | 552 | 207.4 | 126.3 | 49.9 | 42 | B |
| GLU | CG | 552 | 207.0 | 125.1 | 49.2 | 40 | B |
| GLU | CD | 552 | 208.0 | 124.0 | 49.2 | 40 | B |
| GLU | OE1 | 552 | 209.1 | 124.1 | 49.7 | 41 | B |
| GLU | OE2 | 552 | 207.7 | 122.9 | 48.6 | 40 | B |
| GLU | C | 552 | 206.6 | 128.3 | 51.1 | 45 | B |
| GLU | O | 552 | 206.0 | 128.2 | 52.2 | 45 | B |
| GLU | N | 553 | 207.4 | 129.4 | 50.8 | 48 | B |
| GLU | CA | 553 | 207.6 | 130.4 | 51.8 | 50 | B |
| GLU | CB | 553 | 208.8 | 131.3 | 51.5 | 54 | B |
| GLU | CG | 553 | 210.2 | 130.9 | 52.1 | 59 | B |
| GLU | CD | 553 | 210.2 | 130.9 | 53.7 | 63 | B |
| GLU | OE1 | 553 | 210.9 | 130.0 | 54.3 | 64 | B |
| GLU | OE2 | 553 | 209.5 | 131.7 | 54.3 | 65 | B |
| GLU | C | 553 | 206.4 | 131.2 | 52.1 | 49 | B |
| GLU | O | 553 | 206.0 | 131.5 | 53.3 | 49 | B |
| LYS | N | 554 | 205.6 | 131.7 | 51.1 | 49 | B |
| LYS | CA | 554 | 204.4 | 132.5 | 51.3 | 49 | B |
| LYS | CB | 554 | 203.9 | 132.9 | 49.9 | 51 | B |
| LYS | CG | 554 | 204.9 | 133.5 | 49.0 | 55 | B |
| LYS | CD | 554 | 204.3 | 133.9 | 47.6 | 58 | B |
| LYS | CE | 554 | 203.9 | 132.7 | 46.7 | 58 | B |
| LYS | NZ | 554 | 203.4 | 133.2 | 45.3 | 58 | B |
| LYS | C | 554 | 203.4 | 131.6 | 52.0 | 49 | B |
| LYS | O | 554 | 202.5 | 132.2 | 52.7 | 48 | B |
| ILE | N | 555 | 203.4 | 130.3 | 51.8 | 49 | B |
| ILE | CA | 555 | 202.5 | 129.4 | 52.4 | 49 | B |
| ILE | CB | 555 | 202.4 | 128.1 | 51.7 | 49 | B |
| ILE | CG2 | 555 | 201.4 | 127.1 | 52.4 | 49 | B |
| ILE | CG1 | 555 | 201.9 | 128.2 | 50.2 | 49 | B |
| ILE | CD1 | 555 | 200.5 | 128.9 | 50.1 | 48 | B |
| ILE | C | 555 | 202.9 | 129.2 | 53.9 | 49 | B |
| ILE | O | 555 | 202.1 | 129.2 | 54.8 | 50 | B |
| GLN | N | 556 | 204.2 | 129.0 | 54.1 | 50 | B |
| GLN | CA | 556 | 204.7 | 128.8 | 55.4 | 51 | B |
| GLN | CB | 556 | 206.2 | 128.7 | 55.4 | 51 | B |
| GLN | CG | 556 | 206.8 | 128.3 | 56.8 | 53 | B |
| GLN | CD | 556 | 206.3 | 127.0 | 57.4 | 54 | B |
| GLN | OE1 | 556 | 206.8 | 125.9 | 57.2 | 54 | B |
| GLN | NE2 | 556 | 205.2 | 127.1 | 58.1 | 54 | B |
| GLN | C | 556 | 204.2 | 129.9 | 56.3 | 53 | B |
| GLN | O | 556 | 203.5 | 129.6 | 57.3 | 53 | B |
| GLU | N | 557 | 204.4 | 131.1 | 55.8 | 54 | B |
| GLU | CA | 557 | 203.9 | 132.3 | 56.6 | 54 | B |
| GLU | CB | 557 | 203.9 | 133.6 | 55.7 | 58 | B |
| GLU | CG | 557 | 205.3 | 134.1 | 55.4 | 62 | B |
| GLU | CD | 557 | 205.3 | 135.3 | 54.5 | 65 | B |
| GLU | OE1 | 557 | 204.3 | 136.0 | 54.4 | 66 | B |
| GLU | OE2 | 557 | 206.4 | 135.6 | 53.8 | 66 | B |
| GLU | C | 557 | 202.5 | 132.1 | 57.0 | 53 | B |
| GLU | O | 557 | 202.2 | 132.2 | 58.2 | 55 | B |
| VAL | N | 558 | 201.6 | 131.8 | 56.1 | 50 | B |
| VAL | CA | 558 | 200.2 | 131.6 | 56.4 | 49 | B |
| VAL | CB | 558 | 199.4 | 131.1 | 55.2 | 49 | B |
| VAL | CG1 | 558 | 198.0 | 130.7 | 55.6 | 48 | B |
| VAL | CG2 | 558 | 199.3 | 132.2 | 54.1 | 48 | B |
| VAL | C | 558 | 200.0 | 130.5 | 57.5 | 48 | B |
| VAL | O | 558 | 199.3 | 130.7 | 58.4 | 49 | B |
| PHE | N | 559 | 200.8 | 129.5 | 57.3 | 48 | B |
| PHE | CA | 559 | 200.7 | 128.4 | 58.3 | 47 | B |
| PHE | CB | 559 | 201.6 | 127.2 | 57.9 | 44 | B |
| PHE | CG | 559 | 201.0 | 126.4 | 56.8 | 42 | B |
| PHE | CD1 | 559 | 201.7 | 125.4 | 56.1 | 42 | B |
| PHE | CD2 | 559 | 199.6 | 126.5 | 56.4 | 42 | B |

TABLE 2-continued

| | | | | | | | |
|---|---|---|---|---|---|---|---|
| PHE | CE1 | 559 | 201.2 | 124.6 | 55.1 | 41 | B |
| PHE | CE2 | 559 | 199.1 | 125.8 | 55.4 | 41 | B |
| PHE | CZ | 559 | 199.8 | 124.8 | 54.8 | 41 | B |
| PHE | C | 559 | 201.1 | 129.0 | 59.7 | 48 | B |
| PHE | O | 559 | 200.3 | 129.0 | 60.6 | 48 | B |
| SER | N | 560 | 202.3 | 129.5 | 59.8 | 50 | B |
| SER | CA | 560 | 202.8 | 130.1 | 61.0 | 52 | B |
| SER | CB | 560 | 204.2 | 130.5 | 60.9 | 52 | B |
| SER | OG | 560 | 205.0 | 129.3 | 60.6 | 54 | B |
| SER | C | 560 | 202.0 | 131.3 | 61.4 | 55 | B |
| SER | O | 560 | 202.3 | 131.9 | 62.5 | 55 | B |
| SER | N | 561 | 201.0 | 131.7 | 60.6 | 58 | B |
| SER | CA | 561 | 200.2 | 132.9 | 61.0 | 62 | B |
| SER | CB | 561 | 199.0 | 132.9 | 60.1 | 64 | B |
| SER | OG | 561 | 198.1 | 134.0 | 60.5 | 66 | B |
| SER | C | 561 | 199.8 | 133.0 | 62.4 | 65 | B |
| SER | O | 561 | 199.9 | 134.0 | 63.1 | 66 | B |
| TYR | N | 562 | 199.4 | 131.8 | 63.0 | 69 | B |
| TYR | CA | 562 | 198.9 | 131.6 | 64.3 | 71 | B |
| TYR | CB | 562 | 198.3 | 130.2 | 64.4 | 72 | B |
| TYR | CG | 562 | 197.3 | 130.0 | 63.3 | 74 | B |
| TYR | CD1 | 562 | 197.7 | 129.4 | 62.1 | 74 | B |
| TYR | CE1 | 562 | 196.9 | 129.3 | 61.0 | 75 | B |
| TYR | CD2 | 562 | 196.1 | 130.6 | 63.3 | 75 | B |
| TYR | CE2 | 562 | 195.2 | 130.5 | 62.2 | 75 | B |
| TYR | CZ | 562 | 195.6 | 129.9 | 61.1 | 75 | B |
| TYR | OH | 562 | 194.8 | 129.9 | 60.0 | 76 | B |
| TYR | C | 562 | 200.0 | 131.8 | 65.4 | 72 | B |
| TYR | O | 562 | 199.8 | 132.6 | 66.3 | 71 | B |
| LYS | N | 563 | 201.1 | 131.1 | 65.3 | 73 | B |
| LYS | CA | 563 | 202.2 | 131.1 | 66.2 | 74 | B |
| LYS | CB | 563 | 203.4 | 130.3 | 65.6 | 76 | B |
| LYS | CG | 563 | 203.0 | 128.9 | 65.2 | 79 | B |
| LYS | CD | 563 | 204.2 | 128.1 | 64.7 | 80 | B |
| LYS | CE | 563 | 203.8 | 126.6 | 64.3 | 81 | B |
| LYS | NZ | 563 | 204.9 | 125.8 | 63.8 | 82 | B |
| LYS | C | 563 | 202.6 | 132.5 | 66.5 | 74 | B |
| LYS | O | 563 | 202.6 | 133.0 | 67.6 | 73 | B |
| PHE | N | 564 | 202.9 | 133.3 | 65.4 | 75 | B |
| PHE | CA | 564 | 203.4 | 134.7 | 65.6 | 77 | B |
| PHE | CB | 564 | 203.6 | 135.3 | 64.2 | 80 | B |
| PHE | CG | 564 | 204.8 | 134.8 | 63.5 | 83 | B |
| PHE | CD1 | 564 | 205.1 | 133.5 | 63.2 | 85 | B |
| PHE | CD2 | 564 | 205.8 | 135.8 | 63.0 | 85 | B |
| PHE | CE1 | 564 | 206.2 | 133.1 | 62.5 | 85 | B |
| PHE | CE2 | 564 | 206.9 | 135.4 | 62.3 | 86 | B |
| PHE | CZ | 564 | 207.1 | 134.0 | 62.0 | 86 | B |
| PHE | C | 564 | 202.4 | 135.6 | 66.3 | 76 | B |
| PHE | O | 564 | 202.8 | 136.4 | 67.1 | 75 | B |
| ASN | N | 565 | 201.1 | 135.4 | 66.1 | 75 | B |
| ASN | CA | 565 | 200.1 | 136.3 | 66.7 | 73 | B |
| ASN | CB | 565 | 199.0 | 136.6 | 65.7 | 75 | B |
| ASN | CG | 565 | 199.5 | 137.5 | 64.6 | 76 | B |
| ASN | OD1 | 565 | 199.7 | 138.7 | 64.8 | 76 | B |
| ASN | ND2 | 565 | 199.7 | 137.0 | 63.4 | 76 | B |
| ASN | C | 565 | 199.5 | 135.9 | 68.0 | 71 | B |
| ASN | O | 565 | 198.8 | 136.7 | 68.6 | 71 | B |
| HIS | N | 566 | 199.7 | 134.7 | 68.5 | 68 | B |
| HIS | CA | 566 | 199.3 | 134.2 | 69.8 | 66 | B |
| HIS | CB | 566 | 199.9 | 135.1 | 70.9 | 64 | B |
| HIS | CG | 566 | 201.4 | 135.3 | 70.7 | 63 | B |
| HIS | CD2 | 566 | 202.4 | 134.4 | 70.7 | 62 | B |
| HIS | ND1 | 566 | 201.9 | 136.5 | 70.4 | 62 | B |
| HIS | CE1 | 566 | 203.2 | 136.3 | 70.2 | 62 | B |
| HIS | NE2 | 566 | 203.5 | 135.1 | 70.4 | 62 | B |
| HIS | C | 566 | 197.8 | 134.1 | 70.0 | 66 | B |
| HIS | O | 566 | 197.2 | 134.6 | 71.0 | 64 | B |
| LEU | N | 567 | 197.2 | 133.4 | 69.0 | 67 | B |
| LEU | CA | 567 | 195.8 | 133.1 | 69.0 | 69 | B |
| LEU | CB | 567 | 195.1 | 133.9 | 67.9 | 68 | B |
| LEU | CG | 567 | 195.3 | 135.4 | 68.0 | 68 | B |
| LEU | CD1 | 567 | 194.9 | 136.0 | 66.7 | 68 | B |
| LEU | CD2 | 567 | 194.5 | 135.9 | 69.2 | 68 | B |
| LEU | C | 567 | 195.7 | 131.6 | 68.8 | 71 | B |
| LEU | O | 567 | 196.7 | 131.0 | 68.4 | 71 | B |
| VAL | N | 568 | 194.5 | 131.0 | 69.0 | 72 | B |
| VAL | CA | 568 | 194.3 | 129.6 | 68.8 | 72 | B |
| VAL | CB | 568 | 193.3 | 129.0 | 69.8 | 71 | B |
| VAL | CG1 | 568 | 193.8 | 127.7 | 70.3 | 71 | B |
| VAL | CG2 | 568 | 193.1 | 130.0 | 71.0 | 71 | B |
| VAL | C | 568 | 193.8 | 129.5 | 67.3 | 72 | B |
| VAL | O | 568 | 193.0 | 130.4 | 66.9 | 73 | B |
| PRO | N | 569 | 194.4 | 128.6 | 66.5 | 73 | B |
| PRO | CD | 569 | 195.5 | 127.6 | 66.8 | 72 | B |
| PRO | CA | 569 | 193.9 | 128.5 | 65.1 | 72 | B |
| PRO | CB | 569 | 194.8 | 127.3 | 64.5 | 71 | B |
| PRO | CG | 569 | 196.0 | 127.4 | 65.4 | 72 | B |
| PRO | C | 569 | 192.4 | 128.1 | 65.0 | 71 | B |
| PRO | O | 569 | 191.9 | 127.2 | 65.7 | 71 | B |
| ARG | N | 570 | 191.7 | 128.9 | 64.2 | 70 | B |
| ARG | CA | 570 | 190.2 | 128.6 | 64.1 | 70 | B |
| ARG | CB | 570 | 189.4 | 129.5 | 64.9 | 71 | B |
| ARG | CG | 570 | 188.4 | 128.7 | 65.8 | 73 | B |
| ARG | CD | 570 | 187.6 | 129.5 | 66.7 | 74 | B |
| ARG | NE | 570 | 186.5 | 130.2 | 65.9 | 76 | B |
| ARG | CZ | 570 | 185.2 | 129.9 | 66.0 | 76 | B |
| ARG | NH1 | 570 | 184.8 | 128.9 | 66.8 | 76 | B |
| ARG | NH2 | 570 | 184.3 | 130.6 | 65.3 | 76 | B |
| ARG | C | 570 | 189.9 | 128.7 | 62.6 | 69 | B |
| ARG | O | 570 | 189.5 | 129.8 | 62.1 | 70 | B |
| LEU | N | 571 | 189.9 | 127.5 | 61.9 | 65 | B |
| LEU | CA | 571 | 189.6 | 127.4 | 60.5 | 61 | B |
| LEU | CB | 571 | 190.0 | 126.1 | 59.9 | 60 | B |
| LEU | CG | 571 | 191.4 | 125.9 | 59.4 | 59 | B |
| LEU | CD1 | 571 | 192.5 | 126.2 | 60.4 | 58 | B |
| LEU | CD2 | 571 | 191.6 | 124.5 | 58.8 | 57 | B |
| LEU | C | 571 | 188.1 | 127.7 | 60.3 | 59 | B |
| LEU | O | 571 | 187.3 | 127.0 | 60.9 | 59 | B |
| VAL | N | 572 | 187.7 | 128.7 | 59.6 | 57 | B |
| VAL | CA | 572 | 186.4 | 129.1 | 59.4 | 57 | B |
| VAL | CB | 572 | 185.9 | 130.3 | 60.3 | 57 | B |
| VAL | CG1 | 572 | 184.4 | 130.6 | 60.1 | 57 | B |
| VAL | CG2 | 572 | 186.3 | 130.0 | 61.7 | 58 | B |
| VAL | C | 572 | 186.1 | 129.5 | 57.9 | 55 | B |
| VAL | O | 572 | 187.0 | 130.1 | 57.3 | 56 | B |
| LEU | N | 573 | 185.0 | 129.1 | 57.3 | 53 | B |
| LEU | CA | 573 | 184.7 | 129.5 | 55.9 | 52 | B |
| LEU | CB | 573 | 183.9 | 128.3 | 55.3 | 52 | B |
| LEU | CG | 573 | 183.3 | 128.6 | 53.9 | 51 | B |
| LEU | CD1 | 573 | 184.5 | 128.8 | 52.9 | 51 | B |
| LEU | CD2 | 573 | 182.4 | 127.5 | 53.5 | 49 | B |
| LEU | C | 573 | 183.8 | 130.7 | 56.0 | 52 | B |
| LEU | O | 573 | 182.7 | 130.7 | 56.3 | 51 | B |
| GLN | N | 574 | 184.4 | 131.9 | 55.6 | 51 | B |
| GLN | CA | 574 | 183.7 | 133.2 | 55.6 | 52 | B |
| GLN | CB | 574 | 184.7 | 134.3 | 55.1 | 53 | B |
| GLN | CG | 574 | 186.1 | 134.3 | 55.9 | 57 | B |
| GLN | CD | 574 | 185.9 | 134.6 | 57.4 | 58 | B |
| GLN | OE1 | 574 | 186.4 | 133.9 | 58.2 | 58 | B |
| GLN | NE2 | 574 | 185.2 | 135.7 | 57.7 | 59 | B |
| GLN | C | 574 | 182.6 | 133.1 | 54.6 | 52 | B |
| GLN | O | 574 | 182.5 | 133.9 | 53.7 | 52 | B |
| ARG | N | 575 | 181.6 | 132.3 | 55.0 | 51 | B |
| ARG | CA | 575 | 180.4 | 132.0 | 54.2 | 52 | B |
| ARG | CB | 575 | 179.6 | 131.0 | 55.0 | 52 | B |
| ARG | CG | 575 | 178.4 | 130.4 | 54.2 | 53 | B |
| ARG | CD | 575 | 177.6 | 129.5 | 55.1 | 53 | B |
| ARG | NE | 575 | 178.5 | 128.3 | 55.5 | 53 | B |
| ARG | CZ | 575 | 178.3 | 127.1 | 55.0 | 54 | B |
| ARG | NH1 | 575 | 177.3 | 126.8 | 54.1 | 54 | B |
| ARG | NH2 | 575 | 179.1 | 126.1 | 55.3 | 54 | B |
| ARG | C | 575 | 179.6 | 133.3 | 53.9 | 52 | B |
| ARG | O | 575 | 179.0 | 133.4 | 52.9 | 51 | B |
| GLU | N | 576 | 179.4 | 134.2 | 54.9 | 54 | B |
| GLU | CA | 576 | 178.6 | 135.4 | 54.7 | 56 | B |
| GLU | CB | 576 | 178.3 | 136.1 | 56.0 | 59 | B |
| GLU | CG | 576 | 177.0 | 135.5 | 56.7 | 63 | B |
| GLU | CD | 576 | 175.8 | 135.4 | 55.7 | 66 | B |
| GLU | OE1 | 576 | 175.5 | 134.3 | 55.2 | 66 | B |
| GLU | OE2 | 576 | 175.2 | 136.5 | 55.4 | 67 | B |
| GLU | C | 576 | 179.3 | 136.3 | 53.7 | 55 | B |
| GLU | O | 576 | 178.7 | 136.8 | 52.8 | 54 | B |
| LYS | N | 577 | 180.6 | 136.5 | 54.0 | 54 | B |
| LYS | CA | 577 | 181.4 | 137.4 | 53.1 | 53 | B |
| LYS | CB | 577 | 182.9 | 137.5 | 53.7 | 55 | B |
| LYS | CG | 577 | 183.3 | 139.0 | 53.8 | 58 | B |
| LYS | CD | 577 | 182.4 | 139.9 | 54.7 | 59 | B |
| LYS | CE | 577 | 181.2 | 140.4 | 54.0 | 61 | B |

TABLE 2-continued

| | | | | | | | |
|---|---|---|---|---|---|---|---|
| LYS | NZ | 577 | 180.2 | 141.0 | 55.0 | 61 | B |
| LYS | C | 577 | 181.5 | 136.9 | 51.7 | 51 | B |
| LYS | O | 577 | 181.4 | 137.7 | 50.7 | 51 | B |
| HIS | N | 578 | 181.5 | 135.5 | 51.5 | 48 | B |
| HIS | CA | 578 | 181.5 | 134.9 | 50.2 | 44 | B |
| HIS | CB | 578 | 181.8 | 133.4 | 50.3 | 40 | B |
| HIS | CG | 578 | 183.2 | 133.1 | 50.8 | 38 | B |
| HIS | CD2 | 578 | 183.7 | 132.0 | 51.4 | 37 | B |
| HIS | ND1 | 578 | 184.2 | 134.0 | 50.8 | 38 | B |
| HIS | CE1 | 578 | 185.3 | 133.4 | 51.3 | 37 | B |
| HIS | NE2 | 578 | 185.1 | 132.2 | 51.7 | 36 | B |
| HIS | C | 578 | 180.1 | 135.0 | 49.5 | 43 | B |
| HIS | O | 578 | 180.0 | 135.2 | 48.3 | 43 | B |
| PHE | N | 579 | 179.1 | 134.9 | 50.4 | 43 | B |
| PHE | CA | 579 | 177.7 | 135.0 | 49.9 | 44 | B |
| PHE | CB | 579 | 176.7 | 134.7 | 51.0 | 46 | B |
| PHE | CG | 579 | 175.3 | 135.1 | 50.7 | 48 | B |
| PHE | CD1 | 579 | 174.6 | 134.4 | 49.7 | 48 | B |
| PHE | CD2 | 579 | 174.7 | 136.1 | 51.4 | 49 | B |
| PHE | CE1 | 579 | 173.3 | 134.8 | 49.4 | 49 | B |
| PHE | CE2 | 579 | 173.4 | 136.5 | 51.1 | 50 | B |
| PHE | CZ | 579 | 172.7 | 135.8 | 50.0 | 50 | B |
| PHE | C | 579 | 177.4 | 136.3 | 49.4 | 44 | B |
| PHE | O | 579 | 176.7 | 136.5 | 48.4 | 45 | B |
| HIS | N | 580 | 177.9 | 137.4 | 50.0 | 46 | B |
| HIS | CA | 580 | 177.7 | 138.7 | 49.6 | 47 | B |
| HIS | CB | 580 | 178.0 | 139.7 | 50.7 | 52 | B |
| HIS | CG | 580 | 177.2 | 139.3 | 52.0 | 55 | B |
| HIS | CD2 | 580 | 175.9 | 139.1 | 52.2 | 56 | B |
| HIS | ND1 | 580 | 177.9 | 139.0 | 53.2 | 57 | B |
| HIS | CE1 | 580 | 177.0 | 138.7 | 54.1 | 57 | B |
| HIS | NE2 | 580 | 175.8 | 138.7 | 53.5 | 57 | B |
| HIS | C | 580 | 178.4 | 139.1 | 48.3 | 46 | B |
| HIS | O | 580 | 178.0 | 139.9 | 47.5 | 46 | B |
| TYR | N | 581 | 179.5 | 138.4 | 48.1 | 44 | B |
| TYR | CA | 581 | 180.4 | 138.6 | 46.9 | 43 | B |
| TYR | CB | 581 | 181.7 | 137.8 | 47.1 | 43 | B |
| TYR | CG | 581 | 182.7 | 137.6 | 45.9 | 42 | B |
| TYR | CD1 | 581 | 183.0 | 138.7 | 45.1 | 42 | B |
| TYR | CE1 | 581 | 183.9 | 138.5 | 44.1 | 41 | B |
| TYR | CD2 | 581 | 183.3 | 136.4 | 45.7 | 42 | B |
| TYR | CE2 | 581 | 184.2 | 136.2 | 44.7 | 40 | B |
| TYR | CZ | 581 | 184.5 | 137.3 | 43.9 | 40 | B |
| TYR | OH | 581 | 185.4 | 137.1 | 42.9 | 40 | B |
| TYR | C | 581 | 179.7 | 137.9 | 45.7 | 42 | B |
| TYR | O | 581 | 179.4 | 138.6 | 44.6 | 41 | B |
| LEU | N | 582 | 179.3 | 136.7 | 45.9 | 41 | B |
| LEU | CA | 582 | 178.6 | 135.9 | 44.9 | 40 | B |
| LEU | CB | 582 | 178.3 | 134.5 | 45.4 | 38 | B |
| LEU | CG | 582 | 179.6 | 133.7 | 45.7 | 36 | B |
| LEU | CD1 | 582 | 179.3 | 132.5 | 46.5 | 36 | B |
| LEU | CD2 | 582 | 180.3 | 133.3 | 44.4 | 36 | B |
| LEU | C | 582 | 177.2 | 136.6 | 44.5 | 43 | B |
| LEU | O | 582 | 176.9 | 136.8 | 43.3 | 43 | B |
| LYS | N | 583 | 176.5 | 136.9 | 45.5 | 48 | B |
| LYS | CA | 583 | 175.2 | 137.5 | 45.4 | 51 | B |
| LYS | CB | 583 | 174.6 | 137.8 | 46.8 | 54 | B |
| LYS | CG | 583 | 173.3 | 138.6 | 46.8 | 59 | B |
| LYS | CD | 583 | 172.8 | 139.0 | 48.3 | 61 | B |
| LYS | CE | 583 | 171.6 | 139.9 | 48.2 | 64 | B |
| LYS | NZ | 583 | 170.9 | 140.2 | 49.5 | 65 | B |
| LYS | C | 583 | 175.2 | 138.8 | 44.5 | 51 | B |
| LYS | O | 583 | 174.2 | 139.1 | 43.8 | 51 | B |
| ARG | N | 584 | 176.3 | 139.5 | 44.6 | 52 | B |
| ARG | CA | 584 | 176.5 | 140.8 | 43.8 | 53 | B |
| ARG | CB | 584 | 177.6 | 141.6 | 44.5 | 55 | B |
| ARG | CG | 584 | 177.1 | 142.5 | 45.6 | 59 | B |
| ARG | CD | 584 | 176.8 | 143.9 | 45.2 | 61 | B |
| ARG | NE | 584 | 176.0 | 143.9 | 44.0 | 63 | B |
| ARG | CZ | 584 | 176.2 | 144.6 | 42.9 | 65 | B |
| ARG | NH1 | 584 | 177.3 | 145.4 | 42.8 | 65 | B |
| ARG | NH2 | 584 | 175.4 | 144.5 | 41.9 | 66 | B |
| ARG | C | 584 | 176.9 | 140.5 | 42.4 | 52 | B |
| ARG | O | 584 | 176.4 | 141.1 | 41.4 | 51 | B |
| GLY | N | 585 | 177.8 | 139.5 | 42.2 | 52 | B |
| GLY | CA | 585 | 178.3 | 139.1 | 40.9 | 49 | B |
| GLY | C | 585 | 177.2 | 138.5 | 40.0 | 48 | B |
| GLY | O | 585 | 177.4 | 138.5 | 38.8 | 47 | B |
| LEU | N | 586 | 176.2 | 137.9 | 40.6 | 47 | B |

TABLE 2-continued

| | | | | | | | |
|---|---|---|---|---|---|---|---|
| LEU | CA | 586 | 175.1 | 137.3 | 39.8 | 47 | B |
| LEU | CB | 586 | 174.2 | 136.5 | 40.7 | 46 | B |
| LEU | CG | 586 | 173.1 | 135.7 | 40.0 | 47 | B |
| LEU | CD1 | 586 | 173.7 | 134.7 | 39.0 | 46 | B |
| LEU | CD2 | 586 | 172.2 | 135.1 | 40.9 | 47 | B |
| LEU | C | 586 | 174.3 | 138.4 | 39.2 | 48 | B |
| LEU | O | 586 | 173.6 | 138.2 | 38.2 | 49 | B |
| ARG | N | 587 | 174.4 | 139.6 | 39.7 | 49 | B |
| ARG | CA | 587 | 173.7 | 140.8 | 39.2 | 48 | B |
| ARG | CB | 587 | 173.1 | 141.6 | 40.4 | 51 | B |
| ARG | CG | 587 | 172.6 | 143.0 | 40.1 | 55 | B |
| ARG | CD | 587 | 171.5 | 142.9 | 39.1 | 58 | B |
| ARG | NE | 587 | 171.3 | 144.2 | 38.5 | 62 | B |
| ARG | CZ | 587 | 171.4 | 144.5 | 37.2 | 64 | B |
| ARG | NH1 | 587 | 171.2 | 145.8 | 36.7 | 65 | B |
| ARG | NH2 | 587 | 171.6 | 143.6 | 36.3 | 65 | B |
| ARG | C | 587 | 174.4 | 141.7 | 38.3 | 47 | B |
| ARG | O | 587 | 173.9 | 142.2 | 37.3 | 45 | B |
| GLN | N | 588 | 175.7 | 142.0 | 38.6 | 46 | B |
| GLN | CA | 588 | 176.5 | 142.8 | 37.8 | 46 | B |
| GLN | CB | 588 | 176.0 | 144.3 | 37.8 | 46 | B |
| GLN | CG | 588 | 176.4 | 145.0 | 39.0 | 47 | B |
| GLN | CD | 588 | 175.9 | 146.4 | 39.1 | 47 | B |
| GLN | OE1 | 588 | 175.1 | 146.8 | 38.3 | 47 | B |
| GLN | NE2 | 588 | 176.3 | 147.1 | 40.1 | 47 | B |
| GLN | C | 588 | 178.0 | 142.8 | 38.1 | 46 | B |
| GLN | O | 588 | 178.4 | 142.6 | 39.3 | 45 | B |
| LEU | N | 589 | 178.9 | 143.0 | 37.1 | 45 | B |
| LEU | CA | 589 | 180.3 | 142.9 | 37.3 | 45 | B |
| LEU | CB | 589 | 180.9 | 141.7 | 36.6 | 43 | B |
| LEU | CG | 589 | 180.3 | 140.4 | 37.0 | 41 | B |
| LEU | CD1 | 589 | 180.4 | 139.3 | 36.0 | 41 | B |
| LEU | CD2 | 589 | 180.9 | 140.0 | 38.3 | 41 | B |
| LEU | C | 589 | 180.9 | 144.2 | 36.7 | 44 | B |
| LEU | O | 589 | 180.3 | 144.8 | 35.8 | 45 | B |
| THR | N | 590 | 182.1 | 144.6 | 37.2 | 44 | B |
| THR | CA | 590 | 182.8 | 145.8 | 36.7 | 45 | B |
| THR | CB | 590 | 184.0 | 146.1 | 37.7 | 45 | B |
| THR | OG1 | 590 | 184.9 | 145.1 | 37.7 | 45 | B |
| THR | CG2 | 590 | 183.5 | 146.5 | 39.1 | 45 | B |
| THR | C | 590 | 183.4 | 145.5 | 35.4 | 45 | B |
| THR | O | 590 | 183.4 | 144.4 | 34.9 | 47 | B |
| ASP | N | 591 | 184.0 | 146.5 | 34.7 | 45 | B |
| ASP | CA | 591 | 184.6 | 146.3 | 33.4 | 45 | B |
| ASP | CB | 591 | 185.0 | 147.7 | 32.8 | 45 | B |
| ASP | CG | 591 | 185.8 | 148.5 | 33.7 | 46 | B |
| ASP | OD1 | 591 | 185.6 | 149.8 | 33.6 | 48 | B |
| ASP | OD2 | 591 | 186.6 | 148.0 | 34.5 | 46 | B |
| ASP | C | 591 | 185.8 | 145.4 | 33.5 | 45 | B |
| ASP | O | 591 | 186.4 | 145.1 | 32.5 | 48 | B |
| ALA | N | 592 | 186.2 | 145.0 | 34.7 | 43 | B |
| ALA | CA | 592 | 187.3 | 144.1 | 34.9 | 41 | B |
| ALA | CB | 592 | 187.7 | 144.1 | 36.4 | 41 | B |
| ALA | C | 592 | 187.0 | 142.8 | 34.4 | 40 | B |
| ALA | O | 592 | 187.8 | 141.9 | 34.2 | 40 | B |
| TYR | N | 593 | 185.7 | 142.6 | 34.1 | 39 | B |
| TYR | CA | 593 | 185.1 | 141.3 | 33.6 | 37 | B |
| TYR | CB | 593 | 183.9 | 140.9 | 34.4 | 38 | B |
| TYR | CG | 593 | 184.3 | 140.0 | 35.6 | 38 | B |
| TYR | CD1 | 593 | 184.4 | 140.5 | 36.9 | 37 | B |
| TYR | CE1 | 593 | 184.9 | 139.7 | 37.9 | 37 | B |
| TYR | CD2 | 593 | 184.5 | 138.7 | 35.4 | 38 | B |
| TYR | CE2 | 593 | 185.0 | 137.8 | 36.4 | 38 | B |
| TYR | CZ | 593 | 185.1 | 138.3 | 37.7 | 37 | B |
| TYR | OH | 593 | 185.6 | 137.5 | 38.7 | 36 | B |
| TYR | C | 593 | 184.8 | 141.4 | 32.1 | 37 | B |
| TYR | O | 593 | 184.0 | 140.6 | 31.6 | 38 | B |
| GLU | N | 594 | 185.3 | 142.4 | 31.5 | 35 | B |
| GLU | CA | 594 | 185.1 | 142.5 | 30.0 | 34 | B |
| GLU | CB | 594 | 185.7 | 143.8 | 29.5 | 35 | B |
| GLU | CG | 594 | 184.9 | 145.1 | 29.8 | 37 | B |
| GLU | CD | 594 | 185.6 | 146.4 | 29.4 | 38 | B |
| GLU | OE1 | 594 | 184.9 | 147.4 | 29.2 | 39 | B |
| GLU | OE2 | 594 | 186.9 | 146.4 | 29.3 | 39 | B |
| GLU | C | 594 | 185.8 | 141.3 | 29.3 | 32 | B |
| GLU | O | 594 | 185.4 | 141.0 | 28.2 | 31 | B |
| CYS | N | 595 | 186.8 | 140.8 | 30.0 | 32 | B |
| CYS | CA | 595 | 187.6 | 139.6 | 29.5 | 31 | B |
| CYS | CB | 595 | 188.9 | 139.5 | 30.2 | 31 | B |

TABLE 2-continued

| | | | | | | | |
|---|---|---|---|---|---|---|---|
| CYS | SG | 595 | 188.9 | 139.1 | 32.0 | 33 | B |
| CYS | C | 595 | 186.9 | 138.3 | 29.5 | 29 | B |
| CYS | O | 595 | 187.4 | 137.3 | 28.9 | 27 | B |
| LEU | N | 596 | 185.8 | 138.2 | 30.2 | 28 | B |
| LEU | CA | 596 | 184.9 | 137.0 | 30.3 | 27 | B |
| LEU | CB | 596 | 184.8 | 136.6 | 31.8 | 26 | B |
| LEU | CG | 596 | 186.0 | 135.8 | 32.3 | 26 | B |
| LEU | CD1 | 596 | 185.8 | 135.6 | 33.8 | 27 | B |
| LEU | CD2 | 596 | 186.2 | 134.5 | 31.6 | 25 | B |
| LEU | C | 596 | 183.6 | 137.3 | 29.7 | 28 | B |
| LEU | O | 596 | 182.6 | 136.7 | 30.1 | 28 | B |
| ASP | N | 597 | 183.6 | 138.3 | 28.8 | 29 | B |
| ASP | CA | 597 | 182.4 | 138.8 | 28.1 | 29 | B |
| ASP | CB | 597 | 182.7 | 140.0 | 27.4 | 30 | B |
| ASP | CG | 597 | 181.5 | 140.6 | 26.7 | 31 | B |
| ASP | OD1 | 597 | 180.4 | 140.6 | 27.3 | 32 | B |
| ASP | OD2 | 597 | 181.6 | 141.0 | 25.5 | 32 | B |
| ASP | C | 597 | 181.8 | 137.7 | 27.1 | 29 | B |
| ASP | O | 597 | 180.7 | 137.8 | 26.6 | 29 | B |
| ALA | N | 598 | 182.6 | 136.7 | 26.9 | 28 | B |
| ALA | CA | 598 | 182.2 | 135.6 | 26.0 | 26 | B |
| ALA | CB | 598 | 183.3 | 135.4 | 24.9 | 25 | B |
| ALA | C | 598 | 182.1 | 134.3 | 26.8 | 25 | B |
| ALA | O | 598 | 182.0 | 133.2 | 26.3 | 23 | B |
| SER | N | 599 | 182.0 | 134.4 | 28.2 | 26 | B |
| SER | CA | 599 | 181.9 | 133.3 | 29.1 | 27 | B |
| SER | CB | 599 | 183.2 | 133.1 | 29.9 | 28 | B |
| SER | OG | 599 | 184.3 | 133.0 | 29.0 | 33 | B |
| SER | C | 599 | 180.8 | 133.6 | 30.1 | 27 | B |
| SER | O | 599 | 180.9 | 133.3 | 31.3 | 28 | B |
| ARG | N | 600 | 179.7 | 134.3 | 29.7 | 25 | B |
| ARG | CA | 600 | 178.7 | 134.6 | 30.6 | 25 | B |
| ARG | CB | 600 | 177.8 | 135.8 | 30.1 | 24 | B |
| ARG | CG | 600 | 178.7 | 137.0 | 30.0 | 25 | B |
| ARG | CD | 600 | 178.0 | 138.2 | 29.4 | 25 | B |
| ARG | NE | 600 | 177.0 | 138.7 | 30.2 | 27 | B |
| ARG | CZ | 600 | 176.0 | 139.4 | 29.8 | 27 | B |
| ARG | NH1 | 600 | 175.9 | 139.8 | 28.5 | 28 | B |
| ARG | NH2 | 600 | 175.0 | 139.8 | 30.6 | 28 | B |
| ARG | C | 600 | 177.9 | 133.4 | 31.2 | 26 | B |
| ARG | O | 600 | 177.5 | 133.5 | 32.4 | 27 | B |
| PRO | N | 601 | 177.7 | 132.4 | 30.5 | 26 | B |
| PRO | CD | 601 | 177.7 | 132.2 | 29.0 | 26 | B |
| PRO | CA | 601 | 176.9 | 131.3 | 31.1 | 26 | B |
| PRO | CB | 601 | 176.7 | 130.3 | 30.0 | 25 | B |
| PRO | CG | 601 | 176.5 | 131.2 | 28.8 | 25 | B |
| PRO | C | 601 | 177.8 | 130.7 | 32.2 | 27 | B |
| PRO | O | 601 | 177.4 | 130.0 | 33.1 | 30 | B |
| TRP | N | 602 | 179.1 | 130.9 | 32.1 | 27 | B |
| TRP | CA | 602 | 180.1 | 130.4 | 33.0 | 26 | B |
| TRP | CB | 602 | 181.5 | 130.6 | 32.6 | 24 | B |
| TRP | CG | 602 | 182.0 | 129.4 | 31.7 | 23 | B |
| TRP | CD2 | 602 | 182.3 | 128.1 | 32.1 | 23 | B |
| TRP | CE2 | 602 | 182.7 | 127.4 | 30.9 | 21 | B |
| TRP | CE3 | 602 | 182.3 | 127.4 | 33.3 | 22 | B |
| TRP | CD1 | 602 | 182.2 | 129.5 | 30.3 | 22 | B |
| TRP | NE1 | 602 | 182.6 | 128.3 | 29.9 | 22 | B |
| TRP | CZ2 | 602 | 183.1 | 126.1 | 30.9 | 21 | B |
| TRP | CZ3 | 602 | 182.7 | 126.1 | 33.3 | 22 | B |
| TRP | CH2 | 602 | 183.1 | 125.4 | 32.1 | 21 | B |
| TRP | C | 602 | 179.9 | 131.2 | 34.3 | 29 | B |
| TRP | O | 602 | 179.9 | 130.6 | 35.4 | 31 | B |
| LEU | N | 603 | 179.7 | 132.5 | 34.2 | 30 | B |
| LEU | CA | 603 | 179.6 | 133.3 | 35.4 | 31 | B |
| LEU | CB | 603 | 179.6 | 134.8 | 35.1 | 31 | B |
| LEU | CG | 603 | 181.1 | 135.1 | 34.6 | 32 | B |
| LEU | CD1 | 603 | 181.1 | 136.4 | 33.8 | 31 | B |
| LEU | CD2 | 603 | 182.0 | 135.2 | 35.9 | 32 | B |
| LEU | C | 603 | 178.3 | 132.9 | 36.1 | 33 | B |
| LEU | O | 603 | 178.3 | 132.8 | 37.4 | 35 | B |
| CYS | N | 604 | 177.2 | 132.5 | 35.4 | 33 | B |
| CYS | CA | 604 | 176.0 | 132.1 | 36.0 | 32 | B |
| CYS | CB | 604 | 174.9 | 131.8 | 35.0 | 32 | B |
| CYS | SG | 604 | 174.4 | 133.2 | 34.0 | 36 | B |
| CYS | C | 604 | 176.3 | 130.8 | 36.8 | 33 | B |
| CYS | O | 604 | 176.0 | 130.6 | 38.0 | 35 | B |
| TYR | N | 605 | 177.0 | 129.8 | 36.1 | 31 | B |
| TYR | CA | 605 | 177.3 | 128.5 | 36.7 | 29 | B |
| TYR | CB | 605 | 177.9 | 127.6 | 35.6 | 29 | B |

TABLE 2-continued

| | | | | | | | |
|---|---|---|---|---|---|---|---|
| TYR | CG | 605 | 178.5 | 126.3 | 36.3 | 28 | B |
| TYR | CD1 | 605 | 177.7 | 125.3 | 36.9 | 28 | B |
| TYR | CE1 | 605 | 178.2 | 124.3 | 37.6 | 25 | B |
| TYR | CD2 | 605 | 179.9 | 126.1 | 36.3 | 26 | B |
| TYR | CE2 | 605 | 180.4 | 125.1 | 37.0 | 25 | B |
| TYR | CZ | 605 | 179.6 | 124.1 | 37.6 | 25 | B |
| TYR | OH | 605 | 180.2 | 123.1 | 38.2 | 27 | B |
| TYR | C | 605 | 178.2 | 128.7 | 37.9 | 29 | B |
| TYR | O | 605 | 177.9 | 128.1 | 38.9 | 31 | B |
| TRP | N | 606 | 179.3 | 129.3 | 37.8 | 30 | B |
| TRP | CA | 606 | 180.2 | 129.5 | 38.9 | 31 | B |
| TRP | CB | 606 | 181.4 | 130.3 | 38.6 | 31 | B |
| TRP | CG | 606 | 182.3 | 129.8 | 37.5 | 30 | B |
| TRP | CD2 | 606 | 183.0 | 130.6 | 36.5 | 30 | B |
| TRP | CE2 | 606 | 183.7 | 129.6 | 35.7 | 30 | B |
| TRP | CE3 | 606 | 183.1 | 131.9 | 36.2 | 31 | B |
| TRP | CD1 | 606 | 182.7 | 128.5 | 37.2 | 30 | B |
| TRP | NE1 | 606 | 183.5 | 128.4 | 36.1 | 30 | B |
| TRP | CZ2 | 606 | 184.5 | 130.1 | 34.6 | 30 | B |
| TRP | CZ3 | 606 | 183.9 | 132.3 | 35.1 | 30 | B |
| TRP | CH2 | 606 | 184.6 | 131.4 | 34.3 | 30 | B |
| TRP | C | 606 | 179.6 | 130.1 | 40.2 | 32 | B |
| TRP | O | 606 | 179.7 | 129.6 | 41.3 | 33 | B |
| ILE | N | 607 | 178.8 | 131.1 | 40.0 | 32 | B |
| ILE | CA | 607 | 178.1 | 131.8 | 41.0 | 32 | B |
| ILE | CB | 607 | 177.6 | 133.2 | 40.6 | 32 | B |
| ILE | CG2 | 607 | 176.6 | 133.8 | 41.5 | 32 | B |
| ILE | CG1 | 607 | 178.8 | 134.1 | 40.3 | 30 | B |
| ILE | CD1 | 607 | 178.4 | 135.3 | 39.5 | 30 | B |
| ILE | C | 607 | 177.0 | 131.0 | 41.6 | 32 | B |
| ILE | O | 607 | 176.9 | 130.7 | 42.8 | 33 | B |
| LEU | N | 608 | 176.1 | 130.5 | 40.7 | 31 | B |
| LEU | CA | 608 | 174.9 | 129.6 | 41.1 | 29 | B |
| LEU | CB | 608 | 174.1 | 129.4 | 39.9 | 29 | B |
| LEU | CG | 608 | 172.7 | 130.0 | 39.8 | 30 | B |
| LEU | CD1 | 608 | 172.8 | 131.5 | 40.0 | 30 | B |
| LEU | CD2 | 608 | 172.1 | 129.7 | 38.4 | 31 | B |
| LEU | C | 608 | 175.4 | 128.3 | 41.6 | 30 | B |
| LEU | O | 608 | 174.5 | 127.5 | 41.9 | 31 | B |
| HIS | N | 609 | 176.6 | 128.0 | 41.6 | 29 | B |
| HIS | CA | 609 | 177.1 | 126.7 | 42.1 | 29 | B |
| HIS | CB | 609 | 178.0 | 126.0 | 41.1 | 27 | B |
| HIS | CG | 609 | 178.5 | 124.6 | 41.6 | 25 | B |
| HIS | CD2 | 609 | 179.7 | 124.2 | 41.8 | 24 | B |
| HIS | ND1 | 609 | 177.6 | 123.7 | 42.1 | 25 | B |
| HIS | CE1 | 609 | 178.3 | 122.7 | 42.5 | 25 | B |
| HIS | NE2 | 609 | 179.6 | 122.9 | 42.4 | 24 | B |
| HIS | C | 609 | 177.7 | 126.9 | 43.4 | 31 | B |
| HIS | O | 609 | 177.8 | 126.0 | 44.3 | 32 | B |
| SER | N | 610 | 178.4 | 128.1 | 43.6 | 34 | B |
| SER | CA | 610 | 179.0 | 128.4 | 44.8 | 36 | B |
| SER | CB | 610 | 179.9 | 129.6 | 44.6 | 35 | B |
| SER | OG | 610 | 180.9 | 129.4 | 43.6 | 34 | B |
| SER | C | 610 | 177.9 | 128.6 | 45.9 | 37 | B |
| SER | O | 610 | 177.9 | 128.1 | 47.0 | 37 | B |
| LEU | N | 611 | 176.9 | 129.4 | 45.4 | 38 | B |
| LEU | CA | 611 | 175.7 | 129.6 | 46.3 | 39 | B |
| LEU | CB | 611 | 174.7 | 130.5 | 45.6 | 37 | B |
| LEU | CG | 611 | 175.2 | 131.9 | 45.1 | 37 | B |
| LEU | CD1 | 611 | 174.2 | 132.6 | 44.2 | 35 | B |
| LEU | CD2 | 611 | 175.6 | 132.7 | 46.4 | 36 | B |
| LEU | C | 611 | 175.1 | 128.3 | 46.6 | 41 | B |
| LEU | O | 611 | 174.7 | 128.1 | 47.7 | 43 | B |
| GLU | N | 612 | 175.0 | 127.4 | 45.6 | 42 | B |
| GLU | CA | 612 | 174.5 | 126.1 | 45.8 | 44 | B |
| GLU | CB | 612 | 174.5 | 125.3 | 44.4 | 44 | B |
| GLU | CG | 612 | 173.9 | 123.9 | 44.5 | 45 | B |
| GLU | CD | 612 | 174.6 | 123.0 | 43.6 | 46 | B |
| GLU | OE1 | 612 | 175.2 | 122.0 | 44.1 | 46 | B |
| GLU | OE2 | 612 | 174.7 | 123.2 | 42.3 | 45 | B |
| GLU | C | 612 | 175.2 | 125.3 | 46.8 | 45 | B |
| GLU | O | 612 | 174.7 | 124.5 | 47.5 | 46 | B |
| LEU | N | 613 | 176.5 | 125.5 | 46.8 | 46 | B |
| LEU | CA | 613 | 177.3 | 124.7 | 47.8 | 48 | B |
| LEU | CB | 613 | 178.8 | 124.7 | 47.3 | 48 | B |
| LEU | CG | 613 | 179.1 | 123.6 | 46.3 | 47 | B |
| LEU | CD1 | 613 | 180.1 | 124.2 | 45.3 | 47 | B |
| LEU | CD2 | 613 | 179.8 | 122.4 | 46.9 | 48 | B |
| LEU | C | 613 | 177.3 | 125.3 | 49.2 | 49 | B |

TABLE 2-continued

| | | | | | | | |
|---|---|---|---|---|---|---|---|
| LEU | O | 613 | 177.3 | 124.6 | 50.2 | 49 | B |
| LEU | N | 614 | 177.1 | 126.7 | 49.2 | 50 | B |
| LEU | CA | 614 | 177.1 | 127.4 | 50.5 | 51 | B |
| LEU | CB | 614 | 177.5 | 128.9 | 50.3 | 48 | B |
| LEU | CG | 614 | 178.9 | 129.1 | 49.8 | 46 | B |
| LEU | CD1 | 614 | 179.1 | 130.5 | 49.4 | 44 | B |
| LEU | CD2 | 614 | 179.9 | 128.7 | 50.9 | 44 | B |
| LEU | C | 614 | 175.7 | 127.3 | 51.1 | 54 | B |
| LEU | O | 614 | 175.3 | 127.9 | 52.1 | 55 | B |
| ASP | N | 615 | 174.8 | 126.5 | 50.4 | 57 | B |
| ASP | CA | 615 | 173.5 | 126.3 | 50.8 | 60 | B |
| ASP | CB | 615 | 173.4 | 125.6 | 52.2 | 61 | B |
| ASP | CG | 615 | 172.1 | 125.0 | 52.5 | 62 | B |
| ASP | OD1 | 615 | 171.2 | 125.0 | 51.7 | 63 | B |
| ASP | OD2 | 615 | 172.0 | 124.5 | 53.7 | 63 | B |
| ASP | C | 615 | 172.7 | 127.6 | 50.8 | 61 | B |
| ASP | O | 615 | 171.7 | 127.7 | 51.6 | 62 | B |
| GLU | N | 616 | 173.1 | 128.5 | 50.0 | 63 | B |
| GLU | CA | 616 | 172.4 | 129.8 | 49.9 | 65 | B |
| GLU | CB | 616 | 173.4 | 130.9 | 49.5 | 65 | B |
| GLU | CG | 616 | 174.6 | 131.0 | 50.6 | 66 | B |
| GLU | CD | 616 | 174.2 | 131.8 | 51.8 | 67 | B |
| GLU | OE1 | 616 | 173.1 | 132.4 | 51.9 | 66 | B |
| GLU | OE2 | 616 | 175.0 | 131.8 | 52.8 | 67 | B |
| GLU | C | 616 | 171.2 | 129.7 | 48.9 | 66 | B |
| GLU | O | 616 | 171.2 | 128.8 | 48.2 | 67 | B |
| PRO | N | 617 | 170.3 | 130.7 | 49.0 | 68 | B |
| PRO | CD | 617 | 170.4 | 131.8 | 49.9 | 70 | B |
| PRO | CA | 617 | 169.1 | 130.8 | 48.2 | 69 | B |
| PRO | CB | 617 | 168.3 | 131.8 | 49.0 | 70 | B |
| PRO | CG | 617 | 169.3 | 132.8 | 49.4 | 71 | B |
| PRO | C | 617 | 169.2 | 131.3 | 46.8 | 69 | B |
| PRO | O | 617 | 170.1 | 132.1 | 46.5 | 71 | B |
| ILE | N | 618 | 168.3 | 130.8 | 45.9 | 69 | B |
| ILE | CA | 618 | 168.3 | 131.2 | 44.5 | 69 | B |
| ILE | CB | 618 | 168.6 | 130.0 | 43.6 | 68 | B |
| ILE | CG2 | 618 | 168.8 | 130.5 | 42.1 | 67 | B |
| ILE | CG1 | 618 | 169.8 | 129.1 | 44.1 | 68 | B |
| ILE | CD1 | 618 | 171.1 | 129.8 | 44.3 | 67 | B |
| ILE | C | 618 | 166.9 | 131.7 | 44.2 | 68 | B |
| ILE | O | 618 | 166.1 | 131.0 | 43.6 | 70 | B |
| PRO | N | 619 | 166.6 | 133.0 | 44.7 | 68 | B |
| PRO | CD | 619 | 167.6 | 133.9 | 45.3 | 67 | B |
| PRO | CA | 619 | 165.3 | 133.7 | 44.5 | 67 | B |
| PRO | CB | 619 | 165.7 | 135.1 | 44.5 | 67 | B |
| PRO | CG | 619 | 166.8 | 135.1 | 45.6 | 67 | B |
| PRO | C | 619 | 164.5 | 133.3 | 43.2 | 67 | B |
| PRO | O | 619 | 165.0 | 133.4 | 42.1 | 68 | B |
| GLN | N | 620 | 163.3 | 132.9 | 43.4 | 68 | B |
| GLN | CA | 620 | 162.4 | 132.5 | 42.4 | 69 | B |
| GLN | CB | 620 | 161.0 | 132.2 | 42.9 | 71 | B |
| GLN | CG | 620 | 160.9 | 131.1 | 44.0 | 73 | B |
| GLN | CD | 620 | 159.6 | 130.5 | 44.3 | 74 | B |
| GLN | OE1 | 620 | 158.5 | 131.0 | 43.9 | 75 | B |
| GLN | NE2 | 620 | 159.6 | 129.3 | 45.0 | 74 | B |
| GLN | C | 620 | 162.3 | 133.5 | 41.2 | 68 | B |
| GLN | O | 620 | 161.7 | 133.1 | 40.2 | 68 | B |
| ILE | N | 621 | 162.8 | 134.7 | 41.4 | 66 | B |
| ILE | CA | 621 | 162.8 | 135.7 | 40.4 | 65 | B |
| ILE | CB | 621 | 162.4 | 137.1 | 41.0 | 66 | B |
| ILE | CG2 | 621 | 162.1 | 138.1 | 39.9 | 65 | B |
| ILE | CG1 | 621 | 161.3 | 137.0 | 42.0 | 67 | B |
| ILE | CD1 | 621 | 161.6 | 136.5 | 43.4 | 67 | B |
| ILE | C | 621 | 164.2 | 135.8 | 39.7 | 63 | B |
| ILE | O | 621 | 164.2 | 136.0 | 38.5 | 62 | B |
| VAL | N | 622 | 165.2 | 135.7 | 40.5 | 60 | B |
| VAL | CA | 622 | 166.6 | 135.7 | 39.9 | 59 | B |
| VAL | CB | 622 | 167.6 | 135.8 | 41.0 | 59 | B |
| VAL | CG1 | 622 | 167.8 | 134.4 | 41.7 | 59 | B |
| VAL | CG2 | 622 | 168.9 | 136.2 | 40.4 | 60 | B |
| VAL | C | 622 | 166.8 | 134.5 | 39.0 | 57 | B |
| VAL | O | 622 | 167.4 | 134.6 | 37.9 | 56 | B |
| ALA | N | 623 | 166.4 | 133.3 | 39.5 | 56 | B |
| ALA | CA | 623 | 166.5 | 132.1 | 38.7 | 54 | B |
| ALA | CB | 623 | 165.9 | 131.0 | 39.5 | 54 | B |
| ALA | C | 623 | 165.8 | 132.2 | 37.4 | 54 | B |
| ALA | O | 623 | 166.3 | 131.8 | 36.4 | 54 | B |
| THR | N | 624 | 164.7 | 132.9 | 37.4 | 52 | B |
| THR | CA | 624 | 164.0 | 133.2 | 36.2 | 52 | B |

TABLE 2-continued

| | | | | | | | |
|---|---|---|---|---|---|---|---|
| THR | CB | 624 | 162.6 | 133.8 | 36.4 | 53 | B |
| THR | OG1 | 624 | 161.8 | 132.9 | 37.2 | 55 | B |
| THR | CG2 | 624 | 161.9 | 134.2 | 35.1 | 53 | B |
| THR | C | 624 | 164.8 | 134.0 | 35.2 | 52 | B |
| THR | O | 624 | 164.9 | 133.7 | 34.1 | 52 | B |
| ASP | N | 625 | 165.3 | 135.1 | 35.7 | 52 | B |
| ASP | CA | 625 | 166.1 | 136.0 | 34.9 | 51 | B |
| ASP | CB | 625 | 166.7 | 137.2 | 35.7 | 53 | B |
| ASP | CG | 625 | 165.6 | 138.0 | 36.4 | 54 | B |
| ASP | OD1 | 625 | 164.6 | 138.3 | 35.8 | 53 | B |
| ASP | OD2 | 625 | 165.8 | 138.3 | 37.6 | 55 | B |
| ASP | C | 625 | 167.3 | 135.2 | 34.3 | 49 | B |
| ASP | O | 625 | 167.5 | 135.3 | 33.1 | 49 | B |
| VAL | N | 626 | 167.9 | 134.4 | 35.1 | 46 | B |
| VAL | CA | 626 | 169.0 | 133.6 | 34.7 | 44 | B |
| VAL | CB | 626 | 169.6 | 132.6 | 31.7 | 42 | B |
| VAL | CG1 | 626 | 170.6 | 131.7 | 35.1 | 40 | B |
| VAL | CG2 | 626 | 170.3 | 133.5 | 36.8 | 41 | B |
| VAL | C | 626 | 168.5 | 132.7 | 33.5 | 44 | B |
| VAL | O | 626 | 169.1 | 132.6 | 32.5 | 44 | B |
| CYS | N | 627 | 167.3 | 132.1 | 33.7 | 44 | B |
| CYS | CA | 627 | 166.7 | 131.3 | 32.7 | 44 | B |
| CYS | CB | 627 | 165.4 | 130.6 | 33.1 | 44 | B |
| CYS | SG | 627 | 165.5 | 129.4 | 34.4 | 45 | B |
| CYS | C | 627 | 166.4 | 132.0 | 31.4 | 45 | B |
| CYS | O | 627 | 166.6 | 131.5 | 30.3 | 45 | B |
| GLN | N | 628 | 166.0 | 133.3 | 31.6 | 47 | B |
| GLN | CA | 628 | 165.6 | 134.2 | 30.5 | 48 | B |
| GLN | CB | 628 | 164.8 | 135.3 | 31.1 | 52 | B |
| GLN | CG | 628 | 164.6 | 136.6 | 30.1 | 57 | B |
| GLN | CD | 628 | 163.7 | 137.6 | 30.8 | 60 | B |
| GLN | OE1 | 628 | 162.6 | 137.9 | 30.3 | 62 | B |
| GLN | NE2 | 628 | 164.2 | 138.2 | 31.9 | 61 | B |
| GLN | C | 628 | 166.8 | 134.7 | 29.8 | 46 | B |
| GLN | O | 628 | 166.8 | 134.9 | 28.6 | 46 | B |
| PHE | N | 629 | 167.9 | 134.8 | 30.5 | 43 | B |
| PHE | CA | 629 | 169.2 | 135.3 | 30.0 | 41 | B |
| PHE | CB | 629 | 170.1 | 135.8 | 31.1 | 39 | B |
| PHE | CG | 629 | 171.5 | 136.1 | 30.6 | 39 | B |
| PHE | CD1 | 629 | 171.7 | 137.1 | 29.6 | 40 | B |
| PHE | CD2 | 629 | 172.6 | 135.4 | 31.0 | 39 | B |
| PHE | CE1 | 629 | 173.0 | 137.4 | 29.1 | 39 | B |
| PHE | CE2 | 629 | 173.9 | 135.7 | 30.5 | 38 | B |
| PHE | CZ | 629 | 174.1 | 136.7 | 29.5 | 38 | B |
| PHE | C | 629 | 169.8 | 134.2 | 29.1 | 40 | B |
| PHE | O | 629 | 170.2 | 134.4 | 28.0 | 40 | B |
| LEU | N | 630 | 169.9 | 133.0 | 29.7 | 39 | B |
| LEU | CA | 630 | 170.5 | 131.8 | 29.0 | 36 | B |
| LEU | CB | 630 | 170.5 | 130.6 | 30.0 | 33 | B |
| LEU | CG | 630 | 171.4 | 130.7 | 31.2 | 31 | B |
| LEU | CD1 | 630 | 171.4 | 129.4 | 32.0 | 30 | B |
| LEU | CD2 | 630 | 172.8 | 131.0 | 30.7 | 31 | B |
| LEU | C | 630 | 169.7 | 131.5 | 27.7 | 38 | B |
| LEU | O | 630 | 170.3 | 131.1 | 26.7 | 38 | B |
| GLU | N | 631 | 168.4 | 131.8 | 27.7 | 39 | B |
| GLU | CA | 631 | 167.6 | 131.6 | 26.6 | 42 | B |
| GLU | CB | 631 | 166.1 | 131.9 | 26.9 | 46 | B |
| GLU | CG | 631 | 165.1 | 131.3 | 26.0 | 52 | B |
| GLU | CD | 631 | 163.7 | 131.0 | 26.8 | 56 | B |
| GLU | OE1 | 631 | 163.0 | 130.1 | 26.3 | 58 | B |
| GLU | OE2 | 631 | 163.4 | 131.8 | 27.7 | 57 | B |
| GLU | C | 631 | 168.1 | 132.5 | 25.4 | 42 | B |
| GLU | O | 631 | 168.0 | 132.2 | 24.3 | 42 | B |
| LEU | N | 632 | 168.6 | 133.7 | 25.8 | 42 | B |
| LEU | CA | 632 | 169.2 | 134.7 | 24.9 | 42 | B |
| LEU | CB | 632 | 169.3 | 136.0 | 25.6 | 42 | B |
| LEU | CG | 632 | 168.0 | 136.8 | 25.8 | 42 | B |
| LEU | CD1 | 632 | 168.0 | 137.8 | 27.0 | 42 | B |
| LEU | CD2 | 632 | 167.6 | 137.5 | 24.5 | 41 | B |
| LEU | C | 632 | 170.6 | 134.3 | 24.4 | 42 | B |
| LEU | O | 632 | 171.0 | 134.7 | 23.4 | 42 | B |
| CYS | N | 633 | 171.3 | 133.5 | 25.2 | 42 | B |
| CYS | CA | 633 | 172.6 | 132.9 | 24.9 | 42 | B |
| CYS | CB | 633 | 173.3 | 132.5 | 26.2 | 40 | B |
| CYS | SG | 633 | 173.8 | 133.8 | 27.2 | 40 | B |
| CYS | C | 633 | 172.5 | 131.8 | 23.9 | 43 | B |
| CYS | O | 633 | 173.3 | 131.6 | 23.1 | 44 | B |
| GLN | N | 634 | 171.4 | 131.0 | 24.1 | 43 | B |
| GLN | CA | 634 | 171.1 | 129.8 | 23.3 | 43 | B |

TABLE 2-continued

| | | | | | | | |
|---|---|---|---|---|---|---|---|
| GLN | CB | 634 | 169.9 | 129.1 | 23.7 | 42 | B |
| GLN | CG | 634 | 169.6 | 127.7 | 23.2 | 41 | B |
| GLN | CD | 634 | 168.5 | 127.0 | 23.9 | 41 | B |
| GLN | OE1 | 634 | 168.6 | 125.8 | 24.1 | 41 | B |
| GLN | NE2 | 634 | 167.5 | 127.7 | 24.2 | 41 | B |
| GLN | C | 634 | 171.0 | 130.1 | 21.8 | 43 | B |
| GLN | O | 634 | 170.4 | 131.1 | 21.4 | 43 | B |
| SER | N | 635 | 171.6 | 129.3 | 20.9 | 44 | B |
| SER | CA | 635 | 171.6 | 129.5 | 19.5 | 45 | B |
| SER | CB | 635 | 173.0 | 129.0 | 18.9 | 44 | B |
| SER | OG | 635 | 173.0 | 129.1 | 17.5 | 44 | B |
| SER | C | 635 | 170.5 | 128.7 | 18.7 | 47 | B |
| SER | O | 635 | 170.0 | 127.7 | 19.2 | 47 | B |
| PRO | N | 636 | 170.0 | 129.4 | 17.7 | 47 | B |
| PRO | CD | 636 | 170.3 | 130.7 | 17.2 | 47 | B |
| PRO | CA | 636 | 168.9 | 128.7 | 16.9 | 48 | B |
| PRO | CB | 636 | 168.5 | 129.8 | 15.9 | 48 | B |
| PRO | CG | 636 | 169.8 | 130.6 | 15.7 | 48 | B |
| PRO | C | 636 | 169.4 | 127.4 | 16.2 | 49 | B |
| PRO | O | 636 | 168.7 | 126.6 | 15.7 | 50 | B |
| ASP | N | 637 | 170.7 | 127.2 | 16.3 | 48 | B |
| ASP | CA | 637 | 171.3 | 126.0 | 15.7 | 47 | B |
| ASP | CB | 637 | 172.7 | 126.4 | 15.0 | 50 | B |
| ASP | CG | 637 | 172.4 | 127.3 | 13.8 | 53 | B |
| ASP | OD1 | 637 | 171.4 | 127.1 | 13.1 | 54 | B |
| ASP | OD2 | 637 | 173.3 | 128.2 | 13.6 | 53 | B |
| ASP | C | 637 | 171.6 | 125.0 | 16.9 | 46 | B |
| ASP | O | 637 | 172.1 | 123.9 | 16.6 | 46 | B |
| GLY | N | 638 | 171.2 | 125.4 | 18.1 | 43 | B |
| GLY | CA | 638 | 171.4 | 124.6 | 19.2 | 39 | B |
| GLY | C | 638 | 172.6 | 124.9 | 20.0 | 38 | B |
| GLY | O | 638 | 173.6 | 125.5 | 19.5 | 38 | B |
| GLY | N | 639 | 172.6 | 124.6 | 21.3 | 37 | B |
| GLY | CA | 639 | 173.8 | 124.9 | 22.1 | 35 | B |
| GLY | C | 639 | 173.7 | 126.4 | 22.6 | 34 | B |
| GLY | O | 639 | 172.8 | 127.1 | 22.4 | 33 | B |
| PHE | N | 640 | 174.8 | 126.8 | 23.4 | 33 | B |
| PHE | CA | 640 | 174.8 | 128.1 | 23.9 | 34 | B |
| PHE | CB | 640 | 174.7 | 128.1 | 25.4 | 35 | B |
| PHE | CG | 640 | 173.4 | 127.5 | 25.9 | 36 | B |
| PHE | CD1 | 640 | 173.2 | 126.2 | 25.9 | 38 | B |
| PHE | CD2 | 640 | 172.3 | 128.4 | 26.2 | 37 | B |
| PHE | CE1 | 640 | 171.9 | 125.6 | 26.3 | 39 | B |
| PHE | CE2 | 640 | 171.1 | 127.9 | 26.6 | 38 | B |
| PHE | CZ | 640 | 170.9 | 126.5 | 26.6 | 40 | B |
| PHE | C | 640 | 176.0 | 128.9 | 23.6 | 33 | B |
| PHE | O | 640 | 177.1 | 128.4 | 23.5 | 34 | B |
| GLY | N | 641 | 175.8 | 130.3 | 23.4 | 31 | B |
| GLY | CA | 641 | 177.0 | 131.1 | 23.1 | 31 | B |
| GLY | C | 641 | 177.5 | 131.7 | 24.4 | 32 | B |
| GLY | O | 641 | 177.0 | 131.4 | 25.5 | 33 | B |
| GLY | N | 642 | 178.5 | 132.6 | 24.3 | 33 | B |
| GLY | CA | 642 | 179.1 | 133.2 | 25.6 | 33 | B |
| GLY | C | 642 | 178.3 | 134.4 | 26.1 | 32 | B |
| GLY | O | 642 | 178.6 | 134.9 | 27.2 | 32 | B |
| GLY | N | 643 | 177.3 | 134.8 | 25.3 | 32 | B |
| GLY | CA | 643 | 176.5 | 135.9 | 25.7 | 31 | B |
| GLY | C | 643 | 175.4 | 136.0 | 24.6 | 32 | B |
| GLY | O | 643 | 175.4 | 135.3 | 23.6 | 32 | B |
| PRO | N | 644 | 174.4 | 137.0 | 24.8 | 32 | B |
| PRO | CD | 644 | 174.1 | 137.9 | 25.9 | 32 | B |
| PRO | CA | 644 | 173.4 | 137.1 | 23.7 | 32 | B |
| PRO | CB | 644 | 172.6 | 138.3 | 24.2 | 32 | B |
| PRO | CG | 644 | 172.7 | 138.2 | 25.7 | 31 | B |
| PRO | C | 644 | 174.0 | 137.3 | 22.4 | 31 | B |
| PRO | O | 644 | 174.9 | 138.1 | 22.2 | 33 | B |
| GLY | N | 645 | 173.6 | 136.4 | 21.4 | 32 | B |
| GLY | CA | 645 | 174.1 | 136.6 | 20.1 | 33 | B |
| GLY | C | 645 | 175.4 | 136.0 | 19.7 | 35 | B |
| GLY | O | 645 | 175.9 | 136.2 | 18.5 | 37 | B |
| GLN | N | 646 | 176.1 | 135.2 | 20.6 | 33 | B |
| GLN | CA | 646 | 177.4 | 134.6 | 20.2 | 32 | B |
| GLN | CB | 646 | 178.3 | 134.6 | 21.5 | 31 | B |
| GLN | CG | 646 | 178.7 | 136.0 | 21.9 | 29 | B |
| GLN | CD | 646 | 179.4 | 136.0 | 23.2 | 27 | B |
| GLN | OE1 | 646 | 179.1 | 136.9 | 24.0 | 29 | B |
| GLN | NE2 | 646 | 180.3 | 135.1 | 23.4 | 27 | B |
| GLN | C | 646 | 177.2 | 133.2 | 19.7 | 32 | B |
| GLN | O | 646 | 176.3 | 132.5 | 20.2 | 33 | B |

TABLE 2-continued

| | | | | | | | |
|---|---|---|---|---|---|---|---|
| TYR | N | 647 | 178.0 | 132.8 | 18.8 | 30 | B |
| TYR | CA | 647 | 178.0 | 131.5 | 18.2 | 29 | B |
| TYR | CB | 647 | 179.2 | 131.3 | 17.3 | 28 | B |
| TYR | CG | 647 | 179.2 | 132.2 | 16.1 | 29 | B |
| TYR | CD1 | 647 | 180.3 | 132.4 | 15.3 | 29 | B |
| TYR | CE1 | 647 | 180.2 | 133.2 | 14.2 | 30 | B |
| TYR | CD2 | 647 | 178.0 | 133.0 | 15.8 | 29 | B |
| TYR | CE2 | 647 | 178.0 | 133.8 | 14.7 | 29 | B |
| TYR | CZ | 647 | 179.0 | 133.9 | 13.9 | 30 | B |
| TYR | OH | 647 | 178.9 | 134.7 | 12.8 | 33 | B |
| TYR | C | 647 | 178.1 | 130.4 | 19.3 | 29 | B |
| TYR | O | 647 | 178.9 | 130.6 | 20.3 | 30 | B |
| PRO | N | 648 | 177.3 | 129.4 | 19.3 | 28 | B |
| PRO | CD | 648 | 176.4 | 128.9 | 18.2 | 27 | B |
| PRO | CA | 648 | 177.3 | 128.3 | 20.3 | 25 | B |
| PRO | CB | 648 | 176.3 | 127.3 | 19.8 | 25 | B |
| PRO | CG | 648 | 176.4 | 127.4 | 18.4 | 26 | B |
| PRO | C | 648 | 178.7 | 127.8 | 20.5 | 24 | B |
| PRO | O | 648 | 179.4 | 127.7 | 19.5 | 27 | B |
| HIS | N | 649 | 179.0 | 127.3 | 21.7 | 21 | B |
| HIS | CA | 649 | 180.4 | 126.8 | 21.9 | 19 | B |
| HIS | CB | 649 | 181.3 | 128.0 | 22.4 | 18 | B |
| HIS | CG | 649 | 182.7 | 127.6 | 22.6 | 15 | B |
| HIS | CD2 | 649 | 183.8 | 128.1 | 22.0 | 14 | B |
| HIS | ND1 | 649 | 183.1 | 126.8 | 23.7 | 14 | B |
| HIS | CE1 | 649 | 184.4 | 126.8 | 23.7 | 13 | B |
| HIS | NE2 | 649 | 184.9 | 127.6 | 22.7 | 12 | B |
| HIS | C | 649 | 180.1 | 125.8 | 23.0 | 20 | B |
| HIS | O | 649 | 179.3 | 126.0 | 23.9 | 21 | B |
| LEU | N | 650 | 180.8 | 124.7 | 23.0 | 21 | B |
| LEU | CA | 650 | 180.6 | 123.6 | 24.0 | 21 | B |
| LEU | CB | 650 | 181.4 | 122.3 | 23.6 | 20 | B |
| LEU | CG | 650 | 180.7 | 121.4 | 22.6 | 19 | B |
| LEU | CD1 | 650 | 181.6 | 120.2 | 22.4 | 18 | B |
| LEU | CD2 | 650 | 179.4 | 120.9 | 23.1 | 18 | B |
| LEU | C | 650 | 180.9 | 124.0 | 25.4 | 23 | B |
| LEU | O | 650 | 180.3 | 123.5 | 26.4 | 24 | B |
| ALA | N | 651 | 181.9 | 124.9 | 25.7 | 24 | B |
| ALA | CA | 651 | 182.2 | 125.3 | 27.1 | 25 | B |
| ALA | CB | 651 | 183.5 | 126.1 | 27.2 | 23 | B |
| ALA | C | 651 | 181.0 | 126.1 | 27.7 | 26 | B |
| ALA | O | 651 | 180.5 | 125.7 | 28.8 | 25 | B |
| PRO | N | 652 | 180.4 | 127.1 | 27.0 | 26 | B |
| PRO | CD | 652 | 181.0 | 127.8 | 25.8 | 27 | B |
| PRO | CA | 652 | 179.3 | 127.9 | 27.5 | 27 | B |
| PRO | CB | 652 | 179.1 | 129.0 | 26.4 | 27 | B |
| PRO | CG | 652 | 180.4 | 129.2 | 25.9 | 27 | B |
| PRO | C | 652 | 178.0 | 126.9 | 27.6 | 28 | B |
| PRO | O | 652 | 177.1 | 127.1 | 28.4 | 29 | B |
| THR | N | 653 | 177.9 | 126.0 | 26.6 | 26 | B |
| THR | CA | 653 | 176.8 | 125.0 | 26.5 | 24 | B |
| THR | CB | 653 | 176.9 | 124.1 | 25.3 | 23 | B |
| THR | OG1 | 653 | 176.8 | 124.9 | 24.1 | 21 | B |
| THR | CG2 | 653 | 175.8 | 123.0 | 25.3 | 23 | B |
| THR | C | 653 | 176.8 | 124.1 | 27.8 | 23 | B |
| THR | O | 653 | 175.8 | 123.9 | 28.5 | 24 | B |
| TYR | N | 654 | 178.0 | 123.6 | 28.1 | 23 | B |
| TYR | CA | 654 | 178.2 | 122.8 | 29.3 | 22 | B |
| TYR | CB | 654 | 179.6 | 122.4 | 29.5 | 19 | B |
| TYR | CG | 654 | 180.0 | 122.0 | 30.9 | 18 | B |
| TYR | CD1 | 654 | 179.8 | 120.7 | 31.3 | 17 | B |
| TYR | CE1 | 654 | 180.2 | 120.2 | 32.5 | 17 | B |
| TYR | CD2 | 654 | 180.6 | 122.9 | 31.8 | 18 | B |
| TYR | CE2 | 654 | 181.0 | 122.4 | 33.1 | 17 | B |
| TYR | CZ | 654 | 180.8 | 121.1 | 33.4 | 18 | B |
| TYR | OH | 654 | 181.2 | 120.7 | 34.7 | 19 | B |
| TYR | C | 654 | 177.7 | 123.6 | 30.5 | 24 | B |
| TYR | O | 654 | 177.0 | 123.2 | 31.4 | 25 | B |
| ALA | N | 655 | 178.2 | 124.9 | 30.6 | 27 | B |
| ALA | CA | 655 | 177.9 | 125.8 | 31.7 | 27 | B |
| ALA | CB | 655 | 178.7 | 127.0 | 31.6 | 26 | B |
| ALA | C | 655 | 176.4 | 126.1 | 31.8 | 27 | B |
| ALA | O | 655 | 175.8 | 126.0 | 32.9 | 27 | B |
| ALA | N | 656 | 175.8 | 126.5 | 30.7 | 27 | B |
| ALA | CA | 656 | 174.4 | 126.8 | 30.6 | 28 | B |
| ALA | CB | 656 | 174.0 | 127.2 | 29.2 | 27 | B |
| ALA | C | 656 | 173.6 | 125.7 | 31.2 | 30 | B |
| ALA | O | 656 | 172.7 | 125.8 | 32.0 | 32 | B |
| VAL | N | 657 | 173.8 | 124.5 | 30.6 | 31 | B |

TABLE 2-continued

| | | | | | | | |
|---|---|---|---|---|---|---|---|
| VAL | CA | 657 | 173.1 | 123.3 | 31.1 | 31 | B |
| VAL | CB | 657 | 173.4 | 122.0 | 30.2 | 30 | B |
| VAL | CG1 | 657 | 172.6 | 120.8 | 30.6 | 29 | B |
| VAL | CG2 | 657 | 173.2 | 122.3 | 28.8 | 29 | B |
| VAL | C | 657 | 173.2 | 123.0 | 32.6 | 32 | B |
| VAL | O | 657 | 172.3 | 122.8 | 33.2 | 33 | B |
| ASN | N | 658 | 174.5 | 123.1 | 33.1 | 32 | B |
| ASN | CA | 658 | 174.7 | 122.9 | 34.5 | 31 | B |
| ASN | CB | 658 | 176.2 | 122.9 | 34.8 | 30 | B |
| ASN | CG | 658 | 176.7 | 121.6 | 34.9 | 30 | B |
| ASN | OD1 | 658 | 176.1 | 120.6 | 34.5 | 31 | B |
| ASN | ND2 | 658 | 177.9 | 121.4 | 35.5 | 30 | B |
| ASN | C | 658 | 173.9 | 124.0 | 35.3 | 33 | B |
| ASN | O | 658 | 173.3 | 123.6 | 36.3 | 33 | B |
| ALA | N | 659 | 173.9 | 125.2 | 34.8 | 34 | B |
| ALA | CA | 659 | 173.2 | 126.3 | 35.5 | 34 | B |
| ALA | CB | 659 | 173.4 | 127.6 | 34.8 | 33 | B |
| ALA | C | 659 | 171.7 | 125.9 | 35.6 | 35 | B |
| ALA | O | 659 | 171.2 | 125.7 | 36.7 | 34 | B |
| LEU | N | 660 | 171.1 | 125.8 | 34.4 | 35 | B |
| LEU | CA | 660 | 169.7 | 125.4 | 34.3 | 35 | B |
| LEU | CB | 660 | 169.4 | 125.1 | 32.9 | 35 | B |
| LEU | CG | 660 | 169.4 | 126.3 | 31.9 | 36 | B |
| LEU | CD1 | 660 | 169.2 | 125.8 | 30.5 | 36 | B |
| LEU | CD2 | 660 | 168.3 | 127.2 | 32.3 | 35 | B |
| LEU | C | 660 | 169.3 | 124.2 | 35.2 | 37 | B |
| LEU | O | 660 | 168.2 | 124.2 | 35.8 | 38 | B |
| CYS | N | 661 | 170.2 | 123.2 | 35.4 | 38 | B |
| CYS | CA | 661 | 169.9 | 122.1 | 36.3 | 39 | B |
| CYS | CB | 661 | 170.8 | 120.9 | 35.9 | 39 | B |
| CYS | SG | 661 | 170.4 | 120.1 | 34.4 | 39 | B |
| CYS | C | 661 | 170.0 | 122.5 | 37.7 | 40 | B |
| CYS | O | 661 | 169.3 | 121.9 | 38.6 | 42 | B |
| ILE | N | 662 | 171.0 | 123.4 | 38.1 | 41 | B |
| ILE | CA | 662 | 171.1 | 123.8 | 39.5 | 40 | B |
| ILE | CB | 662 | 172.3 | 124.8 | 39.6 | 39 | B |
| ILE | CG2 | 662 | 172.4 | 125.3 | 41.1 | 38 | B |
| ILE | CG1 | 662 | 173.6 | 124.0 | 39.3 | 38 | B |
| ILE | CD1 | 662 | 174.9 | 124.9 | 39.6 | 37 | B |
| ILE | C | 662 | 169.8 | 124.4 | 39.9 | 41 | B |
| ILE | O | 662 | 169.3 | 124.2 | 41.0 | 40 | B |
| ILE | N | 663 | 169.2 | 125.3 | 39.0 | 42 | B |
| ILE | CA | 663 | 168.0 | 125.9 | 39.3 | 44 | B |
| ILE | CB | 663 | 167.5 | 126.8 | 38.2 | 44 | B |
| ILE | CG2 | 663 | 166.1 | 127.4 | 38.5 | 44 | B |
| ILE | CG1 | 663 | 168.5 | 128.0 | 38.1 | 44 | B |
| ILE | CD1 | 663 | 168.3 | 128.9 | 36.9 | 43 | B |
| ILE | C | 663 | 167.0 | 124.7 | 39.4 | 47 | B |
| ILE | O | 663 | 166.5 | 124.3 | 40.4 | 49 | B |
| GLY | N | 664 | 166.9 | 123.9 | 38.3 | 48 | B |
| GLY | CA | 664 | 166.1 | 122.7 | 38.2 | 49 | B |
| GLY | C | 664 | 164.5 | 122.9 | 38.3 | 50 | B |
| GLY | O | 664 | 163.9 | 122.3 | 39.2 | 51 | B |
| THR | N | 665 | 163.9 | 123.5 | 37.4 | 49 | B |
| THR | CA | 665 | 162.5 | 123.7 | 37.4 | 48 | B |
| THR | CB | 665 | 162.2 | 125.2 | 37.7 | 48 | B |
| THR | OG1 | 665 | 162.6 | 126.0 | 36.6 | 48 | B |
| THR | CG2 | 665 | 162.9 | 125.6 | 39.0 | 48 | B |
| THR | C | 665 | 162.0 | 123.5 | 36.0 | 50 | B |
| THR | O | 665 | 162.7 | 123.7 | 35.0 | 50 | B |
| GLU | N | 666 | 160.7 | 123.2 | 35.9 | 51 | B |
| GLU | CA | 666 | 160.1 | 123.0 | 34.5 | 53 | B |
| GLU | CB | 666 | 158.6 | 123.1 | 34.6 | 56 | B |
| GLU | CG | 666 | 157.9 | 121.8 | 35.0 | 59 | B |
| GLU | CD | 666 | 158.4 | 120.6 | 34.2 | 61 | B |
| GLU | OE1 | 666 | 159.0 | 119.7 | 34.9 | 62 | B |
| GLU | OE2 | 666 | 158.3 | 120.5 | 33.0 | 61 | B |
| GLU | C | 666 | 160.6 | 124.1 | 33.6 | 53 | B |
| GLU | O | 666 | 160.9 | 123.8 | 32.4 | 53 | B |
| GLU | N | 667 | 160.6 | 125.4 | 34.0 | 52 | B |
| GLU | CA | 667 | 161.0 | 126.5 | 33.3 | 51 | B |
| GLU | CB | 667 | 160.9 | 127.8 | 34.1 | 53 | B |
| GLU | CG | 667 | 161.4 | 129.0 | 33.3 | 54 | B |
| GLU | CD | 667 | 161.4 | 130.3 | 34.2 | 55 | B |
| GLU | OE1 | 667 | 161.7 | 130.1 | 35.4 | 55 | B |
| GLU | OE2 | 667 | 161.2 | 131.4 | 33.7 | 55 | B |
| GLU | C | 667 | 162.5 | 126.4 | 32.8 | 50 | B |
| GLU | O | 667 | 162.7 | 126.5 | 31.6 | 50 | B |
| ALA | N | 668 | 163.4 | 126.2 | 33.7 | 47 | B |

TABLE 2-continued

| | | | | | | | |
|---|---|---|---|---|---|---|---|
| ALA | CA | 668 | 164.8 | 126.1 | 33.4 | 46 | B |
| ALA | CB | 668 | 165.6 | 125.9 | 34.7 | 46 | B |
| ALA | C | 668 | 165.1 | 125.0 | 32.4 | 46 | B |
| ALA | O | 668 | 165.6 | 125.2 | 31.3 | 47 | B |
| TYR | N | 669 | 164.6 | 123.8 | 32.8 | 44 | B |
| TYR | CA | 669 | 164.8 | 122.6 | 31.9 | 43 | B |
| TYR | CB | 669 | 164.0 | 121.4 | 32.5 | 41 | B |
| TYR | CG | 669 | 164.5 | 120.9 | 33.8 | 39 | B |
| TYR | CD1 | 669 | 163.6 | 120.2 | 34.7 | 39 | B |
| TYR | CE1 | 669 | 164.0 | 119.7 | 35.9 | 38 | B |
| TYR | CD2 | 669 | 165.8 | 120.9 | 34.2 | 39 | B |
| TYR | CE2 | 669 | 166.2 | 120.4 | 35.4 | 39 | B |
| TYR | CZ | 669 | 165.3 | 119.8 | 36.2 | 38 | B |
| TYR | OH | 669 | 165.7 | 119.3 | 37.4 | 37 | B |
| TYR | C | 669 | 164.2 | 122.9 | 30.6 | 44 | B |
| TYR | O | 669 | 164.8 | 122.5 | 29.5 | 45 | B |
| ASN | N | 670 | 163.0 | 123.6 | 30.5 | 43 | B |
| ASN | CA | 670 | 162.4 | 123.9 | 29.3 | 44 | B |
| ASN | CB | 670 | 160.9 | 124.3 | 29.5 | 47 | B |
| ASN | CG | 670 | 160.0 | 123.2 | 29.8 | 49 | B |
| ASN | OD1 | 670 | 160.4 | 122.0 | 29.9 | 51 | B |
| ASN | ND2 | 670 | 158.7 | 123.5 | 30.0 | 51 | B |
| ASN | C | 670 | 163.1 | 124.9 | 28.4 | 45 | B |
| ASN | O | 670 | 162.7 | 125.1 | 27.2 | 46 | B |
| VAL | N | 671 | 164.1 | 125.6 | 28.9 | 43 | B |
| VAL | CA | 671 | 164.9 | 126.5 | 28.1 | 40 | B |
| VAL | CB | 671 | 165.9 | 127.4 | 29.0 | 40 | B |
| VAL | CG1 | 671 | 166.7 | 128.3 | 28.1 | 39 | B |
| VAL | CG2 | 671 | 165.1 | 128.2 | 30.0 | 40 | B |
| VAL | C | 671 | 165.8 | 125.8 | 27.1 | 40 | B |
| VAL | O | 671 | 165.9 | 126.2 | 25.9 | 40 | B |
| ILE | N | 672 | 166.3 | 124.6 | 27.5 | 39 | B |
| ILE | CA | 672 | 167.1 | 123.7 | 26.7 | 37 | B |
| ILE | CB | 672 | 167.7 | 122.6 | 27.6 | 34 | B |
| ILE | CG2 | 672 | 168.8 | 121.9 | 26.8 | 34 | B |
| ILE | CG1 | 672 | 168.3 | 123.1 | 28.9 | 32 | B |
| ILE | CD1 | 672 | 168.8 | 122.1 | 29.8 | 29 | B |
| ILE | C | 672 | 166.4 | 123.0 | 25.5 | 39 | B |
| ILE | O | 672 | 165.5 | 122.2 | 25.7 | 40 | B |
| ASN | N | 673 | 166.8 | 123.4 | 24.3 | 39 | B |
| ASN | CA | 673 | 166.2 | 122.8 | 23.1 | 39 | B |
| ASN | CB | 673 | 166.3 | 123.8 | 21.9 | 39 | B |
| ASN | CG | 673 | 165.8 | 123.2 | 20.6 | 41 | B |
| ASN | OD1 | 673 | 165.7 | 122.0 | 20.4 | 41 | B |
| ASN | ND2 | 673 | 165.4 | 124.2 | 19.8 | 40 | B |
| ASN | C | 673 | 167.0 | 121.5 | 22.8 | 39 | B |
| ASN | O | 673 | 168.1 | 121.6 | 22.1 | 38 | B |
| ARG | N | 674 | 166.5 | 120.4 | 23.2 | 40 | B |
| ARG | CA | 674 | 167.1 | 119.1 | 23.0 | 40 | B |
| ARG | CB | 674 | 166.3 | 118.1 | 23.8 | 38 | B |
| ARG | CG | 674 | 166.3 | 118.3 | 25.3 | 37 | B |
| ARG | CD | 674 | 165.3 | 117.3 | 25.9 | 38 | B |
| ARG | NE | 674 | 165.7 | 115.9 | 25.7 | 38 | B |
| ARG | CZ | 674 | 165.1 | 115.0 | 24.9 | 37 | B |
| ARG | NH1 | 674 | 164.0 | 115.3 | 24.2 | 38 | B |
| ARG | NH2 | 674 | 165.5 | 113.8 | 24.9 | 37 | B |
| ARG | C | 674 | 167.2 | 118.5 | 21.6 | 41 | B |
| ARG | O | 674 | 168.1 | 117.7 | 21.3 | 41 | B |
| GLU | N | 675 | 166.3 | 119.0 | 20.7 | 44 | B |
| GLU | CA | 675 | 166.3 | 118.5 | 19.3 | 47 | B |
| GLU | CB | 675 | 164.9 | 118.7 | 18.6 | 51 | B |
| GLU | CG | 675 | 163.9 | 119.7 | 19.3 | 57 | B |
| GLU | CD | 675 | 163.4 | 119.1 | 20.7 | 59 | B |
| GLU | OE1 | 675 | 163.5 | 119.8 | 21.7 | 60 | B |
| GLU | OE2 | 675 | 162.8 | 118.0 | 20.7 | 61 | B |
| GLU | C | 675 | 167.4 | 119.3 | 18.6 | 46 | B |
| GLU | O | 675 | 168.0 | 118.8 | 17.6 | 47 | B |
| LYS | N | 676 | 167.6 | 120.5 | 19.0 | 44 | B |
| LYS | CA | 676 | 168.6 | 121.4 | 18.4 | 41 | B |
| LYS | CB | 676 | 168.3 | 122.8 | 18.6 | 42 | B |
| LYS | CG | 676 | 167.4 | 123.3 | 17.5 | 45 | B |
| LYS | CD | 676 | 168.1 | 123.4 | 16.2 | 47 | B |
| LYS | CE | 676 | 167.2 | 123.8 | 15.1 | 50 | B |
| LYS | NZ | 676 | 166.4 | 125.0 | 15.4 | 52 | B |
| LYS | C | 676 | 170.0 | 121.1 | 19.0 | 39 | B |
| LYS | O | 676 | 171.0 | 121.2 | 18.3 | 38 | B |
| LEU | N | 677 | 170.0 | 120.7 | 20.2 | 35 | B |
| LEU | CA | 677 | 171.3 | 120.4 | 20.9 | 33 | B |
| LEU | CB | 677 | 171.0 | 120.1 | 22.4 | 31 | B |

TABLE 2-continued

| | | | | | | | |
|---|---|---|---|---|---|---|---|
| LEU | CG | 677 | 172.2 | 119.9 | 23.4 | 29 | B |
| LEU | CD1 | 677 | 173.2 | 121.0 | 23.3 | 29 | B |
| LEU | CD2 | 677 | 171.6 | 119.9 | 24.8 | 28 | B |
| LEU | C | 677 | 172.0 | 119.1 | 20.3 | 34 | B |
| LEU | O | 677 | 173.2 | 119.1 | 20.2 | 34 | B |
| LEU | N | 678 | 171.2 | 118.2 | 19.8 | 34 | B |
| LEU | CA | 678 | 171.7 | 117.0 | 19.2 | 34 | B |
| LEU | CB | 678 | 170.7 | 115.9 | 19.0 | 35 | B |
| LEU | CG | 678 | 170.8 | 114.6 | 19.7 | 35 | B |
| LEU | CD1 | 678 | 169.9 | 113.5 | 19.1 | 35 | B |
| LEU | CD2 | 678 | 172.2 | 114.1 | 19.6 | 35 | B |
| LEU | C | 678 | 172.3 | 117.4 | 17.8 | 35 | B |
| LEU | O | 678 | 173.4 | 117.0 | 17.5 | 35 | B |
| GLN | N | 679 | 171.6 | 118.2 | 17.1 | 36 | B |
| GLN | CA | 679 | 172.1 | 118.7 | 15.8 | 39 | B |
| GLN | CB | 679 | 171.2 | 119.8 | 15.2 | 42 | B |
| GLN | CG | 679 | 169.9 | 119.4 | 14.7 | 47 | B |
| GLN | CD | 679 | 169.0 | 120.6 | 14.3 | 50 | B |
| GLN | OE1 | 679 | 169.5 | 121.7 | 14.0 | 51 | B |
| GLN | NE2 | 679 | 167.7 | 120.4 | 14.6 | 52 | B |
| GLN | C | 679 | 173.4 | 119.3 | 16.0 | 38 | B |
| GLN | O | 679 | 174.4 | 119.0 | 15.2 | 39 | B |
| TYR | N | 680 | 173.5 | 120.2 | 16.9 | 37 | B |
| TYR | CA | 680 | 174.8 | 120.9 | 17.3 | 34 | B |
| TYR | CB | 680 | 174.5 | 121.9 | 18.4 | 33 | B |
| TYR | CG | 680 | 175.7 | 122.6 | 18.9 | 31 | B |
| TYR | CD1 | 680 | 176.5 | 123.4 | 18.0 | 31 | B |
| TYR | CE1 | 680 | 177.6 | 124.0 | 18.4 | 31 | B |
| TYR | CD2 | 680 | 176.2 | 122.5 | 20.2 | 31 | B |
| TYR | CE2 | 680 | 177.3 | 123.1 | 20.6 | 30 | B |
| TYR | CZ | 680 | 178.0 | 123.8 | 19.7 | 30 | B |
| TYR | OH | 680 | 179.2 | 124.4 | 20.2 | 32 | B |
| TYR | C | 680 | 175.8 | 120.0 | 17.6 | 33 | B |
| TYR | O | 680 | 176.9 | 120.0 | 17.1 | 33 | B |
| LEU | N | 681 | 175.6 | 119.1 | 18.6 | 31 | B |
| LEU | CA | 681 | 176.5 | 118.1 | 19.0 | 30 | B |
| LEU | CB | 681 | 176.0 | 117.1 | 20.0 | 28 | B |
| LEU | CG | 681 | 175.7 | 117.6 | 21.4 | 26 | B |
| LEU | CD1 | 681 | 175.4 | 116.5 | 22.4 | 26 | B |
| LEU | CD2 | 681 | 176.9 | 118.4 | 21.8 | 25 | B |
| LEU | C | 681 | 177.0 | 117.3 | 17.8 | 31 | B |
| LEU | O | 681 | 178.2 | 117.0 | 17.7 | 33 | B |
| TYR | N | 682 | 176.1 | 116.9 | 16.9 | 31 | B |
| TYR | CA | 682 | 176.5 | 116.2 | 15.8 | 33 | B |
| TYR | CB | 682 | 175.3 | 115.6 | 15.0 | 35 | B |
| TYR | CG | 682 | 174.9 | 114.3 | 15.5 | 38 | B |
| TYR | CD1 | 682 | 173.5 | 114.0 | 15.9 | 39 | B |
| TYR | CE1 | 682 | 173.1 | 112.7 | 16.2 | 38 | B |
| TYR | CD2 | 682 | 175.8 | 113.2 | 15.4 | 39 | B |
| TYR | CE2 | 682 | 175.3 | 111.9 | 15.7 | 39 | B |
| TYR | CZ | 682 | 174.0 | 111.7 | 16.1 | 39 | B |
| TYR | OH | 682 | 173.6 | 110.4 | 16.3 | 40 | B |
| TYR | C | 682 | 177.3 | 117.0 | 14.8 | 33 | B |
| TYR | O | 682 | 178.2 | 116.6 | 14.1 | 33 | B |
| SER | N | 683 | 177.1 | 118.3 | 14.8 | 33 | B |
| SER | CA | 683 | 177.8 | 119.3 | 14.0 | 33 | B |
| SER | CB | 683 | 177.1 | 120.7 | 13.9 | 34 | B |
| SER | OG | 683 | 177.6 | 121.5 | 15.0 | 36 | B |
| SER | C | 683 | 179.3 | 119.4 | 14.3 | 32 | B |
| SER | O | 683 | 180.1 | 119.7 | 13.4 | 33 | B |
| LEU | N | 684 | 179.7 | 119.1 | 15.5 | 31 | B |
| LEU | CA | 684 | 181.0 | 119.2 | 16.0 | 29 | B |
| LEU | CB | 684 | 181.1 | 119.8 | 17.4 | 28 | B |
| LEU | CG | 684 | 180.2 | 121.0 | 17.7 | 26 | B |
| LEU | CD1 | 684 | 180.3 | 121.4 | 19.1 | 26 | B |
| LEU | CD2 | 684 | 180.5 | 122.1 | 16.8 | 26 | B |
| LEU | C | 684 | 181.8 | 117.9 | 15.9 | 30 | B |
| LEU | O | 684 | 183.0 | 117.9 | 15.9 | 31 | B |
| LYS | N | 685 | 181.1 | 116.8 | 15.9 | 31 | B |
| LYS | CA | 685 | 181.6 | 115.5 | 15.9 | 29 | B |
| LYS | CB | 685 | 180.5 | 114.4 | 15.8 | 29 | B |
| LYS | CG | 685 | 180.9 | 113.0 | 16.0 | 29 | B |
| LYS | CD | 685 | 181.6 | 112.8 | 17.3 | 29 | B |
| LYS | CE | 685 | 181.5 | 111.4 | 17.8 | 30 | B |
| LYS | NZ | 685 | 182.0 | 110.4 | 16.9 | 32 | B |
| LYS | C | 685 | 182.6 | 115.2 | 14.8 | 29 | B |
| LYS | O | 685 | 182.4 | 115.5 | 13.6 | 29 | B |
| GLN | N | 686 | 183.8 | 114.7 | 15.2 | 30 | B |
| GLN | CA | 686 | 184.9 | 114.4 | 14.3 | 31 | B |

TABLE 2-continued

| | | | | | | | |
|---|---|---|---|---|---|---|---|
| GLN | CB | 686 | 186.2 | 114.8 | 14.9 | 31 | B |
| GLN | CG | 686 | 186.3 | 116.2 | 15.1 | 31 | B |
| GLN | CD | 686 | 186.1 | 116.9 | 13.8 | 32 | B |
| GLN | OE1 | 686 | 187.1 | 117.0 | 13.0 | 33 | B |
| GLN | NE2 | 686 | 184.9 | 117.4 | 13.5 | 33 | B |
| GLN | C | 686 | 185.0 | 112.9 | 14.0 | 32 | B |
| GLN | O | 686 | 184.7 | 112.0 | 14.8 | 33 | B |
| PRO | N | 687 | 185.5 | 112.6 | 12.7 | 32 | B |
| PRO | CD | 687 | 185.8 | 113.5 | 11.6 | 32 | B |
| PRO | CA | 687 | 185.6 | 111.2 | 12.3 | 31 | B |
| PRO | CB | 687 | 186.3 | 111.3 | 11.0 | 32 | B |
| PRO | CG | 687 | 185.7 | 112.6 | 10.4 | 32 | B |
| PRO | C | 687 | 186.5 | 110.4 | 13.3 | 31 | B |
| PRO | O | 687 | 186.2 | 109.2 | 13.5 | 33 | B |
| ASP | N | 688 | 187.5 | 111.0 | 13.9 | 28 | B |
| ASP | CA | 688 | 188.3 | 110.3 | 14.9 | 26 | B |
| ASP | CB | 688 | 189.8 | 110.8 | 14.9 | 28 | B |
| ASP | CG | 688 | 189.9 | 112.1 | 15.6 | 31 | B |
| ASP | OD1 | 688 | 188.9 | 112.8 | 15.9 | 31 | B |
| ASP | OD2 | 688 | 191.1 | 112.5 | 15.8 | 32 | B |
| ASP | C | 688 | 187.8 | 110.1 | 16.3 | 25 | B |
| ASP | O | 688 | 188.5 | 109.6 | 17.1 | 26 | B |
| GLY | N | 689 | 186.6 | 110.6 | 16.5 | 24 | B |
| GLY | CA | 689 | 185.9 | 110.4 | 17.8 | 24 | B |
| GLY | C | 689 | 185.9 | 111.7 | 18.6 | 24 | B |
| GLY | O | 689 | 185.1 | 111.7 | 19.6 | 25 | B |
| SER | N | 690 | 186.7 | 112.7 | 18.3 | 23 | B |
| SER | CA | 690 | 186.7 | 113.9 | 19.1 | 24 | B |
| SER | CB | 690 | 188.1 | 114.6 | 18.9 | 23 | B |
| SER | OG | 690 | 188.3 | 115.0 | 17.6 | 21 | B |
| SER | C | 690 | 185.6 | 114.8 | 18.5 | 26 | B |
| SER | O | 690 | 185.1 | 114.5 | 17.4 | 28 | B |
| PHE | N | 691 | 185.4 | 115.9 | 19.2 | 25 | B |
| PHE | CA | 691 | 184.4 | 117.0 | 18.8 | 24 | B |
| PHE | CB | 691 | 183.3 | 117.2 | 19.8 | 23 | B |
| PHE | CG | 691 | 182.4 | 116.0 | 20.0 | 22 | B |
| PHE | CD1 | 691 | 182.8 | 114.9 | 20.8 | 21 | B |
| PHE | CD2 | 691 | 181.1 | 116.0 | 19.5 | 20 | B |
| PHE | CE1 | 691 | 182.0 | 113.8 | 21.1 | 20 | B |
| PHE | CE2 | 691 | 180.3 | 114.9 | 19.7 | 21 | B |
| PHE | CZ | 691 | 180.7 | 113.9 | 20.5 | 21 | B |
| PHE | C | 691 | 185.2 | 118.3 | 18.7 | 24 | B |
| PHE | O | 691 | 186.2 | 118.4 | 19.4 | 26 | B |
| LEU | N | 692 | 184.6 | 119.2 | 18.0 | 25 | B |
| LEU | CA | 692 | 185.3 | 120.6 | 17.9 | 25 | B |
| LEU | CB | 692 | 184.9 | 121.3 | 16.7 | 25 | B |
| LEU | CG | 692 | 185.1 | 120.7 | 15.3 | 25 | B |
| LEU | CD1 | 692 | 184.4 | 121.5 | 14.2 | 24 | B |
| LEU | CD2 | 692 | 186.6 | 120.5 | 15.0 | 25 | B |
| LEU | C | 692 | 184.6 | 121.3 | 19.1 | 26 | B |
| LEU | O | 692 | 183.5 | 120.8 | 19.6 | 28 | B |
| MET | N | 693 | 185.2 | 122.4 | 19.6 | 24 | B |
| MET | CA | 693 | 184.5 | 123.1 | 20.7 | 23 | B |
| MET | CB | 693 | 185.5 | 123.9 | 21.5 | 22 | B |
| MET | CG | 693 | 186.5 | 123.1 | 22.4 | 21 | B |
| MET | SD | 693 | 185.7 | 122.3 | 23.7 | 23 | B |
| MET | CE | 693 | 185.1 | 123.7 | 24.7 | 21 | B |
| MET | C | 693 | 183.4 | 123.9 | 20.1 | 22 | B |
| MET | O | 693 | 182.4 | 124.2 | 20.8 | 23 | B |
| HIS | N | 694 | 183.6 | 124.4 | 18.9 | 20 | B |
| HIS | CA | 694 | 182.6 | 125.2 | 18.2 | 22 | B |
| HIS | CB | 694 | 182.6 | 126.6 | 18.7 | 21 | B |
| HIS | CG | 694 | 183.8 | 127.4 | 18.5 | 21 | B |
| HIS | CD2 | 694 | 185.1 | 127.3 | 19.1 | 20 | B |
| HIS | ND1 | 694 | 184.0 | 128.4 | 17.6 | 21 | B |
| HIS | CE1 | 694 | 185.2 | 128.9 | 17.6 | 21 | B |
| HIS | NE2 | 694 | 185.9 | 128.3 | 18.5 | 21 | B |
| HIS | C | 694 | 182.9 | 125.0 | 16.7 | 24 | B |
| HIS | O | 694 | 184.0 | 124.5 | 16.3 | 25 | B |
| VAL | N | 695 | 182.0 | 125.4 | 15.9 | 26 | B |
| VAL | CA | 695 | 182.2 | 125.4 | 14.4 | 27 | B |
| VAL | CB | 695 | 180.9 | 125.8 | 13.7 | 27 | B |
| VAL | CG1 | 695 | 181.2 | 125.9 | 12.2 | 26 | B |
| VAL | CG2 | 695 | 179.8 | 124.9 | 13.9 | 26 | B |
| VAL | C | 695 | 183.4 | 126.2 | 14.0 | 27 | B |
| VAL | O | 695 | 183.5 | 127.4 | 14.3 | 30 | B |
| GLY | N | 696 | 184.4 | 125.5 | 13.4 | 27 | B |
| GLY | CA | 696 | 185.6 | 126.2 | 13.1 | 27 | B |
| GLY | C | 696 | 186.5 | 126.4 | 14.2 | 27 | B |

TABLE 2-continued

| | | | | | | | |
|---|---|---|---|---|---|---|---|
| GLY | O | 696 | 187.5 | 127.1 | 14.1 | 28 | B |
| GLY | N | 697 | 186.2 | 125.7 | 15.4 | 25 | B |
| GLY | CA | 697 | 187.0 | 125.9 | 16.6 | 23 | B |
| GLY | C | 697 | 188.0 | 124.7 | 16.8 | 23 | B |
| GLY | O | 697 | 187.9 | 123.7 | 16.1 | 25 | B |
| GLU | N | 698 | 188.8 | 124.8 | 17.9 | 20 | B |
| GLU | CA | 698 | 189.7 | 123.8 | 18.3 | 18 | B |
| GLU | CB | 698 | 190.7 | 124.4 | 19.3 | 18 | B |
| GLU | CG | 698 | 190.1 | 124.6 | 20.7 | 17 | B |
| GLU | CD | 698 | 189.3 | 125.9 | 20.9 | 18 | B |
| GLU | OE1 | 698 | 189.0 | 126.6 | 19.9 | 17 | B |
| GLU | OE2 | 698 | 189.0 | 126.2 | 22.1 | 18 | B |
| GLU | C | 698 | 189.2 | 122.5 | 18.8 | 18 | B |
| GLU | O | 698 | 188.0 | 122.4 | 19.2 | 19 | B |
| VAL | N | 699 | 190.1 | 121.5 | 18.9 | 18 | B |
| VAL | CA | 699 | 189.7 | 120.2 | 19.4 | 18 | B |
| VAL | CB | 699 | 189.9 | 119.1 | 18.4 | 18 | B |
| VAL | CG1 | 699 | 189.8 | 117.7 | 19.0 | 18 | B |
| VAL | CG2 | 699 | 188.8 | 119.3 | 17.3 | 17 | B |
| VAL | C | 699 | 190.7 | 119.8 | 20.6 | 19 | B |
| VAL | O | 699 | 191.9 | 120.0 | 20.5 | 20 | B |
| ASP | N | 700 | 190.1 | 119.3 | 21.7 | 20 | B |
| ASP | CA | 700 | 190.9 | 118.9 | 22.9 | 20 | B |
| ASP | CB | 700 | 191.6 | 120.0 | 23.6 | 19 | B |
| ASP | CG | 700 | 190.7 | 121.1 | 24.1 | 20 | B |
| ASP | OD1 | 700 | 190.0 | 120.8 | 25.0 | 19 | B |
| ASP | OD2 | 700 | 190.8 | 122.2 | 23.6 | 20 | B |
| ASP | C | 700 | 189.8 | 118.2 | 23.7 | 21 | B |
| ASP | O | 700 | 188.7 | 118.4 | 23.5 | 23 | B |
| VAL | N | 701 | 190.3 | 117.4 | 24.8 | 22 | B |
| VAL | CA | 701 | 189.3 | 116.7 | 25.6 | 22 | B |
| VAL | CB | 701 | 189.9 | 115.9 | 26.8 | 21 | B |
| VAL | CG1 | 701 | 189.2 | 114.6 | 27.0 | 21 | B |
| VAL | CG2 | 701 | 191.4 | 115.7 | 26.6 | 23 | B |
| VAL | C | 701 | 188.1 | 117.4 | 26.2 | 23 | B |
| VAL | O | 701 | 187.1 | 116.8 | 26.5 | 23 | B |
| ARG | N | 702 | 188.2 | 118.7 | 26.4 | 23 | B |
| ARG | CA | 702 | 187.1 | 119.5 | 27.0 | 23 | B |
| ARG | CB | 702 | 187.3 | 121.0 | 27.0 | 22 | B |
| ARG | CG | 702 | 188.5 | 121.5 | 27.9 | 19 | B |
| ARG | CD | 702 | 188.7 | 123.0 | 27.6 | 19 | B |
| ARG | NE | 702 | 189.1 | 123.3 | 26.2 | 19 | B |
| ARG | CZ | 702 | 188.7 | 124.4 | 25.5 | 20 | B |
| ARG | NH1 | 702 | 189.2 | 124.5 | 24.3 | 20 | B |
| ARG | NH2 | 702 | 188.0 | 125.3 | 26.0 | 20 | B |
| ARG | C | 702 | 185.8 | 119.2 | 26.1 | 24 | B |
| ARG | O | 702 | 184.7 | 119.2 | 26.7 | 25 | B |
| SER | N | 703 | 186.0 | 119.2 | 24.8 | 24 | B |
| SER | CA | 703 | 184.8 | 119.0 | 24.0 | 25 | B |
| SER | CB | 703 | 185.2 | 119.0 | 22.5 | 25 | B |
| SER | OG | 703 | 185.9 | 117.8 | 22.2 | 25 | B |
| SER | C | 703 | 184.1 | 117.7 | 24.2 | 26 | B |
| SER | O | 703 | 182.9 | 117.6 | 24.2 | 28 | B |
| ALA | N | 704 | 184.9 | 116.6 | 24.6 | 26 | B |
| ALA | CA | 704 | 184.4 | 115.3 | 24.8 | 27 | B |
| ALA | CB | 704 | 185.5 | 114.3 | 24.9 | 27 | B |
| ALA | C | 704 | 183.5 | 115.3 | 26.1 | 28 | B |
| ALA | O | 704 | 182.4 | 114.7 | 26.1 | 26 | B |
| TYR | N | 705 | 184.0 | 115.9 | 27.2 | 28 | B |
| TYR | CA | 705 | 183.4 | 116.0 | 28.5 | 29 | B |
| TYR | CB | 705 | 184.3 | 116.5 | 29.6 | 29 | B |
| TYR | CG | 705 | 183.7 | 116.9 | 30.9 | 32 | B |
| TYR | CD1 | 705 | 183.1 | 116.0 | 31.7 | 32 | B |
| TYR | CE1 | 705 | 182.5 | 116.3 | 32.9 | 33 | B |
| TYR | CD2 | 705 | 183.7 | 118.2 | 31.3 | 32 | B |
| TYR | CE2 | 705 | 183.1 | 118.6 | 32.5 | 32 | B |
| TYR | CZ | 705 | 182.5 | 117.7 | 33.3 | 33 | B |
| TYR | OH | 705 | 181.9 | 118.0 | 34.5 | 34 | B |
| TYR | C | 705 | 182.1 | 116.9 | 28.4 | 29 | B |
| TYR | O | 705 | 181.0 | 116.6 | 28.9 | 29 | B |
| CYS | N | 706 | 182.3 | 118.0 | 27.7 | 27 | B |
| CYS | CA | 706 | 181.2 | 119.0 | 27.6 | 25 | B |
| CYS | CB | 706 | 181.6 | 120.2 | 26.8 | 25 | B |
| CYS | SG | 706 | 182.7 | 121.2 | 27.7 | 25 | B |
| CYS | C | 706 | 180.0 | 118.3 | 26.8 | 27 | B |
| CYS | O | 706 | 178.9 | 118.4 | 27.3 | 29 | B |
| ALA | N | 707 | 180.3 | 117.6 | 25.7 | 27 | B |
| ALA | CA | 707 | 179.3 | 116.9 | 25.0 | 26 | B |
| ALA | CB | 707 | 179.8 | 116.4 | 23.7 | 25 | B |

TABLE 2-continued

| | | | | | | | |
|---|---|---|---|---|---|---|---|
| ALA | C | 707 | 178.6 | 115.8 | 25.8 | 28 | B |
| ALA | O | 707 | 177.4 | 115.8 | 26.0 | 29 | B |
| ALA | N | 708 | 179.5 | 115.0 | 26.4 | 28 | B |
| ALA | CA | 708 | 179.0 | 113.9 | 27.2 | 29 | B |
| ALA | CB | 708 | 180.1 | 113.0 | 27.7 | 28 | B |
| ALA | C | 708 | 178.1 | 114.3 | 28.4 | 30 | B |
| ALA | O | 708 | 177.1 | 113.7 | 28.7 | 32 | B |
| SER | N | 709 | 178.5 | 115.4 | 29.1 | 31 | B |
| SER | CA | 709 | 177.8 | 115.9 | 30.2 | 30 | B |
| SER | CB | 709 | 178.6 | 117.0 | 30.9 | 30 | B |
| SER | OG | 709 | 177.9 | 117.7 | 31.9 | 30 | B |
| SER | C | 709 | 176.4 | 116.5 | 29.9 | 30 | B |
| SER | O | 709 | 175.4 | 116.2 | 30.5 | 30 | B |
| VAL | N | 710 | 176.3 | 117.3 | 28.8 | 31 | B |
| VAL | CA | 710 | 175.0 | 117.9 | 28.4 | 32 | B |
| VAL | CB | 710 | 175.2 | 119.1 | 27.4 | 33 | B |
| VAL | CG1 | 710 | 175.9 | 120.2 | 28.1 | 33 | B |
| VAL | CG2 | 710 | 175.9 | 118.6 | 26.1 | 33 | B |
| VAL | C | 710 | 174.1 | 116.9 | 27.7 | 34 | B |
| VAL | O | 710 | 172.9 | 116.9 | 27.9 | 35 | B |
| ALA | N | 711 | 174.7 | 116.0 | 26.9 | 35 | B |
| ALA | CA | 711 | 173.9 | 115.0 | 26.1 | 34 | B |
| ALA | CB | 711 | 174.7 | 114.3 | 25.1 | 34 | B |
| ALA | C | 711 | 173.3 | 114.0 | 27.1 | 35 | B |
| ALA | O | 711 | 172.1 | 113.6 | 26.9 | 36 | B |
| SER | N | 712 | 174.1 | 113.5 | 28.1 | 36 | B |
| SER | CA | 712 | 173.5 | 112.5 | 29.0 | 36 | B |
| SER | CB | 712 | 174.7 | 112.0 | 29.9 | 36 | B |
| SER | OG | 712 | 175.4 | 113.0 | 30.5 | 37 | B |
| SER | C | 712 | 172.4 | 113.1 | 29.9 | 37 | B |
| SER | O | 712 | 171.3 | 112.6 | 30.0 | 38 | B |
| LEU | N | 713 | 172.7 | 114.3 | 30.6 | 36 | B |
| LEU | CA | 713 | 171.7 | 114.9 | 31.4 | 35 | B |
| LEU | CB | 713 | 172.3 | 116.3 | 32.0 | 33 | B |
| LEU | CG | 713 | 173.4 | 116.2 | 33.0 | 33 | B |
| LEU | CD1 | 713 | 173.9 | 117.6 | 33.3 | 32 | B |
| LEU | CD2 | 713 | 172.9 | 115.5 | 34.3 | 32 | B |
| LEU | C | 713 | 170.4 | 115.2 | 30.7 | 35 | B |
| LEU | O | 713 | 169.4 | 114.8 | 31.2 | 36 | B |
| THR | N | 714 | 170.5 | 115.7 | 29.5 | 36 | B |
| THR | CA | 714 | 169.3 | 116.0 | 28.7 | 37 | B |
| THR | CB | 714 | 169.4 | 117.2 | 27.7 | 36 | B |
| THR | OG1 | 714 | 170.3 | 116.8 | 26.6 | 37 | B |
| THR | CG2 | 714 | 170.0 | 118.4 | 28.4 | 36 | B |
| THR | C | 714 | 168.8 | 114.8 | 27.9 | 38 | B |
| THR | O | 714 | 167.8 | 114.9 | 27.2 | 39 | B |
| ASN | N | 715 | 169.4 | 113.6 | 28.1 | 39 | B |
| ASN | CA | 715 | 169.0 | 112.4 | 27.4 | 38 | B |
| ASN | CB | 715 | 167.6 | 112.0 | 28.0 | 40 | B |
| ASN | CG | 715 | 167.0 | 110.8 | 27.3 | 41 | B |
| ASN | OD1 | 715 | 167.7 | 109.9 | 26.9 | 42 | B |
| ASN | ND2 | 715 | 165.7 | 110.9 | 27.1 | 41 | B |
| ASN | C | 715 | 168.8 | 112.6 | 25.9 | 39 | B |
| ASN | O | 715 | 167.7 | 112.5 | 25.3 | 40 | B |
| ILE | N | 716 | 169.9 | 112.8 | 25.2 | 36 | B |
| ILE | CA | 716 | 169.9 | 113.0 | 23.7 | 34 | B |
| ILE | CB | 716 | 170.2 | 114.4 | 23.3 | 35 | B |
| ILE | CG2 | 716 | 169.0 | 115.3 | 23.4 | 35 | B |
| ILE | CG1 | 716 | 171.4 | 114.9 | 24.0 | 35 | B |
| ILE | CD1 | 716 | 172.0 | 116.1 | 23.4 | 36 | B |
| ILE | C | 716 | 170.9 | 112.0 | 23.2 | 33 | B |
| ILE | O | 716 | 171.2 | 112.1 | 22.0 | 31 | B |
| ILE | N | 717 | 171.5 | 111.2 | 24.0 | 32 | B |
| ILE | CA | 717 | 172.5 | 110.2 | 23.5 | 34 | B |
| ILE | CB | 717 | 173.3 | 109.6 | 24.7 | 33 | B |
| ILE | CG2 | 717 | 174.5 | 108.8 | 24.0 | 31 | B |
| ILE | CG1 | 717 | 173.9 | 110.6 | 25.6 | 32 | B |
| ILE | CD1 | 717 | 174.8 | 110.0 | 26.6 | 31 | B |
| ILE | C | 717 | 171.9 | 109.1 | 22.6 | 36 | B |
| ILE | O | 717 | 171.2 | 108.2 | 23.1 | 37 | B |
| THR | N | 718 | 172.2 | 109.3 | 21.3 | 38 | B |
| THR | CA | 718 | 171.8 | 108.3 | 20.4 | 41 | B |
| THR | CB | 718 | 171.8 | 108.9 | 19.0 | 41 | B |
| THR | OG1 | 718 | 173.2 | 109.2 | 18.6 | 42 | B |
| THR | CG2 | 718 | 171.0 | 110.2 | 18.9 | 41 | B |
| THR | C | 718 | 172.8 | 107.2 | 20.4 | 42 | B |
| THR | O | 718 | 173.8 | 107.2 | 21.2 | 43 | B |
| PRO | N | 719 | 172.6 | 106.1 | 19.6 | 44 | B |
| PRO | CD | 719 | 171.5 | 105.8 | 18.7 | 44 | B |

TABLE 2-continued

| | | | | | | | |
|---|---|---|---|---|---|---|---|
| PRO | CA | 719 | 173.6 | 105.0 | 19.6 | 43 | B |
| PRO | CB | 719 | 172.9 | 103.9 | 18.8 | 44 | B |
| PRO | CG | 719 | 172.1 | 104.8 | 17.8 | 45 | B |
| PRO | C | 719 | 175.0 | 105.3 | 19.0 | 43 | B |
| PRO | O | 719 | 176.0 | 104.8 | 19.4 | 43 | B |
| ASP | N | 720 | 175.0 | 106.2 | 18.0 | 40 | B |
| ASP | CA | 720 | 176.3 | 106.5 | 17.4 | 40 | B |
| ASP | CB | 720 | 176.1 | 106.4 | 15.8 | 41 | B |
| ASP | CG | 720 | 175.3 | 107.4 | 15.2 | 43 | B |
| ASP | OD1 | 720 | 175.5 | 107.8 | 14.1 | 45 | B |
| ASP | OD2 | 720 | 174.3 | 107.8 | 15.9 | 44 | B |
| ASP | C | 720 | 176.8 | 107.9 | 17.7 | 39 | B |
| ASP | O | 720 | 177.8 | 108.4 | 17.0 | 38 | B |
| LEU | N | 721 | 176.2 | 108.6 | 18.6 | 37 | B |
| LEU | CA | 721 | 176.7 | 110.0 | 19.0 | 35 | B |
| LEU | CB | 721 | 175.8 | 110.5 | 20.1 | 34 | B |
| LEU | CG | 721 | 176.3 | 111.9 | 20.6 | 33 | B |
| LEU | CD1 | 721 | 176.4 | 112.9 | 19.5 | 32 | B |
| LEU | CD2 | 721 | 175.4 | 112.4 | 21.7 | 33 | B |
| LEU | C | 721 | 178.2 | 110.0 | 19.4 | 35 | B |
| LEU | O | 721 | 178.9 | 110.7 | 18.7 | 35 | B |
| PHE | N | 722 | 178.5 | 109.2 | 20.4 | 34 | B |
| PHE | CA | 722 | 179.9 | 109.2 | 20.9 | 36 | B |
| PHE | CB | 722 | 179.8 | 109.1 | 22.4 | 36 | B |
| PHE | CG | 722 | 179.2 | 110.3 | 23.1 | 36 | B |
| PHE | CD1 | 722 | 178.0 | 110.3 | 23.7 | 35 | B |
| PHE | CD2 | 722 | 179.9 | 111.5 | 23.0 | 35 | B |
| PHE | CE1 | 722 | 177.4 | 111.4 | 24.3 | 34 | B |
| PHE | CE2 | 722 | 179.4 | 112.7 | 23.6 | 34 | B |
| PHE | CZ | 722 | 178.1 | 112.6 | 24.2 | 34 | B |
| PHE | C | 722 | 180.7 | 108.0 | 20.3 | 37 | B |
| PHE | O | 722 | 181.6 | 107.5 | 21.0 | 37 | B |
| GLU | N | 723 | 180.4 | 107.7 | 19.1 | 40 | B |
| GLU | CA | 723 | 181.1 | 106.6 | 18.4 | 41 | B |
| GLU | CB | 723 | 180.6 | 106.4 | 17.0 | 45 | B |
| GLU | CG | 723 | 180.9 | 105.1 | 16.3 | 50 | B |
| GLU | CD | 723 | 179.9 | 104.0 | 16.7 | 54 | B |
| GLU | OE1 | 723 | 179.0 | 103.7 | 15.9 | 56 | B |
| GLU | OE2 | 723 | 180.0 | 103.5 | 17.8 | 57 | B |
| GLU | C | 723 | 182.6 | 106.9 | 18.3 | 39 | B |
| GLU | O | 723 | 183.0 | 107.8 | 17.6 | 38 | B |
| GLY | N | 724 | 183.4 | 106.0 | 18.9 | 37 | B |
| GLY | CA | 724 | 184.9 | 106.2 | 18.8 | 35 | B |
| GLY | C | 724 | 185.4 | 107.3 | 19.8 | 34 | B |
| GLY | O | 724 | 186.6 | 107.5 | 19.8 | 35 | B |
| THR | N | 725 | 184.5 | 107.9 | 20.6 | 34 | B |
| THR | CA | 725 | 184.9 | 108.9 | 21.5 | 33 | B |
| THR | CB | 725 | 183.7 | 109.7 | 22.1 | 34 | B |
| THR | OG1 | 725 | 183.0 | 110.3 | 21.0 | 30 | B |
| THR | CG2 | 725 | 184.2 | 110.8 | 23.0 | 30 | B |
| THR | C | 725 | 185.7 | 108.4 | 22.7 | 32 | B |
| THR | O | 725 | 186.7 | 109.0 | 23.1 | 33 | B |
| ALA | N | 726 | 185.4 | 107.2 | 23.2 | 30 | B |
| ALA | CA | 726 | 186.1 | 106.6 | 24.3 | 30 | B |
| ALA | CB | 726 | 185.4 | 105.4 | 24.9 | 30 | B |
| ALA | C | 726 | 187.5 | 106.3 | 23.9 | 31 | B |
| ALA | O | 726 | 188.5 | 106.3 | 24.7 | 32 | B |
| GLU | N | 727 | 187.7 | 105.9 | 22.6 | 30 | B |
| GLU | CA | 727 | 189.0 | 105.5 | 22.1 | 30 | B |
| GLU | CB | 727 | 188.8 | 104.7 | 20.8 | 32 | B |
| GLU | CG | 727 | 188.4 | 103.3 | 21.0 | 34 | B |
| GLU | CD | 727 | 186.9 | 103.1 | 21.3 | 36 | B |
| GLU | OE1 | 727 | 186.5 | 102.0 | 21.8 | 38 | B |
| GLU | OE2 | 727 | 186.1 | 104.0 | 20.9 | 36 | B |
| GLU | C | 727 | 189.9 | 106.7 | 21.9 | 29 | B |
| GLU | O | 727 | 191.1 | 106.6 | 22.1 | 30 | B |
| TRP | N | 728 | 189.4 | 107.8 | 21.5 | 28 | B |
| TRP | CA | 728 | 190.2 | 109.0 | 21.3 | 27 | B |
| TRP | CB | 728 | 189.3 | 110.1 | 20.7 | 25 | B |
| TRP | CG | 728 | 190.1 | 111.3 | 20.2 | 24 | B |
| TRP | CD2 | 728 | 190.4 | 112.4 | 21.0 | 25 | B |
| TRP | CE2 | 728 | 191.2 | 113.2 | 20.2 | 25 | B |
| TRP | CE3 | 728 | 190.0 | 112.9 | 22.3 | 25 | B |
| TRP | CD1 | 728 | 190.8 | 111.4 | 19.1 | 24 | B |
| TRP | NE1 | 728 | 191.4 | 112.6 | 19.0 | 25 | B |
| TRP | CZ2 | 728 | 191.7 | 114.5 | 20.6 | 24 | B |
| TRP | CZ3 | 728 | 190.5 | 114.1 | 22.7 | 23 | B |
| TRP | CH2 | 728 | 191.3 | 114.9 | 21.8 | 23 | B |
| TRP | C | 728 | 190.6 | 109.5 | 22.7 | 27 | B |

TABLE 2-continued

| | | | | | | | |
|---|---|---|---|---|---|---|---|
| TRP | O | 728 | 191.8 | 109.8 | 23.0 | 28 | B |
| ILE | N | 729 | 189.7 | 109.6 | 23.7 | 26 | B |
| ILE | CA | 729 | 190.0 | 110.0 | 25.0 | 24 | B |
| ILE | CB | 729 | 188.8 | 110.0 | 25.9 | 22 | B |
| ILE | CG2 | 729 | 189.1 | 110.3 | 27.3 | 22 | B |
| ILE | CG1 | 729 | 187.7 | 111.0 | 25.4 | 23 | B |
| ILE | CD1 | 729 | 186.4 | 111.0 | 26.2 | 24 | B |
| ILE | C | 729 | 191.1 | 109.1 | 25.7 | 25 | B |
| ILE | O | 729 | 191.9 | 109.6 | 26.4 | 27 | B |
| ALA | N | 730 | 191.1 | 107.8 | 25.3 | 26 | B |
| ALA | CA | 730 | 192.1 | 106.9 | 25.9 | 26 | B |
| ALA | CB | 730 | 191.6 | 105.4 | 25.7 | 26 | B |
| ALA | C | 730 | 193.4 | 107.1 | 25.2 | 25 | B |
| ALA | O | 730 | 194.5 | 106.7 | 25.7 | 26 | B |
| ARG | N | 731 | 193.4 | 107.8 | 24.0 | 25 | B |
| ARG | CA | 731 | 194.7 | 108.1 | 23.4 | 24 | B |
| ARG | CB | 731 | 194.4 | 108.4 | 21.9 | 25 | B |
| ARG | CG | 731 | 194.0 | 107.1 | 21.1 | 25 | B |
| ARG | CD | 731 | 194.6 | 107.2 | 19.7 | 25 | B |
| ARG | NE | 731 | 193.9 | 108.1 | 18.9 | 28 | B |
| ARG | CZ | 731 | 194.4 | 109.1 | 18.1 | 28 | B |
| ARG | NH1 | 731 | 195.7 | 109.3 | 18.2 | 26 | B |
| ARG | NH2 | 731 | 193.6 | 109.8 | 17.3 | 28 | B |
| ARG | C | 731 | 195.3 | 109.3 | 24.0 | 25 | B |
| ARG | O | 731 | 196.5 | 109.6 | 23.8 | 27 | B |
| CYS | N | 732 | 194.5 | 110.1 | 24.8 | 23 | B |
| CYS | CA | 732 | 195.0 | 111.3 | 25.5 | 22 | B |
| CYS | CB | 732 | 193.9 | 112.2 | 25.8 | 22 | B |
| CYS | SG | 732 | 193.0 | 112.8 | 24.3 | 23 | B |
| CYS | C | 732 | 195.8 | 110.9 | 26.7 | 23 | B |
| CYS | O | 732 | 196.6 | 111.6 | 27.2 | 23 | B |
| GLN | N | 733 | 195.7 | 109.6 | 27.2 | 23 | B |
| GLN | CA | 733 | 196.4 | 109.1 | 28.3 | 24 | B |
| GLN | CB | 733 | 195.8 | 107.8 | 28.9 | 24 | B |
| GLN | CG | 733 | 196.6 | 107.3 | 30.1 | 25 | B |
| GLN | CD | 733 | 195.9 | 106.2 | 30.9 | 26 | B |
| GLN | OE1 | 733 | 195.5 | 105.2 | 30.3 | 27 | B |
| GLN | NE2 | 733 | 195.8 | 106.4 | 32.2 | 24 | B |
| GLN | C | 733 | 197.9 | 108.8 | 27.9 | 25 | B |
| GLN | O | 733 | 198.1 | 108.0 | 27.0 | 26 | B |
| ASN | N | 734 | 198.9 | 109.5 | 28.5 | 26 | B |
| ASN | CA | 734 | 200.3 | 109.3 | 28.2 | 25 | B |
| ASN | CB | 734 | 200.9 | 110.7 | 27.9 | 25 | B |
| ASN | CG | 734 | 201.2 | 111.4 | 29.2 | 25 | B |
| ASN | OD1 | 734 | 200.7 | 111.0 | 30.2 | 24 | B |
| ASN | ND2 | 734 | 202.0 | 112.5 | 29.1 | 26 | B |
| ASN | C | 734 | 201.1 | 108.5 | 29.1 | 25 | B |
| ASN | O | 734 | 200.6 | 108.0 | 30.1 | 26 | B |
| TRP | N | 735 | 202.4 | 108.5 | 28.9 | 24 | B |
| TRP | CA | 735 | 203.4 | 107.8 | 29.8 | 24 | B |
| TRP | CB | 735 | 204.8 | 108.0 | 29.3 | 23 | B |
| TRP | CG | 735 | 205.2 | 109.5 | 29.2 | 22 | B |
| TRP | CD2 | 735 | 205.9 | 110.3 | 30.1 | 20 | B |
| TRP | CE2 | 735 | 206.0 | 111.6 | 29.6 | 20 | B |
| TRP | CE3 | 735 | 206.6 | 110.0 | 31.3 | 20 | B |
| TRP | CD1 | 735 | 204.8 | 110.4 | 28.2 | 22 | B |
| TRP | NE1 | 735 | 205.3 | 111.6 | 28.5 | 21 | B |
| TRP | CZ2 | 735 | 206.6 | 112.6 | 30.3 | 19 | B |
| TRP | CZ3 | 735 | 207.2 | 111.0 | 32.0 | 20 | B |
| TRP | CH2 | 735 | 207.2 | 112.3 | 31.5 | 20 | B |
| TRP | C | 735 | 203.4 | 108.1 | 31.3 | 27 | B |
| TRP | O | 735 | 203.9 | 107.4 | 32.1 | 28 | B |
| GLU | N | 736 | 202.7 | 109.2 | 31.7 | 27 | B |
| GLU | CA | 736 | 202.7 | 109.7 | 33.1 | 26 | B |
| GLU | CB | 736 | 202.5 | 111.2 | 33.1 | 26 | B |
| GLU | CG | 736 | 203.5 | 112.0 | 32.3 | 27 | B |
| GLU | CD | 736 | 203.2 | 113.5 | 32.4 | 27 | B |
| GLU | OE1 | 736 | 202.8 | 114.1 | 31.3 | 27 | B |
| GLU | OE2 | 736 | 203.3 | 114.2 | 33.4 | 28 | B |
| GLU | C | 736 | 201.5 | 109.0 | 33.8 | 25 | B |
| GLU | O | 736 | 201.4 | 109.2 | 35.1 | 27 | B |
| GLY | N | 737 | 200.5 | 108.4 | 33.1 | 23 | B |
| GLY | CA | 737 | 199.4 | 107.8 | 33.8 | 20 | B |
| GLY | C | 737 | 198.3 | 108.8 | 33.7 | 20 | B |
| GLY | O | 737 | 197.1 | 108.4 | 33.8 | 21 | B |
| GLY | N | 738 | 198.6 | 110.1 | 33.4 | 21 | B |
| GLY | CA | 738 | 197.5 | 111.1 | 33.3 | 20 | B |
| GLY | C | 738 | 197.1 | 111.3 | 31.9 | 20 | B |
| GLY | O | 738 | 197.6 | 110.7 | 30.9 | 21 | B |

TABLE 2-continued

| | | | | | | | |
|---|---|---|---|---|---|---|---|
| ILE | N | 739 | 196.1 | 112.2 | 31.7 | 19 | B |
| ILE | CA | 739 | 195.5 | 112.5 | 30.4 | 19 | B |
| ILE | CB | 739 | 194.0 | 112.3 | 30.5 | 17 | B |
| ILE | CG2 | 739 | 193.3 | 112.6 | 29.2 | 18 | B |
| ILE | CG1 | 739 | 193.7 | 110.9 | 31.0 | 15 | B |
| ILE | CD1 | 739 | 192.3 | 110.5 | 30.9 | 14 | B |
| ILE | C | 739 | 195.9 | 113.9 | 29.9 | 20 | B |
| ILE | O | 739 | 196.0 | 114.8 | 30.7 | 24 | B |
| GLY | N | 740 | 196.2 | 114.1 | 28.6 | 20 | B |
| GLY | CA | 740 | 196.6 | 115.4 | 28.1 | 17 | B |
| GLY | C | 740 | 195.4 | 116.0 | 27.3 | 17 | B |
| GLY | O | 740 | 194.4 | 115.4 | 27.1 | 17 | B |
| GLY | N | 741 | 195.6 | 117.2 | 26.7 | 18 | B |
| GLY | CA | 741 | 194.6 | 117.9 | 26.0 | 18 | B |
| GLY | C | 741 | 194.2 | 117.1 | 24.7 | 19 | B |
| GLY | O | 741 | 193.0 | 117.1 | 24.3 | 19 | B |
| VAL | N | 742 | 195.2 | 116.6 | 24.0 | 21 | B |
| VAL | CA | 742 | 195.0 | 115.8 | 22.8 | 21 | B |
| VAL | CB | 742 | 195.3 | 116.7 | 21.5 | 20 | B |
| VAL | CG1 | 742 | 194.2 | 117.7 | 21.3 | 19 | B |
| VAL | CG2 | 742 | 196.7 | 117.4 | 21.6 | 19 | B |
| VAL | C | 742 | 196.1 | 114.7 | 22.8 | 21 | B |
| VAL | O | 742 | 197.0 | 114.8 | 23.6 | 23 | B |
| PRO | N | 743 | 195.9 | 113.6 | 22.1 | 20 | B |
| PRO | CD | 743 | 194.8 | 113.2 | 21.2 | 18 | B |
| PRO | CA | 743 | 196.9 | 112.5 | 22.2 | 20 | B |
| PRO | CB | 743 | 196.5 | 111.6 | 21.0 | 19 | B |
| PRO | CG | 743 | 195.1 | 111.7 | 21.0 | 19 | B |
| PRO | C | 743 | 198.4 | 113.1 | 21.9 | 21 | B |
| PRO | O | 743 | 198.6 | 113.9 | 21.0 | 21 | B |
| GLY | N | 744 | 199.3 | 112.7 | 22.8 | 22 | B |
| GLY | CA | 744 | 200.7 | 113.2 | 22.7 | 22 | B |
| GLY | C | 744 | 201.1 | 114.3 | 23.7 | 24 | B |
| GLY | O | 744 | 202.2 | 114.5 | 23.9 | 23 | B |
| MET | N | 745 | 200.0 | 114.9 | 24.2 | 23 | B |
| MET | CA | 745 | 200.3 | 116.0 | 25.2 | 24 | B |
| MET | CB | 745 | 199.3 | 117.1 | 25.0 | 25 | B |
| MET | CG | 745 | 199.6 | 118.0 | 23.9 | 27 | B |
| MET | SD | 745 | 200.8 | 119.3 | 24.3 | 30 | B |
| MET | CE | 745 | 202.2 | 118.5 | 24.9 | 28 | B |
| MET | C | 745 | 200.5 | 115.6 | 26.6 | 24 | B |
| MET | O | 745 | 200.1 | 114.5 | 27.1 | 25 | B |
| GLU | N | 746 | 201.2 | 116.5 | 27.4 | 24 | B |
| GLU | CA | 746 | 201.5 | 116.4 | 28.8 | 23 | B |
| GLU | CB | 746 | 202.3 | 117.6 | 29.3 | 24 | B |
| GLU | CG | 746 | 202.8 | 117.5 | 30.7 | 26 | B |
| GLU | CD | 746 | 203.4 | 118.8 | 31.1 | 28 | B |
| GLU | OE1 | 746 | 203.2 | 119.9 | 30.4 | 29 | B |
| GLU | OE2 | 746 | 204.0 | 118.9 | 32.2 | 30 | B |
| GLU | C | 746 | 200.2 | 116.2 | 29.6 | 21 | B |
| GLU | O | 746 | 199.2 | 116.8 | 29.4 | 22 | B |
| ALA | N | 747 | 200.3 | 115.3 | 30.6 | 21 | B |
| ALA | CA | 747 | 199.2 | 115.0 | 31.5 | 19 | B |
| ALA | CB | 747 | 199.5 | 113.9 | 32.4 | 19 | B |
| ALA | C | 747 | 198.9 | 116.3 | 32.2 | 18 | B |
| ALA | O | 747 | 199.8 | 116.9 | 32.8 | 17 | B |
| HIS | N | 748 | 197.6 | 116.6 | 32.2 | 18 | B |
| HIS | CA | 748 | 197.2 | 117.9 | 32.9 | 19 | B |
| HIS | CB | 748 | 196.8 | 118.8 | 31.7 | 18 | B |
| HIS | CG | 748 | 196.5 | 120.2 | 32.2 | 19 | B |
| HIS | CD2 | 748 | 197.3 | 121.3 | 32.3 | 19 | B |
| HIS | ND1 | 748 | 195.3 | 120.5 | 32.7 | 21 | B |
| HIS | CE1 | 748 | 195.3 | 121.8 | 33.0 | 21 | B |
| HIS | NE2 | 748 | 196.5 | 122.3 | 32.8 | 21 | B |
| HIS | C | 748 | 195.9 | 117.6 | 33.7 | 20 | B |
| HIS | O | 748 | 195.1 | 116.8 | 33.2 | 23 | B |
| GLY | N | 749 | 195.8 | 118.2 | 34.8 | 21 | B |
| GLY | CA | 749 | 194.7 | 118.0 | 35.7 | 20 | B |
| GLY | C | 749 | 193.3 | 118.3 | 35.2 | 21 | B |
| GLY | O | 749 | 192.3 | 117.7 | 35.5 | 22 | B |
| GLY | N | 750 | 193.2 | 119.5 | 34.5 | 21 | B |
| GLY | CA | 750 | 191.8 | 119.9 | 34.0 | 20 | B |
| GLY | C | 750 | 191.4 | 119.0 | 32.9 | 22 | B |
| GLY | O | 750 | 190.2 | 118.8 | 32.7 | 24 | B |
| TYR | N | 751 | 192.4 | 118.4 | 32.1 | 23 | B |
| TYR | CA | 751 | 192.1 | 117.6 | 31.0 | 21 | B |
| TYR | CB | 751 | 193.2 | 117.6 | 29.9 | 21 | B |
| TYR | CG | 751 | 193.3 | 118.9 | 29.2 | 22 | B |
| TYR | CD1 | 751 | 194.5 | 119.6 | 29.0 | 21 | B |

TABLE 2-continued

| | | | | | | | |
|---|---|---|---|---|---|---|---|
| TYR | CE1 | 751 | 194.5 | 120.8 | 28.3 | 21 | B |
| TYR | CD2 | 751 | 192.1 | 119.4 | 28.6 | 22 | B |
| TYR | CE2 | 751 | 192.2 | 120.6 | 27.8 | 21 | B |
| TYR | CZ | 751 | 193.4 | 121.3 | 27.7 | 22 | B |
| TYR | OH | 751 | 193.4 | 122.4 | 26.9 | 23 | B |
| TYR | C | 751 | 191.8 | 116.1 | 31.4 | 21 | B |
| TYR | O | 751 | 191.1 | 115.4 | 30.8 | 22 | B |
| THR | N | 752 | 192.5 | 115.7 | 32.5 | 20 | B |
| THR | CA | 752 | 192.4 | 114.4 | 33.1 | 21 | B |
| THR | CB | 752 | 193.4 | 114.1 | 34.1 | 21 | B |
| THR | OG1 | 752 | 194.7 | 114.2 | 33.6 | 20 | B |
| THR | CG2 | 752 | 193.3 | 112.7 | 34.6 | 20 | B |
| THR | C | 752 | 191.0 | 114.3 | 33.7 | 23 | B |
| THR | O | 752 | 190.4 | 113.2 | 33.6 | 27 | B |
| PHE | N | 753 | 190.5 | 115.4 | 34.3 | 24 | B |
| PHE | CA | 753 | 189.1 | 115.3 | 34.8 | 23 | B |
| PHE | CB | 753 | 188.8 | 116.6 | 35.6 | 22 | B |
| PHE | CG | 753 | 187.3 | 116.7 | 36.0 | 22 | B |
| PHE | CD1 | 753 | 186.8 | 116.0 | 37.1 | 23 | B |
| PHE | CD2 | 753 | 186.5 | 117.4 | 35.2 | 23 | B |
| PHE | CE1 | 753 | 185.5 | 116.0 | 37.4 | 23 | B |
| PHE | CE2 | 753 | 185.1 | 117.4 | 35.4 | 24 | B |
| PHE | CZ | 753 | 184.6 | 116.7 | 36.5 | 23 | B |
| PHE | C | 753 | 188.2 | 115.2 | 33.6 | 24 | B |
| PHE | O | 753 | 187.2 | 114.4 | 33.7 | 28 | B |
| CYS | N | 754 | 188.4 | 116.0 | 32.6 | 24 | B |
| CYS | CA | 754 | 187.5 | 115.9 | 31.4 | 24 | B |
| CYS | CB | 754 | 187.9 | 116.9 | 30.3 | 23 | B |
| CYS | SG | 754 | 187.5 | 118.6 | 30.8 | 19 | B |
| CYS | C | 754 | 187.5 | 114.5 | 30.8 | 25 | B |
| CYS | O | 754 | 186.4 | 114.0 | 30.5 | 25 | B |
| GLY | N | 755 | 188.6 | 113.9 | 30.7 | 25 | B |
| GLY | CA | 755 | 188.7 | 112.5 | 30.1 | 25 | B |
| GLY | C | 755 | 188.1 | 111.5 | 31.0 | 26 | B |
| GLY | O | 755 | 187.2 | 110.8 | 30.5 | 26 | B |
| LEU | N | 756 | 188.5 | 111.4 | 32.3 | 26 | B |
| LEU | CA | 756 | 188.0 | 110.4 | 33.2 | 26 | B |
| LEU | CB | 756 | 188.7 | 110.5 | 34.5 | 26 | B |
| LEU | CG | 756 | 188.2 | 109.4 | 35.5 | 28 | B |
| LEU | CD1 | 756 | 188.4 | 108.0 | 34.9 | 29 | B |
| LEU | CD2 | 756 | 189.0 | 109.5 | 36.8 | 27 | B |
| LEU | C | 756 | 186.5 | 110.6 | 33.3 | 27 | B |
| LEU | O | 756 | 185.7 | 109.7 | 33.0 | 29 | B |
| ALA | N | 757 | 186.0 | 111.8 | 33.7 | 26 | B |
| ALA | CA | 757 | 184.6 | 112.0 | 33.8 | 26 | B |
| ALA | CB | 757 | 184.3 | 113.4 | 34.2 | 25 | B |
| ALA | C | 757 | 183.8 | 111.7 | 32.6 | 27 | B |
| ALA | O | 757 | 182.6 | 111.2 | 32.6 | 28 | B |
| ALA | N | 758 | 184.4 | 112.0 | 31.4 | 27 | B |
| ALA | CA | 758 | 183.7 | 111.7 | 30.1 | 27 | B |
| ALA | CB | 758 | 184.5 | 112.3 | 29.0 | 26 | B |
| ALA | C | 758 | 183.6 | 110.2 | 30.0 | 28 | B |
| ALA | O | 758 | 182.6 | 109.7 | 29.5 | 30 | B |
| LEU | N | 759 | 184.6 | 109.4 | 30.4 | 29 | B |
| LEU | CA | 759 | 184.6 | 108.0 | 30.3 | 29 | B |
| LEU | CB | 759 | 186.0 | 107.4 | 30.4 | 28 | B |
| LEU | CG | 759 | 186.9 | 107.6 | 29.2 | 28 | B |
| LEU | CD1 | 759 | 188.3 | 107.0 | 29.4 | 27 | B |
| LEU | CD2 | 759 | 186.3 | 106.9 | 28.0 | 27 | B |
| LEU | C | 759 | 183.6 | 107.4 | 31.3 | 30 | B |
| LEU | O | 759 | 183.0 | 106.4 | 31.0 | 30 | B |
| VAL | N | 760 | 183.5 | 108.0 | 32.5 | 30 | B |
| VAL | CA | 760 | 182.6 | 107.5 | 33.5 | 29 | B |
| VAL | CB | 760 | 182.7 | 108.3 | 34.8 | 29 | B |
| VAL | CG1 | 760 | 181.5 | 108.0 | 35.7 | 27 | B |
| VAL | CG2 | 760 | 184.0 | 108.1 | 35.4 | 29 | B |
| VAL | C | 760 | 181.1 | 107.6 | 32.9 | 31 | B |
| VAL | O | 760 | 180.3 | 106.7 | 33.0 | 32 | B |
| ILE | N | 761 | 180.9 | 108.8 | 32.3 | 32 | B |
| ILE | CA | 761 | 179.5 | 109.0 | 31.7 | 33 | B |
| ILE | CB | 761 | 179.5 | 110.4 | 31.1 | 33 | B |
| ILE | CG2 | 761 | 178.1 | 110.6 | 30.4 | 33 | B |
| ILE | CG1 | 761 | 179.7 | 111.5 | 32.1 | 32 | B |
| ILE | CD1 | 761 | 179.6 | 112.9 | 31.6 | 32 | B |
| ILE | C | 761 | 179.3 | 107.9 | 30.6 | 35 | B |
| ILE | O | 761 | 178.2 | 107.2 | 30.7 | 35 | B |
| LEU | N | 762 | 180.2 | 107.7 | 29.7 | 36 | B |
| LEU | CA | 762 | 180.1 | 106.7 | 28.6 | 36 | B |
| LEU | CB | 762 | 181.2 | 107.0 | 27.6 | 33 | B |

TABLE 2-continued

| | | | | | | | |
|---|---|---|---|---|---|---|---|
| LEU | CG | 762 | 181.1 | 108.3 | 26.8 | 30 | B |
| LEU | CD1 | 762 | 182.2 | 108.3 | 25.7 | 29 | B |
| LEU | CD2 | 762 | 179.7 | 108.4 | 26.1 | 29 | B |
| LEU | C | 762 | 180.2 | 105.3 | 29.2 | 39 | B |
| LEU | O | 762 | 180.0 | 104.3 | 28.4 | 39 | B |
| LYS | N | 763 | 180.5 | 105.2 | 30.5 | 43 | B |
| LYS | CA | 763 | 180.6 | 103.9 | 31.1 | 45 | B |
| LYS | CB | 763 | 179.2 | 103.2 | 31.0 | 47 | B |
| LYS | CG | 763 | 178.1 | 104.1 | 31.4 | 51 | B |
| LYS | CD | 763 | 176.7 | 103.4 | 31.1 | 55 | B |
| LYS | CE | 763 | 175.8 | 103.6 | 32.3 | 57 | B |
| LYS | NZ | 763 | 174.6 | 102.7 | 32.3 | 59 | B |
| LYS | C | 763 | 181.7 | 103.1 | 30.6 | 45 | B |
| LYS | O | 763 | 181.6 | 101.9 | 30.4 | 46 | B |
| LYS | N | 764 | 182.8 | 103.8 | 30.3 | 46 | B |
| LYS | CA | 764 | 184.0 | 103.2 | 29.8 | 46 | B |
| LYS | CB | 764 | 184.1 | 103.6 | 28.3 | 46 | B |
| LYS | CG | 764 | 183.0 | 103.0 | 27.5 | 48 | B |
| LYS | CD | 764 | 183.2 | 103.3 | 26.0 | 48 | B |
| LYS | CE | 764 | 182.1 | 102.5 | 25.2 | 50 | B |
| LYS | NZ | 764 | 182.1 | 101.1 | 25.5 | 50 | B |
| LYS | C | 764 | 185.3 | 103.6 | 30.5 | 46 | B |
| LYS | O | 764 | 186.4 | 103.6 | 29.8 | 47 | B |
| GLU | N | 765 | 185.3 | 103.9 | 31.7 | 47 | B |
| GLU | CA | 765 | 186.5 | 104.2 | 32.5 | 47 | B |
| GLU | CB | 765 | 186.2 | 104.2 | 34.0 | 48 | B |
| GLU | CG | 765 | 184.9 | 104.8 | 34.4 | 51 | B |
| GLU | CD | 765 | 183.8 | 103.7 | 34.4 | 53 | B |
| GLU | OE1 | 765 | 183.1 | 103.6 | 33.4 | 53 | B |
| GLU | OE2 | 765 | 183.5 | 103.1 | 35.5 | 54 | B |
| GLU | C | 765 | 187.6 | 103.2 | 32.2 | 48 | B |
| GLU | O | 765 | 188.8 | 103.6 | 32.1 | 49 | B |
| ARG | N | 766 | 187.2 | 102.0 | 32.1 | 49 | B |
| ARG | CA | 766 | 188.1 | 100.9 | 31.8 | 49 | B |
| ARG | CB | 766 | 187.3 | 99.6 | 31.9 | 52 | B |
| ARG | CG | 766 | 187.3 | 98.9 | 33.3 | 56 | B |
| ARG | CD | 766 | 186.0 | 98.3 | 33.7 | 59 | B |
| ARG | NE | 766 | 185.1 | 99.3 | 34.4 | 62 | B |
| ARG | CZ | 766 | 185.3 | 99.7 | 35.6 | 62 | B |
| ARG | NH1 | 766 | 184.5 | 100.7 | 36.1 | 62 | B |
| ARG | NH2 | 766 | 186.2 | 99.2 | 36.4 | 63 | B |
| ARG | C | 766 | 188.9 | 101.0 | 30.5 | 47 | B |
| ARG | O | 766 | 189.8 | 100.1 | 30.3 | 47 | B |
| SER | N | 767 | 188.7 | 102.0 | 29.7 | 43 | B |
| SER | CA | 767 | 189.4 | 102.1 | 28.4 | 42 | B |
| SER | CB | 767 | 188.8 | 103.1 | 27.5 | 42 | B |
| SER | OG | 767 | 187.6 | 102.5 | 26.9 | 43 | B |
| SER | C | 767 | 190.8 | 102.7 | 28.8 | 41 | B |
| SER | O | 767 | 191.6 | 103.0 | 27.9 | 43 | B |
| LEU | N | 768 | 191.0 | 103.0 | 30.1 | 40 | B |
| LEU | CA | 768 | 192.3 | 103.6 | 30.6 | 39 | B |
| LEU | CB | 768 | 192.0 | 104.8 | 31.3 | 40 | B |
| LEU | CG | 768 | 191.3 | 106.0 | 30.6 | 41 | B |
| LEU | CD1 | 768 | 191.0 | 107.1 | 31.6 | 41 | B |
| LEU | CD2 | 768 | 192.1 | 106.4 | 29.5 | 42 | B |
| LEU | C | 768 | 193.0 | 102.6 | 31.5 | 39 | B |
| LEU | O | 768 | 192.5 | 101.6 | 31.9 | 40 | B |
| ASN | N | 769 | 194.3 | 103.0 | 31.8 | 36 | B |
| ASN | CA | 769 | 195.0 | 102.2 | 32.8 | 34 | B |
| ASN | CB | 769 | 196.5 | 102.1 | 32.5 | 33 | B |
| ASN | CG | 769 | 197.3 | 101.5 | 33.5 | 32 | B |
| ASN | OD1 | 769 | 196.8 | 101.3 | 34.7 | 33 | B |
| ASN | ND2 | 769 | 198.5 | 101.1 | 33.2 | 33 | B |
| ASN | C | 769 | 194.8 | 102.9 | 34.1 | 34 | B |
| ASN | O | 769 | 195.4 | 103.9 | 34.3 | 35 | B |
| LEU | N | 770 | 193.8 | 102.5 | 34.8 | 35 | B |
| LEU | CA | 770 | 193.4 | 103.1 | 36.1 | 33 | B |
| LEU | CB | 770 | 192.0 | 102.6 | 36.6 | 31 | B |
| LEU | CG | 770 | 190.9 | 102.7 | 35.5 | 31 | B |
| LEU | CD1 | 770 | 189.6 | 102.0 | 36.0 | 30 | B |
| LEU | CD2 | 770 | 190.6 | 104.2 | 35.3 | 30 | B |
| LEU | C | 770 | 194.4 | 103.0 | 37.2 | 35 | B |
| LEU | O | 770 | 194.4 | 103.7 | 38.1 | 36 | B |
| LYS | N | 771 | 195.3 | 102.1 | 37.0 | 37 | B |
| LYS | CA | 771 | 196.3 | 101.9 | 38.0 | 40 | B |
| LYS | CB | 771 | 197.1 | 100.6 | 37.8 | 43 | B |
| LYS | CG | 771 | 196.4 | 99.4 | 38.4 | 46 | B |
| LYS | CD | 771 | 196.5 | 99.3 | 39.9 | 50 | B |
| LYS | CE | 771 | 195.6 | 100.3 | 40.7 | 51 | B |

TABLE 2-continued

| | | | | | | | |
|---|---|---|---|---|---|---|---|
| LYS | NZ | 771 | 194.2 | 99.9 | 40.7 | 52 | B |
| LYS | C | 771 | 197.2 | 103.1 | 38.0 | 41 | B |
| LYS | O | 771 | 197.2 | 104.0 | 38.8 | 43 | B |
| SER | N | 772 | 197.9 | 103.3 | 36.8 | 42 | B |
| SER | CA | 772 | 198.8 | 104.4 | 36.6 | 40 | B |
| SER | CB | 772 | 199.6 | 104.3 | 35.3 | 40 | B |
| SER | OG | 772 | 198.6 | 104.3 | 34.2 | 40 | B |
| SER | C | 772 | 198.1 | 105.8 | 36.7 | 39 | B |
| SER | O | 772 | 198.7 | 106.7 | 37.2 | 40 | B |
| LEU | N | 773 | 196.9 | 105.8 | 36.3 | 37 | B |
| LEU | CA | 773 | 196.1 | 107.1 | 36.4 | 36 | B |
| LEU | CB | 773 | 194.8 | 107.0 | 35.8 | 33 | B |
| LEU | CG | 773 | 193.7 | 108.1 | 36.1 | 31 | B |
| LEU | CD1 | 773 | 194.3 | 109.4 | 35.9 | 32 | B |
| LEU | CD2 | 773 | 192.6 | 107.9 | 35.1 | 32 | B |
| LEU | C | 773 | 196.1 | 107.4 | 37.9 | 38 | B |
| LEU | O | 773 | 196.3 | 108.6 | 38.3 | 40 | B |
| LEU | N | 774 | 195.8 | 106.4 | 38.7 | 37 | B |
| LEU | CA | 774 | 195.7 | 106.6 | 40.2 | 37 | B |
| LEU | CB | 774 | 195.2 | 105.3 | 40.9 | 37 | B |
| LEU | CG | 774 | 195.0 | 105.4 | 42.4 | 36 | B |
| LEU | CD1 | 774 | 193.9 | 106.5 | 42.7 | 35 | B |
| LEU | CD2 | 774 | 194.5 | 104.1 | 42.9 | 36 | B |
| LEU | C | 774 | 197.0 | 107.1 | 40.8 | 37 | B |
| LEU | O | 774 | 197.0 | 108.0 | 41.6 | 39 | B |
| GLN | N | 775 | 198.1 | 106.5 | 40.4 | 37 | B |
| GLN | CA | 775 | 199.4 | 106.9 | 40.9 | 38 | B |
| GLN | CB | 775 | 200.5 | 105.9 | 40.4 | 40 | B |
| GLN | CG | 775 | 201.9 | 106.4 | 39.9 | 45 | B |
| GLN | CD | 775 | 202.0 | 106.6 | 38.4 | 48 | B |
| GLN | OE1 | 775 | 202.4 | 105.6 | 37.7 | 49 | B |
| GLN | NE2 | 775 | 201.6 | 107.7 | 37.8 | 50 | B |
| GLN | C | 775 | 199.8 | 108.3 | 40.5 | 37 | B |
| GLN | O | 775 | 200.3 | 109.1 | 41.3 | 37 | B |
| TRP | N | 776 | 199.3 | 108.7 | 39.2 | 33 | B |
| TRP | CA | 776 | 199.6 | 110.0 | 38.7 | 29 | B |
| TRP | CB | 776 | 199.2 | 110.1 | 37.3 | 28 | B |
| TRP | CG | 776 | 199.5 | 111.5 | 36.7 | 27 | B |
| TRP | CD2 | 776 | 198.4 | 112.5 | 36.5 | 26 | B |
| TRP | CE2 | 776 | 199.1 | 113.7 | 35.9 | 26 | B |
| TRP | CE3 | 776 | 197.1 | 112.6 | 36.6 | 25 | B |
| TRP | CD1 | 776 | 200.6 | 112.1 | 36.3 | 27 | B |
| TRP | NE1 | 776 | 200.4 | 113.4 | 35.8 | 26 | B |
| TRP | CZ2 | 776 | 198.4 | 114.9 | 35.6 | 26 | B |
| TRP | CZ3 | 776 | 196.4 | 113.8 | 36.3 | 25 | B |
| TRP | CH2 | 776 | 197.1 | 114.9 | 35.8 | 25 | B |
| TRP | C | 776 | 198.8 | 111.1 | 39.5 | 27 | B |
| TRP | O | 776 | 199.4 | 112.0 | 40.1 | 27 | B |
| VAL | N | 777 | 197.5 | 110.9 | 39.6 | 27 | B |
| VAL | CA | 777 | 196.7 | 111.9 | 40.4 | 28 | B |
| VAL | CB | 777 | 195.1 | 111.5 | 40.3 | 27 | B |
| VAL | CG1 | 777 | 194.8 | 110.3 | 41.1 | 27 | B |
| VAL | CG2 | 777 | 194.3 | 112.7 | 40.7 | 26 | B |
| VAL | C | 777 | 197.1 | 112.1 | 41.8 | 30 | B |
| VAL | O | 777 | 197.3 | 113.2 | 42.3 | 31 | B |
| THR | N | 778 | 197.3 | 111.0 | 42.5 | 31 | B |
| THR | CA | 778 | 197.8 | 111.0 | 43.9 | 31 | B |
| THR | CB | 778 | 197.8 | 109.6 | 44.5 | 30 | B |
| THR | OG1 | 778 | 198.8 | 108.8 | 43.8 | 29 | B |
| THR | CG2 | 778 | 196.4 | 109.0 | 44.5 | 30 | B |
| THR | C | 778 | 199.2 | 111.7 | 44.0 | 32 | B |
| THR | O | 778 | 199.5 | 112.2 | 45.1 | 34 | B |
| SER | N | 779 | 200.0 | 111.7 | 43.0 | 31 | B |
| SER | CA | 779 | 201.2 | 112.3 | 43.1 | 29 | B |
| SER | CB | 779 | 202.1 | 111.8 | 42.0 | 28 | B |
| SER | OG | 779 | 202.3 | 110.4 | 42.1 | 29 | B |
| SER | C | 779 | 201.1 | 113.8 | 43.0 | 29 | B |
| SER | O | 779 | 202.0 | 114.6 | 43.3 | 30 | B |
| ARG | N | 780 | 199.9 | 114.3 | 42.5 | 28 | B |
| ARG | CA | 780 | 199.7 | 115.7 | 42.3 | 28 | B |
| ARG | CB | 780 | 198.5 | 115.9 | 41.3 | 27 | B |
| ARG | CG | 780 | 198.8 | 115.2 | 39.9 | 24 | B |
| ARG | CD | 780 | 199.7 | 116.0 | 39.0 | 20 | B |
| ARG | NE | 780 | 201.1 | 116.0 | 39.5 | 20 | B |
| ARG | CZ | 780 | 201.9 | 114.9 | 39.4 | 20 | B |
| ARG | NH1 | 780 | 201.5 | 113.8 | 38.9 | 21 | B |
| ARG | NH2 | 780 | 203.1 | 115.0 | 39.9 | 21 | B |
| ARG | C | 780 | 199.4 | 116.5 | 43.5 | 31 | B |
| ARG | O | 780 | 199.3 | 117.7 | 43.4 | 32 | B |

TABLE 2-continued

| | | | | | | | |
|---|---|---|---|---|---|---|---|
| GLN | N | 781 | 199.2 | 115.9 | 44.7 | 33 | B |
| GLN | CA | 781 | 198.9 | 116.6 | 45.9 | 33 | B |
| GLN | CB | 781 | 198.2 | 115.8 | 46.9 | 33 | B |
| GLN | CG | 781 | 197.8 | 116.7 | 48.1 | 33 | B |
| GLN | CD | 781 | 196.8 | 116.0 | 49.0 | 32 | B |
| GLN | OE1 | 781 | 196.8 | 114.8 | 49.2 | 35 | B |
| GLN | NE2 | 781 | 195.8 | 116.8 | 49.4 | 31 | B |
| GLN | C | 781 | 200.3 | 117.0 | 46.4 | 34 | B |
| GLN | O | 781 | 201.2 | 116.2 | 46.5 | 34 | B |
| MET | N | 782 | 200.4 | 118.3 | 46.8 | 36 | B |
| MET | CA | 782 | 201.6 | 118.9 | 47.3 | 38 | B |
| MET | CB | 782 | 201.6 | 120.4 | 47.2 | 38 | B |
| MET | CG | 782 | 201.4 | 120.9 | 45.8 | 38 | B |
| MET | SD | 782 | 202.5 | 120.2 | 44.6 | 37 | B |
| MET | CE | 782 | 203.9 | 121.3 | 44.8 | 36 | B |
| MET | C | 782 | 201.8 | 118.5 | 48.8 | 40 | B |
| MET | O | 782 | 201.1 | 119.0 | 49.7 | 39 | B |
| ARG | N | 783 | 202.9 | 117.7 | 49.0 | 41 | B |
| ARG | CA | 783 | 203.2 | 117.2 | 50.4 | 41 | B |
| ARG | CB | 783 | 204.5 | 116.4 | 50.3 | 40 | B |
| ARG | CG | 783 | 205.7 | 117.2 | 49.9 | 41 | B |
| ARG | CD | 783 | 206.8 | 116.3 | 49.3 | 42 | B |
| ARG | NE | 783 | 207.1 | 115.2 | 50.2 | 44 | B |
| ARG | CZ | 783 | 207.2 | 114.0 | 49.8 | 46 | B |
| ARG | NH1 | 783 | 207.2 | 113.6 | 48.5 | 45 | B |
| ARG | NH2 | 783 | 207.4 | 113.0 | 50.7 | 47 | B |
| ARG | C | 783 | 203.3 | 118.4 | 51.4 | 41 | B |
| ARG | O | 783 | 202.8 | 118.2 | 52.5 | 42 | B |
| PHE | N | 784 | 203.9 | 119.5 | 51.0 | 41 | B |
| PHE | CA | 784 | 204.0 | 120.6 | 51.9 | 40 | B |
| PHE | CB | 784 | 205.3 | 121.4 | 51.6 | 40 | B |
| PHE | CG | 784 | 205.5 | 122.5 | 52.5 | 40 | B |
| PHE | CD1 | 784 | 206.4 | 122.4 | 53.6 | 41 | B |
| PHE | CD2 | 784 | 204.8 | 123.7 | 52.4 | 41 | B |
| PHE | CE1 | 784 | 206.5 | 123.4 | 54.5 | 41 | B |
| PHE | CE2 | 784 | 204.9 | 124.7 | 53.3 | 40 | B |
| PHE | CZ | 784 | 205.8 | 124.5 | 54.4 | 41 | B |
| PHE | C | 784 | 202.8 | 121.5 | 51.9 | 39 | B |
| PHE | O | 784 | 202.4 | 122.0 | 52.9 | 42 | B |
| GLU | N | 785 | 202.2 | 121.8 | 50.7 | 37 | B |
| GLU | CA | 785 | 201.1 | 122.7 | 50.7 | 36 | B |
| GLU | CB | 785 | 201.0 | 123.5 | 49.4 | 37 | B |
| GLU | CG | 785 | 202.3 | 124.2 | 49.0 | 37 | B |
| GLU | CD | 785 | 203.2 | 123.4 | 48.1 | 38 | B |
| GLU | OE1 | 785 | 203.4 | 123.9 | 47.0 | 39 | B |
| GLU | OE2 | 785 | 203.7 | 122.4 | 48.6 | 41 | B |
| GLU | C | 785 | 199.8 | 122.1 | 51.1 | 35 | B |
| GLU | O | 785 | 198.9 | 122.8 | 51.6 | 36 | B |
| GLY | N | 786 | 199.6 | 120.9 | 50.6 | 34 | B |
| GLY | CA | 786 | 198.3 | 120.2 | 50.9 | 32 | B |
| GLY | C | 786 | 197.4 | 120.2 | 49.7 | 33 | B |
| GLY | O | 786 | 196.5 | 119.3 | 49.6 | 34 | B |
| GLY | N | 787 | 197.4 | 121.3 | 48.9 | 32 | B |
| GLY | CA | 787 | 196.6 | 121.4 | 47.8 | 31 | B |
| GLY | C | 787 | 197.2 | 120.7 | 46.6 | 30 | B |
| GLY | O | 787 | 198.2 | 120.1 | 46.7 | 29 | B |
| PHE | N | 788 | 196.5 | 120.7 | 45.4 | 29 | B |
| PHE | CA | 788 | 196.9 | 120.0 | 44.2 | 29 | B |
| PHE | CB | 788 | 195.8 | 119.3 | 43.6 | 29 | B |
| PHE | CG | 788 | 195.4 | 118.0 | 44.3 | 30 | B |
| PHE | CD1 | 788 | 194.5 | 118.0 | 45.3 | 29 | B |
| PHE | CD2 | 788 | 196.0 | 116.8 | 43.8 | 30 | B |
| PHE | CE1 | 788 | 194.2 | 116.8 | 45.9 | 29 | B |
| PHE | CE2 | 788 | 195.6 | 115.6 | 44.4 | 30 | B |
| PHE | CZ | 788 | 194.7 | 115.6 | 45.5 | 30 | B |
| PHE | C | 788 | 197.6 | 120.9 | 43.1 | 29 | B |
| PHE | O | 788 | 197.4 | 122.1 | 43.0 | 29 | B |
| GLN | N | 789 | 198.4 | 120.2 | 42.3 | 29 | B |
| GLN | CA | 789 | 199.0 | 120.9 | 41.2 | 28 | B |
| GLN | CB | 789 | 200.5 | 120.6 | 41.2 | 27 | B |
| GLN | CG | 789 | 201.0 | 119.2 | 40.9 | 24 | B |
| GLN | CD | 789 | 202.5 | 119.1 | 41.1 | 24 | B |
| GLN | OE1 | 789 | 203.0 | 118.0 | 41.0 | 26 | B |
| GLN | NE2 | 789 | 203.2 | 120.2 | 41.4 | 24 | B |
| GLN | C | 789 | 198.4 | 120.3 | 39.9 | 27 | B |
| GLN | O | 789 | 197.8 | 119.2 | 40.0 | 29 | B |
| GLY | N | 790 | 198.4 | 121.1 | 38.8 | 26 | B |
| GLY | CA | 790 | 197.7 | 120.6 | 37.6 | 24 | B |
| GLY | C | 790 | 198.6 | 119.7 | 36.8 | 24 | B |

TABLE 2-continued

| | | | | | | | |
|---|---|---|---|---|---|---|---|
| GLY | O | 790 | 198.1 | 118.9 | 36.1 | 23 | B |
| ARG | N | 791 | 199.9 | 119.9 | 36.9 | 23 | B |
| ARG | CA | 791 | 200.9 | 119.2 | 36.2 | 24 | B |
| ARG | CB | 791 | 201.4 | 120.0 | 35.0 | 23 | B |
| ARG | CG | 791 | 200.5 | 120.1 | 33.8 | 23 | B |
| ARG | CD | 791 | 201.1 | 120.8 | 32.6 | 24 | B |
| ARG | NE | 791 | 200.8 | 122.2 | 32.6 | 26 | B |
| ARG | CZ | 791 | 201.4 | 123.1 | 31.9 | 25 | B |
| ARG | NH1 | 791 | 202.4 | 122.7 | 31.0 | 24 | B |
| ARG | NH2 | 791 | 201.1 | 124.4 | 31.9 | 25 | B |
| ARG | C | 791 | 202.1 | 118.9 | 37.0 | 23 | B |
| ARG | O | 791 | 202.5 | 119.6 | 37.9 | 25 | B |
| CYS | N | 792 | 202.8 | 117.7 | 36.8 | 23 | B |
| CYS | CA | 792 | 204.0 | 117.4 | 37.6 | 23 | B |
| CYS | CB | 792 | 204.6 | 116.1 | 37.0 | 22 | B |
| CYS | SG | 792 | 206.2 | 115.8 | 37.9 | 23 | B |
| CYS | C | 792 | 205.0 | 118.5 | 37.5 | 23 | B |
| CYS | O | 792 | 205.2 | 119.1 | 36.5 | 25 | B |
| ASN | N | 793 | 205.5 | 118.9 | 38.7 | 25 | B |
| ASN | CA | 793 | 206.5 | 120.0 | 38.7 | 26 | B |
| ASN | CB | 793 | 207.7 | 119.7 | 37.9 | 26 | B |
| ASN | CG | 793 | 208.8 | 119.0 | 38.6 | 27 | B |
| ASN | OD1 | 793 | 209.1 | 119.3 | 39.8 | 26 | B |
| ASN | ND2 | 793 | 209.5 | 118.0 | 38.0 | 26 | B |
| ASN | C | 793 | 206.0 | 121.4 | 38.4 | 26 | B |
| ASN | O | 793 | 206.7 | 122.2 | 37.9 | 26 | B |
| LYS | N | 794 | 204.7 | 121.6 | 38.7 | 25 | B |
| LYS | CA | 794 | 204.1 | 123.0 | 38.5 | 26 | B |
| LYS | CB | 794 | 202.8 | 123.0 | 37.6 | 26 | B |
| LYS | CG | 794 | 203.1 | 122.7 | 36.2 | 27 | B |
| LYS | CD | 794 | 204.0 | 123.7 | 35.5 | 28 | B |
| LYS | CE | 794 | 203.3 | 125.0 | 35.4 | 30 | B |
| LYS | NZ | 794 | 202.0 | 124.9 | 34.7 | 31 | B |
| LYS | C | 794 | 203.8 | 123.4 | 39.9 | 27 | B |
| LYS | O | 794 | 204.2 | 122.7 | 40.9 | 27 | B |
| LEU | N | 795 | 203.0 | 124.5 | 40.1 | 25 | B |
| LEU | CA | 795 | 202.7 | 124.9 | 41.5 | 24 | B |
| LEU | CB | 795 | 202.9 | 126.5 | 41.5 | 22 | B |
| LEU | CG | 795 | 204.2 | 127.0 | 41.0 | 21 | B |
| LEU | CD1 | 795 | 204.2 | 128.5 | 40.9 | 19 | B |
| LEU | CD2 | 795 | 205.4 | 126.5 | 41.8 | 22 | B |
| LEU | C | 795 | 201.3 | 124.5 | 41.8 | 24 | B |
| LEU | O | 795 | 200.5 | 124.1 | 41.0 | 26 | B |
| VAL | N | 796 | 201.0 | 124.7 | 43.1 | 24 | B |
| VAL | CA | 796 | 199.7 | 124.4 | 43.6 | 25 | B |
| VAL | CB | 796 | 199.6 | 124.6 | 45.1 | 26 | B |
| VAL | CG1 | 796 | 199.0 | 123.3 | 45.8 | 25 | B |
| VAL | CG2 | 796 | 200.9 | 125.0 | 45.7 | 28 | B |
| VAL | C | 796 | 198.7 | 125.5 | 43.0 | 24 | B |
| VAL | O | 796 | 199.2 | 126.6 | 42.7 | 25 | B |
| ASP | N | 797 | 197.5 | 125.1 | 43.0 | 24 | B |
| ASP | CA | 797 | 196.5 | 126.1 | 42.5 | 24 | B |
| ASP | CB | 797 | 196.4 | 126.2 | 41.0 | 24 | B |
| ASP | CG | 797 | 195.4 | 127.2 | 40.5 | 23 | B |
| ASP | OD1 | 797 | 194.6 | 127.7 | 41.3 | 24 | B |
| ASP | OD2 | 797 | 195.3 | 127.4 | 39.3 | 22 | B |
| ASP | C | 797 | 195.1 | 125.6 | 43.0 | 25 | B |
| ASP | O | 797 | 194.7 | 124.5 | 42.7 | 26 | B |
| GLY | N | 798 | 194.4 | 126.5 | 43.7 | 26 | B |
| GLY | CA | 798 | 193.1 | 126.1 | 44.3 | 26 | B |
| GLY | C | 798 | 192.1 | 125.5 | 43.4 | 28 | B |
| GLY | O | 798 | 191.3 | 124.8 | 43.9 | 30 | B |
| CYS | N | 799 | 192.1 | 125.9 | 42.1 | 27 | B |
| CYS | CA | 799 | 191.0 | 125.4 | 41.2 | 26 | B |
| CYS | CB | 799 | 190.9 | 126.1 | 39.9 | 25 | B |
| CYS | SG | 799 | 192.5 | 126.1 | 38.9 | 26 | B |
| CYS | C | 799 | 191.2 | 123.9 | 41.0 | 27 | B |
| CYS | O | 799 | 190.3 | 123.2 | 40.8 | 28 | B |
| TYR | N | 800 | 192.5 | 123.4 | 41.2 | 29 | B |
| TYR | CA | 800 | 192.8 | 122.0 | 41.0 | 32 | B |
| TYR | CB | 800 | 194.3 | 121.8 | 40.8 | 31 | B |
| TYR | CG | 800 | 194.6 | 122.3 | 39.4 | 32 | B |
| TYR | CD1 | 800 | 195.4 | 123.4 | 39.2 | 32 | B |
| TYR | CE1 | 800 | 195.7 | 123.9 | 37.9 | 33 | B |
| TYR | CD2 | 800 | 194.1 | 121.6 | 38.3 | 32 | B |
| TYR | CE2 | 800 | 194.4 | 122.1 | 37.0 | 32 | B |
| TYR | CZ | 800 | 195.1 | 123.2 | 36.8 | 33 | B |
| TYR | OH | 800 | 195.4 | 123.7 | 35.6 | 34 | B |
| TYR | C | 800 | 192.4 | 121.2 | 42.2 | 34 | B |

TABLE 2-continued

| | | | | | | | |
|---|---|---|---|---|---|---|---|
| TYR | O | 800 | 192.6 | 119.9 | 42.2 | 34 | B |
| SER | N | 801 | 191.8 | 121.8 | 43.2 | 35 | B |
| SER | CA | 801 | 191.3 | 121.1 | 44.4 | 34 | B |
| SER | CB | 801 | 190.8 | 122.2 | 45.4 | 36 | B |
| SER | OG | 801 | 191.9 | 123.0 | 45.8 | 36 | B |
| SER | C | 801 | 190.1 | 120.3 | 43.9 | 33 | B |
| SER | O | 801 | 189.7 | 119.3 | 44.5 | 35 | B |
| PHE | N | 802 | 189.5 | 120.8 | 42.8 | 32 | B |
| PHE | CA | 802 | 188.4 | 120.0 | 42.2 | 31 | B |
| PHE | CB | 802 | 187.2 | 120.9 | 41.7 | 31 | B |
| PHE | CG | 802 | 186.2 | 120.0 | 41.0 | 33 | B |
| PHE | CD1 | 802 | 185.3 | 119.2 | 41.8 | 34 | B |
| PHE | CD2 | 802 | 186.1 | 120.0 | 39.6 | 34 | B |
| PHE | CE1 | 802 | 184.4 | 118.4 | 41.1 | 34 | B |
| PHE | CE2 | 802 | 185.1 | 119.2 | 39.0 | 34 | B |
| PHE | CZ | 802 | 184.3 | 118.4 | 39.8 | 34 | B |
| PHE | C | 802 | 188.8 | 119.2 | 41.0 | 30 | B |
| PHE | O | 802 | 188.4 | 118.0 | 40.8 | 30 | B |
| TRP | N | 803 | 189.5 | 119.8 | 40.0 | 27 | B |
| TRP | CA | 803 | 189.9 | 119.1 | 38.8 | 25 | B |
| TRP | CB | 803 | 190.6 | 120.0 | 37.8 | 23 | B |
| TRP | CG | 803 | 189.8 | 121.2 | 37.3 | 20 | B |
| TRP | CD2 | 803 | 188.6 | 121.3 | 36.6 | 18 | B |
| TRP | CE2 | 803 | 188.3 | 122.6 | 36.4 | 18 | B |
| TRP | CE3 | 803 | 187.7 | 120.3 | 36.2 | 18 | B |
| TRP | CD1 | 803 | 190.2 | 122.5 | 37.5 | 18 | B |
| TRP | NE1 | 803 | 189.3 | 123.3 | 36.9 | 19 | B |
| TRP | CZ2 | 803 | 187.2 | 123.0 | 35.7 | 17 | B |
| TRP | CZ3 | 803 | 186.5 | 120.7 | 35.5 | 17 | B |
| TRP | CH2 | 803 | 186.3 | 122.1 | 35.2 | 18 | B |
| TRP | C | 803 | 190.8 | 117.8 | 39.1 | 26 | B |
| TRP | O | 803 | 190.6 | 116.8 | 38.5 | 26 | B |
| GLN | N | 804 | 191.7 | 117.9 | 40.1 | 26 | B |
| GLN | CA | 804 | 192.5 | 116.8 | 40.4 | 28 | B |
| GLN | CB | 804 | 193.9 | 117.3 | 40.9 | 26 | B |
| GLN | CG | 804 | 194.8 | 118.0 | 39.8 | 25 | B |
| GLN | CD | 804 | 195.4 | 117.0 | 38.8 | 25 | B |
| GLN | OE1 | 804 | 194.8 | 116.0 | 38.5 | 25 | B |
| GLN | NE2 | 804 | 196.6 | 117.4 | 38.4 | 24 | B |
| GLN | C | 804 | 191.9 | 115.9 | 41.6 | 32 | B |
| GLN | O | 804 | 191.9 | 114.7 | 41.4 | 32 | B |
| ALA | N | 805 | 191.5 | 116.5 | 42.7 | 34 | B |
| ALA | CA | 805 | 190.9 | 115.8 | 43.8 | 34 | B |
| ALA | CB | 805 | 190.7 | 116.7 | 45.0 | 35 | B |
| ALA | C | 805 | 189.6 | 115.1 | 43.4 | 35 | B |
| ALA | O | 805 | 189.3 | 114.1 | 43.9 | 37 | B |
| GLY | N | 806 | 188.9 | 115.8 | 42.5 | 34 | B |
| GLY | CA | 806 | 187.6 | 115.2 | 42.0 | 33 | B |
| GLY | C | 806 | 187.8 | 113.8 | 41.3 | 34 | B |
| GLY | O | 806 | 186.9 | 113.1 | 41.1 | 35 | B |
| LEU | N | 807 | 189.0 | 113.5 | 40.9 | 34 | B |
| LEU | CA | 807 | 189.4 | 112.3 | 40.1 | 35 | B |
| LEU | CB | 807 | 190.7 | 112.4 | 39.4 | 35 | B |
| LEU | CG | 807 | 190.9 | 113.3 | 38.2 | 35 | B |
| LEU | CD1 | 807 | 192.3 | 113.3 | 37.8 | 35 | B |
| LEU | CD2 | 807 | 190.0 | 112.8 | 37.1 | 33 | B |
| LEU | C | 807 | 189.4 | 111.0 | 41.0 | 36 | B |
| LEU | O | 807 | 189.3 | 109.9 | 40.5 | 38 | B |
| LEU | N | 808 | 189.5 | 111.2 | 42.3 | 37 | B |
| LEU | CA | 808 | 189.5 | 110.1 | 43.2 | 36 | B |
| LEU | CB | 808 | 190.3 | 110.4 | 44.5 | 35 | B |
| LEU | CG | 808 | 191.7 | 110.7 | 44.1 | 35 | B |
| LEU | CD1 | 808 | 192.4 | 111.5 | 45.0 | 35 | B |
| LEU | CD2 | 808 | 192.4 | 109.4 | 43.9 | 34 | B |
| LEU | C | 808 | 188.1 | 109.5 | 43.4 | 35 | B |
| LEU | O | 808 | 188.0 | 108.3 | 43.4 | 38 | B |
| PRO | N | 809 | 187.1 | 110.3 | 43.6 | 32 | B |
| PRO | CD | 809 | 187.1 | 111.8 | 44.0 | 31 | B |
| PRO | CA | 809 | 185.8 | 109.8 | 43.8 | 31 | B |
| PRO | CB | 809 | 184.9 | 111.0 | 43.9 | 30 | B |
| PRO | CG | 809 | 185.7 | 111.9 | 44.6 | 30 | B |
| PRO | C | 809 | 185.4 | 109.0 | 42.5 | 32 | B |
| PRO | O | 809 | 184.8 | 107.9 | 42.5 | 34 | B |
| LEU | N | 810 | 185.8 | 109.6 | 41.4 | 31 | B |
| LEU | CA | 810 | 185.5 | 109.0 | 40.1 | 30 | B |
| LEU | CB | 810 | 186.0 | 109.8 | 38.9 | 29 | B |
| LEU | CG | 810 | 185.2 | 111.2 | 38.8 | 29 | B |
| LEU | CD1 | 810 | 185.5 | 111.8 | 37.5 | 29 | B |
| LEU | CD2 | 810 | 183.8 | 110.9 | 39.0 | 28 | B |

TABLE 2-continued

| | | | | | | | |
|---|---|---|---|---|---|---|---|
| LEU | C | 810 | 186.3 | 107.6 | 40.0 | 31 | B |
| LEU | O | 810 | 185.7 | 106.6 | 39.6 | 30 | B |
| LEU | N | 811 | 187.5 | 107.7 | 40.5 | 33 | B |
| LEU | CA | 811 | 188.4 | 106.5 | 40.5 | 35 | B |
| LEU | CB | 811 | 189.8 | 106.8 | 40.7 | 32 | B |
| LEU | CG | 811 | 190.6 | 107.2 | 39.4 | 29 | B |
| LEU | CD1 | 811 | 192.0 | 107.6 | 39.7 | 28 | B |
| LEU | CD2 | 811 | 190.6 | 106.0 | 38.5 | 27 | B |
| LEU | C | 811 | 188.0 | 105.5 | 41.6 | 38 | B |
| LEU | O | 811 | 188.5 | 104.3 | 41.7 | 40 | B |
| HIS | N | 812 | 187.1 | 105.9 | 42.6 | 41 | B |
| HIS | CA | 812 | 186.7 | 105.0 | 43.6 | 43 | B |
| HIS | CB | 812 | 186.1 | 105.7 | 44.8 | 45 | B |
| HIS | CG | 812 | 186.4 | 105.1 | 46.1 | 47 | B |
| HIS | CD2 | 812 | 185.8 | 104.3 | 46.9 | 47 | B |
| HIS | ND1 | 812 | 187.7 | 105.4 | 46.7 | 47 | B |
| HIS | CE1 | 812 | 187.8 | 104.8 | 47.8 | 47 | B |
| HIS | NE2 | 812 | 186.7 | 104.0 | 48.0 | 47 | B |
| HIS | C | 812 | 185.7 | 104.1 | 42.9 | 45 | B |
| HIS | O | 812 | 185.9 | 102.9 | 42.8 | 45 | B |
| ARG | N | 813 | 184.6 | 104.7 | 42.3 | 47 | B |
| ARG | CA | 813 | 183.6 | 104.0 | 41.6 | 49 | B |
| ARG | CB | 813 | 182.7 | 104.9 | 40.8 | 52 | B |
| ARG | CG | 813 | 181.8 | 105.9 | 41.7 | 56 | B |
| ARG | CD | 813 | 181.3 | 107.1 | 40.8 | 59 | B |
| ARG | NE | 813 | 180.2 | 107.8 | 41.4 | 62 | B |
| ARG | CZ | 813 | 180.2 | 108.4 | 42.6 | 63 | B |
| ARG | NH1 | 813 | 181.3 | 108.4 | 43.4 | 62 | B |
| ARG | NH2 | 813 | 179.2 | 109.2 | 43.0 | 63 | B |
| ARG | C | 813 | 184.2 | 103.1 | 40.6 | 49 | B |
| ARG | O | 813 | 184.1 | 101.8 | 40.7 | 51 | B |
| ALA | N | 814 | 185.0 | 103.6 | 39.7 | 49 | B |
| ALA | CA | 814 | 185.7 | 102.8 | 38.7 | 49 | B |
| ALA | CB | 814 | 186.7 | 103.6 | 37.9 | 49 | B |
| ALA | C | 814 | 186.3 | 101.6 | 39.2 | 50 | B |
| ALA | O | 814 | 185.9 | 100.5 | 38.8 | 50 | B |
| LEU | N | 815 | 187.2 | 101.7 | 40.2 | 50 | B |
| LEU | CA | 815 | 187.9 | 100.6 | 40.8 | 51 | B |
| LEU | CB | 815 | 189.0 | 101.0 | 41.7 | 50 | B |
| LEU | CG | 815 | 190.1 | 101.8 | 41.0 | 51 | B |
| LEU | CD1 | 815 | 191.2 | 102.2 | 42.0 | 51 | B |
| LEU | CD2 | 815 | 190.7 | 101.0 | 39.9 | 51 | B |
| LEU | C | 815 | 187.0 | 99.6 | 41.5 | 52 | B |
| LEU | O | 815 | 187.1 | 98.4 | 41.4 | 52 | B |
| HIS | N | 816 | 186.1 | 100.1 | 42.3 | 52 | B |
| HIS | CA | 816 | 185.2 | 99.3 | 43.1 | 54 | B |
| HIS | CB | 816 | 184.4 | 100.1 | 44.0 | 56 | B |
| HIS | CG | 816 | 183.2 | 99.5 | 44.6 | 59 | B |
| HIS | CD2 | 816 | 183.0 | 98.5 | 45.5 | 60 | B |
| HIS | ND1 | 816 | 181.9 | 99.8 | 44.2 | 61 | B |
| HIS | CE1 | 816 | 181.0 | 99.1 | 44.9 | 61 | B |
| HIS | NE2 | 816 | 181.7 | 98.2 | 45.7 | 62 | B |
| HIS | C | 816 | 184.2 | 98.6 | 42.1 | 54 | B |
| HIS | O | 816 | 183.8 | 97.4 | 42.3 | 53 | B |
| ALA | N | 817 | 184.0 | 99.2 | 40.9 | 54 | B |
| ALA | CA | 817 | 183.2 | 98.7 | 39.9 | 55 | B |
| ALA | CB | 817 | 183.0 | 99.7 | 38.8 | 55 | B |
| ALA | C | 817 | 183.8 | 97.4 | 39.4 | 55 | B |
| ALA | O | 817 | 183.1 | 96.5 | 39.0 | 57 | B |
| GLN | N | 818 | 185.1 | 97.4 | 39.3 | 56 | B |
| GLN | CA | 818 | 185.7 | 96.1 | 38.9 | 57 | B |
| GLN | CB | 818 | 186.9 | 96.4 | 38.0 | 56 | B |
| GLN | CG | 818 | 188.0 | 97.4 | 38.4 | 56 | B |
| GLN | CD | 818 | 188.9 | 97.8 | 37.2 | 56 | B |
| GLN | OE1 | 818 | 188.7 | 97.3 | 36.1 | 56 | B |
| GLN | NE2 | 818 | 189.9 | 98.6 | 37.5 | 56 | B |
| GLN | C | 818 | 186.1 | 95.3 | 40.1 | 58 | B |
| GLN | O | 818 | 187.1 | 94.6 | 40.2 | 58 | B |
| GLY | N | 819 | 185.2 | 95.4 | 41.1 | 58 | B |
| GLY | CA | 819 | 185.3 | 94.8 | 42.4 | 58 | B |
| GLY | C | 819 | 186.6 | 94.8 | 43.1 | 59 | B |
| GLY | O | 819 | 187.3 | 93.8 | 43.2 | 60 | B |
| ASP | N | 820 | 187.1 | 96.0 | 43.5 | 60 | B |
| ASP | CA | 820 | 188.3 | 96.1 | 44.1 | 61 | B |
| ASP | CB | 820 | 189.0 | 97.4 | 43.8 | 62 | B |
| ASP | CG | 820 | 190.5 | 97.3 | 44.0 | 62 | B |
| ASP | OD1 | 820 | 191.3 | 97.8 | 43.1 | 63 | B |
| ASP | OD2 | 820 | 191.0 | 96.8 | 45.1 | 62 | B |
| ASP | C | 820 | 188.1 | 96.0 | 45.6 | 61 | B |

TABLE 2-continued

| | | | | | | |
|---|---|---|---|---|---|---|
| ASP | O | 820 | 187.2 | 96.6 | 46.2 | 61 | B |
| PRO | N | 821 | 188.8 | 95.1 | 46.3 | 62 | B |
| PRO | CD | 821 | 189.5 | 94.0 | 45.6 | 63 | B |
| PRO | CA | 821 | 188.7 | 94.8 | 47.8 | 63 | B |
| PRO | CB | 821 | 189.3 | 93.4 | 47.9 | 63 | B |
| PRO | CG | 821 | 189.2 | 92.8 | 46.5 | 63 | B |
| PRO | C | 821 | 189.4 | 95.8 | 48.6 | 63 | B |
| PRO | O | 821 | 188.9 | 96.3 | 49.6 | 65 | B |
| ALA | N | 822 | 190.7 | 96.1 | 48.3 | 62 | B |
| ALA | CA | 822 | 191.6 | 97.0 | 49.0 | 60 | B |
| ALA | CB | 822 | 193.0 | 97.0 | 48.5 | 59 | B |
| ALA | C | 822 | 191.1 | 98.5 | 49.2 | 59 | B |
| ALA | O | 822 | 191.9 | 99.3 | 49.7 | 59 | B |
| LEU | N | 823 | 189.9 | 98.8 | 48.7 | 59 | B |
| LEU | CA | 823 | 189.4 | 100.2 | 48.8 | 60 | B |
| LEU | CB | 823 | 188.4 | 100.5 | 47.7 | 60 | B |
| LEU | CG | 823 | 188.9 | 100.5 | 46.3 | 60 | B |
| LEU | CD1 | 823 | 187.7 | 100.6 | 45.4 | 59 | B |
| LEU | CD2 | 823 | 189.8 | 101.7 | 46.0 | 60 | B |
| LEU | C | 823 | 188.8 | 100.5 | 50.2 | 61 | B |
| LEU | O | 823 | 188.0 | 99.8 | 50.7 | 62 | B |
| SER | N | 824 | 189.1 | 101.7 | 50.6 | 62 | B |
| SER | CA | 824 | 188.6 | 102.3 | 51.9 | 62 | B |
| SER | CB | 824 | 189.3 | 103.6 | 52.2 | 62 | B |
| SER | OG | 824 | 188.8 | 104.3 | 53.3 | 61 | B |
| SER | C | 824 | 187.1 | 102.5 | 51.9 | 63 | B |
| SER | O | 824 | 186.5 | 102.7 | 50.8 | 63 | B |
| MET | N | 825 | 186.5 | 102.4 | 53.1 | 65 | B |
| MET | CA | 825 | 185.1 | 102.6 | 53.2 | 66 | B |
| MET | CB | 825 | 184.4 | 101.4 | 53.9 | 70 | B |
| MET | CG | 825 | 184.6 | 100.0 | 53.3 | 74 | B |
| MET | SD | 825 | 183.9 | 99.9 | 51.6 | 79 | B |
| MET | CE | 825 | 182.2 | 99.3 | 52.0 | 78 | B |
| MET | C | 825 | 184.7 | 103.9 | 53.9 | 64 | B |
| MET | O | 825 | 183.5 | 104.1 | 54.2 | 64 | B |
| SER | N | 826 | 185.7 | 104.8 | 54.1 | 62 | B |
| SER | CA | 826 | 185.5 | 106.0 | 54.8 | 60 | B |
| SER | CB | 826 | 185.9 | 105.9 | 56.2 | 60 | B |
| SER | OG | 826 | 187.3 | 105.6 | 56.3 | 59 | B |
| SER | C | 826 | 186.2 | 107.3 | 54.1 | 58 | B |
| SER | O | 826 | 185.8 | 108.4 | 54.4 | 57 | B |
| HIS | N | 827 | 187.2 | 107.1 | 53.3 | 57 | B |
| HIS | CA | 827 | 188.0 | 108.2 | 52.8 | 54 | B |
| HIS | CB | 827 | 189.3 | 108.3 | 53.5 | 56 | B |
| HIS | CG | 827 | 189.1 | 108.7 | 55.0 | 58 | B |
| HIS | CD2 | 827 | 189.6 | 108.2 | 56.1 | 58 | B |
| HIS | ND1 | 827 | 188.4 | 109.8 | 55.4 | 58 | B |
| HIS | CE1 | 827 | 188.4 | 110.0 | 56.7 | 59 | B |
| HIS | NE2 | 827 | 189.2 | 109.0 | 57.2 | 59 | B |
| HIS | C | 827 | 188.4 | 108.0 | 51.3 | 51 | B |
| HIS | O | 827 | 188.4 | 106.9 | 50.8 | 51 | B |
| TRP | N | 828 | 188.7 | 109.1 | 50.7 | 46 | B |
| TRP | CA | 828 | 189.1 | 109.1 | 49.3 | 41 | B |
| TRP | CB | 828 | 188.9 | 110.5 | 48.6 | 37 | B |
| TRP | CG | 828 | 187.5 | 110.9 | 48.6 | 32 | B |
| TRP | CD2 | 828 | 186.4 | 110.1 | 48.1 | 31 | B |
| TRP | CE2 | 828 | 185.2 | 110.8 | 48.2 | 30 | B |
| TRP | CE3 | 828 | 186.3 | 108.8 | 47.6 | 31 | B |
| TRP | CD1 | 828 | 186.9 | 112.0 | 49.0 | 31 | B |
| TRP | NE1 | 828 | 185.6 | 112.0 | 48.8 | 31 | B |
| TRP | CZ2 | 828 | 184.0 | 110.4 | 47.8 | 30 | B |
| TRP | CZ3 | 828 | 185.1 | 108.3 | 47.1 | 30 | B |
| TRP | CH2 | 828 | 184.0 | 109.1 | 47.2 | 30 | B |
| TRP | C | 828 | 190.6 | 108.9 | 49.3 | 42 | B |
| TRP | O | 828 | 191.3 | 109.1 | 50.3 | 40 | B |
| MET | N | 829 | 191.2 | 108.5 | 48.1 | 42 | B |
| MET | CA | 829 | 192.6 | 108.2 | 48.1 | 41 | B |
| MET | CB | 829 | 192.9 | 107.2 | 47.0 | 42 | B |
| MET | CG | 829 | 192.2 | 105.8 | 47.3 | 44 | B |
| MET | SD | 829 | 192.6 | 104.4 | 46.3 | 46 | B |
| MET | CE | 829 | 194.4 | 104.5 | 46.4 | 43 | B |
| MET | C | 829 | 193.5 | 109.4 | 47.9 | 41 | B |
| MET | O | 829 | 194.4 | 109.5 | 47.0 | 41 | B |
| PHE | N | 830 | 193.3 | 110.4 | 48.8 | 40 | B |
| PHE | CA | 830 | 194.1 | 111.6 | 49.0 | 39 | B |
| PHE | CB | 830 | 193.7 | 112.6 | 47.9 | 35 | B |
| PHE | CG | 830 | 192.5 | 113.4 | 48.1 | 30 | B |
| PHE | CD1 | 830 | 192.5 | 114.6 | 48.9 | 30 | B |
| PHE | CD2 | 830 | 191.3 | 113.1 | 47.5 | 30 | B |

TABLE 2-continued

| | | | | | | | |
|---|---|---|---|---|---|---|---|
| PHE | CE1 | 830 | 191.4 | 115.4 | 49.0 | 28 | B |
| PHE | CE2 | 830 | 190.1 | 113.8 | 47.7 | 29 | B |
| PHE | CZ | 830 | 190.2 | 115.0 | 48.4 | 29 | B |
| PHE | C | 830 | 193.9 | 112.1 | 50.4 | 40 | B |
| PHE | O | 830 | 193.0 | 111.7 | 51.1 | 41 | B |
| HIS | N | 831 | 194.8 | 113.0 | 50.8 | 42 | B |
| HIS | CA | 831 | 194.7 | 113.6 | 52.2 | 42 | B |
| HIS | CB | 831 | 196.0 | 114.3 | 52.5 | 43 | B |
| HIS | CG | 831 | 196.4 | 114.2 | 54.0 | 44 | B |
| HIS | CD2 | 831 | 195.8 | 114.7 | 55.1 | 45 | B |
| HIS | ND1 | 831 | 197.5 | 113.5 | 54.5 | 45 | B |
| HIS | CE1 | 831 | 197.5 | 113.6 | 55.8 | 45 | B |
| HIS | NE2 | 831 | 196.5 | 114.3 | 56.2 | 46 | B |
| HIS | C | 831 | 193.6 | 114.6 | 52.2 | 42 | B |
| HIS | O | 831 | 193.8 | 115.8 | 51.9 | 42 | B |
| GLN | N | 832 | 192.4 | 114.2 | 52.6 | 43 | B |
| GLN | CA | 832 | 191.2 | 115.1 | 52.7 | 45 | B |
| GLN | CB | 832 | 190.0 | 114.4 | 53.2 | 45 | B |
| GLN | CG | 832 | 189.3 | 113.5 | 52.1 | 45 | B |
| GLN | CD | 832 | 189.1 | 112.1 | 52.5 | 45 | B |
| GLN | OE1 | 832 | 188.0 | 111.7 | 52.6 | 44 | B |
| GLN | NE2 | 832 | 190.2 | 111.4 | 52.7 | 44 | B |
| GLN | C | 832 | 191.5 | 116.2 | 53.7 | 46 | B |
| GLN | O | 832 | 191.0 | 117.4 | 53.5 | 46 | B |
| GLN | N | 833 | 192.2 | 115.9 | 54.8 | 48 | B |
| GLN | CA | 833 | 192.5 | 116.9 | 55.8 | 49 | B |
| GLN | CB | 833 | 193.2 | 116.3 | 57.0 | 52 | B |
| GLN | CG | 833 | 193.3 | 117.2 | 58.2 | 55 | B |
| GLN | CD | 833 | 194.4 | 116.7 | 59.1 | 57 | B |
| GLN | OE1 | 833 | 195.1 | 115.7 | 58.9 | 58 | B |
| GLN | NE2 | 833 | 194.6 | 117.5 | 60.2 | 57 | B |
| GLN | C | 833 | 193.4 | 118.0 | 55.2 | 48 | B |
| GLN | O | 833 | 193.0 | 119.2 | 55.2 | 48 | B |
| ALA | N | 834 | 194.5 | 117.7 | 54.7 | 46 | B |
| ALA | CA | 834 | 195.5 | 118.6 | 54.1 | 44 | B |
| ALA | CB | 834 | 196.7 | 117.8 | 53.5 | 42 | B |
| ALA | C | 834 | 194.9 | 119.5 | 53.0 | 44 | B |
| ALA | O | 834 | 195.1 | 120.7 | 53.0 | 45 | B |
| LEU | N | 835 | 194.0 | 119.0 | 52.1 | 43 | B |
| LEU | CA | 835 | 193.4 | 119.8 | 51.1 | 42 | B |
| LEU | CB | 835 | 192.6 | 118.9 | 50.1 | 42 | B |
| LEU | CG | 835 | 191.9 | 119.8 | 49.0 | 41 | B |
| LEU | CD1 | 835 | 192.9 | 120.5 | 48.2 | 40 | B |
| LEU | CD2 | 835 | 190.9 | 119.0 | 48.2 | 39 | B |
| LEU | C | 835 | 192.4 | 120.8 | 51.7 | 43 | B |
| LEU | O | 835 | 192.2 | 121.9 | 51.2 | 44 | B |
| GLN | N | 836 | 191.7 | 120.5 | 52.8 | 42 | B |
| GLN | CA | 836 | 190.8 | 121.4 | 53.5 | 40 | B |
| GLN | CB | 836 | 189.9 | 120.6 | 54.4 | 40 | B |
| GLN | CG | 836 | 189.0 | 119.7 | 53.8 | 40 | B |
| GLN | CD | 836 | 188.0 | 119.1 | 54.7 | 41 | B |
| GLN | OE1 | 836 | 187.2 | 119.8 | 55.4 | 41 | B |
| GLN | NE2 | 836 | 188.1 | 117.8 | 54.9 | 42 | B |
| GLN | C | 836 | 191.5 | 122.5 | 54.2 | 39 | B |
| GLN | O | 836 | 191.1 | 123.6 | 54.4 | 38 | B |
| GLU | N | 837 | 192.7 | 122.2 | 54.7 | 38 | B |
| GLU | CA | 837 | 193.6 | 123.1 | 55.4 | 37 | B |
| GLU | CB | 837 | 194.7 | 122.5 | 56.2 | 37 | B |
| GLU | CG | 837 | 194.1 | 121.7 | 57.3 | 37 | B |
| GLU | CD | 837 | 195.1 | 121.0 | 58.3 | 37 | B |
| GLU | OE1 | 837 | 196.3 | 121.2 | 58.1 | 37 | B |
| GLU | OE2 | 837 | 194.6 | 120.3 | 59.1 | 38 | B |
| GLU | C | 837 | 194.1 | 124.1 | 54.4 | 37 | B |
| GLU | O | 837 | 193.9 | 125.3 | 54.6 | 38 | B |
| TYR | N | 838 | 194.6 | 123.6 | 53.3 | 37 | B |
| TYR | CA | 838 | 195.1 | 124.5 | 52.2 | 35 | B |
| TYR | CB | 838 | 195.5 | 123.7 | 50.9 | 36 | B |
| TYR | CG | 838 | 196.0 | 124.6 | 49.8 | 35 | B |
| TYR | CD1 | 838 | 197.3 | 125.2 | 49.9 | 36 | B |
| TYR | CE1 | 838 | 197.7 | 126.2 | 49.0 | 35 | B |
| TYR | CD2 | 838 | 195.2 | 125.0 | 48.8 | 35 | B |
| TYR | CE2 | 838 | 195.6 | 126.0 | 47.8 | 34 | B |
| TYR | CZ | 838 | 196.8 | 126.6 | 48.0 | 34 | B |
| TYR | OH | 838 | 197.3 | 127.6 | 47.1 | 32 | B |
| TYR | C | 838 | 194.0 | 125.5 | 51.8 | 34 | B |
| TYR | O | 838 | 194.3 | 126.7 | 51.9 | 34 | B |
| ILE | N | 839 | 192.9 | 125.0 | 51.4 | 32 | B |
| ILE | CA | 839 | 191.8 | 125.9 | 51.0 | 31 | B |
| ILE | CB | 839 | 190.6 | 125.0 | 50.5 | 29 | B |

TABLE 2-continued

| | | | | | | | |
|---|---|---|---|---|---|---|---|
| ILE | CG2 | 839 | 189.4 | 126.0 | 50.0 | 28 | B |
| ILE | CG1 | 839 | 191.0 | 124.1 | 49.4 | 28 | B |
| ILE | CD1 | 839 | 189.9 | 123.4 | 48.7 | 28 | B |
| ILE | C | 839 | 191.3 | 126.9 | 52.1 | 34 | B |
| ILE | O | 839 | 191.3 | 128.1 | 51.8 | 36 | B |
| LEU | N | 840 | 190.9 | 126.4 | 53.2 | 33 | B |
| LEU | CA | 840 | 190.5 | 127.2 | 54.3 | 32 | B |
| LEU | CB | 840 | 190.1 | 126.4 | 55.5 | 30 | B |
| LEU | CG | 840 | 188.9 | 125.5 | 55.3 | 29 | B |
| LEU | CD1 | 840 | 188.8 | 124.5 | 56.4 | 28 | B |
| LEU | CD2 | 840 | 187.6 | 126.3 | 55.2 | 28 | B |
| LEU | C | 840 | 191.5 | 128.3 | 54.8 | 32 | B |
| LEU | O | 840 | 191.2 | 129.4 | 54.9 | 33 | B |
| MET | N | 841 | 192.8 | 127.8 | 54.9 | 33 | B |
| MET | CA | 841 | 193.8 | 128.7 | 55.4 | 34 | B |
| MET | CB | 841 | 195.0 | 128.0 | 56.0 | 35 | B |
| MET | CG | 841 | 194.7 | 127.4 | 57.5 | 37 | B |
| MET | SD | 841 | 196.2 | 126.8 | 58.3 | 40 | B |
| MET | CE | 841 | 195.9 | 125.0 | 58.3 | 39 | B |
| MET | C | 841 | 194.4 | 129.6 | 54.3 | 36 | B |
| MET | O | 841 | 194.6 | 130.8 | 54.5 | 36 | B |
| CYS | N | 842 | 194.8 | 129.0 | 53.1 | 36 | B |
| CYS | CA | 842 | 195.4 | 129.7 | 52.0 | 34 | B |
| CYS | CB | 842 | 196.6 | 128.9 | 51.5 | 33 | B |
| CYS | SG | 842 | 197.7 | 128.2 | 52.7 | 34 | B |
| CYS | C | 842 | 194.6 | 130.3 | 50.9 | 34 | B |
| CYS | O | 842 | 195.1 | 131.3 | 50.3 | 36 | B |
| CYS | N | 843 | 193.5 | 129.7 | 50.5 | 34 | B |
| CYS | CA | 843 | 192.7 | 130.2 | 49.4 | 33 | B |
| CYS | CB | 843 | 192.3 | 129.0 | 48.5 | 32 | B |
| CYS | SG | 843 | 193.6 | 127.9 | 48.1 | 33 | B |
| CYS | C | 843 | 191.4 | 131.0 | 49.6 | 33 | B |
| CYS | O | 843 | 190.6 | 131.2 | 48.7 | 33 | B |
| GLN | N | 844 | 191.3 | 131.6 | 50.8 | 35 | B |
| GLN | CA | 844 | 190.1 | 132.4 | 51.1 | 37 | B |
| GLN | CB | 844 | 189.6 | 132.0 | 52.4 | 37 | B |
| GLN | CG | 844 | 188.1 | 132.1 | 52.6 | 37 | B |
| GLN | CD | 844 | 187.6 | 131.1 | 53.6 | 37 | B |
| GLN | OE1 | 844 | 186.4 | 130.9 | 53.7 | 38 | B |
| GLN | NE2 | 844 | 188.5 | 130.5 | 54.4 | 35 | B |
| GLN | C | 844 | 190.4 | 133.9 | 51.0 | 37 | B |
| GLN | O | 844 | 191.4 | 134.4 | 51.5 | 38 | B |
| CYS | N | 845 | 189.5 | 134.7 | 50.4 | 37 | B |
| CYS | CA | 845 | 189.7 | 136.1 | 50.3 | 39 | B |
| CYS | CB | 845 | 189.2 | 136.7 | 49.0 | 39 | B |
| CYS | SG | 845 | 189.4 | 138.5 | 48.9 | 39 | B |
| CYS | C | 845 | 188.9 | 136.8 | 51.4 | 40 | B |
| CYS | O | 845 | 187.7 | 136.5 | 51.5 | 41 | B |
| PRO | N | 846 | 189.5 | 137.6 | 52.3 | 41 | B |
| PRO | CD | 846 | 190.9 | 138.0 | 52.2 | 41 | B |
| PRO | CA | 846 | 188.9 | 138.3 | 53.4 | 41 | B |
| PRO | CB | 846 | 189.9 | 139.3 | 53.8 | 41 | B |
| PRO | CG | 846 | 191.2 | 138.5 | 53.6 | 40 | B |
| PRO | C | 846 | 187.6 | 139.0 | 53.0 | 42 | B |
| PRO | O | 846 | 186.5 | 138.8 | 53.6 | 43 | B |
| ALA | N | 847 | 187.7 | 139.7 | 51.9 | 41 | B |
| ALA | CA | 847 | 186.5 | 140.4 | 51.3 | 40 | B |
| ALA | CB | 847 | 187.0 | 141.4 | 50.3 | 40 | B |
| ALA | C | 847 | 185.5 | 139.5 | 50.6 | 39 | B |
| ALA | O | 847 | 184.5 | 140.0 | 50.2 | 41 | B |
| GLY | N | 848 | 185.8 | 138.2 | 50.6 | 38 | B |
| GLY | CA | 848 | 184.8 | 137.3 | 49.9 | 38 | B |
| GLY | C | 848 | 185.5 | 136.7 | 48.7 | 37 | B |
| GLY | O | 848 | 186.3 | 137.3 | 48.1 | 38 | B |
| GLY | N | 849 | 185.1 | 135.5 | 48.3 | 35 | B |
| GLY | CA | 849 | 185.6 | 134.9 | 47.1 | 32 | B |
| GLY | C | 849 | 186.9 | 134.1 | 47.5 | 31 | B |
| GLY | O | 849 | 187.5 | 134.4 | 48.5 | 29 | B |
| LEU | N | 850 | 187.2 | 133.1 | 46.7 | 30 | B |
| LEU | CA | 850 | 188.4 | 132.3 | 46.9 | 28 | B |
| LEU | CB | 850 | 188.0 | 130.8 | 47.0 | 29 | B |
| LEU | CG | 850 | 187.2 | 130.1 | 48.1 | 30 | B |
| LEU | CD1 | 850 | 188.0 | 130.0 | 49.3 | 30 | B |
| LEU | CD2 | 850 | 185.9 | 130.8 | 48.3 | 30 | B |
| LEU | C | 850 | 189.4 | 132.5 | 45.8 | 28 | B |
| LEU | O | 850 | 189.1 | 133.2 | 44.8 | 27 | B |
| LEU | N | 851 | 190.6 | 131.9 | 46.0 | 28 | B |
| LEU | CA | 851 | 191.6 | 132.2 | 45.0 | 29 | B |
| LEU | CB | 851 | 192.3 | 133.5 | 45.3 | 31 | B |
| LEU | CG | 851 | 192.5 | 133.7 | 46.8 | 32 | B |
| LEU | CD1 | 851 | 193.8 | 133.2 | 47.3 | 34 | B |
| LEU | CD2 | 851 | 192.4 | 135.2 | 47.1 | 32 | B |
| LEU | C | 851 | 192.6 | 131.1 | 44.7 | 31 | B |
| LEU | O | 851 | 192.6 | 130.1 | 45.4 | 32 | B |
| ASP | N | 852 | 193.4 | 131.3 | 43.7 | 30 | B |
| ASP | CA | 852 | 194.5 | 130.4 | 43.3 | 30 | B |
| ASP | CB | 852 | 195.3 | 131.1 | 42.2 | 31 | B |
| ASP | CG | 852 | 196.5 | 130.3 | 41.7 | 31 | B |
| ASP | OD1 | 852 | 197.1 | 129.5 | 42.5 | 32 | B |
| ASP | OD2 | 852 | 196.9 | 130.5 | 40.6 | 32 | B |
| ASP | C | 852 | 195.3 | 130.1 | 44.5 | 30 | B |
| ASP | O | 852 | 195.4 | 128.9 | 44.9 | 31 | B |
| LYS | N | 853 | 196.1 | 131.0 | 45.0 | 31 | B |
| LYS | CA | 853 | 196.9 | 130.8 | 46.1 | 31 | B |
| LYS | CB | 853 | 198.3 | 130.3 | 45.6 | 29 | B |
| LYS | CG | 853 | 199.0 | 131.2 | 44.7 | 27 | B |
| LYS | CD | 853 | 200.4 | 130.7 | 44.5 | 27 | B |
| LYS | CE | 853 | 200.4 | 129.3 | 43.9 | 28 | B |
| LYS | NZ | 853 | 199.9 | 129.1 | 42.6 | 27 | B |
| LYS | C | 853 | 197.1 | 132.2 | 46.7 | 33 | B |
| LYS | O | 853 | 196.6 | 133.2 | 46.1 | 33 | B |
| PRO | N | 854 | 197.8 | 132.3 | 47.9 | 36 | B |
| PRO | CD | 854 | 198.3 | 131.2 | 48.7 | 37 | B |
| PRO | CA | 854 | 198.0 | 133.6 | 48.5 | 38 | B |
| PRO | CB | 854 | 198.8 | 133.3 | 49.7 | 38 | B |
| PRO | CG | 854 | 199.4 | 132.0 | 49.4 | 37 | B |
| PRO | C | 854 | 198.7 | 134.7 | 47.5 | 39 | B |
| PRO | O | 854 | 199.7 | 134.4 | 46.9 | 40 | B |
| GLY | N | 855 | 198.1 | 135.9 | 47.4 | 40 | B |
| GLY | CA | 855 | 198.6 | 136.9 | 46.6 | 40 | B |
| GLY | C | 855 | 197.8 | 137.1 | 45.3 | 41 | B |
| GLY | O | 855 | 197.5 | 138.2 | 44.9 | 43 | B |
| LYS | N | 856 | 197.3 | 135.9 | 44.8 | 40 | B |
| LYS | CA | 856 | 196.5 | 135.9 | 43.6 | 39 | B |
| LYS | CB | 856 | 196.2 | 134.4 | 43.2 | 39 | B |
| LYS | CG | 856 | 197.5 | 133.6 | 42.9 | 38 | B |
| LYS | CD | 856 | 198.0 | 134.2 | 41.6 | 40 | B |
| LYS | CE | 856 | 199.1 | 133.3 | 41.0 | 40 | B |
| LYS | NZ | 856 | 199.3 | 133.6 | 39.6 | 42 | B |
| LYS | C | 856 | 195.2 | 136.6 | 43.8 | 39 | B |
| LYS | O | 856 | 194.7 | 136.7 | 45.0 | 40 | B |
| SER | N | 857 | 194.6 | 137.1 | 42.8 | 40 | B |
| SER | CA | 857 | 193.3 | 137.8 | 43.0 | 41 | B |
| SER | CB | 857 | 193.1 | 138.8 | 41.9 | 43 | B |
| SER | OG | 857 | 194.0 | 139.9 | 41.9 | 46 | B |
| SER | C | 857 | 192.1 | 136.8 | 43.0 | 41 | B |
| SER | O | 857 | 192.3 | 135.7 | 42.5 | 41 | B |
| ARG | N | 858 | 191.0 | 137.3 | 43.5 | 40 | B |
| ARG | CA | 858 | 189.8 | 136.5 | 43.6 | 39 | B |
| ARG | CB | 858 | 188.9 | 136.9 | 44.8 | 39 | B |
| ARG | CG | 858 | 188.1 | 138.1 | 44.5 | 39 | B |
| ARG | CD | 858 | 187.5 | 138.7 | 45.7 | 39 | B |
| ARG | NE | 858 | 186.7 | 139.9 | 45.4 | 40 | B |
| ARG | CZ | 858 | 186.1 | 140.6 | 46.4 | 40 | B |
| ARG | NH1 | 858 | 186.2 | 140.3 | 47.6 | 41 | B |
| ARG | NH2 | 858 | 185.3 | 141.7 | 46.0 | 40 | B |
| ARG | C | 858 | 189.0 | 136.6 | 42.3 | 37 | B |
| ARG | O | 858 | 189.0 | 137.6 | 41.6 | 38 | B |
| ASP | N | 859 | 188.2 | 135.5 | 42.1 | 34 | B |
| ASP | CA | 859 | 187.3 | 135.4 | 41.0 | 31 | B |
| ASP | CB | 859 | 188.1 | 135.3 | 39.6 | 31 | B |
| ASP | CG | 859 | 189.0 | 134.0 | 39.6 | 31 | B |
| ASP | OD1 | 859 | 188.5 | 132.9 | 39.4 | 31 | B |
| ASP | OD2 | 859 | 190.2 | 134.2 | 39.8 | 33 | B |
| ASP | C | 859 | 186.4 | 134.3 | 41.2 | 30 | B |
| ASP | O | 859 | 186.6 | 133.4 | 42.0 | 28 | B |
| PHE | N | 860 | 185.3 | 134.3 | 40.4 | 30 | B |
| PHE | CA | 860 | 184.2 | 133.3 | 40.5 | 29 | B |
| PHE | CB | 860 | 183.0 | 133.7 | 39.7 | 29 | B |
| PHE | CG | 860 | 182.6 | 135.1 | 40.1 | 30 | B |
| PHE | CD1 | 860 | 182.7 | 136.2 | 39.1 | 31 | B |
| PHE | CD2 | 860 | 182.3 | 135.4 | 41.4 | 30 | B |
| PHE | CE1 | 860 | 182.4 | 137.5 | 39.5 | 30 | B |
| PHE | CE2 | 860 | 182.0 | 136.7 | 41.8 | 30 | B |
| PHE | CZ | 860 | 182.0 | 137.8 | 40.8 | 30 | B |
| PHE | C | 860 | 184.6 | 131.9 | 40.1 | 28 | B |
| PHE | O | 860 | 184.1 | 130.9 | 40.6 | 31 | B |
| TYR | N | 861 | 185.7 | 131.8 | 39.3 | 26 | B |

TABLE 2-continued

| | | | | | | | |
|---|---|---|---|---|---|---|---|
| TYR | CA | 861 | 186.1 | 130.4 | 38.8 | 23 | B |
| TYR | CB | 861 | 187.1 | 130.6 | 37.6 | 22 | B |
| TYR | CG | 861 | 187.9 | 129.4 | 37.3 | 19 | B |
| TYR | CD1 | 861 | 187.4 | 128.3 | 36.6 | 19 | B |
| TYR | CE1 | 861 | 188.2 | 127.2 | 36.4 | 18 | B |
| TYR | CD2 | 861 | 189.2 | 129.4 | 37.8 | 18 | B |
| TYR | CE2 | 861 | 190.0 | 128.3 | 37.6 | 18 | B |
| TYR | CZ | 861 | 189.5 | 127.2 | 36.9 | 17 | B |
| TYR | OH | 861 | 190.3 | 126.1 | 36.8 | 19 | B |
| TYR | C | 861 | 186.8 | 129.7 | 39.9 | 23 | B |
| TYR | O | 861 | 186.5 | 128.6 | 40.2 | 23 | B |
| HIS | N | 862 | 187.7 | 130.4 | 40.6 | 25 | B |
| HIS | CA | 862 | 188.4 | 129.8 | 41.8 | 25 | B |
| HIS | CB | 862 | 189.6 | 130.6 | 42.2 | 23 | B |
| HIS | CG | 862 | 190.7 | 130.5 | 41.2 | 23 | B |
| HIS | CD2 | 862 | 191.7 | 129.5 | 41.1 | 22 | B |
| HIS | ND1 | 862 | 191.0 | 131.4 | 40.3 | 24 | B |
| HIS | CE1 | 862 | 192.0 | 131.1 | 39.5 | 25 | B |
| HIS | NE2 | 862 | 192.5 | 129.9 | 40.0 | 23 | B |
| HIS | C | 862 | 187.4 | 129.6 | 43.0 | 27 | B |
| HIS | O | 862 | 187.6 | 128.8 | 43.8 | 28 | B |
| THR | N | 863 | 186.5 | 130.6 | 43.0 | 30 | B |
| THR | CA | 863 | 185.5 | 130.5 | 44.1 | 32 | B |
| THR | CB | 863 | 184.5 | 131.8 | 44.1 | 32 | B |
| THR | OG1 | 863 | 185.3 | 133.0 | 44.5 | 32 | B |
| THR | CG2 | 863 | 183.4 | 131.7 | 45.1 | 33 | B |
| THR | C | 863 | 184.7 | 129.2 | 43.9 | 31 | B |
| THR | O | 863 | 184.6 | 128.4 | 44.8 | 34 | B |
| CYS | N | 864 | 184.2 | 129.0 | 42.7 | 30 | B |
| CYS | CA | 864 | 183.5 | 127.9 | 42.3 | 29 | B |
| CYS | CB | 864 | 183.0 | 127.9 | 40.9 | 30 | B |
| CYS | SG | 864 | 182.4 | 126.4 | 40.1 | 30 | B |
| CYS | C | 864 | 184.3 | 126.6 | 42.5 | 29 | B |
| CYS | O | 864 | 183.7 | 125.6 | 43.0 | 31 | B |
| TYR | N | 865 | 185.6 | 126.6 | 42.2 | 28 | B |
| TYR | CA | 865 | 186.4 | 125.4 | 42.3 | 28 | B |
| TYR | CB | 865 | 187.3 | 125.2 | 41.1 | 26 | B |
| TYR | CG | 865 | 186.5 | 125.0 | 39.8 | 25 | B |
| TYR | CD1 | 865 | 186.3 | 126.0 | 38.8 | 25 | B |
| TYR | CE1 | 865 | 185.5 | 125.7 | 37.7 | 25 | B |
| TYR | CD2 | 865 | 185.9 | 123.8 | 39.6 | 24 | B |
| TYR | CE2 | 865 | 185.0 | 123.5 | 38.5 | 24 | B |
| TYR | CZ | 865 | 184.8 | 124.5 | 37.6 | 25 | B |
| TYR | OH | 865 | 184.0 | 124.3 | 36.5 | 26 | B |
| TYR | C | 865 | 187.0 | 125.1 | 43.6 | 29 | B |
| TYR | O | 865 | 187.3 | 123.9 | 43.9 | 29 | B |
| CYS | N | 866 | 187.4 | 126.1 | 44.4 | 29 | B |
| CYS | CA | 866 | 188.0 | 125.8 | 45.7 | 29 | B |
| CYS | CB | 866 | 188.5 | 127.1 | 46.3 | 29 | B |
| CYS | SG | 866 | 190.1 | 127.7 | 45.7 | 30 | B |
| CYS | C | 866 | 186.8 | 125.3 | 46.6 | 29 | B |
| CYS | O | 866 | 187.0 | 124.4 | 47.4 | 29 | B |
| LEU | N | 867 | 185.6 | 125.9 | 46.4 | 27 | B |
| LEU | CA | 867 | 184.5 | 125.4 | 47.2 | 29 | B |
| LEU | CB | 867 | 183.3 | 126.3 | 47.0 | 26 | B |
| LEU | CG | 867 | 183.5 | 127.7 | 47.7 | 25 | B |
| LEU | CD1 | 867 | 182.3 | 128.6 | 47.5 | 25 | B |
| LEU | CD2 | 867 | 183.7 | 127.5 | 49.1 | 25 | B |
| LEU | C | 867 | 184.1 | 123.9 | 46.7 | 32 | B |
| LEU | O | 867 | 183.9 | 123.1 | 47.6 | 33 | B |
| SER | N | 868 | 184.1 | 123.7 | 45.4 | 34 | B |
| SER | CA | 868 | 183.8 | 122.3 | 44.9 | 33 | B |
| SER | CB | 868 | 183.8 | 122.3 | 43.4 | 33 | B |
| SER | OG | 868 | 182.7 | 123.0 | 42.8 | 32 | B |
| SER | C | 868 | 184.8 | 121.3 | 45.5 | 33 | B |
| SER | O | 868 | 184.4 | 120.2 | 45.8 | 34 | B |
| GLY | N | 869 | 186.0 | 121.7 | 45.6 | 34 | B |
| GLY | CA | 869 | 187.1 | 120.9 | 46.1 | 35 | B |
| GLY | C | 869 | 187.0 | 120.6 | 47.6 | 36 | B |
| GLY | O | 869 | 187.3 | 119.5 | 48.1 | 37 | B |
| LEU | N | 870 | 186.5 | 121.6 | 48.3 | 35 | B |
| LEU | CA | 870 | 186.4 | 121.5 | 49.8 | 34 | B |
| LEU | CB | 870 | 185.9 | 122.9 | 50.4 | 32 | B |
| LEU | CG | 870 | 185.8 | 123.0 | 51.9 | 32 | B |
| LEU | CD1 | 870 | 187.2 | 122.6 | 52.5 | 30 | B |
| LEU | CD2 | 870 | 185.4 | 124.4 | 52.3 | 30 | B |
| LEU | C | 870 | 185.3 | 120.5 | 50.1 | 34 | B |
| LEU | O | 870 | 185.5 | 119.5 | 50.8 | 32 | B |
| SER | N | 871 | 184.2 | 120.6 | 49.3 | 36 | B |

TABLE 2-continued

| | | | | | | | |
|---|---|---|---|---|---|---|---|
| SER | CA | 871 | 183.1 | 119.7 | 49.4 | 38 | B |
| SER | CB | 871 | 182.0 | 120.1 | 48.5 | 38 | B |
| SER | OG | 871 | 180.8 | 119.3 | 48.7 | 39 | B |
| SER | C | 871 | 183.5 | 118.2 | 49.0 | 39 | B |
| SER | O | 871 | 183.0 | 117.3 | 49.6 | 41 | B |
| ILE | N | 872 | 184.4 | 118.1 | 48.0 | 40 | B |
| ILE | CA | 872 | 184.8 | 116.8 | 47.7 | 40 | B |
| ILE | CB | 872 | 185.8 | 116.7 | 46.4 | 38 | B |
| ILE | CG2 | 872 | 186.5 | 115.4 | 46.3 | 36 | B |
| ILE | CG1 | 872 | 185.0 | 117.0 | 45.1 | 38 | B |
| ILE | CD1 | 872 | 184.0 | 115.8 | 44.7 | 38 | B |
| ILE | C | 872 | 185.6 | 116.2 | 48.9 | 41 | B |
| ILE | O | 872 | 185.2 | 115.2 | 49.4 | 43 | B |
| ALA | N | 873 | 186.5 | 117.0 | 49.4 | 44 | B |
| ALA | CA | 873 | 187.3 | 116.7 | 50.6 | 46 | B |
| ALA | CB | 873 | 188.3 | 117.8 | 50.8 | 47 | B |
| ALA | C | 873 | 186.5 | 116.4 | 51.9 | 46 | B |
| ALA | O | 873 | 186.9 | 115.6 | 52.7 | 45 | B |
| GLN | N | 874 | 185.4 | 117.0 | 52.1 | 48 | B |
| GLN | CA | 874 | 184.6 | 116.8 | 53.3 | 50 | B |
| GLN | CB | 874 | 183.7 | 118.1 | 53.6 | 49 | B |
| GLN | CG | 874 | 184.4 | 119.3 | 53.9 | 47 | B |
| GLN | CD | 874 | 183.4 | 120.5 | 53.9 | 47 | B |
| GLN | OE1 | 874 | 182.3 | 120.4 | 53.2 | 47 | B |
| GLN | NE2 | 874 | 183.7 | 121.6 | 54.5 | 47 | B |
| GLN | C | 874 | 183.6 | 115.7 | 53.2 | 51 | B |
| GLN | O | 874 | 183.1 | 115.2 | 54.2 | 53 | B |
| HIS | N | 875 | 183.3 | 115.2 | 52.0 | 52 | B |
| HIS | CA | 875 | 182.3 | 114.1 | 51.9 | 53 | B |
| HIS | CB | 875 | 181.0 | 114.7 | 51.3 | 53 | B |
| HIS | CG | 875 | 180.6 | 116.0 | 51.9 | 52 | B |
| HIS | CD2 | 875 | 180.8 | 117.3 | 51.5 | 53 | B |
| HIS | ND1 | 875 | 179.8 | 116.0 | 53.0 | 53 | B |
| HIS | CE1 | 875 | 179.5 | 117.3 | 53.2 | 52 | B |
| HIS | NE2 | 875 | 180.1 | 118.1 | 52.4 | 53 | B |
| HIS | C | 875 | 182.7 | 112.9 | 51.1 | 55 | B |
| HIS | O | 875 | 183.0 | 112.9 | 49.9 | 55 | B |
| PHE | N | 876 | 182.7 | 111.8 | 51.9 | 57 | B |
| PHE | CA | 876 | 183.0 | 110.5 | 51.3 | 59 | B |
| PHE | CB | 876 | 184.0 | 109.7 | 52.1 | 57 | B |
| PHE | CG | 876 | 184.3 | 108.3 | 51.6 | 57 | B |
| PHE | CD1 | 876 | 185.2 | 108.1 | 50.6 | 56 | B |
| PHE | CD2 | 876 | 183.6 | 107.2 | 52.1 | 56 | B |
| PHE | CE1 | 876 | 185.5 | 106.8 | 50.1 | 56 | B |
| PHE | CE2 | 876 | 183.8 | 106.0 | 51.6 | 56 | B |
| PHE | CZ | 876 | 184.7 | 105.7 | 50.6 | 56 | B |
| PHE | C | 876 | 181.7 | 109.6 | 51.1 | 61 | B |
| PHE | O | 876 | 180.7 | 109.9 | 51.8 | 61 | B |
| GLY | N | 877 | 181.8 | 108.7 | 50.2 | 64 | B |
| GLY | CA | 877 | 180.7 | 107.8 | 50.0 | 68 | B |
| GLY | C | 877 | 181.2 | 106.5 | 49.4 | 71 | B |
| GLY | O | 877 | 182.4 | 106.5 | 49.0 | 72 | B |
| SER | N | 878 | 180.5 | 105.4 | 49.5 | 73 | B |
| SER | CA | 878 | 181.0 | 104.1 | 49.0 | 74 | B |
| SER | CB | 878 | 182.2 | 103.6 | 49.7 | 74 | B |
| SER | OG | 878 | 182.7 | 102.3 | 49.2 | 74 | B |
| SER | C | 878 | 179.8 | 103.0 | 49.1 | 75 | B |
| SER | O | 878 | 180.0 | 101.9 | 49.6 | 76 | B |
| GLY | N | 879 | 178.7 | 103.4 | 48.6 | 76 | B |
| GLY | CA | 879 | 177.5 | 102.5 | 48.6 | 77 | B |
| GLY | C | 879 | 176.5 | 103.1 | 49.6 | 77 | B |
| GLY | O | 879 | 175.6 | 103.8 | 49.3 | 77 | B |
| ALA | N | 880 | 176.8 | 102.8 | 50.9 | 78 | B |
| ALA | CA | 880 | 176.0 | 103.3 | 52.0 | 77 | B |
| ALA | CB | 880 | 175.1 | 102.1 | 52.5 | 78 | B |
| ALA | C | 880 | 176.9 | 103.8 | 53.1 | 77 | B |
| ALA | O | 880 | 176.5 | 104.0 | 54.2 | 77 | B |
| MET | N | 881 | 178.2 | 103.9 | 52.8 | 76 | B |
| MET | CA | 881 | 179.2 | 104.4 | 53.7 | 75 | B |
| MET | CB | 881 | 180.6 | 104.0 | 53.3 | 76 | B |
| MET | CG | 881 | 180.7 | 102.6 | 52.8 | 77 | B |
| MET | SD | 881 | 180.8 | 101.4 | 54.2 | 78 | B |
| MET | CE | 881 | 179.1 | 101.1 | 54.5 | 78 | B |
| MET | C | 881 | 179.1 | 106.0 | 53.6 | 73 | B |
| MET | O | 881 | 178.8 | 106.5 | 52.5 | 73 | B |
| LEU | N | 882 | 179.3 | 106.7 | 54.7 | 72 | B |
| LEU | CA | 882 | 179.2 | 108.1 | 54.7 | 71 | B |
| LEU | CB | 882 | 177.7 | 108.6 | 54.9 | 72 | B |
| LEU | CG | 882 | 177.0 | 109.3 | 53.8 | 73 | B |

TABLE 2-continued

| | | | | | | | |
|---|---|---|---|---|---|---|---|
| LEU | CD1 | 882 | 177.8 | 110.5 | 53.3 | 74 | B |
| LEU | CD2 | 882 | 176.6 | 108.4 | 52.7 | 73 | B |
| LEU | C | 882 | 180.1 | 108.9 | 55.7 | 70 | B |
| LEU | O | 882 | 179.6 | 109.5 | 56.6 | 71 | B |
| HIS | N | 883 | 181.4 | 108.8 | 55.5 | 68 | B |
| HIS | CA | 883 | 182.4 | 109.5 | 56.3 | 66 | B |
| HIS | CB | 883 | 183.6 | 108.6 | 56.6 | 66 | B |
| HIS | CG | 883 | 184.5 | 109.1 | 57.6 | 67 | B |
| HIS | CD2 | 883 | 185.4 | 108.4 | 58.4 | 67 | B |
| HIS | ND1 | 883 | 184.7 | 110.4 | 58.0 | 67 | B |
| HIS | CE1 | 883 | 185.6 | 110.5 | 58.9 | 67 | B |
| HIS | NE2 | 883 | 186.0 | 109.3 | 59.2 | 67 | B |
| HIS | C | 883 | 182.8 | 110.9 | 55.9 | 64 | B |
| HIS | O | 883 | 183.9 | 111.1 | 55.3 | 64 | B |
| ASP | N | 884 | 182.0 | 111.8 | S6.4 | 61 | B |
| ASP | CA | 884 | 182.3 | 113.2 | 56.1 | 59 | B |
| ASP | CB | 884 | 181.0 | 114.1 | 56.3 | 59 | B |
| ASP | CG | 884 | 179.9 | 113.7 | 55.3 | 60 | B |
| ASP | OD1 | 884 | 178.8 | 114.2 | 55.5 | 59 | B |
| ASP | OD2 | 884 | 180.1 | 112.7 | 54.5 | 60 | B |
| ASP | C | 884 | 183.4 | 113.7 | 57.1 | 57 | B |
| ASP | O | 884 | 183.5 | 113.2 | 58.2 | 56 | B |
| VAL | N | 885 | 184.3 | 114.6 | 56.6 | 55 | B |
| VAL | CA | 885 | 185.4 | 115.1 | 57.4 | 53 | B |
| VAL | CB | 885 | 186.7 | 114.7 | 56.8 | 52 | B |
| VAL | CG1 | 885 | 187.9 | 115.3 | 57.5 | 51 | B |
| VAL | CG2 | 885 | 186.8 | 113.2 | 56.8 | 52 | B |
| VAL | C | 885 | 185.3 | 116.6 | 57.3 | 52 | B |
| VAL | O | 885 | 185.6 | 117.2 | 56.2 | 52 | B |
| VAL | N | 886 | 184.8 | 117.3 | 58.3 | 50 | B |
| VAL | CA | 886 | 184.7 | 118.7 | 58.3 | 51 | B |
| VAL | CB | 886 | 183.4 | 119.3 | 58.7 | 51 | B |
| VAL | CG1 | 886 | 183.3 | 120.8 | 58.5 | 49 | B |
| VAL | CG2 | 886 | 182.3 | 118.6 | 57.8 | 50 | B |
| VAL | C | 886 | 185.8 | 119.4 | 59.1 | 53 | B |
| VAL | O | 886 | 185.8 | 119.3 | 60.3 | 54 | B |
| MET | N | 887 | 186.7 | 120.1 | 58.4 | 54 | B |
| MET | CA | 887 | 187.8 | 120.8 | 59.1 | 53 | B |
| MET | CB | 887 | 188.9 | 121.1 | 58.1 | 53 | B |
| MET | CG | 887 | 190.2 | 120.6 | 58.5 | 53 | B |
| MET | SD | 887 | 190.1 | 118.9 | 59.0 | 52 | B |
| MET | CE | 887 | 191.4 | 118.9 | 60.2 | 53 | B |
| MET | C | 887 | 187.3 | 122.1 | 59.7 | 54 | B |
| MET | O | 887 | 186.5 | 122.9 | 59.1 | 52 | B |
| GLY | N | 888 | 187.7 | 122.4 | 61.0 | 55 | B |
| GLY | CA | 888 | 187.3 | 123.5 | 61.7 | 57 | B |
| GLY | C | 888 | 185.9 | 123.6 | 62.1 | 57 | B |
| GLY | O | 888 | 185.1 | 122.6 | 62.2 | 56 | B |
| VAL | N | 889 | 185.4 | 124.9 | 62.3 | 58 | B |
| VAL | CA | 889 | 184.0 | 125.2 | 62.6 | 58 | B |
| VAL | CB | 889 | 183.8 | 126.7 | 62.4 | 58 | B |
| VAL | CG1 | 889 | 182.4 | 127.1 | 62.6 | 59 | B |
| VAL | CG2 | 889 | 184.7 | 127.4 | 63.4 | 57 | B |
| VAL | C | 889 | 183.1 | 124.3 | 61.7 | 59 | B |
| VAL | O | 889 | 183.1 | 124.5 | 60.5 | 60 | B |
| PRO | N | 890 | 182.3 | 123.4 | 62.3 | 61 | B |
| PRO | CD | 890 | 182.0 | 123.4 | 63.8 | 62 | B |
| PRO | CA | 890 | 181.4 | 122.5 | 61.6 | 62 | B |
| PRO | CB | 890 | 180.7 | 121.8 | 62.8 | 62 | B |
| PRO | CG | 890 | 180.6 | 122.9 | 63.8 | 62 | B |
| PRO | C | 890 | 180.4 | 123.2 | 60.7 | 62 | B |
| PRO | O | 890 | 179.6 | 122.6 | 60.0 | 63 | B |
| GLU | N | 891 | 180.4 | 124.6 | 60.8 | 63 | B |
| GLU | CA | 891 | 179.5 | 125.4 | 59.9 | 63 | B |
| GLU | CB | 891 | 179.3 | 126.8 | 60.5 | 66 | B |
| GLU | CG | 891 | 178.3 | 126.9 | 61.6 | 70 | B |
| GLU | CD | 891 | 178.6 | 126.1 | 62.9 | 72 | B |
| GLU | OE1 | 891 | 179.7 | 126.2 | 63.4 | 72 | B |
| GLU | OE2 | 891 | 177.7 | 125.4 | 63.4 | 74 | B |
| GLU | C | 891 | 180.2 | 125.5 | 58.6 | 61 | B |
| GLU | O | 891 | 179.7 | 126.1 | 57.6 | 61 | B |
| ASN | N | 892 | 181.4 | 124.9 | 58.5 | 59 | B |
| ASN | CA | 892 | 182.3 | 124.9 | 57.3 | 56 | B |
| ASN | CB | 892 | 183.8 | 124.7 | 57.6 | 53 | B |
| ASN | CG | 892 | 184.3 | 125.9 | 58.5 | 50 | B |
| ASN | OD1 | 892 | 185.4 | 125.8 | 59.0 | 49 | B |
| ASN | ND2 | 892 | 183.6 | 127.0 | 58.5 | 49 | B |
| ASN | C | 892 | 181.8 | 123.9 | 56.3 | 56 | B |
| ASN | O | 892 | 182.2 | 123.9 | 55.1 | 57 | B |

TABLE 2-continued

| | | | | | | | |
|---|---|---|---|---|---|---|---|
| VAL | N | 893 | 181.0 | 122.9 | 56.7 | 55 | B |
| VAL | CA | 893 | 180.5 | 121.8 | 55.8 | 54 | B |
| VAL | CB | 893 | 179.8 | 120.8 | 56.5 | 54 | B |
| VAL | CG1 | 893 | 178.5 | 121.4 | 57.2 | 54 | B |
| VAL | CG2 | 893 | 179.4 | 119.7 | 55.6 | 53 | B |
| VAL | C | 893 | 179.7 | 122.4 | 54.7 | 54 | B |
| VAL | O | 893 | 178.8 | 123.2 | 54.9 | 54 | B |
| LEU | N | 894 | 179.9 | 121.9 | 53.5 | 53 | B |
| LEU | CA | 894 | 179.2 | 122.3 | 52.3 | 52 | B |
| LEU | CB | 894 | 180.2 | 122.6 | 51.2 | 52 | B |
| LEU | CG | 894 | 181.4 | 123.6 | 51.4 | 51 | B |
| LEU | CD1 | 894 | 182.4 | 123.6 | 50.3 | 50 | B |
| LEU | CD2 | 894 | 180.8 | 125.0 | 51.7 | 51 | B |
| LEU | C | 894 | 178.3 | 121.3 | 51.7 | 51 | B |
| LEU | O | 894 | 178.4 | 120.1 | 52.1 | 50 | B |
| GLN | N | 895 | 177.3 | 121.7 | 51.0 | 51 | B |
| GLN | CA | 895 | 176.4 | 120.8 | 50.3 | 50 | B |
| GLN | CB | 895 | 175.3 | 121.6 | 49.5 | 52 | B |
| GLN | CG | 895 | 174.3 | 122.3 | 50.4 | 55 | B |
| GLN | CD | 895 | 173.7 | 121.3 | 51.5 | 56 | B |
| GLN | OE1 | 895 | 172.8 | 120.6 | 51.3 | 56 | B |
| GLN | NE2 | 895 | 174.3 | 121.4 | 52.7 | 57 | B |
| GLN | C | 895 | 177.2 | 119.9 | 49.4 | 49 | B |
| GLN | O | 895 | 178.3 | 120.3 | 49.0 | 50 | B |
| PRO | N | 896 | 176.7 | 118.7 | 49.1 | 47 | B |
| PRO | CD | 896 | 175.4 | 118.1 | 49.7 | 46 | B |
| PRO | CA | 896 | 177.4 | 117.8 | 48.3 | 46 | B |
| PRO | CB | 896 | 176.7 | 116.5 | 48.5 | 47 | B |
| PRO | CG | 896 | 175.9 | 116.7 | 49.8 | 47 | B |
| PRO | C | 896 | 177.4 | 118.2 | 46.8 | 45 | B |
| PRO | O | 896 | 176.5 | 118.9 | 46.3 | 45 | B |
| THR | N | 897 | 178.4 | 117.7 | 46.1 | 42 | B |
| THR | CA | 897 | 178.5 | 117.9 | 44.7 | 40 | B |
| THR | CB | 897 | 179.6 | 119.0 | 44.3 | 39 | B |
| THR | OG1 | 897 | 179.3 | 119.5 | 43.0 | 39 | B |
| THR | CG2 | 897 | 181.0 | 118.5 | 44.5 | 38 | B |
| THR | C | 897 | 178.8 | 116.6 | 44.0 | 39 | B |
| THR | O | 897 | 179.5 | 115.7 | 44.5 | 39 | B |
| HIS | N | 898 | 178.3 | 116.4 | 42.8 | 39 | B |
| HIS | CA | 898 | 178.4 | 115.2 | 42.0 | 38 | B |
| HIS | CB | 898 | 177.3 | 115.1 | 40.9 | 38 | B |
| HIS | CG | 898 | 177.2 | 113.8 | 40.3 | 39 | B |
| HIS | CD2 | 898 | 176.1 | 113.2 | 39.8 | 40 | B |
| HIS | ND1 | 898 | 178.2 | 112.9 | 40.1 | 40 | B |
| HIS | CE1 | 898 | 177.7 | 111.8 | 39.5 | 39 | B |
| HIS | NE2 | 898 | 176.4 | 111.9 | 39.4 | 40 | B |
| HIS | C | 898 | 179.8 | 115.2 | 41.3 | 38 | B |
| HIS | O | 898 | 180.1 | 116.1 | 40.5 | 38 | B |
| PRO | N | 899 | 180.7 | 114.2 | 41.6 | 37 | B |
| PRO | CD | 899 | 180.5 | 113.0 | 42.5 | 38 | B |
| PRO | CA | 899 | 182.0 | 114.2 | 41.0 | 36 | B |
| PRO | CB | 899 | 182.7 | 113.0 | 41.7 | 37 | B |
| PRO | CG | 899 | 181.6 | 112.1 | 42.0 | 37 | B |
| PRO | C | 899 | 182.2 | 114.0 | 39.5 | 35 | B |
| PRO | O | 899 | 183.3 | 113.9 | 38.9 | 36 | B |
| VAL | N | 900 | 181.1 | 114.1 | 38.7 | 32 | B |
| VAL | CA | 900 | 181.1 | 114.0 | 37.3 | 30 | B |
| VAL | CB | 900 | 180.3 | 112.8 | 36.8 | 29 | B |
| VAL | CG1 | 900 | 180.2 | 112.8 | 35.3 | 28 | B |
| VAL | CG2 | 900 | 180.9 | 111.5 | 37.2 | 27 | B |
| VAL | C | 900 | 180.6 | 115.3 | 36.7 | 31 | B |
| VAL | O | 900 | 181.3 | 115.9 | 35.8 | 32 | B |
| TYR | N | 901 | 179.4 | 115.8 | 37.2 | 30 | B |
| TYR | CA | 901 | 178.8 | 117.0 | 36.7 | 30 | B |
| TYR | CB | 901 | 177.3 | 116.8 | 36.7 | 30 | B |
| TYR | CG | 901 | 176.9 | 115.7 | 35.8 | 30 | B |
| TYR | CD1 | 901 | 176.6 | 114.4 | 36.4 | 29 | B |
| TYR | CE1 | 901 | 176.2 | 113.4 | 35.6 | 30 | B |
| TYR | CD2 | 901 | 176.8 | 115.8 | 34.5 | 30 | B |
| TYR | CE2 | 901 | 176.4 | 114.8 | 33.6 | 31 | B |
| TYR | CZ | 901 | 176.1 | 113.6 | 34.2 | 31 | B |
| TYR | OH | 901 | 175.7 | 112.5 | 33.4 | 32 | B |
| TYR | C | 901 | 179.2 | 118.2 | 37.4 | 31 | B |
| TYR | O | 901 | 179.2 | 119.3 | 36.9 | 32 | B |
| ASN | N | 902 | 179.7 | 118.1 | 38.6 | 31 | B |
| ASN | CA | 902 | 180.0 | 119.2 | 39.5 | 31 | B |
| ASN | CB | 902 | 181.2 | 120.0 | 39.0 | 32 | B |
| ASN | CG | 902 | 181.7 | 120.9 | 40.1 | 32 | B |
| ASN | OD1 | 902 | 181.7 | 120.6 | 41.3 | 33 | B |

TABLE 2-continued

| | | | | | | | |
|---|---|---|---|---|---|---|---|
| ASN | ND2 | 902 | 182.2 | 122.0 | 39.7 | 32 | B |
| ASN | C | 902 | 178.8 | 120.0 | 39.8 | 31 | B |
| ASN | O | 902 | 178.9 | 121.3 | 39.6 | 30 | B |
| ILE | N | 903 | 177.7 | 119.4 | 40.0 | 33 | B |
| ILE | CA | 903 | 176.5 | 120.0 | 40.4 | 34 | B |
| ILE | CB | 903 | 175.4 | 120.2 | 39.3 | 32 | B |
| ILE | CG2 | 903 | 175.8 | 121.2 | 38.3 | 32 | B |
| ILE | CG1 | 903 | 175.0 | 118.9 | 38.7 | 31 | B |
| ILE | CD1 | 903 | 173.7 | 119.0 | 37.8 | 27 | B |
| ILE | C | 903 | 175.9 | 119.1 | 41.5 | 35 | B |
| ILE | O | 903 | 176.2 | 117.9 | 41.4 | 35 | B |
| GLY | N | 904 | 175.2 | 119.6 | 42.4 | 37 | B |
| GLY | CA | 904 | 174.6 | 118.8 | 43.5 | 38 | B |
| GLY | C | 904 | 174.0 | 117.5 | 43.0 | 39 | B |
| GLY | O | 904 | 173.2 | 117.5 | 42.1 | 39 | B |
| PRO | N | 905 | 174.4 | 116.4 | 43.6 | 39 | B |
| PRO | CD | 905 | 175.3 | 116.3 | 44.7 | 39 | B |
| PRO | CA | 905 | 173.9 | 115.0 | 43.2 | 40 | B |
| PRO | CB | 905 | 174.5 | 114.2 | 44.3 | 40 | B |
| PRO | CG | 905 | 174.8 | 115.1 | 45.4 | 40 | B |
| PRO | C | 905 | 172.4 | 114.9 | 43.1 | 41 | B |
| PRO | O | 905 | 171.9 | 114.1 | 42.3 | 41 | B |
| ASP | N | 906 | 171.7 | 115.8 | 43.8 | 42 | B |
| ASP | CA | 906 | 170.3 | 115.8 | 43.7 | 44 | B |
| ASP | CB | 906 | 169.7 | 116.5 | 45.0 | 49 | B |
| ASP | CG | 906 | 170.3 | 117.9 | 45.2 | 52 | B |
| ASP | OD1 | 906 | 171.3 | 118.0 | 46.1 | 54 | B |
| ASP | OD2 | 906 | 169.9 | 118.9 | 44.6 | 53 | B |
| ASP | C | 906 | 169.7 | 116.5 | 42.5 | 43 | B |
| ASP | O | 906 | 168.7 | 116.0 | 42.0 | 43 | B |
| LYS | N | 907 | 170.4 | 117.5 | 42.0 | 42 | B |
| LYS | CA | 907 | 170.0 | 118.2 | 40.8 | 40 | B |
| LYS | CB | 907 | 170.9 | 119.5 | 40.6 | 39 | B |
| LYS | CG | 907 | 170.6 | 120.5 | 41.7 | 39 | B |
| LYS | CD | 907 | 169.2 | 121.0 | 41.5 | 41 | B |
| LYS | CE | 907 | 168.6 | 121.6 | 42.8 | 42 | B |
| LYS | NZ | 907 | 169.4 | 122.7 | 43.4 | 43 | B |
| LYS | C | 907 | 170.3 | 117.3 | 39.6 | 39 | B |
| LYS | O | 907 | 169.6 | 117.4 | 38.6 | 38 | B |
| VAL | N | 908 | 171.4 | 116.5 | 39.7 | 39 | B |
| VAL | CA | 908 | 171.8 | 115.6 | 38.6 | 40 | B |
| VAL | CB | 908 | 173.0 | 114.8 | 39.0 | 40 | B |
| VAL | CG1 | 908 | 173.4 | 113.8 | 38.0 | 41 | B |
| VAL | CG2 | 908 | 174.2 | 115.8 | 39.2 | 40 | B |
| VAL | C | 908 | 170.6 | 114.6 | 38.5 | 42 | B |
| VAL | O | 908 | 170.0 | 114.5 | 37.5 | 43 | B |
| ILE | N | 909 | 170.3 | 113.9 | 39.6 | 43 | B |
| ILE | CA | 909 | 169.3 | 112.9 | 39.6 | 45 | B |
| ILE | CB | 909 | 169.0 | 112.3 | 41.0 | 44 | B |
| ILE | CG2 | 909 | 167.7 | 111.5 | 41.0 | 44 | B |
| ILE | CG1 | 909 | 170.2 | 111.4 | 41.4 | 44 | B |
| ILE | CD1 | 909 | 170.2 | 110.9 | 42.8 | 43 | B |
| ILE | C | 909 | 167.9 | 113.5 | 39.1 | 46 | B |
| ILE | O | 909 | 167.2 | 112.9 | 38.3 | 48 | B |
| GLN | N | 910 | 167.6 | 114.7 | 39.7 | 47 | B |
| GLN | CA | 910 | 166.4 | 115.3 | 39.3 | 49 | B |
| GLN | CB | 910 | 166.2 | 116.6 | 40.2 | 50 | B |
| GLN | CG | 910 | 164.9 | 117.4 | 40.0 | 52 | B |
| GLN | CD | 910 | 164.9 | 118.6 | 40.8 | 53 | B |
| GLN | OE1 | 910 | 164.4 | 119.7 | 40.3 | 54 | B |
| GLN | NE2 | 910 | 165.4 | 118.6 | 42.0 | 55 | B |
| GLN | C | 910 | 166.3 | 115.7 | 37.8 | 50 | B |
| GLN | O | 910 | 165.2 | 115.5 | 37.2 | 50 | B |
| ALA | N | 911 | 167.4 | 116.2 | 37.2 | 49 | B |
| ALA | CA | 911 | 167.4 | 116.5 | 35.8 | 49 | B |
| ALA | CB | 911 | 168.7 | 117.4 | 35.5 | 49 | B |
| ALA | C | 911 | 167.4 | 115.3 | 34.9 | 48 | B |
| ALA | O | 911 | 166.5 | 115.3 | 34.0 | 48 | B |
| THR | N | 912 | 168.3 | 114.4 | 35.1 | 48 | B |
| THR | CA | 912 | 168.3 | 113.2 | 34.2 | 50 | B |
| THR | CB | 912 | 169.3 | 112.1 | 34.6 | 49 | B |
| THR | OG1 | 912 | 168.9 | 111.5 | 35.8 | 51 | B |
| THR | CG2 | 912 | 170.7 | 112.8 | 34.9 | 48 | B |
| THR | C | 912 | 166.9 | 112.5 | 34.1 | 50 | B |
| THR | O | 912 | 166.4 | 112.2 | 33.0 | 52 | B |
| THR | N | 913 | 166.3 | 112.3 | 35.2 | 50 | B |
| THR | CA | 913 | 165.0 | 111.6 | 35.2 | 50 | B |
| THR | CB | 913 | 164.5 | 111.3 | 36.7 | 51 | B |
| THR | OG1 | 913 | 164.3 | 112.5 | 37.4 | 53 | B |

TABLE 2-continued

| | | | | | | | |
|---|---|---|---|---|---|---|---|
| THR | CG2 | 913 | 165.6 | 110.5 | 37.4 | 51 | B |
| THR | C | 913 | 163.9 | 112.4 | 34.5 | 48 | B |
| THR | O | 913 | 163.1 | 111.9 | 33.9 | 49 | B |
| HIS | N | 914 | 164.0 | 113.8 | 34.7 | 47 | B |
| HIS | CA | 914 | 163.0 | 114.6 | 34.1 | 45 | B |
| HIS | CB | 914 | 163.1 | 116.1 | 34.5 | 44 | B |
| HIS | CG | 914 | 162.4 | 117.0 | 33.6 | 44 | B |
| HIS | CD2 | 914 | 161.1 | 117.4 | 33.6 | 44 | B |
| HIS | ND1 | 914 | 163.0 | 117.5 | 32.5 | 44 | B |
| HIS | CE1 | 914 | 162.1 | 118.3 | 31.8 | 44 | B |
| HIS | NE2 | 914 | 160.9 | 118.2 | 32.5 | 44 | B |
| HIS | C | 914 | 163.1 | 114.5 | 32.5 | 45 | B |
| HIS | O | 914 | 162.1 | 114.6 | 31.8 | 44 | B |
| PHE | N | 915 | 164.3 | 114.5 | 32.0 | 46 | B |
| PHE | CA | 915 | 164.5 | 114.5 | 30.6 | 46 | B |
| PHE | CB | 915 | 165.9 | 115.0 | 30.3 | 44 | B |
| PHE | CG | 915 | 166.0 | 116.5 | 30.3 | 42 | B |
| PHE | CD1 | 915 | 166.7 | 117.1 | 31.4 | 41 | B |
| PHE | CD2 | 915 | 165.5 | 117.2 | 29.3 | 41 | B |
| PHE | CE1 | 915 | 166.8 | 118.5 | 31.5 | 41 | B |
| PHE | CE2 | 915 | 165.6 | 118.6 | 29.4 | 40 | B |
| PHE | CZ | 915 | 166.2 | 119.2 | 30.5 | 41 | B |
| PHE | C | 915 | 164.4 | 113.0 | 30.1 | 48 | B |
| PHE | O | 915 | 164.3 | 112.8 | 28.9 | 48 | B |
| LEU | N | 916 | 164.5 | 112.1 | 31.1 | 50 | B |
| LEU | CA | 916 | 164.4 | 110.7 | 30.8 | 53 | B |
| LEU | CB | 916 | 164.8 | 109.9 | 32.0 | 52 | B |
| LEU | CG | 916 | 165.6 | 108.6 | 31.7 | 52 | B |
| LEU | CD1 | 916 | 166.4 | 108.8 | 30.4 | 52 | B |
| LEU | CD2 | 916 | 166.5 | 108.4 | 32.9 | 52 | B |
| LEU | C | 916 | 162.9 | 110.3 | 30.4 | 55 | B |
| LEU | O | 916 | 162.7 | 109.3 | 29.7 | 56 | B |
| GLN | N | 917 | 161.9 | 111.2 | 30.7 | 58 | B |
| GLN | CA | 917 | 160.6 | 111.0 | 30.2 | 60 | B |
| GLN | CB | 917 | 159.6 | 111.5 | 31.3 | 62 | B |
| GLN | CG | 917 | 159.5 | 113.0 | 31.5 | 64 | B |
| GLN | CD | 917 | 159.1 | 113.4 | 32.9 | 65 | B |
| GLN | OE1 | 917 | 159.2 | 112.6 | 33.8 | 66 | B |
| GLN | NE2 | 917 | 158.7 | 114.6 | 33.0 | 65 | B |
| GLN | C | 917 | 160.3 | 111.6 | 28.9 | 61 | B |
| GLN | O | 917 | 159.2 | 111.8 | 28.5 | 62 | B |
| LYS | N | 918 | 161.4 | 111.9 | 28.2 | 63 | B |
| LYS | CA | 918 | 161.4 | 112.5 | 26.8 | 64 | B |
| LYS | CB | 918 | 162.1 | 113.8 | 26.8 | 64 | B |
| LYS | CG | 918 | 161.3 | 115.1 | 27.2 | 63 | B |
| LYS | CD | 918 | 161.1 | 115.1 | 28.7 | 64 | B |
| LYS | CE | 918 | 160.2 | 116.3 | 29.1 | 64 | B |
| LYS | NZ | 918 | 161.0 | 117.6 | 28.8 | 65 | B |
| LYS | C | 918 | 162.1 | 111.5 | 26.0 | 65 | B |
| LYS | O | 918 | 163.1 | 110.8 | 26.4 | 64 | B |
| PRO | N | 919 | 161.7 | 111.3 | 24.7 | 66 | B |
| PRO | CD | 919 | 160.5 | 111.8 | 24.0 | 67 | B |
| PRO | CA | 919 | 162.4 | 110.3 | 23.9 | 67 | B |
| PRO | CB | 919 | 161.4 | 110.0 | 22.8 | 67 | B |
| PRO | CG | 919 | 160.8 | 111.4 | 22.6 | 67 | B |
| PRO | C | 919 | 163.7 | 111.0 | 23.4 | 68 | B |
| PRO | O | 919 | 163.7 | 112.2 | 23.1 | 68 | B |
| VAL | N | 920 | 164.7 | 110.2 | 23.2 | 68 | B |
| VAL | CA | 920 | 166.0 | 110.6 | 22.7 | 70 | B |
| VAL | CB | 920 | 167.0 | 109.5 | 22.5 | 69 | B |
| VAL | CG1 | 920 | 168.2 | 109.9 | 21.6 | 68 | B |
| VAL | CG2 | 920 | 167.4 | 109.0 | 23.8 | 68 | B |
| VAL | C | 920 | 165.6 | 111.1 | 21.3 | 73 | B |
| VAL | O | 920 | 164.8 | 110.5 | 20.6 | 73 | B |
| PRO | N | 921 | 166.0 | 112.3 | 20.9 | 75 | B |
| PRO | CD | 921 | 166.7 | 113.4 | 21.7 | 75 | B |
| PRO | CA | 921 | 165.7 | 112.9 | 19.5 | 76 | B |
| PRO | CB | 921 | 166.4 | 114.2 | 19.6 | 76 | B |
| PRO | CG | 921 | 166.3 | 114.6 | 21.0 | 75 | B |
| PRO | C | 921 | 166.2 | 112.0 | 18.4 | 79 | B |
| PRO | O | 921 | 167.2 | 112.2 | 17.8 | 79 | B |
| GLY | N | 922 | 165.4 | 110.9 | 18.2 | 82 | B |
| GLY | CA | 922 | 165.7 | 109.9 | 17.2 | 86 | B |
| GLY | C | 922 | 165.3 | 110.4 | 15.8 | 89 | B |
| GLY | O | 922 | 164.2 | 111.0 | 15.6 | 89 | B |
| PHE | N | 923 | 166.2 | 110.2 | 14.8 | 92 | B |
| PHE | CA | 923 | 165.9 | 110.6 | 13.4 | 93 | B |
| PHE | CB | 923 | 166.3 | 112.1 | 13.2 | 94 | B |
| PHE | CG | 923 | 167.4 | 112.6 | 14.0 | 95 | B |

TABLE 2-continued

| | | | | | | | |
|---|---|---|---|---|---|---|---|
| PHE | CD1 | 923 | 167.5 | 113.9 | 14.5 | 96 | B |
| PHE | CD2 | 923 | 168.5 | 111.7 | 14.3 | 95 | B |
| PHE | CE1 | 923 | 168.6 | 114.4 | 15.2 | 96 | B |
| PHE | CE2 | 923 | 169.6 | 112.2 | 15.1 | 95 | B |
| PHE | CZ | 923 | 169.7 | 113.6 | 15.5 | 96 | B |
| PHE | C | 923 | 166.6 | 109.7 | 12.4 | 94 | B |
| PHE | OT1 | 923 | 166.2 | 109.8 | 11.2 | 94 | B |
| PHE | OT2 | 923 | 167.5 | 108.9 | 12.7 | 94 | B |
| ZIN | ZN | 1000 | 193.5 | 128.0 | 39.2 | 30 | Z |
| HFP | P1 | 2001 | 197.8 | 126.1 | 32.7 | 41 | H |
| HFP | C1 | 2001 | 197.2 | 125.9 | 30.9 | 42 | H |
| HFP | C2 | 2001 | 195.7 | 125.6 | 31.0 | 40 | H |
| HFP | O1 | 2001 | 198.9 | 126.9 | 32.6 | 42 | H |
| HFP | O2 | 2001 | 198.1 | 124.7 | 33.2 | 41 | H |
| HFP | O9 | 2001 | 197.4 | 127.1 | 30.2 | 44 | H |
| HFP | C3 | 2001 | 195.1 | 124.8 | 30.1 | 36 | H |
| HFP | C5 | 2001 | 193.6 | 124.5 | 30.1 | 34 | H |
| HFP | C6 | 2001 | 193.1 | 124.2 | 31.6 | 31 | H |
| HFP | C7 | 2001 | 191.9 | 123.4 | 31.6 | 29 | H |
| HFP | C8 | 2001 | 191.1 | 123.3 | 32.7 | 26 | H |
| HFP | C10 | 2001 | 189.8 | 122.4 | 32.7 | 22 | H |
| HFP | C4 | 2001 | 195.9 | 124.1 | 28.9 | 35 | H |
| HFP | C11 | 2001 | 188.8 | 122.9 | 31.8 | 20 | H |
| HFP | C12 | 2001 | 187.5 | 122.1 | 31.9 | 19 | H |
| HFP | C13 | 2001 | 186.3 | 122.4 | 31.3 | 19 | H |
| HFP | C14 | 2001 | 186.2 | 123.6 | 30.4 | 18 | H |
| HFP | C15 | 2001 | 185.1 | 121.5 | 31.6 | 18 | H |
| HFP | O3 | 2001 | 196.6 | 126.7 | 33.5 | 41 | H |
| HFP | C9 | 2001 | 191.4 | 124.1 | 33.9 | 25 | H |
| HOH | OH2 | 1001 | 195.3 | 125.2 | 22.4 | 19 | W |
| HOH | OH2 | 1002 | 205.3 | 121.6 | 32.9 | 14 | W |
| HOH | OH2 | 1003 | 198.6 | 118.6 | 19.3 | 18 | W |
| HOH | OH2 | 1004 | 200.1 | 127.0 | 30.2 | 16 | W |
| HOH | OH2 | 1005 | 197.3 | 135.0 | 28.0 | 21 | W |
| HOH | OH2 | 1006 | 194.1 | 124.4 | 18.1 | 17 | W |
| HOH | OH2 | 1007 | 190.0 | 131.1 | 16.9 | 17 | W |
| HOH | OH2 | 1008 | 192.4 | 122.1 | 17.0 | 26 | W |
| HOH | OH2 | 1009 | 183.4 | 140.4 | 23.9 | 19 | W |
| HOH | OH2 | 1010 | 207.0 | 125.9 | 37.1 | 32 | W |
| HOH | OH2 | 1011 | 206.7 | 121.1 | 35.1 | 19 | W |
| HOH | OH2 | 1012 | 205.4 | 118.4 | 25.5 | 19 | W |
| HOH | OH2 | 1013 | 185.7 | 136.5 | 27.0 | 20 | W |
| HOH | OH2 | 1014 | 199.9 | 116.3 | 20.3 | 25 | W |
| HOH | OH2 | 1015 | 182.0 | 129.2 | 15.7 | 24 | W |
| HOH | OH2 | 1016 | 186.1 | 132.2 | 24.9 | 20 | W |
| HOH | OH2 | 1017 | 203.7 | 128.9 | 36.9 | 47 | W |
| HOH | OH2 | 1018 | 190.9 | 131.9 | 25.5 | 20 | W |
| HOH | OH2 | 1019 | 193.8 | 145.4 | 6.5 | 35 | W |
| HOH | OH2 | 1020 | 204.7 | 110.3 | 24.0 | 26 | W |
| HOH | OH2 | 1021 | 190.7 | 121.4 | 14.3 | 36 | W |
| HOH | OH2 | 1022 | 189.0 | 132.2 | 33.9 | 26 | W |
| HOH | OH2 | 1023 | 202.7 | 108.8 | 26.0 | 37 | W |
| HOH | OH2 | 1024 | 186.0 | 133.7 | 27.2 | 25 | W |
| HOH | OH2 | 1025 | 203.0 | 111.2 | 38.8 | 33 | W |
| HOH | OH2 | 1026 | 177.9 | 139.1 | 26.5 | 25 | W |
| HOH | OH2 | 1027 | 209.0 | 135.8 | 17.2 | 38 | W |
| HOH | OH2 | 1028 | 192.1 | 141.0 | 25.0 | 26 | W |
| HOH | OH2 | 1029 | 188.3 | 132.6 | 28.9 | 21 | W |
| HOH | OH2 | 1030 | 195.3 | 123.1 | 25.0 | 33 | W |
| HOH | OH2 | 1031 | 202.0 | 99.5 | 32.0 | 52 | W |
| HOH | OH2 | 1032 | 178.2 | 161.7 | 22.7 | 55 | W |
| HOH | OH2 | 1033 | 179.8 | 112.9 | 46.4 | 55 | W |
| HOH | OH2 | 1034 | 193.3 | 99.3 | 34.7 | 24 | W |
| HOH | OH2 | 1035 | 203.2 | 106.6 | 18.6 | 59 | W |
| HOH | OH2 | 1036 | 206.0 | 119.0 | 41.7 | 31 | W |
| HOH | OH2 | 1037 | 194.1 | 143.5 | 18.5 | 41 | W |
| HOH | OH2 | 1038 | 181.0 | 141.1 | 43.3 | 36 | W |
| HOH | OH2 | 1039 | 207.5 | 125.2 | 39.8 | 31 | W |
| HOH | OH2 | 1040 | 211.7 | 126.1 | 33.2 | 26 | W |
| HOH | OH2 | 1041 | 201.2 | 127.4 | 34.1 | 55 | W |
| HOH | OH2 | 1042 | 202.2 | 126.6 | 38.1 | 42 | W |
| HOH | OH2 | 1043 | 201.8 | 116.1 | 34.8 | 21 | W |
| HOH | OH2 | 1044 | 214.1 | 122.8 | 16.0 | 38 | W |
| HOH | OH2 | 1045 | 213.4 | 125.5 | 17.1 | 41 | W |
| HOH | OH2 | 1046 | 189.0 | 134.2 | 35.5 | 33 | W |
| HOH | OH2 | 1047 | 210.3 | 117.3 | 41.7 | 37 | W |
| HOH | OH2 | 1048 | 193.1 | 123.1 | 22.6 | 36 | W |
| HOH | OH2 | 1049 | 190.1 | 138.1 | 27.3 | 29 | W |
| HOH | OH2 | 1050 | 193.6 | 126.4 | 20.8 | 28 | W |

TABLE 2-continued

| | | | | | | | |
|---|---|---|---|---|---|---|---|
| HOH | OH2 | 1051 | 209.4 | 135.7 | 31.8 | 65 | W |
| HOH | OH2 | 1052 | 196.9 | 122.4 | 17.3 | 30 | W |
| HOH | OH2 | 1053 | 201.5 | 108.1 | 44.1 | 35 | W |
| HOH | OH2 | 1054 | 187.1 | 128.5 | 21.1 | 27 | W |
| HOH | OH2 | 1055 | 205.6 | 113.4 | 35.0 | 28 | W |
| HOH | OH2 | 1056 | 193.3 | 138.0 | 30.0 | 54 | W |
| HOH | OH2 | 1057 | 168.3 | 139.7 | 39.2 | 41 | W |
| HOH | OH2 | 1058 | 172.8 | 155.7 | 11.8 | 41 | W |
| HOH | OH2 | 1059 | 214.6 | 89.0 | 34.3 | 48 | W |
| HOH | OH2 | 1060 | 178.8 | 142.9 | 49.1 | 50 | W |
| HOH | OH2 | 1061 | 198.5 | 112.4 | 25.7 | 27 | W |
| HOH | OH2 | 1062 | 217.0 | 94.7 | 49.2 | 59 | W |
| HOH | OH2 | 1063 | 189.2 | 113.4 | 12.5 | 51 | W |
| HOH | OH2 | 1064 | 188.9 | 139.7 | 36.7 | 44 | W |
| HOH | OH2 | 1065 | 176.8 | 142.5 | 30.0 | 30 | W |
| HOH | OH2 | 1066 | 195.7 | 140.7 | 5.7 | 26 | W |
| HOH | OH2 | 1067 | 208.4 | 121.0 | 41.7 | 37 | W |
| HOH | OH2 | 1068 | 179.0 | 145.6 | 24.4 | 34 | W |
| HOH | OH2 | 1069 | 197.8 | 124.7 | 21.0 | 28 | W |
| HOH | OH2 | 1070 | 187.5 | 127.5 | 24.0 | 21 | W |
| HOH | OH2 | 1071 | 202.7 | 132.1 | 28.7 | 27 | W |
| HOH | OH2 | 1072 | 198.3 | 129.7 | 35.9 | 36 | W |
| HOH | OH2 | 1073 | 186.4 | 160.2 | 7.7 | 56 | W |
| HOH | OH2 | 1074 | 190.6 | 115.5 | 16.4 | 39 | W |
| HOH | OH2 | 1075 | 174.5 | 109.8 | 39.4 | 51 | W |
| HOH | OH2 | 1076 | 200.6 | 104.3 | 31.8 | 41 | W |
| HOH | OH2 | 1077 | 191.9 | 134.0 | 27.1 | 42 | W |
| HOH | OH2 | 1078 | 189.6 | 107.5 | 46.3 | 32 | W |
| HOH | OH2 | 1079 | 192.4 | 103.8 | 21.2 | 42 | W |
| HOH | OH2 | 1080 | 182.4 | 122.3 | 36.5 | 29 | W |
| HOH | OH2 | 1081 | 188.2 | 130.9 | 31.1 | 31 | W |
| HOH | OH2 | 1082 | 207.2 | 103.7 | 26.6 | 36 | W |
| HOH | OH2 | 1083 | 204.8 | 133.1 | 27.2 | 37 | W |
| HOH | OH2 | 1084 | 214.0 | 126.7 | 29.6 | 29 | W |
| HOH | OH2 | 1085 | 194.6 | 122.8 | 45.5 | 43 | W |
| HOH | OH2 | 1086 | 198.3 | 108.5 | 19.3 | 52 | W |
| HOH | OH2 | 1087 | 203.6 | 125.2 | 44.6 | 21 | W |
| HOH | OH2 | 1088 | 195.8 | 141.0 | 8.5 | 35 | W |
| HOH | OH2 | 1089 | 186.5 | 150.2 | 37.0 | 64 | W |
| HOH | OH2 | 1090 | 203.2 | 138.6 | 27.6 | 62 | W |
| HOH | OH2 | 1091 | 206.1 | 128.0 | 33.8 | 48 | W |
| HOH | OH2 | 1092 | 218.2 | 128.9 | 36.9 | 61 | W |
| HOH | OH2 | 1093 | 188.3 | 110.9 | 60.4 | 76 | W |
| HOH | OH2 | 1094 | 174.2 | 131.4 | 16.3 | 43 | W |
| HOH | OH2 | 1095 | 186.1 | 139.1 | 40.9 | 34 | W |
| HOH | OH2 | 1096 | 171.6 | 110.3 | 38.2 | 54 | W |
| HOH | OH2 | 1097 | 201.1 | 134.0 | 30.1 | 48 | W |
| HOH | OH2 | 1098 | 173.9 | 123.1 | 14.6 | 38 | W |
| HOH | OH2 | 1099 | 203.2 | 112.0 | 25.5 | 34 | W |
| HOH | OH2 | 1100 | 209.2 | 127.4 | 33.4 | 42 | W |
| HOH | OH2 | 1101 | 183.6 | 103.7 | 21.0 | 44 | W |
| HOH | OH2 | 1102 | 194.1 | 134.0 | 39.6 | 31 | W |
| HOH | OH2 | 1103 | 206.5 | 123.1 | 41.5 | 35 | W |
| HOH | OH2 | 1104 | 212.8 | 134.7 | 16.5 | 49 | W |
| HOH | OH2 | 1105 | 215.0 | 130.6 | 21.3 | 41 | W |
| HOH | OH2 | 1106 | 183.4 | 141.7 | 41.0 | 43 | W |
| HOH | OH2 | 1107 | 203.0 | 116.0 | 53.9 | 30 | W |
| HOH | OH2 | 1108 | 197.1 | 125.1 | 18.1 | 35 | W |
| HOH | OH2 | 1109 | 195.9 | 119.6 | 10.2 | 36 | W |
| HOH | OH2 | 1110 | 197.7 | 127.3 | −0.2 | 43 | W |
| HOH | OH2 | 1111 | 206.4 | 131.4 | 42.7 | 33 | W |
| HOH | OH2 | 1112 | 163.5 | 127.2 | 24.4 | 51 | W |
| HOH | OH2 | 1113 | 196.5 | 143.6 | 9.4 | 54 | W |
| HOH | OH2 | 1114 | 188.8 | 128.8 | 18.2 | 25 | W |
| HOH | OH2 | 1115 | 202.5 | 103.3 | 39.3 | 70 | W |
| HOH | OH2 | 1116 | 202.5 | 127.7 | 31.4 | 41 | W |
| HOH | OH2 | 1117 | 196.3 | 120.1 | 19.2 | 41 | W |
| HOH | OH2 | 1118 | 185.3 | 130.9 | 30.7 | 39 | W |
| HOH | OH2 | 1119 | 193.6 | 119.5 | 18.4 | 45 | W |
| HOH | OH2 | 1120 | 181.9 | 134.9 | 21.2 | 42 | W |
| HOH | OH2 | 1121 | 192.8 | 101.8 | 25.5 | 60 | W |
| HOH | OH2 | 1122 | 188.4 | 149.2 | 27.6 | 63 | W |
| HOH | OH2 | 1123 | 220.5 | 117.5 | 28.3 | 64 | W |
| HOH | OH2 | 1124 | 187.0 | 131.2 | 16.7 | 36 | W |
| HOH | OH2 | 1125 | 212.6 | 128.7 | 27.8 | 36 | W |
| HOH | OH2 | 1126 | 172.3 | 122.7 | 12.5 | 52 | W |
| HOH | OH2 | 1127 | 192.9 | 133.2 | 41.8 | 23 | W |
| HOH | OH2 | 1128 | 189.2 | 150.4 | 12.3 | 60 | W |
| HOH | OH2 | 1129 | 165.9 | 130.2 | 23.5 | 53 | W |

TABLE 2-continued

| | | | | | | | |
|---|---|---|---|---|---|---|---|
| HOH | OH2 | 1130 | 191.0 | 132.6 | 36.8 | 38 | W |
| HOH | OH2 | 1131 | 172.0 | 141.0 | 21.7 | 49 | W |
| HOH | OH2 | 1132 | 216.5 | 127.0 | 35.0 | 40 | W |
| HOH | OH2 | 1133 | 204.7 | 101.1 | 37.6 | 54 | W |
| HOH | OH2 | 1134 | 205.2 | 135.8 | 10.8 | 53 | W |
| HOH | OH2 | 1135 | 182.9 | 105.9 | 23.3 | 43 | W |
| HOH | OH2 | 1136 | 192.8 | 135.4 | 2.0 | 36 | W |
| HOH | OH2 | 1137 | 169.9 | 124.1 | 22.1 | 35 | W |
| HOH | OH2 | 1138 | 194.9 | 103.6 | 27.6 | 57 | W |
| HOH | OH2 | 1139 | 193.8 | 147.5 | 10.8 | 53 | W |
| HOH | OH2 | 1140 | 175.0 | 124.9 | 56.2 | 55 | W |
| HOH | OH2 | 1141 | 175.6 | 146.8 | 25.5 | 50 | W |
| HOH | OH2 | 1142 | 198.9 | 144.5 | 17.4 | 56 | W |
| HOH | OH2 | 1143 | 176.4 | 119.9 | 31.9 | 43 | W |
| HOH | OH2 | 1144 | 204.6 | 113.4 | 44.0 | 53 | W |
| HOH | OH2 | 1145 | 184.2 | 100.6 | 31.8 | 48 | W |
| HOH | OH2 | 1146 | 215.1 | 118.7 | 43.6 | 24 | W |
| HOH | OH2 | 1147 | 203.6 | 116.3 | 46.7 | 40 | W |
| HOH | OH2 | 1148 | 167.9 | 119.4 | 38.0 | 32 | W |
| HOH | OH2 | 1149 | 199.1 | 124.3 | 35.8 | 46 | W |
| HOH | OH2 | 1150 | 213.7 | 90.9 | 37.9 | 46 | W |
| HOH | OH2 | 1151 | 194.9 | 128.5 | 29.0 | 40 | W |
| HOH | OH2 | 1152 | 189.5 | 135.1 | 29.3 | 47 | W |
| HOH | OH2 | 1153 | 205.0 | 133.8 | 13.0 | 36 | W |
| HOH | OH2 | 1154 | 203.0 | 109.0 | 22.1 | 57 | W |
| HOH | OH2 | 1155 | 176.2 | 147.6 | 5.4 | 53 | W |
| HOH | OH2 | 1156 | 183.7 | 123.1 | 11.6 | 49 | W |
| HOH | OH2 | 1157 | 164.3 | 135.4 | 26.2 | 45 | W |
| HOH | OH2 | 1158 | 192.1 | 146.7 | 25.8 | 55 | W |
| HOH | OH2 | 1159 | 188.8 | 137.1 | 36.1 | 45 | W |
| HOH | OH2 | 1160 | 168.6 | 109.3 | 38.1 | 52 | W |
| HOH | OH2 | 1161 | 205.0 | 129.0 | 9.2 | 28 | W |
| HOH | OH2 | 1162 | 213.2 | 124.2 | 30.3 | 32 | W |
| HOH | OH2 | 1163 | 185.7 | 122.1 | 56.4 | 33 | W |
| HOH | OH2 | 1164 | 206.4 | 139.7 | 24.1 | 62 | W |
| HOH | OH2 | 1165 | 214.0 | 128.2 | 25.6 | 41 | W |
| HOH | OH2 | 1166 | 173.6 | 145.4 | 28.5 | 54 | W |
| HOH | OH2 | 1167 | 163.7 | 129.1 | 41.6 | 44 | W |
| HOH | OH2 | 1168 | 175.7 | 141.9 | 48.5 | 72 | W |
| HOH | OH2 | 1169 | 187.5 | 123.0 | 13.4 | 44 | W |
| HOH | OH2 | 1170 | 185.2 | 142.8 | 39.4 | 63 | W |
| HOH | OH2 | 1171 | 211.2 | 114.1 | 9.6 | 52 | W |
| HOH | OH2 | 1172 | 201.7 | 110.9 | 19.4 | 58 | W |
| HOH | OH2 | 1173 | 206.6 | 119.5 | 5.6 | 48 | W |
| HOH | OH2 | 1174 | 213.9 | 111.4 | 12.7 | 60 | W |
| HOH | OH2 | 1175 | 184.1 | 119.6 | 10.4 | 64 | W |
| HOH | OH2 | 1176 | 213.8 | 127.8 | 32.1 | 38 | W |
| HOH | OH2 | 1177 | 209.4 | 125.7 | 11.5 | 48 | W |
| HOH | OH2 | 1178 | 206.0 | 109.5 | 46.6 | 61 | W |
| HOH | OH2 | 1179 | 201.2 | 131.8 | 37.5 | 90 | W |
| HOH | OH2 | 1180 | 192.5 | 136.9 | 26.2 | 69 | W |
| HOH | OH2 | 1181 | 218.0 | 119.6 | 49.4 | 67 | W |
| HOH | OH2 | 1182 | 176.4 | 102.9 | 16.1 | 68 | W |
| HOH | OH2 | 1183 | 173.6 | 140.7 | 17.1 | 67 | W |
| HOH | OH2 | 1184 | 189.8 | 116.1 | 13.4 | 60 | W |
| HOH | OH2 | 1185 | 181.9 | 136.3 | 0.1 | 92 | W |
| HOH | OH2 | 1186 | 167.2 | 136.3 | 31.9 | 37 | W |
| HOH | OH2 | 1187 | 162.5 | 114.2 | 22.1 | 49 | W |
| HOH | OH2 | 1188 | 196.4 | 109.8 | 48.5 | 42 | W |
| HOH | OH2 | 1189 | 212.8 | 120.4 | 15.5 | 39 | W |
| HOH | OH2 | 1190 | 191.0 | 102.6 | 23.4 | 50 | W |
| HOH | OH2 | 1191 | 196.4 | 141.1 | 45.8 | 56 | W |
| HOH | OH2 | 1192 | 204.0 | 108.8 | 40.4 | 77 | W |
| HOH | OH2 | 1193 | 193.1 | 143.8 | 10.7 | 46 | W |
| HOH | OH2 | 1194 | 207.6 | 120.3 | 49.0 | 57 | W |
| HOH | OH2 | 1195 | 190.8 | 106.9 | 18.7 | 55 | W |
| HOH | OH2 | 1196 | 194.3 | 126.0 | 35.2 | 45 | W |
| HOH | OH2 | 1197 | 161.7 | 128.1 | 30.0 | 35 | W |
| HOH | OH2 | 1198 | 204.3 | 124.3 | 60.4 | 54 | W |
| HOH | OH2 | 1199 | 163.7 | 107.4 | 23.3 | 49 | W |
| HOH | OH2 | 1200 | 215.5 | 108.1 | 19.5 | 34 | W |
| HOH | OH2 | 1201 | 164.4 | 143.9 | 24.4 | 59 | W |
| HOH | OH2 | 1202 | 188.5 | 149.1 | 30.8 | 65 | W |
| HOH | OH2 | 1203 | 192.2 | 141.0 | 28.2 | 61 | W |
| HOH | OH2 | 1204 | 184.8 | 103.8 | 15.9 | 63 | W |
| HOH | OH2 | 1205 | 197.7 | 114.2 | 18.5 | 67 | W |
| HOH | OH2 | 1206 | 219.5 | 112.6 | 23.4 | 60 | W |
| HOH | OH2 | 1207 | 210.2 | 138.0 | 22.1 | 58 | W |
| HOH | OH2 | 1208 | 216.3 | 128.9 | 32.8 | 50 | W |

TABLE 2-continued

| | | | | | | | |
|---|---|---|---|---|---|---|---|
| HOH | OH2 | 1209 | 186.2 | 134.3 | 37.1 | 47 | W |
| HOH | OH2 | 1210 | 195.7 | 144.3 | 4.7 | 59 | W |
| HOH | OH2 | 1211 | 180.3 | 104.4 | 34.4 | 62 | W |
| HOH | OH2 | 1212 | 165.3 | 121.4 | 43.1 | 62 | W |
| HOH | OH2 | 1213 | 195.6 | 137.0 | 40.0 | 46 | W |
| HOH | OH2 | 1214 | 196.9 | 112.1 | 47.4 | 54 | W |
| HOH | OH2 | 1215 | 220.4 | 116.7 | 31.0 | 75 | W |
| HOH | OH2 | 1216 | 181.5 | 128.7 | 58.4 | 40 | W |
| HOH | OH2 | 1217 | 180.2 | 142.6 | 41.3 | 49 | W |
| HOH | OH2 | 1218 | 200.6 | 110.1 | 24.4 | 39 | W |
| HOH | OH2 | 1219 | 176.3 | 153.6 | 20.3 | 58 | W |
| HOH | OH2 | 1220 | 179.4 | 142.4 | 24.9 | 45 | W |
| HOH | OH2 | 1221 | 179.6 | 133.8 | 57.6 | 57 | W |
| HOH | OH2 | 1222 | 192.3 | 149.2 | 13.6 | 40 | W |
| HOH | OH2 | 1223 | 204.6 | 123.8 | 65.8 | 54 | W |
| HOH | OH2 | 1224 | 195.9 | 132.1 | 38.7 | 42 | W |
| HOH | OH2 | 1225 | 197.4 | 139.1 | 40.7 | 58 | W |
| HOH | OH2 | 1226 | 199.8 | 123.6 | 38.6 | 36 | W |
| HOH | OH2 | 1227 | 215.3 | 112.9 | 39.2 | 44 | W |
| HOH | OH2 | 1228 | 176.6 | 107.3 | 21.6 | 45 | W |
| HOH | OH2 | 1229 | 210.1 | 129.6 | 31.6 | 43 | W |
| HOH | OH2 | 1230 | 190.7 | 144.2 | 1.5 | 81 | W |
| HOH | OH2 | 1231 | 205.1 | 108.5 | 13.9 | 70 | W |
| HOH | OH2 | 1232 | 205.7 | 136.4 | 7.1 | 73 | W |
| HOH | OH2 | 1233 | 189.5 | 141.8 | 28.2 | 70 | W |
| HOH | OH2 | 1234 | 179.7 | 145.5 | 41.4 | 56 | W |
| HOH | OH2 | 1235 | 192.4 | 132.0 | 53.2 | 63 | W |
| HOH | OH2 | 1236 | 214.4 | 110.1 | 18.2 | 41 | W |
| HOH | OH2 | 1237 | 207.6 | 131.5 | 5.1 | 66 | W |
| HOH | OH2 | 1238 | 180.4 | 127.4 | 16.8 | 43 | W |
| HOH | OH2 | 1239 | 201.9 | 142.7 | 8.5 | 93 | W |
| HOH | OH2 | 1240 | 176.1 | 137.1 | 9.7 | 56 | W |
| HOH | OH2 | 1241 | 169.1 | 111.6 | 31.5 | 45 | W |
| HOH | OH2 | 1242 | 181.9 | 141.6 | 47.9 | 66 | W |
| HOH | OH2 | 1243 | 203.1 | 106.0 | 34.8 | 61 | W |
| HOH | OH2 | 1244 | 183.4 | 102.5 | 18.1 | 67 | W |
| HOH | OH2 | 1245 | 191.6 | 159.6 | 22.3 | 31 | W |
| HOH | OH2 | 1246 | 199.3 | 120.5 | 54.1 | 51 | W |
| HOH | OH2 | 1247 | 214.5 | 112.6 | 51.3 | 72 | W |
| HOH | OH2 | 1248 | 205.0 | 112.7 | 11.6 | 40 | W |
| HOH | OH2 | 1249 | 195.7 | 142.0 | 22.5 | 56 | W |
| HOH | OH2 | 1250 | 162.7 | 131.3 | 30.6 | 61 | W |
| HOH | OH2 | 1251 | 173.0 | 152.1 | 20.0 | 59 | W |
| HOH | OH2 | 1252 | 181.5 | 121.4 | 11.9 | 63 | W |
| HOH | OH2 | 1253 | 186.6 | 115.3 | 22.2 | 44 | W |
| HOH | OH2 | 1254 | 182.7 | 149.4 | 35.4 | 74 | W |
| HOH | OH2 | 1255 | 162.9 | 129.2 | 38.0 | 60 | W |
| HOH | OH2 | 1256 | 203.7 | 141.7 | 25.4 | 66 | W |
| HOH | OH2 | 1257 | 212.6 | 118.9 | 42.3 | 40 | W |
| HOH | OH2 | 1258 | 179.7 | 144.8 | 45.6 | 67 | W |
| HOH | OH2 | 1259 | 198.8 | 108.3 | 22.4 | 87 | W |
| HOH | OH2 | 1260 | 196.9 | 142.5 | 25.8 | 62 | W |
| HOH | OH2 | 1261 | 212.8 | 130.7 | 30.8 | 52 | W |
| HOH | OH2 | 1262 | 214.3 | 93.0 | 39.5 | 54 | W |
| HOH | OH2 | 1263 | 178.4 | 153.2 | 22.4 | 67 | W |
| HOH | OH2 | 1264 | 204.7 | 135.9 | 25.3 | 46 | W |
| HOH | OH2 | 1265 | 212.6 | 117.4 | 9.9 | 60 | W |
| HOH | OH2 | 1266 | 179.6 | 100.0 | 28.4 | 67 | W |
| HOH | OH2 | 1267 | 219.8 | 115.1 | 20.1 | 65 | W |
| HOH | OH2 | 1268 | 158.1 | 126.2 | 30.7 | 59 | W |
| HOH | OH2 | 1269 | 171.9 | 134.2 | 54.2 | 60 | W |
| HOH | OH2 | 1270 | 184.0 | 106.3 | 37.7 | 58 | W |
| HOH | OH2 | 1271 | 173.8 | 118.6 | 46.9 | 49 | W |
| HOH | OH2 | 1272 | 215.9 | 126.1 | 44.5 | 41 | W |
| HOH | OH2 | 1273 | 212.1 | 135.4 | 24.2 | 56 | W |
| HOH | OH2 | 1274 | 181.4 | 140.5 | 50.8 | 55 | W |
| HOH | OH2 | 1275 | 210.9 | 115.0 | 48.8 | 59 | W |
| HOH | OH2 | 1276 | 189.9 | 152.6 | 15.8 | 38 | W |
| HOH | OH2 | 1277 | 195.5 | 129.7 | 32.0 | 47 | W |
| HOH | OH2 | 1278 | 181.3 | 134.6 | 11.0 | 72 | W |
| HOH | OH2 | 1279 | 199.4 | 154.9 | 21.0 | 84 | W |
| HOH | OH2 | 1280 | 202.8 | 101.8 | 44.1 | 59 | W |
| HOH | OH2 | 1281 | 190.8 | 99.5 | 33.5 | 60 | W |
| HOH | OH2 | 1282 | 203.1 | 141.8 | 21.0 | 57 | W |
| HOH | OH2 | 1283 | 211.2 | 117.6 | 47.8 | 54 | W |
| HOH | OH2 | 1284 | 203.8 | 113.8 | 51.8 | 56 | W |
| GLY | C | 0 | 194.2 | 132.2 | 35.3 | 45 | P |
| GLY | O | 0 | 195.2 | 131.9 | 34.7 | 46 | P |
| GLY | CA | 0 | 194.0 | 133.5 | 36.2 | 46 | P |

TABLE 2-continued

| | | | | | | | |
|---|---|---|---|---|---|---|---|
| CYS | N | 1 | 193.1 | 131.4 | 35.4 | 42 | P |
| CYS | CA | 1 | 193.1 | 130.2 | 34.6 | 39 | P |
| CYS | CB | 1 | 192.8 | 129.1 | 35.6 | 40 | P |
| CYS | SG | 1 | 194.0 | 129.0 | 36.9 | 40 | P |
| CYS | C | 1 | 192.1 | 130.3 | 33.5 | 38 | P |
| CYS | O | 1 | 190.9 | 130.5 | 33.8 | 38 | P |
| VAL | N | 2 | 192.6 | 130.3 | 32.3 | 36 | P |
| VAL | CA | 2 | 191.7 | 130.4 | 31.1 | 35 | P |
| VAL | CB | 2 | 192.5 | 131.0 | 29.9 | 35 | P |
| VAL | CG1 | 2 | 191.7 | 131.1 | 28.7 | 35 | P |
| VAL | CG2 | 2 | 193.0 | 132.4 | 30.3 | 36 | P |
| VAL | C | 2 | 191.3 | 129.0 | 30.7 | 34 | P |
| VAL | O | 2 | 192.1 | 128.1 | 30.3 | 35 | P |
| ILE | N | 3 | 190.0 | 128.7 | 30.9 | 32 | P |
| ILE | CA | 3 | 189.4 | 127.4 | 30.6 | 29 | P |
| ILE | CB | 3 | 188.5 | 126.8 | 31.7 | 27 | P |
| ILE | CG2 | 3 | 189.4 | 126.6 | 33.0 | 24 | P |
| ILE | CG1 | 3 | 187.3 | 127.6 | 32.0 | 25 | P |
| ILE | CD1 | 3 | 186.4 | 127.0 | 33.0 | 23 | P |
| ILE | C | 3 | 188.7 | 127.3 | 29.2 | 28 | P |
| ILE | O | 3 | 188.2 | 126.2 | 28.8 | 26 | P |
| MET | N | 4 | 188.5 | 128.4 | 28.5 | 28 | P |
| MET | CA | 4 | 188.0 | 128.5 | 27.2 | 29 | P |
| MET | CB | 4 | 186.5 | 128.0 | 27.1 | 31 | P |
| MET | CG | 4 | 185.4 | 128.8 | 26.3 | 34 | P |
| MET | CE | 4 | 183.3 | 130.4 | 25.9 | 33 | P |
| MET | SD | 4 | 184.2 | 129.9 | 27.3 | 36 | P |
| MET | C | 4 | 188.3 | 129.8 | 26.4 | 31 | P |
| MET | OT1 | 4 | 188.0 | 129.8 | 25.2 | 32 | P |
| MET | OT2 | 4 | 189.0 | 130.7 | 26.9 | 30 | P |

TABLE 3

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| GLY C | 54 | 192.3 | 151.6 | 9.2 | 83 | A |
| GLY O | 54 | 191.1 | 151.5 | 9.3 | 83 | A |
| GLY N | 54 | 193.3 | 151.1 | 7.0 | 84 | A |
| GLY CA | 54 | 192.9 | 152.2 | 7.9 | 83 | A |
| PHE N | 55 | 193.2 | 151.2 | 10.1 | 82 | A |
| PHE CA | 55 | 192.8 | 150.6 | 11.4 | 81 | A |
| PHE CB | 55 | 193.7 | 149.4 | 11.7 | 81 | A |
| PHE CG | 55 | 193.1 | 148.1 | 11.2 | 82 | A |
| PHE CD1 | 55 | 193.7 | 147.4 | 10.1 | 82 | A |
| PHE CD2 | 55 | 192.1 | 147.4 | 11.9 | 81 | A |
| PHE CE1 | 55 | 193.2 | 146.2 | 9.7 | 82 | A |
| PHE CE2 | 55 | 191.6 | 146.2 | 11.5 | 82 | A |
| PHE CZ | 55 | 192.2 | 145.6 | 10.4 | 82 | A |
| PHE C | 55 | 192.8 | 151.6 | 12.5 | 79 | A |
| PHE O | 55 | 193.8 | 152.4 | 12.6 | 79 | A |
| LEU N | 56 | 191.8 | 151.7 | 13.3 | 76 | A |
| LEU CA | 56 | 191.7 | 152.6 | 14.4 | 73 | A |
| LEU CB | 56 | 190.5 | 153.4 | 14.5 | 72 | A |
| LEU CG | 56 | 190.6 | 154.9 | 14.7 | 72 | A |
| LEU CD1 | 56 | 189.3 | 155.5 | 15.1 | 72 | A |
| LEU CD2 | 56 | 191.7 | 155.2 | 15.8 | 72 | A |
| LEU C | 56 | 191.9 | 151.7 | 15.7 | 70 | A |
| LEU O | 56 | 190.9 | 151.2 | 16.2 | 70 | A |
| SER N | 57 | 193.1 | 151.6 | 16.2 | 66 | A |
| SER CA | 57 | 193.4 | 150.8 | 17.4 | 63 | A |
| SER CB | 57 | 194.9 | 151.0 | 17.8 | 64 | A |
| SER OG | 57 | 195.2 | 150.3 | 19.0 | 64 | A |
| SER C | 57 | 192.5 | 151.1 | 18.6 | 61 | A |
| SER O | 57 | 192.2 | 152.2 | 18.9 | 60 | A |
| LEU N | 58 | 192.0 | 150.0 | 19.2 | 59 | A |
| LEU CA | 58 | 191.2 | 150.1 | 20.4 | 57 | A |
| LEU CB | 58 | 190.9 | 148.7 | 20.9 | 55 | A |
| LEU CG | 58 | 189.4 | 148.2 | 20.8 | 54 | A |
| LEU CD1 | 58 | 189.3 | 146.8 | 21.4 | 54 | A |
| LEU CD2 | 58 | 188.5 | 149.2 | 21.6 | 53 | A |
| LEU C | 58 | 191.8 | 150.9 | 21.5 | 57 | A |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| LEU O | 58 | 191.2 | 151.4 | 22.4 | 57 | A |
| ASP N | 59 | 193.2 | 150.9 | 21.5 | 56 | A |
| ASP CA | 59 | 194.0 | 151.7 | 22.4 | 56 | A |
| ASP CB | 59 | 195.2 | 150.9 | 22.8 | 59 | A |
| ASP CG | 59 | 195.1 | 150.1 | 24.1 | 62 | A |
| ASP OD1 | 59 | 194.5 | 149.0 | 24.0 | 63 | A |
| ASP OD2 | 59 | 195.7 | 150.6 | 25.1 | 63 | A |
| ASP C | 59 | 194.4 | 153.1 | 22.0 | 52 | A |
| ASP O | 59 | 194.9 | 153.9 | 22.9 | 51 | A |
| SER N | 60 | 194.2 | 153.4 | 20.8 | 49 | A |
| SER CA | 60 | 194.5 | 154.7 | 20.2 | 46 | A |
| SER CB | 60 | 194.0 | 154.7 | 18.8 | 46 | A |
| SER OG | 60 | 194.1 | 156.0 | 18.2 | 47 | A |
| SER C | 60 | 193.9 | 155.8 | 21.0 | 45 | A |
| SER O | 60 | 192.8 | 155.7 | 21.4 | 45 | A |
| PRO N | 61 | 194.7 | 156.9 | 21.2 | 43 | A |
| PRO CD | 61 | 196.1 | 157.2 | 20.8 | 43 | A |
| PRO CA | 61 | 194.2 | 158.0 | 22.0 | 42 | A |
| PRO CB | 61 | 195.4 | 158.9 | 22.2 | 42 | A |
| PRO CG | 61 | 196.2 | 158.7 | 20.9 | 42 | A |
| PRO C | 61 | 193.0 | 158.7 | 21.3 | 41 | A |
| PRO O | 61 | 192.1 | 159.3 | 21.9 | 41 | A |
| THR N | 62 | 193.0 | 158.5 | 19.9 | 40 | A |
| THR CA | 62 | 192.0 | 159.1 | 19.1 | 40 | A |
| THR CB | 62 | 192.6 | 159.9 | 17.9 | 40 | A |
| THR OG1 | 62 | 193.4 | 159.0 | 17.1 | 40 | A |
| THR CG2 | 62 | 193.6 | 161.0 | 18.4 | 40 | A |
| THR C | 62 | 191.0 | 158.1 | 18.6 | 40 | A |
| THR O | 62 | 190.3 | 158.4 | 17.6 | 42 | A |
| TYR N | 63 | 190.8 | 157.0 | 19.3 | 39 | A |
| TYR CA | 63 | 189.8 | 156.0 | 18.9 | 37 | A |
| TYR CB | 63 | 190.0 | 154.7 | 19.7 | 37 | A |
| TYR CG | 63 | 188.9 | 153.7 | 19.6 | 36 | A |
| TYR CD1 | 63 | 188.9 | 152.7 | 18.5 | 36 | A |
| TYR CE1 | 63 | 187.9 | 151.8 | 18.4 | 35 | A |
| TYR CD2 | 63 | 187.8 | 153.7 | 20.5 | 36 | A |
| TYR CE2 | 63 | 186.8 | 152.7 | 20.3 | 35 | A |
| TYR CZ | 63 | 186.8 | 151.8 | 19.3 | 35 | A |
| TYR OH | 63 | 185.8 | 150.9 | 19.2 | 34 | A |
| TYR C | 63 | 188.5 | 156.6 | 19.2 | 36 | A |
| TYR O | 63 | 188.3 | 157.3 | 20.1 | 36 | A |
| VAL N | 64 | 187.5 | 156.4 | 18.3 | 36 | A |
| VAL CA | 64 | 186.2 | 156.9 | 18.5 | 35 | A |
| VAL CB | 64 | 185.8 | 158.0 | 17.4 | 35 | A |
| VAL CG1 | 64 | 186.7 | 159.3 | 17.6 | 34 | A |
| VAL CG2 | 64 | 186.0 | 157.5 | 16.0 | 35 | A |
| VAL C | 64 | 185.1 | 155.8 | 18.4 | 36 | A |
| VAL O | 64 | 185.3 | 154.8 | 17.6 | 37 | A |
| LEU N | 65 | 184.1 | 155.9 | 19.2 | 35 | A |
| LEU CA | 65 | 183.0 | 154.9 | 19.2 | 34 | A |
| LEU CB | 65 | 181.9 | 155.3 | 20.2 | 31 | A |
| LEU CG | 65 | 182.4 | 155.4 | 21.6 | 30 | A |
| LEU CD1 | 65 | 181.2 | 155.8 | 22.5 | 31 | A |
| LEU CD2 | 65 | 182.9 | 154.1 | 22.2 | 30 | A |
| LEU C | 65 | 182.4 | 154.7 | 17.8 | 36 | A |
| LEU O | 65 | 182.4 | 155.7 | 17.1 | 37 | A |
| TYR N | 66 | 182.0 | 153.6 | 17.5 | 38 | A |
| TYR CA | 66 | 181.4 | 153.3 | 16.2 | 39 | A |
| TYR CB | 66 | 181.0 | 151.8 | 16.0 | 38 | A |
| TYR CG | 66 | 182.2 | 150.9 | 15.7 | 37 | A |
| TYR CD1 | 66 | 183.0 | 150.5 | 16.7 | 36 | A |
| TYR CE1 | 66 | 184.1 | 149.8 | 16.3 | 36 | A |
| TYR CD2 | 66 | 182.4 | 150.6 | 14.3 | 36 | A |
| TYR CE2 | 66 | 183.6 | 149.9 | 14.0 | 35 | A |
| TYR CZ | 66 | 184.4 | 149.5 | 15.0 | 35 | A |
| TYR OH | 66 | 185.6 | 148.8 | 14.7 | 35 | A |
| TYR C | 66 | 180.2 | 154.2 | 15.8 | 40 | A |
| TYR O | 66 | 179.9 | 154.5 | 14.7 | 40 | A |
| ARG N | 67 | 179.5 | 154.6 | 16.9 | 41 | A |
| ARG CA | 67 | 178.3 | 155.4 | 16.7 | 43 | A |
| ARG CB | 67 | 177.4 | 155.4 | 17.9 | 44 | A |
| ARG CG | 67 | 178.0 | 155.9 | 19.2 | 45 | A |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| ARG CD | 67 | 176.9 | 156.1 | 20.3 | 46 | A |
| ARG NE | 67 | 177.4 | 156.6 | 21.5 | 47 | A |
| ARG CZ | 67 | 177.6 | 155.9 | 22.6 | 48 | A |
| ARG NH1 | 67 | 177.3 | 154.6 | 22.7 | 49 | A |
| ARG NH2 | 67 | 178.0 | 156.5 | 23.7 | 49 | A |
| ARG C | 67 | 178.7 | 156.9 | 16.4 | 44 | A |
| ARG O | 67 | 177.8 | T57.7 | 16.1 | 45 | A |
| ASP N | 68 | 179.9 | 157.2 | 16.5 | 44 | A |
| ASP CA | 68 | 180.4 | 158.6 | 16.2 | 43 | A |
| ASP CB | 68 | 181.3 | 159.1 | 17.3 | 42 | A |
| ASP CG | 68 | 180.6 | 159.4 | 18.6 | 42 | A |
| ASP OD1 | 68 | 179.3 | 159.7 | 18.6 | 42 | A |
| ASP OD2 | 68 | 181.2 | 159.3 | 19.7 | 41 | A |
| ASP C | 68 | 181.1 | 158.5 | 14.9 | 44 | A |
| ASP O | 68 | 181.8 | 159.4 | 14.5 | 45 | A |
| ARG N | 69 | 181.0 | 157.4 | 14.2 | 45 | A |
| ARG CA | 69 | 181.7 | 157.1 | 12.9 | 47 | A |
| ARG CB | 69 | 182.4 | 155.8 | 12.9 | 46 | A |
| ARG CG | 69 | 183.3 | 155.5 | 14.1 | 45 | A |
| ARG CD | 69 | 184.3 | 154.4 | 13.8 | 44 | A |
| ARG NE | 69 | 185.1 | 153.9 | 15.0 | 42 | A |
| ARG CZ | 69 | 186.1 | 153.1 | 14.9 | 41 | A |
| ARG NH1 | 69 | 186.5 | 152.6 | 13.8 | 40 | A |
| ARG NH2 | 69 | 186.7 | 152.7 | 16.0 | 41 | A |
| ARG C | 69 | 180.8 | 157.3 | 11.7 | 48 | A |
| ARG O | 69 | 179.8 | 156.6 | 11.5 | 49 | A |
| ALA N | 70 | 181.3 | 158.2 | 10.8 | 51 | A |
| ALA CA | 70 | 180.6 | 158.5 | 9.5 | 52 | A |
| ALA CB | 70 | 181.3 | 159.7 | 8.8 | 53 | A |
| ALA C | 70 | 180.4 | 157.4 | 8.6 | 53 | A |
| ALA O | 70 | 179.4 | 157.3 | 7.9 | 54 | A |
| GLU N | 71 | 181.3 | 156.5 | 8.5 | 53 | A |
| GLU CA | 71 | 181.3 | 155.3 | 7.6 | 54 | A |
| GLU CB | 71 | 182.7 | 154.9 | 7.2 | 55 | A |
| GLU CG | 71 | 183.6 | 154.3 | 8.4 | 56 | A |
| GLU CD | 71 | 183.9 | 155.3 | 9.5 | 56 | A |
| GLU OE1 | 71 | 184.0 | 154.9 | 10.7 | 56 | A |
| GLU OE2 | 71 | 184.0 | 156.5 | 9.2 | 57 | A |
| GLU C | 71 | 180.5 | 154.2 | 8.3 | 53 | A |
| GLU O | 71 | 180.5 | 153.0 | 7.7 | 53 | A |
| TRP N | 72 | 179.9 | 154.4 | 9.4 | 54 | A |
| TRP CA | 72 | 179.1 | 153.5 | 10.2 | 55 | A |
| TRP CB | 72 | 179.9 | 153.1 | 11.5 | 54 | A |
| TRP CG | 72 | 180.9 | 152.0 | 11.3 | 52 | A |
| TRP CD2 | 72 | 180.7 | 150.6 | 11.1 | 51 | A |
| TRP CE2 | 72 | 181.9 | 150.0 | 10.8 | 51 | A |
| TRP CE3 | 72 | 179.5 | 149.8 | 11.0 | 51 | A |
| TRP CD1 | 72 | 182.2 | 152.2 | 11.2 | 52 | A |
| TRP NE1 | 72 | 182.9 | 151.0 | 10.9 | 52 | A |
| TRP CZ2 | 72 | 182.0 | 148.6 | 10.6 | 51 | A |
| TRP CZ3 | 72 | 179.6 | 148.5 | 10.8 | 51 | A |
| TRP CH2 | 72 | 180.9 | 147.9 | 10.6 | 51 | A |
| TRP C | 72 | 177.7 | 154.0 | 10.6 | 58 | A |
| TRP O | 72 | 176.9 | 153.2 | 11.2 | 58 | A |
| ALA N | 73 | 177.4 | 155.2 | 10.3 | 60 | A |
| ALA CA | 73 | 176.1 | 155.8 | 10.6 | 61 | A |
| ALA CB | 73 | 176.2 | 157.3 | 10.5 | 61 | A |
| ALA C | 73 | 175.0 | 155.2 | 9.8 | 62 | A |
| ALA O | 73 | 173.8 | 155.2 | 10.2 | 63 | A |
| ASP N | 74 | 175.3 | 154.7 | 8.6 | 61 | A |
| ASP CA | 74 | 174.3 | 154.1 | 7.7 | 61 | A |
| ASP CB | 74 | 174.9 | 153.8 | 6.4 | 61 | A |
| ASP CG | 74 | 175.9 | 152.7 | 6.4 | 61 | A |
| ASP OD1 | 74 | 175.6 | 151.6 | 5.8 | 62 | A |
| ASP OD2 | 74 | 176.9 | 152.8 | 7.1 | 61 | A |
| ASP C | 74 | 173.7 | 152.8 | 8.3 | 61 | A |
| ASP O | 74 | 172.5 | 152.4 | 8.0 | 61 | A |
| ILE N | 75 | 174.4 | 152.1 | 9.2 | 60 | A |
| ILE CA | 75 | 174.0 | 150.9 | 9.8 | 59 | A |
| ILE CB | 75 | 175.1 | 149.8 | 9.8 | 58 | A |
| ILE CG2 | 75 | 175.9 | 149.9 | 11.1 | 58 | A |
| ILE CG1 | 75 | 174.5 | 148.4 | 9.7 | 58 | A |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| ILE CD1 | 75 | 175.5 | 147.3 | 9.7 | 58 | A |
| ILE C | 75 | 173.4 | 151.1 | 11.2 | 58 | A |
| ILE O | 75 | 173.9 | 152.0 | 12.0 | 59 | A |
| ASP N | 76 | 172.4 | 150.4 | 11.6 | 58 | A |
| ASP CA | 76 | 171.7 | 150.5 | 12.8 | 58 | A |
| ASP CB | 76 | 170.2 | 150.2 | 12.7 | 60 | A |
| ASP CG | 76 | 169.3 | 151.4 | 12.8 | 62 | A |
| ASP OD1 | 76 | 169.3 | 152.3 | 11.9 | 63 | A |
| ASP OD2 | 76 | 168.6 | 151.5 | 13.9 | 63 | A |
| ASP C | 76 | 172.2 | 149.5 | 13.9 | 56 | A |
| ASP O | 76 | 172.1 | 148.3 | 13.6 | 55 | A |
| PRO N | 77 | 172.8 | 149.9 | 15.0 | 54 | A |
| PRO CD | 77 | 173.1 | 151.3 | 15.3 | 54 | A |
| PRO CA | 77 | 173.3 | 149.0 | 16.0 | 53 | A |
| PRO CB | 77 | 174.0 | 149.9 | 17.0 | 53 | A |
| PRO CG | 77 | 173.3 | 151.2 | 16.8 | 54 | A |
| PRO C | 77 | 172.2 | 148.2 | 16.7 | 52 | A |
| PRO O | 77 | 171.1 | 148.7 | 16.9 | 51 | A |
| VAL N | 78 | 172.5 | 147.0 | 17.0 | 51 | A |
| VAL CA | 78 | 171.5 | 146.1 | 17.6 | 49 | A |
| VAL CB | 78 | 171.4 | 144.7 | 16.8 | 49 | A |
| VAL CG1 | 78 | 170.5 | 143.8 | 17.5 | 49 | A |
| VAL CG2 | 78 | 171.1 | 145.0 | 15.4 | 49 | A |
| VAL C | 78 | 172.0 | 145.8 | 19.0 | 50 | A |
| VAL O | 78 | 173.0 | 145.1 | 19.2 | 50 | A |
| PRO N | 79 | 171.3 | 146.3 | 20.0 | 50 | A |
| PRO CD | 79 | 170.3 | 147.3 | 19.9 | 50 | A |
| PRO CA | 79 | 171.7 | 146.1 | 21.4 | 50 | A |
| PRO CB | 79 | 170.8 | 147.2 | 22.2 | 50 | A |
| PRO CG | 79 | 169.6 | 147.3 | 21.3 | 50 | A |
| PRO C | 79 | 171.4 | 144.7 | 21.9 | 50 | A |
| PRO O | 79 | 170.5 | 144.0 | 21.4 | 50 | A |
| GLN N | 80 | 172.1 | 144.2 | 22.9 | 49 | A |
| GLN CA | 80 | 171.9 | 142.9 | 23.4 | 49 | A |
| GLN CB | 80 | 173.1 | 142.5 | 24.4 | 48 | A |
| GLN CG | 80 | 173.0 | 141.1 | 24.9 | 45 | A |
| GLN CD | 80 | 174.3 | 140.6 | 25.5 | 45 | A |
| GLN OE1 | 80 | 175.1 | 139.9 | 24.9 | 45 | A |
| GLN NE2 | 80 | 174.4 | 140.9 | 26.8 | 45 | A |
| GLN C | 80 | 170.6 | 142.8 | 24.1 | 50 | A |
| GLN O | 80 | 170.2 | 143.6 | 24.9 | 51 | A |
| ASN N | 81 | 169.9 | 141.7 | 23.9 | 51 | A |
| ASN CA | 81 | 168.7 | 141.4 | 24.5 | 50 | A |
| ASN CB | 81 | 167.7 | 140.9 | 23.4 | 51 | A |
| ASN CG | 81 | 166.3 | 140.5 | 24.0 | 52 | A |
| ASN OD1 | 81 | 166.0 | 140.9 | 25.1 | 52 | A |
| ASN ND2 | 81 | 165.6 | 139.7 | 23.2 | 53 | A |
| ASN C | 81 | 168.8 | 140.3 | 25.6 | 50 | A |
| ASN O | 81 | 168.9 | 139.1 | 25.3 | 50 | A |
| ASP N | 82 | 168.9 | 140.8 | 26.8 | 51 | A |
| ASP CA | 82 | 169.1 | 139.9 | 28.0 | 52 | A |
| ASP CB | 82 | 170.0 | 140.6 | 29.0 | 53 | A |
| ASP CG | 82 | 171.5 | 140.5 | 28.6 | 54 | A |
| ASP OD1 | 82 | 171.8 | 139.6 | 27.8 | 53 | A |
| ASP OD2 | 82 | 172.3 | 141.2 | 29.3 | 54 | A |
| ASP C | 82 | 167.7 | 139.7 | 28.6 | 53 | A |
| ASP O | 82 | 167.7 | 139.1 | 29.7 | 53 | A |
| GLY N | 83 | 166.7 | 140.2 | 28.0 | 53 | A |
| GLY CA | 83 | 165.3 | 140.1 | 28.5 | 55 | A |
| GLY C | 83 | 165.0 | 141.1 | 29.6 | 56 | A |
| GLY O | 83 | 165.9 | 141.7 | 30.2 | 57 | A |
| PRO N | 84 | 163.7 | 141.3 | 29.8 | 56 | A |
| PRO CD | 84 | 162.6 | 140.5 | 29.2 | 55 | A |
| PRO CA | 84 | 163.2 | 142.3 | 30.8 | 55 | A |
| PRO CB | 84 | 161.7 | 142.0 | 30.8 | 56 | A |
| PRO CG | 84 | 161.6 | 140.6 | 30.4 | 56 | A |
| PRO C | 84 | 163.8 | 142.1 | 32.2 | 55 | A |
| PRO O | 84 | 163.8 | 143.1 | 32.9 | 55 | A |
| SER N | 85 | 164.2 | 140.9 | 32.5 | 54 | A |
| SER CA | 85 | 164.8 | 140.7 | 33.8 | 53 | A |
| SER CB | 85 | 163.8 | 139.9 | 34.7 | 54 | A |
| SER OG | 85 | 162.5 | 140.6 | 34.8 | 55 | A |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| SER C | 85 | 166.0 | 139.9 | 33.7 | 53 | A |
| SER O | 85 | 166.0 | 138.7 | 33.9 | 53 | A |
| PRO N | 86 | 167.2 | 140.6 | 33.5 | 51 | A |
| PRO CD | 86 | 167.2 | 142.0 | 33.2 | 51 | A |
| PRO CA | 86 | 168.5 | 140.0 | 33.4 | 50 | A |
| PRO CB | 86 | 169.4 | 141.2 | 33.1 | 50 | A |
| PRO CG | 86 | 168.5 | 142.1 | 32.3 | 50 | A |
| PRO C | 86 | 169.0 | 139.2 | 34.6 | 48 | A |
| PRO O | 86 | 168.6 | 139.4 | 35.7 | 48 | A |
| VAL N | 87 | 169.9 | 138.3 | 34.3 | 45 | A |
| VAL CA | 87 | 170.6 | 137.5 | 35.3 | 41 | A |
| VAL CB | 87 | 170.1 | 136.0 | 35.4 | 41 | A |
| VAL CG1 | 87 | 168.9 | 136.0 | 36.4 | 41 | A |
| VAL CG2 | 87 | 169.6 | 135.5 | 34.1 | 41 | A |
| VAL C | 87 | 172.1 | 137.5 | 34.8 | 39 | A |
| VAL O | 87 | 172.3 | 137.7 | 33.6 | 38 | A |
| VAL N | 88 | 173.0 | 137.3 | 35.7 | 36 | A |
| VAL CA | 88 | 174.4 | 137.3 | 35.4 | 35 | A |
| VAL CB | 88 | 175.0 | 135.9 | 35.1 | 34 | A |
| VAL CG1 | 88 | 174.9 | 135.0 | 36.3 | 33 | A |
| VAL CG2 | 88 | 174.4 | 135.3 | 33.9 | 33 | A |
| VAL C | 88 | 174.7 | 138.3 | 34.3 | 36 | A |
| VAL O | 88 | 175.3 | 138.0 | 33.3 | 37 | A |
| GLN N | 89 | 174.2 | 139.5 | 34.5 | 36 | A |
| GLN CA | 89 | 174.3 | 140.6 | 33.6 | 36 | A |
| GLN CB | 89 | 173.1 | 141.6 | 33.8 | 36 | A |
| GLN CG | 89 | 173.2 | 142.8 | 33.0 | 38 | A |
| GLN CD | 89 | 172.1 | 143.8 | 33.3 | 38 | A |
| GLN OE1 | 89 | 171.8 | 144.1 | 34.4 | 38 | A |
| GLN NE2 | 89 | 171.5 | 144.2 | 32.2 | 38 | A |
| GLN C | 89 | 175.6 | 141.4 | 33.7 | 37 | A |
| GLN O | 89 | 176.0 | 141.8 | 34.8 | 37 | A |
| ILE N | 90 | 176.3 | 141.6 | 32.6 | 35 | A |
| ILE CA | 90 | 177.6 | 142.2 | 32.7 | 35 | A |
| ILE CB | 90 | 178.5 | 141.6 | 31.7 | 34 | A |
| ILE CG2 | 90 | 179.9 | 142.2 | 31.8 | 34 | A |
| ILE CG1 | 90 | 178.6 | 140.0 | 31.9 | 33 | A |
| ILE CD1 | 90 | 179.2 | 139.2 | 30.8 | 32 | A |
| ILE C | 90 | 177.5 | 143.7 | 32.3 | 35 | A |
| ILE O | 90 | 177.0 | 144.1 | 31.2 | 36 | A |
| ILE N | 91 | 177.9 | 144.5 | 33.3 | 36 | A |
| ILE CA | 91 | 177.8 | 146.0 | 33.1 | 37 | A |
| ILE CB | 91 | 177.9 | 146.7 | 34.4 | 37 | A |
| ILE CG2 | 91 | 177.9 | 148.3 | 34.2 | 38 | A |
| ILE CG1 | 91 | 176.8 | 146.3 | 35.4 | 37 | A |
| ILE CD1 | 91 | 175.4 | 146.6 | 34.8 | 38 | A |
| ILE C | 91 | 178.9 | 146.4 | 32.1 | 36 | A |
| ILE O | 91 | 180.0 | 146.9 | 32.5 | 36 | A |
| TYR N | 92 | 178.7 | 146.2 | 30.8 | 36 | A |
| TYR CA | 92 | 179.7 | 146.5 | 29.8 | 38 | A |
| TYR CB | 92 | 179.2 | 146.2 | 28.4 | 37 | A |
| TYR CG | 92 | 178.6 | 144.8 | 28.2 | 37 | A |
| TYR CD1 | 92 | 177.4 | 144.7 | 27.7 | 37 | A |
| TYR CE1 | 92 | 176.8 | 143.4 | 27.6 | 37 | A |
| TYR CD2 | 92 | 179.3 | 143.7 | 28.6 | 37 | A |
| TYR CE2 | 92 | 178.8 | 142.4 | 28.5 | 37 | A |
| TYR CZ | 92 | 177.5 | 142.3 | 28.0 | 36 | A |
| TYR OH | 92 | 176.8 | 141.1 | 27.9 | 36 | A |
| TYR C | 92 | 180.1 | 147.9 | 29.9 | 39 | A |
| TYR O | 92 | 179.3 | 148.8 | 30.2 | 39 | A |
| SER N | 93 | 181.3 | 148.2 | 29.5 | 40 | A |
| SER CA | 93 | 181.9 | 149.5 | 29.4 | 41 | A |
| SER CB | 93 | 163.4 | 149.5 | 29.2 | 42 | A |
| SER OG | 93 | 183.7 | 148.8 | 28.0 | 43 | A |
| SER C | 93 | 181.2 | 150.0 | 28.1 | 42 | A |
| SER O | 93 | 180.5 | 149.3 | 27.4 | 42 | A |
| GLU N | 94 | 181.4 | 151.3 | 27.7 | 43 | A |
| GLU CA | 94 | 180.8 | 151.9 | 26.5 | 44 | A |
| GLU CB | 94 | 180.8 | 153.4 | 26.6 | 47 | A |
| GLU CG | 94 | 180.0 | 154.0 | 25.5 | 50 | A |
| GLU CD | 94 | 179.0 | 154.9 | 26.2 | 53 | A |
| GLU OE1 | 94 | 178.0 | 154.5 | 26.8 | 53 | A |
| GLU OE2 | 94 | 179.3 | 156.2 | 26.1 | 54 | A |
| GLU C | 94 | 181.4 | 151.4 | 25.2 | 42 | A |
| GLU O | 94 | 180.7 | 151.3 | 24.2 | 41 | A |
| LYS N | 95 | 182.7 | 151.3 | 25.2 | 42 | A |
| LYS CA | 95 | 183.4 | 150.9 | 24.0 | 41 | A |
| LYS CB | 95 | 185.0 | 150.9 | 24.3 | 41 | A |
| LYS CG | 95 | 185.5 | 152.3 | 24.7 | 42 | A |
| LYS CD | 95 | 187.0 | 152.1 | 25.1 | 43 | A |
| LYS CE | 95 | 187.8 | 151.4 | 24.1 | 43 | A |
| LYS NZ | 95 | 189.2 | 151.0 | 24.6 | 43 | A |
| LYS C | 95 | 183.0 | 149.4 | 23.8 | 40 | A |
| LYS O | 95 | 182.7 | 149.1 | 22.6 | 41 | A |
| PHE N | 96 | 183.0 | 148.6 | 24.8 | 39 | A |
| PHE CA | 96 | 182.7 | 147.2 | 24.7 | 37 | A |
| PHE CB | 96 | 182.7 | 146.5 | 26.0 | 35 | A |
| PHE CG | 96 | 182.5 | 145.0 | 25.9 | 34 | A |
| PHE CD1 | 96 | 183.6 | 144.1 | 26.0 | 34 | A |
| PHE CD2 | 96 | 181.3 | 144.5 | 25.7 | 34 | A |
| PHE CE1 | 96 | 183.4 | 142.7 | 25.9 | 33 | A |
| PHE CE2 | 96 | 181.0 | 143.1 | 25.6 | 32 | A |
| PHE CZ | 96 | 182.1 | 142.2 | 25.7 | 33 | A |
| PHE C | 96 | 181.2 | 147.1 | 24.1 | 38 | A |
| PHE O | 96 | 181.0 | 146.6 | 23.0 | 38 | A |
| ARG N | 97 | 180.3 | 147.7 | 24.9 | 40 | A |
| ARG CA | 97 | 178.9 | 147.7 | 24.5 | 41 | A |
| ARG CB | 97 | 178.1 | 148.6 | 25.4 | 43 | A |
| ARG CG | 97 | 176.7 | 148.2 | 25.6 | 47 | A |
| ARG CD | 97 | 175.8 | 149.4 | 26.0 | 50 | A |
| ARG NE | 97 | 176.3 | 150.2 | 27.1 | 53 | A |
| ARG CZ | 97 | 177.0 | 151.3 | 26.9 | 55 | A |
| ARG NH1 | 97 | 177.3 | 151.8 | 25.7 | 56 | A |
| ARG NH2 | 97 | 177.5 | 151.9 | 28.0 | 55 | A |
| ARG C | 97 | 178.8 | 148.2 | 23.0 | 40 | A |
| ARG O | 97 | 178.1 | 147.6 | 22.2 | 41 | A |
| ASP N | 98 | 179.4 | 149.4 | 22.8 | 39 | A |
| ASP CA | 98 | 179.4 | 150.0 | 21.4 | 38 | A |
| ASP CB | 98 | 180.3 | 151.3 | 21.5 | 38 | A |
| ASP CG | 98 | 180.5 | 151.9 | 20.1 | 38 | A |
| ASP OD1 | 98 | 179.6 | 152.6 | 19.6 | 39 | A |
| ASP OD2 | 98 | 181.5 | 151.7 | 19.5 | 37 | A |
| ASP C | 98 | 179.8 | 149.1 | 20.3 | 36 | A |
| ASP O | 98 | 179.1 | 148.9 | 19.3 | 36 | A |
| VAL N | 99 | 181.0 | 148.4 | 20.4 | 34 | A |
| VAL CA | 99 | 181.5 | 147.5 | 19.4 | 32 | A |
| VAL CB | 99 | 182.9 | 147.0 | 19.7 | 31 | A |
| VAL CG1 | 99 | 183.3 | 145.8 | 18.8 | 29 | A |
| VAL CG2 | 99 | 183.9 | 148.1 | 19.5 | 30 | A |
| VAL C | 99 | 180.6 | 146.3 | 19.1 | 32 | A |
| VAL O | 99 | 180.3 | 145.9 | 18.0 | 32 | A |
| TYR N | 100 | 180.0 | 145.8 | 20.2 | 32 | A |
| TYR CA | 100 | 179.2 | 144.6 | 20.1 | 31 | A |
| TYR CB | 100 | 179.1 | 143.9 | 21.4 | 29 | A |
| TYR CG | 100 | 180.3 | 142.9 | 21.5 | 27 | A |
| TYR CD1 | 100 | 181.4 | 143.3 | 22.1 | 26 | A |
| TYR CE1 | 100 | 182.5 | 142.5 | 22.1 | 25 | A |
| TYR CD2 | 100 | 180.2 | 141.7 | 20.8 | 27 | A |
| TYR CE2 | 100 | 181.3 | 140.9 | 20.8 | 26 | A |
| TYR CZ | 100 | 182.5 | 141.3 | 21.4 | 26 | A |
| TYR OH | 100 | 183.5 | 140.4 | 21.4 | 26 | A |
| TYR C | 100 | 177.8 | 145.0 | 19.5 | 33 | A |
| TYR O | 100 | 177.3 | 144.2 | 18.6 | 36 | A |
| ASP N | 101 | 177.2 | 146.1 | 19.9 | 34 | A |
| ASP CA | 101 | 175.9 | 146.5 | 19.3 | 34 | A |
| ASP CB | 101 | 175.5 | 147.8 | 19.8 | 36 | A |
| ASP CG | 101 | 174.9 | 147.8 | 21.2 | 37 | A |
| ASP OD1 | 101 | 174.8 | 146.8 | 21.8 | 37 | A |
| ASP OD2 | 101 | 174.5 | 148.9 | 21.6 | 39 | A |
| ASP C | 101 | 176.1 | 146.5 | 17.8 | 34 | A |
| ASP O | 101 | 175.3 | 146.1 | 17.0 | 35 | A |
| TYR N | 102 | 177.3 | 147.0 | 17.4 | 35 | A |
| TYR CA | 102 | 177.6 | 147.1 | 16.0 | 36 | A |
| TYR CB | 102 | 178.7 | 148.1 | 15.7 | 37 | A |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| TYR CG | 102 | 178.1 | 149.5 | 15.4 | 38 | A |
| TYR CD1 | 102 | 177.8 | 149.8 | 14.1 | 39 | A |
| TYR CE1 | 102 | 177.2 | 151.0 | 13.8 | 39 | A |
| TYR CD2 | 102 | 177.9 | 150.4 | 16.4 | 36 | A |
| TYR CE2 | 102 | 177.2 | 151.6 | 16.2 | 39 | A |
| TYR CZ | 102 | 176.9 | 151.9 | 14.9 | 40 | A |
| TYR OH | 102 | 176.3 | 153.1 | 14.6 | 40 | A |
| TYR C | 102 | 177.9 | 145.7 | 15.4 | 36 | A |
| TYR O | 102 | 177.4 | 145.4 | 14.2 | 36 | A |
| PHE N | 103 | 178.5 | 144.8 | 16.1 | 36 | A |
| PHE CA | 103 | 178.8 | 143.4 | 15.6 | 36 | A |
| PHE CB | 103 | 179.7 | 142.6 | 16.6 | 33 | A |
| PHE CG | 103 | 179.9 | 141.1 | 16.2 | 32 | A |
| PHE CD1 | 103 | 180.7 | 140.8 | 15.1 | 32 | A |
| PHE CD2 | 103 | 179.2 | 140.1 | 16.8 | 31 | A |
| PHE CE1 | 103 | 180.9 | 139.5 | 14.7 | 30 | A |
| PHE CE2 | 103 | 179.3 | 138.8 | 16.4 | 29 | A |
| PHE CZ | 103 | 180.1 | 138.4 | 15.3 | 29 | A |
| PHE C | 103 | 177.4 | 142.8 | 15.4 | 37 | A |
| PHE O | 103 | 177.2 | 142.2 | 14.3 | 37 | A |
| ARG N | 104 | 176.6 | 142.8 | 16.4 | 39 | A |
| ARG CA | 104 | 175.2 | 142.2 | 16.3 | 40 | A |
| ARG CB | 104 | 174.3 | 142.6 | 17.5 | 40 | A |
| ARG CG | 104 | 174.8 | 141.9 | 18.7 | 41 | A |
| ARG CD | 104 | 174.0 | 142.4 | 19.9 | 42 | A |
| ARG NE | 104 | 174.6 | 142.0 | 21.1 | 45 | A |
| ARG CZ | 104 | 175.4 | 142.8 | 21.9 | 46 | A |
| ARG NH1 | 104 | 175.6 | 144.1 | 21.6 | 46 | A |
| ARG NH2 | 104 | 176.0 | 142.3 | 23.0 | 47 | A |
| ARG C | 104 | 174.5 | 142.7 | 15.0 | 40 | A |
| ARG O | 104 | 173.8 | 141.9 | 14.3 | 40 | A |
| ALA N | 105 | 174.7 | 144.0 | 14.7 | 40 | A |
| ALA CA | 105 | 174.1 | 144.5 | 13.5 | 41 | A |
| ALA CB | 105 | 174.3 | 146.0 | 13.4 | 41 | A |
| ALA C | 105 | 174.6 | 143.9 | 12.2 | 41 | A |
| ALA O | 105 | 173.8 | 143.4 | 11.4 | 42 | A |
| VAL N | 106 | 175.9 | 143.8 | 12.1 | 42 | A |
| VAL CA | 106 | 176.6 | 143.3 | 10.9 | 43 | A |
| VAL CB | 106 | 178.1 | 143.6 | 10.9 | 43 | A |
| VAL CG1 | 106 | 178.9 | 142.6 | 10.1 | 44 | A |
| VAL CG2 | 106 | 178.4 | 145.0 | 10.4 | 43 | A |
| VAL C | 106 | 176.4 | 141.8 | 10.8 | 43 | A |
| VAL O | 106 | 176.2 | 141.2 | 9.7 | 42 | A |
| LEU N | 107 | 176.4 | 141.1 | 11.9 | 43 | A |
| LEU CA | 107 | 176.2 | 139.7 | 12.0 | 45 | A |
| LEU CB | 107 | 176.4 | 139.1 | 13.4 | 43 | A |
| LEU CG | 107 | 176.3 | 137.6 | 13.5 | 42 | A |
| LEU CD1 | 107 | 177.5 | 137.1 | 12.7 | 42 | A |
| LEU CD2 | 107 | 176.4 | 137.1 | 14.9 | 41 | A |
| LEU C | 107 | 174.8 | 139.4 | 11.5 | 47 | A |
| LEU O | 107 | 174.5 | 138.6 | 10.6 | 47 | A |
| GLN N | 108 | 173.8 | 140.1 | 12.1 | 51 | A |
| GLN CA | 108 | 172.4 | 139.9 | 11.8 | 54 | A |
| GLN CB | 108 | 171.6 | 141.1 | 12.4 | 56 | A |
| GLN CG | 108 | 170.6 | 140.8 | 13.6 | 59 | A |
| GLN CD | 108 | 171.3 | 140.4 | 14.9 | 61 | A |
| GLN OE1 | 108 | 170.8 | 140.8 | 16.0 | 63 | A |
| GLN NE2 | 108 | 172.4 | 139.8 | 14.8 | 62 | A |
| GLN C | 108 | 172.1 | 139.9 | 10.3 | 54 | A |
| GLN O | 108 | 171.5 | 139.0 | 9.8 | 55 | A |
| ARG N | 109 | 172.6 | 140.9 | 9.6 | 53 | A |
| ARG CA | 109 | 172.5 | 141.0 | 8.2 | 53 | A |
| ARG CB | 109 | 172.5 | 142.5 | 7.8 | 55 | A |
| ARG CG | 109 | 173.8 | 143.2 | 8.1 | 58 | A |
| ARG CD | 109 | 173.7 | 144.7 | 7.7 | 59 | A |
| ARG NE | 109 | 172.7 | 145.4 | 8.4 | 62 | A |
| ARG CZ | 109 | 171.9 | 146.3 | 7.9 | 63 | A |
| ARG NH1 | 109 | 172.1 | 146.7 | 6.6 | 64 | A |
| ARG NH2 | 109 | 171.0 | 147.0 | 8.6 | 63 | A |
| ARG C | 109 | 173.5 | 140.2 | 7.5 | 51 | A |
| ARG O | 109 | 173.5 | 140.3 | 6.2 | 51 | A |
| ASP N | 110 | 174.4 | 139.6 | 8.2 | 49 | A |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| ASP CA | 110 | 175.5 | 138.8 | 7.5 | 48 | A |
| ASP CB | 110 | 174.9 | 137.5 | 6.9 | 48 | A |
| ASP CG | 110 | 176.0 | 136.6 | 6.3 | 48 | A |
| ASP OD1 | 110 | 177.0 | 136.5 | 6.9 | 48 | A |
| ASP OD2 | 110 | 175.7 | 136.1 | 5.2 | 48 | A |
| ASP C | 110 | 176.1 | 139.7 | 6.5 | 47 | A |
| ASP O | 110 | 176.3 | 139.3 | 5.3 | 47 | A |
| GLU N | 111 | 176.5 | 140.8 | 6.9 | 47 | A |
| GLU CA | 111 | 177.2 | 141.8 | 6.1 | 47 | A |
| GLU CB | 111 | 177.1 | 143.2 | 6.7 | 47 | A |
| GLU CG | 111 | 177.6 | 144.3 | 5.8 | 47 | A |
| GLU CD | 111 | 177.7 | 145.6 | 6.6 | 47 | A |
| GLU OE1 | 111 | 178.9 | 146.1 | 6.7 | 47 | A |
| GLU OE2 | 111 | 176.7 | 146.1 | 7.1 | 47 | A |
| GLU C | 111 | 178.6 | 141.3 | 6.0 | 47 | A |
| GLU O | 111 | 179.4 | 141.4 | 6.9 | 47 | A |
| ARG N | 112 | 179.0 | 140.8 | 4.8 | 47 | A |
| ARG CA | 112 | 180.4 | 140.3 | 4.6 | 46 | A |
| ARG CB | 112 | 180.3 | 139.0 | 3.9 | 46 | A |
| ARG CG | 112 | 179.5 | 138.0 | 4.6 | 47 | A |
| ARG CD | 112 | 179.4 | 136.7 | 3.9 | 48 | A |
| ARG NE | 112 | 178.5 | 135.8 | 4.6 | 48 | A |
| ARG CZ | 112 | 178.3 | 134.5 | 4.4 | 49 | A |
| ARG NH1 | 112 | 179.0 | 133.9 | 3.4 | 49 | A |
| ARG NH2 | 112 | 177.5 | 133.8 | 5.1 | 49 | A |
| ARG C | 112 | 181.2 | 141.4 | 4.0 | 47 | A |
| ARG O | 112 | 181.7 | 141.2 | 2.9 | 47 | A |
| SER N | 113 | 181.5 | 142.4 | 4.7 | 47 | A |
| SER CA | 113 | 182.3 | 143.5 | 4.2 | 46 | A |
| SER CB | 113 | 181.5 | 144.8 | 4.3 | 46 | A |
| SER OG | 113 | 181.2 | 145.2 | 5.7 | 46 | A |
| SER C | 113 | 183.6 | 143.7 | 5.0 | 45 | A |
| SER O | 113 | 183.8 | 143.2 | 6.1 | 44 | A |
| GLU N | 114 | 184.5 | 144.5 | 4.3 | 44 | A |
| GLU CA | 114 | 185.8 | 144.8 | 4.8 | 44 | A |
| GLU CB | 114 | 186.5 | 145.7 | 3.8 | 45 | A |
| GLU CG | 114 | 187.8 | 146.2 | 4.2 | 47 | A |
| GLU CD | 114 | 188.8 | 145.1 | 4.4 | 48 | A |
| GLU OE1 | 114 | 189.6 | 145.2 | 5.4 | 49 | A |
| GLU OE2 | 114 | 188.9 | 144.1 | 3.7 | 48 | A |
| GLU C | 114 | 185.7 | 145.6 | 6.1 | 43 | A |
| GLU O | 114 | 186.5 | 145.4 | 7.0 | 43 | A |
| ARG N | 115 | 184.6 | 146.4 | 6.3 | 43 | A |
| ARG CA | 115 | 184.4 | 147.1 | 7.5 | 43 | A |
| ARG CB | 115 | 183.4 | 148.3 | 7.3 | 43 | A |
| ARG CG | 115 | 182.0 | 147.8 | 6.9 | 44 | A |
| ARG CD | 115 | 181.1 | 149.0 | 6.9 | 46 | A |
| ARG NE | 115 | 179.7 | 148.7 | 6.6 | 48 | A |
| ARG CZ | 115 | 178.6 | 149.4 | 6.9 | 48 | A |
| ARG NH1 | 115 | 177.4 | 149.0 | 6.6 | 49 | A |
| ARG NH2 | 115 | 178.7 | 150.5 | 7.6 | 49 | A |
| ARG C | 115 | 184.0 | 146.1 | 8.6 | 42 | A |
| ARG O | 115 | 184.3 | 146.3 | 9.7 | 43 | A |
| ALA N | 116 | 183.2 | 145.1 | 8.2 | 40 | A |
| ALA CA | 116 | 182.7 | 144.1 | 9.1 | 39 | A |
| ALA CB | 116 | 181.7 | 143.2 | 8.5 | 38 | A |
| ALA C | 116 | 183.9 | 143.3 | 9.6 | 38 | A |
| ALA O | 116 | 184.1 | 142.9 | 10.8 | 37 | A |
| PHE N | 117 | 184.9 | 143.2 | 8.7 | 36 | A |
| PHE CA | 117 | 186.1 | 142.5 | 8.9 | 35 | A |
| PHE CB | 117 | 186.9 | 142.3 | 7.6 | 34 | A |
| PHE CG | 117 | 188.2 | 141.7 | 7.8 | 33 | A |
| PHE CD1 | 117 | 188.3 | 140.3 | 8.1 | 32 | A |
| PHE CD2 | 117 | 189.4 | 142.4 | 7.6 | 33 | A |
| PHE CE1 | 117 | 189.6 | 139.7 | 8.3 | 32 | A |
| PHE CE2 | 117 | 190.6 | 141.8 | 7.8 | 31 | A |
| PHE CZ | 117 | 190.7 | 140.5 | 8.2 | 31 | A |
| PHE C | 117 | 187.0 | 143.2 | 9.9 | 34 | A |
| PHE O | 117 | 187.5 | 142.6 | 10.9 | 34 | A |
| LYS N | 118 | 187.1 | 144.5 | 9.8 | 33 | A |
| LYS CA | 118 | 187.9 | 145.3 | 10.7 | 33 | A |
| LYS CB | 118 | 188.2 | 146.7 | 10.2 | 35 | A |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| LYS CG | 118 | 189.1 | 146.7 | 8.9 | 37 | A |
| LYS CD | 118 | 189.7 | 148.1 | 8.7 | 39 | A |
| LYS CE | 118 | 190.5 | 148.2 | 7.4 | 40 | A |
| LYS NZ | 118 | 189.5 | 148.1 | 6.2 | 41 | A |
| LYS C | 118 | 187.2 | 145.4 | 12.1 | 31 | A |
| LYS O | 118 | 187.9 | 145.5 | 13.1 | 30 | A |
| LEU N | 119 | 185.9 | 145.3 | 12.1 | 30 | A |
| LEU CA | 119 | 185.2 | 145.4 | 13.4 | 28 | A |
| LEU CB | 119 | 183.7 | 145.7 | 13.2 | 27 | A |
| LEU CG | 119 | 182.8 | 145.5 | 14.4 | 26 | A |
| LEU CD1 | 119 | 183.2 | 146.5 | 15.5 | 27 | A |
| LEU CD2 | 119 | 181.4 | 145.8 | 14.0 | 27 | A |
| LEU C | 119 | 185.4 | 144.1 | 14.3 | 28 | A |
| LEU O | 119 | 185.3 | 144.2 | 15.5 | 27 | A |
| THR N | 120 | 185.5 | 143.0 | 13.6 | 28 | A |
| THR CA | 120 | 185.6 | 141.7 | 14.3 | 28 | A |
| THR CB | 120 | 185.7 | 140.5 | 13.4 | 27 | A |
| THR OG1 | 120 | 186.8 | 140.7 | 12.4 | 26 | A |
| THR CG2 | 120 | 184.4 | 140.3 | 12.7 | 27 | A |
| THR C | 120 | 186.9 | 141.8 | 15.1 | 28 | A |
| THR O | 120 | 187.0 | 141.3 | 16.2 | 29 | A |
| ARG N | 121 | 187.9 | 142.4 | 14.5 | 28 | A |
| ARG CA | 121 | 189.2 | 142.6 | 15.2 | 29 | A |
| ARG CB | 121 | 190.2 | 143.3 | 14.4 | 31 | A |
| ARG CG | 121 | 191.5 | 143.6 | 15.2 | 35 | A |
| ARG CD | 121 | 192.3 | 144.6 | 14.5 | 39 | A |
| ARG NE | 121 | 193.1 | 144.0 | 13.5 | 43 | A |
| ARG CZ | 121 | 194.4 | 144.2 | 13.4 | 45 | A |
| ARG NH1 | 121 | 195.1 | 143.6 | 12.4 | 45 | A |
| ARG NH2 | 121 | 195.1 | 144.9 | 14.4 | 45 | A |
| ARG C | 121 | 189.1 | 143.3 | 16.5 | 30 | A |
| ARG O | 121 | 189.8 | 143.0 | 17.5 | 30 | A |
| ASP N | 122 | 188.2 | 144.3 | 16.6 | 28 | A |
| ASP CA | 122 | 187.9 | 145.1 | 17.8 | 27 | A |
| ASP CB | 122 | 187.2 | 146.4 | 17.5 | 27 | A |
| ASP CG | 122 | 188.2 | 147.5 | 17.0 | 28 | A |
| ASP OD1 | 122 | 189.4 | 147.4 | 17.2 | 28 | A |
| ASP OD2 | 122 | 187.7 | 148.5 | 16.5 | 30 | A |
| ASP C | 122 | 187.1 | 144.3 | 18.8 | 26 | A |
| ASP O | 122 | 187.3 | 144.4 | 20.0 | 25 | A |
| ALA N | 123 | 186.1 | 143.5 | 18.3 | 26 | A |
| ALA CA | 123 | 185.2 | 142.7 | 19.1 | 25 | A |
| ALA CB | 123 | 184.1 | 142.1 | 18.2 | 24 | A |
| ALA C | 123 | 186.1 | 141.5 | 19.7 | 25 | A |
| ALA O | 123 | 185.9 | 141.2 | 20.8 | 27 | A |
| ILE N | 124 | 187.0 | 141.0 | 18.9 | 25 | A |
| ILE CA | 124 | 187.9 | 139.9 | 19.3 | 25 | A |
| ILE CB | 124 | 188.7 | 139.4 | 18.2 | 23 | A |
| ILE CG2 | 124 | 190.0 | 138.8 | 18.7 | 23 | A |
| ILE CG1 | 124 | 187.9 | 138.5 | 17.3 | 23 | A |
| ILE CD1 | 124 | 188.5 | 138.1 | 16.0 | 21 | A |
| ILE C | 124 | 188.8 | 140.5 | 20.4 | 26 | A |
| ILE O | 124 | 189.0 | 139.9 | 21.4 | 27 | A |
| GLU N | 125 | 189.3 | 141.7 | 20.1 | 28 | A |
| GLU CA | 125 | 190.2 | 142.3 | 21.1 | 30 | A |
| GLU CB | 125 | 190.8 | 143.6 | 20.5 | 34 | A |
| GLU CG | 125 | 192.0 | 144.1 | 21.1 | 41 | A |
| GLU CD | 125 | 192.7 | 145.3 | 20.4 | 45 | A |
| GLU OE1 | 125 | 193.6 | 146.0 | 21.0 | 47 | A |
| GLU OE2 | 125 | 192.3 | 145.5 | 19.2 | 47 | A |
| GLU C | 125 | 189.5 | 142.6 | 22.4 | 29 | A |
| GLU O | 125 | 190.2 | 142.6 | 23.5 | 29 | A |
| LEU N | 126 | 188.2 | 142.8 | 22.4 | 28 | A |
| LEU CA | 126 | 187.4 | 143.1 | 23.6 | 25 | A |
| LEU CB | 126 | 186.1 | 143.8 | 23.2 | 25 | A |
| LEU CG | 126 | 186.3 | 145.3 | 22.8 | 24 | A |
| LEU CD1 | 126 | 185.0 | 145.8 | 22.3 | 24 | A |
| LEU CD2 | 126 | 186.7 | 146.1 | 24.0 | 24 | A |
| LEU C | 126 | 187.1 | 141.8 | 24.4 | 25 | A |
| LEU O | 126 | 187.1 | 141.8 | 25.6 | 26 | A |
| ASN N | 127 | 186.9 | 140.7 | 23.7 | 24 | A |
| ASN CA | 127 | 186.7 | 139.4 | 24.3 | 23 | A |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| ASN CB | 127 | 185.3 | 139.2 | 24.7 | 21 | A |
| ASN CG | 127 | 185.0 | 137.9 | 25.3 | 19 | A |
| ASN OD1 | 127 | 186.0 | 137.3 | 25.8 | 20 | A |
| ASN ND2 | 127 | 183.8 | 137.4 | 25.3 | 19 | A |
| ASN C | 127 | 187.2 | 138.3 | 23.4 | 23 | A |
| ASN O | 127 | 186.5 | 137.8 | 22.6 | 24 | A |
| ALA N | 128 | 188.5 | 138.0 | 23.5 | 22 | A |
| ALA CA | 128 | 189.1 | 137.0 | 22.6 | 22 | A |
| ALA CB | 128 | 190.6 | 137.0 | 22.9 | 21 | A |
| ALA C | 128 | 188.6 | 135.6 | 22.7 | 23 | A |
| ALA O | 128 | 188.9 | 134.8 | 21.9 | 24 | A |
| ALA N | 129 | 187.7 | 135.4 | 23.7 | 22 | A |
| ALA CA | 129 | 187.1 | 134.1 | 23.9 | 20 | A |
| ALA CB | 129 | 187.0 | 133.8 | 25.4 | 19 | A |
| ALA C | 129 | 185.8 | 134.0 | 23.2 | 22 | A |
| ALA O | 129 | 185.0 | 133.0 | 23.4 | 22 | A |
| ASN N | 130 | 185.4 | 135.0 | 22.5 | 21 | A |
| ASN CA | 130 | 184.1 | 135.0 | 21.9 | 22 | A |
| ASN CB | 130 | 183.6 | 136.5 | 21.6 | 24 | A |
| ASN CG | 130 | 182.1 | 136.5 | 21.3 | 25 | A |
| ASN OD1 | 130 | 181.6 | 135.7 | 20.5 | 27 | A |
| ASN ND2 | 130 | 181.3 | 137.4 | 21.9 | 26 | A |
| ASN C | 130 | 184.2 | 134.3 | 20.5 | 21 | A |
| ASN O | 130 | 184.6 | 134.8 | 19.5 | 21 | A |
| TYR N | 131 | 183.9 | 133.0 | 20.6 | 22 | A |
| TYR CA | 131 | 184.0 | 132.0 | 19.5 | 21 | A |
| TYR CB | 131 | 183.8 | 130.6 | 19.9 | 20 | A |
| TYR CG | 131 | 182.5 | 130.3 | 20.6 | 20 | A |
| TYR CD1 | 131 | 181.4 | 130.0 | 19.8 | 19 | A |
| TYR CE1 | 131 | 180.1 | 129.9 | 20.4 | 19 | A |
| TYR CD2 | 131 | 182.3 | 130.5 | 22.0 | 19 | A |
| TYR CE2 | 131 | 181.1 | 130.4 | 22.6 | 19 | A |
| TYR CZ | 131 | 179.9 | 130.1 | 21.8 | 20 | A |
| TYR OH | 131 | 178.7 | 130.0 | 22.4 | 20 | A |
| TYR C | 131 | 183.1 | 132.3 | 18.3 | 23 | A |
| TYR O | 131 | 183.3 | 131.8 | 17.2 | 26 | A |
| THR N | 132 | 182.0 | 133.1 | 18.5 | 23 | A |
| THR CA | 132 | 181.1 | 133.5 | 17.5 | 22 | A |
| THR CB | 132 | 179.8 | 134.1 | 18.1 | 23 | A |
| THR OG1 | 132 | 179.1 | 133.1 | 18.8 | 24 | A |
| THR CG2 | 132 | 178.9 | 134.6 | 17.0 | 24 | A |
| THR C | 132 | 181.7 | 134.5 | 16.6 | 22 | A |
| THR O | 132 | 181.6 | 134.5 | 15.4 | 23 | A |
| VAL N | 133 | 182.4 | 135.4 | 17.2 | 22 | A |
| VAL CA | 133 | 183.1 | 136.5 | 16.4 | 22 | A |
| VAL CB | 133 | 183.7 | 137.6 | 17.3 | 22 | A |
| VAL CG1 | 133 | 184.4 | 138.6 | 16.4 | 22 | A |
| VAL CG2 | 133 | 182.5 | 138.4 | 18.0 | 21 | A |
| VAL C | 133 | 184.2 | 135.8 | 15.6 | 23 | A |
| VAL O | 133 | 184.4 | 136.1 | 14.5 | 25 | A |
| TRP N | 134 | 185.0 | 134.9 | 16.3 | 23 | A |
| TRP CA | 134 | 186.1 | 134.2 | 15.7 | 24 | A |
| TRP CB | 134 | 186.8 | 133.3 | 16.6 | 21 | A |
| TRP CG | 134 | 187.8 | 133.9 | 17.5 | 19 | A |
| TRP CD2 | 134 | 189.1 | 134.5 | 17.0 | 19 | A |
| TRP CE2 | 134 | 189.8 | 135.0 | 18.1 | 18 | A |
| TRP CE3 | 134 | 189.7 | 134.6 | 15.7 | 19 | A |
| TRP CD1 | 134 | 187.8 | 134.2 | 18.8 | 19 | A |
| TRP NE1 | 134 | 189.0 | 134.8 | 19.2 | 18 | A |
| TRP CZ2 | 134 | 191.0 | 135.6 | 18.0 | 19 | A |
| TRP CZ3 | 134 | 190.9 | 135.2 | 15.6 | 19 | A |
| TRP CH2 | 134 | 191.6 | 135.7 | 16.7 | 20 | A |
| TRP C | 134 | 185.6 | 133.5 | 14.4 | 26 | A |
| TRP O | 134 | 186.2 | 133.5 | 13.4 | 27 | A |
| HIS N | 135 | 184.4 | 132.9 | 14.5 | 28 | A |
| HIS CA | 135 | 183.8 | 132.1 | 13.4 | 31 | A |
| HIS CB | 135 | 182.6 | 131.4 | 13.9 | 33 | A |
| HIS CG | 135 | 181.8 | 130.7 | 12.8 | 35 | A |
| HIS CD2 | 135 | 181.0 | 131.2 | 11.9 | 36 | A |
| HIS ND1 | 135 | 181.8 | 129.4 | 12.6 | 36 | A |
| HIS CE1 | 135 | 181.1 | 129.1 | 11.5 | 37 | A |
| HIS NE2 | 135 | 180.6 | 130.2 | 11.1 | 36 | A |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| HIS C | 135 | 183.4 | 133.0 | 12.3 | 32 | A |
| HIS O | 135 | 183.7 | 132.7 | 11.1 | 32 | A |
| PHE N | 136 | 182.7 | 134.1 | 12.6 | 31 | A |
| PHE CA | 136 | 182.4 | 135.1 | 11.6 | 30 | A |
| PHE CB | 136 | 181.5 | 136.2 | 12.2 | 32 | A |
| PHE CG | 136 | 181.0 | 137.2 | 11.2 | 34 | A |
| PHE CD1 | 136 | 180.0 | 136.8 | 10.2 | 35 | A |
| PHE CD2 | 136 | 181.4 | 138.5 | 11.1 | 35 | A |
| PHE CE1 | 136 | 179.5 | 137.6 | 9.2 | 35 | A |
| PHE CE2 | 136 | 180.9 | 139.4 | 10.2 | 35 | A |
| PHE CZ | 136 | 180.0 | 139.0 | 9.2 | 35 | A |
| PHE C | 136 | 183.6 | 135.7 | 10.9 | 29 | A |
| PHE O | 136 | 183.6 | 135.9 | 9.7 | 30 | A |
| ARG N | 137 | 184.7 | 135.9 | 11.6 | 27 | A |
| ARG CA | 137 | 185.9 | 136.4 | 11.0 | 26 | A |
| ARG CB | 137 | 187.0 | 136.7 | 12.1 | 25 | A |
| ARG CG | 137 | 188.2 | 137.3 | 11.5 | 23 | A |
| ARG CD | 137 | 189.3 | 137.5 | 12.6 | 22 | A |
| ARG NE | 137 | 190.5 | 138.2 | 12.1 | 22 | A |
| ARG CZ | 137 | 190.6 | 139.5 | 11.9 | 21 | A |
| ARG NH1 | 137 | 189.6 | 140.3 | 12.2 | 21 | A |
| ARG NH2 | 137 | 191.8 | 139.9 | 11.5 | 21 | A |
| ARG C | 137 | 186.4 | 135.4 | 10.0 | 26 | A |
| ARG O | 137 | 186.9 | 135.8 | 9.0 | 27 | A |
| ARG N | 138 | 186.3 | 134.1 | 10.3 | 26 | A |
| ARG CA | 138 | 186.8 | 133.1 | 9.3 | 25 | A |
| ARG CB | 138 | 186.8 | 131.7 | 10.0 | 25 | A |
| ARG CG | 138 | 188.2 | 131.0 | 10.0 | 23 | A |
| ARG CD | 138 | 188.6 | 130.8 | 11.4 | 22 | A |
| ARG NE | 138 | 187.7 | 129.9 | 12.1 | 21 | A |
| ARG CZ | 138 | 187.6 | 129.9 | 13.5 | 21 | A |
| ARG NH1 | 138 | 188.4 | 130.6 | 14.2 | 20 | A |
| ARG NH2 | 138 | 186.7 | 129.2 | 14.1 | 20 | A |
| ARG C | 138 | 185.9 | 133.2 | 8.1 | 26 | A |
| ARG O | 138 | 186.4 | 133.1 | 7.0 | 25 | A |
| VAL N | 139 | 184.6 | 133.4 | 8.3 | 26 | A |
| VAL CA | 139 | 183.7 | 133.5 | 7.2 | 27 | A |
| VAL CB | 139 | 182.2 | 133.8 | 7.7 | 27 | A |
| VAL CG1 | 139 | 181.3 | 134.2 | 6.6 | 26 | A |
| VAL CG2 | 139 | 181.7 | 132.6 | 8.5 | 26 | A |
| VAL C | 139 | 184.1 | 134.7 | 6.2 | 28 | A |
| VAL O | 139 | 184.3 | 134.5 | 5.0 | 28 | A |
| LEU N | 140 | 184.4 | 135.8 | 6.8 | 28 | A |
| LEU CA | 140 | 184.8 | 137.0 | 6.1 | 27 | A |
| LEU CB | 140 | 184.9 | 138.2 | 7.0 | 27 | A |
| LEU CG | 140 | 183.5 | 138.6 | 7.5 | 28 | A |
| LEU CD1 | 140 | 183.6 | 139.7 | 8.5 | 28 | A |
| LEU CD2 | 140 | 182.7 | 139.0 | 6.3 | 27 | A |
| LEU C | 140 | 186.2 | 136.7 | 5.4 | 29 | A |
| LEU O | 140 | 186.4 | 137.2 | 4.3 | 29 | A |
| LEU N | 141 | 187.0 | 136.0 | 6.1 | 30 | A |
| LEU CA | 141 | 188.4 | 135.7 | 5.6 | 31 | A |
| LEU CB | 141 | 189.1 | 134.8 | 6.5 | 29 | A |
| LEU CG | 141 | 189.9 | 135.4 | 7.7 | 27 | A |
| LEU CD1 | 141 | 190.7 | 134.3 | 8.4 | 25 | A |
| LEU CD2 | 141 | 190.9 | 136.4 | 7.2 | 26 | A |
| LEU C | 141 | 188.2 | 134.9 | 4.3 | 34 | A |
| LEU O | 141 | 189.0 | 135.1 | 3.4 | 34 | A |
| ARG N | 142 | 187.1 | 134.1 | 4.2 | 38 | A |
| ARG CA | 142 | 186.8 | 133.4 | 3.0 | 42 | A |
| ARG CB | 142 | 185.8 | 132.2 | 3.3 | 46 | A |
| ARG CG | 142 | 186.3 | 131.3 | 4.4 | 50 | A |
| ARG CD | 142 | 185.2 | 130.4 | 5.0 | 53 | A |
| ARG NE | 142 | 185.2 | 130.3 | 6.5 | 57 | A |
| ARG CZ | 142 | 184.6 | 129.4 | 7.2 | 57 | A |
| ARG NH1 | 142 | 183.9 | 128.4 | 6.7 | 59 | A |
| ARG NH2 | 142 | 184.7 | 129.4 | 8.6 | 57 | A |
| ARG C | 142 | 186.1 | 134.3 | 1.9 | 42 | A |
| ARG O | 142 | 186.6 | 134.4 | 0.8 | 41 | A |
| SER N | 143 | 185.1 | 135.0 | 2.3 | 41 | A |
| SER CA | 143 | 184.4 | 135.8 | 1.4 | 42 | A |
| SER CB | 143 | 183.2 | 136.5 | 2.0 | 41 | A |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| SER OG | 143 | 182.4 | 135.4 | 2.7 | 44 | A |
| SER C | 143 | 185.2 | 136.9 | 0.7 | 42 | A |
| SER O | 143 | 185.2 | 137.1 | −0.5 | 44 | A |
| LEU N | 144 | 185.9 | 137.7 | 1.6 | 41 | A |
| LEU CA | 144 | 186.7 | 138.8 | 1.0 | 41 | A |
| LEU CB | 144 | 186.9 | 139.9 | 2.1 | 39 | A |
| LEU CG | 144 | 185.9 | 140.1 | 3.2 | 38 | A |
| LEU CD1 | 144 | 186.3 | 141.2 | 4.1 | 38 | A |
| LEU CD2 | 144 | 184.5 | 140.5 | 2.6 | 37 | A |
| LEU C | 144 | 188.1 | 138.4 | 0.5 | 41 | A |
| LEU O | 144 | 188.9 | 139.2 | 0.0 | 43 | A |
| GLN N | 145 | 188.3 | 137.0 | 0.5 | 42 | A |
| GLN CA | 145 | 189.6 | 136.5 | 0.0 | 41 | A |
| GLN CB | 145 | 189.7 | 136.4 | −1.5 | 45 | A |
| GLN CG | 145 | 188.7 | 135.4 | −2.0 | 49 | A |
| GLN CD | 145 | 188.8 | 135.3 | −3.5 | 52 | A |
| GLN OE1 | 145 | 188.6 | 136.3 | −4.2 | 54 | A |
| GLN NE2 | 145 | 189.0 | 134.1 | −4.0 | 54 | A |
| GLN C | 145 | 190.8 | 137.3 | 0.6 | 39 | A |
| GLN O | 145 | 191.5 | 137.9 | −0.2 | 39 | A |
| LYS N | 146 | 190.9 | 137.3 | 1.9 | 37 | A |
| LYS CA | 146 | 191.9 | 138.1 | 2.6 | 35 | A |
| LYS CB | 146 | 191.5 | 138.2 | 4.0 | 35 | A |
| LYS CG | 146 | 190.2 | 139.0 | 4.3 | 35 | A |
| LYS CD | 146 | 190.3 | 140.4 | 3.7 | 35 | A |
| LYS CE | 146 | 191.4 | 141.2 | 4.3 | 36 | A |
| LYS NZ | 146 | 191.3 | 142.6 | 3.7 | 36 | A |
| LYS C | 146 | 193.2 | 137.3 | 2.5 | 34 | A |
| LYS O | 146 | 193.2 | 136.1 | 2.4 | 33 | A |
| ASP N | 147 | 194.3 | 138.0 | 2.5 | 35 | A |
| ASP CA | 147 | 195.6 | 137.5 | 2.5 | 34 | A |
| ASP CB | 147 | 196.7 | 138.6 | 2.3 | 34 | A |
| ASP CG | 147 | 198.1 | 138.0 | 2.2 | 34 | A |
| ASP OD1 | 147 | 198.5 | 137.2 | 3.1 | 35 | A |
| ASP OD2 | 147 | 198.8 | 138.4 | 1.3 | 36 | A |
| ASP C | 147 | 195.8 | 136.8 | 3.8 | 35 | A |
| ASP O | 147 | 195.8 | 137.4 | 4.9 | 35 | A |
| LEU N | 148 | 195.8 | 135.4 | 3.8 | 34 | A |
| LEU CA | 148 | 196.0 | 134.6 | 5.0 | 31 | A |
| LEU CB | 148 | 195.6 | 133.1 | 4.7 | 30 | A |
| LEU CG | 148 | 194.2 | 132.9 | 4.2 | 29 | A |
| LEU CD1 | 148 | 193.9 | 131.5 | 4.0 | 30 | A |
| LEU CD2 | 148 | 193.2 | 133.4 | 5.2 | 29 | A |
| LEU C | 148 | 197.4 | 134.7 | 5.6 | 31 | A |
| LEU O | 148 | 197.5 | 134.3 | 6.8 | 31 | A |
| GLN N | 149 | 198.4 | 135.1 | 4.9 | 31 | A |
| GLN CA | 149 | 199.7 | 135.2 | 5.5 | 32 | A |
| GLN CB | 149 | 200.8 | 135.3 | 4.5 | 34 | A |
| GLN CG | 149 | 202.1 | 134.7 | 5.0 | 36 | A |
| GLN CD | 149 | 202.0 | 133.4 | 5.7 | 38 | A |
| GLN OE1 | 149 | 201.7 | 132.4 | 5.1 | 38 | A |
| GLN NE2 | 149 | 202.2 | 133.4 | 7.0 | 38 | A |
| GLN C | 149 | 199.7 | 136.4 | 6.4 | 33 | A |
| GLN O | 149 | 200.5 | 136.5 | 7.3 | 34 | A |
| GLU N | 150 | 198.9 | 137.4 | 6.1 | 34 | A |
| GLU CA | 150 | 198.8 | 138.6 | 6.8 | 35 | A |
| GLU CB | 150 | 198.0 | 139.7 | 6.0 | 38 | A |
| GLU CG | 150 | 199.0 | 140.8 | 5.5 | 44 | A |
| GLU CD | 150 | 200.2 | 140.3 | 4.7 | 47 | A |
| GLU OE1 | 150 | 201.3 | 140.6 | 5.2 | 49 | A |
| GLU OE2 | 150 | 200.0 | 139.7 | 3.7 | 48 | A |
| GLU C | 150 | 198.0 | 138.2 | 8.1 | 33 | A |
| GLU O | 150 | 198.3 | 138.7 | 9.2 | 33 | A |
| GLU N | 151 | 197.0 | 137.4 | 7.9 | 31 | A |
| GLU CA | 151 | 196.2 | 136.9 | 9.0 | 30 | A |
| GLU CB | 151 | 195.0 | 136.1 | 8.5 | 29 | A |
| GLU CG | 151 | 194.0 | 135.6 | 9.6 | 28 | A |
| GLU CD | 151 | 193.2 | 136.7 | 10.4 | 28 | A |
| GLU OE1 | 151 | 193.4 | 137.9 | 10.1 | 28 | A |
| GLU OE2 | 151 | 192.4 | 136.3 | 11.2 | 27 | A |
| GLU C | 151 | 197.1 | 136.0 | 10.0 | 29 | A |
| GLU O | 151 | 196.9 | 136.1 | 11.2 | 30 | A |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| MET N | 152 | 198.0 | 135.3 | 9.4 | 28 | A |
| MET CA | 152 | 198.9 | 134.5 | 10.3 | 27 | A |
| MET CB | 152 | 199.9 | 133.8 | 9.4 | 27 | A |
| MET CG | 152 | 199.4 | 132.5. | 8.9 | 28 | A |
| MET SD | 152 | 199.4 | 131.2 | 10.2 | 28 | A |
| MET CE | 152 | 201.0 | 130.6 | 10.1 | 29 | A |
| MET C | 152 | 199.6 | 135.5 | 11.2 | 27 | A |
| MET O | 152 | 199.8 | 135.3 | 12.4 | 27 | A |
| ASN N | 153 | 200.0 | 136.7 | 10.6 | 26 | A |
| ASN CA | 153 | 200.7 | 137.7 | 11.3 | 27 | A |
| ASN CB | 153 | 201.1 | 138.8 | 10.4 | 28 | A |
| ASN CG | 153 | 202.1 | 138.4 | 9.3 | 29 | A |
| ASN OD1 | 153 | 202.6 | 137.3 | 9.3 | 28 | A |
| ASN ND2 | 153 | 202.4 | 139.4 | 8.4 | 30 | A |
| ASN C | 153 | 199.9 | 138.2 | 12.5 | 26 | A |
| ASN O | 153 | 200.4 | 138.3 | 13.6 | 24 | A |
| TYR N | 154 | 198.6 | 138.4 | 12.2 | 25 | A |
| TYR CA | 154 | 197.6 | 138.8 | 13.2 | 25 | A |
| TYR CB | 154 | 196.3 | 139.1 | 12.5 | 24 | A |
| TYR CG | 154 | 195.2 | 139.4 | 13.4 | 26 | A |
| TYR CD1 | 154 | 195.1 | 140.6 | 14.1 | 26 | A |
| TYR CE1 | 154 | 194.1 | 140.8 | 15.1 | 25 | A |
| TYR CD2 | 154 | 194.2 | 138.4 | 13.6 | 27 | A |
| TYR CE2 | 154 | 193.2 | 138.6 | 14.5 | 27 | A |
| TYR CZ | 154 | 193.2 | 139.8 | 15.3 | 26 | A |
| TYR OH | 154 | 192.2 | 140.0 | 16.2 | 28 | A |
| TYR C | 154 | 197.5 | 137.8 | 14.3 | 25 | A |
| TYR O | 154 | 197.7 | 138.2 | 15.5 | 26 | A |
| ILE N | 155 | 197.2 | 136.6 | 14.0 | 24 | A |
| ILE CA | 155 | 197.0 | 135.5 | 15.0 | 22 | A |
| ILE CB | 155 | 196.4 | 134.2 | 14.4 | 21 | A |
| ILE CG2 | 155 | 197.5 | 133.4 | 13.8 | 21 | A |
| ILE CG1 | 155 | 195.7 | 133.4 | 15.5 | 20 | A |
| ILE CD1 | 155 | 194.5 | 134.2 | 16.0 | 19 | A |
| ILE C | 155 | 198.3 | 135.3 | 15.8 | 20 | A |
| ILE O | 155 | 198.2 | 135.0 | 17.0 | 20 | A |
| THR N | 156 | 199.4 | 135.6 | 15.2 | 20 | A |
| THR CA | 156 | 200.7 | 135.4 | 15.9 | 20 | A |
| THR CB | 156 | 201.8 | 135.7 | 14.9 | 21 | A |
| THR OG1 | 156 | 201.8 | 134.6 | 13.9 | 21 | A |
| THR CG2 | 156 | 203.2 | 135.7 | 15.6 | 20 | A |
| THR C | 156 | 200.7 | 136.4 | 17.1 | 22 | A |
| THR O | 156 | 201.1 | 136.1 | 18.2 | 22 | A |
| ALA N | 157 | 200.3 | 137.7 | 16.8 | 23 | A |
| ALA CA | 157 | 200.4 | 138.8 | 17.7 | 23 | A |
| ALA CB | 157 | 200.0 | 140.1 | 17.1 | 21 | A |
| ALA C | 157 | 199.4 | 138.5 | 18.9 | 23 | A |
| ALA O | 157 | 199.8 | 138.6 | 20.1 | 24 | A |
| ILE N | 158 | 198.2 | 138.2 | 18.5 | 23 | A |
| ILE CA | 158 | 197.1 | 137.9 | 19.5 | 23 | A |
| ILE CB | 158 | 195.8 | 137.6 | 18.8 | 23 | A |
| ILE CG2 | 158 | 194.7 | 137.2 | 19.8 | 24 | A |
| ILE CG1 | 158 | 195.4 | 138.7 | 18.0 | 24 | A |
| ILE CD1 | 158 | 195.0 | 140.0 | 18.8 | 25 | A |
| ILE C | 158 | 197.5 | 136.7 | 20.4 | 23 | A |
| ILE O | 158 | 197.2 | 136.8 | 21.6 | 24 | A |
| ILE N | 159 | 198.0 | 135.6 | 19.9 | 21 | A |
| ILE CA | 159 | 198.4 | 134.5 | 20.7 | 21 | A |
| ILE CB | 159 | 198.9 | 133.3 | 19.9 | 20 | A |
| ILE CG2 | 159 | 199.4 | 132.2 | 20.8 | 18 | A |
| ILE CG1 | 159 | 197.7 | 132.7 | 19.1 | 19 | A |
| ILE CD1 | 159 | 198.2 | 131.6 | 18.1 | 17 | A |
| ILE C | 159 | 199.5 | 135.0 | 21.7 | 22 | A |
| ILE O | 159 | 199.5 | 134.7 | 22.9 | 21 | A |
| GLU N | 160 | 200.5 | 135.7 | 21.2 | 23 | A |
| GLU CA | 160 | 201.6 | 136.1 | 22.0 | 24 | A |
| GLU CB | 160 | 202.6 | 137.0 | 21.3 | 24 | A |
| GLU CG | 160 | 203.4 | 136.3 | 20.2 | 23 | A |
| GLU CD | 160 | 204.6 | 135.6 | 20.6 | 24 | A |
| GLU OE1 | 160 | 205.0 | 135.8 | 21.8 | 23 | A |
| GLU OE2 | 160 | 205.3 | 135.0 | 19.8 | 23 | A |
| GLU C | 160 | 201.0 | 136.9 | 23.2 | 26 | A |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| GLU O | 160 | 201.5 | 136.8 | 24.3 | 27 | A |
| GLU N | 161 | 200.0 | 137.8 | 23.0 | 26 | A |
| GLU CA | 161 | 199.4 | 138.5 | 24.1 | 29 | A |
| GLU CB | 161 | 198.8 | 139.8 | 23.6 | 30 | A |
| GLU CG | 161 | 197.8 | 139.8 | 22.6 | 34 | A |
| GLU CD | 161 | 197.6 | 141.1 | 21.8 | 36 | A |
| GLU OE1 | 161 | 198.7 | 141.7 | 21.4 | 37 | A |
| GLU OE2 | 161 | 196.5 | 141.5 | 21.6 | 38 | A |
| GLU C | 161 | 198.5 | 137.7 | 25.0 | 28 | A |
| GLU O | 161 | 198.5 | 137.9 | 26.2 | 29 | A |
| GLN N | 162 | 197.8 | 136.7 | 24.5 | 27 | A |
| GLN CA | 162 | 197.0 | 135.8 | 25.3 | 26 | A |
| GLN CB | 162 | 195.5 | 136.4 | 25.4 | 29 | A |
| GLN CG | 162 | 194.8 | 136.9 | 24.2 | 33 | A |
| GLN CD | 162 | 193.6 | 137.7 | 24.6 | 35 | A |
| GLN OE1 | 162 | 192.8 | 137.4 | 25.6 | 34 | A |
| GLN NE2 | 162 | 193.4 | 138.9 | 23.9 | 36 | A |
| GLN C | 162 | 197.0 | 134.4 | 24.8 | 23 | A |
| GLN O | 162 | 196.1 | 133.9 | 24.1 | 23 | A |
| PRO N | 163 | 198.1 | 133.6 | 25.2 | 20 | A |
| PRO CD | 163 | 199.1 | 134.1 | 26.1 | 17 | A |
| PRO CA | 163 | 198.3 | 132.3 | 24.8 | 18 | A |
| PRO CB | 163 | 199.8 | 132.1 | 25.0 | 17 | A |
| PRO CG | 163 | 200.0 | 132.9 | 26.3 | 17 | A |
| PRO C | 163 | 197.5 | 131.2 | 25.5 | 19 | A |
| PRO O | 163 | 197.7 | 130.0 | 25.2 | 19 | A |
| LYS N | 164 | 196.7 | 131.6 | 26.4 | 20 | A |
| LYS CA | 164 | 195.9 | 130.6 | 27.1 | 20 | A |
| LYS CB | 164 | 196.1 | 130.7 | 28.7 | 20 | A |
| LYS CG | 164 | 197.4 | 130.2 | 29.1 | 22 | A |
| LYS CD | 164 | 197.5 | 130.0 | 30.6 | 22 | A |
| LYS CE | 164 | 198.9 | 129.6 | 31.0 | 23 | A |
| LYS NZ | 164 | 198.9 | 129.4 | 32.5 | 24 | A |
| LYS C | 164 | 194.4 | 131.0 | 26.8 | 20 | A |
| LYS O | 164 | 193.8 | 131.7 | 27.5 | 21 | A |
| ASN N | 165 | 194.1 | 130.6 | 25.6 | 20 | A |
| ASN CA | 165 | 192.8 | 130.9 | 25.0 | 19 | A |
| ASN CB | 165 | 192.8 | 132.2 | 24.3 | 20 | A |
| ASN CG | 165 | 191.5 | 132.5 | 23.5 | 21 | A |
| ASN OD1 | 165 | 191.2 | 131.9 | 22.6 | 22 | A |
| ASN ND2 | 165 | 190.8 | 133.6 | 24.0 | 22 | A |
| ASN C | 165 | 192.6 | 129.8 | 24.0 | 18 | A |
| ASN O | 165 | 193.6 | 129.4 | 23.3 | 19 | A |
| TYR N | 166 | 191.4 | 129.2 | 23.9 | 18 | A |
| TYR CA | 166 | 191.1 | 128.1 | 23.0 | 17 | A |
| TYR CB | 166 | 189.9 | 127.3 | 23.5 | 17 | A |
| TYR CG | 166 | 190.2 | 126.3 | 24.6 | 18 | A |
| TYR CD1 | 166 | 189.8 | 126.6 | 25.9 | 18 | A |
| TYR CE1 | 166 | 190.0 | 125.7 | 27.0 | 18 | A |
| TYR CD2 | 166 | 190.8 | 125.1 | 24.4 | 18 | A |
| TYR CE2 | 166 | 191.0 | 124.1 | 25.4 | 19 | A |
| TYR CZ | 166 | 190.6 | 124.5 | 26.7 | 18 | A |
| TYR OH | 166 | 190.7 | 123.6 | 27.8 | 18 | A |
| TYR C | 166 | 190.9 | 128.5 | 21.6 | 18 | A |
| TYR O | 166 | 191.3 | 127.8 | 20.6 | 18 | A |
| GLN N | 167 | 190.3 | 129.7 | 21.4 | 17 | A |
| GLN CA | 167 | 189.9 | 130.2 | 20.1 | 17 | A |
| GLN CB | 167 | 188.9 | 131.3 | 20.2 | 16 | A |
| GLN CG | 167 | 187.5 | 130.9 | 20.6 | 16 | A |
| GLN CD | 167 | 187.4 | 130.5 | 22.1 | 19 | A |
| GLN OE1 | 167 | 188.1 | 131.0 | 22.9 | 20 | A |
| GLN NE2 | 167 | 186.6 | 129.5 | 22.4 | 19 | A |
| GLN C | 167 | 191.1 | 130.6 | 19.2 | 16 | A |
| GLN O | 167 | 191.1 | 130.4 | 18.0 | 17 | A |
| VAL N | 168 | 192.1 | 131.3 | 19.9 | 16 | A |
| VAL CA | 168 | 193.2 | 131.8 | 19.2 | 15 | A |
| VAL CB | 168 | 194.1 | 132.7 | 20.0 | 14 | A |
| VAL CG1 | 168 | 193.4 | 134.0 | 20.5 | 12 | A |
| VAL CG2 | 168 | 194.7 | 132.0 | 21.2 | 13 | A |
| VAL C | 168 | 194.0 | 130.6 | 18.6 | 17 | A |
| VAL O | 168 | 194.3 | 130.6 | 17.4 | 20 | A |
| TRP N | 169 | 194.3 | 129.6 | 19.4 | 17 | A |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| TRP CA | 169 | 195.0 | 128.5 | 18.8 | 16 | A |
| TRP CB | 169 | 195.5 | 127.5 | 19.9 | 15 | A |
| TRP CG | 169 | 196.5 | 128.1 | 20.8 | 15 | A |
| TRP CD2 | 169 | 197.9 | 128.1 | 20.5 | 14 | A |
| TRP CE2 | 169 | 198.6 | 128.8 | 21.6 | 14 | A |
| TRP CE3 | 169 | 198.7 | 127.6 | 19.4 | 14 | A |
| TRP CD1 | 169 | 196.4 | 128.8 | 22.0 | 15 | A |
| TRP NE1 | 169 | 197.6 | 129.1 | 22.5 | 15 | A |
| TRP CZ2 | 169 | 200.0 | 128.9 | 21.6 | 14 | A |
| TRP CZ3 | 169 | 200.1 | 127.8 | 19.5 | 14 | A |
| TRP CH2 | 169 | 200.7 | 128.4 | 20.6 | 14 | A |
| TRP C | 169 | 194.3 | 127.7 | 17.8 | 16 | A |
| TRP O | 169 | 194.9 | 127.3 | 16.8 | 15 | A |
| HIS N | 170 | 193.0 | 127.6 | 17.9 | 17 | A |
| HIS CA | 170 | 192.2 | 126.9 | 16.9 | 19 | A |
| HIS CB | 170 | 190.8 | 126.6 | 17.3 | 19 | A |
| HIS CG | 170 | 190.0 | 125.8 | 16.3 | 20 | A |
| HIS CD2 | 170 | 189.0 | 126.2 | 15.4 | 21 | A |
| HIS ND1 | 170 | 190.3 | 124.5 | 15.9 | 20 | A |
| HIS CE1 | 170 | 189.5 | 124.1 | 14.9 | 21 | A |
| HIS NE2 | 170 | 188.7 | 125.2 | 14.6 | 21 | A |
| HIS C | 170 | 192.2 | 127.7 | 15.6 | 20 | A |
| HIS O | 170 | 192.1 | 127.1 | 14.5 | 20 | A |
| HIS N | 171 | 192.1 | 129.0 | 15.7 | 20 | A |
| HIS CA | 171 | 192.1 | 129.9 | 14.6 | 20 | A |
| HIS CB | 171 | 191.9 | 131.3 | 15.0 | 19 | A |
| HIS CG | 171 | 191.8 | 132.3 | 13.8 | 20 | A |
| HIS CD2 | 171 | 192.7 | 133.1 | 13.2 | 19 | A |
| HIS ND1 | 171 | 190.6 | 132.5 | 13.2 | 19 | A |
| HIS CE1 | 171 | 190.8 | 133.4 | 12.2 | 18 | A |
| HIS NE2 | 171 | 192.0 | 133.8 | 12.3 | 18 | A |
| HIS C | 171 | 193.4 | 129.7 | 13.8 | 20 | A |
| HIS O | 171 | 193.4 | 129.6 | 12.6 | 22 | A |
| ARG N | 172 | 194.5 | 129.6 | 14.6 | 20 | A |
| ARG CA | 172 | 195.8 | 129.4 | 14.0 | 19 | A |
| ARG CB | 172 | 196.9 | 129.5 | 15.0 | 16 | A |
| ARG CG | 172 | 198.3 | 129.3 | 14.4 | 14 | A |
| ARG CD | 172 | 199.4 | 129.8 | 15.2 | 14 | A |
| ARG NE | 172 | 200.6 | 129.7 | 14.5 | 14 | A |
| ARG CZ | 172 | 201.4 | 130.8 | 14.3 | 15 | A |
| ARG NH1 | 172 | 201.0 | 132.0 | 14.7 | 15 | A |
| ARG NH2 | 172 | 202.6 | 130.6 | 13.6 | 16 | A |
| ARG C | 172 | 195.9 | 128.1 | 13.2 | 20 | A |
| ARG O | 172 | 196.6 | 128.1 | 12.2 | 23 | A |
| ARG N | 173 | 195.3 | 127.1 | 13.7 | 21 | A |
| ARG CA | 173 | 195.3 | 125.8 | 13.1 | 21 | A |
| ARG CB | 173 | 194.8 | 124.7 | 14.0 | 23 | A |
| ARG CG | 173 | 194.4 | 123.4 | 13.3 | 26 | A |
| ARG CD | 173 | 193.9 | 122.4 | 14.3 | 31 | A |
| ARG NE | 173 | 193.3 | 121.3 | 13.6 | 34 | A |
| ARG CZ | 173 | 193.3 | 120.0 | 14.1 | 36 | A |
| ARG NH1 | 173 | 193.9 | 119.7 | 15.2 | 37 | A |
| ARG NH2 | 173 | 192.7 | 119.1 | 13.4 | 38 | A |
| ARG C | 173 | 194.5 | 125.8 | 11.8 | 22 | A |
| ARG O | 173 | 194.9 | 125.2 | 10.9 | 23 | A |
| VAL N | 174 | 193.4 | 126.5 | 11.8 | 23 | A |
| VAL CA | 174 | 192.6 | 126.6 | 10.6 | 24 | A |
| VAL CB | 174 | 191.3 | 127.3 | 10.9 | 23 | A |
| VAL CG1 | 174 | 190.5 | 127.5 | 9.6 | 23 | A |
| VAL CG2 | 174 | 190.4 | 126.5 | 11.8 | 21 | A |
| VAL C | 174 | 193.4 | 127.2 | 9.5 | 25 | A |
| VAL O | 174 | 193.3 | 126.7 | 8.3 | 27 | A |
| LEU N | 175 | 194.2 | 128.3 | 9.8 | 25 | A |
| LEU CA | 175 | 194.9 | 129.0 | 8.8 | 24 | A |
| LEU CB | 175 | 195.6 | 130.2 | 9.3 | 22 | A |
| LEU CG | 175 | 194.7 | 131.3 | 9.9 | 22 | A |
| LEU CD1 | 175 | 195.6 | 132.5 | 10.5 | 20 | A |
| LEU CD2 | 175 | 193.7 | 131.9 | 8.9 | 20 | A |
| LEU C | 175 | 196.0 | 128.1 | 8.2 | 25 | A |
| LEU O | 175 | 196.2 | 128.1 | 7.0 | 26 | A |
| VAL N | 176 | 196.7 | 127.4 | 9.1 | 26 | A |
| VAL CA | 176 | 197.8 | 126.4 | 8.6 | 25 | A |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| VAL CB | 176 | 198.5 | 125.8 | 9.9 | 25 | A |
| VAL CG1 | 176 | 199.4 | 124.7 | 9.4 | 25 | A |
| VAL CG2 | 176 | 199.3 | 126.9 | 10.6 | 24 | A |
| VAL C | 176 | 197.2 | 125.3 | 7.8 | 25 | A |
| VAL O | 176 | 197.9 | 124.8 | 6.9 | 25 | A |
| GLU N | 177 | 196.0 | 124.9 | 8.0 | 26 | A |
| GLU CA | 177 | 195.3 | 123.9 | 7.2 | 27 | A |
| GLU CB | 177 | 194.1 | 123.5 | 7.9 | 27 | A |
| GLU CG | 177 | 194.3 | 122.6 | 9.1 | 28 | A |
| GLU CD | 177 | 193.0 | 122.2 | 9.8 | 30 | A |
| GLU OE1 | 177 | 193.1 | 121.2 | 10.6 | 30 | A |
| GLU OE2 | 177 | 192.0 | 122.9 | 9.7 | 31 | A |
| GLU C | 177 | 195.0 | 124.5 | 5.9 | 27 | A |
| GLU O | 177 | 195.5 | 124.0 | 4.8 | 29 | A |
| TRP N | 178 | 194.4 | 125.6 | 5.8 | 27 | A |
| TRP CA | 178 | 194.0 | 126.3 | 4.6 | 26 | A |
| TRP CB | 178 | 193.4 | 127.7 | 5.0 | 25 | A |
| TRP CG | 178 | 192.0 | 127.7 | 5.3 | 22 | A |
| TRP CD2 | 178 | 191.2 | 128.7 | 5.9 | 21 | A |
| TRP CE2 | 178 | 189.9 | 128.3 | 6.0 | 20 | A |
| TRP CE3 | 178 | 191.5 | 130.1 | 6.2 | 20 | A |
| TRP CD1 | 178 | 191.1 | 126.6 | 5.2 | 21 | A |
| TRP NE1 | 178 | 189.9 | 127.0 | 5.6 | 21 | A |
| TRP CZ2 | 178 | 188.9 | 129.1 | 6.5 | 20 | A |
| TRP CZ3 | 178 | 190.5 | 130.9 | 6.7 | 20 | A |
| TRP CH2 | 178 | 189.2 | 130.4 | 6.9 | 20 | A |
| TRP C | 178 | 195.2 | 126.5 | 3.7 | 28 | A |
| TRP O | 178 | 195.3 | 126.0 | 2.6 | 30 | A |
| LEU N | 179 | 196.3 | 127.1 | 4.3 | 29 | A |
| LEU CA | 179 | 197.5 | 127.3 | 3.6 | 30 | A |
| LEU CB | 179 | 198.4 | 128.3 | 4.3 | 31 | A |
| LEU CG | 179 | 197.8 | 129.7 | 4.7 | 32 | A |
| LEU CD1 | 179 | 198.8 | 130.4 | 5.6 | 31 | A |
| LEU CD2 | 179 | 197.6 | 130.5 | 3.4 | 32 | A |
| LEU C | 179 | 198.4 | 126.0 | 3.4 | 32 | A |
| LEU O | 179 | 199.3 | 126.1 | 2.6 | 33 | A |
| LYS N | 180 | 198.1 | 125.0 | 4.1 | 34 | A |
| LYS CA | 180 | 198.9 | 123.8 | 4.0 | 34 | A |
| LYS CB | 180 | 198.8 | 123.2 | 2.7 | 35 | A |
| LYS CG | 180 | 197.4 | 122.6 | 2.5 | 38 | A |
| LYS CD | 180 | 196.9 | 122.9 | 1.1 | 40 | A |
| LYS CE | 180 | 195.5 | 122.3 | 1.0 | 42 | A |
| LYS NZ | 180 | 195.4 | 120.9 | 1.4 | 42 | A |
| LYS C | 180 | 200.4 | 124.2 | 4.3 | 34 | A |
| LYS O | 180 | 201.3 | 123.8 | 3.6 | 35 | A |
| ASP N | 181 | 200.6 | 125.1 | 5.2 | 34 | A |
| ASP CA | 181 | 201.9 | 125.7 | 5.5 | 34 | A |
| ASP CB | 181 | 202.0 | 127.1 | 5.0 | 33 | A |
| ASP CG | 181 | 203.4 | 127.7 | 4.9 | 33 | A |
| ASP OD1 | 181 | 204.3 | 126.9 | 5.2 | 33 | A |
| ASP OD2 | 181 | 203.5 | 128.8 | 4.5 | 34 | A |
| ASP C | 181 | 202.3 | 125.6 | 6.9 | 35 | A |
| ASP O | 181 | 201.9 | 126.4 | 7.8 | 35 | A |
| PRO N | 182 | 203.2 | 124.6 | 7.3 | 34 | A |
| PRO CD | 182 | 203.5 | 123.4 | 6.5 | 34 | A |
| PRO CA | 182 | 203.7 | 124.5 | 8.7 | 34 | A |
| PRO CB | 182 | 203.8 | 123.0 | 8.8 | 35 | A |
| PRO CG | 182 | 204.4 | 122.6 | 7.4 | 33 | A |
| PRO C | 182 | 205.0 | 125.1 | 8.9 | 34 | A |
| PRO O | 182 | 205.6 | 124.9 | 9.9 | 36 | A |
| SER N | 183 | 205.5 | 125.8 | 7.9 | 34 | A |
| SER CA | 183 | 206.9 | 126.4 | 8.0 | 34 | A |
| SER CB | 183 | 207.3 | 127.0 | 6.7 | 35 | A |
| SER OG | 183 | 206.5 | 128.1 | 6.4 | 38 | A |
| SER C | 183 | 207.2 | 127.3 | 9.2 | 34 | A |
| SER O | 183 | 208.3 | 127.3 | 9.6 | 35 | A |
| GLN N | 184 | 206.3 | 128.1 | 9.7 | 33 | A |
| GLN CA | 184 | 206.6 | 128.9 | 10.8 | 32 | A |
| GLN CB | 184 | 206.2 | 130.4 | 10.5 | 34 | A |
| GLN CG | 184 | 204.8 | 130.6 | 10.1 | 37 | A |
| GLN CD | 184 | 204.5 | 132.0 | 9.5 | 38 | A |
| GLN OE1 | 184 | 204.5 | 133.0 | 10.2 | 38 | A |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| GLN NE2 | 184 | 204.3 | 132.0 | 8.2 | 37 | A |
| GLN C | 184 | 206.1 | 128.5 | 12.2 | 30 | A |
| GLN O | 184 | 206.4 | 129.1 | 13.2 | 30 | A |
| GLU N | 185 | 205.6 | 127.3 | 12.2 | 26 | A |
| GLU CA | 185 | 205.0 | 126.7 | 13.4 | 24 | A |
| GLU CB | 185 | 204.1 | 125.5 | 13.1 | 22 | A |
| GLU CG | 185 | 202.9 | 125.8 | 12.2 | 21 | A |
| GLU CD | 185 | 202.2 | 127.1 | 12.6 | 22 | A |
| GLU OE1 | 185 | 201.3 | 127.0 | 13.4 | 22 | A |
| GLU OE2 | 185 | 202.5 | 128.2 | 12.0 | 23 | A |
| GLU C | 185 | 206.0 | 126.3 | 14.6 | 23 | A |
| GLU O | 185 | 205.8 | 126.8 | 15.7 | 23 | A |
| LEU N | 186 | 206.9 | 125.5 | 14.3 | 22 | A |
| LEU CA | 186 | 207.8 | 125.1 | 15.4 | 23 | A |
| LEU CB | 186 | 208.8 | 124.0 | 14.9 | 21 | A |
| LEU CG | 186 | 208.2 | 122.7 | 14.4 | 21 | A |
| LEU CD1 | 186 | 209.3 | 121.7 | 14.0 | 21 | A |
| LEU CD2 | 186 | 207.3 | 122.1 | 15.4 | 19 | A |
| LEU C | 186 | 208.6 | 126.2 | 16.0 | 25 | A |
| LEU O | 186 | 208.8 | 126.3 | 17.2 | 27 | A |
| GLU N | 187 | 208.9 | 127.2 | 15.2 | 26 | A |
| GLU CA | 187 | 209.6 | 128.4 | 15.6 | 27 | A |
| GLU CB | 187 | 210.1 | 129.2 | 14.5 | 31 | A |
| GLU CG | 187 | 210.7 | 130.5 | 14.8 | 35 | A |
| GLU CD | 187 | 211.4 | 131.2 | 13.6 | 38 | A |
| GLU OE1 | 187 | 211.4 | 130.7 | 12.5 | 40 | A |
| GLU OE2 | 187 | 212.1 | 132.2 | 13.9 | 40 | A |
| GLU C | 187 | 208.6 | 129.3 | 16.5 | 26 | A |
| GLU O | 187 | 209.0 | 129.8 | 17.5 | 26 | A |
| PHE N | 188 | 207.4 | 129.6 | 16.0 | 23 | A |
| PHE CA | 188 | 206.4 | 130.4 | 16.7 | 22 | A |
| PHE CB | 188 | 205.2 | 130.5 | 15.9 | 21 | A |
| PHE CG | 188 | 204.0 | 131.0 | 16.7 | 21 | A |
| PHE CD1 | 188 | 204.1 | 132.3 | 17.3 | 21 | A |
| PHE CD2 | 188 | 203.0 | 130.2 | 17.0 | 21 | A |
| PHE CE1 | 188 | 203.0 | 132.8 | 18.1 | 20 | A |
| PHE CE2 | 188 | 201.9 | 130.7 | 17.8 | 21 | A |
| PHE CZ | 188 | 202.0 | 132.0 | 18.3 | 20 | A |
| PHE C | 188 | 206.1 | 129.7 | 18.0 | 21 | A |
| PHE O | 188 | 206.1 | 130.4 | 19.1 | 22 | A |
| ILE N | 189 | 205.8 | 128.4 | 18.0 | 22 | A |
| ILE CA | 189 | 205.5 | 127.6 | 19.2 | 23 | A |
| ILE CB | 189 | 205.2 | 126.2 | 18.9 | 21 | A |
| ILE CG2 | 189 | 204.8 | 125.4 | 20.1 | 21 | A |
| ILE CG1 | 189 | 203.9 | 126.2 | 18.0 | 20 | A |
| ILE CD1 | 189 | 203.6 | 124.8 | 17.4 | 19 | A |
| ILE C | 189 | 206.7 | 127.7 | 20.2 | 23 | A |
| ILE O | 189 | 206.5 | 127.8 | 21.5 | 24 | A |
| ALA N | 190 | 207.9 | 127.6 | 19.7 | 23 | A |
| ALA CA | 190 | 209.1 | 127.7 | 20.6 | 23 | A |
| ALA CB | 190 | 210.4 | 127.4 | 19.8 | 22 | A |
| ALA C | 190 | 209.2 | 129.0 | 21.2 | 23 | A |
| ALA O | 190 | 209.8 | 129.2 | 22.3 | 24 | A |
| ASP N | 191 | 208.7 | 130.1 | 20.6 | 25 | A |
| ASP CA | 191 | 208.7 | 131.4 | 21.2 | 26 | A |
| ASP CB | 191 | 208.5 | 132.5 | 20.2 | 28 | A |
| ASP CG | 191 | 208.6 | 133.9 | 20.9 | 32 | A |
| ASP OD1 | 191 | 209.7 | 134.2 | 21.4 | 33 | A |
| ASP OD2 | 191 | 207.5 | 134.6 | 20.9 | 33 | A |
| ASP C | 191 | 207.7 | 131.5 | 22.3 | 25 | A |
| ASP O | 191 | 208.0 | 132.2 | 23.3 | 27 | A |
| ILE N | 192 | 206.5 | 130.9 | 22.2 | 23 | A |
| ILE CA | 192 | 205.5 | 130.9 | 23.2 | 22 | A |
| ILE CB | 192 | 204.2 | 130.3 | 22.7 | 20 | A |
| ILE CG2 | 192 | 203.2 | 130.2 | 23.8 | 20 | A |
| ILE CG1 | 192 | 203.7 | 131.2 | 21.5 | 19 | A |
| ILE CD1 | 192 | 203.2 | 132.5 | 22.0 | 19 | A |
| ILE C | 192 | 206.0 | 130.1 | 24.4 | 22 | A |
| ILE O | 192 | 205.9 | 130.5 | 25.6 | 22 | A |
| LEU N | 193 | 206.5 | 128.9 | 24.1 | 23 | A |
| LEU CA | 193 | 207.1 | 128.0 | 25.1 | 24 | A |
| LEU CB | 193 | 207.5 | 126.6 | 24.6 | 21 | A |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| LEU CG | 193 | 206.3 | 125.8 | 24.0 | 21 | A |
| LEU CD1 | 193 | 206.9 | 124.5 | 23.4 | 21 | A |
| LEU CD2 | 193 | 205.3 | 125.5 | 25.1 | 20 | A |
| LEU C | 193 | 208.3 | 128.6 | 25.8 | 25 | A |
| LEU O | 193 | 208.8 | 128.1 | 26.8 | 27 | A |
| ASN N | 194 | 208.8 | 129.6 | 25.2 | 25 | A |
| ASN CA | 194 | 210.0 | 130.3 | 25.8 | 26 | A |
| ASN CB | 194 | 210.8 | 131.0 | 24.7 | 28 | A |
| ASN CG | 194 | 212.0 | 131.7 | 25.3 | 30 | A |
| ASN OD1 | 194 | 212.1 | 132.9 | 25.4 | 33 | A |
| ASN ND2 | 194 | 213.0 | 130.9 | 25.8 | 30 | A |
| ASN C | 194 | 209.5 | 131.2 | 26.9 | 27 | A |
| ASN O | 194 | 210.3 | 131.6 | 27.8 | 28 | A |
| GLN N | 195 | 208.2 | 131.6 | 26.8 | 26 | A |
| GLN CA | 195 | 207.6 | 132.5 | 27.8 | 25 | A |
| GLN CB | 195 | 206.6 | 133.4 | 27.0 | 26 | A |
| GLN CG | 195 | 207.4 | 134.2 | 26.0 | 27 | A |
| GLN CD | 195 | 206.5 | 134.9 | 25.0 | 27 | A |
| GLN OE1 | 195 | 205.7 | 135.7 | 25.3 | 29 | A |
| GLN NE2 | 195 | 206.7 | 134.6 | 23.7 | 27 | A |
| GLN C | 195 | 206.9 | 131.7 | 28.9 | 25 | A |
| GLN O | 195 | 206.9 | 132.1 | 30.0 | 27 | A |
| ASP N | 196 | 206.3 | 130.6 | 28.5 | 23 | A |
| ASP CA | 196 | 205.6 | 129.6 | 29.4 | 19 | A |
| ASP CB | 196 | 204.1 | 129.9 | 29.5 | 18 | A |
| ASP CG | 196 | 203.4 | 128.9 | 30.4 | 17 | A |
| ASP OD1 | 196 | 204.0 | 128.0 | 30.9 | 17 | A |
| ASP OD2 | 196 | 202.2 | 129.0 | 30.5 | 17 | A |
| ASP C | 196 | 205.9 | 128.3 | 28.8 | 19 | A |
| ASP O | 196 | 205.2 | 127.8 | 27.9 | 20 | A |
| ALA N | 197 | 206.9 | 127.6 | 29.3 | 18 | A |
| ALA CA | 197 | 207.3 | 126.3 | 28.9 | 18 | A |
| ALA CB | 197 | 208.7 | 125.9 | 29.5 | 18 | A |
| ALA C | 197 | 206.3 | 125.2 | 29.1 | 18 | A |
| ALA O | 197 | 206.6 | 124.0 | 28.7 | 18 | A |
| LYS N | 198 | 205.2 | 125.4 | 29.7 | 18 | A |
| LYS CA | 198 | 204.2 | 124.4 | 29.9 | 18 | A |
| LYS CB | 198 | 204.1 | 124.1 | 31.4 | 19 | A |
| LYS CG | 198 | 205.5 | 123.7 | 32.0 | 22 | A |
| LYS CD | 198 | 205.4 | 123.6 | 33.5 | 21 | A |
| LYS CE | 198 | 206.7 | 123.1 | 34.1 | 22 | A |
| LYS NZ | 198 | 206.5 | 122.6 | 35.5 | 22 | A |
| LYS C | 198 | 202.9 | 124.7 | 29.4 | 18 | A |
| LYS O | 198 | 201.9 | 124.1 | 29.8 | 20 | A |
| ASN N | 199 | 202.8 | 125.7 | 28.5 | 18 | A |
| ASN CA | 199 | 201.5 | 126.1 | 27.9 | 18 | A |
| ASN CB | 199 | 201.7 | 127.3 | 27.0 | 18 | A |
| ASN CG | 199 | 200.3 | 127.8 | 26.4 | 19 | A |
| ASN OD1 | 199 | 199.7 | 127.1 | 25.6 | 20 | A |
| ASN ND2 | 199 | 199.9 | 129.0 | 26.8 | 18 | A |
| ASN C | 199 | 200.9 | 124.9 | 27.2 | 20 | A |
| ASN O | 199 | 201.5 | 124.3 | 26.3 | 23 | A |
| TYR N | 200 | 199.8 | 124.5 | 27.7 | 19 | A |
| TYR CA | 200 | 199.1 | 123.3 | 27.2 | 19 | A |
| TYR CB | 200 | 197.9 | 123.0 | 28.0 | 18 | A |
| TYR CG | 200 | 197.5 | 121.6 | 28.0 | 19 | A |
| TYR CD1 | 200 | 197.9 | 120.7 | 29.0 | 19 | A |
| TYR CE1 | 200 | 197.6 | 119.3 | 29.0 | 18 | A |
| TYR CD2 | 200 | 196.6 | 121.1 | 27.0 | 18 | A |
| TYR CE2 | 200 | 196.3 | 119.8 | 27.0 | 17 | A |
| TYR CZ | 200 | 196.8 | 118.9 | 27.9 | 17 | A |
| TYR OH | 200 | 196.4 | 117.6 | 27.8 | 15 | A |
| TYR C | 200 | 198.7 | 123.4 | 25.7 | 18 | A |
| TYR O | 200 | 199.0 | 122.4 | 25.0 | 18 | A |
| HIS N | 201 | 198.1 | 124.5 | 25.3 | 17 | A |
| HIS CA | 201 | 197.7 | 124.7 | 24.0 | 17 | A |
| HIS CB | 201 | 197.0 | 126.0 | 23.9 | 16 | A |
| HIS CG | 201 | 195.9 | 126.2 | 24.9 | 16 | A |
| HIS CD2 | 201 | 196.0 | 126.9 | 26.1 | 14 | A |
| HIS ND1 | 201 | 194.6 | 125.7 | 24.8 | 14 | A |
| HIS CE1 | 201 | 193.9 | 126.1 | 25.9 | 14 | A |
| HIS NE2 | 201 | 194.7 | 126.7 | 26.7 | 13 | A |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| HIS C | 201 | 198.9 | 124.7 | 23.0 | 16 | A |
| HIS O | 201 | 198.8 | 124.1 | 21.9 | 16 | A |
| ALA N | 202 | 200.0 | 125.3 | 23.4 | 17 | A |
| ALA CA | 202 | 201.2 | 125.4 | 22.6 | 17 | A |
| ALA CB | 202 | 202.2 | 126.2 | 23.3 | 17 | A |
| ALA C | 202 | 201.8 | 124.0 | 22.3 | 19 | A |
| ALA O | 202 | 202.1 | 123.7 | 21.2 | 22 | A |
| TRP N | 203 | 201.9 | 123.2 | 23.4 | 19 | A |
| TRP CA | 203 | 202.4 | 121.8 | 23.3 | 17 | A |
| TRP CB | 203 | 202.5 | 121.2 | 24.7 | 16 | A |
| TRP CG | 203 | 203.7 | 121.6 | 25.4 | 15 | A |
| TRP CD2 | 203 | 205.0 | 121.3 | 24.9 | 15 | A |
| TRP CE2 | 203 | 205.9 | 121.9 | 25.9 | 15 | A |
| TRP CE3 | 203 | 205.6 | 120.6 | 23.9 | 15 | A |
| TRP CD1 | 203 | 203.8 | 122.3 | 26.5 | 14 | A |
| TRP NE1 | 203 | 205.1 | 122.5 | 26.8 | 15 | A |
| TRP CZ2 | 203 | 207.3 | 121.8 | 25.8 | 15 | A |
| TRP CZ3 | 203 | 207.0 | 120.5 | 23.8 | 15 | A |
| TRP CH2 | 203 | 207.8 | 121.1 | 24.7 | 15 | A |
| TRP C | 203 | 201.5 | 121.0 | 22.4 | 19 | A |
| TRP O | 203 | 201.9 | 120.2 | 21.5 | 20 | A |
| GLN N | 204 | 200.1 | 121.1 | 22.6 | 20 | A |
| GLN CA | 204 | 199.1 | 120.4 | 21.8 | 20 | A |
| GLN CB | 204 | 197.8 | 120.6 | 22.4 | 20 | A |
| GLN CG | 204 | 196.7 | 119.8 | 21.8 | 20 | A |
| GLN CD | 204 | 195.3 | 120.0 | 22.5 | 21 | A |
| GLN OE1 | 204 | 194.3 | 120.1 | 21.8 | 22 | A |
| GLN NE2 | 204 | 195.4 | 120.0 | 23.8 | 21 | A |
| GLN C | 204 | 199.2 | 120.8 | 20.3 | 21 | A |
| GLN O | 204 | 199.0 | 120.0 | 19.4 | 20 | A |
| HIS N | 205 | 199.4 | 122.1 | 20.1 | 20 | A |
| HIS CA | 205 | 199.4 | 122.6 | 18.7 | 20 | A |
| HIS CB | 205 | 199.5 | 124.1 | 18.7 | 19 | A |
| HIS CG | 205 | 199.4 | 124.7 | 17.3 | 19 | A |
| HIS CD2 | 205 | 200.3 | 125.4 | 16.6 | 18 | A |
| HIS ND1 | 205 | 198.3 | 124.6 | 16.6 | 19 | A |
| HIS CE1 | 205 | 198.4 | 125.2 | 15.4 | 17 | A |
| HIS NE2 | 205 | 199.7 | 125.7 | 15.4 | 17 | A |
| HIS C | 205 | 200.7 | 122.0 | 18.1 | 21 | A |
| HIS O | 205 | 200.7 | 121.5 | 17.0 | 24 | A |
| ARG N | 206 | 201.8 | 122.0 | 18.9 | 21 | A |
| ARG CA | 206 | 203.1 | 121.5 | 18.4 | 20 | A |
| ARG CB | 206 | 204.1 | 121.6 | 19.5 | 19 | A |
| ARG CG | 206 | 205.6 | 121.5 | 19.1 | 18 | A |
| ARG CD | 206 | 206.6 | 121.9 | 20.1 | 18 | A |
| ARG NE | 206 | 207.9 | 121.9 | 19.5 | 20 | A |
| ARG CZ | 206 | 208.6 | 122.9 | 19.0 | 21 | A |
| ARG NH1 | 206 | 208.0 | 124.1 | 19.0 | 21 | A |
| ARG NH2 | 206 | 209.8 | 122.7 | 18.5 | 21 | A |
| ARG C | 206 | 202.9 | 120.0 | 18.0 | 21 | A |
| ARG O | 206 | 203.4 | 119.6 | 17.0 | 22 | A |
| GLN N | 207 | 202.2 | 119.2 | 18.8 | 20 | A |
| GLN CA | 207 | 202.0 | 117.8 | 18.5 | 20 | A |
| GLN CB | 207 | 201.4 | 117.0 | 19.6 | 19 | A |
| GLN CG | 207 | 202.2 | 116.9 | 20.9 | 20 | A |
| GLN CD | 207 | 201.6 | 115.9 | 21.8 | 20 | A |
| GLN OE1 | 207 | 200.5 | 115.4 | 21.7 | 20 | A |
| GLN NE2 | 207 | 202.5 | 115.5 | 22.8 | 19 | A |
| GLN C | 207 | 201.2 | 117.6 | 17.2 | 21 | A |
| GLN O | 207 | 201.5 | 116.7 | 16.4 | 22 | A |
| TRP N | 208 | 200.2 | 118.4 | 17.0 | 21 | A |
| TRP CA | 208 | 199.4 | 118.3 | 15.8 | 22 | A |
| TRP CB | 208 | 198.2 | 119.3 | 15.9 | 20 | A |
| TRP CG | 208 | 197.4 | 119.4 | 14.6 | 20 | A |
| TRP CD2 | 208 | 197.5 | 120.5 | 13.7 | 20 | A |
| TRP CE2 | 208 | 196.7 | 120.2 | 12.6 | 19 | A |
| TRP CE3 | 208 | 198.2 | 121.7 | 13.6 | 21 | A |
| TRP CD1 | 208 | 196.6 | 118.5 | 14.1 | 20 | A |
| TRP NE1 | 208 | 196.1 | 119.0 | 12.9 | 20 | A |
| TRP CZ2 | 208 | 196.6 | 121.0 | 11.5 | 19 | A |
| TRP CZ3 | 208 | 198.1 | 122.5 | 12.5 | 20 | A |
| TRP CH2 | 208 | 197.3 | 122.2 | 11.5 | 19 | A |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| TRP C | 208 | 200.2 | 118.7 | 14.5 | 23 | A |
| TRP O | 208 | 200.1 | 118.0 | 13.5 | 24 | A |
| VAL N | 209 | 201.0 | 119.8 | 14.6 | 24 | A |
| VAL CA | 209 | 201.8 | 120.2 | 13.4 | 24 | A |
| VAL CB | 209 | 202.5 | 121.5 | 13.7 | 24 | A |
| VAL CG1 | 209 | 203.3 | 121.9 | 12.5 | 25 | A |
| VAL CG2 | 209 | 201.5 | 122.6 | 14.0 | 25 | A |
| VAL C | 209 | 202.8 | 119.1 | 13.1 | 25 | A |
| VAL O | 209 | 203.0 | 118.7 | 11.9 | 26 | A |
| ILE N | 210 | 203.5 | 118.6 | 14.1 | 26 | A |
| ILE CA | 210 | 204.5 | 117.5 | 13.9 | 25 | A |
| ILE CB | 210 | 205.2 | 117.2 | 15.2 | 24 | A |
| ILE CG2 | 210 | 206.2 | 116.0 | 15.0 | 24 | A |
| ILE CG1 | 210 | 206.1 | 118.3 | 15.7 | 23 | A |
| ILE CD1 | 210 | 206.8 | 118.0 | 16.9 | 22 | A |
| ILE C | 210 | 203.9 | 116.3 | 13.4 | 27 | A |
| ILE O | 210 | 204.4 | 115.7 | 12.4 | 27 | A |
| GLN N | 211 | 202.7 | 115.9 | 13.9 | 29 | A |
| GLN CA | 211 | 202.1 | 114.7 | 13.4 | 32 | A |
| GLN CB | 211 | 201.0 | 114.2 | 14.4 | 35 | A |
| GLN CG | 211 | 200.4 | 112.9 | 14.2 | 38 | A |
| GLN CD | 211 | 200.0 | 112.2 | 15.5 | 40 | A |
| GLN OE1 | 211 | 199.5 | 112.8 | 16.4 | 42 | A |
| GLN NE2 | 211 | 200.3 | 110.9 | 15.6 | 41 | A |
| GLN C | 211 | 201.4 | 114.8 | 12.1 | 33 | A |
| GLN O | 211 | 201.5 | 113.9 | 11.3 | 34 | A |
| GLU N | 212 | 200.8 | 116.0 | 11.8 | 35 | A |
| GLU CA | 212 | 200.2 | 116.2 | 10.5 | 37 | A |
| GLU CB | 212 | 199.4 | 117.5 | 10.6 | 40 | A |
| GLU CG | 212 | 198.1 | 117.2 | 11.3 | 45 | A |
| GLU CD | 212 | 197.3 | 116.0 | 10.7 | 48 | A |
| GLU OE1 | 212 | 196.8 | 116.2 | 9.6 | 49 | A |
| GLU OE2 | 212 | 197.4 | 115.0 | 11.4 | 48 | A |
| GLU C | 212 | 201.2 | 116.4 | 9.3 | 37 | A |
| GLU O | 212 | 200.9 | 115.8 | 8.2 | 38 | A |
| PHE N | 213 | 202.2 | 117.1 | 9.6 | 36 | A |
| PHE CA | 213 | 203.2 | 117.4 | 8.6 | 34 | A |
| PHE CB | 213 | 203.6 | 118.9 | 8.6 | 31 | A |
| PHE CG | 213 | 202.4 | 119.8 | 8.3 | 31 | A |
| PHE CD1 | 213 | 201.5 | 120.1 | 9.4 | 30 | A |
| PHE CD2 | 213 | 202.1 | 120.2 | 7.1 | 30 | A |
| PHE CE1 | 213 | 200.4 | 120.8 | 9.1 | 30 | A |
| PHE CE2 | 213 | 200.9 | 120.9 | 6.8 | 30 | A |
| PHE CZ | 213 | 200.0 | 121.2 | 7.8 | 30 | A |
| PHE C | 213 | 204.5 | 116.6 | 8.7 | 35 | A |
| PHE O | 213 | 205.5 | 116.9 | 8.1 | 37 | A |
| ARG N | 214 | 204.4 | 115.5 | 9.5 | 36 | A |
| ARG CA | 214 | 205.5 | 114.6 | 9.7 | 37 | A |
| ARG CB | 214 | 205.7 | 113.7 | 8.5 | 40 | A |
| ARG CG | 214 | 204.7 | 112.6 | 8.5 | 45 | A |
| ARG CD | 214 | 204.1 | 112.3 | 7.1 | 49 | A |
| ARG NE | 214 | 202.7 | 112.6 | 7.1 | 54 | A |
| ARG CZ | 214 | 201.7 | 111.8 | 7.5 | 57 | A |
| ARG NH1 | 214 | 200.4 | 112.2 | 7.5 | 57 | A |
| ARG NH2 | 214 | 201.9 | 110.6 | 7.9 | 59 | A |
| ARG C | 214 | 206.8 | 115.4 | 10.0 | 36 | A |
| ARG O | 214 | 207.9 | 115.1 | 9.3 | 36 | A |
| LEU N | 215 | 206.8 | 116.4 | 10.8 | 34 | A |
| LEU CA | 215 | 208.0 | 117.1 | 11.2 | 32 | A |
| LEU CB | 215 | 207.7 | 118.6 | 11.3 | 32 | A |
| LEU CG | 215 | 206.9 | 119.3 | 10.2 | 32 | A |
| LEU CD1 | 215 | 206.8 | 120.8 | 10.6 | 33 | A |
| LEU CD2 | 215 | 207.6 | 119.2 | 8.9 | 33 | A |
| LEU C | 215 | 208.7 | 116.6 | 12.4 | 32 | A |
| LEU O | 215 | 209.0 | 117.3 | 13.3 | 32 | A |
| TRP N | 216 | 209.1 | 115.3 | 12.4 | 33 | A |
| TRP CA | 216 | 209.7 | 114.6 | 13.5 | 33 | A |
| TRP CB | 216 | 209.5 | 113.1 | 13.4 | 31 | A |
| TRP CG | 216 | 208.1 | 112.7 | 13.3 | 30 | A |
| TRP CD2 | 216 | 207.1 | 112.6 | 14.4 | 29 | A |
| TRP CE2 | 216 | 205.9 | 112.3 | 13.9 | 29 | A |
| TRP CE3 | 216 | 207.2 | 112.8 | 15.8 | 29 | A |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| TRP CD1 | 216 | 207.3 | 112.5 | 12.2 | 30 | A |
| TRP NE1 | 216 | 206.0 | 112.2 | 12.5 | 29 | A |
| TRP CZ2 | 216 | 204.7 | 112.1 | 14.7 | 28 | A |
| TRP CZ3 | 216 | 206.1 | 112.6 | 16.6 | 27 | A |
| TRP CH2 | 216 | 204.9 | 112.3 | 16.0 | 27 | A |
| TRP C | 216 | 211.2 | 114.8 | 13.7 | 35 | A |
| TRP O | 216 | 211.7 | 114.9 | 14.9 | 37 | A |
| ASP N | 217 | 212.0 | 114.9 | 12.6 | 37 | A |
| ASP CA | 217 | 213.4 | 115.1 | 12.7 | 38 | A |
| ASP CB | 217 | 214.0 | 115.5 | 11.4 | 39 | A |
| ASP CG | 217 | 213.5 | 114.5 | 10.3 | 41 | A |
| ASP OD1 | 217 | 213.5 | 115.0 | 9.1 | 43 | A |
| ASP OD2 | 217 | 213.1 | 113.4 | 10.6 | 41 | A |
| ASP C | 217 | 214.2 | 115.8 | 13.8 | 38 | A |
| ASP O | 217 | 215.1 | 115.2 | 14.4 | 38 | A |
| ASN N | 218 | 213.8 | 117.0 | 14.2 | 38 | A |
| ASN CA | 218 | 214.5 | 117.7 | 15.2 | 38 | A |
| ASN CB | 218 | 215.0 | 119.0 | 14.8 | 40 | A |
| ASN CG | 218 | 215.6 | 119.0 | 13.4 | 42 | A |
| ASN OD1 | 218 | 214.9 | 119.2 | 12.4 | 44 | A |
| ASN ND2 | 218 | 216.9 | 118.6 | 13.3 | 43 | A |
| ASN C | 218 | 213.8 | 117.8 | 16.6 | 35 | A |
| ASN O | 218 | 214.2 | 118.6 | 17.4 | 35 | A |
| GLU N | 219 | 212.7 | 117.1 | 16.7 | 34 | A |
| GLU CA | 219 | 211.9 | 117.3 | 18.0 | 33 | A |
| GLU CB | 219 | 210.5 | 116.8 | 17.8 | 32 | A |
| GLU CG | 219 | 209.6 | 117.2 | 19.0 | 31 | A |
| GLU CD | 219 | 209.4 | 118.7 | 19.2 | 31 | A |
| GLU OE1 | 219 | 210.0 | 119.5 | 18.4 | 30 | A |
| GLU OE2 | 219 | 208.7 | 119.1 | 20.1 | 29 | A |
| GLU C | 219 | 212.6 | 116.7 | 19.2 | 32 | A |
| GLU O | 219 | 212.5 | 117.3 | 20.3 | 31 | A |
| LEU N | 220 | 213.3 | 115.5 | 19.1 | 33 | A |
| LEU CA | 220 | 213.9 | 114.9 | 20.3 | 32 | A |
| LEU CB | 220 | 214.4 | 113.5 | 20.0 | 32 | A |
| LEU CG | 220 | 214.7 | 112.7 | 21.3 | 32 | A |
| LEU CD1 | 220 | 213.5 | 112.7 | 22.2 | 33 | A |
| LEU CD2 | 220 | 215.1 | 111.3 | 20.9 | 31 | A |
| LEU C | 220 | 215.1 | 115.8 | 20.7 | 33 | A |
| LEU O | 220 | 215.4 | 115.9 | 21.9 | 34 | A |
| GLN N | 221 | 215.6 | 116.6 | 19.8 | 34 | A |
| GLN CA | 221 | 216.7 | 117.5 | 20.1 | 35 | A |
| GLN CB | 221 | 217.4 | 117.9 | 18.8 | 39 | A |
| GLN CG | 221 | 218.4 | 119.0 | 18.9 | 44 | A |
| GLN CD | 221 | 219.0 | 119.4 | 17.5 | 47 | A |
| GLN OE1 | 221 | 219.5 | 118.6 | 16.8 | 48 | A |
| GLN NE2 | 221 | 218.8 | 120.7 | 17.2 | 49 | A |
| GLN C | 221 | 216.2 | 118.7 | 20.8 | 34 | A |
| GLN O | 221 | 216.9 | 119.3 | 21.7 | 34 | A |
| TYR N | 222 | 215.0 | 119.1 | 20.4 | 32 | A |
| TYR CA | 222 | 214.3 | 120.2 | 21.1 | 30 | A |
| TYR CB | 222 | 213.1 | 120.6 | 20.3 | 28 | A |
| TYR CG | 222 | 212.4 | 121.8 | 20.9 | 27 | A |
| TYR CD1 | 222 | 213.0 | 123.0 | 21.0 | 26 | A |
| TYR CE1 | 222 | 212.3 | 124.1 | 21.5 | 26 | A |
| TYR CD2 | 222 | 211.1 | 121.7 | 21.4 | 27 | A |
| TYR CE2 | 222 | 210.4 | 122.7 | 22.0 | 26 | A |
| TYR CZ | 222 | 211.0 | 124.0 | 22.0 | 27 | A |
| TYR OH | 222 | 210.4 | 125.0 | 22.6 | 26 | A |
| TYR C | 222 | 214.0 | 119.8 | 22.5 | 31 | A |
| TYR O | 222 | 214.2 | 120.6 | 23.5 | 31 | A |
| VAL N | 223 | 213.5 | 118.6 | 22.7 | 32 | A |
| VAL CA | 223 | 213.1 | 118.0 | 24.0 | 32 | A |
| VAL CB | 223 | 212.5 | 116.6 | 23.8 | 31 | A |
| VAL CG1 | 223 | 212.7 | 115.8 | 25.1 | 30 | A |
| VAL CG2 | 223 | 211.0 | 116.8 | 23.5 | 30 | A |
| VAL C | 223 | 214.4 | 118.0 | 24.9 | 32 | A |
| VAL O | 223 | 214.3 | 118.3 | 26.1 | 34 | A |
| ASP N | 224 | 215.5 | 117.5 | 24.4 | 33 | A |
| ASP CA | 224 | 216.7 | 117.5 | 25.1 | 34 | A |
| ASP CB | 224 | 217.8 | 116.8 | 24.4 | 34 | A |
| ASP CG | 224 | 217.7 | 115.4 | 24.2 | 34 | A |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| ASP OD1 | 224 | 217.0 | 114.7 | 25.1 | 34 | A |
| ASP OD2 | 224 | 218.1 | 114.8 | 23.2 | 34 | A |
| ASP C | 224 | 217.1 | 118.9 | 25.6 | 35 | A |
| ASP O | 224 | 217.7 | 119.1 | 26.7 | 35 | A |
| GLN N | 225 | 216.9 | 119.9 | 24.8 | 35 | A |
| GLN CA | 225 | 217.2 | 121.2 | 25.1 | 35 | A |
| GLN CB | 225 | 216.9 | 122.2 | 23.9 | 37 | A |
| GLN CG | 225 | 217.0 | 123.6 | 24.2 | 40 | A |
| GLN CD | 225 | 216.3 | 124.5 | 23.1 | 43 | A |
| GLN OE1 | 225 | 216.4 | 124.2 | 21.9 | 44 | A |
| GLN NE2 | 225 | 215.7 | 125.6 | 23.5 | 43 | A |
| GLN C | 225 | 216.3 | 121.7 | 26.3 | 34 | A |
| GLN O | 225 | 216.8 | 122.2 | 27.3 | 34 | A |
| LEU N | 226 | 215.0 | 121.5 | 26.2 | 33 | A |
| LEU CA | 226 | 214.1 | 121.9 | 27.3 | 32 | A |
| LEU CB | 226 | 212.6 | 121.9 | 26.8 | 31 | A |
| LEU CG | 226 | 212.2 | 122.8 | 25.7 | 31 | A |
| LEU CD1 | 226 | 210.8 | 123.3 | 25.9 | 30 | A |
| LEU CD2 | 226 | 213.1 | 124.1 | 25.8 | 31 | A |
| LEU C | 226 | 214.3 | 121.1 | 28.6 | 33 | A |
| LEU O | 226 | 214.1 | 121.7 | 29.7 | 32 | A |
| LEU N | 227 | 214.6 | 119.8 | 28.5 | 34 | A |
| LEU CA | 227 | 214.8 | 119.0 | 29.7 | 35 | A |
| LEU CB | 227 | 215.0 | 117.5 | 29.4 | 34 | A |
| LEU CG | 227 | 213.7 | 116.8 | 29.2 | 34 | A |
| LEU CD1 | 227 | 214.0 | 115.3 | 28.7 | 33 | A |
| LEU CD2 | 227 | 212.8 | 116.8 | 30.4 | 32 | A |
| LEU C | 227 | 216.1 | 119.5 | 30.5 | 36 | A |
| LEU O | 227 | 216.1 | 119.5 | 31.7 | 36 | A |
| LYS N | 228 | 217.0 | 120.1 | 29.7 | 37 | A |
| LYS CA | 228 | 218.2 | 120.6 | 30.2 | 37 | A |
| LYS CB | 228 | 219.2 | 120.8 | 29.1 | 39 | A |
| LYS CG | 228 | 220.6 | 121.1 | 29.4 | 43 | A |
| LYS CD | 228 | 221.5 | 120.9 | 28.2 | 46 | A |
| LYS CE | 228 | 222.9 | 121.4 | 28.4 | 49 | A |
| LYS NZ | 228 | 223.7 | 121.3 | 27.2 | 50 | A |
| LYS C | 228 | 217.9 | 121.9 | 31.0 | 37 | A |
| LYS O | 228 | 218.6 | 122.2 | 32.0 | 37 | A |
| GLU N | 229 | 217.0 | 122.7 | 30.5 | 35 | A |
| GLU CA | 229 | 216.6 | 123.9 | 31.1 | 33 | A |
| GLU CB | 229 | 215.8 | 124.8 | 30.1 | 33 | A |
| GLU CG | 229 | 216.5 | 125.0 | 28.8 | 34 | A |
| GLU CD | 229 | 215.9 | 126.0 | 27.9 | 34 | A |
| GLU OE1 | 229 | 214.7 | 126.2 | 28.0 | 35 | A |
| GLU OE2 | 229 | 216.6 | 126.5 | 27.1 | 36 | A |
| GLU C | 229 | 215.8 | 123.7 | 32.4 | 32 | A |
| GLU O | 229 | 215.8 | 124.4 | 33.3 | 32 | A |
| ASP N | 230 | 215.0 | 122.6 | 32.3 | 31 | A |
| ASP CA | 230 | 214.1 | 122.3 | 33.5 | 30 | A |
| ASP CB | 230 | 212.9 | 123.2 | 33.6 | 29 | A |
| ASP CG | 230 | 212.2 | 123.0 | 34.9 | 29 | A |
| ASP OD1 | 230 | 212.6 | 122.1 | 35.7 | 30 | A |
| ASP OD2 | 230 | 211.2 | 123.8 | 35.1 | 29 | A |
| ASP C | 230 | 213.7 | 120.8 | 33.4 | 30 | A |
| ASP O | 230 | 212.7 | 120.5 | 32.8 | 31 | A |
| VAL N | 231 | 214.6 | 120.0 | 34.0 | 30 | A |
| VAL CA | 231 | 214.3 | 118.5 | 34.0 | 30 | A |
| VAL CB | 231 | 215.6 | 117.7 | 34.6 | 31 | A |
| VAL CG1 | 231 | 215.6 | 117.9 | 36.1 | 31 | A |
| VAL CG2 | 231 | 215.5 | 116.3 | 34.1 | 30 | A |
| VAL C | 231 | 213.0 | 118.1 | 34.7 | 30 | A |
| VAL O | 231 | 212.6 | 117.0 | 34.6 | 31 | A |
| ARG N | 232 | 212.4 | 119.1 | 35.3 | 30 | A |
| ARG CA | 232 | 211.2 | 118.8 | 36.0 | 30 | A |
| ARG CB | 232 | 211.1 | 119.6 | 37.3 | 30 | A |
| ARG CG | 232 | 212.2 | 119.4 | 38.3 | 31 | A |
| ARG CD | 232 | 211.8 | 120.1 | 39.7 | 32 | A |
| ARG NE | 232 | 212.7 | 119.7 | 40.8 | 34 | A |
| ARG CZ | 232 | 213.9 | 120.3 | 41.0 | 35 | A |
| ARG NH1 | 232 | 214.3 | 121.3 | 40.2 | 35 | A |
| ARG NH2 | 232 | 214.7 | 120.0 | 42.0 | 35 | A |
| ARG C | 232 | 210.0 | 119.2 | 35.1 | 28 | A |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| ARG O | 232 | 208.8 | 119.2 | 35.5 | 28 | A |
| ASN N | 233 | 210.2 | 119.5 | 33.8 | 26 | A |
| ASN CA | 233 | 209.1 | 119.9 | 33.0 | 25 | A |
| ASN CB | 233 | 209.6 | 120.8 | 31.8 | 25 | A |
| ASN CG | 233 | 208.4 | 121.4 | 31.0 | 25 | A |
| ASN OD1 | 233 | 207.3 | 120.9 | 31.0 | 27 | A |
| ASN ND2 | 233 | 208.7 | 122.5 | 30.4 | 24 | A |
| ASN C | 233 | 208.4 | 118.7 | 32.5 | 25 | A |
| ASN O | 233 | 208.9 | 118.0 | 31.5 | 27 | A |
| ASN N | 234 | 207.3 | 118.4 | 33.0 | 26 | A |
| ASN CA | 234 | 206.5 | 117.3 | 32.7 | 25 | A |
| ASN CB | 234 | 205.3 | 117.1 | 33.6 | 26 | A |
| ASN CG | 234 | 204.9 | 115.7 | 33.7 | 25 | A |
| ASN OD1 | 234 | 205.6 | 114.8 | 34.0 | 25 | A |
| ASN ND2 | 234 | 203.6 | 115.5 | 33.5 | 26 | A |
| ASN C | 234 | 206.0 | 117.3 | 31.2 | 25 | A |
| ASN O | 234 | 205.8 | 116.3 | 30.6 | 25 | A |
| SER N | 235 | 205.7 | 118.5 | 30.7 | 23 | A |
| SER CA | 235 | 205.3 | 118.7 | 29.3 | 21 | A |
| SER CB | 235 | 205.0 | 120.2 | 29.1 | 19 | A |
| SER OG | 235 | 203.9 | 120.6 | 29.9 | 17 | A |
| SER C | 235 | 206.3 | 118.2 | 28.3 | 21 | A |
| SER O | 235 | 206.0 | 117.7 | 27.3 | 20 | A |
| VAL N | 236 | 207.6 | 118.3 | 28.7 | 22 | A |
| VAL CA | 236 | 208.7 | 117.9 | 27.9 | 22 | A |
| VAL CB | 236 | 209.9 | 118.7 | 28.3 | 21 | A |
| VAL CG1 | 236 | 211.1 | 118.3 | 27.3 | 22 | A |
| VAL CG2 | 236 | 209.7 | 120.1 | 28.2 | 20 | A |
| VAL C | 236 | 208.9 | 116.4 | 28.0 | 23 | A |
| VAL O | 236 | 209.3 | 115.8 | 27.1 | 25 | A |
| TRP N | 237 | 208.7 | 115.8 | 29.2 | 24 | A |
| TRP CA | 237 | 208.8 | 114.4 | 29.3 | 26 | A |
| TRP CB | 237 | 208.7 | 113.9 | 30.8 | 26 | A |
| TRP CG | 237 | 209.9 | 114.2 | 31.6 | 26 | A |
| TRP CD2 | 237 | 211.1 | 113.4 | 31.6 | 26 | A |
| TRP CE2 | 237 | 212.0 | 114.0 | 32.5 | 25 | A |
| TRP CE3 | 237 | 211.5 | 112.2 | 31.0 | 25 | A |
| TRP CD1 | 237 | 210.2 | 115.3 | 32.4 | 25 | A |
| TRP NE1 | 237 | 211.4 | 115.2 | 32.9 | 26 | A |
| TRP CZ2 | 237 | 213.3 | 113.5 | 32.8 | 24 | A |
| TRP CZ3 | 237 | 212.8 | 111.7 | 31.3 | 24 | A |
| TRP CH2 | 237 | 213.6 | 112.3 | 32.1 | 24 | A |
| TRP C | 237 | 207.7 | 113.8 | 28.5 | 26 | A |
| TRP O | 237 | 207.9 | 112.8 | 27.8 | 26 | A |
| ASN N | 238 | 206.5 | 114.5 | 28.5 | 25 | A |
| ASN CA | 238 | 205.4 | 114.0 | 27.7 | 24 | A |
| ASN CB | 238 | 204.2 | 114.8 | 27.9 | 24 | A |
| ASN CG | 238 | 203.0 | 114.3 | 27.1 | 25 | A |
| ASN OD1 | 238 | 202.6 | 113.2 | 27.3 | 25 | A |
| ASN ND2 | 238 | 202.5 | 115.1 | 26.2 | 24 | A |
| ASN C | 238 | 205.8 | 114.0 | 26.2 | 23 | A |
| ASN O | 238 | 205.6 | 113.1 | 25.5 | 24 | A |
| GLN N | 239 | 206.4 | 115.1 | 25.8 | 23 | A |
| GLN CA | 239 | 206.9 | 115.3 | 24.4 | 23 | A |
| GLN CB | 239 | 207.4 | 116.7 | 24.1 | 23 | A |
| GLN CG | 239 | 207.6 | 117.1 | 22.7 | 23 | A |
| GLN CD | 239 | 206.2 | 117.3 | 21.9 | 24 | A |
| GLN OE1 | 239 | 205.2 | 116.8 | 22.4 | 25 | A |
| GLN NE2 | 239 | 206.3 | 117.9 | 20.8 | 23 | A |
| GLN C | 239 | 207.9 | 114.3 | 24.0 | 24 | A |
| GLN O | 239 | 207.9 | 113.9 | 22.8 | 24 | A |
| ARG N | 240 | 208.8 | 113.9 | 24.9 | 25 | A |
| ARG CA | 240 | 209.8 | 113.0 | 24.7 | 25 | A |
| ARG CB | 240 | 210.7 | 112.8 | 25.9 | 25 | A |
| ARG CG | 240 | 211.9 | 111.9 | 25.7 | 26 | A |
| ARG CD | 240 | 212.7 | 111.7 | 27.0 | 26 | A |
| ARG NE | 240 | 214.0 | 111.2 | 26.6 | 27 | A |
| ARG CZ | 240 | 215.0 | 111.9 | 26.0 | 29 | A |
| ARG NH1 | 240 | 214.7 | 113.2 | 25.8 | 30 | A |
| ARG NH2 | 240 | 216.0 | 111.4 | 25.5 | 30 | A |
| ARG C | 240 | 209.2 | 111.6 | 24.3 | 26 | A |
| ARG O | 240 | 209.6 | 111.0 | 23.4 | 30 | A |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| HIS N | 241 | 208.2 | 111.2 | 25.1 | 26 | A |
| HIS CA | 241 | 207.4 | 110.0 | 24.9 | 24 | A |
| HIS CB | 241 | 206.5 | 109.7 | 26.0 | 24 | A |
| HIS CG | 241 | 205.9 | 108.4 | 26.0 | 24 | A |
| HIS CD2 | 241 | 206.2 | 107.2 | 26.6 | 24 | A |
| HIS ND1 | 241 | 204.8 | 108.1 | 25.3 | 23 | A |
| HIS CE1 | 241 | 204.4 | 106.8 | 25.4 | 24 | A |
| HIS NE2 | 241 | 205.3 | 106.3 | 26.3 | 24 | A |
| HIS C | 241 | 206.7 | 110.0 | 23.6 | 24 | A |
| HIS O | 241 | 206.7 | 109.1 | 22.8 | 25 | A |
| PHE N | 242 | 206.0 | 111.2 | 23.3 | 24 | A |
| PHE CA | 242 | 205.2 | 111.3 | 22.0 | 23 | A |
| PHE CB | 242 | 204.6 | 112.7 | 22.0 | 22 | A |
| PHE CG | 242 | 203.9 | 113.0 | 20.7 | 22 | A |
| PHE CD1 | 242 | 202.7 | 112.5 | 20.4 | 21 | A |
| PHE CD2 | 242 | 204.4 | 114.0 | 19.8 | 22 | A |
| PHE CE1 | 242 | 202.0 | 112.9 | 19.2 | 21 | A |
| PHE CE2 | 242 | 203.8 | 114.4 | 18.7 | 22 | A |
| PHE CZ | 242 | 202.5 | 113.8 | 18.4 | 21 | A |
| PHE C | 242 | 206.2 | 111.2 | 20.8 | 24 | A |
| PHE O | 242 | 205.8 | 110.5 | 19.9 | 24 | A |
| VAL N | 243 | 207.3 | 111.8 | 20.9 | 25 | A |
| VAL CA | 243 | 208.3 | 111.7 | 19.8 | 27 | A |
| VAL CB | 243 | 209.5 | 112.7 | 20.0 | 27 | A |
| VAL CG1 | 243 | 210.6 | 112.5 | 19.0 | 26 | A |
| VAL CG2 | 243 | 208.9 | 114.1 | 20.0 | 27 | A |
| VAL C | 243 | 208.8 | 110.3 | 19.6 | 28 | A |
| VAL O | 243 | 208.7 | 109.7 | 18.5 | 28 | A |
| ILE N | 244 | 209.3 | 109.7 | 20.7 | 28 | A |
| ILE CA | 244 | 209.9 | 108.3 | 20.6 | 28 | A |
| ILE CB | 244 | 210.5 | 107.9 | 21.9 | 27 | A |
| ILE CG2 | 244 | 211.1 | 106.5 | 21.9 | 27 | A |
| ILE CG1 | 244 | 211.7 | 108.8 | 22.2 | 25 | A |
| ILE CD1 | 244 | 212.4 | 108.5 | 23.5 | 23 | A |
| ILE C | 244 | 208.8 | 107.4 | 20.2 | 29 | A |
| ILE O | 244 | 209.0 | 106.7 | 19.2 | 29 | A |
| SER N | 245 | 207.6 | 107.4 | 20.8 | 29 | A |
| SER CA | 245 | 206.6 | 106.5 | 20.4 | 31 | A |
| SER CB | 245 | 205.3 | 106.9 | 21.2 | 31 | A |
| SER OG | 245 | 205.5 | 106.7 | 22.6 | 35 | A |
| SER C | 245 | 206.2 | 106.6 | 19.0 | 33 | A |
| SER O | 245 | 205.9 | 105.5 | 18.4 | 35 | A |
| ASN N | 246 | 206.2 | 107.7 | 18.4 | 34 | A |
| ASN CA | 246 | 205.8 | 107.8 | 17.0 | 34 | A |
| ASN CB | 246 | 205.0 | 109.1 | 16.7 | 33 | A |
| ASN CG | 246 | 203.7 | 109.1 | 17.6 | 32 | A |
| ASN OD1 | 246 | 203.7 | 109.7 | 18.7 | 32 | A |
| ASN ND2 | 246 | 202.6 | 108.6 | 17.1 | 32 | A |
| ASN C | 246 | 206.9 | 107.7 | 15.9 | 34 | A |
| ASN O | 246 | 206.6 | 107.7 | 14.7 | 34 | A |
| THR N | 247 | 208.1 | 107.6 | 16.4 | 34 | A |
| THR CA | 247 | 209.2 | 107.4 | 15.5 | 34 | A |
| THR CB | 247 | 210.3 | 108.5 | 15.8 | 33 | A |
| THR OG1 | 247 | 210.7 | 108.6 | 17.2 | 33 | A |
| THR CG2 | 247 | 209.8 | 109.9 | 15.4 | 32 | A |
| THR C | 247 | 209.8 | 106.0 | 15.6 | 35 | A |
| THR O | 247 | 209.3 | 105.1 | 15.0 | 36 | A |
| THR N | 248 | 210.7 | 105.8 | 16.6 | 36 | A |
| THR CA | 248 | 211.3 | 104.4 | 16.8 | 36 | A |
| THR CB | 248 | 212.7 | 104.6 | 17.4 | 36 | A |
| THR OG1 | 248 | 212.5 | 105.1 | 18.8 | 37 | A |
| THR CG2 | 248 | 213.6 | 105.5 | 16.7 | 36 | A |
| THR C | 248 | 210.5 | 103.5 | 17.6 | 37 | A |
| THR O | 248 | 210.5 | 102.3 | 17.4 | 39 | A |
| GLY N | 249 | 209.9 | 104.0 | 18.7 | 38 | A |
| GLY CA | 249 | 209.1 | 103.1 | 19.6 | 37 | A |
| GLY C | 249 | 210.1 | 102.7 | 20.7 | 38 | A |
| GLY O | 249 | 211.3 | 103.0 | 20.6 | 37 | A |
| TYR N | 250 | 209.6 | 102.0 | 21.7 | 40 | A |
| TYR CA | 250 | 210.4 | 101.5 | 22.8 | 42 | A |
| TYR CB | 250 | 209.8 | 101.8 | 24.1 | 41 | A |
| TYR CG | 250 | 209.7 | 103.3 | 24.4 | 41 | A |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| TYR CD1 | 250 | 208.7 | 104.1 | 23.8 | 40 | A |
| TYR CE1 | 250 | 208.5 | 105.4 | 24.1 | 40 | A |
| TYR CD2 | 250 | 210.5 | 103.9 | 25.3 | 40 | A |
| TYR CE2 | 250 | 210.4 | 105.2 | 25.7 | 41 | A |
| TYR CZ | 250 | 209.4 | 106.0 | 25.1 | 40 | A |
| TYR OH | 250 | 209.2 | 107.3 | 25.4 | 40 | A |
| TYR C | 250 | 210.7 | 100.0 | 22.7 | 44 | A |
| TYR O | 250 | 211.1 | 99.4 | 23.7 | 44 | A |
| SER N | 251 | 210.3 | 99.4 | 21.6 | 46 | A |
| SER CA | 251 | 210.6 | 98.0 | 21.4 | 48 | A |
| SER CB | 251 | 209.7 | 97.5 | 20.2 | 49 | A |
| SER OG | 251 | 208.4 | 97.6 | 20.5 | 51 | A |
| SER C | 251 | 212.0 | 97.7 | 21.1 | 49 | A |
| SER O | 251 | 212.6 | 96.7 | 21.5 | 50 | A |
| ASP N | 252 | 212.6 | 98.7 | 20.4 | 51 | A |
| ASP CA | 252 | 214.1 | 98.7 | 20.2 | 52 | A |
| ASP CB | 252 | 214.5 | 99.9 | 19.3 | 55 | A |
| ASP CG | 252 | 215.9 | 99.8 | 18.8 | 57 | A |
| ASP OD1 | 252 | 216.6 | 98.8 | 19.0 | 59 | A |
| ASP OD2 | 252 | 216.3 | 100.8 | 18.1 | 58 | A |
| ASP C | 252 | 214.8 | 98.7 | 21.5 | 52 | A |
| ASP O | 252 | 214.7 | 99.7 | 22.2 | 51 | A |
| ARG N | 253 | 215.4 | 97.5 | 21.9 | 52 | A |
| ARG CA | 253 | 216.1 | 97.4 | 23.1 | 51 | A |
| ARG CB | 253 | 216.8 | 96.0 | 23.1 | 54 | A |
| ARG CG | 253 | 215.9 | 94.8 | 23.2 | 58 | A |
| ARG CD | 253 | 216.8 | 93.5 | 22.9 | 60 | A |
| ARG NE | 253 | 216.0 | 92.3 | 23.2 | 62 | A |
| ARG CZ | 253 | 216.3 | 91.1 | 22.6 | 63 | A |
| ARG NH1 | 253 | 217.2 | 91.0 | 21.6 | 62 | A |
| ARG NH2 | 253 | 215.6 | 90.1 | 22.9 | 63 | A |
| ARG C | 253 | 217.2 | 98.4 | 23.3 | 49 | A |
| ARG O | 253 | 217.6 | 98.8 | 24.4 | 48 | A |
| ALA N | 254 | 217.7 | 98.9 | 22.1 | 47 | A |
| ALA CA | 254 | 218.7 | 100.0 | 22.2 | 45 | A |
| ALA CB | 254 | 219.4 | 100.0 | 20.8 | 45 | A |
| ALA C | 254 | 218.1 | 101.3 | 22.5 | 43 | A |
| ALA O | 254 | 218.7 | 102.1 | 23.3 | 43 | A |
| VAL N | 255 | 217.0 | 101.6 | 22.0 | 43 | A |
| VAL CA | 255 | 216.3 | 102.9 | 22.3 | 42 | A |
| VAL CB | 255 | 215.1 | 103.1 | 21.4 | 42 | A |
| VAL CG1 | 255 | 214.3 | 104.3 | 21.9 | 42 | A |
| VAL CG2 | 255 | 215.5 | 103.3 | 20.0 | 42 | A |
| VAL C | 255 | 215.8 | 102.8 | 23.8 | 42 | A |
| VAL O | 255 | 216.0 | 103.7 | 24.5 | 43 | A |
| LEU N | 256 | 215.3 | 101.6 | 24.1 | 42 | A |
| LEU CA | 256 | 214.8 | 101.3 | 25.5 | 42 | A |
| LEU CB | 256 | 214.3 | 99.9 | 25.6 | 41 | A |
| LEU CG | 256 | 213.6 | 99.4 | 26.8 | 41 | A |
| LEU CD1 | 256 | 212.3 | 100.2 | 27.2 | 40 | A |
| LEU CD2 | 256 | 213.2 | 98.0 | 26.5 | 41 | A |
| LEU C | 256 | 216.0 | 101.5 | 26.5 | 44 | A |
| LEU O | 256 | 215.9 | 102.3 | 27.4 | 44 | A |
| GLU N | 257 | 217.1 | 100.9 | 26.2 | 45 | A |
| GLU CA | 257 | 218.3 | 101.0 | 27.1 | 46 | A |
| GLU CB | 257 | 219.4 | 100.1 | 26.5 | 48 | A |
| GLU CG | 257 | 220.8 | 100.4 | 27.1 | 51 | A |
| GLU CD | 257 | 220.9 | 99.7 | 28.5 | 54 | A |
| GLU OE1 | 257 | 220.3 | 100.1 | 29.5 | 54 | A |
| GLU OE2 | 257 | 221.8 | 98.8 | 28.6 | 56 | A |
| GLU C | 257 | 218.7 | 102.5 | 27.2 | 44 | A |
| GLU O | 257 | 218.9 | 102.9 | 28.4 | 44 | A |
| ARG N | 258 | 218.8 | 103.1 | 26.1 | 44 | A |
| ARG CA | 258 | 219.2 | 104.5 | 26.1 | 43 | A |
| ARG CB | 258 | 219.1 | 105.1 | 24.6 | 42 | A |
| ARG CG | 258 | 219.6 | 106.5 | 24.5 | 43 | A |
| ARG CD | 258 | 219.1 | 107.2 | 23.2 | 43 | A |
| ARG NE | 258 | 217.7 | 107.4 | 23.2 | 44 | A |
| ARG CZ | 258 | 217.0 | 107.4 | 22.1 | 44 | A |
| ARG NH1 | 258 | 217.5 | 107.2 | 20.9 | 44 | A |
| ARG NH2 | 258 | 215.6 | 107.5 | 22.1 | 44 | A |
| ARG C | 258 | 218.4 | 105.4 | 27.0 | 42 | A |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| ARG O | 258 | 218.8 | 106.3 | 27.7 | 43 | A |
| GLU N | 259 | 217.0 | 105.2 | 26.9 | 41 | A |
| GLU CA | 259 | 216.0 | 105.9 | 27.6 | 40 | A |
| GLU CB | 259 | 214.6 | 105.6 | 27.1 | 40 | A |
| GLU CG | 259 | 214.4 | 106.3 | 25.7 | 40 | A |
| GLU CD | 259 | 214.6 | 107.8 | 25.7 | 40 | A |
| GLU OE1 | 259 | 213.9 | 108.5 | 26.5 | 40 | A |
| GLU OE2 | 259 | 215.5 | 108.3 | 25.0 | 38 | A |
| GLU C | 259 | 216.1 | 105.6 | 29.1 | 39 | A |
| GLU O | 259 | 216.0 | 106.5 | 29.9 | 39 | A |
| VAL N | 260 | 216.1 | 104.3 | 29.4 | 40 | A |
| VAL CA | 260 | 216.2 | 103.8 | 30.8 | 41 | A |
| VAL CB | 260 | 216.0 | 102.3 | 30.9 | 41 | A |
| VAL CG1 | 260 | 216.3 | 101.8 | 32.3 | 41 | A |
| VAL CG2 | 260 | 214.6 | 101.9 | 30.5 | 41 | A |
| VAL C | 260 | 217.4 | 104.3 | 31.5 | 42 | A |
| VAL O | 260 | 217.4 | 104.8 | 32.6 | 42 | A |
| GLN N | 261 | 218.5 | 104.2 | 30.8 | 43 | A |
| GLN CA | 261 | 219.8 | 104.7 | 31.3 | 44 | A |
| GLN CB | 261 | 220.9 | 104.4 | 30.4 | 47 | A |
| GLN CG | 261 | 222.3 | 104.2 | 31.1 | 51 | A |
| GLN CD | 261 | 222.5 | 102.8 | 31.7 | 52 | A |
| GLN OE1 | 261 | 222.4 | 101.8 | 31.0 | 53 | A |
| GLN NE2 | 261 | 222.7 | 102.8 | 33.1 | 53 | A |
| GLN C | 261 | 219.7 | 106.2 | 31.6 | 43 | A |
| GLN O | 261 | 220.0 | 106.7 | 32.7 | 44 | A |
| TYR N | 262 | 219.4 | 107.0 | 30.5 | 42 | A |
| TYR CA | 262 | 219.2 | 108.4 | 30.6 | 40 | A |
| TYR CB | 262 | 218.6 | 109.0 | 29.3 | 40 | A |
| TYR CG | 262 | 218.1 | 110.4 | 29.5 | 40 | A |
| TYR CD1 | 262 | 219.0 | 111.4 | 29.6 | 40 | A |
| TYR CE1 | 262 | 218.5 | 112.7 | 29.8 | 39 | A |
| TYR CD2 | 262 | 216.7 | 110.7 | 29.6 | 40 | A |
| TYR CE2 | 262 | 216.3 | 112.0 | 29.8 | 39 | A |
| TYR CZ | 262 | 217.2 | 113.0 | 29.8 | 39 | A |
| TYR OH | 262 | 216.8 | 114.3 | 30.0 | 38 | A |
| TYR C | 262 | 218.4 | 108.9 | 31.8 | 39 | A |
| TYR O | 262 | 218.7 | 109.8 | 32.5 | 40 | A |
| THR N | 263 | 217.2 | 108.2 | 31.9 | 39 | A |
| THR CA | 263 | 216.2 | 108.5 | 32.9 | 39 | A |
| THR CB | 263 | 214.9 | 107.7 | 32.7 | 38 | A |
| THR OG1 | 263 | 214.5 | 107.9 | 31.4 | 37 | A |
| THR CG2 | 263 | 213.8 | 108.2 | 33.6 | 37 | A |
| THR C | 263 | 216.8 | 108.2 | 34.3 | 40 | A |
| THR O | 263 | 216.7 | 109.0 | 35.2 | 41 | A |
| LEU N | 264 | 217.4 | 107.0 | 34.5 | 41 | A |
| LEU CA | 264 | 218.1 | 106.7 | 35.7 | 43 | A |
| LEU CB | 264 | 218.7 | 105.3 | 35.6 | 43 | A |
| LEU CG | 264 | 217.8 | 104.1 | 35.6 | 42 | A |
| LEU CD1 | 264 | 218.7 | 102.8 | 35.4 | 42 | A |
| LEU CD2 | 264 | 217.0 | 103.9 | 36.9 | 42 | A |
| LEU C | 264 | 219.1 | 107.7 | 36.1 | 44 | A |
| LEU O | 264 | 219.2 | 108.2 | 37.2 | 44 | A |
| GLU N | 265 | 219.9 | 108.2 | 35.1 | 46 | A |
| GLU CA | 265 | 220.9 | 109.2 | 35.3 | 48 | A |
| GLU CB | 265 | 221.7 | 109.5 | 34.0 | 50 | A |
| GLU CG | 265 | 222.2 | 108.3 | 33.3 | 54 | A |
| GLU CD | 265 | 223.0 | 107.4 | 34.2 | 57 | A |
| GLU OE1 | 265 | 222.5 | 106.3 | 34.7 | 57 | A |
| GLU OE2 | 265 | 224.2 | 107.7 | 34.4 | 58 | A |
| GLU C | 265 | 220.2 | 110.5 | 35.8 | 48 | A |
| GLU O | 265 | 220.7 | 111.1 | 36.7 | 49 | A |
| MET N | 266 | 219.0 | 110.8 | 35.3 | 47 | A |
| MET CA | 266 | 218.3 | 112.0 | 35.7 | 45 | A |
| MET CB | 266 | 217.1 | 112.3 | 34.7 | 44 | A |
| MET CG | 266 | 217.5 | 112.6 | 33.3 | 44 | A |
| MET SD | 266 | 219.0 | 113.6 | 33.3 | 44 | A |
| MET CE | 266 | 218.3 | 115.1 | 32.9 | 45 | A |
| MET C | 266 | 217.8 | 111.8 | 37.1 | 45 | A |
| MET O | 266 | 217.7 | 112.8 | 37.8 | 45 | A |
| ILE N | 267 | 217.4 | 110.6 | 37.4 | 45 | A |
| ILE CA | 267 | 216.9 | 110.3 | 38.7 | 46 | A |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| ILE CB | 267 | 216.4 | 108.8 | 38.8 | 45 | A |
| ILE CG2 | 267 | 216.0 | 108.5 | 40.2 | 45 | A |
| ILE CG1 | 267 | 215.2 | 108.7 | 37.9 | 44 | A |
| ILE CD1 | 267 | 214.7 | 107.3 | 37.7 | 44 | A |
| ILE C | 267 | 218.0 | 110.5 | 39.8 | 47 | A |
| ILE O | 267 | 217.9 | 111.2 | 40.8 | 47 | A |
| LYS N | 268 | 219.2 | 109.9 | 39.5 | 48 | A |
| LYS CA | 268 | 220.3 | 110.1 | 40.3 | 50 | A |
| LYS CB | 268 | 221.6 | 109.5 | 39.7 | 52 | A |
| LYS CG | 268 | 221.4 | 108.0 | 39.5 | 56 | A |
| LYS CD | 268 | 222.5 | 107.3 | 38.7 | 59 | A |
| LYS CE | 268 | 222.2 | 105.9 | 38.2 | 61 | A |
| LYS NZ | 268 | 223.3 | 105.2 | 37.6 | 62 | A |
| LYS C | 268 | 220.6 | 111.5 | 40.7 | 50 | A |
| LYS O | 268 | 220.7 | 111.9 | 41.8 | 51 | A |
| LEU N | 269 | 220.5 | 112.4 | 39.7 | 50 | A |
| LEU CA | 269 | 220.6 | 113.9 | 39.9 | 48 | A |
| LEU CB | 269 | 220.8 | 114.6 | 38.5 | 48 | A |
| LEU CG | 269 | 221.8 | 114.2 | 37.5 | 48 | A |
| LEU CD1 | 269 | 222.2 | 115.5 | 36.7 | 48 | A |
| LEU CD2 | 269 | 223.0 | 113.6 | 38.0 | 49 | A |
| LEU C | 269 | 219.6 | 114.6 | 40.7 | 47 | A |
| LEU O | 269 | 219.9 | 115.4 | 41.6 | 48 | A |
| VAL N | 270 | 218.3 | 114.3 | 40.3 | 44 | A |
| VAL CA | 270 | 217.2 | 115.0 | 41.1 | 43 | A |
| VAL CB | 270 | 216.5 | 116.1 | 40.2 | 41 | A |
| VAL CG1 | 270 | 215.6 | 117.0 | 41.0 | 39 | A |
| VAL CG2 | 270 | 217.5 | 116.9 | 39.4 | 39 | A |
| VAL C | 270 | 216.2 | 113.9 | 41.5 | 43 | A |
| VAL O | 270 | 215.1 | 113.8 | 41.0 | 43 | A |
| PRO N | 271 | 216.7 | 113.1 | 42.5 | 44 | A |
| PRO CD | 271 | 217.9 | 113.3 | 43.3 | 44 | A |
| PRO CA | 271 | 215.9 | 112.0 | 43.2 | 44 | A |
| PRO CB | 271 | 216.8 | 111.8 | 44.4 | 44 | A |
| PRO CG | 271 | 218.1 | 112.0 | 44.0 | 44 | A |
| PRO C | 271 | 214.5 | 112.2 | 43.5 | 44 | A |
| PRO O | 271 | 213.7 | 111.3 | 43.6 | 44 | A |
| HIS N | 272 | 214.1 | 113.5 | 43.8 | 44 | A |
| HIS CA | 272 | 212.7 | 113.8 | 44.2 | 43 | A |
| HIS CB | 272 | 212.7 | 114.7 | 45.4 | 45 | A |
| HIS CG | 272 | 213.2 | 114.1 | 46.6 | 46 | A |
| HIS CD2 | 272 | 214.4 | 113.9 | 47.2 | 46 | A |
| HIS ND1 | 272 | 212.3 | 113.4 | 47.5 | 47 | A |
| HIS CE1 | 272 | 213.0 | 112.9 | 48.5 | 47 | A |
| HIS NE2 | 272 | 214.3 | 113.2 | 48.3 | 47 | A |
| HIS C | 272 | 211.9 | 114.4 | 43.0 | 42 | A |
| HIS O | 272 | 210.8 | 114.9 | 43.3 | 42 | A |
| ASN N | 273 | 212.4 | 114.3 | 41.8 | 39 | A |
| ASN CA | 273 | 211.7 | 114.8 | 40.6 | 37 | A |
| ASN CB | 273 | 212.7 | 115.2 | 39.5 | 35 | A |
| ASN CG | 273 | 212.0 | 115.5 | 38.2 | 33 | A |
| ASN OD1 | 273 | 210.8 | 116.0 | 38.2 | 32 | A |
| ASN ND2 | 273 | 212.7 | 115.4 | 37.1 | 32 | A |
| ASN C | 273 | 210.9 | 113.7 | 40.2 | 35 | A |
| ASN O | 273 | 211.3 | 112.7 | 39.6 | 35 | A |
| GLU N | 274 | 209.6 | 113.8 | 40.4 | 35 | A |
| GLU CA | 274 | 208.6 | 112.8 | 40.0 | 34 | A |
| GLU CB | 274 | 207.2 | 113.2 | 40.5 | 35 | A |
| GLU CG | 274 | 206.2 | 112.2 | 40.3 | 37 | A |
| GLU CD | 274 | 204.9 | 112.6 | 40.8 | 39 | A |
| GLU OE1 | 274 | 203.9 | 112.2 | 40.3 | 41 | A |
| GLU OE2 | 274 | 204.9 | 113.4 | 41.8 | 41 | A |
| GLU C | 274 | 208.5 | 112.5 | 38.5 | 34 | A |
| GLU O | 274 | 208.2 | 111.4 | 38.1 | 35 | A |
| SER N | 275 | 208.8 | 113.5 | 37.7 | 33 | A |
| SER CA | 275 | 208.6 | 113.3 | 36.2 | 31 | A |
| SER CB | 275 | 208.9 | 114.6 | 35.4 | 31 | A |
| SER OG | 275 | 207.8 | 115.5 | 35.6 | 31 | A |
| SER C | 275 | 209.5 | 112.2 | 35.7 | 32 | A |
| SER O | 275 | 209.1 | 111.4 | 34.9 | 31 | A |
| ALA N | 276 | 210.8 | 112.2 | 36.1 | 32 | A |
| ALA CA | 276 | 211.7 | 111.2 | 35.6 | 32 | A |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| ALA CB | 276 | 213.1 | 111.5 | 36.0 | 32 | A |
| ALA C | 276 | 211.2 | 109.8 | 36.1 | 32 | A |
| ALA O | 276 | 211.3 | 108.8 | 35.4 | 32 | A |
| TRP N | 277 | 210.6 | 109.8 | 37.3 | 33 | A |
| TRP CA | 277 | 210.1 | 108.6 | 37.9 | 34 | A |
| TRP CB | 277 | 209.7 | 108.8 | 39.3 | 35 | A |
| TRP CG | 277 | 210.9 | 108.7 | 40.2 | 37 | A |
| TRP CD2 | 277 | 211.6 | 107.5 | 40.6 | 38 | A |
| TRP CE2 | 277 | 212.7 | 107.9 | 41.4 | 38 | A |
| TRP CE3 | 277 | 211.5 | 106.1 | 40.3 | 37 | A |
| TRP CD1 | 277 | 211.6 | 109.7 | 40.8 | 38 | A |
| TRP NE1 | 277 | 212.6 | 109.3 | 41.6 | 39 | A |
| TRP CZ2 | 277 | 213.6 | 107.0 | 42.0 | 38 | A |
| TRP CZ3 | 277 | 212.4 | 105.2 | 40.9 | 37 | A |
| TRP CH2 | 277 | 213.4 | 105.6 | 41.7 | 37 | A |
| TRP C | 277 | 208.9 | 108.0 | 37.1 | 33 | A |
| TRP O | 277 | 208.8 | 106.9 | 36.9 | 33 | A |
| ASN N | 278 | 208.0 | 108.9 | 36.8 | 34 | A |
| ASN CA | 278 | 206.8 | 108.6 | 36.1 | 34 | A |
| ASN CB | 278 | 205.8 | 109.8 | 36.1 | 34 | A |
| ASN CG | 278 | 205.2 | 110.1 | 37.4 | 35 | A |
| ASN OD1 | 278 | 205.5 | 109.4 | 38.4 | 35 | A |
| ASN ND2 | 278 | 204.5 | 111.2 | 37.5 | 36 | A |
| ASN C | 278 | 207.1 | 108.1 | 34.7 | 33 | A |
| ASN O | 278 | 206.3 | 107.3 | 34.1 | 33 | A |
| TYR N | 279 | 208.2 | 108.7 | 34.1 | 32 | A |
| TYR CA | 279 | 208.6 | 108.3 | 32.8 | 31 | A |
| TYR CB | 279 | 209.5 | 109.4 | 32.2 | 31 | A |
| TYR CG | 279 | 210.0 | 109.1 | 30.8 | 31 | A |
| TYR CD1 | 279 | 209.1 | 109.3 | 29.7 | 30 | A |
| TYR CE1 | 279 | 209.5 | 109.0 | 28.4 | 30 | A |
| TYR CD2 | 279 | 211.3 | 108.7 | 30.5 | 30 | A |
| TYR CE2 | 279 | 211.7 | 108.4 | 29.2 | 31 | A |
| TYR CZ | 279 | 210.8 | 108.6 | 28.2 | 30 | A |
| TYR OH | 279 | 211.3 | 108.4 | 26.9 | 31 | A |
| TYR C | 279 | 209.3 | 106.9 | 32.8 | 32 | A |
| TYR O | 279 | 209.0 | 106.1 | 31.9 | 33 | A |
| LEU N | 280 | 210.1 | 106.7 | 33.9 | 33 | A |
| LEU CA | 280 | 210.8 | 105.4 | 34.0 | 33 | A |
| LEU CB | 280 | 211.6 | 105.3 | 35.3 | 33 | A |
| LEU CG | 280 | 212.4 | 104.1 | 35.6 | 33 | A |
| LEU CD1 | 280 | 213.4 | 103.8 | 34.4 | 32 | A |
| LEU CD2 | 280 | 213.1 | 104.2 | 36.9 | 32 | A |
| LEU C | 280 | 209.7 | 104.2 | 34.1 | 34 | A |
| LEU O | 280 | 209.8 | 103.2 | 33.4 | 33 | A |
| LYS N | 281 | 208.7 | 104.5 | 34.9 | 35 | A |
| LYS CA | 281 | 207.7 | 103.5 | 35.1 | 37 | A |
| LYS CB | 281 | 206.8 | 103.9 | 36.2 | 38 | A |
| LYS CG | 281 | 205.7 | 102.9 | 36.6 | 40 | A |
| LYS CD | 281 | 205.1 | 103.2 | 37.9 | 42 | A |
| LYS CE | 281 | 204.3 | 104.5 | 37.8 | 44 | A |
| LYS NZ | 281 | 204.2 | 105.2 | 39.2 | 44 | A |
| LYS C | 281 | 206.9 | 103.4 | 33.8 | 38 | A |
| LYS O | 281 | 206.7 | 102.3 | 33.3 | 39 | A |
| GLY N | 282 | 206.5 | 104.6 | 33.2 | 38 | A |
| GLY CA | 282 | 205.8 | 104.6 | 32.0 | 37 | A |
| GLY C | 282 | 206.3 | 103.8 | 30.8 | 38 | A |
| GLY O | 282 | 205.6 | 103.3 | 30.1 | 39 | A |
| ILE N | 283 | 207.7 | 103.8 | 30.6 | 39 | A |
| ILE CA | 283 | 208.2 | 103.1 | 29.5 | 40 | A |
| ILE CB | 283 | 209.5 | 103.8 | 29.0 | 39 | A |
| ILE CG2 | 283 | 209.2 | 105.2 | 28.6 | 39 | A |
| ILE CG1 | 283 | 210.6 | 103.8 | 30.0 | 37 | A |
| ILE CD1 | 283 | 211.9 | 104.4 | 29.6 | 36 | A |
| ILE C | 283 | 208.5 | 101.6 | 29.7 | 42 | A |
| ILE O | 283 | 208.7 | 100.8 | 28.8 | 43 | A |
| LEU N | 284 | 208.6 | 101.2 | 31.0 | 46 | A |
| LEU CA | 284 | 208.9 | 99.8 | 31.4 | 47 | A |
| LEU CB | 284 | 209.8 | 99.6 | 32.5 | 46 | A |
| LEU CG | 284 | 211.2 | 100.2 | 32.4 | 46 | A |
| LEU CD1 | 284 | 212.0 | 100.1 | 33.7 | 46 | A |
| LEU CD2 | 284 | 212.0 | 99.5 | 31.3 | 46 | A |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| LEU C | 284 | 207.6 | 99.0 | 31.7 | 49 | A |
| LEU O | 284 | 207.4 | 97.9 | 31.4 | 49 | A |
| GLN N | 285 | 206.7 | 99.7 | 32.4 | 53 | A |
| GLN CA | 285 | 205.4 | 99.2 | 32.9 | 56 | A |
| GLN CB | 285 | 204.5 | 100.3 | 33.5 | 58 | A |
| GLN CG | 285 | 203.8 | 101.2 | 32.5 | 59 | A |
| GLN CD | 285 | 202.8 | 102.2 | 33.1 | 61 | A |
| GLN OE1 | 285 | 202.0 | 102.8 | 32.4 | 62 | A |
| GLN NE2 | 285 | 202.9 | 102.4 | 34.4 | 61 | A |
| GLN C | 285 | 204.6 | 98.5 | 31.8 | 58 | A |
| GLN O | 285 | 203.7 | 97.8 | 32.0 | 59 | A |
| ASP N | 286 | 204.9 | 98.9 | 30.5 | 61 | A |
| ASP CA | 286 | 204.2 | 98.3 | 29.4 | 63 | A |
| ASP CB | 286 | 203.8 | 99.4 | 28.4 | 66 | A |
| ASP CG | 286 | 202.3 | 99.7 | 28.3 | 68 | A |
| ASP OD1 | 286 | 201.8 | 99.5 | 27.1 | 69 | A |
| ASP OD2 | 286 | 201.7 | 100.0 | 29.3 | 69 | A |
| ASP C | 286 | 204.9 | 97.1 | 28.8 | 64 | A |
| ASP O | 286 | 205.2 | 97.1 | 27.7 | 65 | A |
| ARG N | 287 | 205.1 | 96.1 | 29.7 | 63 | A |
| ARG CA | 287 | 205.8 | 94.8 | 29.4 | 62 | A |
| ARG CB | 287 | 207.1 | 95.0 | 28.7 | 63 | A |
| ARG CG | 287 | 207.7 | 93.6 | 28.4 | 65 | A |
| ARG CD | 287 | 209.2 | 93.6 | 28.1 | 67 | A |
| ARG NE | 287 | 209.9 | 92.4 | 28.4 | 69 | A |
| ARG CZ | 287 | 210.7 | 91.7 | 27.6 | 69 | A |
| ARG NH1 | 287 | 211.1 | 92.3 | 26.4 | 69 | A |
| ARG NH2 | 287 | 211.2 | 90.5 | 27.9 | 69 | A |
| ARG C | 287 | 205.9 | 94.1 | 30.7 | 60 | A |
| ARG O | 287 | 206.0 | 92.8 | 30.8 | 60 | A |
| GLY N | 288 | 206.0 | 94.8 | 31.8 | 58 | A |
| GLY CA | 288 | 206.1 | 94.3 | 33.1 | 55 | A |
| GLY C | 288 | 207.4 | 94.6 | 33.7 | 54 | A |
| GLY O | 288 | 208.5 | 94.3 | 33.2 | 55 | A |
| LEU N | 289 | 207.4 | 95.3 | 34.9 | 52 | A |
| LEU CA | 289 | 208.6 | 95.7 | 35.6 | 51 | A |
| LEU CB | 289 | 208.3 | 96.5 | 36.8 | 50 | A |
| LEU CG | 289 | 208.3 | 98.1 | 36.8 | 49 | A |
| LEU CD1 | 289 | 208.1 | 98.6 | 35.4 | 49 | A |
| LEU CD2 | 289 | 207.2 | 98.6 | 37.7 | 48 | A |
| LEU C | 289 | 209.5 | 94.4 | 36.0 | 51 | A |
| LEU O | 289 | 210.7 | 94.5 | 36.0 | 52 | A |
| SER N | 290 | 208.8 | 93.3 | 36.2 | 51 | A |
| SER CA | 290 | 209.4 | 92.1 | 36.6 | 51 | A |
| SER CB | 290 | 208.4 | 91.1 | 37.2 | 51 | A |
| SER OG | 290 | 207.4 | 90.8 | 36.3 | 52 | A |
| SER C | 290 | 210.3 | 91.4 | 35.5 | 50 | A |
| SER O | 290 | 211.0 | 90.4 | 35.8 | 49 | A |
| ARG N | 291 | 210.1 | 91.8 | 34.2 | 50 | A |
| ARG CA | 291 | 210.9 | 91.2 | 33.1 | 50 | A |
| ARG CB | 291 | 210.1 | 91.4 | 31.8 | 52 | A |
| ARG CG | 291 | 209.1 | 90.3 | 31.6 | 56 | A |
| ARG CD | 291 | 208.4 | 90.5 | 30.3 | 60 | A |
| ARG NE | 291 | 208.2 | 89.2 | 29.6 | 64 | A |
| ARG CZ | 291 | 208.1 | 89.0 | 28.3 | 65 | A |
| ARG NH1 | 291 | 207.9 | 87.8 | 27.7 | 66 | A |
| ARG NH2 | 291 | 208.3 | 90.1 | 27.5 | 66 | A |
| ARG C | 291 | 212.3 | 91.9 | 33.0 | 49 | A |
| ARG O | 291 | 213.0 | 91.7 | 32.1 | 48 | A |
| TYR N | 292 | 212.6 | 92.7 | 34.0 | 47 | A |
| TYR CA | 292 | 213.8 | 93.4 | 34.2 | 46 | A |
| TYR CB | 292 | 213.6 | 94.9 | 33.9 | 43 | A |
| TYR CG | 292 | 212.9 | 95.2 | 32.6 | 42 | A |
| TYR CD1 | 292 | 211.5 | 95.5 | 32.6 | 41 | A |
| TYR CE1 | 292 | 210.9 | 95.6 | 31.3 | 41 | A |
| TYR CD2 | 292 | 213.6 | 95.1 | 31.4 | 41 | A |
| TYR CE2 | 292 | 213.0 | 95.2 | 30.2 | 40 | A |
| TYR CZ | 292 | 211.6 | 95.5 | 30.2 | 40 | A |
| TYR OH | 292 | 211.0 | 95.8 | 28.9 | 39 | A |
| TYR C | 292 | 214.4 | 93.2 | 35.6 | 46 | A |
| TYR O | 292 | 214.2 | 93.9 | 36.5 | 46 | A |
| PRO N | 293 | 215.1 | 92.0 | 35.7 | 47 | A |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| PRO CD | 293 | 215.3 | 91.0 | 34.6 | 46 | A |
| PRO CA | 293 | 215.7 | 91.6 | 37.0 | 47 | A |
| PRO CB | 293 | 216.2 | 90.2 | 36.6 | 46 | A |
| PRO CG | 293 | 216.5 | 90.3 | 35.2 | 45 | A |
| PRO C | 293 | 216.7 | 92.5 | 37.6 | 48 | A |
| PRO O | 293 | 216.7 | 92.6 | 38.8 | 50 | A |
| ASN N | 294 | 217.6 | 93.1 | 36.8 | 49 | A |
| ASN CA | 294 | 218.7 | 94.0 | 37.4 | 50 | A |
| ASN CB | 294 | 219.6 | 94.4 | 36.3 | 48 | A |
| ASN CG | 294 | 220.2 | 93.2 | 35.5 | 47 | A |
| ASN OD1 | 294 | 220.1 | 93.1 | 34.3 | 47 | A |
| ASN ND2 | 294 | 220.8 | 92.3 | 36.3 | 47 | A |
| ASN C | 294 | 218.1 | 95.2 | 38.0 | 52 | A |
| ASN O | 294 | 218.5 | 95.7 | 39.0 | 52 | A |
| LEU N | 295 | 217.0 | 95.7 | 37.3 | 54 | A |
| LEU CA | 295 | 216.3 | 96.9 | 37.7 | 55 | A |
| LEU CB | 295 | 215.0 | 97.0 | 37.0 | 56 | A |
| LEU CG | 295 | 214.2 | 98.3 | 36.9 | 56 | A |
| LEU CD1 | 295 | 215.0 | 99.3 | 36.0 | 56 | A |
| LEU CD2 | 295 | 212.8 | 98.0 | 36.4 | 56 | A |
| LEU C | 295 | 216.2 | 97.0 | 39.3 | 56 | A |
| LEU O | 295 | 216.6 | 98.0 | 39.9 | 56 | A |
| LEU N | 296 | 215.6 | 96.0 | 39.9 | 56 | A |
| LEU CA | 296 | 215.3 | 96.0 | 41.3 | 58 | A |
| LEU CB | 296 | 214.7 | 94.7 | 41.8 | 56 | A |
| LEU CG | 296 | 214.5 | 94.6 | 43.3 | 56 | A |
| LEU CD1 | 296 | 213.7 | 95.8 | 43.9 | 55 | A |
| LEU CD2 | 296 | 213.7 | 93.3 | 43.6 | 56 | A |
| LEU C | 296 | 216.6 | 96.3 | 42.1 | 60 | A |
| LEU O | 296 | 216.6 | 97.2 | 43.0 | 60 | A |
| ASN N | 297 | 217.7 | 95.7 | 41.7 | 62 | A |
| ASN CA | 297 | 219.0 | 95.9 | 42.4 | 65 | A |
| ASN CB | 297 | 220.1 | 95.1 | 41.7 | 66 | A |
| ASN CG | 297 | 219.8 | 93.7 | 41.6 | 68 | A |
| ASN OD1 | 297 | 218.8 | 93.2 | 42.0 | 69 | A |
| ASN ND2 | 297 | 220.8 | 92.9 | 41.1 | 68 | A |
| ASN C | 297 | 219.3 | 97.4 | 42.3 | 65 | A |
| ASN O | 297 | 219.3 | 98.1 | 43.3 | 65 | A |
| GLN N | 298 | 219.6 | 97.9 | 41.1 | 65 | A |
| GLN CA | 298 | 220.0 | 99.3 | 40.8 | 66 | A |
| GLN CB | 298 | 219.8 | 99.6 | 39.4 | 67 | A |
| GLN CG | 298 | 219.5 | 98.5 | 38.4 | 68 | A |
| GLN CD | 298 | 220.7 | 97.7 | 38.0 | 68 | A |
| GLN OE1 | 298 | 221.1 | 96.8 | 38.8 | 70 | A |
| GLN NE2 | 298 | 221.1 | 97.8 | 36.8 | 68 | A |
| GLN C | 298 | 219.2 | 100.2 | 41.7 | 67 | A |
| GLN O | 298 | 219.8 | 101.2 | 42.3 | 67 | A |
| LEU N | 299 | 217.9 | 100.0 | 41.9 | 67 | A |
| LEU CA | 299 | 217.0 | 100.8 | 42.7 | 68 | A |
| LEU CB | 299 | 215.5 | 100.6 | 42.4 | 67 | A |
| LEU CG | 299 | 214.9 | 101.1 | 41.1 | 67 | A |
| LEU CD1 | 299 | 213.4 | 101.1 | 41.3 | 66 | A |
| LEU CD2 | 299 | 215.4 | 102.5 | 40.7 | 66 | A |
| LEU C | 299 | 217.3 | 100.7 | 44.1 | 69 | A |
| LEU O | 299 | 217.5 | 101.7 | 44.9 | 68 | A |
| LEU N | 300 | 217.4 | 99.4 | 44.6 | 70 | A |
| LEU CA | 300 | 217.6 | 99.1 | 46.0 | 72 | A |
| LEU CB | 300 | 217.7 | 97.6 | 46.1 | 72 | A |
| LEU CG | 300 | 216.6 | 96.9 | 46.8 | 72 | A |
| LEU CD1 | 300 | 215.3 | 97.6 | 46.6 | 72 | A |
| LEU CD2 | 300 | 216.5 | 95.4 | 46.4 | 72 | A |
| LEU C | 300 | 219.0 | 99.7 | 46.4 | 73 | A |
| LEU O | 300 | 219.1 | 100.2 | 47.5 | 73 | A |
| ASP N | 301 | 219.9 | 99.8 | 45.4 | 75 | A |
| ASP CA | 301 | 221.2 | 100.4 | 45.7 | 77 | A |
| ASP CB | 301 | 222.1 | 100.2 | 44.5 | 78 | A |
| ASP CG | 301 | 222.4 | 98.7 | 44.3 | 78 | A |
| ASP OD1 | 301 | 221.9 | 97.8 | 45.1 | 79 | A |
| ASP OD2 | 301 | 223.2 | 98.3 | 43.4 | 78 | A |
| ASP C | 301 | 221.1 | 101.9 | 46.0 | 78 | A |
| ASP O | 301 | 221.8 | 102.4 | 46.8 | 79 | A |
| LEU N | 302 | 220.2 | 102.6 | 45.3 | 79 | A |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| LEU CA | 302 | 220.0 | 104.1 | 45.5 | 79 | A |
| LEU CB | 302 | 219.3 | 104.7 | 44.3 | 80 | A |
| LEU CG | 302 | 220.1 | 104.8 | 42.9 | 80 | A |
| LEU CD1 | 302 | 219.3 | 105.7 | 42.0 | 80 | A |
| LEU CD2 | 302 | 221.5 | 105.3 | 43.1 | 80 | A |
| LEU C | 302 | 219.3 | 104.4 | 46.8 | 79 | A |
| LEU O | 302 | 219.3 | 105.5 | 47.3 | 78 | A |
| GLN N | 303 | 218.7 | 103.3 | 47.4 | 79 | A |
| GLN CA | 303 | 217.9 | 103.4 | 48.6 | 80 | A |
| GLN CB | 303 | 217.7 | 102.1 | 49.3 | 79 | A |
| GLN CG | 303 | 216.4 | 101.4 | 48.9 | 79 | A |
| GLN CD | 303 | 215.3 | 102.1 | 49.6 | 80 | A |
| GLN OE1 | 303 | 215.1 | 103.3 | 49.6 | 80 | A |
| GLN NE2 | 303 | 214.4 | 101.3 | 50.2 | 80 | A |
| GLN C | 303 | 218.6 | 104.4 | 49.7 | 81 | A |
| GLN O | 303 | 217.9 | 105.1 | 50.4 | 81 | A |
| PRO N | 304 | 219.9 | 104.3 | 49.8 | 81 | A |
| PRO CD | 304 | 220.8 | 103.1 | 49.5 | 81 | A |
| PRO CA | 304 | 220.6 | 105.2 | 50.8 | 81 | A |
| PRO CB | 304 | 221.8 | 104.3 | 51.3 | 81 | A |
| PRO CG | 304 | 222.1 | 103.6 | 50.0 | 81 | A |
| PRO C | 304 | 221.0 | 106.6 | 50.3 | 81 | A |
| PRO O | 304 | 220.6 | 107.6 | 51.0 | 81 | A |
| SER N | 305 | 221.7 | 106.6 | 49.2 | 81 | A |
| SER CA | 305 | 222.2 | 107.9 | 48.7 | 81 | A |
| SER CB | 305 | 223.6 | 107.7 | 48.0 | 80 | A |
| SER OG | 305 | 223.6 | 106.6 | 47.2 | 80 | A |
| SER C | 305 | 221.3 | 108.7 | 47.7 | 80 | A |
| SER O | 305 | 221.5 | 109.9 | 47.6 | 80 | A |
| HIS N | 306 | 220.3 | 108.1 | 47.1 | 80 | A |
| HIS CA | 306 | 219.4 | 108.8 | 46.2 | 79 | A |
| HIS CB | 306 | 219.8 | 108.5 | 44.7 | 80 | A |
| HIS CG | 306 | 221.1 | 109.0 | 44.3 | 82 | A |
| HIS CD2 | 306 | 221.9 | 108.6 | 43.2 | 82 | A |
| HIS ND1 | 306 | 221.9 | 109.9 | 45.0 | 82 | A |
| HIS CE1 | 306 | 223.0 | 110.1 | 44.4 | 83 | A |
| HIS NE2 | 306 | 223.1 | 109.4 | 43.3 | 83 | A |
| HIS C | 306 | 218.0 | 108.4 | 46.5 | 77 | A |
| HIS O | 306 | 217.3 | 108.0 | 45.6 | 77 | A |
| SER N | 307 | 217.7 | 108.4 | 47.7 | 75 | A |
| SER CA | 307 | 216.3 | 108.0 | 48.2 | 73 | A |
| SER CB | 307 | 216.4 | 107.6 | 49.6 | 74 | A |
| SER OG | 307 | 215.2 | 107.0 | 50.0 | 75 | A |
| SER C | 307 | 215.3 | 109.1 | 48.0 | 72 | A |
| SER O | 307 | 215.6 | 110.3 | 48.0 | 73 | A |
| SER N | 308 | 214.0 | 108.7 | 47.9 | 70 | A |
| SER CA | 308 | 212.9 | 109.6 | 47.7 | 68 | A |
| SER CB | 308 | 212.9 | 110.2 | 46.3 | 68 | A |
| SER OG | 308 | 212.6 | 109.3 | 45.3 | 68 | A |
| SER C | 308 | 211.7 | 108.7 | 47.8 | 65 | A |
| SER O | 308 | 211.8 | 107.5 | 47.5 | 65 | A |
| PRO N | 309 | 210.5 | 109.2 | 48.3 | 63 | A |
| PRO CD | 309 | 210.2 | 110.6 | 48.7 | 63 | A |
| PRO CA | 309 | 209.4 | 108.3 | 48.4 | 61 | A |
| PRO CB | 309 | 208.3 | 109.2 | 49.0 | 62 | A |
| PRO CG | 309 | 208.7 | 110.6 | 48.5 | 62 | A |
| PRO C | 309 | 209.0 | 107.7 | 47.1 | 60 | A |
| PRO O | 309 | 208.1 | 106.8 | 47.0 | 61 | A |
| TYR N | 310 | 209.6 | 108.2 | 46.0 | 57 | A |
| TYR CA | 310 | 209.3 | 107.7 | 44.6 | 55 | A |
| TYR CB | 310 | 209.9 | 108.7 | 43.6 | 55 | A |
| TYR CG | 310 | 209.4 | 110.1 | 43.9 | 55 | A |
| TYR CD1 | 310 | 210.2 | 111.0 | 44.5 | 56 | A |
| TYR CE1 | 310 | 209.6 | 112.3 | 44.8 | 56 | A |
| TYR CD2 | 310 | 208.0 | 110.4 | 43.6 | 55 | A |
| TYR CE2 | 310 | 207.5 | 111.6 | 43.9 | 56 | A |
| TYR CZ | 310 | 208.3 | 112.5 | 44.6 | 57 | A |
| TYR OH | 310 | 207.8 | 113.7 | 45.0 | 58 | A |
| TYR C | 310 | 210.0 | 106.3 | 44.5 | 53 | A |
| TYR O | 310 | 209.5 | 105.4 | 43.8 | 52 | A |
| LEU N | 311 | 211.2 | 106.2 | 45.0 | 50 | A |
| LEU CA | 311 | 212.0 | 105.0 | 44.9 | 49 | A |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| LEU CB | 311 | 213.3 | 105.2 | 45.7 | 48 | A |
| LEU CG | 311 | 214.3 | 104.1 | 45.7 | 48 | A |
| LEU CD1 | 311 | 214.7 | 103.7 | 44.3 | 48 | A |
| LEU CD2 | 311 | 215.6 | 104.6 | 46.4 | 48 | A |
| LEU C | 311 | 211.2 | 103.9 | 45.7 | 47 | A |
| LEU O | 311 | 210.9 | 102.8 | 45.1 | 46 | A |
| ILE N | 312 | 210.7 | 104.2 | 46.9 | 46 | A |
| ILE CA | 312 | 209.9 | 103.3 | 47.7 | 46 | A |
| ILE CB | 312 | 209.4 | 104.0 | 49.0 | 46 | A |
| ILE CG2 | 312 | 208.8 | 102.9 | 49.9 | 46 | A |
| ILE CG1 | 312 | 210.6 | 104.6 | 49.8 | 47 | A |
| ILE CD1 | 312 | 211.6 | 103.6 | 50.3 | 46 | A |
| ILE C | 312 | 208.7 | 102.9 | 46.9 | 46 | A |
| ILE O | 312 | 208.4 | 101.7 | 46.9 | 48 | A |
| ALA N | 313 | 208.0 | 103.8 | 46.2 | 45 | A |
| ALA CA | 313 | 206.8 | 103.4 | 45.5 | 43 | A |
| ALA CB | 313 | 206.0 | 104.6 | 45.1 | 43 | A |
| ALA C | 313 | 207.2 | 102.5 | 44.2 | 42 | A |
| ALA O | 313 | 206.4 | 101.6 | 43.9 | 41 | A |
| PHE N | 314 | 208.3 | 102.8 | 43.6 | 41 | A |
| PHE CA | 314 | 208.7 | 102.0 | 42.5 | 40 | A |
| PHE CB | 314 | 209.9 | 102.6 | 41.8 | 40 | A |
| PHE CG | 314 | 210.0 | 102.4 | 40.3 | 40 | A |
| PHE CD1 | 314 | 209.8 | 103.5 | 39.4 | 41 | A |
| PHE CD2 | 314 | 210.3 | 101.2 | 39.8 | 40 | A |
| PHE CE1 | 314 | 209.8 | 103.3 | 38.0 | 41 | A |
| PHE CE2 | 314 | 210.4 | 101.0 | 38.4 | 40 | A |
| PHE CZ | 314 | 210.1 | 102.0 | 37.5 | 41 | A |
| PHE C | 314 | 208.9 | 100.6 | 42.8 | 41 | A |
| PHE O | 314 | 208.6 | 99.7 | 42.1 | 41 | A |
| LEU N | 315 | 209.6 | 100.3 | 44.0 | 41 | A |
| LEU CA | 315 | 209.8 | 99.0 | 44.5 | 39 | A |
| LEU CB | 315 | 210.6 | 99.0 | 45.8 | 40 | A |
| LEU CG | 315 | 211.9 | 99.9 | 45.8 | 41 | A |
| LEU CD1 | 315 | 212.3 | 100.0 | 47.3 | 40 | A |
| LEU CD2 | 315 | 213.0 | 99.3 | 44.9 | 40 | A |
| LEU C | 315 | 208.5 | 98.2 | 44.7 | 40 | A |
| LEU O | 315 | 208.4 | 97.1 | 44.4 | 41 | A |
| VAL N | 316 | 207.5 | 98.9 | 45.3 | 40 | A |
| VAL CA | 316 | 206.2 | 98.3 | 45.5 | 41 | A |
| VAL CB | 316 | 205.3 | 99.3 | 46.3 | 41 | A |
| VAL CG1 | 316 | 203.9 | 98.6 | 46.5 | 40 | A |
| VAL CG2 | 316 | 205.8 | 99.7 | 47.6 | 41 | A |
| VAL C | 316 | 205.6 | 98.0 | 44.1 | 43 | A |
| VAL O | 316 | 204.9 | 97.0 | 44.0 | 44 | A |
| ASP N | 317 | 206.0 | 98.8 | 43.1 | 44 | A |
| ASP CA | 317 | 205.5 | 98.6 | 41.8 | 45 | A |
| ASP CB | 317 | 205.8 | 99.8 | 40.8 | 46 | A |
| ASP CG | 317 | 204.9 | 100.9 | 41.1 | 48 | A |
| ASP OD1 | 317 | 203.7 | 100.7 | 41.4 | 48 | A |
| ASP OD2 | 317 | 205.4 | 102.1 | 41.1 | 48 | A |
| ASP C | 317 | 206.1 | 97.3 | 41.2 | 44 | A |
| ASP O | 317 | 205.5 | 96.6 | 40.5 | 44 | A |
| ILE N | 318 | 207.4 | 97.1 | 41.4 | 44 | A |
| ILE CA | 318 | 208.1 | 95.9 | 41.0 | 44 | A |
| ILE CB | 318 | 209.6 | 96.0 | 41.3 | 43 | A |
| ILE CG2 | 318 | 210.3 | 94.7 | 40.8 | 44 | A |
| ILE CG1 | 318 | 210.2 | 97.2 | 40.5 | 43 | A |
| ILE CD1 | 318 | 211.7 | 97.3 | 40.7 | 42 | A |
| ILE C | 318 | 207.5 | 94.7 | 41.6 | 45 | A |
| ILE O | 318 | 207.1 | 93.7 | 41.0 | 45 | A |
| TYR N | 319 | 207.4 | 94.8 | 43.0 | 47 | A |
| TYR CA | 319 | 206.9 | 93.7 | 43.7 | 50 | A |
| TYR CB | 319 | 206.9 | 94.0 | 45.2 | 50 | A |
| TYR CG | 319 | 208.3 | 94.1 | 45.8 | 50 | A |
| TYR CD1 | 319 | 208.6 | 94.8 | 47.0 | 50 | A |
| TYR CE1 | 319 | 209.9 | 95.0 | 47.4 | 50 | A |
| TYR CD2 | 319 | 209.4 | 93.6 | 45.1 | 50 | A |
| TYR CE2 | 319 | 210.7 | 93.7 | 45.6 | 50 | A |
| TYR CZ | 319 | 210.9 | 94.4 | 46.7 | 50 | A |
| TYR OH | 319 | 212.2 | 94.5 | 47.2 | 51 | A |
| TYR C | 319 | 205.5 | 93.3 | 43.3 | 52 | A |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| TYR O | 319 | 205.2 | 92.1 | 43.1 | 53 | A |
| GLU N | 320 | 204.7 | 94.3 | 43.0 | 54 | A |
| GLU CA | 320 | 203.3 | 94.0 | 42.5 | 56 | A |
| GLU CB | 320 | 202.6 | 95.4 | 42.2 | 58 | A |
| GLU CG | 320 | 202.2 | 96.2 | 43.4 | 61 | A |
| GLU CD | 320 | 201.8 | 97.6 | 43.0 | 63 | A |
| GLU OE1 | 320 | 200.7 | 98.1 | 43.4 | 65 | A |
| GLU OE2 | 320 | 202.6 | 98.4 | 42.4 | 64 | A |
| GLU C | 320 | 203.3 | 93.2 | 41.3 | 56 | A |
| GLU O | 320 | 202.7 | 92.2 | 41.2 | 56 | A |
| ASP N | 321 | 204.2 | 93.6 | 40.4 | 56 | A |
| ASP CA | 321 | 204.3 | 92.8 | 39.1 | 56 | A |
| ASP CB | 321 | 205.0 | 93.7 | 38.0 | 55 | A |
| ASP CG | 321 | 204.9 | 93.0 | 36.7 | 55 | A |
| ASP OD1 | 321 | 203.8 | 92.7 | 36.3 | 55 | A |
| ASP OD2 | 321 | 205.9 | 92.8 | 36.0 | 54 | A |
| ASP C | 321 | 205.0 | 91.5 | 39.2 | 58 | A |
| ASP O | 321 | 204.7 | 90.6 | 38.4 | 58 | A |
| MET N | 322 | 205.9 | 91.3 | 40.2 | 60 | A |
| MET CA | 322 | 206.5 | 90.0 | 40.3 | 61 | A |
| MET CB | 322 | 207.7 | 90.1 | 41.3 | 61 | A |
| MET CG | 322 | 208.9 | 90.9 | 40.7 | 61 | A |
| MET SD | 322 | 210.5 | 90.5 | 41.5 | 61 | A |
| MET CE | 322 | 210.3 | 91.5 | 42.9 | 59 | A |
| MET C | 322 | 205.5 | 89.0 | 40.8 | 63 | A |
| MET O | 322 | 205.5 | 87.9 | 40.3 | 64 | A |
| LEU N | 323 | 204.7 | 89.4 | 41.8 | 66 | A |
| LEU CA | 323 | 203.7 | 88.5 | 42.3 | 69 | A |
| LEU CB | 323 | 202.9 | 89.1 | 43.4 | 68 | A |
| LEU CG | 323 | 203.3 | 88.8 | 44.9 | 68 | A |
| LEU CD1 | 323 | 204.8 | 88.9 | 45.1 | 67 | A |
| LEU CD2 | 323 | 202.6 | 89.8 | 45.8 | 68 | A |
| LEU C | 323 | 202.8 | 88.1 | 41.2 | 72 | A |
| LEU O | 323 | 202.5 | 86.9 | 40.9 | 73 | A |
| GLU N | 324 | 202.3 | 89.1 | 40.4 | 75 | A |
| GLU CA | 324 | 201.4 | 88.9 | 39.3 | 78 | A |
| GLU CB | 324 | 201.2 | 90.2 | 38.5 | 79 | A |
| GLU CG | 324 | 200.3 | 91.3 | 39.3 | 81 | A |
| GLU CD | 324 | 200.5 | 92.7 | 38.6 | 83 | A |
| GLU OE1 | 324 | 200.6 | 92.8 | 37.4 | 83 | A |
| GLU OE2 | 324 | 200.4 | 93.7 | 39.4 | 83 | A |
| GLU C | 324 | 202.0 | 87.9 | 38.3 | 79 | A |
| GLU O | 324 | 201.3 | 87.1 | 37.8 | 79 | A |
| ASN N | 325 | 203.3 | 88.0 | 38.1 | 80 | A |
| ASN CA | 325 | 204.0 | 87.1 | 37.1 | 81 | A |
| ASN CB | 325 | 205.0 | 87.9 | 36.3 | 81 | A |
| ASN CG | 325 | 204.3 | 89.0 | 35.4 | 81 | A |
| ASN OD1 | 325 | 204.6 | 90.1 | 35.3 | 81 | A |
| ASN ND2 | 325 | 203.2 | 88.5 | 34.8 | 81 | A |
| ASN C | 325 | 204.7 | 85.9 | 37.8 | 81 | A |
| ASN O | 325 | 205.8 | 85.5 | 37.4 | 81 | A |
| GLN N | 326 | 204.0 | 85.4 | 38.8 | 84 | A |
| GLN CA | 326 | 204.4 | 84.3 | 39.6 | 86 | A |
| GLN CB | 326 | 203.9 | 83.0 | 38.9 | 87 | A |
| GLN CG | 326 | 202.5 | 83.0 | 38.3 | 87 | A |
| GLN CD | 326 | 202.4 | 83.3 | 36.8 | 88 | A |
| GLN OE1 | 326 | 202.9 | 82.5 | 36.0 | 88 | A |
| GLN NE2 | 326 | 201.7 | 84.4 | 36.5 | 88 | A |
| GLN C | 326 | 205.9 | 84.2 | 39.9 | 87 | A |
| GLN O | 326 | 206.6 | 83.2 | 39.5 | 87 | A |
| CYS N | 327 | 206.4 | 85.1 | 40.6 | 89 | A |
| CYS CA | 327 | 207.8 | 55.1 | 41.0 | 90 | A |
| CYS CB | 327 | 208.3 | 86.5 | 41.5 | 89 | A |
| CYS SG | 327 | 207.7 | 87.0 | 43.1 | 88 | A |
| CYS C | 327 | 208.0 | 84.2 | 42.2 | 92 | A |
| CYS O | 327 | 207.0 | 83.8 | 42.8 | 92 | A |
| ASP N | 328 | 209.2 | 83.7 | 42.4 | 93 | A |
| ASP CA | 328 | 209.5 | 82.8 | 43.5 | 94 | A |
| ASP CB | 328 | 210.7 | 81.9 | 43.2 | 95 | A |
| ASP CG | 328 | 210.3 | 80.4 | 43.4 | 96 | A |
| ASP OD1 | 328 | 210.3 | 79.7 | 42.4 | 97 | A |
| ASP OD2 | 328 | 210.0 | 80.0 | 44.6 | 96 | A |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| ASP C | 328 | 209.8 | 83.7 | 44.7 | 94 | A |
| ASP O | 328 | 210.3 | 84.9 | 44.6 | 95 | A |
| ASN N | 329 | 209.5 | 83.3 | 45.9 | 94 | A |
| ASN CA | 329 | 209.6 | 84.0 | 47.2 | 94 | A |
| ASN CB | 329 | 210.7 | 85.0 | 47.2 | 94 | A |
| ASN CG | 329 | 212.1 | 84.4 | 47.2 | 95 | A |
| ASN OD1 | 329 | 212.5 | 83.7 | 46.2 | 95 | A |
| ASN ND2 | 329 | 212.8 | 84.5 | 48.3 | 95 | A |
| ASN C | 329 | 208.3 | 84.7 | 47.5 | 94 | A |
| ASN O | 329 | 208.3 | 85.6 | 48.3 | 93 | A |
| LYS N | 330 | 207.2 | 84.3 | 46.8 | 93 | A |
| LYS CA | 330 | 205.9 | 85.0 | 47.0 | 93 | A |
| LYS CB | 330 | 204.8 | 84.0 | 46.5 | 93 | A |
| LYS CG | 330 | 203.8 | 84.7 | 45.6 | 95 | A |
| LYS CD | 330 | 202.8 | 83.7 | 45.0 | 95 | A |
| LYS CE | 330 | 201.8 | 84.4 | 44.0 | 95 | A |
| LYS NZ | 330 | 202.5 | 84.8 | 42.8 | 94 | A |
| LYS C | 330 | 205.6 | 85.4 | 48.4 | 92 | A |
| LYS O | 330 | 205.3 | 86.6 | 48.6 | 92 | A |
| GLU N | 331 | 205.9 | 84.6 | 49.4 | 92 | A |
| GLU CA | 331 | 205.7 | 84.9 | 50.8 | 91 | A |
| GLU CB | 331 | 206.0 | 83.7 | 51.7 | 93 | A |
| GLU CG | 331 | 205.1 | 82.4 | 51.5 | 94 | A |
| GLU CD | 331 | 203.8 | 82.5 | 52.1 | 95 | A |
| GLU OE1 | 331 | 203.0 | 81.5 | 51.9 | 95 | A |
| GLU OE2 | 331 | 203.4 | 83.5 | 52.7 | 96 | A |
| GLU C | 331 | 206.6 | 86.1 | 51.2 | 89 | A |
| GLU O | 331 | 206.1 | 87.0 | 51.9 | 89 | A |
| ASP N | 332 | 207.9 | 85.9 | 50.9 | 87 | A |
| ASP CA | 332 | 208.9 | 86.9 | 51.2 | 85 | A |
| ASP CB | 332 | 210.3 | 86.2 | 50.7 | 87 | A |
| ASP CG | 332 | 211.4 | 87.2 | 50.7 | 88 | A |
| ASP OD1 | 332 | 212.2 | 87.2 | 49.7 | 88 | A |
| ASP OD2 | 332 | 211.6 | 88.0 | 51.7 | 89 | A |
| ASP C | 332 | 208.7 | 88.2 | 50.5 | 83 | A |
| ASP O | 332 | 208.5 | 89.3 | 51.1 | 83 | A |
| ILE N | 333 | 208.7 | 88.2 | 49.1 | 81 | A |
| ILE CA | 333 | 208.6 | 89.4 | 48.4 | 77 | A |
| ILE CB | 333 | 208.7 | 89.1 | 46.8 | 77 | A |
| ILE CG2 | 333 | 208.0 | 90.2 | 46.0 | 77 | A |
| ILE CG1 | 333 | 210.2 | 89.0 | 46.5 | 76 | A |
| ILE CD1 | 333 | 210.5 | 88.8 | 45.1 | 76 | A |
| ILE C | 333 | 207.3 | 90.2 | 48.7 | 76 | A |
| ILE O | 333 | 207.2 | 91.4 | 48.8 | 76 | A |
| LEU N | 334 | 206.2 | 89.4 | 49.0 | 74 | A |
| LEU CA | 334 | 204.9 | 90.0 | 49.4 | 73 | A |
| LEU CB | 334 | 203.9 | 89.0 | 49.7 | 73 | A |
| LEU CG | 334 | 202.5 | 89.4 | 50.3 | 73 | A |
| LEU CD1 | 334 | 201.9 | 90.5 | 49.4 | 73 | A |
| LEU CD2 | 334 | 201.6 | 88.2 | 50.3 | 73 | A |
| LEU C | 334 | 205.1 | 90.9 | 50.7 | 73 | A |
| LEU O | 334 | 204.8 | 92.0 | 50.7 | 74 | A |
| ASN N | 335 | 205.8 | 90.3 | 51.7 | 73 | A |
| ASN CA | 335 | 206.0 | 91.0 | 53.0 | 73 | A |
| ASN CB | 335 | 206.8 | 90.2 | 53.9 | 74 | A |
| ASN CG | 335 | 206.1 | 89.0 | 54.5 | 74 | A |
| ASN OD1 | 335 | 205.0 | 89.2 | 55.1 | 75 | A |
| ASN ND2 | 335 | 206.6 | 87.8 | 54.4 | 74 | A |
| ASN C | 335 | 206.6 | 92.4 | 52.8 | 71 | A |
| ASN O | 335 | 206.2 | 93.4 | 53.4 | 71 | A |
| LYS N | 336 | 207.7 | 92.4 | 51.9 | 70 | A |
| LYS CA | 336 | 208.3 | 93.6 | 51.6 | 69 | A |
| LYS CB | 336 | 209.5 | 93.4 | 50.6 | 70 | A |
| LYS CG | 336 | 210.9 | 93.4 | 51.3 | 71 | A |
| LYS CD | 336 | 211.9 | 92.6 | 50.4 | 72 | A |
| LYS CE | 336 | 211.5 | 91.2 | 50.1 | 72 | A |
| LYS NZ | 336 | 212.4 | 90.5 | 49.2 | 73 | A |
| LYS C | 336 | 207.3 | 94.6 | 51.0 | 68 | A |
| LYS O | 336 | 207.2 | 95.7 | 51.6 | 67 | A |
| ALA N | 337 | 206.7 | 94.2 | 50.0 | 66 | A |
| ALA CA | 337 | 205.7 | 95.1 | 49.3 | 64 | A |
| ALA CB | 337 | 204.9 | 94.2 | 48.3 | 63 | A |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| ALA C | 337 | 204.7 | 95.7 | 50.4 | 63 | A |
| ALA O | 337 | 204.5 | 96.9 | 50.4 | 63 | A |
| LEU N | 338 | 204.2 | 94.8 | 51.2 | 62 | A |
| LEU CA | 338 | 203.2 | 95.2 | 52.3 | 61 | A |
| LEU CB | 338 | 202.6 | 94.0 | 52.9 | 61 | A |
| LEU CG | 338 | 201.7 | 93.1 | 52.1 | 61 | A |
| LEU CD1 | 338 | 201.6 | 91.7 | 52.7 | 61 | A |
| LEU CD2 | 338 | 200.3 | 93.7 | 51.9 | 61 | A |
| LEU C | 338 | 203.9 | 96.1 | 53.3 | 60 | A |
| LEU O | 338 | 203.2 | 97.0 | 53.9 | 59 | A |
| GLU N | 339 | 205.2 | 95.9 | 53.6 | 60 | A |
| GLU CA | 339 | 205.9 | 96.7 | 54.6 | 61 | A |
| GLU CB | 339 | 207.3 | 96.1 | 54.8 | 64 | A |
| GLU CG | 339 | 208.2 | 96.9 | 55.8 | 67 | A |
| GLU CD | 339 | 209.7 | 96.5 | 55.6 | 69 | A |
| GLU OE1 | 339 | 210.0 | 95.3 | 55.7 | 70 | A |
| GLU OE2 | 339 | 210.5 | 97.4 | 55.5 | 70 | A |
| GLU C | 339 | 206.0 | 98.1 | 54.1 | 59 | A |
| GLU O | 339 | 205.7 | 99.1 | 54.8 | 58 | A |
| LEU N | 340 | 206.5 | 98.2 | 52.8 | 57 | A |
| LEU CA | 340 | 206.7 | 99.5 | 52.2 | 55 | A |
| LEU CB | 340 | 207.3 | 99.3 | 50.8 | 54 | A |
| LEU CG | 340 | 208.6 | 98.4 | 50.7 | 54 | A |
| LEU CD1 | 340 | 209.3 | 98.7 | 49.3 | 53 | A |
| LEU CD2 | 340 | 209.5 | 98.7 | 51.8 | 54 | A |
| LEU C | 340 | 205.4 | 100.2 | 52.1 | 55 | A |
| LEU O | 340 | 205.3 | 101.4 | 52.5 | 55 | A |
| CYS N | 341 | 204.3 | 99.5 | 51.8 | 55 | A |
| CYS CA | 341 | 203.0 | 100.1 | 51.7 | 55 | A |
| CYS CB | 341 | 201.9 | 99.1 | 51.3 | 54 | A |
| CYS SG | 341 | 202.0 | 95.5 | 49.6 | 54 | A |
| CYS C | 341 | 202.6 | 100.8 | 53.1 | 55 | A |
| CYS O | 341 | 201.9 | 101.8 | 53.1 | 55 | A |
| GLU N | 342 | 203.1 | 100.2 | 54.1 | 55 | A |
| GLU CA | 342 | 202.8 | 100.7 | 55.5 | 55 | A |
| GLU CB | 342 | 202.9 | 99.6 | 56.5 | 56 | A |
| GLU CG | 342 | 202.1 | 100.0 | 57.8 | 57 | A |
| GLU CD | 342 | 200.7 | 100.5 | 57.5 | 58 | A |
| GLU OE1 | 342 | 200.3 | 101.6 | 57.9 | 58 | A |
| GLU OE2 | 342 | 199.9 | 99.7 | 56.8 | 58 | A |
| GLU C | 342 | 203.8 | 101.8 | 55.8 | 55 | A |
| GLU O | 342 | 203.4 | 102.8 | 56.4 | 54 | A |
| ILE N | 343 | 205.1 | 101.7 | 55.5 | 54 | A |
| ILE CA | 343 | 206.1 | 102.7 | 55.7 | 54 | A |
| ILE CB | 343 | 207.4 | 102.4 | 55.1 | 53 | A |
| ILE CG2 | 343 | 208.4 | 103.6 | 55.2 | 53 | A |
| ILE CG1 | 343 | 208.1 | 101.2 | 55.8 | 53 | A |
| ILE CD1 | 343 | 209.5 | 100.9 | 55.3 | 53 | A |
| ILE C | 343 | 205.5 | 104.0 | 55.1 | 54 | A |
| ILE O | 343 | 205.5 | 105.1 | 55.7 | 55 | A |
| LEU N | 344 | 205.1 | 103.9 | 53.8 | 53 | A |
| LEU CA | 344 | 204.6 | 105.0 | 53.1 | 52 | A |
| LEU CB | 344 | 204.2 | 104.5 | 51.6 | 51 | A |
| LEU CG | 344 | 205.4 | 104.1 | 50.7 | 50 | A |
| LEU CD1 | 344 | 204.9 | 103.5 | 49.4 | 49 | A |
| LEU CD2 | 344 | 206.3 | 105.3 | 50.4 | 50 | A |
| LEU C | 344 | 203.3 | 105.5 | 53.7 | 53 | A |
| LEU O | 344 | 203.2 | 106.6 | 54.2 | 54 | A |
| ALA N | 345 | 202.3 | 104.6 | 53.9 | 54 | A |
| ALA CA | 345 | 201.1 | 105.0 | 54.5 | 55 | A |
| ALA CB | 345 | 200.2 | 103.8 | 54.7 | 55 | A |
| ALA C | 345 | 201.2 | 105.7 | 55.9 | 56 | A |
| ALA O | 345 | 200.4 | 106.7 | 56.1 | 57 | A |
| LYS N | 346 | 202.0 | 105.2 | 56.8 | 58 | A |
| LYS CA | 346 | 202.2 | 105.8 | 58.1 | 60 | A |
| LYS CB | 346 | 202.6 | 104.7 | 59.1 | 62 | A |
| LYS CG | 346 | 201.5 | 103.9 | 59.7 | 64 | A |
| LYS CD | 346 | 202.1 | 102.9 | 60.7 | 67 | A |
| LYS CE | 346 | 201.1 | 101.8 | 61.2 | 68 | A |
| LYS NZ | 346 | 201.7 | 100.8 | 62.1 | 69 | A |
| LYS C | 346 | 203.3 | 106.9 | 58.2 | 60 | A |
| LYS O | 346 | 203.1 | 107.8 | 59.0 | 60 | A |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| GLU N | 347 | 204.3 | 106.7 | 57.4 | 60 | A |
| GLU CA | 347 | 205.5 | 107.6 | 57.5 | 60 | A |
| GLU CB | 347 | 206.7 | 106.8 | 58.0 | 62 | A |
| GLU CG | 347 | 208.0 | 107.6 | 58.0 | 65 | A |
| GLU CD | 347 | 209.2 | 106.7 | 58.4 | 67 | A |
| GLU OE1 | 347 | 210.0 | 107.3 | 59.2 | 69 | A |
| GLU OE2 | 347 | 209.3 | 105.6 | 57.9 | 68 | A |
| GLU C | 347 | 205.9 | 108.4 | 56.3 | 58 | A |
| GLU O | 347 | 205.8 | 109.6 | 56.3 | 57 | A |
| LYS N | 348 | 206.4 | 107.7 | 55.2 | 56 | A |
| LYS CA | 348 | 206.9 | 108.4 | 54.0 | 55 | A |
| LYS CB | 348 | 207.7 | 107.4 | 53.2 | 57 | A |
| LYS CG | 348 | 208.7 | 106.6 | 54.0 | 57 | A |
| LYS CD | 348 | 209.8 | 107.5 | 54.5 | 58 | A |
| LYS CE | 348 | 210.9 | 106.7 | 55.3 | 59 | A |
| LYS NZ | 348 | 211.5 | 105.6 | 54.5 | 59 | A |
| LYS C | 348 | 205.9 | 109.1 | 53.1 | 54 | A |
| LYS O | 348 | 206.3 | 110.1 | 52.4 | 54 | A |
| ASP N | 349 | 204.7 | 108.7 | 53.0 | 51 | A |
| ASP CA | 349 | 203.8 | 109.3 | 52.0 | 49 | A |
| ASP CB | 349 | 203.8 | 108.6 | 50.7 | 49 | A |
| ASP CG | 349 | 203.4 | 109.5 | 49.5 | 50 | A |
| ASP OD1 | 349 | 203.2 | 110.8 | 49.7 | 50 | A |
| ASP OD2 | 349 | 203.4 | 109.0 | 48.4 | 51 | A |
| ASP C | 349 | 202.3 | 109.3 | 52.6 | 48 | A |
| ASP O | 349 | 201.4 | 108.9 | 51.9 | 48 | A |
| THR N | 350 | 202.2 | 109.9 | 53.8 | 46 | A |
| THR CA | 350 | 200.9 | 109.9 | 54.5 | 46 | A |
| THR CB | 350 | 201.1 | 110.5 | 55.9 | 46 | A |
| THR OG1 | 350 | 201.4 | 111.9 | 55.8 | 47 | A |
| THR CG2 | 350 | 202.2 | 109.8 | 56.6 | 46 | A |
| THR C | 350 | 199.7 | 110.6 | 53.8 | 45 | A |
| THR O | 350 | 198.6 | 110.3 | 54.1 | 44 | A |
| ILE N | 351 | 200.0 | 111.5 | 52.9 | 45 | A |
| ILE CA | 351 | 199.0 | 112.3 | 52.2 | 43 | A |
| ILE CB | 351 | 199.6 | 113.4 | 51.3 | 41 | A |
| ILE CG2 | 351 | 200.3 | 112.8 | 50.1 | 41 | A |
| ILE CG1 | 351 | 198.5 | 114.3 | 50.9 | 40 | A |
| ILE CD1 | 351 | 198.1 | 115.3 | 52.0 | 39 | A |
| ILE C | 351 | 198.1 | 111.2 | 51.4 | 43 | A |
| ILE O | 351 | 196.8 | 111.4 | 51.4 | 43 | A |
| ARG N | 352 | 198.6 | 110.1 | 51.0 | 43 | A |
| ARG CA | 352 | 197.8 | 109.1 | 50.3 | 45 | A |
| ARG CB | 352 | 198.2 | 108.9 | 48.8 | 44 | A |
| ARG CG | 352 | 199.7 | 109.0 | 48.5 | 44 | A |
| ARG CD | 352 | 199.9 | 109.7 | 47.1 | 43 | A |
| ARG NE | 352 | 201.1 | 110.4 | 47.1 | 44 | A |
| ARG CZ | 352 | 201.3 | 111.8 | 47.1 | 44 | A |
| ARG NH1 | 352 | 200.2 | 112.6 | 47.0 | 44 | A |
| ARG NH2 | 352 | 202.5 | 112.3 | 47.2 | 44 | A |
| ARG C | 352 | 197.9 | 107.8 | 51.1 | 46 | A |
| ARG O | 352 | 198.1 | 106.7 | 50.5 | 46 | A |
| LYS N | 353 | 197.6 | 107.9 | 52.4 | 47 | A |
| LYS CA | 353 | 197.5 | 106.7 | 53.3 | 46 | A |
| LYS CB | 353 | 197.3 | 107.2 | 54.7 | 45 | A |
| LYS CG | 353 | 196.0 | 107.9 | 55.0 | 45 | A |
| LYS CD | 353 | 196.0 | 108.7 | 56.3 | 45 | A |
| LYS CE | 353 | 194.6 | 109.4 | 56.5 | 45 | A |
| LYS NZ | 353 | 194.5 | 110.3 | 57.7 | 45 | A |
| LYS C | 353 | 196.3 | 105.9 | 52.8 | 47 | A |
| LYS O | 353 | 196.4 | 104.6 | 52.8 | 46 | A |
| GLU N | 354 | 195.3 | 106.5 | 52.4 | 48 | A |
| GLU CA | 354 | 194.1 | 105.8 | 51.9 | 49 | A |
| GLU CB | 354 | 193.0 | 106.8 | 51.5 | 51 | A |
| GLU CG | 354 | 192.2 | 107.4 | 52.7 | 54 | A |
| GLU CD | 354 | 191.5 | 106.3 | 53.5 | 56 | A |
| GLU OE1 | 354 | 191.9 | 106.1 | 54.7 | 57 | A |
| GLU OE2 | 354 | 190.5 | 105.7 | 53.1 | 57 | A |
| GLU C | 354 | 194.4 | 104.9 | 50.7 | 48 | A |
| GLU O | 354 | 194.0 | 103.8 | 50.5 | 49 | A |
| TYR N | 355 | 195.3 | 105.4 | 49.8 | 47 | A |
| TYR CA | 355 | 195.7 | 104.7 | 48.6 | 46 | A |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| TYR CB | 355 | 196.3 | 105.7 | 47.6 | 43 | A |
| TYR CG | 355 | 197.0 | 104.9 | 46.4 | 39 | A |
| TYR CD1 | 355 | 196.3 | 104.4 | 45.4 | 38 | A |
| TYR CE1 | 355 | 196.9 | 103.7 | 44.3 | 37 | A |
| TYR CD2 | 355 | 198.4 | 104.8 | 46.4 | 38 | A |
| TYR CE2 | 355 | 199.0 | 104.1 | 45.4 | 37 | A |
| TYR CZ | 355 | 198.3 | 103.5 | 44.4 | 37 | A |
| TYR OH | 355 | 198.9 | 102.8 | 43.3 | 37 | A |
| TYR C | 355 | 196.7 | 103.6 | 48.9 | 47 | A |
| TYR O | 355 | 196.5 | 102.5 | 48.5 | 48 | A |
| TRP N | 356 | 197.7 | 104.0 | 49.6 | 48 | A |
| TRP CA | 356 | 198.8 | 103.0 | 50.0 | 50 | A |
| TRP CB | 356 | 199.9 | 103.7 | 50.7 | 50 | A |
| TRP CG | 356 | 200.8 | 104.4 | 49.7 | 50 | A |
| TRP CD2 | 356 | 201.5 | 103.8 | 48.6 | 50 | A |
| TRP CE2 | 356 | 202.1 | 104.8 | 47.9 | 50 | A |
| TRP CE3 | 356 | 201.6 | 102.5 | 48.2 | 50 | A |
| TRP CD1 | 356 | 201.0 | 105.8 | 49.6 | 50 | A |
| TRP NE1 | 356 | 201.8 | 106.0 | 48.5 | 50 | A |
| TRP CZ2 | 356 | 202.9 | 104.6 | 46.8 | 50 | A |
| TRP CZ3 | 356 | 202.4 | 102.2 | 47.0 | 50 | A |
| TRP CH2 | 356 | 203.0 | 103.3 | 46.4 | 50 | A |
| TRP C | 356 | 198.3 | 101.8 | 50.8 | 51 | A |
| TRP O | 356 | 198.8 | 100.7 | 50.7 | 51 | A |
| ARG N | 357 | 197.3 | 102.0 | 51.7 | 52 | A |
| ARG CA | 357 | 196.7 | 100.9 | 52.4 | 53 | A |
| ARG CB | 357 | 196.0 | 101.4 | 53.6 | 55 | A |
| ARG CG | 357 | 196.8 | 101.5 | 54.9 | 57 | A |
| ARG CD | 357 | 196.8 | 102.9 | 55.5 | 58 | A |
| ARG NE | 357 | 195.4 | 103.2 | 55.7 | 60 | A |
| ARG CZ | 357 | 195.0 | 104.2 | 56.6 | 61 | A |
| ARG NH1 | 357 | 193.7 | 104.4 | 56.7 | 61 | A |
| ARG NH2 | 357 | 195.9 | 104.9 | 57.2 | 61 | A |
| ARG C | 357 | 195.9 | 100.1 | 51.5 | 53 | A |
| ARG O | 357 | 196.0 | 98.8 | 51.6 | 54 | A |
| TYR N | 358 | 195.2 | 100.7 | 50.6 | 52 | A |
| TYR CA | 358 | 194.4 | 100.0 | 49.6 | 51 | A |
| TYR CB | 358 | 193.7 | 100.9 | 48.7 | 51 | A |
| TYR CG | 358 | 193.2 | 100.3 | 47.4 | 51 | A |
| TYR CD1 | 358 | 192.0 | 99.6 | 47.3 | 50 | A |
| TYR CE1 | 358 | 191.6 | 99.0 | 46.1 | 50 | A |
| TYR CD2 | 358 | 194.1 | 100.3 | 46.3 | 50 | A |
| TYR CE2 | 358 | 193.7 | 99.7 | 45.1 | 49 | A |
| TYR CZ | 358 | 192.5 | 99.0 | 45.0 | 50 | A |
| TYR OH | 358 | 192.2 | 98.4 | 43.9 | 50 | A |
| TYR C | 358 | 195.3 | 99.0 | 48.9 | 51 | A |
| TYR O | 358 | 194.9 | 97.9 | 48.6 | 50 | A |
| ILE N | 359 | 196.5 | 99.4 | 48.6 | 51 | A |
| ILE CA | 359 | 197.5 | 98.6 | 47.9 | 51 | A |
| ILE CB | 359 | 198.8 | 99.4 | 47.6 | 50 | A |
| ILE CG2 | 359 | 199.8 | 98.5 | 47.0 | 49 | A |
| ILE CG1 | 359 | 198.4 | 100.5 | 46.6 | 50 | A |
| ILE CD1 | 359 | 197.8 | 99.9 | 45.3 | 49 | A |
| ILE C | 359 | 197.9 | 97.4 | 48.8 | 52 | A |
| ILE O | 359 | 198.1 | 96.3 | 48.3 | 51 | A |
| GLY N | 360 | 197.9 | 97.6 | 50.1 | 53 | A |
| GLY CA | 360 | 198.3 | 96.6 | 51.1 | 54 | A |
| GLY C | 360 | 197.1 | 95.6 | 51.0 | 55 | A |
| GLY O | 360 | 197.4 | 94.4 | 50.7 | 55 | A |
| ARG N | 361 | 195.9 | 96.1 | 51.2 | 57 | A |
| ARG CA | 361 | 194.7 | 95.2 | 51.2 | 58 | A |
| ARG CB | 361 | 193.5 | 96.0 | 51.4 | 59 | A |
| ARG CG | 361 | 193.0 | 96.1 | 52.9 | 60 | A |
| ARG CD | 361 | 192.8 | 97.5 | 53.4 | 61 | A |
| ARG NE | 361 | 191.7 | 98.1 | 52.6 | 62 | A |
| ARG CZ | 361 | 191.7 | 99.5 | 52.4 | 62 | A |
| ARG NH1 | 361 | 190.7 | 100.0 | 51.6 | 63 | A |
| ARG NH2 | 361 | 192.7 | 100.2 | 52.9 | 63 | A |
| ARG C | 361 | 194.6 | 94.4 | 49.9 | 59 | A |
| ARG O | 361 | 194.2 | 93.3 | 49.9 | 61 | A |
| SER N | 362 | 194.9 | 95.1 | 48.8 | 60 | A |
| SER CA | 362 | 194.8 | 94.4 | 47.5 | 60 | A |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| SER CB | 362 | 195.0 | 95.4 | 46.3 | 59 | A |
| SER OG | 362 | 193.8 | 96.1 | 46.1 | 59 | A |
| SER C | 362 | 195.9 | 93.3 | 47.4 | 59 | A |
| SER O | 362 | 195.6 | 92.2 | 47.1 | 59 | A |
| LEU N | 363 | 197.1 | 93.7 | 47.8 | 60 | A |
| LEU CA | 363 | 198.2 | 92.7 | 47.8 | 62 | A |
| LEU CB | 363 | 199.5 | 93.4 | 48.3 | 62 | A |
| LEU CG | 363 | 200.5 | 93.8 | 47.2 | 62 | A |
| LEU CD1 | 363 | 199.8 | 94.7 | 46.1 | 62 | A |
| LEU CD2 | 363 | 201.6 | 94.6 | 47.8 | 62 | A |
| LEU C | 363 | 197.9 | 91.6 | 48.7 | 63 | A |
| LEU O | 363 | 198.4 | 90.5 | 48.6 | 62 | A |
| GLN N | 364 | 197.1 | 91.9 | 49.7 | 65 | A |
| GLN CA | 364 | 196.6 | 90.9 | 50.7 | 67 | A |
| GLN CB | 364 | 195.8 | 91.6 | 51.8 | 68 | A |
| GLN CG | 364 | 195.9 | 91.0 | 53.1 | 69 | A |
| GLN CD | 364 | 197.3 | 91.2 | 53.7 | 70 | A |
| GLN OE1 | 364 | 197.4 | 92.0 | 54.7 | 71 | A |
| GLN NE2 | 364 | 198.3 | 90.4 | 53.3 | 70 | A |
| GLN C | 364 | 195.8 | 89.8 | 50.0 | 68 | A |
| GLN O | 364 | 195.8 | 88.7 | 50.5 | 69 | A |
| SER N | 365 | 195.0 | 90.2 | 49.0 | 69 | A |
| SER CA | 365 | 194.2 | 89.1 | 48.3 | 70 | A |
| SER CB | 365 | 192.8 | 89.6 | 48.2 | 70 | A |
| SER OG | 365 | 192.6 | 90.7 | 47.4 | 71 | A |
| SER C | 365 | 194.8 | 88.7 | 47.0 | 72 | A |
| SER O | 365 | 194.0 | 88.4 | 46.1 | 72 | A |
| LYS N | 366 | 196.1 | 88.6 | 46.8 | 74 | A |
| LYS CA | 366 | 196.8 | 88.2 | 45.6 | 77 | A |
| LYS CB | 366 | 196.3 | 88.9 | 44.4 | 78 | A |
| LYS CG | 366 | 196.5 | 90.4 | 44.3 | 80 | A |
| LYS CD | 366 | 195.3 | 91.2 | 44.6 | 81 | A |
| LYS CE | 366 | 194.1 | 90.8 | 43.8 | 82 | A |
| LYS NZ | 366 | 192.8 | 91.6 | 44.3 | 83 | A |
| LYS C | 366 | 198.3 | 88.1 | 45.7 | 77 | A |
| LYS OT1 | 366 | 198.8 | 87.5 | 46.7 | 77 | A |
| LYS OT2 | 366 | 199.0 | 88.6 | 44.7 | 76 | A |
| LEU CB | 523 | 194.6 | 121.6 | 61.6 | 44 | B |
| LEU CG | 523 | 193.3 | 122.3 | 62.1 | 44 | B |
| LEU CD1 | 523 | 193.5 | 123.8 | 61.8 | 44 | B |
| LEU CD2 | 523 | 192.1 | 121.8 | 61.4 | 44 | B |
| LEU C | 523 | 195.8 | 119.4 | 61.4 | 46 | B |
| LEU O | 523 | 196.9 | 119.6 | 61.9 | 46 | B |
| LEU N | 523 | 194.6 | 119.9 | 63.4 | 47 | B |
| LEU CA | 523 | 194.5 | 120.1 | 62.0 | 45 | B |
| TYR N | 524 | 195.5 | 118.4 | 60.5 | 47 | B |
| TYR CA | 524 | 196.6 | 117.6 | 59.9 | 46 | B |
| TYR CB | 524 | 196.0 | 116.7 | 58.9 | 45 | B |
| TYR CG | 524 | 197.0 | 116.0 | 58.0 | 45 | B |
| TYR CD1 | 524 | 197.6 | 114.8 | 58.3 | 44 | B |
| TYR CE1 | 524 | 198.6 | 114.1 | 57.5 | 44 | B |
| TYR CD2 | 524 | 197.3 | 116.5 | 56.7 | 44 | B |
| TYR CE2 | 524 | 198.3 | 115.9 | 55.9 | 43 | B |
| TYR CZ | 524 | 198.9 | 114.7 | 56.3 | 43 | B |
| TYR OH | 524 | 199.7 | 114.1 | 55.4 | 41 | B |
| TYR C | 524 | 197.7 | 118.4 | 59.3 | 47 | B |
| TYR O | 524 | 198.9 | 118.1 | 59.5 | 47 | B |
| SER N | 525 | 197.3 | 119.5 | 58.7 | 48 | B |
| SER CA | 525 | 198.3 | 120.4 | 58.0 | 50 | B |
| SER CB | 525 | 197.6 | 121.3 | 57.0 | 49 | B |
| SER OG | 525 | 196.6 | 122.0 | 57.6 | 49 | B |
| SER C | 525 | 199.1 | 121.2 | 59.1 | 52 | B |
| SER O | 525 | 200.3 | 121.5 | 58.8 | 53 | B |
| LEU N | 526 | 198.5 | 121.5 | 60.2 | 54 | B |
| LEU CA | 526 | 199.1 | 122.3 | 61.2 | 56 | B |
| LEU CB | 526 | 198.0 | 123.0 | 62.0 | 56 | B |
| LEU CG | 526 | 198.2 | 124.6 | 62.1 | 56 | B |
| LEU CD1 | 526 | 199.1 | 125.0 | 60.9 | 57 | B |
| LEU CD2 | 526 | 196.8 | 125.2 | 61.9 | 56 | B |
| LEU C | 526 | 200.0 | 121.4 | 62.1 | 57 | B |
| LEU O | 526 | 200.6 | 121.9 | 63.1 | 57 | B |
| ARG N | 527 | 200.0 | 120.1 | 61.8 | 58 | B |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| ARG CA | 527 | 200.8 | 119.2 | 62.6 | 58 | B |
| ARG CB | 527 | 200.4 | 117.8 | 62.1 | 59 | B |
| ARG CG | 527 | 200.7 | 116.7 | 63.1 | 59 | B |
| ARG CD | 527 | 199.9 | 115.4 | 62.8 | 60 | B |
| ARG NE | 527 | 198.5 | 115.7 | 63.1 | 60 | B |
| ARG CZ | 527 | 197.5 | 114.9 | 62.5 | 60 | B |
| ARG NH1 | 527 | 197.8 | 113.9 | 61.7 | 60 | B |
| ARG NH2 | 527 | 196.3 | 115.2 | 62.8 | 60 | B |
| ARG C | 527 | 202.2 | 119.4 | 62.4 | 59 | B |
| ARG O | 527 | 202.7 | 119.8 | 61.4 | 61 | B |
| PRO N | 528 | 203.0 | 119.2 | 63.5 | 60 | B |
| PRO CD | 528 | 202.6 | 119.0 | 64.9 | 61 | B |
| PRO CA | 528 | 204.5 | 119.5 | 63.5 | 61 | B |
| PRO CB | 528 | 204.9 | 119.1 | 65.0 | 61 | B |
| PRO CG | 528 | 203.7 | 119.6 | 65.7 | 60 | B |
| PRO C | 528 | 205.3 | 118.7 | 62.6 | 61 | B |
| PRO O | 528 | 206.3 | 119.1 | 62.0 | 61 | B |
| GLU N | 529 | 204.9 | 117.4 | 62.3 | 62 | B |
| GLU CA | 529 | 205.7 | 116.6 | 61.4 | 63 | B |
| GLU CB | 529 | 205.3 | 115.1 | 61.7 | 65 | B |
| GLU CG | 529 | 203.8 | 114.8 | 61.9 | 67 | B |
| GLU CD | 529 | 203.4 | 114.8 | 63.3 | 69 | B |
| GLU OE1 | 529 | 202.7 | 113.8 | 63.7 | 70 | B |
| GLU OE2 | 529 | 203.7 | 115.8 | 64.1 | 70 | B |
| GLU C | 529 | 205.4 | 116.9 | 60.0 | 63 | B |
| GLU O | 529 | 206.2 | 116.6 | 59.1 | 62 | B |
| HIS N | 530 | 204.2 | 117.5 | 59.7 | 62 | B |
| HIS CA | 530 | 203.8 | 117.9 | 58.4 | 61 | B |
| HIS CB | 530 | 202.4 | 118.5 | 58.4 | 62 | B |
| HIS CG | 530 | 201.9 | 119.0 | 57.1 | 62 | B |
| HIS CD2 | 530 | 201.2 | 118.4 | 56.1 | 62 | B |
| HIS ND1 | 530 | 202.1 | 120.3 | 56.6 | 62 | B |
| HIS CE1 | 530 | 201.5 | 120.4 | 55.5 | 62 | B |
| HIS NE2 | 530 | 201.0 | 119.3 | 55.1 | 62 | B |
| HIS C | 530 | 204.8 | 118.8 | 57.7 | 60 | B |
| HIS O | 530 | 204.8 | 118.9 | 56.5 | 60 | B |
| ALA N | 531 | 205.6 | 119.5 | 58.5 | 60 | B |
| ALA CA | 531 | 206.6 | 120.4 | 58.0 | 59 | B |
| ALA CB | 531 | 207.3 | 121.2 | 59.1 | 60 | B |
| ALA C | 531 | 207.7 | 119.6 | 57.2 | 58 | B |
| ALA O | 531 | 208.4 | 120.2 | 56.3 | 58 | B |
| ARG N | 532 | 207.8 | 118.3 | 57.4 | 57 | B |
| ARG CA | 532 | 208.8 | 117.5 | 56.7 | 56 | B |
| ARG CB | 532 | 209.0 | 116.2 | 57.5 | 59 | B |
| ARG CG | 532 | 209.9 | 116.3 | 58.7 | 63 | B |
| ARG CD | 532 | 209.1 | 116.1 | 60.0 | 65 | B |
| ARG NE | 532 | 208.9 | 114.6 | 60.2 | 68 | B |
| ARG CZ | 532 | 208.6 | 114.1 | 61.4 | 69 | B |
| ARG NH1 | 532 | 208.3 | 114.9 | 62.5 | 69 | B |
| ARG NH2 | 532 | 208.4 | 112.8 | 61.5 | 69 | B |
| ARG C | 532 | 208.3 | 117.3 | 55.3 | 54 | B |
| ARG O | 532 | 209.1 | 116.8 | 54.4 | 53 | B |
| GLU N | 533 | 207.0 | 117.6 | 55.1 | 51 | B |
| GLU CA | 533 | 206.4 | 117.4 | 53.8 | 50 | B |
| GLU CB | 533 | 204.9 | 117.3 | 53.9 | 49 | B |
| GLU CG | 533 | 204.4 | 116.0 | 54.6 | 47 | B |
| GLU CD | 533 | 204.9 | 114.7 | 53.8 | 46 | B |
| GLU OE1 | 533 | 204.0 | 114.0 | 53.3 | 46 | B |
| GLU OE2 | 533 | 206.1 | 114.4 | 53.7 | 45 | B |
| GLU C | 533 | 206.8 | 118.5 | 52.8 | 50 | B |
| GLU O | 533 | 206.3 | 118.6 | 51.7 | 50 | B |
| ARG N | 534 | 207.7 | 119.3 | 53.2 | 50 | B |
| ARG CA | 534 | 208.2 | 120.4 | 52.4 | 49 | B |
| ARG CB | 534 | 209.1 | 121.3 | 53.3 | 50 | B |
| ARG CG | 534 | 208.9 | 122.8 | 53.0 | 52 | B |
| ARG CD | 534 | 207.6 | 123.3 | 53.5 | 53 | B |
| ARG NE | 534 | 207.3 | 124.7 | 53.1 | 55 | B |
| ARG CZ | 534 | 208.2 | 125.7 | 53.4 | 56 | B |
| ARG NH1 | 534 | 209.3 | 125.4 | 54.0 | 58 | B |
| ARG NH2 | 534 | 207.8 | 126.9 | 53.2 | 57 | B |
| ARG C | 534 | 209.0 | 119.9 | 51.2 | 48 | B |
| ARG O | 534 | 209.6 | 118.9 | 51.3 | 48 | B |
| LEU N | 535 | 208.9 | 120.7 | 50.2 | 47 | B |
| LEU CA | 535 | 209.6 | 120.3 | 48.9 | 46 | B |
| LEU CB | 535 | 209.4 | 121.4 | 47.9 | 44 | B |
| LEU CG | 535 | 210.2 | 121.2 | 46.5 | 43 | B |
| LEU CD1 | 535 | 209.6 | 120.1 | 45.7 | 42 | B |
| LEU CD2 | 535 | 210.2 | 122.5 | 45.8 | 43 | B |
| LEU C | 535 | 211.1 | 120.1 | 49.2 | 46 | B |
| LEU O | 535 | 211.7 | 120.9 | 49.9 | 46 | B |
| GLN N | 536 | 211.7 | 119.1 | 48.5 | 47 | B |
| GLN CA | 536 | 213.1 | 118.8 | 48.5 | 49 | B |
| GLN CB | 536 | 213.3 | 117.4 | 49.0 | 50 | B |
| GLN CG | 536 | 212.7 | 117.1 | 50.3 | 52 | B |
| GLN CD | 536 | 213.2 | 115.9 | 51.0 | 53 | B |
| GLN OE1 | 536 | 212.5 | 115.1 | 51.5 | 54 | B |
| GLN NE2 | 536 | 214.5 | 115.7 | 50.9 | 53 | B |
| GLN C | 536 | 213.7 | 119.0 | 47.2 | 50 | B |
| GLN O | 536 | 213.6 | 118.1 | 46.4 | 51 | B |
| ASP N | 537 | 214.2 | 120.2 | 46.9 | 51 | B |
| ASP CA | 537 | 214.8 | 120.5 | 45.6 | 52 | B |
| ASP CB | 537 | 214.9 | 122.0 | 45.4 | 53 | B |
| ASP CG | 537 | 216.2 | 122.6 | 45.9 | 53 | B |
| ASP OD1 | 537 | 216.8 | 122.0 | 46.9 | 54 | B |
| ASP OD2 | 537 | 216.7 | 123.6 | 45.4 | 53 | B |
| ASP C | 537 | 216.1 | 119.8 | 45.1 | 52 | B |
| ASP O | 537 | 216.6 | 120.1 | 44.1 | 52 | B |
| ASP N | 538 | 216.6 | 118.9 | 46.0 | 53 | B |
| ASP CA | 538 | 217.9 | 118.2 | 45.7 | 53 | B |
| ASP CB | 538 | 217.7 | 117.3 | 44.5 | 53 | B |
| ASP CG | 538 | 216.6 | 116.2 | 44.8 | 55 | B |
| ASP OD1 | 538 | 216.7 | 115.6 | 45.8 | 55 | B |
| ASP OD2 | 538 | 215.7 | 116.0 | 43.9 | 55 | B |
| ASP C | 538 | 219.0 | 119.2 | 45.4 | 52 | B |
| ASP O | 538 | 220.1 | 118.8 | 44.9 | 52 | B |
| SER N | 539 | 218.8 | 120.4 | 45.7 | 51 | B |
| SER CA | 539 | 219.8 | 121.5 | 45.5 | 52 | B |
| SER CB | 539 | 221.1 | 121.1 | 46.2 | 53 | B |
| SER OG | 539 | 220.9 | 121.0 | 47.6 | 54 | B |
| SER C | 539 | 220.1 | 121.7 | 44.0 | 52 | B |
| SER O | 539 | 221.2 | 122.1 | 43.6 | 53 | B |
| VAL N | 540 | 219.1 | 121.4 | 43.2 | 50 | B |
| VAL CA | 540 | 219.1 | 121.6 | 41.8 | 48 | B |
| VAL CB | 540 | 219.1 | 120.3 | 41.0 | 47 | B |
| VAL CG1 | 540 | 219.1 | 120.6 | 39.5 | 47 | B |
| VAL CG2 | 540 | 220.2 | 119.4 | 41.4 | 47 | B |
| VAL C | 540 | 217.9 | 122.4 | 41.5 | 48 | B |
| VAL O | 540 | 216.8 | 121.9 | 41.4 | 48 | B |
| GLU N | 541 | 218.0 | 123.8 | 41.4 | 47 | B |
| GLU CA | 541 | 216.9 | 124.6 | 41.2 | 46 | B |
| GLU CB | 541 | 217.1 | 126.0 | 41.7 | 49 | B |
| GLU CG | 541 | 217.8 | 126.1 | 43.0 | 54 | B |
| GLU CD | 541 | 218.0 | 127.6 | 43.4 | 56 | B |
| GLU OE1 | 541 | 218.3 | 128.4 | 42.5 | 58 | B |
| GLU OE2 | 541 | 217.7 | 127.9 | 44.6 | 58 | B |
| GLU C | 541 | 216.5 | 124.7 | 39.7 | 44 | B |
| GLU O | 541 | 217.4 | 124.8 | 38.9 | 44 | B |
| THR N | 542 | 215.2 | 124.7 | 39.5 | 42 | B |
| THR CA | 542 | 214.7 | 124.9 | 38.1 | 39 | B |
| THR CB | 542 | 214.3 | 123.6 | 37.5 | 39 | B |
| THR OG1 | 542 | 213.4 | 122.9 | 38.3 | 39 | B |
| THR CG2 | 542 | 215.6 | 122.8 | 37.3 | 39 | B |
| THR C | 542 | 213.5 | 125.8 | 38.3 | 38 | B |
| THR O | 542 | 213.0 | 126.0 | 39.5 | 39 | B |
| VAL N | 543 | 212.9 | 126.4 | 37.2 | 35 | B |
| VAL CA | 543 | 211.8 | 127.2 | 37.3 | 32 | B |
| VAL CB | 543 | 211.2 | 127.5 | 35.9 | 31 | B |
| VAL CG1 | 543 | 210.0 | 128.5 | 36.1 | 30 | B |
| VAL CG2 | 543 | 212.3 | 128.1 | 35.1 | 32 | B |
| VAL C | 543 | 210.7 | 126.5 | 38.1 | 32 | B |
| VAL O | 543 | 210.0 | 127.2 | 38.9 | 32 | B |
| THR N | 544 | 210.5 | 125.2 | 38.0 | 32 | B |
| THR CA | 544 | 209.5 | 124.4 | 38.6 | 31 | B |
| THR CB | 544 | 209.5 | 122.9 | 38.1 | 32 | B |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| THR OG1 | 544 | 209.4 | 122.9 | 36.7 | 32 | B |
| THR CG2 | 544 | 208.3 | 122.2 | 38.7 | 32 | B |
| THR C | 544 | 209.6 | 124.4 | 40.2 | 30 | B |
| THR O | 544 | 208.7 | 124.6 | 40.8 | 30 | B |
| SER N | 545 | 210.8 | 124.1 | 40.7 | 31 | B |
| SER CA | 545 | 211.0 | 124.0 | 42.1 | 32 | B |
| SER CB | 545 | 212.4 | 123.4 | 42.5 | 31 | B |
| SER OG | 545 | 213.4 | 123.9 | 41.7 | 32 | B |
| SER C | 545 | 210.9 | 125.4 | 42.7 | 32 | B |
| SER O | 545 | 210.3 | 125.6 | 43.7 | 34 | B |
| ILE N | 546 | 211.5 | 126.4 | 42.0 | 33 | B |
| ILE CA | 546 | 211.5 | 127.8 | 42.4 | 32 | B |
| ILE CB | 546 | 212.1 | 128.7 | 41.3 | 32 | B |
| ILE CG2 | 546 | 211.8 | 130.1 | 41.5 | 31 | B |
| ILE CG1 | 546 | 213.6 | 128.4 | 41.3 | 32 | B |
| ILE CD1 | 546 | 214.4 | 129.1 | 40.2 | 33 | B |
| ILE C | 546 | 210.0 | 128.2 | 42.6 | 33 | B |
| ILE O | 546 | 209.7 | 128.9 | 43.6 | 35 | B |
| GLU N | 547 | 209.1 | 127.9 | 41.7 | 33 | B |
| GLU CA | 547 | 207.7 | 128.3 | 41.8 | 32 | B |
| GLU CB | 547 | 207.0 | 128.2 | 40.5 | 34 | B |
| GLU CG | 547 | 207.6 | 129.2 | 39.4 | 35 | B |
| GLU CD | 547 | 207.4 | 130.6 | 39.9 | 36 | B |
| GLU OE1 | 547 | 206.3 | 131.0 | 40.3 | 37 | B |
| GLU OE2 | 547 | 208.4 | 131.4 | 39.8 | 38 | B |
| GLU C | 547 | 207.0 | 127.5 | 42.8 | 32 | B |
| GLU O | 547 | 206.0 | 128.0 | 43.5 | 31 | B |
| GLN N | 548 | 207.3 | 126.2 | 42.9 | 32 | B |
| GLN CA | 548 | 206.6 | 125.3 | 43.9 | 33 | B |
| GLN CB | 548 | 207.1 | 123.9 | 43.7 | 31 | B |
| GLN CG | 548 | 206.4 | 122.8 | 44.7 | 31 | B |
| GLN CD | 548 | 204.9 | 122.8 | 44.8 | 32 | B |
| GLN OE1 | 548 | 204.3 | 122.6 | 45.8 | 32 | B |
| GLN NE2 | 548 | 204.3 | 123.1 | 43.6 | 33 | B |
| GLN C | 548 | 207.0 | 125.8 | 45.3 | 33 | B |
| GLN O | 548 | 206.1 | 126.0 | 46.2 | 33 | B |
| ALA N | 549 | 208.3 | 126.2 | 45.5 | 34 | B |
| ALA CA | 549 | 208.8 | 126.8 | 46.7 | 35 | B |
| ALA CB | 549 | 210.3 | 127.0 | 46.6 | 34 | B |
| ALA C | 549 | 208.1 | 128.1 | 47.1 | 36 | B |
| ALA O | 549 | 207.8 | 128.3 | 48.3 | 37 | B |
| LYS N | 550 | 207.8 | 128.9 | 46.1 | 37 | B |
| LYS CA | 550 | 207.1 | 130.2 | 46.4 | 39 | B |
| LYS CB | 550 | 207.0 | 131.0 | 45.2 | 41 | B |
| LYS CG | 550 | 208.3 | 131.5 | 44.6 | 43 | B |
| LYS CD | 550 | 208.1 | 132.4 | 43.4 | 45 | B |
| LYS CE | 550 | 209.4 | 132.8 | 42.7 | 46 | B |
| LYS NZ | 550 | 209.2 | 133.7 | 41.5 | 47 | B |
| LYS C | 550 | 205.8 | 129.9 | 47.0 | 40 | B |
| LYS O | 550 | 205.3 | 130.5 | 47.9 | 41 | B |
| VAL N | 551 | 205.1 | 128.9 | 46.3 | 40 | B |
| VAL CA | 551 | 203.7 | 128.5 | 46.8 | 40 | B |
| VAL CB | 551 | 203.1 | 127.5 | 45.8 | 40 | B |
| VAL CG1 | 551 | 201.8 | 127.0 | 46.4 | 40 | B |
| VAL CG2 | 551 | 202.8 | 128.2 | 44.5 | 40 | B |
| VAL C | 551 | 203.7 | 128.0 | 48.2 | 41 | B |
| VAL O | 551 | 203.0 | 128.5 | 49.0 | 41 | B |
| GLU N | 552 | 204.6 | 127.0 | 48.4 | 41 | B |
| GLU CA | 552 | 204.7 | 126.4 | 49.7 | 43 | B |
| GLU CB | 552 | 205.7 | 125.3 | 49.8 | 41 | B |
| GLU CG | 552 | 205.4 | 124.1 | 49.0 | 39 | B |
| GLU CD | 552 | 206.4 | 123.0 | 49.1 | 38 | B |
| GLU OE1 | 552 | 207.5 | 123.3 | 49.7 | 37 | B |
| GLU OE2 | 552 | 206.1 | 121.9 | 48.7 | 38 | B |
| GLU C | 552 | 204.9 | 127.4 | 50.8 | 45 | B |
| GLU O | 552 | 204.2 | 127.4 | 51.8 | 46 | B |
| GLU N | 553 | 205.8 | 128.4 | 50.6 | 48 | B |
| GLU CA | 553 | 206.1 | 129.4 | 51.5 | 50 | B |
| GLU CB | 553 | 207.1 | 130.4 | 50.9 | 53 | B |
| GLU CG | 553 | 207.4 | 131.6 | 51.8 | 57 | B |
| GLU CD | 553 | 208.8 | 131.6 | 52.3 | 60 | B |
| GLU OE1 | 553 | 209.1 | 130.6 | 53.1 | 61 | B |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| GLU OE2 | 553 | 209.6 | 132.5 | 52.0 | 61 | B |
| GLU C | 553 | 204.8 | 130.2 | 51.9 | 49 | B |
| GLU O | 553 | 204.6 | 130.4 | 53.1 | 49 | B |
| LYS N | 554 | 204.1 | 130.6 | 51.0 | 49 | B |
| LYS CA | 554 | 202.8 | 131.3 | 51.3 | 51 | B |
| LYS CB | 554 | 202.1 | 131.8 | 50.0 | 53 | B |
| LYS CG | 554 | 203.0 | 132.7 | 49.2 | 57 | B |
| LYS CD | 554 | 202.2 | 133.2 | 47.9 | 61 | B |
| LYS CE | 554 | 203.0 | 134.2 | 47.1 | 63 | B |
| LYS NZ | 554 | 202.1 | 135.0 | 46.2 | 64 | B |
| LYS C | 554 | 201.9 | 130.5 | 52.1 | 51 | B |
| LYS O | 554 | 201.2 | 131.0 | 53.0 | 51 | B |
| ILE N | 555 | 201.7 | 129.2 | 51.7 | 51 | B |
| ILE CA | 555 | 200.8 | 128.3 | 52.4 | 50 | B |
| ILE CB | 555 | 200.7 | 126.9 | 51.7 | 49 | B |
| ILE CG2 | 555 | 199.7 | 126.1 | 52.4 | 48 | B |
| ILE CG1 | 555 | 200.4 | 127.1 | 50.2 | 49 | B |
| ILE CD1 | 555 | 199.2 | 127.9 | 49.9 | 49 | B |
| ILE C | 555 | 201.3 | 128.1 | 53.8 | 50 | B |
| ILE O | 555 | 200.5 | 128.2 | 54.8 | 50 | B |
| GLN N | 556 | 202.6 | 127.9 | 54.0 | 50 | B |
| GLN CA | 556 | 203.2 | 127.8 | 55.3 | 51 | B |
| GLN CB | 556 | 204.7 | 127.8 | 55.1 | 51 | B |
| GLN CG | 556 | 205.5 | 127.7 | 56.4 | 53 | B |
| GLN CD | 556 | 205.1 | 126.4 | 57.2 | 53 | B |
| GLN OE1 | 556 | 205.9 | 125.4 | 57.1 | 55 | B |
| GLN NE2 | 556 | 204.0 | 126.4 | 57.9 | 53 | B |
| GLN C | 556 | 202.7 | 128.9 | 56.1 | 53 | B |
| GLN O | 556 | 202.1 | 128.7 | 57.1 | 54 | B |
| GLU N | 557 | 203.0 | 130.2 | 55.7 | 53 | B |
| GLU CA | 557 | 202.6 | 131.3 | 56.4 | 54 | B |
| GLU CB | 557 | 202.9 | 132.6 | 55.6 | 57 | B |
| GLU CG | 557 | 204.4 | 132.7 | 55.2 | 60 | B |
| GLU CD | 557 | 204.7 | 133.9 | 54.3 | 62 | B |
| GLU OE1 | 557 | 203.9 | 134.8 | 54.2 | 63 | B |
| GLU OE2 | 557 | 205.9 | 134.0 | 53.8 | 62 | B |
| GLU C | 557 | 201.1 | 131.3 | 56.8 | 54 | B |
| GLU O | 557 | 200.8 | 131.8 | 57.9 | 55 | B |
| VAL N | 558 | 200.3 | 130.8 | 56.0 | 54 | B |
| VAL CA | 558 | 198.8 | 130.7 | 56.3 | 53 | B |
| VAL CB | 558 | 198.0 | 130.2 | 55.1 | 53 | B |
| VAL CG1 | 558 | 196.6 | 129.9 | 55.5 | 53 | B |
| VAL CG2 | 558 | 198.0 | 131.2 | 53.9 | 53 | B |
| VAL C | 558 | 198.6 | 129.7 | 57.4 | 52 | B |
| VAL O | 558 | 197.9 | 130.0 | 58.4 | 52 | B |
| PHE N | 559 | 199.2 | 128.6 | 57.4 | 52 | B |
| PHE CA | 559 | 199.1 | 127.6 | 58.4 | 52 | B |
| PHE CB | 559 | 199.9 | 126.3 | 58.0 | 50 | B |
| PHE CG | 559 | 199.3 | 125.6 | 56.8 | 49 | B |
| PHE CD1 | 559 | 200.0 | 124.7 | 56.1 | 49 | B |
| PHE CD2 | 559 | 197.9 | 125.8 | 56.5 | 48 | B |
| PHE CE1 | 559 | 199.4 | 123.9 | 55.0 | 47 | B |
| P HE CE2 | 559 | 197.3 | 125.0 | 55.5 | 47 | B |
| PHE CZ | 559 | 198.1 | 124.1 | 54.7 | 48 | B |
| PHE C | 559 | 199.5 | 128.1 | 59.8 | 53 | B |
| PHE O | 559 | 198.8 | 128.0 | 60.7 | 53 | B |
| SER N | 560 | 200.7 | 128.8 | 59.8 | 54 | B |
| SER CA | 560 | 201.2 | 129.3 | 61.0 | 56 | B |
| SER CB | 560 | 202.7 | 129.6 | 60.9 | 55 | B |
| SER OG | 560 | 203.4 | 128.4 | 60.4 | 55 | B |
| SER C | 560 | 200.5 | 130.6 | 61.4 | 58 | B |
| SER O | 560 | 200.8 | 131.1 | 62.5 | 57 | B |
| SER N | 561 | 199.6 | 131.2 | 60.6 | 61 | B |
| SER CA | 561 | 199.0 | 132.4 | 61.0 | 64 | B |
| SER CB | 561 | 198.0 | 132.9 | 59.9 | 64 | B |
| SER OG | 561 | 196.9 | 132.0 | 59.8 | 64 | B |
| SER C | 561 | 198.2 | 132.1 | 62.3 | 66 | B |
| SER O | 561 | 198.2 | 132.9 | 63.2 | 66 | B |
| TYR N | 562 | 197.7 | 130.9 | 62.4 | 70 | B |
| TYR CA | 562 | 196.9 | 130.4 | 63.5 | 73 | B |
| TYR CB | 562 | 196.3 | 129.0 | 63.2 | 73 | B |
| TYR CG | 562 | 195.2 | 129.0 | 62.2 | 73 | B |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| TYR CD1 | 562 | 195.4 | 128.5 | 60.9 | 73 | B |
| TYR CE1 | 562 | 194.4 | 128.5 | 59.9 | 74 | B |
| TYR CD2 | 562 | 194.0 | 129.6 | 62.5 | 73 | B |
| TYR CE2 | 562 | 193.0 | 129.7 | 61.5 | 74 | B |
| TYR CZ | 562 | 193.2 | 129.1 | 60.2 | 74 | B |
| TYR OH | 562 | 192.2 | 129.2 | 59.3 | 74 | B |
| TYR C | 562 | 197.8 | 130.3 | 64.8 | 75 | B |
| TYR O | 562 | 197.5 | 131.0 | 65.8 | 75 | B |
| LYS N | 563 | 198.8 | 129.5 | 64.7 | 77 | B |
| LYS CA | 563 | 199.8 | 129.3 | 65.7 | 79 | B |
| LYS CB | 563 | 200.7 | 128.1 | 65.2 | 81 | B |
| LYS CG | 563 | 201.1 | 127.1 | 66.2 | 82 | B |
| LYS CD | 563 | 201.5 | 125.8 | 65.6 | 83 | B |
| LYS CE | 563 | 202.8 | 125.9 | 64.7 | 84 | B |
| LYS NZ | 563 | 203.8 | 124.8 | 65.0 | 84 | B |
| LYS C | 563 | 200.7 | 130.5 | 65.9 | 80 | B |
| LYS O | 563 | 201.9 | 130.4 | 66.1 | 79 | B |
| PHE N | 564 | 200.0 | 131.7 | 66.0 | 82 | B |
| PHE CA | 564 | 200.7 | 133.0 | 66.2 | 85 | B |
| PHE CB | 564 | 200.4 | 133.8 | 65.0 | 87 | B |
| PHE CG | 564 | 201.1 | 135.2 | 65.0 | 90 | B |
| PHE CD1 | 564 | 202.4 | 135.4 | 64.6 | 91 | B |
| PHE CD2 | 564 | 200.4 | 136.3 | 65.5 | 91 | B |
| PHE CE1 | 564 | 203.0 | 136.7 | 64.6 | 92 | B |
| PHE CE2 | 564 | 200.9 | 137.6 | 65.6 | 92 | B |
| PHE CZ | 564 | 202.3 | 137.8 | 65.2 | 93 | B |
| PHE C | 564 | 200.3 | 133.7 | 67.5 | 85 | B |
| PHE O | 564 | 199.4 | 134.6 | 67.4 | 85 | B |
| ASN N | 565 | 200.9 | 133.3 | 68.6 | 84 | B |
| ASN CA | 565 | 200.6 | 133.9 | 69.9 | 82 | B |
| ASN CB | 565 | 201.4 | 135.2 | 70.1 | 84 | B |
| ASN CG | 565 | 202.7 | 135.0 | 70.8 | 86 | B |
| ASN OD1 | 565 | 203.0 | 133.9 | 71.2 | 87 | B |
| ASN ND2 | 565 | 203.5 | 136.1 | 70.9 | 87 | B |
| ASN C | 565 | 199.2 | 134.4 | 70.0 | 81 | B |
| ASN O | 565 | 198.9 | 135.4 | 70.6 | 80 | B |
| HIS N | 566 | 198.3 | 133.7 | 69.4 | 79 | B |
| HIS CA | 566 | 196.9 | 134.2 | 69.4 | 78 | B |
| HIS CB | 566 | 196.7 | 134.8 | 68.0 | 81 | B |
| HIS CG | 566 | 196.4 | 136.3 | 68.0 | 82 | B |
| HIS CD2 | 566 | 195.3 | 137.0 | 68.2 | 83 | B |
| HIS ND1 | 566 | 197.5 | 137.2 | 67.9 | 83 | B |
| HIS CE1 | 566 | 197.0 | 138.5 | 67.9 | 83 | B |
| HIS NE2 | 566 | 195.6 | 138.4 | 68.1 | 83 | B |
| HIS C | 566 | 195.8 | 133.4 | 69.8 | 76 | B |
| HIS O | 566 | 195.4 | 133.3 | 70.9 | 75 | B |
| LEU N | 567 | 195.1 | 132.9 | 68.7 | 75 | B |
| LEU CA | 567 | 193.9 | 132.2 | 68.9 | 74 | B |
| LEU CB | 567 | 192.8 | 132.7 | 68.0 | 74 | B |
| LEU CG | 567 | 192.6 | 134.2 | 67.8 | 74 | B |
| LEU CD1 | 567 | 192.9 | 135.0 | 69.1 | 73 | B |
| LEU CD2 | 567 | 193.5 | 134.7 | 66.6 | 73 | B |
| LEU C | 567 | 194.0 | 130.7 | 68.7 | 74 | B |
| LEU O | 567 | 195.2 | 130.2 | 68.5 | 75 | B |
| VAL N | 568 | 192.9 | 130.0 | 68.6 | 74 | B |
| VAL CA | 568 | 192.8 | 128.6 | 68.4 | 73 | B |
| VAL CB | 568 | 191.8 | 127.9 | 69.4 | 73 | B |
| VAL CG1 | 568 | 191.9 | 126.4 | 69.4 | 73 | B |
| VAL CG2 | 568 | 192.1 | 128.5 | 70.8 | 72 | B |
| VAL C | 568 | 192.2 | 128.5 | 67.0 | 72 | B |
| VAL O | 568 | 191.2 | 129.1 | 66.7 | 73 | B |
| PRO N | 569 | 192.8 | 127.7 | 66.1 | 71 | B |
| PRO CD | 569 | 194.0 | 126.9 | 66.2 | 71 | B |
| PRO CA | 569 | 192.2 | 127.6 | 64.7 | 71 | B |
| PRO CB | 569 | 193.1 | 126.6 | 64.0 | 71 | B |
| PRO CG | 569 | 193.8 | 125.9 | 65.1 | 71 | B |
| PRO C | 569 | 190.7 | 127.2 | 64.7 | 70 | B |
| PRO O | 569 | 190.3 | 126.2 | 65.2 | 70 | B |
| ARG N | 570 | 189.9 | 128.1 | 64.1 | 70 | B |
| ARG CA | 570 | 188.5 | 127.9 | 63.9 | 70 | B |
| ARG CB | 570 | 187.8 | 129.2 | 64.4 | 73 | B |
| ARG CG | 570 | 187.7 | 129.3 | 65.9 | 77 | B |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| ARG CD | 570 | 186.3 | 128.8 | 66.4 | 80 | B |
| ARG NE | 570 | 186.3 | 127.4 | 66.4 | 82 | B |
| ARG CZ | 570 | 185.7 | 126.7 | 67.4 | 84 | B |
| ARG NH1 | 570 | 185.1 | 127.3 | 68.4 | 85 | B |
| ARG NH2 | 570 | 185.8 | 125.3 | 67.4 | 85 | B |
| ARG C | 570 | 188.3 | 127.7 | 62.4 | 68 | B |
| ARG O | 570 | 188.3 | 128.7 | 61.7 | 68 | B |
| LEU N | 571 | 188.2 | 126.5 | 62.0 | 63 | B |
| LEU CA | 571 | 188.0 | 126.3 | 60.6 | 59 | B |
| LEU CB | 571 | 188.4 | 124.9 | 60.1 | 59 | B |
| LEU CG | 571 | 189.7 | 124.8 | 59.3 | 58 | B |
| LEU CD1 | 571 | 190.9 | 125.3 | 60.1 | 57 | B |
| LEU CD2 | 571 | 189.9 | 123.4 | 58.7 | 57 | B |
| LEU C | 571 | 186.5 | 126.6 | 60.3 | 57 | B |
| LEU O | 571 | 185.6 | 125.9 | 60.9 | 57 | B |
| VAL N | 572 | 186.2 | 127.6 | 59.5 | 55 | B |
| VAL CA | 572 | 184.8 | 128.0 | 59.3 | 53 | B |
| VAL CB | 572 | 184.4 | 129.2 | 60.2 | 53 | B |
| VAL CG1 | 572 | 183.0 | 129.6 | 59.9 | 53 | B |
| VAL CG2 | 572 | 184.7 | 128.9 | 61.6 | 54 | B |
| VAL C | 572 | 184.6 | 128.4 | 57.8 | 53 | B |
| VAL O | 572 | 185.4 | 129.2 | 57.2 | 53 | B |
| LEU N | 573 | 183.5 | 128.0 | 57.2 | 51 | B |
| LEU CA | 573 | 183.2 | 128.3 | 55.9 | 49 | B |
| LEU CB | 573 | 182.4 | 127.2 | 55.2 | 48 | B |
| LEU CG | 573 | 181.9 | 127.5 | 53.8 | 48 | B |
| LEU CD1 | 573 | 183.1 | 127.2 | 52.8 | 47 | B |
| LEU CD2 | 573 | 180.7 | 126.6 | 53.5 | 47 | B |
| LEU C | 573 | 182.3 | 129.6 | 55.9 | 48 | B |
| LEU O | 573 | 181.1 | 129.6 | 56.4 | 47 | B |
| GLN N | 574 | 182.8 | 130.7 | 55.5 | 48 | B |
| GLN CA | 574 | 182.1 | 132.0 | 55.5 | 48 | B |
| GLN CB | 574 | 183.0 | 133.1 | 55.0 | 49 | B |
| GLN CG | 574 | 184.4 | 133.1 | 55.7 | 51 | B |
| GLN CD | 574 | 184.3 | 133.2 | 57.2 | 52 | B |
| GLN OE1 | 574 | 185.2 | 132.8 | 57.9 | 54 | B |
| GLN NE2 | 574 | 183.2 | 133.7 | 57.8 | 52 | B |
| GLN C | 574 | 180.9 | 132.0 | 54.6 | 48 | B |
| GLN O | 574 | 180.8 | 132.7 | 53.5 | 48 | B |
| ARG N | 575 | 179.9 | 131.2 | 55.0 | 48 | B |
| ARG CA | 575 | 178.6 | 131.0 | 54.2 | 48 | B |
| ARG CB | 575 | 177.7 | 130.2 | 55.0 | 49 | B |
| ARG CG | 575 | 178.1 | 128.7 | 55.2 | 50 | B |
| ARG CD | 575 | 177.2 | 128.1 | 56.2 | 51 | B |
| ARG NE | 575 | 177.2 | 126.6 | 56.1 | 51 | B |
| ARG CZ | 575 | 176.6 | 125.9 | 55.1 | 51 | B |
| ARG NH1 | 575 | 175.8 | 126.5 | 54.3 | 50 | B |
| ARG NH2 | 575 | 176.7 | 124.6 | 55.1 | 51 | B |
| ARG C | 575 | 177.9 | 132.3 | 53.8 | 49 | B |
| ARG O | 575 | 177.5 | 132.5 | 52.7 | 48 | B |
| GLU N | 576 | 177.7 | 133.2 | 54.8 | 49 | B |
| GLU CA | 576 | 177.0 | 434.4 | 54.6 | 49 | B |
| GLU CB | 576 | 176.7 | 135.2 | 55.9 | 52 | B |
| GLU CG | 576 | 176.5 | 134.4 | 57.1 | 55 | B |
| GLU CD | 576 | 175.3 | 133.4 | 57.0 | 57 | B |
| GLU OE1 | 576 | 174.3 | 133.8 | 56.3 | 58 | B |
| GLU OE2 | 576 | 175.4 | 132.3 | 57.5 | 58 | B |
| GLU C | 576 | 177.7 | 135.3 | 53.6 | 47 | B |
| GLU O | 576 | 177.1 | 135.8 | 52.6 | 46 | B |
| LYS N | 577 | 179.0 | 135.3 | 53.7 | 46 | B |
| LYS CA | 577 | 179.9 | 136.1 | 52.9 | 45 | B |
| LYS CB | 577 | 181.3 | 136.0 | 53.4 | 46 | B |
| LYS CG | 577 | 181.9 | 137.3 | 53.9 | 48 | B |
| LYS CD | 577 | 180.9 | 138.1 | 54.8 | 50 | B |
| LYS CE | 577 | 180.7 | 139.5 | 54.4 | 51 | B |
| LYS NZ | 577 | 179.6 | 139.8 | 53.5 | 52 | B |
| LYS C | 577 | 179.8 | 135.5 | 51.4 | 43 | B |
| LYS O | 577 | 179.6 | 136.3 | 50.5 | 43 | B |
| HIS N | 578 | 179.9 | 134.2 | 51.3 | 41 | B |
| HIS CA | 578 | 179.8 | 133.6 | 50.0 | 38 | B |
| HIS CB | 578 | 180.0 | 132.1 | 50.1 | 34 | B |
| HIS CG | 578 | 181.3 | 131.7 | 50.7 | 31 | B |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| HIS CD2 | 578 | 181.8 | 130.6 | 51.3 | 30 | B |
| HIS ND1 | 578 | 182.4 | 132.6 | 50.7 | 30 | B |
| HIS CE1 | 578 | 183.5 | 131.9 | 51.3 | 29 | B |
| HIS NE2 | 578 | 183.1 | 130.7 | 51.6 | 29 | B |
| HIS C | 578 | 178.4 | 133.8 | 49.4 | 39 | B |
| HIS O | 578 | 178.2 | 134.0 | 48.2 | 39 | B |
| PHE N | 579 | 177.4 | 133.7 | 50.3 | 40 | B |
| PHE CA | 579 | 176.0 | 133.9 | 49.9 | 41 | B |
| PHE CB | 579 | 175.1 | 133.6 | 51.0 | 41 | B |
| PHE CG | 579 | 173.7 | 133.9 | 50.7 | 41 | B |
| PHE CD1 | 579 | 172.9 | 133.1 | 49.9 | 42 | B |
| PHE CD2 | 579 | 173.1 | 135.1 | 51.2 | 42 | B |
| PHE CE1 | 579 | 171.6 | 133.4 | 49.5 | 42 | B |
| PHE CE2 | 579 | 171.8 | 135.4 | 50.8 | 43 | B |
| PHE CZ | 579 | 171.1 | 134.6 | 50.0 | 43 | B |
| PHE C | 579 | 175.7 | 135.2 | 49.2 | 43 | B |
| PHE O | 579 | 175.0 | 135.2 | 48.2 | 44 | B |
| HIS N | 580 | 176.2 | 136.3 | 49.8 | 46 | B |
| HIS CA | 580 | 175.9 | 137.6 | 49.3 | 47 | B |
| HIS CB | 580 | 176.3 | 138.7 | 50.4 | 52 | B |
| HIS CG | 580 | 175.8 | 138.4 | 51.7 | 55 | B |
| HIS CD2 | 580 | 174.5 | 138.2 | 52.2 | 57 | B |
| HIS ND1 | 580 | 176.6 | 138.3 | 52.8 | 57 | B |
| HIS CE1 | 580 | 175.9 | 138.0 | 53.9 | 58 | B |
| HIS NE2 | 580 | 174.6 | 137.9 | 53.5 | 58 | B |
| HIS C | 580 | 176.6 | 137.9 | 48.0 | 46 | B |
| HIS O | 580 | 176.2 | 138.6 | 47.2 | 45 | B |
| TYR N | 581 | 177.8 | 137.3 | 48.0 | 44 | B |
| TYR CA | 581 | 178.7 | 137.4 | 46.8 | 43 | B |
| TYR CB | 581 | 180.0 | 136.7 | 47.1 | 42 | B |
| TYR CG | 581 | 181.0 | 136.5 | 45.9 | 43 | B |
| TYR CD1 | 581 | 181.3 | 137.6 | 45.1 | 43 | B |
| TYR CE1 | 581 | 182.1 | 137.5 | 44.0 | 44 | B |
| TYR CD2 | 581 | 181.6 | 135.3 | 45.7 | 43 | B |
| TYR CE2 | 581 | 182.5 | 135.2 | 44.6 | 43 | B |
| TYR CZ | 581 | 182.7 | 136.3 | 43.8 | 43 | B |
| TYR OH | 581 | 183.6 | 136.1 | 42.7 | 43 | B |
| TYR C | 581 | 178.0 | 136.7 | 45.6 | 42 | B |
| TYR O | 581 | 177.8 | 137.4 | 44.5 | 41 | B |
| LEU N | 582 | 177.6 | 135.5 | 45.8 | 41 | B |
| LEU CA | 582 | 176.9 | 134.7 | 44.8 | 40 | B |
| LEU CB | 582 | 176.7 | 133.3 | 45.4 | 38 | B |
| LEU CG | 582 | 177.9 | 132.5 | 45.6 | 36 | B |
| LEU CD1 | 582 | 177.8 | 131.4 | 46.6 | 35 | B |
| LEU CD2 | 582 | 178.4 | 131.8 | 44.3 | 36 | B |
| LEU C | 582 | 175.5 | 135.3 | 44.5 | 42 | B |
| LEU O | 582 | 175.2 | 135.4 | 43.3 | 42 | B |
| LYS N | 583 | 174.9 | 135.8 | 45.5 | 45 | B |
| LYS CA | 583 | 173.6 | 136.4 | 45.4 | 47 | B |
| LYS CB | 583 | 173.1 | 136.8 | 46.8 | 50 | B |
| LYS CG | 583 | 171.8 | 137.6 | 47.0 | 53 | B |
| LYS CD | 583 | 171.6 | 138.0 | 48.5 | 55 | B |
| LYS CE | 583 | 170.6 | 139.2 | 48.6 | 56 | B |
| LYS NZ | 583 | 169.2 | 138.9 | 48.4 | 56 | B |
| LYS C | 583 | 173.6 | 137.7 | 44.5 | 47 | B |
| LYS O | 583 | 172.7 | 137.8 | 43.6 | 47 | B |
| ARG N | 584 | 174.6 | 138.6 | 44.6 | 48 | B |
| ARG CA | 584 | 174.6 | 139.7 | 43.7 | 49 | B |
| ARG CB | 584 | 175.3 | 140.9 | 44.2 | 53 | B |
| ARG CG | 584 | 174.5 | 142.2 | 44.0 | 58 | B |
| ARG CD | 584 | 175.2 | 143.5 | 44.0 | 62 | B |
| ARG NE | 584 | 175.9 | 143.8 | 42.8 | 66 | B |
| ARG CZ | 584 | 177.1 | 144.5 | 42.7 | 68 | B |
| ARG NH1 | 584 | 177.7 | 144.9 | 43.8 | 69 | B |
| ARG NH2 | 584 | 177.7 | 144.7 | 41.5 | 68 | B |
| ARG C | 584 | 175.2 | 139.4 | 42.3 | 47 | B |
| ARG O | 584 | 174.8 | 140.0 | 41.3 | 45 | B |
| GLY N | 585 | 176.1 | 138.4 | 42.3 | 46 | B |
| GLY CA | 585 | 176.7 | 138.0 | 41.0 | 44 | B |
| GLY C | 585 | 175.7 | 137.3 | 40.1 | 42 | B |
| GLY O | 585 | 175.8 | 137.3 | 38.9 | 40 | B |
| LEU N | 586 | 174.6 | 136.7 | 40.7 | 41 | B |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| LEU CA | 586 | 173.6 | 136.0 | 39.9 | 40 | B |
| LEU CB | 586 | 172.7 | 135.2 | 40.8 | 40 | B |
| LEU CG | 586 | 171.6 | 134.3 | 40.1 | 41 | B |
| LEU CD1 | 586 | 172.3 | 133.4 | 39.1 | 40 | B |
| LEU CD2 | 586 | 170.8 | 133.5 | 41.1 | 40 | B |
| LEU C | 586 | 172.8 | 137.1 | 39.2 | 40 | B |
| LEU O | 586 | 172.2 | 136.8 | 38.2 | 40 | B |
| ARG N | 587 | 172.8 | 138.3 | 39.7 | 41 | B |
| ARG CA | 587 | 172.1 | 139.4 | 39.0 | 41 | B |
| ARG CB | 587 | 171.3 | 140.2 | 40.1 | 43 | B |
| ARG CG | 587 | 169.8 | 140.1 | 40.0 | 46 | B |
| ARG CD | 587 | 169.4 | 138.6 | 40.2 | 48 | B |
| ARG NE | 587 | 168.0 | 138.5 | 40.6 | 51 | B |
| ARG CZ | 587 | 166.9 | 138.5 | 39.7 | 52 | B |
| ARG NH1 | 587 | 167.2 | 138.6 | 38.4 | 52 | B |
| ARG NH2 | 587 | 165.7 | 138.4 | 40.2 | 53 | B |
| ARG C | 587 | 172.9 | 140.3 | 38.2 | 40 | B |
| ARG O | 587 | 172.5 | 140.6 | 37.1 | 39 | B |
| GLN N | 588 | 174.1 | 140.7 | 38.7 | 39 | B |
| GLN CA | 588 | 174.9 | 141.6 | 37.9 | 39 | B |
| GLN CB | 588 | 174.5 | 143.1 | 38.0 | 41 | B |
| GLN CG | 588 | 174.8 | 143.7 | 39.3 | 46 | B |
| GLN CD | 588 | 174.4 | 145.2 | 39.3 | 48 | B |
| GLN OE1 | 588 | 173.7 | 145.7 | 38.4 | 49 | B |
| GLN NE2 | 588 | 174.8 | 145.9 | 40.4 | 50 | B |
| GLN C | 588 | 176.4 | 141.5 | 38.2 | 37 | B |
| GLN O | 588 | 176.8 | 141.2 | 39.4 | 36 | B |
| LEU N | 589 | 177.2 | 141.7 | 37.2 | 34 | B |
| LEU CA | 589 | 178.7 | 141.7 | 37.4 | 33 | B |
| LEU CB | 589 | 179.2 | 140.4 | 36.8 | 31 | B |
| LEU CG | 589 | 178.5 | 139.1 | 37.1 | 29 | B |
| LEU CD1 | 589 | 178.5 | 138.2 | 35.9 | 30 | B |
| LEU CD2 | 589 | 179.3 | 138.4 | 38.2 | 28 | B |
| LEU C | 589 | 179.3 | 142.9 | 36.8 | 33 | B |
| LEU O | 589 | 178.7 | 143.5 | 35.9 | 31 | B |
| THR N | 590 | 180.5 | 143.3 | 37.3 | 33 | B |
| THR CA | 590 | 181.2 | 144.4 | 36.7 | 34 | B |
| THR CB | 590 | 182.3 | 144.9 | 37.7 | 35 | B |
| THR OG1 | 590 | 183.4 | 143.9 | 37.7 | 36 | B |
| THR CG2 | 590 | 181.8 | 145.0 | 39.1 | 36 | B |
| THR C | 590 | 181.8 | 144.1 | 35.4 | 35 | B |
| THR O | 590 | 181.8 | 143.0 | 35.0 | 36 | B |
| ASP N | 591 | 182.3 | 145.1 | 34.7 | 33 | B |
| ASP CA | 591 | 182.8 | 144.9 | 33.4 | 33 | B |
| ASP CB | 591 | 183.1 | 146.2 | 32.6 | 33 | B |
| ASP CG | 591 | 184.0 | 147.1 | 33.3 | 35 | B |
| ASP OD1 | 591 | 184.4 | 148.2 | 32.7 | 36 | B |
| ASP OD2 | 591 | 184.5 | 146.8 | 34.5 | 35 | B |
| ASP C | 591 | 184.1 | 144.1 | 33.4 | 32 | B |
| ASP O | 591 | 184.7 | 143.8 | 32.3 | 34 | B |
| ALA N | 592 | 184.5 | 143.7 | 34.6 | 30 | B |
| ALA CA | 592 | 185.7 | 142.8 | 34.7 | 28 | B |
| ALA CB | 592 | 186.1 | 142.7 | 36.2 | 27 | B |
| ALA C | 592 | 185.4 | 141.5 | 34.2 | 28 | B |
| ALA O | 592 | 186.2 | 140.6 | 34.0 | 28 | B |
| TYR N | 593 | 184.1 | 141.2 | 34.0 | 28 | B |
| TYR CA | 593 | 183.5 | 140.0 | 33.5 | 28 | B |
| TYR CB | 593 | 182.3 | 139.6 | 34.2 | 26 | B |
| TYR CG | 593 | 182.6 | 138.9 | 35.5 | 26 | B |
| TYR CD1 | 593 | 182.9 | 139.6 | 36.7 | 26 | B |
| TYR CE1 | 593 | 183.4 | 138.9 | 37.8 | 26 | B |
| TYR CD2 | 593 | 182.8 | 137.5 | 35.4 | 26 | B |
| TYR CE2 | 593 | 183.3 | 136.8 | 36.6 | 26 | B |
| TYR CZ | 593 | 183.6 | 137.5 | 37.7 | 26 | B |
| TYR OH | 593 | 184.1 | 136.9 | 38.8 | 27 | B |
| TYR C | 593 | 183.3 | 140.0 | 32.0 | 28 | B |
| TYR O | 593 | 182.6 | 139.1 | 31.5 | 29 | B |
| GLU N | 594 | 183.8 | 141.1 | 31.3 | 28 | B |
| GLU CA | 594 | 183.6 | 141.2 | 29.9 | 28 | B |
| GLU CB | 594 | 184.2 | 142.5 | 29.4 | 29 | B |
| GLU CG | 594 | 183.4 | 143.7 | 29.8 | 31 | B |
| GLU CD | 594 | 184.0 | 145.0 | 29.3 | 33 | B |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| GLU OE1 | 594 | 183.3 | 146.0 | 29.1 | 34 | B |
| GLU OE2 | 594 | 185.2 | 145.0 | 29.1 | 34 | B |
| GLU C | 594 | 184.2 | 140.0 | 29.2 | 26 | B |
| GLU O | 594 | 183.7 | 139.5 | 28.2 | 27 | B |
| CYS N | 595 | 185.3 | 139.5 | 29.8 | 26 | B |
| CYS CA | 595 | 186.0 | 138.3 | 29.2 | 25 | B |
| CYS CB | 595 | 187.4 | 138.1 | 30.0 | 24 | B |
| CYS SG | 595 | 187.3 | 137.7 | 31.7 | 23 | B |
| CYS C | 595 | 185.2 | 137.0 | 29.4 | 24 | B |
| CYS O | 595 | 185.6 | 135.9 | 28.8 | 23 | B |
| LEU N | 596 | 184.1 | 137.0 | 30.1 | 23 | B |
| LEU CA | 596 | 183.2 | 135.9 | 30.3 | 22 | B |
| LEU CB | 596 | 183.1 | 135.6 | 31.8 | 22 | B |
| LEU CG | 596 | 184.2 | 134.8 | 32.4 | 22 | B |
| LEU CD1 | 596 | 183.9 | 134.4 | 33.8 | 22 | B |
| LEU CD2 | 596 | 184.6 | 133.5 | 31.7 | 22 | B |
| LEU C | 596 | 181.9 | 136.2 | 29.7 | 22 | B |
| LEU O | 596 | 180.9 | 135.5 | 30.0 | 22 | B |
| ASP N | 597 | 181.9 | 137.1 | 28.7 | 24 | B |
| ASP CA | 597 | 180.7 | 137.5 | 28.0 | 24 | B |
| ASP CB | 597 | 180.9 | 138.7 | 27.1 | 24 | B |
| ASP CG | 597 | 179.6 | 139.2 | 26.5 | 24 | B |
| ASP OD1 | 597 | 178.6 | 139.2 | 27.3 | 25 | B |
| ASP OD2 | 597 | 179.6 | 139.7 | 25.4 | 25 | B |
| ASP C | 597 | 180.2 | 136.3 | 27.1 | 26 | B |
| ASP O | 597 | 179.0 | 136.4 | 26.6 | 27 | B |
| ALA N | 598 | 181.0 | 135.3 | 26.8 | 26 | B |
| ALA CA | 598 | 180.6 | 134.1 | 26.0 | 26 | B |
| ALA CB | 598 | 181.6 | 133.9 | 24.9 | 25 | B |
| ALA C | 598 | 180.5 | 132.9 | 26.9 | 27 | B |
| ALA O | 598 | 180.6 | 131.8 | 26.4 | 27 | B |
| SER N | 599 | 180.4 | 133.1 | 28.2 | 27 | B |
| SER CA | 599 | 180.3 | 132.0 | 29.2 | 26 | B |
| SER CB | 599 | 181.6 | 131.8 | 29.9 | 25 | B |
| SER OG | 599 | 182.6 | 131.3 | 29.1 | 25 | B |
| SER C | 599 | 179.2 | 132.3 | 30.1 | 26 | B |
| SER O | 599 | 179.3 | 132.0 | 31.3 | 27 | B |
| ARG N | 600 | 178.1 | 133.0 | 29.7 | 27 | B |
| ARG CA | 600 | 177.1 | 133.3 | 30.6 | 28 | B |
| ARG CB | 600 | 176.2 | 134.5 | 30.1 | 28 | B |
| ARG CG | 600 | 177.1 | 135.7 | 30.1 | 28 | B |
| ARG CD | 600 | 176.4 | 136.9 | 29.5 | 30 | B |
| ARG NE | 600 | 175.4 | 137.4 | 30.5 | 30 | B |
| ARG CZ | 600 | 174.3 | 138.1 | 30.1 | 30 | B |
| ARG NH1 | 600 | 174.1 | 138.4 | 28.8 | 30 | B |
| ARG NH2 | 600 | 173.4 | 138.5 | 31.0 | 32 | B |
| ARG C | 600 | 176.3 | 132.1 | 31.2 | 28 | B |
| ARG O | 600 | 176.0 | 132.1 | 32.4 | 31 | B |
| PRO N | 601 | 176.1 | 131.1 | 30.5 | 26 | B |
| PRO CD | 601 | 176.0 | 130.9 | 29.0 | 26 | B |
| PRO CA | 601 | 175.4 | 130.0 | 31.1 | 25 | B |
| PRO CB | 601 | 175.1 | 129.0 | 30.0 | 24 | B |
| PRO CG | 601 | 174.9 | 129.9 | 28.8 | 24 | B |
| PRO C | 601 | 176.3 | 129.4 | 32.2 | 25 | B |
| PRO O | 601 | 175.8 | 128.8 | 33.1 | 27 | B |
| TRP N | 602 | 177.6 | 129.6 | 32.0 | 26 | B |
| TRP CA | 602 | 178.5 | 129.0 | 33.0 | 26 | B |
| TRP CB | 602 | 180.0 | 129.2 | 32.5 | 25 | B |
| TRP CG | 602 | 180.5 | 128.1 | 31.7 | 26 | B |
| TRP CD2 | 602 | 180.7 | 126.7 | 32.1 | 26 | B |
| TRP CE2 | 602 | 181.2 | 126.0 | 30.9 | 25 | B |
| TRP CE3 | 602 | 180.5 | 126.0 | 33.3 | 26 | B |
| TRP CD1 | 602 | 180.9 | 128.1 | 30.3 | 25 | B |
| TRP NE1 | 602 | 181.3 | 126.9 | 29.9 | 26 | B |
| TRP CZ2 | 602 | 181.5 | 124.6 | 31.0 | 26 | B |
| TRP CZ3 | 602 | 180.8 | 124.6 | 33.3 | 26 | B |
| TRP CH2 | 602 | 181.3 | 124.0 | 32.2 | 26 | B |
| TRP C | 602 | 178.4 | 129.8 | 34.3 | 26 | B |
| TRP O | 602 | 178.5 | 129.2 | 35.3 | 27 | B |
| LEU N | 603 | 178.2 | 131.1 | 34.2 | 28 | B |
| LEU CA | 603 | 178.0 | 131.9 | 35.4 | 28 | B |
| LEU CB | 603 | 178.1 | 133.4 | 35.0 | 29 | B |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| LEU CG | 603 | 179.5 | 133.9 | 34.7 | 30 | B |
| LEU CD1 | 603 | 179.5 | 135.2 | 34.0 | 29 | B |
| LEU CD2 | 603 | 180.4 | 133.9 | 36.0 | 28 | B |
| LEU C | 603 | 176.8 | 131.5 | 36.1 | 28 | B |
| LEU O | 603 | 176.8 | 131.5 | 37.3 | 29 | B |
| CYS N | 604 | 175.7 | 131.2 | 35.4 | 28 | B |
| CYS CA | 604 | 174.5 | 130.8 | 36.0 | 28 | B |
| CYS CB | 604 | 173.4 | 130.6 | 34.9 | 29 | B |
| CYS SG | 604 | 172.8 | 132.0 | 34.1 | 33 | B |
| CYS C | 604 | 174.7 | 129.4 | 36.7 | 28 | B |
| CYS O | 604 | 174.4 | 129.3 | 37.9 | 30 | B |
| TYR N | 605 | 175.4 | 128.5 | 36.0 | 26 | B |
| TYR CA | 605 | 175.6 | 127.2 | 36.6 | 24 | B |
| TYR CB | 605 | 176.3 | 126.2 | 35.6 | 23 | B |
| TYR CG | 605 | 176.9 | 125.0 | 36.3 | 22 | B |
| TYR CD1 | 605 | 176.1 | 124.1 | 37.0 | 22 | B |
| TYR CE1 | 605 | 176.7 | 123.0 | 37.7 | 21 | B |
| TYR CD2 | 605 | 178.3 | 124.8 | 36.3 | 22 | B |
| TYR CE2 | 605 | 178.8 | 123.8 | 37.0 | 23 | B |
| TYR CZ | 605 | 178.0 | 122.9 | 37.7 | 22 | B |
| TYR OH | 605 | 178.7 | 121.8 | 38.3 | 24 | B |
| TYR C | 605 | 176.5 | 127.3 | 37.8 | 25 | B |
| TYR O | 605 | 176.2 | 126.8 | 38.9 | 25 | B |
| TRP N | 606 | 177.6 | 128.0 | 37.7 | 27 | B |
| TRP CA | 606 | 178.6 | 128.2 | 38.8 | 28 | B |
| TRP CB | 606 | 179.8 | 129.1 | 38.4 | 28 | B |
| TRP CG | 606 | 180.7 | 128.5 | 37.3 | 28 | B |
| TRP CD2 | 606 | 181.5 | 129.2 | 36.4 | 28 | B |
| TRP CE2 | 606 | 182.3 | 128.3 | 35.6 | 28 | B |
| TRP CE3 | 606 | 181.7 | 130.6 | 36.1 | 29 | B |
| TRP CD1 | 606 | 181.1 | 127.2 | 37.1 | 27 | B |
| TRP NE1 | 606 | 182.0 | 127.1 | 36.1 | 26 | B |
| TRP CZ2 | 606 | 183.1 | 128.7 | 34.6 | 28 | B |
| TRP CZ3 | 606 | 182.5 | 131.0 | 35.1 | 28 | B |
| TRP CH2 | 606 | 183.3 | 130.1 | 34.3 | 28 | B |
| TRP C | 606 | 177.9 | 128.8 | 40.0 | 29 | B |
| TRP O | 606 | 178.1 | 128.2 | 41.1 | 31 | B |
| ILE N | 607 | 177.2 | 129.8 | 39.8 | 31 | B |
| ILE CA | 607 | 176.5 | 130.5 | 41.0 | 32 | B |
| ILE CB | 607 | 176.0 | 131.9 | 40.6 | 31 | B |
| ILE CG2 | 607 | 175.1 | 132.5 | 41.7 | 30 | B |
| ILE CG1 | 607 | 177.2 | 132.8 | 40.2 | 30 | B |
| ILE CD1 | 607 | 176.9 | 134.0 | 39.4 | 30 | B |
| ILE C | 607 | 175.3 | 129.6 | 41.5 | 32 | B |
| ILE O | 607 | 175.4 | 129.2 | 42.7 | 32 | B |
| LEU N | 608 | 174.4 | 129.3 | 40.7 | 32 | B |
| LEU CA | 608 | 173.2 | 128.4 | 41.1 | 31 | B |
| LEU CB | 608 | 172.4 | 128.1 | 39.9 | 30 | B |
| LEU CG | 608 | 170.9 | 128.6 | 39.8 | 30 | B |
| LEU CD1 | 608 | 170.8 | 130.0 | 40.4 | 30 | B |
| LEU CD2 | 608 | 170.6 | 128.7 | 38.3 | 31 | B |
| LEU C | 608 | 173.7 | 127.1 | 41.7 | 31 | B |
| LEU O | 608 | 172.9 | 126.6 | 42.5 | 33 | B |
| HIS N | 609 | 174.8 | 126.7 | 41.4 | 30 | B |
| HIS CA | 609 | 175.3 | 125.4 | 42.0 | 30 | B |
| HIS CB | 609 | 176.3 | 124.7 | 41.0 | 27 | B |
| HIS CG | 609 | 176.8 | 123.4 | 41.6 | 25 | B |
| HIS CD2 | 609 | 178.1 | 123.0 | 41.8 | 24 | B |
| HIS ND1 | 609 | 176.1 | 122.4 | 42.1 | 24 | B |
| HIS CE1 | 609 | 176.9 | 121.5 | 42.6 | 24 | B |
| HIS NE2 | 609 | 178.1 | 121.8 | 42.5 | 24 | B |
| HIS C | 609 | 176.0 | 125.7 | 43.3 | 31 | B |
| HIS O | 609 | 175.8 | 124.9 | 44.2 | 31 | B |
| SER N | 610 | 176.7 | 126.7 | 43.4 | 32 | B |
| SER CA | 610 | 177.4 | 127.1 | 44.7 | 35 | B |
| SER CB | 610 | 178.2 | 128.3 | 44.5 | 35 | B |
| SER OG | 610 | 179.2 | 128.1 | 43.5 | 35 | B |
| SER C | 610 | 176.3 | 127.3 | 45.8 | 35 | B |
| SER O | 610 | 176.4 | 126.8 | 46.9 | 34 | B |
| LEU N | 611 | 175.2 | 128.0 | 45.4 | 36 | B |
| LEU CA | 611 | 174.1 | 128.2 | 46.3 | 37 | B |
| LEU CB | 611 | 173.0 | 129.1 | 45.6 | 36 | B |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| LEU CG | 611 | 173.5 | 130.5 | 45.2 | 35 | B |
| LEU CD1 | 611 | 172.3 | 131.2 | 44.5 | 35 | B |
| LEU CD2 | 611 | 173.9 | 131.2 | 46.4 | 35 | B |
| LEU C | 611 | 173.5 | 126.9 | 46.7 | 39 | B |
| LEU O | 611 | 173.3 | 126.6 | 47.9 | 40 | B |
| GLU N | 612 | 173.3 | 126.0 | 45.7 | 40 | B |
| GLU CA | 612 | 172.7 | 124.7 | 46.0 | 41 | B |
| GLU CB | 612 | 172.7 | 123.9 | 44.6 | 43 | B |
| GLU CG | 612 | 172.4 | 122.4 | 44.8 | 44 | B |
| GLU CD | 612 | 173.2 | 121.5 | 43.8 | 45 | B |
| GLU OE1 | 612 | 174.0 | 120.7 | 44.4 | 45 | B |
| GLU OE2 | 612 | 173.1 | 121.7 | 42.6 | 45 | B |
| GLU C | 612 | 173.6 | 123.9 | 47.0 | 41 | B |
| GLU O | 612 | 173.1 | 123.3 | 47.9 | 42 | B |
| LEU N | 613 | 174.9 | 124.1 | 46.8 | 41 | B |
| LEU CA | 613 | 175.8 | 123.4 | 47.8 | 42 | B |
| LEU CB | 613 | 177.2 | 123.5 | 47.3 | 40 | B |
| LEU CG | 613 | 177.6 | 122.5 | 46.2 | 40 | B |
| LEU CD1 | 613 | 178.8 | 123.0 | 45.4 | 39 | B |
| LEU CD2 | 613 | 178.0 | 121.1 | 46.9 | 40 | B |
| LEU C | 613 | 175.7 | 124.1 | 49.2 | 44 | B |
| LEU O | 613 | 175.7 | 123.4 | 50.2 | 44 | B |
| LEU N | 614 | 175.5 | 125.4 | 49.2 | 46 | B |
| LEU CA | 614 | 175.4 | 126.2 | 50.4 | 48 | B |
| LEU CB | 614 | 175.8 | 127.6 | 50.2 | 47 | B |
| LEU CG | 614 | 177.2 | 128.0 | 49.7 | 47 | B |
| LEU CD1 | 614 | 177.2 | 129.4 | 49.2 | 46 | B |
| LEU CD2 | 614 | 178.1 | 127.8 | 50.9 | 47 | B |
| LEU C | 614 | 174.0 | 126.1 | 50.9 | 50 | B |
| LEU O | 614 | 173.6 | 126.8 | 51.9 | 50 | B |
| ASP N | 615 | 173.2 | 125.2 | 50.3 | 52 | B |
| ASP CA | 615 | 171.8 | 125.1 | 50.7 | 55 | B |
| ASP CB | 615 | 171.7 | 124.4 | 52.1 | 55 | B |
| ASP CG | 615 | 170.3 | 123.7 | 52.3 | 54 | B |
| ASP OD1 | 615 | 169.4 | 123.8 | 51.5 | 54 | B |
| ASP OD2 | 615 | 170.2 | 123.1 | 53.4 | 54 | B |
| ASP C | 615 | 171.0 | 126.4 | 50.7 | 56 | B |
| ASP O | 615 | 170.0 | 126.5 | 51.4 | 58 | B |
| GLU N | 616 | 171.5 | 127.3 | 49.9 | 57 | B |
| GLU CA | 616 | 170.8 | 128.6 | 49.8 | 59 | B |
| GLU CB | 616 | 171.7 | 129.7 | 49.5 | 61 | B |
| GLU CG | 616 | 172.9 | 129.8 | 50.4 | 63 | B |
| GLU CD | 616 | 172.6 | 130.3 | 51.8 | 64 | B |
| GLU OE1 | 616 | 171.4 | 130.6 | 52.1 | 65 | B |
| GLU OE2 | 616 | 173.6 | 130.5 | 52.6 | 65 | B |
| GLU C | 616 | 169.8 | 128.4 | 48.7 | 60 | B |
| GLU O | 616 | 170.1 | 127.7 | 47.7 | 60 | B |
| PRO N | 617 | 168.6 | 128.9 | 48.9 | 61 | B |
| PRO CD | 617 | 168.2 | 129.8 | 50.0 | 62 | B |
| PRO CA | 617 | 167.4 | 128.8 | 47.9 | 62 | B |
| PRO CB | 617 | 166.3 | 129.4 | 48.7 | 63 | B |
| PRO CG | 617 | 167.0 | 130.5 | 49.5 | 63 | B |
| PRO C | 617 | 167.6 | 129.6 | 46.7 | 62 | B |
| PRO O | 617 | 168.3 | 130.6 | 46.6 | 62 | B |
| ILE N | 618 | 166.9 | 129.1 | 45.6 | 63 | B |
| ILE CA | 618 | 166.9 | 129.7 | 44.3 | 63 | B |
| ILE CB | 618 | 167.4 | 128.6 | 43.2 | 63 | B |
| ILE CG2 | 618 | 167.3 | 129.2 | 41.8 | 63 | B |
| ILE CG1 | 618 | 168.9 | 128.2 | 43.5 | 62 | B |
| ILE CD1 | 618 | 169.1 | 127.1 | 44.5 | 62 | B |
| ILE C | 618 | 165.5 | 130.2 | 44.0 | 62 | B |
| ILE O | 618 | 164.8 | 129.6 | 43.1 | 63 | B |
| PRO N | 619 | 165.0 | 131.2 | 44.7 | 60 | B |
| PRO CD | 619 | 165.9 | 132.1 | 45.5 | 60 | B |
| PRO CA | 619 | 163.7 | 131.8 | 44.6 | 59 | B |
| PRO CB | 619 | 164.0 | 133.3 | 44.9 | 60 | B |
| PRO CG | 619 | 165.0 | 133.2 | 46.0 | 60 | B |
| PRO C | 619 | 163.0 | 131.7 | 43.3 | 59 | B |
| PRO O | 619 | 163.4 | 132.0 | 42.2 | 59 | B |
| GLN N | 620 | 161.7 | 131.2 | 43.4 | 59 | B |
| GLN CA | 620 | 160.9 | 130.9 | 42.3 | 59 | B |
| GLN CB | 620 | 159.4 | 130.7 | 42.8 | 61 | B |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| GLN CG | 620 | 159.4 | 129.8 | 44.1 | 64 | B |
| GLN CD | 620 | 158.0 | 129.1 | 44.3 | 65 | B |
| GLN OE1 | 620 | 157.0 | 129.4 | 43.6 | 65 | B |
| GLN NE2 | 620 | 158.0 | 128.2 | 45.3 | 65 | B |
| GLN C | 620 | 160.9 | 132.0 | 41.2 | 58 | B |
| GLN O | 620 | 161.0 | 131.6 | 40.0 | 58 | B |
| ILE N | 621 | 161.0 | 133.2 | 41.5 | 57 | B |
| ILE CA | 621 | 161.1 | 134.3 | 40.5 | 56 | B |
| ILE CB | 621 | 160.8 | 135.7 | 41.2 | 57 | B |
| ILE CG2 | 621 | 160.6 | 136.8 | 40.1 | 56 | B |
| ILE CG1 | 621 | 159.5 | 135.6 | 42.0 | 57 | B |
| ILE CD1 | 621 | 159.6 | 135.0 | 43.4 | 56 | B |
| ILE C | 621 | 162.5 | 134.5 | 39.8 | 54 | B |
| ILE O | 621 | 162.6 | 134.8 | 38.6 | 51 | B |
| VAL N | 622 | 163.6 | 134.2 | 40.6 | 51 | B |
| VAL CA | 622 | 164.9 | 134.3 | 40.0 | 50 | B |
| VAL CB | 622 | 166.0 | 134.3 | 41.1 | 49 | B |
| VAL CG1 | 622 | 166.2 | 132.9 | 41.6 | 49 | B |
| VAL CG2 | 622 | 167.2 | 134.9 | 40.5 | 50 | B |
| VAL C | 622 | 165.0 | 133.2 | 39.1 | 50 | B |
| VAL O | 622 | 165.6 | 133.3 | 37.9 | 49 | B |
| ALA N | 623 | 164.5 | 132.0 | 39.5 | 49 | B |
| ALA CA | 623 | 164.6 | 130.8 | 38.7 | 47 | B |
| ALA CB | 623 | 163.9 | 129.7 | 39.4 | 47 | B |
| ALA C | 623 | 164.0 | 131.0 | 37.3 | 47 | B |
| ALA O | 623 | 164.6 | 130.7 | 36.3 | 47 | B |
| THR N | 624 | 162.8 | 131.6 | 37.3 | 47 | B |
| THR CA | 624 | 162.1 | 131.9 | 36.0 | 46 | B |
| THR CB | 624 | 160.8 | 132.7 | 36.3 | 46 | B |
| THR OG1 | 624 | 160.0 | 131.9 | 37.1 | 46 | B |
| THR CG2 | 624 | 160.1 | 133.0 | 35.0 | 44 | B |
| THR C | 624 | 163.0 | 132.8 | 35.1 | 47 | B |
| THR O | 624 | 163.1 | 132.6 | 33.9 | 48 | B |
| ASP N | 625 | 163.6 | 133.8 | 35.8 | 48 | B |
| ASP CA | 625 | 164.5 | 134.7 | 35.1 | 47 | B |
| ASP CB | 625 | 165.1 | 135.8 | 36.0 | 49 | B |
| ASP CG | 625 | 164.0 | 136.7 | 36.6 | 50 | B |
| ASP OD1 | 625 | 162.9 | 136.9 | 35.9 | 50 | B |
| ASP OD2 | 625 | 164.1 | 137.2 | 37.8 | 50 | B |
| ASP C | 625 | 165.6 | 133.9 | 34.4 | 44 | B |
| ASP O | 625 | 165.9 | 134.0 | 33.2 | 44 | B |
| VAL N | 626 | 166.3 | 133.0 | 35.2 | 41 | B |
| VAL CA | 626 | 167.3 | 132.2 | 34.7 | 40 | B |
| VAL CB | 626 | 167.9 | 131.2 | 35.7 | 39 | B |
| VAL CG1 | 626 | 168.9 | 130.4 | 35.1 | 39 | B |
| VAL CG2 | 626 | 168.4 | 131.9 | 37.0 | 39 | B |
| VAL C | 626 | 166.8 | 131.5 | 33.5 | 41 | B |
| VAL O | 626 | 167.4 | 131.5 | 32.5 | 42 | B |
| CYS N | 627 | 165.6 | 130.9 | 33.7 | 40 | B |
| CYS CA | 627 | 165.0 | 130.1 | 32.6 | 40 | B |
| CYS CB | 627 | 163.6 | 129.5 | 33.1 | 39 | B |
| CYS SG | 627 | 163.8 | 128.2 | 34.3 | 39 | B |
| CYS C | 627 | 164.8 | 130.9 | 31.3 | 40 | B |
| CYS O | 627 | 165.1 | 130.4 | 30.3 | 39 | B |
| GLN N | 628 | 164.2 | 132.1 | 31.5 | 40 | B |
| GLN CA | 628 | 163.9 | 132.9 | 30.3 | 40 | B |
| GLN CB | 628 | 163.1 | 134.1 | 30.7 | 42 | B |
| GLN CG | 628 | 161.7 | 133.7 | 31.1 | 45 | B |
| GLN CD | 628 | 160.8 | 134.8 | 31.5 | 47 | B |
| GLN OE1 | 628 | 161.0 | 136.0 | 31.1 | 47 | B |
| GLN NE2 | 628 | 159.8 | 134.6 | 32.4 | 48 | B |
| GLN C | 628 | 165.2 | 133.4 | 29.7 | 39 | B |
| GLN O | 628 | 165.2 | 133.5 | 28.4 | 38 | B |
| PHE N | 629 | 166.2 | 133.6 | 30.5 | 38 | B |
| PHE CA | 629 | 167.5 | 134.0 | 29.9 | 37 | B |
| PHE CB | 629 | 168.5 | 134.5 | 31.0 | 36 | B |
| PHE CG | 629 | 169.9 | 134.8 | 30.5 | 35 | B |
| PHE CD1 | 629 | 170.1 | 135.8 | 29.6 | 35 | B |
| PHE CD2 | 629 | 171.0 | 134.1 | 31.0 | 35 | B |
| PHE CE1 | 629 | 171.4 | 136.0 | 29.1 | 35 | B |
| PHE CE2 | 629 | 172.3 | 134.3 | 30.6 | 34 | B |
| PHE CZ | 629 | 172.5 | 135.3 | 29.6 | 34 | B |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| PHE C | 629 | 168.2 | 132.9 | 29.1 | 37 | B |
| PHE O | 629 | 168.6 | 133.1 | 28.0 | 37 | B |
| LEU N | 630 | 168.3 | 131.7 | 29.7 | 36 | B |
| LEU CA | 630 | 168.8 | 130.5 | 29.1 | 35 | B |
| LEU CB | 630 | 168.9 | 129.3 | 30.0 | 31 | B |
| LEU CG | 630 | 169.9 | 129.5 | 31.2 | 29 | B |
| LEU CD1 | 630 | 169.8 | 128.4 | 32.2 | 28 | B |
| LEU CD2 | 630 | 171.3 | 129.6 | 30.6 | 27 | B |
| LEU C | 630 | 168.1 | 130.2 | 27.8 | 37 | B |
| LEU O | 630 | 168.7 | 129.6 | 26.8 | 38 | B |
| GLU N | 631 | 166.8 | 130.6 | 27.7 | 38 | B |
| GLU CA | 631 | 166.1 | 130.4 | 26.5 | 40 | B |
| GLU CB | 631 | 164.6 | 130.8 | 26.7 | 43 | B |
| GLU CG | 631 | 163.8 | 129.8 | 27.6 | 48 | B |
| GLU CD | 631 | 162.3 | 130.0 | 27.4 | 51 | B |
| GLU OE1 | 631 | 161.6 | 130.6 | 28.2 | 51 | B |
| GLU OE2 | 631 | 161.8 | 129.6 | 26.3 | 52 | B |
| GLU C | 631 | 166.6 | 131.3 | 25.4 | 38 | B |
| GLU O | 631 | 166.5 | 130.9 | 24.2 | 37 | B |
| LEU N | 632 | 167.1 | 132.5 | 25.8 | 37 | B |
| LEU CA | 632 | 167.6 | 133.4 | 24.8 | 37 | B |
| LEU CB | 632 | 167.7 | 134.8 | 25.4 | 38 | B |
| LEU CG | 632 | 166.5 | 135.5 | 25.9 | 38 | B |
| LEU CD1 | 632 | 166.8 | 136.7 | 26.8 | 39 | B |
| LEU CD2 | 632 | 165.6 | 135.9 | 24.8 | 39 | B |
| LEU C | 632 | 169.0 | 133.0 | 24.3 | 36 | B |
| LEU O | 632 | 169.4 | 133.2 | 23.2 | 36 | B |
| CYS N | 633 | 169.7 | 132.3 | 25.2 | 35 | B |
| CYS CA | 633 | 171.0 | 131.7 | 24.9 | 35 | B |
| CYS CB | 633 | 171.7 | 131.2 | 26.1 | 34 | B |
| CYS SG | 633 | 172.2 | 132.6 | 27.2 | 34 | B |
| CYS C | 633 | 170.8 | 130.5 | 23.9 | 35 | B |
| CYS O | 633 | 171.7 | 130.3 | 23.1 | 35 | B |
| GLN N | 634 | 169.7 | 129.8 | 24.1 | 35 | B |
| GLN CA | 634 | 169.5 | 128.6 | 23.3 | 35 | B |
| GLN CB | 634 | 168.2 | 128.0 | 23.8 | 34 | B |
| GLN CG | 634 | 167.9 | 126.7 | 23.0 | 34 | B |
| GLN CD | 634 | 166.8 | 125.9 | 23.7 | 34 | B |
| GLN OE1 | 634 | 165.8 | 126.4 | 24.1 | 35 | B |
| GLN NE2 | 634 | 167.1 | 124.6 | 23.9 | 34 | B |
| GLN C | 634 | 169.4 | 128.9 | 21.8 | 35 | B |
| GLN O | 634 | 168.8 | 129.9 | 21.4 | 35 | B |
| SER N | 635 | 170.0 | 128.1 | 21.0 | 35 | B |
| SER CA | 635 | 170.0 | 128.3 | 19.6 | 35 | B |
| SER CB | 635 | 171.3 | 127.7 | 19.0 | 34 | B |
| SER OG | 635 | 171.3 | 127.6 | 17.6 | 33 | B |
| SER C | 635 | 168.8 | 127.6 | 18.8 | 37 | B |
| SER O | 635 | 168.3 | 126.5 | 19.3 | 37 | B |
| PRO N | 636 | 168.4 | 128.1 | 17.7 | 38 | B |
| PRO CD | 636 | 168.9 | 129.4 | 17.1 | 39 | B |
| PRO CA | 636 | 167.3 | 127.5 | 16.9 | 40 | B |
| PRO CB | 636 | 167.0 | 128.6 | 15.9 | 39 | B |
| PRO CG | 636 | 168.4 | 129.3 | 15.6 | 40 | B |
| PRO C | 636 | 167.8 | 126.3 | 16.2 | 40 | B |
| PRO O | 636 | 167.1 | 125.7 | 15.4 | 41 | B |
| ASP N | 637 | 169.1 | 125.9 | 16.5 | 42 | B |
| ASP CA | 637 | 169.7 | 124.7 | 15.9 | 41 | B |
| ASP CB | 637 | 170.9 | 125.1 | 15.1 | 44 | B |
| ASP CG | 637 | 170.5 | 126.0 | 14.0 | 48 | B |
| ASP OD1 | 637 | 169.4 | 125.9 | 13.4 | 49 | B |
| ASP OD2 | 637 | 171.3 | 126.9 | 13.7 | 48 | B |
| ASP C | 637 | 170.1 | 123.7 | 17.1 | 39 | B |
| ASP O | 637 | 170.8 | 122.8 | 16.8 | 41 | B |
| GLY N | 638 | 169.5 | 124.0 | 18.3 | 37 | B |
| GLY CA | 638 | 169.9 | 123.1 | 19.4 | 33 | B |
| GLY C | 638 | 171.1 | 123.6 | 20.1 | 31 | B |
| GLY O | 638 | 172.0 | 124.2 | 19.5 | 32 | B |
| GLY N | 639 | 171.2 | 123.3 | 21.4 | 30 | B |
| GLY CA | 639 | 172.4 | 123.7 | 22.1 | 29 | B |
| GLY C | 639 | 172.3 | 125.2 | 22.5 | 29 | B |
| GLY O | 639 | 171.4 | 125.9 | 22.0 | 28 | B |
| PHE N | 640 | 173.2 | 125.6 | 23.4 | 29 | B |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| PHE CA | 640 | 173.2 | 127.0 | 23.9 | 28 | B |
| PHE CB | 640 | 172.9 | 127.0 | 25.4 | 28 | B |
| PHE CG | 640 | 171.7 | 126.3 | 25.8 | 29 | B |
| PHE CD1 | 640 | 171.6 | 124.9 | 25.9 | 30 | B |
| PHE CD2 | 640 | 170.5 | 127.0 | 26.2 | 30 | B |
| PHE CE1 | 640 | 170.4 | 124.2 | 26.2 | 30 | B |
| PHE CE2 | 640 | 169.3 | 126.3 | 26.5 | 31 | B |
| PHE CZ | 640 | 169.3 | 124.9 | 26.5 | 31 | B |
| PHE C | 640 | 174.4 | 127.7 | 23.6 | 28 | B |
| PHE O | 640 | 175.5 | 127.1 | 23.7 | 29 | B |
| GLY N | 641 | 174.3 | 129.0 | 23.4 | 28 | B |
| GLY CA | 641 | 175.5 | 129.8 | 23.1 | 27 | B |
| GLY C | 641 | 176.0 | 130.4 | 24.4 | 26 | B |
| GLY O | 641 | 175.3 | 130.2 | 25.5 | 27 | B |
| GLY N | 642 | 177.1 | 131.2 | 24.4 | 26 | B |
| GLY CA | 642 | 177.6 | 131.8 | 25.6 | 26 | B |
| GLY C | 642 | 176.8 | 133.0 | 26.1 | 27 | B |
| GLY O | 642 | 177.1 | 133.6 | 27.1 | 28 | B |
| GLY N | 643 | 175.8 | 133.4 | 25.3 | 27 | B |
| GLY CA | 643 | 175.1 | 134.6 | 25.6 | 26 | B |
| GLY C | 643 | 174.0 | 134.7 | 24.6 | 28 | B |
| GLY O | 643 | 174.0 | 133.9 | 23.6 | 28 | B |
| PRO N | 644 | 172.9 | 135.5 | 24.8 | 29 | B |
| PRO CD | 644 | 172.7 | 136.5 | 25.9 | 29 | B |
| PRO CA | 644 | 171.9 | 135.6 | 23.8 | 30 | B |
| PRO CB | 644 | 171.1 | 136.8 | 24.3 | 29 | B |
| PRO CG | 644 | 171.2 | 136.7 | 25.8 | 28 | B |
| PRO C | 644 | 172.4 | 135.9 | 22.4 | 31 | B |
| PRO O | 644 | 173.3 | 136.8 | 22.3 | 33 | B |
| GLY N | 645 | 172.0 | 135.1 | 21.5 | 33 | B |
| GLY CA | 645 | 172.4 | 135.2 | 20.1 | 33 | B |
| GLY C | 645 | 173.7 | 134.7 | 19.6 | 34 | B |
| GLY O | 645 | 174.2 | 134.9 | 18.5 | 34 | B |
| GLN N | 646 | 174.4 | 133.9 | 20.5 | 32 | B |
| GLN CA | 646 | 175.7 | 133.3 | 20.1 | 32 | B |
| GLN CB | 646 | 176.6 | 133.4 | 21.3 | 32 | B |
| GLN CG | 646 | 177.0 | 134.8 | 21.8 | 31 | B |
| GLN CD | 646 | 177.8 | 134.8 | 23.1 | 31 | B |
| GLN OE1 | 646 | 177.6 | 135.7 | 23.9 | 32 | B |
| GLN NE2 | 646 | 178.7 | 133.8 | 23.3 | 31 | B |
| GLN C | 646 | 175.5 | 131.9 | 19.6 | 32 | B |
| GLN O | 646 | 174.6 | 131.2 | 20.1 | 33 | B |
| TYR N | 647 | 176.3 | 131.5 | 18.7 | 30 | B |
| TYR CA | 647 | 176.2 | 130.1 | 18.1 | 28 | B |
| TYR CB | 647 | 177.4 | 129.9 | 17.2 | 28 | B |
| TYR CG | 647 | 177.4 | 130.8 | 16.0 | 2B | B |
| TYR CD1 | 647 | 178.5 | 131.0 | 15.2 | 28 | B |
| TYR CE1 | 647 | 178.5 | 131.8 | 14.1 | 29 | B |
| TYR CD2 | 647 | 176.2 | 131.6 | 15.7 | 27 | B |
| TYR CE2 | 647 | 176.2 | 132.4 | 14.7 | 27 | B |
| TYR CZ | 647 | 177.3 | 132.5 | 13.8 | 28 | B |
| TYR OH | 647 | 177.3 | 133.3 | 12.7 | 31 | B |
| TYR C | 647 | 176.4 | 129.2 | 19.3 | 28 | B |
| TYR O | 647 | 177.0 | 129.5 | 20.3 | 29 | B |
| PRO N | 648 | 175.7 | 128.0 | 19.2 | 27 | B |
| PRO CD | 648 | 174.9 | 127.5 | 18.1 | 27 | B |
| PRO CA | 648 | 175.8 | 127.1 | 20.3 | 25 | B |
| PRO CB | 648 | 174.7 | 126.1 | 20.0 | 25 | B |
| PRO CG | 648 | 174.7 | 126.0 | 18.5 | 27 | B |
| PRO C | 648 | 177.2 | 126.4 | 20.4 | 24 | B |
| PRO O | 648 | 177.8 | 126.2 | 19.4 | 25 | B |
| HIS N | 649 | 177.6 | 126.2 | 21.7 | 21 | B |
| HIS CA | 649 | 178.9 | 125.6 | 22.0 | 21 | B |
| HIS CB | 649 | 179.8 | 126.8 | 22.4 | 19 | B |
| HIS CG | 649 | 181.2 | 126.4 | 22.7 | 17 | B |
| HIS CD2 | 649 | 182.3 | 126.8 | 22.1 | 17 | B |
| HIS ND1 | 649 | 181.6 | 125.7 | 23.8 | 17 | B |
| HIS CE1 | 649 | 182.9 | 125.7 | 23.9 | 16 | B |
| HIS NE2 | 649 | 183.4 | 126.3 | 22.8 | 17 | B |
| HIS C | 649 | 178.6 | 124.6 | 23.1 | 23 | B |
| HIS O | 649 | 177.7 | 124.8 | 23.9 | 24 | B |
| LEU N | 650 | 179.3 | 123.5 | 23.0 | 23 | B |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| LEU CA | 650 | 179.0 | 122.4 | 24.0 | 23 | B |
| LEU CB | 650 | 179.8 | 121.1 | 23.7 | 22 | B |
| LEU CG | 650 | 179.2 | 120.1 | 22.7 | 21 | B |
| LEU CD1 | 650 | 180.1 | 119.0 | 22.5 | 21 | B |
| LEU CD2 | 650 | 177.9 | 119.6 | 23.3 | 20 | B |
| LEU C | 650 | 179.2 | 122.8 | 25.5 | 25 | B |
| LEU O | 650 | 178.5 | 122.3 | 26.3 | 26 | B |
| ALA N | 651 | 180.2 | 123.6 | 25.8 | 23 | B |
| ALA CA | 651 | 180.5 | 124.0 | 27.2 | 22 | B |
| ALA CB | 651 | 181.8 | 124.7 | 27.4 | 22 | B |
| ALA C | 651 | 179.3 | 124.9 | 27.7 | 23 | B |
| ALA O | 651 | 178.8 | 124.6 | 28.8 | 24 | B |
| PRO N | 652 | 178.9 | 125.9 | 27.0 | 23 | B |
| PRO CD | 652 | 179.7 | 126.7 | 26.0 | 23 | B |
| PRO CA | 652 | 177.7 | 126.7 | 27.4 | 23 | B |
| PRO CB | 652 | 177.6 | 127.8 | 26.4 | 23 | B |
| PRO CG | 652 | 179.1 | 128.1 | 26.2 | 21 | B |
| PRO C | 652 | 176.5 | 125.8 | 27.5 | 25 | B |
| PRO O | 652 | 175.6 | 126.0 | 28.3 | 27 | B |
| THR N | 653 | 176.4 | 124.8 | 26.6 | 25 | B |
| THR CA | 653 | 175.3 | 123.8 | 26.6 | 23 | B |
| THR CB | 653 | 175.3 | 122.9 | 25.3 | 24 | B |
| THR OG1 | 653 | 175.2 | 123.7 | 24.2 | 25 | B |
| THR CG2 | 653 | 174.2 | 121.9 | 25.4 | 24 | B |
| THR C | 653 | 175.3 | 123.0 | 27.8 | 23 | B |
| THR O | 653 | 174.2 | 122.7 | 28.5 | 24 | B |
| TYR N | 654 | 176.4 | 122.4 | 28.2 | 22 | B |
| TYR CA | 654 | 176.5 | 121.6 | 29.4 | 22 | B |
| TYR CB | 654 | 177.9 | 121.2 | 29.6 | 22 | B |
| TYR CG | 654 | 178.2 | 120.7 | 31.0 | 21 | B |
| TYR CD1 | 654 | 178.0 | 119.3 | 31.4 | 20 | B |
| TYR CE1 | 654 | 178.4 | 118.9 | 32.7 | 20 | B |
| TYR CD2 | 654 | 178.9 | 121.5 | 32.0 | 21 | B |
| TYR CE2 | 654 | 179.2 | 121.0 | 33.2 | 21 | B |
| TYR CZ | 654 | 179.0 | 119.7 | 33.6 | 21 | B |
| TYR OH | 654 | 179.4 | 119.3 | 34.8 | 21 | B |
| TYR C | 654 | 176.0 | 122.5 | 30.6 | 24 | B |
| TYR O | 654 | 175.2 | 122.1 | 31.4 | 24 | B |
| ALA N | 655 | 176.6 | 123.7 | 30.7 | 25 | B |
| ALA CA | 655 | 176.3 | 124.7 | 31.7 | 25 | B |
| ALA CB | 655 | 177.1 | 125.9 | 31.5 | 24 | B |
| ALA C | 655 | 174.8 | 125.0 | 31.8 | 25 | B |
| ALA O | 655 | 174.2 | 125.0 | 32.8 | 26 | B |
| ALA N | 656 | 174.2 | 125.3 | 30.6 | 26 | B |
| ALA CA | 656 | 172.8 | 125.6 | 30.6 | 26 | B |
| ALA CB | 656 | 172.4 | 126.0 | 29.2 | 24 | B |
| ALA C | 656 | 172.0 | 124.5 | 31.1 | 28 | B |
| ALA O | 656 | 171.2 | 124.6 | 32.1 | 29 | B |
| VAL N | 657 | 172.1 | 123.3 | 30.4 | 29 | B |
| VAL CA | 657 | 171.4 | 122.1 | 30.8 | 29 | B |
| VAL CB | 657 | 171.8 | 120.9 | 29.9 | 29 | B |
| VAL CG1 | 657 | 171.1 | 119.6 | 30.4 | 29 | B |
| VAL CG2 | 657 | 171.3 | 121.2 | 28.5 | 27 | B |
| VAL C | 657 | 171.6 | 121.8 | 32.3 | 29 | B |
| VAL O | 657 | 170.6 | 121.6 | 33.0 | 31 | B |
| ASN N | 658 | 172.8 | 121.8 | 32.9 | 30 | B |
| ASN CA | 658 | 173.0 | 121.6 | 34.3 | 29 | B |
| ASN CB | 658 | 174.5 | 121.6 | 34.7 | 29 | B |
| ASN CG | 658 | 175.1 | 120.3 | 34.9 | 30 | B |
| ASN OD1 | 658 | 174.6 | 119.3 | 34.4 | 32 | B |
| ASN ND2 | 658 | 176.2 | 120.2 | 35.7 | 31 | B |
| ASN C | 658 | 172.3 | 122.6 | 35.2 | 30 | B |
| ASN O | 658 | 171.7 | 122.2 | 36.2 | 30 | B |
| ALA N | 659 | 172.3 | 123.9 | 34.8 | 30 | B |
| ALA CA | 659 | 171.7 | 124.9 | 35.5 | 29 | B |
| ALA CB | 659 | 171.9 | 126.3 | 34.8 | 28 | B |
| ALA C | 659 | 170.2 | 124.6 | 35.5 | 30 | B |
| ALA O | 659 | 169.6 | 124.5 | 36.6 | 31 | B |
| LEU N | 660 | 169.6 | 124.5 | 34.3 | 31 | B |
| LEU CA | 660 | 168.1 | 124.2 | 34.2 | 32 | B |
| LEU CB | 660 | 167.8 | 123.9 | 32.7 | 30 | B |
| LEU CG | 660 | 167.8 | 125.1 | 31.8 | 30 | B |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| LEU CD1 | 660 | 167.5 | 124.7 | 30.4 | 30 | B |
| LEU CD2 | 660 | 166.8 | 126.2 | 32.3 | 30 | B |
| LEU C | 660 | 167.7 | 123.0 | 35.1 | 33 | B |
| LEU O | 660 | 166.6 | 122.9 | 35.7 | 34 | B |
| CYS N | 661 | 168.6 | 122.0 | 35.2 | 34 | B |
| CYS CA | 661 | 168.4 | 120.9 | 36.0 | 36 | B |
| CYS CB | 661 | 169.4 | 119.7 | 35.7 | 35 | B |
| CYS SG | 661 | 168.9 | 118.8 | 34.2 | 33 | B |
| CYS C | 661 | 168.4 | 121.2 | 37.5 | 38 | B |
| CYS O | 661 | 167.7 | 120.5 | 38.3 | 39 | B |
| ILE N | 662 | 169.3 | 122.1 | 38.0 | 40 | B |
| ILE CA | 662 | 169.4 | 122.4 | 39.4 | 40 | B |
| ILE CB | 662 | 170.6 | 123.3 | 39.7 | 41 | B |
| ILE CG2 | 662 | 170.7 | 123.6 | 41.2 | 42 | B |
| ILE CG1 | 662 | 171.9 | 122.7 | 39.2 | 41 | B |
| ILE CD1 | 662 | 173.1 | 123.5 | 39.5 | 41 | B |
| ILE C | 662 | 168.1 | 123.1 | 39.8 | 40 | B |
| ILE O | 662 | 167.6 | 122.9 | 40.9 | 40 | B |
| ILE N | 663 | 167.5 | 123.9 | 38.8 | 39 | B |
| ILE CA | 663 | 166.2 | 124.5 | 39.1 | 39 | B |
| ILE CB | 663 | 166.0 | 125.6 | 38.0 | 37 | B |
| ILE CG2 | 663 | 164.6 | 126.2 | 38.1 | 37 | B |
| ILE CG1 | 663 | 167.0 | 126.7 | 38.1 | 36 | B |
| ILE CD1 | 663 | 166.9 | 127.8 | 37.0 | 34 | B |
| ILE C | 663 | 165.1 | 123.5 | 39.1 | 41 | B |
| ILE O | 663 | 164.1 | 123.6 | 39.7 | 42 | B |
| CLY N | 664 | 165.3 | 122.3 | 38.4 | 40 | B |
| GLY CA | 664 | 164.4 | 121.3 | 38.4 | 41 | B |
| GLY C | 664 | 162.9 | 121.5 | 38.2 | 41 | B |
| GLY O | 664 | 162.1 | 120.6 | 38.6 | 42 | B |
| THR N | 665 | 162.4 | 122.6 | 37.7 | 41 | B |
| THR CA | 665 | 161.0 | 122.8 | 37.5 | 42 | B |
| THR CB | 665 | 160.6 | 124.3 | 37.7 | 41 | B |
| THR OG1 | 665 | 160.9 | 125.0 | 36.5 | 41 | B |
| THR CG2 | 665 | 161.3 | 125.0 | 38.8 | 41 | B |
| THR C | 665 | 160.6 | 122.4 | 36.2 | 43 | B |
| THR O | 665 | 161.4 | 122.3 | 35.3 | 42 | B |
| GLU N | 666 | 159.3 | 122.1 | 36.0 | 46 | B |
| GLU CA | 666 | 158.8 | 121.7 | 34.7 | 48 | B |
| GLU CB | 666 | 157.3 | 121.2 | 34.8 | 50 | B |
| GLU CG | 666 | 157.2 | 119.7 | 35.0 | 53 | B |
| GLU CD | 666 | 157.9 | 119.1 | 36.3 | 54 | B |
| GLU OE1 | 666 | 158.0 | 119.9 | 37.2 | 56 | B |
| GLU OE2 | 666 | 158.2 | 117.9 | 36.3 | 55 | B |
| GLU C | 666 | 159.0 | 122.8 | 33.7 | 49 | B |
| GLU O | 666 | 158.9 | 122.6 | 32.5 | 50 | B |
| GLU N | 667 | 159.2 | 124.0 | 34.2 | 48 | B |
| GLU CA | 667 | 159.5 | 125.2 | 33.4 | 47 | B |
| GLU CB | 667 | 159.2 | 126.5 | 34.1 | 48 | B |
| GLU CG | 667 | 159.5 | 127.7 | 33.3 | 50 | B |
| GLU CD | 667 | 159.7 | 129.0 | 34.1 | 51 | B |
| GLU OE1 | 667 | 159.9 | 128.9 | 35.4 | 51 | B |
| GLU OE2 | 667 | 159.8 | 130.1 | 33.6 | 52 | B |
| GLU C | 667 | 160.9 | 125.2 | 32.9 | 45 | B |
| GLU O | 667 | 161.2 | 125.5 | 31.7 | 45 | B |
| ALA N | 668 | 161.8 | 124.8 | 33.8 | 42 | B |
| ALA CA | 668 | 163.2 | 124.7 | 33.4 | 40 | B |
| ALA CB | 668 | 164.0 | 124.3 | 34.7 | 40 | B |
| ALA C | 668 | 163.4 | 123.6 | 32.4 | 39 | B |
| ALA O | 668 | 163.8 | 123.8 | 31.3 | 38 | B |
| TYR N | 669 | 162.9 | 122.4 | 32.7 | 37 | B |
| TYR CA | 669 | 163.0 | 121.2 | 31.8 | 35 | B |
| TYR CB | 669 | 162.3 | 120.0 | 32.4 | 34 | B |
| TYR CG | 669 | 162.7 | 119.5 | 33.7 | 32 | B |
| TYR CD1 | 669 | 161.8 | 119.0 | 34.6 | 31 | B |
| TYR CE1 | 669 | 162.2 | 118.5 | 35.9 | 30 | B |
| TYR CD2 | 669 | 164.1 | 119.5 | 34.1 | 31 | B |
| TYR CE2 | 669 | 164.5 | 119.0 | 35.4 | 31 | B |
| TYR CZ | 669 | 163.5 | 118.5 | 36.2 | 30 | B |
| TYR OH | 669 | 163.9 | 118.0 | 37.5 | 28 | B |
| TYR C | 669 | 162.4 | 121.6 | 30.5 | 36 | B |
| TYR O | 669 | 163.0 | 121.2 | 29.4 | 37 | B |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| ASN N | 670 | 161.3 | 122.3 | 30.5 | 36 | B |
| ASN CA | 670 | 160.7 | 122.6 | 29.2 | 37 | B |
| ASN CB | 670 | 159.3 | 123.2 | 29.4 | 39 | B |
| ASN CG | 670 | 158.3 | 122.0 | 29.7 | 39 | B |
| ASN OD1 | 670 | 158.6 | 121.0 | 30.2 | 39 | B |
| ASN ND2 | 670 | 157.0 | 122.3 | 29.4 | 40 | B |
| ASN C | 670 | 161.5 | 123.6 | 28.3 | 37 | B |
| ASN O | 670 | 161.2 | 123.8 | 27.2 | 38 | B |
| VAL N | 671 | 162.5 | 124.2 | 28.9 | 36 | B |
| VAL CA | 671 | 163.3 | 125.2 | 28.2 | 36 | B |
| VAL CB | 671 | 164.3 | 125.9 | 29.1 | 36 | B |
| VAL CG1 | 671 | 165.2 | 126.7 | 28.2 | 36 | B |
| VAL CG2 | 671 | 163.5 | 126.7 | 30.1 | 36 | B |
| VAL C | 671 | 164.0 | 124.4 | 27.1 | 36 | B |
| VAL O | 671 | 164.2 | 124.9 | 25.9 | 36 | B |
| ILE N | 672 | 164.6 | 123.3 | 27.4 | 35 | B |
| ILE CA | 672 | 165.4 | 122.5 | 26.5 | 34 | B |
| ILE CB | 672 | 166.1 | 121.3 | 27.3 | 32 | B |
| ILE CG2 | 672 | 167.1 | 120.6 | 26.4 | 31 | B |
| ILE CG1 | 672 | 166.8 | 121.8 | 28.6 | 30 | B |
| ILE CD1 | 672 | 167.3 | 120.7 | 29.5 | 28 | B |
| ILE C | 672 | 164.7 | 121.8 | 25.4 | 35 | B |
| ILE O | 672 | 163.7 | 121.1 | 25.6 | 36 | B |
| ASN N | 673 | 165.1 | 122.2 | 24.1 | 35 | B |
| ASN CA | 673 | 164.5 | 121.6 | 22.9 | 37 | B |
| ASN CB | 673 | 164.6 | 122.6 | 21.8 | 37 | B |
| ASN CG | 673 | 164.1 | 122.1 | 20.5 | 39 | B |
| ASN OD1 | 673 | 164.2 | 121.0 | 20.2 | 40 | B |
| ASN ND2 | 673 | 163.4 | 123.0 | 19.7 | 39 | B |
| ASN C | 673 | 165.2 | 120.4 | 22.6 | 38 | B |
| ASN O | 673 | 166.3 | 120.4 | 21.9 | 39 | B |
| ARG N | 674 | 164.7 | 119.2 | 23.0 | 40 | B |
| ARG CA | 674 | 165.4 | 118.0 | 22.8 | 40 | B |
| ARG CB | 674 | 164.7 | 116.9 | 23.7 | 39 | B |
| ARG CG | 674 | 164.7 | 117.2 | 25.1 | 39 | B |
| ARG CD | 674 | 163.8 | 116.3 | 25.9 | 40 | B |
| ARG NE | 674 | 164.1 | 114.8 | 25.7 | 41 | B |
| ARG CZ | 674 | 163.6 | 114.0 | 24.9 | 42 | B |
| ARG NH1 | 674 | 162.5 | 114.4 | 24.1 | 42 | B |
| ARG NH2 | 674 | 163.9 | 112.7 | 24.9 | 42 | B |
| ARG C | 674 | 165.6 | 117.4 | 21.4 | 41 | B |
| ARG O | 674 | 166.7 | 116.9 | 21.1 | 41 | B |
| GLU N | 675 | 164.6 | 117.6 | 20.6 | 43 | B |
| GLU CA | 675 | 164.8 | 117.1 | 19.2 | 45 | B |
| GLU CB | 675 | 163.5 | 117.2 | 18.4 | 49 | B |
| GLU CG | 675 | 162.4 | 118.2 | 19.0 | 55 | B |
| GLU CD | 675 | 161.7 | 117.8 | 20.3 | 57 | B |
| GLU OE1 | 675 | 161.9 | 118.5 | 21.3 | 58 | B |
| GLU OE2 | 675 | 161.0 | 116.7 | 20.3 | 59 | B |
| GLU C | 675 | 165.9 | 117.8 | 18.5 | 45 | B |
| GLU O | 675 | 166.7 | 117.3 | 17.7 | 44 | B |
| LYS N | 676 | 166.1 | 119.1 | 18.9 | 43 | B |
| LYS CA | 676 | 167.2 | 119.9 | 18.3 | 41 | B |
| LYS CB | 676 | 166.7 | 121.4 | 18.1 | 43 | B |
| LYS CG | 676 | 166.2 | 121.5 | 16.6 | 46 | B |
| LYS CD | 676 | 166.0 | 123.0 | 16.3 | 49 | B |
| LYS CE | 676 | 164.9 | 123.6 | 17.0 | 51 | B |
| LYS NZ | 676 | 164.6 | 125.0 | 16.7 | 52 | B |
| LYS C | 676 | 168.5 | 119.8 | 19.0 | 38 | B |
| LYS O | 676 | 169.5 | 120.0 | 18.4 | 37 | B |
| LEU N | 677 | 168.4 | 119.5 | 20.3 | 35 | B |
| LEU CA | 677 | 169.7 | 119.3 | 21.1 | 33 | B |
| LEU CB | 677 | 169.4 | 119.0 | 22.5 | 31 | B |
| LEU CG | 677 | 170.5 | 118.7 | 23.5 | 30 | B |
| LEU CD1 | 677 | 171.6 | 119.8 | 23.2 | 31 | B |
| LEU CD2 | 677 | 170.1 | 118.7 | 24.9 | 30 | B |
| LEU C | 677 | 170.4 | 118.1 | 20.4 | 33 | B |
| LEU O | 677 | 171.6 | 118.3 | 20.1 | 33 | B |
| LEU N | 678 | 169.7 | 117.0 | 20.2 | 35 | B |
| LEU CA | 678 | 170.2 | 115.8 | 19.5 | 34 | B |
| LEU CB | 678 | 169.1 | 114.8 | 19.4 | 35 | B |
| LEU CG | 678 | 169.3 | 113.3 | 19.3 | 36 | B |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| LEU CD1 | 678 | 168.5 | 112.7 | 18.2 | 36 | B |
| LEU CD2 | 678 | 170.8 | 113.0 | 19.1 | 37 | B |
| LEU C | 678 | 170.8 | 116.1 | 18.2 | 34 | B |
| LEU O | 678 | 171.9 | 115.7 | 17.8 | 34 | B |
| GLN N | 679 | 170.0 | 116.9 | 17.4 | 34 | B |
| GLN CA | 679 | 170.3 | 117.3 | 16.1 | 36 | B |
| GLN CB | 679 | 169.3 | 118.3 | 15.5 | 39 | B |
| GLN CG | 679 | 169.5 | 118.9 | 14.2 | 43 | B |
| GLN CD | 679 | 168.3 | 119.6 | 13.6 | 46 | B |
| GLN OE1 | 679 | 168.3 | 120.8 | 13.4 | 4B | B |
| GLN NE2 | 679 | 167.2 | 118.8 | 13.4 | 46 | B |
| GLN C | 679 | 171.7 | 118.0 | 16.1 | 35 | B |
| GLN O | 679 | 172.5 | 117.7 | 15.2 | 35 | B |
| TYR N | 680 | 171.9 | 118.8 | 17.1 | 34 | B |
| TYR CA | 680 | 173.1 | 119.6 | 17.3 | 31 | B |
| TYR CB | 680 | 172.9 | 120.5 | 18.5 | 30 | B |
| TYR CG | 680 | 174.1 | 121.3 | 18.9 | 29 | B |
| TYR CD1 | 680 | 174.7 | 122.2 | 17.9 | 28 | B |
| TYR CE1 | 680 | 175.9 | 122.9 | 18.2 | 28 | B |
| TYR CD2 | 680 | 174.7 | 121.3 | 20.1 | 28 | B |
| TYR CE2 | 680 | 175.8 | 122.0 | 20.4 | 27 | B |
| TYR CZ | 680 | 176.4 | 122.8 | 19.5 | 27 | B |
| TYR OH | 680 | 177.6 | 123.4 | 19.8 | 29 | B |
| TYR C | 680 | 174.3 | 118.6 | 17.6 | 29 | B |
| TYR O | 680 | 175.3 | 118.7 | 17.0 | 29 | B |
| LEU N | 681 | 174.1 | 117.7 | 18.6 | 27 | B |
| LEU CA | 681 | 175.2 | 116.8 | 19.0 | 27 | B |
| LEU CB | 681 | 174.7 | 115.8 | 20.1 | 26 | B |
| LEU CG | 681 | 174.3 | 116.5 | 21.4 | 26 | B |
| LEU CD1 | 681 | 174.0 | 115.4 | 22.5 | 25 | B |
| LEU CD2 | 681 | 175.4 | 117.3 | 21.9 | 25 | B |
| LEU C | 681 | 175.6 | 116.0 | 17.8 | 27 | B |
| LEU O | 681 | 176.8 | 115.8 | 17.6 | 26 | B |
| TYR N | 682 | 174.7 | 115.6 | 16.9 | 28 | B |
| TYR CA | 682 | 175.0 | 114.9 | 15.8 | 29 | B |
| TYR CB | 682 | 173.8 | 114.4 | 15.0 | 31 | B |
| TYR CG | 682 | 173.3 | 113.0 | 15.3 | 32 | B |
| TYR CD1 | 682 | 172.0 | 112.8 | 15.8 | 32 | B |
| TYR CE1 | 682 | 171.6 | 111.5 | 16.1 | 32 | B |
| TYR CD2 | 682 | 174.2 | 111.9 | 15.2 | 32 | B |
| TYR CE2 | 682 | 173.7 | 110.6 | 15.5 | 32 | B |
| TYR CZ | 682 | 172.4 | 110.4 | 15.9 | 33 | B |
| TYR OH | 682 | 172.0 | 109.2 | 16.2 | 33 | B |
| TYR C | 682 | 175.9 | 115.8 | 14.8 | 29 | B |
| TYR O | 682 | 176.8 | 115.3 | 14.2 | 30 | B |
| SER N | 683 | 175.6 | 117.1 | 14.8 | 30 | B |
| SER CA | 683 | 176.4 | 118.0 | 13.9 | 29 | B |
| SER CB | 683 | 175.7 | 119.4 | 13.8 | 30 | B |
| SER OG | 683 | 175.9 | 120.2 | 15.0 | 30 | B |
| SER C | 683 | 177.8 | 118.2 | 14.4 | 29 | B |
| SER O | 683 | 178.6 | 118.7 | 13.6 | 29 | B |
| LEU N | 684 | 178.1 | 117.7 | 15.6 | 28 | B |
| LEU CA | 684 | 179.5 | 117.9 | 16.1 | 27 | B |
| LEU CB | 684 | 179.4 | 118.4 | 17.5 | 24 | B |
| LEU CG | 684 | 178.6 | 119.7 | 17.7 | 23 | B |
| LEU CD1 | 684 | 178.7 | 120.1 | 19.2 | 22 | B |
| LEU CD2 | 684 | 179.1 | 120.8 | 16.8 | 20 | B |
| LEU C | 684 | 180.3 | 116.5 | 16.1 | 27 | B |
| LEU O | 684 | 181.5 | 116.5 | 16.0 | 29 | B |
| LYS N | 685 | 179.5 | 115.4 | 16.1 | 27 | B |
| LYS CA | 685 | 180.1 | 114.1 | 16.0 | 26 | B |
| LYS CB | 685 | 179.0 | 113.0 | 15.8 | 27 | B |
| LYS CG | 685 | 179.1 | 111.8 | 16.7 | 27 | B |
| LYS CD | 685 | 180.5 | 111.3 | 16.8 | 27 | B |
| LYS CE | 685 | 180.6 | 110.0 | 17.7 | 28 | B |
| LYS NZ | 685 | 179.9 | 108.9 | 17.1 | 27 | B |
| LYS C | 685 | 181.1 | 114.0 | 14.9 | 27 | B |
| LYS O | 685 | 180.9 | 114.4 | 13.8 | 26 | B |
| GLN N | 686 | 182.3 | 113.3 | 15.2 | 27 | B |
| GLN CA | 686 | 183.3 | 113.1 | 14.3 | 28 | B |
| GLN CB | 686 | 184.7 | 113.6 | 14.9 | 28 | B |
| GLN CG | 686 | 184.7 | 115.1 | 15.1 | 28 | B |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| GLN CD | 686 | 184.6 | 115.8 | 13.9 | 30 | B |
| GLN OE1 | 686 | 185.5 | 115.8 | 13.0 | 32 | B |
| GLN NE2 | 686 | 183.4 | 116.4 | 13.7 | 30 | B |
| GLN C | 686 | 183.5 | 111.6 | 14.1 | 29 | B |
| GLN O | 686 | 183.1 | 110.8 | 14.9 | 30 | B |
| PRO N | 687 | 184.0 | 111.2 | 12.9 | 30 | B |
| PRO CD | 687 | 184.4 | 112.1 | 11.8 | 30 | B |
| PRO CA | 687 | 184.2 | 109.8 | 12.5 | 29 | B |
| PRO CB | 687 | 184.8 | 110.0 | 11.1 | 30 | B |
| PRO CG | 687 | 184.3 | 111.2 | 10.6 | 31 | B |
| PRO C | 687 | 185.1 | 109.1 | 13.5 | 29 | B |
| PRO O | 687 | 184.9 | 107.9 | 13.7 | 29 | B |
| ASP N | 688 | 186.1 | 109.8 | 14.0 | 28 | B |
| ASP CA | 688 | 187.0 | 109.1 | 15.0 | 27 | B |
| ASP CB | 688 | 188.3 | 109.8 | 15.1 | 27 | B |
| ASP CG | 688 | 188.3 | 111.1 | 15.7 | 28 | B |
| ASP OD1 | 688 | 187.2 | 111.6 | 16.1 | 28 | B |
| ASP OD2 | 688 | 189.4 | 111.7 | 15.8 | 29 | B |
| ASP C | 688 | 186.3 | 108.9 | 16.3 | 26 | B |
| ASP O | 688 | 186.9 | 108.4 | 17.3 | 28 | B |
| GLY N | 689 | 185.1 | 109.4 | 16.5 | 23 | B |
| GLY CA | 689 | 184.4 | 109.3 | 17.8 | 23 | B |
| GLY C | 689 | 184.4 | 110.5 | 18.6 | 22 | B |
| GLY O | 689 | 183.6 | 110.6 | 19.5 | 22 | B |
| SER N | 690 | 185.2 | 111.5 | 18.3 | 22 | B |
| SER CA | 690 | 185.2 | 112.8 | 19.0 | 20 | B |
| SER CB | 690 | 186.5 | 113.5 | 18.9 | 20 | B |
| SER OG | 690 | 186.8 | 113.7 | 17.5 | 18 | B |
| SER C | 690 | 184.0 | 113.7 | 18.6 | 21 | B |
| SER O | 690 | 183.2 | 113.3 | 17.8 | 23 | B |
| PHE N | 691 | 183.9 | 114.8 | 19.3 | 22 | B |
| PHE CA | 691 | 182.9 | 115.8 | 19.0 | 19 | B |
| PHE CB | 691 | 181.9 | 115.9 | 20.1 | 19 | B |
| PHE CG | 691 | 180.9 | 114.8 | 20.2 | 19 | B |
| PHE CD1 | 691 | 181.2 | 113.6 | 21.0 | 19 | B |
| PHE CD2 | 691 | 179.7 | 114.8 | 19.6 | 19 | B |
| PHE CE1 | 691 | 180.3 | 112.6 | 21.1 | 19 | B |
| PHE CE2 | 691 | 178.7 | 113.8 | 19.7 | 18 | B |
| PHE CZ | 691 | 179.0 | 112.7 | 20.5 | 18 | B |
| PHE C | 691 | 183.6 | 117.2 | 18.9 | 19 | B |
| PHE O | 691 | 184.6 | 117.4 | 19.6 | 18 | B |
| LEU N | 692 | 183.1 | 118.1 | 18.1 | 20 | B |
| LEU CA | 692 | 183.7 | 119.4 | 18.0 | 21 | B |
| LEU CB | 692 | 183.3 | 120.1 | 16.8 | 21 | B |
| LEU CG | 692 | 183.6 | 119.5 | 15.4 | 20 | B |
| LEU CD1 | 692 | 182.8 | 120.3 | 14.4 | 20 | B |
| LEU CD2 | 692 | 185.1 | 119.4 | 15.1 | 18 | B |
| LEU C | 692 | 183.1 | 120.1 | 19.3 | 23 | B |
| LEU O | 692 | 182.1 | 119.6 | 19.8 | 23 | B |
| MET N | 693 | 183.7 | 121.2 | 19.7 | 23 | B |
| MET CA | 693 | 183.1 | 121.9 | 20.8 | 22 | B |
| MET CB | 693 | 184.1 | 122.9 | 21.5 | 21 | B |
| MET CG | 693 | 185.2 | 122.1 | 22.4 | 22 | B |
| MET SD | 693 | 184.4 | 121.2 | 23.7 | 25 | B |
| MET CE | 693 | 183.8 | 122.4 | 24.8 | 23 | B |
| MET C | 693 | 182.0 | 122.8 | 20.3 | 22 | B |
| MET O | 693 | 181.0 | 123.1 | 21.0 | 21 | B |
| HIS N | 694 | 182.1 | 123.1 | 19.0 | 22 | B |
| HIS CA | 694 | 181.0 | 123.9 | 18.3 | 23 | B |
| HIS CB | 694 | 181.0 | 125.3 | 18.7 | 22 | B |
| HIS CG | 694 | 182.2 | 126.1 | 18.5 | 22 | B |
| HIS CD2 | 694 | 183.4 | 126.1 | 19.1 | 20 | B |
| HIS ND1 | 694 | 182.3 | 127.1 | 17.5 | 22 | B |
| HIS CE1 | 694 | 183.5 | 127.6 | 17.5 | 21 | B |
| HIS NE2 | 694 | 184.2 | 127.0 | 18.5 | 21 | B |
| HIS C | 694 | 181.4 | 123.8 | 16.8 | 25 | B |
| HIS O | 694 | 182.5 | 123.3 | 16.4 | 26 | B |
| VAL N | 695 | 180.5 | 124.2 | 15.9 | 25 | B |
| VAL CA | 695 | 180.7 | 124.1 | 14.5 | 25 | B |
| VAL CB | 695 | 179.5 | 124.5 | 13.7 | 26 | B |
| VAL CG1 | 695 | 179.8 | 124.7 | 12.2 | 26 | B |
| VAL CG2 | 695 | 178.3 | 123.5 | 13.9 | 25 | B |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| VAL C | 695 | 181.9 | 125.0 | 14.1 | 26 | B |
| VAL O | 695 | 181.9 | 126.2 | 14.3 | 28 | B |
| GLY N | 696 | 182.9 | 124.4 | 13.5 | 26 | B |
| GLY CA | 696 | 184.1 | 125.1 | 13.1 | 26 | B |
| GLY C | 696 | 185.0 | 125.2 | 14.2 | 26 | B |
| GLY O | 696 | 186.1 | 125.8 | 14.1 | 26 | B |
| GLY N | 697 | 184.6 | 124.6 | 15.4 | 24 | B |
| GLY CA | 697 | 185.5 | 124.7 | 16.6 | 22 | B |
| GLY C | 697 | 186.5 | 123.6 | 16.8 | 22 | B |
| GLY O | 697 | 186.7 | 122.7 | 16.0 | 23 | B |
| GLU N | 698 | 187.1 | 123.6 | 18.0 | 20 | B |
| GLU CA | 698 | 188.1 | 122.7 | 18.4 | 20 | B |
| GLU CB | 698 | 189.1 | 123.4 | 19.4 | 20 | B |
| GLU CG | 698 | 188.7 | 123.6 | 20.8 | 21 | B |
| GLU CD | 698 | 187.7 | 124.8 | 21.0 | 22 | B |
| GLU OE1 | 698 | 187.4 | 125.6 | 20.1 | 22 | B |
| GLU OE2 | 698 | 187.4 | 125.0 | 22.2 | 22 | B |
| GLU C | 698 | 187.6 | 121.4 | 19.0 | 19 | B |
| GLU O | 698 | 186.4 | 121.3 | 19.3 | 19 | B |
| VAL N | 699 | 188.4 | 120.4 | 19.0 | 19 | B |
| VAL CA | 699 | 188.1 | 119.0 | 19.6 | 18 | B |
| VAL CB | 699 | 188.3 | 117.9 | 18.5 | 17 | B |
| VAL CG1 | 699 | 188.2 | 116.5 | 19.2 | 16 | B |
| VAL CG2 | 699 | 187.2 | 118.0 | 17.4 | 18 | B |
| VAL C | 699 | 189.0 | 118.7 | 20.7 | 18 | B |
| VAL O | 699 | 190.2 | 118.8 | 20.6 | 18 | B |
| ASP N | 700 | 188.5 | 118.3 | 21.9 | 18 | B |
| ASP CA | 700 | 189.3 | 117.8 | 23.0 | 19 | B |
| ASP CB | 700 | 190.1 | 118.9 | 23.7 | 20 | B |
| ASP CG | 700 | 189.3 | 120.0 | 24.3 | 22 | B |
| ASP OD1 | 700 | 188.4 | 119.7 | 25.1 | 22 | B |
| ASP OD2 | 700 | 189.5 | 121.1 | 23.9 | 22 | B |
| ASP C | 700 | 188.2 | 117.1 | 23.9 | 19 | B |
| ASP O | 700 | 187.0 | 117.2 | 23.7 | 19 | B |
| VAL N | 701 | 188.7 | 116.3 | 24.9 | 20 | B |
| VAL CA | 701 | 187.7 | 115.6 | 25.8 | 20 | B |
| VAL CB | 701 | 188.3 | 114.8 | 27.0 | 20 | B |
| VAL CG1 | 701 | 188.1 | 113.3 | 26.8 | 18 | B |
| VAL CG2 | 701 | 189.7 | 115.1 | 27.2 | 20 | B |
| VAL C | 701 | 186.6 | 116.3 | 26.4 | 21 | B |
| VAL O | 701 | 185.6 | 115.7 | 26.7 | 23 | B |
| ARG N | 702 | 186.7 | 117.6 | 26.5 | 22 | B |
| ARG CA | 702 | 185.6 | 118.4 | 27.2 | 22 | B |
| ARG CB | 702 | 185.8 | 119.9 | 27.2 | 21 | B |
| ARG CG | 702 | 187.0 | 120.4 | 28.1 | 19 | B |
| ARG CD | 702 | 187.3 | 121.9 | 27.8 | 19 | B |
| ARG NE | 702 | 187.6 | 122.1 | 26.4 | 19 | B |
| ARG CZ | 702 | 187.4 | 123.2 | 25.6 | 18 | B |
| ARG NH1 | 702 | 187.8 | 123.3 | 24.4 | 17 | B |
| ARG NH2 | 702 | 186.7 | 124.2 | 26.1 | 18 | B |
| ARG C | 702 | 184.3 | 118.1 | 26.4 | 24 | B |
| ARG O | 702 | 183.2 | 118.0 | 27.0 | 25 | B |
| SER N | 703 | 184.4 | 118.0 | 25.1 | 25 | B |
| SER CA | 703 | 183.2 | 117.8 | 24.2 | 25 | B |
| SER CB | 703 | 183.6 | 117.9 | 22.8 | 26 | B |
| SER OG | 703 | 184.3 | 116.8 | 22.3 | 25 | B |
| SER C | 703 | 182.5 | 116.5 | 24.5 | 26 | B |
| SER O | 703 | 181.3 | 116.4 | 24.5 | 27 | B |
| ALA N | 704 | 183.3 | 115.4 | 24.7 | 26 | B |
| ALA CA | 704 | 182.8 | 114.1 | 25.0 | 26 | B |
| ALA CB | 704 | 183.9 | 113.1 | 25.1 | 26 | B |
| ALA C | 704 | 181.9 | 114.0 | 26.2 | 27 | B |
| ALA O | 704 | 180.9 | 113.4 | 26.2 | 28 | B |
| TYR N | 705 | 182.4 | 114.7 | 27.3 | 27 | B |
| TYR CA | 705 | 181.7 | 114.8 | 28.6 | 27 | B |
| TYR CB | 705 | 182.7 | 115.4 | 29.6 | 27 | B |
| TYR CG | 705 | 182.1 | 115.7 | 30.9 | 27 | B |
| TYR CD1 | 705 | 181.4 | 114.8 | 31.7 | 27 | B |
| TYR CE1 | 705 | 180.8 | 115.1 | 32.9 | 28 | B |
| TYR CD2 | 705 | 182.1 | 117.0 | 31.4 | 27 | B |
| TYR CE2 | 705 | 181.5 | 117.4 | 32.6 | 28 | B |
| TYR CZ | 705 | 180.9 | 116.4 | 33.4 | 28 | B |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| TYR OH | 705 | 180.3 | 116.8 | 34.6 | 28 | B |
| TYR C | 705 | 180.5 | 115.8 | 28.5 | 26 | B |
| TYR O | 705 | 179.4 | 115.4 | 29.0 | 24 | B |
| CYS N | 706 | 180.7 | 117.0 | 27.9 | 25 | B |
| CYS CA | 706 | 179.5 | 117.9 | 27.8 | 26 | B |
| CYS CB | 706 | 180.0 | 119.1 | 27.0 | 26 | B |
| CYS SG | 706 | 181.1 | 120.2 | 27.9 | 25 | B |
| CYS C | 706 | 178.4 | 117.2 | 27.0 | 27 | B |
| CYS O | 706 | 177.3 | 117.2 | 27.5 | 28 | B |
| ALA N | 707 | 178.7 | 116.5 | 25.9 | 26 | B |
| ALA CA | 707 | 177.7 | 115.8 | 25.1 | 24 | B |
| ALA CB | 707 | 178.4 | 115.3 | 23.8 | 22 | B |
| ALA C | 707 | 177.1 | 114.6 | 25.9 | 23 | B |
| ALA O | 707 | 175.9 | 114.5 | 26.0 | 23 | B |
| ALA N | 708 | 177.9 | 113.8 | 26.5 | 24 | B |
| ALA CA | 708 | 177.4 | 112.6 | 27.3 | 24 | B |
| ALA CB | 708 | 178.5 | 111.7 | 27.7 | 23 | B |
| ALA C | 708 | 176.6 | 113.0 | 28.5 | 26 | B |
| ALA O | 708 | 175.8 | 112.2 | 28.9 | 27 | B |
| SER N | 709 | 176.8 | 114.2 | 29.0 | 27 | B |
| SER CA | 709 | 176.1 | 114.7 | 30.2 | 27 | B |
| SER CB | 709 | 176.9 | 115.9 | 30.9 | 27 | B |
| SER OG | 709 | 176.2 | 116.4 | 32.0 | 27 | B |
| SER C | 709 | 174.7 | 115.2 | 29.8 | 28 | B |
| SER O | 709 | 173.8 | 114.9 | 30.4 | 28 | B |
| VAL N | 710 | 174.7 | 116.1 | 28.8 | 29 | B |
| VAL CA | 710 | 173.4 | 116.6 | 28.3 | 29 | B |
| VAL CB | 710 | 173.6 | 117.8 | 27.4 | 28 | B |
| VAL CG1 | 710 | 174.4 | 118.9 | 28.1 | 28 | B |
| VAL CG2 | 710 | 174.2 | 117.4 | 26.1 | 27 | B |
| VAL C | 710 | 172.5 | 115.6 | 27.6 | 29 | B |
| VAL O | 710 | 171.3 | 115.5 | 27.9 | 29 | B |
| ALA N | 711 | 173.1 | 114.7 | 26.8 | 30 | B |
| ALA CA | 711 | 172.3 | 113.7 | 26.1 | 30 | B |
| ALA CB | 711 | 173.1 | 113.0 | 25.1 | 28 | B |
| ALA C | 711 | 171.7 | 112.7 | 27.1 | 30 | B |
| ALA O | 711 | 170.6 | 112.2 | 26.9 | 31 | B |
| SER N | 712 | 172.5 | 112.3 | 28.1 | 31 | B |
| SER CA | 712 | 172.0 | 111.3 | 29.1 | 33 | B |
| SER CB | 712 | 173.1 | 110.8 | 30.0 | 34 | B |
| SER OG | 712 | 173.8 | 111.8 | 30.7 | 35 | B |
| SER C | 712 | 170.9 | 111.9 | 29.9 | 33 | B |
| SER O | 712 | 169.8 | 111.3 | 30.0 | 34 | B |
| LEU N | 713 | 171.2 | 113.1 | 30.5 | 33 | B |
| LEU CA | 713 | 170.2 | 113.8 | 31.4 | 32 | B |
| LEU CB | 713 | 170.7 | 115.2 | 31.8 | 31 | B |
| LEU CG | 713 | 171.7 | 115.1 | 33.0 | 30 | B |
| LEU CD1 | 713 | 172.3 | 116.5 | 33.2 | 29 | B |
| LEU CD2 | 713 | 171.1 | 114.6 | 34.3 | 29 | B |
| LEU C | 713 | 168.9 | 114.0 | 30.6 | 34 | B |
| LEU O | 713 | 167.8 | 113.8 | 31.2 | 34 | B |
| THR N | 714 | 168.9 | 114.4 | 29.4 | 35 | B |
| THR CA | 714 | 167.7 | 114.6 | 28.6 | 35 | B |
| THR CB | 714 | 167.9 | 115.8 | 27.6 | 34 | B |
| THR OG1 | 714 | 169.0 | 115.6 | 26.7 | 34 | B |
| THR CG2 | 714 | 168.2 | 117.1 | 28.4 | 32 | B |
| THR C | 714 | 167.2 | 113.4 | 27.9 | 36 | B |
| THR O | 714 | 166.2 | 113.5 | 27.1 | 37 | B |
| ASN N | 715 | 167.8 | 112.2 | 28.1 | 36 | B |
| ASN CA | 715 | 167.4 | 111.0 | 27.4 | 35 | B |
| ASN CB | 715 | 166.0 | 110.6 | 28.1 | 36 | B |
| ASN CG | 715 | 165.4 | 109.4 | 27.5 | 37 | B |
| ASN OD1 | 715 | 166.0 | 108.3 | 27.2 | 38 | B |
| ASN ND2 | 715 | 164.1 | 109.5 | 27.2 | 37 | B |
| ASN C | 715 | 167.2 | 111.1 | 25.9 | 34 | B |
| ASN O | 715 | 166.2 | 110.9 | 25.3 | 34 | B |
| ILE N | 716 | 168.3 | 111.5 | 25.3 | 31 | B |
| ILE CA | 716 | 168.3 | 111.7 | 23.8 | 29 | B |
| ILE CB | 716 | 168.5 | 113.1 | 23.3 | 29 | B |
| ILE CG2 | 716 | 167.4 | 114.0 | 23.8 | 28 | B |
| ILE CG1 | 716 | 169.8 | 113.7 | 23.9 | 30 | B |
| ILE CD1 | 716 | 170.3 | 115.0 | 23.3 | 30 | B |
| ILE C | 716 | 169.4 | 110.8 | 23.2 | 29 | B |
| ILE O | 716 | 169.7 | 111.0 | 22.1 | 28 | B |
| ILE N | 717 | 169.9 | 109.9 | 24.0 | 29 | B |
| ILE CA | 717 | 170.9 | 109.0 | 23.5 | 32 | B |
| ILE CB | 717 | 171.6 | 108.3 | 24.7 | 31 | B |
| ILE CG2 | 717 | 172.7 | 107.3 | 24.2 | 31 | B |
| ILE CG1 | 717 | 172.3 | 109.3 | 25.6 | 31 | B |
| ILE CD1 | 717 | 173.2 | 108.7 | 26.7 | 30 | B |
| ILE C | 717 | 170.4 | 107.9 | 22.6 | 33 | B |
| ILE O | 717 | 169.7 | 107.0 | 23.0 | 34 | B |
| THR N | 718 | 170.7 | 108.1 | 21.3 | 35 | B |
| THR CA | 718 | 170.3 | 107.1 | 20.3 | 35 | B |
| THR CB | 718 | 170.3 | 107.8 | 18.9 | 35 | B |
| THR OG1 | 718 | 171.6 | 108.2 | 18.5 | 36 | B |
| THR CG2 | 718 | 169.3 | 109.0 | 18.9 | 35 | B |
| THR C | 718 | 171.4 | 106.0 | 20.3 | 38 | B |
| THR O | 718 | 172.3 | 106.0 | 21.1 | 38 | B |
| PRO N | 719 | 171.2 | 105.0 | 19.4 | 39 | B |
| PRO CD | 719 | 170.0 | 104.8 | 18.5 | 40 | B |
| PRO CA | 719 | 172.2 | 103.9 | 19.3 | 39 | B |
| PRO CB | 719 | 171.5 | 103.0 | 18.3 | 40 | B |
| PRO CG | 719 | 170.0 | 103.3 | 18.5 | 40 | B |
| PRO C | 719 | 173.6 | 104.2 | 18.8 | 39 | B |
| PRO O | 719 | 174.6 | 103.7 | 19.4 | 38 | B |
| ASP N | 720 | 173.7 | 105.0 | 17.8 | 38 | B |
| ASP CA | 720 | 175.0 | 105.4 | 17.2 | 39 | B |
| ASP CB | 720 | 174.9 | 105.4 | 15.7 | 40 | B |
| ASP CG | 720 | 173.9 | 106.5 | 15.2 | 41 | B |
| ASP OD1 | 720 | 174.0 | 106.9 | 14.0 | 43 | B |
| ASP OD2 | 720 | 173.1 | 106.9 | 16.0 | 41 | B |
| ASP C | 720 | 175.6 | 106.7 | 17.7 | 38 | B |
| ASP O | 720 | 176.7 | 107.1 | 17.2 | 37 | B |
| LEU N | 721 | 174.9 | 107.5 | 18.5 | 37 | B |
| LEU CA | 721 | 175.4 | 108.8 | 19.0 | 35 | B |
| LEU CB | 721 | 174.4 | 109.4 | 20.1 | 34 | B |
| LEU CG | 721 | 174.9 | 110.8 | 20.5 | 33 | B |
| LEU CD1 | 721 | 175.1 | 111.7 | 19.3 | 31 | B |
| LEU CD2 | 721 | 173.9 | 111.3 | 21.5 | 31 | B |
| LEU C | 721 | 176.8 | 108.7 | 19.5 | 36 | B |
| LEU O | 721 | 177.7 | 109.4 | 19.0 | 36 | B |
| PHE N | 722 | 177.1 | 107.9 | 20.5 | 35 | B |
| PHE CA | 722 | 178.4 | 107.8 | 21.0 | 36 | B |
| PHE CB | 722 | 178.3 | 107.8 | 22.6 | 36 | B |
| PHE CG | 722 | 177.7 | 109.0 | 23.1 | 36 | B |
| PHE CD1 | 722 | 176.4 | 109.0 | 23.7 | 36 | B |
| PHE CD2 | 722 | 178.3 | 110.3 | 23.0 | 37 | B |
| PHE CE1 | 722 | 175.8 | 110.1 | 24.2 | 36 | B |
| PHE CE2 | 722 | 177.6 | 111.4 | 23.4 | 37 | B |
| PHE CZ | 722 | 176.4 | 111.3 | 24.0 | 36 | B |
| PHE C | 722 | 179.2 | 106.7 | 20.5 | 36 | B |
| PHE O | 722 | 180.1 | 106.1 | 21.2 | 36 | B |
| GLU N | 723 | 178.9 | 106.3 | 19.3 | 37 | B |
| GLU CA | 723 | 179.6 | 105.2 | 18.6 | 37 | B |
| GLU CB | 723 | 179.1 | 105.0 | 17.2 | 41 | B |
| GLU CG | 723 | 179.2 | 103.5 | 16.8 | 45 | B |
| GLU CD | 723 | 178.9 | 102.6 | 18.0 | 48 | B |
| GLU OE1 | 723 | 177.7 | 102.7 | 18.5 | 49 | B |
| GLU OE2 | 723 | 179.8 | 101.9 | 18.5 | 49 | B |
| GLU C | 723 | 181.1 | 105.6 | 18.5 | 34 | B |
| GLU O | 723 | 181.4 | 106.6 | 17.9 | 34 | B |
| GLY N | 724 | 181.9 | 104.8 | 19.2 | 32 | B |
| GLY CA | 724 | 183.3 | 105.1 | 19.1 | 31 | B |
| GLY C | 724 | 183.9 | 106.1 | 20.0 | 28 | B |
| GLY O | 724 | 185.1 | 106.3 | 20.0 | 28 | B |
| THR N | 725 | 183.1 | 106.8 | 20.8 | 28 | B |
| THR CA | 725 | 183.6 | 107.9 | 21.6 | 28 | B |
| THR CB | 725 | 182.7 | 109.1 | 21.9 | 29 | B |
| THR OG1 | 725 | 182.2 | 109.1 | 23.3 | 31 | B |
| THR CG2 | 725 | 181.5 | 109.0 | 21.0 | 27 | B |
| THR C | 725 | 184.3 | 107.3 | 22.9 | 27 | B |
| THR O | 725 | 185.3 | 107.9 | 23.3 | 28 | B |
| ALA N | 726 | 183.9 | 106.2 | 23.3 | 25 | B |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| ALA CA | 726 | 184.6 | 105.6 | 24.5 | 25 | B |
| ALA CB | 726 | 183.8 | 104.3 | 24.9 | 25 | B |
| ALA C | 726 | 186.0 | 105.2 | 24.0 | 26 | B |
| ALA O | 726 | 186.9 | 105.3 | 24.8 | 27 | B |
| GLU N | 727 | 186.1 | 104.8 | 22.8 | 25 | B |
| GLU CA | 727 | 187.4 | 104.3 | 22.2 | 24 | B |
| GLU CB | 727 | 187.2 | 103.6 | 20.9 | 25 | B |
| GLU CG | 727 | 186.7 | 102.1 | 21.1 | 26 | B |
| GLU CD | 727 | 185.2 | 101.9 | 21.3 | 26 | B |
| GLU OE1 | 727 | 184.7 | 100.8 | 21.7 | 27 | B |
| GLU OE2 | 727 | 184.4 | 102.8 | 21.0 | 27 | B |
| GLU C | 727 | 188.3 | 105.5 | 22.0 | 23 | B |
| GLU O | 727 | 189.4 | 105.5 | 22.3 | 23 | B |
| TRP N | 728 | 187.7 | 106.6 | 21.5 | 21 | B |
| TRP CA | 728 | 188.5 | 107.8 | 21.3 | 21 | B |
| TRP CB | 728 | 187.7 | 108.9 | 20.6 | 21 | B |
| TRP CG | 728 | 188.5 | 110.1 | 20.3 | 20 | B |
| TRP CD2 | 728 | 188.7 | 111.2 | 21.1 | 21 | B |
| TRP CE2 | 728 | 189.6 | 112.1 | 20.4 | 21 | B |
| TRP CE3 | 728 | 188.2 | 111.7 | 22.3 | 21 | B |
| TRP CD1 | 728 | 189.2 | 110.2 | 19.2 | 20 | B |
| TRP NE1 | 728 | 189.9 | 111.4 | 19.2 | 21 | B |
| TRP CZ2 | 728 | 190.0 | 113.3 | 20.8 | 21 | B |
| TRP CZ3 | 728 | 188.7 | 112.9 | 22.8 | 21 | B |
| TRP CH2 | 728 | 189.5 | 113.7 | 22.1 | 21 | B |
| TRP C | 728 | 189.0 | 108.3 | 22.6 | 22 | B |
| TRP O | 728 | 190.2 | 108.6 | 22.8 | 23 | B |
| ILE N | 729 | 188.1 | 108.4 | 23.6 | 23 | B |
| ILE CA | 729 | 188.5 | 108.9 | 25.0 | 21 | B |
| ILE CB | 729 | 187.3 | 108.9 | 26.0 | 21 | B |
| ILE CG2 | 729 | 187.8 | 109.2 | 27.4 | 20 | B |
| ILE CG1 | 729 | 186.2 | 109.8 | 25.5 | 19 | B |
| ILE CD1 | 729 | 184.9 | 109.7 | 26.2 | 19 | B |
| ILE C | 729 | 189.6 | 108.0 | 25.6 | 22 | B |
| ILE O | 729 | 190.6 | 108.5 | 26.1 | 23 | B |
| ALA N | 730 | 189.5 | 106.7 | 25.4 | 22 | B |
| ALA CA | 730 | 190.5 | 105.7 | 25.9 | 21 | B |
| ALA CB | 730 | 190.1 | 104.3 | 25.6 | 22 | B |
| ALA C | 730 | 191.9 | 106.0 | 25.3 | 23 | B |
| ALA O | 730 | 192.9 | 105.6 | 25.8 | 22 | B |
| ARG N | 731 | 191.9 | 106.7 | 24.1 | 24 | B |
| ARG CA | 731 | 193.2 | 107.0 | 23.5 | 24 | B |
| ARG CB | 731 | 193.0 | 107.3 | 22.0 | 25 | B |
| ARG CG | 731 | 192.7 | 106.0 | 21.2 | 25 | B |
| ARG CD | 731 | 193.1 | 106.1 | 19.8 | 25 | B |
| ARG NE | 731 | 192.3 | 107.0 | 19.0 | 25 | B |
| ARC CZ | 731 | 192.8 | 108.0 | 18.3 | 27 | B |
| ARG NH1 | 731 | 194.1 | 108.2 | 18.2 | 25 | B |
| ARG NH2 | 731 | 192.0 | 108.8 | 17.6 | 27 | B |
| ARG C | 731 | 193.8 | 108.3 | 24.1 | 24 | B |
| ARG O | 731 | 195.0 | 108.7 | 23.7 | 22 | B |
| CYS N | 732 | 193.1 | 109.0 | 24.9 | 24 | B |
| CYS CA | 732 | 193.5 | 110.2 | 25.6 | 23 | B |
| CYS CB | 732 | 192.4 | 111.0 | 25.9 | 22 | B |
| CYS SG | 732 | 191.6 | 111.7 | 24.4 | 22 | B |
| CYS C | 732 | 194.3 | 109.8 | 26.8 | 23 | B |
| CYS O | 732 | 195.1 | 110.6 | 27.4 | 24 | B |
| GLN N | 733 | 194.2 | 108.5 | 27.2 | 23 | B |
| GLN CA | 733 | 195.0 | 108.0 | 28.4 | 23 | B |
| GLN CB | 733 | 194.4 | 106.8 | 29.0 | 23 | B |
| GLN CG | 733 | 195.1 | 106.3 | 30.3 | 23 | B |
| GLN CD | 733 | 194.5 | 105.1 | 31.0 | 24 | B |
| GLN OE1 | 733 | 193.9 | 104.2 | 30.4 | 25 | B |
| GLN NE2 | 733 | 194.6 | 105.1 | 32.3 | 24 | B |
| GLN C | 733 | 196.4 | 107.8 | 27.9 | 23 | B |
| GLN O | 733 | 196.7 | 107.1 | 26.9 | 24 | B |
| ASN N | 734 | 197.4 | 108.4 | 28.6 | 24 | B |
| ASN CA | 734 | 198.8 | 108.3 | 28.2 | 23 | B |
| ASN CB | 734 | 199.4 | 109.7 | 27.9 | 23 | B |
| ASN CG | 734 | 199.8 | 110.4 | 29.2 | 23 | B |
| ASN OD1 | 734 | 199.3 | 110.0 | 30.3 | 22 | B |
| ASN ND2 | 734 | 200.5 | 111.5 | 29.1 | 22 | B |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| ASN C | 734 | 199.7 | 107.5 | 29.2 | 22 | B |
| ASN O | 734 | 199.2 | 106.9 | 30.1 | 23 | B |
| TRP N | 735 | 201.0 | 107.5 | 28.9 | 22 | B |
| TRP CA | 735 | 202.0 | 106.8 | 29.8 | 23 | B |
| TRP CB | 735 | 203.4 | 107.1 | 29.3 | 21 | B |
| TRP CG | 735 | 203.7 | 108.6 | 29.2 | 21 | B |
| TRP CD2 | 735 | 204.4 | 109.3 | 30.2 | 21 | B |
| TRP CE2 | 735 | 204.5 | 110.7 | 29.7 | 21 | B |
| TRP CE3 | 735 | 205.0 | 109.0 | 31.4 | 21 | B |
| TRP CD1 | 735 | 203.4 | 109.5 | 28.2 | 22 | B |
| TRP NE1 | 735 | 203.8 | 110.7 | 28.5 | 21 | B |
| TRP CZ2 | 735 | 205.1 | 111.7 | 30.5 | 22 | B |
| TRP CZ3 | 735 | 205.7 | 110.0 | 32.1 | 21 | B |
| TRP CH2 | 735 | 205.7 | 111.3 | 31.6 | 21 | B |
| TRP C | 735 | 201.9 | 107.2 | 31.3 | 26 | B |
| TRP O | 735 | 202.3 | 106.3 | 32.1 | 27 | B |
| GLU N | 736 | 201.4 | 108.3 | 31.6 | 26 | B |
| GLU CA | 736 | 201.3 | 108.8 | 33.0 | 25 | B |
| GLU CB | 736 | 201.0 | 110.3 | 33.0 | 25 | B |
| GLU CG | 736 | 202.1 | 111.2 | 32.5 | 25 | B |
| GLU CD | 736 | 201.8 | 112.7 | 32.5 | 25 | B |
| GLU OE1 | 736 | 201.4 | 113.2 | 31.4 | 24 | B |
| GLU OE2 | 736 | 201.8 | 113.3 | 33.6 | 25 | B |
| GLU C | 736 | 200.2 | 108.1 | 33.8 | 25 | B |
| GLU O | 736 | 200.3 | 108.1 | 35.0 | 29 | B |
| GLY N | 737 | 199.1 | 107.7 | 33.1 | 23 | B |
| GLY CA | 737 | 198.0 | 107.1 | 33.9 | 21 | B |
| GLY C | 737 | 196.8 | 108.0 | 33.8 | 21 | B |
| GLY O | 737 | 195.7 | 107.6 | 33.9 | 22 | B |
| GLY N | 738 | 197.1 | 109.3 | 33.5 | 20 | B |
| GLY CA | 738 | 196.0 | 110.3 | 33.4 | 19 | B |
| GLY C | 738 | 195.5 | 110.4 | 32.0 | 18 | B |
| GLY O | 738 | 196.0 | 109.6 | 31.1 | 18 | B |
| ILE N | 739 | 194.6 | 111.3 | 31.8 | 17 | B |
| ILE CA | 739 | 194.1 | 111.6 | 30.5 | 17 | B |
| ILE CB | 739 | 192.5 | 111.4 | 30.5 | 16 | B |
| ILE CG2 | 739 | 191.9 | 111.8 | 29.2 | 16 | B |
| ILE CG1 | 739 | 192.2 | 109.9 | 30.9 | 16 | B |
| ILE CD1 | 739 | 190.8 | 109.6 | 31.0 | 15 | B |
| ILE C | 739 | 194.4 | 113.0 | 30.0 | 17 | B |
| ILE O | 739 | 194.3 | 113.9 | 30.8 | 18 | B |
| GLY N | 740 | 194.8 | 113.1 | 28.7 | 17 | B |
| GLY CA | 740 | 195.0 | 114.4 | 28.1 | 15 | B |
| GLY C | 740 | 193.9 | 114.9 | 27.4 | 16 | B |
| GLY O | 740 | 192.8 | 114.2 | 27.2 | 16 | B |
| GLY N | 741 | 194.0 | 116.1 | 26.8 | 17 | B |
| GLY CA | 741 | 192.9 | 116.7 | 26.0 | 19 | B |
| GLY C | 741 | 192.6 | 116.0 | 24.7 | 19 | B |
| GLY O | 741 | 191.4 | 115.9 | 24.3 | 20 | B |
| VAL N | 742 | 193.6 | 115.4 | 24.1 | 20 | B |
| VAL CA | 742 | 193.5 | 114.7 | 22.8 | 20 | B |
| VAL CB | 742 | 193.8 | 115.6 | 21.6 | 19 | B |
| VAL CG1 | 742 | 192.7 | 116.6 | 21.5 | 18 | B |
| VAL CG2 | 742 | 195.2 | 116.2 | 21.7 | 19 | B |
| VAL C | 742 | 194.6 | 113.6 | 22.9 | 20 | B |
| VAL O | 742 | 195.5 | 113.8 | 23.7 | 21 | B |
| PRO N | 743 | 194.5 | 112.6 | 22.1 | 20 | B |
| PRO CD | 743 | 193.5 | 112.1 | 21.2 | 19 | B |
| PRO CA | 743 | 195.6 | 111.6 | 22.2 | 20 | B |
| PRO CB | 743 | 195.2 | 110.6 | 21.1 | 19 | B |
| PRO CG | 743 | 193.7 | 110.6 | 21.2 | 19 | B |
| PRO C | 743 | 197.0 | 112.1 | 22.0 | 21 | B |
| PRO O | 743 | 197.2 | 113.0 | 21.1 | 23 | B |
| GLY N | 744 | 197.9 | 111.7 | 22.9 | 21 | B |
| GLY CA | 744 | 199.3 | 112.2 | 22.8 | 21 | B |
| GLY C | 744 | 199.6 | 113.3 | 23.8 | 22 | B |
| GLY O | 744 | 200.8 | 113.5 | 24.1 | 22 | B |
| MET N | 745 | 198.6 | 114.0 | 24.3 | 21 | B |
| MET CA | 745 | 198.9 | 115.1 | 25.2 | 21 | B |
| MET CB | 745 | 197.8 | 116.2 | 25.1 | 21 | B |
| MET CG | 745 | 198.2 | 117.2 | 24.0 | 19 | B |
| MET SD | 745 | 199.8 | 117.9 | 24.3 | 21 | B |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| MET CE | 745 | 199.4 | 119.1 | 25.4 | 21 | B |
| MET C | 745 | 199.1 | 114.7 | 26.7 | 22 | B |
| MET O | 745 | 198.7 | 113.6 | 27.1 | 22 | B |
| GLU N | 746 | 199.7 | 115.6 | 27.4 | 22 | B |
| GLU CA | 746 | 200.0 | 115.4 | 28.8 | 22 | B |
| GLU CB | 746 | 200.8 | 116.7 | 29.3 | 22 | B |
| GLU CG | 746 | 201.2 | 116.6 | 30.7 | 25 | B |
| GLU CD | 746 | 201.8 | 117.9 | 31.2 | 26 | B |
| GLU OE1 | 746 | 201.6 | 118.9 | 30.5 | 27 | B |
| GLU OE2 | 746 | 202.4 | 117.9 | 32.3 | 27 | B |
| GLU C | 746 | 198.8 | 115.2 | 29.6 | 22 | B |
| GLU O | 746 | 197.7 | 115.9 | 29.4 | 24 | B |
| ALA N | 747 | 198.8 | 114.4 | 30.6 | 22 | B |
| ALA CA | 747 | 197.7 | 114.1 | 31.5 | 22 | B |
| ALA CB | 747 | 198.0 | 112.9 | 32.4 | 21 | B |
| ALA C | 747 | 197.3 | 115.3 | 32.3 | 21 | B |
| ALA O | 747 | 198.2 | 115.9 | 33.0 | 23 | B |
| HIS N | 748 | 196.0 | 115.7 | 32.4 | 21 | B |
| HIS CA | 748 | 195.5 | 116.9 | 33.1 | 20 | B |
| HIS CB | 748 | 195.3 | 118.0 | 32.2 | 17 | B |
| HIS CG | 748 | 195.3 | 119.4 | 32.8 | 15 | B |
| HIS CD2 | 748 | 196.3 | 120.3 | 33.0 | 14 | B |
| HIS ND1 | 748 | 194.2 | 119.9 | 33.4 | 15 | B |
| HIS CE1 | 748 | 194.5 | 121.1 | 34.0 | 14 | B |
| HIS NE2 | 748 | 195.8 | 121.3 | 33.7 | 14 | B |
| HIS C | 748 | 194.3 | 116.5 | 33.9 | 21 | B |
| HIS O | 748 | 193.5 | 115.7 | 33.5 | 22 | B |
| GLY N | 749 | 194.1 | 117.1 | 35.1 | 22 | B |
| GLY CA | 749 | 192.9 | 116.9 | 35.9 | 20 | B |
| GLY C | 749 | 191.6 | 117.3 | 35.2 | 20 | B |
| GLY O | 749 | 190.6 | 116.6 | 35.3 | 23 | B |
| GLY N | 750 | 191.5 | 118.4 | 34.6 | 20 | B |
| GLY CA | 750 | 190.3 | 118.9 | 34.0 | 18 | B |
| GLY C | 750 | 189.9 | 117.9 | 32.9 | 19 | B |
| GLY O | 750 | 188.7 | 117.6 | 32.7 | 20 | B |
| TYR N | 751 | 190.8 | 117.4 | 32.1 | 18 | B |
| TYR CA | 751 | 190.6 | 116.5 | 31.0 | 17 | B |
| TYR CB | 751 | 191.7 | 116.5 | 30.0 | 14 | B |
| TYR CG | 751 | 191.8 | 117.7 | 29.2 | 12 | B |
| TYR CD1 | 751 | 193.0 | 118.4 | 29.0 | 12 | B |
| TYR CE1 | 751 | 193.1 | 119.6 | 28.3 | 13 | B |
| TYR CD2 | 751 | 190.7 | 118.3 | 28.6 | 12 | B |
| TYR CE2 | 751 | 190.7 | 119.5 | 27.9 | 12 | B |
| TYR CZ | 751 | 191.9 | 120.1 | 27.8 | 13 | B |
| TYR OH | 751 | 192.0 | 121.3 | 27.1 | 15 | B |
| TYR C | 751 | 190.3 | 115.1 | 31.5 | 18 | B |
| TYR O | 751 | 189.5 | 114.4 | 31.0 | 18 | B |
| THR N | 752 | 191.1 | 114.7 | 32.6 | 18 | B |
| THR CA | 752 | 190.9 | 113.4 | 33.2 | 19 | B |
| THR CB | 752 | 191.9 | 113.1 | 34.2 | 19 | B |
| THR OG1 | 752 | 193.2 | 113.3 | 33.6 | 18 | B |
| THR CG2 | 752 | 191.8 | 111.6 | 34.7 | 19 | B |
| THR C | 752 | 189.5 | 113.2 | 33.8 | 21 | B |
| THR O | 752 | 188.9 | 112.1 | 33.8 | 22 | B |
| PHE N | 753 | 188.9 | 114.3 | 34.3 | 21 | B |
| PHE CA | 753 | 187.6 | 114.2 | 34.9 | 20 | B |
| PHE CB | 753 | 187.3 | 115.5 | 35.7 | 18 | B |
| PHE CG | 753 | 185.9 | 115.5 | 36.2 | 18 | B |
| PHE CD1 | 753 | 185.5 | 114.7 | 37.3 | 17 | B |
| PHE CD2 | 753 | 184.9 | 116.1 | 35.5 | 17 | B |
| PHE CE1 | 753 | 184.1 | 114.6 | 37.6 | 17 | B |
| PHE CE2 | 753 | 183.6 | 116.0 | 35.8 | 18 | B |
| PHE CZ | 753 | 183.2 | 115.2 | 36.9 | 18 | B |
| PHE C | 753 | 186.6 | 114.1 | 33.7 | 21 | B |
| PHE O | 753 | 185.7 | 113.3 | 33.8 | 22 | B |
| CYS N | 754 | 186.8 | 114.9 | 32.7 | 22 | B |
| CYS CA | 754 | 185.9 | 114.8 | 31.5 | 23 | B |
| CYS CB | 754 | 186.3 | 115.8 | 30.4 | 22 | B |
| CYS SG | 754 | 186.0 | 117.5 | 30.9 | 21 | B |
| CYS C | 754 | 186.0 | 113.4 | 30.9 | 23 | B |
| CYS O | 754 | 184.9 | 112.8 | 30.6 | 22 | B |
| GLY N | 755 | 187.2 | 112.8 | 30.8 | 23 | B |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| GLY CA | 755 | 187.4 | 111.5 | 30.3 | 24 | B |
| GLY C | 755 | 186.7 | 110.4 | 31.1 | 26 | B |
| GLY O | 755 | 185.8 | 109.7 | 30.5 | 26 | B |
| LEU N | 756 | 187.1 | 110.3 | 32.3 | 26 | B |
| LEU CA | 756 | 186.5 | 109.3 | 33.2 | 26 | B |
| LEU CB | 756 | 187.2 | 109.2 | 34.5 | 25 | B |
| LEU CG | 756 | 186.7 | 108.1 | 35.5 | 25 | B |
| LEU CD1 | 756 | 186.8 | 106.7 | 34.8 | 25 | B |
| LEU CD2 | 756 | 187.5 | 108.1 | 36.7 | 24 | B |
| LEU C | 756 | 185.0 | 109.4 | 33.4 | 27 | B |
| LEU O | 756 | 184.2 | 108.5 | 33.1 | 28 | B |
| ALA N | 757 | 184.5 | 110.6 | 33.7 | 27 | B |
| ALA CA | 757 | 183.1 | 110.8 | 33.9 | 25 | B |
| ALA CB | 757 | 182.8 | 112.3 | 34.4 | 24 | B |
| ALA C | 757 | 182.3 | 110.5 | 32.6 | 25 | B |
| ALA O | 757 | 181.1 | 110.0 | 32.7 | 25 | B |
| ALA N | 758 | 182.8 | 110.8 | 31.5 | 26 | B |
| ALA CA | 758 | 182.2 | 110.5 | 30.2 | 26 | B |
| ALA CB | 758 | 182.9 | 111.1 | 29.1 | 25 | B |
| ALA C | 758 | 182.0 | 109.0 | 30.0 | 26 | B |
| ALA O | 758 | 181.0 | 108.5 | 29.6 | 27 | B |
| LEU N | 759 | 183.1 | 108.3 | 30.4 | 27 | B |
| LEU CA | 759 | 183.1 | 106.8 | 30.3 | 27 | B |
| LEU CB | 759 | 184.5 | 106.2 | 30.5 | 25 | B |
| LEU CG | 759 | 185.4 | 106.5 | 29.3 | 25 | B |
| LEU CD1 | 759 | 186.8 | 105.9 | 29.5 | 24 | B |
| LEU CD2 | 759 | 184.8 | 105.9 | 28.0 | 24 | B |
| LEU C | 759 | 182.0 | 106.2 | 31.3 | 28 | B |
| LEU O | 759 | 181.3 | 105.3 | 30.9 | 28 | B |
| VAL N | 760 | 181.9 | 106.8 | 32.4 | 28 | B |
| VAL CA | 760 | 181.0 | 106.3 | 33.4 | 27 | B |
| VAL CB | 760 | 181.1 | 107.1 | 34.7 | 27 | B |
| VAL CG1 | 760 | 180.0 | 106.9 | 35.7 | 27 | B |
| VAL CG2 | 760 | 182.4 | 106.7 | 35.5 | 27 | B |
| VAL C | 760 | 179.6 | 106.5 | 32.9 | 28 | B |
| VAL O | 760 | 178.8 | 105.6 | 33.0 | 30 | B |
| ILE N | 761 | 179.3 | 107.6 | 32.2 | 28 | B |
| ILE CA | 761 | 178.0 | 107.8 | 31.7 | 28 | B |
| ILE CB | 761 | 177.9 | 109.3 | 31.1 | 27 | B |
| ILE CG2 | 761 | 176.5 | 109.4 | 30.5 | 27 | B |
| ILE CG1 | 761 | 178.1 | 110.3 | 32.1 | 27 | B |
| ILE CD1 | 761 | 178.0 | 111.8 | 31.7 | 27 | B |
| ILE C | 761 | 177.8 | 106.8 | 30.6 | 29 | B |
| ILE O | 761 | 176.7 | 106.3 | 30.4 | 29 | B |
| LEU N | 762 | 178.8 | 106.5 | 29.8 | 31 | B |
| LEU CA | 762 | 178.7 | 105.5 | 28.7 | 32 | B |
| LEU CB | 762 | 179.8 | 105.8 | 27.7 | 30 | B |
| LEU CG | 762 | 179.6 | 107.1 | 26.9 | 29 | B |
| LEU CD1 | 762 | 180.7 | 107.2 | 25.9 | 29 | B |
| LEU CD2 | 762 | 178.3 | 107.2 | 26.3 | 28 | B |
| LEU C | 762 | 178.9 | 104.1 | 29.2 | 33 | B |
| LEU O | 762 | 178.7 | 103.1 | 28.5 | 33 | B |
| LYS N | 763 | 179.1 | 103.9 | 30.5 | 35 | B |
| LYS CA | 763 | 179.3 | 102.6 | 31.2 | 37 | B |
| LYS CB | 763 | 178.0 | 101.8 | 31.0 | 39 | B |
| LYS CG | 763 | 176.8 | 102.4 | 31.5 | 43 | B |
| LYS CD | 763 | 175.6 | 102.0 | 30.7 | 46 | B |
| LYS CE | 763 | 174.2 | 102.4 | 31.2 | 47 | B |
| LYS NZ | 763 | 173.1 | 101.9 | 30.4 | 48 | B |
| LYS C | 763 | 180.5 | 101.9 | 30.5 | 37 | B |
| LYS O | 763 | 180.4 | 100.7 | 30.4 | 38 | B |
| LYS N | 764 | 181.5 | 102.6 | 30.2 | 36 | B |
| LYS CA | 764 | 182.7 | 102.1 | 29.6 | 37 | B |
| LYS CB | 764 | 182.9 | 102.7 | 28.2 | 37 | B |
| LYS CG | 764 | 181.9 | 102.4 | 27.2 | 38 | B |
| LYS CD | 764 | 181.7 | 100.9 | 27.0 | 39 | B |
| LYS CE | 764 | 180.7 | 100.7 | 25.9 | 41 | B |
| LYS NZ | 764 | 179.7 | 101.7 | 26.0 | 43 | B |
| LYS C | 764 | 184.0 | 102.3 | 30.3 | 37 | B |
| LYS O | 764 | 185.1 | 102.2 | 29.7 | 37 | B |
| GLU N | 765 | 183.9 | 102.7 | 31.6 | 39 | B |
| GLU CA | 765 | 185.2 | 102.9 | 32.4 | 41 | B |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| GLU CB | 765 | 184.9 | 103.1 | 33.9 | 41 | B |
| GLU CG | 765 | 183.6 | 103.7 | 34.2 | 42 | B |
| GLU CD | 765 | 182.6 | 102.6 | 34.4 | 42 | B |
| GLU OE1 | 765 | 182.7 | 101.8 | 35.4 | 44 | B |
| GLU OE2 | 765 | 181.7 | 102.5 | 33.5 | 42 | B |
| GLU C | 765 | 186.2 | 101.9 | 32.2 | 42 | B |
| GLU O | 765 | 187.4 | 102.2 | 32.3 | 42 | B |
| ARG N | 766 | 185.8 | 100.6 | 32.0 | 43 | B |
| ARG CA | 766 | 186.7 | 99.5 | 31.8 | 45 | B |
| ARG CB | 766 | 185.9 | 98.2 | 31.6 | 48 | B |
| ARG CG | 766 | 185.5 | 97.5 | 32.9 | 53 | B |
| ARG CD | 766 | 184.1 | 98.0 | 33.4 | 57 | B |
| ARG NE | 766 | 184.1 | 98.3 | 34.8 | 60 | B |
| ARG CZ | 766 | 183.0 | 98.8 | 35.4 | 61 | B |
| ARG NH1 | 766 | 183.1 | 99.0 | 36.7 | 62 | B |
| ARG NH2 | 766 | 181.9 | 99.1 | 34.8 | 61 | B |
| ARG C | 766 | 187.6 | 99.7 | 30.6 | 43 | B |
| ARG O | 766 | 188.6 | 99.0 | 30.5 | 43 | B |
| SER N | 767 | 187.3 | 100.7 | 29.7 | 42 | B |
| SER CA | 767 | 188.2 | 101.0 | 28.5 | 42 | B |
| SER CB | 767 | 187.4 | 101.9 | 27.6 | 42 | B |
| SER OG | 767 | 186.1 | 101.4 | 27.3 | 44 | B |
| SER C | 767 | 189.5 | 101.6 | 28.9 | 41 | B |
| SER O | 767 | 190.3 | 102.0 | 28.0 | 41 | B |
| LEU N | 768 | 189.7 | 101.9 | 30.2 | 39 | B |
| LEU CA | 768 | 190.9 | 102.6 | 30.7 | 38 | B |
| LEU CB | 768 | 190.5 | 103.9 | 31.4 | 38 | B |
| LEU CG | 768 | 189.7 | 105.0 | 30.8 | 39 | B |
| LEU CD1 | 768 | 189.3 | 106.0 | 31.8 | 39 | B |
| LEU CD2 | 768 | 190.5 | 105.7 | 29.7 | 38 | B |
| LEU C | 768 | 191.6 | 101.7 | 31.6 | 38 | B |
| LEU O | 768 | 191.1 | 100.8 | 32.2 | 39 | B |
| ASN N | 769 | 192.9 | 102.0 | 31.8 | 35 | B |
| ASN CA | 769 | 193.7 | 101.2 | 32.8 | 34 | B |
| ASN CB | 769 | 195.2 | 101.3 | 32.5 | 34 | B |
| ASN CG | 769 | 196.0 | 100.6 | 33.5 | 36 | B |
| ASN OD1 | 769 | 195.5 | 100.4 | 34.6 | 36 | B |
| ASN ND2 | 769 | 197.2 | 100.2 | 33.1 | 37 | B |
| ASN C | 769 | 193.4 | 102.0 | 34.1 | 34 | B |
| ASN O | 769 | 194.0 | 103.0 | 34.4 | 34 | B |
| LEU N | 770 | 192.4 | 101.5 | 34.8 | 33 | B |
| LEU CA | 770 | 191.9 | 102.1 | 36.0 | 32 | B |
| LEU CB | 770 | 190.6 | 101.5 | 36.5 | 30 | B |
| LEU CG | 770 | 189.4 | 101.6 | 35.6 | 29 | B |
| LEU CD1 | 770 | 188.2 | 101.0 | 36.2 | 29 | B |
| LEU CD2 | 770 | 189.2 | 103.1 | 35.1 | 29 | B |
| LEU C | 770 | 193.0 | 102.1 | 37.1 | 33 | B |
| LEU O | 770 | 193.0 | 102.9 | 38.1 | 34 | B |
| LYS N | 771 | 194.0 | 101.2 | 37.0 | 35 | B |
| LYS CA | 771 | 195.0 | 101.1 | 38.0 | 37 | B |
| LYS CB | 771 | 195.7 | 99.8 | 38.1 | 40 | B |
| LYS CG | 771 | 195.0 | 98.8 | 39.0 | 45 | B |
| LYS CD | 771 | 194.7 | 99.4 | 40.4 | 48 | B |
| LYS CE | 771 | 193.8 | 98.4 | 41.2 | 50 | B |
| LYS NZ | 771 | 192.4 | 98.2 | 40.8 | 51 | B |
| LYS C | 771 | 196.0 | 102.3 | 37.9 | 36 | B |
| LYS O | 771 | 196.3 | 103.0 | 38.9 | 36 | B |
| SER N | 772 | 196.5 | 102.5 | 36.7 | 35 | B |
| SER CA | 772 | 197.5 | 103.5 | 36.4 | 35 | B |
| SER CB | 772 | 196.0 | 103.4 | 35.0 | 35 | B |
| SER OG | 772 | 197.0 | 103.4 | 34.0 | 36 | B |
| SER C | 772 | 196.8 | 104.8 | 36.6 | 34 | B |
| SER O | 772 | 197.4 | 105.8 | 37.0 | 35 | B |
| LEU N | 773 | 195.5 | 104.9 | 36.3 | 33 | B |
| LEU CA | 773 | 194.7 | 106.1 | 36.4 | 34 | B |
| LEU CB | 773 | 193.4 | 105.9 | 35.7 | 33 | B |
| LEU CG | 773 | 192.3 | 107.0 | 36.0 | 33 | B |
| LEU CD1 | 773 | 192.8 | 108.4 | 36.0 | 34 | B |
| LEU CD2 | 773 | 191.1 | 106.8 | 35.0 | 33 | B |
| LEU C | 773 | 194.6 | 106.4 | 37.9 | 35 | B |
| LEU O | 773 | 194.9 | 107.5 | 38.3 | 36 | B |
| LEU N | 774 | 194.3 | 105.3 | 38.7 | 36 | B |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| LEU CA | 774 | 194.1 | 105.5 | 40.1 | 35 | B |
| LEU CB | 774 | 193.8 | 104.2 | 40.8 | 35 | B |
| LEU CG | 774 | 193.8 | 104.2 | 42.3 | 34 | B |
| LEU CD1 | 774 | 192.7 | 105.2 | 42.8 | 33 | B |
| LEU CD2 | 774 | 193.5 | 102.8 | 42.9 | 34 | B |
| LEU C | 774 | 195.4 | 106.0 | 40.7 | 34 | B |
| LEU O | 774 | 195.4 | 107.0 | 41.5 | 35 | B |
| GLN N | 775 | 196.5 | 105.5 | 40.3 | 35 | B |
| GLN CA | 775 | 197.8 | 105.8 | 40.8 | 35 | B |
| GLN CB | 775 | 198.9 | 104.9 | 40.3 | 37 | B |
| GLN CG | 775 | 200.3 | 105.2 | 40.7 | 43 | B |
| GLN CD | 775 | 201.3 | 104.1 | 40.3 | 47 | B |
| GLN OE1 | 775 | 202.2 | 103.8 | 41.1 | 49 | B |
| GLN NE2 | 775 | 201.0 | 103.5 | 39.1 | 48 | B |
| GLN C | 775 | 198.2 | 107.3 | 40.5 | 35 | B |
| GLN O | 775 | 198.8 | 108.0 | 41.3 | 35 | B |
| TRP N | 776 | 197.9 | 107.7 | 39.3 | 33 | B |
| TRP CA | 776 | 198.2 | 109.1 | 38.8 | 30 | B |
| TRP CB | 776 | 198.0 | 109.2 | 37.3 | 27 | B |
| TRP CG | 776 | 198.2 | 110.6 | 36.8 | 24 | B |
| TRP CD2 | 776 | 197.1 | 111.5 | 36.5 | 23 | B |
| TRP CE2 | 776 | 197.7 | 112.7 | 36.0 | 22 | B |
| TRP CE3 | 776 | 195.7 | 111.5 | 36.8 | 24 | B |
| TRP CD1 | 776 | 199.3 | 111.1 | 36.4 | 23 | B |
| TRP NE1 | 776 | 199.1 | 112.4 | 35.9 | 23 | B |
| TRP CZ2 | 776 | 197.0 | 113.8 | 35.7 | 24 | B |
| TRP CZ3 | 776 | 195.0 | 112.6 | 36.4 | 24 | B |
| TRP CH2 | 776 | 195.6 | 113.8 | 35.9 | 24 | B |
| TRP C | 776 | 197.3 | 110.2 | 39.6 | 29 | B |
| TRP O | 776 | 197.9 | 111.1 | 40.1 | 29 | B |
| VAL N | 777 | 196.0 | 110.0 | 39.7 | 29 | B |
| VAL CA | 777 | 195.2 | 110.9 | 40.4 | 28 | B |
| VAL CB | 777 | 193.7 | 110.6 | 40.3 | 27 | B |
| VAL CG1 | 777 | 193.4 | 109.3 | 40.9 | 26 | B |
| VAL CG2 | 777 | 192.8 | 111.6 | 40.9 | 27 | B |
| VAL C | 777 | 195.6 | 111.1 | 41.8 | 30 | B |
| VAL O | 777 | 195.7 | 112.3 | 42.3 | 30 | B |
| THR N | 778 | 195.9 | 110.0 | 42.5 | 30 | B |
| THR CA | 778 | 196.3 | 110.1 | 43.9 | 29 | B |
| THR CB | 778 | 196.4 | 108.7 | 44.6 | 28 | B |
| THR OG1 | 778 | 197.3 | 107.9 | 43.9 | 28 | B |
| THR CG2 | 778 | 195.0 | 108.0 | 44.5 | 28 | B |
| THR C | 778 | 197.6 | 110.8 | 44.1 | 30 | B |
| THR O | 778 | 197.9 | 111.6 | 45.0 | 32 | B |
| SER N | 779 | 198.5 | 110.6 | 43.1 | 29 | B |
| SER CA | 779 | 199.8 | 111.3 | 43.1 | 28 | B |
| SER CB | 779 | 200.7 | 110.7 | 41.9 | 28 | B |
| SER OG | 779 | 201.0 | 109.4 | 42.1 | 30 | B |
| SER C | 779 | 199.7 | 112.8 | 42.9 | 28 | B |
| SER O | 779 | 200.6 | 113.5 | 43.1 | 29 | B |
| ARG N | 780 | 198.5 | 113.3 | 42.5 | 27 | B |
| ARG CA | 780 | 198.3 | 114.7 | 42.3 | 27 | B |
| ARG CB | 780 | 197.2 | 114.9 | 41.2 | 26 | B |
| ARG CG | 780 | 197.4 | 114.2 | 39.9 | 25 | B |
| ARG CD | 780 | 198.3 | 114.9 | 38.9 | 22 | B |
| ARG NE | 780 | 199.7 | 115.0 | 39.4 | 21 | B |
| ARG CZ | 780 | 200.5 | 114.0 | 39.4 | 21 | B |
| ARG NH1 | 780 | 200.1 | 112.8 | 39.0 | 22 | B |
| ARG NH2 | 780 | 201.8 | 114.1 | 39.9 | 22 | B |
| ARG C | 780 | 198.0 | 115.5 | 43.5 | 29 | B |
| ARG O | 780 | 198.0 | 116.7 | 43.4 | 30 | B |
| GLN N | 781 | 197.7 | 114.8 | 44.6 | 31 | B |
| GLN CA | 781 | 197.4 | 115.6 | 45.8 | 32 | B |
| GLN CB | 781 | 196.7 | 114.7 | 46.9 | 33 | B |
| GLN CG | 781 | 196.1 | 115.6 | 48.0 | 33 | B |
| GLN CD | 781 | 195.1 | 114.8 | 48.9 | 34 | B |
| GLN OE1 | 781 | 195.0 | 113.6 | 48.9 | 35 | B |
| GLN NE2 | 781 | 194.2 | 115.6 | 49.5 | 33 | B |
| GLN C | 781 | 198.8 | 116.0 | 46.4 | 32 | B |
| GLN O | 781 | 199.7 | 115.2 | 46.4 | 32 | B |
| MET N | 782 | 198.8 | 117.3 | 46.7 | 32 | B |
| MET CA | 782 | 200.1 | 117.9 | 47.2 | 32 | B |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| MET CB | 782 | 200.1 | 119.4 | 47.0 | 31 | B |
| MET CG | 782 | 199.8 | 119.9 | 45.6 | 31 | B |
| MET SD | 782 | 200.9 | 119.1 | 44.4 | 30 | B |
| MET CE | 782 | 202.4 | 120.0 | 44.6 | 29 | B |
| MET C | 782 | 200.3 | 117.6 | 48.7 | 33 | B |
| MET O | 782 | 199.4 | 118.0 | 49.6 | 33 | B |
| ARG N | 783 | 201.3 | 116.8 | 49.0 | 35 | B |
| ARG CA | 783 | 201.7 | 116.4 | 50.4 | 37 | B |
| ARG CB | 783 | 203.0 | 115.6 | 50.4 | 37 | B |
| ARG CG | 783 | 204.1 | 116.4 | 49.9 | 40 | B |
| ARG CD | 783 | 205.2 | 115.6 | 49.2 | 42 | B |
| ARG NE | 783 | 205.6 | 114.5 | 50.1 | 45 | B |
| ARG CZ | 783 | 205.9 | 113.3 | 49.7 | 47 | B |
| ARG NH1 | 783 | 206.0 | 113.0 | 48.4 | 47 | B |
| ARG NH2 | 783 | 206.3 | 112.4 | 50.6 | 47 | B |
| ARG C | 783 | 201.8 | 117.5 | 51.4 | 37 | B |
| ARG O | 783 | 201.4 | 117.4 | 52.6 | 39 | B |
| PHE N | 784 | 202.2 | 118.7 | 51.0 | 37 | B |
| PHE CA | 784 | 202.3 | 119.8 | 51.8 | 35 | B |
| PHE CB | 784 | 203.6 | 120.7 | 51.5 | 36 | B |
| PHE CG | 784 | 203.8 | 121.8 | 52.5 | 36 | B |
| PHE CD1 | 784 | 204.6 | 121.5 | 53.6 | 36 | B |
| PHE CD2 | 784 | 203.2 | 123.0 | 52.4 | 37 | B |
| PHE CE1 | 784 | 204.8 | 122.5 | 54.6 | 37 | B |
| PHE CE2 | 784 | 203.3 | 123.9 | 53.4 | 37 | B |
| PHE CZ | 784 | 204.1 | 123.7 | 54.5 | 37 | B |
| PHE C | 784 | 201.1 | 120.7 | 51.9 | 34 | B |
| PHE O | 784 | 200.5 | 120.9 | 52.9 | 36 | B |
| GLU N | 785 | 200.7 | 121.2 | 50.7 | 32 | B |
| GLU CA | 785 | 199.5 | 122.0 | 50.6 | 30 | B |
| GLU CB | 785 | 199.4 | 122.8 | 49.3 | 30 | B |
| GLU CG | 785 | 200.7 | 123.6 | 49.0 | 32 | B |
| GLU CD | 785 | 201.7 | 122.7 | 48.2 | 33 | B |
| GLU OE1 | 785 | 201.6 | 122.6 | 47.0 | 35 | B |
| GLU OE2 | 785 | 202.6 | 122.1 | 48.8 | 34 | B |
| GLU C | 785 | 198.2 | 121.3 | 50.9 | 30 | B |
| GLU O | 785 | 197.2 | 121.9 | 51.3 | 29 | B |
| GLY N | 786 | 198.2 | 120.0 | 50.6 | 29 | B |
| GLY CA | 786 | 197.0 | 119.2 | 50.7 | 29 | B |
| GLY C | 786 | 195.9 | 119.3 | 49.6 | 30 | B |
| GLY O | 786 | 195.0 | 118.5 | 49.5 | 29 | B |
| GLY N | 787 | 196.0 | 120.4 | 48.8 | 29 | B |
| GLY CA | 787 | 195.1 | 120.6 | 47.7 | 29 | B |
| GLY C | 787 | 195.7 | 119.8 | 46.5 | 28 | B |
| GLY O | 787 | 196.8 | 119.2 | 46.6 | 28 | B |
| PHE N | 788 | 195.0 | 119.8 | 45.4 | 28 | B |
| PHE CA | 788 | 195.4 | 119.0 | 44.2 | 26 | B |
| PHE CB | 788 | 194.3 | 118.3 | 43.6 | 25 | B |
| PHE CG | 788 | 194.0 | 116.9 | 44.3 | 26 | B |
| PHE CD1 | 788 | 193.0 | 116.9 | 45.3 | 26 | B |
| PHE CD2 | 788 | 194.5 | 115.8 | 43.9 | 26 | B |
| PHE CE1 | 788 | 192.7 | 115.7 | 45.9 | 25 | B |
| PHE CE2 | 788 | 194.2 | 114.5 | 44.5 | 25 | B |
| PHE CZ | 788 | 193.3 | 114.5 | 45.5 | 25 | B |
| PHE C | 788 | 196.1 | 119.9 | 43.1 | 25 | B |
| PHE O | 788 | 195.7 | 121.1 | 43.0 | 25 | B |
| GLN N | 789 | 197.0 | 119.3 | 42.4 | 25 | B |
| GLN CA | 789 | 197.7 | 120.0 | 41.3 | 25 | B |
| GLN CB | 789 | 199.2 | 119.7 | 41.2 | 24 | B |
| GLN CG | 789 | 199.5 | 118.2 | 40.9 | 24 | B |
| GLN CD | 789 | 201.0 | 117.9 | 41.0 | 24 | B |
| GLN OE1 | 789 | 201.4 | 116.8 | 40.8 | 25 | B |
| GLN NE2 | 789 | 201.8 | 118.9 | 41.2 | 26 | B |
| GLN C | 789 | 197.0 | 119.5 | 40.0 | 24 | B |
| GLN O | 789 | 196.5 | 118.4 | 39.9 | 25 | B |
| GLY N | 790 | 197.1 | 120.4 | 38.9 | 24 | B |
| GLY CA | 790 | 196.4 | 120.0 | 37.7 | 22 | B |
| GLY C | 790 | 197.1 | 118.9 | 36.9 | 21 | B |
| GLY O | 790 | 196.5 | 118.1 | 36.3 | 21 | B |
| ARG N | 791 | 198.5 | 118.9 | 37.0 | 21 | B |
| ARG CA | 791 | 199.2 | 118.0 | 36.3 | 22 | B |
| ARG CB | 791 | 199.4 | 118.3 | 34.8 | 21 | B |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| ARG CG | 791 | 199.5 | 119.8 | 34.5 | 21 | B |
| ARG CD | 791 | 199.6 | 120.2 | 33.0 | 20 | B |
| ARG NE | 791 | 199.5 | 121.7 | 32.9 | 19 | B |
| ARG CZ | 791 | 200.0 | 122.3 | 31.8 | 19 | B |
| ARG NH1 | 791 | 200.7 | 121.7 | 30.9 | 19 | B |
| ARG NH2 | 791 | 199.9 | 123.7 | 31.8 | 18 | B |
| ARG C | 791 | 200.6 | 117.9 | 37.0 | 23 | B |
| ARG O | 791 | 201.0 | 118.8 | 37.7 | 24 | B |
| CYS N | 792 | 201.3 | 116.8 | 36.9 | 23 | B |
| CYS CA | 792 | 202.5 | 116.6 | 37.5 | 24 | B |
| CYS CB | 792 | 203.2 | 115.3 | 37.0 | 22 | B |
| CYS SG | 792 | 204.7 | 114.9 | 37.8 | 25 | B |
| CYS C | 792 | 203.5 | 117.7 | 37.4 | 25 | B |
| CYS O | 792 | 203.7 | 118.3 | 36.3 | 27 | B |
| ASN N | 793 | 204.1 | 118.1 | 38.5 | 26 | B |
| ASN CA | 793 | 205.1 | 119.2 | 38.5 | 27 | B |
| ASN CB | 793 | 206.3 | 118.8 | 37.7 | 27 | B |
| ASN CG | 793 | 207.5 | 118.2 | 38.5 | 27 | B |
| ASN OD1 | 793 | 207.7 | 118.6 | 39.6 | 28 | B |
| ASN ND2 | 793 | 208.2 | 117.3 | 37.9 | 26 | B |
| ASN C | 793 | 204.6 | 120.6 | 38.2 | 26 | B |
| ASN O | 793 | 205.3 | 121.4 | 37.7 | 26 | B |
| LYS N | 794 | 203.3 | 120.7 | 38.5 | 26 | B |
| LYS CA | 794 | 202.6 | 122.0 | 38.3 | 25 | B |
| LYS CB | 794 | 201.4 | 121.8 | 37.4 | 25 | B |
| LYS CG | 794 | 201.2 | 122.8 | 36.4 | 26 | B |
| LYS CD | 794 | 202.3 | 122.9 | 35.4 | 25 | B |
| LYS CE | 794 | 201.9 | 123.9 | 34.3 | 24 | B |
| LYS NZ | 794 | 201.5 | 125.2 | 34.8 | 22 | B |
| LYS C | 794 | 202.2 | 122.5 | 39.7 | 26 | B |
| LYS O | 794 | 202.6 | 121.9 | 40.7 | 25 | B |
| LEU N | 795 | 201.4 | 123.5 | 39.8 | 26 | B |
| LEU CA | 795 | 201.0 | 124.1 | 41.1 | 25 | B |
| LEU CB | 795 | 201.2 | 125.6 | 41.2 | 23 | B |
| LEU CG | 795 | 202.6 | 126.2 | 40.8 | 22 | B |
| LEU CD1 | 795 | 202.5 | 127.7 | 40.9 | 21 | B |
| LEU CD2 | 795 | 203.6 | 125.6 | 41.7 | 21 | B |
| LEU C | 795 | 199.6 | 123.7 | 41.6 | 25 | B |
| LEU O | 795 | 198.8 | 123.5 | 40.8 | 26 | B |
| VAL N | 796 | 199.4 | 123.8 | 42.9 | 26 | B |
| VAL CA | 796 | 198.1 | 123.5 | 43.5 | 26 | B |
| VAL CB | 796 | 198.0 | 123.7 | 45.0 | 27 | B |
| VAL CG1 | 796 | 197.4 | 122.5 | 45.7 | 28 | B |
| VAL CG2 | 796 | 199.3 | 124.2 | 45.5 | 28 | B |
| VAL C | 796 | 197.1 | 124.6 | 43.0 | 25 | B |
| VAL O | 796 | 197.5 | 125.7 | 42.6 | 27 | B |
| ASP N | 797 | 195.8 | 124.2 | 43.0 | 24 | B |
| ASP CA | 797 | 194.8 | 125.2 | 42.6 | 23 | B |
| ASP CB | 797 | 194.7 | 125.3 | 41.0 | 21 | B |
| ASP CG | 797 | 193.6 | 126.1 | 40.5 | 20 | B |
| ASP OD1 | 797 | 192.6 | 126.5 | 41.2 | 22 | B |
| ASP OD2 | 797 | 193.6 | 126.4 | 39.3 | 20 | B |
| ASP C | 797 | 193.5 | 124.6 | 43.1 | 23 | B |
| ASP O | 797 | 193.1 | 123.5 | 42.9 | 25 | B |
| GLY N | 798 | 192.8 | 125.5 | 43.8 | 24 | B |
| GLY CA | 798 | 191.5 | 125.1 | 44.4 | 24 | B |
| GLY C | 798 | 190.5 | 124.4 | 43.6 | 25 | B |
| GLY O | 798 | 189.7 | 123.5 | 44.1 | 26 | B |
| CYS N | 799 | 190.4 | 124.7 | 42.3 | 25 | B |
| CYS CA | 799 | 189.3 | 124.1 | 41.4 | 24 | B |
| CYS CB | 799 | 189.2 | 124.8 | 40.1 | 25 | B |
| CYS SG | 799 | 190.6 | 124.9 | 39.0 | 26 | B |
| CYS C | 799 | 189.6 | 122.7 | 41.2 | 24 | B |
| CYS O | 799 | 188.7 | 121.9 | 40.9 | 24 | B |
| TYR N | 800 | 190.9 | 122.2 | 41.4 | 24 | B |
| TYR CA | 800 | 191.2 | 120.8 | 41.2 | 27 | B |
| TYR CB | 800 | 192.7 | 120.6 | 40.9 | 26 | B |
| TYR CG | 800 | 193.2 | 121.3 | 39.6 | 27 | B |
| TYR CD1 | 800 | 194.3 | 122.1 | 39.7 | 27 | B |
| TYR CE1 | 800 | 194.7 | 122.7 | 38.5 | 28 | B |
| TYR CD2 | 800 | 192.5 | 121.1 | 38.4 | 27 | B |
| TYR CE2 | 800 | 192.9 | 121.7 | 37.3 | 28 | B |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| TYR CZ | 800 | 194.0 | 122.6 | 37.3 | 29 | B |
| TYR OH | 800 | 194.4 | 123.2 | 36.2 | 29 | B |
| TYR C | 800 | 190.7 | 120.0 | 42.4 | 29 | B |
| TYR O | 800 | 190.9 | 118.8 | 42.4 | 30 | B |
| SER N | 801 | 190.2 | 120.7 | 43.4 | 30 | B |
| SER CA | 801 | 189.7 | 119.9 | 44.6 | 30 | B |
| SER CB | 801 | 189.2 | 121.0 | 45.6 | 31 | B |
| SER OG | 801 | 190.2 | 121.8 | 46.0 | 31 | B |
| SER C | 801 | 188.5 | 119.1 | 44.0 | 29 | B |
| SER O | 801 | 188.2 | 118.1 | 44.6 | 30 | B |
| PHE N | 802 | 187.9 | 119.6 | 42.9 | 29 | B |
| PHE CA | 802 | 186.8 | 118.9 | 42.3 | 28 | B |
| PHE CB | 802 | 185.7 | 119.7 | 41.8 | 28 | B |
| PHE CG | 802 | 184.6 | 118.9 | 41.1 | 29 | B |
| PHE CD1 | 802 | 183.6 | 118.2 | 41.9 | 28 | B |
| PHE CD2 | 802 | 184.6 | 118.8 | 39.7 | 29 | B |
| PHE CE1 | 802 | 182.7 | 117.4 | 41.2 | 29 | B |
| PHE CE2 | 802 | 183.7 | 118.0 | 39.1 | 29 | B |
| PHE CZ | 802 | 182.7 | 117.3 | 39.8 | 29 | B |
| PHE C | 802 | 187.3 | 118.0 | 41.1 | 28 | B |
| PHE O | 802 | 187.0 | 116.8 | 41.0 | 30 | B |
| TRP N | 803 | 187.9 | 118.7 | 40.1 | 26 | B |
| TRP CA | 803 | 188.4 | 118.0 | 38.9 | 24 | B |
| TRP CB | 803 | 189.2 | 119.0 | 38.0 | 20 | B |
| TRP CG | 803 | 188.4 | 120.2 | 37.6 | 17 | B |
| TRP CD2 | 803 | 187.1 | 120.2 | 36.9 | 17 | B |
| TRP CE2 | 803 | 186.8 | 121.5 | 36.6 | 16 | B |
| TRP CE3 | 803 | 186.2 | 119.2 | 36.4 | 18 | B |
| TRP CD1 | 803 | 188.8 | 121.4 | 37.7 | 16 | B |
| TRP NE1 | 803 | 187.8 | 122.3 | 37.1 | 17 | B |
| TRP CZ2 | 803 | 185.7 | 121.9 | 35.9 | 17 | B |
| TRP CZ3 | 803 | 185.1 | 119.6 | 35.8 | 18 | B |
| TRP CH2 | 803 | 184.8 | 121.0 | 35.5 | 18 | B |
| TRP C | 803 | 189.2 | 116.8 | 39.1 | 24 | B |
| TRP O | 803 | 189.1 | 115.8 | 38.4 | 26 | B |
| GLN N | 804 | 190.1 | 116.9 | 40.1 | 26 | B |
| GLN CA | 804 | 191.0 | 115.8 | 40.5 | 26 | B |
| GLN CB | 804 | 192.3 | 116.3 | 41.0 | 25 | B |
| GLN CG | 804 | 193.1 | 117.0 | 39.9 | 25 | B |
| GLN CD | 804 | 193.9 | 116.1 | 39.0 | 26 | B |
| GLN OE1 | 804 | 193.3 | 115.0 | 38.6 | 26 | B |
| GLN NE2 | 804 | 195.1 | 116.4 | 38.6 | 25 | B |
| GLN C | 804 | 190.3 | 114.9 | 41.6 | 27 | B |
| GLN O | 804 | 190.1 | 113.7 | 41.4 | 29 | B |
| ALA N | 805 | 190.0 | 115.5 | 42.8 | 28 | B |
| ALA CA | 805 | 189.5 | 114.7 | 43.9 | 28 | B |
| ALA CB | 805 | 189.3 | 115.5 | 45.1 | 28 | B |
| ALA C | 805 | 188.1 | 114.1 | 43.5 | 28 | B |
| ALA O | 805 | 187.8 | 113.0 | 44.0 | 30 | B |
| GLY N | 806 | 187.4 | 114.7 | 42.5 | 29 | B |
| GLY CA | 806 | 186.2 | 114.2 | 42.1 | 29 | B |
| GLY C | 806 | 186.3 | 112.8 | 41.4 | 31 | B |
| GLY O | 806 | 185.4 | 112.1 | 41.3 | 31 | B |
| LEU N | 807 | 187.6 | 112.6 | 40.9 | 31 | B |
| LEU CA | 807 | 187.9 | 111.3 | 40.3 | 33 | B |
| LEU CB | 807 | 189.3 | 111.3 | 39.6 | 33 | B |
| LEU CG | 807 | 189.5 | 112.1 | 38.3 | 33 | B |
| LEU CD1 | 807 | 191.0 | 112.3 | 38.1 | 33 | B |
| LEU CD2 | 807 | 188.9 | 111.3 | 37.2 | 33 | B |
| LEU C | 807 | 187.8 | 110.1 | 41.2 | 33 | B |
| LEU O | 807 | 187.4 | 109.0 | 40.7 | 33 | B |
| LEU N | 808 | 188.1 | 110.2 | 42.5 | 33 | B |
| LEU CA | 808 | 188.0 | 109.2 | 43.4 | 32 | B |
| LEU CB | 808 | 188.8 | 109.6 | 44.7 | 31 | B |
| LEU CG | 808 | 190.2 | 109.6 | 44.1 | 32 | B |
| LEU CD1 | 808 | 191.1 | 110.7 | 44.7 | 32 | B |
| LEU CD2 | 808 | 190.9 | 108.3 | 44.2 | 31 | B |
| LEU C | 808 | 186.6 | 108.6 | 43.6 | 32 | B |
| LEU O | 808 | 186.5 | 107.3 | 43.8 | 33 | B |
| PRO N | 809 | 185.6 | 109.4 | 43.7 | 31 | B |
| PRO CD | 809 | 185.5 | 110.8 | 44.0 | 31 | B |
| PRO CA | 809 | 184.3 | 108.8 | 43.9 | 31 | B |
| PRO CB | 809 | 183.3 | 110.0 | 44.0 | 31 | B |
| PRO CG | 809 | 184.2 | 111.0 | 44.6 | 31 | B |
| PRO C | 809 | 184.0 | 107.9 | 42.7 | 33 | B |
| PRO O | 809 | 183.6 | 106.8 | 42.8 | 33 | B |
| LEU N | 810 | 184.3 | 108.5 | 41.5 | 33 | B |
| LEU CA | 810 | 184.1 | 107.8 | 40.2 | 32 | B |
| LEU CB | 810 | 184.5 | 108.7 | 39.1 | 30 | B |
| LEU CG | 810 | 183.7 | 109.9 | 38.9 | 29 | B |
| LEU CD1 | 810 | 184.1 | 110.7 | 37.7 | 30 | B |
| LEU CD2 | 810 | 182.2 | 109.5 | 38.7 | 29 | B |
| LEU C | 810 | 184.8 | 106.5 | 40.1 | 33 | B |
| LEU O | 810 | 184.3 | 105.5 | 39.7 | 34 | B |
| LEU N | 811 | 186.1 | 106.5 | 40.6 | 35 | B |
| LEU CA | 811 | 186.9 | 105.3 | 40.6 | 37 | B |
| LEU CB | 811 | 188.4 | 105.6 | 40.8 | 34 | B |
| LEU CG | 811 | 189.2 | 106.1 | 39.6 | 32 | B |
| LEU CD1 | 811 | 190.5 | 106.6 | 40.1 | 30 | B |
| LEU CD2 | 811 | 189.3 | 105.0 | 38.6 | 30 | B |
| LEU C | 811 | 186.4 | 104.2 | 41.6 | 41 | B |
| LEU O | 811 | 186.7 | 103.1 | 41.5 | 42 | B |
| HIS N | 812 | 185.7 | 104.7 | 42.6 | 44 | B |
| HIS CA | 812 | 185.1 | 103.8 | 43.6 | 46 | B |
| HIS CB | 812 | 184.6 | 104.5 | 44.8 | 48 | B |
| HIS CG | 812 | 184.8 | 103.9 | 46.1 | 50 | B |
| HIS CD2 | 812 | 184.2 | 102.9 | 46.8 | 50 | B |
| HIS ND1 | 812 | 186.0 | 104.1 | 46.8 | 51 | B |
| HIS CE1 | 812 | 186.0 | 103.3 | 47.9 | 51 | B |
| HIS NE2 | 812 | 184.9 | 102.6 | 47.9 | 51 | B |
| HIS C | 812 | 184.1 | 103.0 | 42.9 | 47 | B |
| HIS O | 812 | 184.1 | 101.7 | 43.0 | 47 | B |
| ARG N | 813 | 183.1 | 103.6 | 42.3 | 48 | B |
| ARG CA | 813 | 182.0 | 103.0 | 41.5 | 49 | B |
| ARG CB | 813 | 181.3 | 104.0 | 40.6 | 52 | B |
| ARG CG | 813 | 180.3 | 104.9 | 41.3 | 57 | B |
| ARG CD | 813 | 179.9 | 106.1 | 40.4 | 60 | B |
| ARG NE | 813 | 178.8 | 106.9 | 41.0 | 63 | B |
| ARG CZ | 813 | 178.7 | 107.5 | 42.1 | 64 | B |
| ARG NH1 | 813 | 179.8 | 107.6 | 42.9 | 64 | B |
| ARG NH2 | 813 | 177.6 | 108.2 | 42.5 | 64 | B |
| ARG C | 813 | 182.6 | 101.9 | 40.6 | 48 | B |
| ARG O | 813 | 182.4 | 100.8 | 40.8 | 48 | B |
| ALA N | 814 | 183.5 | 102.4 | 39.7 | 47 | B |
| ALA CA | 814 | 184.1 | 101.5 | 38.8 | 46 | B |
| ALA CB | 814 | 185.1 | 102.3 | 37.9 | 45 | B |
| ALA C | 814 | 184.8 | 100.3 | 39.4 | 46 | B |
| ALA O | 814 | 184.4 | 99.2 | 39.1 | 47 | B |
| LEU N | 815 | 185.8 | 100.5 | 40.3 | 47 | B |
| LEU CA | 815 | 186.5 | 99.4 | 40.9 | 48 | B |
| LEU CB | 815 | 187.6 | 99.9 | 41.9 | 47 | B |
| LEU CG | 815 | 188.8 | 100.6 | 41.3 | 48 | B |
| LEU CD1 | 815 | 189.8 | 101.1 | 42.4 | 47 | B |
| LEU CD2 | 815 | 189.6 | 99.6 | 40.4 | 48 | B |
| LEU C | 815 | 185.6 | 98.5 | 41.6 | 48 | B |
| LEU O | 815 | 185.6 | 97.3 | 41.5 | 49 | B |
| HIS N | 816 | 184.6 | 99.1 | 42.4 | 49 | B |
| HIS CA | 816 | 183.7 | 98.3 | 43.1 | 51 | B |
| HIS CB | 816 | 182.9 | 99.2 | 44.1 | 53 | B |
| HIS CG | 816 | 181.8 | 98.5 | 44.8 | 55 | B |
| HIS CD2 | 816 | 181.9 | 97.6 | 45.8 | 56 | B |
| HIS ND1 | 816 | 180.5 | 98.7 | 44.5 | 56 | B |
| HIS CE1 | 816 | 179.8 | 97.9 | 45.3 | 57 | B |
| HIS NE2 | 816 | 180.6 | 97.2 | 46.0 | 57 | B |
| HIS C | 816 | 182.7 | 97.5 | 42.2 | 52 | B |
| HIS O | 816 | 182.2 | 96.5 | 42.7 | 52 | B |
| ALA N | 817 | 182.5 | 98.0 | 41.0 | 52 | B |
| ALA CA | 817 | 181.6 | 97.3 | 40.1 | 52 | B |
| ALA CB | 817 | 181.2 | 98.2 | 39.0 | 52 | B |
| ALA C | 817 | 182.3 | 96.1 | 39.6 | 53 | B |
| ALA O | 817 | 181.6 | 95.2 | 38.9 | 53 | B |
| GLN N | 818 | 183.6 | 96.0 | 39.8 | 54 | B |
| GLN CA | 818 | 184.3 | 94.8 | 39.4 | 55 | B |
| GLN CB | 818 | 185.7 | 95.2 | 38.8 | 55 | B |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| GLN CG | 818 | 185.5 | 96.0 | 37.5 | 56 | B |
| GLN CD | 818 | 186.7 | 96.8 | 37.2 | 57 | B |
| GLN OE1 | 818 | 187.8 | 96.5 | 37.5 | 57 | B |
| GLN NE2 | 818 | 186.4 | 97.9 | 36.5 | 57 | B |
| GLN C | 818 | 184.5 | 94.1 | 40.7 | 55 | B |
| GLN O | 818 | 185.4 | 93.2 | 40.9 | 55 | B |
| GLY N | 819 | 183.7 | 94.4 | 41.7 | 56 | B |
| GLY CA | 819 | 183.7 | 93.8 | 43.0 | 57 | B |
| GLY C | 819 | 185.1 | 93.9 | 43.6 | 57 | B |
| GLY O | 819 | 185.6 | 92.8 | 44.1 | 58 | B |
| ASP N | 820 | 185.7 | 95.0 | 43.6 | 57 | B |
| ASP CA | 820 | 187.1 | 95.1 | 44.2 | 57 | B |
| ASP CB | 820 | 187.7 | 96.5 | 44.0 | 56 | B |
| ASP CG | 820 | 189.2 | 96.5 | 44.1 | 56 | B |
| ASP OD1 | 820 | 189.9 | 96.7 | 43.0 | 56 | B |
| ASP OD2 | 820 | 189.8 | 96.2 | 45.2 | 54 | B |
| ASP C | 820 | 186.8 | 94.9 | 45.7 | 57 | B |
| ASP O | 820 | 185.8 | 95.5 | 46.3 | 57 | B |
| PRO N | 821 | 187.5 | 94.0 | 46.3 | 57 | B |
| PRO CD | 821 | 188.3 | 92.9 | 45.7 | 57 | B |
| PRO CA | 821 | 187.3 | 93.7 | 47.8 | 58 | B |
| PRO CB | 821 | 187.9 | 92.2 | 47.9 | 58 | B |
| PRO CG | 821 | 189.0 | 92.2 | 46.8 | 58 | B |
| PRO C | 821 | 188.1 | 94.6 | 48.7 | 58 | B |
| PRO O | 821 | 187.7 | 94.9 | 49.8 | 60 | B |
| ALA N | 822 | 189.3 | 95.2 | 48.2 | 57 | B |
| ALA CA | 822 | 190.1 | 96.1 | 49.0 | 55 | B |
| ALA CB | 822 | 191.5 | 96.1 | 48.3 | 54 | B |
| ALA C | 822 | 189.6 | 97.5 | 49.1 | 55 | B |
| ALA O | 822 | 190.2 | 98.3 | 49.8 | 55 | B |
| LEU N | 823 | 188.4 | 97.8 | 48.6 | 55 | B |
| LEU CA | 823 | 187.8 | 99.1 | 48.7 | 56 | B |
| LEU CB | 823 | 186.8 | 99.3 | 47.6 | 55 | B |
| LEU CG | 823 | 187.2 | 99.3 | 46.2 | 55 | B |
| LEU CD1 | 823 | 186.0 | 99.6 | 45.3 | 54 | B |
| LEU CD2 | 823 | 188.3 | 100.2 | 46.0 | 55 | B |
| LEU C | 823 | 187.2 | 99.5 | 50.0 | 57 | B |
| LEU O | 823 | 186.2 | 98.9 | 50.4 | 59 | B |
| SER N | 824 | 187.7 | 100.6 | 50.6 | 58 | B |
| SER CA | 824 | 187.2 | 101.1 | 51.9 | 58 | B |
| SER CB | 824 | 188.0 | 102.3 | 52.4 | 58 | B |
| SER OG | 824 | 187.5 | 102.9 | 53.6 | 57 | B |
| SER C | 824 | 185.7 | 101.4 | 51.9 | 59 | B |
| SER O | 824 | 185.2 | 101.7 | 50.9 | 58 | B |
| MET N | 825 | 185.1 | 101.2 | 53.0 | 60 | B |
| MET CA | 825 | 183.6 | 101.4 | 53.1 | 60 | B |
| MET CB | 825 | 182.9 | 100.2 | 53.8 | 63 | B |
| MET CG | 825 | 183.1 | 98.8 | 53.1 | 66 | B |
| MET SD | 825 | 182.2 | 98.5 | 51.5 | 69 | B |
| MET CE | 825 | 183.4 | 97.4 | 50.6 | 68 | B |
| MET C | 825 | 183.4 | 102.7 | 53.9 | 59 | B |
| MET O | 825 | 182.3 | 102.8 | 54.5 | 59 | B |
| SER N | 826 | 184.3 | 103.6 | 53.9 | 58 | B |
| SER CA | 826 | 184.2 | 104.9 | 54.6 | 56 | B |
| SER CB | 826 | 184.6 | 104.7 | 56.1 | 56 | B |
| SER OG | 826 | 186.0 | 104.4 | 56.2 | 56 | B |
| SER C | 826 | 184.8 | 106.1 | 54.0 | 55 | B |
| SER O | 826 | 184.3 | 107.2 | 54.1 | 54 | B |
| HIS N | 827 | 185.9 | 105.9 | 53.3 | 53 | B |
| HIS CA | 827 | 186.7 | 107.0 | 52.7 | 50 | B |
| HIS CB | 827 | 187.9 | 107.3 | 53.6 | 53 | B |
| HIS CG | 827 | 187.7 | 107.6 | 55.0 | 55 | B |
| HIS CD2 | 827 | 188.1 | 107.0 | 56.2 | 55 | B |
| HIS ND1 | 827 | 186.9 | 108.7 | 55.4 | 55 | B |
| HIS CE1 | 827 | 186.8 | 108.8 | 56.7 | 55 | B |
| HIS NE2 | 827 | 187.6 | 107.8 | 57.2 | 56 | B |
| HIS C | 827 | 187.2 | 106.9 | 51.3 | 47 | B |
| HIS O | 827 | 187.6 | 105.8 | 50.9 | 45 | B |
| TRP N | 828 | 187.2 | 108.0 | 50.6 | 43 | B |
| TRP CA | 828 | 187.7 | 108.0 | 49.2 | 39 | B |
| TRP CB | 828 | 187.4 | 109.4 | 48.6 | 35 | B |
| TRP CG | 828 | 185.9 | 109.7 | 48.6 | 31 | B |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| TRP CD2 | 828 | 184.9 | 108.9 | 48.1 | 29 | B |
| TRP CE2 | 828 | 183.7 | 109.7 | 48.2 | 29 | B |
| TRP CE3 | 828 | 184.8 | 107.6 | 47.5 | 29 | B |
| TRP CD1 | 828 | 185.4 | 110.9 | 49.0 | 30 | B |
| TRP NE1 | 828 | 184.0 | 110.8 | 48.8 | 30 | B |
| TRP CZ2 | 828 | 182.5 | 109.2 | 47.8 | 29 | B |
| TRP CZ3 | 828 | 183.6 | 107.2 | 47.1 | 29 | B |
| TRP CH2 | 828 | 182.4 | 107.9 | 47.2 | 29 | B |
| TRP C | 828 | 189.1 | 107.8 | 49.3 | 38 | B |
| TRP O | 828 | 189.7 | 108.1 | 50.4 | 38 | B |
| MET N | 829 | 189.8 | 107.4 | 48.2 | 38 | B |
| MET CA | 829 | 191.2 | 107.2 | 48.2 | 38 | B |
| MET CB | 829 | 191.5 | 106.1 | 47.2 | 38 | B |
| MET CG | 829 | 190.7 | 104.8 | 47.4 | 39 | B |
| MET SD | 829 | 191.3 | 103.4 | 46.4 | 39 | B |
| MET CE | 829 | 193.1 | 103.6 | 46.6 | 36 | B |
| MET C | 829 | 192.1 | 108.3 | 48.1 | 38 | B |
| MET O | 829 | 193.1 | 108.4 | 47.3 | 38 | B |
| PHE N | 830 | 191.9 | 109.3 | 49.0 | 38 | B |
| PHE CA | 830 | 192.7 | 110.5 | 49.1 | 37 | B |
| PHE CB | 830 | 192.4 | 111.6 | 48.0 | 33 | B |
| PHE CG | 830 | 191.1 | 112.3 | 48.1 | 29 | B |
| PHE CD1 | 830 | 191.1 | 113.6 | 48.7 | 28 | B |
| PHE CD2 | 830 | 189.9 | 111.8 | 47.6 | 28 | B |
| PHE CE1 | 830 | 189.9 | 114.3 | 48.8 | 28 | B |
| PHE CE2 | 830 | 188.7 | 112.6 | 47.7 | 28 | B |
| PHE CZ | 830 | 188.7 | 113.8 | 48.3 | 28 | B |
| PHE C | 830 | 192.5 | 111.1 | 50.5 | 38 | B |
| PHE O | 830 | 191.5 | 110.8 | 51.2 | 38 | B |
| HIS N | 831 | 193.5 | 112.0 | 50.9 | 39 | B |
| HIS CA | 831 | 193.3 | 112.6 | 52.2 | 39 | B |
| HIS CB | 831 | 194.6 | 113.2 | 52.6 | 39 | B |
| HIS CG | 831 | 194.9 | 113.3 | 54.1 | 40 | B |
| HIS CD2 | 831 | 194.2 | 113.9 | 55.1 | 40 | B |
| HIS ND1 | 831 | 196.0 | 112.6 | 54.6 | 40 | B |
| HIS CE1 | 831 | 196.0 | 112.8 | 55.9 | 40 | B |
| HIS NE2 | 831 | 194.9 | 113.6 | 56.2 | 41 | B |
| HIS C | 831 | 192.2 | 113.6 | 52.2 | 39 | B |
| HIS O | 831 | 192.4 | 114.8 | 51.9 | 40 | B |
| GLN N | 832 | 191.0 | 113.2 | 52.6 | 39 | B |
| GLN CA | 832 | 189.8 | 114.1 | 52.6 | 39 | B |
| GLN CB | 832 | 188.6 | 113.4 | 53.0 | 39 | B |
| GLN CG | 832 | 188.1 | 112.3 | 52.0 | 37 | B |
| GLN CD | 832 | 187.1 | 111.3 | 52.6 | 36 | B |
| GLN OE1 | 832 | 186.1 | 111.8 | 53.1 | 35 | B |
| GLN NE2 | 832 | 187.3 | 110.1 | 52.5 | 34 | B |
| GLN C | 832 | 190.0 | 115.3 | 53.6 | 41 | B |
| GLN O | 832 | 189.5 | 116.4 | 53.4 | 40 | B |
| GLN N | 833 | 190.7 | 115.0 | 54.6 | 42 | B |
| GLN CA | 833 | 191.0 | 115.9 | 55.7 | 43 | B |
| GLN CB | 833 | 191.8 | 115.3 | 56.9 | 44 | B |
| GLN CG | 833 | 191.5 | 115.9 | 58.2 | 45 | B |
| GLN CD | 833 | 192.7 | 115.8 | 59.2 | 45 | B |
| GLN OE1 | 833 | 193.5 | 114.8 | 59.1 | 45 | B |
| GLN NE2 | 833 | 192.8 | 116.7 | 60.1 | 45 | B |
| GLN C | 833 | 191.9 | 117.1 | 55.2 | 42 | B |
| GLN O | 833 | 191.5 | 118.3 | 55.3 | 42 | B |
| ALA N | 834 | 193.0 | 116.8 | 54.6 | 41 | B |
| ALA CA | 834 | 194.0 | 117.8 | 54.0 | 39 | B |
| ALA CB | 834 | 195.2 | 117.1 | 53.5 | 39 | B |
| ALA C | 834 | 193.3 | 118.6 | 53.0 | 39 | B |
| ALA O | 834 | 193.5 | 119.8 | 53.0 | 40 | B |
| LEU N | 835 | 192.6 | 118.0 | 52.1 | 39 | B |
| LEU CA | 835 | 191.9 | 118.8 | 51.0 | 39 | B |
| LEU CB | 835 | 191.2 | 117.9 | 50.0 | 39 | B |
| LEU CG | 835 | 190.4 | 118.7 | 49.0 | 39 | B |
| LEU CD1 | 835 | 191.3 | 119.7 | 48.2 | 39 | B |
| LEU CD2 | 835 | 189.7 | 117.7 | 48.0 | 39 | B |
| LEU C | 835 | 190.9 | 119.8 | 51.7 | 39 | B |
| LEU O | 835 | 190.9 | 121.0 | 51.3 | 41 | B |
| GLN N | 836 | 190.2 | 119.4 | 52.7 | 38 | B |
| GLN CA | 836 | 189.2 | 120.2 | 53.4 | 39 | B |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| GLN CB | 836 | 188.4 | 119.5 | 54.4 | 39 | B |
| GLN CG | 836 | 187.2 | 118.7 | 53.8 | 39 | B |
| GLN CD | 836 | 186.3 | 118.1 | 54.9 | 39 | B |
| GLN OE1 | 836 | 185.7 | 118.8 | 55.7 | 38 | B |
| GLN NE2 | 836 | 186.2 | 116.8 | 54.9 | 39 | B |
| GLN C | 836 | 189.9 | 121.4 | 54.1 | 38 | B |
| GLN O | 836 | 189.4 | 122.5 | 54.2 | 38 | B |
| GLU N | 837 | 191.1 | 121.1 | 54.6 | 38 | B |
| GLU CA | 837 | 191.9 | 122.1 | 55.3 | 39 | B |
| GLU CB | 837 | 193.0 | 121.5 | 56.1 | 38 | B |
| GLU CG | 837 | 192.5 | 120.7 | 57.3 | 39 | B |
| GLU CD | 837 | 193.6 | 120.0 | 58.1 | 40 | B |
| GLU OE1 | 837 | 194.8 | 120.3 | 58.0 | 40 | B |
| GLU OE2 | 837 | 193.2 | 119.1 | 58.9 | 41 | B |
| GLU C | 837 | 192.4 | 123.1 | 54.3 | 39 | B |
| GLU O | 837 | 192.0 | 124.3 | 54.4 | 40 | B |
| TYR N | 838 | 193.1 | 122.7 | 53.3 | 39 | B |
| TYR CA | 838 | 193.6 | 123.6 | 52.2 | 36 | B |
| TYR CB | 838 | 194.1 | 122.8 | 51.0 | 37 | B |
| TYR CG | 838 | 194.5 | 123.6 | 49.8 | 38 | B |
| TYR CD1 | 838 | 195.7 | 124.4 | 49.9 | 37 | B |
| TYR CE1 | 838 | 196.0 | 125.4 | 48.9 | 37 | B |
| TYR CD2 | 838 | 193.7 | 123.8 | 48.7 | 37 | B |
| TYR CE2 | 838 | 194.0 | 124.8 | 47.7 | 36 | B |
| TYR CZ | 838 | 195.2 | 125.6 | 47.9 | 36 | B |
| TYR OH | 838 | 195.4 | 126.6 | 47.0 | 36 | B |
| TYR C | 838 | 192.4 | 124.5 | 51.8 | 35 | B |
| TYR O | 838 | 192.6 | 125.7 | 51.8 | 35 | B |
| ILE N | 839 | 191.3 | 123.9 | 51.4 | 34 | B |
| ILE CA | 839 | 190.2 | 124.7 | 51.0 | 33 | B |
| ILE CB | 839 | 189.0 | 123.9 | 50.5 | 32 | B |
| ILE CG2 | 839 | 187.8 | 124.8 | 50.1 | 31 | B |
| ILE CG1 | 839 | 189.3 | 123.0 | 49.3 | 32 | B |
| ILE CD1 | 839 | 188.1 | 122.3 | 48.7 | 31 | B |
| ILE C | 839 | 189.7 | 125.7 | 52.0 | 34 | B |
| ILE O | 839 | 189.4 | 126.9 | 51.7 | 36 | B |
| LEU N | 840 | 189.5 | 125.2 | 53.3 | 35 | B |
| LEU CA | 840 | 189.1 | 126.1 | 54.3 | 34 | B |
| LEU CB | 840 | 188.6 | 125.3 | 55.5 | 33 | B |
| LEU CG | 840 | 187.2 | 124.6 | 55.2 | 32 | B |
| LEU CD1 | 840 | 186.9 | 123.6 | 56.3 | 32 | B |
| LEU CD2 | 840 | 186.1 | 125.7 | 55.2 | 31 | B |
| LEU C | 840 | 190.1 | 127.2 | 54.8 | 35 | B |
| LEU O | 840 | 189.7 | 128.4 | 55.0 | 35 | B |
| MET N | 841 | 191.3 | 126.8 | 54.9 | 35 | B |
| MET CA | 841 | 192.4 | 127.7 | 55.3 | 36 | B |
| MET CB | 841 | 193.5 | 127.0 | 55.9 | 37 | B |
| MET CG | 841 | 193.2 | 126.4 | 57.3 | 38 | B |
| MET SD | 841 | 194.6 | 125.9 | 58.2 | 40 | B |
| MET CE | 841 | 194.6 | 124.2 | 58.0 | 38 | B |
| MET C | 841 | 192.9 | 128.6 | 54.2 | 36 | B |
| MET O | 841 | 193.1 | 129.8 | 54.3 | 37 | B |
| CYS N | 842 | 193.3 | 128.0 | 53.0 | 37 | B |
| CYS CA | 842 | 193.9 | 128.7 | 51.9 | 36 | B |
| CYS CB | 842 | 195.0 | 127.9 | 51.3 | 36 | B |
| CYS SG | 842 | 196.1 | 127.3 | 52.6 | 37 | B |
| CYS C | 842 | 193.0 | 129.3 | 50.8 | 36 | B |
| CYS O | 842 | 193.4 | 130.4 | 50.3 | 37 | B |
| CYS N | 843 | 191.9 | 128.7 | 50.4 | 35 | B |
| CYS CA | 843 | 191.1 | 129.2 | 49.3 | 36 | B |
| CYS CB | 843 | 190.8 | 128.0 | 48.4 | 34 | B |
| CYS SG | 843 | 192.3 | 127.0 | 48.1 | 33 | B |
| CYS C | 843 | 189.8 | 129.9 | 49.5 | 37 | B |
| CYS O | 843 | 188.9 | 129.9 | 48.7 | 38 | B |
| GLN N | 844 | 189.7 | 130.6 | 50.7 | 38 | B |
| GLN CA | 844 | 188.5 | 131.4 | 51.0 | 39 | B |
| GLN CB | 844 | 188.0 | 130.9 | 52.3 | 38 | B |
| GLN CG | 844 | 186.5 | 131.2 | 52.5 | 38 | B |
| GLN CD | 844 | 185.9 | 130.2 | 53.4 | 38 | B |
| GLN OE1 | 844 | 184.7 | 130.0 | 53.4 | 38 | B |
| GLN NE2 | 844 | 186.7 | 129.5 | 54.3 | 38 | B |
| GLN C | 844 | 188.8 | 132.9 | 51.0 | 40 | B |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| GLN O | 844 | 189.9 | 133.3 | 51.5 | 40 | B |
| CYS N | 845 | 187.9 | 133.7 | 50.4 | 40 | B |
| CYS CA | 845 | 188.1 | 135.1 | 50.4 | 42 | B |
| CYS CB | 845 | 187.7 | 135.7 | 49.0 | 42 | B |
| CYS SG | 845 | 187.8 | 137.5 | 49.0 | 43 | B |
| CYS C | 845 | 187.2 | 135.7 | 51.5 | 43 | B |
| CYS O | 845 | 186.0 | 135.4 | 51.6 | 43 | B |
| PRO N | 846 | 187.8 | 136.5 | 52.4 | 44 | B |
| PRO CD | 846 | 189.2 | 137.0 | 52.4 | 44 | B |
| PRO CA | 846 | 187.1 | 137.2 | 53.5 | 43 | B |
| PRO CB | 846 | 188.1 | 138.2 | 54.0 | 44 | B |
| PRO CG | 846 | 189.4 | 137.5 | 53.8 | 44 | B |
| PRO C | 846 | 185.8 | 137.9 | 53.0 | 43 | B |
| PRO O | 846 | 184.8 | 137.7 | 53.6 | 44 | B |
| ALA N | 847 | 185.9 | 138.6 | 51.9 | 42 | B |
| ALA CA | 847 | 184.8 | 139.3 | 51.3 | 41 | B |
| ALA CB | 847 | 185.3 | 140.4 | 50.4 | 41 | B |
| ALA C | 847 | 183.7 | 138.4 | 50.6 | 40 | B |
| ALA O | 847 | 182.6 | 138.9 | 50.2 | 40 | B |
| GLY N | 848 | 184.0 | 137.1 | 50.6 | 39 | B |
| GLY CA | 848 | 183.1 | 136.2 | 49.9 | 39 | B |
| GLY C | 848 | 183.8 | 135.7 | 48.7 | 39 | B |
| GLY O | 848 | 184.7 | 136.4 | 48.1 | 40 | B |
| GLY N | 849 | 183.5 | 134.4 | 48.3 | 37 | B |
| GLY CA | 849 | 184.2 | 133.9 | 47.1 | 34 | B |
| GLY C | 849 | 185.4 | 133.0 | 47.5 | 33 | B |
| GLY O | 849 | 186.0 | 133.1 | 48.6 | 32 | B |
| LEU N | 850 | 185.6 | 132.0 | 46.7 | 32 | B |
| LEU CA | 850 | 186.7 | 131.0 | 46.9 | 31 | B |
| LEU CB | 850 | 186.1 | 129.6 | 46.8 | 31 | B |
| LEU CG | 850 | 185.3 | 129.0 | 48.0 | 31 | B |
| LEU CD1 | 850 | 186.1 | 128.8 | 49.2 | 30 | B |
| LEU CD2 | 850 | 184.0 | 129.7 | 48.2 | 29 | B |
| LEU C | 850 | 187.7 | 131.3 | 45.8 | 29 | B |
| LEU O | 850 | 187.4 | 131.9 | 44.8 | 28 | B |
| LEU N | 851 | 188.9 | 130.7 | 45.9 | 29 | B |
| LEU CA | 851 | 189.9 | 131.0 | 44.9 | 31 | B |
| LEU CB | 851 | 190.6 | 132.3 | 45.3 | 32 | B |
| LEU CG | 851 | 190.9 | 132.5 | 46.8 | 32 | B |
| LEU CD1 | 851 | 192.3 | 132.0 | 47.1 | 32 | B |
| LEU CD2 | 851 | 190.8 | 134.0 | 47.2 | 32 | B |
| LEU C | 851 | 190.9 | 129.9 | 44.6 | 31 | B |
| LEU O | 851 | 190.9 | 128.8 | 45.2 | 33 | B |
| ASP N | 852 | 191.8 | 130.2 | 43.7 | 30 | B |
| ASP CA | 852 | 192.8 | 129.3 | 43.2 | 29 | B |
| ASP CB | 852 | 193.7 | 130.0 | 42.2 | 28 | B |
| ASP CG | 852 | 194.9 | 129.2 | 41.7 | 28 | B |
| ASP OD1 | 852 | 195.4 | 128.4 | 42.4 | 29 | B |
| ASP OD2 | 852 | 195.3 | 129.4 | 40.5 | 29 | B |
| ASP C | 852 | 193.7 | 128.9 | 44.5 | 29 | B |
| ASP O | 852 | 193.6 | 127.8 | 45.0 | 29 | B |
| LYS N | 853 | 194.5 | 129.9 | 44.9 | 29 | B |
| LYS CA | 853 | 195.4 | 129.7 | 46.0 | 28 | B |
| LYS CB | 853 | 196.7 | 129.2 | 45.6 | 26 | B |
| LYS CG | 853 | 197.5 | 130.1 | 44.6 | 24 | B |
| LYS CD | 853 | 198.9 | 129.6 | 44.3 | 23 | B |
| LYS CE | 853 | 198.9 | 128.3 | 43.5 | 24 | B |
| LYS NZ | 853 | 198.2 | 128.3 | 42.2 | 24 | B |
| LYS C | 853 | 195.5 | 131.1 | 46.6 | 30 | B |
| LYS O | 853 | 195.0 | 132.1 | 46.0 | 28 | B |
| PRO N | 854 | 196.1 | 131.3 | 47.8 | 31 | B |
| PRO CD | 854 | 196.6 | 130.2 | 48.7 | 31 | B |
| PRO CA | 854 | 196.3 | 132.6 | 48.3 | 32 | B |
| PRO CB | 854 | 196.9 | 132.3 | 49.7 | 32 | B |
| PRO CG | 854 | 197.6 | 131.0 | 49.5 | 32 | B |
| PRO C | 854 | 197.1 | 133.5 | 47.4 | 33 | B |
| PRO O | 854 | 198.1 | 133.2 | 46.9 | 33 | B |
| GLY N | 855 | 196.6 | 134.7 | 47.2 | 34 | B |
| GLY CA | 855 | 197.2 | 135.7 | 46.4 | 36 | B |
| GLY C | 855 | 196.4 | 135.9 | 45.1 | 36 | B |
| GLY O | 855 | 196.5 | 136.9 | 44.5 | 38 | B |
| LYS N | 856 | 195.6 | 134.9 | 44.7 | 35 | B |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| LYS CA | 856 | 194.8 | 134.9 | 43.5 | 34 | B |
| LYS CB | 856 | 194.6 | 133.5 | 43.1 | 34 | B |
| LYS CG | 856 | 195.8 | 132.8 | 42.6 | 34 | B |
| LYS CD | 856 | 196.5 | 133.6 | 41.6 | 35 | B |
| LYS CE | 856 | 197.9 | 133.1 | 41.2 | 37 | B |
| LYS NZ | 856 | 197.8 | 132.0 | 40.2 | 38 | B |
| LYS C | 856 | 193.5 | 135.5 | 43.9 | 34 | B |
| LYS O | 856 | 193.2 | 135.6 | 45.1 | 34 | B |
| SER N | 857 | 192.8 | 136.1 | 42.9 | 34 | B |
| SER CA | 857 | 191.5 | 136.7 | 43.0 | 32 | B |
| SER CB | 857 | 191.2 | 137.7 | 41.9 | 33 | B |
| SER OG | 857 | 191.8 | 138.9 | 42.1 | 36 | B |
| SER C | 857 | 190.4 | 135.7 | 43.1 | 32 | B |
| SER O | 857 | 190.5 | 134.6 | 42.5 | 32 | B |
| ARG N | 858 | 189.3 | 136.1 | 43.6 | 31 | B |
| ARG CA | 858 | 188.1 | 135.3 | 43.7 | 31 | B |
| ARG CB | 858 | 187.2 | 135.8 | 44.9 | 32 | B |
| ARG CG | 858 | 186.5 | 137.1 | 44.6 | 33 | B |
| ARG CD | 858 | 186.0 | 137.8 | 45.9 | 34 | B |
| ARG NE | 858 | 185.1 | 138.9 | 45.6 | 35 | B |
| ARG CZ | 858 | 184.2 | 139.4 | 46.5 | 35 | B |
| ARG NH1 | 858 | 184.1 | 138.9 | 47.7 | 36 | B |
| ARG NH2 | 858 | 183.4 | 140.3 | 46.1 | 35 | B |
| ARG C | 858 | 187.3 | 135.4 | 42.4 | 30 | B |
| ARG O | 858 | 187.4 | 136.3 | 41.7 | 31 | B |
| ASP N | 859 | 186.5 | 134.3 | 42.2 | 28 | B |
| ASP CA | 859 | 185.6 | 134.3 | 41.0 | 28 | B |
| ASP CB | 859 | 186.4 | 134.1 | 39.7 | 28 | B |
| ASP CG | 859 | 187.3 | 132.9 | 39.7 | 28 | B |
| ASP OD1 | 859 | 186.7 | 131.8 | 39.5 | 29 | B |
| ASP OD2 | 859 | 188.5 | 133.0 | 39.7 | 30 | B |
| ASP C | 859 | 184.6 | 133.1 | 41.2 | 27 | B |
| ASP O | 859 | 184.9 | 132.2 | 42.0 | 27 | B |
| PHE N | 860 | 183.5 | 133.2 | 40.5 | 28 | B |
| PHE CA | 860 | 182.5 | 132.2 | 40.6 | 28 | B |
| PHE CB | 860 | 181.3 | 132.7 | 39.8 | 28 | B |
| PHE CG | 860 | 180.9 | 134.1 | 40.2 | 28 | B |
| PHE CD1 | 860 | 181.2 | 135.2 | 39.5 | 29 | B |
| PHE CD2 | 860 | 180.2 | 134.3 | 41.4 | 29 | B |
| PHE CE1 | 860 | 180.9 | 136.4 | 39.9 | 29 | B |
| PHE CE2 | 860 | 179.8 | 135.6 | 41.8 | 29 | B |
| PHE CZ | 860 | 180.2 | 136.7 | 41.1 | 28 | B |
| PHE C | 860 | 182.9 | 130.8 | 40.2 | 28 | B |
| PHE O | 860 | 182.5 | 129.8 | 40.8 | 30 | B |
| TYR N | 861 | 183.8 | 130.7 | 39.2 | 26 | B |
| TYR CA | 861 | 184.4 | 129.4 | 38.7 | 23 | B |
| TYR CB | 861 | 185.4 | 129.6 | 37.6 | 20 | B |
| TYR CG | 861 | 186.2 | 128.4 | 37.3 | 17 | B |
| TYR CD1 | 861 | 185.7 | 127.2 | 36.9 | 16 | B |
| TYR CE1 | 861 | 186.4 | 126.1 | 36.7 | 14 | B |
| TYR CD2 | 861 | 187.6 | 128.4 | 37.5 | 15 | B |
| TYR CE2 | 861 | 188.4 | 127.3 | 37.3 | 14 | B |
| TYR CZ | 861 | 187.8 | 126.1 | 36.9 | 14 | B |
| TYR OH | 861 | 188.5 | 125.0 | 36.7 | 14 | B |
| TYR C | 861 | 185.0 | 128.7 | 39.9 | 23 | B |
| TYR O | 861 | 184.7 | 127.5 | 40.2 | 23 | B |
| HIS N | 862 | 185.9 | 129.4 | 40.6 | 23 | B |
| HIS CA | 862 | 186.6 | 128.8 | 41.7 | 25 | B |
| HIS CB | 862 | 187.8 | 129.5 | 42.1 | 22 | B |
| HIS CG | 862 | 188.9 | 129.5 | 41.1 | 21 | B |
| HIS CD2 | 862 | 190.0 | 128.7 | 41.0 | 20 | B |
| HIS ND1 | 862 | 189.0 | 130.4 | 40.1 | 22 | B |
| HIS CE1 | 862 | 190.1 | 130.2 | 39.4 | 22 | B |
| HIS NE2 | 862 | 190.8 | 129.2 | 40.0 | 20 | B |
| HIS C | 862 | 185.7 | 128.6 | 42.9 | 27 | B |
| HIS O | 862 | 185.9 | 127.7 | 43.8 | 28 | B |
| THR N | 863 | 184.7 | 129.5 | 43.0 | 28 | B |
| THR CA | 863 | 183.7 | 129.4 | 44.1 | 30 | B |
| THR CB | 863 | 182.6 | 130.6 | 44.1 | 30 | B |
| THR OG1 | 863 | 183.3 | 131.8 | 44.2 | 32 | B |
| THR CG2 | 863 | 181.6 | 130.4 | 45.2 | 30 | B |
| THR C | 863 | 183.1 | 128.1 | 44.0 | 30 | B |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| THR O | 863 | 183.1 | 127.2 | 44.8 | 32 | B |
| CYS N | 864 | 182.6 | 127.8 | 42.7 | 29 | B |
| CYS CA | 864 | 181.9 | 126.6 | 42.4 | 28 | B |
| CYS CB | 864 | 181.4 | 126.7 | 40.9 | 28 | B |
| CYS SG | 864 | 180.7 | 125.1 | 40.3 | 28 | B |
| CYS C | 864 | 182.7 | 125.4 | 42.6 | 27 | B |
| CYS O | 864 | 182.2 | 124.4 | 43.1 | 29 | B |
| TYR N | 865 | 183.9 | 125.3 | 42.1 | 26 | B |
| TYR CA | 865 | 184.7 | 124.1 | 42.3 | 26 | B |
| TYR CB | 865 | 185.6 | 123.9 | 41.0 | 25 | B |
| TYR CG | 865 | 184.8 | 123.6 | 39.8 | 23 | B |
| TYR CD1 | 865 | 184.5 | 124.7 | 38.9 | 24 | B |
| TYR CE1 | 865 | 183.6 | 124.5 | 37.8 | 24 | B |
| TYR CD2 | 865 | 184.3 | 122.4 | 39.5 | 22 | B |
| TYR CE2 | 865 | 183.4 | 122.2 | 38.4 | 22 | B |
| TYR CZ | 865 | 183.1 | 123.2 | 37.6 | 23 | B |
| TYR OH | 865 | 182.2 | 123.0 | 36.5 | 23 | B |
| TYR C | 865 | 185.4 | 123.9 | 43.6 | 27 | B |
| TYR O | 865 | 185.6 | 122.7 | 43.9 | 28 | B |
| CYS N | 866 | 185.7 | 124.9 | 44.3 | 29 | B |
| CYS CA | 866 | 186.3 | 124.8 | 45.7 | 29 | B |
| CYS CB | 866 | 186.7 | 126.1 | 46.2 | 30 | B |
| CYS SG | 866 | 188.2 | 126.7 | 45.6 | 32 | B |
| CYS C | 866 | 185.2 | 124.2 | 46.6 | 29 | B |
| CYS O | 866 | 185.4 | 123.2 | 47.3 | 29 | B |
| LEU N | 867 | 183.9 | 124.7 | 46.4 | 28 | B |
| LEU CA | 867 | 182.8 | 124.2 | 47.2 | 29 | B |
| LEU CB | 867 | 181.6 | 125.1 | 47.0 | 27 | B |
| LEU CG | 867 | 181.8 | 126.5 | 47.6 | 27 | B |
| LEU CD1 | 867 | 180.6 | 127.4 | 47.4 | 27 | B |
| LEU CD2 | 867 | 182.2 | 126.4 | 49.1 | 27 | B |
| LEU C | 867 | 182.5 | 122.8 | 46.8 | 31 | B |
| LEU O | 867 | 182.4 | 121.9 | 47.6 | 32 | B |
| SER N | 868 | 182.4 | 122.5 | 45.5 | 32 | B |
| SER CA | 868 | 182.1 | 121.2 | 44.9 | 31 | B |
| SER CB | 868 | 182.2 | 121.2 | 43.4 | 29 | B |
| SER OG | 868 | 181.1 | 122.0 | 42.8 | 29 | B |
| SER C | 868 | 183.1 | 120.2 | 45.5 | 31 | B |
| SER O | 868 | 182.7 | 119.1 | 46.0 | 32 | B |
| GLY N | 869 | 184.4 | 120.5 | 45.5 | 32 | B |
| GLY CA | 869 | 185.4 | 119.6 | 46.0 | 33 | B |
| GLY C | 869 | 185.4 | 119.4 | 47.5 | 35 | B |
| GLY O | 869 | 185.9 | 118.4 | 48.0 | 36 | B |
| LEU N | 870 | 184.8 | 120.4 | 48.2 | 37 | B |
| LEU CA | 870 | 184.7 | 120.3 | 49.7 | 36 | B |
| LEU CB | 870 | 184.3 | 121.6 | 50.3 | 35 | B |
| LEU CG | 870 | 184.2 | 121.8 | 51.8 | 34 | B |
| LEU CD1 | 870 | 185.7 | 121.6 | 52.3 | 33 | B |
| LEU CD2 | 870 | 183.7 | 123.1 | 52.2 | 32 | B |
| LEU C | 870 | 183.6 | 119.3 | 50.0 | 36 | B |
| LEU O | 870 | 183.9 | 118.3 | 50.7 | 36 | B |
| SER N | 871 | 182.5 | 119.4 | 49.3 | 37 | B |
| SER CA | 871 | 181.3 | 118.6 | 49.5 | 38 | B |
| SER CB | 871 | 180.2 | 119.0 | 48.4 | 38 | B |
| SER OG | 871 | 179.1 | 118.2 | 48.6 | 38 | B |
| SER C | 871 | 181.8 | 117.1 | 49.2 | 39 | B |
| SER O | 871 | 181.4 | 116.2 | 49.9 | 40 | B |
| ILE N | 872 | 182.6 | 116.9 | 48.1 | 39 | B |
| ILE CA | 872 | 183.1 | 115.6 | 47.8 | 39 | B |
| ILE CB | 872 | 183.7 | 115.6 | 46.3 | 37 | B |
| ILE CG2 | 872 | 184.6 | 114.4 | 46.2 | 35 | B |
| ILE CG1 | 872 | 182.5 | 115.5 | 45.3 | 37 | B |
| ILE CD1 | 872 | 183.0 | 115.5 | 43.9 | 38 | B |
| ILE C | 872 | 184.0 | 115.1 | 48.9 | 39 | B |
| ILE O | 872 | 183.9 | 113.9 | 49.3 | 39 | B |
| ALA N | 873 | 184.9 | 115.9 | 49.3 | 40 | B |
| ALA CA | 873 | 185.9 | 115.5 | 50.3 | 41 | B |
| ALA CB | 873 | 187.0 | 116.6 | 50.5 | 41 | B |
| ALA C | 873 | 185.3 | 115.2 | 51.7 | 42 | B |
| ALA O | 873 | 185.9 | 114.5 | 52.5 | 42 | B |
| GLN N | 874 | 184.1 | 115.7 | 51.9 | 42 | B |
| GLN CA | 874 | 183.4 | 115.4 | 53.2 | 43 | B |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| GLN CB | 874 | 183.0 | 116.8 | 53.8 | 42 | B |
| GLN CG | 874 | 181.8 | 117.4 | 53.1 | 40 | B |
| GLN CD | 874 | 181.5 | 118.8 | 53.7 | 39 | B |
| GLN OE1 | 874 | 180.5 | 119.4 | 53.4 | 40 | B |
| GLN NE2 | 874 | 182.5 | 119.3 | 54.5 | 37 | B |
| GLN C | 874 | 182.3 | 114.4 | 53.2 | 45 | B |
| GLN O | 874 | 181.8 | 114.0 | 54.2 | 45 | B |
| HIS N | 875 | 181.9 | 114.0 | 52.0 | 46 | B |
| HIS CA | 875 | 180.8 | 113.1 | 51.9 | 46 | B |
| HIS CB | 875 | 179.6 | 113.7 | 51.1 | 45 | B |
| HIS CG | 875 | 178.9 | 114.8 | 51.7 | 45 | B |
| HIS CD2 | 875 | 178.1 | 115.8 | 51.2 | 45 | B |
| HIS ND1 | 875 | 179.0 | 115.0 | 53.1 | 45 | B |
| HIS CE1 | 875 | 178.2 | 116.1 | 53.4 | 45 | B |
| HIS NE2 | 875 | 177.7 | 116.6 | 52.3 | 44 | B |
| HIS C | 875 | 181.2 | 111.8 | 51.2 | 48 | B |
| HIS O | 875 | 181.5 | 111.8 | 50.0 | 48 | B |
| PHE N | 876 | 181.1 | 110.7 | 52.0 | 51 | B |
| PHE CA | 876 | 181.4 | 109.4 | 51.4 | 54 | B |
| PHE CB | 876 | 182.5 | 108.6 | 52.3 | 52 | B |
| PHE CG | 876 | 182.7 | 107.2 | 51.7 | 51 | B |
| PHE CD1 | 876 | 183.7 | 107.0 | 50.8 | 51 | B |
| PHE CD2 | 876 | 181.9 | 106.2 | 52.1 | 51 | B |
| PHE CE1 | 876 | 183.9 | 105.7 | 50.3 | 51 | B |
| PHE CE2 | 876 | 182.0 | 104.9 | 51.6 | 51 | B |
| PHE CZ | 876 | 183.1 | 104.7 | 50.7 | 52 | B |
| PHE C | 876 | 180.1 | 108.6 | 51.4 | 56 | B |
| PHE O | 876 | 179.2 | 108.7 | 52.2 | 57 | B |
| GLY N | 877 | 180.1 | 107.7 | 50.4 | 60 | B |
| GLY CA | 877 | 178.9 | 106.8 | 50.2 | 63 | B |
| GLY C | 877 | 179.3 | 105.6 | 49.3 | 64 | B |
| GLY O | 877 | 180.1 | 105.8 | 48.4 | 65 | B |
| SER N | 878 | 178.8 | 104.4 | 49.6 | 66 | B |
| SER CA | 878 | 179.2 | 103.2 | 48.8 | 67 | B |
| SER CB | 878 | 180.6 | 102.7 | 49.2 | 66 | B |
| SER OG | 878 | 181.1 | 102.0 | 48.1 | 66 | B |
| SER C | 878 | 178.1 | 102.2 | 49.1 | 68 | B |
| SER O | 878 | 178.3 | 101.2 | 49.8 | 69 | B |
| GLY N | 879 | 176.9 | 102.3 | 48.4 | 69 | B |
| GLY CA | 879 | 175.9 | 101.4 | 48.6 | 71 | B |
| GLY C | 879 | 175.1 | 101.8 | 49.9 | 71 | B |
| GLY O | 879 | 174.6 | 102.9 | 49.9 | 72 | B |
| ALA N | 880 | 175.2 | 101.0 | 50.9 | 72 | B |
| ALA CA | 880 | 174.5 | 101.3 | 52.2 | 72 | B |
| ALA CB | 880 | 174.2 | 100.0 | 53.0 | 73 | B |
| ALA C | 880 | 175.5 | 102.2 | 53.1 | 72 | B |
| ALA O | 880 | 175.0 | 102.8 | 54.0 | 73 | B |
| MET N | 881 | 176.7 | 102.3 | 52.7 | 72 | B |
| MET CA | 881 | 177.7 | 103.2 | 53.3 | 71 | B |
| MET CB | 881 | 179.1 | 102.9 | 52.8 | 72 | B |
| MET CG | 881 | 179.8 | 101.6 | 53.4 | 73 | B |
| MET SD | 881 | 178.8 | 100.2 | 53.2 | 75 | B |
| MET CE | 881 | 178.5 | 99.9 | 55.0 | 75 | B |
| MET C | 881 | 177.5 | 104.6 | 53.1 | 70 | B |
| MET O | 881 | 177.2 | 105.1 | 52.0 | 69 | B |
| LEU N | 882 | 177.7 | 105.4 | 54.2 | 68 | B |
| LEU CA | 882 | 177.6 | 106.9 | 54.2 | 66 | B |
| LEU CB | 882 | 176.1 | 107.3 | 54.3 | 67 | B |
| LEU CG | 882 | 175.2 | 107.4 | 53.1 | 67 | B |
| LEU CD1 | 882 | 175.9 | 108.0 | 52.0 | 67 | B |
| LEU CD2 | 882 | 174.6 | 106.0 | 52.7 | 67 | B |
| LEU C | 882 | 178.5 | 107.5 | 55.3 | 65 | B |
| LEU O | 882 | 178.0 | 107.6 | 56.4 | 66 | B |
| HIS N | 883 | 179.7 | 107.8 | 55.0 | 64 | B |
| HIS CA | 883 | 180.6 | 108.4 | 56.0 | 61 | B |
| HIS CB | 883 | 181.8 | 107.6 | 56.2 | 61 | B |
| HIS CG | 883 | 182.7 | 108.0 | 57.3 | 62 | B |
| HIS CD2 | 883 | 183.3 | 109.2 | 57.5 | 62 | B |
| HIS ND1 | 883 | 183.1 | 107.2 | 58.4 | 62 | B |
| HIS CE1 | 883 | 183.9 | 107.9 | 59.2 | 62 | B |
| HIS NE2 | 883 | 184.0 | 109.2 | 58.7 | 62 | B |
| HIS C | 883 | 181.0 | 109.9 | 55.7 | 60 | B |
| HIS O | 883 | 181.6 | 110.1 | 54.7 | 60 | B |
| ASP N | 884 | 180.6 | 110.8 | 56.6 | 56 | B |
| ASP CA | 884 | 181.0 | 112.2 | 56.4 | 53 | B |
| ASP CB | 884 | 179.8 | 113.1 | 56.8 | 52 | B |
| ASP CG | 884 | 178.6 | 113.0 | 55.8 | 52 | B |
| ASP OD1 | 884 | 177.8 | 113.9 | 55.8 | 52 | B |
| ASP OD2 | 884 | 178.6 | 112.0 | 55.0 | 53 | B |
| ASP C | 884 | 182.1 | 112.5 | 57.3 | 52 | B |
| ASP O | 884 | 182.3 | 111.9 | 58.3 | 52 | B |
| VAL N | 885 | 182.9 | 113.5 | 56.8 | 50 | B |
| VAL CA | 885 | 184.1 | 114.0 | 57.6 | 49 | B |
| VAL CB | 885 | 185.5 | 113.5 | 57.0 | 48 | B |
| VAL CG1 | 885 | 186.6 | 114.2 | 57.7 | 47 | B |
| VAL CG2 | 885 | 185.6 | 112.0 | 57.1 | 47 | B |
| VAL C | 885 | 183.9 | 115.5 | 57.4 | 49 | B |
| VAL O | 885 | 184.0 | 115.9 | 56.2 | 50 | B |
| VAL N | 886 | 183.6 | 116.2 | 58.4 | 48 | B |
| VAL CA | 886 | 183.4 | 117.6 | 58.2 | 49 | B |
| VAL CB | 886 | 182.0 | 118.1 | 58.7 | 48 | B |
| VAL CG1 | 886 | 181.9 | 119.6 | 58.5 | 48 | B |
| VAL CG2 | 886 | 181.0 | 117.3 | 57.9 | 48 | B |
| VAL C | 886 | 184.5 | 118.3 | 59.1 | 50 | B |
| VAL O | 886 | 184.6 | 117.9 | 60.3 | 51 | B |
| MET N | 887 | 185.3 | 119.2 | 58.5 | 51 | B |
| MET CA | 887 | 186.3 | 119.9 | 59.2 | 51 | B |
| MET CB | 887 | 187.5 | 120.1 | 58.3 | 50 | B |
| MET CG | 887 | 188.2 | 118.8 | 57.9 | 50 | B |
| MET SD | 887 | 188.6 | 117.8 | 59.3 | 49 | B |
| MET CE | 887 | 190.1 | 118.7 | 59.8 | 49 | B |
| MET C | 887 | 185.9 | 121.2 | 59.8 | 52 | B |
| MET O | 887 | 185.1 | 121.9 | 59.2 | 52 | B |
| GLY N | 888 | 186.4 | 121.5 | 61.0 | 52 | B |
| GLY CA | 888 | 186.1 | 122.7 | 61.7 | 53 | B |
| GLY C | 888 | 184.6 | 122.8 | 62.2 | 53 | B |
| GLY O | 888 | 184.0 | 121.7 | 62.5 | 53 | B |
| VAL N | 889 | 184.0 | 123.9 | 62.2 | 54 | B |
| VAL CA | 889 | 182.7 | 124.0 | 62.7 | 56 | B |
| VAL CB | 889 | 182.3 | 125.5 | 62.7 | 56 | B |
| VAL CG1 | 889 | 181.9 | 126.0 | 61.4 | 56 | B |
| VAL CG2 | 889 | 181.1 | 125.7 | 63.7 | 56 | B |
| VAL C | 889 | 181.8 | 123.2 | 61.9 | 57 | B |
| VAL O | 889 | 181.8 | 123.2 | 60.6 | 58 | B |
| PRO N | 890 | 180.9 | 122.3 | 62.5 | 58 | B |
| PRO CD | 890 | 180.7 | 122.2 | 63.9 | 58 | B |
| PRO CA | 890 | 180.0 | 121.4 | 61.8 | 58 | B |
| PRO CB | 890 | 179.3 | 120.7 | 62.9 | 58 | B |
| PRO CG | 890 | 179.3 | 121.7 | 64.0 | 58 | B |
| PRO C | 890 | 179.0 | 122.1 | 60.8 | 57 | B |
| PRO O | 890 | 178.4 | 121.4 | 60.0 | 57 | B |
| GLU N | 891 | 178.9 | 123.4 | 61.0 | 57 | B |
| GLU CA | 891 | 178.0 | 124.2 | 60.1 | 58 | B |
| GLU CB | 891 | 177.8 | 125.6 | 60.6 | 59 | B |
| GLU CG | 891 | 176.8 | 125.8 | 61.8 | 61 | B |
| GLU CD | 891 | 177.2 | 125.0 | 63.0 | 63 | B |
| GLU OE1 | 891 | 178.4 | 124.8 | 63.3 | 63 | B |
| GLU OE2 | 891 | 176.2 | 124.7 | 63.8 | 64 | B |
| GLU C | 891 | 178.6 | 124.2 | 58.7 | 57 | B |
| GLU O | 891 | 178.0 | 124.6 | 57.7 | 57 | B |
| ASN N | 892 | 179.9 | 123.7 | 58.6 | 54 | B |
| ASN CA | 892 | 180.6 | 123.7 | 57.4 | 52 | B |
| ASN CB | 892 | 182.1 | 123.5 | 57.7 | 49 | B |
| ASN CG | 892 | 182.8 | 124.7 | 58.4 | 47 | B |
| ASN OD1 | 892 | 183.9 | 124.5 | 58.9 | 45 | B |
| ASN ND2 | 892 | 182.1 | 125.8 | 58.4 | 45 | B |
| ASN C | 892 | 180.2 | 122.6 | 56.4 | 51 | B |
| ASN O | 892 | 180.7 | 122.5 | 55.3 | 53 | B |
| VAL N | 893 | 179.2 | 121.8 | 56.8 | 49 | B |
| VAL CA | 893 | 178.8 | 120.7 | 55.9 | 48 | B |
| VAL CB | 893 | 178.1 | 119.5 | 56.6 | 49 | B |
| VAL CG1 | 893 | 176.7 | 119.8 | 57.0 | 49 | B |
| VAL CG2 | 893 | 178.2 | 118.3 | 55.7 | 49 | B |
| VAL C | 893 | 177.9 | 121.3 | 54.8 | 47 | B |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| VAL O | 893 | 176.9 | 122.0 | 55.0 | 47 | B |
| LEU N | 894 | 178.2 | 120.8 | 53.5 | 46 | B |
| LEU CA | 894 | 177.5 | 121.3 | 52.3 | 44 | B |
| LEU CB | 894 | 178.6 | 121.6 | 51.2 | 43 | B |
| LEU CG | 894 | 179.6 | 122.6 | 51.6 | 42 | B |
| LEU CD1 | 894 | 180.8 | 122.6 | 50.6 | 41 | B |
| LEU CD2 | 894 | 179.0 | 124.0 | 51.6 | 42 | B |
| LEU C | 894 | 176.6 | 120.2 | 51.8 | 43 | B |
| LEU O | 894 | 176.8 | 119.0 | 52.2 | 42 | B |
| GLN N | 895 | 175.6 | 120.6 | 51.0 | 41 | B |
| GLN CA | 895 | 174.7 | 119.6 | 50.4 | 41 | B |
| GLN CB | 895 | 173.7 | 120.4 | 49.6 | 42 | B |
| GLN CG | 895 | 172.7 | 121.1 | 50.4 | 43 | B |
| GLN CD | 895 | 171.9 | 120.1 | 51.2 | 44 | B |
| GLN OE1 | 895 | 170.9 | 119.5 | 50.8 | 44 | B |
| GLN NE2 | 895 | 172.3 | 119.9 | 52.5 | 45 | B |
| LN C | 895 | 175.6 | 118.8 | 49.5 | 40 | B |
| GLN O | 895 | 176.6 | 119.2 | 48.9 | 41 | B |
| PRO N | 896 | 175.2 | 117.5 | 49.3 | 39 | B |
| PRO CD | 896 | 174.1 | 116.8 | 49.9 | 38 | B |
| PRO CA | 896 | 176.0 | 116.6 | 48.4 | 38 | B |
| PRO CB | 896 | 175.5 | 115.2 | 48.8 | 38 | B |
| PRO CG | 896 | 174.0 | 115.5 | 49.0 | 38 | B |
| PRO C | 896 | 175.9 | 116.9 | 46.9 | 37 | B |
| PRO O | 896 | 174.9 | 117.5 | 46.5 | 37 | B |
| THR N | 897 | 176.9 | 116.5 | 46.2 | 36 | B |
| THR CA | 897 | 177.0 | 116.7 | 44.8 | 34 | B |
| THR CB | 897 | 178.1 | 117.8 | 44.4 | 35 | B |
| THR OG1 | 897 | 178.0 | 118.2 | 43.0 | 36 | B |
| THR CG2 | 897 | 179.5 | 117.3 | 44.7 | 33 | B |
| THR C | 897 | 177.3 | 115.4 | 44.1 | 32 | B |
| THR O | 897 | 178.1 | 114.6 | 44.5 | 32 | B |
| HIS N | 898 | 176.6 | 115.2 | 42.9 | 31 | B |
| HIS CA | 898 | 176.8 | 114.0 | 42.1 | 31 | B |
| HIS CB | 898 | 175.7 | 113.9 | 41.1 | 31 | B |
| HIS CG | 898 | 175.5 | 112.6 | 40.4 | 32 | B |
| HIS CD2 | 898 | 174.4 | 111.8 | 40.2 | 32 | B |
| HIS ND1 | 898 | 176.6 | 111.9 | 39.8 | 32 | B |
| HIS CE1 | 898 | 176.1 | 110.8 | 39.3 | 31 | B |
| HIS NE2 | 898 | 174.8 | 110.7 | 39.5 | 32 | B |
| HIS C | 898 | 178.2 | 114.1 | 41.5 | 31 | B |
| HIS O | 898 | 178.4 | 115.0 | 40.7 | 31 | B |
| PRO N | 899 | 179.1 | 113.1 | 41.7 | 30 | B |
| PRO CD | 899 | 178.9 | 111.9 | 42.5 | 31 | B |
| PRO CA | 899 | 180.4 | 113.1 | 41.1 | 31 | B |
| PRO CB | 899 | 181.1 | 112.0 | 41.8 | 31 | B |
| PRO CG | 899 | 180.0 | 111.0 | 42.0 | 32 | B |
| PRO C | 899 | 180.6 | 113.0 | 39.6 | 30 | B |
| PRO O | 899 | 181.7 | 113.3 | 39.1 | 31 | B |
| VAL N | 900 | 179.5 | 112.8 | 38.9 | 28 | B |
| VAL CA | 900 | 179.6 | 112.7 | 37.4 | 26 | B |
| VAL CB | 900 | 178.7 | 111.5 | 36.8 | 24 | B |
| VAL CG1 | 900 | 178.6 | 111.5 | 35.3 | 22 | B |
| VAL CG2 | 900 | 179.3 | 110.2 | 37.3 | 23 | B |
| VAL C | 900 | 179.1 | 114.0 | 36.8 | 26 | B |
| VAL O | 900 | 179.8 | 114.6 | 36.0 | 26 | B |
| TYR N | 901 | 177.9 | 114.5 | 37.3 | 26 | B |
| TYR CA | 901 | 177.3 | 115.7 | 36.8 | 26 | B |
| TYR CB | 901 | 175.8 | 115.5 | 36.7 | 25 | B |
| TYR CG | 901 | 175.3 | 114.4 | 35.8 | 26 | B |
| TYR CD1 | 901 | 175.0 | 113.1 | 36.3 | 27 | B |
| TYR CE1 | 901 | 174.6 | 112.1 | 35.5 | 27 | B |
| TYR CD2 | 901 | 175.2 | 114.6 | 34.5 | 27 | B |
| TYR CE2 | 901 | 174.8 | 113.5 | 33.6 | 27 | B |
| TYR CZ | 901 | 174.5 | 112.3 | 34.1 | 26 | B |
| TYR OH | 901 | 174.1 | 111.2 | 33.3 | 24 | B |
| TYR C | 901 | 177.6 | 117.0 | 37.6 | 27 | B |
| TYR O | 901 | 177.4 | 118.1 | 37.0 | 27 | B |
| ASN N | 902 | 178.0 | 116.8 | 38.8 | 28 | B |
| ASN CA | 902 | 178.3 | 117.9 | 39.7 | 29 | B |
| ASN CB | 902 | 179.5 | 118.8 | 39.2 | 30 | B |
| ASN CG | 902 | 180.1 | 119.6 | 40.3 | 30 | B |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| ASN OD1 | 902 | 180.0 | 119.2 | 41.5 | 30 | B |
| ASN ND2 | 902 | 180.7 | 120.7 | 40.0 | 30 | B |
| ASN C | 902 | 177.1 | 118.8 | 39.9 | 29 | B |
| ASN O | 902 | 177.2 | 120.0 | 39.7 | 30 | B |
| ILE N | 903 | 176.0 | 118.2 | 40.3 | 30 | B |
| ILE CA | 903 | 174.8 | 118.9 | 40.6 | 30 | B |
| ILE CB | 903 | 173.8 | 119.1 | 39.4 | 29 | B |
| ILE CG2 | 903 | 174.5 | 119.8 | 38.3 | 28 | B |
| ILE CG1 | 903 | 173.2 | 117.8 | 38.9 | 28 | B |
| ILE CD1 | 903 | 172.1 | 118.0 | 37.9 | 27 | B |
| ILE C | 903 | 174.2 | 117.9 | 41.6 | 32 | B |
| ILE O | 903 | 174.6 | 116.7 | 41.7 | 33 | B |
| GLY N | 904 | 173.3 | 11a.4 | 42.5 | 35 | B |
| GLY CA | 904 | 172.7 | 117.6 | 43.6 | 36 | B |
| GLY C | 904 | 172.2 | 116.3 | 43.1 | 36 | B |
| GLY O | 904 | 171.6 | 116.2 | 42.0 | 37 | B |
| PRO N | 905 | 172.6 | 115.2 | 43.8 | 35 | B |
| PRO CD | 905 | 173.4 | 115.3 | 45.0 | 35 | B |
| PRO CA | 905 | 172.2 | 113.8 | 43.5 | 36 | B |
| PRO CB | 905 | 172.6 | 113.1 | 44.7 | 35 | B |
| PRO CG | 905 | 173.8 | 113.8 | 45.2 | 35 | B |
| PRO C | 905 | 170.7 | 113.7 | 43.2 | 38 | B |
| PRO O | 905 | 170.3 | 112.9 | 42.3 | 39 | B |
| ASP N | 906 | 169.9 | 114.5 | 43.9 | 40 | B |
| ASP CA | 906 | 168.5 | 114.5 | 43.7 | 42 | B |
| ASP CB | 906 | 167.9 | 115.3 | 44.9 | 45 | B |
| ASP CG | 906 | 168.6 | 116.6 | 45.2 | 48 | B |
| ASP OD1 | 906 | 169.6 | 116.6 | 45.9 | 51 | B |
| ASP OD2 | 906 | 168.1 | 117.7 | 44.8 | 50 | B |
| ASP C | 906 | 168.0 | 115.2 | 42.4 | 42 | B |
| ASP O | 906 | 167.0 | 114.9 | 41.9 | 42 | B |
| LYS N | 907 | 168.8 | 116.2 | 42.0 | 41 | B |
| LYS CA | 907 | 168.6 | 116.9 | 40.8 | 41 | B |
| LYS CB | 907 | 169.4 | 118.1 | 40.6 | 41 | B |
| LYS CG | 907 | 169.1 | 119.2 | 41.7 | 41 | B |
| LYS CD | 907 | 167.7 | 119.6 | 41.6 | 42 | B |
| LYS CE | 907 | 167.3 | 120.5 | 42.7 | 43 | B |
| LYS NZ | 907 | 166.0 | 121.2 | 42.5 | 44 | B |
| LYS C | 907 | 168.8 | 115.9 | 39.6 | 40 | B |
| LYS O | 907 | 168.1 | 115.9 | 38.6 | 40 | B |
| VAL N | 908 | 169.9 | 115.1 | 39.8 | 40 | B |
| VAL CA | 908 | 170.2 | 114.1 | 38.7 | 41 | B |
| VAL CB | 908 | 171.4 | 113.3 | 39.1 | 40 | B |
| VAL CG1 | 908 | 171.6 | 112.2 | 38.2 | 41 | B |
| VAL CG2 | 908 | 172.7 | 114.2 | 39.1 | 40 | B |
| VAL C | 908 | 169.0 | 113.2 | 38.6 | 42 | B |
| VAL O | 908 | 168.4 | 113.1 | 37.6 | 42 | B |
| ILE N | 909 | 168.6 | 112.6 | 39.7 | 41 | B |
| ILE CA | 909 | 167.5 | 111.7 | 39.8 | 42 | B |
| ILE CB | 909 | 167.2 | 111.2 | 41.2 | 41 | B |
| ILE CG2 | 909 | 165.9 | 110.3 | 41.2 | 41 | B |
| ILE CG1 | 909 | 168.4 | 110.4 | 41.7 | 41 | B |
| ILE CD1 | 909 | 168.4 | 110.1 | 43.2 | 41 | B |
| ILE C | 909 | 166.2 | 112.4 | 39.2 | 42 | B |
| ILE O | 909 | 165.6 | 111.9 | 38.2 | 44 | B |
| GLN N | 910 | 165.9 | 113.5 | 39.8 | 42 | B |
| GLN CA | 910 | 164.7 | 114.2 | 39.4 | 42 | B |
| GLN CB | 910 | 164.6 | 115.6 | 40.1 | 44 | B |
| GLN CG | 910 | 163.3 | 116.3 | 39.9 | 46 | B |
| GLN CD | 910 | 163.3 | 117.6 | 40.7 | 47 | B |
| GLN OE1 | 910 | 162.5 | 118.5 | 40.4 | 47 | B |
| GLN NE2 | 910 | 164.1 | 117.8 | 41.7 | 48 | B |
| GLN C | 910 | 164.7 | 114.5 | 37.8 | 42 | B |
| GLN O | 910 | 163.7 | 114.2 | 37.1 | 42 | B |
| ALA N | 911 | 165.8 | 115.0 | 37.3 | 42 | B |
| ALA CA | 911 | 165.8 | 115.3 | 35.9 | 41 | B |
| ALA CB | 911 | 167.1 | 116.1 | 35.5 | 41 | B |
| ALA C | 911 | 165.8 | 114.1 | 35.0 | 40 | B |
| ALA O | 911 | 165.0 | 114.1 | 34.0 | 39 | B |
| THR N | 912 | 166.5 | 113.0 | 35.3 | 41 | B |
| THR CA | 912 | 166.6 | 111.8 | 34.5 | 42 | B |
| THR CB | 912 | 167.6 | 110.8 | 35.0 | 42 | B |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| THR OG1 | 912 | 167.3 | 110.4 | 36.3 | 44 | B |
| THR CG2 | 912 | 169.0 | 111.5 | 35.0 | 42 | B |
| THR C | 912 | 165.2 | 111.1 | 34.4 | 42 | B |
| THR O | 912 | 164.8 | 110.8 | 33.3 | 43 | B |
| THR N | 913 | 164.6 | 110.9 | 35.5 | 42 | B |
| THR CA | 913 | 163.2 | 110.2 | 35.4 | 41 | B |
| THR CB | 913 | 162.7 | 109.8 | 36.8 | 40 | B |
| THR OG1 | 913 | 161.8 | 110.7 | 37.3 | 41 | B |
| THR CG2 | 913 | 163.9 | 109.5 | 37.8 | 41 | B |
| THR C | 913 | 162.2 | 111.1 | 34.7 | 40 | B |
| THR O | 913 | 161.3 | 110.6 | 34.0 | 41 | B |
| HIS N | 914 | 162.3 | 112.4 | 34.8 | 38 | B |
| HIS CA | 914 | 161.4 | 113.3 | 34.1 | 37 | B |
| HIS CB | 914 | 161.5 | 114.7 | 34.6 | 36 | B |
| HIS CG | 914 | 160.8 | 115.7 | 33.7 | 34 | B |
| HIS CD2 | 914 | 159.6 | 116.2 | 33.8 | 34 | B |
| HIS ND1 | 914 | 161.3 | 116.1 | 32.5 | 34 | B |
| HIS CE1 | 914 | 160.4 | 116.9 | 31.9 | 33 | B |
| HIS NE2 | 914 | 159.3 | 116.9 | 32.6 | 34 | B |
| HIS C | 914 | 161.5 | 113.2 | 32.6 | 38 | B |
| HIS O | 914 | 160.5 | 113.2 | 31.9 | 38 | B |
| PHE N | 915 | 162.7 | 113.2 | 32.1 | 39 | B |
| PHE CA | 915 | 163.0 | 113.2 | 30.7 | 38 | B |
| PHE CB | 915 | 164.4 | 113.7 | 30.4 | 37 | B |
| PHE CG | 915 | 164.5 | 115.2 | 30.5 | 35 | B |
| PHE CD1 | 915 | 165.2 | 115.7 | 31.5 | 35 | B |
| PHE CD2 | 915 | 164.0 | 116.0 | 29.5 | 35 | B |
| PHE CE1 | 915 | 165.3 | 117.1 | 31.6 | 35 | B |
| PHE CE2 | 915 | 164.0 | 117.4 | 29.6 | 34 | B |
| PHE CZ | 915 | 164.7 | 117.9 | 30.7 | 34 | B |
| PHE C | 915 | 162.7 | 111.8 | 30.1 | 39 | B |
| PHE O | 915 | 162.6 | 111.6 | 28.9 | 39 | B |
| LEU N | 916 | 162.7 | 110.8 | 31.0 | 41 | B |
| LEU CA | 916 | 162.4 | 109.5 | 30.7 | 43 | B |
| LEU CB | 916 | 162.8 | 108.5 | 31.9 | 43 | B |
| LEU CG | 916 | 164.0 | 107.7 | 31.8 | 43 | B |
| LEU CD1 | 916 | 165.0 | 108.2 | 30.7 | 44 | B |
| LEU CD2 | 916 | 164.7 | 107.5 | 33.1 | 43 | B |
| LEU C | 916 | 161.0 | 109.3 | 30.2 | 45 | B |
| LEU O | 916 | 160.7 | 108.5 | 29.4 | 45 | B |
| GLN N | 917 | 160.1 | 110.2 | 30.7 | 46 | B |
| GLN CA | 917 | 158.7 | 110.2 | 30.3 | 48 | B |
| GLN CB | 917 | 157.9 | 111.3 | 31.0 | 50 | B |
| GLN CG | 917 | 158.0 | 111.4 | 32.5 | 53 | B |
| GLN CD | 917 | 157.5 | 112.7 | 33.0 | 54 | B |
| GLN OE1 | 917 | 158.1 | 113.4 | 33.8 | 57 | B |
| GLN NE2 | 917 | 156.4 | 113.2 | 32.5 | 55 | B |
| GLN C | 917 | 158.6 | 110.5 | 28.8 | 48 | B |
| GLN O | 917 | 157.6 | 110.3 | 28.2 | 48 | B |
| LYS N | 918 | 159.7 | 111.1 | 28.3 | 49 | B |
| LYS CA | 918 | 159.7 | 111.4 | 26.9 | 50 | B |
| LYS CB | 918 | 160.4 | 112.8 | 26.7 | 50 | B |
| LYS CG | 918 | 159.6 | 113.9 | 27.4 | 51 | B |
| LYS CD | 918 | 160.0 | 114.1 | 28.9 | 50 | B |
| LYS CE | 918 | 158.9 | 114.9 | 29.6 | 50 | B |
| LYS NZ | 918 | 158.6 | 116.2 | 28.9 | 50 | B |
| LYS C | 918 | 160.5 | 110.4 | 26.1 | 51 | B |
| LYS O | 918 | 161.4 | 109.7 | 26.6 | 51 | B |
| PRO N | 919 | 160.1 | 110.1 | 24.8 | 52 | B |
| PRO CD | 919 | 159.0 | 110.6 | 24.0 | 52 | B |
| PRO CA | 919 | 160.9 | 109.1 | 24.1 | 53 | B |
| PRO CB | 919 | 159.9 | 108.7 | 23.0 | 52 | B |
| PRO CG | 919 | 159.3 | 110.0 | 22.7 | 52 | B |
| PRO C | 919 | 162.1 | 109.8 | 23.5 | 54 | B |
| PRO O | 919 | 162.1 | 111.0 | 23.3 | 54 | B |
| VAL N | 920 | 163.2 | 109.0 | 23.4 | 55 | B |
| VAL CA | 920 | 164.4 | 109.5 | 22.7 | 56 | B |
| VAL CB | 920 | 165.4 | 108.4 | 22.5 | 55 | B |
| VAL CG1 | 920 | 166.6 | 108.8 | 21.7 | 54 | B |
| VAL CG2 | 920 | 165.9 | 107.8 | 23.9 | 53 | B |
| VAL C | 920 | 163.9 | 110.0 | 21.4 | 60 | B |
| VAL O | 920 | 163.2 | 109.3 | 20.7 | 60 | B |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| PRO N | 921 | 164.3 | 111.3 | 21.0 | 63 | B |
| PRO CD | 921 | 165.0 | 112.3 | 21.7 | 63 | B |
| PRO CA | 921 | 163.9 | 111.8 | 19.6 | 66 | B |
| PRO CB | 921 | 164.7 | 113.1 | 19.5 | 64 | B |
| PRO CG | 921 | 164.8 | 113.6 | 20.9 | 63 | B |
| PRO C | 921 | 164.1 | 110.8 | 18.5 | 69 | B |
| PRO O | 921 | 165.2 | 110.7 | 18.0 | 69 | B |
| GLY N | 922 | 163.1 | 110.0 | 18.3 | 74 | B |
| GLY CA | 922 | 163.2 | 108.9 | 17.3 | 80 | B |
| GLY C | 922 | 163.0 | 109.3 | 15.8 | 84 | B |
| GLY O | 922 | 162.6 | 110.4 | 15.5 | 85 | B |
| PHE N | 923 | 163.4 | 108.3 | 15.0 | 88 | B |
| PHE CA | 923 | 163.3 | 108.5 | 13.5 | 91 | B |
| PHE CB | 923 | 164.8 | 108.5 | 13.0 | 93 | B |
| PHE CG | 923 | 165.8 | 109.0 | 13.9 | 94 | B |
| PHE CD1 | 923 | 166.1 | 110.3 | 14.0 | 95 | B |
| PHE CD2 | 923 | 166.5 | 108.1 | 14.8 | 95 | B |
| PHE CE1 | 923 | 167.1 | 110.8 | 14.9 | 95 | B |
| PHE CE2 | 923 | 167.4 | 108.6 | 15.7 | 95 | B |
| PHE CZ | 923 | 167.8 | 109.9 | 15.7 | 95 | B |
| PHE C | 923 | 162.5 | 107.4 | 13.0 | 92 | B |
| PHE OT1 | 923 | 163.0 | 106.2 | 13.0 | 93 | B |
| PHE OT2 | 923 | 161.3 | 107.6 | 12.8 | 93 | B |
| ZIN ZN | 1000 | 191.8 | 126.9 | 39.0 | 28 | Z |
| FPP P | 2001 | 197.0 | 126.1 | 33.2 | 22 | F |
| FPP O | 2001 | 196.9 | 127.7 | 33.2 | 22 | F |
| FPP 01 | 2001 | 198.5 | 125.8 | 32.7 | 22 | F |
| FPP 02 | 2001 | 196.7 | 125.5 | 34.6 | 24 | F |
| FPP 03 | 2001 | 196.0 | 125.5 | 32.1 | 22 | F |
| FPP C | 2001 | 195.9 | 124.2 | 31.7 | 22 | F |
| FPP C1 | 2001 | 193.8 | 123.3 | 30.4 | 22 | F |
| FPP C2 | 2001 | 194.4 | 123.7 | 31.5 | 22 | F |
| FPP C3 | 2001 | 192.4 | 122.7 | 30.4 | 22 | F |
| FPP C4 | 2001 | 194.4 | 123.4 | 29.0 | 21 | F |
| FPP C5 | 2001 | 191.8 | 122.4 | 31.8 | 22 | F |
| FPP C6 | 2001 | 189.4 | 122.1 | 32.6 | 20 | F |
| FPP C7 | 2001 | 190.4 | 121.8 | 31.7 | 21 | F |
| FPP C8 | 2001 | 189.5 | 123.1 | 33.7 | 20 | F |
| FPP C9 | 2001 | 188.2 | 121.2 | 32.6 | 19 | F |
| FPP C10 | 2001 | 187.0 | 121.9 | 31.9 | 18 | F |
| FPP C11 | 2001 | 185.7 | 121.1 | 32.0 | 17 | F |
| FPP C12 | 2001 | 184.6 | 121.4 | 31.4 | 17 | F |
| FPP C13 | 2001 | 184.4 | 122.6 | 30.5 | 18 | F |
| FPP C14 | 2001 | 183.4 | 120.5 | 31.5 | 17 | F |
| FPP P1 | 2001 | 197.6 | 124.4 | 35.2 | 24 | F |
| FPP 04 | 2001 | 196.9 | 124.0 | 36.6 | 24 | F |
| FPP 05 | 2001 | 197.6 | 123.1 | 34.3 | 24 | F |
| FPP 06 | 2001 | 199.0 | 124.9 | 35.5 | 24 | F |
| SCH C1 | 2002 | 184.9 | 127.1 | 32.3 | 26 | I |
| SCH N2 | 2002 | 185.7 | 128.1 | 31.9 | 26 | I |
| SCH C3 | 2002 | 187.0 | 128.1 | 32.3 | 25 | I |
| SCH C4 | 2002 | 187.6 | 127.1 | 33.1 | 25 | I |
| SCH C5 | 2002 | 186.7 | 126.1 | 33.5 | 25 | I |
| SCH C6 | 2002 | 185.4 | 126.1 | 33.1 | 25 | I |
| SCH C9 | 2002 | 187.8 | 129.2 | 31.8 | 26 | I |
| SCH C10 | 2002 | 189.0 | 128.9 | 30.9 | 25 | I |
| SCH C11 | 2002 | 189.9 | 127.9 | 31.2 | 27 | I |
| SCH C12 | 2002 | 190.0 | 126.9 | 32.4 | 26 | I |
| SCH C13 | 2002 | 189.0 | 127.2 | 33.5 | 26 | I |
| SCH C18 | 2002 | 189.1 | 129.7 | 29.8 | 24 | I |
| SCH C19 | 2002 | 190.1 | 129.5 | 28.9 | 26 | I |
| SCH C20 | 2002 | 191.1 | 128.5 | 29.1 | 27 | I |
| SCH C21 | 2002 | 191.0 | 127.7 | 30.3 | 27 | I |
| SCH C24 | 2002 | 188.3 | 130.2 | 33.0 | 27 | I |
| SCH C25 | 2002 | 188.4 | 131.6 | 32.5 | 27 | I |
| SCH C26 | 2002 | 188.6 | 132.7 | 33.6 | 29 | I |
| SCH N27 | 2002 | 187.8 | 132.5 | 34.8 | 30 | I |
| SCH C28 | 2002 | 187.7 | 131.1 | 35.3 | 30 | I |
| SCH C29 | 2002 | 187.3 | 130.1 | 34.2 | 28 | I |
| SCHBR38 | 2002 | 184.2 | 124.7 | 33.7 | 28 | I |
| SCHBR39 | 2002 | 192.3 | 126.4 | 30.6 | 31 | I |
| SCHCL40 | 2002 | 192.4 | 128.2 | 28.1 | 25 | I |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| SCH C41 | 2002 | 187.2 | 133.5 | 35.4 | 30 | I |
| SCH 042 | 2002 | 186.5 | 133.4 | 36.4 | 33 | I |
| SCH C43 | 2002 | 187.5 | 134.9 | 34.9 | 31 | I |
| SCH C44 | 2002 | 187.2 | 136.0 | 35.9 | 30 | I |
| SCH C47 | 2002 | 187.1 | 137.4 | 35.3 | 30 | I |
| SCH C48 | 2002 | 187.1 | 138.6 | 36.3 | 30 | I |
| SCH N49 | 2002 | 188.1 | 138.4 | 37.3 | 31 | I |
| SCH C50 | 2002 | 188.0 | 137.1 | 38.1 | 30 | I |
| SCH C51 | 2002 | 188.2 | 136.0 | 37.1 | 30 | I |
| SCH C61 | 2002 | 189.1 | 139.2 | 37.6 | 33 | I |
| SCH 062 | 2002 | 190.0 | 138.9 | 38.3 | 35 | I |
| SCH N63 | 2002 | 189.0 | 140.4 | 36.9 | 34 | I |
| HOH OH2 | 1001 | 195.7 | 134.3 | 28.0 | 21 | W |
| HOH OH2 | 1002 | 188.3 | 129.9 | 17.0 | 15 | W |
| HOH OH2 | 1003 | 202.0 | 124.3 | 44.4 | 17 | W |
| HOH OH2 | 1004 | 203.6 | 117.7 | 25.9 | 14 | W |
| HOH OH2 | 1005 | 198.5 | 115.4 | 20.3 | 19 | W |
| HOH OH2 | 1006 | 188.9 | 124.1 | 29.9 | 18 | W |
| HOH OH2 | 1007 | 200.2 | 114.9 | 34.8 | 16 | W |
| HOH OH2 | 1008 | 185.9 | 127.8 | 28.3 | 24 | W |
| HOH OH2 | 1009 | 192.7 | 123.5 | 18.2 | 23 | W |
| HOH OH2 | 1010 | 198.3 | 126.1 | 29.8 | 16 | W |
| HOH OH2 | 1011 | 197.4 | 117.7 | 19.3 | 17 | W |
| HOH OH2 | 1012 | 205.3 | 120.2 | 34.9 | 16 | W |
| HOH OH2 | 1013 | 189.2 | 130.4 | 25.4 | 17 | W |
| HOH OH2 | 1014 | 192.1 | 125.3 | 20.7 | 19 | W |
| HOH OH2 | 1015 | 186.7 | 125.5 | 28.8 | 22 | W |
| HOH OH2 | 1046 | 203.0 | 109.6 | 23.6 | 23 | W |
| HOH OH2 | 1017 | 184.6 | 130.1 | 30.4 | 25 | W |
| HOH OH2 | 1018 | 193.9 | 124.3 | 22.5 | 20 | W |
| HOH OH2 | 1019 | 194.6 | 119.0 | 18.9 | 23 | W |
| HOH OH2 | 1020 | 180.1 | 133.7 | 21.3 | 20 | W |
| HOH OH2 | 1021 | 203.8 | 120.4 | 32.7 | 18 | W |
| HOH OH2 | 1022 | 207.4 | 126.4 | 33.4 | 25 | W |
| HOH OH2 | 1023 | 204.4 | 127.6 | 36.9 | 26 | W |
| HOH OH2 | 1024 | 181.7 | 104.6 | 22.8 | 27 | W |
| HOH OH2 | 1025 | 191.7 | 121.8 | 22.7 | 27 | W |
| HOH OH2 | 1026 | 178.3 | 138.0 | 20.2 | 30 | W |
| HOH OH2 | 1027 | 186.2 | 126.7 | 23.9 | 21 | W |
| HOH OH2 | 1028 | 200.2 | 125.5 | 37.8 | 22 | W |
| HOH OH2 | 1029 | 188.3 | 136.9 | 26.9 | 28 | W |
| HOH OH2 | 1030 | 200.0 | 132.8 | 29.9 | 28 | W |
| HOH OH2 | 1031 | 182.4 | 129.5 | 26.2 | 27 | W |
| HOH OH2 | 1032 | 205.7 | 125.0 | 37.1 | 27 | W |
| HOH OH2 | 1033 | 198.2 | 103.7 | 28.2 | 38 | W |
| HOH OH2 | 1034 | 203.8 | 119.9 | 48.2 | 26 | W |
| HOH OH2 | 1035 | 195.9 | 127.4 | 29.4 | 25 | W |
| HOH OH2 | 1036 | 183.5 | 127.3 | 27.5 | 30 | W |
| HOH OH2 | 1037 | 180.9 | 120.8 | 36.7 | 28 | W |
| HOH OH2 | 1038 | 190.7 | 120.8 | 17.0 | 31 | W |
| HOH OH2 | 1039 | 210.0 | 125.3 | 33.1 | 21 | W |
| HOH OH2 | 1040 | 198.4 | 122.5 | 38.2 | 21 | W |
| HOH OH2 | 1041 | 201.1 | 130.7 | 28.8 | 21 | W |
| HOH OH2 | 1042 | 192.9 | 121.5 | 45.2 | 26 | W |
| HOH OH2 | 1043 | 201.4 | 127.9 | 36.7 | 34 | W |
| HOH OH2 | 1044 | 194.2 | 139.9 | 8.6 | 22 | W |
| HOH OH2 | 1045 | 192.1 | 118.4 | 18.4 | 24 | W |
| HOH OH2 | 1046 | 202.1 | 115.3 | 46.7 | 34 | W |
| HOH OH2 | 1047 | 190.2 | 132.1 | 37.4 | 30 | W |
| HOH OH2 | 1048 | 189.4 | 132.3 | 27.3 | 29 | W |
| HOH OH2 | 1049 | 190.8 | 134.8 | 26.7 | 31 | W |
| HOH OH2 | 1050 | 180.2 | 127.9 | 15.7 | 32 | W |
| HOH OH2 | 1051 | 190.3 | 139.4 | 25.4 | 37 | W |
| HOH OH2 | 1052 | 206.5 | 133.6 | 14.1 | 30 | W |
| HOH OH2 | 1053 | 186.9 | 129.2 | 25.4 | 23 | W |
| HOH OH2 | 1054 | 191.5 | 116.0 | 17.4 | 30 | W |
| HOH OH2 | 1055 | 194.2 | 139.4 | 5.7 | 21 | W |
| HOH OH2 | 1056 | 184.1 | 132.3 | 27.3 | 28 | W |
| HOH OH2 | 1057 | 200.9 | 126.4 | 31.4 | 26 | W |
| HOH OH2 | 1058 | 201.8 | 128.9 | 33.9 | 36 | W |
| HOH OH2 | 1059 | 192.4 | 131.0 | 32.5 | 31 | W |
| HOH OH2 | 1060 | 184.6 | 130.9 | 25.1 | 22 | W |
| HOH OH2 | 1061 | 176.2 | 138.0 | 26.3 | 28 | W |
| HOH OH2 | 1062 | 193.6 | 121.5 | 24.9 | 28 | W |
| HOH OH2 | 1063 | 202.9 | 139.3 | 14.3 | 32 | W |
| HOH OH2 | 1064 | 195.8 | 113.6 | 18.6 | 31 | W |
| HOH OH2 | 1065 | 207.7 | 124.8 | 11.6 | 24 | W |
| HOH OH2 | 1066 | 179.3 | 139.3 | 43.4 | 31 | W |
| HOH OH2 | 1067 | 185.6 | 130.0 | 16.5 | 27 | W |
| HOH OH2 | 1068 | 186.7 | 126.1 | 10.3 | 34 | W |
| HOH OH2 | 1069 | 191.9 | 136.7 | 37.9 | 34 | W |
| HOH OH2 | 1070 | 185.7 | 114.5 | 21.9 | 22 | W |
| HOH OH2 | 1071 | 207.2 | 108.9 | 11.3 | 37 | W |
| HOH OH2 | 1072 | 196.1 | 126.3 | 38.0 | 24 | W |
| HOH OH2 | 1073 | 201.9 | 111.1 | 25.6 | 24 | W |
| HOH OH2 | 1074 | 201.0 | 107.7 | 25.9 | 33 | W |
| HOH OH2 | 1075 | 211.9 | 126.6 | 31.8 | 25 | W |
| HOH OH2 | 1076 | 207.5 | 134.5 | 17.0 | 33 | W |
| HOH OH2 | 1077 | 204.3 | 112.7 | 35.1 | 26 | W |
| HOH OH2 | 1078 | 208.1 | 128.8 | 31.9 | 24 | W |
| HOH OH2 | 1079 | 187.7 | 134.2 | 29.9 | 32 | W |
| HOH OH2 | 1080 | 187.6 | 112.2 | 12.6 | 34 | W |
| HOH OH2 | 1081 | 203.7 | 111.6 | 11.6 | 32 | W |
| HOH OH2 | 1082 | 178.2 | 126.1 | 16.8 | 34 | W |
| HOH OH2 | 1083 | 192.6 | 132.5 | 30.4 | 39 | W |
| HOH OH2 | 1084 | 174.9 | 122.4 | 14.5 | 29 | W |
| HOH OH2 | 1085 | 203.2 | 127.9 | 9.2 | 20 | W |
| HOH OH2 | 1086 | 192.4 | 132.6 | 39.4 | 27 | W |
| HOH OH2 | 1087 | 208.5 | 137.2 | 22.2 | 48 | W |
| HOH OH2 | 1088 | 183.9 | 133.3 | 37.3 | 35 | W |
| HOH OH2 | 1089 | 212.1 | 129.9 | 29.3 | 34 | W |
| HOH OH2 | 1090 | 179.3 | 103.2 | 34.5 | 36 | W |
| HOH OH2 | 1091 | 185.0 | 128.3 | 11.2 | 36 | W |
| HOH OH2 | 1092 | 212.5 | 125.8 | 29.3 | 25 | W |
| HOH OH2 | 1093 | 201.7 | 110.0 | 39.1 | 35 | W |
| HOH OH2 | 1094 | 192.5 | 126.8 | 35.8 | 34 | W |
| HOH OH2 | 1095 | 199.2 | 109.1 | 24.5 | 34 | W |
| HOH OH2 | 1096 | 187.9 | 124.2 | 12.1 | 33 | W |
| HOH OH2 | 1097 | 190.7 | 103.0 | 22.2 | 32 | W |
| HOH OH2 | 1098 | 185.2 | 158.5 | 8.1 | 42 | W |
| HOH OH2 | 1099 | 187.2 | 127.8 | 18.2 | 30 | W |
| HOH OH2 | 1100 | 187.5 | 124.9 | 8.1 | 45 | W |
| HOH OH2 | 1101 | 191.4 | 132.1 | 41.9 | 27 | W |
| HOH OH2 | 1102 | 201.1 | 137.1 | 27.9 | 52 | W |
| HOH OH2 | 1103 | 192.3 | 141.9 | 18.2 | 34 | W |
| HOH OH2 | 1104 | 213.6 | 113.9 | 16.5 | 30 | W |
| HOH OH2 | 1105 | 204.4 | 118.0 | 41.4 | 29 | W |
| HOH OH2 | 1106 | 188.1 | 106.4 | 46.2 | 29 | W |
| HOH OH2 | 1107 | 179.1 | 115.3 | 47.8 | 34 | W |
| HOH OH2 | 1108 | 190.4 | 134.8 | 39.6 | 25 | W |
| HOH OH2 | 1109 | 189.3 | 101.2 | 23.8 | 42 | W |
| HOH OH2 | 1110 | 204.6 | 130.6 | 42.5 | 29 | W |
| HOH OH2 | 1111 | 211.6 | 123.4 | 30.0 | 26 | W |
| HOH OH2 | 1112 | 177.0 | 127.9 | 13.1 | 37 | W |
| HOH OH2 | 1113 | 200.4 | 107.2 | 44.1 | 36 | W |
| HOH OH2 | 1114 | 186.9 | 98.8 | 21.9 | 41 | W |
| HOH OH2 | 1115 | 198.5 | 142.5 | 12.8 | 47 | W |
| HOH OH2 | 1116 | 174.9 | 118.7 | 31.8 | 27 | W |
| HOH OH2 | 1117 | 220.9 | 119.9 | 25.1 | 38 | W |
| HOH OH2 | 1118 | 208.9 | 132.7 | 48.8 | 41 | W |
| HOH OH2 | 1119 | 175.2 | 108.3 | 35.5 | 40 | W |
| HOH OH2 | 1120 | 182.8 | 100.1 | 23.2 | 42 | W |
| HOH OH2 | 1121 | 201.5 | 132.1 | 32.9 | 48 | W |
| HOH OH2 | 1122 | 197.6 | 114.9 | 15.1 | 38 | W |
| HOH OH2 | 1123 | 211.1 | 127.7 | 27.8 | 29 | W |
| HOH OH2 | 1124 | 162.9 | 134.0 | 25.3 | 39 | W |
| HOH OH2 | 1125 | 213.9 | 127.7 | 21.6 | 37 | W |
| HOH OH2 | 1126 | 220.3 | 126.0 | 32.0 | 48 | W |
| HOH OH2 | 1127 | 199.0 | 103.3 | 31.6 | 35 | W |
| HOH OH2 | 1128 | 210.7 | 135.2 | 24.4 | 40 | W |
| HOH OH2 | 1129 | 201.4 | 108.1 | 22.0 | 45 | W |
| HOH OH2 | 1130 | 172.4 | 144.0 | 28.1 | 37 | W |
| HOH OH2 | 1131 | 195.5 | 111.4 | 47.4 | 31 | W |
| HOH OH2 | 1132 | 202.4 | 109.2 | 13.1 | 50 | W |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| HOH OH2 | 1133 | 215.0 | 130.3 | 29.5 | 39 | W |
| HOH OH2 | 1134 | 212.0 | 124.5 | 17.4 | 34 | W |
| HOH OH2 | 1135 | 189.1 | 114.6 | 16.2 | 34 | W |
| HOH OH2 | 1136 | 168.5 | 122.8 | 22.2 | 29 | W |
| HOH OH2 | 1137 | 177.9 | 141.2 | 24.4 | 33 | W |
| HOH OH2 | 1138 | 219.4 | 124.1 | 26.2 | 45 | W |
| HOH OH2 | 1139 | 195.1 | 141.5 | 4.4 | 36 | W |
| HOH OH2 | 1140 | 211.3 | 120.0 | 16.0 | 29 | W |
| HOH OH2 | 1141 | 181.7 | 139.1 | 23.9 | 32 | W |
| HOH OH2 | 1142 | 178.0 | 111.9 | 46.4 | 57 | W |
| HOH OH2 | 1143 | 185.8 | 151.8 | 10.3 | 36 | W |
| HOH OH2 | 1144 | 172.6 | 139.1 | 17.9 | 44 | W |
| HOH OH2 | 1145 | 215.2 | 102.2 | 15.8 | 43 | W |
| HOH OH2 | 1146 | 214.1 | 107.1 | 19.7 | 33 | W |
| HOH OH2 | 1147 | 218.4 | 123.1 | 49.2 | 44 | W |
| HOH OH2 | 1148 | 200.9 | 96.8 | 26.4 | 50 | W |
| HOH OH2 | 1149 | 211.2 | 133.4 | 16.9 | 44 | W |
| HOH OH2 | 1150 | 203.4 | 135.4 | 11.0 | 36 | W |
| HOH OH2 | 1151 | 178.2 | 141.2 | 41.7 | 34 | W |
| HOH OH2 | 1152 | 221.1 | 124.3 | 40.7 | 49 | W |
| HOH OH2 | 1153 | 184.0 | 135.1 | 27.0 | 29 | W |
| HOH OH2 | 1154 | 191.9 | 133.7 | 36.2 | 62 | W |
| HOH OH2 | 1155 | 195.9 | 123.9 | 17.9 | 29 | W |
| HOH OH2 | 1156 | 175.1 | 101.7 | 16.1 | 47 | W |
| HOH OH2 | 1157 | 203.6 | 135.6 | 7.7 | 38 | W |
| HOH OH2 | 1158 | 189.6 | 107.1 | 17.8 | 40 | W |
| HOH OH2 | 1159 | 177.2 | 144.0 | 24.6 | 30 | W |
| HOH OH2 | 1160 | 196.4 | 123.9 | 20.9 | 26 | W |
| HOH OH2 | 1161 | 205.2 | 103.6 | 15.1 | 64 | W |
| HOH OH2 | 1162 | 172.1 | 121.8 | 14.4 | 36 | W |
| HOH OH2 | 1163 | 194.1 | 143.8 | 17.6 | 42 | W |
| HOH OH2 | 1164 | 194.3 | 141.0 | 1.6 | 39 | W |
| HOH OH2 | 1165 | 214.4 | 127.7 | 33.0 | 34 | W |
| HOH OH2 | 1166 | 211.0 | 129.1 | 31.6 | 30 | W |
| HOH OH2 | 1167 | 179.3 | 120.7 | 11.7 | 48 | W |
| HOH OH2 | 1168 | 205.3 | 122.0 | 41.5 | 29 | W |
| HOH OH2 | 1169 | 170.0 | 142.6 | 37.6 | 41 | W |
| HOH OH2 | 1170 | 205.7 | 118.3 | 45.8 | 46 | W |
| HOH OH2 | 1171 | 202.4 | 120.9 | 3.1 | 50 | W |
| HOH OH2 | 1172 | 216.3 | 115.3 | 17.3 | 33 | W |
| HOH OH2 | 1173 | 208.6 | 116.8 | 41.5 | 36 | W |
| HOH OH2 | 1174 | 218.9 | 125.1 | 46.6 | 52 | W |
| HOH OH2 | 1175 | 157.0 | 125.0 | 36.3 | 41 | W |
| HOH OH2 | 1176 | 206.4 | 130.8 | 33.0 | 33 | W |
| HOH OH2 | 1177 | 206.3 | 119.2 | 48.5 | 41 | W |
| HOH OH2 | 1178 | 204.4 | 132.7 | 13.1 | 34 | W |
| HOH OH2 | 1179 | 191.2 | 100.7 | 25.7 | 45 | W |
| HOH OH2 | 1180 | 193.7 | 130.2 | 38.5 | 48 | W |
| HOH OH2 | 1181 | 172.8 | 130.2 | 16.3 | 43 | W |
| HOH OH2 | 1182 | 159.9 | 126.5 | 29.7 | 41 | W |
| HOH OH2 | 1183 | 207.9 | 122.8 | 7.1 | 42 | W |
| HOH OH2 | 1184 | 215.5 | 121.5 | 17.4 | 41 | W |
| HOH OH2 | 1185 | 204.1 | 127.5 | 33.6 | 39 | W |
| HOH OH2 | 1186 | 192.1 | 144.1 | 6.6 | 45 | W |
| HOH OH2 | 1187 | 207.0 | 137.1 | 17.1 | 57 | W |
| HOH OH2 | 1188 | 212.1 | 90.1 | 38.0 | 44 | W |
| HOH OH2 | 1189 | 201.5 | 105.9 | 19.3 | 56 | W |
| HOH OH2 | 1190 | 205.4 | 136.6 | 12.5 | 48 | W |
| HOH OH2 | 1191 | 177.6 | 133.6 | 8.1 | 37 | W |
| HOH OH2 | 1192 | 198.3 | 126.5 | 39.4 | 33 | W |
| HOH OH2 | 1193 | 187.4 | 141.5 | 31.1 | 31 | W |
| HOH OH2 | 1194 | 205.9 | 124.2 | 39.8 | 35 | W |
| HOH OH2 | 1195 | 205.5 | 103.4 | 26.6 | 45 | W |
| HOH OH2 | 1196 | 176.5 | 151.9 | 22.0 | 47 | W |
| HOH OH2 | 1197 | 188.2 | 114.7 | 13.3 | 48 | W |
| HOH OH2 | 1198 | 204.9 | 138.7 | 24.2 | 41 | W |
| HOH OH2 | 1199 | 186.7 | 131.8 | 29.0 | 39 | W |
| HOH OH2 | 1200 | 194.5 | 118.3 | 9.7 | 55 | W |
| HOH OH2 | 1201 | 160.4 | 118.0 | 26.8 | 51 | W |
| HOH OH2 | 1202 | 186.1 | 122.4 | 13.3 | 41 | W |
| HOH OH2 | 1203 | 181.4 | 147.9 | 35.9 | 38 | W |
| HOH OH2 | 1204 | 189.3 | 120.5 | 14.5 | 48 | W |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| HOH OH2 | 1205 | 173.4 | 108.1 | 39.7 | 55 | W |
| HOH OH2 | 1206 | 216.7 | 122.8 | 19.7 | 40 | W |
| HOH OH2 | 1207 | 207.1 | 120.0 | 42.1 | 39 | W |
| HOH OH2 | 1208 | 213.8 | 117.9 | 43.6 | 36 | W |
| HOH OH2 | 1209 | 211.4 | 127.4 | 23.1 | 36 | W |
| HOH OH2 | 1210 | 193.6 | 116.9 | 16.0 | 41 | W |
| HOH OH2 | 1211 | 191.5 | 123.3 | 65.6 | 49 | W |
| HOH OH2 | 1212 | 178.6 | 142.2 | 45.4 | 50 | W |
| HOH OH2 | 1213 | 182.5 | 99.9 | 31.8 | 39 | W |
| HOH OH2 | 1214 | 211.4 | 120.7 | 10.9 | 47 | W |
| HOH OH2 | 1215 | 209.3 | 127.0 | 12.3 | 33 | W |
| HOH OH2 | 1216 | 211.5 | 130.4 | 18.5 | 38 | W |
| HOH OH2 | 1217 | 165.4 | 105.5 | 27.3 | 51 | W |
| HOH OH2 | 1218 | 193.9 | 128.8 | 33.1 | 41 | W |
| HOH OH2 | 1219 | 190.6 | 122.7 | 5.9 | 43 | W |
| HOH OH2 | 1220 | 209.8 | 116.6 | 47.5 | 45 | W |
| HOH OH2 | 1221 | 196.7 | 107.4 | 19.1 | 52 | W |
| HOH OH2 | 1222 | 183.8 | 158.5 | 20.1 | 34 | W |
| HOH OH2 | 1223 | 215.7 | 128.2 | 24.5 | 55 | W |
| HOH OH2 | 1224 | 175.1 | 145.8 | 5.0 | 47 | W |
| HOH OH2 | 1225 | 200.8 | 105.3 | 36.7 | 40 | W |
| HOH OH2 | 1226 | 191.3 | 142.8 | 10.8 | 42 | W |
| HOH OH2 | 1227 | 157.5 | 122.3 | 38.9 | 58 | W |
| HOH OH2 | 1228 | 210.8 | 130.8 | 38.5 | 40 | W |
| HOH OH2 | 1229 | 209.6 | 123.1 | 9.8 | 42 | W |
| HOH OH2 | 1230 | 196.6 | 119.6 | 6.9 | 48 | W |
| HOH OH2 | 1231 | 175.1 | 141.0 | 30.1 | 35 | W |
| HOH OH2 | 1232 | 190.0 | 159.7 | 15.0 | 42 | W |
| HOH OH2 | 1233 | 172.1 | 118.0 | 46.7 | 37 | W |
| HOH OH2 | 1234 | 162.7 | 119.4 | 27.6 | 40 | W |
| HOH OH2 | 1235 | 208.8 | 98.3 | 25.8 | 52 | W |
| HOH OH2 | 1236 | 202.0 | 100.9 | 43.9 | 38 | W |
| HOH OH2 | 1237 | 209.2 | 131.4 | 36.1 | 43 | W |
| HOH OH2 | 1238 | 185.7 | 149.3 | 10.1 | 38 | W |
| HOH OH2 | 1239 | 212.0 | 125.6 | 12.7 | 46 | W |
| HOH OH2 | 1240 | 213.0 | 109.0 | 18.2 | 39 | W |
| HOH OH2 | 1241 | 218.0 | 120.9 | 34.6 | 49 | W |
| HOH OH2 | 1242 | 212.3 | 95.1 | 26.6 | 47 | W |
| HOH OH2 | 1243 | 192.9 | 146.6 | 23.8 | 53 | W |
| HOH OH2 | 1244 | 189.9 | 145.2 | 26.6 | 56 | W |
| HOH OH2 | 1245 | 169.1 | 108.3 | 26.3 | 39 | W |
| HOH OH2 | 1246 | 170.5 | 147.1 | 12.2 | 56 | W |
| HOH OH2 | 1247 | 195.4 | 108.8 | 48.1 | 37 | W |
| HOH OH2 | 1248 | 211.4 | 118.7 | 13.7 | 36 | W |
| HOH OH2 | 1249 | 201.6 | 114.9 | 53.7 | 37 | W |
| HOH OH2 | 1250 | 187.0 | 149.7 | 6.3 | 48 | W |
| HOH OH2 | 1251 | 217.1 | 128.4 | 31.3 | 55 | W |
| HOH OH2 | 1252 | 180.0 | 127.2 | 58.1 | 39 | W |
| HOH OH2 | 1253 | 202.9 | 103.1 | 28.9 | 41 | W |
| HOH OH2 | 1254 | 213.5 | 123.4 | 13.5 | 48 | W |
| HOH OH2 | 1255 | 196.2 | 116.2 | 17.3 | 55 | W |
| HOH OH2 | 1256 | 196.9 | 143.3 | 17.1 | 58 | W |
| HOH OH2 | 1257 | 213.8 | 126.4 | 19.0 | 48 | W |
| HOH OH2 | 1258 | 175.8 | 138.7 | 21.9 | 55 | W |
| HOH OH2 | 1259 | 183.0 | 158.8 | 22.8 | 43 | W |
| HOH OH2 | 1260 | 212.3 | 118.9 | 53.4 | 45 | W |
| HOH OH2 | 1261 | 204.2 | 138.7 | 6.1 | 55 | W |
| HOH OH2 | 1262 | 185.5 | 127.5 | 20.9 | 34 | W |
| HOH OH2 | 1263 | 200.6 | 141.7 | 8.4 | 54 | W |
| HOH OH2 | 1264 | 203.3 | 134.7 | 25.5 | 39 | W |
| HOH OH2 | 1265 | 219.5 | 123.6 | 37.2 | 48 | W |
| HOH OH2 | 1266 | 204.2 | 132.5 | 32.5 | 53 | W |
| HOH OH2 | 1267 | 211.3 | 109.9 | 12.2 | 44 | W |
| HOH OH2 | 1268 | 192.1 | 113.4 | 18.0 | 45 | W |
| HOH OH2 | 1269 | 184.3 | 98.6 | 28.0 | 50 | W |
| HOH OH2 | 1270 | 169.6 | 121.6 | 47.1 | 68 | W |
| HOH OH2 | 1271 | 210.6 | 125.5 | 8.8 | 50 | W |
| HOH OH2 | 1272 | 180.5 | 140.5 | 48.1 | 54 | W |
| HOH OH2 | 1273 | 200.0 | 109.5 | 19.4 | 56 | W |
| HOH OH2 | 1274 | 199.7 | 107.7 | 58.8 | 51 | W |
| HOH OH2 | 1275 | 205.3 | 118.6 | 5.8 | 43 | W |
| HOH OH2 | 1276 | 207.2 | 115.9 | 5.7 | 46 | W |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| HOH OH2 | 1277 | 171.7 | 131.5 | 20.7 | 39 | W |
| HOH OH2 | 1278 | 161.2 | 127.6 | 37.2 | 47 | W |
| HOH OH2 | 1279 | 212.6 | 102.9 | 53.5 | 54 | W |
| HOH OH2 | 1280 | 194.2 | 135.9 | 40.1 | 44 | W |
| HOH OH2 | 1281 | 221.6 | 113.4 | 44.5 | 55 | W |
| HOH OH2 | 1282 | 190.2 | 140.7 | 30.9 | 60 | W |
| HOH OH2 | 1283 | 172.5 | 148.6 | 25.3 | 56 | W |
| HOH OH2 | 1284 | 177.6 | 110.8 | 52.9 | 44 | W |
| HOH OH2 | 1285 | 203.9 | 115.7 | 42.8 | 49 | W |
| HOH OH2 | 1286 | 169.0 | 105.5 | 26.1 | 57 | W |
| HOH OH2 | 1287 | 192.6 | 124.0 | 2.2 | 51 | W |
| HOH OH2 | 1288 | 174.0 | 145.7 | 24.9 | 42 | W |
| HOH OH2 | 1289 | 197.3 | 111.6 | 25.9 | 33 | W |
| HOH OH2 | 1290 | 166.5 | 118.1 | 38.0 | 33 | W |
| HOH OH2 | 1291 | 181.2 | 141.4 | 39.7 | 48 | W |
| HOH OH2 | 1292 | 212.6 | 127.9 | 25.6 | 40 | W |
| HOH OH2 | 1293 | 191.1 | 134.2 | 1.8 | 40 | W |
| HOH OH2 | 1294 | 199.2 | 129.2 | 37.5 | 60 | W |
| HOH OH2 | 1295 | 189.7 | 110.1 | 53.2 | 41 | W |
| HOH OH2 | 1296 | 179.2 | 131.6 | 58.4 | 52 | W |
| HOH OH2 | 1297 | 204.0 | 96.4 | 34.8 | 57 | W |
| HOH OH2 | 1298 | 210.9 | 120.8 | 56.3 | 55 | W |
| HOH OH2 | 1299 | 206.0 | 129.3 | 3.1 | 61 | W |
| HOH OH2 | 1300 | 194.0 | 142.3 | 9.6 | 48 | W |
| HOH OH2 | 1301 | 195.3 | 113.3 | 60.3 | 52 | W |
| HOH OH2 | 1302 | 180.3 | 112.8 | 47.7 | 55 | W |
| HOH OH2 | 1303 | 209.1 | 113.8 | 48.1 | 49 | W |
| HOH OH2 | 1304 | 164.8 | 126.3 | 20.2 | 59 | W |
| HOH OH2 | 1305 | 219.8 | 118.8 | 21.9 | 52 | W |
| HOH OH2 | 1306 | 179.2 | 133.3 | 10.6 | 54 | W |
| HOH OH2 | 1307 | 202.5 | 109.0 | 36.6 | 37 | W |
| HOH OH2 | 1308 | 162.2 | 128.0 | 42.5 | 56 | W |
| HOH OH2 | 1309 | 203.8 | 106.7 | 35.2 | 42 | W |
| HOH OH2 | 1310 | 198.5 | 118.9 | 53.9 | 41 | W |
| HOH OH2 | 1311 | 217.4 | 104.5 | 15.9 | 53 | W |
| HOH OH2 | 1312 | 160.6 | 113.1 | 21.2 | 50 | W |
| HOH OH2 | 1313 | 219.5 | 104.4 | 19.6 | 52 | W |
| HOH OH2 | 1314 | 214.0 | 111.2 | 16.1 | 45 | W |
| HOH OH2 | 1315 | 187.6 | 133.5 | 55.7 | 48 | W |
| HOH OH2 | 1316 | 201.5 | 104.9 | 26.4 | 62 | W |
| HOH OH2 | 1317 | 206.8 | 106.0 | 38.8 | 53 | W |
| HOH OH2 | 1318 | 191.4 | 112.2 | 55.4 | 46 | W |
| HOH OH2 | 1319 | 190.9 | 130.8 | 53.0 | 46 | W |
| HOH OH2 | 1320 | 188.4 | 150.6 | 14.7 | 46 | W |
| HOH OH2 | 1321 | 181.3 | 107.7 | 14.5 | 47 | W |
| HOH OH2 | 1322 | 195.5 | 147.7 | 17.4 | 63 | W |
| HOH OH2 | 1323 | 199.1 | 99.5 | 54.4 | 52 | W |
| HOH OH2 | 1324 | 189.3 | 152.0 | 27.7 | 59 | W |
| HOH OH2 | 1325 | 163.4 | 120.7 | 41.4 | 52 | W |
| HOH OH2 | 1326 | 206.6 | 130.9 | 35.8 | 45 | W |
| HOH OH2 | 1327 | 184.0 | 148.8 | 37.1 | 60 | W |
| HOH OH2 | 1328 | 203.8 | 139.2 | 17.2 | 58 | W |
| HOH OH2 | 1329 | 187.0 | 149.4 | 12.4 | 51 | W |
| HOH OH2 | 1330 | 190.4 | 122.6 | 12.1 | 53 | W |
| HOH OH2 | 1331 | 207.3 | 106.0 | 41.7 | 49 | W |
| HOH OH2 | 1332 | 200.1 | 98.4 | 32.1 | 70 | W |
| HOH OH2 | 1333 | 201.5 | 140.8 | 20.6 | 55 | W |
| HOH OH2 | 1334 | 187.3 | 124.3 | 5.4 | 60 | W |
| HOH OH2 | 1335 | 184.8 | 138.3 | 41.1 | 47 | W |
| HOH OH2 | 1336 | 189.8 | 157.8 | 22.5 | 34 | W |
| HOH OH2 | 1337 | 186.6 | 147.6 | 28.0 | 66 | W |
| HOH OH2 | 1338 | 202.8 | 140.6 | 23.7 | 58 | W |
| HOH OH2 | 1339 | 170.4 | 139.7 | 21.8 | 54 | W |
| HOH OH2 | 1340 | 159.5 | 121.5 | 41.4 | 69 | W |
| HOH OH2 | 1341 | 187.1 | 105.8 | 18.3 | 42 | W |
| HOH OH2 | 1342 | 174.7 | 128.1 | 14.1 | 53 | W |
| HOH OH2 | 1343 | 173.4 | 135.2 | 9.1 | 45 | W |
| HOH OH2 | 1344 | 184.3 | 121.0 | 56.3 | 41 | W |
| HOH OH2 | 1345 | 190.3 | 147.8 | 14.4 | 41 | W |
| HOH OH2 | 1346 | 194.7 | 121.3 | 4.8 | 50 | W |
| HOH OH2 | 1347 | 176.9 | 130.9 | 9.9 | 63 | W |
| HOH OH2 | 1348 | 174.0 | 118.2 | 54.2 | 53 | W |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| HOH OH2 | 1349 | 202.0 | 131.5 | 43.1 | 61 | W |
| HOH OH2 | 1350 | 175.9 | 137.5 | 18.7 | 50 | W |
| HOH OH2 | 1351 | 179.9 | 138.8 | 50.5 | 47 | W |
| HOH OH2 | 1352 | 195.2 | 114.9 | 13.3 | 55 | W |
| HOH OH2 | 1353 | 198.4 | 103.4 | 58.2 | 47 | W |
| HOH OH2 | 1354 | 187.5 | 144.3 | 31.3 | 45 | W |
| HOH OH2 | 1355 | 174.7 | 124.0 | 52.8 | 38 | W |
| HOH OH2 | 1356 | 184.2 | 148.4 | 3.6 | 56 | W |
| HOH OH2 | 1357 | 170.1 | 144.7 | 27.3 | 56 | W |
| HOH OH2 | 1358 | 167.5 | 142.6 | 19.8 | 64 | W |
| HOH OH2 | 1359 | 162.2 | 125.8 | 24.1 | 52 | W |
| HOH OH2 | 1360 | 175.5 | 135.6 | 10.6 | 49 | W |
| HOH OH2 | 1361 | 193.8 | 115.4 | 62.4 | 59 | W |
| HOH OH2 | 1362 | 177.6 | 109.6 | 14.3 | 70 | W |
| HOH OH2 | 1363 | 203.0 | 130.4 | 6.8 | 42 | W |
| HOH OH2 | 1364 | 196.6 | 101.3 | 22.1 | 55 | W |
| HOH OH2 | 1365 | 156.8 | 125.3 | 30.2 | 57 | W |
| HOH OH2 | 1366 | 203.7 | 96.6 | 38.5 | 57 | W |
| HOH OH2 | 1367 | 193.9 | 130.5 | 57.4 | 48 | W |
| HOH OH2 | 1368 | 180.9 | 149.6 | 33.7 | 61 | W |
| HOH OH2 | 1369 | 219.1 | 125.3 | 34.8 | 54 | W |
| HOH OH2 | 1370 | 187.5 | 144.2 | 28.0 | 51 | W |
| HOH OH2 | 1371 | 183.7 | 151.1 | 20.7 | 39 | W |
| HOH OH2 | 1372 | 176.3 | 148.8 | 29.7 | 48 | W |
| HOH OH2 | 1373 | 191.8 | 142.0 | 0.7 | 61 | W |
| HOH OH2 | 1374 | 214.3 | 125.3 | 43.9 | 44 | W |
| HOH OH2 | 1375 | 176.9 | 104.4 | 21.0 | 49 | W |
| HOH OH2 | 1376 | 216.9 | 112.9 | 14.1 | 55 | W |
| HOH OH2 | 1377 | 197.5 | 153.1 | 18.0 | 56 | W |
| HOH OH2 | 1378 | 184.6 | 145.4 | 1.0 | 59 | W |
| HOH OH2 | 1379 | 209.6 | 120.7 | 42.2 | 41 | W |
| HOH OH2 | 1380 | 184.5 | 110.0 | 54.8 | 38 | W |
| HOH OH2 | 1381 | 214.9 | 114.0 | 37.4 | 50 | W |
| HOH OH2 | 1382 | 212.7 | 122.2 | 16.4 | 47 | W |
| HOH OH2 | 1383 | 187.8 | 143.4 | 1.3 | 57 | W |
| HOH OH2 | 1384 | 206.9 | 100.8 | 20.9 | 54 | W |
| HOH OH2 | 1385 | 158.7 | 131.8 | 32.0 | 56 | W |
| HOH OH2 | 1386 | 174.4 | 146.8 | 28.4 | 55 | W |
| HOH OH2 | 1387 | 191.2 | 129.5 | 35.7 | 64 | W |
| HOH OH2 | 1388 | 173.2 | 135.9 | 54.4 | 52 | W |
| HOH OH2 | 1389 | 218.0 | 116.4 | 28.2 | 59 | W |
| HOH OH2 | 1390 | 217.1 | 97.1 | 26.2 | 42 | W |
| HOH OH2 | 1391 | 175.7 | 125.5 | 15.2 | 56 | W |
| HOH OH2 | 1392 | 207.0 | 117.2 | 43.7 | 58 | W |
| HOH OH2 | 1393 | 169.1 | 124.4 | 46.5 | 68 | W |
| HOH OH2 | 1394 | 179.7 | 134.1 | 56.6 | 52 | W |
| HOH OH2 | 1395 | 169.8 | 108.4 | 29.2 | 55 | W |
| HOH OH2 | 1396 | 173.8 | 143.2 | 4.1 | 60 | W |
| HOH OH2 | 1397 | 159.5 | 118.6 | 39.2 | 54 | W |
| HOH OH2 | 1398 | 190.6 | 124.9 | 7.7 | 53 | W |
| HOH OH2 | 1399 | 212.3 | 92.4 | 39.4 | 51 | W |
| HOH OH2 | 1400 | 196.9 | 142.7 | 5.8 | 73 | W |
| HOH OH2 | 1401 | 212.8 | 127.2 | 16.6 | 55 | W |
| HOH OH2 | 1402 | 166.2 | 131.2 | 21.6 | 60 | W |
| HOH OH2 | 1403 | 203.3 | 132.5 | 27.3 | 43 | W |
| HOH OH2 | 1404 | 177.7 | 103.3 | 25.9 | 55 | W |
| HOH OH2 | 1405 | 175.0 | 106.0 | 21.9 | 52 | W |
| HOH OH2 | 1406 | 213.2 | 130.3 | 21.4 | 68 | W |
| HOH OH2 | 1407 | 214.8 | 129.1 | 27.1 | 65 | W |
| HOH OH2 | 1408 | 183.9 | 141.8 | 39.5 | 64 | W |
| HOH OH2 | 1409 | 164.1 | 128.8 | 24.2 | 59 | W |
| HOH OH2 | 1410 | 216.7 | 118.7 | 49.3 | 59 | W |
| HOH OH2 | 1411 | 210.9 | 118.2 | 42.3 | 48 | W |
| HOH OH2 | 1412 | 178.6 | 148.0 | 37.5 | 58 | W |
| HOH OH2 | 1413 | 185.6 | 136.2 | 55.8 | 56 | W |
| HOH OH2 | 1414 | 218.9 | 91.1 | 39.8 | 58 | W |
| HOH OH2 | 1415 | 207.9 | 131.5 | 13.5 | 54 | W |
| HOH OH2 | 1416 | 204.3 | 130.2 | 38.5 | 61 | W |
| HOH OH2 | 1417 | 165.9 | 136.6 | 32.5 | 43 | W |
| HOH OH2 | 1418 | 188.0 | 141.4 | 28.3 | 48 | W |
| HOH OH2 | 1419 | 207.9 | 133.3 | 32.2 | 67 | W |
| HOH OH2 | 1420 | 187.2 | 146.8 | 31.2 | 61 | W |

TABLE 3-continued

The following table lists the atomic structure coordinates for FPT in complex with FPP and the inhibitor SCH66381 as derived by X-ray diffraction from crystals of that complex. The abbreviations are the same as those used in Table 2.

| RES ATOM | # | X | Y | Z | B | C |
|---|---|---|---|---|---|---|
| HOH OH2 | 1421 | 189.5 | 104.8 | 19.3 | 62 | W |
| HOH OH2 | 1422 | 208.7 | 111.0 | 9.3 | 63 | W |
| HOH OH2 | 1423 | 202.4 | 133.7 | 59.8 | 75 | W |
| HOH OH2 | 1424 | 216.4 | 127.7 | 36.3 | 65 | W |
| HOH OH2 | 1425 | 217.8 | 116.9 | 15.4 | 53 | W |
| HOH OH2 | 1426 | 160.4 | 118.6 | 29.6 | 54 | W |
| HOH OH2 | 1427 | 174.7 | 133.2 | 7.4 | 58 | W |
| HOH OH2 | 1428 | 181.4 | 102.2 | 21.5 | 62 | W |
| HOH OH2 | 1429 | 171.7 | 109.9 | 34.7 | 66 | W |
| HOH OH2 | 1430 | 197.8 | 111.1 | 58.3 | 74 | W |
| HOH OH2 | 1431 | 183.9 | 105.6 | 11.6 | 52 | W |
| HOH OH2 | 1432 | 195.3 | 153.9 | 15.5 | 62 | W |
| HOH OH2 | 1433 | 202.0 | 138.1 | 3.0 | 48 | W |
| HOH OH2 | 1434 | 194.9 | 148.2 | 21.5 | 60 | W |
| HOH OH2 | 1435 | 204.3 | 111.4 | 54.3 | 54 | W |
| HOH OH2 | 1436 | 216.4 | 107.6 | 18.0 | 65 | W |
| HOH OH2 | 1437 | 174.7 | 145.5 | 31.2 | 59 | W |
| HOH OH2 | 1438 | 182.0 | 156.5 | 25.2 | 66 | W |

TABLE 4

The following table lists the atomic structure coordinates for FPT in complex with FPP and the inhibitor SCH66701 as derived by X-ray diffraction from crystals of that complex The abbreviations are the same as those used in Table 2

| RES | ATOM | # | X | Y | Z | B | C |
|---|---|---|---|---|---|---|---|
| GLY | C | 54 | 192.9 | 151.9 | 9.4 | 80 | A |
| GLY | O | 54 | 191.7 | 151.8 | 9.5 | 81 | A |
| GLY | N | 54 | 193.8 | 151.4 | 7.1 | 80 | A |
| GLY | CA | 54 | 193.5 | 152.5 | 8.1 | 80 | A |
| PHE | N | 55 | 193.8 | 151.5 | 10.3 | 80 | A |
| PHE | CA | 55 | 193.4 | 150.9 | 11.5 | 78 | A |
| PHE | CB | 55 | 194.3 | 149.7 | 11.8 | 79 | A |
| PHE | CG | 55 | 193.7 | 148.4 | 11.3 | 80 | A |
| PHE | CD1 | 55 | 194.2 | 147.8 | 10.1 | 80 | A |
| PHE | CD2 | 55 | 192.7 | 147.7 | 12.0 | 80 | A |
| PHE | CE1 | 55 | 193.7 | 146.6 | 9.7 | 80 | A |
| PHE | CE2 | 55 | 192.2 | 146.5 | 11.5 | 80 | A |
| PHE | CZ | 55 | 192.7 | 145.9 | 10.4 | 80 | A |
| PHE | C | 55 | 193.5 | 151.8 | 12.7 | 77 | A |
| PHE | O | 55 | 194.6 | 152.3 | 13.1 | 77 | A |
| LEU | N | 56 | 192.4 | 152.1 | 13.4 | 74 | A |
| LEU | CA | 56 | 192.4 | 152.9 | 14.6 | 71 | A |
| LEU | CB | 56 | 191.3 | 153.9 | 14.6 | 72 | A |
| LEU | CG | 56 | 191.6 | 155.4 | 14.8 | 73 | A |
| LEU | CD1 | 56 | 190.4 | 156.3 | 14.8 | 73 | A |
| LEU | CD2 | 56 | 192.4 | 155.6 | 16.1 | 72 | A |
| LEU | C | 56 | 192.5 | 152.1 | 15.8 | 69 | A |
| LEU | O | 56 | 191.6 | 151.4 | 16.2 | 69 | A |
| SER | N | 57 | 193.7 | 152.1 | 16.4 | 66 | A |
| SER | CA | 57 | 194.0 | 151.3 | 17.6 | 64 | A |
| SER | CB | 57 | 195.4 | 151.6 | 18.1 | 64 | A |
| SER | OG | 57 | 195.8 | 150.9 | 19.3 | 64 | A |
| SER | C | 57 | 193.0 | 151.5 | 18.7 | 62 | A |
| SER | O | 57 | 192.5 | 152.6 | 19.0 | 61 | A |
| LEU | N | 58 | 192.6 | 150.4 | 19.4 | 59 | A |
| LEU | CA | 58 | 191.7 | 150.5 | 20.5 | 57 | A |
| LEU | CB | 58 | 191.3 | 149.1 | 21.0 | 56 | A |
| LEU | CG | 58 | 189.9 | 148.6 | 20.9 | 56 | A |
| LEU | CD1 | 58 | 189.8 | 147.2 | 21.4 | 56 | A |
| LEU | CD2 | 58 | 188.9 | 149.5 | 21.6 | 55 | A |
| LEU | C | 58 | 192.4 | 151.2 | 21.6 | 57 | A |
| LEU | O | 58 | 191.8 | 151.7 | 22.6 | 57 | A |
| ASP | N | 59 | 193.7 | 151.3 | 21.5 | 57 | A |
| ASP | CA | 59 | 194.6 | 152.0 | 22.4 | 56 | A |
| ASP | CB | 59 | 195.9 | 151.2 | 22.6 | 60 | A |
| ASP | CG | 59 | 195.7 | 150.0 | 23.6 | 62 | A |

TABLE 4-continued

The following table lists the atomic structure coordinates for FPT in complex with FPP and the inhibitor SCH66701 as derived by X-ray diffraction from crystals of that complex The abbreviations are the same as those used in Table 2

| RES | ATOM | # | X | Y | Z | B | C |
|---|---|---|---|---|---|---|---|
| ASP | OD1 | 59 | 195.1 | 149.0 | 23.2 | 62 | A |
| ASP | OD2 | 59 | 196.2 | 150.1 | 24.7 | 62 | A |
| ASP | C | 59 | 195.0 | 153.4 | 22.0 | 54 | A |
| ASP | O | 59 | 195.6 | 154.2 | 22.8 | 54 | A |
| SER | N | 60 | 194.7 | 153.8 | 20.8 | 51 | A |
| SER | CA | 60 | 195.0 | 155.1 | 20.2 | 48 | A |
| SER | CB | 60 | 194.5 | 155.2 | 18.8 | 47 | A |
| SER | OG | 60 | 194.9 | 156.4 | 18.3 | 47 | A |
| SER | C | 60 | 194.5 | 156.2 | 21.1 | 46 | A |
| SER | O | 60 | 193.3 | 156.1 | 21.5 | 46 | A |
| PRO | N | 61 | 195.3 | 157.2 | 21.4 | 44 | A |
| PRO | CD | 61 | 196.6 | 157.5 | 20.8 | 43 | A |
| PRO | CA | 61 | 194.8 | 158.3 | 22.2 | 43 | A |
| PRO | CB | 61 | 196.0 | 159.2 | 22.4 | 43 | A |
| PRO | CG | 61 | 196.7 | 159.0 | 21.1 | 43 | A |
| PRO | C | 61 | 193.7 | 159.0 | 21.5 | 41 | A |
| PRO | O | 61 | 192.9 | 159.8 | 22.1 | 40 | A |
| THR | N | 62 | 193.6 | 158.8 | 20.2 | 39 | A |
| THR | CA | 62 | 192.5 | 159.5 | 19.4 | 39 | A |
| THR | CB | 62 | 193.2 | 160.2 | 18.3 | 38 | A |
| THR | OG1 | 62 | 194.2 | 159.4 | 17.6 | 37 | A |
| THR | CG2 | 62 | 194.0 | 161.4 | 18.8 | 38 | A |
| THR | C | 62 | 191.5 | 158.5 | 18.8 | 39 | A |
| THR | O | 62 | 190.9 | 158.7 | 17.8 | 39 | A |
| TYR | N | 63 | 191.3 | 157.4 | 19.6 | 37 | A |
| TYR | CA | 63 | 190.3 | 156.4 | 19.2 | 35 | A |
| TYR | CB | 63 | 190.5 | 155.1 | 19.9 | 35 | A |
| TYR | CG | 63 | 189.4 | 154.0 | 19.8 | 35 | A |
| TYR | CD1 | 63 | 189.4 | 153.1 | 18.7 | 35 | A |
| TYR | CE1 | 63 | 188.4 | 152.2 | 18.6 | 34 | A |
| TYR | CD2 | 63 | 188.3 | 154.0 | 20.6 | 34 | A |
| TYR | CE2 | 63 | 187.2 | 153.1 | 20.5 | 34 | A |
| TYR | CZ | 63 | 187.3 | 152.2 | 19.4 | 34 | A |
| TYR | OH | 63 | 186.3 | 151.2 | 19.3 | 34 | A |
| TYR | C | 63 | 188.9 | 157.0 | 19.4 | 35 | A |
| TYR | O | 63 | 188.7 | 157.5 | 20.5 | 34 | A |
| VAL | N | 64 | 188.0 | 156.8 | 18.5 | 33 | A |
| VAL | CA | 64 | 186.7 | 157.3 | 18.6 | 32 | A |
| VAL | CB | 64 | 186.3 | 158.4 | 17.4 | 32 | A |
| VAL | CG1 | 64 | 187.0 | 159.7 | 17.7 | 32 | A |
| VAL | CG2 | 64 | 186.8 | 157.8 | 16.1 | 32 | A |
| VAL | C | 64 | 185.7 | 156.2 | 18.5 | 31 | A |
| VAL | O | 64 | 185.9 | 155.2 | 17.8 | 31 | A |
| LEU | N | 65 | 184.6 | 156.2 | 19.3 | 31 | A |
| LEU | CA | 65 | 183.6 | 155.2 | 19.4 | 30 | A |
| LEU | CB | 65 | 182.5 | 155.5 | 20.4 | 27 | A |
| LEU | CG | 65 | 183.0 | 155.7 | 21.8 | 26 | A |
| LEU | CD1 | 65 | 181.9 | 156.2 | 22.7 | 26 | A |
| LEU | CD2 | 65 | 183.5 | 154.5 | 22.4 | 27 | A |
| LEU | C | 65 | 182.9 | 155.1 | 18.0 | 32 | A |
| LEU | O | 65 | 182.8 | 156.1 | 17.3 | 33 | A |
| TYR | N | 66 | 182.6 | 153.9 | 17.6 | 34 | A |
| TYR | CA | 66 | 182.0 | 153.6 | 16.3 | 35 | A |
| TYR | CB | 66 | 181.5 | 152.2 | 16.1 | 34 | A |
| TYR | CG | 66 | 182.7 | 151.3 | 15.7 | 32 | A |
| TYR | CD1 | 66 | 183.6 | 150.9 | 16.7 | 32 | A |
| TYR | CE1 | 66 | 184.7 | 150.2 | 16.3 | 31 | A |
| TYR | CD2 | 66 | 182.9 | 150.9 | 14.4 | 31 | A |
| TYR | CE2 | 66 | 184.0 | 150.2 | 14.1 | 31 | A |
| TYR | CZ | 66 | 184.9 | 149.8 | 15.0 | 30 | A |
| TYR | OH | 66 | 186.0 | 149.1 | 14.6 | 29 | A |
| TYR | C | 66 | 180.8 | 154.5 | 15.9 | 36 | A |
| TYR | O | 66 | 180.5 | 154.8 | 14.7 | 35 | A |
| ARG | N | 67 | 180.0 | 154.9 | 16.9 | 38 | A |
| ARG | CA | 67 | 178.8 | 155.8 | 16.7 | 42 | A |
| ARG | CB | 67 | 177.9 | 155.7 | 17.9 | 42 | A |
| ARG | CG | 67 | 178.5 | 156.4 | 19.2 | 44 | A |
| ARG | CD | 67 | 177.5 | 156.6 | 20.2 | 45 | A |
| ARG | NE | 67 | 178.1 | 156.9 | 21.5 | 47 | A |
| ARG | CZ | 67 | 178.3 | 156.1 | 22.5 | 48 | A |
| ARG | NH1 | 67 | 178.1 | 154.8 | 22.3 | 50 | A |
| ARG | NH2 | 67 | 178.9 | 156.5 | 23.6 | 49 | A |

TABLE 4-continued

The following table lists the atomic structure coordinates for FPT in complex with FPP and the inhibitor SCH66701 as derived by X-ray diffraction from crystals of that complex The abbreviations are the same as those used in Table 2

| RES | ATOM | # | X | Y | Z | B | C |
|---|---|---|---|---|---|---|---|
| ARG | C | 67 | 179.2 | 157.2 | 16.4 | 43 | A |
| ARG | O | 67 | 178.3 | 158.0 | 16.0 | 45 | A |
| ASP | N | 68 | 180.5 | 157.6 | 16.5 | 43 | A |
| ASP | CA | 68 | 180.9 | 158.9 | 16.2 | 42 | A |
| ASP | CB | 68 | 181.8 | 159.5 | 17.3 | 41 | A |
| ASP | CG | 68 | 181.1 | 159.6 | 18.6 | 40 | A |
| ASP | OD1 | 68 | 179.9 | 160.0 | 18.7 | 39 | A |
| ASP | OD2 | 68 | 181.8 | 159.4 | 19.7 | 39 | A |
| ASP | C | 68 | 181.7 | 158.9 | 14.9 | 43 | A |
| ASP | O | 68 | 182.3 | 159.9 | 14.5 | 44 | A |
| ARG | N | 69 | 181.6 | 157.8 | 14.2 | 44 | A |
| ARG | CA | 69 | 182.3 | 157.6 | 12.9 | 46 | A |
| ARG | CB | 69 | 183.0 | 156.2 | 12.9 | 46 | A |
| ARG | CG | 69 | 183.8 | 155.9 | 14.2 | 45 | A |
| ARG | CD | 69 | 185.0 | 154.9 | 14.0 | 44 | A |
| ARG | NE | 69 | 185.6 | 154.3 | 15.1 | 43 | A |
| ARG | CZ | 69 | 186.5 | 153.3 | 15.0 | 42 | A |
| ARG | NH1 | 69 | 186.9 | 152.9 | 13.8 | 42 | A |
| ARG | NH2 | 69 | 187.0 | 152.8 | 16.1 | 42 | A |
| ARG | C | 69 | 181.5 | 157.7 | 11.6 | 47 | A |
| ARG | O | 69 | 180.4 | 157.0 | 11.5 | 47 | A |
| ALA | N | 70 | 182.0 | 158.5 | 10.7 | 49 | A |
| ALA | CA | 70 | 181.3 | 158.8 | 9.4 | 50 | A |
| ALA | CB | 70 | 182.0 | 159.9 | 8.7 | 50 | A |
| ALA | C | 70 | 181.1 | 157.6 | 8.4 | 52 | A |
| ALA | O | 70 | 180.3 | 157.6 | 7.6 | 53 | A |
| GLU | N | 71 | 182.0 | 156.6 | 8.6 | 53 | A |
| GLU | CA | 71 | 181.9 | 155.4 | 7.7 | 54 | A |
| GLU | CB | 71 | 183.4 | 154.9 | 7.5 | 54 | A |
| GLU | CG | 71 | 184.2 | 154.5 | 8.7 | 55 | A |
| GLU | CD | 71 | 184.6 | 155.6 | 9.6 | 54 | A |
| GLU | OE1 | 71 | 185.1 | 155.3 | 10.8 | 53 | A |
| GLU | OE2 | 71 | 184.5 | 156.8 | 9.3 | 55 | A |
| GLU | C | 71 | 181.1 | 154.3 | 8.4 | 55 | A |
| GLU | O | 71 | 181.0 | 153.2 | 7.8 | 55 | A |
| TRP | N | 72 | 180.6 | 154.6 | 9.6 | 56 | A |
| TRP | CA | 72 | 179.8 | 153.7 | 10.4 | 58 | A |
| TRP | CB | 72 | 180.6 | 153.3 | 11.6 | 58 | A |
| TRP | CG | 72 | 181.6 | 152.2 | 11.4 | 57 | A |
| TRP | CD2 | 72 | 181.3 | 150.8 | 11.1 | 57 | A |
| TRP | CE2 | 72 | 182.5 | 150.2 | 10.9 | 57 | A |
| TRP | CE3 | 72 | 180.1 | 150.1 | 10.9 | 57 | A |
| TRP | CD1 | 72 | 182.9 | 152.3 | 11.4 | 57 | A |
| TRP | NE1 | 72 | 183.5 | 151.1 | 11.1 | 57 | A |
| TRP | CZ2 | 72 | 182.6 | 148.8 | 10.7 | 57 | A |
| TRP | CZ3 | 72 | 180.2 | 148.7 | 10.7 | 57 | A |
| TRP | CH2 | 72 | 181.5 | 148.1 | 10.5 | 57 | A |
| TRP | C | 72 | 178.5 | 154.4 | 10.8 | 59 | A |
| TRP | O | 72 | 177.8 | 153.9 | 11.8 | 59 | A |
| ALA | N | 73 | 178.0 | 155.4 | 10.1 | 60 | A |
| ALA | CA | 73 | 176.8 | 156.1 | 10.5 | 62 | A |
| ALA | CB | 73 | 176.9 | 157.6 | 10.4 | 62 | A |
| ALA | C | 73 | 175.6 | 155.6 | 9.6 | 62 | A |
| ALA | O | 73 | 174.4 | 155.9 | 9.8 | 62 | A |
| ASP | N | 74 | 176.0 | 154.8 | 8.5 | 62 | A |
| ASP | CA | 74 | 175.0 | 154.3 | 7.6 | 62 | A |
| ASP | CB | 74 | 175.6 | 154.0 | 6.3 | 62 | A |
| ASP | CG | 74 | 176.6 | 152.9 | 6.3 | 63 | A |
| ASP | OD1 | 74 | 176.4 | 151.9 | 5.7 | 63 | A |
| ASP | OD2 | 74 | 177.6 | 153.1 | 7.1 | 63 | A |
| ASP | C | 74 | 174.4 | 153.0 | 8.2 | 61 | A |
| ASP | O | 74 | 173.4 | 152.5 | 7.6 | 62 | A |
| ILE | N | 75 | 175.0 | 152.5 | 9.3 | 60 | A |
| ILE | CA | 75 | 174.5 | 151.3 | 9.9 | 60 | A |
| ILE | CB | 75 | 175.5 | 150.2 | 9.8 | 59 | A |
| ILE | CG2 | 75 | 176.9 | 150.6 | 10.3 | 59 | A |
| ILE | CG1 | 75 | 175.1 | 149.0 | 10.6 | 60 | A |
| ILE | CD1 | 75 | 175.9 | 147.7 | 10.5 | 60 | A |
| ILE | C | 75 | 174.0 | 151.5 | 11.3 | 60 | A |
| ILE | O | 75 | 174.6 | 152.2 | 12.1 | 60 | A |
| ASP | N | 76 | 172.9 | 150.9 | 11.6 | 59 | A |
| ASP | CA | 76 | 172.2 | 150.9 | 12.9 | 59 | A |

TABLE 4-continued

The following table lists the atomic structure coordinates for FPT in complex with FPP and the inhibitor SCH66701 as derived by X-ray diffraction from crystals of that complex The abbreviations are the same as those used in Table 2

| RES | ATOM | # | X | Y | Z | B | C |
|---|---|---|---|---|---|---|---|
| ASP | CB | 76 | 170.7 | 150.7 | 12.8 | 61 | A |
| ASP | CG | 76 | 169.9 | 151.9 | 12.8 | 63 | A |
| ASP | OD1 | 76 | 169.8 | 152.7 | 11.8 | 64 | A |
| ASP | OD2 | 76 | 169.2 | 152.2 | 13.9 | 63 | A |
| ASP | C | 76 | 172.8 | 149.9 | 13.9 | 58 | A |
| ASP | O | 76 | 172.8 | 148.7 | 13.6 | 57 | A |
| PRO | N | 77 | 173.4 | 150.3 | 15.0 | 56 | A |
| PRO | CD | 77 | 173.7 | 151.7 | 15.4 | 56 | A |
| PRO | CA | 77 | 173.9 | 149.4 | 15.9 | 56 | A |
| PRO | CB | 77 | 174.7 | 150.2 | 16.9 | 55 | A |
| PRO | CG | 77 | 173.9 | 151.5 | 16.9 | 56 | A |
| PRO | C | 77 | 172.8 | 148.6 | 16.6 | 55 | A |
| PRO | O | 77 | 171.7 | 149.1 | 16.8 | 55 | A |
| VAL | N | 78 | 173.1 | 147.3 | 17.0 | 54 | A |
| VAL | CA | 78 | 172.1 | 146.5 | 17.6 | 53 | A |
| VAL | CB | 78 | 172.0 | 145.2 | 16.8 | 53 | A |
| VAL | CG1 | 78 | 170.9 | 144.3 | 17.5 | 53 | A |
| VAL | CG2 | 78 | 171.6 | 145.4 | 15.4 | 52 | A |
| VAL | C | 78 | 172.5 | 146.2 | 19.1 | 53 | A |
| VAL | O | 78 | 173.5 | 145.4 | 19.3 | 53 | A |
| PRO | N | 79 | 171.9 | 146.8 | 20.0 | 53 | A |
| PRO | CD | 79 | 170.9 | 147.9 | 19.9 | 52 | A |
| PRO | CA | 79 | 172.2 | 146.5 | 21.4 | 52 | A |
| PRO | CB | 79 | 171.4 | 147.6 | 22.2 | 52 | A |
| PRO | CG | 79 | 170.2 | 147.8 | 21.3 | 52 | A |
| PRO | C | 79 | 171.9 | 145.1 | 21.9 | 52 | A |
| PRO | O | 79 | 170.9 | 144.5 | 21.4 | 51 | A |
| GLN | N | 80 | 172.7 | 144.6 | 22.7 | 52 | A |
| GLN | CA | 80 | 172.5 | 143.2 | 23.2 | 52 | A |
| GLN | CB | 80 | 173.6 | 142.8 | 24.2 | 51 | A |
| GLN | CG | 80 | 173.5 | 141.4 | 24.7 | 50 | A |
| GLN | CD | 80 | 174.7 | 140.9 | 25.5 | 50 | A |
| GLN | OE1 | 80 | 175.7 | 140.3 | 24.9 | 50 | A |
| GLN | NE2 | 80 | 174.7 | 141.3 | 26.7 | 50 | A |
| GLN | C | 80 | 171.2 | 143.0 | 24.0 | 52 | A |
| GLN | O | 80 | 170.8 | 143.8 | 24.8 | 53 | A |
| ASN | N | 81 | 170.4 | 142.0 | 23.7 | 52 | A |
| ASN | CA | 81 | 169.2 | 141.7 | 24.3 | 52 | A |
| ASN | CB | 81 | 168.2 | 141.1 | 23.3 | 53 | A |
| ASN | CG | 81 | 166.8 | 140.8 | 23.9 | 53 | A |
| ASN | OD1 | 81 | 166.5 | 141.2 | 25.1 | 53 | A |
| ASN | ND2 | 81 | 165.9 | 140.2 | 23.1 | 54 | A |
| ASN | C | 81 | 169.3 | 140.7 | 25.4 | 52 | A |
| ASN | O | 81 | 169.2 | 139.4 | 25.2 | 52 | A |
| ASP | N | 82 | 169.4 | 141.2 | 26.7 | 52 | A |
| ASP | CA | 82 | 169.5 | 140.3 | 27.8 | 53 | A |
| ASP | CB | 82 | 170.4 | 141.0 | 28.9 | 53 | A |
| ASP | CG | 82 | 171.8 | 140.8 | 28.8 | 53 | A |
| ASP | OD1 | 82 | 172.2 | 140.0 | 27.8 | 53 | A |
| ASP | OD2 | 82 | 172.6 | 141.4 | 29.5 | 53 | A |
| ASP | C | 82 | 168.1 | 140.0 | 28.4 | 53 | A |
| ASP | O | 82 | 168.0 | 139.3 | 29.4 | 53 | A |
| GLY | N | 83 | 167.1 | 140.6 | 27.7 | 54 | A |
| GLY | CA | 83 | 165.7 | 140.4 | 28.2 | 55 | A |
| GLY | C | 83 | 165.4 | 141.4 | 29.3 | 55 | A |
| GLY | O | 83 | 166.2 | 142.0 | 29.9 | 56 | A |
| PRO | N | 84 | 164.1 | 141.6 | 29.5 | 55 | A |
| PRO | CD | 84 | 162.9 | 140.8 | 29.0 | 55 | A |
| PRO | CA | 84 | 163.6 | 142.5 | 30.6 | 54 | A |
| PRO | CB | 84 | 162.1 | 142.3 | 30.6 | 55 | A |
| PRO | CG | 84 | 162.0 | 140.9 | 30.1 | 55 | A |
| PRO | C | 84 | 164.2 | 142.3 | 32.0 | 54 | A |
| PRO | O | 84 | 164.4 | 143.3 | 32.7 | 53 | A |
| SER | N | 85 | 164.5 | 141.1 | 32.3 | 53 | A |
| SER | CA | 85 | 165.0 | 140.8 | 33.7 | 52 | A |
| SER | CB | 85 | 164.0 | 140.1 | 34.5 | 53 | A |
| SER | OG | 85 | 162.9 | 140.9 | 34.8 | 54 | A |
| SER | C | 85 | 166.3 | 140.0 | 33.6 | 52 | A |
| SER | O | 85 | 166.3 | 138.8 | 33.9 | 51 | A |
| PRO | N | 86 | 167.4 | 140.6 | 33.3 | 51 | A |
| PRO | CD | 86 | 167.4 | 142.1 | 33.1 | 51 | A |
| PRO | CA | 86 | 168.8 | 140.1 | 33.2 | 50 | A |

TABLE 4-continued

The following table lists the atomic structure coordinates for FPT in complex with FPP and the inhibitor SCH66701 as derived by X-ray diffraction from crystals of that complex
The abbreviations are the same as those used in Table 2

| RES | ATOM | # | X | Y | Z | B | C |
|---|---|---|---|---|---|---|---|
| PRO | CB | 86 | 169.6 | 141.3 | 33.0 | 51 | A |
| PRO | CG | 86 | 168.7 | 142.3 | 32.3 | 51 | A |
| PRO | C | 86 | 169.3 | 139.3 | 34.4 | 48 | A |
| PRO | O | 86 | 168.7 | 139.5 | 35.5 | 48 | A |
| VAL | N | 87 | 170.2 | 138.4 | 34.2 | 46 | A |
| VAL | CA | 87 | 170.9 | 137.6 | 35.2 | 43 | A |
| VAL | CB | 87 | 170.4 | 136.2 | 35.3 | 43 | A |
| VAL | CG1 | 87 | 169.6 | 136.0 | 36.6 | 43 | A |
| VAL | CG2 | 87 | 169.6 | 135.8 | 34.1 | 42 | A |
| VAL | C | 87 | 172.4 | 137.7 | 34.8 | 41 | A |
| VAL | O | 87 | 172.7 | 137.9 | 33.6 | 40 | A |
| VAL | N | 88 | 173.3 | 137.4 | 35.7 | 39 | A |
| VAL | CA | 88 | 174.7 | 137.5 | 35.5 | 38 | A |
| VAL | CB | 88 | 175.4 | 136.1 | 35.2 | 37 | A |
| VAL | CG1 | 88 | 175.4 | 135.3 | 36.5 | 37 | A |
| VAL | CG2 | 88 | 174.7 | 135.4 | 34.1 | 37 | A |
| VAL | C | 88 | 175.0 | 138.4 | 34.3 | 39 | A |
| VAL | O | 88 | 175.6 | 138.0 | 33.3 | 39 | A |
| GLN | N | 89 | 174.5 | 139.7 | 34.5 | 39 | A |
| GLN | CA | 89 | 174.7 | 140.7 | 33.5 | 39 | A |
| GLN | CB | 89 | 173.5 | 141.7 | 33.7 | 40 | A |
| GLN | CG | 89 | 173.7 | 143.0 | 32.9 | 42 | A |
| GLN | CD | 89 | 172.5 | 144.0 | 33.1 | 43 | A |
| GLN | OE1 | 89 | 172.2 | 144.3 | 34.3 | 43 | A |
| GLN | NE2 | 89 | 171.8 | 144.3 | 32.1 | 44 | A |
| GLN | C | 89 | 176.0 | 141.5 | 33.7 | 39 | A |
| GLN | O | 89 | 176.4 | 141.8 | 34.8 | 40 | A |
| ILE | N | 90 | 176.6 | 141.8 | 32.6 | 38 | A |
| ILE | CA | 90 | 177.9 | 142.5 | 32.6 | 38 | A |
| ILE | CB | 90 | 178.9 | 141.8 | 31.7 | 37 | A |
| ILE | CG2 | 90 | 180.3 | 142.4 | 31.9 | 38 | A |
| ILE | CG1 | 90 | 179.0 | 140.3 | 31.9 | 37 | A |
| ILE | CD1 | 90 | 179.5 | 139.5 | 30.8 | 35 | A |
| ILE | C | 90 | 177.8 | 144.0 | 32.3 | 38 | A |
| ILE | O | 90 | 177.3 | 144.4 | 31.2 | 39 | A |
| ILE | N | 91 | 178.2 | 144.8 | 33.2 | 37 | A |
| ILE | CA | 91 | 178.2 | 146.3 | 33.0 | 38 | A |
| ILE | CB | 91 | 178.4 | 147.0 | 34.4 | 38 | A |
| ILE | CG2 | 91 | 178.2 | 148.5 | 34.1 | 38 | A |
| ILE | CG1 | 91 | 177.4 | 146.6 | 35.4 | 38 | A |
| ILE | CD1 | 91 | 175.9 | 146.7 | 35.0 | 38 | A |
| ILE | C | 91 | 179.4 | 146.7 | 32.1 | 37 | A |
| ILE | O | 91 | 180.4 | 147.1 | 32.5 | 37 | A |
| TYR | N | 92 | 179.1 | 146.5 | 30.8 | 36 | A |
| TYR | CA | 92 | 180.2 | 146.8 | 29.9 | 36 | A |
| TYR | CB | 92 | 179.8 | 146.4 | 28.4 | 36 | A |
| TYR | CG | 92 | 179.2 | 145.1 | 28.3 | 36 | A |
| TYR | CD1 | 92 | 177.9 | 145.0 | 27.6 | 36 | A |
| TYR | CE1 | 92 | 177.3 | 143.8 | 27.4 | 36 | A |
| TYR | CD2 | 92 | 179.7 | 143.9 | 28.8 | 35 | A |
| TYR | CE2 | 92 | 179.1 | 142.7 | 28.6 | 35 | A |
| TYR | CZ | 92 | 177.9 | 142.6 | 27.9 | 36 | A |
| TYR | OH | 92 | 177.2 | 141.4 | 27.8 | 35 | A |
| TYR | C | 92 | 180.7 | 148.2 | 29.9 | 37 | A |
| TYR | O | 92 | 180.0 | 149.1 | 30.2 | 37 | A |
| SER | N | 93 | 182.0 | 148.3 | 29.5 | 38 | A |
| SER | CA | 93 | 182.6 | 149.6 | 29.4 | 39 | A |
| SER | CB | 93 | 184.1 | 149.4 | 29.1 | 39 | A |
| SER | OG | 93 | 184.2 | 148.8 | 27.8 | 39 | A |
| SER | C | 93 | 181.9 | 150.2 | 28.2 | 40 | A |
| SER | O | 93 | 181.1 | 149.5 | 27.5 | 41 | A |
| GLU | N | 94 | 182.1 | 151.5 | 27.8 | 42 | A |
| GLU | CA | 94 | 181.4 | 152.0 | 26.7 | 43 | A |
| GLU | CB | 94 | 181.3 | 153.5 | 26.7 | 46 | A |
| GLU | CG | 94 | 180.4 | 154.1 | 25.7 | 49 | A |
| GLU | CD | 94 | 179.5 | 155.1 | 26.2 | 51 | A |
| GLU | OE1 | 94 | 178.5 | 154.7 | 26.9 | 51 | A |
| GLU | OE2 | 94 | 179.8 | 156.3 | 26.1 | 52 | A |
| GLU | C | 94 | 182.0 | 151.6 | 25.4 | 42 | A |
| GLU | O | 94 | 181.3 | 151.6 | 24.3 | 42 | A |
| LYS | N | 95 | 183.3 | 151.3 | 25.4 | 41 | A |
| LYS | CA | 95 | 184.0 | 150.9 | 24.1 | 41 | A |
| LYS | CB | 95 | 185.5 | 151.0 | 24.3 | 41 | A |
| LYS | CG | 95 | 186.1 | 152.4 | 24.4 | 43 | A |
| LYS | CD | 95 | 187.4 | 152.4 | 25.1 | 43 | A |
| LYS | CE | 95 | 188.5 | 151.7 | 24.2 | 43 | A |
| LYS | NZ | 95 | 189.7 | 151.4 | 25.0 | 43 | A |
| LYS | C | 95 | 183.6 | 149.5 | 23.8 | 40 | A |
| LYS | O | 95 | 183.2 | 149.1 | 22.7 | 40 | A |
| PHE | N | 96 | 183.6 | 148.6 | 24.9 | 39 | A |
| PHE | CA | 96 | 183.2 | 147.2 | 24.7 | 38 | A |
| PHE | CB | 96 | 183.2 | 146.5 | 26.1 | 37 | A |
| PHE | CG | 96 | 183.0 | 145.1 | 26.0 | 36 | A |
| PHE | CD1 | 96 | 184.1 | 144.2 | 26.2 | 35 | A |
| PHE | CD2 | 96 | 181.8 | 144.5 | 25.7 | 36 | A |
| PHE | CE1 | 96 | 183.9 | 142.8 | 26.1 | 35 | A |
| PHE | CE2 | 96 | 181.6 | 143.2 | 25.6 | 35 | A |
| PHE | CZ | 96 | 182.7 | 142.3 | 25.8 | 35 | A |
| PHE | C | 96 | 181.8 | 147.2 | 24.2 | 39 | A |
| PHE | O | 96 | 181.6 | 146.7 | 23.1 | 39 | A |
| ARG | N | 97 | 180.9 | 147.9 | 24.8 | 39 | A |
| ARG | CA | 97 | 179.6 | 148.0 | 24.4 | 39 | A |
| ARG | CB | 97 | 178.7 | 148.8 | 25.3 | 41 | A |
| ARG | CG | 97 | 177.3 | 148.4 | 25.4 | 45 | A |
| ARG | CD | 97 | 176.3 | 149.4 | 25.9 | 48 | A |
| ARG | NE | 97 | 176.8 | 150.2 | 27.0 | 50 | A |
| ARG | CZ | 97 | 177.3 | 151.5 | 26.9 | 52 | A |
| ARG | NH1 | 97 | 177.4 | 152.1 | 25.7 | 53 | A |
| ARG | NH2 | 97 | 177.8 | 152.1 | 28.0 | 53 | A |
| ARG | C | 97 | 179.5 | 148.6 | 23.0 | 38 | A |
| ARG | O | 97 | 178.7 | 148.1 | 22.1 | 39 | A |
| ASP | N | 98 | 180.2 | 149.6 | 22.7 | 37 | A |
| ASP | CA | 98 | 180.2 | 150.3 | 21.4 | 36 | A |
| ASP | CB | 98 | 181.1 | 151.5 | 21.4 | 37 | A |
| ASP | CG | 98 | 181.2 | 152.1 | 20.0 | 38 | A |
| ASP | OD1 | 98 | 180.3 | 152.9 | 19.6 | 39 | A |
| ASP | OD2 | 98 | 182.3 | 151.9 | 19.3 | 38 | A |
| ASP | C | 98 | 180.5 | 149.3 | 20.2 | 35 | A |
| ASP | O | 98 | 179.8 | 149.3 | 19.2 | 36 | A |
| VAL | N | 99 | 181.7 | 148.6 | 20.3 | 33 | A |
| VAL | CA | 99 | 182.1 | 147.7 | 19.3 | 31 | A |
| VAL | CB | 99 | 183.5 | 147.1 | 19.6 | 30 | A |
| VAL | CG1 | 99 | 183.9 | 146.0 | 18.6 | 29 | A |
| VAL | CG2 | 99 | 184.5 | 148.2 | 19.6 | 29 | A |
| VAL | C | 99 | 181.1 | 146.6 | 19.0 | 30 | A |
| VAL | O | 99 | 180.7 | 146.3 | 17.9 | 29 | A |
| TYR | N | 100 | 180.7 | 146.0 | 20.1 | 30 | A |
| TYR | CA | 100 | 179.7 | 144.9 | 20.0 | 30 | A |
| TYR | CB | 100 | 179.6 | 144.2 | 21.4 | 30 | A |
| TYR | CG | 100 | 180.8 | 143.2 | 21.5 | 30 | A |
| TYR | CD1 | 100 | 181.8 | 143.5 | 22.3 | 30 | A |
| TYR | CE1 | 100 | 182.9 | 142.6 | 22.3 | 30 | A |
| TYR | CD2 | 100 | 180.8 | 142.1 | 20.6 | 30 | A |
| TYR | CE2 | 100 | 181.9 | 141.2 | 20.7 | 30 | A |
| TYR | CZ | 100 | 182.9 | 141.5 | 21.5 | 29 | A |
| TYR | OH | 100 | 184.0 | 140.7 | 21.5 | 29 | A |
| TYR | C | 100 | 178.4 | 145.2 | 19.5 | 32 | A |
| TYR | O | 100 | 177.9 | 144.5 | 18.6 | 32 | A |
| ASP | N | 101 | 177.8 | 146.3 | 19.9 | 32 | A |
| ASP | CA | 101 | 176.5 | 146.8 | 19.4 | 33 | A |
| ASP | CB | 101 | 176.1 | 148.1 | 19.9 | 34 | A |
| ASP | CG | 101 | 175.4 | 148.0 | 21.3 | 36 | A |
| ASP | OD1 | 101 | 175.3 | 146.9 | 21.8 | 36 | A |
| ASP | OD2 | 101 | 174.9 | 149.0 | 21.8 | 38 | A |
| ASP | C | 101 | 176.7 | 146.8 | 17.9 | 33 | A |
| ASP | O | 101 | 175.8 | 146.5 | 17.1 | 32 | A |
| TYR | N | 102 | 177.8 | 147.3 | 17.4 | 34 | A |
| TYR | CA | 102 | 178.1 | 147.3 | 16.0 | 36 | A |
| TYR | CB | 102 | 179.2 | 148.3 | 15.7 | 37 | A |
| TYR | CG | 102 | 178.7 | 149.7 | 15.3 | 38 | A |
| TYR | CD1 | 102 | 178.4 | 150.1 | 14.0 | 39 | A |
| TYR | CE1 | 102 | 177.8 | 151.3 | 13.7 | 40 | A |
| TYR | CD2 | 102 | 178.3 | 150.6 | 16.3 | 39 | A |
| TYR | CE2 | 102 | 177.7 | 151.8 | 16.0 | 39 | A |

TABLE 4-continued

The following table lists the atomic structure coordinates for FPT in complex with FPP and the inhibitor SCH66701 as derived by X-ray diffraction from crystals of that complex The abbreviations are the same as those used in Table 2

| RES | ATOM | # | X | Y | Z | B | C |
|---|---|---|---|---|---|---|---|
| TYR | CZ | 102 | 177.5 | 152.2 | 14.7 | 40 | A |
| TYR | OH | 102 | 176.8 | 153.4 | 14.4 | 40 | A |
| TYR | C | 102 | 178.4 | 146.0 | 15.4 | 35 | A |
| TYR | O | 102 | 178.0 | 145.7 | 14.2 | 35 | A |
| PHE | N | 103 | 179.0 | 145.1 | 16.1 | 36 | A |
| PHE | CA | 103 | 179.3 | 143.7 | 15.6 | 36 | A |
| PHE | CB | 103 | 180.1 | 142.9 | 16.6 | 35 | A |
| PHE | CG | 103 | 180.4 | 141.5 | 16.1 | 34 | A |
| PHE | CD1 | 103 | 181.3 | 141.2 | 15.1 | 34 | A |
| PHE | CD2 | 103 | 179.7 | 140.4 | 16.7 | 33 | A |
| PHE | CE1 | 103 | 181.5 | 140.0 | 14.6 | 33 | A |
| PHE | CE2 | 103 | 179.9 | 139.1 | 16.2 | 32 | A |
| PHE | CZ | 103 | 180.8 | 138.9 | 15.1 | 32 | A |
| PHE | C | 103 | 177.9 | 143.0 | 15.4 | 37 | A |
| PHE | O | 103 | 177.7 | 142.5 | 14.3 | 37 | A |
| ARG | N | 104 | 177.0 | 143.1 | 16.4 | 38 | A |
| ARG | CA | 104 | 175.7 | 142.4 | 16.2 | 38 | A |
| ARG | CB | 104 | 174.8 | 142.8 | 17.4 | 38 | A |
| ARG | CG | 104 | 175.4 | 142.3 | 18.7 | 38 | A |
| ARG | CD | 104 | 174.5 | 142.7 | 19.8 | 39 | A |
| ARG | NE | 104 | 175.1 | 142.3 | 21.1 | 41 | A |
| ARG | CZ | 104 | 175.9 | 143.1 | 21.8 | 42 | A |
| ARG | NH1 | 104 | 176.3 | 144.3 | 21.3 | 42 | A |
| ARG | NH2 | 104 | 176.5 | 142.7 | 22.9 | 42 | A |
| ARG | C | 104 | 175.1 | 143.0 | 14.9 | 38 | A |
| ARG | O | 104 | 174.5 | 142.2 | 14.2 | 38 | A |
| ALA | N | 105 | 175.2 | 144.3 | 14.7 | 38 | A |
| ALA | CA | 105 | 174.6 | 144.9 | 13.6 | 38 | A |
| ALA | CB | 105 | 175.0 | 146.4 | 13.6 | 39 | A |
| ALA | C | 105 | 175.2 | 144.3 | 12.3 | 39 | A |
| ALA | O | 105 | 174.4 | 143.9 | 11.5 | 39 | A |
| VAL | N | 106 | 176.5 | 144.2 | 12.2 | 39 | A |
| VAL | CA | 106 | 177.1 | 143.7 | 11.0 | 39 | A |
| VAL | CB | 106 | 178.7 | 144.0 | 11.0 | 39 | A |
| VAL | CG1 | 106 | 179.5 | 142.9 | 10.3 | 40 | A |
| VAL | CG2 | 106 | 178.9 | 145.3 | 10.4 | 39 | A |
| VAL | C | 106 | 176.9 | 142.2 | 10.8 | 39 | A |
| VAL | O | 106 | 176.6 | 141.7 | 9.7 | 38 | A |
| LEU | N | 107 | 176.9 | 141.4 | 11.9 | 40 | A |
| LEU | CA | 107 | 176.7 | 140.0 | 11.9 | 41 | A |
| LEU | CB | 107 | 176.9 | 139.4 | 13.3 | 39 | A |
| LEU | CG | 107 | 176.8 | 137.9 | 13.5 | 38 | A |
| LEU | CD1 | 107 | 177.9 | 137.3 | 12.7 | 37 | A |
| LEU | CD2 | 107 | 176.9 | 137.5 | 15.0 | 37 | A |
| LEU | C | 107 | 175.3 | 139.7 | 11.5 | 43 | A |
| LEU | O | 107 | 175.0 | 138.8 | 10.7 | 43 | A |
| GLN | N | 108 | 174.4 | 140.5 | 12.1 | 47 | A |
| GLN | CA | 108 | 172.9 | 140.4 | 11.8 | 49 | A |
| GLN | CB | 108 | 172.2 | 141.6 | 12.4 | 51 | A |
| GLN | CG | 108 | 170.9 | 141.4 | 13.1 | 52 | A |
| GLN | CD | 108 | 171.1 | 141.1 | 14.6 | 53 | A |
| GLN | OE1 | 108 | 170.1 | 141.3 | 15.3 | 54 | A |
| GLN | NE2 | 108 | 172.3 | 140.7 | 15.0 | 52 | A |
| GLN | C | 108 | 172.7 | 140.3 | 10.4 | 50 | A |
| GLN | O | 108 | 172.1 | 139.3 | 9.8 | 51 | A |
| ARG | N | 109 | 173.2 | 141.3 | 9.7 | 51 | A |
| ARG | CA | 109 | 173.0 | 141.4 | 8.2 | 52 | A |
| ARG | CB | 109 | 173.0 | 142.8 | 7.8 | 54 | A |
| ARG | CG | 109 | 174.2 | 143.6 | 8.1 | 56 | A |
| ARG | CD | 109 | 174.2 | 145.0 | 7.7 | 58 | A |
| ARG | NE | 109 | 173.1 | 145.8 | 8.4 | 60 | A |
| ARG | CZ | 109 | 172.5 | 146.9 | 7.9 | 61 | A |
| ARG | NH1 | 109 | 172.8 | 147.3 | 6.6 | 62 | A |
| ARG | NH2 | 109 | 171.6 | 147.5 | 8.6 | 61 | A |
| ARG | C | 109 | 174.0 | 140.6 | 7.5 | 51 | A |
| ARG | O | 109 | 174.0 | 140.5 | 6.3 | 51 | A |
| ASP | N | 110 | 174.9 | 139.9 | 8.2 | 50 | A |
| ASP | CA | 110 | 176.0 | 139.1 | 7.7 | 49 | A |
| ASP | CB | 110 | 175.5 | 137.8 | 7.1 | 49 | A |
| ASP | CG | 110 | 176.6 | 137.0 | 6.4 | 49 | A |
| ASP | OD1 | 110 | 177.6 | 136.8 | 7.1 | 49 | A |
| ASP | OD2 | 110 | 176.3 | 136.4 | 5.3 | 49 | A |

TABLE 4-continued

The following table lists the atomic structure coordinates for FPT in complex with FPP and the inhibitor SCH66701 as derived by X-ray diffraction from crystals of that complex The abbreviations are the same as those used in Table 2

| RES | ATOM | # | X | Y | Z | B | C |
|---|---|---|---|---|---|---|---|
| ASP | C | 110 | 176.6 | 140.0 | 6.6 | 49 | A |
| ASP | O | 110 | 176.6 | 139.7 | 5.4 | 48 | A |
| GLU | N | 111 | 177.2 | 141.1 | 7.1 | 48 | A |
| GLU | CA | 111 | 177.8 | 142.1 | 6.2 | 48 | A |
| GLU | CB | 111 | 177.8 | 143.4 | 6.9 | 48 | A |
| GLU | CG | 111 | 178.0 | 144.6 | 6.0 | 47 | A |
| GLU | CD | 111 | 178.2 | 145.9 | 6.8 | 47 | A |
| GLU | OE1 | 111 | 179.4 | 146.4 | 6.7 | 47 | A |
| GLU | OE2 | 111 | 177.3 | 146.3 | 7.5 | 47 | A |
| GLU | C | 111 | 179.3 | 141.7 | 6.0 | 47 | A |
| GLU | O | 111 | 180.1 | 141.9 | 6.8 | 48 | A |
| ARG | N | 112 | 179.5 | 141.0 | 4.8 | 46 | A |
| ARG | CA | 112 | 180.9 | 140.6 | 4.5 | 45 | A |
| ARG | CB | 112 | 180.8 | 139.3 | 3.7 | 46 | A |
| ARG | CG | 112 | 180.2 | 138.2 | 4.4 | 47 | A |
| ARG | CD | 112 | 179.9 | 137.0 | 3.6 | 48 | A |
| ARG | NE | 112 | 179.0 | 136.1 | 4.5 | 50 | A |
| ARG | CZ | 112 | 178.8 | 134.8 | 4.2 | 51 | A |
| ARG | NH1 | 112 | 179.3 | 134.2 | 3.2 | 51 | A |
| ARG | NH2 | 112 | 178.0 | 134.2 | 5.1 | 52 | A |
| ARG | C | 112 | 181.8 | 141.6 | 3.9 | 45 | A |
| ARG | O | 112 | 182.3 | 141.4 | 2.8 | 44 | A |
| SER | N | 113 | 182.0 | 142.7 | 4.7 | 44 | A |
| SER | CA | 113 | 182.8 | 143.8 | 4.2 | 43 | A |
| SER | CB | 113 | 182.0 | 145.1 | 4.3 | 44 | A |
| SER | OG | 113 | 181.7 | 145.5 | 5.7 | 43 | A |
| SER | C | 113 | 184.1 | 144.0 | 5.0 | 42 | A |
| SER | O | 113 | 184.2 | 143.6 | 6.1 | 41 | A |
| GLU | N | 114 | 185.0 | 144.7 | 4.3 | 42 | A |
| GLU | CA | 114 | 186.3 | 145.1 | 4.8 | 42 | A |
| GLU | CB | 114 | 187.0 | 145.9 | 3.7 | 43 | A |
| GLU | CG | 114 | 188.3 | 146.4 | 4.1 | 45 | A |
| GLU | CD | 114 | 189.3 | 145.2 | 4.3 | 46 | A |
| GLU | OE1 | 114 | 190.0 | 145.1 | 5.3 | 47 | A |
| GLU | OE2 | 114 | 189.4 | 144.4 | 3.3 | 46 | A |
| GLU | C | 114 | 186.3 | 145.9 | 6.1 | 42 | A |
| GLU | O | 114 | 187.2 | 145.8 | 6.9 | 41 | A |
| ARG | N | 115 | 185.2 | 146.6 | 6.3 | 42 | A |
| ARG | CA | 115 | 185.0 | 147.4 | 7.6 | 42 | A |
| ARG | CB | 115 | 184.0 | 148.5 | 7.4 | 43 | A |
| ARG | CG | 115 | 182.6 | 148.1 | 7.0 | 44 | A |
| ARG | CD | 115 | 181.7 | 149.3 | 7.1 | 45 | A |
| ARG | NE | 115 | 180.3 | 149.0 | 6.7 | 46 | A |
| ARG | CZ | 115 | 179.2 | 149.7 | 7.0 | 46 | A |
| ARG | NH1 | 115 | 178.0 | 149.3 | 6.6 | 46 | A |
| ARG | NH2 | 115 | 179.3 | 150.7 | 7.8 | 46 | A |
| ARG | C | 115 | 184.6 | 146.4 | 8.7 | 42 | A |
| ARG | O | 115 | 185.0 | 146.5 | 9.8 | 42 | A |
| ALA | N | 116 | 183.7 | 145.5 | 8.3 | 42 | A |
| ALA | CA | 116 | 183.2 | 144.5 | 9.2 | 42 | A |
| ALA | CB | 116 | 182.3 | 143.5 | 8.6 | 41 | A |
| ALA | C | 116 | 184.5 | 143.7 | 9.7 | 41 | A |
| ALA | O | 116 | 184.7 | 143.5 | 10.9 | 41 | A |
| PHE | N | 117 | 185.3 | 143.4 | 8.7 | 40 | A |
| PHE | CA | 117 | 186.6 | 142.7 | 9.0 | 38 | A |
| PHE | CB | 117 | 187.3 | 142.5 | 7.7 | 38 | A |
| PHE | CG | 117 | 188.7 | 141.8 | 7.8 | 37 | A |
| PHE | CD1 | 117 | 188.8 | 140.5 | 8.2 | 37 | A |
| PHE | CD2 | 117 | 189.8 | 142.6 | 7.7 | 37 | A |
| PHE | CE1 | 117 | 190.0 | 140.0 | 8.4 | 37 | A |
| PHE | CE2 | 117 | 191.1 | 142.0 | 7.9 | 36 | A |
| PHE | CZ | 117 | 191.2 | 140.7 | 8.3 | 37 | A |
| PHE | C | 117 | 187.5 | 143.5 | 9.9 | 38 | A |
| PHE | O | 117 | 188.2 | 142.9 | 10.7 | 39 | A |
| LYS | N | 118 | 187.5 | 144.8 | 9.8 | 35 | A |
| LYS | CA | 118 | 188.4 | 145.5 | 10.8 | 32 | A |
| LYS | CB | 118 | 188.7 | 146.9 | 10.2 | 34 | A |
| LYS | CG | 118 | 189.6 | 146.9 | 8.9 | 36 | A |
| LYS | CD | 118 | 190.2 | 148.3 | 8.7 | 37 | A |
| LYS | CE | 118 | 190.9 | 148.4 | 7.3 | 38 | A |
| LYS | NZ | 118 | 190.0 | 148.2 | 6.1 | 39 | A |
| LYS | C | 118 | 187.8 | 145.7 | 12.1 | 30 | A |

TABLE 4-continued

The following table lists the atomic structure coordinates for FPT in complex with FPP and the inhibitor SCH66701 as derived by X-ray diffraction from crystals of that complex The abbreviations are the same as those used in Table 2

| RES | ATOM | # | X | Y | Z | B | C |
|---|---|---|---|---|---|---|---|
| LYS | O | 118 | 188.5 | 145.8 | 13.1 | 30 | A |
| LEU | N | 119 | 186.4 | 145.6 | 12.2 | 28 | A |
| LEU | CA | 119 | 185.7 | 145.7 | 13.5 | 27 | A |
| LEU | CB | 119 | 184.2 | 146.0 | 13.2 | 26 | A |
| LEU | CG | 119 | 183.3 | 145.9 | 14.5 | 25 | A |
| LEU | CD1 | 119 | 183.8 | 146.9 | 15.5 | 25 | A |
| LEU | CD2 | 119 | 181.9 | 146.2 | 14.2 | 25 | A |
| LEU | C | 119 | 185.9 | 144.4 | 14.3 | 27 | A |
| LEU | O | 119 | 185.9 | 144.5 | 15.5 | 26 | A |
| THR | N | 120 | 185.9 | 143.3 | 13.6 | 27 | A |
| THR | CA | 120 | 186.1 | 142.0 | 14.3 | 26 | A |
| THR | CB | 120 | 186.1 | 140.8 | 13.4 | 26 | A |
| THR | OG1 | 120 | 187.1 | 141.1 | 12.4 | 25 | A |
| THR | CG2 | 120 | 184.8 | 140.6 | 12.8 | 27 | A |
| THR | C | 120 | 187.4 | 142.1 | 15.1 | 27 | A |
| THR | O | 120 | 187.5 | 141.6 | 16.2 | 28 | A |
| ARG | N | 121 | 188.4 | 142.7 | 14.5 | 28 | A |
| ARG | CA | 121 | 189.7 | 142.8 | 15.2 | 29 | A |
| ARG | CB | 121 | 190.7 | 143.5 | 14.4 | 30 | A |
| ARG | CG | 121 | 191.9 | 143.9 | 15.2 | 33 | A |
| ARG | CD | 121 | 192.7 | 145.0 | 14.6 | 36 | A |
| ARG | NE | 121 | 193.6 | 144.4 | 13.6 | 39 | A |
| ARG | CZ | 121 | 194.9 | 144.6 | 13.6 | 40 | A |
| ARG | NH1 | 121 | 195.6 | 144.0 | 12.6 | 40 | A |
| ARG | NH2 | 121 | 195.4 | 145.4 | 14.5 | 41 | A |
| ARG | C | 121 | 189.6 | 143.4 | 16.5 | 30 | A |
| ARG | O | 121 | 190.2 | 143.0 | 17.5 | 31 | A |
| ASP | N | 122 | 188.8 | 144.5 | 16.6 | 31 | A |
| ASP | CA | 122 | 188.5 | 145.2 | 17.9 | 30 | A |
| ASP | CB | 122 | 187.9 | 146.6 | 17.7 | 31 | A |
| ASP | CG | 122 | 188.8 | 147.6 | 17.1 | 32 | A |
| ASP | OD1 | 122 | 190.0 | 147.7 | 17.5 | 32 | A |
| ASP | OD2 | 122 | 188.3 | 148.4 | 16.2 | 32 | A |
| ASP | C | 122 | 187.7 | 144.4 | 18.8 | 30 | A |
| ASP | O | 122 | 187.8 | 144.4 | 20.0 | 30 | A |
| ALA | N | 123 | 186.7 | 143.8 | 18.2 | 30 | A |
| ALA | CA | 123 | 185.7 | 142.9 | 19.0 | 29 | A |
| ALA | CB | 123 | 184.6 | 142.4 | 18.1 | 29 | A |
| ALA | C | 123 | 186.6 | 141.8 | 19.6 | 29 | A |
| ALA | O | 123 | 186.4 | 141.4 | 20.7 | 30 | A |
| ILE | N | 124 | 187.6 | 141.3 | 18.8 | 27 | A |
| ILE | CA | 124 | 188.4 | 140.2 | 19.2 | 26 | A |
| ILE | CB | 124 | 189.3 | 139.7 | 18.1 | 25 | A |
| ILE | CG2 | 124 | 190.6 | 139.2 | 18.6 | 25 | A |
| ILE | CG1 | 124 | 188.5 | 138.7 | 17.3 | 24 | A |
| ILE | CD1 | 124 | 189.2 | 138.1 | 16.1 | 24 | A |
| ILE | C | 124 | 189.3 | 140.8 | 20.4 | 26 | A |
| ILE | O | 124 | 189.5 | 140.2 | 21.4 | 26 | A |
| GLU | N | 125 | 189.9 | 141.9 | 20.1 | 27 | A |
| GLU | CA | 125 | 190.7 | 142.5 | 21.1 | 28 | A |
| GLU | CB | 125 | 191.2 | 143.9 | 20.7 | 32 | A |
| GLU | CG | 125 | 192.6 | 144.3 | 21.2 | 37 | A |
| GLU | CD | 125 | 193.1 | 145.6 | 20.6 | 41 | A |
| GLU | OE1 | 125 | 193.7 | 146.5 | 21.3 | 42 | A |
| GLU | OE2 | 125 | 192.9 | 145.8 | 19.3 | 42 | A |
| GLU | C | 125 | 190.0 | 142.7 | 22.5 | 27 | A |
| GLU | O | 125 | 190.5 | 142.4 | 23.5 | 25 | A |
| LEU | N | 126 | 188.7 | 143.1 | 22.4 | 25 | A |
| LEU | CA | 126 | 187.9 | 143.3 | 23.6 | 24 | A |
| LEU | CB | 126 | 186.7 | 144.1 | 23.2 | 22 | A |
| LEU | CG | 126 | 187.1 | 145.5 | 22.8 | 21 | A |
| LEU | CD1 | 126 | 186.0 | 146.1 | 22.0 | 22 | A |
| LEU | CD2 | 126 | 187.4 | 146.3 | 24.0 | 20 | A |
| LEU | C | 126 | 187.6 | 142.0 | 24.4 | 23 | A |
| LEU | O | 126 | 187.6 | 142.0 | 25.6 | 23 | A |
| ASN | N | 127 | 187.4 | 140.9 | 23.6 | 23 | A |
| ASN | CA | 127 | 187.2 | 139.6 | 24.3 | 23 | A |
| ASN | CB | 127 | 185.7 | 139.4 | 24.6 | 23 | A |
| ASN | CG | 127 | 185.5 | 138.1 | 25.4 | 23 | A |
| ASN | OD1 | 127 | 186.5 | 137.6 | 25.9 | 25 | A |
| ASN | ND2 | 127 | 184.3 | 137.6 | 25.5 | 23 | A |
| ASN | C | 127 | 187.6 | 138.5 | 23.3 | 22 | A |

TABLE 4-continued

The following table lists the atomic structure coordinates for FPT in complex with FPP and the inhibitor SCH66701 as derived by X-ray diffraction from crystals of that complex The abbreviations are the same as those used in Table 2

| RES | ATOM | # | X | Y | Z | B | C |
|---|---|---|---|---|---|---|---|
| ASN | O | 127 | 186.8 | 137.9 | 22.6 | 22 | A |
| ALA | N | 128 | 188.9 | 138.3 | 23.3 | 21 | A |
| ALA | CA | 128 | 189.6 | 137.3 | 22.5 | 21 | A |
| ALA | CB | 128 | 191.1 | 137.3 | 22.7 | 20 | A |
| ALA | C | 128 | 189.0 | 135.9 | 22.6 | 20 | A |
| ALA | O | 128 | 189.3 | 135.1 | 21.8 | 22 | A |
| ALA | N | 129 | 188.1 | 135.7 | 23.6 | 18 | A |
| ALA | CA | 129 | 187.5 | 134.4 | 23.7 | 17 | A |
| ALA | CB | 129 | 187.4 | 134.1 | 25.2 | 17 | A |
| ALA | C | 129 | 186.1 | 134.3 | 23.1 | 18 | A |
| ALA | O | 129 | 185.4 | 133.3 | 23.2 | 17 | A |
| ASN | N | 130 | 185.7 | 135.4 | 22.4 | 18 | A |
| ASN | CA | 130 | 184.4 | 135.4 | 21.8 | 17 | A |
| ASN | CB | 130 | 183.9 | 136.8 | 21.5 | 19 | A |
| ASN | CG | 130 | 182.4 | 136.7 | 21.0 | 20 | A |
| ASN | OD1 | 130 | 182.1 | 135.9 | 20.2 | 22 | A |
| ASN | ND2 | 130 | 181.6 | 137.6 | 21.5 | 21 | A |
| ASN | C | 130 | 184.6 | 134.6 | 20.5 | 16 | A |
| ASN | O | 130 | 185.0 | 135.2 | 19.5 | 16 | A |
| TYR | N | 131 | 184.3 | 133.3 | 20.6 | 15 | A |
| TYR | CA | 131 | 184.4 | 132.4 | 19.5 | 15 | A |
| TYR | CB | 131 | 184.2 | 131.0 | 19.9 | 13 | A |
| TYR | CG | 131 | 182.9 | 130.7 | 20.5 | 13 | A |
| TYR | CD1 | 131 | 181.8 | 130.3 | 19.7 | 13 | A |
| TYR | CE1 | 131 | 180.5 | 130.1 | 20.3 | 12 | A |
| TYR | CD2 | 131 | 182.6 | 130.9 | 21.9 | 13 | A |
| TYR | CE2 | 131 | 181.3 | 130.8 | 22.4 | 13 | A |
| TYR | CZ | 131 | 180.3 | 130.4 | 21.6 | 12 | A |
| TYR | OH | 131 | 179.1 | 130.3 | 22.2 | 12 | A |
| TYR | C | 131 | 183.5 | 132.7 | 18.3 | 15 | A |
| TYR | O | 131 | 183.6 | 132.1 | 17.2 | 17 | A |
| THR | N | 132 | 182.4 | 133.4 | 18.5 | 15 | A |
| THR | CA | 132 | 181.5 | 133.7 | 17.5 | 15 | A |
| THR | CB | 132 | 180.2 | 134.4 | 18.0 | 15 | A |
| THR | OG1 | 132 | 179.5 | 133.5 | 18.9 | 15 | A |
| THR | CG2 | 132 | 179.3 | 134.6 | 16.8 | 16 | A |
| THR | C | 132 | 182.1 | 134.7 | 16.6 | 16 | A |
| THR | O | 132 | 181.8 | 134.8 | 15.4 | 16 | A |
| VAL | N | 133 | 182.9 | 135.6 | 17.1 | 17 | A |
| VAL | CA | 133 | 183.5 | 136.6 | 16.3 | 18 | A |
| VAL | CB | 133 | 184.1 | 137.8 | 17.2 | 18 | A |
| VAL | CG1 | 133 | 184.6 | 138.9 | 16.3 | 18 | A |
| VAL | CG2 | 133 | 183.0 | 138.3 | 18.1 | 18 | A |
| VAL | C | 133 | 184.6 | 136.0 | 15.5 | 20 | A |
| VAL | O | 133 | 184.7 | 136.3 | 14.3 | 22 | A |
| TRP | N | 134 | 185.4 | 135.1 | 16.1 | 20 | A |
| TRP | CA | 134 | 186.5 | 134.4 | 15.5 | 21 | A |
| TRP | CB | 134 | 187.2 | 133.5 | 16.4 | 19 | A |
| TRP | CG | 134 | 188.2 | 134.1 | 17.3 | 18 | A |
| TRP | CD2 | 134 | 189.5 | 134.7 | 16.9 | 17 | A |
| TRP | CE2 | 134 | 190.1 | 135.2 | 18.0 | 17 | A |
| TRP | CE3 | 134 | 190.1 | 134.7 | 15.6 | 17 | A |
| TRP | CD1 | 134 | 188.1 | 134.4 | 18.6 | 17 | A |
| TRP | NE1 | 134 | 189.3 | 135.0 | 19.1 | 16 | A |
| TRP | CZ2 | 134 | 191.4 | 135.7 | 17.9 | 17 | A |
| TRP | CZ3 | 134 | 191.4 | 135.3 | 15.6 | 16 | A |
| TRP | CH2 | 134 | 192.0 | 135.8 | 16.7 | 17 | A |
| TRP | C | 134 | 185.9 | 133.7 | 14.3 | 23 | A |
| TRP | O | 134 | 186.6 | 133.6 | 13.2 | 22 | A |
| HIS | N | 135 | 184.7 | 133.2 | 14.4 | 25 | A |
| HIS | CA | 135 | 184.1 | 132.4 | 13.3 | 28 | A |
| HIS | CB | 135 | 182.8 | 131.7 | 13.8 | 30 | A |
| HIS | CG | 135 | 182.0 | 131.1 | 12.7 | 32 | A |
| HIS | CD2 | 135 | 181.1 | 131.6 | 11.9 | 33 | A |
| HIS | ND1 | 135 | 182.3 | 129.8 | 12.3 | 33 | A |
| HIS | CE1 | 135 | 181.5 | 129.6 | 11.2 | 34 | A |
| HIS | NE2 | 135 | 180.8 | 130.7 | 11.0 | 34 | A |
| HIS | C | 135 | 183.7 | 133.4 | 12.2 | 29 | A |
| HIS | O | 135 | 184.1 | 133.1 | 11.0 | 29 | A |
| PHE | N | 136 | 183.0 | 134.5 | 12.5 | 29 | A |
| PHE | CA | 136 | 182.6 | 135.4 | 11.5 | 29 | A |
| PHE | CB | 136 | 181.8 | 136.6 | 12.1 | 31 | A |

TABLE 4-continued

The following table lists the atomic structure coordinates for FPT in complex with FPP and the inhibitor SCH66701 as derived by X-ray diffraction from crystals of that complex
The abbreviations are the same as those used in Table 2

| RES | ATOM | # | X | Y | Z | B | C |
|---|---|---|---|---|---|---|---|
| PHE | CG | 136 | 181.3 | 137.6 | 11.1 | 33 | A |
| PHE | CD1 | 136 | 180.3 | 137.2 | 10.1 | 34 | A |
| PHE | CD2 | 136 | 181.7 | 138.9 | 11.1 | 34 | A |
| PHE | CE1 | 136 | 179.8 | 138.1 | 9.2 | 34 | A |
| PHE | CE2 | 136 | 181.2 | 139.8 | 10.1 | 35 | A |
| PHE | CZ | 136 | 180.3 | 139.4 | 9.2 | 34 | A |
| PHE | C | 136 | 183.9 | 136.0 | 10.8 | 28 | A |
| PHE | O | 136 | 183.9 | 136.3 | 9.6 | 29 | A |
| ARG | N | 137 | 185.0 | 136.1 | 11.5 | 27 | A |
| ARG | CA | 137 | 186.2 | 136.6 | 10.9 | 25 | A |
| ARG | CB | 137 | 187.3 | 136.8 | 12.0 | 24 | A |
| ARG | CG | 137 | 188.5 | 137.4 | 11.5 | 23 | A |
| ARG | CD | 137 | 189.4 | 137.8 | 12.6 | 23 | A |
| ARG | NE | 137 | 190.7 | 138.2 | 12.1 | 23 | A |
| ARG | CZ | 137 | 191.1 | 139.5 | 11.9 | 22 | A |
| ARG | NH1 | 137 | 190.2 | 140.5 | 12.2 | 22 | A |
| ARG | NH2 | 137 | 192.3 | 139.8 | 11.5 | 22 | A |
| ARG | C | 137 | 186.8 | 135.6 | 9.9 | 25 | A |
| ARG | O | 137 | 187.2 | 136.0 | 8.8 | 25 | A |
| ARG | N | 138 | 186.8 | 134.3 | 10.2 | 25 | A |
| ARG | CA | 138 | 187.3 | 133.4 | 9.3 | 23 | A |
| ARG | CB | 138 | 187.2 | 132.0 | 9.8 | 22 | A |
| ARG | CG | 138 | 188.5 | 131.3 | 10.0 | 21 | A |
| ARG | CD | 138 | 188.9 | 131.2 | 11.4 | 20 | A |
| ARG | NE | 138 | 188.1 | 130.3 | 12.2 | 19 | A |
| ARG | CZ | 138 | 188.1 | 130.2 | 13.5 | 19 | A |
| ARG | NH1 | 138 | 188.9 | 130.9 | 14.3 | 19 | A |
| ARG | NH2 | 138 | 187.3 | 129.2 | 14.1 | 19 | A |
| ARG | C | 138 | 186.4 | 133.5 | 8.0 | 23 | A |
| ARG | O | 138 | 186.9 | 133.5 | 6.9 | 22 | A |
| VAL | N | 139 | 185.1 | 133.7 | 8.2 | 23 | A |
| VAL | CA | 139 | 184.2 | 133.9 | 7.1 | 24 | A |
| VAL | CB | 139 | 182.8 | 134.2 | 7.7 | 24 | A |
| VAL | CG1 | 139 | 181.8 | 134.5 | 6.5 | 24 | A |
| VAL | CG2 | 139 | 182.2 | 132.9 | 8.4 | 24 | A |
| VAL | C | 139 | 184.6 | 135.0 | 6.2 | 24 | A |
| VAL | O | 139 | 184.8 | 134.9 | 5.0 | 23 | A |
| LEU | N | 140 | 184.8 | 136.2 | 6.8 | 25 | A |
| LEU | CA | 140 | 185.3 | 137.4 | 6.1 | 26 | A |
| LEU | CB | 140 | 185.4 | 138.6 | 7.0 | 25 | A |
| LEU | CG | 140 | 183.9 | 139.0 | 7.4 | 25 | A |
| LEU | CD1 | 140 | 184.0 | 140.1 | 8.4 | 25 | A |
| LEU | CD2 | 140 | 183.2 | 139.3 | 6.2 | 24 | A |
| LEU | C | 140 | 186.6 | 137.1 | 5.4 | 28 | A |
| LEU | O | 140 | 186.8 | 137.4 | 4.2 | 29 | A |
| LEU | N | 141 | 187.5 | 136.4 | 6.1 | 29 | A |
| LEU | CA | 141 | 188.8 | 136.0 | 5.5 | 31 | A |
| LEU | CB | 141 | 189.6 | 135.2 | 6.5 | 29 | A |
| LEU | CG | 141 | 190.4 | 135.8 | 7.6 | 28 | A |
| LEU | CD1 | 141 | 191.0 | 134.7 | 8.4 | 28 | A |
| LEU | CD2 | 141 | 191.4 | 136.8 | 7.1 | 27 | A |
| LEU | C | 141 | 188.6 | 135.3 | 4.2 | 34 | A |
| LEU | O | 141 | 189.4 | 135.4 | 3.3 | 35 | A |
| ARG | N | 142 | 187.5 | 134.5 | 4.1 | 38 | A |
| ARG | CA | 142 | 187.3 | 133.7 | 2.9 | 41 | A |
| ARG | CB | 142 | 186.3 | 132.5 | 3.2 | 44 | A |
| ARG | CG | 142 | 186.6 | 131.8 | 4.5 | 48 | A |
| ARG | CD | 142 | 185.3 | 131.0 | 5.1 | 51 | A |
| ARG | NE | 142 | 185.3 | 130.8 | 6.5 | 53 | A |
| ARG | CZ | 142 | 184.9 | 129.8 | 7.2 | 54 | A |
| ARG | NH1 | 142 | 184.4 | 128.7 | 6.6 | 56 | A |
| ARG | NH2 | 142 | 184.8 | 129.8 | 8.6 | 54 | A |
| ARG | C | 142 | 186.7 | 134.6 | 1.8 | 41 | A |
| ARG | O | 142 | 187.2 | 134.7 | 0.7 | 40 | A |
| SER | N | 143 | 185.5 | 135.2 | 2.2 | 40 | A |
| SER | CA | 143 | 184.8 | 136.1 | 1.3 | 39 | A |
| SER | CB | 143 | 183.6 | 136.6 | 2.0 | 39 | A |
| SER | OG | 143 | 183.2 | 135.7 | 2.9 | 41 | A |
| SER | C | 143 | 185.6 | 137.2 | 0.7 | 39 | A |
| SER | O | 143 | 185.6 | 137.5 | −0.5 | 39 | A |
| LEU | N | 144 | 186.4 | 137.9 | 1.5 | 38 | A |
| LEU | CA | 144 | 187.2 | 139.0 | 1.0 | 37 | A |

TABLE 4-continued

The following table lists the atomic structure coordinates for FPT in complex with FPP and the inhibitor SCH66701 as derived by X-ray diffraction from crystals of that complex
The abbreviations are the same as those used in Table 2

| RES | ATOM | # | X | Y | Z | B | C |
|---|---|---|---|---|---|---|---|
| LEU | CB | 144 | 187.4 | 140.1 | 2.2 | 37 | A |
| LEU | CG | 144 | 186.3 | 140.5 | 3.1 | 36 | A |
| LEU | CD1 | 144 | 186.9 | 141.4 | 4.2 | 36 | A |
| LEU | CD2 | 144 | 185.2 | 141.2 | 2.5 | 35 | A |
| LEU | C | 144 | 188.5 | 138.6 | 0.5 | 37 | A |
| LEU | O | 144 | 189.3 | 139.4 | 0.0 | 37 | A |
| GLN | N | 145 | 188.8 | 137.3 | 0.5 | 37 | A |
| GLN | CA | 145 | 190.1 | 136.7 | 0.0 | 38 | A |
| GLN | CB | 145 | 190.1 | 136.7 | −1.5 | 40 | A |
| GLN | CG | 145 | 189.1 | 135.7 | −2.0 | 44 | A |
| GLN | CD | 145 | 189.4 | 135.4 | −3.5 | 46 | A |
| GLN | OE1 | 145 | 189.3 | 136.3 | −4.3 | 48 | A |
| GLN | NE2 | 145 | 189.6 | 134.2 | −3.8 | 48 | A |
| GLN | C | 145 | 191.2 | 137.5 | 0.6 | 36 | A |
| GLN | O | 145 | 192.0 | 138.1 | −0.2 | 35 | A |
| LYS | N | 146 | 191.4 | 137.6 | 1.9 | 35 | A |
| LYS | CA | 146 | 192.4 | 138.3 | 2.5 | 34 | A |
| LYS | CB | 146 | 192.1 | 138.5 | 4.0 | 34 | A |
| LYS | CG | 146 | 190.7 | 139.2 | 4.3 | 35 | A |
| LYS | CD | 146 | 190.7 | 140.6 | 3.7 | 35 | A |
| LYS | CE | 146 | 191.8 | 141.4 | 4.2 | 35 | A |
| LYS | NZ | 146 | 191.6 | 142.8 | 3.7 | 35 | A |
| LYS | C | 146 | 193.7 | 137.6 | 2.4 | 35 | A |
| LYS | O | 146 | 193.7 | 136.3 | 2.3 | 34 | A |
| ASP | N | 147 | 194.8 | 138.3 | 2.5 | 34 | A |
| ASP | CA | 147 | 196.1 | 137.7 | 2.5 | 34 | A |
| ASP | CB | 147 | 197.2 | 138.8 | 2.3 | 34 | A |
| ASP | CG | 147 | 198.6 | 138.3 | 2.2 | 34 | A |
| ASP | OD1 | 147 | 199.1 | 137.7 | 3.1 | 36 | A |
| ASP | OD2 | 147 | 199.2 | 138.5 | 1.1 | 35 | A |
| ASP | C | 147 | 196.3 | 137.0 | 3.8 | 33 | A |
| ASP | O | 147 | 196.5 | 137.6 | 4.8 | 34 | A |
| LEU | N | 148 | 196.3 | 135.6 | 3.7 | 33 | A |
| LEU | CA | 148 | 196.5 | 134.8 | 4.9 | 32 | A |
| LEU | CB | 148 | 196.1 | 133.4 | 4.5 | 31 | A |
| LEU | CG | 148 | 194.6 | 133.2 | 4.1 | 31 | A |
| LEU | CD1 | 148 | 194.3 | 131.7 | 3.7 | 31 | A |
| LEU | CD2 | 148 | 193.7 | 133.6 | 5.2 | 31 | A |
| LEU | C | 148 | 197.9 | 134.9 | 5.5 | 31 | A |
| LEU | O | 148 | 198.1 | 134.6 | 6.7 | 31 | A |
| GLN | N | 149 | 198.9 | 135.3 | 4.7 | 32 | A |
| GLN | CA | 149 | 200.2 | 135.3 | 5.3 | 33 | A |
| GLN | CB | 149 | 201.2 | 135.5 | 4.2 | 34 | A |
| GLN | CG | 149 | 202.6 | 135.0 | 4.7 | 36 | A |
| GLN | CD | 149 | 202.4 | 133.6 | 5.4 | 37 | A |
| GLN | OE1 | 149 | 202.2 | 132.6 | 4.8 | 38 | A |
| GLN | NE2 | 149 | 202.5 | 133.7 | 6.7 | 39 | A |
| GLN | C | 149 | 200.2 | 136.5 | 6.2 | 34 | A |
| GLN | O | 149 | 201.1 | 136.6 | 7.0 | 35 | A |
| GLU | N | 150 | 199.4 | 137.5 | 5.9 | 36 | A |
| GLU | CA | 150 | 199.3 | 138.7 | 6.7 | 38 | A |
| GLU | CB | 150 | 198.7 | 139.9 | 6.0 | 41 | A |
| GLU | CG | 150 | 199.6 | 141.0 | 5.7 | 46 | A |
| GLU | CD | 150 | 200.9 | 140.6 | 4.8 | 49 | A |
| GLU | OE1 | 150 | 202.0 | 141.0 | 5.2 | 51 | A |
| GLU | OE2 | 150 | 200.7 | 140.1 | 3.7 | 50 | A |
| GLU | C | 150 | 198.5 | 138.4 | 8.0 | 37 | A |
| GLU | O | 150 | 198.9 | 138.8 | 9.1 | 37 | A |
| GLU | N | 151 | 197.5 | 137.6 | 7.8 | 34 | A |
| GLU | CA | 151 | 196.6 | 137.1 | 8.9 | 32 | A |
| GLU | CB | 151 | 195.4 | 136.4 | 8.4 | 31 | A |
| GLU | CG | 151 | 194.5 | 135.9 | 9.5 | 30 | A |
| GLU | CD | 151 | 193.7 | 137.0 | 10.2 | 30 | A |
| GLU | OE1 | 151 | 193.5 | 138.1 | 9.7 | 30 | A |
| GLU | OE2 | 151 | 193.3 | 136.7 | 11.4 | 30 | A |
| GLU | C | 151 | 197.5 | 136.3 | 9.8 | 31 | A |
| GLU | O | 151 | 197.3 | 136.3 | 11.0 | 31 | A |
| MET | N | 152 | 198.5 | 135.6 | 9.3 | 29 | A |
| MET | CA | 152 | 199.4 | 134.8 | 10.1 | 28 | A |
| MET | CB | 152 | 200.5 | 134.1 | 9.2 | 27 | A |
| MET | CG | 152 | 200.0 | 132.8 | 8.6 | 26 | A |
| MET | SD | 152 | 199.9 | 131.5 | 9.9 | 25 | A |

TABLE 4-continued

The following table lists the atomic structure coordinates for FPT in complex with FPP and the inhibitor SCH66701 as derived by X-ray diffraction from crystals of that complex
The abbreviations are the same as those used in Table 2

| RES | ATOM | # | X | Y | Z | B | C |
|---|---|---|---|---|---|---|---|
| MET | CE | 152 | 201.4 | 131.8 | 10.8 | 24 | A |
| MET | C | 152 | 200.1 | 135.8 | 11.0 | 28 | A |
| MET | O | 152 | 200.1 | 135.6 | 12.2 | 28 | A |
| ASN | N | 153 | 200.5 | 136.9 | 10.4 | 28 | A |
| ASN | CA | 153 | 201.2 | 137.9 | 11.2 | 28 | A |
| ASN | CB | 153 | 201.6 | 139.0 | 10.2 | 30 | A |
| ASN | CG | 153 | 202.6 | 138.6 | 9.2 | 30 | A |
| ASN | OD1 | 153 | 202.9 | 137.4 | 9.2 | 31 | A |
| ASN | ND2 | 153 | 203.0 | 139.5 | 8.3 | 30 | A |
| ASN | C | 153 | 200.3 | 138.5 | 12.3 | 28 | A |
| ASN | O | 153 | 200.8 | 138.7 | 13.4 | 27 | A |
| TYR | N | 154 | 199.0 | 138.6 | 12.1 | 27 | A |
| TYR | CA | 154 | 198.1 | 139.1 | 13.1 | 26 | A |
| TYR | CB | 154 | 196.7 | 139.2 | 12.4 | 25 | A |
| TYR | CG | 154 | 195.6 | 139.5 | 13.4 | 26 | A |
| TYR | CD1 | 154 | 195.5 | 140.7 | 14.1 | 27 | A |
| TYR | CE1 | 154 | 194.5 | 140.9 | 15.0 | 27 | A |
| TYR | CD2 | 154 | 194.6 | 138.5 | 13.7 | 27 | A |
| TYR | CE2 | 154 | 193.6 | 138.7 | 14.6 | 28 | A |
| TYR | CZ | 154 | 193.6 | 140.0 | 15.3 | 28 | A |
| TYR | OH | 154 | 192.6 | 140.1 | 16.3 | 30 | A |
| TYR | C | 154 | 198.0 | 138.1 | 14.2 | 25 | A |
| TYR | O | 154 | 198.3 | 138.4 | 15.4 | 26 | A |
| ILE | N | 155 | 197.7 | 136.9 | 13.8 | 24 | A |
| ILE | CA | 155 | 197.5 | 135.8 | 14.8 | 22 | A |
| ILE | CB | 155 | 197.0 | 134.5 | 14.2 | 21 | A |
| ILE | CG2 | 155 | 198.1 | 133.7 | 13.6 | 21 | A |
| ILE | CG1 | 155 | 196.2 | 133.7 | 15.2 | 21 | A |
| ILE | CD1 | 155 | 195.0 | 134.4 | 15.7 | 21 | A |
| ILE | C | 155 | 198.8 | 135.6 | 15.6 | 21 | A |
| ILE | O | 155 | 198.8 | 135.2 | 16.8 | 21 | A |
| THR | N | 156 | 199.9 | 135.9 | 15.0 | 20 | A |
| THR | CA | 156 | 201.2 | 135.8 | 15.8 | 21 | A |
| THR | CB | 156 | 202.4 | 136.1 | 14.8 | 21 | A |
| THR | OG1 | 156 | 202.3 | 135.2 | 13.7 | 22 | A |
| THR | CG2 | 156 | 203.7 | 135.8 | 15.5 | 21 | A |
| THR | C | 156 | 201.2 | 136.8 | 16.9 | 21 | A |
| THR | O | 156 | 201.6 | 136.4 | 18.1 | 21 | A |
| ALA | N | 157 | 200.8 | 138.0 | 16.7 | 22 | A |
| ALA | CA | 157 | 200.8 | 139.1 | 17.7 | 22 | A |
| ALA | CB | 157 | 200.5 | 140.4 | 17.0 | 22 | A |
| ALA | C | 157 | 199.9 | 138.8 | 18.8 | 22 | A |
| ALA | O | 157 | 200.3 | 138.9 | 19.9 | 21 | A |
| ILE | N | 158 | 198.6 | 138.5 | 18.5 | 22 | A |
| ILE | CA | 158 | 197.6 | 138.3 | 19.5 | 22 | A |
| ILE | CB | 158 | 196.2 | 137.9 | 18.8 | 23 | A |
| ILE | CG2 | 158 | 195.3 | 137.6 | 19.9 | 24 | A |
| ILE | CG1 | 158 | 195.7 | 139.1 | 18.0 | 25 | A |
| ILE | CD1 | 158 | 195.4 | 140.3 | 18.9 | 26 | A |
| ILE | C | 158 | 198.0 | 137.1 | 20.4 | 22 | A |
| ILE | O | 158 | 197.7 | 137.2 | 21.6 | 23 | A |
| ILE | N | 159 | 198.5 | 136.0 | 19.8 | 22 | A |
| ILE | CA | 159 | 198.9 | 134.9 | 20.6 | 21 | A |
| ILE | CB | 159 | 199.4 | 133.7 | 19.8 | 20 | A |
| ILE | CG2 | 159 | 199.8 | 132.6 | 20.7 | 20 | A |
| ILE | CG1 | 159 | 198.3 | 133.2 | 18.9 | 22 | A |
| ILE | CD1 | 159 | 198.7 | 132.1 | 17.9 | 22 | A |
| ILE | C | 159 | 200.0 | 135.4 | 21.6 | 21 | A |
| ILE | O | 159 | 199.9 | 135.2 | 22.8 | 21 | A |
| GLU | N | 160 | 201.0 | 136.1 | 21.0 | 22 | A |
| GLU | CA | 160 | 202.1 | 136.5 | 21.8 | 23 | A |
| GLU | CB | 160 | 203.1 | 137.4 | 21.1 | 23 | A |
| GLU | CG | 160 | 203.9 | 136.6 | 20.0 | 22 | A |
| GLU | CD | 160 | 205.2 | 136.0 | 20.6 | 22 | A |
| GLU | OE1 | 160 | 205.5 | 136.2 | 21.8 | 22 | A |
| GLU | OE2 | 160 | 205.9 | 135.4 | 19.8 | 21 | A |
| GLU | C | 160 | 201.5 | 137.3 | 23.0 | 24 | A |
| GLU | O | 160 | 202.1 | 137.2 | 24.1 | 25 | A |
| GLU | N | 161 | 200.4 | 138.1 | 22.8 | 26 | A |
| GLU | CA | 161 | 199.9 | 138.8 | 24.0 | 28 | A |
| GLU | CB | 161 | 199.3 | 140.2 | 23.5 | 30 | A |
| GLU | CG | 161 | 198.2 | 140.1 | 22.5 | 33 | A |
| GLU | CD | 161 | 198.0 | 141.4 | 21.7 | 36 | A |
| GLU | OE1 | 161 | 199.0 | 141.9 | 21.1 | 37 | A |
| GLU | OE2 | 161 | 196.8 | 141.8 | 21.6 | 38 | A |
| GLU | C | 161 | 199.0 | 138.0 | 24.9 | 27 | A |
| GLU | O | 161 | 198.9 | 138.3 | 26.1 | 29 | A |
| GLN | N | 162 | 198.3 | 137.0 | 24.3 | 27 | A |
| GLN | CA | 162 | 197.4 | 136.1 | 25.1 | 26 | A |
| GLN | CB | 162 | 196.0 | 136.6 | 25.2 | 28 | A |
| GLN | CG | 162 | 195.3 | 137.2 | 23.9 | 31 | A |
| GLN | CD | 162 | 194.1 | 138.1 | 24.3 | 34 | A |
| GLN | OE1 | 162 | 193.3 | 137.7 | 25.2 | 33 | A |
| GLN | NE2 | 162 | 194.0 | 139.3 | 23.7 | 34 | A |
| GLN | C | 162 | 197.5 | 134.7 | 24.6 | 24 | A |
| GLN | O | 162 | 196.6 | 134.2 | 23.9 | 24 | A |
| PRO | N | 163 | 198.6 | 134.0 | 24.9 | 22 | A |
| PRO | CD | 163 | 199.6 | 134.4 | 25.9 | 21 | A |
| PRO | CA | 163 | 198.9 | 132.6 | 24.5 | 21 | A |
| PRO | CB | 163 | 200.4 | 132.5 | 24.8 | 20 | A |
| PRO | CG | 163 | 200.4 | 133.2 | 26.2 | 20 | A |
| PRO | C | 163 | 198.1 | 131.5 | 25.2 | 21 | A |
| PRO | O | 163 | 198.4 | 130.3 | 25.0 | 21 | A |
| LYS | N | 164 | 197.3 | 131.9 | 26.2 | 21 | A |
| LYS | CA | 164 | 196.5 | 131.0 | 27.0 | 20 | A |
| LYS | CB | 164 | 196.7 | 131.2 | 28.5 | 19 | A |
| LYS | CG | 164 | 198.0 | 130.7 | 28.9 | 20 | A |
| LYS | CD | 164 | 198.0 | 130.6 | 30.4 | 19 | A |
| LYS | CE | 164 | 199.4 | 130.2 | 30.8 | 20 | A |
| LYS | NZ | 164 | 199.3 | 130.0 | 32.3 | 21 | A |
| LYS | C | 164 | 195.0 | 131.2 | 26.6 | 20 | A |
| LYS | O | 164 | 194.2 | 131.6 | 27.4 | 22 | A |
| ASN | N | 165 | 194.7 | 130.9 | 25.3 | 20 | A |
| ASN | CA | 165 | 193.3 | 131.1 | 24.8 | 18 | A |
| ASN | CB | 165 | 193.2 | 132.5 | 24.2 | 17 | A |
| ASN | CG | 165 | 192.1 | 132.6 | 23.3 | 18 | A |
| ASN | OD1 | 165 | 191.9 | 131.7 | 22.4 | 20 | A |
| ASN | ND2 | 165 | 191.3 | 133.7 | 23.3 | 18 | A |
| ASN | C | 165 | 193.2 | 130.0 | 23.8 | 18 | A |
| ASN | O | 165 | 194.1 | 129.6 | 23.2 | 18 | A |
| TYR | N | 166 | 192.0 | 129.4 | 23.8 | 17 | A |
| TYR | CA | 166 | 191.7 | 128.3 | 22.8 | 17 | A |
| TYR | CB | 166 | 190.5 | 127.5 | 23.3 | 18 | A |
| TYR | CG | 166 | 190.7 | 126.6 | 24.5 | 20 | A |
| TYR | CD1 | 166 | 190.6 | 127.1 | 25.8 | 21 | A |
| TYR | CE1 | 166 | 190.8 | 126.3 | 26.9 | 22 | A |
| TYR | CD2 | 166 | 191.0 | 125.3 | 24.3 | 22 | A |
| TYR | CE2 | 166 | 191.2 | 124.4 | 25.4 | 23 | A |
| TYR | CZ | 166 | 191.0 | 124.9 | 26.7 | 22 | A |
| TYR | OH | 166 | 191.2 | 124.1 | 27.8 | 23 | A |
| TYR | C | 166 | 191.5 | 128.8 | 21.4 | 16 | A |
| TYR | O | 166 | 192.0 | 128.1 | 20.5 | 18 | A |
| GLN | N | 167 | 190.8 | 129.9 | 21.2 | 14 | A |
| GLN | CA | 167 | 190.5 | 130.4 | 19.9 | 12 | A |
| GLN | CB | 167 | 189.5 | 131.5 | 19.9 | 12 | A |
| GLN | CG | 167 | 188.1 | 131.1 | 20.3 | 12 | A |
| GLN | CD | 167 | 188.1 | 130.7 | 21.8 | 13 | A |
| GLN | OE1 | 167 | 188.8 | 131.2 | 22.6 | 13 | A |
| GLN | NE2 | 167 | 187.2 | 129.8 | 22.1 | 14 | A |
| GLN | C | 167 | 191.7 | 130.9 | 19.1 | 12 | A |
| GLN | O | 167 | 191.8 | 130.7 | 17.8 | 12 | A |
| VAL | N | 168 | 192.6 | 131.6 | 19.7 | 11 | A |
| VAL | CA | 168 | 193.8 | 132.2 | 19.1 | 11 | A |
| VAL | CB | 168 | 194.7 | 133.0 | 20.0 | 11 | A |
| VAL | CG1 | 168 | 194.0 | 134.2 | 20.6 | 10 | A |
| VAL | CG2 | 168 | 195.3 | 132.2 | 21.1 | 11 | A |
| VAL | C | 168 | 194.6 | 131.1 | 18.4 | 13 | A |
| VAL | O | 168 | 194.7 | 131.0 | 17.2 | 15 | A |
| TRP | N | 169 | 194.9 | 130.0 | 19.2 | 13 | A |
| TRP | CA | 169 | 195.6 | 128.9 | 18.6 | 11 | A |
| TRP | CB | 169 | 196.0 | 127.9 | 19.7 | 10 | A |
| TRP | CG | 169 | 197.0 | 128.5 | 20.6 | 10 | A |
| TRP | CD2 | 169 | 198.4 | 128.5 | 20.4 | 11 | A |
| TRP | CE2 | 169 | 199.0 | 129.1 | 21.6 | 11 | A |

TABLE 4-continued

The following table lists the atomic structure coordinates for FPT in complex with FPP and the inhibitor SCH66701 as derived by X-ray diffraction from crystals of that complex The abbreviations are the same as those used in Table 2

| RES | ATOM | # | X | Y | Z | B | C |
|---|---|---|---|---|---|---|---|
| TRP | CE3 | 169 | 199.3 | 128.1 | 19.4 | 11 | A |
| TRP | CD1 | 169 | 196.8 | 129.1 | 21.9 | 10 | A |
| TRP | NE1 | 169 | 198.0 | 129.4 | 22.4 | 11 | A |
| TRP | CZ2 | 169 | 200.4 | 129.2 | 21.7 | 12 | A |
| TRP | CZ3 | 169 | 200.6 | 128.2 | 19.5 | 11 | A |
| TRP | CH2 | 169 | 201.2 | 128.8 | 20.6 | 12 | A |
| TRP | C | 169 | 194.9 | 128.2 | 17.6 | 12 | A |
| TRP | O | 169 | 195.4 | 128.0 | 16.5 | 12 | A |
| HIS | N | 170 | 193.6 | 127.9 | 17.8 | 13 | A |
| HIS | CA | 170 | 192.8 | 127.2 | 16.8 | 15 | A |
| HIS | CB | 170 | 191.4 | 126.9 | 17.2 | 17 | A |
| HIS | CG | 170 | 190.6 | 126.2 | 16.2 | 19 | A |
| HIS | CD2 | 170 | 189.4 | 126.5 | 15.6 | 21 | A |
| HIS | ND1 | 170 | 190.9 | 124.9 | 15.8 | 21 | A |
| HIS | CE1 | 170 | 190.1 | 124.5 | 14.9 | 22 | A |
| HIS | NE2 | 170 | 189.1 | 125.4 | 14.8 | 21 | A |
| HIS | C | 170 | 192.7 | 128.0 | 15.5 | 16 | A |
| HIS | O | 170 | 192.4 | 127.4 | 14.4 | 17 | A |
| HIS | N | 171 | 192.8 | 129.3 | 15.6 | 17 | A |
| HIS | CA | 171 | 192.7 | 130.2 | 14.5 | 17 | A |
| HIS | CB | 171 | 192.6 | 131.6 | 14.9 | 17 | A |
| HIS | CG | 171 | 192.3 | 132.5 | 13.8 | 17 | A |
| HIS | CD2 | 171 | 193.0 | 133.6 | 13.3 | 18 | A |
| HIS | ND1 | 171 | 191.2 | 132.4 | 13.0 | 17 | A |
| HIS | CE1 | 171 | 191.2 | 133.4 | 12.1 | 17 | A |
| HIS | NE2 | 171 | 192.3 | 134.1 | 12.2 | 18 | A |
| HIS | C | 171 | 194.0 | 130.0 | 13.7 | 18 | A |
| HIS | O | 171 | 194.0 | 129.8 | 12.5 | 18 | A |
| ARG | N | 172 | 195.1 | 129.9 | 14.5 | 18 | A |
| ARG | CA | 172 | 196.4 | 129.7 | 13.8 | 18 | A |
| ARG | CB | 172 | 197.5 | 129.7 | 14.9 | 17 | A |
| ARG | CG | 172 | 198.8 | 129.8 | 14.3 | 15 | A |
| ARG | CD | 172 | 199.9 | 130.2 | 15.2 | 15 | A |
| ARG | NE | 172 | 201.2 | 130.0 | 14.6 | 17 | A |
| ARG | CZ | 172 | 201.9 | 130.9 | 14.1 | 18 | A |
| ARG | NH1 | 172 | 201.6 | 132.2 | 14.2 | 18 | A |
| ARG | NH2 | 172 | 203.0 | 130.6 | 13.4 | 19 | A |
| ARG | C | 172 | 196.4 | 128.4 | 13.1 | 19 | A |
| ARG | O | 172 | 196.9 | 128.3 | 12.0 | 20 | A |
| ARG | N | 173 | 195.8 | 127.4 | 13.7 | 21 | A |
| ARG | CA | 173 | 195.8 | 126.0 | 13.1 | 22 | A |
| ARG | CB | 173 | 195.1 | 125.1 | 14.0 | 23 | A |
| ARG | CG | 173 | 194.8 | 123.7 | 13.3 | 25 | A |
| ARG | CD | 173 | 194.3 | 122.8 | 14.4 | 27 | A |
| ARG | NE | 173 | 193.8 | 121.6 | 13.7 | 30 | A |
| ARG | CZ | 173 | 194.0 | 120.4 | 14.2 | 31 | A |
| ARG | NH1 | 173 | 194.7 | 120.1 | 15.2 | 32 | A |
| ARG | NH2 | 173 | 193.5 | 119.3 | 13.5 | 32 | A |
| ARG | C | 173 | 195.0 | 126.1 | 11.8 | 21 | A |
| ARG | O | 173 | 195.4 | 125.4 | 10.8 | 22 | A |
| VAL | N | 174 | 193.9 | 126.8 | 11.8 | 22 | A |
| VAL | CA | 174 | 193.1 | 126.9 | 10.6 | 22 | A |
| VAL | CB | 174 | 191.8 | 127.6 | 10.8 | 20 | A |
| VAL | CG1 | 174 | 191.1 | 127.9 | 9.6 | 19 | A |
| VAL | CG2 | 174 | 191.0 | 126.8 | 11.8 | 20 | A |
| VAL | C | 174 | 193.9 | 127.6 | 9.4 | 24 | A |
| VAL | O | 174 | 193.8 | 127.2 | 8.3 | 26 | A |
| LEU | N | 175 | 194.6 | 128.7 | 9.7 | 24 | A |
| LEU | CA | 175 | 195.4 | 129.3 | 8.7 | 25 | A |
| LEU | CB | 175 | 196.1 | 130.6 | 9.3 | 25 | A |
| LEU | CG | 175 | 195.1 | 131.7 | 9.8 | 25 | A |
| LEU | CD1 | 175 | 196.0 | 132.9 | 10.3 | 26 | A |
| LEU | CD2 | 175 | 194.2 | 132.2 | 8.7 | 24 | A |
| LEU | C | 175 | 196.5 | 128.4 | 8.1 | 26 | A |
| LEU | O | 175 | 196.5 | 128.3 | 6.9 | 26 | A |
| VAL | N | 176 | 197.2 | 127.7 | 9.0 | 26 | A |
| VAL | CA | 176 | 198.3 | 126.8 | 8.5 | 26 | A |
| VAL | CB | 176 | 199.1 | 126.2 | 9.7 | 26 | A |
| VAL | CG1 | 176 | 200.1 | 125.2 | 9.2 | 25 | A |
| VAL | CG2 | 176 | 199.8 | 127.3 | 10.4 | 26 | A |
| VAL | C | 176 | 197.7 | 125.7 | 7.6 | 26 | A |
| VAL | O | 176 | 198.4 | 125.2 | 6.8 | 27 | A |

TABLE 4-continued

The following table lists the atomic structure coordinates for FPT in complex with FPP and the inhibitor SCH66701 as derived by X-ray diffraction from crystals of that complex The abbreviations are the same as those used in Table 2

| RES | ATOM | # | X | Y | Z | B | C |
|---|---|---|---|---|---|---|---|
| GLU | N | 177 | 196.5 | 125.3 | 7.9 | 27 | A |
| GLU | CA | 177 | 195.8 | 124.3 | 7.1 | 28 | A |
| GLU | CB | 177 | 194.6 | 123.8 | 7.8 | 29 | A |
| GLU | CG | 177 | 194.9 | 123.0 | 9.0 | 30 | A |
| GLU | CD | 177 | 193.7 | 122.4 | 9.7 | 32 | A |
| GLU | OE1 | 177 | 193.8 | 121.4 | 10.4 | 33 | A |
| GLU | OE2 | 177 | 192.6 | 123.0 | 9.5 | 33 | A |
| GLU | C | 177 | 195.5 | 124.9 | 5.7 | 28 | A |
| GLU | O | 177 | 195.8 | 124.3 | 4.7 | 28 | A |
| TRP | N | 178 | 194.8 | 126.0 | 5.7 | 28 | A |
| TRP | CA | 178 | 194.4 | 126.7 | 4.5 | 28 | A |
| TRP | CB | 178 | 193.8 | 128.1 | 4.8 | 28 | A |
| TRP | CG | 178 | 192.4 | 128.1 | 5.2 | 27 | A |
| TRP | CD2 | 178 | 191.7 | 129.2 | 5.8 | 27 | A |
| TRP | CE2 | 178 | 190.4 | 128.8 | 6.0 | 26 | A |
| TRP | CE3 | 178 | 192.1 | 130.5 | 6.2 | 27 | A |
| TRP | CD1 | 178 | 191.5 | 127.2 | 5.0 | 27 | A |
| TRP | NE1 | 178 | 190.3 | 127.6 | 5.5 | 26 | A |
| TRP | CZ2 | 178 | 189.4 | 129.7 | 6.5 | 26 | A |
| TRP | CZ3 | 178 | 191.2 | 131.3 | 6.8 | 26 | A |
| TRP | CH2 | 178 | 189.8 | 130.9 | 7.0 | 26 | A |
| TRP | C | 178 | 195.7 | 126.9 | 3.6 | 29 | A |
| TRP | O | 178 | 195.6 | 126.7 | 2.4 | 30 | A |
| LEU | N | 179 | 196.7 | 127.4 | 4.3 | 29 | A |
| LEU | CA | 179 | 198.0 | 127.7 | 3.6 | 30 | A |
| LEU | CB | 179 | 198.8 | 128.6 | 4.5 | 30 | A |
| LEU | CG | 179 | 198.5 | 130.1 | 4.6 | 29 | A |
| LEU | CD1 | 179 | 199.6 | 130.8 | 5.4 | 30 | A |
| LEU | CD2 | 179 | 198.3 | 130.8 | 3.3 | 29 | A |
| LEU | C | 179 | 198.8 | 126.4 | 3.4 | 31 | A |
| LEU | O | 179 | 199.7 | 126.5 | 2.6 | 31 | A |
| LYS | N | 180 | 198.6 | 125.4 | 4.1 | 33 | A |
| LYS | CA | 180 | 199.4 | 124.2 | 4.0 | 34 | A |
| LYS | CB | 180 | 199.2 | 123.6 | 2.6 | 36 | A |
| LYS | CG | 180 | 197.8 | 123.3 | 2.2 | 39 | A |
| LYS | CD | 180 | 197.6 | 123.0 | 0.8 | 41 | A |
| LYS | CE | 180 | 196.1 | 122.5 | 0.5 | 42 | A |
| LYS | NZ | 180 | 195.8 | 121.2 | 1.3 | 43 | A |
| LYS | C | 180 | 200.9 | 124.5 | 4.2 | 34 | A |
| LYS | O | 180 | 201.8 | 123.9 | 3.7 | 35 | A |
| ASP | N | 181 | 201.1 | 125.6 | 5.1 | 32 | A |
| ASP | CA | 181 | 202.4 | 126.1 | 5.3 | 32 | A |
| ASP | CB | 181 | 202.5 | 127.5 | 4.9 | 32 | A |
| ASP | CG | 181 | 203.9 | 128.1 | 4.8 | 33 | A |
| ASP | OD1 | 181 | 204.8 | 127.4 | 5.3 | 32 | A |
| ASP | OD2 | 181 | 204.0 | 129.2 | 4.3 | 33 | A |
| ASP | C | 181 | 202.8 | 126.0 | 6.8 | 32 | A |
| ASP | O | 181 | 202.4 | 126.8 | 7.6 | 33 | A |
| PRO | N | 182 | 203.7 | 125.0 | 7.2 | 32 | A |
| PRO | CD | 182 | 203.9 | 123.8 | 6.4 | 31 | A |
| PRO | CA | 182 | 204.1 | 124.8 | 8.5 | 31 | A |
| PRO | CB | 182 | 204.3 | 123.3 | 8.6 | 31 | A |
| PRO | CG | 182 | 204.8 | 123.0 | 7.3 | 31 | A |
| PRO | C | 182 | 205.5 | 125.4 | 8.8 | 30 | A |
| PRO | O | 182 | 206.0 | 125.3 | 9.9 | 31 | A |
| SER | N | 183 | 206.1 | 126.0 | 7.7 | 30 | A |
| SER | CA | 183 | 207.4 | 126.6 | 7.8 | 31 | A |
| SER | CB | 183 | 207.7 | 127.4 | 6.6 | 32 | A |
| SER | OG | 183 | 207.0 | 128.7 | 6.7 | 34 | A |
| SER | C | 183 | 207.7 | 127.4 | 9.1 | 31 | A |
| SER | O | 183 | 208.8 | 127.2 | 9.6 | 32 | A |
| GLN | N | 184 | 206.8 | 128.3 | 9.5 | 30 | A |
| GLN | CA | 184 | 207.1 | 129.1 | 10.7 | 29 | A |
| GLN | CB | 184 | 206.7 | 130.6 | 10.4 | 31 | A |
| GLN | CG | 184 | 205.3 | 130.8 | 9.7 | 33 | A |
| GLN | CD | 184 | 205.0 | 132.2 | 9.4 | 34 | A |
| GLN | OE1 | 184 | 205.3 | 133.1 | 10.1 | 35 | A |
| GLN | NE2 | 184 | 204.3 | 132.4 | 8.3 | 33 | A |
| GLN | C | 184 | 206.7 | 128.7 | 12.1 | 28 | A |
| GLN | O | 184 | 207.1 | 129.3 | 13.1 | 27 | A |
| GLU | N | 185 | 205.9 | 127.6 | 12.1 | 26 | A |
| GLU | CA | 185 | 205.4 | 127.0 | 13.4 | 23 | A |

TABLE 4-continued

The following table lists the atomic structure coordinates for FPT in complex with FPP and the inhibitor SCH66701 as derived by X-ray diffraction from crystals of that complex
The abbreviations are the same as those used in Table 2

| RES | ATOM | # | X | Y | Z | B | C |
|---|---|---|---|---|---|---|---|
| GLU | CB | 185 | 204.5 | 125.8 | 13.2 | 22 | A |
| GLU | CG | 185 | 203.4 | 126.0 | 12.2 | 21 | A |
| GLU | CD | 185 | 202.6 | 127.3 | 12.5 | 21 | A |
| GLU | OE1 | 185 | 201.8 | 127.4 | 13.4 | 20 | A |
| GLU | OE2 | 185 | 202.9 | 128.3 | 11.7 | 22 | A |
| GLU | C | 185 | 206.4 | 126.6 | 14.5 | 22 | A |
| GLU | O | 185 | 206.4 | 127.1 | 15.6 | 22 | A |
| LEU | N | 186 | 207.4 | 125.7 | 14.2 | 22 | A |
| LEU | CA | 186 | 208.3 | 125.3 | 15.2 | 23 | A |
| LEU | CB | 186 | 209.2 | 124.2 | 14.7 | 22 | A |
| LEU | CG | 186 | 208.5 | 122.9 | 14.3 | 22 | A |
| LEU | CD1 | 186 | 209.4 | 121.8 | 14.0 | 23 | A |
| LEU | CD2 | 186 | 207.6 | 122.5 | 15.5 | 21 | A |
| LEU | C | 186 | 209.1 | 126.4 | 15.9 | 24 | A |
| LEU | O | 186 | 209.4 | 126.3 | 17.1 | 24 | A |
| GLU | N | 187 | 209.3 | 127.5 | 15.2 | 27 | A |
| GLU | CA | 187 | 210.0 | 128.7 | 15.7 | 28 | A |
| GLU | CB | 187 | 210.6 | 129.5 | 14.5 | 31 | A |
| GLU | CG | 187 | 211.5 | 130.6 | 14.9 | 34 | A |
| GLU | CD | 187 | 211.8 | 131.5 | 13.8 | 36 | A |
| GLU | OE1 | 187 | 211.9 | 130.9 | 12.6 | 37 | A |
| GLU | OE2 | 187 | 211.9 | 132.7 | 14.0 | 37 | A |
| GLU | C | 187 | 209.1 | 129.5 | 16.5 | 27 | A |
| GLU | O | 187 | 209.5 | 129.9 | 17.7 | 27 | A |
| PHE | N | 188 | 207.9 | 129.9 | 16.0 | 25 | A |
| PHE | CA | 188 | 207.0 | 130.7 | 16.7 | 23 | A |
| PHE | CB | 188 | 205.7 | 130.9 | 15.9 | 24 | A |
| PHE | CG | 188 | 204.5 | 131.3 | 16.7 | 25 | A |
| PHE | CD1 | 188 | 204.5 | 132.6 | 17.3 | 25 | A |
| PHE | CD2 | 188 | 203.5 | 130.5 | 16.8 | 25 | A |
| PHE | CE1 | 188 | 203.5 | 133.0 | 18.1 | 25 | A |
| PHE | CE2 | 188 | 202.4 | 130.9 | 17.6 | 25 | A |
| PHE | CZ | 188 | 202.4 | 132.1 | 18.2 | 25 | A |
| PHE | C | 188 | 206.6 | 130.0 | 18.0 | 22 | A |
| PHE | O | 188 | 206.6 | 130.7 | 19.1 | 21 | A |
| ILE | N | 189 | 206.3 | 128.8 | 18.0 | 21 | A |
| ILE | CA | 189 | 205.9 | 128.0 | 19.2 | 20 | A |
| ILE | CB | 189 | 205.6 | 126.5 | 18.8 | 18 | A |
| ILE | CG2 | 189 | 205.1 | 125.8 | 20.1 | 18 | A |
| ILE | CG1 | 189 | 204.5 | 126.4 | 17.8 | 17 | A |
| ILE | CD1 | 189 | 204.1 | 125.1 | 17.4 | 16 | A |
| ILE | C | 189 | 207.0 | 128.0 | 20.2 | 20 | A |
| ILE | O | 189 | 206.8 | 128.1 | 21.4 | 19 | A |
| ALA | N | 190 | 208.3 | 127.9 | 19.7 | 21 | A |
| ALA | CA | 190 | 209.4 | 127.9 | 20.7 | 21 | A |
| ALA | CB | 190 | 210.7 | 127.5 | 20.0 | 21 | A |
| ALA | C | 190 | 209.6 | 129.3 | 21.3 | 21 | A |
| ALA | O | 190 | 210.2 | 129.4 | 22.3 | 21 | A |
| ASP | N | 191 | 209.1 | 130.4 | 20.6 | 22 | A |
| ASP | CA | 191 | 209.2 | 131.7 | 21.2 | 22 | A |
| ASP | CB | 191 | 209.0 | 132.8 | 20.3 | 24 | A |
| ASP | CG | 191 | 209.1 | 134.2 | 20.9 | 28 | A |
| ASP | OD1 | 191 | 210.1 | 134.4 | 21.6 | 29 | A |
| ASP | OD2 | 191 | 208.2 | 135.1 | 20.8 | 28 | A |
| ASP | C | 191 | 208.1 | 131.8 | 22.4 | 22 | A |
| ASP | O | 191 | 208.4 | 132.3 | 23.4 | 23 | A |
| ILE | N | 192 | 206.9 | 131.3 | 22.1 | 20 | A |
| ILE | CA | 192 | 205.9 | 131.3 | 23.1 | 18 | A |
| ILE | CB | 192 | 204.6 | 130.7 | 22.6 | 17 | A |
| ILE | CG2 | 192 | 203.6 | 130.6 | 23.6 | 17 | A |
| ILE | CG1 | 192 | 204.1 | 131.6 | 21.4 | 16 | A |
| ILE | CD1 | 192 | 203.7 | 133.0 | 21.9 | 16 | A |
| ILE | C | 192 | 206.4 | 130.4 | 24.3 | 18 | A |
| ILE | O | 192 | 206.4 | 130.8 | 25.4 | 17 | A |
| LEU | N | 193 | 206.9 | 129.2 | 24.0 | 19 | A |
| LEU | CA | 193 | 207.4 | 128.3 | 25.0 | 21 | A |
| LEU | CB | 193 | 207.8 | 127.0 | 24.3 | 19 | A |
| LEU | CG | 193 | 206.7 | 126.1 | 23.9 | 19 | A |
| LEU | CD1 | 193 | 207.3 | 124.8 | 23.5 | 19 | A |
| LEU | CD2 | 193 | 205.8 | 125.9 | 25.1 | 20 | A |
| LEU | C | 193 | 208.6 | 128.9 | 25.7 | 22 | A |
| LEU | O | 193 | 209.0 | 128.4 | 26.7 | 23 | A |

TABLE 4-continued

The following table lists the atomic structure coordinates for FPT in complex with FPP and the inhibitor SCH66701 as derived by X-ray diffraction from crystals of that complex
The abbreviations are the same as those used in Table 2

| RES | ATOM | # | X | Y | Z | B | C |
|---|---|---|---|---|---|---|---|
| ASN | N | 194 | 209.2 | 129.9 | 25.1 | 23 | A |
| ASN | CA | 194 | 210.3 | 130.5 | 25.7 | 24 | A |
| ASN | CB | 194 | 211.2 | 131.3 | 24.7 | 27 | A |
| ASN | CG | 194 | 212.4 | 131.9 | 25.3 | 29 | A |
| ASN | OD1 | 194 | 212.5 | 133.1 | 25.4 | 31 | A |
| ASN | ND2 | 194 | 213.3 | 131.0 | 25.7 | 30 | A |
| ASN | C | 194 | 209.8 | 131.4 | 26.8 | 24 | A |
| ASN | O | 194 | 210.5 | 131.7 | 27.8 | 24 | A |
| GLN | N | 195 | 208.6 | 131.9 | 26.7 | 24 | A |
| GLN | CA | 195 | 208.0 | 132.8 | 27.6 | 23 | A |
| GLN | CB | 195 | 207.0 | 133.7 | 26.9 | 24 | A |
| GLN | CG | 195 | 207.7 | 134.6 | 25.9 | 25 | A |
| GLN | CD | 195 | 206.8 | 135.2 | 24.8 | 26 | A |
| GLN | OE1 | 195 | 205.8 | 135.9 | 25.0 | 27 | A |
| GLN | NE2 | 195 | 207.2 | 134.9 | 23.5 | 26 | A |
| GLN | C | 195 | 207.3 | 132.0 | 28.8 | 23 | A |
| GLN | O | 195 | 207.4 | 132.4 | 29.9 | 24 | A |
| ASP | N | 196 | 206.7 | 130.9 | 28.4 | 22 | A |
| ASP | CA | 196 | 206.1 | 130.0 | 29.4 | 20 | A |
| ASP | CB | 196 | 204.6 | 130.2 | 29.4 | 20 | A |
| ASP | CG | 196 | 203.8 | 129.3 | 30.3 | 21 | A |
| ASP | OD1 | 196 | 204.4 | 128.3 | 30.8 | 21 | A |
| ASP | OD2 | 196 | 202.6 | 129.5 | 30.4 | 22 | A |
| ASP | C | 196 | 206.3 | 128.6 | 28.8 | 19 | A |
| ASP | O | 196 | 205.7 | 128.1 | 27.9 | 18 | A |
| ALA | N | 197 | 207.3 | 127.9 | 29.4 | 18 | A |
| ALA | CA | 197 | 207.7 | 126.6 | 29.0 | 17 | A |
| ALA | CB | 197 | 209.0 | 126.2 | 29.6 | 17 | A |
| ALA | C | 197 | 206.7 | 125.4 | 29.1 | 17 | A |
| ALA | O | 197 | 206.9 | 124.3 | 28.7 | 17 | A |
| LYS | N | 198 | 205.5 | 125.8 | 29.7 | 16 | A |
| LYS | CA | 198 | 204.5 | 124.7 | 29.9 | 15 | A |
| LYS | CB | 198 | 204.4 | 124.5 | 31.4 | 15 | A |
| LYS | CG | 198 | 205.7 | 124.2 | 32.1 | 15 | A |
| LYS | CD | 198 | 205.6 | 123.8 | 33.6 | 16 | A |
| LYS | CE | 198 | 206.9 | 123.4 | 34.1 | 17 | A |
| LYS | NZ | 198 | 206.9 | 123.1 | 35.6 | 17 | A |
| LYS | C | 198 | 203.2 | 125.1 | 29.3 | 15 | A |
| LYS | O | 198 | 202.1 | 124.6 | 29.7 | 16 | A |
| ASN | N | 199 | 203.2 | 126.1 | 28.4 | 13 | A |
| ASN | CA | 199 | 201.9 | 126.5 | 27.8 | 14 | A |
| ASN | CB | 199 | 202.1 | 127.6 | 26.8 | 15 | A |
| ASN | CG | 199 | 200.9 | 128.3 | 26.4 | 16 | A |
| ASN | OD1 | 199 | 200.0 | 127.8 | 25.7 | 17 | A |
| ASN | ND2 | 199 | 200.7 | 129.5 | 26.9 | 18 | A |
| ASN | C | 199 | 201.3 | 125.3 | 27.1 | 15 | A |
| ASN | O | 199 | 201.7 | 124.8 | 26.1 | 19 | A |
| TYR | N | 200 | 200.3 | 124.7 | 27.8 | 14 | A |
| TYR | CA | 200 | 199.6 | 123.6 | 27.2 | 12 | A |
| TYR | CB | 200 | 198.3 | 123.3 | 28.1 | 14 | A |
| TYR | CG | 200 | 197.9 | 121.9 | 28.1 | 14 | A |
| TYR | CD1 | 200 | 198.4 | 120.9 | 28.9 | 15 | A |
| TYR | CE1 | 200 | 198.1 | 119.5 | 28.8 | 14 | A |
| TYR | CD2 | 200 | 196.9 | 121.4 | 27.2 | 15 | A |
| TYR | CE2 | 200 | 196.6 | 120.1 | 27.1 | 14 | A |
| TYR | CZ | 200 | 197.1 | 119.2 | 27.9 | 14 | A |
| TYR | OH | 200 | 196.7 | 117.9 | 27.7 | 14 | A |
| TYR | C | 200 | 199.1 | 123.7 | 25.8 | 12 | A |
| TYR | O | 200 | 199.3 | 122.9 | 25.0 | 12 | A |
| HIS | N | 201 | 198.6 | 124.9 | 25.5 | 12 | A |
| HIS | CA | 201 | 198.2 | 125.2 | 24.1 | 12 | A |
| HIS | CB | 201 | 197.5 | 126.6 | 24.0 | 13 | A |
| HIS | CG | 201 | 196.4 | 126.7 | 25.0 | 12 | A |
| HIS | CD2 | 201 | 196.3 | 127.0 | 26.3 | 12 | A |
| HIS | ND1 | 201 | 195.1 | 126.5 | 24.6 | 13 | A |
| HIS | CE1 | 201 | 194.3 | 126.6 | 25.7 | 12 | A |
| HIS | NE2 | 201 | 195.0 | 127.0 | 26.7 | 12 | A |
| HIS | C | 201 | 199.4 | 125.1 | 23.2 | 13 | A |
| HIS | O | 201 | 199.4 | 124.4 | 22.2 | 14 | A |
| ALA | N | 202 | 200.5 | 125.8 | 23.6 | 14 | A |
| ALA | CA | 202 | 201.7 | 125.8 | 22.8 | 14 | A |
| ALA | CB | 202 | 202.8 | 126.5 | 23.5 | 13 | A |

TABLE 4-continued

The following table lists the atomic structure coordinates for FPT in complex with FPP and the inhibitor SCH66701 as derived by X-ray diffraction from crystals of that complex The abbreviations are the same as those used in Table 2

| RES | ATOM | # | X | Y | Z | B | C |
|---|---|---|---|---|---|---|---|
| ALA | C | 202 | 202.2 | 124.4 | 22.4 | 14 | A |
| ALA | O | 202 | 202.4 | 124.1 | 21.2 | 15 | A |
| TRP | N | 203 | 202.4 | 123.5 | 23.4 | 13 | A |
| TRP | CA | 203 | 202.8 | 122.1 | 23.2 | 12 | A |
| TRP | CB | 203 | 203.0 | 121.5 | 24.6 | 11 | A |
| TRP | CG | 203 | 204.2 | 121.9 | 25.2 | 10 | A |
| TRP | CD2 | 203 | 205.6 | 121.5 | 24.8 | 10 | A |
| TRP | CE2 | 203 | 206.4 | 122.1 | 25.8 | 9 | A |
| TRP | CE3 | 203 | 206.1 | 120.8 | 23.8 | 9 | A |
| TRP | CD1 | 203 | 204.3 | 122.6 | 26.4 | 9 | A |
| TRP | NE1 | 203 | 205.7 | 122.7 | 26.7 | 10 | A |
| TRP | CZ2 | 203 | 207.8 | 122.0 | 25.7 | 9 | A |
| TRP | CZ3 | 203 | 207.5 | 120.7 | 23.7 | 9 | A |
| TRP | CH2 | 203 | 208.3 | 121.2 | 24.7 | 9 | A |
| TRP | C | 203 | 201.8 | 121.3 | 22.4 | 14 | A |
| TRP | O | 203 | 202.2 | 120.6 | 21.5 | 15 | A |
| GLN | N | 204 | 200.5 | 121.5 | 22.7 | 15 | A |
| GLN | CA | 204 | 199.5 | 120.7 | 21.9 | 15 | A |
| GLN | CB | 204 | 198.1 | 121.0 | 22.5 | 15 | A |
| GLN | CG | 204 | 197.1 | 120.1 | 21.8 | 15 | A |
| GLN | CD | 204 | 195.6 | 120.4 | 22.3 | 15 | A |
| GLN | OE1 | 204 | 194.7 | 120.4 | 21.4 | 15 | A |
| GLN | NE2 | 204 | 195.4 | 120.6 | 23.6 | 15 | A |
| GLN | C | 204 | 199.5 | 121.1 | 20.5 | 15 | A |
| GLN | O | 204 | 199.3 | 120.3 | 19.6 | 15 | A |
| HIS | N | 205 | 199.8 | 122.4 | 20.2 | 16 | A |
| HIS | CA | 205 | 199.8 | 122.9 | 18.8 | 18 | A |
| HIS | CB | 205 | 199.9 | 124.4 | 18.8 | 19 | A |
| HIS | CG | 205 | 199.9 | 125.0 | 17.4 | 20 | A |
| HIS | CD2 | 205 | 200.7 | 125.9 | 16.8 | 20 | A |
| HIS | ND1 | 205 | 198.9 | 124.7 | 16.5 | 21 | A |
| HIS | CE1 | 205 | 199.1 | 125.3 | 15.4 | 20 | A |
| HIS | NE2 | 205 | 200.2 | 126.1 | 15.5 | 20 | A |
| HIS | C | 205 | 201.1 | 122.3 | 18.2 | 19 | A |
| HIS | O | 205 | 201.0 | 121.8 | 17.1 | 20 | A |
| ARG | N | 206 | 202.2 | 122.4 | 19.0 | 19 | A |
| ARG | CA | 206 | 203.5 | 121.9 | 18.6 | 17 | A |
| ARG | CB | 206 | 204.5 | 122.0 | 19.7 | 16 | A |
| ARG | CG | 206 | 205.9 | 121.8 | 19.2 | 15 | A |
| ARG | CD | 206 | 206.9 | 122.2 | 20.3 | 16 | A |
| ARG | NE | 206 | 208.3 | 122.2 | 19.8 | 17 | A |
| ARG | CZ | 206 | 208.9 | 123.2 | 19.2 | 19 | A |
| ARG | NH1 | 206 | 208.3 | 124.3 | 19.0 | 20 | A |
| ARG | NH2 | 206 | 210.1 | 123.1 | 18.7 | 19 | A |
| ARG | C | 206 | 203.3 | 120.5 | 18.1 | 17 | A |
| ARG | O | 206 | 203.7 | 120.1 | 17.0 | 19 | A |
| GLN | N | 207 | 202.7 | 119.6 | 18.9 | 16 | A |
| GLN | CA | 207 | 202.5 | 118.2 | 18.6 | 17 | A |
| GLN | CB | 207 | 201.8 | 117.4 | 19.7 | 17 | A |
| GLN | CG | 207 | 202.8 | 117.2 | 20.9 | 17 | A |
| GLN | CD | 207 | 202.2 | 116.2 | 22.0 | 17 | A |
| GLN | OE1 | 207 | 201.0 | 115.8 | 21.9 | 17 | A |
| GLN | NE2 | 207 | 203.0 | 115.9 | 23.0 | 15 | A |
| GLN | C | 207 | 201.7 | 118.0 | 17.2 | 17 | A |
| GLN | O | 207 | 202.1 | 117.2 | 16.4 | 18 | A |
| TRP | N | 208 | 200.7 | 118.8 | 17.0 | 18 | A |
| TRP | CA | 208 | 199.9 | 118.6 | 15.8 | 18 | A |
| TRP | CB | 208 | 198.6 | 119.4 | 15.9 | 16 | A |
| TRP | CG | 208 | 197.9 | 119.6 | 14.6 | 15 | A |
| TRP | CD2 | 208 | 198.1 | 120.8 | 13.7 | 15 | A |
| TRP | CE2 | 208 | 197.3 | 120.6 | 12.6 | 15 | A |
| TRP | CE3 | 208 | 198.9 | 121.9 | 13.8 | 16 | A |
| TRP | CD1 | 208 | 197.0 | 118.8 | 14.0 | 15 | A |
| TRP | NE1 | 208 | 196.7 | 119.4 | 12.8 | 15 | A |
| TRP | CZ2 | 208 | 197.2 | 121.5 | 11.5 | 15 | A |
| TRP | CZ3 | 208 | 198.8 | 122.8 | 12.8 | 16 | A |
| TRP | CH2 | 208 | 198.0 | 122.6 | 11.6 | 15 | A |
| TRP | C | 208 | 200.7 | 119.1 | 14.6 | 20 | A |
| TRP | O | 208 | 200.4 | 118.5 | 13.5 | 21 | A |
| VAL | N | 209 | 201.5 | 120.1 | 14.7 | 20 | A |
| VAL | CA | 209 | 202.3 | 120.5 | 13.5 | 21 | A |
| VAL | CB | 209 | 203.0 | 121.8 | 13.7 | 21 | A |

TABLE 4-continued

The following table lists the atomic structure coordinates for FPT in complex with FPP and the inhibitor SCH66701 as derived by X-ray diffraction from crystals of that complex The abbreviations are the same as those used in Table 2

| RES | ATOM | # | X | Y | Z | B | C |
|---|---|---|---|---|---|---|---|
| VAL | CG1 | 209 | 203.8 | 122.2 | 12.5 | 21 | A |
| VAL | CG2 | 209 | 202.1 | 122.9 | 14.1 | 22 | A |
| VAL | C | 209 | 203.3 | 119.4 | 13.2 | 22 | A |
| VAL | O | 209 | 203.5 | 119.1 | 12.0 | 23 | A |
| ILE | N | 210 | 204.0 | 118.9 | 14.2 | 22 | A |
| ILE | CA | 210 | 205.0 | 117.8 | 14.0 | 21 | A |
| ILE | CB | 210 | 205.7 | 117.4 | 15.3 | 19 | A |
| ILE | CG2 | 210 | 206.5 | 116.2 | 15.1 | 18 | A |
| ILE | CG1 | 210 | 206.5 | 118.6 | 15.8 | 17 | A |
| ILE | CD1 | 210 | 207.3 | 118.2 | 17.0 | 15 | A |
| ILE | C | 210 | 204.3 | 116.6 | 13.4 | 24 | A |
| ILE | O | 210 | 204.8 | 116.0 | 12.5 | 25 | A |
| GLN | N | 211 | 203.2 | 116.2 | 14.0 | 28 | A |
| GLN | CA | 211 | 202.5 | 115.0 | 13.5 | 32 | A |
| GLN | CB | 211 | 201.4 | 114.6 | 14.5 | 34 | A |
| GLN | CG | 211 | 200.8 | 113.2 | 14.3 | 37 | A |
| GLN | CD | 211 | 200.5 | 112.4 | 15.6 | 39 | A |
| GLN | OE1 | 211 | 200.0 | 113.0 | 16.6 | 40 | A |
| GLN | NE2 | 211 | 200.7 | 111.1 | 15.6 | 39 | A |
| GLN | C | 211 | 202.0 | 115.1 | 12.1 | 33 | A |
| GLN | O | 211 | 202.2 | 114.3 | 11.3 | 34 | A |
| GLU | N | 212 | 201.4 | 116.3 | 11.8 | 36 | A |
| GLU | CA | 212 | 200.8 | 116.5 | 10.5 | 38 | A |
| GLU | CB | 212 | 200.0 | 117.8 | 10.5 | 40 | A |
| GLU | CG | 212 | 198.7 | 117.7 | 11.2 | 44 | A |
| GLU | CD | 212 | 197.9 | 116.5 | 10.5 | 46 | A |
| GLU | OE1 | 212 | 197.6 | 116.7 | 9.3 | 48 | A |
| GLU | OE2 | 212 | 197.6 | 115.5 | 11.2 | 47 | A |
| GLU | C | 212 | 201.8 | 116.6 | 9.4 | 38 | A |
| GLU | O | 212 | 201.7 | 115.9 | 8.4 | 38 | A |
| PHE | N | 213 | 202.8 | 117.5 | 9.5 | 37 | A |
| PHE | CA | 213 | 203.8 | 117.7 | 8.5 | 36 | A |
| PHE | CB | 213 | 204.1 | 119.2 | 8.4 | 35 | A |
| PHE | CG | 213 | 202.9 | 120.0 | 8.2 | 33 | A |
| PHE | CD1 | 213 | 202.1 | 120.3 | 9.2 | 33 | A |
| PHE | CD2 | 213 | 202.7 | 120.5 | 6.9 | 33 | A |
| PHE | CE1 | 213 | 200.9 | 121.0 | 9.0 | 33 | A |
| PHE | CE2 | 213 | 201.5 | 121.2 | 6.7 | 32 | A |
| PHE | CZ | 213 | 200.6 | 121.5 | 7.7 | 32 | A |
| PHE | C | 213 | 205.1 | 116.8 | 8.7 | 37 | A |
| PHE | O | 213 | 206.1 | 117.1 | 8.0 | 38 | A |
| ARG | N | 214 | 205.0 | 115.8 | 9.5 | 38 | A |
| ARG | CA | 214 | 206.1 | 114.9 | 9.7 | 39 | A |
| ARG | CB | 214 | 206.3 | 114.1 | 8.5 | 42 | A |
| ARG | CG | 214 | 205.3 | 112.9 | 8.4 | 46 | A |
| ARG | CD | 214 | 204.8 | 112.7 | 7.0 | 50 | A |
| ARG | NE | 214 | 203.3 | 113.0 | 6.9 | 54 | A |
| ARG | CZ | 214 | 202.4 | 112.2 | 7.4 | 56 | A |
| ARG | NH1 | 214 | 201.1 | 112.6 | 7.3 | 57 | A |
| ARG | NH2 | 214 | 202.7 | 111.1 | 8.0 | 57 | A |
| ARG | C | 214 | 207.4 | 115.6 | 10.0 | 38 | A |
| ARG | O | 214 | 208.5 | 115.2 | 9.6 | 39 | A |
| LEU | N | 215 | 207.3 | 116.7 | 10.9 | 35 | A |
| LEU | CA | 215 | 208.5 | 117.4 | 11.3 | 33 | A |
| LEU | CB | 215 | 208.2 | 118.9 | 11.4 | 32 | A |
| LEU | CG | 215 | 207.3 | 119.5 | 10.3 | 32 | A |
| LEU | CD1 | 215 | 206.9 | 120.9 | 10.7 | 32 | A |
| LEU | CD2 | 215 | 208.1 | 119.4 | 9.0 | 32 | A |
| LEU | C | 215 | 209.2 | 116.9 | 12.5 | 32 | A |
| LEU | O | 215 | 209.4 | 117.6 | 13.5 | 32 | A |
| TRP | N | 216 | 209.6 | 115.6 | 12.5 | 32 | A |
| TRP | CA | 216 | 210.2 | 114.9 | 13.6 | 31 | A |
| TRP | CB | 216 | 209.9 | 113.4 | 13.6 | 28 | A |
| TRP | CG | 216 | 208.5 | 113.0 | 13.5 | 25 | A |
| TRP | CD2 | 216 | 207.5 | 112.9 | 14.5 | 24 | A |
| TRP | CE2 | 216 | 206.3 | 112.6 | 13.9 | 24 | A |
| TRP | CE3 | 216 | 207.6 | 113.1 | 15.9 | 23 | A |
| TRP | CD1 | 216 | 207.8 | 112.8 | 12.3 | 25 | A |
| TRP | NE1 | 216 | 206.5 | 112.5 | 12.6 | 24 | A |
| TRP | CZ2 | 216 | 205.1 | 112.4 | 14.7 | 24 | A |
| TRP | CZ3 | 216 | 206.5 | 112.9 | 16.7 | 23 | A |
| TRP | CH2 | 216 | 205.2 | 112.6 | 16.1 | 23 | A |

TABLE 4-continued

The following table lists the atomic structure coordinates for FPT in complex with FPP and the inhibitor SCH66701 as derived by X-ray diffraction from crystals of that complex
The abbreviations are the same as those used in Table 2

| RES | ATOM | # | X | Y | Z | B | C |
|---|---|---|---|---|---|---|---|
| TRP | C | 216 | 211.7 | 115.2 | 13.9 | 33 | A |
| TRP | O | 216 | 212.1 | 115.4 | 15.0 | 34 | A |
| ASP | N | 217 | 212.5 | 115.1 | 12.8 | 35 | A |
| ASP | CA | 217 | 213.9 | 115.2 | 12.8 | 37 | A |
| ASP | CB | 217 | 214.4 | 115.7 | 11.5 | 39 | A |
| ASP | CG | 217 | 214.0 | 114.8 | 10.3 | 41 | A |
| ASP | OD1 | 217 | 214.4 | 115.1 | 9.2 | 42 | A |
| ASP | OD2 | 217 | 213.2 | 113.8 | 10.6 | 41 | A |
| ASP | C | 217 | 214.6 | 115.9 | 13.9 | 36 | A |
| ASP | O | 217 | 215.6 | 115.4 | 14.5 | 36 | A |
| ASN | N | 218 | 214.2 | 117.1 | 14.2 | 37 | A |
| ASN | CA | 218 | 214.9 | 117.9 | 15.3 | 37 | A |
| ASN | CB | 218 | 215.3 | 119.2 | 14.7 | 38 | A |
| ASN | CG | 218 | 215.9 | 119.1 | 13.3 | 39 | A |
| ASN | OD1 | 218 | 215.2 | 119.3 | 12.3 | 40 | A |
| ASN | ND2 | 218 | 217.2 | 118.8 | 13.3 | 39 | A |
| ASN | C | 218 | 214.1 | 118.1 | 16.6 | 36 | A |
| ASN | O | 218 | 214.6 | 118.9 | 17.4 | 37 | A |
| GLU | N | 219 | 213.0 | 117.4 | 16.8 | 34 | A |
| GLU | CA | 219 | 212.3 | 117.6 | 18.0 | 33 | A |
| GLU | CB | 219 | 210.8 | 117.1 | 17.9 | 33 | A |
| GLU | CG | 219 | 209.9 | 117.6 | 19.0 | 32 | A |
| GLU | CD | 219 | 209.8 | 119.1 | 19.2 | 32 | A |
| GLU | OE1 | 219 | 210.5 | 119.9 | 18.4 | 32 | A |
| GLU | OE2 | 219 | 209.1 | 119.6 | 20.1 | 32 | A |
| GLU | C | 219 | 212.9 | 117.0 | 19.3 | 33 | A |
| GLU | O | 219 | 212.8 | 117.6 | 20.4 | 33 | A |
| LEU | N | 220 | 213.6 | 115.9 | 19.2 | 32 | A |
| LEU | CA | 220 | 214.2 | 115.3 | 20.3 | 32 | A |
| LEU | CB | 220 | 214.7 | 113.8 | 20.1 | 32 | A |
| LEU | CG | 220 | 215.3 | 113.0 | 21.2 | 31 | A |
| LEU | CD1 | 220 | 214.5 | 113.2 | 22.5 | 32 | A |
| LEU | CD2 | 220 | 215.5 | 111.6 | 20.9 | 31 | A |
| LEU | C | 220 | 215.4 | 116.2 | 20.8 | 33 | A |
| LEU | O | 220 | 215.7 | 116.2 | 22.0 | 34 | A |
| GLN | N | 221 | 216.0 | 116.9 | 19.9 | 34 | A |
| GLN | CA | 221 | 217.1 | 117.8 | 20.2 | 36 | A |
| GLN | CB | 221 | 217.7 | 118.3 | 18.9 | 39 | A |
| GLN | CG | 221 | 218.8 | 119.4 | 19.1 | 42 | A |
| GLN | CD | 221 | 219.5 | 119.7 | 17.8 | 45 | A |
| GLN | OE1 | 221 | 220.0 | 118.8 | 17.1 | 46 | A |
| GLN | NE2 | 221 | 219.5 | 121.0 | 17.5 | 46 | A |
| GLN | C | 221 | 216.6 | 119.0 | 21.0 | 35 | A |
| GLN | O | 221 | 217.2 | 119.4 | 21.9 | 35 | A |
| TYR | N | 222 | 215.4 | 119.5 | 20.6 | 34 | A |
| TYR | CA | 222 | 214.8 | 120.6 | 21.2 | 33 | A |
| TYR | CB | 222 | 213.5 | 120.9 | 20.5 | 31 | A |
| TYR | CG | 222 | 212.7 | 122.1 | 21.0 | 31 | A |
| TYR | CD1 | 222 | 213.3 | 123.3 | 21.2 | 30 | A |
| TYR | CE1 | 222 | 212.6 | 124.4 | 21.7 | 30 | A |
| TYR | CD2 | 222 | 211.4 | 121.9 | 21.4 | 30 | A |
| TYR | CE2 | 222 | 210.7 | 123.0 | 21.9 | 29 | A |
| TYR | CZ | 222 | 211.3 | 124.2 | 22.1 | 30 | A |
| TYR | OH | 222 | 210.6 | 125.3 | 22.6 | 29 | A |
| TYR | C | 222 | 214.4 | 120.1 | 22.7 | 33 | A |
| TYR | O | 222 | 214.5 | 120.9 | 23.6 | 32 | A |
| VAL | N | 223 | 213.9 | 118.9 | 22.8 | 33 | A |
| VAL | CA | 223 | 213.6 | 118.3 | 24.1 | 32 | A |
| VAL | CB | 223 | 212.9 | 116.9 | 23.9 | 31 | A |
| VAL | CG1 | 223 | 213.0 | 116.1 | 25.2 | 31 | A |
| VAL | CG2 | 223 | 211.5 | 117.1 | 23.5 | 30 | A |
| VAL | C | 223 | 214.8 | 118.3 | 25.0 | 33 | A |
| VAL | O | 223 | 214.7 | 118.7 | 26.2 | 33 | A |
| ASP | N | 224 | 215.9 | 117.9 | 24.5 | 33 | A |
| ASP | CA | 224 | 217.1 | 117.8 | 25.4 | 35 | A |
| ASP | CB | 224 | 218.3 | 117.2 | 24.6 | 35 | A |
| ASP | CG | 224 | 218.1 | 115.8 | 24.3 | 36 | A |
| ASP | OD1 | 224 | 217.6 | 115.0 | 25.1 | 36 | A |
| ASP | OD2 | 224 | 218.4 | 115.5 | 23.1 | 36 | A |
| ASP | C | 224 | 217.4 | 119.3 | 25.8 | 35 | A |
| ASP | O | 224 | 217.9 | 119.5 | 26.9 | 35 | A |
| GLN | N | 225 | 217.2 | 120.2 | 24.9 | 35 | A |

TABLE 4-continued

The following table lists the atomic structure coordinates for FPT in complex with FPP and the inhibitor SCH66701 as derived by X-ray diffraction from crystals of that complex
The abbreviations are the same as those used in Table 2

| RES | ATOM | # | X | Y | Z | B | C |
|---|---|---|---|---|---|---|---|
| GLN | CA | 225 | 217.4 | 121.6 | 25.2 | 36 | A |
| GLN | CB | 225 | 217.1 | 122.5 | 24.0 | 37 | A |
| GLN | CG | 225 | 217.3 | 124.0 | 24.2 | 40 | A |
| GLN | CD | 225 | 216.7 | 124.9 | 23.1 | 42 | A |
| GLN | OE1 | 225 | 216.7 | 124.5 | 21.9 | 42 | A |
| GLN | NE2 | 225 | 216.3 | 126.1 | 23.4 | 42 | A |
| GLN | C | 225 | 216.6 | 122.0 | 26.4 | 35 | A |
| GLN | O | 225 | 217.2 | 122.4 | 27.4 | 35 | A |
| LEU | N | 226 | 215.3 | 121.9 | 26.3 | 34 | A |
| LEU | CA | 226 | 214.4 | 122.3 | 27.4 | 32 | A |
| LEU | CB | 226 | 213.0 | 122.3 | 27.0 | 31 | A |
| LEU | CG | 226 | 212.7 | 123.2 | 25.8 | 30 | A |
| LEU | CD1 | 226 | 211.2 | 123.3 | 25.6 | 31 | A |
| LEU | CD2 | 226 | 213.2 | 124.6 | 26.0 | 30 | A |
| LEU | C | 226 | 214.6 | 121.6 | 28.7 | 32 | A |
| LEU | O | 226 | 214.6 | 122.1 | 29.8 | 32 | A |
| LEU | N | 227 | 214.9 | 120.3 | 28.6 | 33 | A |
| LEU | CA | 227 | 215.2 | 119.4 | 29.8 | 33 | A |
| LEU | CB | 227 | 215.3 | 117.9 | 29.4 | 31 | A |
| LEU | CG | 227 | 214.1 | 117.1 | 29.3 | 30 | A |
| LEU | CD1 | 227 | 214.5 | 115.7 | 28.8 | 30 | A |
| LEU | CD2 | 227 | 213.3 | 117.1 | 30.6 | 29 | A |
| LEU | C | 227 | 216.4 | 119.9 | 30.5 | 34 | A |
| LEU | O | 227 | 216.5 | 119.7 | 31.8 | 33 | A |
| LYS | N | 228 | 217.4 | 120.4 | 29.8 | 35 | A |
| LYS | CA | 228 | 218.6 | 121.0 | 30.3 | 36 | A |
| LYS | CB | 228 | 219.6 | 121.3 | 29.2 | 38 | A |
| LYS | CG | 228 | 220.9 | 121.7 | 29.6 | 42 | A |
| LYS | CD | 228 | 221.8 | 121.7 | 28.4 | 45 | A |
| LYS | CE | 228 | 223.3 | 121.9 | 28.7 | 47 | A |
| LYS | NZ | 228 | 224.1 | 121.6 | 27.5 | 48 | A |
| LYS | C | 228 | 218.2 | 122.2 | 31.0 | 36 | A |
| LYS | O | 228 | 218.7 | 122.5 | 32.2 | 36 | A |
| GLU | N | 229 | 217.4 | 123.0 | 30.4 | 35 | A |
| GLU | CA | 229 | 216.9 | 124.3 | 31.0 | 33 | A |
| GLU | CB | 229 | 216.1 | 125.1 | 30.0 | 33 | A |
| GLU | CG | 229 | 216.9 | 125.4 | 28.7 | 33 | A |
| GLU | CD | 229 | 216.2 | 126.4 | 27.8 | 34 | A |
| GLU | OE1 | 229 | 215.2 | 127.0 | 28.2 | 35 | A |
| GLU | OE2 | 229 | 216.7 | 126.6 | 26.7 | 34 | A |
| GLU | C | 229 | 216.1 | 124.0 | 32.3 | 32 | A |
| GLU | O | 229 | 216.3 | 124.7 | 33.3 | 32 | A |
| ASP | N | 230 | 215.3 | 123.0 | 32.2 | 31 | A |
| ASP | CA | 230 | 214.5 | 122.6 | 33.4 | 31 | A |
| ASP | CB | 230 | 213.3 | 123.5 | 33.5 | 30 | A |
| ASP | CG | 230 | 212.6 | 123.3 | 34.9 | 30 | A |
| ASP | OD1 | 230 | 213.0 | 122.5 | 35.7 | 30 | A |
| ASP | OD2 | 230 | 211.6 | 124.0 | 35.1 | 29 | A |
| ASP | C | 230 | 214.1 | 121.1 | 33.4 | 30 | A |
| ASP | O | 230 | 213.1 | 120.7 | 32.8 | 30 | A |
| VAL | N | 231 | 215.0 | 120.3 | 34.0 | 30 | A |
| VAL | CA | 231 | 214.7 | 118.8 | 34.1 | 30 | A |
| VAL | CB | 231 | 215.8 | 118.1 | 34.8 | 30 | A |
| VAL | CG1 | 231 | 215.8 | 118.3 | 36.3 | 29 | A |
| VAL | CG2 | 231 | 215.7 | 116.6 | 34.5 | 30 | A |
| VAL | C | 231 | 213.3 | 118.5 | 34.7 | 30 | A |
| VAL | O | 231 | 212.8 | 117.4 | 34.6 | 30 | A |
| ARG | N | 232 | 212.8 | 119.5 | 35.5 | 29 | A |
| ARG | CA | 232 | 211.5 | 119.2 | 36.1 | 28 | A |
| ARG | CB | 232 | 211.5 | 120.1 | 37.4 | 27 | A |
| ARG | CG | 232 | 212.6 | 119.8 | 38.4 | 28 | A |
| ARG | CD | 232 | 212.2 | 120.5 | 39.7 | 29 | A |
| ARG | NE | 232 | 213.2 | 120.2 | 40.8 | 30 | A |
| ARG | CZ | 232 | 214.3 | 120.8 | 41.0 | 30 | A |
| ARG | NH1 | 232 | 214.7 | 121.7 | 40.2 | 30 | A |
| ARG | NH2 | 232 | 215.1 | 120.5 | 42.1 | 30 | A |
| ARG | C | 232 | 210.3 | 119.6 | 35.2 | 27 | A |
| ARG | O | 232 | 209.2 | 119.6 | 35.7 | 27 | A |
| ASN | N | 233 | 210.6 | 120.0 | 34.0 | 25 | A |
| ASN | CA | 233 | 209.5 | 120.3 | 33.1 | 24 | A |
| ASN | CB | 233 | 210.0 | 121.2 | 31.9 | 24 | A |
| ASN | CG | 233 | 208.8 | 121.7 | 31.1 | 24 | A |

TABLE 4-continued

The following table lists the atomic structure coordinates for FPT in complex with FPP and the inhibitor SCH66701 as derived by X-ray diffraction from crystals of that complex The abbreviations are the same as those used in Table 2

| RES | ATOM | # | X | Y | Z | B | C |
|---|---|---|---|---|---|---|---|
| ASN | OD1 | 233 | 207.7 | 121.2 | 31.1 | 25 | A |
| ASN | ND2 | 233 | 209.1 | 122.8 | 30.4 | 23 | A |
| ASN | C | 233 | 208.8 | 119.1 | 32.6 | 24 | A |
| ASN | O | 233 | 209.1 | 118.5 | 31.6 | 25 | A |
| ASN | N | 234 | 207.7 | 118.8 | 33.3 | 24 | A |
| ASN | CA | 234 | 206.9 | 117.6 | 32.8 | 23 | A |
| ASN | CB | 234 | 205.7 | 117.4 | 33.8 | 23 | A |
| ASN | CG | 234 | 205.4 | 115.9 | 33.9 | 23 | A |
| ASN | OD1 | 234 | 206.1 | 115.2 | 34.7 | 23 | A |
| ASN | ND2 | 234 | 204.4 | 115.4 | 33.3 | 24 | A |
| ASN | C | 234 | 206.4 | 117.7 | 31.4 | 23 | A |
| ASN | O | 234 | 206.3 | 116.6 | 30.7 | 23 | A |
| SER | N | 235 | 206.2 | 118.8 | 30.9 | 21 | A |
| SER | CA | 235 | 205.7 | 119.0 | 29.5 | 20 | A |
| SER | CB | 235 | 205.3 | 120.4 | 29.2 | 20 | A |
| SER | OG | 235 | 204.2 | 120.8 | 30.0 | 21 | A |
| SER | C | 235 | 206.8 | 118.5 | 28.5 | 20 | A |
| SER | O | 235 | 206.5 | 117.9 | 27.4 | 19 | A |
| VAL | N | 236 | 208.1 | 118.7 | 28.9 | 19 | A |
| VAL | CA | 236 | 209.2 | 118.3 | 28.0 | 18 | A |
| VAL | CB | 236 | 210.4 | 118.9 | 28.4 | 18 | A |
| VAL | CG1 | 236 | 211.5 | 118.6 | 27.4 | 19 | A |
| VAL | CG2 | 236 | 210.2 | 120.4 | 28.5 | 18 | A |
| VAL | C | 236 | 209.3 | 116.8 | 28.1 | 18 | A |
| VAL | O | 236 | 209.5 | 116.1 | 27.0 | 18 | A |
| TRP | N | 237 | 209.2 | 116.2 | 29.3 | 18 | A |
| TRP | CA | 237 | 209.3 | 114.7 | 29.4 | 19 | A |
| TRP | CB | 237 | 209.2 | 114.3 | 30.9 | 19 | A |
| TRP | CG | 237 | 210.4 | 114.5 | 31.7 | 20 | A |
| TRP | CD2 | 237 | 211.6 | 113.6 | 31.7 | 21 | A |
| TRP | CE2 | 237 | 212.5 | 114.2 | 32.5 | 21 | A |
| TRP | CE3 | 237 | 211.9 | 112.5 | 31.0 | 21 | A |
| TRP | CD1 | 237 | 210.7 | 115.5 | 32.5 | 21 | A |
| TRP | NE1 | 237 | 211.9 | 115.4 | 33.0 | 21 | A |
| TRP | CZ2 | 237 | 213.8 | 113.7 | 32.8 | 20 | A |
| TRP | CZ3 | 237 | 213.2 | 111.9 | 31.3 | 21 | A |
| TRP | CH2 | 237 | 214.1 | 112.5 | 32.1 | 21 | A |
| TRP | C | 237 | 208.1 | 114.2 | 28.6 | 19 | A |
| TRP | O | 237 | 208.3 | 113.2 | 27.9 | 20 | A |
| ASN | N | 238 | 207.0 | 114.8 | 28.7 | 19 | A |
| ASN | CA | 238 | 205.9 | 114.3 | 27.9 | 20 | A |
| ASN | CB | 238 | 204.6 | 115.0 | 28.2 | 21 | A |
| ASN | CG | 238 | 203.5 | 114.5 | 27.3 | 22 | A |
| ASN | OD1 | 238 | 203.2 | 113.3 | 27.3 | 23 | A |
| ASN | ND2 | 238 | 203.0 | 115.4 | 26.4 | 23 | A |
| ASN | C | 238 | 206.2 | 114.4 | 26.4 | 19 | A |
| ASN | O | 238 | 206.0 | 113.4 | 25.7 | 19 | A |
| GLN | N | 239 | 206.9 | 115.5 | 26.0 | 20 | A |
| GLN | CA | 239 | 207.2 | 115.7 | 24.6 | 21 | A |
| GLN | CB | 239 | 207.8 | 117.1 | 24.3 | 20 | A |
| GLN | CG | 239 | 208.1 | 117.4 | 22.9 | 19 | A |
| GLN | CD | 239 | 206.8 | 117.7 | 22.0 | 19 | A |
| GLN | OE1 | 239 | 205.7 | 117.4 | 22.5 | 19 | A |
| GLN | NE2 | 239 | 207.0 | 118.2 | 20.9 | 18 | A |
| GLN | C | 239 | 208.2 | 114.7 | 24.1 | 22 | A |
| GLN | O | 239 | 208.2 | 114.3 | 22.9 | 22 | A |
| ARG | N | 240 | 209.1 | 114.3 | 25.0 | 23 | A |
| ARG | CA | 240 | 210.2 | 113.3 | 24.7 | 23 | A |
| ARG | CB | 240 | 211.0 | 113.1 | 26.0 | 23 | A |
| ARG | CG | 240 | 212.2 | 112.3 | 25.8 | 23 | A |
| ARG | CD | 240 | 213.0 | 112.2 | 27.1 | 24 | A |
| ARG | NE | 240 | 214.3 | 111.6 | 26.7 | 25 | A |
| ARG | CZ | 240 | 215.4 | 112.2 | 26.2 | 26 | A |
| ARG | NH1 | 240 | 215.3 | 113.6 | 26.1 | 27 | A |
| ARG | NH2 | 240 | 216.3 | 111.6 | 25.7 | 27 | A |
| ARG | C | 240 | 209.5 | 112.0 | 24.4 | 23 | A |
| ARG | O | 240 | 209.7 | 111.4 | 23.3 | 26 | A |
| HIS | N | 241 | 208.6 | 111.5 | 25.2 | 22 | A |
| HIS | CA | 241 | 207.9 | 110.3 | 25.0 | 22 | A |
| HIS | CB | 241 | 206.9 | 110.1 | 26.1 | 23 | A |
| HIS | CG | 241 | 206.3 | 108.7 | 26.1 | 24 | A |
| HIS | CD2 | 241 | 206.6 | 107.6 | 26.9 | 24 | A |

TABLE 4-continued

The following table lists the atomic structure coordinates for FPT in complex with FPP and the inhibitor SCH66701 as derived by X-ray diffraction from crystals of that complex The abbreviations are the same as those used in Table 2

| RES | ATOM | # | X | Y | Z | B | C |
|---|---|---|---|---|---|---|---|
| HIS | ND1 | 241 | 205.3 | 108.3 | 25.3 | 24 | A |
| HIS | CE1 | 241 | 204.9 | 107.1 | 25.5 | 24 | A |
| HIS | NE2 | 241 | 205.7 | 106.6 | 26.5 | 25 | A |
| HIS | C | 241 | 207.1 | 110.4 | 23.6 | 22 | A |
| HIS | O | 241 | 207.1 | 109.4 | 22.9 | 23 | A |
| PHE | N | 242 | 206.5 | 111.5 | 23.3 | 21 | A |
| PHE | CA | 242 | 205.7 | 111.6 | 22.1 | 20 | A |
| PHE | CB | 242 | 205.0 | 113.0 | 22.1 | 20 | A |
| PHE | CG | 242 | 204.3 | 113.4 | 20.8 | 19 | A |
| PHE | CD1 | 242 | 203.1 | 112.9 | 20.4 | 19 | A |
| PHE | CD2 | 242 | 204.9 | 114.3 | 19.9 | 19 | A |
| PHE | CE1 | 242 | 202.4 | 113.3 | 19.3 | 18 | A |
| PHE | CE2 | 242 | 204.3 | 114.7 | 18.7 | 19 | A |
| PHE | CZ | 242 | 203.0 | 114.2 | 18.4 | 18 | A |
| PHE | C | 242 | 206.6 | 111.5 | 20.9 | 21 | A |
| PHE | O | 242 | 206.3 | 110.8 | 19.9 | 21 | A |
| VAL | N | 243 | 207.8 | 112.1 | 21.0 | 21 | A |
| VAL | CA | 243 | 208.8 | 112.0 | 19.9 | 22 | A |
| VAL | CB | 243 | 210.0 | 113.0 | 20.2 | 22 | A |
| VAL | CG1 | 243 | 211.1 | 112.7 | 19.3 | 22 | A |
| VAL | CG2 | 243 | 209.5 | 114.4 | 20.0 | 23 | A |
| VAL | C | 243 | 209.3 | 110.6 | 19.6 | 22 | A |
| VAL | O | 243 | 209.3 | 110.1 | 18.5 | 22 | A |
| ILE | N | 244 | 209.8 | 109.9 | 20.7 | 22 | A |
| ILE | CA | 244 | 210.4 | 108.6 | 20.6 | 22 | A |
| ILE | CB | 244 | 211.0 | 108.2 | 21.9 | 21 | A |
| ILE | CG2 | 244 | 211.6 | 106.8 | 21.8 | 22 | A |
| ILE | CG1 | 244 | 212.1 | 109.2 | 22.3 | 19 | A |
| ILE | CD1 | 244 | 212.7 | 108.8 | 23.6 | 18 | A |
| ILE | C | 244 | 209.2 | 107.6 | 20.2 | 22 | A |
| ILE | O | 244 | 209.3 | 106.9 | 19.3 | 21 | A |
| SER | N | 245 | 208.1 | 107.7 | 20.9 | 24 | A |
| SER | CA | 245 | 207.0 | 106.9 | 20.6 | 26 | A |
| SER | CB | 245 | 205.8 | 107.4 | 21.3 | 27 | A |
| SER | OG | 245 | 205.9 | 107.1 | 22.7 | 30 | A |
| SER | C | 245 | 206.6 | 106.9 | 19.1 | 29 | A |
| SER | O | 245 | 206.2 | 105.9 | 18.6 | 30 | A |
| ASN | N | 246 | 206.6 | 108.1 | 18.5 | 31 | A |
| ASN | CA | 246 | 206.2 | 108.1 | 17.1 | 31 | A |
| ASN | CB | 246 | 205.4 | 109.4 | 16.8 | 31 | A |
| ASN | CG | 246 | 204.1 | 109.4 | 17.6 | 31 | A |
| ASN | OD1 | 246 | 204.0 | 109.7 | 18.8 | 31 | A |
| ASN | ND2 | 246 | 203.0 | 109.1 | 16.9 | 32 | A |
| ASN | C | 246 | 207.3 | 108.0 | 16.1 | 32 | A |
| ASN | O | 246 | 207.2 | 108.1 | 14.9 | 32 | A |
| THR | N | 247 | 208.5 | 107.8 | 16.6 | 32 | A |
| THR | CA | 247 | 209.7 | 107.6 | 15.7 | 33 | A |
| THR | CB | 247 | 210.7 | 108.8 | 15.9 | 32 | A |
| THR | OG1 | 247 | 211.1 | 108.8 | 17.3 | 32 | A |
| THR | CG2 | 247 | 210.1 | 110.1 | 15.6 | 31 | A |
| THR | C | 247 | 210.3 | 106.2 | 15.8 | 34 | A |
| THR | O | 247 | 209.9 | 105.3 | 15.0 | 34 | A |
| THR | N | 248 | 211.1 | 106.0 | 16.8 | 34 | A |
| THR | CA | 248 | 211.7 | 104.7 | 17.0 | 35 | A |
| THR | CB | 248 | 213.1 | 104.9 | 17.6 | 34 | A |
| THR | OG1 | 248 | 213.1 | 105.4 | 18.9 | 34 | A |
| THR | CG2 | 248 | 213.8 | 106.0 | 16.7 | 34 | A |
| THR | C | 248 | 211.0 | 103.7 | 18.0 | 36 | A |
| THR | O | 248 | 211.3 | 102.5 | 18.0 | 38 | A |
| GLY | N | 249 | 210.1 | 104.2 | 18.9 | 37 | A |
| GLY | CA | 249 | 209.5 | 103.4 | 19.8 | 38 | A |
| GLY | C | 249 | 210.5 | 102.9 | 20.9 | 39 | A |
| GLY | O | 249 | 211.7 | 103.2 | 20.8 | 39 | A |
| TYR | N | 250 | 210.0 | 102.3 | 21.9 | 40 | A |
| TYR | CA | 250 | 210.8 | 101.8 | 23.0 | 41 | A |
| TYR | CB | 250 | 210.2 | 102.1 | 24.3 | 40 | A |
| TYR | CG | 250 | 210.1 | 103.6 | 24.6 | 40 | A |
| TYR | CD1 | 250 | 209.1 | 104.4 | 24.0 | 39 | A |
| TYR | CE1 | 250 | 209.0 | 105.7 | 24.3 | 40 | A |
| TYR | CD2 | 250 | 210.9 | 104.2 | 25.6 | 40 | A |
| TYR | CE2 | 250 | 210.8 | 105.5 | 25.9 | 40 | A |
| TYR | CZ | 250 | 209.9 | 106.3 | 25.2 | 40 | A |

TABLE 4-continued

The following table lists the atomic structure coordinates for FPT in complex with FPP and the inhibitor SCH66701 as derived by X-ray diffraction from crystals of that complex
The abbreviations are the same as those used in Table 2

| RES | ATOM | # | X | Y | Z | B | C |
|---|---|---|---|---|---|---|---|
| TYR | OH | 250 | 209.7 | 107.6 | 25.6 | 41 | A |
| TYR | C | 250 | 211.2 | 100.4 | 22.9 | 43 | A |
| TYR | O | 250 | 211.9 | 99.8 | 23.8 | 43 | A |
| SER | N | 251 | 210.7 | 99.7 | 21.9 | 44 | A |
| SER | CA | 251 | 211.0 | 98.3 | 21.6 | 45 | A |
| SER | CB | 251 | 210.2 | 97.8 | 20.4 | 45 | A |
| SER | OG | 251 | 208.8 | 98.0 | 20.7 | 46 | A |
| SER | C | 251 | 212.5 | 98.1 | 21.4 | 46 | A |
| SER | O | 251 | 213.1 | 97.2 | 22.0 | 46 | A |
| ASP | N | 252 | 213.0 | 99.0 | 20.5 | 47 | A |
| ASP | CA | 252 | 214.4 | 98.9 | 20.2 | 49 | A |
| ASP | CB | 252 | 214.8 | 100.1 | 19.3 | 51 | A |
| ASP | CG | 252 | 216.2 | 100.0 | 18.7 | 53 | A |
| ASP | OD1 | 252 | 216.9 | 99.0 | 18.9 | 54 | A |
| ASP | OD2 | 252 | 216.5 | 100.9 | 17.9 | 55 | A |
| ASP | C | 252 | 215.2 | 99.0 | 21.5 | 49 | A |
| ASP | O | 252 | 215.3 | 100.0 | 22.2 | 49 | A |
| ARG | N | 253 | 215.8 | 97.9 | 21.9 | 49 | A |
| ARG | CA | 253 | 216.6 | 97.7 | 23.1 | 48 | A |
| ARG | CB | 253 | 217.3 | 96.3 | 23.1 | 51 | A |
| ARG | CG | 253 | 216.4 | 95.1 | 23.2 | 54 | A |
| ARG | CD | 253 | 217.2 | 93.8 | 23.0 | 57 | A |
| ARG | NE | 253 | 216.5 | 92.6 | 23.4 | 59 | A |
| ARG | CZ | 253 | 216.5 | 91.5 | 22.8 | 60 | A |
| ARG | NH1 | 253 | 217.3 | 91.3 | 21.7 | 60 | A |
| ARG | NH2 | 253 | 215.8 | 90.5 | 23.2 | 60 | A |
| ARG | C | 253 | 217.7 | 98.8 | 23.3 | 46 | A |
| ARG | O | 253 | 218.0 | 99.1 | 24.5 | 45 | A |
| ALA | N | 254 | 218.2 | 99.3 | 22.2 | 44 | A |
| ALA | CA | 254 | 219.2 | 100.3 | 22.2 | 42 | A |
| ALA | CB | 254 | 219.8 | 100.5 | 20.9 | 43 | A |
| ALA | C | 254 | 218.6 | 101.6 | 22.7 | 42 | A |
| ALA | O | 254 | 219.1 | 102.3 | 23.5 | 41 | A |
| VAL | N | 255 | 217.4 | 101.9 | 22.1 | 41 | A |
| VAL | CA | 255 | 216.7 | 103.1 | 22.5 | 40 | A |
| VAL | CB | 255 | 215.5 | 103.4 | 21.6 | 40 | A |
| VAL | CG1 | 255 | 214.8 | 104.7 | 22.0 | 41 | A |
| VAL | CG2 | 255 | 215.9 | 103.4 | 20.2 | 40 | A |
| VAL | C | 255 | 216.3 | 103.0 | 23.9 | 40 | A |
| VAL | O | 255 | 216.5 | 103.8 | 24.8 | 40 | A |
| LEU | N | 256 | 215.6 | 101.9 | 24.2 | 39 | A |
| LEU | CA | 256 | 215.2 | 101.6 | 25.6 | 39 | A |
| LEU | CB | 256 | 214.6 | 100.2 | 25.7 | 38 | A |
| LEU | CG | 256 | 214.0 | 99.6 | 26.9 | 37 | A |
| LEU | CD1 | 256 | 213.1 | 100.5 | 27.7 | 37 | A |
| LEU | CD2 | 256 | 213.2 | 98.4 | 26.5 | 37 | A |
| LEU | C | 256 | 216.3 | 101.8 | 26.6 | 40 | A |
| LEU | O | 256 | 216.2 | 102.7 | 27.5 | 40 | A |
| GLU | N | 257 | 217.4 | 101.1 | 26.4 | 41 | A |
| GLU | CA | 257 | 218.6 | 101.2 | 27.3 | 42 | A |
| GLU | CB | 257 | 219.7 | 100.4 | 26.7 | 43 | A |
| GLU | CG | 257 | 221.1 | 100.6 | 27.2 | 46 | A |
| GLU | CD | 257 | 221.4 | 100.0 | 28.6 | 49 | A |
| GLU | OE1 | 257 | 220.5 | 100.0 | 29.5 | 50 | A |
| GLU | OE2 | 257 | 222.5 | 99.5 | 28.7 | 50 | A |
| GLU | C | 257 | 219.0 | 102.7 | 27.5 | 41 | A |
| GLU | O | 257 | 219.2 | 103.1 | 28.6 | 40 | A |
| ARG | N | 258 | 219.2 | 103.4 | 26.4 | 40 | A |
| ARG | CA | 258 | 219.6 | 104.8 | 26.3 | 40 | A |
| ARG | CB | 258 | 219.6 | 105.3 | 24.9 | 39 | A |
| ARG | CG | 258 | 220.0 | 106.8 | 24.8 | 39 | A |
| ARG | CD | 258 | 219.6 | 107.4 | 23.5 | 38 | A |
| ARG | NE | 258 | 218.1 | 107.6 | 23.4 | 39 | A |
| ARG | CZ | 258 | 217.4 | 107.6 | 22.3 | 39 | A |
| ARG | NH1 | 258 | 218.0 | 107.5 | 21.1 | 39 | A |
| ARG | NH2 | 258 | 216.1 | 107.7 | 22.4 | 39 | A |
| ARG | C | 258 | 218.8 | 105.7 | 27.2 | 40 | A |
| ARG | O | 258 | 219.3 | 106.6 | 27.9 | 41 | A |
| GLU | N | 259 | 217.5 | 105.5 | 27.1 | 40 | A |
| GLU | CA | 259 | 216.5 | 106.3 | 27.8 | 39 | A |
| GLU | CB | 259 | 215.1 | 106.0 | 27.3 | 39 | A |
| GLU | CG | 259 | 214.8 | 106.6 | 25.9 | 39 | A |

TABLE 4-continued

The following table lists the atomic structure coordinates for FPT in complex with FPP and the inhibitor SCH66701 as derived by X-ray diffraction from crystals of that complex
The abbreviations are the same as those used in Table 2

| RES | ATOM | # | X | Y | Z | B | C |
|---|---|---|---|---|---|---|---|
| GLU | CD | 259 | 215.0 | 108.1 | 26.0 | 39 | A |
| GLU | OE1 | 259 | 214.4 | 108.8 | 26.9 | 40 | A |
| GLU | OE2 | 259 | 215.7 | 108.7 | 25.1 | 39 | A |
| GLU | C | 259 | 216.5 | 105.9 | 29.3 | 40 | A |
| GLU | O | 259 | 216.6 | 106.7 | 30.1 | 40 | A |
| VAL | N | 260 | 216.6 | 104.6 | 29.5 | 41 | A |
| VAL | CA | 260 | 216.6 | 104.0 | 30.9 | 41 | A |
| VAL | CB | 260 | 216.5 | 102.5 | 30.9 | 41 | A |
| VAL | CG1 | 260 | 216.8 | 102.0 | 32.3 | 41 | A |
| VAL | CG2 | 260 | 215.1 | 102.1 | 30.6 | 41 | A |
| VAL | C | 260 | 217.8 | 104.5 | 31.6 | 42 | A |
| VAL | O | 260 | 217.7 | 104.9 | 32.8 | 42 | A |
| GLN | N | 261 | 219.0 | 104.6 | 30.9 | 42 | A |
| GLN | CA | 261 | 220.2 | 105.0 | 31.5 | 43 | A |
| GLN | CB | 261 | 221.3 | 104.8 | 30.5 | 46 | A |
| GLN | CG | 261 | 222.7 | 104.5 | 31.2 | 49 | A |
| GLN | CD | 261 | 222.8 | 103.1 | 31.8 | 50 | A |
| GLN | OE1 | 261 | 222.7 | 102.1 | 31.0 | 50 | A |
| GLN | NE2 | 261 | 223.0 | 102.9 | 33.1 | 51 | A |
| GLN | C | 261 | 220.1 | 106.5 | 31.8 | 42 | A |
| GLN | O | 261 | 220.2 | 106.9 | 33.0 | 42 | A |
| TYR | N | 262 | 219.9 | 107.3 | 30.8 | 40 | A |
| TYR | CA | 262 | 219.7 | 108.8 | 30.9 | 38 | A |
| TYR | CB | 262 | 219.1 | 109.3 | 29.6 | 38 | A |
| TYR | CG | 262 | 218.6 | 110.7 | 29.8 | 38 | A |
| TYR | CD1 | 262 | 219.4 | 111.8 | 30.1 | 38 | A |
| TYR | CE1 | 262 | 219.0 | 113.1 | 30.3 | 38 | A |
| TYR | CD2 | 262 | 217.2 | 111.0 | 29.6 | 38 | A |
| TYR | CE2 | 262 | 216.8 | 112.3 | 29.8 | 38 | A |
| TYR | CZ | 262 | 217.6 | 113.3 | 30.1 | 38 | A |
| TYR | OH | 262 | 217.2 | 114.6 | 30.3 | 38 | A |
| TYR | C | 262 | 218.8 | 109.2 | 32.0 | 38 | A |
| TYR | O | 262 | 219.1 | 110.1 | 32.8 | 37 | A |
| THR | N | 263 | 217.6 | 108.6 | 32.0 | 37 | A |
| THR | CA | 263 | 216.6 | 108.9 | 33.0 | 37 | A |
| THR | CB | 263 | 215.3 | 108.1 | 32.8 | 36 | A |
| THR | OG1 | 263 | 214.9 | 108.2 | 31.4 | 35 | A |
| THR | CG2 | 263 | 214.2 | 108.6 | 33.6 | 35 | A |
| THR | C | 263 | 217.1 | 108.6 | 34.4 | 38 | A |
| THR | O | 263 | 217.0 | 109.4 | 35.3 | 37 | A |
| LEU | N | 264 | 217.8 | 107.4 | 34.6 | 40 | A |
| LEU | CA | 264 | 218.3 | 107.0 | 35.9 | 42 | A |
| LEU | CB | 264 | 219.0 | 105.6 | 35.8 | 42 | A |
| LEU | CG | 264 | 218.1 | 104.4 | 36.0 | 41 | A |
| LEU | CD1 | 264 | 218.8 | 103.2 | 35.7 | 41 | A |
| LEU | CD2 | 264 | 217.4 | 104.4 | 37.4 | 41 | A |
| LEU | C | 264 | 219.4 | 108.1 | 36.2 | 44 | A |
| LEU | O | 264 | 219.5 | 108.5 | 37.4 | 44 | A |
| GLU | N | 265 | 220.1 | 108.5 | 35.2 | 46 | A |
| GLU | CA | 265 | 221.2 | 109.6 | 35.4 | 49 | A |
| GLU | CB | 265 | 221.9 | 109.9 | 34.1 | 52 | A |
| GLU | CG | 265 | 222.4 | 108.6 | 33.3 | 56 | A |
| GLU | CD | 265 | 223.3 | 107.7 | 34.1 | 59 | A |
| GLU | OE1 | 265 | 222.8 | 106.5 | 34.4 | 60 | A |
| GLU | OE2 | 265 | 224.4 | 108.1 | 34.5 | 61 | A |
| GLU | C | 265 | 220.5 | 110.8 | 36.0 | 49 | A |
| GLU | O | 265 | 221.1 | 111.5 | 36.9 | 50 | A |
| MET | N | 266 | 219.3 | 111.2 | 35.5 | 49 | A |
| MET | CA | 266 | 218.6 | 112.3 | 35.9 | 48 | A |
| MET | CB | 266 | 217.4 | 112.6 | 34.9 | 47 | A |
| MET | CG | 266 | 217.8 | 112.8 | 33.5 | 46 | A |
| MET | SD | 266 | 219.3 | 113.9 | 33.4 | 46 | A |
| MET | CE | 266 | 218.6 | 115.4 | 32.9 | 47 | A |
| MET | C | 266 | 218.1 | 112.1 | 37.3 | 48 | A |
| MET | O | 266 | 218.0 | 113.1 | 38.1 | 48 | A |
| ILE | N | 267 | 217.7 | 110.9 | 37.6 | 48 | A |
| ILE | CA | 267 | 217.2 | 110.5 | 38.9 | 49 | A |
| ILE | CB | 267 | 216.7 | 109.1 | 39.0 | 48 | A |
| ILE | CG2 | 267 | 216.2 | 108.8 | 40.4 | 48 | A |
| ILE | CG1 | 267 | 215.4 | 109.0 | 38.0 | 48 | A |
| ILE | CD1 | 267 | 214.8 | 107.6 | 38.0 | 48 | A |
| ILE | C | 267 | 218.4 | 110.7 | 39.9 | 50 | A |

TABLE 4-continued

The following table lists the atomic structure coordinates for FPT in complex with FPP and the inhibitor SCH66701 as derived by X-ray diffraction from crystals of that complex
The abbreviations are the same as those used in Table 2

| RES | ATOM | # | X | Y | Z | B | C |
|---|---|---|---|---|---|---|---|
| ILE | O | 267 | 218.2 | 111.2 | 41.0 | 51 | A |
| LYS | N | 268 | 219.6 | 110.3 | 39.5 | 51 | A |
| LYS | CA | 268 | 220.7 | 110.5 | 40.4 | 52 | A |
| LYS | CB | 268 | 222.0 | 109.9 | 39.7 | 55 | A |
| LYS | CG | 268 | 221.9 | 108.4 | 39.6 | 58 | A |
| LYS | CD | 268 | 223.2 | 107.8 | 39.0 | 60 | A |
| LYS | CE | 268 | 222.9 | 106.3 | 38.7 | 62 | A |
| LYS | NZ | 268 | 223.9 | 105.7 | 37.7 | 63 | A |
| LYS | C | 268 | 220.9 | 112.0 | 40.7 | 51 | A |
| LYS | O | 268 | 220.9 | 112.3 | 41.9 | 52 | A |
| LEU | N | 269 | 220.8 | 112.8 | 39.7 | 51 | A |
| LEU | CA | 269 | 221.0 | 114.2 | 39.9 | 49 | A |
| LEU | CB | 269 | 221.2 | 115.0 | 38.6 | 50 | A |
| LEU | CG | 269 | 222.2 | 114.6 | 37.5 | 50 | A |
| LEU | CD1 | 269 | 222.8 | 115.8 | 36.9 | 51 | A |
| LEU | CD2 | 269 | 223.2 | 113.6 | 38.0 | 51 | A |
| LEU | C | 269 | 219.9 | 114.9 | 40.7 | 48 | A |
| LEU | O | 269 | 220.3 | 115.7 | 41.7 | 49 | A |
| VAL | N | 270 | 218.7 | 114.7 | 40.4 | 46 | A |
| VAL | CA | 270 | 217.6 | 115.3 | 41.2 | 44 | A |
| VAL | CB | 270 | 216.8 | 116.4 | 40.3 | 43 | A |
| VAL | CG1 | 270 | 216.0 | 117.3 | 41.2 | 42 | A |
| VAL | CG2 | 270 | 217.8 | 117.2 | 39.5 | 42 | A |
| VAL | C | 270 | 216.7 | 114.2 | 41.7 | 43 | A |
| VAL | O | 270 | 215.5 | 114.1 | 41.2 | 43 | A |
| PRO | N | 271 | 217.1 | 113.5 | 42.7 | 43 | A |
| PRO | CD | 271 | 218.3 | 113.7 | 43.4 | 43 | A |
| PRO | CA | 271 | 216.4 | 112.3 | 43.3 | 43 | A |
| PRO | CB | 271 | 217.2 | 112.0 | 44.5 | 43 | A |
| PRO | CG | 271 | 218.5 | 112.3 | 44.0 | 42 | A |
| PRO | C | 271 | 214.9 | 112.6 | 43.6 | 43 | A |
| PRO | O | 271 | 214.1 | 111.6 | 43.7 | 43 | A |
| HIS | N | 272 | 214.5 | 113.8 | 43.9 | 43 | A |
| HIS | CA | 272 | 213.2 | 114.2 | 44.3 | 43 | A |
| HIS | CB | 272 | 213.2 | 115.1 | 45.5 | 44 | A |
| HIS | CG | 272 | 213.7 | 114.4 | 46.8 | 46 | A |
| HIS | CD2 | 272 | 214.9 | 114.4 | 47.3 | 46 | A |
| HIS | ND1 | 272 | 212.8 | 113.7 | 47.6 | 47 | A |
| HIS | CE1 | 272 | 213.5 | 113.2 | 48.6 | 47 | A |
| HIS | NE2 | 272 | 214.8 | 113.6 | 48.5 | 47 | A |
| HIS | C | 272 | 212.3 | 114.7 | 43.2 | 41 | A |
| HIS | O | 272 | 211.3 | 115.3 | 43.4 | 41 | A |
| ASN | N | 273 | 212.8 | 114.6 | 41.9 | 39 | A |
| ASN | CA | 273 | 212.1 | 115.1 | 40.7 | 37 | A |
| ASN | CB | 273 | 213.1 | 115.5 | 39.6 | 36 | A |
| ASN | CG | 273 | 212.4 | 115.8 | 38.3 | 35 | A |
| ASN | OD1 | 273 | 211.2 | 116.2 | 38.3 | 34 | A |
| ASN | ND2 | 273 | 213.1 | 115.7 | 37.2 | 34 | A |
| ASN | C | 273 | 211.2 | 114.0 | 40.2 | 36 | A |
| ASN | O | 273 | 211.7 | 113.0 | 39.7 | 35 | A |
| GLU | N | 274 | 210.0 | 114.2 | 40.4 | 35 | A |
| GLU | CA | 274 | 209.0 | 113.2 | 40.0 | 34 | A |
| GLU | CB | 274 | 207.6 | 113.6 | 40.5 | 35 | A |
| GLU | CG | 274 | 206.6 | 112.6 | 40.3 | 37 | A |
| GLU | CD | 274 | 205.3 | 113.0 | 40.9 | 39 | A |
| GLU | OE1 | 274 | 204.2 | 112.6 | 40.3 | 41 | A |
| GLU | OE2 | 274 | 205.3 | 113.6 | 42.0 | 40 | A |
| GLU | C | 274 | 208.9 | 112.9 | 38.5 | 33 | A |
| GLU | O | 274 | 208.5 | 111.8 | 38.2 | 34 | A |
| SER | N | 275 | 209.2 | 113.9 | 37.7 | 33 | A |
| SER | CA | 275 | 209.0 | 113.7 | 36.2 | 33 | A |
| SER | CB | 275 | 209.3 | 114.9 | 35.5 | 33 | A |
| SER | OG | 275 | 208.5 | 116.0 | 35.9 | 33 | A |
| SER | C | 275 | 209.9 | 112.5 | 35.7 | 34 | A |
| SER | O | 275 | 209.5 | 111.6 | 35.0 | 34 | A |
| ALA | N | 276 | 211.2 | 112.6 | 36.1 | 34 | A |
| ALA | CA | 276 | 212.1 | 111.5 | 35.6 | 33 | A |
| ALA | CB | 276 | 213.5 | 111.8 | 36.2 | 33 | A |
| ALA | C | 276 | 211.6 | 110.2 | 36.2 | 33 | A |
| ALA | O | 276 | 211.7 | 109.2 | 35.5 | 33 | A |
| TRP | N | 277 | 211.1 | 110.2 | 37.4 | 33 | A |
| TRP | CA | 277 | 210.5 | 109.0 | 38.0 | 32 | A |

TABLE 4-continued

The following table lists the atomic structure coordinates for FPT in complex with FPP and the inhibitor SCH66701 as derived by X-ray diffraction from crystals of that complex
The abbreviations are the same as those used in Table 2

| RES | ATOM | # | X | Y | Z | B | C |
|---|---|---|---|---|---|---|---|
| TRP | CB | 277 | 210.2 | 109.3 | 39.4 | 33 | A |
| TRP | CG | 277 | 211.3 | 109.1 | 40.3 | 35 | A |
| TRP | CD2 | 277 | 212.0 | 107.9 | 40.7 | 36 | A |
| TRP | CE2 | 277 | 212.9 | 108.2 | 41.7 | 36 | A |
| TRP | CE3 | 277 | 211.8 | 106.5 | 40.3 | 36 | A |
| TRP | CD1 | 277 | 211.9 | 110.1 | 41.1 | 35 | A |
| TRP | NE1 | 277 | 212.9 | 109.5 | 41.9 | 36 | A |
| TRP | CZ2 | 277 | 213.8 | 107.2 | 42.2 | 36 | A |
| TRP | CZ3 | 277 | 212.7 | 105.6 | 40.8 | 36 | A |
| TRP | CH2 | 277 | 213.6 | 105.9 | 41.8 | 36 | A |
| TRP | C | 277 | 209.3 | 108.4 | 37.2 | 31 | A |
| TRP | O | 277 | 209.3 | 107.3 | 36.9 | 31 | A |
| ASN | N | 278 | 208.3 | 109.3 | 37.0 | 30 | A |
| ASN | CA | 278 | 207.1 | 108.9 | 36.3 | 29 | A |
| ASN | CB | 278 | 206.1 | 110.0 | 36.3 | 30 | A |
| ASN | CG | 278 | 205.6 | 110.4 | 37.6 | 30 | A |
| ASN | OD1 | 278 | 206.0 | 109.8 | 38.6 | 30 | A |
| ASN | ND2 | 278 | 204.8 | 111.5 | 37.7 | 31 | A |
| ASN | C | 278 | 207.5 | 108.5 | 34.9 | 29 | A |
| ASN | O | 278 | 206.7 | 107.8 | 34.2 | 29 | A |
| TYR | N | 279 | 208.6 | 109.0 | 34.4 | 28 | A |
| TYR | CA | 279 | 209.0 | 108.6 | 33.0 | 27 | A |
| TYR | CB | 279 | 210.0 | 109.7 | 32.5 | 26 | A |
| TYR | CG | 279 | 210.4 | 109.4 | 31.0 | 25 | A |
| TYR | CD1 | 279 | 209.5 | 109.7 | 30.0 | 24 | A |
| TYR | CE1 | 279 | 209.8 | 109.4 | 28.7 | 24 | A |
| TYR | CD2 | 279 | 211.6 | 108.9 | 30.7 | 25 | A |
| TYR | CE2 | 279 | 212.0 | 108.7 | 29.4 | 24 | A |
| TYR | CZ | 279 | 211.1 | 109.0 | 28.4 | 24 | A |
| TYR | OH | 279 | 211.6 | 108.8 | 27.1 | 24 | A |
| TYR | C | 279 | 209.6 | 107.3 | 33.0 | 27 | A |
| TYR | O | 279 | 209.4 | 106.5 | 32.1 | 28 | A |
| LEU | N | 280 | 210.4 | 107.0 | 34.1 | 28 | A |
| LEU | CA | 280 | 211.1 | 105.7 | 34.2 | 29 | A |
| LEU | CB | 280 | 211.9 | 105.6 | 35.5 | 28 | A |
| LEU | CG | 280 | 212.8 | 104.4 | 35.7 | 27 | A |
| LEU | CD1 | 280 | 213.7 | 104.1 | 34.5 | 26 | A |
| LEU | CD2 | 280 | 213.6 | 104.5 | 37.0 | 25 | A |
| LEU | C | 280 | 210.1 | 104.6 | 34.2 | 31 | A |
| LEU | O | 280 | 210.1 | 103.7 | 33.4 | 31 | A |
| LYS | N | 281 | 209.1 | 104.8 | 35.1 | 33 | A |
| LYS | CA | 281 | 208.0 | 103.8 | 35.2 | 35 | A |
| LYS | CB | 281 | 207.1 | 104.3 | 36.4 | 34 | A |
| LYS | CG | 281 | 206.0 | 103.2 | 36.7 | 35 | A |
| LYS | CD | 281 | 205.4 | 103.5 | 38.0 | 37 | A |
| LYS | CE | 281 | 204.6 | 104.8 | 38.0 | 38 | A |
| LYS | NZ | 281 | 204.5 | 105.5 | 39.3 | 39 | A |
| LYS | C | 281 | 207.2 | 103.8 | 34.0 | 36 | A |
| LYS | O | 281 | 206.9 | 102.7 | 33.5 | 37 | A |
| GLY | N | 282 | 206.9 | 104.9 | 33.3 | 37 | A |
| GLY | CA | 282 | 206.2 | 105.0 | 32.1 | 38 | A |
| GLY | C | 282 | 206.7 | 104.1 | 31.0 | 39 | A |
| GLY | O | 282 | 205.9 | 103.4 | 30.4 | 39 | A |
| ILE | N | 283 | 208.0 | 104.1 | 30.7 | 40 | A |
| ILE | CA | 283 | 208.6 | 103.4 | 29.6 | 41 | A |
| ILE | CB | 283 | 209.9 | 104.1 | 29.1 | 40 | A |
| ILE | CG2 | 283 | 209.6 | 105.5 | 28.8 | 41 | A |
| ILE | CG1 | 283 | 211.0 | 104.1 | 30.1 | 40 | A |
| ILE | CD1 | 283 | 212.2 | 104.7 | 29.6 | 39 | A |
| ILE | C | 283 | 208.8 | 101.9 | 29.9 | 43 | A |
| ILE | O | 283 | 208.8 | 101.1 | 28.9 | 44 | A |
| LEU | N | 284 | 209.0 | 101.5 | 31.1 | 45 | A |
| LEU | CA | 284 | 209.3 | 100.1 | 31.5 | 47 | A |
| LEU | CB | 284 | 210.2 | 99.9 | 32.6 | 46 | A |
| LEU | CG | 284 | 211.6 | 100.6 | 32.5 | 45 | A |
| LEU | CD1 | 284 | 212.3 | 100.4 | 33.9 | 46 | A |
| LEU | CD2 | 284 | 212.5 | 99.9 | 31.4 | 45 | A |
| LEU | C | 284 | 208.0 | 99.4 | 31.8 | 49 | A |
| LEU | O | 284 | 207.7 | 98.2 | 31.4 | 49 | A |
| GLN | N | 285 | 207.1 | 100.1 | 32.6 | 52 | A |
| GLN | CA | 285 | 205.8 | 99.6 | 33.0 | 55 | A |
| GLN | CB | 285 | 204.9 | 100.7 | 33.7 | 56 | A |

TABLE 4-continued

The following table lists the atomic structure coordinates for FPT in complex with FPP and the inhibitor SCH66701 as derived by X-ray diffraction from crystals of that complex
The abbreviations are the same as those used in Table 2

| RES | ATOM | # | X | Y | Z | B | C |
|---|---|---|---|---|---|---|---|
| GLN | CG | 285 | 204.2 | 101.5 | 32.6 | 57 | A |
| GLN | CD | 285 | 203.2 | 102.6 | 33.2 | 59 | A |
| GLN | OE1 | 285 | 202.5 | 103.2 | 32.5 | 59 | A |
| GLN | NE2 | 285 | 203.2 | 102.7 | 34.6 | 59 | A |
| GLN | C | 285 | 205.0 | 99.0 | 31.9 | 56 | A |
| GLN | O | 285 | 204.0 | 98.4 | 32.2 | 57 | A |
| ASP | N | 286 | 205.4 | 99.2 | 30.7 | 58 | A |
| ASP | CA | 286 | 204.6 | 98.6 | 29.6 | 60 | A |
| ASP | CB | 286 | 204.4 | 99.6 | 28.5 | 63 | A |
| ASP | CG | 286 | 202.9 | 99.9 | 28.2 | 65 | A |
| ASP | OD1 | 286 | 202.5 | 99.7 | 27.0 | 66 | A |
| ASP | OD2 | 286 | 202.1 | 100.2 | 29.1 | 66 | A |
| ASP | C | 286 | 205.1 | 97.3 | 29.1 | 60 | A |
| ASP | O | 286 | 204.9 | 96.9 | 27.9 | 61 | A |
| ARG | N | 287 | 205.9 | 96.6 | 29.9 | 59 | A |
| ARG | CA | 287 | 206.4 | 95.2 | 29.6 | 59 | A |
| ARG | CB | 287 | 207.7 | 95.3 | 28.8 | 60 | A |
| ARG | CG | 287 | 208.2 | 93.9 | 28.2 | 61 | A |
| ARG | CD | 287 | 209.7 | 93.9 | 27.9 | 62 | A |
| ARG | NE | 287 | 210.3 | 92.7 | 28.3 | 63 | A |
| ARG | CZ | 287 | 211.3 | 92.0 | 27.5 | 63 | A |
| ARG | NH1 | 287 | 211.7 | 92.5 | 26.4 | 62 | A |
| ARG | NH2 | 287 | 211.7 | 90.8 | 28.0 | 63 | A |
| ARG | C | 287 | 206.6 | 94.4 | 30.9 | 58 | A |
| ARG | O | 287 | 206.8 | 93.2 | 30.9 | 58 | A |
| GLY | N | 288 | 206.5 | 95.1 | 32.0 | 56 | A |
| GLY | CA | 288 | 206.6 | 94.5 | 33.3 | 54 | A |
| GLY | C | 288 | 207.9 | 94.9 | 34.0 | 52 | A |
| GLY | O | 288 | 209.0 | 94.6 | 33.5 | 53 | A |
| LEU | N | 289 | 207.8 | 95.6 | 35.1 | 51 | A |
| LEU | CA | 289 | 209.1 | 96.0 | 35.8 | 50 | A |
| LEU | CB | 289 | 208.7 | 96.8 | 37.0 | 49 | A |
| LEU | CG | 289 | 208.7 | 98.4 | 36.9 | 48 | A |
| LEU | CD1 | 289 | 208.5 | 98.8 | 35.4 | 48 | A |
| LEU | CD2 | 289 | 207.6 | 98.9 | 37.7 | 48 | A |
| LEU | C | 289 | 209.9 | 94.8 | 36.2 | 50 | A |
| LEU | O | 289 | 211.1 | 94.9 | 36.4 | 50 | A |
| SER | N | 290 | 209.2 | 93.6 | 36.4 | 50 | A |
| SER | CA | 290 | 209.8 | 92.4 | 36.8 | 50 | A |
| SER | CB | 290 | 208.8 | 91.4 | 37.3 | 50 | A |
| SER | OG | 290 | 207.8 | 91.1 | 36.4 | 49 | A |
| SER | C | 290 | 210.7 | 91.7 | 35.7 | 50 | A |
| SER | O | 290 | 211.5 | 90.8 | 36.0 | 49 | A |
| ARG | N | 291 | 210.5 | 92.2 | 34.4 | 50 | A |
| ARG | CA | 291 | 211.3 | 91.6 | 33.3 | 50 | A |
| ARG | CB | 291 | 210.6 | 91.8 | 32.0 | 52 | A |
| ARG | CG | 291 | 209.8 | 90.5 | 31.7 | 55 | A |
| ARG | CD | 291 | 209.1 | 90.7 | 30.4 | 59 | A |
| ARG | NE | 291 | 208.8 | 89.4 | 29.7 | 63 | A |
| ARG | CZ | 291 | 208.7 | 89.2 | 28.4 | 65 | A |
| ARG | NH1 | 291 | 208.5 | 88.0 | 27.9 | 66 | A |
| ARG | NH2 | 291 | 208.9 | 90.3 | 27.6 | 66 | A |
| ARG | C | 291 | 212.7 | 92.3 | 33.2 | 49 | A |
| ARG | O | 291 | 213.4 | 92.2 | 32.2 | 49 | A |
| TYR | N | 292 | 213.0 | 93.1 | 34.3 | 47 | A |
| TYR | CA | 292 | 214.2 | 93.8 | 34.4 | 45 | A |
| TYR | CB | 292 | 213.9 | 95.3 | 34.2 | 42 | A |
| TYR | CG | 292 | 213.3 | 95.5 | 32.8 | 39 | A |
| TYR | CD1 | 292 | 212.0 | 95.8 | 32.7 | 38 | A |
| TYR | CE1 | 292 | 211.4 | 95.9 | 31.4 | 37 | A |
| TYR | CD2 | 292 | 214.1 | 95.4 | 31.6 | 38 | A |
| TYR | CE2 | 292 | 213.5 | 95.5 | 30.4 | 37 | A |
| TYR | CZ | 292 | 212.1 | 95.7 | 30.3 | 36 | A |
| TYR | OH | 292 | 211.6 | 95.8 | 29.0 | 34 | A |
| TYR | C | 292 | 214.8 | 93.6 | 35.8 | 46 | A |
| TYR | O | 292 | 214.7 | 94.4 | 36.7 | 46 | A |
| PRO | N | 293 | 215.4 | 92.4 | 36.0 | 46 | A |
| PRO | CD | 293 | 215.7 | 91.4 | 34.8 | 45 | A |
| PRO | CA | 293 | 216.0 | 91.9 | 37.2 | 46 | A |
| PRO | CB | 293 | 216.6 | 90.5 | 36.8 | 46 | A |
| PRO | CG | 293 | 216.9 | 90.7 | 35.3 | 45 | A |
| PRO | C | 293 | 217.1 | 92.7 | 37.8 | 47 | A |

TABLE 4-continued

The following table lists the atomic structure coordinates for FPT in complex with FPP and the inhibitor SCH66701 as derived by X-ray diffraction from crystals of that complex
The abbreviations are the same as those used in Table 2

| RES | ATOM | # | X | Y | Z | B | C |
|---|---|---|---|---|---|---|---|
| PRO | O | 293 | 217.3 | 92.7 | 39.0 | 48 | A |
| ASN | N | 294 | 217.9 | 93.5 | 37.0 | 48 | A |
| ASN | CA | 294 | 219.0 | 94.3 | 37.5 | 50 | A |
| ASN | CB | 294 | 219.9 | 94.8 | 36.4 | 49 | A |
| ASN | CG | 294 | 220.5 | 93.6 | 35.7 | 48 | A |
| ASN | OD1 | 294 | 220.1 | 93.3 | 34.5 | 48 | A |
| ASN | ND2 | 294 | 221.5 | 92.9 | 36.2 | 48 | A |
| ASN | C | 294 | 218.4 | 95.6 | 38.2 | 51 | A |
| ASN | O | 294 | 218.9 | 96.0 | 39.2 | 51 | A |
| LEU | N | 295 | 217.3 | 96.1 | 37.6 | 53 | A |
| LEU | CA | 295 | 216.6 | 97.3 | 38.0 | 55 | A |
| LEU | CB | 295 | 215.3 | 97.4 | 37.3 | 56 | A |
| LEU | CG | 295 | 214.5 | 98.7 | 37.2 | 57 | A |
| LEU | CD1 | 295 | 215.3 | 99.7 | 36.5 | 57 | A |
| LEU | CD2 | 295 | 213.2 | 98.4 | 36.5 | 57 | A |
| LEU | C | 295 | 216.5 | 97.4 | 39.5 | 55 | A |
| LEU | O | 295 | 216.9 | 98.4 | 40.1 | 54 | A |
| LEU | N | 296 | 215.8 | 96.4 | 40.1 | 56 | A |
| LEU | CA | 296 | 215.6 | 96.4 | 41.6 | 57 | A |
| LEU | CB | 296 | 215.0 | 95.1 | 42.1 | 56 | A |
| LEU | CG | 296 | 214.6 | 95.1 | 43.6 | 56 | A |
| LEU | CD1 | 296 | 213.6 | 96.1 | 43.9 | 56 | A |
| LEU | CD2 | 296 | 214.1 | 93.7 | 43.9 | 56 | A |
| LEU | C | 296 | 216.9 | 96.7 | 42.4 | 59 | A |
| LEU | O | 296 | 216.9 | 97.5 | 43.3 | 59 | A |
| ASN | N | 297 | 218.0 | 96.1 | 41.9 | 62 | A |
| ASN | CA | 297 | 219.3 | 96.2 | 42.5 | 65 | A |
| ASN | CB | 297 | 220.4 | 95.5 | 41.8 | 67 | A |
| ASN | CG | 297 | 220.1 | 94.0 | 41.5 | 69 | A |
| ASN | OD1 | 297 | 218.9 | 93.6 | 41.5 | 70 | A |
| ASN | ND2 | 297 | 221.1 | 93.2 | 41.3 | 69 | A |
| ASN | C | 297 | 219.6 | 97.7 | 42.6 | 65 | A |
| ASN | O | 297 | 219.4 | 98.4 | 43.6 | 65 | A |
| GLN | N | 298 | 220.0 | 98.3 | 41.4 | 66 | A |
| GLN | CA | 298 | 220.4 | 99.7 | 41.3 | 66 | A |
| GLN | CB | 298 | 220.3 | 100.1 | 39.8 | 66 | A |
| GLN | CG | 298 | 219.9 | 99.0 | 38.8 | 66 | A |
| GLN | CD | 298 | 221.0 | 98.2 | 38.3 | 66 | A |
| GLN | OE1 | 298 | 221.5 | 97.3 | 39.1 | 66 | A |
| GLN | NE2 | 298 | 221.4 | 98.3 | 37.1 | 65 | A |
| GLN | C | 298 | 219.6 | 100.6 | 42.1 | 67 | A |
| GLN | O | 298 | 220.1 | 101.3 | 43.0 | 68 | A |
| LEU | N | 299 | 218.2 | 100.5 | 42.0 | 68 | A |
| LEU | CA | 299 | 217.4 | 101.4 | 42.8 | 69 | A |
| LEU | CB | 299 | 215.9 | 101.1 | 42.5 | 68 | A |
| LEU | CG | 299 | 215.3 | 101.4 | 41.1 | 68 | A |
| LEU | CD1 | 299 | 213.8 | 101.2 | 41.2 | 68 | A |
| LEU | CD2 | 299 | 215.7 | 102.8 | 40.7 | 67 | A |
| LEU | C | 299 | 217.6 | 101.2 | 44.3 | 69 | A |
| LEU | O | 299 | 217.8 | 102.2 | 45.0 | 68 | A |
| LEU | N | 300 | 217.7 | 99.9 | 44.7 | 71 | A |
| LEU | CA | 300 | 218.0 | 99.6 | 46.1 | 72 | A |
| LEU | CB | 300 | 218.0 | 98.1 | 46.2 | 72 | A |
| LEU | CG | 300 | 216.8 | 97.2 | 46.7 | 73 | A |
| LEU | CD1 | 300 | 215.6 | 97.9 | 46.2 | 74 | A |
| LEU | CD2 | 300 | 217.0 | 95.8 | 46.2 | 73 | A |
| LEU | C | 300 | 219.3 | 100.2 | 46.5 | 73 | A |
| LEU | O | 300 | 219.4 | 100.6 | 47.7 | 73 | A |
| ASP | N | 301 | 220.3 | 100.2 | 45.6 | 75 | A |
| ASP | CA | 301 | 221.6 | 100.7 | 45.9 | 76 | A |
| ASP | CB | 301 | 222.5 | 100.5 | 44.7 | 76 | A |
| ASP | CG | 301 | 222.8 | 99.0 | 44.4 | 77 | A |
| ASP | OD1 | 301 | 222.2 | 98.1 | 45.1 | 77 | A |
| ASP | OD2 | 301 | 223.5 | 98.6 | 43.4 | 77 | A |
| ASP | C | 301 | 221.5 | 102.2 | 46.2 | 77 | A |
| ASP | O | 301 | 222.2 | 102.6 | 47.2 | 77 | A |
| LEU | N | 302 | 220.7 | 102.9 | 45.5 | 77 | A |
| LEU | CA | 302 | 220.6 | 104.4 | 45.8 | 78 | A |
| LEU | CB | 302 | 219.9 | 105.1 | 44.6 | 79 | A |
| LEU | CG | 302 | 220.7 | 105.2 | 43.3 | 79 | A |
| LEU | CD1 | 302 | 220.0 | 106.1 | 42.2 | 79 | A |
| LEU | CD2 | 302 | 222.1 | 105.7 | 43.5 | 79 | A |

TABLE 4-continued

The following table lists the atomic structure coordinates for FPT in complex with FPP and the inhibitor SCH66701 as derived by X-ray diffraction from crystals of that complex
The abbreviations are the same as those used in Table 2

| RES | ATOM | # | X | Y | Z | B | C |
|---|---|---|---|---|---|---|---|
| LEU | C | 302 | 219.8 | 104.7 | 47.0 | 78 | A |
| LEU | O | 302 | 219.7 | 105.8 | 47.5 | 78 | A |
| GLN | N | 303 | 219.2 | 103.6 | 47.6 | 79 | A |
| GLN | CA | 303 | 218.4 | 103.8 | 48.9 | 80 | A |
| GLN | CB | 303 | 218.2 | 102.4 | 49.5 | 79 | A |
| GLN | CG | 303 | 216.9 | 101.7 | 49.1 | 80 | A |
| GLN | CD | 303 | 215.7 | 102.3 | 49.8 | 80 | A |
| GLN | OE1 | 303 | 215.6 | 103.5 | 49.9 | 79 | A |
| GLN | NE2 | 303 | 214.8 | 101.4 | 50.3 | 80 | A |
| GLN | C | 303 | 219.0 | 104.7 | 49.8 | 81 | A |
| GLN | O | 303 | 218.4 | 105.7 | 50.3 | 81 | A |
| PRO | N | 304 | 220.3 | 104.5 | 50.2 | 82 | A |
| PRO | CD | 304 | 221.2 | 103.4 | 49.9 | 81 | A |
| PRO | CA | 304 | 220.9 | 105.4 | 51.2 | 82 | A |
| PRO | CB | 304 | 222.1 | 104.7 | 51.6 | 82 | A |
| PRO | CG | 304 | 222.5 | 103.9 | 50.4 | 82 | A |
| PRO | C | 304 | 221.3 | 106.8 | 50.6 | 82 | A |
| PRO | O | 304 | 220.9 | 107.8 | 51.1 | 82 | A |
| SER | N | 305 | 222.0 | 106.8 | 49.4 | 82 | A |
| SER | CA | 305 | 222.4 | 108.0 | 48.8 | 82 | A |
| SER | CB | 305 | 223.8 | 107.8 | 48.0 | 82 | A |
| SER | OG | 305 | 223.7 | 106.7 | 47.1 | 83 | A |
| SER | C | 305 | 221.5 | 108.9 | 48.0 | 82 | A |
| SER | O | 305 | 221.4 | 110.1 | 48.1 | 82 | A |
| HIS | N | 306 | 220.7 | 108.2 | 47.1 | 81 | A |
| HIS | CA | 306 | 219.7 | 109.0 | 46.3 | 80 | A |
| HIS | CB | 306 | 220.0 | 108.8 | 44.8 | 81 | A |
| HIS | CG | 306 | 221.4 | 109.2 | 44.4 | 82 | A |
| HIS | CD2 | 306 | 222.1 | 108.9 | 43.3 | 82 | A |
| HIS | ND1 | 306 | 222.1 | 110.1 | 45.1 | 82 | A |
| HIS | CE1 | 306 | 223.3 | 110.3 | 44.6 | 82 | A |
| HIS | NE2 | 306 | 223.3 | 109.6 | 43.4 | 82 | A |
| HIS | C | 306 | 218.3 | 108.7 | 46.6 | 79 | A |
| HIS | O | 306 | 217.4 | 108.5 | 45.8 | 80 | A |
| SER | N | 307 | 218.0 | 108.7 | 47.9 | 78 | A |
| SER | CA | 307 | 216.7 | 108.4 | 48.5 | 76 | A |
| SER | CB | 307 | 216.9 | 108.3 | 50.0 | 76 | A |
| SER | OG | 307 | 215.9 | 107.4 | 50.6 | 76 | A |
| SER | C | 307 | 215.7 | 109.5 | 48.2 | 75 | A |
| SER | O | 307 | 216.0 | 110.6 | 48.0 | 76 | A |
| SER | N | 308 | 214.4 | 109.0 | 48.1 | 73 | A |
| SER | CA | 308 | 213.3 | 109.9 | 47.8 | 70 | A |
| SER | CB | 308 | 213.4 | 110.5 | 46.4 | 70 | A |
| SER | OG | 308 | 213.1 | 109.6 | 45.4 | 69 | A |
| SER | C | 308 | 212.1 | 109.0 | 47.9 | 68 | A |
| SER | O | 308 | 212.1 | 107.9 | 47.4 | 69 | A |
| PRO | N | 309 | 210.9 | 109.5 | 48.4 | 66 | A |
| PRO | CD | 309 | 210.5 | 110.8 | 48.8 | 66 | A |
| PRO | CA | 309 | 209.8 | 108.6 | 48.5 | 64 | A |
| PRO | CB | 309 | 208.7 | 109.5 | 49.1 | 65 | A |
| PRO | CG | 309 | 209.0 | 110.8 | 48.6 | 65 | A |
| PRO | C | 309 | 209.3 | 108.0 | 47.1 | 63 | A |
| PRO | O | 309 | 208.5 | 107.1 | 47.0 | 62 | A |
| TYR | N | 310 | 210.0 | 108.5 | 46.0 | 60 | A |
| TYR | CA | 310 | 209.7 | 108.0 | 44.7 | 57 | A |
| TYR | CB | 310 | 210.2 | 109.1 | 43.7 | 57 | A |
| TYR | CG | 310 | 209.7 | 110.4 | 44.0 | 57 | A |
| TYR | CD1 | 310 | 210.5 | 111.4 | 44.6 | 57 | A |
| TYR | CE1 | 310 | 209.9 | 112.6 | 45.0 | 58 | A |
| TYR | CD2 | 310 | 208.3 | 110.7 | 43.8 | 56 | A |
| TYR | CE2 | 310 | 207.8 | 111.9 | 44.2 | 57 | A |
| TYR | CZ | 310 | 208.6 | 112.9 | 44.8 | 58 | A |
| TYR | OH | 310 | 208.0 | 114.0 | 45.3 | 59 | A |
| TYR | C | 310 | 210.4 | 106.7 | 44.5 | 55 | A |
| TYR | O | 310 | 209.9 | 105.8 | 43.7 | 55 | A |
| LEU | N | 311 | 211.6 | 106.5 | 45.1 | 52 | A |
| LEU | CA | 311 | 212.3 | 105.3 | 45.0 | 49 | A |
| LEU | CB | 311 | 213.7 | 105.5 | 45.7 | 49 | A |
| LEU | CG | 311 | 214.7 | 104.3 | 45.8 | 49 | A |
| LEU | CD1 | 311 | 215.2 | 104.0 | 44.4 | 49 | A |
| LEU | CD2 | 311 | 215.9 | 104.7 | 46.6 | 49 | A |
| LEU | C | 311 | 211.6 | 104.3 | 45.8 | 47 | A |

TABLE 4-continued

The following table lists the atomic structure coordinates for FPT in complex with FPP and the inhibitor SCH66701 as derived by X-ray diffraction from crystals of that complex
The abbreviations are the same as those used in Table 2

| RES | ATOM | # | X | Y | Z | B | C |
|---|---|---|---|---|---|---|---|
| LEU | O | 311 | 211.3 | 103.2 | 45.3 | 46 | A |
| ILE | N | 312 | 211.1 | 104.6 | 47.0 | 46 | A |
| ILE | CA | 312 | 210.4 | 103.7 | 47.9 | 45 | A |
| ILE | CB | 312 | 209.9 | 104.4 | 49.2 | 45 | A |
| ILE | CG2 | 312 | 209.1 | 103.4 | 50.1 | 45 | A |
| ILE | CG1 | 312 | 211.0 | 104.9 | 50.1 | 46 | A |
| ILE | CD1 | 312 | 211.9 | 103.9 | 50.7 | 46 | A |
| ILE | C | 312 | 209.2 | 103.2 | 47.1 | 44 | A |
| ILE | O | 312 | 209.0 | 102.0 | 47.1 | 45 | A |
| ALA | N | 313 | 208.4 | 104.1 | 46.5 | 43 | A |
| ALA | CA | 313 | 207.2 | 103.7 | 45.8 | 41 | A |
| ALA | CB | 313 | 206.3 | 104.9 | 45.5 | 41 | A |
| ALA | C | 313 | 207.5 | 102.9 | 44.5 | 39 | A |
| ALA | O | 313 | 206.7 | 102.1 | 44.0 | 39 | A |
| PHE | N | 314 | 208.7 | 103.1 | 43.9 | 38 | A |
| PHE | CA | 314 | 209.1 | 102.4 | 42.7 | 38 | A |
| PHE | CB | 314 | 210.4 | 103.0 | 42.0 | 37 | A |
| PHE | CG | 314 | 210.5 | 102.7 | 40.5 | 37 | A |
| PHE | CD1 | 314 | 210.4 | 103.7 | 39.6 | 37 | A |
| PHE | CD2 | 314 | 210.6 | 101.4 | 40.1 | 37 | A |
| PHE | CE1 | 314 | 210.5 | 103.4 | 38.2 | 37 | A |
| PHE | CE2 | 314 | 210.6 | 101.1 | 38.7 | 37 | A |
| PHE | CZ | 314 | 210.6 | 102.1 | 37.8 | 37 | A |
| PHE | C | 314 | 209.2 | 100.9 | 43.1 | 38 | A |
| PHE | O | 314 | 208.7 | 100.0 | 42.4 | 39 | A |
| LEU | N | 315 | 209.9 | 100.7 | 44.2 | 37 | A |
| LEU | CA | 315 | 210.2 | 99.3 | 44.6 | 36 | A |
| LEU | CB | 315 | 210.9 | 99.3 | 46.0 | 35 | A |
| LEU | CG | 315 | 212.2 | 100.1 | 45.9 | 35 | A |
| LEU | CD1 | 315 | 212.9 | 100.2 | 47.3 | 34 | A |
| LEU | CD2 | 315 | 213.2 | 99.6 | 44.9 | 34 | A |
| LEU | C | 315 | 208.9 | 98.6 | 44.8 | 36 | A |
| LEU | O | 315 | 208.8 | 97.5 | 44.3 | 37 | A |
| VAL | N | 316 | 207.9 | 99.2 | 45.4 | 37 | A |
| VAL | CA | 316 | 206.6 | 98.6 | 45.5 | 38 | A |
| VAL | CB | 316 | 205.5 | 99.5 | 46.2 | 37 | A |
| VAL | CG1 | 316 | 204.2 | 98.7 | 46.3 | 37 | A |
| VAL | CG2 | 316 | 206.0 | 99.8 | 47.6 | 37 | A |
| VAL | C | 316 | 206.0 | 98.3 | 44.1 | 39 | A |
| VAL | O | 316 | 205.4 | 97.2 | 43.9 | 39 | A |
| ASP | N | 317 | 206.2 | 99.2 | 43.2 | 40 | A |
| ASP | CA | 317 | 205.8 | 99.0 | 41.8 | 41 | A |
| ASP | CB | 317 | 206.0 | 100.2 | 40.9 | 42 | A |
| ASP | CG | 317 | 205.2 | 101.4 | 41.3 | 43 | A |
| ASP | OD1 | 317 | 204.0 | 101.2 | 41.7 | 44 | A |
| ASP | OD2 | 317 | 205.7 | 102.5 | 41.3 | 44 | A |
| ASP | C | 317 | 206.5 | 97.7 | 41.2 | 41 | A |
| ASP | O | 317 | 205.9 | 97.1 | 40.4 | 40 | A |
| ILE | N | 318 | 207.7 | 97.5 | 41.5 | 41 | A |
| ILE | CA | 318 | 208.4 | 96.3 | 41.0 | 42 | A |
| ILE | CB | 318 | 210.0 | 96.4 | 41.3 | 42 | A |
| ILE | CG2 | 318 | 210.6 | 95.1 | 40.9 | 42 | A |
| ILE | CG1 | 318 | 210.6 | 97.6 | 40.7 | 41 | A |
| ILE | CD1 | 318 | 212.1 | 97.6 | 40.8 | 40 | A |
| ILE | C | 318 | 207.9 | 95.1 | 41.7 | 43 | A |
| ILE | O | 318 | 207.5 | 94.2 | 41.0 | 44 | A |
| TYR | N | 319 | 207.8 | 95.1 | 43.0 | 45 | A |
| TYR | CA | 319 | 207.3 | 94.0 | 43.7 | 48 | A |
| TYR | CB | 319 | 207.3 | 94.3 | 45.2 | 48 | A |
| TYR | CG | 319 | 208.6 | 94.5 | 45.8 | 48 | A |
| TYR | CD1 | 319 | 208.8 | 95.1 | 47.1 | 48 | A |
| TYR | CE1 | 319 | 210.1 | 95.3 | 47.6 | 48 | A |
| TYR | CD2 | 319 | 209.8 | 94.0 | 45.2 | 48 | A |
| TYR | CE2 | 319 | 211.0 | 94.2 | 45.7 | 48 | A |
| TYR | CZ | 319 | 211.2 | 94.8 | 46.9 | 48 | A |
| TYR | OH | 319 | 212.4 | 94.9 | 47.5 | 49 | A |
| TYR | C | 319 | 205.9 | 93.6 | 43.3 | 50 | A |
| TYR | O | 319 | 205.7 | 92.4 | 43.0 | 51 | A |
| GLU | N | 320 | 205.0 | 94.6 | 43.1 | 52 | A |
| GLU | CA | 320 | 203.7 | 94.3 | 42.6 | 54 | A |
| GLU | CB | 320 | 202.9 | 95.6 | 42.4 | 56 | A |
| GLU | CG | 320 | 202.6 | 96.5 | 43.6 | 58 | A |

TABLE 4-continued

The following table lists the atomic structure coordinates for FPT in complex with FPP and the inhibitor SCH66701 as derived by X-ray diffraction from crystals of that complex The abbreviations are the same as those used in Table 2

| RES | ATOM | # | X | Y | Z | B | C |
|---|---|---|---|---|---|---|---|
| GLU | CD | 320 | 202.4 | 98.0 | 43.3 | 60 | A |
| GLU | OE1 | 320 | 201.7 | 98.7 | 44.2 | 61 | A |
| GLU | OE2 | 320 | 202.8 | 98.5 | 42.3 | 61 | A |
| GLU | C | 320 | 203.7 | 93.5 | 41.3 | 53 | A |
| GLU | O | 320 | 203.1 | 92.5 | 41.2 | 53 | A |
| ASP | N | 321 | 204.6 | 93.9 | 40.4 | 54 | A |
| ASP | CA | 321 | 204.7 | 93.2 | 39.2 | 55 | A |
| ASP | CB | 321 | 205.4 | 94.0 | 38.1 | 53 | A |
| ASP | CG | 321 | 205.3 | 93.4 | 36.7 | 53 | A |
| ASP | OD1 | 321 | 204.1 | 93.2 | 36.3 | 53 | A |
| ASP | OD2 | 321 | 206.3 | 93.1 | 36.1 | 52 | A |
| ASP | C | 321 | 205.3 | 91.8 | 39.3 | 56 | A |
| ASP | O | 321 | 205.0 | 91.0 | 38.5 | 57 | A |
| MET | N | 322 | 206.2 | 91.7 | 40.2 | 58 | A |
| MET | CA | 322 | 206.9 | 90.4 | 40.4 | 60 | A |
| MET | CB | 322 | 208.0 | 90.5 | 41.3 | 59 | A |
| MET | CG | 322 | 209.2 | 91.3 | 40.8 | 58 | A |
| MET | SD | 322 | 210.8 | 91.0 | 41.5 | 57 | A |
| MET | CE | 322 | 210.7 | 91.6 | 43.1 | 56 | A |
| MET | C | 322 | 205.8 | 89.3 | 40.8 | 62 | A |
| MET | O | 322 | 205.8 | 88.3 | 40.3 | 62 | A |
| LEU | N | 323 | 205.0 | 89.7 | 41.8 | 65 | A |
| LEU | CA | 323 | 204.0 | 88.8 | 42.3 | 68 | A |
| LEU | CB | 323 | 203.2 | 89.4 | 43.4 | 68 | A |
| LEU | CG | 323 | 203.6 | 89.3 | 44.9 | 68 | A |
| LEU | CD1 | 323 | 205.1 | 89.4 | 45.1 | 68 | A |
| LEU | CD2 | 323 | 202.9 | 90.3 | 45.7 | 68 | A |
| LEU | C | 323 | 203.1 | 88.4 | 41.2 | 70 | A |
| LEU | O | 323 | 202.9 | 87.2 | 40.8 | 70 | A |
| GLU | N | 324 | 202.6 | 89.4 | 40.5 | 74 | A |
| GLU | CA | 324 | 201.7 | 89.3 | 39.3 | 77 | A |
| GLU | CB | 324 | 201.5 | 90.6 | 38.6 | 78 | A |
| GLU | CG | 324 | 200.6 | 91.6 | 39.5 | 80 | A |
| GLU | CD | 324 | 200.7 | 93.1 | 39.0 | 81 | A |
| GLU | OE1 | 324 | 201.1 | 93.4 | 37.8 | 82 | A |
| GLU | OE2 | 324 | 200.4 | 94.0 | 39.8 | 82 | A |
| GLU | C | 324 | 202.3 | 88.3 | 38.3 | 78 | A |
| GLU | O | 324 | 201.6 | 87.5 | 37.7 | 78 | A |
| ASN | N | 325 | 203.6 | 88.3 | 38.2 | 79 | A |
| ASN | CA | 325 | 204.3 | 87.4 | 37.3 | 80 | A |
| ASN | CB | 325 | 205.3 | 88.2 | 36.4 | 80 | A |
| ASN | CG | 325 | 204.6 | 89.3 | 35.5 | 81 | A |
| ASN | OD1 | 325 | 205.0 | 90.4 | 35.4 | 81 | A |
| ASN | ND2 | 325 | 203.4 | 88.9 | 35.0 | 81 | A |
| ASN | C | 325 | 205.1 | 86.3 | 37.9 | 81 | A |
| ASN | O | 325 | 206.2 | 86.0 | 37.6 | 81 | A |
| GLN | N | 326 | 204.4 | 85.6 | 38.9 | 83 | A |
| GLN | CA | 326 | 204.9 | 84.5 | 39.6 | 85 | A |
| GLN | CB | 326 | 204.6 | 83.2 | 38.8 | 85 | A |
| GLN | CG | 326 | 203.2 | 83.1 | 38.2 | 86 | A |
| GLN | CD | 326 | 203.0 | 83.3 | 36.7 | 86 | A |
| GLN | OE1 | 326 | 203.7 | 82.6 | 35.9 | 86 | A |
| GLN | NE2 | 326 | 202.2 | 84.2 | 36.3 | 86 | A |
| GLN | C | 326 | 206.4 | 84.5 | 40.1 | 85 | A |
| GLN | O | 326 | 207.1 | 83.6 | 39.7 | 85 | A |
| CYS | N | 327 | 206.8 | 85.5 | 40.8 | 86 | A |
| CYS | CA | 327 | 208.1 | 85.6 | 41.3 | 87 | A |
| CYS | CB | 327 | 208.4 | 87.0 | 41.8 | 87 | A |
| CYS | SG | 327 | 207.9 | 87.3 | 43.5 | 86 | A |
| CYS | C | 327 | 208.4 | 84.7 | 42.4 | 89 | A |
| CYS | O | 327 | 207.5 | 84.3 | 43.2 | 89 | A |
| ASP | N | 328 | 209.7 | 84.2 | 42.5 | 90 | A |
| ASP | CA | 328 | 210.0 | 83.2 | 43.5 | 91 | A |
| ASP | CB | 328 | 211.2 | 82.3 | 43.1 | 92 | A |
| ASP | CG | 328 | 210.9 | 80.9 | 43.5 | 93 | A |
| ASP | OD1 | 328 | 210.6 | 80.0 | 42.6 | 93 | A |
| ASP | OD2 | 328 | 210.9 | 80.5 | 44.7 | 93 | A |
| ASP | C | 328 | 210.4 | 84.1 | 44.7 | 91 | A |
| ASP | O | 328 | 211.0 | 85.1 | 44.6 | 91 | A |
| ASN | N | 329 | 209.9 | 83.7 | 45.9 | 91 | A |
| ASN | CA | 329 | 210.0 | 84.3 | 47.2 | 90 | A |
| ASN | CB | 329 | 211.2 | 85.3 | 47.2 | 90 | A |

TABLE 4-continued

The following table lists the atomic structure coordinates for FPT in complex with FPP and the inhibitor SCH66701 as derived by X-ray diffraction from crystals of that complex The abbreviations are the same as those used in Table 2

| RES | ATOM | # | X | Y | Z | B | C |
|---|---|---|---|---|---|---|---|
| ASN | CG | 329 | 212.5 | 84.6 | 47.3 | 90 | A |
| ASN | OD1 | 329 | 212.9 | 83.8 | 46.4 | 90 | A |
| ASN | ND2 | 329 | 213.3 | 84.8 | 48.3 | 91 | A |
| ASN | C | 329 | 208.8 | 85.1 | 47.5 | 90 | A |
| ASN | O | 329 | 208.8 | 86.0 | 48.3 | 90 | A |
| LYS | N | 330 | 207.7 | 84.7 | 46.9 | 90 | A |
| LYS | CA | 330 | 206.4 | 85.3 | 47.0 | 90 | A |
| LYS | CB | 330 | 205.2 | 84.4 | 46.6 | 90 | A |
| LYS | CG | 330 | 204.3 | 85.0 | 45.5 | 91 | A |
| LYS | CD | 330 | 203.3 | 84.1 | 45.0 | 91 | A |
| LYS | CE | 330 | 202.4 | 84.7 | 43.9 | 91 | A |
| LYS | NZ | 330 | 203.2 | 85.1 | 42.7 | 90 | A |
| LYS | C | 330 | 206.1 | 85.8 | 48.5 | 90 | A |
| LYS | O | 330 | 205.9 | 87.0 | 48.7 | 89 | A |
| GLU | N | 331 | 206.3 | 84.9 | 49.4 | 90 | A |
| GLU | CA | 331 | 206.1 | 85.1 | 50.8 | 90 | A |
| GLU | CB | 331 | 206.5 | 83.9 | 51.7 | 92 | A |
| GLU | CG | 331 | 205.9 | 82.6 | 51.3 | 93 | A |
| GLU | CD | 331 | 204.6 | 82.3 | 52.0 | 94 | A |
| GLU | OE1 | 331 | 203.8 | 81.4 | 51.6 | 94 | A |
| GLU | OE2 | 331 | 204.3 | 83.0 | 53.0 | 95 | A |
| GLU | C | 331 | 207.0 | 86.3 | 51.3 | 89 | A |
| GLU | O | 331 | 206.6 | 87.2 | 51.9 | 88 | A |
| ASP | N | 332 | 208.3 | 86.2 | 50.9 | 87 | A |
| ASP | CA | 332 | 209.3 | 87.2 | 51.2 | 86 | A |
| ASP | CB | 332 | 210.7 | 86.6 | 50.8 | 87 | A |
| ASP | CG | 332 | 211.8 | 87.6 | 50.8 | 88 | A |
| ASP | OD1 | 332 | 212.7 | 87.5 | 49.9 | 88 | A |
| ASP | OD2 | 332 | 211.9 | 88.4 | 51.7 | 89 | A |
| ASP | C | 332 | 209.1 | 88.5 | 50.5 | 84 | A |
| ASP | O | 332 | 208.9 | 89.5 | 51.2 | 84 | A |
| ILE | N | 333 | 209.1 | 88.6 | 49.2 | 82 | A |
| ILE | CA | 333 | 208.9 | 89.8 | 48.4 | 79 | A |
| ILE | CB | 333 | 208.9 | 89.5 | 46.9 | 79 | A |
| ILE | CG2 | 333 | 208.2 | 90.5 | 46.1 | 78 | A |
| ILE | CG1 | 333 | 210.4 | 89.4 | 46.4 | 78 | A |
| ILE | CD1 | 333 | 210.6 | 88.7 | 45.1 | 78 | A |
| ILE | C | 333 | 207.6 | 90.5 | 48.9 | 78 | A |
| ILE | O | 333 | 207.7 | 91.7 | 49.1 | 78 | A |
| LEU | N | 334 | 206.6 | 89.8 | 49.1 | 76 | A |
| LEU | CA | 334 | 205.3 | 90.4 | 49.5 | 75 | A |
| LEU | CB | 334 | 204.2 | 89.3 | 49.7 | 75 | A |
| LEU | CG | 334 | 202.9 | 89.7 | 50.4 | 74 | A |
| LEU | CD1 | 334 | 202.2 | 90.8 | 49.6 | 74 | A |
| LEU | CD2 | 334 | 202.1 | 88.5 | 50.4 | 74 | A |
| LEU | C | 334 | 205.5 | 91.2 | 50.8 | 75 | A |
| LEU | O | 334 | 205.0 | 92.3 | 50.8 | 76 | A |
| ASN | N | 335 | 206.1 | 90.6 | 51.8 | 75 | A |
| ASN | CA | 335 | 206.3 | 91.3 | 53.1 | 75 | A |
| ASN | CB | 335 | 207.1 | 90.5 | 54.1 | 76 | A |
| ASN | CG | 335 | 206.3 | 89.3 | 54.6 | 77 | A |
| ASN | OD1 | 335 | 205.1 | 89.4 | 55.0 | 77 | A |
| ASN | ND2 | 335 | 206.9 | 88.1 | 54.6 | 77 | A |
| ASN | C | 335 | 206.9 | 92.7 | 52.9 | 74 | A |
| ASN | O | 335 | 206.5 | 93.7 | 53.5 | 74 | A |
| LYS | N | 336 | 207.9 | 92.7 | 52.0 | 72 | A |
| LYS | CA | 336 | 208.6 | 94.0 | 51.8 | 71 | A |
| LYS | CB | 336 | 209.7 | 93.8 | 50.7 | 72 | A |
| LYS | CG | 336 | 211.1 | 93.9 | 51.3 | 72 | A |
| LYS | CD | 336 | 212.1 | 93.1 | 50.4 | 73 | A |
| LYS | CE | 336 | 211.7 | 91.6 | 50.4 | 73 | A |
| LYS | NZ | 336 | 212.7 | 90.8 | 49.6 | 74 | A |
| LYS | C | 336 | 207.6 | 95.0 | 51.2 | 70 | A |
| LYS | O | 336 | 207.4 | 96.0 | 51.9 | 69 | A |
| ALA | N | 337 | 207.0 | 94.6 | 50.1 | 68 | A |
| ALA | CA | 337 | 206.0 | 95.4 | 49.5 | 66 | A |
| ALA | CB | 337 | 205.2 | 94.6 | 48.4 | 66 | A |
| ALA | C | 337 | 205.0 | 96.0 | 50.5 | 65 | A |
| ALA | O | 337 | 204.7 | 97.2 | 50.5 | 65 | A |
| LEU | N | 338 | 204.5 | 95.2 | 51.4 | 64 | A |
| LEU | CA | 338 | 203.6 | 95.6 | 52.4 | 63 | A |
| LEU | CB | 338 | 202.9 | 94.4 | 53.1 | 63 | A |

TABLE 4-continued

The following table lists the atomic structure coordinates for FPT in complex with FPP and the inhibitor SCH66701 as derived by X-ray diffraction from crystals of that complex The abbreviations are the same as those used in Table 2

| RES | ATOM | # | X | Y | Z | B | C |
|---|---|---|---|---|---|---|---|
| LEU | CG | 338 | 202.1 | 93.5 | 52.2 | 63 | A |
| LEU | CD1 | 338 | 201.7 | 92.3 | 52.9 | 62 | A |
| LEU | CD2 | 338 | 200.8 | 94.3 | 51.7 | 62 | A |
| LEU | C | 338 | 204.2 | 96.5 | 53.5 | 63 | A |
| LEU | O | 338 | 203.6 | 97.5 | 54.0 | 63 | A |
| GLU | N | 339 | 205.5 | 96.3 | 53.8 | 63 | A |
| GLU | CA | 339 | 206.2 | 97.1 | 54.8 | 63 | A |
| GLU | CB | 339 | 207.6 | 96.5 | 55.1 | 65 | A |
| GLU | CG | 339 | 208.3 | 97.2 | 56.2 | 68 | A |
| GLU | CD | 339 | 209.8 | 97.1 | 56.2 | 69 | A |
| GLU | OE1 | 339 | 210.3 | 95.9 | 56.0 | 70 | A |
| GLU | OE2 | 339 | 210.5 | 98.1 | 56.2 | 70 | A |
| GLU | C | 339 | 206.4 | 98.5 | 54.2 | 61 | A |
| GLU | O | 339 | 206.1 | 99.5 | 54.9 | 60 | A |
| LEU | N | 340 | 206.9 | 98.6 | 53.0 | 59 | A |
| LEU | CA | 340 | 207.1 | 99.8 | 52.3 | 57 | A |
| LEU | CB | 340 | 207.7 | 99.6 | 50.9 | 56 | A |
| LEU | CG | 340 | 209.0 | 98.7 | 50.8 | 56 | A |
| LEU | CD1 | 340 | 209.5 | 98.7 | 49.3 | 56 | A |
| LEU | CD2 | 340 | 210.1 | 99.3 | 51.7 | 56 | A |
| LEU | C | 340 | 205.8 | 100.5 | 52.2 | 57 | A |
| LEU | O | 340 | 205.7 | 101.7 | 52.5 | 57 | A |
| CYS | N | 341 | 204.7 | 99.8 | 51.9 | 56 | A |
| CYS | CA | 341 | 203.4 | 100.4 | 51.8 | 55 | A |
| CYS | CB | 341 | 202.3 | 99.4 | 51.4 | 55 | A |
| CYS | SG | 341 | 202.3 | 98.9 | 49.7 | 54 | A |
| CYS | C | 341 | 203.0 | 101.1 | 53.1 | 55 | A |
| CYS | O | 341 | 202.3 | 102.1 | 53.1 | 55 | A |
| GLU | N | 342 | 203.4 | 100.5 | 54.2 | 55 | A |
| GLU | CA | 342 | 203.1 | 101.0 | 55.5 | 55 | A |
| GLU | CB | 342 | 203.2 | 99.9 | 56.6 | 56 | A |
| GLU | CG | 342 | 202.3 | 100.3 | 57.8 | 57 | A |
| GLU | CD | 342 | 200.9 | 100.7 | 57.4 | 58 | A |
| GLU | OE1 | 342 | 200.2 | 101.2 | 58.3 | 59 | A |
| GLU | OE2 | 342 | 200.4 | 100.5 | 56.3 | 58 | A |
| GLU | C | 342 | 204.0 | 102.2 | 55.9 | 55 | A |
| GLU | O | 342 | 203.6 | 103.2 | 56.4 | 55 | A |
| ILE | N | 343 | 205.3 | 102.0 | 55.5 | 55 | A |
| ILE | CA | 343 | 206.3 | 103.1 | 55.8 | 54 | A |
| ILE | CB | 343 | 207.7 | 102.7 | 55.2 | 54 | A |
| ILE | CG2 | 343 | 208.6 | 103.9 | 55.3 | 54 | A |
| ILE | CG1 | 343 | 208.3 | 101.6 | 56.1 | 55 | A |
| ILE | CD1 | 343 | 209.8 | 101.3 | 55.7 | 55 | A |
| ILE | C | 343 | 205.8 | 104.3 | 55.1 | 53 | A |
| ILE | O | 343 | 205.8 | 105.4 | 55.7 | 54 | A |
| LEU | N | 344 | 205.4 | 104.1 | 53.9 | 52 | A |
| LEU | CA | 344 | 204.9 | 105.2 | 53.0 | 52 | A |
| LEU | CB | 344 | 204.5 | 104.6 | 51.6 | 50 | A |
| LEU | CG | 344 | 205.7 | 104.3 | 50.7 | 49 | A |
| LEU | CD1 | 344 | 205.2 | 103.9 | 49.4 | 48 | A |
| LEU | CD2 | 344 | 206.5 | 105.6 | 50.5 | 49 | A |
| LEU | C | 344 | 203.6 | 105.8 | 53.7 | 53 | A |
| LEU | O | 344 | 203.6 | 107.0 | 53.9 | 53 | A |
| ALA | N | 345 | 202.6 | 105.0 | 54.0 | 54 | A |
| ALA | CA | 345 | 201.4 | 105.4 | 54.6 | 55 | A |
| ALA | CB | 345 | 200.4 | 104.3 | 54.6 | 55 | A |
| ALA | C | 345 | 201.5 | 106.0 | 56.0 | 56 | A |
| ALA | O | 345 | 200.8 | 107.0 | 56.3 | 56 | A |
| LYS | N | 346 | 202.4 | 105.5 | 56.8 | 58 | A |
| LYS | CA | 346 | 202.6 | 105.9 | 58.2 | 59 | A |
| LYS | CB | 346 | 203.1 | 104.8 | 59.1 | 61 | A |
| LYS | CG | 346 | 202.0 | 104.1 | 59.9 | 64 | A |
| LYS | CD | 346 | 202.6 | 103.0 | 60.9 | 65 | A |
| LYS | CE | 346 | 201.6 | 102.1 | 61.5 | 66 | A |
| LYS | NZ | 346 | 202.1 | 101.0 | 62.4 | 66 | A |
| LYS | C | 346 | 203.6 | 107.0 | 58.3 | 60 | A |
| LYS | O | 346 | 203.5 | 107.9 | 59.1 | 60 | A |
| GLU | N | 347 | 204.6 | 107.0 | 57.5 | 59 | A |
| GLU | CA | 347 | 205.7 | 108.0 | 57.6 | 59 | A |
| GLU | CB | 347 | 206.9 | 107.3 | 58.2 | 60 | A |
| GLU | CG | 347 | 208.2 | 108.2 | 58.2 | 62 | A |
| GLU | CD | 347 | 209.5 | 107.4 | 58.3 | 63 | A |

TABLE 4-continued

The following table lists the atomic structure coordinates for FPT in complex with FPP and the inhibitor SCH66701 as derived by X-ray diffraction from crystals of that complex The abbreviations are the same as those used in Table 2

| RES | ATOM | # | X | Y | Z | B | C |
|---|---|---|---|---|---|---|---|
| GLU | OE1 | 347 | 210.5 | 108.1 | 58.4 | 64 | A |
| GLU | OE2 | 347 | 209.4 | 106.2 | 58.3 | 64 | A |
| GLU | C | 347 | 206.2 | 108.8 | 56.3 | 57 | A |
| GLU | O | 347 | 206.1 | 110.0 | 56.3 | 57 | A |
| LYS | N | 348 | 206.7 | 108.1 | 55.3 | 56 | A |
| LYS | CA | 348 | 207.3 | 108.7 | 54.1 | 54 | A |
| LYS | CB | 348 | 208.1 | 107.7 | 53.4 | 55 | A |
| LYS | CG | 348 | 209.2 | 107.0 | 54.2 | 56 | A |
| LYS | CD | 348 | 210.2 | 107.9 | 54.8 | 56 | A |
| LYS | CE | 348 | 211.3 | 107.2 | 55.6 | 57 | A |
| LYS | NZ | 348 | 212.0 | 106.1 | 54.8 | 57 | A |
| LYS | C | 348 | 206.4 | 109.4 | 53.2 | 52 | A |
| LYS | O | 348 | 206.8 | 110.4 | 52.5 | 52 | A |
| ASP | N | 349 | 205.1 | 109.0 | 53.0 | 50 | A |
| ASP | CA | 349 | 204.2 | 109.6 | 52.1 | 48 | A |
| ASP | CB | 349 | 204.3 | 108.9 | 50.8 | 49 | A |
| ASP | CG | 349 | 203.8 | 109.7 | 49.6 | 49 | A |
| ASP | OD1 | 349 | 203.6 | 110.9 | 49.7 | 50 | A |
| ASP | OD2 | 349 | 203.5 | 109.0 | 48.5 | 50 | A |
| ASP | C | 349 | 202.8 | 109.6 | 52.6 | 47 | A |
| ASP | O | 349 | 201.9 | 109.2 | 52.0 | 46 | A |
| THR | N | 350 | 202.6 | 110.3 | 53.8 | 46 | A |
| THR | CA | 350 | 201.3 | 110.3 | 54.4 | 46 | A |
| THR | CB | 350 | 201.5 | 110.8 | 55.9 | 46 | A |
| THR | OG1 | 350 | 201.7 | 112.2 | 55.9 | 47 | A |
| THR | CG2 | 350 | 202.7 | 110.2 | 56.6 | 46 | A |
| THR | C | 350 | 200.1 | 110.9 | 53.8 | 45 | A |
| THR | O | 350 | 199.0 | 110.5 | 54.0 | 46 | A |
| ILE | N | 351 | 200.3 | 112.0 | 53.0 | 45 | A |
| ILE | CA | 351 | 199.2 | 112.7 | 52.3 | 43 | A |
| ILE | CB | 351 | 199.7 | 113.8 | 51.4 | 42 | A |
| ILE | CG2 | 351 | 200.4 | 113.2 | 50.1 | 41 | A |
| ILE | CG1 | 351 | 198.6 | 114.8 | 51.1 | 41 | A |
| ILE | CD1 | 351 | 198.4 | 115.7 | 52.2 | 40 | A |
| ILE | C | 351 | 198.3 | 111.6 | 51.5 | 42 | A |
| ILE | O | 351 | 197.1 | 111.8 | 51.4 | 41 | A |
| ARG | N | 352 | 198.9 | 110.5 | 51.2 | 42 | A |
| ARG | CA | 352 | 198.2 | 109.5 | 50.5 | 43 | A |
| ARG | CB | 352 | 198.7 | 109.3 | 49.0 | 43 | A |
| ARG | CG | 352 | 200.1 | 109.4 | 48.8 | 44 | A |
| ARG | CD | 352 | 200.4 | 110.0 | 47.4 | 44 | A |
| ARG | NE | 352 | 201.6 | 110.8 | 47.4 | 44 | A |
| ARG | CZ | 352 | 201.7 | 112.2 | 47.3 | 44 | A |
| ARG | NH1 | 352 | 200.6 | 112.9 | 47.1 | 44 | A |
| ARG | NH2 | 352 | 202.9 | 112.8 | 47.4 | 45 | A |
| ARG | C | 352 | 198.2 | 108.1 | 51.2 | 44 | A |
| ARG | O | 352 | 198.4 | 107.1 | 50.6 | 44 | A |
| LYS | N | 353 | 198.0 | 108.2 | 52.5 | 44 | A |
| LYS | CA | 353 | 198.0 | 107.0 | 53.4 | 44 | A |
| LYS | CB | 353 | 197.7 | 107.4 | 54.8 | 44 | A |
| LYS | CG | 353 | 196.3 | 108.0 | 55.0 | 44 | A |
| LYS | CD | 353 | 196.2 | 108.9 | 56.3 | 43 | A |
| LYS | CE | 353 | 194.9 | 109.7 | 56.3 | 42 | A |
| LYS | NZ | 353 | 194.9 | 110.7 | 57.4 | 42 | A |
| LYS | C | 353 | 196.9 | 106.1 | 52.8 | 45 | A |
| LYS | O | 353 | 197.0 | 104.9 | 52.7 | 44 | A |
| GLU | N | 354 | 195.8 | 106.8 | 52.5 | 45 | A |
| GLU | CA | 354 | 194.6 | 106.1 | 51.9 | 46 | A |
| GLU | CB | 354 | 193.6 | 107.1 | 51.5 | 47 | A |
| GLU | CG | 354 | 192.8 | 107.7 | 52.7 | 49 | A |
| GLU | CD | 354 | 192.0 | 106.8 | 53.4 | 50 | A |
| GLU | OE1 | 354 | 192.3 | 106.4 | 54.6 | 51 | A |
| GLU | OE2 | 354 | 190.9 | 106.3 | 52.9 | 50 | A |
| GLU | C | 354 | 195.0 | 105.2 | 50.7 | 46 | A |
| GLU | O | 354 | 194.5 | 104.0 | 50.6 | 46 | A |
| TYR | N | 355 | 195.7 | 105.8 | 49.7 | 44 | A |
| TYR | CA | 355 | 196.1 | 105.0 | 48.6 | 43 | A |
| TYR | CB | 355 | 196.7 | 105.9 | 47.5 | 41 | A |
| TYR | CG | 355 | 197.4 | 105.2 | 46.4 | 38 | A |
| TYR | CD1 | 355 | 196.7 | 104.6 | 45.3 | 37 | A |
| TYR | CE1 | 355 | 197.3 | 103.9 | 44.3 | 36 | A |
| TYR | CD2 | 355 | 198.8 | 105.0 | 46.4 | 36 | A |

TABLE 4-continued

The following table lists the atomic structure coordinates for FPT in complex with FPP and the inhibitor SCH66701 as derived by X-ray diffraction from crystals of that complex The abbreviations are the same as those used in Table 2

| RES | ATOM | # | X | Y | Z | B | C |
|---|---|---|---|---|---|---|---|
| TYR | CE2 | 355 | 199.4 | 104.4 | 45.4 | 36 | A |
| TYR | CZ | 355 | 198.7 | 103.8 | 44.4 | 36 | A |
| TYR | OH | 355 | 199.4 | 103.2 | 43.4 | 36 | A |
| TYR | C | 355 | 197.1 | 103.9 | 49.0 | 44 | A |
| TYR | O | 355 | 196.8 | 102.7 | 48.7 | 45 | A |
| TRP | N | 356 | 198.2 | 104.3 | 49.6 | 46 | A |
| TRP | CA | 356 | 199.2 | 103.3 | 50.0 | 48 | A |
| TRP | CB | 356 | 200.4 | 104.1 | 50.6 | 47 | A |
| TRP | CG | 356 | 201.2 | 104.6 | 49.6 | 47 | A |
| TRP | CD2 | 356 | 201.8 | 103.9 | 48.5 | 47 | A |
| TRP | CE2 | 356 | 202.4 | 104.9 | 47.7 | 47 | A |
| TRP | CE3 | 356 | 201.8 | 102.6 | 48.1 | 47 | A |
| TRP | CD1 | 356 | 201.5 | 106.0 | 49.4 | 47 | A |
| TRP | NE1 | 356 | 202.3 | 106.1 | 48.3 | 47 | A |
| TRP | CZ2 | 356 | 203.1 | 104.5 | 46.5 | 47 | A |
| TRP | CZ3 | 356 | 202.4 | 102.2 | 46.9 | 47 | A |
| TRP | CH2 | 356 | 203.1 | 103.2 | 46.2 | 48 | A |
| TRP | C | 356 | 198.7 | 102.2 | 50.9 | 49 | A |
| TRP | O | 356 | 199.3 | 101.1 | 50.9 | 49 | A |
| ARG | N | 357 | 197.7 | 102.4 | 51.7 | 50 | A |
| ARG | CA | 357 | 197.1 | 101.3 | 52.5 | 51 | A |
| ARG | CB | 357 | 196.4 | 101.9 | 53.7 | 52 | A |
| ARG | CG | 357 | 197.3 | 102.0 | 54.9 | 55 | A |
| ARG | CD | 357 | 197.2 | 103.3 | 55.6 | 56 | A |
| ARG | NE | 357 | 195.8 | 103.6 | 56.0 | 58 | A |
| ARG | CZ | 357 | 195.4 | 104.4 | 57.0 | 59 | A |
| ARG | NH1 | 357 | 194.1 | 104.5 | 57.3 | 59 | A |
| ARG | NH2 | 357 | 196.3 | 105.1 | 57.7 | 58 | A |
| ARG | C | 357 | 196.3 | 100.4 | 51.7 | 50 | A |
| ARG | O | 357 | 196.3 | 99.2 | 51.9 | 51 | A |
| TYR | N | 358 | 195.6 | 101.0 | 50.7 | 50 | A |
| TYR | CA | 358 | 194.8 | 100.2 | 49.8 | 49 | A |
| TYR | CB | 358 | 194.1 | 101.1 | 48.8 | 48 | A |
| TYR | CG | 358 | 193.6 | 100.5 | 47.5 | 47 | A |
| TYR | CD1 | 358 | 192.4 | 99.8 | 47.5 | 47 | A |
| TYR | CE1 | 358 | 191.9 | 99.2 | 46.3 | 46 | A |
| TYR | CD2 | 358 | 194.3 | 100.6 | 46.3 | 47 | A |
| TYR | CE2 | 358 | 193.8 | 100.0 | 45.2 | 46 | A |
| TYR | CZ | 358 | 192.6 | 99.3 | 45.2 | 46 | A |
| TYR | OH | 358 | 192.2 | 98.7 | 44.0 | 46 | A |
| TYR | C | 358 | 195.7 | 99.2 | 49.0 | 49 | A |
| TYR | O | 358 | 195.2 | 98.2 | 48.6 | 48 | A |
| ILE | N | 359 | 196.9 | 99.7 | 48.7 | 51 | A |
| ILE | CA | 359 | 197.9 | 98.9 | 48.0 | 52 | A |
| ILE | CB | 359 | 199.2 | 99.7 | 47.7 | 50 | A |
| ILE | CG2 | 359 | 200.3 | 98.8 | 47.3 | 50 | A |
| ILE | CG1 | 359 | 198.8 | 100.6 | 46.5 | 50 | A |
| ILE | CD1 | 359 | 198.3 | 99.9 | 45.3 | 49 | A |
| ILE | C | 359 | 198.3 | 97.7 | 49.0 | 53 | A |
| ILE | O | 359 | 198.5 | 96.6 | 48.5 | 52 | A |
| GLY | N | 360 | 198.4 | 98.0 | 50.2 | 54 | A |
| GLY | CA | 360 | 198.7 | 97.0 | 51.2 | 56 | A |
| GLY | C | 360 | 197.6 | 96.0 | 51.2 | 57 | A |
| GLY | O | 360 | 197.8 | 94.8 | 51.0 | 57 | A |
| ARG | N | 361 | 196.4 | 96.5 | 51.2 | 58 | A |
| ARG | CA | 361 | 195.2 | 95.7 | 51.2 | 59 | A |
| ARG | CB | 361 | 193.9 | 96.5 | 51.4 | 60 | A |
| ARG | CG | 361 | 193.2 | 96.4 | 52.7 | 61 | A |
| ARG | CD | 361 | 192.9 | 97.8 | 53.3 | 62 | A |
| ARG | NE | 361 | 192.0 | 98.5 | 52.5 | 63 | A |
| ARG | CZ | 361 | 192.0 | 99.9 | 52.3 | 64 | A |
| ARG | NH1 | 361 | 191.2 | 100.5 | 51.5 | 64 | A |
| ARG | NH2 | 361 | 193.0 | 100.6 | 53.0 | 64 | A |
| ARG | C | 361 | 195.0 | 94.8 | 50.0 | 60 | A |
| ARG | O | 361 | 194.8 | 93.6 | 50.1 | 60 | A |
| SER | N | 362 | 195.2 | 95.4 | 48.8 | 60 | A |
| SER | CA | 362 | 195.2 | 94.6 | 47.5 | 60 | A |
| SER | CB | 362 | 195.2 | 95.5 | 46.3 | 60 | A |
| SER | OG | 362 | 193.9 | 96.1 | 46.1 | 61 | A |
| SER | C | 362 | 196.3 | 93.6 | 47.5 | 60 | A |
| SER | O | 362 | 196.0 | 92.4 | 47.2 | 60 | A |
| LEU | N | 363 | 197.5 | 94.0 | 47.8 | 60 | A |

TABLE 4-continued

The following table lists the atomic structure coordinates for FPT in complex with FPP and the inhibitor SCH66701 as derived by X-ray diffraction from crystals of that complex The abbreviations are the same as those used in Table 2

| RES | ATOM | # | X | Y | Z | B | C |
|---|---|---|---|---|---|---|---|
| LEU | CA | 363 | 198.6 | 93.1 | 47.8 | 61 | A |
| LEU | CB | 363 | 199.9 | 93.8 | 48.2 | 60 | A |
| LEU | CG | 363 | 200.8 | 94.3 | 47.1 | 59 | A |
| LEU | CD1 | 363 | 200.1 | 94.9 | 46.0 | 59 | A |
| LEU | CD2 | 363 | 201.8 | 95.3 | 47.7 | 59 | A |
| LEU | C | 363 | 198.3 | 92.0 | 48.7 | 61 | A |
| LEU | O | 363 | 198.8 | 90.8 | 48.5 | 61 | A |
| GLN | N | 364 | 197.5 | 92.3 | 49.7 | 63 | A |
| GLN | CA | 364 | 197.1 | 91.3 | 50.7 | 64 | A |
| GLN | CB | 364 | 196.4 | 92.0 | 51.9 | 65 | A |
| GLN | CG | 364 | 196.5 | 91.3 | 53.2 | 66 | A |
| GLN | CD | 364 | 198.0 | 91.3 | 53.7 | 66 | A |
| GLN | OE1 | 364 | 198.3 | 92.1 | 54.6 | 67 | A |
| GLN | NE2 | 364 | 198.9 | 90.6 | 53.0 | 66 | A |
| GLN | C | 364 | 196.3 | 90.2 | 50.2 | 65 | A |
| GLN | O | 364 | 196.1 | 89.2 | 50.8 | 66 | A |
| SER | N | 365 | 195.6 | 90.4 | 49.1 | 65 | A |
| SER | CA | 365 | 194.8 | 89.4 | 48.5 | 66 | A |
| SER | CB | 365 | 193.3 | 89.8 | 48.4 | 66 | A |
| SER | OG | 365 | 193.1 | 91.0 | 47.7 | 67 | A |
| SER | C | 365 | 195.2 | 88.9 | 47.2 | 68 | A |
| SER | O | 365 | 194.4 | 88.6 | 46.3 | 68 | A |
| LYS | N | 366 | 196.6 | 88.8 | 47.0 | 70 | A |
| LYS | CA | 366 | 197.2 | 88.3 | 45.7 | 72 | A |
| LYS | CB | 366 | 196.6 | 89.0 | 44.5 | 73 | A |
| LYS | CG | 366 | 196.7 | 90.5 | 44.4 | 74 | A |
| LYS | CD | 366 | 195.4 | 91.2 | 44.8 | 75 | A |
| LYS | CE | 366 | 194.2 | 90.8 | 44.1 | 76 | A |
| LYS | NZ | 366 | 192.9 | 91.5 | 44.5 | 77 | A |
| LYS | C | 366 | 198.8 | 88.4 | 45.7 | 72 | A |
| LYS | OT1 | 366 | 199.3 | 87.9 | 46.7 | 72 | A |
| LYS | OT2 | 366 | 199.4 | 88.8 | 44.7 | 71 | A |
| LEU | CB | 523 | 194.7 | 121.9 | 61.8 | 46 | B |
| LEU | CG | 523 | 193.4 | 122.7 | 62.0 | 46 | B |
| LEU | CD1 | 523 | 193.7 | 124.2 | 61.8 | 47 | B |
| LEU | CD2 | 523 | 192.3 | 122.1 | 61.1 | 46 | B |
| LEU | C | 523 | 195.9 | 119.7 | 61.6 | 47 | B |
| LEU | O | 523 | 197.0 | 119.9 | 62.1 | 46 | B |
| LEU | N | 523 | 194.6 | 120.2 | 63.5 | 48 | B |
| LEU | CA | 523 | 194.7 | 120.4 | 62.1 | 47 | B |
| TYR | N | 524 | 195.7 | 118.9 | 60.6 | 47 | B |
| TYR | CA | 524 | 196.8 | 118.1 | 60.0 | 47 | B |
| TYR | CB | 524 | 196.2 | 117.2 | 58.9 | 46 | B |
| TYR | CG | 524 | 197.3 | 116.4 | 58.1 | 47 | B |
| TYR | CD1 | 524 | 198.0 | 115.3 | 58.6 | 46 | B |
| TYR | CE1 | 524 | 198.9 | 114.6 | 57.8 | 46 | B |
| TYR | CD2 | 524 | 197.5 | 116.8 | 56.8 | 46 | B |
| TYR | CE2 | 524 | 198.4 | 116.1 | 56.0 | 46 | B |
| TYR | CZ | 524 | 199.1 | 115.0 | 56.5 | 46 | B |
| TYR | OH | 524 | 199.9 | 114.3 | 55.6 | 45 | B |
| TYR | C | 524 | 198.0 | 118.9 | 59.5 | 47 | B |
| TYR | O | 524 | 199.1 | 118.7 | 59.9 | 48 | B |
| SER | N | 525 | 197.7 | 119.9 | 58.6 | 48 | B |
| SER | CA | 525 | 198.7 | 120.7 | 58.0 | 50 | B |
| SER | CB | 525 | 198.1 | 121.6 | 57.0 | 49 | B |
| SER | OG | 525 | 196.8 | 122.0 | 57.4 | 50 | B |
| SER | C | 525 | 199.5 | 121.5 | 59.1 | 51 | B |
| SER | O | 525 | 200.7 | 121.8 | 58.9 | 51 | B |
| LEU | N | 526 | 198.9 | 121.8 | 60.2 | 52 | B |
| LEU | CA | 526 | 199.5 | 122.6 | 61.3 | 53 | B |
| LEU | CB | 526 | 198.5 | 123.3 | 62.1 | 54 | B |
| LEU | CG | 526 | 198.2 | 124.8 | 61.8 | 54 | B |
| LEU | CD1 | 526 | 199.5 | 125.5 | 61.4 | 55 | B |
| LEU | CD2 | 526 | 197.2 | 124.9 | 60.6 | 54 | B |
| LEU | C | 526 | 200.3 | 121.6 | 62.2 | 54 | B |
| LEU | O | 526 | 201.0 | 122.1 | 63.1 | 54 | B |
| ARG | N | 527 | 200.3 | 120.3 | 61.9 | 55 | B |
| ARG | CA | 527 | 201.0 | 119.4 | 62.7 | 57 | B |
| ARG | CB | 527 | 200.7 | 118.0 | 62.3 | 58 | B |
| ARG | CG | 527 | 201.0 | 116.9 | 63.3 | 59 | B |
| ARG | CD | 527 | 200.2 | 115.6 | 63.0 | 60 | B |
| ARG | NE | 527 | 198.8 | 115.8 | 63.1 | 61 | B |

TABLE 4-continued

The following table lists the atomic structure coordinates for FPT in complex with FPP and the inhibitor SCH66701 as derived by X-ray diffraction from crystals of that complex The abbreviations are the same as those used in Table 2

| RES | ATOM | # | X | Y | Z | B | C |
|---|---|---|---|---|---|---|---|
| ARG | CZ | 527 | 197.9 | 115.1 | 62.5 | 61 | B |
| ARG | NH1 | 527 | 198.3 | 114.1 | 61.7 | 61 | B |
| ARG | NH2 | 527 | 196.6 | 115.3 | 62.7 | 61 | B |
| ARG | C | 527 | 202.5 | 119.6 | 62.5 | 58 | B |
| ARG | O | 527 | 203.0 | 119.9 | 61.4 | 59 | B |
| PRO | N | 528 | 203.3 | 119.5 | 63.6 | 59 | B |
| PRO | CD | 528 | 202.8 | 119.4 | 65.0 | 60 | B |
| PRO | CA | 528 | 204.8 | 119.7 | 63.6 | 59 | B |
| PRO | CB | 528 | 205.2 | 119.3 | 65.0 | 59 | B |
| PRO | CG | 528 | 204.0 | 119.8 | 65.8 | 60 | B |
| PRO | C | 528 | 205.6 | 119.0 | 62.6 | 60 | B |
| PRO | O | 528 | 206.4 | 119.5 | 61.8 | 59 | B |
| GLU | N | 529 | 205.3 | 117.7 | 62.5 | 61 | B |
| GLU | CA | 529 | 206.0 | 116.8 | 61.6 | 62 | B |
| GLU | CB | 529 | 205.6 | 115.3 | 61.9 | 63 | B |
| GLU | CG | 529 | 204.1 | 115.1 | 62.2 | 65 | B |
| GLU | CD | 529 | 203.8 | 115.1 | 63.7 | 66 | B |
| GLU | OE1 | 529 | 202.9 | 114.3 | 64.0 | 67 | B |
| GLU | OE2 | 529 | 204.4 | 115.8 | 64.5 | 67 | B |
| GLU | C | 529 | 205.7 | 117.2 | 60.1 | 61 | B |
| GLU | O | 529 | 206.5 | 116.9 | 59.2 | 62 | B |
| HIS | N | 530 | 204.5 | 117.8 | 59.9 | 61 | B |
| HIS | CA | 530 | 204.1 | 118.2 | 58.6 | 60 | B |
| HIS | CB | 530 | 202.7 | 118.8 | 58.6 | 61 | B |
| HIS | CG | 530 | 202.2 | 119.4 | 57.3 | 60 | B |
| HIS | CD2 | 530 | 201.4 | 118.9 | 56.3 | 60 | B |
| HIS | ND1 | 530 | 202.6 | 120.7 | 56.9 | 60 | B |
| HIS | CE1 | 530 | 202.0 | 121.0 | 55.8 | 60 | B |
| HIS | NE2 | 530 | 201.3 | 119.9 | 55.4 | 60 | B |
| HIS | C | 530 | 205.1 | 119.1 | 57.9 | 59 | B |
| HIS | O | 530 | 205.1 | 119.2 | 56.6 | 59 | B |
| ALA | N | 531 | 205.9 | 119.8 | 58.6 | 58 | B |
| ALA | CA | 531 | 206.8 | 120.7 | 58.0 | 58 | B |
| ALA | CB | 531 | 207.5 | 121.5 | 59.1 | 59 | B |
| ALA | C | 531 | 207.9 | 119.9 | 57.2 | 58 | B |
| ALA | O | 531 | 208.5 | 120.5 | 56.3 | 57 | B |
| ARG | N | 532 | 208.1 | 118.7 | 57.5 | 57 | B |
| ARG | CA | 532 | 209.0 | 117.8 | 56.8 | 57 | B |
| ARG | CB | 532 | 209.2 | 116.5 | 57.5 | 58 | B |
| ARG | CG | 532 | 210.1 | 116.5 | 58.7 | 60 | B |
| ARG | CD | 532 | 209.4 | 116.3 | 60.0 | 62 | B |
| ARG | NE | 532 | 209.2 | 114.9 | 60.3 | 64 | B |
| ARG | CZ | 532 | 209.0 | 114.4 | 61.6 | 65 | B |
| ARG | NH1 | 532 | 208.9 | 115.2 | 62.6 | 65 | B |
| ARG | NH2 | 532 | 208.9 | 113.1 | 61.8 | 65 | B |
| ARG | C | 532 | 208.6 | 117.6 | 55.4 | 56 | B |
| ARG | O | 532 | 209.4 | 117.4 | 54.5 | 56 | B |
| GLU | N | 533 | 207.3 | 117.7 | 55.1 | 54 | B |
| GLU | CA | 533 | 206.7 | 117.6 | 53.8 | 53 | B |
| GLU | CB | 533 | 205.2 | 117.3 | 53.9 | 53 | B |
| GLU | CG | 533 | 204.9 | 116.0 | 54.6 | 53 | B |
| GLU | CD | 533 | 205.3 | 114.8 | 53.7 | 54 | B |
| GLU | OE1 | 533 | 204.3 | 114.1 | 53.1 | 54 | B |
| GLU | OE2 | 533 | 206.5 | 114.5 | 53.6 | 54 | B |
| GLU | C | 533 | 207.0 | 118.8 | 52.9 | 52 | B |
| GLU | O | 533 | 206.3 | 119.0 | 51.9 | 52 | B |
| ARG | N | 534 | 208.0 | 119.5 | 53.2 | 50 | B |
| ARG | CA | 534 | 208.4 | 120.7 | 52.5 | 49 | B |
| ARG | CB | 534 | 209.2 | 121.6 | 53.4 | 50 | B |
| ARG | CG | 534 | 209.2 | 123.0 | 53.0 | 51 | B |
| ARG | CD | 534 | 207.9 | 123.6 | 53.6 | 52 | B |
| ARG | NE | 534 | 207.7 | 125.0 | 53.1 | 54 | B |
| ARG | CZ | 534 | 208.4 | 126.1 | 53.5 | 55 | B |
| ARG | NH1 | 534 | 209.4 | 125.9 | 54.3 | 56 | B |
| ARG | NH2 | 534 | 208.1 | 127.3 | 53.0 | 56 | B |
| ARG | C | 534 | 209.2 | 120.2 | 51.3 | 48 | B |
| ARG | O | 534 | 209.9 | 119.2 | 51.4 | 48 | B |
| LEU | N | 535 | 209.2 | 121.0 | 50.2 | 47 | B |
| LEU | CA | 535 | 210.0 | 120.7 | 49.0 | 46 | B |
| LEU | CB | 535 | 209.7 | 121.8 | 47.9 | 44 | B |
| LEU | CG | 535 | 210.5 | 121.6 | 46.6 | 43 | B |
| LEU | CD1 | 535 | 209.8 | 120.5 | 45.8 | 43 | B |

TABLE 4-continued

The following table lists the atomic structure coordinates for FPT in complex with FPP and the inhibitor SCH66701 as derived by X-ray diffraction from crystals of that complex The abbreviations are the same as those used in Table 2

| RES | ATOM | # | X | Y | Z | B | C |
|---|---|---|---|---|---|---|---|
| LEU | CD2 | 535 | 210.7 | 122.9 | 45.9 | 43 | B |
| LEU | C | 535 | 211.5 | 120.6 | 49.2 | 47 | B |
| LEU | O | 535 | 212.0 | 121.3 | 50.0 | 47 | B |
| GLN | N | 536 | 212.1 | 119.6 | 48.5 | 48 | B |
| GLN | CA | 536 | 213.5 | 119.3 | 48.6 | 49 | B |
| GLN | CB | 536 | 213.7 | 117.9 | 49.0 | 50 | B |
| GLN | CG | 536 | 212.9 | 117.5 | 50.3 | 52 | B |
| GLN | CD | 536 | 213.5 | 116.4 | 51.0 | 53 | B |
| GLN | OE1 | 536 | 212.9 | 115.5 | 51.6 | 54 | B |
| GLN | NE2 | 536 | 214.9 | 116.5 | 51.1 | 54 | B |
| GLN | C | 536 | 214.1 | 119.5 | 47.2 | 50 | B |
| GLN | O | 536 | 214.2 | 118.5 | 46.5 | 51 | B |
| ASP | N | 537 | 214.6 | 120.7 | 47.0 | 51 | B |
| ASP | CA | 537 | 215.2 | 121.0 | 45.7 | 52 | B |
| ASP | CB | 537 | 215.3 | 122.5 | 45.5 | 52 | B |
| ASP | CG | 537 | 216.6 | 123.1 | 45.9 | 52 | B |
| ASP | OD1 | 537 | 217.2 | 122.5 | 46.8 | 53 | B |
| ASP | OD2 | 537 | 217.1 | 124.1 | 45.3 | 53 | B |
| ASP | C | 537 | 216.5 | 120.3 | 45.2 | 53 | B |
| ASP | O | 537 | 216.9 | 120.6 | 44.1 | 53 | B |
| ASP | N | 538 | 217.0 | 119.5 | 46.1 | 54 | B |
| ASP | CA | 538 | 218.3 | 118.8 | 45.7 | 55 | B |
| ASP | CB | 538 | 218.1 | 117.8 | 44.6 | 55 | B |
| ASP | CG | 538 | 217.0 | 116.7 | 44.9 | 56 | B |
| ASP | OD1 | 538 | 216.9 | 116.3 | 46.1 | 56 | B |
| ASP | OD2 | 538 | 216.4 | 116.2 | 43.9 | 56 | B |
| ASP | C | 538 | 219.5 | 119.7 | 45.4 | 54 | B |
| ASP | O | 538 | 220.5 | 119.3 | 44.9 | 54 | B |
| SER | N | 539 | 219.3 | 121.0 | 45.7 | 55 | B |
| SER | CA | 539 | 220.3 | 122.0 | 45.5 | 55 | B |
| SER | CB | 539 | 221.6 | 121.6 | 46.2 | 57 | B |
| SER | OG | 539 | 221.3 | 121.3 | 47.6 | 58 | B |
| SER | C | 539 | 220.6 | 122.2 | 44.0 | 55 | B |
| SER | O | 539 | 221.6 | 122.6 | 43.6 | 55 | B |
| VAL | N | 540 | 219.5 | 121.9 | 43.2 | 53 | B |
| VAL | CA | 540 | 219.5 | 122.0 | 41.8 | 51 | B |
| VAL | CB | 540 | 219.5 | 120.6 | 41.0 | 51 | B |
| VAL | CG1 | 540 | 219.5 | 120.8 | 39.6 | 50 | B |
| VAL | CG2 | 540 | 220.7 | 119.8 | 41.5 | 51 | B |
| VAL | C | 540 | 218.2 | 122.7 | 41.5 | 50 | B |
| VAL | O | 540 | 217.2 | 122.0 | 41.4 | 51 | B |
| GLU | N | 541 | 218.3 | 124.0 | 41.5 | 49 | B |
| GLU | CA | 541 | 217.0 | 124.7 | 41.3 | 48 | B |
| GLU | CB | 541 | 217.0 | 126.0 | 42.1 | 50 | B |
| GLU | CG | 541 | 218.4 | 126.5 | 42.4 | 53 | B |
| GLU | CD | 541 | 218.4 | 127.8 | 43.1 | 55 | B |
| GLU | OE1 | 541 | 218.5 | 128.9 | 42.4 | 56 | B |
| GLU | OE2 | 541 | 218.2 | 127.9 | 44.4 | 56 | B |
| GLU | C | 541 | 216.8 | 125.0 | 39.9 | 46 | B |
| GLU | O | 541 | 217.7 | 125.2 | 39.1 | 47 | B |
| THR | N | 542 | 215.5 | 125.0 | 39.5 | 43 | B |
| THR | CA | 542 | 215.0 | 125.3 | 38.1 | 40 | B |
| THR | CB | 542 | 214.7 | 124.0 | 37.4 | 40 | B |
| THR | OG1 | 542 | 213.7 | 123.3 | 38.2 | 40 | B |
| THR | CG2 | 542 | 215.9 | 123.1 | 37.4 | 40 | B |
| THR | C | 542 | 213.8 | 126.1 | 38.3 | 38 | B |
| THR | O | 542 | 213.3 | 126.3 | 39.4 | 38 | B |
| VAL | N | 543 | 213.3 | 126.7 | 37.2 | 36 | B |
| VAL | CA | 543 | 212.1 | 127.6 | 37.3 | 34 | B |
| VAL | CB | 543 | 211.6 | 127.9 | 36.0 | 33 | B |
| VAL | CG1 | 543 | 210.4 | 128.9 | 36.1 | 33 | B |
| VAL | CG2 | 543 | 212.6 | 128.4 | 35.0 | 33 | B |
| VAL | C | 543 | 211.0 | 126.9 | 38.1 | 34 | B |
| VAL | O | 543 | 210.3 | 127.6 | 38.8 | 35 | B |
| THR | N | 544 | 210.9 | 125.6 | 38.0 | 33 | B |
| THR | CA | 544 | 209.9 | 124.8 | 38.7 | 33 | B |
| THR | CB | 544 | 209.9 | 123.4 | 38.2 | 33 | B |
| THR | OG1 | 544 | 209.7 | 123.4 | 36.8 | 32 | B |
| THR | CG2 | 544 | 208.7 | 122.6 | 38.9 | 32 | B |
| THR | C | 544 | 210.0 | 124.8 | 40.2 | 33 | B |
| THR | O | 544 | 209.1 | 125.1 | 40.9 | 33 | B |
| SER | N | 545 | 211.2 | 124.4 | 40.8 | 33 | B |

TABLE 4-continued

The following table lists the atomic structure coordinates for FPT in complex with FPP and the inhibitor SCH66701 as derived by X-ray diffraction from crystals of that complex The abbreviations are the same as those used in Table 2

| RES | ATOM | # | X | Y | Z | B | C |
|---|---|---|---|---|---|---|---|
| SER | CA | 545 | 211.4 | 124.3 | 42.2 | 32 | B |
| SER | CB | 545 | 212.7 | 123.6 | 42.5 | 32 | B |
| SER | OG | 545 | 213.8 | 124.3 | 41.7 | 31 | B |
| SER | C | 545 | 211.3 | 125.7 | 42.8 | 33 | B |
| SER | O | 545 | 210.7 | 125.9 | 43.9 | 34 | B |
| ILE | N | 546 | 211.8 | 126.7 | 42.1 | 33 | B |
| ILE | CA | 546 | 211.8 | 128.1 | 42.5 | 32 | B |
| ILE | CB | 546 | 212.4 | 129.0 | 41.4 | 32 | B |
| ILE | CG2 | 546 | 212.2 | 130.4 | 41.8 | 32 | B |
| ILE | CG1 | 546 | 213.9 | 128.7 | 41.4 | 32 | B |
| ILE | CD1 | 546 | 214.6 | 129.4 | 40.2 | 33 | B |
| ILE | C | 546 | 210.3 | 128.5 | 42.7 | 32 | B |
| ILE | O | 546 | 210.0 | 129.0 | 43.8 | 33 | B |
| GLU | N | 547 | 209.4 | 128.3 | 41.7 | 32 | B |
| GLU | CA | 547 | 208.0 | 128.7 | 41.8 | 32 | B |
| GLU | CB | 547 | 207.3 | 128.6 | 40.5 | 33 | B |
| GLU | CG | 547 | 207.9 | 129.5 | 39.4 | 35 | B |
| GLU | CD | 547 | 208.0 | 131.0 | 39.9 | 37 | B |
| GLU | OE1 | 547 | 207.0 | 131.5 | 40.4 | 37 | B |
| GLU | OE2 | 547 | 209.1 | 131.5 | 39.8 | 38 | B |
| GLU | C | 547 | 207.3 | 127.9 | 42.8 | 31 | B |
| GLU | O | 547 | 206.5 | 128.5 | 43.6 | 31 | B |
| GLN | N | 548 | 207.4 | 126.6 | 42.8 | 31 | B |
| GLN | CA | 548 | 206.8 | 125.7 | 43.8 | 32 | B |
| GLN | CB | 548 | 207.2 | 124.3 | 43.7 | 30 | B |
| GLN | CG | 548 | 206.8 | 123.3 | 44.8 | 28 | B |
| GLN | CD | 548 | 205.3 | 123.2 | 44.9 | 27 | B |
| GLN | OE1 | 548 | 204.8 | 123.2 | 46.1 | 27 | B |
| GLN | NE2 | 548 | 204.6 | 123.2 | 43.8 | 27 | B |
| GLN | C | 548 | 207.1 | 126.3 | 45.2 | 33 | B |
| GLN | O | 548 | 206.3 | 126.5 | 46.1 | 32 | B |
| ALA | N | 549 | 208.4 | 126.5 | 45.4 | 34 | B |
| ALA | CA | 549 | 209.0 | 127.0 | 46.6 | 35 | B |
| ALA | CB | 549 | 210.5 | 127.2 | 46.5 | 35 | B |
| ALA | C | 549 | 208.4 | 128.3 | 47.1 | 35 | B |
| ALA | O | 549 | 208.4 | 128.6 | 48.2 | 35 | B |
| LYS | N | 550 | 208.0 | 129.2 | 46.1 | 36 | B |
| LYS | CA | 550 | 207.4 | 130.4 | 46.5 | 38 | B |
| LYS | CB | 550 | 207.2 | 131.3 | 45.2 | 39 | B |
| LYS | CG | 550 | 208.5 | 131.9 | 44.7 | 41 | B |
| LYS | CD | 550 | 208.3 | 132.8 | 43.5 | 42 | B |
| LYS | CE | 550 | 209.6 | 133.0 | 42.8 | 42 | B |
| LYS | NZ | 550 | 209.4 | 133.8 | 41.5 | 43 | B |
| LYS | C | 550 | 206.0 | 130.2 | 47.1 | 38 | B |
| LYS | O | 550 | 205.7 | 130.7 | 48.1 | 39 | B |
| VAL | N | 551 | 205.3 | 129.3 | 46.4 | 39 | B |
| VAL | CA | 551 | 203.9 | 128.9 | 46.8 | 39 | B |
| VAL | CB | 551 | 203.2 | 127.9 | 46.0 | 38 | B |
| VAL | CG1 | 551 | 201.9 | 127.5 | 46.5 | 38 | B |
| VAL | CG2 | 551 | 203.1 | 128.3 | 44.5 | 38 | B |
| VAL | C | 551 | 204.0 | 128.4 | 48.3 | 40 | B |
| VAL | O | 551 | 203.3 | 129.0 | 49.2 | 40 | B |
| GLU | N | 552 | 204.8 | 127.4 | 48.5 | 41 | B |
| GLU | CA | 552 | 204.9 | 126.8 | 49.8 | 42 | B |
| GLU | CB | 552 | 206.0 | 125.7 | 49.8 | 41 | B |
| GLU | CG | 552 | 205.7 | 124.5 | 48.9 | 38 | B |
| GLU | CD | 552 | 206.7 | 123.4 | 49.2 | 37 | B |
| GLU | OE1 | 552 | 207.7 | 123.6 | 49.8 | 36 | B |
| GLU | OE2 | 552 | 206.4 | 122.3 | 48.7 | 37 | B |
| GLU | C | 552 | 205.1 | 127.8 | 50.9 | 44 | B |
| GLU | O | 552 | 204.4 | 127.7 | 51.9 | 45 | B |
| GLU | N | 553 | 206.0 | 128.7 | 50.7 | 47 | B |
| GLU | CA | 553 | 206.3 | 129.7 | 51.6 | 49 | B |
| GLU | CB | 553 | 207.4 | 130.6 | 51.1 | 51 | B |
| GLU | CG | 553 | 207.9 | 131.6 | 52.2 | 55 | B |
| GLU | CD | 553 | 209.4 | 131.7 | 52.2 | 57 | B |
| GLU | OE1 | 553 | 210.0 | 130.7 | 52.4 | 59 | B |
| GLU | OE2 | 553 | 209.9 | 132.8 | 51.9 | 58 | B |
| GLU | C | 553 | 205.0 | 130.6 | 52.0 | 49 | B |
| GLU | O | 553 | 204.8 | 130.9 | 53.2 | 49 | B |
| LYS | N | 554 | 204.3 | 131.0 | 51.0 | 50 | B |
| LYS | CA | 554 | 203.1 | 131.7 | 51.3 | 52 | B |

TABLE 4-continued

The following table lists the atomic structure coordinates for FPT in complex with FPP and the inhibitor SCH66701 as derived by X-ray diffraction from crystals of that complex The abbreviations are the same as those used in Table 2

| RES | ATOM | # | X | Y | Z | B | C |
|---|---|---|---|---|---|---|---|
| LYS | CB | 554 | 202.4 | 132.2 | 50.0 | 54 | B |
| LYS | CG | 554 | 203.3 | 132.8 | 49.0 | 57 | B |
| LYS | CD | 554 | 202.7 | 133.1 | 47.7 | 59 | B |
| LYS | CE | 554 | 203.5 | 133.9 | 46.8 | 61 | B |
| LYS | NZ | 554 | 202.7 | 134.7 | 45.8 | 63 | B |
| LYS | C | 554 | 202.1 | 130.9 | 52.0 | 52 | B |
| LYS | O | 554 | 201.4 | 131.4 | 52.9 | 51 | B |
| ILE | N | 555 | 202.0 | 129.6 | 51.7 | 52 | B |
| ILE | CA | 555 | 201.1 | 128.7 | 52.3 | 51 | B |
| ILE | CB | 555 | 201.1 | 127.3 | 51.6 | 50 | B |
| ILE | CG2 | 555 | 200.1 | 126.4 | 52.4 | 50 | B |
| ILE | CG1 | 555 | 200.7 | 127.5 | 50.2 | 50 | B |
| ILE | CD1 | 555 | 199.3 | 128.1 | 49.9 | 50 | B |
| ILE | C | 555 | 201.5 | 128.5 | 53.7 | 52 | B |
| ILE | O | 555 | 200.7 | 128.5 | 54.7 | 51 | B |
| GLN | N | 556 | 202.8 | 128.4 | 53.9 | 53 | B |
| GLN | CA | 556 | 203.4 | 128.2 | 55.2 | 54 | B |
| GLN | CB | 556 | 204.9 | 128.2 | 55.1 | 55 | B |
| GLN | CG | 556 | 205.6 | 128.2 | 56.4 | 55 | B |
| GLN | CD | 556 | 205.4 | 126.9 | 57.1 | 56 | B |
| GLN | OE1 | 556 | 206.3 | 126.0 | 57.2 | 57 | B |
| GLN | NE2 | 556 | 204.2 | 126.7 | 57.7 | 56 | B |
| GLN | C | 556 | 202.9 | 129.3 | 56.1 | 55 | B |
| GLN | O | 556 | 202.2 | 129.1 | 57.1 | 56 | B |
| GLU | N | 557 | 203.2 | 130.5 | 55.7 | 56 | B |
| GLU | CA | 557 | 202.8 | 131.7 | 56.5 | 58 | B |
| GLU | CB | 557 | 203.1 | 133.0 | 55.7 | 60 | B |
| GLU | CG | 557 | 204.6 | 133.1 | 55.3 | 63 | B |
| GLU | CD | 557 | 205.0 | 134.4 | 54.5 | 65 | B |
| GLU | OE1 | 557 | 204.1 | 135.3 | 54.3 | 65 | B |
| GLU | OE2 | 557 | 206.1 | 134.5 | 53.9 | 65 | B |
| GLU | C | 557 | 201.3 | 131.7 | 56.9 | 57 | B |
| GLU | O | 557 | 201.0 | 132.3 | 57.9 | 57 | B |
| VAL | N | 558 | 200.5 | 131.1 | 56.1 | 56 | B |
| VAL | CA | 558 | 199.1 | 131.0 | 56.4 | 55 | B |
| VAL | CB | 558 | 198.2 | 130.5 | 55.1 | 55 | B |
| VAL | CG1 | 558 | 196.8 | 130.0 | 55.6 | 55 | B |
| VAL | CG2 | 558 | 198.1 | 131.6 | 54.1 | 55 | B |
| VAL | C | 558 | 198.8 | 130.0 | 57.5 | 55 | B |
| VAL | O | 558 | 198.1 | 130.4 | 58.5 | 55 | B |
| PHE | N | 559 | 199.5 | 128.9 | 57.5 | 55 | B |
| PHE | CA | 559 | 199.3 | 127.9 | 58.5 | 55 | B |
| PHE | CB | 559 | 200.1 | 126.6 | 58.2 | 54 | B |
| PHE | CG | 559 | 199.5 | 125.9 | 57.0 | 53 | B |
| PHE | CD1 | 559 | 200.2 | 125.0 | 56.2 | 52 | B |
| PHE | CD2 | 559 | 198.1 | 126.1 | 56.7 | 52 | B |
| PHE | CE1 | 559 | 199.6 | 124.4 | 55.1 | 52 | B |
| PHE | CE2 | 559 | 197.5 | 125.4 | 55.6 | 51 | B |
| PHE | CZ | 559 | 198.3 | 124.6 | 54.8 | 51 | B |
| PHE | C | 559 | 199.8 | 128.5 | 59.9 | 56 | B |
| PHE | O | 559 | 199.1 | 128.4 | 60.9 | 56 | B |
| SER | N | 560 | 201.0 | 129.1 | 59.8 | 58 | B |
| SER | CA | 560 | 201.5 | 129.7 | 61.0 | 60 | B |
| SER | CB | 560 | 203.0 | 130.0 | 60.9 | 59 | B |
| SER | OG | 560 | 203.7 | 128.8 | 60.6 | 59 | B |
| SER | C | 560 | 200.8 | 131.0 | 61.6 | 62 | B |
| SER | O | 560 | 201.1 | 131.4 | 62.7 | 63 | B |
| SER | N | 561 | 199.9 | 131.5 | 60.8 | 64 | B |
| SER | CA | 561 | 199.2 | 132.7 | 61.3 | 67 | B |
| SER | CB | 561 | 198.2 | 133.2 | 60.3 | 67 | B |
| SER | OG | 561 | 197.2 | 132.3 | 60.0 | 67 | B |
| SER | C | 561 | 198.5 | 132.3 | 62.6 | 69 | B |
| SER | O | 561 | 198.4 | 133.1 | 63.5 | 70 | B |
| TYR | N | 562 | 197.9 | 131.1 | 62.6 | 72 | B |
| TYR | CA | 562 | 197.2 | 130.5 | 63.7 | 74 | B |
| TYR | CB | 562 | 196.7 | 129.1 | 63.3 | 73 | B |
| TYR | CG | 562 | 195.5 | 129.3 | 62.4 | 73 | B |
| TYR | CD1 | 562 | 195.6 | 128.8 | 61.0 | 73 | B |
| TYR | CE1 | 562 | 194.6 | 129.0 | 60.1 | 73 | B |
| TYR | CD2 | 562 | 194.3 | 129.9 | 62.7 | 73 | B |
| TYR | CE2 | 562 | 193.3 | 130.1 | 61.8 | 73 | B |
| TYR | CZ | 562 | 193.4 | 129.7 | 60.5 | 73 | B |

TABLE 4-continued

The following table lists the atomic structure coordinates for FPT in complex with FPP and the inhibitor SCH66701 as derived by X-ray diffraction from crystals of that complex The abbreviations are the same as those used in Table 2

| RES | ATOM | # | X | Y | Z | B | C |
|---|---|---|---|---|---|---|---|
| TYR | OH | 562 | 192.4 | 129.9 | 59.6 | 73 | B |
| TYR | C | 562 | 198.1 | 130.4 | 64.9 | 76 | B |
| TYR | O | 562 | 197.8 | 131.0 | 66.0 | 76 | B |
| LYS | N | 563 | 199.3 | 129.8 | 64.7 | 78 | B |
| LYS | CA | 563 | 200.3 | 129.6 | 65.8 | 80 | B |
| LYS | CB | 563 | 201.3 | 128.5 | 65.3 | 81 | B |
| LYS | CG | 563 | 200.9 | 127.1 | 65.7 | 81 | B |
| LYS | CD | 563 | 201.3 | 126.1 | 64.6 | 82 | B |
| LYS | CE | 563 | 202.7 | 126.1 | 64.2 | 82 | B |
| LYS | NZ | 563 | 203.5 | 124.9 | 64.7 | 82 | B |
| LYS | C | 563 | 201.0 | 130.9 | 66.0 | 81 | B |
| LYS | O | 563 | 202.2 | 130.9 | 66.2 | 81 | B |
| PHE | N | 564 | 200.3 | 132.0 | 66.1 | 83 | B |
| PHE | CA | 564 | 200.9 | 133.3 | 66.3 | 85 | B |
| PHE | CB | 564 | 200.7 | 134.2 | 65.1 | 88 | B |
| PHE | CG | 564 | 201.1 | 135.6 | 65.3 | 90 | B |
| PHE | CD1 | 564 | 202.5 | 135.9 | 65.4 | 91 | B |
| PHE | CD2 | 564 | 200.2 | 136.7 | 65.3 | 91 | B |
| PHE | CE1 | 564 | 202.9 | 137.3 | 65.6 | 92 | B |
| PHE | CE2 | 564 | 200.6 | 138.0 | 65.5 | 91 | B |
| PHE | CZ | 564 | 202.0 | 138.3 | 65.7 | 92 | B |
| PHE | C | 564 | 200.5 | 134.0 | 67.6 | 86 | B |
| PHE | O | 564 | 199.7 | 134.9 | 67.6 | 85 | B |
| ASN | N | 565 | 201.0 | 133.6 | 68.8 | 86 | B |
| ASN | CA | 565 | 200.8 | 134.2 | 70.1 | 85 | B |
| ASN | CB | 565 | 201.6 | 135.5 | 70.3 | 86 | B |
| ASN | CG | 565 | 202.9 | 135.2 | 71.0 | 88 | B |
| ASN | OD1 | 565 | 203.1 | 134.1 | 71.5 | 89 | B |
| ASN | ND2 | 565 | 203.7 | 136.3 | 71.2 | 89 | B |
| ASN | C | 565 | 199.4 | 134.6 | 70.3 | 84 | B |
| ASN | O | 565 | 199.1 | 135.4 | 71.1 | 84 | B |
| HIS | N | 566 | 198.5 | 134.0 | 69.5 | 84 | B |
| HIS | CA | 566 | 197.1 | 134.5 | 69.5 | 84 | B |
| HIS | CB | 566 | 196.7 | 135.0 | 68.1 | 86 | B |
| HIS | CG | 566 | 196.8 | 136.5 | 68.0 | 88 | B |
| HIS | CD2 | 566 | 195.9 | 137.5 | 68.3 | 89 | B |
| HIS | ND1 | 566 | 198.0 | 137.2 | 67.7 | 89 | B |
| HIS | CE1 | 566 | 197.8 | 138.5 | 67.8 | 90 | B |
| HIS | NE2 | 566 | 196.5 | 138.7 | 68.2 | 90 | B |
| HIS | C | 566 | 196.0 | 133.6 | 70.0 | 82 | B |
| HIS | O | 566 | 195.9 | 133.4 | 71.2 | 81 | B |
| LEU | N | 567 | 195.2 | 133.2 | 69.1 | 81 | B |
| LEU | CA | 567 | 194.0 | 132.4 | 69.4 | 80 | B |
| LEU | CB | 567 | 192.7 | 133.0 | 68.7 | 80 | B |
| LEU | CG | 567 | 192.8 | 134.1 | 67.7 | 80 | B |
| LEU | CD1 | 567 | 193.3 | 135.4 | 68.4 | 80 | B |
| LEU | CD2 | 567 | 193.7 | 133.8 | 66.5 | 80 | B |
| LEU | C | 567 | 194.3 | 131.0 | 68.9 | 80 | B |
| LEU | O | 567 | 195.4 | 130.7 | 68.4 | 80 | B |
| VAL | N | 568 | 193.2 | 130.2 | 68.9 | 79 | B |
| VAL | CA | 568 | 193.2 | 128.8 | 68.5 | 77 | B |
| VAL | CB | 568 | 192.4 | 127.9 | 69.4 | 77 | B |
| VAL | CG1 | 568 | 192.7 | 126.4 | 69.2 | 77 | B |
| VAL | CG2 | 568 | 192.7 | 128.2 | 70.9 | 76 | B |
| VAL | C | 568 | 192.7 | 128.7 | 67.0 | 76 | B |
| VAL | O | 568 | 191.8 | 129.5 | 66.7 | 76 | B |
| PRO | N | 569 | 193.2 | 127.9 | 66.1 | 75 | B |
| PRO | CD | 569 | 194.4 | 127.0 | 66.2 | 74 | B |
| PRO | CA | 569 | 192.7 | 127.9 | 64.8 | 74 | B |
| PRO | CB | 569 | 193.5 | 126.8 | 64.1 | 74 | B |
| PRO | CG | 569 | 194.0 | 125.9 | 65.2 | 74 | B |
| PRO | C | 569 | 191.2 | 127.5 | 64.7 | 73 | B |
| PRO | O | 569 | 190.7 | 126.5 | 65.2 | 73 | B |
| ARG | N | 570 | 190.4 | 128.5 | 64.2 | 72 | B |
| ARG | CA | 570 | 189.0 | 128.3 | 64.0 | 71 | B |
| ARG | CB | 570 | 188.3 | 129.6 | 64.5 | 73 | B |
| ARG | CG | 570 | 188.1 | 129.8 | 66.0 | 76 | B |
| ARG | CD | 570 | 186.8 | 129.2 | 66.4 | 78 | B |
| ARG | NE | 570 | 186.8 | 127.7 | 66.3 | 79 | B |
| ARG | CZ | 570 | 186.1 | 126.9 | 67.1 | 81 | B |
| ARG | NH1 | 570 | 185.4 | 127.5 | 68.1 | 81 | B |
| ARG | NH2 | 570 | 186.1 | 125.6 | 67.0 | 82 | B |

TABLE 4-continued

The following table lists the atomic structure coordinates for FPT in complex with FPP and the inhibitor SCH66701 as derived by X-ray diffraction from crystals of that complex The abbreviations are the same as those used in Table 2

| RES | ATOM | # | X | Y | Z | B | C |
|---|---|---|---|---|---|---|---|
| ARG | C | 570 | 188.6 | 128.1 | 62.6 | 69 | B |
| ARG | O | 570 | 188.3 | 129.1 | 61.9 | 70 | B |
| LEU | N | 571 | 188.7 | 126.9 | 62.1 | 66 | B |
| LEU | CA | 571 | 188.4 | 126.7 | 60.7 | 62 | B |
| LEU | CB | 571 | 188.8 | 125.3 | 60.2 | 62 | B |
| LEU | CG | 571 | 190.1 | 125.3 | 59.3 | 62 | B |
| LEU | CD1 | 571 | 191.3 | 125.8 | 60.1 | 61 | B |
| LEU | CD2 | 571 | 190.4 | 123.9 | 58.8 | 62 | B |
| LEU | C | 571 | 186.9 | 126.9 | 60.5 | 60 | B |
| LEU | O | 571 | 186.0 | 126.2 | 61.0 | 59 | B |
| VAL | N | 572 | 186.5 | 127.9 | 59.7 | 57 | B |
| VAL | CA | 572 | 185.2 | 128.2 | 59.4 | 55 | B |
| VAL | CB | 572 | 184.7 | 129.4 | 60.3 | 56 | B |
| VAL | CG1 | 572 | 183.3 | 129.8 | 60.1 | 56 | B |
| VAL | CG2 | 572 | 185.0 | 129.1 | 61.8 | 56 | B |
| VAL | C | 572 | 185.0 | 128.7 | 58.0 | 54 | B |
| VAL | O | 572 | 185.8 | 129.3 | 57.4 | 55 | B |
| LEU | N | 573 | 183.8 | 128.3 | 57.4 | 52 | B |
| LEU | CA | 573 | 183.6 | 128.6 | 56.0 | 50 | B |
| LEU | CB | 573 | 182.9 | 127.4 | 55.2 | 48 | B |
| LEU | CG | 573 | 182.3 | 127.8 | 53.9 | 46 | B |
| LEU | CD1 | 573 | 183.4 | 127.8 | 52.9 | 46 | B |
| LEU | CD2 | 573 | 181.2 | 126.9 | 53.5 | 46 | B |
| LEU | C | 573 | 182.6 | 129.8 | 56.0 | 49 | B |
| LEU | O | 573 | 181.4 | 129.7 | 56.2 | 49 | B |
| GLN | N | 574 | 183.1 | 131.0 | 55.6 | 49 | B |
| GLN | CA | 574 | 182.4 | 132.2 | 55.5 | 49 | B |
| GLN | CB | 574 | 183.2 | 133.4 | 54.9 | 50 | B |
| GLN | CG | 574 | 184.5 | 133.5 | 55.7 | 51 | B |
| GLN | CD | 574 | 184.4 | 133.4 | 57.2 | 52 | B |
| GLN | OE1 | 574 | 185.1 | 132.7 | 57.8 | 54 | B |
| GLN | NE2 | 574 | 183.4 | 134.2 | 57.7 | 52 | B |
| GLN | C | 574 | 181.1 | 132.1 | 54.6 | 49 | B |
| GLN | O | 574 | 181.0 | 132.9 | 53.6 | 50 | B |
| ARG | N | 575 | 180.1 | 131.4 | 55.0 | 48 | B |
| ARG | CA | 575 | 178.9 | 131.2 | 54.2 | 49 | B |
| ARG | CB | 575 | 177.9 | 130.3 | 55.0 | 49 | B |
| ARG | CG | 575 | 178.5 | 129.1 | 55.6 | 50 | B |
| ARG | CD | 575 | 177.5 | 128.4 | 56.5 | 50 | B |
| ARG | NE | 575 | 177.5 | 126.9 | 56.2 | 50 | B |
| ARG | CZ | 575 | 176.9 | 126.4 | 55.2 | 50 | B |
| ARG | NH1 | 575 | 176.1 | 127.1 | 54.4 | 49 | B |
| ARG | NH2 | 575 | 177.0 | 125.1 | 55.0 | 50 | B |
| ARG | C | 575 | 178.2 | 132.5 | 53.8 | 49 | B |
| ARG | O | 575 | 177.7 | 132.6 | 52.7 | 48 | B |
| GLU | N | 576 | 178.0 | 133.4 | 54.8 | 50 | B |
| GLU | CA | 576 | 177.3 | 134.6 | 54.5 | 51 | B |
| GLU | CB | 576 | 177.0 | 135.4 | 55.9 | 53 | B |
| GLU | CG | 576 | 176.8 | 134.5 | 57.1 | 55 | B |
| GLU | CD | 576 | 175.9 | 133.3 | 57.0 | 57 | B |
| GLU | OE1 | 576 | 174.8 | 133.5 | 56.4 | 57 | B |
| GLU | OE2 | 576 | 176.2 | 132.2 | 57.4 | 57 | B |
| GLU | C | 576 | 178.0 | 135.4 | 53.6 | 50 | B |
| GLU | O | 576 | 177.5 | 136.0 | 52.6 | 50 | B |
| LYS | N | 577 | 179.3 | 135.5 | 53.8 | 48 | B |
| LYS | CA | 577 | 180.2 | 136.3 | 52.9 | 46 | B |
| LYS | CB | 577 | 181.6 | 136.3 | 53.4 | 47 | B |
| LYS | CG | 577 | 182.0 | 137.7 | 53.9 | 48 | B |
| LYS | CD | 577 | 181.0 | 138.2 | 55.0 | 49 | B |
| LYS | CE | 577 | 180.7 | 139.7 | 54.8 | 49 | B |
| LYS | NZ | 577 | 179.7 | 140.0 | 53.7 | 50 | B |
| LYS | C | 577 | 180.1 | 135.8 | 51.4 | 44 | B |
| LYS | O | 577 | 179.7 | 136.5 | 50.5 | 43 | B |
| HIS | N | 578 | 180.2 | 134.4 | 51.3 | 41 | B |
| HIS | CA | 578 | 180.1 | 133.8 | 49.9 | 39 | B |
| HIS | CB | 578 | 180.4 | 132.3 | 50.0 | 36 | B |
| HIS | CG | 578 | 181.7 | 132.0 | 50.6 | 34 | B |
| HIS | CD2 | 578 | 182.1 | 130.8 | 51.3 | 34 | B |
| HIS | ND1 | 578 | 182.8 | 132.8 | 50.7 | 34 | B |
| HIS | CE1 | 578 | 183.8 | 132.2 | 51.4 | 34 | B |
| HIS | NE2 | 578 | 183.3 | 131.0 | 51.7 | 33 | B |
| HIS | C | 578 | 178.7 | 134.0 | 49.4 | 39 | B |

TABLE 4-continued

The following table lists the atomic structure coordinates for FPT in complex with FPP and the inhibitor SCH66701 as derived by X-ray diffraction from crystals of that complex
The abbreviations are the same as those used in Table 2

| RES | ATOM | # | X | Y | Z | B | C |
|---|---|---|---|---|---|---|---|
| HIS | O | 578 | 178.5 | 134.1 | 48.2 | 39 | B |
| PHE | N | 579 | 177.7 | 134.0 | 50.3 | 39 | B |
| PHE | CA | 579 | 176.3 | 134.0 | 49.9 | 40 | B |
| PHE | CB | 579 | 175.4 | 133.9 | 51.1 | 40 | B |
| PHE | CG | 579 | 174.0 | 134.1 | 50.8 | 39 | B |
| PHE | CD1 | 579 | 173.3 | 133.2 | 50.0 | 39 | B |
| PHE | CD2 | 579 | 173.3 | 135.3 | 51.1 | 40 | B |
| PHE | CE1 | 579 | 172.0 | 133.5 | 49.5 | 39 | B |
| PHE | CE2 | 579 | 172.0 | 135.6 | 50.7 | 40 | B |
| PHE | CZ | 579 | 171.4 | 134.7 | 49.9 | 40 | B |
| PHE | C | 579 | 176.0 | 135.3 | 49.3 | 41 | B |
| PHE | O | 579 | 175.4 | 135.4 | 48.2 | 41 | B |
| HIS | N | 580 | 176.3 | 136.4 | 49.9 | 44 | B |
| HIS | CA | 580 | 176.1 | 137.8 | 49.4 | 46 | B |
| HIS | CB | 580 | 176.4 | 138.8 | 50.5 | 49 | B |
| HIS | CG | 580 | 175.9 | 138.5 | 51.8 | 53 | B |
| HIS | CD2 | 580 | 174.6 | 138.2 | 52.2 | 54 | B |
| HIS | ND1 | 580 | 176.7 | 138.3 | 52.9 | 54 | B |
| HIS | CE1 | 580 | 175.9 | 138.0 | 54.0 | 54 | B |
| HIS | NE2 | 580 | 174.7 | 137.9 | 53.6 | 54 | B |
| HIS | C | 580 | 176.8 | 138.0 | 48.1 | 45 | B |
| HIS | O | 580 | 176.4 | 138.8 | 47.2 | 45 | B |
| TYR | N | 581 | 178.0 | 137.4 | 48.0 | 44 | B |
| TYR | CA | 581 | 178.9 | 137.5 | 46.9 | 43 | B |
| TYR | CB | 581 | 180.2 | 136.8 | 47.2 | 43 | B |
| TYR | CG | 581 | 181.1 | 136.7 | 46.0 | 44 | B |
| TYR | CD1 | 581 | 181.3 | 137.8 | 45.1 | 44 | B |
| TYR | CE1 | 581 | 182.2 | 137.6 | 44.1 | 44 | B |
| TYR | CD2 | 581 | 181.8 | 135.5 | 45.7 | 44 | B |
| TYR | CE2 | 581 | 182.6 | 135.3 | 44.7 | 44 | B |
| TYR | CZ | 581 | 182.8 | 136.4 | 43.8 | 44 | B |
| TYR | OH | 581 | 183.7 | 136.3 | 42.8 | 45 | B |
| TYR | C | 581 | 178.2 | 136.9 | 45.7 | 43 | B |
| TYR | O | 581 | 178.0 | 137.5 | 44.6 | 42 | B |
| LEU | N | 582 | 177.8 | 135.6 | 45.8 | 42 | B |
| LEU | CA | 582 | 177.2 | 134.8 | 44.8 | 41 | B |
| LEU | CB | 582 | 177.0 | 133.4 | 45.3 | 39 | B |
| LEU | CG | 582 | 178.2 | 132.6 | 45.4 | 37 | B |
| LEU | CD1 | 582 | 178.1 | 131.7 | 46.6 | 36 | B |
| LEU | CD2 | 582 | 178.5 | 131.8 | 44.2 | 37 | B |
| LEU | C | 582 | 175.8 | 135.4 | 44.5 | 43 | B |
| LEU | O | 582 | 175.4 | 135.5 | 43.3 | 43 | B |
| LYS | N | 583 | 175.2 | 135.9 | 45.5 | 45 | B |
| LYS | CA | 583 | 173.9 | 136.5 | 45.5 | 48 | B |
| LYS | CB | 583 | 173.4 | 136.9 | 46.9 | 50 | B |
| LYS | CG | 583 | 172.0 | 137.5 | 47.0 | 52 | B |
| LYS | CD | 583 | 171.8 | 138.2 | 48.4 | 54 | B |
| LYS | CE | 583 | 170.8 | 139.4 | 48.3 | 55 | B |
| LYS | NZ | 583 | 169.3 | 139.1 | 48.0 | 55 | B |
| LYS | C | 583 | 173.8 | 137.7 | 44.5 | 49 | B |
| LYS | O | 583 | 172.8 | 137.8 | 43.8 | 49 | B |
| ARG | N | 584 | 174.8 | 138.6 | 44.5 | 50 | B |
| ARG | CA | 584 | 174.7 | 139.8 | 43.7 | 51 | B |
| ARG | CB | 584 | 175.4 | 141.1 | 44.2 | 53 | B |
| ARG | CG | 584 | 174.7 | 142.4 | 43.7 | 57 | B |
| ARG | CD | 584 | 175.6 | 143.6 | 43.8 | 59 | B |
| ARG | NE | 584 | 176.3 | 143.8 | 42.5 | 62 | B |
| ARG | CZ | 584 | 177.5 | 144.5 | 42.3 | 63 | B |
| ARG | NH1 | 584 | 178.0 | 145.1 | 43.4 | 64 | B |
| ARG | NH2 | 584 | 178.0 | 144.7 | 41.1 | 63 | B |
| ARG | C | 584 | 175.3 | 139.6 | 42.3 | 50 | B |
| ARG | O | 584 | 174.9 | 140.2 | 41.3 | 49 | B |
| GLY | N | 585 | 176.3 | 138.6 | 42.2 | 48 | B |
| GLY | CA | 585 | 176.9 | 138.3 | 40.9 | 47 | B |
| GLY | C | 585 | 175.9 | 137.6 | 40.1 | 46 | B |
| GLY | O | 585 | 176.0 | 137.6 | 38.8 | 45 | B |
| LEU | N | 586 | 174.9 | 137.0 | 40.7 | 45 | B |
| LEU | CA | 586 | 173.8 | 136.3 | 39.9 | 44 | B |
| LEU | CB | 586 | 173.0 | 135.4 | 40.8 | 45 | B |
| LEU | CG | 586 | 171.9 | 134.5 | 40.2 | 45 | B |
| LEU | CD1 | 586 | 172.5 | 133.4 | 39.3 | 45 | B |
| LEU | CD2 | 586 | 171.1 | 133.8 | 41.3 | 45 | B |

TABLE 4-continued

The following table lists the atomic structure coordinates for FPT in complex with FPP and the inhibitor SCH66701 as derived by X-ray diffraction from crystals of that complex
The abbreviations are the same as those used in Table 2

| RES | ATOM | # | X | Y | Z | B | C |
|---|---|---|---|---|---|---|---|
| LEU | C | 586 | 173.0 | 137.3 | 39.2 | 44 | B |
| LEU | O | 586 | 172.3 | 137.0 | 38.2 | 43 | B |
| ARG | N | 587 | 173.1 | 138.6 | 39.6 | 44 | B |
| ARG | CA | 587 | 172.4 | 139.7 | 39.0 | 45 | B |
| ARG | CB | 587 | 171.6 | 140.5 | 40.1 | 46 | B |
| ARG | CG | 587 | 170.1 | 140.4 | 40.0 | 48 | B |
| ARG | CD | 587 | 169.6 | 138.9 | 40.2 | 49 | B |
| ARG | NE | 587 | 168.2 | 138.8 | 40.5 | 50 | B |
| ARG | CZ | 587 | 167.3 | 138.9 | 39.5 | 51 | B |
| ARG | NH1 | 587 | 167.6 | 139.0 | 38.2 | 51 | B |
| ARG | NH2 | 587 | 166.0 | 138.8 | 39.8 | 51 | B |
| ARG | C | 587 | 173.2 | 140.6 | 38.1 | 44 | B |
| ARG | O | 587 | 172.8 | 141.0 | 37.0 | 43 | B |
| GLN | N | 588 | 174.4 | 141.0 | 38.6 | 43 | B |
| GLN | CA | 588 | 175.2 | 141.9 | 37.8 | 43 | B |
| GLN | CB | 588 | 174.8 | 143.3 | 37.9 | 46 | B |
| GLN | CG | 588 | 174.8 | 143.8 | 39.3 | 49 | B |
| GLN | CD | 588 | 174.7 | 145.3 | 39.4 | 50 | B |
| GLN | OE1 | 588 | 174.4 | 145.9 | 38.3 | 51 | B |
| GLN | NE2 | 588 | 174.9 | 145.9 | 40.5 | 51 | B |
| GLN | C | 588 | 176.7 | 141.8 | 38.2 | 41 | B |
| GLN | O | 588 | 177.1 | 141.6 | 39.4 | 40 | B |
| LEU | N | 589 | 177.6 | 142.0 | 37.2 | 38 | B |
| LEU | CA | 589 | 179.0 | 142.0 | 37.4 | 36 | B |
| LEU | CB | 589 | 179.5 | 140.7 | 36.7 | 34 | B |
| LEU | CG | 589 | 178.9 | 139.4 | 37.1 | 32 | B |
| LEU | CD1 | 589 | 178.7 | 138.6 | 35.8 | 31 | B |
| LEU | CD2 | 589 | 179.8 | 138.6 | 38.1 | 31 | B |
| LEU | C | 589 | 179.6 | 143.2 | 36.7 | 35 | B |
| LEU | O | 589 | 179.2 | 143.6 | 35.6 | 34 | B |
| THR | N | 590 | 180.8 | 143.6 | 37.2 | 35 | B |
| THR | CA | 590 | 181.6 | 144.7 | 36.7 | 36 | B |
| THR | CB | 590 | 182.7 | 145.0 | 37.7 | 36 | B |
| THR | OG1 | 590 | 183.6 | 143.8 | 37.9 | 37 | B |
| THR | CG2 | 590 | 182.1 | 145.4 | 39.0 | 37 | B |
| THR | C | 590 | 182.3 | 144.3 | 35.4 | 35 | B |
| THR | O | 590 | 182.4 | 143.1 | 35.1 | 35 | B |
| ASP | N | 591 | 182.7 | 145.3 | 34.6 | 35 | B |
| ASP | CA | 591 | 183.3 | 145.1 | 33.3 | 35 | B |
| ASP | CB | 591 | 183.6 | 146.4 | 32.6 | 35 | B |
| ASP | CG | 591 | 184.5 | 147.3 | 33.4 | 37 | B |
| ASP | OD1 | 591 | 184.7 | 148.5 | 32.9 | 37 | B |
| ASP | OD2 | 591 | 185.1 | 146.9 | 34.5 | 36 | B |
| ASP | C | 591 | 184.6 | 144.2 | 33.4 | 34 | B |
| ASP | O | 591 | 185.1 | 143.9 | 32.4 | 35 | B |
| ALA | N | 592 | 185.0 | 143.9 | 34.6 | 32 | B |
| ALA | CA | 592 | 186.2 | 143.0 | 34.8 | 31 | B |
| ALA | CB | 592 | 186.6 | 143.0 | 36.2 | 32 | B |
| ALA | C | 592 | 185.8 | 141.6 | 34.4 | 30 | B |
| ALA | O | 592 | 186.6 | 140.7 | 34.5 | 29 | B |
| TYR | N | 593 | 184.5 | 141.4 | 33.9 | 29 | B |
| TYR | CA | 593 | 184.0 | 140.2 | 33.4 | 28 | B |
| TYR | CB | 593 | 182.7 | 139.8 | 34.1 | 27 | B |
| TYR | CG | 593 | 182.9 | 139.1 | 35.4 | 27 | B |
| TYR | CD1 | 593 | 183.0 | 139.7 | 36.6 | 27 | B |
| TYR | CE1 | 593 | 183.4 | 139.0 | 37.8 | 27 | B |
| TYR | CD2 | 593 | 183.3 | 137.7 | 35.4 | 27 | B |
| TYR | CE2 | 593 | 183.6 | 137.0 | 36.5 | 26 | B |
| TYR | CZ | 593 | 183.7 | 137.7 | 37.7 | 26 | B |
| TYR | OH | 593 | 184.1 | 137.0 | 38.8 | 27 | B |
| TYR | C | 593 | 183.7 | 140.2 | 31.9 | 29 | B |
| TYR | O | 593 | 183.0 | 139.3 | 31.4 | 29 | B |
| GLU | N | 594 | 184.2 | 141.3 | 31.3 | 28 | B |
| GLU | CA | 594 | 184.0 | 141.4 | 29.9 | 28 | B |
| GLU | CB | 594 | 184.6 | 142.6 | 29.3 | 30 | B |
| GLU | CG | 594 | 183.9 | 143.9 | 29.7 | 32 | B |
| GLU | CD | 594 | 184.6 | 145.1 | 29.4 | 33 | B |
| GLU | OE1 | 594 | 184.0 | 146.1 | 28.9 | 34 | B |
| GLU | OE2 | 594 | 185.9 | 145.1 | 29.5 | 34 | B |
| GLU | C | 594 | 184.6 | 140.2 | 29.2 | 27 | B |
| GLU | O | 594 | 184.2 | 139.8 | 28.1 | 27 | B |
| CYS | N | 595 | 185.6 | 139.6 | 29.8 | 26 | B |

TABLE 4-continued

The following table lists the atomic structure coordinates for FPT in complex with FPP and the inhibitor SCH66701 as derived by X-ray diffraction from crystals of that complex
The abbreviations are the same as those used in Table 2

| RES | ATOM | # | X | Y | Z | B | C |
|---|---|---|---|---|---|---|---|
| CYS | CA | 595 | 186.3 | 138.4 | 29.3 | 24 | B |
| CYS | CB | 595 | 187.6 | 138.1 | 30.0 | 22 | B |
| CYS | SG | 595 | 187.6 | 137.9 | 31.8 | 19 | B |
| CYS | C | 595 | 185.4 | 137.2 | 29.3 | 24 | B |
| CYS | O | 595 | 185.4 | 136.3 | 28.4 | 24 | B |
| LEU | N | 596 | 184.6 | 137.1 | 30.4 | 22 | B |
| LEU | CA | 596 | 183.6 | 136.0 | 30.5 | 20 | B |
| LEU | CB | 596 | 183.4 | 135.6 | 31.9 | 20 | B |
| LEU | CG | 596 | 184.5 | 134.6 | 32.4 | 20 | B |
| LEU | CD1 | 596 | 184.7 | 134.7 | 33.9 | 20 | B |
| LEU | CD2 | 596 | 184.2 | 133.2 | 31.9 | 20 | B |
| LEU | C | 596 | 182.3 | 136.4 | 29.8 | 20 | B |
| LEU | O | 596 | 181.3 | 135.7 | 29.9 | 19 | B |
| ASP | N | 597 | 182.3 | 137.4 | 29.0 | 21 | B |
| ASP | CA | 597 | 181.1 | 137.8 | 28.2 | 21 | B |
| ASP | CB | 597 | 181.4 | 139.2 | 27.5 | 20 | B |
| ASP | CG | 597 | 180.3 | 139.5 | 26.6 | 19 | B |
| ASP | OD1 | 597 | 179.1 | 139.6 | 27.0 | 19 | B |
| ASP | OD2 | 597 | 180.6 | 139.8 | 25.4 | 20 | B |
| ASP | C | 597 | 180.7 | 136.8 | 27.2 | 23 | B |
| ASP | O | 597 | 179.7 | 137.0 | 26.5 | 25 | B |
| ALA | N | 598 | 181.4 | 135.7 | 27.0 | 24 | B |
| ALA | CA | 598 | 181.0 | 134.6 | 26.1 | 24 | B |
| ALA | CB | 598 | 181.9 | 134.5 | 24.9 | 24 | B |
| ALA | C | 598 | 180.9 | 133.3 | 26.8 | 25 | B |
| ALA | O | 598 | 180.7 | 132.2 | 26.2 | 25 | B |
| SER | N | 599 | 180.9 | 133.3 | 28.1 | 26 | B |
| SER | CA | 599 | 180.8 | 132.2 | 29.0 | 27 | B |
| SER | CB | 599 | 182.1 | 131.9 | 29.7 | 27 | B |
| SER | OG | 599 | 183.2 | 131.7 | 28.8 | 28 | B |
| SER | C | 599 | 179.7 | 132.5 | 30.1 | 27 | B |
| SER | O | 599 | 179.9 | 132.2 | 31.2 | 27 | B |
| ARG | N | 600 | 178.6 | 133.1 | 29.6 | 27 | B |
| ARG | CA | 600 | 177.6 | 133.5 | 30.6 | 27 | B |
| ARG | CB | 600 | 176.7 | 134.6 | 30.1 | 27 | B |
| ARG | CG | 600 | 177.5 | 135.9 | 29.9 | 28 | B |
| ARG | CD | 600 | 176.7 | 137.0 | 29.3 | 29 | B |
| ARG | NE | 600 | 175.8 | 137.6 | 30.3 | 30 | B |
| ARG | CZ | 600 | 174.8 | 138.4 | 30.1 | 31 | B |
| ARG | NH1 | 600 | 174.6 | 138.7 | 28.8 | 31 | B |
| ARG | NH2 | 600 | 174.0 | 138.9 | 31.0 | 32 | B |
| ARG | C | 600 | 176.8 | 132.3 | 31.2 | 27 | B |
| ARG | O | 600 | 176.6 | 132.3 | 32.4 | 29 | B |
| PRO | N | 601 | 176.5 | 131.3 | 30.4 | 25 | B |
| PRO | CD | 601 | 176.4 | 131.1 | 29.0 | 26 | B |
| PRO | CA | 601 | 175.8 | 130.2 | 31.1 | 24 | B |
| PRO | CB | 601 | 175.5 | 129.2 | 30.0 | 24 | B |
| PRO | CG | 601 | 175.3 | 130.1 | 28.8 | 24 | B |
| PRO | C | 601 | 176.7 | 129.7 | 32.2 | 24 | B |
| PRO | O | 601 | 176.2 | 129.2 | 33.2 | 25 | B |
| TRP | N | 602 | 178.0 | 129.7 | 32.0 | 23 | B |
| TRP | CA | 602 | 178.8 | 129.2 | 33.1 | 23 | B |
| TRP | CB | 602 | 180.3 | 129.3 | 32.7 | 23 | B |
| TRP | CG | 602 | 180.7 | 128.3 | 31.8 | 23 | B |
| TRP | CD2 | 602 | 181.1 | 126.9 | 32.1 | 23 | B |
| TRP | CE2 | 602 | 181.5 | 126.3 | 30.9 | 23 | B |
| TRP | CE3 | 602 | 181.0 | 126.1 | 33.3 | 23 | B |
| TRP | CD1 | 602 | 181.0 | 128.4 | 30.4 | 23 | B |
| TRP | NE1 | 602 | 181.5 | 127.2 | 29.9 | 23 | B |
| TRP | CZ2 | 602 | 181.9 | 124.9 | 30.9 | 23 | B |
| TRP | CZ3 | 602 | 181.4 | 124.8 | 33.2 | 22 | B |
| TRP | CH2 | 602 | 181.8 | 124.2 | 32.1 | 22 | B |
| TRP | C | 602 | 178.6 | 130.1 | 34.3 | 24 | B |
| TRP | O | 602 | 178.3 | 129.5 | 35.4 | 24 | B |
| LEU | N | 603 | 178.6 | 131.4 | 34.1 | 25 | B |
| LEU | CA | 603 | 178.3 | 132.3 | 35.2 | 26 | B |
| LEU | CB | 603 | 178.3 | 133.7 | 34.7 | 26 | B |
| LEU | CG | 603 | 179.7 | 134.3 | 34.4 | 27 | B |
| LEU | CD1 | 603 | 179.7 | 135.6 | 33.6 | 26 | B |
| LEU | CD2 | 603 | 180.4 | 134.5 | 35.7 | 26 | B |
| LEU | C | 603 | 177.1 | 131.9 | 36.0 | 27 | B |
| LEU | O | 603 | 177.1 | 132.1 | 37.2 | 28 | B |

TABLE 4-continued

The following table lists the atomic structure coordinates for FPT in complex with FPP and the inhibitor SCH66701 as derived by X-ray diffraction from crystals of that complex
The abbreviations are the same as those used in Table 2

| RES | ATOM | # | X | Y | Z | B | C |
|---|---|---|---|---|---|---|---|
| CYS | N | 604 | 176.0 | 131.5 | 35.3 | 26 | B |
| CYS | CA | 604 | 174.8 | 131.0 | 36.0 | 25 | B |
| CYS | CB | 604 | 173.7 | 130.8 | 35.0 | 25 | B |
| CYS | SG | 604 | 173.2 | 132.2 | 34.1 | 28 | B |
| CYS | C | 604 | 175.2 | 129.8 | 36.7 | 25 | B |
| CYS | O | 604 | 175.2 | 129.8 | 38.0 | 25 | B |
| TYR | N | 605 | 175.5 | 128.7 | 36.0 | 24 | B |
| TYR | CA | 605 | 175.9 | 127.4 | 36.6 | 22 | B |
| TYR | CB | 605 | 176.5 | 126.5 | 35.6 | 21 | B |
| TYR | CG | 605 | 177.1 | 125.2 | 36.3 | 21 | B |
| TYR | CD1 | 605 | 176.4 | 124.3 | 37.0 | 21 | B |
| TYR | CE1 | 605 | 177.0 | 123.2 | 37.6 | 20 | B |
| TYR | CD2 | 605 | 178.5 | 125.1 | 36.3 | 21 | B |
| TYR | CE2 | 605 | 179.1 | 124.0 | 36.9 | 21 | B |
| TYR | CZ | 605 | 178.4 | 123.1 | 37.6 | 21 | B |
| TYR | OH | 605 | 179.0 | 122.1 | 38.2 | 22 | B |
| TYR | C | 605 | 176.8 | 127.6 | 37.8 | 23 | B |
| TYR | O | 605 | 176.5 | 127.2 | 39.0 | 22 | B |
| TRP | N | 606 | 178.0 | 128.2 | 37.6 | 24 | B |
| TRP | CA | 606 | 178.9 | 128.4 | 38.7 | 25 | B |
| TRP | CB | 606 | 180.1 | 129.3 | 38.2 | 26 | B |
| TRP | CG | 606 | 181.1 | 128.7 | 37.2 | 27 | B |
| TRP | CD2 | 606 | 181.8 | 129.5 | 36.2 | 28 | B |
| TRP | CE2 | 606 | 182.6 | 128.6 | 35.6 | 27 | B |
| TRP | CE3 | 606 | 181.8 | 130.8 | 35.9 | 29 | B |
| TRP | CD1 | 606 | 181.5 | 127.4 | 37.1 | 26 | B |
| TRP | NE1 | 606 | 182.4 | 127.3 | 36.1 | 26 | B |
| TRP | CZ2 | 606 | 183.5 | 129.0 | 34.5 | 28 | B |
| TRP | CZ3 | 606 | 182.6 | 131.2 | 34.8 | 29 | B |
| TRP | CH2 | 606 | 183.5 | 130.3 | 34.2 | 28 | B |
| TRP | C | 606 | 178.3 | 128.9 | 39.9 | 26 | B |
| TRP | O | 606 | 178.5 | 128.5 | 41.0 | 26 | B |
| ILE | N | 607 | 177.5 | 130.0 | 39.7 | 27 | B |
| ILE | CA | 607 | 176.8 | 130.6 | 40.9 | 28 | B |
| ILE | CB | 607 | 176.4 | 132.1 | 40.5 | 27 | B |
| ILE | CG2 | 607 | 175.6 | 132.7 | 41.7 | 27 | B |
| ILE | CG1 | 607 | 177.6 | 132.9 | 40.2 | 26 | B |
| ILE | CD1 | 607 | 177.3 | 134.2 | 39.4 | 26 | B |
| ILE | C | 607 | 175.7 | 129.8 | 41.4 | 28 | B |
| ILE | O | 607 | 175.7 | 129.4 | 42.6 | 29 | B |
| LEU | N | 608 | 174.7 | 129.6 | 40.6 | 28 | B |
| LEU | CA | 608 | 173.5 | 128.8 | 40.9 | 28 | B |
| LEU | CB | 608 | 172.7 | 128.5 | 39.7 | 27 | B |
| LEU | CG | 608 | 171.2 | 128.9 | 39.7 | 27 | B |
| LEU | CD1 | 608 | 170.9 | 130.2 | 40.4 | 27 | B |
| LEU | CD2 | 608 | 170.7 | 128.9 | 38.2 | 27 | B |
| LEU | C | 608 | 173.9 | 127.5 | 41.6 | 28 | B |
| LEU | O | 608 | 173.2 | 126.9 | 42.4 | 30 | B |
| HIS | N | 609 | 175.1 | 126.9 | 41.2 | 28 | B |
| HIS | CA | 609 | 175.6 | 125.7 | 41.8 | 29 | B |
| HIS | CB | 609 | 176.5 | 124.9 | 40.9 | 28 | B |
| HIS | CG | 609 | 177.1 | 123.7 | 41.5 | 28 | B |
| HIS | CD2 | 609 | 178.4 | 123.3 | 41.8 | 28 | B |
| HIS | ND1 | 609 | 176.4 | 122.7 | 42.0 | 27 | B |
| HIS | CE1 | 609 | 177.1 | 121.7 | 42.6 | 27 | B |
| HIS | NE2 | 609 | 178.4 | 122.1 | 42.4 | 28 | B |
| HIS | C | 609 | 176.2 | 125.9 | 43.2 | 30 | B |
| HIS | O | 609 | 176.0 | 125.1 | 44.1 | 30 | B |
| SER | N | 610 | 176.9 | 127.0 | 43.4 | 32 | B |
| SER | CA | 610 | 177.6 | 127.3 | 44.6 | 33 | B |
| SER | CB | 610 | 178.5 | 128.5 | 44.5 | 34 | B |
| SER | OG | 610 | 179.4 | 128.4 | 43.4 | 34 | B |
| SER | C | 610 | 176.5 | 127.5 | 45.7 | 34 | B |
| SER | O | 610 | 176.7 | 127.1 | 46.9 | 33 | B |
| LEU | N | 611 | 175.5 | 128.2 | 45.4 | 35 | B |
| LEU | CA | 611 | 174.4 | 128.5 | 46.3 | 35 | B |
| LEU | CB | 611 | 173.3 | 129.3 | 45.6 | 34 | B |
| LEU | CG | 611 | 173.6 | 130.7 | 45.0 | 34 | B |
| LEU | CD1 | 611 | 172.4 | 131.4 | 44.4 | 33 | B |
| LEU | CD2 | 611 | 174.2 | 131.6 | 46.1 | 33 | B |
| LEU | C | 611 | 173.8 | 127.1 | 46.6 | 36 | B |
| LEU | O | 611 | 173.7 | 126.8 | 47.8 | 38 | B |

TABLE 4-continued

The following table lists the atomic structure coordinates for FPT in complex with FPP and the inhibitor SCH66701 as derived by X-ray diffraction from crystals of that complex The abbreviations are the same as those used in Table 2

| RES | ATOM | # | X | Y | Z | B | C |
|---|---|---|---|---|---|---|---|
| GLU | N | 612 | 173.5 | 126.3 | 45.6 | 37 | B |
| GLU | CA | 612 | 173.1 | 125.0 | 45.8 | 37 | B |
| GLU | CB | 612 | 173.0 | 124.2 | 44.5 | 37 | B |
| GLU | CG | 612 | 172.5 | 122.8 | 44.6 | 37 | B |
| GLU | CD | 612 | 173.3 | 121.9 | 43.7 | 37 | B |
| GLU | OE1 | 612 | 173.8 | 120.9 | 44.2 | 37 | B |
| GLU | OE2 | 612 | 173.3 | 122.1 | 42.4 | 36 | B |
| GLU | C | 612 | 173.9 | 124.2 | 46.8 | 38 | B |
| GLU | O | 612 | 173.4 | 123.6 | 47.7 | 38 | B |
| LEU | N | 613 | 175.2 | 124.4 | 46.8 | 39 | B |
| LEU | CA | 613 | 176.1 | 123.7 | 47.7 | 41 | B |
| LEU | CB | 613 | 177.6 | 123.8 | 47.2 | 40 | B |
| LEU | CG | 613 | 178.0 | 122.9 | 46.0 | 40 | B |
| LEU | CD1 | 613 | 179.1 | 123.6 | 45.2 | 40 | B |
| LEU | CD2 | 613 | 178.5 | 121.6 | 46.6 | 41 | B |
| LEU | C | 613 | 176.0 | 124.3 | 49.1 | 42 | B |
| LEU | O | 613 | 175.8 | 123.6 | 50.1 | 42 | B |
| LEU | N | 614 | 176.0 | 125.6 | 49.2 | 44 | B |
| LEU | CA | 614 | 175.9 | 126.3 | 50.5 | 46 | B |
| LEU | CB | 614 | 176.2 | 127.8 | 50.3 | 45 | B |
| LEU | CG | 614 | 177.5 | 128.2 | 49.8 | 44 | B |
| LEU | CD1 | 614 | 177.4 | 129.4 | 49.0 | 44 | B |
| LEU | CD2 | 614 | 178.5 | 128.3 | 50.9 | 45 | B |
| LEU | C | 614 | 174.6 | 126.1 | 51.1 | 47 | B |
| LEU | O | 614 | 174.3 | 126.4 | 52.3 | 47 | B |
| ASP | N | 615 | 173.6 | 125.6 | 50.3 | 50 | B |
| ASP | CA | 615 | 172.3 | 125.3 | 50.7 | 52 | B |
| ASP | CB | 615 | 172.2 | 124.6 | 52.0 | 52 | B |
| ASP | CG | 615 | 170.8 | 124.0 | 52.3 | 53 | B |
| ASP | OD1 | 615 | 169.9 | 124.0 | 51.4 | 53 | B |
| ASP | OD2 | 615 | 170.7 | 123.5 | 53.4 | 52 | B |
| ASP | C | 615 | 171.4 | 126.6 | 50.7 | 53 | B |
| ASP | O | 615 | 170.6 | 126.7 | 51.5 | 55 | B |
| GLU | N | 616 | 171.8 | 127.5 | 49.8 | 55 | B |
| GLU | CA | 616 | 171.0 | 128.7 | 49.7 | 56 | B |
| GLU | CB | 616 | 171.9 | 129.9 | 49.4 | 58 | B |
| GLU | CG | 616 | 173.2 | 129.9 | 50.3 | 60 | B |
| GLU | CD | 616 | 172.9 | 130.4 | 51.7 | 61 | B |
| GLU | OE1 | 616 | 171.7 | 130.6 | 52.1 | 62 | B |
| GLU | OE2 | 616 | 173.9 | 130.5 | 52.5 | 62 | B |
| GLU | C | 616 | 169.9 | 128.5 | 48.7 | 57 | B |
| GLU | O | 616 | 170.1 | 127.7 | 47.8 | 57 | B |
| PRO | N | 617 | 168.8 | 129.2 | 48.8 | 58 | B |
| PRO | CD | 617 | 168.6 | 130.3 | 49.7 | 59 | B |
| PRO | CA | 617 | 167.7 | 129.1 | 47.8 | 59 | B |
| PRO | CB | 617 | 166.6 | 129.9 | 48.6 | 59 | B |
| PRO | CG | 617 | 167.4 | 131.1 | 49.1 | 59 | B |
| PRO | C | 617 | 167.9 | 129.8 | 46.5 | 59 | B |
| PRO | O | 617 | 168.7 | 130.8 | 46.4 | 59 | B |
| ILE | N | 618 | 167.2 | 129.3 | 45.5 | 60 | B |
| ILE | CA | 618 | 167.3 | 129.9 | 44.1 | 61 | B |
| ILE | CB | 618 | 167.8 | 128.8 | 43.1 | 61 | B |
| ILE | CG2 | 618 | 167.6 | 129.1 | 41.7 | 60 | B |
| ILE | CG1 | 618 | 169.3 | 128.5 | 43.3 | 61 | B |
| ILE | CD1 | 618 | 169.8 | 127.9 | 44.6 | 60 | B |
| ILE | C | 618 | 165.8 | 130.3 | 43.8 | 60 | B |
| ILE | O | 618 | 165.1 | 129.6 | 43.1 | 61 | B |
| PRO | N | 619 | 165.4 | 131.4 | 44.4 | 60 | B |
| PRO | CD | 619 | 166.3 | 132.3 | 45.2 | 60 | B |
| PRO | CA | 619 | 164.1 | 132.1 | 44.3 | 59 | B |
| PRO | CB | 619 | 164.4 | 133.5 | 44.5 | 59 | B |
| PRO | CG | 619 | 165.3 | 133.5 | 45.6 | 59 | B |
| PRO | C | 619 | 163.3 | 131.8 | 43.0 | 58 | B |
| PRO | O | 619 | 163.8 | 132.0 | 41.9 | 58 | B |
| GLN | N | 620 | 162.0 | 131.6 | 43.2 | 58 | B |
| GLN | CA | 620 | 161.1 | 131.3 | 42.1 | 59 | B |
| GLN | CB | 620 | 159.7 | 131.1 | 42.6 | 60 | B |
| GLN | CG | 620 | 159.6 | 130.4 | 44.1 | 62 | B |
| GLN | CD | 620 | 158.5 | 129.5 | 44.3 | 63 | B |
| GLN | OE1 | 620 | 157.4 | 129.6 | 43.6 | 64 | B |
| GLN | NE2 | 620 | 158.6 | 128.6 | 45.3 | 63 | B |
| GLN | C | 620 | 161.2 | 132.3 | 41.0 | 57 | B |

TABLE 4-continued

The following table lists the atomic structure coordinates for FPT in complex with FPP and the inhibitor SCH66701 as derived by X-ray diffraction from crystals of that complex The abbreviations are the same as those used in Table 2

| RES | ATOM | # | X | Y | Z | B | C |
|---|---|---|---|---|---|---|---|
| GLN | O | 620 | 160.9 | 131.9 | 39.8 | 57 | B |
| ILE | N | 621 | 161.6 | 133.5 | 41.3 | 56 | B |
| ILE | CA | 621 | 161.7 | 134.6 | 40.3 | 56 | B |
| ILE | CB | 621 | 161.3 | 136.0 | 40.9 | 56 | B |
| ILE | CG2 | 621 | 161.2 | 137.0 | 39.8 | 55 | B |
| ILE | CG1 | 621 | 160.0 | 135.9 | 41.7 | 57 | B |
| ILE | CD1 | 621 | 160.2 | 135.2 | 43.1 | 57 | B |
| ILE | C | 621 | 163.0 | 134.7 | 39.6 | 54 | B |
| ILE | O | 621 | 163.1 | 134.8 | 38.4 | 53 | B |
| VAL | N | 622 | 164.1 | 134.6 | 40.4 | 52 | B |
| VAL | CA | 622 | 165.4 | 134.7 | 39.8 | 51 | B |
| VAL | CB | 622 | 166.5 | 134.6 | 40.9 | 51 | B |
| VAL | CG1 | 622 | 166.7 | 133.2 | 41.5 | 50 | B |
| VAL | CG2 | 622 | 167.8 | 135.2 | 40.4 | 51 | B |
| VAL | C | 622 | 165.6 | 133.5 | 38.9 | 51 | B |
| VAL | O | 622 | 166.2 | 133.5 | 37.8 | 50 | B |
| ALA | N | 623 | 164.9 | 132.4 | 39.3 | 51 | B |
| ALA | CA | 623 | 164.9 | 131.1 | 38.5 | 50 | B |
| ALA | CB | 623 | 164.1 | 130.0 | 39.3 | 49 | B |
| ALA | C | 623 | 164.2 | 131.3 | 37.2 | 49 | B |
| ALA | O | 623 | 164.8 | 130.9 | 36.2 | 50 | B |
| THR | N | 624 | 163.1 | 132.0 | 37.1 | 48 | B |
| THR | CA | 624 | 162.4 | 132.2 | 35.8 | 47 | B |
| THR | CB | 624 | 161.1 | 133.0 | 36.0 | 46 | B |
| THR | OG1 | 624 | 160.3 | 132.2 | 36.8 | 47 | B |
| THR | CG2 | 624 | 160.4 | 133.2 | 34.6 | 45 | B |
| THR | C | 624 | 163.3 | 133.1 | 34.9 | 48 | B |
| THR | O | 624 | 163.4 | 132.9 | 33.7 | 47 | B |
| ASP | N | 625 | 164.0 | 134.0 | 35.5 | 48 | B |
| ASP | CA | 625 | 164.9 | 134.9 | 34.8 | 47 | B |
| ASP | CB | 625 | 165.4 | 136.0 | 35.7 | 49 | B |
| ASP | CG | 625 | 164.3 | 136.9 | 36.3 | 50 | B |
| ASP | OD1 | 625 | 163.3 | 137.2 | 35.6 | 50 | B |
| ASP | OD2 | 625 | 164.4 | 137.3 | 37.5 | 50 | B |
| ASP | C | 625 | 166.1 | 134.1 | 34.2 | 45 | B |
| ASP | O | 625 | 166.3 | 134.2 | 33.0 | 45 | B |
| VAL | N | 626 | 166.7 | 133.3 | 35.1 | 43 | B |
| VAL | CA | 626 | 167.8 | 132.4 | 34.6 | 42 | B |
| VAL | CB | 626 | 168.2 | 131.5 | 35.7 | 42 | B |
| VAL | CG1 | 626 | 169.2 | 130.5 | 35.1 | 42 | B |
| VAL | CG2 | 626 | 168.8 | 132.2 | 36.9 | 42 | B |
| VAL | C | 626 | 167.2 | 131.7 | 33.4 | 42 | B |
| VAL | O | 626 | 167.8 | 131.6 | 32.4 | 43 | B |
| CYS | N | 627 | 166.0 | 131.1 | 33.6 | 43 | B |
| CYS | CA | 627 | 165.4 | 130.3 | 32.5 | 43 | B |
| CYS | CB | 627 | 164.1 | 129.7 | 32.9 | 42 | B |
| CYS | SG | 627 | 164.2 | 128.4 | 34.1 | 43 | B |
| CYS | C | 627 | 165.2 | 131.1 | 31.2 | 44 | B |
| CYS | O | 627 | 165.8 | 130.8 | 30.2 | 44 | B |
| GLN | N | 628 | 164.5 | 132.2 | 31.3 | 44 | B |
| GLN | CA | 628 | 164.2 | 133.1 | 30.2 | 43 | B |
| GLN | CB | 628 | 163.4 | 134.3 | 30.7 | 46 | B |
| GLN | CG | 628 | 161.9 | 134.1 | 30.8 | 47 | B |
| GLN | CD | 628 | 161.2 | 135.4 | 31.3 | 48 | B |
| GLN | OE1 | 628 | 161.5 | 136.6 | 31.0 | 48 | B |
| GLN | NE2 | 628 | 160.2 | 135.2 | 32.2 | 49 | B |
| GLN | C | 628 | 165.5 | 133.5 | 29.6 | 42 | B |
| GLN | O | 628 | 165.5 | 133.7 | 28.3 | 41 | B |
| PHE | N | 629 | 166.6 | 133.7 | 30.4 | 40 | B |
| PHE | CA | 629 | 167.9 | 134.1 | 29.8 | 39 | B |
| PHE | CB | 629 | 168.8 | 134.6 | 31.0 | 38 | B |
| PHE | CG | 629 | 170.2 | 135.0 | 30.5 | 38 | B |
| PHE | CD1 | 629 | 170.4 | 136.0 | 29.6 | 38 | B |
| PHE | CD2 | 629 | 171.3 | 134.2 | 30.9 | 38 | B |
| PHE | CE1 | 629 | 171.6 | 136.3 | 29.1 | 38 | B |
| PHE | CE2 | 629 | 172.6 | 134.5 | 30.4 | 37 | B |
| PHE | CZ | 629 | 172.7 | 135.6 | 29.5 | 37 | B |
| PHE | C | 629 | 168.6 | 133.0 | 29.0 | 38 | B |
| PHE | O | 629 | 169.0 | 133.2 | 27.9 | 37 | B |
| LEU | N | 630 | 168.6 | 131.8 | 29.6 | 36 | B |
| LEU | CA | 630 | 169.2 | 130.7 | 29.0 | 35 | B |
| LEU | CB | 630 | 169.3 | 129.5 | 29.9 | 32 | B |

TABLE 4-continued

The following table lists the atomic structure coordinates for FPT in complex with FPP and the inhibitor SCH66701 as derived by X-ray diffraction from crystals of that complex The abbreviations are the same as those used in Table 2

| RES | ATOM | # | X | Y | Z | B | C |
|---|---|---|---|---|---|---|---|
| LEU | CG | 630 | 170.2 | 129.7 | 31.1 | 31 | B |
| LEU | CD1 | 630 | 170.1 | 128.7 | 32.2 | 30 | B |
| LEU | CD2 | 630 | 171.6 | 129.8 | 30.6 | 30 | B |
| LEU | C | 630 | 168.5 | 130.3 | 27.7 | 37 | B |
| LEU | O | 630 | 169.0 | 129.7 | 26.7 | 37 | B |
| GLU | N | 631 | 167.2 | 130.8 | 27.6 | 38 | B |
| GLU | CA | 631 | 166.4 | 130.7 | 26.4 | 40 | B |
| GLU | CB | 631 | 165.0 | 131.0 | 26.7 | 43 | B |
| GLU | CG | 631 | 164.2 | 130.0 | 27.6 | 46 | B |
| GLU | CD | 631 | 162.7 | 130.3 | 27.6 | 49 | B |
| GLU | OE1 | 631 | 162.2 | 130.7 | 28.7 | 50 | B |
| GLU | OE2 | 631 | 162.1 | 130.1 | 26.6 | 50 | B |
| GLU | C | 631 | 167.0 | 131.6 | 25.3 | 39 | B |
| GLU | O | 631 | 166.8 | 131.4 | 24.1 | 39 | B |
| LEU | N | 632 | 167.5 | 132.7 | 25.8 | 39 | B |
| LEU | CA | 632 | 168.0 | 133.8 | 24.9 | 39 | B |
| LEU | CB | 632 | 168.1 | 135.1 | 25.6 | 39 | B |
| LEU | CG | 632 | 166.8 | 135.8 | 25.7 | 39 | B |
| LEU | CD1 | 632 | 166.9 | 137.0 | 26.7 | 39 | B |
| LEU | CD2 | 632 | 166.4 | 136.3 | 24.4 | 38 | B |
| LEU | C | 632 | 169.3 | 133.3 | 24.3 | 38 | B |
| LEU | O | 632 | 169.7 | 133.6 | 23.2 | 39 | B |
| CYS | N | 633 | 170.1 | 132.6 | 25.2 | 38 | B |
| CYS | CA | 633 | 171.4 | 132.1 | 24.7 | 37 | B |
| CYS | CB | 633 | 172.2 | 131.6 | 25.9 | 36 | B |
| CYS | SG | 633 | 172.6 | 132.9 | 27.0 | 36 | B |
| CYS | C | 633 | 171.2 | 130.9 | 23.7 | 37 | B |
| CYS | O | 633 | 171.9 | 130.8 | 22.7 | 36 | B |
| GLN | N | 634 | 170.2 | 130.0 | 24.0 | 37 | B |
| GLN | CA | 634 | 169.9 | 128.9 | 23.2 | 37 | B |
| GLN | CB | 634 | 168.6 | 128.2 | 23.7 | 36 | B |
| GLN | CG | 634 | 168.2 | 127.0 | 22.9 | 36 | B |
| GLN | CD | 634 | 167.3 | 126.1 | 23.8 | 36 | B |
| GLN | OE1 | 634 | 166.2 | 126.5 | 24.2 | 37 | B |
| GLN | NE2 | 634 | 167.7 | 124.9 | 24.0 | 36 | B |
| GLN | C | 634 | 169.8 | 129.2 | 21.7 | 37 | B |
| GLN | O | 634 | 169.1 | 130.1 | 21.3 | 37 | B |
| SER | N | 635 | 170.5 | 128.3 | 20.9 | 37 | B |
| SER | CA | 635 | 170.5 | 128.5 | 19.5 | 38 | B |
| SER | CB | 635 | 171.8 | 127.9 | 18.9 | 38 | B |
| SER | OG | 635 | 171.7 | 127.6 | 17.5 | 38 | B |
| SER | C | 635 | 169.4 | 127.9 | 18.8 | 39 | B |
| SER | O | 635 | 168.7 | 126.9 | 19.3 | 40 | B |
| PRO | N | 636 | 169.0 | 128.4 | 17.7 | 39 | B |
| PRO | CD | 636 | 169.4 | 129.7 | 17.1 | 39 | B |
| PRO | CA | 636 | 167.9 | 127.9 | 16.9 | 40 | B |
| PRO | CB | 636 | 167.5 | 129.0 | 15.9 | 40 | B |
| PRO | CG | 636 | 168.9 | 129.7 | 15.7 | 40 | B |
| PRO | C | 636 | 168.4 | 126.6 | 16.1 | 40 | B |
| PRO | O | 636 | 167.8 | 126.3 | 15.1 | 39 | B |
| ASP | N | 637 | 169.5 | 126.1 | 16.5 | 40 | B |
| ASP | CA | 637 | 170.1 | 124.9 | 15.9 | 41 | B |
| ASP | CB | 637 | 171.3 | 125.3 | 15.1 | 43 | B |
| ASP | CG | 637 | 170.9 | 126.2 | 13.9 | 46 | B |
| ASP | OD1 | 637 | 169.8 | 126.0 | 13.3 | 47 | B |
| ASP | OD2 | 637 | 171.6 | 127.2 | 13.6 | 48 | B |
| ASP | C | 637 | 170.6 | 124.0 | 17.0 | 39 | B |
| ASP | O | 637 | 171.6 | 123.3 | 16.8 | 39 | B |
| GLY | N | 638 | 169.9 | 124.1 | 18.2 | 37 | B |
| GLY | CA | 638 | 170.2 | 123.3 | 19.3 | 34 | B |
| GLY | C | 638 | 171.5 | 123.8 | 20.0 | 33 | B |
| GLY | O | 638 | 172.2 | 124.5 | 19.4 | 33 | B |
| GLY | N | 639 | 171.6 | 123.4 | 21.3 | 32 | B |
| GLY | CA | 639 | 172.8 | 123.9 | 22.0 | 32 | B |
| GLY | C | 639 | 172.7 | 125.4 | 22.4 | 32 | B |
| GLY | O | 639 | 171.9 | 126.1 | 21.8 | 32 | B |
| PHE | N | 640 | 173.5 | 125.8 | 23.3 | 31 | B |
| PHE | CA | 640 | 173.5 | 127.2 | 23.8 | 31 | B |
| PHE | CB | 640 | 173.3 | 127.1 | 25.3 | 32 | B |
| PHE | CG | 640 | 172.0 | 126.5 | 25.7 | 32 | B |
| PHE | CD1 | 640 | 172.0 | 125.1 | 25.8 | 33 | B |
| PHE | CD2 | 640 | 170.9 | 127.2 | 26.1 | 33 | B |
| PHE | CE1 | 640 | 170.8 | 124.4 | 26.2 | 33 | B |
| PHE | CE2 | 640 | 169.7 | 126.6 | 26.5 | 33 | B |
| PHE | CZ | 640 | 169.7 | 125.2 | 26.5 | 34 | B |
| PHE | C | 640 | 174.7 | 128.0 | 23.4 | 30 | B |
| PHE | O | 640 | 175.8 | 127.5 | 23.2 | 31 | B |
| GLY | N | 641 | 174.5 | 129.3 | 23.2 | 28 | B |
| GLY | CA | 641 | 175.6 | 130.2 | 22.8 | 26 | B |
| GLY | C | 641 | 176.1 | 130.7 | 24.2 | 25 | B |
| GLY | O | 641 | 175.5 | 130.4 | 25.2 | 25 | B |
| GLY | N | 642 | 177.3 | 131.4 | 24.1 | 24 | B |
| GLY | CA | 642 | 177.8 | 131.9 | 25.4 | 24 | B |
| GLY | C | 642 | 177.2 | 133.1 | 26.0 | 24 | B |
| GLY | O | 642 | 177.6 | 133.6 | 27.1 | 25 | B |
| GLY | N | 643 | 176.2 | 133.6 | 25.3 | 23 | B |
| GLY | CA | 643 | 175.4 | 134.8 | 25.7 | 22 | B |
| GLY | C | 643 | 174.4 | 135.0 | 24.7 | 23 | B |
| GLY | O | 643 | 174.5 | 134.4 | 23.6 | 23 | B |
| PRO | N | 644 | 173.3 | 135.8 | 24.9 | 23 | B |
| PRO | CD | 644 | 173.1 | 136.7 | 26.1 | 23 | B |
| PRO | CA | 644 | 172.2 | 136.0 | 24.0 | 23 | B |
| PRO | CB | 644 | 171.5 | 137.3 | 24.5 | 22 | B |
| PRO | CG | 644 | 171.7 | 137.1 | 26.0 | 22 | B |
| PRO | C | 644 | 172.8 | 136.3 | 22.6 | 24 | B |
| PRO | O | 644 | 173.6 | 137.2 | 22.4 | 26 | B |
| GLY | N | 645 | 172.3 | 135.5 | 21.6 | 26 | B |
| GLY | CA | 645 | 172.8 | 135.7 | 20.3 | 28 | B |
| GLY | C | 645 | 174.0 | 135.0 | 19.8 | 28 | B |
| GLY | O | 645 | 174.3 | 135.0 | 18.6 | 29 | B |
| GLN | N | 646 | 174.8 | 134.3 | 20.7 | 28 | B |
| GLN | CA | 646 | 176.0 | 133.7 | 20.2 | 29 | B |
| GLN | CB | 646 | 177.0 | 133.6 | 21.4 | 29 | B |
| GLN | CG | 646 | 177.5 | 135.0 | 21.7 | 29 | B |
| GLN | CD | 646 | 178.1 | 135.1 | 23.1 | 29 | B |
| GLN | OE1 | 646 | 177.7 | 135.9 | 23.9 | 30 | B |
| GLN | NE2 | 646 | 178.9 | 134.1 | 23.5 | 30 | B |
| GLN | C | 646 | 175.8 | 132.3 | 19.6 | 28 | B |
| GLN | O | 646 | 174.8 | 131.6 | 20.0 | 29 | B |
| TYR | N | 647 | 176.6 | 131.9 | 18.7 | 27 | B |
| TYR | CA | 647 | 176.6 | 130.6 | 18.1 | 26 | B |
| TYR | CB | 647 | 177.7 | 130.4 | 17.1 | 25 | B |
| TYR | CG | 647 | 177.7 | 131.4 | 15.9 | 24 | B |
| TYR | CD1 | 647 | 178.7 | 131.4 | 15.0 | 25 | B |
| TYR | CE1 | 647 | 178.7 | 132.2 | 13.9 | 25 | B |
| TYR | CD2 | 647 | 176.5 | 132.1 | 15.6 | 24 | B |
| TYR | CE2 | 647 | 176.5 | 132.9 | 14.5 | 24 | B |
| TYR | CZ | 647 | 177.6 | 132.9 | 13.6 | 25 | B |
| TYR | OH | 647 | 177.5 | 133.6 | 12.4 | 26 | B |
| TYR | C | 647 | 176.7 | 129.6 | 19.2 | 26 | B |
| TYR | O | 647 | 177.5 | 129.8 | 20.1 | 26 | B |
| PRO | N | 648 | 176.1 | 128.4 | 19.1 | 25 | B |
| PRO | CD | 648 | 175.4 | 127.9 | 17.9 | 26 | B |
| PRO | CA | 648 | 176.2 | 127.4 | 20.1 | 25 | B |
| PRO | CB | 648 | 175.1 | 126.4 | 19.7 | 25 | B |
| PRO | CG | 648 | 175.3 | 126.4 | 18.2 | 26 | B |
| PRO | C | 648 | 177.5 | 126.8 | 20.3 | 24 | B |
| PRO | O | 648 | 178.3 | 126.6 | 19.3 | 24 | B |
| HIS | N | 649 | 177.9 | 126.4 | 21.5 | 22 | B |
| HIS | CA | 649 | 179.2 | 125.9 | 21.8 | 21 | B |
| HIS | CB | 649 | 180.0 | 127.1 | 22.1 | 21 | B |
| HIS | CG | 649 | 181.5 | 126.7 | 22.4 | 20 | B |
| HIS | CD2 | 649 | 182.6 | 127.1 | 21.8 | 20 | B |
| HIS | ND1 | 649 | 181.9 | 126.1 | 23.6 | 20 | B |
| HIS | CE1 | 649 | 183.2 | 126.1 | 23.6 | 20 | B |
| HIS | NE2 | 649 | 183.7 | 126.6 | 22.5 | 20 | B |
| HIS | C | 649 | 179.0 | 124.9 | 22.9 | 22 | B |
| HIS | O | 649 | 178.3 | 125.3 | 23.9 | 23 | B |
| LEU | N | 650 | 179.5 | 123.7 | 22.8 | 21 | B |
| LEU | CA | 650 | 179.4 | 122.7 | 23.9 | 20 | B |
| LEU | CB | 650 | 180.2 | 121.5 | 23.5 | 20 | B |
| LEU | CG | 650 | 179.5 | 120.5 | 22.6 | 18 | B |
| LEU | CD1 | 650 | 180.5 | 119.5 | 22.1 | 18 | B |
| LEU | CD2 | 650 | 178.4 | 119.7 | 23.4 | 17 | B |

TABLE 4-continued

The following table lists the atomic structure coordinates for FPT in complex with FPP and the inhibitor SCH66701 as derived by X-ray diffraction from crystals of that complex
The abbreviations are the same as those used in Table 2

| RES | ATOM | # | X | Y | Z | B | C |
|---|---|---|---|---|---|---|---|
| LEU | C | 650 | 179.6 | 123.2 | 25.3 | 20 | B |
| LEU | O | 650 | 179.0 | 122.7 | 26.2 | 21 | B |
| ALA | N | 651 | 180.6 | 124.1 | 25.6 | 21 | B |
| ALA | CA | 651 | 180.9 | 124.5 | 27.0 | 20 | B |
| ALA | CB | 651 | 182.1 | 125.3 | 27.1 | 19 | B |
| ALA | C | 651 | 179.7 | 125.2 | 27.6 | 20 | B |
| ALA | O | 651 | 179.3 | 125.0 | 28.7 | 20 | B |
| PRO | N | 652 | 179.1 | 126.2 | 26.9 | 20 | B |
| PRO | CD | 652 | 179.8 | 127.0 | 25.7 | 20 | B |
| PRO | CA | 652 | 178.0 | 127.0 | 27.4 | 21 | B |
| PRO | CB | 652 | 177.8 | 128.0 | 26.3 | 21 | B |
| PRO | CG | 652 | 179.1 | 128.3 | 25.9 | 20 | B |
| PRO | C | 652 | 176.8 | 126.0 | 27.4 | 22 | B |
| PRO | O | 652 | 176.0 | 126.0 | 28.4 | 23 | B |
| THR | N | 653 | 176.6 | 125.1 | 26.4 | 21 | B |
| THR | CA | 653 | 175.6 | 124.1 | 26.4 | 20 | B |
| THR | CB | 653 | 175.7 | 123.2 | 25.2 | 20 | B |
| THR | OG1 | 653 | 175.7 | 124.0 | 24.0 | 21 | B |
| THR | CG2 | 653 | 174.6 | 122.2 | 25.2 | 19 | B |
| THR | C | 653 | 175.6 | 123.2 | 27.7 | 21 | B |
| THR | O | 653 | 174.6 | 123.0 | 28.3 | 22 | B |
| TYR | N | 654 | 176.8 | 122.8 | 28.1 | 20 | B |
| TYR | CA | 654 | 176.9 | 121.9 | 29.2 | 20 | B |
| TYR | CB | 654 | 178.4 | 121.5 | 29.5 | 19 | B |
| TYR | CG | 654 | 178.7 | 121.0 | 30.8 | 18 | B |
| TYR | CD1 | 654 | 178.4 | 119.7 | 31.2 | 18 | B |
| TYR | CE1 | 654 | 178.8 | 119.3 | 32.5 | 19 | B |
| TYR | CD2 | 654 | 179.3 | 121.9 | 31.8 | 18 | B |
| TYR | CE2 | 654 | 179.6 | 121.4 | 33.0 | 19 | B |
| TYR | CZ | 654 | 179.4 | 120.1 | 33.4 | 19 | B |
| TYR | OH | 654 | 179.8 | 119.6 | 34.6 | 19 | B |
| TYR | C | 654 | 176.4 | 122.8 | 30.4 | 21 | B |
| TYR | O | 654 | 175.6 | 122.3 | 31.1 | 22 | B |
| ALA | N | 655 | 176.9 | 124.0 | 30.5 | 23 | B |
| ALA | CA | 655 | 176.6 | 124.9 | 31.6 | 23 | B |
| ALA | CB | 655 | 177.5 | 126.1 | 31.5 | 22 | B |
| ALA | C | 655 | 175.1 | 125.3 | 31.7 | 23 | B |
| ALA | O | 655 | 174.6 | 125.3 | 32.8 | 23 | B |
| ALA | N | 656 | 174.5 | 125.5 | 30.5 | 22 | B |
| ALA | CA | 656 | 173.1 | 125.9 | 30.5 | 23 | B |
| ALA | CB | 656 | 172.7 | 126.2 | 29.1 | 21 | B |
| ALA | C | 656 | 172.3 | 124.7 | 31.1 | 24 | B |
| ALA | O | 656 | 171.7 | 124.8 | 32.1 | 24 | B |
| VAL | N | 657 | 172.4 | 123.6 | 30.3 | 26 | B |
| VAL | CA | 657 | 171.7 | 122.4 | 30.7 | 27 | B |
| VAL | CB | 657 | 172.1 | 121.2 | 29.8 | 26 | B |
| VAL | CG1 | 657 | 171.3 | 119.9 | 30.2 | 27 | B |
| VAL | CG2 | 657 | 171.8 | 121.6 | 28.4 | 26 | B |
| VAL | C | 657 | 171.9 | 122.1 | 32.2 | 27 | B |
| VAL | O | 657 | 171.0 | 121.7 | 32.9 | 28 | B |
| ASN | N | 658 | 173.1 | 122.2 | 32.8 | 27 | B |
| ASN | CA | 658 | 173.4 | 122.0 | 34.2 | 28 | B |
| ASN | CB | 658 | 174.8 | 122.0 | 34.5 | 27 | B |
| ASN | CG | 658 | 175.5 | 120.7 | 34.6 | 27 | B |
| ASN | OD1 | 658 | 175.1 | 119.8 | 33.9 | 26 | B |
| ASN | ND2 | 658 | 176.4 | 120.6 | 35.6 | 28 | B |
| ASN | C | 658 | 172.6 | 122.9 | 35.0 | 29 | B |
| ASN | O | 658 | 172.0 | 122.6 | 36.0 | 30 | B |
| ALA | N | 659 | 172.6 | 124.2 | 34.6 | 29 | B |
| ALA | CA | 659 | 171.9 | 125.3 | 35.3 | 28 | B |
| ALA | CB | 659 | 172.1 | 126.6 | 34.7 | 28 | B |
| ALA | C | 659 | 170.4 | 124.9 | 35.4 | 28 | B |
| ALA | O | 659 | 169.9 | 124.6 | 36.4 | 28 | B |
| LEU | N | 660 | 169.9 | 124.8 | 34.2 | 28 | B |
| LEU | CA | 660 | 168.5 | 124.4 | 34.0 | 28 | B |
| LEU | CB | 660 | 168.2 | 124.2 | 32.5 | 27 | B |
| LEU | CG | 660 | 168.2 | 125.4 | 31.7 | 26 | B |
| LEU | CD1 | 660 | 167.8 | 125.2 | 30.3 | 26 | B |
| LEU | CD2 | 660 | 167.3 | 126.5 | 32.3 | 26 | B |
| LEU | C | 660 | 168.1 | 123.2 | 34.9 | 30 | B |
| LEU | O | 660 | 167.0 | 123.2 | 35.5 | 31 | B |
| CYS | N | 661 | 169.0 | 122.2 | 35.0 | 32 | B |

TABLE 4-continued

The following table lists the atomic structure coordinates for FPT in complex with FPP and the inhibitor SCH66701 as derived by X-ray diffraction from crystals of that complex
The abbreviations are the same as those used in Table 2

| RES | ATOM | # | X | Y | Z | B | C |
|---|---|---|---|---|---|---|---|
| CYS | CA | 661 | 168.7 | 121.1 | 35.8 | 33 | B |
| CYS | CB | 661 | 169.6 | 119.9 | 35.4 | 32 | B |
| CYS | SG | 661 | 169.1 | 119.2 | 33.9 | 31 | B |
| CYS | C | 661 | 168.8 | 121.4 | 37.3 | 35 | B |
| CYS | O | 661 | 168.0 | 120.8 | 38.1 | 36 | B |
| ILE | N | 662 | 169.6 | 122.3 | 37.7 | 37 | B |
| ILE | CA | 662 | 169.7 | 122.7 | 39.1 | 39 | B |
| ILE | CB | 662 | 170.9 | 123.6 | 39.4 | 39 | B |
| ILE | CG2 | 662 | 171.0 | 123.9 | 40.9 | 39 | B |
| ILE | CG1 | 662 | 172.2 | 123.0 | 38.9 | 39 | B |
| ILE | CD1 | 662 | 173.5 | 123.7 | 39.3 | 39 | B |
| ILE | C | 662 | 168.4 | 123.4 | 39.5 | 39 | B |
| ILE | O | 662 | 167.9 | 123.2 | 40.6 | 40 | B |
| ILE | N | 663 | 167.8 | 124.2 | 38.6 | 39 | B |
| ILE | CA | 663 | 166.5 | 124.8 | 38.8 | 39 | B |
| ILE | CB | 663 | 166.3 | 125.9 | 37.7 | 38 | B |
| ILE | CG2 | 663 | 164.9 | 126.4 | 37.8 | 38 | B |
| ILE | CG1 | 663 | 167.3 | 127.0 | 37.8 | 37 | B |
| ILE | CD1 | 663 | 167.1 | 128.0 | 36.7 | 37 | B |
| ILE | C | 663 | 165.4 | 123.8 | 38.9 | 39 | B |
| ILE | O | 663 | 164.4 | 124.0 | 39.4 | 40 | B |
| GLY | N | 664 | 165.7 | 122.6 | 38.3 | 39 | B |
| GLY | CA | 664 | 164.8 | 121.5 | 38.2 | 40 | B |
| GLY | C | 664 | 163.3 | 121.7 | 38.1 | 39 | B |
| GLY | O | 664 | 162.5 | 120.9 | 38.6 | 40 | B |
| THR | N | 665 | 162.8 | 122.8 | 37.5 | 39 | B |
| THR | CA | 665 | 161.4 | 123.0 | 37.4 | 40 | B |
| THR | CB | 665 | 161.0 | 124.5 | 37.6 | 39 | B |
| THR | OG1 | 665 | 161.2 | 125.2 | 36.3 | 38 | B |
| THR | CG2 | 665 | 161.8 | 125.1 | 38.7 | 39 | B |
| THR | C | 665 | 161.0 | 122.6 | 36.0 | 41 | B |
| THR | O | 665 | 161.8 | 122.5 | 35.1 | 41 | B |
| GLU | N | 666 | 159.7 | 122.3 | 35.9 | 44 | B |
| GLU | CA | 666 | 159.1 | 122.0 | 34.6 | 46 | B |
| GLU | CB | 666 | 157.7 | 121.4 | 34.7 | 48 | B |
| GLU | CG | 666 | 157.6 | 119.9 | 34.8 | 50 | B |
| GLU | CD | 666 | 158.2 | 119.2 | 36.1 | 50 | B |
| GLU | OE1 | 666 | 158.3 | 119.9 | 37.2 | 51 | B |
| GLU | OE2 | 666 | 158.6 | 118.0 | 36.1 | 51 | B |
| GLU | C | 666 | 159.2 | 123.1 | 33.6 | 47 | B |
| GLU | O | 666 | 158.9 | 123.0 | 32.4 | 47 | B |
| GLU | N | 667 | 159.7 | 124.3 | 34.2 | 46 | B |
| GLU | CA | 667 | 159.9 | 125.5 | 33.3 | 46 | B |
| GLU | CB | 667 | 159.8 | 126.7 | 34.2 | 47 | B |
| GLU | CG | 667 | 160.2 | 128.0 | 33.4 | 47 | B |
| GLU | CD | 667 | 160.1 | 129.3 | 34.2 | 48 | B |
| GLU | OE1 | 667 | 160.2 | 129.2 | 35.4 | 48 | B |
| GLU | OE2 | 667 | 159.8 | 130.3 | 33.5 | 49 | B |
| GLU | C | 667 | 161.3 | 125.4 | 32.8 | 44 | B |
| GLU | O | 667 | 161.5 | 125.6 | 31.6 | 45 | B |
| ALA | N | 668 | 162.2 | 125.1 | 33.7 | 43 | B |
| ALA | CA | 668 | 163.6 | 125.0 | 33.3 | 40 | B |
| ALA | CB | 668 | 164.5 | 124.6 | 34.5 | 41 | B |
| ALA | C | 668 | 163.7 | 123.9 | 32.3 | 39 | B |
| ALA | O | 668 | 164.1 | 124.1 | 31.1 | 39 | B |
| TYR | N | 669 | 163.3 | 122.6 | 32.6 | 38 | B |
| TYR | CA | 669 | 163.4 | 121.5 | 31.7 | 37 | B |
| TYR | CB | 669 | 162.7 | 120.3 | 32.3 | 35 | B |
| TYR | CG | 669 | 163.2 | 119.7 | 33.6 | 32 | B |
| TYR | CD1 | 669 | 162.3 | 119.2 | 34.6 | 31 | B |
| TYR | CE1 | 669 | 162.7 | 118.8 | 35.8 | 30 | B |
| TYR | CD2 | 669 | 164.6 | 119.8 | 34.0 | 31 | B |
| TYR | CE2 | 669 | 165.0 | 119.3 | 35.3 | 30 | B |
| TYR | CZ | 669 | 164.1 | 118.8 | 36.2 | 29 | B |
| TYR | OH | 669 | 164.4 | 118.4 | 37.4 | 27 | B |
| TYR | C | 669 | 162.8 | 121.8 | 30.4 | 37 | B |
| TYR | O | 669 | 163.4 | 121.5 | 29.3 | 38 | B |
| ASN | N | 670 | 161.8 | 122.6 | 30.4 | 38 | B |
| ASN | CA | 670 | 161.1 | 122.9 | 29.1 | 39 | B |
| ASN | CB | 670 | 159.7 | 123.4 | 29.4 | 42 | B |
| ASN | CG | 670 | 158.7 | 122.3 | 29.5 | 44 | B |
| ASN | OD1 | 670 | 159.1 | 121.2 | 30.1 | 45 | B |

TABLE 4-continued

The following table lists the atomic structure coordinates for FPT in complex with FPP and the inhibitor SCH66701 as derived by X-ray diffraction from crystals of that complex The abbreviations are the same as those used in Table 2

| RES | ATOM | # | X | Y | Z | B | C |
|---|---|---|---|---|---|---|---|
| ASN | ND2 | 670 | 157.5 | 122.5 | 28.9 | 45 | B |
| ASN | C | 670 | 161.9 | 123.9 | 28.2 | 39 | B |
| ASN | O | 670 | 161.5 | 124.1 | 27.1 | 39 | B |
| VAL | N | 671 | 162.9 | 124.6 | 28.8 | 38 | B |
| VAL | CA | 671 | 163.7 | 125.5 | 28.0 | 37 | B |
| VAL | CB | 671 | 164.7 | 126.2 | 28.9 | 38 | B |
| VAL | CG1 | 671 | 165.6 | 127.0 | 28.0 | 38 | B |
| VAL | CG2 | 671 | 164.1 | 127.0 | 30.0 | 38 | B |
| VAL | C | 671 | 164.4 | 124.7 | 26.9 | 36 | B |
| VAL | O | 671 | 164.3 | 125.1 | 25.7 | 36 | B |
| ILE | N | 672 | 165.1 | 123.6 | 27.3 | 35 | B |
| ILE | CA | 672 | 165.9 | 122.8 | 26.4 | 33 | B |
| ILE | CB | 672 | 166.5 | 121.6 | 27.2 | 31 | B |
| ILE | CG2 | 672 | 167.5 | 120.9 | 26.3 | 32 | B |
| ILE | CG1 | 672 | 167.2 | 122.2 | 28.4 | 31 | B |
| ILE | CD1 | 672 | 167.8 | 121.1 | 29.3 | 30 | B |
| ILE | C | 672 | 165.1 | 122.1 | 25.3 | 33 | B |
| ILE | O | 672 | 164.1 | 121.4 | 25.5 | 35 | B |
| ASN | N | 673 | 165.5 | 122.4 | 24.0 | 34 | B |
| ASN | CA | 673 | 164.9 | 121.9 | 22.8 | 35 | B |
| ASN | CB | 673 | 165.0 | 122.9 | 21.7 | 35 | B |
| ASN | CG | 673 | 164.5 | 122.3 | 20.4 | 35 | B |
| ASN | OD1 | 673 | 164.7 | 121.2 | 20.0 | 36 | B |
| ASN | ND2 | 673 | 163.9 | 123.2 | 19.6 | 34 | B |
| ASN | C | 673 | 165.6 | 120.6 | 22.5 | 37 | B |
| ASN | O | 673 | 166.6 | 120.6 | 21.7 | 38 | B |
| ARG | N | 674 | 165.2 | 119.5 | 23.1 | 38 | B |
| ARG | CA | 674 | 165.8 | 118.2 | 22.9 | 38 | B |
| ARG | CB | 674 | 165.1 | 117.1 | 23.8 | 37 | B |
| ARG | CG | 674 | 165.1 | 117.4 | 25.2 | 38 | B |
| ARG | CD | 674 | 164.2 | 116.4 | 26.0 | 39 | B |
| ARG | NE | 674 | 164.5 | 115.0 | 25.8 | 39 | B |
| ARG | CZ | 674 | 163.9 | 114.2 | 24.9 | 39 | B |
| ARG | NH1 | 674 | 162.9 | 114.6 | 24.1 | 39 | B |
| ARG | NH2 | 674 | 164.4 | 113.0 | 24.8 | 38 | B |
| ARG | C | 674 | 166.0 | 117.6 | 21.5 | 40 | B |
| ARG | O | 674 | 167.0 | 117.0 | 21.3 | 40 | B |
| GLU | N | 675 | 165.1 | 117.9 | 20.6 | 41 | B |
| GLU | CA | 675 | 165.3 | 117.3 | 19.3 | 44 | B |
| GLU | CB | 675 | 164.0 | 117.4 | 18.5 | 47 | B |
| GLU | CG | 675 | 163.0 | 118.6 | 18.9 | 51 | B |
| GLU | CD | 675 | 162.3 | 118.4 | 20.3 | 53 | B |
| GLU | OE1 | 675 | 162.6 | 119.2 | 21.2 | 54 | B |
| GLU | OE2 | 675 | 161.5 | 117.4 | 20.4 | 55 | B |
| GLU | C | 675 | 166.4 | 118.0 | 18.6 | 43 | B |
| GLU | O | 675 | 167.1 | 117.4 | 17.8 | 42 | B |
| LYS | N | 676 | 166.6 | 119.3 | 18.9 | 42 | B |
| LYS | CA | 676 | 167.6 | 120.1 | 18.2 | 41 | B |
| LYS | CB | 676 | 167.2 | 121.5 | 18.0 | 42 | B |
| LYS | CG | 676 | 166.6 | 121.7 | 16.6 | 43 | B |
| LYS | CD | 676 | 166.6 | 123.1 | 16.1 | 46 | B |
| LYS | CE | 676 | 165.7 | 124.0 | 17.0 | 48 | B |
| LYS | NZ | 676 | 165.5 | 125.4 | 16.6 | 49 | B |
| LYS | C | 676 | 168.9 | 120.0 | 19.0 | 39 | B |
| LYS | O | 676 | 170.0 | 120.1 | 18.3 | 39 | B |
| LEU | N | 677 | 168.9 | 119.8 | 20.3 | 36 | B |
| LEU | CA | 677 | 170.1 | 119.7 | 21.0 | 35 | B |
| LEU | CB | 677 | 169.8 | 119.4 | 22.5 | 33 | B |
| LEU | CG | 677 | 170.9 | 119.0 | 23.4 | 32 | B |
| LEU | CD1 | 677 | 172.2 | 119.8 | 23.2 | 33 | B |
| LEU | CD2 | 677 | 170.5 | 119.1 | 24.8 | 32 | B |
| LEU | C | 677 | 170.9 | 118.5 | 20.4 | 35 | B |
| LEU | O | 677 | 172.1 | 118.6 | 20.2 | 35 | B |
| LEU | N | 678 | 170.2 | 117.5 | 20.1 | 36 | B |
| LEU | CA | 678 | 170.8 | 116.2 | 19.5 | 36 | B |
| LEU | CB | 678 | 169.7 | 115.1 | 19.6 | 36 | B |
| LEU | CG | 678 | 169.8 | 113.7 | 19.0 | 36 | B |
| LEU | CD1 | 678 | 169.2 | 113.6 | 17.6 | 36 | B |
| LEU | CD2 | 678 | 171.2 | 113.1 | 19.0 | 36 | B |
| LEU | C | 678 | 171.2 | 116.5 | 18.1 | 35 | B |
| LEU | O | 678 | 172.3 | 116.0 | 17.7 | 35 | B |
| GLN | N | 679 | 170.4 | 117.2 | 17.3 | 36 | B |

TABLE 4-continued

The following table lists the atomic structure coordinates for FPT in complex with FPP and the inhibitor SCH66701 as derived by X-ray diffraction from crystals of that complex The abbreviations are the same as those used in Table 2

| RES | ATOM | # | X | Y | Z | B | C |
|---|---|---|---|---|---|---|---|
| GLN | CA | 679 | 170.7 | 117.6 | 16.0 | 37 | B |
| GLN | CB | 679 | 169.7 | 118.6 | 15.4 | 39 | B |
| GLN | CG | 679 | 169.8 | 119.0 | 14.0 | 41 | B |
| GLN | CD | 679 | 168.6 | 119.7 | 13.5 | 43 | B |
| GLN | OE1 | 679 | 168.7 | 120.9 | 13.0 | 44 | B |
| GLN | NE2 | 679 | 167.4 | 119.2 | 13.7 | 43 | B |
| GLN | C | 679 | 172.1 | 118.2 | 15.9 | 36 | B |
| GLN | O | 679 | 172.9 | 117.9 | 15.0 | 37 | B |
| TYR | N | 680 | 172.4 | 119.0 | 16.9 | 33 | B |
| TYR | CA | 680 | 173.6 | 119.7 | 17.1 | 30 | B |
| TYR | CB | 680 | 173.5 | 120.7 | 18.3 | 29 | B |
| TYR | CG | 680 | 174.7 | 121.5 | 18.6 | 26 | B |
| TYR | CD1 | 680 | 175.3 | 122.4 | 17.7 | 25 | B |
| TYR | CE1 | 680 | 176.4 | 123.2 | 18.0 | 24 | B |
| TYR | CD2 | 680 | 175.2 | 121.6 | 19.9 | 25 | B |
| TYR | CE2 | 680 | 176.2 | 122.3 | 20.3 | 24 | B |
| TYR | CZ | 680 | 176.8 | 123.1 | 19.3 | 24 | B |
| TYR | OH | 680 | 177.9 | 124.0 | 19.7 | 24 | B |
| TYR | C | 680 | 174.7 | 118.7 | 17.5 | 28 | B |
| TYR | O | 680 | 175.7 | 118.7 | 16.8 | 26 | B |
| LEU | N | 681 | 174.5 | 117.9 | 18.6 | 27 | B |
| LEU | CA | 681 | 175.6 | 117.0 | 19.0 | 27 | B |
| LEU | CB | 681 | 175.1 | 116.1 | 20.1 | 25 | B |
| LEU | CG | 681 | 174.7 | 116.8 | 21.4 | 25 | B |
| LEU | CD1 | 681 | 174.2 | 115.8 | 22.5 | 23 | B |
| LEU | CD2 | 681 | 175.9 | 117.5 | 21.9 | 24 | B |
| LEU | C | 681 | 176.1 | 116.2 | 17.8 | 28 | B |
| LEU | O | 681 | 177.2 | 115.8 | 17.6 | 28 | B |
| TYR | N | 682 | 175.1 | 115.9 | 16.8 | 29 | B |
| TYR | CA | 682 | 175.5 | 115.2 | 15.6 | 30 | B |
| TYR | CB | 682 | 174.3 | 114.7 | 14.8 | 32 | B |
| TYR | CG | 682 | 173.8 | 113.3 | 15.2 | 33 | B |
| TYR | CD1 | 682 | 172.5 | 113.1 | 15.6 | 34 | B |
| TYR | CE1 | 682 | 172.0 | 111.9 | 15.9 | 34 | B |
| TYR | CD2 | 682 | 174.6 | 112.2 | 15.1 | 34 | B |
| TYR | CE2 | 682 | 174.2 | 110.9 | 15.5 | 34 | B |
| TYR | CZ | 682 | 172.9 | 110.8 | 15.9 | 34 | B |
| TYR | OH | 682 | 172.4 | 109.5 | 16.2 | 33 | B |
| TYR | C | 682 | 176.4 | 116.1 | 14.8 | 29 | B |
| TYR | O | 682 | 177.3 | 115.6 | 14.1 | 30 | B |
| SER | N | 683 | 176.2 | 117.4 | 14.8 | 29 | B |
| SER | CA | 683 | 176.9 | 118.3 | 14.0 | 28 | B |
| SER | CB | 683 | 176.2 | 119.7 | 13.9 | 27 | B |
| SER | OG | 683 | 176.2 | 120.4 | 15.1 | 26 | B |
| SER | C | 683 | 178.4 | 118.5 | 14.4 | 27 | B |
| SER | O | 683 | 179.2 | 119.1 | 13.7 | 27 | B |
| LEU | N | 684 | 178.7 | 118.0 | 15.6 | 26 | B |
| LEU | CA | 684 | 180.1 | 118.1 | 16.1 | 26 | B |
| LEU | CB | 684 | 180.0 | 118.7 | 17.5 | 24 | B |
| LEU | CG | 684 | 179.1 | 120.0 | 17.7 | 22 | B |
| LEU | CD1 | 684 | 179.1 | 120.4 | 19.1 | 21 | B |
| LEU | CD2 | 684 | 179.6 | 121.1 | 16.8 | 20 | B |
| LEU | C | 684 | 180.8 | 116.7 | 16.1 | 27 | B |
| LEU | O | 684 | 182.0 | 116.7 | 16.0 | 28 | B |
| LYS | N | 685 | 180.0 | 115.7 | 16.1 | 27 | B |
| LYS | CA | 685 | 180.5 | 114.3 | 16.1 | 26 | B |
| LYS | CB | 685 | 179.4 | 113.3 | 15.9 | 26 | B |
| LYS | CG | 685 | 179.5 | 112.0 | 16.7 | 25 | B |
| LYS | CD | 685 | 180.9 | 111.5 | 16.7 | 26 | B |
| LYS | CE | 685 | 181.1 | 110.3 | 17.6 | 27 | B |
| LYS | NZ | 685 | 180.3 | 109.1 | 17.1 | 28 | B |
| LYS | C | 685 | 181.5 | 114.2 | 14.9 | 25 | B |
| LYS | O | 685 | 181.3 | 114.7 | 13.8 | 25 | B |
| GLN | N | 686 | 182.6 | 113.5 | 15.2 | 25 | B |
| GLN | CA | 686 | 183.7 | 113.3 | 14.2 | 26 | B |
| GLN | CB | 686 | 185.0 | 113.9 | 14.8 | 25 | B |
| GLN | CG | 686 | 185.0 | 115.4 | 15.0 | 26 | B |
| GLN | CD | 686 | 184.8 | 116.1 | 13.7 | 27 | B |
| GLN | OE1 | 686 | 185.8 | 116.3 | 13.0 | 28 | B |
| GLN | NE2 | 686 | 183.6 | 116.7 | 13.5 | 27 | B |
| GLN | C | 686 | 183.8 | 111.8 | 14.0 | 27 | B |
| GLN | O | 686 | 183.4 | 111.0 | 14.8 | 28 | B |

TABLE 4-continued

The following table lists the atomic structure coordinates for FPT in complex with FPP and the inhibitor SCH66701 as derived by X-ray diffraction from crystals of that complex The abbreviations are the same as those used in Table 2

| RES | ATOM | # | X | Y | Z | B | C |
|---|---|---|---|---|---|---|---|
| PRO | N | 687 | 184.5 | 111.5 | 12.8 | 26 | B |
| PRO | CD | 687 | 184.9 | 112.3 | 11.7 | 27 | B |
| PRO | CA | 687 | 184.6 | 110.1 | 12.5 | 26 | B |
| PRO | CB | 687 | 185.4 | 110.1 | 11.2 | 26 | B |
| PRO | CG | 687 | 184.8 | 111.3 | 10.6 | 27 | B |
| PRO | C | 687 | 185.5 | 109.4 | 13.6 | 26 | B |
| PRO | O | 687 | 185.1 | 108.3 | 14.0 | 27 | B |
| ASP | N | 688 | 186.5 | 110.0 | 14.1 | 25 | B |
| ASP | CA | 688 | 187.3 | 109.3 | 15.1 | 25 | B |
| ASP | CB | 688 | 188.7 | 109.9 | 15.2 | 26 | B |
| ASP | CG | 688 | 188.8 | 111.3 | 15.7 | 27 | B |
| ASP | OD1 | 688 | 187.8 | 112.0 | 15.8 | 28 | B |
| ASP | OD2 | 688 | 189.9 | 111.7 | 16.0 | 28 | B |
| ASP | C | 688 | 186.6 | 109.3 | 16.4 | 24 | B |
| ASP | O | 688 | 187.3 | 109.0 | 17.4 | 25 | B |
| GLY | N | 689 | 185.4 | 109.6 | 16.5 | 22 | B |
| GLY | CA | 689 | 184.6 | 109.6 | 17.7 | 21 | B |
| GLY | C | 689 | 184.7 | 110.8 | 18.6 | 20 | B |
| GLY | O | 689 | 184.1 | 110.9 | 19.6 | 21 | B |
| SER | N | 690 | 185.4 | 111.8 | 18.1 | 20 | B |
| SER | CA | 690 | 185.6 | 113.0 | 18.9 | 19 | B |
| SER | CB | 690 | 186.9 | 113.7 | 18.7 | 18 | B |
| SER | OG | 690 | 187.2 | 114.0 | 17.4 | 17 | B |
| SER | C | 690 | 184.4 | 114.0 | 18.5 | 19 | B |
| SER | O | 690 | 183.7 | 113.7 | 17.6 | 20 | B |
| PHE | N | 691 | 184.3 | 115.1 | 19.2 | 19 | B |
| PHE | CA | 691 | 183.3 | 116.1 | 19.0 | 19 | B |
| PHE | CB | 691 | 182.3 | 116.2 | 20.1 | 20 | B |
| PHE | CG | 691 | 181.4 | 115.0 | 20.2 | 19 | B |
| PHE | CD1 | 691 | 181.7 | 113.9 | 21.0 | 19 | B |
| PHE | CD2 | 691 | 180.1 | 115.1 | 19.6 | 19 | B |
| PHE | CE1 | 691 | 180.8 | 112.9 | 21.1 | 19 | B |
| PHE | CE2 | 691 | 179.2 | 114.0 | 19.7 | 19 | B |
| PHE | CZ | 691 | 179.6 | 112.9 | 20.5 | 19 | B |
| PHE | C | 691 | 184.0 | 117.5 | 18.9 | 18 | B |
| PHE | O | 691 | 185.0 | 117.8 | 19.6 | 18 | B |
| LEU | N | 692 | 183.6 | 118.3 | 17.9 | 18 | B |
| LEU | CA | 692 | 184.2 | 119.7 | 17.9 | 18 | B |
| LEU | CB | 692 | 183.6 | 120.4 | 16.7 | 17 | B |
| LEU | CG | 692 | 183.8 | 119.8 | 15.3 | 16 | B |
| LEU | CD1 | 692 | 183.1 | 120.7 | 14.3 | 15 | B |
| LEU | CD2 | 692 | 185.3 | 119.9 | 15.0 | 16 | B |
| LEU | C | 692 | 183.6 | 120.3 | 19.1 | 21 | B |
| LEU | O | 692 | 182.6 | 119.8 | 19.7 | 22 | B |
| MET | N | 693 | 184.1 | 121.5 | 19.6 | 21 | B |
| MET | CA | 693 | 183.6 | 122.2 | 20.7 | 20 | B |
| MET | CB | 693 | 184.6 | 123.1 | 21.4 | 19 | B |
| MET | CG | 693 | 185.6 | 122.3 | 22.3 | 20 | B |
| MET | SD | 693 | 184.7 | 121.5 | 23.6 | 21 | B |
| MET | CE | 693 | 184.3 | 122.8 | 24.8 | 20 | B |
| MET | C | 693 | 182.4 | 123.0 | 20.2 | 20 | B |
| MET | O | 693 | 181.5 | 123.4 | 20.9 | 21 | B |
| HIS | N | 694 | 182.5 | 123.4 | 18.9 | 21 | B |
| HIS | CA | 694 | 181.4 | 124.1 | 18.2 | 21 | B |
| HIS | CB | 694 | 181.4 | 125.5 | 18.7 | 22 | B |
| HIS | CG | 694 | 182.6 | 126.3 | 18.4 | 23 | B |
| HIS | CD2 | 694 | 183.8 | 126.4 | 19.1 | 23 | B |
| HIS | ND1 | 694 | 182.7 | 127.3 | 17.4 | 23 | B |
| HIS | CE1 | 694 | 183.9 | 127.8 | 17.4 | 24 | B |
| HIS | NE2 | 694 | 184.6 | 127.3 | 18.4 | 24 | B |
| HIS | C | 694 | 181.8 | 124.1 | 16.7 | 21 | B |
| HIS | O | 694 | 182.9 | 123.7 | 16.3 | 22 | B |
| VAL | N | 695 | 180.9 | 124.4 | 15.8 | 21 | B |
| VAL | CA | 695 | 181.2 | 124.3 | 14.4 | 21 | B |
| VAL | CB | 695 | 180.0 | 124.8 | 13.5 | 22 | B |
| VAL | CG1 | 695 | 180.4 | 124.8 | 12.1 | 23 | B |
| VAL | CG2 | 695 | 178.8 | 123.9 | 13.7 | 21 | B |
| VAL | C | 695 | 182.4 | 125.2 | 14.0 | 21 | B |
| VAL | O | 695 | 182.5 | 126.3 | 14.5 | 23 | B |
| GLY | N | 696 | 183.3 | 124.6 | 13.3 | 21 | B |
| GLY | CA | 696 | 184.5 | 125.4 | 12.9 | 21 | B |
| GLY | C | 696 | 185.5 | 125.5 | 14.1 | 21 | B |

TABLE 4-continued

The following table lists the atomic structure coordinates for FPT in complex with FPP and the inhibitor SCH66701 as derived by X-ray diffraction from crystals of that complex The abbreviations are the same as those used in Table 2

| RES | ATOM | # | X | Y | Z | B | C |
|---|---|---|---|---|---|---|---|
| GLY | O | 696 | 186.6 | 125.9 | 13.9 | 22 | B |
| GLY | N | 697 | 185.1 | 125.0 | 15.3 | 21 | B |
| GLY | CA | 697 | 185.9 | 125.1 | 16.5 | 20 | B |
| GLY | C | 697 | 186.9 | 123.9 | 16.7 | 20 | B |
| GLY | O | 697 | 187.1 | 123.0 | 15.9 | 20 | B |
| GLU | N | 698 | 187.6 | 124.0 | 17.8 | 20 | B |
| GLU | CA | 698 | 188.6 | 123.0 | 18.3 | 21 | B |
| GLU | CB | 698 | 189.6 | 123.7 | 19.3 | 22 | B |
| GLU | CG | 698 | 189.0 | 123.9 | 20.7 | 23 | B |
| GLU | CD | 698 | 188.1 | 125.0 | 21.0 | 24 | B |
| GLU | OE1 | 698 | 187.7 | 125.8 | 20.0 | 24 | B |
| GLU | OE2 | 698 | 187.7 | 125.3 | 22.2 | 25 | B |
| GLU | C | 698 | 188.0 | 121.7 | 18.8 | 21 | B |
| GLU | O | 698 | 186.8 | 121.6 | 19.1 | 21 | B |
| VAL | N | 699 | 188.9 | 120.7 | 19.0 | 20 | B |
| VAL | CA | 699 | 188.5 | 119.4 | 19.5 | 19 | B |
| VAL | CB | 699 | 188.6 | 118.3 | 18.4 | 19 | B |
| VAL | CG1 | 699 | 188.8 | 116.9 | 18.9 | 18 | B |
| VAL | CG2 | 699 | 187.4 | 118.3 | 17.5 | 19 | B |
| VAL | C | 699 | 189.4 | 118.9 | 20.7 | 20 | B |
| VAL | O | 699 | 190.6 | 119.0 | 20.6 | 19 | B |
| ASP | N | 700 | 188.7 | 118.3 | 21.7 | 20 | B |
| ASP | CA | 700 | 189.4 | 117.8 | 22.9 | 20 | B |
| ASP | CB | 700 | 190.4 | 118.8 | 23.5 | 21 | B |
| ASP | CG | 700 | 189.7 | 119.9 | 24.2 | 22 | B |
| ASP | OD1 | 700 | 188.8 | 119.7 | 25.1 | 22 | B |
| ASP | OD2 | 700 | 190.0 | 121.1 | 23.9 | 23 | B |
| ASP | C | 700 | 188.4 | 117.2 | 23.9 | 21 | B |
| ASP | O | 700 | 187.2 | 117.5 | 23.8 | 21 | B |
| VAL | N | 701 | 188.9 | 116.4 | 24.8 | 20 | B |
| VAL | CA | 701 | 188.0 | 115.8 | 25.8 | 21 | B |
| VAL | CB | 701 | 188.7 | 115.0 | 27.0 | 20 | B |
| VAL | CG1 | 701 | 188.7 | 113.6 | 26.7 | 20 | B |
| VAL | CG2 | 701 | 190.0 | 115.6 | 27.2 | 21 | B |
| VAL | C | 701 | 186.9 | 116.6 | 26.4 | 22 | B |
| VAL | O | 701 | 185.8 | 116.0 | 26.7 | 23 | B |
| ARG | N | 702 | 187.1 | 117.9 | 26.6 | 23 | B |
| ARG | CA | 702 | 186.0 | 118.7 | 27.2 | 23 | B |
| ARG | CB | 702 | 186.3 | 120.2 | 27.1 | 23 | B |
| ARG | CG | 702 | 187.4 | 120.7 | 28.1 | 23 | B |
| ARG | CD | 702 | 187.8 | 122.1 | 27.7 | 24 | B |
| ARG | NE | 702 | 188.2 | 122.2 | 26.2 | 25 | B |
| ARG | CZ | 702 | 187.9 | 123.2 | 25.4 | 25 | B |
| ARG | NH1 | 702 | 188.2 | 123.1 | 24.1 | 25 | B |
| ARG | NH2 | 702 | 187.3 | 124.3 | 25.9 | 26 | B |
| ARG | C | 702 | 184.7 | 118.4 | 26.4 | 24 | B |
| ARG | O | 702 | 183.6 | 118.1 | 27.0 | 24 | B |
| SER | N | 703 | 184.8 | 118.3 | 25.1 | 23 | B |
| SER | CA | 703 | 183.6 | 118.0 | 24.2 | 24 | B |
| SER | CB | 703 | 183.9 | 118.3 | 22.7 | 24 | B |
| SER | OG | 703 | 184.7 | 117.2 | 22.2 | 25 | B |
| SER | C | 703 | 182.9 | 116.7 | 24.4 | 24 | B |
| SER | O | 703 | 181.7 | 116.6 | 24.3 | 26 | B |
| ALA | N | 704 | 183.7 | 115.6 | 24.6 | 24 | B |
| ALA | CA | 704 | 183.2 | 114.3 | 24.8 | 23 | B |
| ALA | CB | 704 | 184.3 | 113.3 | 24.9 | 23 | B |
| ALA | C | 704 | 182.3 | 114.3 | 26.1 | 23 | B |
| ALA | O | 704 | 181.3 | 113.6 | 26.2 | 22 | B |
| TYR | N | 705 | 182.8 | 115.0 | 27.1 | 23 | B |
| TYR | CA | 705 | 182.2 | 115.2 | 28.4 | 24 | B |
| TYR | CB | 705 | 183.1 | 115.6 | 29.4 | 24 | B |
| TYR | CG | 705 | 182.5 | 116.0 | 30.7 | 23 | B |
| TYR | CD1 | 705 | 181.8 | 115.0 | 31.5 | 23 | B |
| TYR | CE1 | 705 | 181.3 | 115.4 | 32.8 | 23 | B |
| TYR | CD2 | 705 | 182.5 | 117.3 | 31.2 | 23 | B |
| TYR | CE2 | 705 | 182.0 | 117.6 | 32.4 | 23 | B |
| TYR | CZ | 705 | 181.4 | 116.7 | 33.2 | 23 | B |
| TYR | OH | 705 | 180.9 | 117.0 | 34.4 | 22 | B |
| TYR | C | 705 | 180.9 | 116.1 | 28.3 | 24 | B |
| TYR | O | 705 | 179.9 | 115.9 | 29.0 | 24 | B |
| CYS | N | 706 | 181.1 | 117.2 | 27.6 | 24 | B |
| CYS | CA | 706 | 179.9 | 118.1 | 27.6 | 24 | B |

TABLE 4-continued

The following table lists the atomic structure coordinates for FPT in complex with FPP and the inhibitor SCH66701 as derived by X-ray diffraction from crystals of that complex The abbreviations are the same as those used in Table 2

| RES | ATOM | # | X | Y | Z | B | C |
|---|---|---|---|---|---|---|---|
| CYS | CB | 706 | 180.3 | 119.4 | 26.8 | 25 | B |
| CYS | SG | 706 | 181.5 | 120.4 | 27.6 | 25 | B |
| CYS | C | 706 | 178.8 | 117.4 | 26.9 | 25 | B |
| CYS | O | 706 | 177.7 | 117.3 | 27.5 | 26 | B |
| ALA | N | 707 | 179.1 | 116.8 | 25.7 | 24 | B |
| ALA | CA | 707 | 178.1 | 116.0 | 25.0 | 23 | B |
| ALA | CB | 707 | 178.7 | 115.5 | 23.7 | 21 | B |
| ALA | C | 707 | 177.5 | 114.8 | 25.8 | 22 | B |
| ALA | O | 707 | 176.3 | 114.7 | 26.0 | 21 | B |
| ALA | N | 708 | 178.4 | 114.0 | 26.4 | 23 | B |
| ALA | CA | 708 | 177.9 | 112.9 | 27.2 | 24 | B |
| ALA | CB | 708 | 179.1 | 112.0 | 27.7 | 24 | B |
| ALA | C | 708 | 177.0 | 113.3 | 28.4 | 26 | B |
| ALA | O | 708 | 176.1 | 112.5 | 28.8 | 27 | B |
| SER | N | 709 | 177.3 | 114.5 | 29.0 | 26 | B |
| SER | CA | 709 | 176.5 | 115.0 | 30.1 | 25 | B |
| SER | CB | 709 | 177.3 | 116.1 | 30.8 | 25 | B |
| SER | OG | 709 | 176.6 | 116.5 | 32.0 | 24 | B |
| SER | C | 709 | 175.1 | 115.5 | 29.7 | 26 | B |
| SER | O | 709 | 174.1 | 115.1 | 30.3 | 26 | B |
| VAL | N | 710 | 175.1 | 116.3 | 28.7 | 27 | B |
| VAL | CA | 710 | 173.8 | 116.9 | 28.2 | 27 | B |
| VAL | CB | 710 | 174.0 | 118.1 | 27.3 | 26 | B |
| VAL | CG1 | 710 | 174.9 | 119.2 | 27.9 | 25 | B |
| VAL | CG2 | 710 | 174.6 | 117.7 | 26.0 | 26 | B |
| VAL | C | 710 | 172.9 | 115.9 | 27.5 | 27 | B |
| VAL | O | 710 | 171.7 | 115.8 | 27.8 | 27 | B |
| ALA | N | 711 | 173.5 | 115.1 | 26.6 | 28 | B |
| ALA | CA | 711 | 172.7 | 114.0 | 25.9 | 28 | B |
| ALA | CB | 711 | 173.5 | 113.3 | 24.9 | 28 | B |
| ALA | C | 711 | 172.1 | 113.0 | 26.9 | 29 | B |
| ALA | O | 711 | 171.0 | 112.6 | 26.7 | 29 | B |
| SER | N | 712 | 172.9 | 112.7 | 27.9 | 30 | B |
| SER | CA | 712 | 172.4 | 111.7 | 28.9 | 31 | B |
| SER | CB | 712 | 173.5 | 111.1 | 29.8 | 30 | B |
| SER | OG | 712 | 174.2 | 112.0 | 30.7 | 30 | B |
| SER | C | 712 | 171.3 | 112.3 | 29.8 | 31 | B |
| SER | O | 712 | 170.2 | 111.7 | 29.9 | 32 | B |
| LEU | N | 713 | 171.6 | 113.5 | 30.4 | 31 | B |
| LEU | CA | 713 | 170.6 | 114.1 | 31.2 | 32 | B |
| LEU | CB | 713 | 171.1 | 115.5 | 31.8 | 31 | B |
| LEU | CG | 713 | 172.1 | 115.4 | 32.9 | 30 | B |
| LEU | CD1 | 713 | 172.4 | 116.8 | 33.4 | 29 | B |
| LEU | CD2 | 713 | 171.5 | 114.7 | 34.1 | 30 | B |
| LEU | C | 713 | 169.3 | 114.3 | 30.5 | 33 | B |
| LEU | O | 713 | 168.2 | 114.0 | 31.1 | 34 | B |
| THR | N | 714 | 169.3 | 114.8 | 29.3 | 34 | B |
| THR | CA | 714 | 168.1 | 115.0 | 28.5 | 33 | B |
| THR | CB | 714 | 168.2 | 116.3 | 27.6 | 33 | B |
| THR | OG1 | 714 | 169.4 | 116.1 | 26.8 | 33 | B |
| THR | CG2 | 714 | 168.4 | 117.5 | 28.4 | 32 | B |
| THR | C | 714 | 167.6 | 113.8 | 27.8 | 34 | B |
| THR | O | 714 | 166.7 | 113.9 | 27.0 | 35 | B |
| ASN | N | 715 | 168.2 | 112.6 | 28.0 | 34 | B |
| ASN | CA | 715 | 167.8 | 111.4 | 27.4 | 33 | B |
| ASN | CB | 715 | 166.5 | 110.9 | 28.0 | 34 | B |
| ASN | CG | 715 | 165.8 | 109.7 | 27.4 | 35 | B |
| ASN | OD1 | 715 | 166.5 | 108.8 | 26.9 | 37 | B |
| ASN | ND2 | 715 | 164.5 | 109.6 | 27.4 | 36 | B |
| ASN | C | 715 | 167.7 | 111.5 | 25.9 | 32 | B |
| ASN | O | 715 | 166.6 | 111.4 | 25.3 | 32 | B |
| ILE | N | 716 | 168.8 | 111.8 | 25.2 | 31 | B |
| ILE | CA | 716 | 168.7 | 111.9 | 23.7 | 31 | B |
| ILE | CB | 716 | 169.0 | 113.4 | 23.3 | 31 | B |
| ILE | CG2 | 716 | 167.8 | 114.2 | 23.6 | 31 | B |
| ILE | CG1 | 716 | 170.2 | 113.9 | 23.9 | 31 | B |
| ILE | CD1 | 716 | 170.7 | 115.2 | 23.2 | 31 | B |
| ILE | C | 716 | 169.8 | 111.1 | 23.1 | 30 | B |
| ILE | O | 716 | 170.2 | 111.3 | 22.0 | 30 | B |
| ILE | N | 717 | 170.4 | 110.2 | 23.9 | 30 | B |
| ILE | CA | 717 | 171.5 | 109.4 | 23.5 | 31 | B |
| ILE | CB | 717 | 172.2 | 108.6 | 24.6 | 31 | B |
| ILE | CG2 | 717 | 173.3 | 107.7 | 24.1 | 31 | B |
| ILE | CG1 | 717 | 172.7 | 109.6 | 25.6 | 31 | B |
| ILE | CD1 | 717 | 173.6 | 109.0 | 26.7 | 30 | B |
| ILE | C | 717 | 170.9 | 108.3 | 22.5 | 33 | B |
| ILE | O | 717 | 170.1 | 107.5 | 22.9 | 33 | B |
| THR | N | 718 | 171.2 | 108.5 | 21.2 | 33 | B |
| THR | CA | 718 | 170.7 | 107.6 | 20.2 | 34 | B |
| THR | CB | 718 | 170.8 | 108.2 | 18.8 | 33 | B |
| THR | OG1 | 718 | 172.2 | 108.5 | 18.5 | 33 | B |
| THR | CG2 | 718 | 170.0 | 109.5 | 18.8 | 32 | B |
| THR | C | 718 | 171.7 | 106.4 | 20.3 | 36 | B |
| THR | O | 718 | 172.3 | 106.2 | 21.3 | 37 | B |
| PRO | N | 719 | 171.8 | 105.5 | 19.3 | 38 | B |
| PRO | CD | 719 | 170.7 | 105.2 | 18.3 | 39 | B |
| PRO | CA | 719 | 172.7 | 104.4 | 19.4 | 38 | B |
| PRO | CB | 719 | 172.0 | 103.4 | 18.5 | 39 | B |
| PRO | CG | 719 | 170.6 | 103.8 | 18.5 | 39 | B |
| PRO | C | 719 | 174.1 | 104.7 | 18.8 | 38 | B |
| PRO | O | 719 | 175.1 | 104.3 | 19.4 | 39 | B |
| ASP | N | 720 | 174.1 | 105.4 | 17.7 | 39 | B |
| ASP | CA | 720 | 175.4 | 105.8 | 17.1 | 39 | B |
| ASP | CB | 720 | 175.3 | 105.7 | 15.6 | 41 | B |
| ASP | CG | 720 | 174.3 | 106.8 | 15.1 | 41 | B |
| ASP | OD1 | 720 | 174.4 | 107.2 | 13.9 | 42 | B |
| ASP | OD2 | 720 | 173.4 | 107.2 | 15.9 | 42 | B |
| ASP | C | 720 | 176.0 | 107.1 | 17.5 | 39 | B |
| ASP | O | 720 | 177.0 | 107.5 | 17.0 | 39 | B |
| LEU | N | 721 | 175.3 | 107.9 | 18.4 | 38 | B |
| LEU | CA | 721 | 175.8 | 109.2 | 18.8 | 38 | B |
| LEU | CB | 721 | 174.8 | 109.8 | 19.9 | 36 | B |
| LEU | CG | 721 | 175.2 | 111.2 | 20.3 | 36 | B |
| LEU | CD1 | 721 | 175.3 | 112.1 | 19.1 | 35 | B |
| LEU | CD2 | 721 | 174.1 | 111.7 | 21.3 | 35 | B |
| LEU | C | 721 | 177.2 | 109.1 | 19.3 | 38 | B |
| LEU | O | 721 | 178.1 | 109.8 | 18.8 | 38 | B |
| PHE | N | 722 | 177.4 | 108.3 | 20.4 | 38 | B |
| PHE | CA | 722 | 178.8 | 108.2 | 20.9 | 38 | B |
| PHE | CB | 722 | 178.6 | 108.1 | 22.5 | 39 | B |
| PHE | CG | 722 | 178.1 | 109.4 | 23.1 | 40 | B |
| PHE | CD1 | 722 | 176.7 | 109.4 | 23.4 | 40 | B |
| PHE | CD2 | 722 | 178.9 | 110.5 | 23.2 | 41 | B |
| PHE | CE1 | 722 | 176.2 | 110.6 | 23.9 | 40 | B |
| PHE | CE2 | 722 | 178.3 | 111.7 | 23.7 | 41 | B |
| PHE | CZ | 722 | 177.0 | 111.7 | 24.0 | 41 | B |
| PHE | C | 722 | 179.6 | 107.1 | 20.4 | 39 | B |
| PHE | O | 722 | 180.5 | 106.6 | 21.0 | 40 | B |
| GLU | N | 723 | 179.3 | 106.7 | 19.2 | 39 | B |
| GLU | CA | 723 | 180.0 | 105.6 | 18.5 | 39 | B |
| GLU | CB | 723 | 179.4 | 105.3 | 17.2 | 42 | B |
| GLU | CG | 723 | 179.5 | 103.8 | 16.8 | 45 | B |
| GLU | CD | 723 | 179.2 | 103.0 | 18.1 | 47 | B |
| GLU | OE1 | 723 | 178.1 | 103.1 | 18.6 | 48 | B |
| GLU | OE2 | 723 | 180.2 | 102.3 | 18.6 | 48 | B |
| GLU | C | 723 | 181.5 | 105.9 | 18.4 | 36 | B |
| GLU | O | 723 | 181.9 | 106.9 | 17.7 | 35 | B |
| GLY | N | 724 | 182.3 | 105.2 | 19.1 | 34 | B |
| GLY | CA | 724 | 183.7 | 105.4 | 19.0 | 32 | B |
| GLY | C | 724 | 184.3 | 106.4 | 20.0 | 30 | B |
| GLY | O | 724 | 185.5 | 106.5 | 20.0 | 30 | B |
| THR | N | 725 | 183.5 | 107.1 | 20.7 | 28 | B |
| THR | CA | 725 | 184.1 | 108.2 | 21.6 | 27 | B |
| THR | CB | 725 | 183.1 | 109.4 | 21.8 | 27 | B |
| THR | OG1 | 725 | 182.7 | 109.5 | 23.2 | 28 | B |
| THR | CG2 | 725 | 181.9 | 109.3 | 20.9 | 27 | B |
| THR | C | 725 | 184.7 | 107.6 | 22.9 | 26 | B |
| THR | O | 725 | 185.5 | 108.3 | 23.5 | 26 | B |
| ALA | N | 726 | 184.4 | 106.4 | 23.2 | 25 | B |
| ALA | CA | 726 | 185.0 | 105.9 | 24.4 | 25 | B |
| ALA | CB | 726 | 184.3 | 104.6 | 24.9 | 26 | B |
| ALA | C | 726 | 186.4 | 105.5 | 24.0 | 25 | B |
| ALA | O | 726 | 187.4 | 105.6 | 24.8 | 25 | B |
| GLU | N | 727 | 186.5 | 105.0 | 22.7 | 25 | B |

TABLE 4-continued

The following table lists the atomic structure coordinates for FPT in complex with FPP and the inhibitor SCH66701 as derived by X-ray diffraction from crystals of that complex
The abbreviations are the same as those used in Table 2

| RES | ATOM | # | X | Y | Z | B | C |
|---|---|---|---|---|---|---|---|
| GLU | CA | 727 | 187.8 | 104.6 | 22.2 | 24 | B |
| GLU | CB | 727 | 187.6 | 104.0 | 20.8 | 25 | B |
| GLU | CG | 727 | 187.2 | 102.5 | 20.7 | 26 | B |
| GLU | CD | 727 | 185.7 | 102.3 | 21.2 | 26 | B |
| GLU | OE1 | 727 | 185.6 | 101.2 | 21.9 | 27 | B |
| GLU | OE2 | 727 | 184.8 | 103.0 | 20.9 | 26 | B |
| GLU | C | 727 | 188.7 | 105.8 | 22.1 | 23 | B |
| GLU | O | 727 | 189.8 | 105.9 | 22.6 | 24 | B |
| TRP | N | 728 | 188.2 | 106.9 | 21.4 | 22 | B |
| TRP | CA | 728 | 189.0 | 108.1 | 21.3 | 21 | B |
| TRP | CB | 728 | 188.2 | 109.2 | 20.6 | 20 | B |
| TRP | CG | 728 | 189.0 | 110.3 | 20.2 | 20 | B |
| TRP | CD2 | 728 | 189.3 | 111.5 | 21.0 | 20 | B |
| TRP | CE2 | 728 | 190.1 | 112.3 | 20.2 | 21 | B |
| TRP | CE3 | 728 | 188.8 | 112.0 | 22.2 | 20 | B |
| TRP | CD1 | 728 | 189.8 | 110.5 | 19.1 | 19 | B |
| TRP | NE1 | 728 | 190.4 | 111.7 | 19.1 | 20 | B |
| TRP | CZ2 | 728 | 190.6 | 113.6 | 20.7 | 21 | B |
| TRP | CZ3 | 728 | 189.2 | 113.2 | 22.7 | 21 | B |
| TRP | CH2 | 728 | 190.1 | 114.0 | 21.9 | 20 | B |
| TRP | C | 728 | 189.4 | 108.6 | 22.7 | 21 | B |
| TRP | O | 728 | 190.6 | 108.8 | 22.9 | 21 | B |
| ILE | N | 729 | 188.4 | 108.8 | 23.6 | 20 | B |
| ILE | CA | 729 | 188.8 | 109.2 | 25.0 | 19 | B |
| ILE | CB | 729 | 187.6 | 109.3 | 25.9 | 17 | B |
| ILE | CG2 | 729 | 188.1 | 109.7 | 27.3 | 15 | B |
| ILE | CG1 | 729 | 186.6 | 110.3 | 25.4 | 17 | B |
| ILE | CD1 | 729 | 185.3 | 110.3 | 26.2 | 18 | B |
| ILE | C | 729 | 189.9 | 108.3 | 25.6 | 20 | B |
| ILE | O | 729 | 190.8 | 108.8 | 26.3 | 21 | B |
| ALA | N | 730 | 189.9 | 107.1 | 25.3 | 22 | B |
| ALA | CA | 730 | 190.9 | 106.1 | 25.8 | 23 | B |
| ALA | CB | 730 | 190.4 | 104.7 | 25.5 | 24 | B |
| ALA | C | 730 | 192.3 | 106.4 | 25.2 | 24 | B |
| ALA | O | 730 | 193.3 | 106.1 | 25.8 | 25 | B |
| ARG | N | 731 | 192.3 | 107.0 | 24.0 | 23 | B |
| ARG | CA | 731 | 193.6 | 107.4 | 23.4 | 23 | B |
| ARG | CB | 731 | 193.4 | 107.5 | 21.9 | 23 | B |
| ARG | CG | 731 | 193.1 | 106.3 | 21.2 | 23 | B |
| ARG | CD | 731 | 193.5 | 106.3 | 19.8 | 22 | B |
| ARG | NE | 731 | 192.7 | 107.3 | 19.0 | 23 | B |
| ARG | CZ | 731 | 193.2 | 108.2 | 18.2 | 24 | B |
| ARG | NH1 | 731 | 194.5 | 108.4 | 18.2 | 24 | B |
| ARG | NH2 | 731 | 192.4 | 109.0 | 17.5 | 24 | B |
| ARG | C | 731 | 194.2 | 108.6 | 24.0 | 24 | B |
| ARG | O | 731 | 195.3 | 109.0 | 23.6 | 24 | B |
| CYS | N | 732 | 193.5 | 109.2 | 24.9 | 22 | B |
| CYS | CA | 732 | 194.0 | 110.4 | 25.6 | 21 | B |
| CYS | CB | 732 | 192.8 | 111.4 | 25.9 | 20 | B |
| CYS | SG | 732 | 192.1 | 111.9 | 24.3 | 22 | B |
| CYS | C | 732 | 194.7 | 110.0 | 26.8 | 21 | B |
| CYS | O | 732 | 195.5 | 110.9 | 27.4 | 23 | B |
| GLN | N | 733 | 194.6 | 108.8 | 27.3 | 20 | B |
| GLN | CA | 733 | 195.4 | 108.4 | 28.5 | 19 | B |
| GLN | CB | 733 | 194.8 | 107.1 | 29.1 | 19 | B |
| GLN | CG | 733 | 195.4 | 106.6 | 30.4 | 18 | B |
| GLN | CD | 733 | 194.7 | 105.4 | 31.0 | 19 | B |
| GLN | OE1 | 733 | 194.1 | 104.6 | 30.2 | 19 | B |
| GLN | NE2 | 733 | 194.8 | 105.2 | 32.3 | 18 | B |
| GLN | C | 733 | 196.8 | 108.2 | 28.0 | 20 | B |
| GLN | O | 733 | 197.0 | 107.5 | 27.1 | 21 | B |
| ASN | N | 734 | 197.8 | 108.8 | 28.7 | 19 | B |
| ASN | CA | 734 | 199.2 | 108.7 | 28.3 | 18 | B |
| ASN | CB | 734 | 199.8 | 110.1 | 28.0 | 17 | B |
| ASN | CG | 734 | 200.2 | 110.8 | 29.3 | 17 | B |
| ASN | OD1 | 734 | 199.9 | 110.4 | 30.4 | 16 | B |
| ASN | ND2 | 734 | 200.9 | 111.9 | 29.1 | 17 | B |
| ASN | C | 734 | 200.1 | 107.9 | 29.3 | 17 | B |
| ASN | O | 734 | 199.6 | 107.3 | 30.2 | 17 | B |
| TRP | N | 735 | 201.4 | 107.9 | 29.0 | 17 | B |
| TRP | CA | 735 | 202.3 | 107.2 | 29.9 | 18 | B |
| TRP | CB | 735 | 203.7 | 107.4 | 29.4 | 17 | B |

TABLE 4-continued

The following table lists the atomic structure coordinates for FPT in complex with FPP and the inhibitor SCH66701 as derived by X-ray diffraction from crystals of that complex
The abbreviations are the same as those used in Table 2

| RES | ATOM | # | X | Y | Z | B | C |
|---|---|---|---|---|---|---|---|
| TRP | CG | 735 | 204.0 | 108.9 | 29.3 | 18 | B |
| TRP | CD2 | 735 | 204.8 | 109.7 | 30.3 | 18 | B |
| TRP | CE2 | 735 | 204.8 | 111.0 | 29.8 | 18 | B |
| TRP | CE3 | 735 | 205.4 | 109.4 | 31.5 | 18 | B |
| TRP | CD1 | 735 | 203.7 | 109.7 | 28.3 | 19 | B |
| TRP | NE1 | 735 | 204.1 | 111.0 | 28.6 | 19 | B |
| TRP | CZ2 | 735 | 205.4 | 112.0 | 30.4 | 19 | B |
| TRP | CZ3 | 735 | 206.0 | 110.4 | 32.2 | 18 | B |
| TRP | CH2 | 735 | 206.0 | 111.7 | 31.6 | 18 | B |
| TRP | C | 735 | 202.2 | 107.5 | 31.4 | 19 | B |
| TRP | O | 735 | 202.7 | 106.8 | 32.3 | 21 | B |
| GLU | N | 736 | 201.7 | 108.7 | 31.7 | 19 | B |
| GLU | CA | 736 | 201.6 | 109.2 | 33.1 | 19 | B |
| GLU | CB | 736 | 201.4 | 110.7 | 33.2 | 19 | B |
| GLU | CG | 736 | 202.6 | 111.5 | 32.8 | 20 | B |
| GLU | CD | 736 | 202.2 | 113.0 | 32.6 | 20 | B |
| GLU | OE1 | 736 | 201.9 | 113.3 | 31.4 | 19 | B |
| GLU | OE2 | 736 | 202.2 | 113.8 | 33.5 | 20 | B |
| GLU | C | 736 | 200.4 | 108.5 | 33.9 | 18 | B |
| GLU | O | 736 | 200.5 | 108.5 | 35.1 | 20 | B |
| GLY | N | 737 | 199.4 | 108.0 | 33.1 | 16 | B |
| GLY | CA | 737 | 198.3 | 107.4 | 33.8 | 14 | B |
| GLY | C | 737 | 197.1 | 108.4 | 33.7 | 13 | B |
| GLY | O | 737 | 196.0 | 108.0 | 33.6 | 14 | B |
| GLY | N | 738 | 197.4 | 109.7 | 33.6 | 12 | B |
| GLY | CA | 738 | 196.4 | 110.7 | 33.4 | 11 | B |
| GLY | C | 738 | 195.9 | 110.7 | 31.9 | 11 | B |
| GLY | O | 738 | 196.3 | 110.0 | 31.1 | 10 | B |
| ILE | N | 739 | 195.0 | 111.7 | 31.7 | 10 | B |
| ILE | CA | 739 | 194.4 | 111.9 | 30.4 | 9 | B |
| ILE | CB | 739 | 192.9 | 111.7 | 30.4 | 9 | B |
| ILE | CG2 | 739 | 192.3 | 112.1 | 29.1 | 9 | B |
| ILE | CG1 | 739 | 192.6 | 110.2 | 30.8 | 8 | B |
| ILE | CD1 | 739 | 191.1 | 109.8 | 30.8 | 7 | B |
| ILE | C | 739 | 194.8 | 113.3 | 29.9 | 9 | B |
| ILE | O | 739 | 194.8 | 114.2 | 30.7 | 10 | B |
| GLY | N | 740 | 195.0 | 113.5 | 28.6 | 9 | B |
| GLY | CA | 740 | 195.3 | 114.8 | 28.0 | 9 | B |
| GLY | C | 740 | 194.2 | 115.3 | 27.2 | 11 | B |
| GLY | O | 740 | 193.1 | 114.7 | 27.0 | 11 | B |
| GLY | N | 741 | 194.3 | 116.5 | 26.7 | 12 | B |
| GLY | CA | 741 | 193.3 | 117.1 | 25.9 | 14 | B |
| GLY | C | 741 | 193.0 | 116.4 | 24.6 | 16 | B |
| GLY | O | 741 | 191.8 | 116.3 | 24.2 | 16 | B |
| VAL | N | 742 | 194.0 | 115.9 | 24.0 | 17 | B |
| VAL | CA | 742 | 194.0 | 115.1 | 22.7 | 16 | B |
| VAL | CB | 742 | 194.3 | 116.0 | 21.5 | 16 | B |
| VAL | CG1 | 742 | 193.2 | 117.0 | 21.3 | 15 | B |
| VAL | CG2 | 742 | 195.6 | 116.7 | 21.6 | 16 | B |
| VAL | C | 742 | 195.1 | 114.1 | 22.9 | 18 | B |
| VAL | O | 742 | 196.1 | 114.4 | 23.7 | 18 | B |
| PRO | N | 743 | 195.1 | 113.0 | 22.2 | 17 | B |
| PRO | CD | 743 | 194.1 | 112.5 | 21.2 | 17 | B |
| PRO | CA | 743 | 196.2 | 112.0 | 22.3 | 17 | B |
| PRO | CB | 743 | 195.8 | 111.0 | 21.2 | 17 | B |
| PRO | CG | 743 | 194.4 | 111.0 | 21.1 | 16 | B |
| PRO | C | 743 | 197.6 | 112.5 | 22.1 | 17 | B |
| PRO | O | 743 | 197.9 | 113.3 | 21.2 | 18 | B |
| GLY | N | 744 | 198.5 | 112.2 | 23.0 | 17 | B |
| GLY | CA | 744 | 199.9 | 112.7 | 22.9 | 17 | B |
| GLY | C | 744 | 200.2 | 113.7 | 23.9 | 19 | B |
| GLY | O | 744 | 201.4 | 113.8 | 24.3 | 18 | B |
| MET | N | 745 | 199.2 | 114.5 | 24.3 | 20 | B |
| MET | CA | 745 | 199.4 | 115.6 | 25.3 | 20 | B |
| MET | CB | 745 | 198.2 | 116.5 | 25.3 | 20 | B |
| MET | CG | 745 | 198.3 | 117.7 | 24.3 | 21 | B |
| MET | SD | 745 | 200.0 | 118.3 | 24.1 | 23 | B |
| MET | CE | 745 | 200.2 | 119.1 | 25.6 | 23 | B |
| MET | C | 745 | 199.6 | 115.2 | 26.7 | 20 | B |
| MET | O | 745 | 199.3 | 114.1 | 27.2 | 20 | B |
| GLU | N | 746 | 200.2 | 116.1 | 27.5 | 20 | B |
| GLU | CA | 746 | 200.6 | 115.8 | 28.9 | 21 | B |

TABLE 4-continued

The following table lists the atomic structure coordinates for FPT in complex with FPP and the inhibitor SCH66701 as derived by X-ray diffraction from crystals of that complex The abbreviations are the same as those used in Table 2

| RES | ATOM | # | X | Y | Z | B | C |
|---|---|---|---|---|---|---|---|
| GLU | CB | 746 | 201.3 | 117.0 | 29.5 | 21 | B |
| GLU | CG | 746 | 201.6 | 116.9 | 30.9 | 23 | B |
| GLU | CD | 746 | 202.2 | 118.2 | 31.4 | 24 | B |
| GLU | OE1 | 746 | 202.0 | 119.3 | 30.8 | 25 | B |
| GLU | OE2 | 746 | 202.9 | 118.1 | 32.5 | 25 | B |
| GLU | C | 746 | 199.3 | 115.5 | 29.7 | 21 | B |
| GLU | O | 746 | 198.2 | 116.1 | 29.4 | 22 | B |
| ALA | N | 747 | 199.4 | 114.7 | 30.7 | 21 | B |
| ALA | CA | 747 | 198.2 | 114.4 | 31.5 | 21 | B |
| ALA | CB | 747 | 198.5 | 113.2 | 32.4 | 22 | B |
| ALA | C | 747 | 197.9 | 115.6 | 32.3 | 21 | B |
| ALA | O | 747 | 198.7 | 116.2 | 33.0 | 20 | B |
| HIS | N | 748 | 196.6 | 116.0 | 32.3 | 21 | B |
| HIS | CA | 748 | 196.0 | 117.1 | 33.0 | 20 | B |
| HIS | CB | 748 | 195.7 | 118.3 | 32.0 | 20 | B |
| HIS | CG | 748 | 195.6 | 119.6 | 32.6 | 20 | B |
| HIS | CD2 | 748 | 196.6 | 120.6 | 32.7 | 21 | B |
| HIS | ND1 | 748 | 194.5 | 120.1 | 33.2 | 20 | B |
| HIS | CE1 | 748 | 194.7 | 121.3 | 33.7 | 20 | B |
| HIS | NE2 | 748 | 196.0 | 121.6 | 33.4 | 21 | B |
| HIS | C | 748 | 194.8 | 116.8 | 33.8 | 20 | B |
| HIS | O | 748 | 193.9 | 116.0 | 33.3 | 21 | B |
| GLY | N | 749 | 194.6 | 117.4 | 35.0 | 20 | B |
| GLY | CA | 749 | 193.5 | 117.1 | 35.8 | 18 | B |
| GLY | C | 749 | 192.1 | 117.5 | 35.2 | 18 | B |
| GLY | O | 749 | 191.2 | 116.8 | 35.3 | 20 | B |
| GLY | N | 750 | 192.0 | 118.7 | 34.7 | 17 | B |
| GLY | CA | 750 | 190.8 | 119.1 | 34.1 | 15 | B |
| GLY | C | 750 | 190.3 | 118.2 | 33.0 | 16 | B |
| GLY | O | 750 | 189.1 | 117.9 | 32.9 | 15 | B |
| TYR | N | 751 | 191.2 | 117.8 | 32.1 | 16 | B |
| TYR | CA | 751 | 190.8 | 116.9 | 31.0 | 17 | B |
| TYR | CB | 751 | 191.9 | 116.9 | 30.0 | 15 | B |
| TYR | CG | 751 | 192.0 | 118.1 | 29.2 | 15 | B |
| TYR | CD1 | 751 | 193.2 | 118.9 | 29.3 | 15 | B |
| TYR | CE1 | 751 | 193.4 | 120.1 | 28.6 | 15 | B |
| TYR | CD2 | 751 | 191.0 | 118.6 | 28.4 | 15 | B |
| TYR | CE2 | 751 | 191.1 | 119.8 | 27.6 | 16 | B |
| TYR | CZ | 751 | 192.3 | 120.5 | 27.7 | 16 | B |
| TYR | OH | 751 | 192.5 | 121.7 | 27.0 | 17 | B |
| TYR | C | 751 | 190.6 | 115.5 | 31.6 | 19 | B |
| TYR | O | 751 | 189.6 | 114.8 | 31.1 | 20 | B |
| THR | N | 752 | 191.4 | 115.0 | 32.5 | 18 | B |
| THR | CA | 752 | 191.3 | 113.7 | 33.1 | 18 | B |
| THR | CB | 752 | 192.4 | 113.5 | 34.1 | 18 | B |
| THR | OG1 | 752 | 193.6 | 113.6 | 33.5 | 19 | B |
| THR | CG2 | 752 | 192.3 | 112.1 | 34.7 | 18 | B |
| THR | C | 752 | 189.9 | 113.5 | 33.8 | 19 | B |
| THR | O | 752 | 189.4 | 112.4 | 33.9 | 21 | B |
| PHE | N | 753 | 189.3 | 114.6 | 34.3 | 18 | B |
| PHE | CA | 753 | 188.0 | 114.5 | 34.9 | 17 | B |
| PHE | CB | 753 | 187.6 | 115.7 | 35.7 | 16 | B |
| PHE | CG | 753 | 186.2 | 115.7 | 36.2 | 16 | B |
| PHE | CD1 | 753 | 185.8 | 114.9 | 37.2 | 16 | B |
| PHE | CD2 | 753 | 185.3 | 116.5 | 35.5 | 16 | B |
| PHE | CE1 | 753 | 184.4 | 114.8 | 37.6 | 15 | B |
| PHE | CE2 | 753 | 183.9 | 116.4 | 35.8 | 16 | B |
| PHE | CZ | 753 | 183.5 | 115.6 | 36.9 | 16 | B |
| PHE | C | 753 | 186.9 | 114.4 | 33.7 | 17 | B |
| PHE | O | 753 | 186.0 | 113.7 | 33.8 | 17 | B |
| CYS | N | 754 | 187.1 | 115.2 | 32.7 | 17 | B |
| CYS | CA | 754 | 186.2 | 115.1 | 31.5 | 18 | B |
| CYS | CB | 754 | 186.6 | 116.1 | 30.5 | 18 | B |
| CYS | SG | 754 | 186.4 | 117.8 | 30.9 | 18 | B |
| CYS | C | 754 | 186.3 | 113.7 | 30.9 | 18 | B |
| CYS | O | 754 | 185.3 | 113.2 | 30.5 | 19 | B |
| GLY | N | 755 | 187.5 | 113.2 | 30.8 | 19 | B |
| GLY | CA | 755 | 187.7 | 111.9 | 30.2 | 19 | B |
| GLY | C | 755 | 187.0 | 110.8 | 31.0 | 20 | B |
| GLY | O | 755 | 186.1 | 110.2 | 30.5 | 21 | B |
| LEU | N | 756 | 187.4 | 110.6 | 32.3 | 20 | B |
| LEU | CA | 756 | 186.8 | 109.6 | 33.1 | 21 | B |

TABLE 4-continued

The following table lists the atomic structure coordinates for FPT in complex with FPP and the inhibitor SCH66701 as derived by X-ray diffraction from crystals of that complex The abbreviations are the same as those used in Table 2

| RES | ATOM | # | X | Y | Z | B | C |
|---|---|---|---|---|---|---|---|
| LEU | CB | 756 | 187.4 | 109.6 | 34.5 | 20 | B |
| LEU | CG | 756 | 187.0 | 108.5 | 35.5 | 19 | B |
| LEU | CD1 | 756 | 187.2 | 107.2 | 34.8 | 19 | B |
| LEU | CD2 | 756 | 187.8 | 108.6 | 36.7 | 19 | B |
| LEU | C | 756 | 185.2 | 109.8 | 33.3 | 22 | B |
| LEU | O | 756 | 184.5 | 108.9 | 33.0 | 23 | B |
| ALA | N | 757 | 184.8 | 111.0 | 33.6 | 22 | B |
| ALA | CA | 757 | 183.3 | 111.2 | 33.8 | 21 | B |
| ALA | CB | 757 | 183.1 | 112.7 | 34.1 | 20 | B |
| ALA | C | 757 | 182.6 | 110.9 | 32.6 | 21 | B |
| ALA | O | 757 | 181.5 | 110.3 | 32.6 | 22 | B |
| ALA | N | 758 | 183.1 | 111.2 | 31.4 | 21 | B |
| ALA | CA | 758 | 182.4 | 110.9 | 30.2 | 20 | B |
| ALA | CB | 758 | 183.2 | 111.5 | 29.0 | 20 | B |
| ALA | C | 758 | 182.3 | 109.4 | 30.0 | 21 | B |
| ALA | O | 758 | 181.3 | 108.9 | 29.6 | 22 | B |
| LEU | N | 759 | 183.4 | 108.6 | 30.3 | 21 | B |
| LEU | CA | 759 | 183.4 | 107.2 | 30.2 | 21 | B |
| LEU | CB | 759 | 184.8 | 106.6 | 30.4 | 20 | B |
| LEU | CG | 759 | 185.8 | 106.8 | 29.3 | 20 | B |
| LEU | CD1 | 759 | 187.1 | 106.2 | 29.6 | 19 | B |
| LEU | CD2 | 759 | 185.3 | 106.2 | 28.0 | 19 | B |
| LEU | C | 759 | 182.3 | 106.6 | 31.2 | 22 | B |
| LEU | O | 759 | 181.5 | 105.8 | 30.8 | 23 | B |
| VAL | N | 760 | 182.4 | 107.1 | 32.4 | 21 | B |
| VAL | CA | 760 | 181.4 | 106.6 | 33.4 | 20 | B |
| VAL | CB | 760 | 181.5 | 107.4 | 34.7 | 20 | B |
| VAL | CG1 | 760 | 180.4 | 107.1 | 35.6 | 20 | B |
| VAL | CG2 | 760 | 182.8 | 107.1 | 35.4 | 20 | B |
| VAL | C | 760 | 180.0 | 106.8 | 32.9 | 21 | B |
| VAL | O | 760 | 179.2 | 105.9 | 33.0 | 23 | B |
| ILE | N | 761 | 179.8 | 107.9 | 32.2 | 22 | B |
| ILE | CA | 761 | 178.5 | 108.1 | 31.6 | 24 | B |
| ILE | CB | 761 | 178.4 | 109.5 | 31.0 | 23 | B |
| ILE | CG2 | 761 | 177.0 | 109.8 | 30.4 | 23 | B |
| ILE | CG1 | 761 | 178.6 | 110.6 | 32.1 | 22 | B |
| ILE | CD1 | 761 | 178.5 | 112.0 | 31.6 | 22 | B |
| ILE | C | 761 | 178.2 | 107.1 | 30.5 | 26 | B |
| ILE | O | 761 | 177.1 | 106.5 | 30.3 | 26 | B |
| LEU | N | 762 | 179.2 | 106.8 | 29.7 | 28 | B |
| LEU | CA | 762 | 179.1 | 105.8 | 28.6 | 30 | B |
| LEU | CB | 762 | 180.2 | 106.2 | 27.5 | 28 | B |
| LEU | CG | 762 | 180.0 | 107.5 | 26.8 | 27 | B |
| LEU | CD1 | 762 | 181.2 | 107.6 | 25.8 | 26 | B |
| LEU | CD2 | 762 | 178.7 | 107.6 | 26.0 | 26 | B |
| LEU | C | 762 | 179.3 | 104.4 | 29.1 | 31 | B |
| LEU | O | 762 | 179.2 | 103.4 | 28.3 | 30 | B |
| LYS | N | 763 | 179.5 | 104.2 | 30.4 | 33 | B |
| LYS | CA | 763 | 179.7 | 103.0 | 31.1 | 35 | B |
| LYS | CB | 763 | 178.4 | 102.1 | 31.0 | 37 | B |
| LYS | CG | 763 | 177.2 | 102.7 | 31.5 | 40 | B |
| LYS | CD | 763 | 176.0 | 102.3 | 30.6 | 41 | B |
| LYS | CE | 763 | 174.7 | 102.6 | 31.2 | 42 | B |
| LYS | NZ | 763 | 173.6 | 102.0 | 30.4 | 44 | B |
| LYS | C | 763 | 180.8 | 102.2 | 30.4 | 36 | B |
| LYS | O | 763 | 180.7 | 101.1 | 30.0 | 37 | B |
| LYS | N | 764 | 181.9 | 102.9 | 30.2 | 35 | B |
| LYS | CA | 764 | 183.1 | 102.3 | 29.6 | 35 | B |
| LYS | CB | 764 | 183.3 | 102.8 | 28.2 | 35 | B |
| LYS | CG | 764 | 182.2 | 102.5 | 27.2 | 36 | B |
| LYS | CD | 764 | 182.0 | 101.1 | 27.1 | 37 | B |
| LYS | CE | 764 | 181.1 | 100.8 | 25.9 | 38 | B |
| LYS | NZ | 764 | 180.0 | 101.8 | 25.8 | 39 | B |
| LYS | C | 764 | 184.4 | 102.5 | 30.3 | 36 | B |
| LYS | O | 764 | 185.5 | 102.4 | 29.8 | 36 | B |
| GLU | N | 765 | 184.3 | 102.9 | 31.6 | 37 | B |
| GLU | CA | 765 | 185.5 | 103.2 | 32.4 | 39 | B |
| GLU | CB | 765 | 185.2 | 103.2 | 33.9 | 39 | B |
| GLU | CG | 765 | 183.8 | 103.8 | 34.3 | 41 | B |
| GLU | CD | 765 | 182.8 | 102.8 | 34.5 | 42 | B |
| GLU | OE1 | 765 | 182.7 | 102.3 | 35.6 | 43 | B |
| GLU | OE2 | 765 | 182.0 | 102.5 | 33.5 | 43 | B |

TABLE 4-continued

The following table lists the atomic structure coordinates for FPT in complex with FPP and the inhibitor SCH66701 as derived by X-ray diffraction from crystals of that complex The abbreviations are the same as those used in Table 2

| RES | ATOM | # | X | Y | Z | B | C |
|---|---|---|---|---|---|---|---|
| GLU | C | 765 | 186.6 | 102.2 | 32.2 | 39 | B |
| GLU | O | 765 | 187.7 | 102.5 | 32.3 | 38 | B |
| ARG | N | 766 | 186.2 | 100.9 | 32.0 | 40 | B |
| ARG | CA | 766 | 187.1 | 99.8 | 31.8 | 41 | B |
| ARG | CB | 766 | 186.4 | 98.5 | 31.7 | 44 | B |
| ARG | CG | 766 | 186.1 | 97.9 | 33.0 | 48 | B |
| ARG | CD | 766 | 184.6 | 98.2 | 33.5 | 51 | B |
| ARG | NE | 766 | 184.6 | 98.7 | 34.9 | 54 | B |
| ARG | CZ | 766 | 183.5 | 99.1 | 35.5 | 55 | B |
| ARG | NH1 | 766 | 183.6 | 99.5 | 36.8 | 55 | B |
| ARG | NH2 | 766 | 182.3 | 99.1 | 34.9 | 55 | B |
| ARG | C | 766 | 188.1 | 100.1 | 30.6 | 40 | B |
| ARG | O | 766 | 189.2 | 99.5 | 30.6 | 40 | B |
| SER | N | 767 | 187.7 | 100.9 | 29.7 | 39 | B |
| SER | CA | 767 | 188.5 | 101.3 | 28.5 | 38 | B |
| SER | CB | 767 | 187.8 | 102.2 | 27.6 | 38 | B |
| SER | OG | 767 | 186.6 | 101.6 | 27.1 | 39 | B |
| SER | C | 767 | 189.8 | 101.9 | 28.9 | 37 | B |
| SER | O | 767 | 190.7 | 102.1 | 28.1 | 38 | B |
| LEU | N | 768 | 190.0 | 102.4 | 30.2 | 36 | B |
| LEU | CA | 768 | 191.2 | 103.0 | 30.6 | 36 | B |
| LEU | CB | 768 | 190.8 | 104.4 | 31.3 | 35 | B |
| LEU | CG | 768 | 190.1 | 105.5 | 30.6 | 35 | B |
| LEU | CD1 | 768 | 189.8 | 106.6 | 31.6 | 34 | B |
| LEU | CD2 | 768 | 191.1 | 106.0 | 29.5 | 35 | B |
| LEU | C | 768 | 191.9 | 102.2 | 31.7 | 35 | B |
| LEU | O | 768 | 191.2 | 101.6 | 32.5 | 37 | B |
| ASN | N | 769 | 193.2 | 102.3 | 31.7 | 34 | B |
| ASN | CA | 769 | 193.9 | 101.5 | 32.7 | 33 | B |
| ASN | CB | 769 | 195.4 | 101.6 | 32.5 | 33 | B |
| ASN | CG | 769 | 196.2 | 100.9 | 33.6 | 33 | B |
| ASN | OD1 | 769 | 195.8 | 100.8 | 34.7 | 34 | B |
| ASN | ND2 | 769 | 197.4 | 100.4 | 33.2 | 34 | B |
| ASN | C | 769 | 193.6 | 102.3 | 34.0 | 33 | B |
| ASN | O | 769 | 194.2 | 103.3 | 34.3 | 34 | B |
| LEU | N | 770 | 192.7 | 101.7 | 34.8 | 31 | B |
| LEU | CA | 770 | 192.3 | 102.4 | 36.0 | 30 | B |
| LEU | CB | 770 | 190.9 | 101.8 | 36.5 | 29 | B |
| LEU | CG | 770 | 189.8 | 102.1 | 35.5 | 28 | B |
| LEU | CD1 | 770 | 188.5 | 101.9 | 36.3 | 28 | B |
| LEU | CD2 | 770 | 189.8 | 103.4 | 34.9 | 29 | B |
| LEU | C | 770 | 193.3 | 102.3 | 37.1 | 30 | B |
| LEU | O | 770 | 193.2 | 103.1 | 38.1 | 30 | B |
| LYS | N | 771 | 194.3 | 101.5 | 37.0 | 32 | B |
| LYS | CA | 771 | 195.3 | 101.5 | 38.1 | 35 | B |
| LYS | CB | 771 | 196.0 | 100.1 | 38.2 | 38 | B |
| LYS | CG | 771 | 195.3 | 99.2 | 39.2 | 43 | B |
| LYS | CD | 771 | 194.9 | 99.9 | 40.5 | 45 | B |
| LYS | CE | 771 | 194.0 | 99.1 | 41.5 | 47 | B |
| LYS | NZ | 771 | 192.6 | 98.8 | 41.0 | 46 | B |
| LYS | C | 771 | 196.3 | 102.6 | 37.9 | 35 | B |
| LYS | O | 771 | 196.6 | 103.3 | 38.9 | 35 | B |
| SER | N | 772 | 196.8 | 102.7 | 36.7 | 35 | B |
| SER | CA | 772 | 197.8 | 103.7 | 36.4 | 35 | B |
| SER | CB | 772 | 198.3 | 103.7 | 35.0 | 35 | B |
| SER | OG | 772 | 197.3 | 103.5 | 34.1 | 35 | B |
| SER | C | 772 | 197.1 | 105.1 | 36.7 | 35 | B |
| SER | O | 772 | 197.7 | 106.0 | 37.3 | 37 | B |
| LEU | N | 773 | 195.9 | 105.2 | 36.2 | 34 | B |
| LEU | CA | 773 | 195.2 | 106.4 | 36.4 | 33 | B |
| LEU | CB | 773 | 193.8 | 106.3 | 35.6 | 33 | B |
| LEU | CG | 773 | 192.7 | 107.3 | 36.0 | 33 | B |
| LEU | CD1 | 773 | 193.1 | 108.7 | 36.2 | 33 | B |
| LEU | CD2 | 773 | 191.6 | 107.1 | 35.0 | 34 | B |
| LEU | C | 773 | 195.0 | 106.6 | 37.9 | 34 | B |
| LEU | O | 773 | 195.3 | 107.7 | 38.3 | 34 | B |
| LEU | N | 774 | 194.6 | 105.6 | 38.6 | 33 | B |
| LEU | CA | 774 | 194.4 | 105.8 | 40.1 | 33 | B |
| LEU | CB | 774 | 194.1 | 104.5 | 40.7 | 34 | B |
| LEU | CG | 774 | 194.2 | 104.5 | 42.3 | 34 | B |
| LEU | CD1 | 774 | 193.1 | 105.5 | 42.8 | 33 | B |
| LEU | CD2 | 774 | 193.9 | 103.1 | 42.9 | 34 | B |

TABLE 4-continued

The following table lists the atomic structure coordinates for FPT in complex with FPP and the inhibitor SCH66701 as derived by X-ray diffraction from crystals of that complex The abbreviations are the same as those used in Table 2

| RES | ATOM | # | X | Y | Z | B | C |
|---|---|---|---|---|---|---|---|
| LEU | C | 774 | 195.7 | 106.3 | 40.7 | 32 | B |
| LEU | O | 774 | 195.7 | 107.2 | 41.5 | 31 | B |
| GLN | N | 775 | 196.8 | 105.8 | 40.2 | 33 | B |
| GLN | CA | 775 | 198.1 | 106.2 | 40.7 | 34 | B |
| GLN | CB | 775 | 199.2 | 105.2 | 40.2 | 35 | B |
| GLN | CG | 775 | 200.6 | 105.6 | 40.8 | 39 | B |
| GLN | CD | 775 | 201.6 | 104.5 | 40.6 | 42 | B |
| GLN | OE1 | 775 | 202.4 | 104.2 | 41.6 | 43 | B |
| GLN | NE2 | 775 | 201.7 | 103.9 | 39.4 | 43 | B |
| GLN | C | 775 | 198.5 | 107.6 | 40.5 | 33 | B |
| GLN | O | 775 | 198.9 | 108.3 | 41.4 | 34 | B |
| TRP | N | 776 | 198.2 | 108.1 | 39.2 | 31 | B |
| TRP | CA | 776 | 198.5 | 109.5 | 38.9 | 29 | B |
| TRP | CB | 776 | 198.5 | 109.6 | 37.4 | 28 | B |
| TRP | CG | 776 | 198.6 | 111.0 | 36.9 | 26 | B |
| TRP | CD2 | 776 | 197.5 | 111.9 | 36.6 | 26 | B |
| TRP | CE2 | 776 | 198.0 | 113.0 | 36.0 | 26 | B |
| TRP | CE3 | 776 | 196.1 | 111.7 | 36.8 | 26 | B |
| TRP | CD1 | 776 | 199.7 | 111.7 | 36.5 | 26 | B |
| TRP | NE1 | 776 | 199.3 | 112.9 | 36.0 | 26 | B |
| TRP | CZ2 | 776 | 197.2 | 114.1 | 35.7 | 26 | B |
| TRP | CZ3 | 776 | 195.3 | 112.8 | 36.4 | 26 | B |
| TRP | CH2 | 776 | 195.8 | 114.0 | 35.8 | 26 | B |
| TRP | C | 776 | 197.7 | 110.5 | 39.6 | 28 | B |
| TRP | O | 776 | 198.2 | 111.4 | 40.3 | 27 | B |
| VAL | N | 777 | 196.3 | 110.3 | 39.7 | 27 | B |
| VAL | CA | 777 | 195.5 | 111.3 | 40.4 | 26 | B |
| VAL | CB | 777 | 193.9 | 110.8 | 40.3 | 26 | B |
| VAL | CG1 | 777 | 193.7 | 109.6 | 41.0 | 26 | B |
| VAL | CG2 | 777 | 193.1 | 111.9 | 40.8 | 25 | B |
| VAL | C | 777 | 195.9 | 111.4 | 41.8 | 27 | B |
| VAL | O | 777 | 195.9 | 112.5 | 42.3 | 26 | B |
| THR | N | 778 | 196.2 | 110.3 | 42.5 | 27 | B |
| THR | CA | 778 | 196.6 | 110.4 | 43.9 | 27 | B |
| THR | CB | 778 | 196.8 | 109.0 | 44.5 | 26 | B |
| THR | OG1 | 778 | 197.8 | 108.2 | 43.8 | 25 | B |
| THR | CG2 | 778 | 195.4 | 108.2 | 44.3 | 26 | B |
| THR | C | 778 | 198.0 | 111.1 | 44.0 | 27 | B |
| THR | O | 778 | 198.3 | 111.7 | 45.1 | 28 | B |
| SER | N | 779 | 198.8 | 111.1 | 43.0 | 27 | B |
| SER | CA | 779 | 200.1 | 111.8 | 43.1 | 28 | B |
| SER | CB | 779 | 201.0 | 111.2 | 42.0 | 28 | B |
| SER | OG | 779 | 201.1 | 109.8 | 42.1 | 28 | B |
| SER | C | 779 | 199.9 | 113.3 | 42.9 | 29 | B |
| SER | O | 779 | 200.8 | 114.1 | 43.2 | 30 | B |
| ARG | N | 780 | 198.7 | 113.7 | 42.4 | 28 | B |
| ARG | CA | 780 | 198.5 | 115.1 | 42.1 | 27 | B |
| ARG | CB | 780 | 197.4 | 115.3 | 41.1 | 27 | B |
| ARG | CG | 780 | 197.6 | 114.6 | 39.8 | 26 | B |
| ARG | CD | 780 | 198.7 | 115.3 | 38.9 | 24 | B |
| ARG | NE | 780 | 200.0 | 115.3 | 39.4 | 22 | B |
| ARG | CZ | 780 | 200.8 | 114.3 | 39.5 | 23 | B |
| ARG | NH1 | 780 | 200.4 | 113.1 | 39.0 | 24 | B |
| ARG | NH2 | 780 | 202.0 | 114.4 | 40.0 | 23 | B |
| ARG | C | 780 | 198.2 | 115.9 | 43.4 | 28 | B |
| ARG | O | 780 | 198.1 | 117.1 | 43.4 | 29 | B |
| GLN | N | 781 | 198.0 | 115.2 | 44.5 | 29 | B |
| GLN | CA | 781 | 197.7 | 115.9 | 45.8 | 30 | B |
| GLN | CB | 781 | 196.9 | 115.0 | 46.8 | 31 | B |
| GLN | CG | 781 | 196.6 | 115.8 | 48.1 | 31 | B |
| GLN | CD | 781 | 195.5 | 115.2 | 48.9 | 31 | B |
| GLN | OE1 | 781 | 195.4 | 114.0 | 49.1 | 31 | B |
| GLN | NE2 | 781 | 194.6 | 116.1 | 49.4 | 31 | B |
| GLN | C | 781 | 199.0 | 116.3 | 46.3 | 31 | B |
| GLN | O | 781 | 199.9 | 115.5 | 46.4 | 31 | B |
| MET | N | 782 | 199.2 | 117.6 | 46.7 | 31 | B |
| MET | CA | 782 | 200.4 | 118.1 | 47.2 | 32 | B |
| MET | CB | 782 | 200.4 | 119.6 | 47.0 | 31 | B |
| MET | CG | 782 | 200.1 | 120.1 | 45.6 | 30 | B |
| MET | SD | 782 | 201.3 | 119.5 | 44.3 | 30 | B |
| MET | CE | 782 | 202.7 | 120.3 | 44.9 | 29 | B |
| MET | C | 782 | 200.6 | 117.9 | 48.7 | 33 | B |

TABLE 4-continued

The following table lists the atomic structure coordinates for FPT in complex with FPP and the inhibitor SCH66701 as derived by X-ray diffraction from crystals of that complex
The abbreviations are the same as those used in Table 2

| RES | ATOM | # | X | Y | Z | B | C |
|---|---|---|---|---|---|---|---|
| MET | O | 782 | 199.8 | 118.3 | 49.5 | 33 | B |
| ARG | N | 783 | 201.6 | 117.1 | 49.1 | 34 | B |
| ARG | CA | 783 | 202.0 | 116.8 | 50.5 | 36 | B |
| ARG | CB | 783 | 203.3 | 116.0 | 50.5 | 37 | B |
| ARG | CG | 783 | 204.4 | 116.8 | 50.0 | 40 | B |
| ARG | CD | 783 | 205.4 | 115.9 | 49.2 | 42 | B |
| ARG | NE | 783 | 205.9 | 114.9 | 50.1 | 45 | B |
| ARG | CZ | 783 | 206.2 | 113.6 | 49.7 | 47 | B |
| ARG | NH1 | 783 | 206.0 | 113.3 | 48.4 | 48 | B |
| ARG | NH2 | 783 | 206.6 | 112.8 | 50.6 | 48 | B |
| ARG | C | 783 | 202.0 | 117.9 | 51.5 | 35 | B |
| ARG | O | 783 | 201.7 | 117.7 | 52.7 | 35 | B |
| PHE | N | 784 | 202.5 | 119.1 | 51.1 | 35 | B |
| PHE | CA | 784 | 202.6 | 120.2 | 52.0 | 34 | B |
| PHE | CB | 784 | 203.8 | 121.1 | 51.6 | 34 | B |
| PHE | CG | 784 | 204.1 | 122.1 | 52.7 | 34 | B |
| PHE | CD1 | 784 | 204.9 | 121.8 | 53.7 | 34 | B |
| PHE | CD2 | 784 | 203.5 | 123.4 | 52.6 | 34 | B |
| PHE | CE1 | 784 | 205.1 | 122.8 | 54.7 | 35 | B |
| PHE | CE2 | 784 | 203.7 | 124.3 | 53.6 | 34 | B |
| PHE | CZ | 784 | 204.5 | 124.0 | 54.6 | 34 | B |
| PHE | C | 784 | 201.3 | 121.1 | 52.0 | 33 | B |
| PHE | O | 784 | 200.8 | 121.4 | 53.0 | 34 | B |
| GLU | N | 785 | 200.9 | 121.5 | 50.8 | 32 | B |
| GLU | CA | 785 | 199.8 | 122.4 | 50.7 | 31 | B |
| GLU | CB | 785 | 199.8 | 123.1 | 49.3 | 31 | B |
| GLU | CG | 785 | 201.0 | 123.9 | 49.0 | 31 | B |
| GLU | CD | 785 | 202.1 | 123.0 | 48.2 | 32 | B |
| GLU | OE1 | 785 | 202.0 | 123.0 | 46.9 | 33 | B |
| GLU | OE2 | 785 | 203.0 | 122.5 | 48.8 | 32 | B |
| GLU | C | 785 | 198.5 | 121.7 | 51.0 | 31 | B |
| GLU | O | 785 | 197.5 | 122.2 | 51.4 | 31 | B |
| GLY | N | 786 | 198.5 | 120.4 | 50.6 | 30 | B |
| GLY | CA | 786 | 197.3 | 119.6 | 50.8 | 28 | B |
| GLY | C | 786 | 196.3 | 119.7 | 49.7 | 27 | B |
| GLY | O | 786 | 195.3 | 118.9 | 49.6 | 27 | B |
| GLY | N | 787 | 196.4 | 120.7 | 48.9 | 26 | B |
| GLY | CA | 787 | 195.5 | 120.9 | 47.7 | 24 | B |
| GLY | C | 787 | 196.1 | 120.1 | 46.6 | 23 | B |
| GLY | O | 787 | 197.2 | 119.5 | 46.7 | 22 | B |
| PHE | N | 788 | 195.4 | 120.1 | 45.4 | 22 | B |
| PHE | CA | 788 | 195.8 | 119.4 | 44.2 | 23 | B |
| PHE | CB | 788 | 194.5 | 118.7 | 43.6 | 22 | B |
| PHE | CG | 788 | 194.3 | 117.3 | 44.2 | 23 | B |
| PHE | CD1 | 788 | 193.4 | 117.2 | 45.3 | 23 | B |
| PHE | CD2 | 788 | 194.9 | 116.2 | 43.8 | 23 | B |
| PHE | CE1 | 788 | 193.1 | 116.0 | 45.9 | 23 | B |
| PHE | CE2 | 788 | 194.7 | 114.9 | 44.3 | 24 | B |
| PHE | CZ | 788 | 193.8 | 114.8 | 45.4 | 23 | B |
| PHE | C | 788 | 196.4 | 120.3 | 43.2 | 23 | B |
| PHE | O | 788 | 196.3 | 121.5 | 43.1 | 24 | B |
| GLN | N | 789 | 197.3 | 119.6 | 42.3 | 22 | B |
| GLN | CA | 789 | 198.0 | 120.3 | 41.3 | 23 | B |
| GLN | CB | 789 | 199.5 | 120.0 | 41.3 | 23 | B |
| GLN | CG | 789 | 199.8 | 118.5 | 41.1 | 23 | B |
| GLN | CD | 789 | 201.3 | 118.3 | 41.0 | 24 | B |
| GLN | OE1 | 789 | 201.8 | 117.2 | 40.7 | 23 | B |
| GLN | NE2 | 789 | 202.1 | 119.3 | 41.2 | 25 | B |
| GLN | C | 789 | 197.4 | 119.9 | 40.0 | 23 | B |
| GLN | O | 789 | 196.9 | 118.8 | 39.8 | 24 | B |
| GLY | N | 790 | 197.4 | 120.8 | 39.0 | 24 | B |
| GLY | CA | 790 | 196.8 | 120.4 | 37.7 | 22 | B |
| GLY | C | 790 | 197.5 | 119.3 | 37.0 | 21 | B |
| GLY | O | 790 | 196.9 | 118.4 | 36.4 | 20 | B |
| ARG | N | 791 | 198.9 | 119.3 | 36.9 | 20 | B |
| ARG | CA | 791 | 199.6 | 118.3 | 36.2 | 20 | B |
| ARG | CB | 791 | 199.9 | 118.7 | 34.8 | 20 | B |
| ARG | CG | 791 | 199.5 | 120.2 | 34.5 | 20 | B |
| ARG | CD | 791 | 199.9 | 120.5 | 33.0 | 20 | B |
| ARG | NE | 791 | 199.8 | 122.0 | 32.9 | 21 | B |
| ARG | CZ | 791 | 200.2 | 122.7 | 31.8 | 21 | B |
| ARG | NH1 | 791 | 200.9 | 122.1 | 30.9 | 22 | B |
| ARG | NH2 | 791 | 200.1 | 124.0 | 31.8 | 21 | B |
| ARG | C | 791 | 201.0 | 118.2 | 37.0 | 22 | B |
| ARG | O | 791 | 201.3 | 119.2 | 37.6 | 22 | B |
| CYS | N | 792 | 201.6 | 117.1 | 36.9 | 22 | B |
| CYS | CA | 792 | 202.9 | 116.9 | 37.6 | 23 | B |
| CYS | CB | 792 | 203.6 | 115.6 | 37.0 | 23 | B |
| CYS | SG | 792 | 205.1 | 115.2 | 37.9 | 24 | B |
| CYS | C | 792 | 203.9 | 118.1 | 37.5 | 24 | B |
| CYS | O | 792 | 203.9 | 118.8 | 36.5 | 26 | B |
| ASN | N | 793 | 204.6 | 118.4 | 38.6 | 24 | B |
| ASN | CA | 793 | 205.6 | 119.5 | 38.6 | 25 | B |
| ASN | CB | 793 | 206.8 | 119.2 | 37.7 | 25 | B |
| ASN | CG | 793 | 207.9 | 118.5 | 38.5 | 25 | B |
| ASN | OD1 | 793 | 207.9 | 118.6 | 39.7 | 26 | B |
| ASN | ND2 | 793 | 208.9 | 117.9 | 37.8 | 24 | B |
| ASN | C | 793 | 205.0 | 120.8 | 38.2 | 24 | B |
| ASN | O | 793 | 205.6 | 121.7 | 37.5 | 23 | B |
| LYS | N | 794 | 203.8 | 121.0 | 38.7 | 24 | B |
| LYS | CA | 794 | 203.0 | 122.3 | 38.5 | 24 | B |
| LYS | CB | 794 | 201.7 | 122.0 | 37.7 | 24 | B |
| LYS | CG | 794 | 201.6 | 122.9 | 36.5 | 25 | B |
| LYS | CD | 794 | 202.7 | 122.8 | 35.6 | 25 | B |
| LYS | CE | 794 | 202.4 | 123.7 | 34.4 | 26 | B |
| LYS | NZ | 794 | 202.0 | 125.1 | 34.6 | 25 | B |
| LYS | C | 794 | 202.6 | 122.7 | 39.9 | 25 | B |
| LYS | O | 794 | 203.1 | 122.2 | 40.9 | 26 | B |
| LEU | N | 795 | 201.8 | 123.8 | 40.0 | 24 | B |
| LEU | CA | 795 | 201.4 | 124.3 | 41.3 | 24 | B |
| LEU | CB | 795 | 201.5 | 125.9 | 41.3 | 23 | B |
| LEU | CG | 795 | 202.8 | 126.5 | 41.0 | 21 | B |
| LEU | CD1 | 795 | 202.7 | 128.0 | 41.2 | 19 | B |
| LEU | CD2 | 795 | 204.0 | 125.9 | 41.7 | 20 | B |
| LEU | C | 795 | 200.0 | 123.9 | 41.8 | 24 | B |
| LEU | O | 795 | 199.2 | 123.4 | 41.0 | 25 | B |
| VAL | N | 796 | 199.8 | 124.2 | 43.1 | 24 | B |
| VAL | CA | 796 | 198.5 | 123.9 | 43.7 | 24 | B |
| VAL | CB | 796 | 198.5 | 124.1 | 45.2 | 25 | B |
| VAL | CG1 | 796 | 198.1 | 122.8 | 45.9 | 27 | B |
| VAL | CG2 | 796 | 199.8 | 124.6 | 45.7 | 25 | B |
| VAL | C | 796 | 197.5 | 124.8 | 43.1 | 23 | B |
| VAL | O | 796 | 197.8 | 125.9 | 42.7 | 24 | B |
| ASP | N | 797 | 196.2 | 124.5 | 43.2 | 20 | B |
| ASP | CA | 797 | 195.1 | 125.4 | 42.8 | 18 | B |
| ASP | CB | 797 | 195.1 | 125.5 | 41.2 | 16 | B |
| ASP | CG | 797 | 194.0 | 126.4 | 40.7 | 15 | B |
| ASP | OD1 | 797 | 193.0 | 126.7 | 41.3 | 16 | B |
| ASP | OD2 | 797 | 194.1 | 126.8 | 39.5 | 15 | B |
| ASP | C | 797 | 193.8 | 124.9 | 43.3 | 19 | B |
| ASP | O | 797 | 193.4 | 123.7 | 43.0 | 19 | B |
| GLY | N | 798 | 193.0 | 125.7 | 43.9 | 19 | B |
| GLY | CA | 798 | 191.7 | 125.4 | 44.4 | 19 | B |
| GLY | C | 798 | 190.7 | 124.6 | 43.4 | 20 | B |
| GLY | O | 798 | 190.2 | 123.6 | 43.9 | 21 | B |
| CYS | N | 799 | 190.6 | 125.0 | 42.2 | 21 | B |
| CYS | CA | 799 | 189.6 | 124.3 | 41.3 | 22 | B |
| CYS | CB | 799 | 189.4 | 125.0 | 40.0 | 23 | B |
| CYS | SG | 799 | 190.9 | 125.3 | 39.0 | 25 | B |
| CYS | C | 799 | 189.9 | 122.9 | 41.2 | 24 | B |
| CYS | O | 799 | 189.0 | 122.1 | 40.9 | 25 | B |
| TYR | N | 800 | 191.2 | 122.5 | 41.3 | 25 | B |
| TYR | CA | 800 | 191.6 | 121.2 | 41.2 | 26 | B |
| TYR | CB | 800 | 193.1 | 121.0 | 41.0 | 26 | B |
| TYR | CG | 800 | 193.5 | 121.6 | 39.6 | 27 | B |
| TYR | CD1 | 800 | 194.7 | 122.3 | 39.5 | 27 | B |
| TYR | CE1 | 800 | 195.0 | 122.8 | 38.3 | 28 | B |
| TYR | CD2 | 800 | 192.8 | 121.3 | 38.5 | 27 | B |
| TYR | CE2 | 800 | 193.1 | 121.8 | 37.3 | 28 | B |
| TYR | CZ | 800 | 194.3 | 122.6 | 37.2 | 28 | B |
| TYR | OH | 800 | 194.6 | 123.2 | 36.0 | 30 | B |
| TYR | C | 800 | 191.2 | 120.3 | 42.4 | 28 | B |
| TYR | O | 800 | 191.4 | 119.1 | 42.4 | 30 | B |
| SER | N | 801 | 190.6 | 121.0 | 43.4 | 27 | B |

TABLE 4-continued

The following table lists the atomic structure coordinates for FPT in complex with FPP and the inhibitor SCH66701 as derived by X-ray diffraction from crystals of that complex
The abbreviations are the same as those used in Table 2

| RES | ATOM | # | X | Y | Z | B | C |
|---|---|---|---|---|---|---|---|
| SER | CA | 801 | 190.2 | 120.3 | 44.5 | 26 | B |
| SER | CB | 801 | 189.7 | 121.3 | 45.6 | 26 | B |
| SER | OG | 801 | 190.8 | 122.1 | 45.9 | 25 | B |
| SER | C | 801 | 189.0 | 119.4 | 44.0 | 27 | B |
| SER | O | 801 | 188.6 | 118.4 | 44.6 | 28 | B |
| PHE | N | 802 | 188.4 | 119.9 | 42.9 | 26 | B |
| PHE | CA | 802 | 187.2 | 119.2 | 42.3 | 25 | B |
| PHE | CB | 802 | 186.1 | 120.0 | 41.8 | 24 | B |
| PHE | CG | 802 | 185.1 | 119.2 | 41.1 | 23 | B |
| PHE | CD1 | 802 | 184.0 | 118.6 | 41.7 | 23 | B |
| PHE | CD2 | 802 | 185.1 | 119.1 | 39.7 | 23 | B |
| PHE | CE1 | 802 | 183.1 | 117.8 | 41.0 | 23 | B |
| PHE | CE2 | 802 | 184.2 | 118.4 | 39.0 | 22 | B |
| PHE | CZ | 802 | 183.2 | 117.7 | 39.7 | 22 | B |
| PHE | C | 802 | 187.6 | 118.3 | 41.1 | 26 | B |
| PHE | O | 802 | 187.3 | 117.2 | 41.0 | 28 | B |
| TRP | N | 803 | 188.3 | 118.9 | 40.1 | 24 | B |
| TRP | CA | 803 | 188.7 | 118.2 | 38.9 | 22 | B |
| TRP | CB | 803 | 189.4 | 119.1 | 37.9 | 20 | B |
| TRP | CG | 803 | 188.6 | 120.4 | 37.5 | 19 | B |
| TRP | CD2 | 803 | 187.4 | 120.5 | 36.7 | 19 | B |
| TRP | CE2 | 803 | 187.2 | 121.9 | 36.5 | 19 | B |
| TRP | CE3 | 803 | 186.5 | 119.6 | 36.2 | 20 | B |
| TRP | CD1 | 803 | 189.0 | 121.7 | 37.7 | 19 | B |
| TRP | NE1 | 803 | 188.2 | 122.5 | 37.1 | 19 | B |
| TRP | CZ2 | 803 | 186.1 | 122.3 | 35.8 | 19 | B |
| TRP | CZ3 | 803 | 185.4 | 120.0 | 35.5 | 20 | B |
| TRP | CH2 | 803 | 185.2 | 121.4 | 35.3 | 20 | B |
| TRP | C | 803 | 189.6 | 117.0 | 39.2 | 22 | B |
| TRP | O | 803 | 189.5 | 116.0 | 38.5 | 23 | B |
| GLN | N | 804 | 190.5 | 117.2 | 40.2 | 22 | B |
| GLN | CA | 804 | 191.4 | 116.1 | 40.6 | 22 | B |
| GLN | CB | 804 | 192.7 | 116.6 | 41.2 | 21 | B |
| GLN | CG | 804 | 193.6 | 117.4 | 40.2 | 22 | B |
| GLN | CD | 804 | 194.2 | 116.5 | 39.2 | 23 | B |
| GLN | OE1 | 804 | 193.6 | 115.5 | 38.8 | 25 | B |
| GLN | NE2 | 804 | 195.3 | 116.9 | 38.7 | 23 | B |
| GLN | C | 804 | 190.7 | 115.2 | 41.6 | 23 | B |
| GLN | O | 804 | 190.4 | 114.1 | 41.3 | 25 | B |
| ALA | N | 805 | 190.5 | 115.7 | 42.8 | 23 | B |
| ALA | CA | 805 | 189.9 | 115.0 | 43.9 | 22 | B |
| ALA | CB | 805 | 189.7 | 115.9 | 45.1 | 22 | B |
| ALA | C | 805 | 188.6 | 114.4 | 43.5 | 22 | B |
| ALA | O | 805 | 188.2 | 113.3 | 44.0 | 22 | B |
| GLY | N | 806 | 187.9 | 115.1 | 42.6 | 21 | B |
| GLY | CA | 806 | 186.6 | 114.5 | 42.1 | 22 | B |
| GLY | C | 806 | 186.8 | 113.2 | 41.4 | 24 | B |
| GLY | O | 806 | 185.8 | 112.4 | 41.3 | 24 | B |
| LEU | N | 807 | 188.0 | 112.9 | 40.9 | 25 | B |
| LEU | CA | 807 | 188.2 | 111.6 | 40.2 | 27 | B |
| LEU | CB | 807 | 189.5 | 111.6 | 39.5 | 26 | B |
| LEU | CG | 807 | 189.8 | 112.4 | 38.2 | 26 | B |
| LEU | CD1 | 807 | 191.3 | 112.6 | 38.0 | 27 | B |
| LEU | CD2 | 807 | 189.1 | 111.8 | 37.0 | 25 | B |
| LEU | C | 807 | 188.1 | 110.4 | 41.1 | 28 | B |
| LEU | O | 807 | 187.8 | 109.3 | 40.7 | 28 | B |
| LEU | N | 808 | 188.3 | 110.7 | 42.4 | 28 | B |
| LEU | CA | 808 | 188.2 | 109.6 | 43.4 | 30 | B |
| LEU | CB | 808 | 188.9 | 109.9 | 44.7 | 30 | B |
| LEU | CG | 808 | 190.4 | 109.9 | 44.2 | 30 | B |
| LEU | CD1 | 808 | 191.2 | 110.9 | 44.9 | 31 | B |
| LEU | CD2 | 808 | 191.0 | 108.6 | 44.3 | 31 | B |
| LEU | C | 808 | 186.8 | 109.0 | 43.5 | 30 | B |
| LEU | O | 808 | 186.7 | 107.7 | 43.6 | 33 | B |
| PRO | N | 809 | 185.8 | 109.8 | 43.7 | 30 | B |
| PRO | CD | 809 | 185.7 | 111.2 | 44.0 | 30 | B |
| PRO | CA | 809 | 184.5 | 109.2 | 43.8 | 30 | B |
| PRO | CB | 809 | 183.5 | 110.4 | 43.8 | 30 | B |
| PRO | CG | 809 | 184.3 | 111.3 | 44.6 | 30 | B |
| PRO | C | 809 | 184.2 | 108.3 | 42.5 | 30 | B |
| PRO | O | 809 | 183.8 | 107.2 | 42.6 | 31 | B |
| LEU | N | 810 | 184.7 | 108.8 | 41.4 | 31 | B |

TABLE 4-continued

The following table lists the atomic structure coordinates for FPT in complex with FPP and the inhibitor SCH66701 as derived by X-ray diffraction from crystals of that complex
The abbreviations are the same as those used in Table 2

| RES | ATOM | # | X | Y | Z | B | C |
|---|---|---|---|---|---|---|---|
| LEU | CA | 810 | 184.5 | 108.1 | 40.1 | 30 | B |
| LEU | CB | 810 | 185.0 | 109.0 | 39.0 | 28 | B |
| LEU | CG | 810 | 184.1 | 110.2 | 38.7 | 27 | B |
| LEU | CD1 | 810 | 184.5 | 111.0 | 37.5 | 26 | B |
| LEU | CD2 | 810 | 182.7 | 109.7 | 38.6 | 26 | B |
| LEU | C | 810 | 185.3 | 106.8 | 40.0 | 32 | B |
| LEU | O | 810 | 184.7 | 105.8 | 39.6 | 32 | B |
| LEU | N | 811 | 186.5 | 106.8 | 40.5 | 33 | B |
| LEU | CA | 811 | 187.3 | 105.6 | 40.5 | 35 | B |
| LEU | CB | 811 | 188.8 | 105.9 | 40.8 | 33 | B |
| LEU | CG | 811 | 189.6 | 106.4 | 39.7 | 32 | B |
| LEU | CD1 | 811 | 190.9 | 106.7 | 40.2 | 31 | B |
| LEU | CD2 | 811 | 189.6 | 105.4 | 38.6 | 30 | B |
| LEU | C | 811 | 186.8 | 104.6 | 41.5 | 38 | B |
| LEU | O | 811 | 187.0 | 103.4 | 41.3 | 39 | B |
| HIS | N | 812 | 186.2 | 105.1 | 42.6 | 40 | B |
| HIS | CA | 812 | 185.6 | 104.2 | 43.6 | 41 | B |
| HIS | CB | 812 | 185.0 | 105.0 | 44.7 | 42 | B |
| HIS | CG | 812 | 185.1 | 104.3 | 46.1 | 42 | B |
| HIS | CD2 | 812 | 184.4 | 103.4 | 46.7 | 42 | B |
| HIS | ND1 | 812 | 186.2 | 104.5 | 46.9 | 43 | B |
| HIS | CE1 | 812 | 186.1 | 103.8 | 48.0 | 42 | B |
| HIS | NE2 | 812 | 185.0 | 103.0 | 47.9 | 42 | B |
| HIS | C | 812 | 184.5 | 103.3 | 42.9 | 42 | B |
| HIS | O | 812 | 184.6 | 102.1 | 42.9 | 42 | B |
| ARG | N | 813 | 183.5 | 104.0 | 42.3 | 44 | B |
| ARG | CA | 813 | 182.5 | 103.3 | 41.5 | 46 | B |
| ARG | CB | 813 | 181.7 | 104.2 | 40.6 | 49 | B |
| ARG | CG | 813 | 180.6 | 105.0 | 41.2 | 52 | B |
| ARG | CD | 813 | 180.1 | 106.1 | 40.2 | 55 | B |
| ARG | NE | 813 | 179.0 | 106.9 | 40.8 | 57 | B |
| ARG | CZ | 813 | 179.1 | 107.8 | 41.8 | 58 | B |
| ARG | NH1 | 813 | 180.2 | 107.9 | 42.5 | 59 | B |
| ARG | NH2 | 813 | 178.0 | 108.5 | 42.2 | 59 | B |
| ARG | C | 813 | 183.1 | 102.2 | 40.6 | 46 | B |
| ARG | O | 813 | 183.0 | 101.0 | 40.9 | 47 | B |
| ALA | N | 814 | 183.8 | 102.7 | 39.6 | 45 | B |
| ALA | CA | 814 | 184.5 | 101.8 | 38.7 | 45 | B |
| ALA | CB | 814 | 185.4 | 102.6 | 37.8 | 45 | B |
| ALA | C | 814 | 185.2 | 100.6 | 39.3 | 45 | B |
| ALA | O | 814 | 184.9 | 99.5 | 39.0 | 45 | B |
| LEU | N | 815 | 186.1 | 100.9 | 40.2 | 46 | B |
| LEU | CA | 815 | 186.9 | 99.8 | 40.9 | 47 | B |
| LEU | CB | 815 | 187.9 | 100.3 | 41.9 | 47 | B |
| LEU | CG | 815 | 189.1 | 101.1 | 41.3 | 47 | B |
| LEU | CD1 | 815 | 190.1 | 101.5 | 42.3 | 48 | B |
| LEU | CD2 | 815 | 189.8 | 100.2 | 40.2 | 47 | B |
| LEU | C | 815 | 185.9 | 98.8 | 41.6 | 48 | B |
| LEU | O | 815 | 185.9 | 97.6 | 41.3 | 49 | B |
| HIS | N | 816 | 185.0 | 99.4 | 42.4 | 49 | B |
| HIS | CA | 816 | 184.1 | 98.6 | 43.1 | 51 | B |
| HIS | CB | 816 | 183.3 | 99.5 | 44.1 | 53 | B |
| HIS | CG | 816 | 182.3 | 98.7 | 44.8 | 54 | B |
| HIS | CD2 | 816 | 182.3 | 97.9 | 45.8 | 55 | B |
| HIS | ND1 | 816 | 180.9 | 98.8 | 44.4 | 55 | B |
| HIS | CE1 | 816 | 180.2 | 98.0 | 45.2 | 56 | B |
| HIS | NE2 | 816 | 181.0 | 97.5 | 46.1 | 56 | B |
| HIS | C | 816 | 183.1 | 97.8 | 42.2 | 52 | B |
| HIS | O | 816 | 182.6 | 96.8 | 42.7 | 52 | B |
| ALA | N | 817 | 182.9 | 98.3 | 41.0 | 52 | B |
| ALA | CA | 817 | 182.0 | 97.6 | 40.1 | 52 | B |
| ALA | CB | 817 | 181.6 | 98.5 | 39.0 | 52 | B |
| ALA | C | 817 | 182.7 | 96.3 | 39.6 | 53 | B |
| ALA | O | 817 | 182.1 | 95.5 | 39.0 | 53 | B |
| GLN | N | 818 | 184.0 | 96.2 | 39.8 | 54 | B |
| GLN | CA | 818 | 184.7 | 95.1 | 39.4 | 55 | B |
| GLN | CB | 818 | 186.1 | 95.5 | 38.8 | 55 | B |
| GLN | CG | 818 | 185.8 | 96.4 | 37.6 | 56 | B |
| GLN | CD | 818 | 187.1 | 97.2 | 37.2 | 56 | B |
| GLN | OE1 | 818 | 188.2 | 96.8 | 37.5 | 57 | B |
| GLN | NE2 | 818 | 186.9 | 98.3 | 36.6 | 57 | B |
| GLN | C | 818 | 185.0 | 94.4 | 40.8 | 55 | B |

TABLE 4-continued

The following table lists the atomic structure coordinates for FPT in complex with FPP and the inhibitor SCH66701 as derived by X-ray diffraction from crystals of that complex The abbreviations are the same as those used in Table 2

| RES | ATOM | # | X | Y | Z | B | C |
|---|---|---|---|---|---|---|---|
| GLN | O | 818 | 186.0 | 93.7 | 41.0 | 55 | B |
| GLY | N | 819 | 184.1 | 94.6 | 41.7 | 55 | B |
| GLY | CA | 819 | 184.1 | 94.0 | 43.0 | 56 | B |
| GLY | C | 819 | 185.5 | 94.1 | 43.7 | 57 | B |
| GLY | O | 819 | 186.0 | 93.1 | 44.1 | 57 | B |
| ASP | N | 820 | 186.1 | 95.2 | 43.6 | 57 | B |
| ASP | CA | 820 | 187.4 | 95.3 | 44.3 | 57 | B |
| ASP | CB | 820 | 188.1 | 96.7 | 44.0 | 57 | B |
| ASP | CG | 820 | 189.6 | 96.7 | 44.0 | 57 | B |
| ASP | OD1 | 820 | 190.2 | 96.9 | 43.0 | 57 | B |
| ASP | OD2 | 820 | 190.2 | 96.5 | 45.1 | 56 | B |
| ASP | C | 820 | 187.2 | 95.1 | 45.7 | 57 | B |
| ASP | O | 820 | 186.2 | 95.6 | 46.3 | 57 | B |
| PRO | N | 821 | 187.9 | 94.2 | 46.4 | 57 | B |
| PRO | CD | 821 | 188.7 | 93.2 | 45.7 | 57 | B |
| PRO | CA | 821 | 187.7 | 93.9 | 47.8 | 57 | B |
| PRO | CB | 821 | 188.3 | 92.5 | 47.9 | 57 | B |
| PRO | CG | 821 | 189.4 | 92.5 | 46.9 | 57 | B |
| PRO | C | 821 | 188.4 | 94.9 | 48.7 | 58 | B |
| PRO | O | 821 | 187.9 | 95.3 | 49.7 | 59 | B |
| ALA | N | 822 | 189.6 | 95.4 | 48.3 | 56 | B |
| ALA | CA | 822 | 190.4 | 96.3 | 49.1 | 55 | B |
| ALA | CB | 822 | 191.9 | 96.3 | 48.6 | 54 | B |
| ALA | C | 822 | 189.9 | 97.8 | 49.2 | 54 | B |
| ALA | O | 822 | 190.6 | 98.6 | 49.8 | 53 | B |
| LEU | N | 823 | 188.8 | 98.1 | 48.7 | 54 | B |
| LEU | CA | 823 | 188.2 | 99.5 | 48.7 | 54 | B |
| LEU | CB | 823 | 187.2 | 99.7 | 47.6 | 54 | B |
| LEU | CG | 823 | 187.6 | 99.7 | 46.2 | 54 | B |
| LEU | CD1 | 823 | 186.5 | 100.0 | 45.3 | 53 | B |
| LEU | CD2 | 823 | 188.8 | 100.7 | 46.0 | 54 | B |
| LEU | C | 823 | 187.6 | 99.8 | 50.0 | 55 | B |
| LEU | O | 823 | 186.6 | 99.2 | 50.5 | 55 | B |
| SER | N | 824 | 188.0 | 101.0 | 50.6 | 55 | B |
| SER | CA | 824 | 187.5 | 101.4 | 51.9 | 55 | B |
| SER | CB | 824 | 188.2 | 102.7 | 52.3 | 55 | B |
| SER | OG | 824 | 187.7 | 103.2 | 53.6 | 55 | B |
| SER | C | 824 | 186.0 | 101.7 | 51.8 | 56 | B |
| SER | O | 824 | 185.3 | 102.0 | 50.8 | 56 | B |
| MET | N | 825 | 185.4 | 101.5 | 53.0 | 58 | B |
| MET | CA | 825 | 183.9 | 101.7 | 53.2 | 59 | B |
| MET | CB | 825 | 183.3 | 100.5 | 53.9 | 61 | B |
| MET | CG | 825 | 183.2 | 99.2 | 53.1 | 63 | B |
| MET | SD | 825 | 182.3 | 99.4 | 51.5 | 66 | B |
| MET | CE | 825 | 183.4 | 98.2 | 50.4 | 66 | B |
| MET | C | 825 | 183.7 | 103.0 | 54.0 | 59 | B |
| MET | O | 825 | 182.7 | 103.0 | 54.7 | 59 | B |
| SER | N | 826 | 184.6 | 103.9 | 53.9 | 58 | B |
| SER | CA | 826 | 184.4 | 105.2 | 54.6 | 57 | B |
| SER | CB | 826 | 184.9 | 105.0 | 56.1 | 57 | B |
| SER | OG | 826 | 186.2 | 104.5 | 56.1 | 57 | B |
| SER | C | 826 | 185.1 | 106.4 | 54.0 | 56 | B |
| SER | O | 826 | 184.6 | 107.6 | 54.2 | 56 | B |
| HIS | N | 827 | 186.2 | 106.3 | 53.3 | 54 | B |
| HIS | CA | 827 | 186.9 | 107.4 | 52.7 | 51 | B |
| HIS | CB | 827 | 188.1 | 107.8 | 53.6 | 53 | B |
| HIS | CG | 827 | 187.9 | 107.9 | 55.0 | 54 | B |
| HIS | CD2 | 827 | 188.3 | 107.2 | 56.1 | 54 | B |
| HIS | ND1 | 827 | 187.1 | 109.0 | 55.6 | 55 | B |
| HIS | CE1 | 827 | 187.1 | 108.9 | 56.9 | 55 | B |
| HIS | NE2 | 827 | 187.8 | 107.9 | 57.2 | 55 | B |
| HIS | C | 827 | 187.5 | 107.2 | 51.3 | 48 | B |
| HIS | O | 827 | 187.9 | 106.1 | 51.0 | 48 | B |
| TRP | N | 828 | 187.5 | 108.3 | 50.5 | 45 | B |
| TRP | CA | 828 | 188.0 | 108.3 | 49.2 | 40 | B |
| TRP | CB | 828 | 187.7 | 109.6 | 48.5 | 36 | B |
| TRP | CG | 828 | 186.3 | 109.9 | 48.6 | 33 | B |
| TRP | CD2 | 828 | 185.2 | 109.2 | 48.0 | 32 | B |
| TRP | CE2 | 828 | 184.1 | 109.9 | 48.3 | 32 | B |
| TRP | CE3 | 828 | 185.1 | 107.9 | 47.4 | 32 | B |
| TRP | CD1 | 828 | 185.8 | 111.0 | 49.1 | 33 | B |
| TRP | NE1 | 828 | 184.4 | 111.1 | 48.9 | 32 | B |

TABLE 4-continued

The following table lists the atomic structure coordinates for FPT in complex with FPP and the inhibitor SCH66701 as derived by X-ray diffraction from crystals of that complex The abbreviations are the same as those used in Table 2

| RES | ATOM | # | X | Y | Z | B | C |
|---|---|---|---|---|---|---|---|
| TRP | CZ2 | 828 | 182.8 | 109.5 | 47.9 | 32 | B |
| TRP | CZ3 | 828 | 183.9 | 107.5 | 47.0 | 32 | B |
| TRP | CH2 | 828 | 182.7 | 108.3 | 47.2 | 32 | B |
| TRP | C | 828 | 189.5 | 108.1 | 49.3 | 40 | B |
| TRP | O | 828 | 190.1 | 108.4 | 50.3 | 40 | B |
| MET | N | 829 | 190.1 | 107.7 | 48.2 | 40 | B |
| MET | CA | 829 | 191.6 | 107.4 | 48.2 | 39 | B |
| MET | CB | 829 | 191.9 | 106.3 | 47.2 | 39 | B |
| MET | CG | 829 | 191.1 | 105.0 | 47.4 | 40 | B |
| MET | SD | 829 | 191.6 | 103.6 | 46.4 | 41 | B |
| MET | CE | 829 | 193.4 | 103.7 | 46.6 | 40 | B |
| MET | C | 829 | 192.4 | 108.7 | 48.1 | 39 | B |
| MET | O | 829 | 193.1 | 108.8 | 47.1 | 39 | B |
| PHE | N | 830 | 192.3 | 109.5 | 49.1 | 38 | B |
| PHE | CA | 830 | 193.1 | 110.8 | 49.1 | 36 | B |
| PHE | CB | 830 | 192.7 | 111.8 | 48.0 | 33 | B |
| PHE | CG | 830 | 191.4 | 112.6 | 48.2 | 29 | B |
| PHE | CD1 | 830 | 191.5 | 113.8 | 49.0 | 28 | B |
| PHE | CD2 | 830 | 190.3 | 112.2 | 47.6 | 28 | B |
| PHE | CE1 | 830 | 190.3 | 114.5 | 49.1 | 28 | B |
| PHE | CE2 | 830 | 189.1 | 113.0 | 47.7 | 28 | B |
| PHE | CZ | 830 | 189.2 | 114.2 | 48.5 | 28 | B |
| PHE | C | 830 | 192.9 | 111.4 | 50.5 | 37 | B |
| PHE | O | 830 | 191.9 | 111.1 | 51.2 | 38 | B |
| HIS | N | 831 | 193.8 | 112.2 | 50.9 | 37 | B |
| HIS | CA | 831 | 193.7 | 112.9 | 52.2 | 37 | B |
| HIS | CB | 831 | 195.0 | 113.5 | 52.6 | 36 | B |
| HIS | CG | 831 | 195.2 | 113.6 | 54.1 | 36 | B |
| HIS | CD2 | 831 | 194.5 | 114.3 | 55.1 | 36 | B |
| HIS | ND1 | 831 | 196.3 | 113.0 | 54.7 | 36 | B |
| HIS | CE1 | 831 | 196.3 | 113.3 | 56.0 | 36 | B |
| HIS | NE2 | 831 | 195.2 | 114.0 | 56.3 | 36 | B |
| HIS | C | 831 | 192.6 | 113.9 | 52.2 | 38 | B |
| HIS | O | 831 | 192.8 | 115.0 | 51.7 | 39 | B |
| GLN | N | 832 | 191.4 | 113.6 | 52.6 | 38 | B |
| GLN | CA | 832 | 190.2 | 114.5 | 52.6 | 38 | B |
| GLN | CB | 832 | 188.9 | 113.8 | 53.0 | 37 | B |
| GLN | CG | 832 | 188.6 | 112.6 | 52.1 | 36 | B |
| GLN | CD | 832 | 187.5 | 111.8 | 52.6 | 35 | B |
| GLN | OE1 | 832 | 186.6 | 112.2 | 53.3 | 34 | B |
| GLN | NE2 | 832 | 187.6 | 110.5 | 52.3 | 34 | B |
| GLN | C | 832 | 190.4 | 115.7 | 53.6 | 39 | B |
| GLN | O | 832 | 189.9 | 116.8 | 53.4 | 38 | B |
| GLN | N | 833 | 191.1 | 115.4 | 54.7 | 41 | B |
| GLN | CA | 833 | 191.3 | 116.3 | 55.8 | 42 | B |
| GLN | CB | 833 | 192.0 | 115.7 | 57.0 | 43 | B |
| GLN | CG | 833 | 191.9 | 116.5 | 58.2 | 44 | B |
| GLN | CD | 833 | 193.0 | 116.1 | 59.2 | 45 | B |
| GLN | OE1 | 833 | 193.8 | 115.2 | 59.0 | 45 | B |
| GLN | NE2 | 833 | 193.1 | 116.9 | 60.3 | 45 | B |
| GLN | C | 833 | 192.2 | 117.5 | 55.2 | 41 | B |
| GLN | O | 833 | 191.9 | 118.6 | 55.4 | 41 | B |
| ALA | N | 834 | 193.3 | 117.1 | 54.6 | 40 | B |
| ALA | CA | 834 | 194.2 | 118.1 | 54.0 | 39 | B |
| ALA | CB | 834 | 195.4 | 117.4 | 53.4 | 38 | B |
| ALA | C | 834 | 193.5 | 118.9 | 53.0 | 38 | B |
| ALA | O | 834 | 193.5 | 120.1 | 53.0 | 39 | B |
| LEU | N | 835 | 192.8 | 118.3 | 52.0 | 37 | B |
| LEU | CA | 835 | 192.1 | 119.0 | 51.0 | 37 | B |
| LEU | CB | 835 | 191.4 | 118.1 | 50.0 | 36 | B |
| LEU | CG | 835 | 190.6 | 118.9 | 49.0 | 36 | B |
| LEU | CD1 | 835 | 191.5 | 119.9 | 48.3 | 36 | B |
| LEU | CD2 | 835 | 190.0 | 117.9 | 47.9 | 36 | B |
| LEU | C | 835 | 191.1 | 120.1 | 51.6 | 37 | B |
| LEU | O | 835 | 191.1 | 121.2 | 51.2 | 37 | B |
| GLN | N | 836 | 190.4 | 119.7 | 52.7 | 37 | B |
| GLN | CA | 836 | 189.5 | 120.6 | 53.4 | 37 | B |
| GLN | CB | 836 | 188.7 | 119.8 | 54.4 | 37 | B |
| GLN | CG | 836 | 187.5 | 119.1 | 53.8 | 38 | B |
| GLN | CD | 836 | 186.6 | 118.4 | 54.9 | 38 | B |
| GLN | OE1 | 836 | 186.1 | 119.0 | 55.8 | 37 | B |
| GLN | NE2 | 836 | 186.4 | 117.1 | 54.7 | 38 | B |

TABLE 4-continued

The following table lists the atomic structure coordinates for FPT in complex with FPP and the inhibitor SCH66701 as derived by X-ray diffraction from crystals of that complex The abbreviations are the same as those used in Table 2

| RES | ATOM | # | X | Y | Z | B | C |
|---|---|---|---|---|---|---|---|
| GLN | C | 836 | 190.3 | 121.7 | 54.1 | 36 | B |
| GLN | O | 836 | 189.8 | 122.8 | 54.1 | 36 | B |
| GLU | N | 837 | 191.4 | 121.4 | 54.6 | 35 | B |
| GLU | CA | 837 | 192.2 | 122.4 | 55.3 | 36 | B |
| GLU | CB | 837 | 193.4 | 121.8 | 56.1 | 34 | B |
| GLU | CG | 837 | 192.8 | 121.1 | 57.3 | 34 | B |
| GLU | CD | 837 | 193.8 | 120.3 | 58.2 | 33 | B |
| GLU | OE1 | 837 | 195.0 | 120.6 | 58.1 | 32 | B |
| GLU | OE2 | 837 | 193.4 | 119.5 | 59.0 | 33 | B |
| GLU | C | 837 | 192.7 | 123.5 | 54.3 | 37 | B |
| GLU | O | 837 | 192.5 | 124.7 | 54.4 | 39 | B |
| TYR | N | 838 | 193.4 | 123.0 | 53.2 | 37 | B |
| TYR | CA | 838 | 193.9 | 124.0 | 52.2 | 35 | B |
| TYR | CB | 838 | 194.5 | 123.2 | 50.9 | 36 | B |
| TYR | CG | 838 | 194.9 | 124.1 | 49.8 | 37 | B |
| TYR | CD1 | 838 | 196.1 | 124.9 | 49.8 | 36 | B |
| TYR | CE1 | 838 | 196.4 | 125.8 | 48.8 | 35 | B |
| TYR | CD2 | 838 | 194.0 | 124.3 | 48.7 | 36 | B |
| TYR | CE2 | 838 | 194.3 | 125.2 | 47.7 | 35 | B |
| TYR | CZ | 838 | 195.5 | 126.0 | 47.7 | 35 | B |
| TYR | OH | 838 | 195.7 | 126.9 | 46.8 | 35 | B |
| TYR | C | 838 | 192.7 | 124.8 | 51.8 | 34 | B |
| TYR | O | 838 | 192.7 | 126.1 | 52.0 | 33 | B |
| ILE | N | 839 | 191.6 | 124.2 | 51.3 | 33 | B |
| ILE | CA | 839 | 190.4 | 124.9 | 50.8 | 31 | B |
| ILE | CB | 839 | 189.3 | 124.0 | 50.4 | 29 | B |
| ILE | CG2 | 839 | 188.1 | 124.8 | 50.0 | 29 | B |
| ILE | CG1 | 839 | 189.6 | 123.1 | 49.2 | 29 | B |
| ILE | CD1 | 839 | 188.5 | 122.3 | 48.7 | 28 | B |
| ILE | C | 839 | 189.9 | 125.9 | 51.8 | 31 | B |
| ILE | O | 839 | 189.4 | 127.0 | 51.4 | 33 | B |
| LEU | N | 840 | 190.0 | 125.6 | 53.1 | 30 | B |
| LEU | CA | 840 | 189.5 | 126.5 | 54.1 | 29 | B |
| LEU | CB | 840 | 189.1 | 125.7 | 55.3 | 28 | B |
| LEU | CG | 840 | 187.8 | 124.9 | 55.2 | 28 | B |
| LEU | CD1 | 840 | 187.8 | 124.0 | 56.4 | 28 | B |
| LEU | CD2 | 840 | 186.6 | 125.9 | 55.2 | 27 | B |
| LEU | C | 840 | 190.6 | 127.6 | 54.6 | 29 | B |
| LEU | O | 840 | 190.2 | 128.8 | 54.7 | 30 | B |
| MET | N | 841 | 191.8 | 127.2 | 54.9 | 29 | B |
| MET | CA | 841 | 192.8 | 128.1 | 55.3 | 30 | B |
| MET | CB | 841 | 193.9 | 127.3 | 56.0 | 30 | B |
| MET | CG | 841 | 193.5 | 126.7 | 57.3 | 30 | B |
| MET | SD | 841 | 194.9 | 126.2 | 58.3 | 31 | B |
| MET | CE | 841 | 194.9 | 124.5 | 58.0 | 30 | B |
| MET | C | 841 | 193.4 | 128.9 | 54.2 | 31 | B |
| MET | O | 841 | 193.5 | 130.1 | 54.4 | 32 | B |
| CYS | N | 842 | 193.6 | 128.3 | 53.1 | 32 | B |
| CYS | CA | 842 | 194.2 | 129.0 | 52.0 | 31 | B |
| CYS | CB | 842 | 195.4 | 128.2 | 51.4 | 30 | B |
| CYS | SG | 842 | 196.5 | 127.7 | 52.7 | 31 | B |
| CYS | C | 842 | 193.4 | 129.6 | 50.8 | 32 | B |
| CYS | O | 842 | 193.8 | 130.6 | 50.3 | 33 | B |
| CYS | N | 843 | 192.3 | 129.0 | 50.5 | 33 | B |
| CYS | CA | 843 | 191.5 | 129.5 | 49.4 | 34 | B |
| CYS | CB | 843 | 191.2 | 128.3 | 48.4 | 33 | B |
| CYS | SG | 843 | 192.7 | 127.4 | 48.1 | 32 | B |
| CYS | C | 843 | 190.2 | 130.2 | 49.6 | 35 | B |
| CYS | O | 843 | 189.3 | 130.3 | 48.7 | 36 | B |
| GLN | N | 844 | 190.1 | 130.9 | 50.7 | 37 | B |
| GLN | CA | 844 | 188.9 | 131.6 | 51.0 | 39 | B |
| GLN | CB | 844 | 188.3 | 131.1 | 52.4 | 39 | B |
| GLN | CG | 844 | 186.9 | 131.4 | 52.6 | 38 | B |
| GLN | CD | 844 | 186.3 | 130.3 | 53.4 | 39 | B |
| GLN | OE1 | 844 | 185.1 | 130.2 | 53.4 | 39 | B |
| GLN | NE2 | 844 | 187.1 | 129.6 | 54.2 | 38 | B |
| GLN | C | 844 | 189.1 | 133.1 | 51.1 | 40 | B |
| GLN | O | 844 | 190.0 | 133.6 | 51.7 | 40 | B |
| CYS | N | 845 | 188.3 | 133.8 | 50.3 | 40 | B |
| CYS | CA | 845 | 188.5 | 135.3 | 50.3 | 41 | B |
| CYS | CB | 845 | 188.1 | 135.9 | 48.9 | 42 | B |
| CYS | SG | 845 | 187.9 | 137.7 | 48.9 | 42 | B |

TABLE 4-continued

The following table lists the atomic structure coordinates for FPT in complex with FPP and the inhibitor SCH66701 as derived by X-ray diffraction from crystals of that complex The abbreviations are the same as those used in Table 2

| RES | ATOM | # | X | Y | Z | B | C |
|---|---|---|---|---|---|---|---|
| CYS | C | 845 | 187.5 | 135.9 | 51.4 | 42 | B |
| CYS | O | 845 | 186.3 | 135.6 | 51.4 | 43 | B |
| PRO | N | 846 | 188.1 | 136.7 | 52.3 | 42 | B |
| PRO | CD | 846 | 189.5 | 137.2 | 52.2 | 42 | B |
| PRO | CA | 846 | 187.4 | 137.3 | 53.4 | 42 | B |
| PRO | CB | 846 | 188.4 | 138.4 | 53.8 | 41 | B |
| PRO | CG | 846 | 189.7 | 137.8 | 53.6 | 41 | B |
| PRO | C | 846 | 186.1 | 137.9 | 53.0 | 42 | B |
| PRO | O | 846 | 185.0 | 137.6 | 53.5 | 43 | B |
| ALA | N | 847 | 186.1 | 138.8 | 51.9 | 41 | B |
| ALA | CA | 847 | 185.0 | 139.5 | 51.4 | 41 | B |
| ALA | CB | 847 | 185.4 | 140.7 | 50.5 | 41 | B |
| ALA | C | 847 | 183.9 | 138.6 | 50.6 | 40 | B |
| ALA | O | 847 | 183.0 | 139.2 | 50.1 | 40 | B |
| GLY | N | 848 | 184.2 | 137.3 | 50.5 | 39 | B |
| GLY | CA | 848 | 183.3 | 136.4 | 49.8 | 38 | B |
| GLY | C | 848 | 184.0 | 135.9 | 48.6 | 37 | B |
| GLY | O | 848 | 184.9 | 136.6 | 48.0 | 37 | B |
| GLY | N | 849 | 183.7 | 134.7 | 48.2 | 36 | B |
| GLY | CA | 849 | 184.4 | 134.1 | 47.0 | 33 | B |
| GLY | C | 849 | 185.6 | 133.3 | 47.5 | 32 | B |
| GLY | O | 849 | 186.1 | 133.5 | 48.6 | 32 | B |
| LEU | N | 850 | 185.8 | 132.2 | 46.7 | 31 | B |
| LEU | CA | 850 | 187.0 | 131.3 | 47.0 | 29 | B |
| LEU | CB | 850 | 186.6 | 129.9 | 47.0 | 28 | B |
| LEU | CG | 850 | 185.8 | 129.1 | 48.1 | 27 | B |
| LEU | CD1 | 850 | 186.6 | 129.0 | 49.4 | 25 | B |
| LEU | CD2 | 850 | 184.4 | 129.8 | 48.3 | 26 | B |
| LEU | C | 850 | 188.0 | 131.6 | 45.9 | 28 | B |
| LEU | O | 850 | 187.6 | 132.2 | 44.9 | 27 | B |
| LEU | N | 851 | 189.2 | 131.1 | 46.0 | 27 | B |
| LEU | CA | 851 | 190.2 | 131.4 | 45.0 | 27 | B |
| LEU | CB | 851 | 190.8 | 132.8 | 45.3 | 27 | B |
| LEU | CG | 851 | 191.2 | 133.1 | 46.8 | 26 | B |
| LEU | CD1 | 851 | 192.5 | 132.4 | 47.2 | 26 | B |
| LEU | CD2 | 851 | 191.2 | 134.6 | 46.9 | 26 | B |
| LEU | C | 851 | 191.2 | 130.4 | 44.8 | 28 | B |
| LEU | O | 851 | 191.4 | 129.5 | 45.6 | 29 | B |
| ASP | N | 852 | 192.0 | 130.5 | 43.6 | 28 | B |
| ASP | CA | 852 | 193.1 | 129.6 | 43.3 | 27 | B |
| ASP | CB | 852 | 193.9 | 130.3 | 42.2 | 28 | B |
| ASP | CG | 852 | 195.1 | 129.5 | 41.7 | 30 | B |
| ASP | OD1 | 852 | 195.6 | 128.6 | 42.4 | 29 | B |
| ASP | OD2 | 852 | 195.6 | 129.8 | 40.6 | 30 | B |
| ASP | C | 852 | 193.9 | 129.2 | 44.5 | 27 | B |
| ASP | O | 852 | 193.9 | 128.1 | 44.9 | 26 | B |
| LYS | N | 853 | 194.7 | 130.2 | 44.9 | 27 | B |
| LYS | CA | 853 | 195.6 | 130.0 | 46.0 | 27 | B |
| LYS | CB | 853 | 196.9 | 129.4 | 45.5 | 25 | B |
| LYS | CG | 853 | 197.7 | 130.4 | 44.7 | 24 | B |
| LYS | CD | 853 | 199.1 | 130.0 | 44.5 | 24 | B |
| LYS | CE | 853 | 199.2 | 128.7 | 43.8 | 24 | B |
| LYS | NZ | 853 | 198.6 | 128.7 | 42.5 | 23 | B |
| LYS | C | 853 | 195.8 | 131.4 | 46.6 | 28 | B |
| LYS | O | 853 | 195.4 | 132.4 | 45.9 | 26 | B |
| PRO | N | 854 | 196.4 | 131.5 | 47.8 | 31 | B |
| PRO | CD | 854 | 196.9 | 130.5 | 48.7 | 32 | B |
| PRO | CA | 854 | 196.6 | 132.9 | 48.3 | 32 | B |
| PRO | CB | 854 | 197.3 | 132.5 | 49.7 | 32 | B |
| PRO | CG | 854 | 198.0 | 131.2 | 49.5 | 32 | B |
| PRO | C | 854 | 197.5 | 133.8 | 47.5 | 33 | B |
| PRO | O | 854 | 198.5 | 133.4 | 46.9 | 34 | B |
| GLY | N | 855 | 197.0 | 135.0 | 47.3 | 34 | B |
| GLY | CA | 855 | 197.7 | 135.9 | 46.4 | 35 | B |
| GLY | C | 855 | 196.9 | 136.1 | 45.2 | 36 | B |
| GLY | O | 855 | 196.9 | 137.2 | 44.6 | 37 | B |
| LYS | N | 856 | 196.1 | 135.1 | 44.8 | 36 | B |
| LYS | CA | 856 | 195.3 | 135.1 | 43.7 | 35 | B |
| LYS | CB | 856 | 195.1 | 133.6 | 43.2 | 35 | B |
| LYS | CG | 856 | 196.4 | 133.0 | 42.7 | 35 | B |
| LYS | CD | 856 | 197.1 | 134.0 | 41.8 | 35 | B |
| LYS | CE | 856 | 198.4 | 133.4 | 41.2 | 36 | B |

TABLE 4-continued

The following table lists the atomic structure coordinates for FPT in complex with FPP and the inhibitor SCH66701 as derived by X-ray diffraction from crystals of that complex The abbreviations are the same as those used in Table 2

| RES | ATOM | # | X | Y | Z | B | C |
|---|---|---|---|---|---|---|---|
| LYS | NZ | 856 | 198.2 | 132.4 | 40.1 | 36 | B |
| LYS | C | 856 | 193.9 | 135.7 | 44.0 | 35 | B |
| LYS | O | 856 | 193.5 | 135.7 | 45.1 | 35 | B |
| SER | N | 857 | 193.3 | 136.2 | 42.9 | 36 | B |
| SER | CA | 857 | 192.0 | 136.8 | 43.0 | 36 | B |
| SER | CB | 857 | 191.8 | 137.8 | 41.9 | 36 | B |
| SER | OG | 857 | 191.6 | 139.1 | 42.3 | 37 | B |
| SER | C | 857 | 190.8 | 135.9 | 43.1 | 36 | B |
| SER | O | 857 | 190.9 | 134.7 | 42.7 | 38 | B |
| ARG | N | 858 | 189.6 | 136.4 | 43.5 | 35 | B |
| ARG | CA | 858 | 188.4 | 135.6 | 43.7 | 34 | B |
| ARG | CB | 858 | 187.6 | 136.1 | 44.8 | 34 | B |
| ARG | CG | 858 | 186.8 | 137.3 | 44.6 | 34 | B |
| ARG | CD | 858 | 186.4 | 138.1 | 45.8 | 34 | B |
| ARG | NE | 858 | 185.4 | 139.1 | 45.5 | 34 | B |
| ARG | CZ | 858 | 184.5 | 139.6 | 46.4 | 33 | B |
| ARG | NH1 | 858 | 184.5 | 139.2 | 47.7 | 33 | B |
| ARG | NH2 | 858 | 183.6 | 140.5 | 46.0 | 33 | B |
| ARG | C | 858 | 187.6 | 135.7 | 42.4 | 33 | B |
| ARG | O | 858 | 187.8 | 136.6 | 41.6 | 33 | B |
| ASP | N | 859 | 186.8 | 134.7 | 42.1 | 32 | B |
| ASP | CA | 859 | 185.9 | 134.6 | 41.0 | 31 | B |
| ASP | CB | 859 | 186.6 | 134.6 | 39.6 | 32 | B |
| ASP | CG | 859 | 187.6 | 133.4 | 39.5 | 33 | B |
| ASP | OD1 | 859 | 187.2 | 132.3 | 39.3 | 33 | B |
| ASP | OD2 | 859 | 188.8 | 133.7 | 39.6 | 34 | B |
| ASP | C | 859 | 185.0 | 133.5 | 41.2 | 31 | B |
| ASP | O | 859 | 185.2 | 132.6 | 42.0 | 30 | B |
| PHE | N | 860 | 183.9 | 133.5 | 40.4 | 30 | B |
| PHE | CA | 860 | 182.8 | 132.4 | 40.5 | 30 | B |
| PHE | CB | 860 | 181.6 | 132.9 | 39.7 | 29 | B |
| PHE | CG | 860 | 181.2 | 134.3 | 40.2 | 30 | B |
| PHE | CD1 | 860 | 181.5 | 135.4 | 39.4 | 30 | B |
| PHE | CD2 | 860 | 180.4 | 134.4 | 41.4 | 30 | B |
| PHE | CE1 | 860 | 181.1 | 136.7 | 39.9 | 30 | B |
| PHE | CE2 | 860 | 180.1 | 135.7 | 41.8 | 30 | B |
| PHE | CZ | 860 | 180.5 | 136.8 | 41.1 | 30 | B |
| PHE | C | 860 | 183.3 | 131.0 | 40.2 | 29 | B |
| PHE | O | 860 | 182.8 | 130.1 | 40.8 | 30 | B |
| TYR | N | 861 | 184.2 | 130.9 | 39.2 | 28 | B |
| TYR | CA | 861 | 184.7 | 129.6 | 38.8 | 25 | B |
| TYR | CB | 861 | 185.6 | 129.8 | 37.5 | 21 | B |
| TYR | CG | 861 | 186.5 | 128.6 | 37.2 | 17 | B |
| TYR | CD1 | 861 | 186.0 | 127.4 | 36.8 | 16 | B |
| TYR | CE1 | 861 | 186.8 | 126.2 | 36.6 | 13 | B |
| TYR | CD2 | 861 | 187.9 | 128.6 | 37.5 | 15 | B |
| TYR | CE2 | 861 | 188.7 | 127.5 | 37.4 | 13 | B |
| TYR | CZ | 861 | 188.1 | 126.3 | 36.9 | 12 | B |
| TYR | OH | 861 | 188.9 | 125.2 | 36.9 | 9 | B |
| TYR | C | 861 | 185.4 | 128.9 | 40.0 | 25 | B |
| TYR | O | 861 | 185.3 | 127.7 | 40.2 | 25 | B |
| HIS | N | 862 | 186.2 | 129.7 | 40.7 | 25 | B |
| HIS | CA | 862 | 186.9 | 129.0 | 41.9 | 26 | B |
| HIS | CB | 862 | 188.1 | 129.8 | 42.3 | 26 | B |
| HIS | CG | 862 | 189.2 | 129.9 | 41.3 | 26 | B |
| HIS | CD2 | 862 | 190.2 | 129.0 | 41.1 | 27 | B |
| HIS | ND1 | 862 | 189.2 | 130.8 | 40.3 | 27 | B |
| HIS | CE1 | 862 | 190.2 | 130.6 | 39.5 | 28 | B |
| HIS | NE2 | 862 | 190.9 | 129.5 | 40.0 | 28 | B |
| HIS | C | 862 | 186.0 | 128.9 | 43.0 | 27 | B |
| HIS | O | 862 | 186.2 | 128.0 | 43.9 | 26 | B |
| THR | N | 863 | 185.0 | 129.8 | 43.2 | 28 | B |
| THR | CA | 863 | 184.0 | 129.7 | 44.2 | 30 | B |
| THR | CB | 863 | 182.9 | 130.8 | 44.1 | 31 | B |
| THR | OG1 | 863 | 183.5 | 132.1 | 44.1 | 32 | B |
| THR | CG2 | 863 | 181.8 | 130.6 | 45.2 | 30 | B |
| THR | C | 863 | 183.3 | 128.3 | 44.0 | 31 | B |
| THR | O | 863 | 183.4 | 127.4 | 44.9 | 32 | B |
| CYS | N | 864 | 182.8 | 128.2 | 42.8 | 30 | B |
| CYS | CA | 864 | 182.1 | 127.0 | 42.4 | 28 | B |
| CYS | CB | 864 | 181.7 | 127.1 | 41.0 | 29 | B |
| CYS | SG | 864 | 181.2 | 125.5 | 40.4 | 30 | B |

TABLE 4-continued

The following table lists the atomic structure coordinates for FPT in complex with FPP and the inhibitor SCH66701 as derived by X-ray diffraction from crystals of that complex The abbreviations are the same as those used in Table 2

| RES | ATOM | # | X | Y | Z | B | C |
|---|---|---|---|---|---|---|---|
| CYS | C | 864 | 183.0 | 125.7 | 42.6 | 27 | B |
| CYS | O | 864 | 182.5 | 124.8 | 43.2 | 28 | B |
| TYR | N | 865 | 184.2 | 125.8 | 42.1 | 26 | B |
| TYR | CA | 865 | 185.0 | 124.6 | 42.2 | 25 | B |
| TYR | CB | 865 | 185.9 | 124.4 | 41.0 | 25 | B |
| TYR | CG | 865 | 185.2 | 124.1 | 39.7 | 24 | B |
| TYR | CD1 | 865 | 184.6 | 125.1 | 38.9 | 24 | B |
| TYR | CE1 | 865 | 183.8 | 124.8 | 37.9 | 25 | B |
| TYR | CD2 | 865 | 184.8 | 122.8 | 39.5 | 24 | B |
| TYR | CE2 | 865 | 184.0 | 122.5 | 38.4 | 25 | B |
| TYR | CZ | 865 | 183.4 | 123.5 | 37.6 | 25 | B |
| TYR | OH | 865 | 182.5 | 123.2 | 36.6 | 27 | B |
| TYR | C | 865 | 185.6 | 124.3 | 43.5 | 24 | B |
| TYR | O | 865 | 185.7 | 123.1 | 43.9 | 25 | B |
| CYS | N | 866 | 185.9 | 125.3 | 44.3 | 24 | B |
| CYS | CA | 866 | 186.5 | 125.0 | 45.7 | 23 | B |
| CYS | CB | 866 | 187.1 | 126.3 | 46.3 | 22 | B |
| CYS | SG | 866 | 188.6 | 126.8 | 45.6 | 23 | B |
| CYS | C | 866 | 185.4 | 124.5 | 46.6 | 23 | B |
| CYS | O | 866 | 185.7 | 123.6 | 47.4 | 22 | B |
| LEU | N | 867 | 184.2 | 124.9 | 46.4 | 23 | B |
| LEU | CA | 867 | 183.1 | 124.4 | 47.2 | 24 | B |
| LEU | CB | 867 | 181.9 | 125.4 | 47.1 | 22 | B |
| LEU | CG | 867 | 182.2 | 126.8 | 47.7 | 22 | B |
| LEU | CD1 | 867 | 180.9 | 127.6 | 47.4 | 22 | B |
| LEU | CD2 | 867 | 182.5 | 126.7 | 49.2 | 21 | B |
| LEU | C | 867 | 182.8 | 123.0 | 46.7 | 26 | B |
| LEU | O | 867 | 182.7 | 122.1 | 47.5 | 26 | B |
| SER | N | 868 | 182.6 | 122.9 | 45.4 | 27 | B |
| SER | CA | 868 | 182.4 | 121.6 | 44.8 | 28 | B |
| SER | CB | 868 | 182.4 | 121.6 | 43.3 | 27 | B |
| SER | OG | 868 | 181.3 | 122.4 | 42.7 | 26 | B |
| SER | C | 868 | 183.4 | 120.5 | 45.4 | 29 | B |
| SER | O | 868 | 183.1 | 119.4 | 45.9 | 29 | B |
| GLY | N | 869 | 184.7 | 120.9 | 45.3 | 30 | B |
| GLY | CA | 869 | 185.8 | 120.1 | 45.8 | 31 | B |
| GLY | C | 869 | 185.8 | 119.9 | 47.3 | 32 | B |
| GLY | O | 869 | 186.3 | 118.9 | 47.8 | 32 | B |
| LEU | N | 870 | 185.2 | 120.8 | 48.0 | 33 | B |
| LEU | CA | 870 | 185.1 | 120.7 | 49.5 | 33 | B |
| LEU | CB | 870 | 184.7 | 122.0 | 50.1 | 32 | B |
| LEU | CG | 870 | 184.6 | 122.2 | 51.6 | 30 | B |
| LEU | CD1 | 870 | 186.0 | 121.8 | 52.2 | 29 | B |
| LEU | CD2 | 870 | 184.2 | 123.6 | 52.0 | 28 | B |
| LEU | C | 870 | 184.1 | 119.6 | 49.9 | 34 | B |
| LEU | O | 870 | 184.3 | 118.7 | 50.6 | 34 | B |
| SER | N | 871 | 182.9 | 119.8 | 49.2 | 35 | B |
| SER | CA | 871 | 181.8 | 118.9 | 49.4 | 36 | B |
| SER | CB | 871 | 180.7 | 119.2 | 48.3 | 36 | B |
| SER | OG | 871 | 179.5 | 118.6 | 48.6 | 37 | B |
| SER | C | 871 | 182.2 | 117.4 | 49.1 | 36 | B |
| SER | O | 871 | 181.9 | 116.6 | 50.0 | 37 | B |
| ILE | N | 872 | 182.9 | 117.2 | 48.1 | 36 | B |
| ILE | CA | 872 | 183.4 | 115.8 | 47.8 | 36 | B |
| ILE | CB | 872 | 184.1 | 115.8 | 46.4 | 34 | B |
| ILE | CG2 | 872 | 185.2 | 114.7 | 46.3 | 34 | B |
| ILE | CG1 | 872 | 183.0 | 115.4 | 45.3 | 33 | B |
| ILE | CD1 | 872 | 183.4 | 115.9 | 44.0 | 32 | B |
| ILE | C | 872 | 184.3 | 115.3 | 48.9 | 36 | B |
| ILE | O | 872 | 184.1 | 114.3 | 49.5 | 36 | B |
| ALA | N | 873 | 185.3 | 116.1 | 49.3 | 36 | B |
| ALA | CA | 873 | 186.2 | 115.7 | 50.3 | 38 | B |
| ALA | CB | 873 | 187.3 | 116.8 | 50.5 | 38 | B |
| ALA | C | 873 | 185.6 | 115.4 | 51.7 | 38 | B |
| ALA | O | 873 | 186.2 | 114.8 | 52.5 | 38 | B |
| GLN | N | 874 | 184.4 | 115.9 | 51.9 | 38 | B |
| GLN | CA | 874 | 183.7 | 115.7 | 53.1 | 39 | B |
| GLN | CB | 874 | 183.3 | 117.1 | 53.7 | 38 | B |
| GLN | CG | 874 | 182.4 | 117.9 | 52.9 | 36 | B |
| GLN | CD | 874 | 182.0 | 119.2 | 53.6 | 36 | B |
| GLN | OE1 | 874 | 180.9 | 119.8 | 53.3 | 35 | B |
| GLN | NE2 | 874 | 182.8 | 119.7 | 54.6 | 34 | B |

TABLE 4-continued

The following table lists the atomic structure coordinates for FPT in complex with FPP and the inhibitor SCH66701 as derived by X-ray diffraction from crystals of that complex
The abbreviations are the same as those used in Table 2

| RES | ATOM | # | X | Y | Z | B | C |
|---|---|---|---|---|---|---|---|
| GLN | C | 874 | 182.5 | 114.8 | 53.1 | 41 | B |
| GLN | O | 874 | 181.9 | 114.5 | 54.1 | 41 | B |
| HIS | N | 875 | 182.2 | 114.2 | 51.9 | 43 | B |
| HIS | CA | 875 | 181.1 | 113.3 | 51.8 | 45 | B |
| HIS | CB | 875 | 180.0 | 113.9 | 51.0 | 44 | B |
| HIS | CG | 875 | 179.3 | 115.1 | 51.6 | 45 | B |
| HIS | CD2 | 875 | 178.3 | 115.9 | 51.2 | 45 | B |
| HIS | ND1 | 875 | 179.5 | 115.4 | 52.9 | 45 | B |
| HIS | CE1 | 875 | 178.8 | 116.5 | 53.3 | 45 | B |
| HIS | NE2 | 875 | 178.0 | 116.8 | 52.2 | 45 | B |
| HIS | C | 875 | 181.5 | 112.0 | 51.1 | 47 | B |
| HIS | O | 875 | 182.0 | 112.0 | 49.9 | 47 | B |
| PHE | N | 876 | 181.5 | 110.9 | 51.8 | 50 | B |
| PHE | CA | 876 | 181.8 | 109.6 | 51.3 | 52 | B |
| PHE | CB | 876 | 182.9 | 108.9 | 52.2 | 51 | B |
| PHE | CG | 876 | 183.1 | 107.5 | 51.7 | 50 | B |
| PHE | CD1 | 876 | 184.1 | 107.2 | 50.8 | 50 | B |
| PHE | CD2 | 876 | 182.3 | 106.5 | 52.1 | 50 | B |
| PHE | CE1 | 876 | 184.3 | 106.0 | 50.3 | 50 | B |
| PHE | CE2 | 876 | 182.4 | 105.2 | 51.6 | 50 | B |
| PHE | CZ | 876 | 183.5 | 104.9 | 50.7 | 50 | B |
| PHE | C | 876 | 180.6 | 108.7 | 51.2 | 54 | B |
| PHE | O | 876 | 179.6 | 108.8 | 52.0 | 54 | B |
| GLY | N | 877 | 180.6 | 107.8 | 50.2 | 57 | B |
| GLY | CA | 877 | 179.5 | 106.9 | 50.0 | 61 | B |
| GLY | C | 877 | 179.9 | 105.7 | 49.2 | 64 | B |
| GLY | O | 877 | 180.6 | 105.8 | 48.2 | 65 | B |
| SER | N | 878 | 179.4 | 104.5 | 49.6 | 65 | B |
| SER | CA | 878 | 179.7 | 103.3 | 48.9 | 67 | B |
| SER | CB | 878 | 181.0 | 102.7 | 49.4 | 67 | B |
| SER | OG | 878 | 181.8 | 102.0 | 48.4 | 67 | B |
| SER | C | 878 | 178.5 | 102.4 | 49.1 | 68 | B |
| SER | O | 878 | 178.6 | 101.4 | 49.8 | 68 | B |
| GLY | N | 879 | 177.4 | 102.7 | 48.4 | 68 | B |
| GLY | CA | 879 | 176.2 | 101.9 | 48.5 | 69 | B |
| GLY | C | 879 | 175.5 | 102.3 | 49.8 | 69 | B |
| GLY | O | 879 | 175.1 | 103.5 | 49.9 | 69 | B |
| ALA | N | 880 | 175.4 | 101.4 | 50.7 | 69 | B |
| ALA | CA | 880 | 174.8 | 101.7 | 52.0 | 69 | B |
| ALA | CB | 880 | 174.4 | 100.3 | 52.7 | 69 | B |
| ALA | C | 880 | 175.7 | 102.5 | 52.9 | 69 | B |
| ALA | O | 880 | 175.4 | 103.0 | 54.0 | 69 | B |
| MET | N | 881 | 177.0 | 102.5 | 52.5 | 68 | B |
| MET | CA | 881 | 178.0 | 103.3 | 53.2 | 67 | B |
| MET | CB | 881 | 179.4 | 102.8 | 52.7 | 67 | B |
| MET | CG | 881 | 180.0 | 101.7 | 53.5 | 68 | B |
| MET | SD | 881 | 178.9 | 100.3 | 53.6 | 69 | B |
| MET | CE | 881 | 178.3 | 100.6 | 55.3 | 69 | B |
| MET | C | 881 | 177.9 | 104.8 | 52.9 | 65 | B |
| MET | O | 881 | 177.6 | 105.2 | 51.8 | 65 | B |
| LEU | N | 882 | 178.2 | 105.5 | 54.0 | 64 | B |
| LEU | CA | 882 | 178.1 | 107.0 | 54.0 | 62 | B |
| LEU | CB | 882 | 176.7 | 107.5 | 54.1 | 62 | B |
| LEU | CG | 882 | 175.7 | 107.6 | 53.0 | 63 | B |
| LEU | CD1 | 882 | 176.4 | 108.2 | 51.7 | 63 | B |
| LEU | CD2 | 882 | 175.1 | 106.3 | 52.6 | 63 | B |
| LEU | C | 882 | 179.0 | 107.5 | 55.1 | 60 | B |
| LEU | O | 882 | 178.6 | 107.4 | 56.3 | 61 | B |
| HIS | N | 883 | 180.1 | 108.1 | 54.8 | 59 | B |
| HIS | CA | 883 | 180.9 | 108.6 | 55.9 | 58 | B |
| HIS | CB | 883 | 182.2 | 107.8 | 56.2 | 57 | B |
| HIS | CG | 883 | 183.0 | 108.3 | 57.3 | 58 | B |
| HIS | CD2 | 883 | 183.8 | 109.4 | 57.4 | 58 | B |
| HIS | ND1 | 883 | 183.3 | 107.5 | 58.4 | 58 | B |
| HIS | CE1 | 883 | 184.0 | 108.2 | 59.3 | 59 | B |
| HIS | NE2 | 883 | 184.4 | 109.3 | 58.7 | 58 | B |
| HIS | C | 883 | 181.3 | 110.1 | 55.6 | 57 | B |
| HIS | O | 883 | 181.9 | 110.4 | 54.6 | 57 | B |
| ASP | N | 884 | 181.0 | 111.0 | 56.5 | 54 | B |
| ASP | CA | 884 | 181.3 | 112.4 | 56.4 | 52 | B |
| ASP | CB | 884 | 180.1 | 113.3 | 56.8 | 52 | B |
| ASP | CG | 884 | 179.0 | 113.2 | 55.8 | 52 | B |

TABLE 4-continued

The following table lists the atomic structure coordinates for FPT in complex with FPP and the inhibitor SCH66701 as derived by X-ray diffraction from crystals of that complex
The abbreviations are the same as those used in Table 2

| RES | ATOM | # | X | Y | Z | B | C |
|---|---|---|---|---|---|---|---|
| ASP | OD1 | 884 | 178.1 | 114.1 | 55.9 | 52 | B |
| ASP | OD2 | 884 | 179.0 | 112.4 | 54.9 | 52 | B |
| ASP | C | 884 | 182.5 | 112.8 | 57.2 | 51 | B |
| ASP | O | 884 | 182.8 | 112.1 | 58.2 | 51 | B |
| VAL | N | 885 | 183.2 | 113.8 | 56.8 | 50 | B |
| VAL | CA | 885 | 184.3 | 114.4 | 57.5 | 49 | B |
| VAL | CB | 885 | 185.7 | 113.9 | 57.0 | 48 | B |
| VAL | CG1 | 885 | 186.8 | 114.6 | 57.7 | 47 | B |
| VAL | CG2 | 885 | 185.9 | 112.4 | 57.2 | 48 | B |
| VAL | C | 885 | 184.2 | 115.9 | 57.3 | 49 | B |
| VAL | O | 885 | 184.4 | 116.4 | 56.2 | 49 | B |
| VAL | N | 886 | 183.8 | 116.6 | 58.3 | 48 | B |
| VAL | CA | 886 | 183.7 | 118.1 | 58.2 | 49 | B |
| VAL | CB | 886 | 182.4 | 118.6 | 58.6 | 49 | B |
| VAL | CG1 | 886 | 182.4 | 120.1 | 58.4 | 49 | B |
| VAL | CG2 | 886 | 181.3 | 118.0 | 57.7 | 49 | B |
| VAL | C | 886 | 184.8 | 118.7 | 59.0 | 50 | B |
| VAL | O | 886 | 185.0 | 118.2 | 60.2 | 51 | B |
| MET | N | 887 | 185.6 | 119.5 | 58.5 | 51 | B |
| MET | CA | 887 | 186.7 | 120.2 | 59.2 | 51 | B |
| MET | CB | 887 | 187.9 | 120.4 | 58.3 | 51 | B |
| MET | CG | 887 | 188.6 | 119.2 | 57.9 | 50 | B |
| MET | SD | 887 | 188.9 | 118.2 | 59.4 | 50 | B |
| MET | CE | 887 | 190.4 | 118.9 | 59.9 | 49 | B |
| MET | C | 887 | 186.2 | 121.5 | 59.8 | 53 | B |
| MET | O | 887 | 185.5 | 122.2 | 59.2 | 52 | B |
| GLY | N | 888 | 186.7 | 121.7 | 61.1 | 54 | B |
| GLY | CA | 888 | 186.3 | 122.9 | 61.8 | 55 | B |
| GLY | C | 888 | 184.8 | 122.9 | 62.2 | 55 | B |
| GLY | O | 888 | 184.2 | 121.9 | 62.5 | 55 | B |
| VAL | N | 889 | 184.3 | 124.1 | 62.3 | 55 | B |
| VAL | CA | 889 | 182.9 | 124.2 | 62.8 | 56 | B |
| VAL | CB | 889 | 182.5 | 125.7 | 62.9 | 57 | B |
| VAL | CG1 | 889 | 181.6 | 126.1 | 61.7 | 57 | B |
| VAL | CG2 | 889 | 181.9 | 125.9 | 64.2 | 58 | B |
| VAL | C | 889 | 182.0 | 123.3 | 61.9 | 55 | B |
| VAL | O | 889 | 182.0 | 123.4 | 60.7 | 55 | B |
| PRO | N | 890 | 181.1 | 122.5 | 62.5 | 55 | B |
| PRO | CD | 890 | 181.0 | 122.3 | 64.0 | 55 | B |
| PRO | CA | 890 | 180.2 | 121.6 | 61.8 | 55 | B |
| PRO | CB | 890 | 179.4 | 121.0 | 63.0 | 55 | B |
| PRO | CG | 890 | 179.6 | 122.0 | 64.1 | 55 | B |
| PRO | C | 890 | 179.3 | 122.3 | 60.8 | 54 | B |
| PRO | O | 890 | 178.7 | 121.6 | 59.9 | 54 | B |
| GLU | N | 891 | 179.2 | 123.6 | 60.9 | 54 | B |
| GLU | CA | 891 | 178.3 | 124.3 | 59.9 | 54 | B |
| GLU | CB | 891 | 178.1 | 125.8 | 60.4 | 55 | B |
| GLU | CG | 891 | 177.1 | 126.0 | 61.6 | 56 | B |
| GLU | CD | 891 | 177.6 | 125.4 | 62.9 | 58 | B |
| GLU | OE1 | 891 | 178.8 | 125.3 | 63.1 | 58 | B |
| GLU | OE2 | 891 | 176.7 | 124.9 | 63.7 | 58 | B |
| GLU | C | 891 | 179.1 | 124.3 | 58.6 | 54 | B |
| GLU | O | 891 | 178.5 | 124.7 | 57.5 | 53 | B |
| ASN | N | 892 | 180.3 | 123.9 | 58.6 | 53 | B |
| ASN | CA | 892 | 181.1 | 123.8 | 57.4 | 51 | B |
| ASN | CB | 892 | 182.6 | 123.7 | 57.7 | 49 | B |
| ASN | CG | 892 | 183.2 | 124.9 | 58.5 | 48 | B |
| ASN | OD1 | 892 | 184.2 | 124.8 | 59.1 | 47 | B |
| ASN | ND2 | 892 | 182.5 | 126.0 | 58.5 | 47 | B |
| ASN | C | 892 | 180.7 | 122.6 | 56.5 | 51 | B |
| ASN | O | 892 | 181.5 | 122.1 | 55.7 | 53 | B |
| VAL | N | 893 | 179.5 | 122.1 | 56.7 | 50 | B |
| VAL | CA | 893 | 179.1 | 121.0 | 55.8 | 49 | B |
| VAL | CB | 893 | 178.4 | 119.9 | 56.6 | 49 | B |
| VAL | CG1 | 893 | 177.1 | 120.4 | 57.3 | 50 | B |
| VAL | CG2 | 893 | 178.0 | 118.7 | 55.7 | 49 | B |
| VAL | C | 893 | 178.2 | 121.5 | 54.7 | 48 | B |
| VAL | O | 893 | 177.1 | 122.1 | 55.0 | 49 | B |
| LEU | N | 894 | 178.6 | 121.2 | 53.5 | 47 | B |
| LEU | CA | 894 | 177.9 | 121.6 | 52.3 | 46 | B |
| LEU | CB | 894 | 178.9 | 122.0 | 51.2 | 46 | B |
| LEU | CG | 894 | 180.1 | 122.8 | 51.4 | 46 | B |

TABLE 4-continued

The following table lists the atomic structure coordinates for FPT in complex with FPP and the inhibitor SCH66701 as derived by X-ray diffraction from crystals of that complex The abbreviations are the same as those used in Table 2

| RES | ATOM | # | X | Y | Z | B | C |
|---|---|---|---|---|---|---|---|
| LEU | CD1 | 894 | 181.0 | 122.8 | 50.2 | 46 | B |
| LEU | CD2 | 894 | 179.8 | 124.2 | 51.8 | 47 | B |
| LEU | C | 894 | 177.0 | 120.5 | 51.8 | 45 | B |
| LEU | O | 894 | 177.2 | 119.3 | 52.1 | 45 | B |
| GLN | N | 895 | 176.0 | 120.9 | 51.0 | 44 | B |
| GLN | CA | 895 | 175.1 | 119.9 | 50.3 | 44 | B |
| GLN | CB | 895 | 174.1 | 120.6 | 49.5 | 44 | B |
| GLN | CG | 895 | 173.0 | 121.3 | 50.3 | 46 | B |
| GLN | CD | 895 | 172.2 | 120.3 | 51.1 | 46 | B |
| GLN | OE1 | 895 | 171.4 | 119.6 | 50.5 | 46 | B |
| GLN | NE2 | 895 | 172.5 | 120.3 | 52.4 | 47 | B |
| GLN | C | 895 | 176.0 | 119.1 | 49.4 | 44 | B |
| GLN | O | 895 | 177.0 | 119.5 | 48.9 | 44 | B |
| PRO | N | 896 | 175.7 | 117.8 | 49.3 | 43 | B |
| PRO | CD | 896 | 174.7 | 117.0 | 50.0 | 43 | B |
| PRO | CA | 896 | 176.5 | 116.9 | 48.4 | 42 | B |
| PRO | CB | 896 | 176.0 | 115.5 | 48.8 | 42 | B |
| PRO | CG | 896 | 174.6 | 115.8 | 49.2 | 42 | B |
| PRO | C | 896 | 176.3 | 117.2 | 46.9 | 41 | B |
| PRO | O | 896 | 175.2 | 117.6 | 46.5 | 41 | B |
| THR | N | 897 | 177.3 | 116.9 | 46.1 | 39 | B |
| THR | CA | 897 | 177.3 | 117.1 | 44.7 | 37 | B |
| THR | CB | 897 | 178.4 | 118.2 | 44.2 | 38 | B |
| THR | OG1 | 897 | 178.2 | 118.5 | 42.8 | 38 | B |
| THR | CG2 | 897 | 179.8 | 117.9 | 44.5 | 37 | B |
| THR | C | 897 | 177.6 | 115.8 | 44.0 | 35 | B |
| THR | O | 897 | 178.4 | 114.9 | 44.5 | 35 | B |
| HIS | N | 898 | 177.0 | 115.5 | 42.9 | 33 | B |
| HIS | CA | 898 | 177.1 | 114.3 | 42.1 | 31 | B |
| HIS | CB | 898 | 176.0 | 114.2 | 41.1 | 32 | B |
| HIS | CG | 898 | 175.9 | 112.9 | 40.4 | 33 | B |
| HIS | CD2 | 898 | 174.8 | 112.2 | 40.0 | 33 | B |
| HIS | ND1 | 898 | 177.0 | 112.2 | 40.0 | 33 | B |
| HIS | CE1 | 898 | 176.6 | 111.1 | 39.3 | 33 | B |
| HIS | NE2 | 898 | 175.2 | 111.1 | 39.3 | 33 | B |
| HIS | C | 898 | 178.5 | 114.4 | 41.3 | 31 | B |
| HIS | O | 898 | 178.6 | 115.2 | 40.5 | 31 | B |
| PRO | N | 899 | 179.4 | 113.5 | 41.6 | 29 | B |
| PRO | CD | 899 | 179.4 | 112.5 | 42.7 | 29 | B |
| PRO | CA | 899 | 180.7 | 113.5 | 41.0 | 28 | B |
| PRO | CB | 899 | 181.5 | 112.4 | 41.7 | 28 | B |
| PRO | CG | 899 | 180.4 | 111.5 | 42.2 | 30 | B |
| PRO | C | 899 | 180.9 | 113.3 | 39.4 | 27 | B |
| PRO | O | 899 | 182.0 | 113.4 | 38.9 | 27 | B |
| VAL | N | 900 | 179.8 | 113.1 | 38.7 | 25 | B |
| VAL | CA | 900 | 179.9 | 113.0 | 37.3 | 23 | B |
| VAL | CB | 900 | 179.1 | 111.9 | 36.6 | 22 | B |
| VAL | CG1 | 900 | 179.0 | 112.1 | 35.1 | 21 | B |
| VAL | CG2 | 900 | 179.7 | 110.5 | 36.9 | 21 | B |
| VAL | C | 900 | 179.5 | 114.3 | 36.7 | 24 | B |
| VAL | O | 900 | 180.3 | 115.0 | 36.0 | 24 | B |
| TYR | N | 901 | 178.3 | 114.8 | 37.1 | 25 | B |
| TYR | CA | 901 | 177.7 | 116.0 | 36.7 | 25 | B |
| TYR | CB | 901 | 176.2 | 115.9 | 36.6 | 23 | B |
| TYR | CG | 901 | 175.8 | 114.8 | 35.7 | 23 | B |
| TYR | CD1 | 901 | 175.5 | 113.5 | 36.3 | 24 | B |
| TYR | CE1 | 901 | 175.1 | 112.4 | 35.5 | 24 | B |
| TYR | CD2 | 901 | 175.6 | 114.9 | 34.4 | 23 | B |
| TYR | CE2 | 901 | 175.2 | 113.9 | 33.6 | 24 | B |
| TYR | CZ | 901 | 174.9 | 112.6 | 34.1 | 24 | B |
| TYR | OH | 901 | 174.6 | 111.6 | 33.3 | 24 | B |
| TYR | C | 901 | 178.0 | 117.3 | 37.5 | 26 | B |
| TYR | O | 901 | 177.8 | 118.4 | 37.1 | 26 | B |
| ASN | N | 902 | 178.5 | 117.0 | 38.7 | 26 | B |
| ASN | CA | 902 | 178.8 | 118.1 | 39.7 | 26 | B |
| ASN | CB | 902 | 180.0 | 118.9 | 39.3 | 26 | B |
| ASN | CG | 902 | 180.5 | 119.8 | 40.3 | 26 | B |
| ASN | OD1 | 902 | 180.6 | 119.4 | 41.5 | 25 | B |
| ASN | ND2 | 902 | 180.7 | 121.1 | 40.0 | 26 | B |
| ASN | C | 902 | 177.6 | 119.0 | 40.0 | 27 | B |
| ASN | O | 902 | 177.7 | 120.2 | 39.8 | 27 | B |
| ILE | N | 903 | 176.5 | 118.4 | 40.3 | 28 | B |

TABLE 4-continued

The following table lists the atomic structure coordinates for FPT in complex with FPP and the inhibitor SCH66701 as derived by X-ray diffraction from crystals of that complex The abbreviations are the same as those used in Table 2

| RES | ATOM | # | X | Y | Z | B | C |
|---|---|---|---|---|---|---|---|
| ILE | CA | 903 | 175.3 | 119.1 | 40.7 | 28 | B |
| ILE | CB | 903 | 174.3 | 119.3 | 39.5 | 27 | B |
| ILE | CG2 | 903 | 175.1 | 119.9 | 38.3 | 27 | B |
| ILE | CG1 | 903 | 173.6 | 118.1 | 39.0 | 26 | B |
| ILE | CD1 | 903 | 172.6 | 118.3 | 37.9 | 24 | B |
| ILE | C | 903 | 174.6 | 118.1 | 41.7 | 31 | B |
| ILE | O | 903 | 175.0 | 117.0 | 41.7 | 32 | B |
| GLY | N | 904 | 173.7 | 118.6 | 42.5 | 34 | B |
| GLY | CA | 904 | 173.1 | 117.8 | 43.5 | 35 | B |
| GLY | C | 904 | 172.6 | 116.5 | 43.0 | 36 | B |
| GLY | O | 904 | 171.8 | 116.5 | 41.9 | 36 | B |
| PRO | N | 905 | 172.9 | 115.4 | 43.6 | 36 | B |
| PRO | CD | 905 | 173.6 | 115.4 | 44.9 | 36 | B |
| PRO | CA | 905 | 172.5 | 114.0 | 43.3 | 37 | B |
| PRO | CB | 905 | 172.7 | 113.2 | 44.5 | 36 | B |
| PRO | CG | 905 | 173.9 | 113.9 | 45.1 | 36 | B |
| PRO | C | 905 | 171.0 | 114.0 | 42.9 | 38 | B |
| PRO | O | 905 | 170.6 | 113.3 | 41.9 | 38 | B |
| ASP | N | 906 | 170.2 | 114.7 | 43.7 | 41 | B |
| ASP | CA | 906 | 168.8 | 114.8 | 43.5 | 44 | B |
| ASP | CB | 906 | 168.2 | 115.5 | 44.7 | 46 | B |
| ASP | CG | 906 | 169.0 | 116.6 | 45.2 | 48 | B |
| ASP | OD1 | 906 | 169.9 | 116.4 | 46.1 | 50 | B |
| ASP | OD2 | 906 | 168.9 | 117.7 | 44.6 | 50 | B |
| ASP | C | 906 | 168.4 | 115.5 | 42.2 | 43 | B |
| ASP | O | 906 | 167.3 | 115.2 | 41.7 | 44 | B |
| LYS | N | 907 | 169.2 | 116.4 | 41.8 | 43 | B |
| LYS | CA | 907 | 168.9 | 117.1 | 40.5 | 43 | B |
| LYS | CB | 907 | 169.8 | 118.4 | 40.4 | 43 | B |
| LYS | CG | 907 | 169.6 | 119.4 | 41.5 | 42 | B |
| LYS | CD | 907 | 168.2 | 119.8 | 41.6 | 43 | B |
| LYS | CE | 907 | 167.9 | 120.7 | 42.7 | 43 | B |
| LYS | NZ | 907 | 166.5 | 121.3 | 42.7 | 44 | B |
| LYS | C | 907 | 169.2 | 116.2 | 39.4 | 42 | B |
| LYS | O | 907 | 168.4 | 116.1 | 38.5 | 42 | B |
| VAL | N | 908 | 170.3 | 115.4 | 39.6 | 42 | B |
| VAL | CA | 908 | 170.7 | 114.4 | 38.6 | 42 | B |
| VAL | CB | 908 | 172.0 | 113.7 | 39.0 | 41 | B |
| VAL | CG1 | 908 | 172.4 | 112.7 | 37.9 | 41 | B |
| VAL | CG2 | 908 | 173.1 | 114.7 | 39.2 | 41 | B |
| VAL | C | 908 | 169.6 | 113.4 | 38.4 | 42 | B |
| VAL | O | 908 | 169.1 | 113.1 | 37.3 | 42 | B |
| ILE | N | 909 | 169.0 | 113.0 | 39.6 | 42 | B |
| ILE | CA | 909 | 168.0 | 112.0 | 39.6 | 42 | B |
| ILE | CB | 909 | 167.7 | 111.5 | 41.1 | 43 | B |
| ILE | CG2 | 909 | 166.4 | 110.7 | 41.1 | 43 | B |
| ILE | CG1 | 909 | 168.9 | 110.7 | 41.6 | 42 | B |
| ILE | CD1 | 909 | 168.9 | 110.4 | 43.0 | 43 | B |
| ILE | C | 909 | 166.7 | 112.6 | 39.1 | 42 | B |
| ILE | O | 909 | 166.1 | 112.1 | 38.1 | 42 | B |
| GLN | N | 910 | 166.3 | 113.8 | 39.6 | 42 | B |
| GLN | CA | 910 | 165.1 | 114.5 | 39.2 | 42 | B |
| GLN | CB | 910 | 165.2 | 115.9 | 39.8 | 44 | B |
| GLN | CG | 910 | 163.9 | 116.7 | 39.8 | 46 | B |
| GLN | CD | 910 | 163.9 | 117.8 | 40.8 | 47 | B |
| GLN | OE1 | 910 | 163.1 | 118.7 | 40.7 | 48 | B |
| GLN | NE2 | 910 | 164.7 | 117.7 | 41.9 | 48 | B |
| GLN | C | 910 | 165.1 | 114.7 | 37.6 | 42 | B |
| GLN | O | 910 | 164.2 | 114.3 | 36.9 | 42 | B |
| ALA | N | 911 | 166.1 | 115.3 | 37.1 | 41 | B |
| ALA | CA | 911 | 166.2 | 115.6 | 35.7 | 40 | B |
| ALA | CB | 911 | 167.4 | 116.4 | 35.3 | 40 | B |
| ALA | C | 911 | 166.1 | 114.4 | 34.8 | 39 | B |
| ALA | O | 911 | 165.4 | 114.4 | 33.8 | 39 | B |
| THR | N | 912 | 166.9 | 113.3 | 35.1 | 40 | B |
| THR | CA | 912 | 166.9 | 112.1 | 34.3 | 40 | B |
| THR | CB | 912 | 168.0 | 111.1 | 34.8 | 40 | B |
| THR | OG1 | 912 | 167.7 | 110.7 | 36.2 | 41 | B |
| THR | CG2 | 912 | 169.4 | 111.6 | 34.7 | 40 | B |
| THR | C | 912 | 165.6 | 111.4 | 34.2 | 41 | B |
| THR | O | 912 | 165.2 | 111.1 | 33.1 | 41 | B |
| THR | N | 913 | 164.9 | 111.2 | 35.3 | 41 | B |

TABLE 4-continued

The following table lists the atomic structure coordinates for FPT in complex with FPP and the inhibitor SCH66701 as derived by X-ray diffraction from crystals of that complex The abbreviations are the same as those used in Table 2

| RES | ATOM | # | X | Y | Z | B | C |
|---|---|---|---|---|---|---|---|
| THR | CA | 913 | 163.6 | 110.5 | 35.3 | 40 | B |
| THR | CB | 913 | 163.1 | 110.1 | 36.7 | 40 | B |
| THR | OG1 | 913 | 162.0 | 110.9 | 37.1 | 40 | B |
| THR | CG2 | 913 | 164.1 | 110.1 | 37.8 | 39 | B |
| THR | C | 913 | 162.6 | 111.4 | 34.5 | 40 | B |
| THR | O | 913 | 161.8 | 110.8 | 33.8 | 41 | B |
| HIS | N | 914 | 162.6 | 112.7 | 34.8 | 40 | B |
| HIS | CA | 914 | 161.7 | 113.5 | 34.1 | 39 | B |
| HIS | CB | 914 | 161.8 | 115.0 | 34.6 | 38 | B |
| HIS | CG | 914 | 161.1 | 115.9 | 33.7 | 38 | B |
| HIS | CD2 | 914 | 159.8 | 116.4 | 33.7 | 38 | B |
| HIS | ND1 | 914 | 161.6 | 116.3 | 32.5 | 37 | B |
| HIS | CE1 | 914 | 160.7 | 117.0 | 31.8 | 37 | B |
| HIS | NE2 | 914 | 159.6 | 117.1 | 32.5 | 39 | B |
| HIS | C | 914 | 161.9 | 113.5 | 32.6 | 39 | B |
| HIS | O | 914 | 160.9 | 113.4 | 31.8 | 39 | B |
| PHE | N | 915 | 163.1 | 113.6 | 32.1 | 40 | B |
| PHE | CA | 915 | 163.4 | 113.6 | 30.7 | 40 | B |
| PHE | CB | 915 | 164.8 | 114.1 | 30.4 | 38 | B |
| PHE | CG | 915 | 165.0 | 115.6 | 30.4 | 36 | B |
| PHE | CD1 | 915 | 165.5 | 116.2 | 31.6 | 36 | B |
| PHE | CD2 | 915 | 164.4 | 116.4 | 29.4 | 35 | B |
| PHE | CE1 | 915 | 165.6 | 117.6 | 31.7 | 35 | B |
| PHE | CE2 | 915 | 164.5 | 117.8 | 29.5 | 35 | B |
| PHE | CZ | 915 | 165.1 | 118.4 | 30.6 | 35 | B |
| PHE | C | 915 | 163.2 | 112.2 | 30.1 | 41 | B |
| PHE | O | 915 | 162.9 | 112.0 | 28.9 | 40 | B |
| LEU | N | 916 | 163.2 | 111.2 | 31.0 | 42 | B |
| LEU | CA | 916 | 162.9 | 109.8 | 30.7 | 44 | B |
| LEU | CB | 916 | 163.2 | 108.9 | 31.9 | 44 | B |
| LEU | CG | 916 | 164.4 | 107.9 | 31.8 | 45 | B |
| LEU | CD1 | 916 | 165.4 | 108.4 | 30.8 | 45 | B |
| LEU | CD2 | 916 | 165.1 | 107.8 | 33.2 | 45 | B |
| LEU | C | 916 | 161.5 | 109.7 | 30.2 | 45 | B |
| LEU | O | 916 | 161.2 | 108.9 | 29.3 | 45 | B |
| GLN | N | 917 | 160.6 | 110.5 | 30.8 | 47 | B |
| GLN | CA | 917 | 159.2 | 110.5 | 30.4 | 49 | B |
| GLN | CB | 917 | 158.4 | 111.6 | 31.0 | 50 | B |
| GLN | CG | 917 | 158.6 | 111.8 | 32.5 | 52 | B |
| GLN | CD | 917 | 158.0 | 113.1 | 33.0 | 54 | B |
| GLN | OE1 | 917 | 158.5 | 113.8 | 33.8 | 55 | B |
| GLN | NE2 | 917 | 156.8 | 113.4 | 32.4 | 54 | B |
| GLN | C | 917 | 159.1 | 110.8 | 28.9 | 49 | B |
| GLN | O | 917 | 158.0 | 110.7 | 28.3 | 49 | B |
| LYS | N | 918 | 160.2 | 111.3 | 28.3 | 51 | B |
| LYS | CA | 918 | 160.2 | 111.6 | 26.9 | 53 | B |
| LYS | CB | 918 | 160.7 | 113.0 | 26.6 | 54 | B |
| LYS | CG | 918 | 159.9 | 114.1 | 27.4 | 55 | B |
| LYS | CD | 918 | 160.5 | 114.3 | 28.8 | 55 | B |
| LYS | CE | 918 | 159.5 | 115.2 | 29.6 | 56 | B |
| LYS | NZ | 918 | 159.2 | 116.5 | 29.0 | 56 | B |
| LYS | C | 918 | 161.0 | 110.6 | 26.1 | 54 | B |
| LYS | O | 918 | 161.9 | 110.0 | 26.6 | 53 | B |
| PRO | N | 919 | 160.7 | 110.4 | 24.8 | 55 | B |
| PRO | CD | 919 | 159.5 | 110.9 | 24.1 | 55 | B |
| PRO | CA | 919 | 161.4 | 109.4 | 24.0 | 56 | B |
| PRO | CB | 919 | 160.4 | 109.1 | 22.9 | 56 | B |
| PRO | CG | 919 | 159.7 | 110.5 | 22.7 | 55 | B |
| PRO | C | 919 | 162.6 | 110.1 | 23.4 | 58 | B |
| PRO | O | 919 | 162.7 | 111.3 | 23.2 | 59 | B |
| VAL | N | 920 | 163.7 | 109.3 | 23.2 | 60 | B |
| VAL | CA | 920 | 164.9 | 109.8 | 22.6 | 61 | B |
| VAL | CB | 920 | 165.9 | 108.7 | 22.4 | 61 | B |
| VAL | CG1 | 920 | 167.1 | 109.1 | 21.5 | 61 | B |
| VAL | CG2 | 920 | 166.4 | 108.1 | 23.7 | 61 | B |
| VAL | C | 920 | 164.4 | 110.3 | 21.2 | 64 | B |
| VAL | O | 920 | 163.7 | 109.5 | 20.6 | 64 | B |
| PRO | N | 921 | 164.7 | 111.5 | 20.8 | 66 | B |
| PRO | CD | 921 | 165.4 | 112.6 | 21.6 | 66 | B |
| PRO | CA | 921 | 164.3 | 112.0 | 19.5 | 68 | B |
| PRO | CB | 921 | 165.1 | 113.3 | 19.3 | 67 | B |
| PRO | CG | 921 | 165.1 | 113.8 | 20.7 | 66 | B |

TABLE 4-continued

The following table lists the atomic structure coordinates for FPT in complex with FPP and the inhibitor SCH66701 as derived by X-ray diffraction from crystals of that complex The abbreviations are the same as those used in Table 2

| RES | ATOM | # | X | Y | Z | B | C |
|---|---|---|---|---|---|---|---|
| PRO | C | 921 | 164.5 | 111.0 | 18.4 | 72 | B |
| PRO | O | 921 | 165.6 | 110.8 | 17.9 | 72 | B |
| GLY | N | 922 | 163.5 | 110.2 | 18.1 | 75 | B |
| GLY | CA | 922 | 163.5 | 109.2 | 17.1 | 80 | B |
| GLY | C | 922 | 163.6 | 109.6 | 15.6 | 83 | B |
| GLY | O | 922 | 163.5 | 110.8 | 15.3 | 84 | B |
| PHE | N | 923 | 163.7 | 108.6 | 14.8 | 87 | B |
| PHE | CA | 923 | 163.7 | 108.8 | 13.3 | 90 | B |
| PHE | CB | 923 | 165.2 | 108.7 | 12.8 | 91 | B |
| PHE | CG | 923 | 166.2 | 109.2 | 13.8 | 93 | B |
| PHE | CD1 | 923 | 166.7 | 110.5 | 13.8 | 93 | B |
| PHE | CD2 | 923 | 166.8 | 108.3 | 14.8 | 93 | B |
| PHE | CE1 | 923 | 167.6 | 111.0 | 14.8 | 93 | B |
| PHE | CE2 | 923 | 167.7 | 108.7 | 15.7 | 93 | B |
| PHE | CZ | 923 | 168.1 | 110.1 | 15.7 | 93 | B |
| PHE | C | 923 | 162.9 | 107.7 | 12.7 | 91 | B |
| PHE | OT1 | 923 | 163.4 | 106.5 | 12.5 | 91 | B |
| PHE | OT2 | 923 | 161.7 | 107.9 | 12.6 | 92 | B |
| ZIN | ZN | 1000 | 192.2 | 127.2 | 39.0 | 29 | Z |
| FPP | P | 2001 | 197.5 | 126.4 | 33.3 | 35 | F |
| FPP | O | 2001 | 197.4 | 128.0 | 33.4 | 36 | F |
| FPP | O1 | 2001 | 199.0 | 126.1 | 32.7 | 36 | F |
| FPP | O2 | 2001 | 197.2 | 125.9 | 34.8 | 37 | F |
| FPP | O3 | 2001 | 196.4 | 125.9 | 32.3 | 34 | F |
| FPP | C | 2001 | 196.2 | 124.5 | 31.9 | 32 | F |
| FPP | C1 | 2001 | 194.1 | 123.9 | 30.6 | 29 | F |
| FPP | C2 | 2001 | 194.8 | 124.1 | 31.7 | 30 | F |
| FPP | C3 | 2001 | 192.6 | 123.6 | 30.6 | 27 | F |
| FPP | C4 | 2001 | 194.7 | 124.0 | 29.2 | 29 | F |
| FPP | C5 | 2001 | 192.2 | 122.5 | 31.7 | 26 | F |
| FPP | C6 | 2001 | 189.8 | 122.3 | 32.6 | 22 | F |
| FPP | C7 | 2001 | 190.7 | 122.1 | 31.6 | 24 | F |
| FPP | C8 | 2001 | 189.9 | 123.4 | 33.6 | 22 | F |
| FPP | C9 | 2001 | 188.5 | 121.5 | 32.6 | 21 | F |
| FPP | C10 | 2001 | 187.4 | 122.1 | 31.8 | 20 | F |
| FPP | C11 | 2001 | 186.1 | 121.4 | 31.9 | 20 | F |
| FPP | C12 | 2001 | 184.9 | 121.6 | 31.2 | 20 | F |
| FPP | C13 | 2001 | 184.8 | 122.8 | 30.3 | 20 | F |
| FPP | C14 | 2001 | 183.7 | 120.7 | 31.2 | 20 | F |
| FPP | P1 | 2001 | 198.0 | 124.6 | 35.3 | 37 | F |
| FPP | O4 | 2001 | 197.4 | 124.2 | 36.8 | 37 | F |
| FPP | O5 | 2001 | 197.7 | 123.3 | 34.3 | 36 | F |
| FPP | O6 | 2001 | 199.6 | 124.9 | 35.5 | 37 | F |
| SCH | C1 | 2002 | 187.7 | 127.3 | 33.2 | 31 | I |
| SCH | C2 | 2002 | 187.2 | 128.3 | 32.5 | 31 | I |
| SCH | C3 | 2002 | 188.0 | 129.4 | 32.1 | 31 | I |
| SCH | C4 | 2002 | 189.1 | 129.2 | 31.1 | 32 | I |
| SCH | C5 | 2002 | 190.1 | 128.2 | 31.3 | 32 | I |
| SCH | C6 | 2002 | 190.2 | 127.2 | 32.5 | 32 | I |
| SCH | C7 | 2002 | 189.2 | 127.4 | 33.7 | 31 | I |
| SCH | C8 | 2002 | 185.9 | 128.2 | 32.1 | 31 | I |
| SCH | C9 | 2002 | 187.0 | 126.2 | 33.6 | 30 | I |
| SCH | C10 | 2002 | 185.6 | 126.1 | 33.2 | 30 | I |
| SCH | C11 | 2002 | 185.1 | 127.2 | 32.4 | 30 | I |
| SCH | N12 | 2002 | 189.2 | 130.0 | 30.0 | 32 | I |
| SCH | C13 | 2002 | 190.1 | 129.9 | 29.1 | 33 | I |
| SCH | C14 | 2002 | 191.2 | 128.9 | 29.2 | 33 | I |
| SCH | C15 | 2002 | 191.1 | 128.1 | 30.4 | 33 | I |
| SCH | C16 | 2002 | 187.8 | 130.6 | 32.7 | 33 | I |
| SCH | C17 | 2002 | 188.7 | 131.8 | 32.5 | 34 | I |
| SCH | C18 | 2002 | 189.1 | 132.5 | 33.8 | 34 | I |
| SCH | N19 | 2002 | 188.0 | 132.6 | 34.7 | 35 | I |
| SCH | C20 | 2002 | 187.4 | 131.3 | 35.0 | 35 | I |
| SCH | C21 | 2002 | 186.7 | 130.7 | 33.8 | 34 | I |
| SCH | BR22 | 2002 | 192.6 | 128.7 | 28.0 | 32 | I |
| SCH | CL23 | 2002 | 184.6 | 124.8 | 33.5 | 30 | I |
| SCH | BR24 | 2002 | 185.1 | 129.6 | 31.1 | 34 | I |
| SCH | C25 | 2002 | 187.5 | 133.7 | 35.3 | 35 | I |
| SCH | O26 | 2002 | 186.6 | 133.8 | 36.1 | 36 | I |
| SCH | C27 | 2002 | 188.3 | 134.9 | 34.8 | 35 | I |
| SCH | C28 | 2002 | 188.0 | 136.1 | 35.7 | 35 | I |
| SCH | C29 | 2002 | 187.2 | 137.1 | 35.2 | 35 | I |

TABLE 4-continued

The following table lists the atomic structure coordinates for FPT in complex with FPP and the inhibitor SCH66701 as derived by X-ray diffraction from crystals of that complex The abbreviations are the same as those used in Table 2

| RES | ATOM | # | X | Y | Z | B | C |
|---|---|---|---|---|---|---|---|
| SCH | C30 | 2002 | 187.0 | 138.3 | 36.0 | 36 | I |
| SCH | N31 | 2002 | 187.5 | 138.4 | 37.2 | 37 | I |
| SCH | C32 | 2002 | 188.3 | 137.4 | 37.8 | 36 | I |
| SCH | C33 | 2002 | 188.5 | 136.2 | 37.0 | 36 | I |
| SCH | O34 | 2002 | 187.3 | 139.5 | 38.0 | 39 | I |
| HOH | OH2 | 1002 | 188.6 | 130.2 | 17.2 | 10 | W |
| HOH | OH2 | 1003 | 202.5 | 124.5 | 44.4 | 7 | W |
| HOH | OH2 | 1004 | 204.1 | 118.0 | 25.8 | 20 | W |
| HOH | OH2 | 1005 | 199.0 | 115.7 | 20.4 | 15 | W |
| HOH | OH2 | 1007 | 200.6 | 115.3 | 35.1 | 19 | W |
| HOH | OH2 | 1009 | 192.7 | 123.7 | 17.5 | 21 | W |
| HOH | OH2 | 1011 | 197.7 | 118.0 | 19.2 | 4 | W |
| HOH | OH2 | 1012 | 205.7 | 120.4 | 35.2 | 14 | W |
| HOH | OH2 | 1016 | 203.8 | 109.9 | 23.4 | 33 | W |
| HOH | OH2 | 1019 | 195.2 | 119.4 | 18.6 | 26 | W |
| HOH | OH2 | 1020 | 180.3 | 133.7 | 21.4 | 15 | W |
| HOH | OH2 | 1021 | 204.3 | 120.9 | 32.8 | 17 | W |
| HOH | OH2 | 1022 | 208.0 | 126.4 | 33.6 | 22 | W |
| HOH | OH2 | 1023 | 205.0 | 127.9 | 36.8 | 27 | W |
| HOH | OH2 | 1024 | 182.3 | 104.6 | 22.8 | 39 | W |
| HOH | OH2 | 1026 | 178.5 | 138.5 | 19.7 | 13 | W |
| HOH | OH2 | 1032 | 205.9 | 125.5 | 36.7 | 19 | W |
| HOH | OH2 | 1033 | 198.8 | 103.8 | 28.4 | 20 | W |
| HOH | OH2 | 1034 | 204.1 | 120.1 | 48.4 | 30 | W |
| HOH | OH2 | 1038 | 191.1 | 121.4 | 16.9 | 36 | W |
| HOH | OH2 | 1039 | 210.6 | 125.7 | 33.2 | 19 | W |
| HOH | OH2 | 1042 | 193.4 | 121.9 | 45.3 | 19 | W |
| HOH | OH2 | 1044 | 194.7 | 140.1 | 8.3 | 21 | W |
| HOH | OH2 | 1045 | 192.7 | 118.9 | 18.4 | 44 | W |
| HOH | OH2 | 1046 | 202.5 | 115.9 | 46.7 | 43 | W |
| HOH | OH2 | 1050 | 180.6 | 128.1 | 15.7 | 40 | W |
| HOH | OH2 | 1051 | 190.8 | 139.7 | 25.1 | 28 | W |
| HOH | OH2 | 1052 | 207.2 | 134.0 | 14.1 | 23 | W |
| HOH | OH2 | 1054 | 191.7 | 116.7 | 17.3 | 34 | W |
| HOH | OH2 | 1055 | 194.9 | 139.9 | 5.6 | 15 | W |
| HOH | OH2 | 1061 | 176.7 | 138.2 | 26.5 | 29 | W |
| HOH | OH2 | 1063 | 203.4 | 139.4 | 14.3 | 31 | W |
| HOH | OH2 | 1064 | 196.2 | 113.7 | 18.7 | 43 | W |
| HOH | OH2 | 1065 | 208.1 | 125.0 | 11.6 | 23 | W |
| HOH | OH2 | 1066 | 179.4 | 139.4 | 43.7 | 51 | W |
| HOH | OH2 | 1067 | 186.2 | 130.2 | 16.2 | 31 | W |
| HOH | OH2 | 1068 | 186.8 | 126.4 | 10.1 | 29 | W |
| HOH | OH2 | 1070 | 186.0 | 115.0 | 21.9 | 53 | W |
| HOH | OH2 | 1071 | 207.5 | 109.0 | 11.3 | 19 | W |
| HOH | OH2 | 1073 | 202.2 | 111.5 | 25.7 | 23 | W |
| HOH | OH2 | 1074 | 201.6 | 108.0 | 25.8 | 30 | W |
| HOH | OH2 | 1075 | 212.3 | 127.0 | 31.7 | 25 | W |
| HOH | OH2 | 1076 | 208.1 | 134.9 | 17.1 | 28 | W |
| HOH | OH2 | 1077 | 204.6 | 113.1 | 35.4 | 16 | W |
| HOH | OH2 | 1078 | 208.3 | 128.4 | 31.9 | 30 | W |
| HOH | OH2 | 1080 | 188.2 | 112.1 | 12.4 | 51 | W |
| HOH | OH2 | 1081 | 204.2 | 111.6 | 11.5 | 19 | W |
| HOH | OH2 | 1082 | 178.8 | 126.3 | 16.7 | 41 | W |
| HOH | OH2 | 1084 | 175.5 | 122.9 | 14.3 | 25 | W |
| HOH | OH2 | 1085 | 204.2 | 128.2 | 9.1 | 24 | W |
| HOH | OH2 | 1087 | 208.8 | 137.6 | 21.9 | 35 | W |
| HOH | OH2 | 1089 | 212.3 | 130.1 | 29.5 | 35 | W |
| HOH | OH2 | 1090 | 180.0 | 103.2 | 35.0 | 49 | W |
| HOH | OH2 | 1091 | 185.5 | 128.6 | 11.0 | 31 | W |
| HOH | OH2 | 1092 | 212.9 | 126.4 | 29.3 | 30 | W |
| HOH | OH2 | 1093 | 202.1 | 109.9 | 39.4 | 39 | W |
| HOH | OH2 | 1095 | 199.7 | 109.4 | 24.5 | 35 | W |
| HOH | OH2 | 1096 | 188.4 | 124.2 | 11.5 | 34 | W |
| HOH | OH2 | 1097 | 190.7 | 103.3 | 22.8 | 33 | W |
| HOH | OH2 | 1098 | 185.6 | 159.1 | 8.2 | 35 | W |
| HOH | OH2 | 1099 | 187.1 | 128.1 | 18.4 | 37 | W |
| HOH | OH2 | 1100 | 188.0 | 125.1 | 8.0 | 39 | W |
| HOH | OH2 | 1102 | 201.5 | 137.5 | 27.9 | 51 | W |
| HOH | OH2 | 1103 | 193.1 | 142.2 | 18.2 | 45 | W |
| HOH | OH2 | 1104 | 214.0 | 114.3 | 16.4 | 13 | W |
| HOH | OH2 | 1105 | 204.5 | 118.2 | 41.3 | 16 | W |
| HOH | OH2 | 1106 | 188.4 | 106.6 | 46.3 | 36 | W |

TABLE 4-continued

The following table lists the atomic structure coordinates for FPT in complex with FPP and the inhibitor SCH66701 as derived by X-ray diffraction from crystals of that complex The abbreviations are the same as those used in Table 2

| RES | ATOM | # | X | Y | Z | B | C |
|---|---|---|---|---|---|---|---|
| HOH | OH2 | 1107 | 179.7 | 115.9 | 47.9 | 42 | W |
| HOH | OH2 | 1109 | 189.2 | 100.9 | 23.9 | 47 | W |
| HOH | OH2 | 1110 | 205.0 | 130.9 | 42.4 | 25 | W |
| HOH | OH2 | 1111 | 212.1 | 123.9 | 29.9 | 30 | W |
| HOH | OH2 | 1112 | 177.1 | 128.5 | 13.5 | 19 | W |
| HOH | OH2 | 1113 | 201.0 | 107.3 | 44.3 | 27 | W |
| HOH | OH2 | 1114 | 187.4 | 99.1 | 21.7 | 34 | W |
| HOH | OH2 | 1115 | 198.8 | 142.7 | 13.6 | 46 | W |
| HOH | OH2 | 1116 | 175.1 | 118.7 | 31.2 | 26 | W |
| HOH | OH2 | 1117 | 221.5 | 119.8 | 25.3 | 32 | W |
| HOH | OH2 | 1118 | 209.4 | 133.2 | 48.8 | 26 | W |
| HOH | OH2 | 1119 | 175.9 | 108.0 | 36.0 | 30 | W |
| HOH | OH2 | 1120 | 183.3 | 100.4 | 23.5 | 44 | W |
| HOH | OH2 | 1121 | 201.6 | 133.0 | 32.9 | 62 | W |
| HOH | OH2 | 1122 | 197.8 | 114.8 | 15.0 | 38 | W |
| HOH | OH2 | 1123 | 211.3 | 128.0 | 27.8 | 25 | W |
| HOH | OH2 | 1124 | 163.2 | 134.5 | 25.1 | 33 | W |
| HOH | OH2 | 1125 | 214.5 | 128.0 | 21.9 | 39 | W |
| HOH | OH2 | 1126 | 221.0 | 126.1 | 31.6 | 48 | W |
| HOH | OH2 | 1127 | 199.4 | 103.8 | 31.4 | 31 | W |
| HOH | OH2 | 1128 | 211.3 | 135.8 | 24.5 | 38 | W |
| HOH | OH2 | 1129 | 201.5 | 109.0 | 21.8 | 42 | W |
| HOH | OH2 | 1130 | 173.1 | 144.3 | 28.1 | 30 | W |
| HOH | OH2 | 1131 | 196.0 | 111.8 | 47.6 | 18 | W |
| HOH | OH2 | 1132 | 202.6 | 109.7 | 13.2 | 55 | W |
| HOH | OH2 | 1133 | 215.3 | 130.2 | 29.7 | 37 | W |
| HOH | OH2 | 1134 | 212.4 | 124.6 | 17.2 | 28 | W |
| HOH | OH2 | 1135 | 189.5 | 114.6 | 16.1 | 40 | W |
| HOH | OH2 | 1136 | 169.0 | 123.2 | 22.2 | 43 | W |
| HOH | OH2 | 1137 | 178.4 | 141.1 | 24.5 | 23 | W |
| HOH | OH2 | 1138 | 219.5 | 124.8 | 26.0 | 40 | W |
| HOH | OH2 | 1139 | 195.1 | 142.1 | 3.9 | 40 | W |
| HOH | OH2 | 1140 | 211.5 | 120.1 | 16.1 | 22 | W |
| HOH | OH2 | 1141 | 182.3 | 139.1 | 23.7 | 36 | W |
| HOH | OH2 | 1142 | 178.3 | 112.2 | 46.7 | 50 | W |
| HOH | OH2 | 1143 | 186.5 | 152.1 | 10.2 | 32 | W |
| HOH | OH2 | 1144 | 173.1 | 139.5 | 17.8 | 40 | W |
| HOH | OH2 | 1145 | 215.5 | 102.4 | 15.6 | 39 | W |
| HOH | OH2 | 1146 | 214.8 | 107.2 | 19.7 | 35 | W |
| HOH | OH2 | 1147 | 219.5 | 123.5 | 49.3 | 46 | W |
| HOH | OH2 | 1148 | 201.0 | 97.3 | 26.4 | 49 | W |
| HOH | OH2 | 1149 | 211.5 | 134.0 | 17.1 | 43 | W |
| HOH | OH2 | 1150 | 204.4 | 135.8 | 11.3 | 36 | W |
| HOH | OH2 | 1151 | 178.7 | 141.7 | 41.7 | 23 | W |
| HOH | OH2 | 1152 | 221.6 | 124.6 | 40.7 | 59 | W |
| HOH | OH2 | 1155 | 196.1 | 124.1 | 18.2 | 20 | W |
| HOH | OH2 | 1156 | 175.6 | 101.4 | 16.5 | 55 | W |
| HOH | OH2 | 1157 | 204.0 | 135.5 | 7.7 | 47 | W |
| HOH | OH2 | 1158 | 190.0 | 107.3 | 17.9 | 23 | W |
| HOH | OH2 | 1159 | 177.8 | 144.0 | 24.6 | 23 | W |
| HOH | OH2 | 1160 | 197.2 | 124.4 | 21.0 | 38 | W |
| HOH | OH2 | 1161 | 205.9 | 104.1 | 15.4 | 64 | W |
| HOH | OH2 | 1162 | 172.1 | 121.8 | 14.1 | 28 | W |
| HOH | OH2 | 1163 | 194.7 | 144.2 | 17.3 | 48 | W |
| HOH | OH2 | 1164 | 194.8 | 141.3 | 1.3 | 37 | W |
| HOH | OH2 | 1165 | 214.8 | 127.8 | 33.0 | 20 | W |
| HOH | OH2 | 1166 | 211.4 | 129.4 | 31.9 | 25 | W |
| HOH | OH2 | 1167 | 179.7 | 121.3 | 11.6 | 45 | W |
| HOH | OH2 | 1168 | 205.6 | 122.7 | 41.4 | 30 | W |
| HOH | OH2 | 1169 | 170.3 | 142.8 | 38.0 | 37 | W |
| HOH | OH2 | 1170 | 205.7 | 118.5 | 45.5 | 39 | W |
| HOH | OH2 | 1171 | 203.2 | 121.1 | 3.2 | 49 | W |
| HOH | OH2 | 1172 | 217.0 | 115.8 | 17.4 | 31 | W |
| HOH | OH2 | 1173 | 209.1 | 117.1 | 41.6 | 29 | W |
| HOH | OH2 | 1174 | 219.8 | 125.2 | 46.6 | 70 | W |
| HOH | OH2 | 1175 | 157.1 | 125.8 | 36.2 | 39 | W |
| HOH | OH2 | 1176 | 207.4 | 131.0 | 33.0 | 22 | W |
| HOH | OH2 | 1177 | 206.9 | 119.2 | 48.3 | 24 | W |
| HOH | OH2 | 1178 | 204.8 | 132.9 | 13.0 | 32 | W |
| HOH | OH2 | 1179 | 191.5 | 101.1 | 25.5 | 37 | W |
| HOH | OH2 | 1181 | 173.0 | 130.7 | 16.4 | 40 | W |
| HOH | OH2 | 1182 | 160.9 | 127.1 | 29.4 | 50 | W |

TABLE 4-continued

The following table lists the atomic structure coordinates for FPT in complex with FPP and the inhibitor SCH66701 as derived by X-ray diffraction from crystals of that complex
The abbreviations are the same as those used in Table 2

| RES | ATOM | # | X | Y | Z | B | C |
|---|---|---|---|---|---|---|---|
| HOH | OH2 | 1183 | 208.7 | 122.6 | 6.7 | 53 | W |
| HOH | OH2 | 1184 | 215.9 | 121.7 | 17.8 | 45 | W |
| HOH | OH2 | 1185 | 205.1 | 127.6 | 33.6 | 54 | W |
| HOH | OH2 | 1186 | 192.8 | 144.2 | 6.3 | 37 | W |
| HOH | OH2 | 1187 | 207.4 | 137.4 | 17.2 | 50 | W |
| HOH | OH2 | 1188 | 213.0 | 90.7 | 38.1 | 44 | W |
| HOH | OH2 | 1189 | 202.0 | 105.9 | 19.5 | 54 | W |
| HOH | OH2 | 1190 | 206.1 | 137.8 | 12.7 | 51 | W |
| HOH | OH2 | 1191 | 178.0 | 133.9 | 8.1 | 25 | W |
| HOH | OH2 | 1193 | 187.1 | 141.4 | 31.8 | 38 | W |
| HOH | OH2 | 1194 | 206.4 | 124.5 | 39.1 | 38 | W |
| HOH | OH2 | 1195 | 205.8 | 103.3 | 26.3 | 39 | W |
| HOH | OH2 | 1196 | 176.7 | 152.4 | 22.1 | 50 | W |
| HOH | OH2 | 1197 | 188.7 | 114.5 | 13.4 | 38 | W |
| HOH | OH2 | 1198 | 205.5 | 139.0 | 23.7 | 33 | W |
| HOH | OH2 | 1200 | 195.1 | 118.4 | 9.4 | 50 | W |
| HOH | OH2 | 1201 | 160.6 | 118.6 | 26.6 | 66 | W |
| HOH | OH2 | 1202 | 186.6 | 122.7 | 13.3 | 31 | W |
| HOH | OH2 | 1203 | 181.4 | 148.1 | 36.0 | 32 | W |
| HOH | OH2 | 1204 | 189.7 | 120.4 | 14.1 | 36 | W |
| HOH | OH2 | 1205 | 173.8 | 108.4 | 39.8 | 56 | W |
| HOH | OH2 | 1206 | 217.2 | 123.1 | 19.6 | 39 | W |
| HOH | OH2 | 1207 | 206.9 | 120.4 | 42.2 | 58 | W |
| HOH | OH2 | 1208 | 214.1 | 118.3 | 43.6 | 40 | W |
| HOH | OH2 | 1209 | 211.8 | 127.7 | 23.2 | 40 | W |
| HOH | OH2 | 1210 | 194.0 | 117.0 | 16.1 | 34 | W |
| HOH | OH2 | 1211 | 191.1 | 123.8 | 65.6 | 46 | W |
| HOH | OH2 | 1212 | 178.7 | 142.5 | 45.3 | 67 | W |
| HOH | OH2 | 1213 | 183.2 | 100.2 | 31.7 | 58 | W |
| HOH | OH2 | 1214 | 212.1 | 121.3 | 11.1 | 54 | W |
| HOH | OH2 | 1215 | 209.7 | 127.4 | 12.2 | 47 | W |
| HOH | OH2 | 1216 | 212.0 | 130.9 | 18.8 | 46 | W |
| HOH | OH2 | 1217 | 165.5 | 105.4 | 27.1 | 75 | W |
| HOH | OH2 | 1219 | 191.2 | 122.8 | 6.5 | 32 | W |
| HOH | OH2 | 1220 | 210.8 | 117.0 | 48.0 | 49 | W |
| HOH | OH2 | 1221 | 197.1 | 108.2 | 19.0 | 76 | W |
| HOH | OH2 | 1222 | 184.5 | 159.0 | 20.2 | 22 | W |
| HOH | OH2 | 1223 | 215.9 | 128.7 | 24.4 | 73 | W |
| HOH | OH2 | 1224 | 175.6 | 146.5 | 5.3 | 46 | W |
| HOH | OH2 | 1225 | 201.5 | 105.4 | 36.8 | 48 | W |
| HOH | OH2 | 1226 | 192.2 | 143.0 | 10.9 | 54 | W |
| HOH | OH2 | 1227 | 157.9 | 122.3 | 39.1 | 54 | W |
| HOH | OH2 | 1228 | 211.3 | 131.4 | 38.7 | 44 | W |
| HOH | OH2 | 1229 | 210.5 | 123.4 | 10.2 | 37 | W |
| HOH | OH2 | 1230 | 197.2 | 119.3 | 7.1 | 52 | W |
| HOH | OH2 | 1231 | 175.7 | 141.4 | 29.8 | 22 | W |
| HOH | OH2 | 1232 | 190.4 | 159.6 | 15.0 | 32 | W |
| HOH | OH2 | 1233 | 172.3 | 118.7 | 46.4 | 37 | W |
| HOH | OH2 | 1234 | 163.0 | 119.4 | 27.7 | 47 | W |
| HOH | OH2 | 1235 | 208.5 | 98.4 | 26.0 | 46 | W |
| HOH | OH2 | 1236 | 202.3 | 101.5 | 43.8 | 29 | W |
| HOH | OH2 | 1237 | 209.7 | 131.9 | 36.2 | 44 | W |
| HOH | OH2 | 1238 | 186.4 | 149.6 | 10.0 | 39 | W |
| HOH | OH2 | 1239 | 212.3 | 126.1 | 13.0 | 42 | W |
| HOH | OH2 | 1240 | 213.5 | 109.0 | 18.1 | 24 | W |
| HOH | OH2 | 1241 | 218.2 | 121.1 | 34.8 | 49 | W |
| HOH | OH2 | 1242 | 213.1 | 95.5 | 26.9 | 52 | W |
| HOH | OH2 | 1243 | 193.4 | 146.8 | 23.9 | 46 | W |
| HOH | OH2 | 1244 | 190.5 | 145.1 | 26.2 | 44 | W |
| HOH | OH2 | 1245 | 169.6 | 108.8 | 26.2 | 43 | W |
| HOH | OH2 | 1246 | 171.1 | 147.8 | 11.7 | 54 | W |
| HOH | OH2 | 1247 | 195.7 | 109.1 | 48.3 | 45 | W |
| HOH | OH2 | 1248 | 212.1 | 119.2 | 13.7 | 36 | W |
| HOH | OH2 | 1249 | 201.7 | 115.2 | 53.9 | 21 | W |
| HOH | OH2 | 1250 | 187.6 | 150.1 | 6.3 | 56 | W |
| HOH | OH2 | 1251 | 217.5 | 128.9 | 31.3 | 73 | W |
| HOH | OH2 | 1252 | 180.3 | 127.5 | 58.1 | 29 | W |
| HOH | OH2 | 1253 | 203.4 | 103.2 | 28.9 | 50 | W |
| HOH | OH2 | 1254 | 213.5 | 123.8 | 13.1 | 52 | W |
| HOH | OH2 | 1255 | 197.0 | 116.2 | 17.2 | 56 | W |
| HOH | OH2 | 1256 | 197.2 | 143.0 | 17.6 | 48 | W |
| HOH | OH2 | 1257 | 214.2 | 126.4 | 19.1 | 53 | W |

TABLE 4-continued

The following table lists the atomic structure coordinates for FPT in complex with FPP and the inhibitor SCH66701 as derived by X-ray diffraction from crystals of that complex
The abbreviations are the same as those used in Table 2

| RES | ATOM | # | X | Y | Z | B | C |
|---|---|---|---|---|---|---|---|
| HOH | OH2 | 1258 | 176.9 | 139.2 | 21.5 | 41 | W |
| HOH | OH2 | 1259 | 183.2 | 159.3 | 23.0 | 52 | W |
| HOH | OH2 | 1260 | 212.9 | 119.1 | 53.6 | 59 | W |
| HOH | OH2 | 1261 | 205.0 | 139.0 | 6.1 | 62 | W |
| HOH | OH2 | 1263 | 200.9 | 142.1 | 8.5 | 60 | W |
| HOH | OH2 | 1264 | 203.8 | 135.0 | 26.3 | 55 | W |
| HOH | OH2 | 1265 | 219.9 | 123.6 | 37.1 | 68 | W |
| HOH | OH2 | 1266 | 204.8 | 132.5 | 32.4 | 57 | W |
| HOH | OH2 | 1267 | 211.7 | 110.0 | 12.4 | 46 | W |
| HOH | OH2 | 1268 | 193.0 | 114.1 | 17.9 | 46 | W |
| HOH | OH2 | 1269 | 184.2 | 98.2 | 27.7 | 51 | W |
| HOH | OH2 | 1270 | 169.9 | 121.7 | 47.4 | 54 | W |
| HOH | OH2 | 1271 | 211.3 | 125.8 | 8.6 | 64 | W |
| HOH | OH2 | 1272 | 181.1 | 141.0 | 48.1 | 56 | W |
| HOH | OH2 | 1273 | 200.6 | 110.1 | 19.4 | 50 | W |
| HOH | OH2 | 1274 | 200.4 | 107.9 | 59.1 | 71 | W |
| HOH | OH2 | 1275 | 206.1 | 119.1 | 5.8 | 37 | W |
| HOH | OH2 | 1276 | 207.5 | 116.6 | 5.3 | 55 | W |
| HOH | OH2 | 1277 | 171.8 | 131.9 | 20.2 | 51 | W |
| HOH | OH2 | 1278 | 161.6 | 127.9 | 37.2 | 49 | W |
| HOH | OH2 | 1279 | 212.4 | 103.5 | 53.7 | 55 | W |
| HOH | OH2 | 1281 | 221.6 | 113.1 | 44.8 | 66 | W |
| HOH | OH2 | 1282 | 190.4 | 141.2 | 30.3 | 98 | W |
| HOH | OH2 | 1283 | 173.0 | 149.1 | 25.5 | 53 | W |
| HOH | OH2 | 1284 | 177.9 | 110.8 | 53.0 | 37 | W |
| HOH | OH2 | 1285 | 204.6 | 116.2 | 43.0 | 39 | W |
| HOH | OH2 | 1286 | 169.2 | 106.0 | 25.8 | 61 | W |
| HOH | OH2 | 1287 | 193.1 | 124.4 | 2.4 | 62 | W |
| HOH | OH2 | 1288 | 174.5 | 146.0 | 24.6 | 42 | W |
| HOH | OH2 | 1289 | 197.7 | 112.1 | 26.0 | 34 | W |
| HOH | OH2 | 1290 | 167.0 | 118.3 | 37.8 | 26 | W |
| HOH | OH2 | 1291 | 181.5 | 141.2 | 39.8 | 54 | W |
| HOH | OH2 | 1292 | 212.9 | 128.2 | 25.6 | 48 | W |
| HOH | OH2 | 1293 | 191.9 | 134.3 | 1.6 | 39 | W |
| HOH | OH2 | 1295 | 190.4 | 110.4 | 53.3 | 40 | W |
| HOH | OH2 | 1296 | 179.3 | 132.2 | 58.2 | 71 | W |
| HOH | OH2 | 1297 | 204.4 | 96.6 | 34.6 | 50 | W |
| HOH | OH2 | 1298 | 211.3 | 121.2 | 56.6 | 51 | W |
| HOH | OH2 | 1299 | 206.7 | 130.1 | 3.5 | 66 | W |
| HOH | OH2 | 1300 | 194.9 | 142.4 | 9.7 | 38 | W |
| HOH | OH2 | 1301 | 195.7 | 113.7 | 60.6 | 42 | W |
| HOH | OH2 | 1302 | 180.8 | 112.9 | 47.5 | 46 | W |
| HOH | OH2 | 1303 | 209.3 | 114.3 | 48.6 | 54 | W |
| HOH | OH2 | 1304 | 165.3 | 126.6 | 19.8 | 56 | W |
| HOH | OH2 | 1305 | 220.5 | 119.4 | 22.1 | 33 | W |
| HOH | OH2 | 1306 | 179.4 | 133.6 | 10.4 | 37 | W |
| HOH | OH2 | 1307 | 203.0 | 109.5 | 36.6 | 34 | W |
| HOH | OH2 | 1308 | 162.5 | 128.4 | 42.1 | 66 | W |
| HOH | OH2 | 1309 | 204.0 | 107.0 | 35.4 | 30 | W |
| HOH | OH2 | 1310 | 198.9 | 119.4 | 54.0 | 45 | W |
| HOH | OH2 | 1311 | 217.8 | 105.2 | 15.6 | 64 | W |
| HOH | OH2 | 1312 | 161.1 | 113.3 | 21.3 | 47 | W |
| HOH | OH2 | 1313 | 220.2 | 105.0 | 19.8 | 52 | W |
| HOH | OH2 | 1314 | 214.4 | 111.3 | 16.0 | 36 | W |
| HOH | OH2 | 1315 | 187.6 | 133.4 | 56.1 | 50 | W |
| HOH | OH2 | 1316 | 201.7 | 105.0 | 26.4 | 65 | W |
| HOH | OH2 | 1317 | 207.2 | 106.3 | 39.0 | 61 | W |
| HOH | OH2 | 1318 | 191.8 | 112.5 | 55.0 | 49 | W |
| HOH | OH2 | 1319 | 191.4 | 130.7 | 53.1 | 57 | W |
| HOH | OH2 | 1320 | 188.7 | 150.9 | 14.6 | 61 | W |
| HOH | OH2 | 1321 | 181.7 | 108.1 | 14.4 | 57 | W |
| HOH | OH2 | 1322 | 194.6 | 147.8 | 17.7 | 67 | W |
| HOH | OH2 | 1323 | 198.6 | 99.1 | 54.4 | 50 | W |
| HOH | OH2 | 1324 | 189.6 | 152.7 | 28.0 | 58 | W |
| HOH | OH2 | 1325 | 164.4 | 121.2 | 41.1 | 49 | W |
| HOH | OH2 | 1326 | 207.0 | 131.5 | 36.1 | 46 | W |
| HOH | OH2 | 1327 | 184.4 | 148.2 | 37.3 | 67 | W |
| HOH | OH2 | 1328 | 205.2 | 139.2 | 17.7 | 64 | W |
| HOH | OH2 | 1329 | 187.4 | 149.5 | 12.4 | 49 | W |
| HOH | OH2 | 1330 | 191.2 | 122.5 | 11.8 | 53 | W |
| HOH | OH2 | 1331 | 207.5 | 106.3 | 42.0 | 46 | W |
| HOH | OH2 | 1332 | 200.4 | 98.8 | 31.5 | 54 | W |

TABLE 4-continued

The following table lists the atomic structure coordinates for FPT in complex with FPP and the inhibitor SCH66701 as derived by X-ray diffraction from crystals of that complex The abbreviations are the same as those used in Table 2

| RES | ATOM | # | X | Y | Z | B | C |
|---|---|---|---|---|---|---|---|
| HOH | OH2 | 1333 | 202.4 | 141.0 | 20.9 | 49 | W |
| HOH | OH2 | 1334 | 187.0 | 125.1 | 5.3 | 68 | W |
| HOH | OH2 | 1335 | 185.3 | 138.4 | 41.1 | 48 | W |
| HOH | OH2 | 1336 | 190.2 | 158.5 | 22.6 | 39 | W |
| HOH | OH2 | 1337 | 187.1 | 147.9 | 27.8 | 63 | W |
| HOH | OH2 | 1338 | 203.5 | 140.9 | 23.5 | 68 | W |
| HOH | OH2 | 1339 | 171.0 | 139.9 | 21.8 | 37 | W |
| HOH | OH2 | 1340 | 160.0 | 121.8 | 41.7 | 68 | W |
| HOH | OH2 | 1341 | 187.8 | 106.1 | 18.4 | 26 | W |
| HOH | OH2 | 1342 | 174.5 | 128.5 | 13.5 | 58 | W |
| HOH | OH2 | 1343 | 173.8 | 135.5 | 8.9 | 42 | W |
| HOH | OH2 | 1344 | 184.7 | 121.5 | 56.7 | 33 | W |
| HOH | OH2 | 1345 | 190.6 | 148.2 | 14.3 | 21 | W |
| HOH | OH2 | 1346 | 194.6 | 121.8 | 4.5 | 76 | W |
| HOH | OH2 | 1347 | 177.2 | 130.9 | 9.8 | 61 | W |
| HOH | OH2 | 1348 | 174.1 | 117.7 | 54.2 | 59 | W |
| HOH | OH2 | 1349 | 202.0 | 131.9 | 43.4 | 58 | W |
| HOH | OH2 | 1350 | 175.9 | 138.1 | 18.8 | 40 | W |
| HOH | OH2 | 1351 | 180.2 | 138.9 | 51.0 | 58 | W |
| HOH | OH2 | 1352 | 195.7 | 114.6 | 13.2 | 71 | W |
| HOH | OH2 | 1353 | 198.6 | 103.3 | 58.0 | 51 | W |
| HOH | OH2 | 1354 | 187.9 | 144.2 | 31.6 | 47 | W |
| HOH | OH2 | 1355 | 175.1 | 123.9 | 53.2 | 44 | W |
| HOH | OH2 | 1356 | 184.6 | 148.8 | 3.9 | 53 | W |
| HOH | OH2 | 1357 | 170.7 | 144.8 | 27.4 | 51 | W |
| HOH | OH2 | 1358 | 168.1 | 142.8 | 19.9 | 74 | W |
| HOH | OH2 | 1359 | 162.6 | 126.0 | 23.8 | 61 | W |
| HOH | OH2 | 1360 | 176.3 | 135.9 | 10.0 | 42 | W |
| HOH | OH2 | 1361 | 193.9 | 116.3 | 62.9 | 75 | W |
| HOH | OH2 | 1362 | 178.5 | 109.7 | 14.7 | 70 | W |
| HOH | OH2 | 1363 | 203.1 | 130.7 | 6.5 | 30 | W |
| HOH | OH2 | 1364 | 197.2 | 107.5 | 22.5 | 62 | W |
| HOH | OH2 | 1365 | 157.0 | 125.6 | 29.6 | 75 | W |
| HOH | OH2 | 1366 | 203.9 | 96.6 | 38.4 | 70 | W |
| HOH | OH2 | 1367 | 194.1 | 130.9 | 57.7 | 42 | W |
| HOH | OH2 | 1368 | 181.4 | 150.1 | 34.0 | 71 | W |
| HOH | OH2 | 1369 | 219.2 | 125.8 | 35.1 | 54 | W |
| HOH | OH2 | 1370 | 188.0 | 145.3 | 28.2 | 47 | W |
| HOH | OH2 | 1371 | 184.3 | 151.2 | 21.2 | 37 | W |
| HOH | OH2 | 1372 | 177.0 | 148.7 | 29.3 | 58 | W |
| HOH | OH2 | 1373 | 192.5 | 142.6 | 0.7 | 53 | W |
| HOH | OH2 | 1374 | 214.4 | 125.4 | 44.0 | 30 | W |
| HOH | OH2 | 1375 | 177.5 | 104.7 | 21.1 | 51 | W |
| HOH | OH2 | 1376 | 217.5 | 112.6 | 14.0 | 64 | W |
| HOH | OH2 | 1377 | 198.3 | 153.2 | 18.0 | 70 | W |
| HOH | OH2 | 1378 | 184.9 | 145.4 | 1.1 | 57 | W |
| HOH | OH2 | 1379 | 209.6 | 120.8 | 42.1 | 40 | W |
| HOH | OH2 | 1380 | 184.6 | 110.5 | 54.9 | 45 | W |
| HOH | OH2 | 1381 | 215.6 | 114.6 | 37.6 | 52 | W |
| HOH | OH2 | 1382 | 213.0 | 122.2 | 16.5 | 45 | W |
| HOH | OH2 | 1383 | 188.4 | 143.5 | 0.9 | 66 | W |
| HOH | OH2 | 1384 | 206.5 | 100.8 | 21.4 | 55 | W |
| HOH | OH2 | 1385 | 159.4 | 132.3 | 31.7 | 68 | W |
| HOH | OH2 | 1386 | 174.7 | 147.4 | 28.1 | 52 | W |
| HOH | OH2 | 1388 | 173.7 | 135.8 | 54.4 | 57 | W |
| HOH | OH2 | 1389 | 218.4 | 116.4 | 28.3 | 54 | W |
| HOH | OH2 | 1390 | 217.6 | 97.3 | 26.8 | 55 | W |
| HOH | OH2 | 1391 | 176.0 | 126.1 | 15.0 | 54 | W |
| HOH | OH2 | 1392 | 207.2 | 117.4 | 43.6 | 61 | W |
| HOH | OH2 | 1393 | 169.0 | 124.7 | 46.2 | 48 | W |
| HOH | OH2 | 1394 | 180.1 | 134.6 | 56.3 | 49 | W |
| HOH | OH2 | 1395 | 170.2 | 108.5 | 29.5 | 47 | W |
| HOH | OH2 | 1396 | 174.5 | 144.0 | 3.9 | 59 | W |
| HOH | OH2 | 1397 | 159.9 | 118.6 | 39.2 | 59 | W |
| HOH | OH2 | 1398 | 191.2 | 125.3 | 7.7 | 52 | W |
| HOH | OH2 | 1399 | 212.9 | 93.2 | 39.5 | 53 | W |
| HOH | OH2 | 1400 | 197.3 | 142.7 | 5.5 | 80 | W |
| HOH | OH2 | 1401 | 213.6 | 127.4 | 16.6 | 66 | W |
| HOH | OH2 | 1402 | 166.6 | 131.6 | 21.1 | 52 | W |
| HOH | OH2 | 1403 | 204.1 | 132.7 | 27.5 | 67 | W |
| HOH | OH2 | 1404 | 177.4 | 102.7 | 26.3 | 73 | W |
| HOH | OH2 | 1405 | 175.4 | 106.5 | 21.8 | 59 | W |
| HOH | OH2 | 1406 | 213.6 | 130.7 | 21.2 | 83 | W |
| HOH | OH2 | 1407 | 215.4 | 129.7 | 26.9 | 69 | W |
| HOH | OH2 | 1408 | 184.6 | 141.9 | 39.8 | 73 | W |
| HOH | OH2 | 1409 | 164.1 | 129.3 | 24.3 | 47 | W |
| HOH | OH2 | 1410 | 216.8 | 119.1 | 49.5 | 61 | W |
| HOH | OH2 | 1411 | 211.3 | 118.4 | 42.3 | 43 | W |
| HOH | OH2 | 1412 | 178.6 | 148.3 | 37.4 | 54 | W |
| HOH | OH2 | 1413 | 185.9 | 136.4 | 56.0 | 64 | W |
| HOH | OH2 | 1414 | 219.2 | 90.5 | 40.6 | 71 | W |
| HOH | OH2 | 1415 | 208.6 | 131.7 | 13.5 | 39 | W |
| HOH | OH2 | 1416 | 205.2 | 130.5 | 38.6 | 69 | W |
| HOH | OH2 | 1417 | 166.1 | 137.4 | 31.9 | 46 | W |
| HOH | OH2 | 1418 | 188.4 | 142.1 | 28.5 | 54 | W |
| HOH | OH2 | 1419 | 207.5 | 134.4 | 32.5 | 60 | W |
| HOH | OH2 | 1420 | 187.7 | 146.9 | 31.3 | 70 | W |
| HOH | OH2 | 1421 | 190.3 | 105.4 | 19.8 | 67 | W |
| HOH | OH2 | 1422 | 209.3 | 111.1 | 9.4 | 64 | W |
| HOH | OH2 | 1423 | 203.0 | 134.3 | 59.8 | 85 | W |
| HOH | OH2 | 1424 | 216.7 | 128.0 | 36.3 | 83 | W |
| HOH | OH2 | 1425 | 218.3 | 117.1 | 15.5 | 46 | W |
| HOH | OH2 | 1426 | 160.6 | 118.7 | 29.7 | 58 | W |
| HOH | OH2 | 1427 | 175.3 | 133.6 | 7.1 | 46 | W |
| HOH | OH2 | 1428 | 182.0 | 102.1 | 21.5 | 54 | W |
| HOH | OH2 | 1429 | 171.9 | 109.5 | 35.5 | 69 | W |
| HOH | OH2 | 1430 | 197.8 | 111.7 | 58.3 | 82 | W |
| HOH | OH2 | 1431 | 184.1 | 105.8 | 11.8 | 52 | W |
| HOH | OH2 | 1432 | 195.8 | 154.6 | 15.7 | 50 | W |
| HOH | OH2 | 1433 | 202.6 | 138.8 | 2.4 | 44 | W |
| HOH | OH2 | 1434 | 195.9 | 148.1 | 20.5 | 60 | W |
| HOH | OH2 | 1435 | 204.9 | 111.7 | 54.5 | 50 | W |
| HOH | OH2 | 1436 | 217.1 | 107.9 | 17.7 | 68 | W |
| HOH | OH2 | 1437 | 175.5 | 146.3 | 31.1 | 70 | W |
| HOH | OH2 | 1438 | 182.4 | 156.6 | 25.6 | 61 | W |

TABLE 5

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| GLY | C | 54 | 191.7 | 151.2 | 9.3 | 81 | A |
| GLY | O | 54 | 190.4 | 151.2 | 9.5 | 82 | A |
| GLY | N | 54 | 192.5 | 150.9 | 7.0 | 81 | A |
| GLY | CA | 54 | 192.2 | 151.9 | 8.0 | 82 | A |
| PHE | N | 55 | 192.6 | 150.8 | 10.1 | 81 | A |
| PHE | CA | 55 | 192.3 | 150.1 | 11.4 | 79 | A |
| PHE | CB | 55 | 193.2 | 148.9 | 11.6 | 80 | A |
| PHE | CG | 55 | 192.6 | 147.6 | 11.1 | 81 | A |
| PHE | CD1 | 55 | 192.9 | 147.1 | 9.8 | 81 | A |
| PHE | CD2 | 55 | 191.8 | 146.8 | 11.9 | 80 | A |
| PHE | CE1 | 55 | 192.4 | 145.9 | 9.4 | 81 | A |
| PHE | CE2 | 55 | 191.3 | 145.6 | 11.4 | 80 | A |
| PHE | CZ | 55 | 191.6 | 145.1 | 10.2 | 80 | A |
| PHE | C | 55 | 192.4 | 151.1 | 12.6 | 78 | A |
| PHE | O | 55 | 193.5 | 151.6 | 12.8 | 78 | A |
| LEU | N | 56 | 191.3 | 151.3 | 13.3 | 75 | A |
| LEU | CA | 56 | 191.4 | 152.1 | 14.5 | 72 | A |
| LEU | CB | 56 | 190.1 | 153.0 | 14.5 | 72 | A |
| LEU | CG | 56 | 190.4 | 154.6 | 14.6 | 72 | A |
| LEU | CD1 | 56 | 189.1 | 155.3 | 14.8 | 72 | A |
| LEU | CD2 | 56 | 191.4 | 154.9 | 15.7 | 72 | A |
| LEU | C | 56 | 191.5 | 151.3 | 15.8 | 69 | A |
| LEU | O | 56 | 190.5 | 150.7 | 16.2 | 69 | A |
| SER | N | 57 | 192.7 | 151.3 | 16.3 | 66 | A |
| SER | CA | 57 | 193.0 | 150.5 | 17.5 | 64 | A |
| SER | CB | 57 | 194.4 | 150.8 | 18.0 | 65 | A |

TABLE 5-continued

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| SER | OG | 57 | 194.8 | 150.1 | 19.1 | 65 | A |
| SER | C | 57 | 192.0 | 150.7 | 18.6 | 62 | A |
| SER | O | 57 | 191.6 | 151.8 | 18.9 | 61 | A |
| LEU | N | 58 | 191.6 | 149.6 | 19.2 | 60 | A |
| LEU | CA | 58 | 190.7 | 149.6 | 20.4 | 58 | A |
| LEU | CB | 58 | 190.4 | 148.2 | 20.8 | 57 | A |
| LEU | CG | 58 | 188.9 | 147.8 | 20.9 | 56 | A |
| LEU | CD1 | 58 | 188.9 | 146.4 | 21.5 | 57 | A |
| LEU | CD2 | 58 | 188.1 | 148.7 | 21.7 | 55 | A |
| LEU | C | 58 | 191.3 | 150.4 | 21.5 | 58 | A |
| LEU | O | 58 | 190.7 | 150.8 | 22.5 | 59 | A |
| ASP | N | 59 | 192.6 | 150.6 | 21.4 | S8 | A |
| ASP | CA | 59 | 193.5 | 151.3 | 22.4 | 58 | A |
| ASP | CB | 59 | 194.7 | 150.4 | 22.7 | 61 | A |
| ASP | CG | 59 | 194.4 | 149.4 | 23.9 | 64 | A |
| ASP | OD1 | 59 | 194.4 | 148.2 | 23.6 | 65 | A |
| ASP | OD2 | 59 | 194.2 | 149.9 | 25.0 | 66 | A |
| ASP | C | 59 | 193.9 | 152.7 | 21.9 | 55 | A |
| ASP | O | 59 | 194.5 | 153.4 | 22.7 | 55 | A |
| SER | N | 60 | 193.7 | 153.0 | 20.7 | 51 | A |
| SER | CA | 60 | 194.1 | 154.2 | 20.1 | 48 | A |
| SER | CB | 60 | 193.5 | 154.3 | 18.7 | 48 | A |
| SER | OG | 60 | 193.8 | 155.6 | 18.2 | 49 | A |
| SER | C | 60 | 193.5 | 155.3 | 21.0 | 46 | A |
| SER | O | 60 | 192.4 | 155.2 | 21.5 | 47 | A |
| PRO | N | 61 | 194.3 | 156.4 | 21.2 | 44 | A |
| PRO | CD | 61 | 195.7 | 156.6 | 20.7 | 44 | A |
| PRO | CA | 61 | 193.8 | 157.5 | 22.1 | 43 | A |
| PRO | CB | 61 | 195.1 | 158.3 | 22.2 | 43 | A |
| PRO | CG | 61 | 195.8 | 158.1 | 20.9 | 43 | A |
| PRO | C | 61 | 192.7 | 158.2 | 21.4 | 42 | A |
| PRO | O | 61 | 191.8 | 158.8 | 22.0 | 42 | A |
| THR | N | 62 | 192.7 | 158.1 | 20.0 | 40 | A |
| THR | CA | 62 | 191.7 | 158.8 | 19.2 | 40 | A |
| THR | CB | 62 | 192.4 | 159.5 | 18.0 | 40 | A |
| THR | OG1 | 62 | 193.1 | 158.5 | 17.2 | 39 | A |
| THR | CG2 | 62 | 193.4 | 160.5 | 18.4 | 39 | A |
| THR | C | 62 | 190.6 | 157.8 | 18.7 | 40 | A |
| THR | O | 62 | 189.9 | 158.1 | 17.7 | 42 | A |
| TYR | N | 63 | 190.4 | 156.7 | 19.4 | 39 | A |
| TYR | CA | 63 | 189.4 | 155.7 | 19.0 | 37 | A |
| TYR | CB | 63 | 189.7 | 154.4 | 19.8 | 36 | A |
| TYR | CG | 63 | 188.6 | 153.3 | 19.7 | 36 | A |
| TYR | CD1 | 63 | 188.6 | 152.4 | 18.6 | 36 | A |
| TYR | CE1 | 63 | 187.6 | 151.4 | 18.5 | 36 | A |
| TYR | CD2 | 63 | 187.6 | 153.3 | 20.6 | 36 | A |
| TYR | CE2 | 63 | 186.5 | 152.3 | 20.5 | 35 | A |
| TYR | CZ | 63 | 186.6 | 151.4 | 19.5 | 36 | A |
| TYR | OH | 63 | 185.5 | 150.5 | 19.4 | 35 | A |
| TYR | C | 63 | 188.0 | 156.2 | 19.4 | 35 | A |
| TYR | O | 63 | 187.8 | 156.8 | 20.4 | 35 | A |
| VAL | N | 64 | 187.1 | 156.1 | 18.4 | 34 | A |
| VAL | CA | 64 | 185.7 | 156.6 | 18.6 | 34 | A |
| VAL | CB | 64 | 185.4 | 157.7 | 17.6 | 34 | A |
| VAL | CG1 | 64 | 186.2 | 159.0 | 17.8 | 33 | A |
| VAL | CG2 | 64 | 185.6 | 157.2 | 16.1 | 34 | A |
| VAL | C | 64 | 184.7 | 155.4 | 18.6 | 34 | A |
| VAL | O | 64 | 185.0 | 154.4 | 17.9 | 35 | A |
| LEU | N | 65 | 183.6 | 155.6 | 19.3 | 34 | A |
| LEU | CA | 65 | 182.6 | 154.5 | 19.3 | 33 | A |
| LEU | CB | 65 | 181.5 | 154.9 | 20.3 | 29 | A |
| LEU | CG | 65 | 181.9 | 155.0 | 21.8 | 28 | A |
| LEU | CD1 | 65 | 180.7 | 155.2 | 22.7 | 28 | A |
| LEU | CD2 | 65 | 182.6 | 153.7 | 22.2 | 27 | A |
| LEU | C | 65 | 182.0 | 154.3 | 18.0 | 35 | A |
| LEU | O | 65 | 181.8 | 155.3 | 17.2 | 37 | A |
| TYR | N | 66 | 181.6 | 153.1 | 17.6 | 37 | A |
| TYR | CA | 66 | 181.1 | 152.8 | 16.3 | 38 | A |
| TYR | CB | 66 | 180.7 | 151.3 | 16.2 | 37 | A |
| TYR | CG | 66 | 181.8 | 150.5 | 15.8 | 36 | A |
| TYR | CD1 | 66 | 182.7 | 150.1 | 16.8 | 35 | A |
| TYR | CE1 | 66 | 183.9 | 149.4 | 16.5 | 35 | A |

TABLE 5-continued

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| TYR | CD2 | 66 | 182.1 | 150.2 | 14.5 | 35 | A |
| TYR | CE2 | 66 | 183.3 | 149.5 | 14.2 | 35 | A |
| TYR | CZ | 66 | 184.2 | 149.1 | 15.2 | 35 | A |
| TYR | OH | 66 | 185.3 | 148.5 | 14.8 | 34 | A |
| TYR | C | 66 | 179.9 | 153.7 | 15.9 | 39 | A |
| TYR | O | 66 | 179.7 | 154.1 | 14.8 | 39 | A |
| ARG | N | 67 | 179.1 | 154.1 | 16.9 | 42 | A |
| ARG | CA | 67 | 177.9 | 154.9 | 16.7 | 45 | A |
| ARG | CB | 67 | 177.0 | 155.0 | 17.9 | 45 | A |
| ARG | CG | 67 | 177.6 | 155.7 | 19.2 | 47 | A |
| ARG | CD | 67 | 176.5 | 155.8 | 20.3 | 48 | A |
| ARG | NE | 67 | 177.0 | 156.2 | 21.5 | 49 | A |
| ARG | CZ | 67 | 177.3 | 155.5 | 22.6 | 50 | A |
| ARG | NH1 | 67 | 177.0 | 154.1 | 22.5 | 51 | A |
| ARG | NH2 | 67 | 177.8 | 156.0 | 23.7 | 50 | A |
| ARG | C | 67 | 178.3 | 156.3 | 16.3 | 46 | A |
| ARG | O | 67 | 177.5 | 157.0 | 15.7 | 47 | A |
| ASP | N | 68 | 179.5 | 156.8 | 16.6 | 45 | A |
| ASP | CA | 68 | 179.9 | 158.1 | 16.3 | 45 | A |
| ASP | CB | 68 | 180.9 | 158.7 | 17.3 | 44 | A |
| ASP | CG | 68 | 180.1 | 159.0 | 18.6 | 44 | A |
| ASP | OD1 | 68 | 178.9 | 159.2 | 18.6 | 44 | A |
| ASP | OD2 | 68 | 180.8 | 159.1 | 19.7 | 43 | A |
| ASP | C | 68 | 180.7 | 158.1 | 14.9 | 46 | A |
| ASP | O | 68 | 181.3 | 159.0 | 14.5 | 46 | A |
| ARG | N | 69 | 180.6 | 156.9 | 14.3 | 47 | A |
| ARG | CA | 69 | 181.3 | 156.7 | 13.0 | 48 | A |
| ARG | CB | 69 | 182.0 | 155.3 | 13.0 | 48 | A |
| ARG | CG | 69 | 182.9 | 155.1 | 14.2 | 47 | A |
| ARG | CD | 69 | 183.8 | 153.9 | 13.9 | 45 | A |
| ARG | NE | 69 | 184.7 | 153.5 | 15.1 | 43 | A |
| ARG | CZ | 69 | 185.7 | 152.6 | 15.0 | 43 | A |
| ARG | NH1 | 69 | 186.0 | 152.1 | 13.9 | 42 | A |
| ARG | NH2 | 69 | 186.3 | 152.3 | 16.1 | 43 | A |
| ARG | C | 69 | 180.4 | 156.9 | 11.7 | 50 | A |
| ARG | O | 69 | 179.4 | 156.2 | 11.5 | 51 | A |
| ALA | N | 70 | 180.9 | 157.7 | 10.8 | 52 | A |
| ALA | CA | 70 | 180.2 | 158.1 | 9.6 | 53 | A |
| ALA | CB | 70 | 180.9 | 159.3 | 8.9 | 54 | A |
| ALA | C | 70 | 180.0 | 156.9 | 8.5 | 54 | A |
| ALA | O | 70 | 179.2 | 157.0 | 7.7 | 56 | A |
| GLU | N | 71 | 180.9 | 155.9 | 8.6 | 55 | A |
| GLU | CA | 71 | 180.8 | 154.8 | 7.7 | 55 | A |
| GLU | CB | 71 | 182.2 | 154.3 | 7.3 | 55 | A |
| GLU | CG | 71 | 183.1 | 153.8 | 8.5 | 57 | A |
| GLU | CD | 71 | 183.5 | 154.9 | 9.5 | 57 | A |
| GLU | OE1 | 71 | 183.7 | 154.6 | 10.7 | 57 | A |
| GLU | OE2 | 71 | 183.5 | 156.1 | 9.1 | 58 | A |
| GLU | C | 71 | 180.0 | 153.7 | 8.4 | 55 | A |
| GLU | O | 71 | 179.9 | 152.6 | 7.8 | 53 | A |
| TRP | N | 72 | 179.4 | 154.0 | 9.5 | 55 | A |
| TRP | CA | 72 | 178.6 | 153.1 | 10.3 | 57 | A |
| TRP | CB | 72 | 179.4 | 152.7 | 11.6 | 56 | A |
| TRP | CG | 72 | 180.4 | 151.7 | 11.4 | 55 | A |
| TRP | CD2 | 72 | 180.2 | 150.3 | 11.2 | 54 | A |
| TRP | CE2 | 72 | 181.5 | 149.7 | 11.1 | 54 | A |
| TRP | CE3 | 72 | 179.1 | 149.5 | 11.2 | 54 | A |
| TRP | CD1 | 72 | 181.8 | 151.9 | 11.4 | 55 | A |
| TRP | NE1 | 72 | 182.4 | 150.7 | 11.2 | 55 | A |
| TRP | CZ2 | 72 | 181.6 | 148.3 | 10.9 | 54 | A |
| TRP | CZ3 | 72 | 179.2 | 148.1 | 11.0 | 54 | A |
| TRP | CH2 | 72 | 180.5 | 147.5 | 10.8 | 54 | A |
| TRP | C | 72 | 177.3 | 153.7 | 10.7 | 59 | A |
| TRP | O | 72 | 176.5 | 153.1 | 11.4 | 59 | A |
| ALA | N | 73 | 177.0 | 154.9 | 10.2 | 60 | A |
| ALA | CA | 73 | 175.7 | 155.6 | 10.5 | 62 | A |
| ALA | CB | 73 | 175.9 | 157.1 | 10.4 | 62 | A |
| ALA | C | 73 | 174.5 | 155.1 | 9.7 | 62 | A |
| ALA | O | 73 | 173.4 | 155.4 | 10.0 | 63 | A |
| ASP | N | 74 | 174.8 | 154.3 | 8.6 | 62 | A |
| ASP | CA | 74 | 173.8 | 153.8 | 7.8 | 62 | A |
| ASP | CB | 74 | 174.4 | 153.5 | 6.4 | 62 | A |

TABLE 5-continued

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| ASP | CG | 74 | 175.3 | 152.3 | 6.5 | 62 | A |
| ASP | OD1 | 74 | 175.0 | 151.2 | 5.9 | 62 | A |
| ASP | OD2 | 74 | 176.4 | 152.4 | 7.1 | 61 | A |
| ASP | C | 74 | 173.2 | 152.6 | 8.4 | 62 | A |
| ASP | O | 74 | 172.0 | 152.3 | 8.1 | 63 | A |
| ILE | N | 75 | 173.9 | 151.9 | 9.2 | 61 | A |
| ILE | CA | 75 | 173.5 | 150.6 | 9.9 | 60 | A |
| ILE | CB | 75 | 174.5 | 149.5 | 9.8 | 59 | A |
| ILE | CG2 | 75 | 175.7 | 149.8 | 10.7 | 59 | A |
| ILE | CG1 | 75 | 173.9 | 148.2 | 10.1 | 59 | A |
| ILE | CD1 | 75 | 174.8 | 147.0 | 9.8 | 60 | A |
| ILE | C | 75 | 173.0 | 150.8 | 11.3 | 60 | A |
| ILE | O | 75 | 173.5 | 151.6 | 12.0 | 61 | A |
| ASP | N | 76 | 171.9 | 150.1 | 11.7 | 60 | A |
| ASP | CA | 76 | 171.3 | 150.2 | 13.0 | 59 | A |
| ASP | CB | 76 | 169.8 | 150.0 | 12.9 | 62 | A |
| ASP | CG | 76 | 169.0 | 151.3 | 12.9 | 64 | A |
| ASP | OD1 | 76 | 169.2 | 152.1 | 12.0 | 65 | A |
| ASP | OD2 | 76 | 168.2 | 151.5 | 13.8 | 64 | A |
| ASP | C | 76 | 171.9 | 149.2 | 14.0 | 57 | A |
| ASP | O | 76 | 171.8 | 148.0 | 13.7 | 56 | A |
| PRO | N | 77 | 172.4 | 149.6 | 15.1 | 55 | A |
| PRO | CD | 77 | 172.7 | 151.0 | 15.4 | 55 | A |
| PRO | CA | 77 | 173.0 | 148.7 | 16.1 | 54 | A |
| PRO | CB | 77 | 173.6 | 149.6 | 17.1 | 54 | A |
| PRO | CG | 77 | 172.9 | 150.9 | 16.9 | 54 | A |
| PRO | C | 77 | 171.8 | 147.9 | 16.7 | 53 | A |
| PRO | O | 77 | 170.7 | 148.4 | 17.0 | 53 | A |
| VAL | N | 78 | 172.1 | 146.7 | 17.0 | 52 | A |
| VAL | CA | 78 | 171.1 | 145.8 | 17.6 | 51 | A |
| VAL | CB | 78 | 171.0 | 144.5 | 16.9 | 51 | A |
| VAL | CG1 | 78 | 170.0 | 143.5 | 17.5 | 51 | A |
| VAL | CG2 | 78 | 170.7 | 144.7 | 15.4 | 51 | A |
| VAL | C | 78 | 171.5 | 145.5 | 19.1 | 52 | A |
| VAL | O | 78 | 172.5 | 144.7 | 19.3 | 53 | A |
| PRO | N | 79 | 170.9 | 146.1 | 20.0 | 51 | A |
| PRO | CD | 79 | 169.8 | 147.2 | 19.9 | 51 | A |
| PRO | CA | 79 | 171.2 | 145.9 | 21.5 | 51 | A |
| PRO | CB | 79 | 170.4 | 147.0 | 22.2 | 51 | A |
| PRO | CG | 79 | 169.2 | 147.1 | 21.3 | 51 | A |
| PRO | C | 79 | 170.8 | 144.5 | 21.9 | 50 | A |
| PRO | O | 79 | 169.9 | 143.9 | 21.4 | 49 | A |
| GLN | N | 80 | 171.6 | 144.0 | 22.9 | 50 | A |
| GLN | CA | 80 | 171.4 | 142.7 | 23.4 | 50 | A |
| GLN | CB | 80 | 172.5 | 142.2 | 24.4 | 48 | A |
| GLN | CG | 80 | 172.4 | 140.8 | 24.8 | 47 | A |
| GLN | CD | 80 | 173.7 | 140.2 | 25.3 | 46 | A |
| GLN | OE1 | 80 | 174.4 | 139.6 | 24.6 | 46 | A |
| GLN | NE2 | 80 | 174.0 | 140.5 | 26.6 | 47 | A |
| GLN | C | 80 | 170.0 | 142.5 | 24.2 | 51 | A |
| GLN | O | 80 | 169.6 | 143.4 | 24.9 | 52 | A |
| ASN | N | 81 | 169.4 | 141.4 | 24.0 | 52 | A |
| ASN | CA | 81 | 168.1 | 141.1 | 24.6 | 53 | A |
| ASN | CB | 81 | 167.1 | 140.6 | 23.5 | 53 | A |
| ASN | CG | 81 | 165.8 | 140.3 | 24.1 | 54 | A |
| ASN | OD1 | 81 | 165.4 | 140.7 | 25.3 | 53 | A |
| ASN | ND2 | 81 | 165.0 | 139.5 | 23.4 | 54 | A |
| ASN | C | 81 | 168.3 | 140.0 | 25.7 | 53 | A |
| ASN | O | 81 | 168.2 | 138.8 | 25.4 | 52 | A |
| ASP | N | 82 | 168.5 | 140.5 | 26.9 | 54 | A |
| ASP | CA | 82 | 168.6 | 139.6 | 28.1 | 55 | A |
| ASP | CB | 82 | 169.5 | 140.2 | 29.1 | 56 | A |
| ASP | CG | 82 | 171.0 | 140.1 | 28.7 | 56 | A |
| ASP | OD1 | 82 | 171.3 | 139.5 | 27.7 | 55 | A |
| ASP | OD2 | 82 | 171.8 | 140.7 | 29.4 | 56 | A |
| ASP | C | 82 | 167.3 | 139.3 | 28.7 | 56 | A |
| ASP | O | 82 | 167.2 | 138.6 | 29.7 | 56 | A |
| GLY | N | 83 | 166.2 | 139.9 | 28.1 | 57 | A |
| GLY | CA | 83 | 164.9 | 139.7 | 28.6 | 58 | A |
| GLY | C | 83 | 164.5 | 140.8 | 29.6 | 59 | A |
| GLY | O | 83 | 165.3 | 141.6 | 30.1 | 60 | A |
| PRO | N | 84 | 163.2 | 140.9 | 29.8 | 58 | A |

TABLE 5-continued

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| PRO | CD | 84 | 162.1 | 140.1 | 29.3 | 58 | A |
| PRO | CA | 84 | 162.6 | 141.9 | 30.7 | 58 | A |
| PRO | CB | 84 | 161.1 | 141.6 | 30.7 | 58 | A |
| PRO | CG | 84 | 161.1 | 140.2 | 30.4 | 58 | A |
| PRO | C | 84 | 163.2 | 141.8 | 32.1 | 57 | A |
| PRO | O | 84 | 163.4 | 142.9 | 32.8 | 57 | A |
| SER | N | 85 | 163.5 | 140.6 | 32.6 | 56 | A |
| SER | CA | 85 | 164.0 | 140.4 | 33.9 | 55 | A |
| SER | CB | 85 | 163.0 | 139.6 | 34.8 | 56 | A |
| SER | OG | 85 | 161.8 | 140.4 | 34.8 | 58 | A |
| SER | C | 85 | 165.3 | 139.5 | 33.8 | 54 | A |
| SER | O | 85 | 165.2 | 138.3 | 33.9 | 54 | A |
| PRO | N | 86 | 166.4 | 140.2 | 33.6 | 52 | A |
| PRO | CD | 86 | 166.5 | 141.6 | 33.4 | 52 | A |
| PRO | CA | 86 | 167.8 | 139.6 | 33.4 | 51 | A |
| PRO | CB | 86 | 168.6 | 140.9 | 33.3 | 52 | A |
| PRO | CG | 86 | 167.7 | 141.8 | 32.6 | 52 | A |
| PRO | C | 86 | 168.3 | 138.7 | 34.6 | 48 | A |
| PRO | O | 86 | 167.7 | 138.7 | 35.7 | 48 | A |
| VAL | N | 87 | 169.3 | 138.0 | 34.3 | 46 | A |
| VAL | CA | 87 | 170.0 | 137.1 | 35.3 | 43 | A |
| VAL | CB | 87 | 169.4 | 135.7 | 35.3 | 43 | A |
| VAL | CG1 | 87 | 168.4 | 135.6 | 36.4 | 43 | A |
| VAL | CG2 | 87 | 168.9 | 135.3 | 34.0 | 42 | A |
| VAL | C | 87 | 171.5 | 137.1 | 34.8 | 41 | A |
| VAL | O | 87 | 171.7 | 137.3 | 33.6 | 40 | A |
| VAL | N | 88 | 172.4 | 136.8 | 35.7 | 38 | A |
| VAL | CA | 88 | 173.8 | 136.8 | 35.4 | 36 | A |
| VAL | CB | 88 | 174.4 | 135.4 | 35.1 | 35 | A |
| VAL | CG1 | 88 | 174.3 | 134.5 | 36.3 | 35 | A |
| VAL | CG2 | 88 | 173.8 | 134.8 | 33.9 | 35 | A |
| VAL | C | 88 | 174.1 | 137.8 | 34.3 | 36 | A |
| VAL | O | 88 | 174.8 | 137.5 | 33.3 | 38 | A |
| GLN | N | 89 | 173.6 | 139.0 | 34.5 | 35 | A |
| GLN | CA | 89 | 173.7 | 140.1 | 33.6 | 34 | A |
| GLN | CB | 89 | 172.6 | 141.1 | 33.8 | 34 | A |
| GLN | CG | 89 | 172.8 | 142.4 | 33.1 | 35 | A |
| GLN | CD | 89 | 171.8 | 143.4 | 33.4 | 35 | A |
| GLN | OE1 | 89 | 171.4 | 143.7 | 34.6 | 36 | A |
| GLN | NE2 | 89 | 171.1 | 143.9 | 32.3 | 35 | A |
| GLN | C | 89 | 175.1 | 140.9 | 33.8 | 35 | A |
| GLN | O | 89 | 175.4 | 141.2 | 34.9 | 36 | A |
| ILE | N | 90 | 175.7 | 141.2 | 32.7 | 34 | A |
| ILE | CA | 90 | 177.0 | 141.8 | 32.7 | 34 | A |
| ILE | CB | 90 | 178.0 | 141.2 | 31.8 | 33 | A |
| ILE | CG2 | 90 | 179.4 | 141.8 | 31.9 | 33 | A |
| ILE | CG1 | 90 | 178.2 | 139.7 | 32.1 | 32 | A |
| ILE | CD1 | 90 | 178.8 | 138.9 | 30.9 | 31 | A |
| ILE | C | 90 | 176.9 | 143.3 | 32.5 | 34 | A |
| ILE | O | 90 | 176.3 | 143.7 | 31.5 | 35 | A |
| ILE | N | 91 | 177.4 | 144.2 | 33.3 | 35 | A |
| ILE | CA | 91 | 177.4 | 145.6 | 33.1 | 35 | A |
| ILE | CB | 91 | 177.5 | 146.4 | 34.5 | 35 | A |
| ILE | CG2 | 91 | 177.5 | 147.9 | 34.2 | 35 | A |
| ILE | CG1 | 91 | 176.3 | 146.0 | 35.4 | 35 | A |
| ILE | CD1 | 91 | 174.9 | 146.4 | 34.8 | 35 | A |
| ILE | C | 91 | 178.5 | 146.0 | 32.2 | 35 | A |
| ILE | O | 91 | 179.5 | 146.5 | 32.6 | 35 | A |
| TYR | N | 92 | 178.2 | 145.8 | 30.9 | 35 | A |
| TYR | CA | 92 | 179.2 | 146.1 | 29.9 | 37 | A |
| TYR | CB | 92 | 178.7 | 145.8 | 28.5 | 35 | A |
| TYR | CG | 92 | 178.1 | 144.5 | 28.3 | 35 | A |
| TYR | CD1 | 92 | 176.8 | 144.3 | 27.8 | 35 | A |
| TYR | CE1 | 92 | 176.2 | 143.1 | 27.6 | 35 | A |
| TYR | CD2 | 92 | 178.8 | 143.3 | 28.6 | 34 | A |
| TYR | CE2 | 92 | 178.2 | 142.0 | 28.5 | 35 | A |
| TYR | CZ | 92 | 176.9 | 141.9 | 28.0 | 35 | A |
| TYR | OH | 92 | 176.3 | 140.7 | 27.9 | 34 | A |
| TYR | C | 92 | 179.7 | 147.5 | 29.9 | 38 | A |
| TYR | O | 92 | 179.0 | 148.4 | 30.4 | 38 | A |
| SER | N | 93 | 180.9 | 147.7 | 29.4 | 40 | A |
| SER | CA | 93 | 181.5 | 149.0 | 29.4 | 41 | A |

TABLE 5-continued

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| SER | CB | 93 | 183.0 | 148.9 | 29.1 | 41 | A |
| SER | OG | 93 | 183.2 | 148.1 | 27.9 | 42 | A |
| SER | C | 93 | 180.8 | 149.6 | 28.2 | 42 | A |
| SER | O | 93 | 179.9 | 149.0 | 27.5 | 43 | A |
| GLU | N | 94 | 181.1 | 150.8 | 27.8 | 44 | A |
| GLU | CA | 94 | 180.5 | 151.5 | 26.7 | 45 | A |
| GLU | CB | 94 | 180.8 | 153.0 | 26.8 | 48 | A |
| GLU | CG | 94 | 180.1 | 153.8 | 25.6 | 50 | A |
| GLU | CD | 94 | 178.9 | 154.5 | 26.1 | 52 | A |
| GLU | OE1 | 94 | 177.9 | 153.9 | 26.5 | 52 | A |
| GLU | OE2 | 94 | 179.0 | 155.8 | 26.1 | 53 | A |
| GLU | C | 94 | 181.0 | 151.0 | 25.4 | 45 | A |
| GLU | O | 94 | 180.2 | 151.0 | 24.4 | 44 | A |
| LYS | N | 95 | 182.3 | 150.8 | 25.3 | 44 | A |
| LYS | CA | 95 | 183.0 | 150.3 | 24.1 | 43 | A |
| LYS | CB | 95 | 184.5 | 150.3 | 24.2 | 44 | A |
| LYS | CG | 95 | 185.1 | 151.7 | 24.6 | 45 | A |
| LYS | CD | 95 | 186.5 | 151.5 | 25.1 | 46 | A |
| LYS | CE | 95 | 187.5 | 150.9 | 24.1 | 47 | A |
| LYS | NZ | 95 | 188.8 | 150.5 | 24.6 | 47 | A |
| LYS | C | 95 | 182.5 | 148.9 | 23.8 | 42 | A |
| LYS | O | 95 | 182.2 | 148.6 | 22.7 | 42 | A |
| PHE | N | 96 | 182.6 | 148.0 | 24.9 | 40 | A |
| PHE | CA | 96 | 182.3 | 146.6 | 24.7 | 38 | A |
| PHE | CB | 96 | 182.3 | 145.9 | 26.1 | 36 | A |
| PHE | CG | 96 | 182.1 | 144.5 | 26.0 | 36 | A |
| PHE | CD1 | 96 | 183.1 | 143.6 | 26.1 | 35 | A |
| PHE | CD2 | 96 | 180.8 | 143.9 | 25.7 | 35 | A |
| PHE | CE1 | 96 | 182.9 | 142.2 | 26.0 | 34 | A |
| PHE | CE2 | 96 | 180.6 | 142.6 | 25.6 | 34 | A |
| PHE | CZ | 96 | 181.7 | 141.7 | 25.7 | 34 | A |
| PHE | C | 96 | 180.9 | 146.6 | 24.2 | 40 | A |
| PHE | O | 96 | 180.6 | 146.1 | 23.1 | 40 | A |
| ARG | N | 97 | 179.9 | 147.2 | 24.9 | 41 | A |
| ARG | CA | 97 | 178.5 | 147.3 | 24.5 | 43 | A |
| ARG | CB | 97 | 177.7 | 148.1 | 25.4 | 44 | A |
| ARG | CG | 97 | 176.3 | 147.7 | 25.6 | 48 | A |
| ARG | CD | 97 | 175.4 | 148.9 | 26.0 | 51 | A |
| ARG | NE | 97 | 176.0 | 149.7 | 27.1 | 53 | A |
| ARG | CZ | 97 | 176.6 | 150.8 | 26.9 | 55 | A |
| ARG | NH1 | 97 | 176.8 | 151.3 | 25.6 | 56 | A |
| ARG | NH2 | 97 | 177.1 | 151.5 | 27.9 | 56 | A |
| ARG | C | 97 | 178.4 | 147.9 | 23.1 | 42 | A |
| ARG | O | 97 | 177.6 | 147.4 | 22.2 | 44 | A |
| ASP | N | 98 | 179.1 | 149.0 | 22.8 | 42 | A |
| ASP | CA | 98 | 179.1 | 149.6 | 21.5 | 41 | A |
| ASP | CB | 98 | 180.0 | 150.9 | 21.5 | 41 | A |
| ASP | CG | 98 | 180.1 | 151.6 | 20.1 | 40 | A |
| ASP | OD1 | 98 | 179.1 | 152.3 | 19.8 | 41 | A |
| ASP | OD2 | 98 | 181.1 | 151.3 | 19.4 | 39 | A |
| ASP | C | 98 | 179.5 | 148.7 | 20.3 | 40 | A |
| ASP | O | 98 | 178.7 | 148.6 | 19.3 | 41 | A |
| VAL | N | 99 | 180.6 | 148.0 | 20.4 | 38 | A |
| VAL | CA | 99 | 181.1 | 147.1 | 19.4 | 35 | A |
| VAL | CB | 99 | 182.5 | 146.5 | 19.7 | 33 | A |
| VAL | CG1 | 99 | 182.9 | 145.4 | 18.8 | 32 | A |
| VAL | CG2 | 99 | 183.5 | 147.6 | 19.7 | 33 | A |
| VAL | C | 99 | 180.2 | 145.9 | 19.1 | 34 | A |
| VAL | O | 99 | 179.9 | 145.5 | 18.0 | 33 | A |
| TYR | N | 100 | 179.6 | 145.4 | 20.2 | 33 | A |
| TYR | CA | 100 | 178.7 | 144.3 | 20.2 | 32 | A |
| TYR | CB | 100 | 178.7 | 143.6 | 21.5 | 30 | A |
| TYR | CG | 100 | 179.8 | 142.6 | 21.5 | 28 | A |
| TYR | CD1 | 100 | 180.9 | 142.9 | 22.2 | 27 | A |
| TYR | CE1 | 100 | 182.0 | 142.0 | 22.1 | 26 | A |
| TYR | CD2 | 100 | 179.7 | 141.4 | 20.8 | 28 | A |
| TYR | CE2 | 100 | 180.7 | 140.6 | 20.7 | 27 | A |
| TYR | CZ | 100 | 181.9 | 140.8 | 21.4 | 27 | A |
| TYR | OH | 100 | 182.9 | 139.9 | 21.3 | 26 | A |
| TYR | C | 100 | 177.4 | 144.6 | 19.6 | 34 | A |
| TYR | O | 100 | 176.9 | 143.9 | 18.7 | 35 | A |
| ASP | N | 101 | 176.8 | 145.7 | 20.0 | 35 | A |

TABLE 5-continued

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| ASP | CA | 101 | 175.5 | 146.1 | 19.4 | 35 | A |
| ASP | CB | 101 | 175.1 | 147.5 | 19.8 | 37 | A |
| ASP | CG | 101 | 174.5 | 147.5 | 21.2 | 38 | A |
| ASP | OD1 | 101 | 174.5 | 146.5 | 21.9 | 38 | A |
| ASP | OD2 | 101 | 174.0 | 148.6 | 21.6 | 39 | A |
| ASP | C | 101 | 175.7 | 146.2 | 17.9 | 35 | A |
| ASP | O | 101 | 174.8 | 145.8 | 17.1 | 35 | A |
| TYR | N | 102 | 176.9 | 146.7 | 17.5 | 35 | A |
| TYR | CA | 102 | 177.1 | 146.7 | 16.0 | 37 | A |
| TYR | CB | 102 | 178.2 | 147.7 | 15.7 | 39 | A |
| TYR | CG | 102 | 177.7 | 149.1 | 15.3 | 40 | A |
| TYR | CD1 | 102 | 177.3 | 149.4 | 14.0 | 40 | A |
| TYR | CE1 | 102 | 176.7 | 150.6 | 13.7 | 41 | A |
| TYR | CD2 | 102 | 177.4 | 150.0 | 16.3 | 40 | A |
| TYR | CE2 | 102 | 176.8 | 151.2 | 16.0 | 40 | A |
| TYR | CZ | 102 | 176.5 | 151.5 | 14.7 | 41 | A |
| TYR | OH | 102 | 175.8 | 152.7 | 14.4 | 41 | A |
| TYR | C | 102 | 177.4 | 145.3 | 15.5 | 37 | A |
| TYR | O | 102 | 177.1 | 145.1 | 14.3 | 36 | A |
| PHE | N | 103 | 178.0 | 144.4 | 16.3 | 37 | A |
| PHE | CA | 103 | 178.3 | 143.1 | 15.8 | 37 | A |
| PHE | CB | 103 | 179.1 | 142.2 | 16.7 | 36 | A |
| PHE | CG | 103 | 179.4 | 140.8 | 16.2 | 34 | A |
| PHE | CD1 | 103 | 180.3 | 140.5 | 15.2 | 34 | A |
| PHE | CD2 | 103 | 178.7 | 139.7 | 16.8 | 33 | A |
| PHE | CE1 | 103 | 180.5 | 139.2 | 14.7 | 32 | A |
| PHE | CE2 | 103 | 178.9 | 138.4 | 16.3 | 31 | A |
| PHE | CZ | 103 | 179.8 | 138.2 | 15.2 | 31 | A |
| PHE | C | 103 | 176.9 | 142.4 | 15.5 | 40 | A |
| PHE | O | 103 | 176.7 | 141.9 | 14.4 | 41 | A |
| ARG | N | 104 | 176.0 | 142.4 | 16.5 | 40 | A |
| ARG | CA | 104 | 174.7 | 141.8 | 16.3 | 41 | A |
| ARG | CB | 104 | 173.8 | 142.1 | 17.4 | 42 | A |
| ARG | CG | 104 | 174.2 | 141.5 | 18.7 | 42 | A |
| ARG | CD | 104 | 173.3 | 141.9 | 19.8 | 43 | A |
| ARG | NE | 104 | 174.0 | 141.6 | 21.1 | 45 | A |
| ARG | CZ | 104 | 174.7 | 142.5 | 21.8 | 46 | A |
| ARG | NH1 | 104 | 174.9 | 143.7 | 21.4 | 47 | A |
| ARG | NH2 | 104 | 175.3 | 142.0 | 22.9 | 47 | A |
| ARG | C | 104 | 174.1 | 142.3 | 15.0 | 41 | A |
| ARG | O | 104 | 173.6 | 141.5 | 14.2 | 41 | A |
| ALA | N | 105 | 174.2 | 143.6 | 14.8 | 42 | A |
| ALA | CA | 105 | 173.6 | 144.3 | 13.6 | 42 | A |
| ALA | CB | 105 | 174.0 | 145.7 | 13.6 | 42 | A |
| ALA | C | 105 | 174.1 | 143.6 | 12.3 | 42 | A |
| ALA | O | 105 | 173.3 | 143.2 | 11.5 | 43 | A |
| VAL | N | 106 | 175.4 | 143.6 | 12.2 | 42 | A |
| VAL | CA | 106 | 176.1 | 143.1 | 11.0 | 43 | A |
| VAL | CB | 106 | 177.6 | 143.5 | 11.0 | 43 | A |
| VAL | CG1 | 106 | 178.6 | 142.3 | 10.9 | 44 | A |
| VAL | CG2 | 106 | 177.9 | 144.6 | 10.0 | 43 | A |
| VAL | C | 106 | 176.0 | 141.6 | 10.8 | 43 | A |
| VAL | O | 106 | 175.8 | 141.1 | 9.7 | 42 | A |
| LEU | N | 107 | 176.0 | 140.8 | 12.0 | 43 | A |
| LEU | CA | 107 | 175.8 | 139.4 | 11.9 | 44 | A |
| LEU | CB | 107 | 176.1 | 138.B | 13.3 | 43 | A |
| LEU | CG | 107 | 175.9 | 137.3 | 13.5 | 42 | A |
| LEU | CD1 | 107 | 176.9 | 136.6 | 12.5 | 41 | A |
| LEU | CD2 | 107 | 176.1 | 136.8 | 14.9 | 40 | A |
| LEU | C | 107 | 174.4 | 139.1 | 11.5 | 47 | A |
| LEU | O | 107 | 174.2 | 138.2 | 10.7 | 47 | A |
| GLN | N | 108 | 173.5 | 139.8 | 12.1 | 50 | A |
| GLN | CA | 108 | 172.1 | 139.7 | 11.9 | 53 | A |
| GLN | CB | 108 | 171.3 | 141.0 | 12.5 | 56 | A |
| GLN | CG | 108 | 170.0 | 140.7 | 13.2 | 58 | A |
| GLN | CD | 108 | 170.2 | 140.5 | 14.7 | 60 | A |
| GLN | OE1 | 108 | 169.4 | 140.9 | 15.5 | 61 | A |
| GLN | NE2 | 108 | 171.4 | 139.9 | 15.1 | 60 | A |
| GLN | C | 108 | 171.8 | 139.7 | 10.4 | 54 | A |
| GLN | O | 108 | 171.3 | 138.7 | 9.9 | 55 | A |
| ARG | N | 109 | 172.2 | 140.7 | 9.7 | 54 | A |
| ARG | CA | 109 | 172.0 | 140.8 | 8.3 | 54 | A |

TABLE 5-continued

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| ARG | CB | 109 | 172.0 | 142.2 | 7.8 | 56 | A |
| ARG | CG | 109 | 173.3 | 142.9 | 8.1 | 59 | A |
| ARG | CD | 109 | 173.2 | 144.4 | 7.6 | 61 | A |
| ARG | NE | 109 | 172.2 | 145.1 | B.4 | 63 | A |
| ARG | CZ | 109 | 171.6 | 146.2 | 7.9 | 65 | A |
| ARG | NH1 | 109 | 171.9 | 146.6 | 6.7 | 66 | A |
| ARG | NH2 | 109 | 170.7 | 146.8 | 8.6 | 65 | A |
| ARG | C | 109 | 173.0 | 140.0 | 7.5 | 52 | A |
| ARG | O | 109 | 173.0 | 139.9 | 6.3 | 52 | A |
| ASP | N | 110 | 173.9 | 139.3 | 8.2 | 50 | A |
| ASP | CA | 110 | 175.0 | 138.5 | 7.6 | 49 | A |
| ASP | CB | 110 | 174.4 | 137.2 | 7.0 | 49 | A |
| ASP | CG | 110 | 175.5 | 136.3 | 6.4 | 50 | A |
| ASP | OD1 | 110 | 176.6 | 136.2 | 7.0 | 50 | A |
| ASP | OD2 | 110 | 175.2 | 135.7 | 5.4 | 51 | A |
| ASP | C | 110 | 175.6 | 139.4 | 6.6 | 48 | A |
| ASP | O | 110 | 175.7 | 139.0 | 5.4 | 47 | A |
| GLU | N | 111 | 176.1 | 140.5 | 7.0 | 48 | A |
| GLU | CA | 111 | 176.8 | 141.5 | 6.1 | 47 | A |
| GLU | CB | 111 | 176.7 | 142.9 | 6.8 | 48 | A |
| GLU | CG | 111 | 177.0 | 144.0 | 5.9 | 48 | A |
| GLU | CD | 111 | 177.2 | 145.3 | 6.7 | 49 | A |
| GLU | OE1 | 111 | 178.4 | 145.8 | 6.6 | 48 | A |
| GLU | OE2 | 111 | 176.3 | 145.8 | 7.3 | 49 | A |
| GLU | C | 111 | 178.2 | 141.0 | 6.0 | 47 | A |
| GLU | O | 111 | 179.0 | 141.1 | 7.0 | 47 | A |
| ARG | N | 112 | 178.6 | 140.5 | 4.9 | 46 | A |
| ARG | CA | 112 | 179.9 | 140.0 | 4.6 | 45 | A |
| ARG | CB | 112 | 179.9 | 138.7 | 3.8 | 45 | A |
| ARG | CG | 112 | 179.0 | 137.7 | 4.4 | 46 | A |
| ARG | CD | 112 | 178.9 | 136.4 | 3.7 | 47 | A |
| ARG | NE | 112 | 178.0 | 135.5 | 4.4 | 49 | A |
| ARG | CZ | 112 | 177.8 | 134.2 | 4.2 | 50 | A |
| ARG | NH1 | 112 | 178.5 | 133.6 | 3.3 | 50 | A |
| ARG | NH2 | 112 | 176.9 | 133.6 | 4.9 | 50 | A |
| ARG | C | 112 | 180.8 | 141.1 | 4.0 | 44 | A |
| ARG | O | 112 | 181.3 | 141.0 | 2.9 | 43 | A |
| SER | N | 113 | 181.0 | 142.2 | 4.8 | 44 | A |
| SER | CA | 113 | 181.7 | 143.3 | 4.3 | 44 | A |
| SER | CB | 113 | 180.9 | 144.6 | 4.5 | 43 | A |
| SER | OG | 113 | 180.8 | 145.0 | 5.9 | 42 | A |
| SER | C | 113 | 183.1 | 143.5 | 5.0 | 44 | A |
| SER | O | 113 | 183.3 | 143.0 | 6.1 | 45 | A |
| GLU | N | 114 | 184.0 | 144.2 | 4.3 | 44 | A |
| GLU | CA | 114 | 185.3 | 144.5 | 4.8 | 44 | A |
| GLU | CB | 114 | 186.0 | 145.4 | 3.8 | 45 | A |
| GLU | CG | 114 | 187.3 | 145.9 | 4.2 | 47 | A |
| GLU | CD | 114 | 188.3 | 144.9 | 4.4 | 49 | A |
| GLU | OE1 | 114 | 189.1 | 145.0 | 5.4 | 50 | A |
| GLU | OE2 | 114 | 188.3 | 143.9 | 3.6 | 50 | A |
| GLU | C | 114 | 185.2 | 145.2 | 6.2 | 44 | A |
| GLU | O | 114 | 186.1 | 145.1 | 7.0 | 44 | A |
| ARG | N | 115 | 184.2 | 146.0 | 6.4 | 44 | A |
| ARG | CA | 115 | 184.0 | 146.7 | 7.6 | 44 | A |
| ARG | CB | 115 | 183.0 | 147.9 | 7.5 | 44 | A |
| ARG | CG | 115 | 181.7 | 147.5 | 7.0 | 45 | A |
| ARG | CD | 115 | 180.8 | 148.7 | 7.1 | 47 | A |
| ARG | NE | 115 | 179.4 | 148.4 | 6.8 | 48 | A |
| ARG | CZ | 115 | 178.3 | 149.2 | 7.1 | 49 | A |
| ARG | NH1 | 115 | 177.1 | 148.7 | 6.8 | 50 | A |
| ARG | NH2 | 115 | 178.4 | 150.3 | 7.7 | 49 | A |
| ARG | C | 115 | 183.5 | 145.7 | 8.7 | 44 | A |
| ARG | O | 115 | 183.9 | 145.8 | 9.9 | 45 | A |
| ALA | N | 116 | 182.7 | 144.8 | 8.3 | 43 | A |
| ALA | CA | 116 | 182.2 | 143.8 | 9.3 | 41 | A |
| ALA | CB | 116 | 181.2 | 142.8 | 8.6 | 40 | A |
| ALA | C | 116 | 183.5 | 143.0 | 9.7 | 41 | A |
| ALA | O | 116 | 183.6 | 142.6 | 10.8 | 41 | A |
| PHE | N | 117 | 184.4 | 142.8 | 8.7 | 39 | A |
| PHE | CA | 117 | 185.6 | 142.1 | 8.9 | 37 | A |
| PHE | CB | 117 | 186.4 | 141.9 | 7.6 | 35 | A |
| PHE | CG | 117 | 187.8 | 141.3 | 7.8 | 34 | A |

TABLE 5-continued

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| PHE | CD1 | 117 | 187.9 | 140.0 | 8.2 | 33 | A |
| PHE | CD2 | 117 | 188.9 | 142.0 | 7.7 | 34 | A |
| PHE | CE1 | 117 | 189.1 | 139.4 | 8.4 | 32 | A |
| PHE | CE2 | 117 | 190.2 | 141.4 | 7.9 | 32 | A |
| PHE | CZ | 117 | 190.3 | 140.1 | 8.3 | 32 | A |
| PHE | C | 117 | 186.5 | 142.9 | 9.9 | 36 | A |
| PHE | O | 117 | 187.0 | 142.2 | 10.8 | 37 | A |
| LYS | N | 118 | 186.6 | 144.2 | 9.8 | 34 | A |
| LYS | CA | 118 | 187.4 | 145.0 | 10.8 | 32 | A |
| LYS | CB | 118 | 187.6 | 146.3 | 10.2 | 34 | A |
| LYS | CG | 118 | 188.6 | 146.3 | 9.0 | 36 | A |
| LYS | CD | 118 | 189.2 | 147.7 | 8.8 | 37 | A |
| LYS | CE | 118 | 190.0 | 147.8 | 7.5 | 39 | A |
| LYS | NZ | 118 | 189.2 | 147.6 | 6.3 | 39 | A |
| LYS | C | 118 | 186.7 | 145.1 | 12.1 | 31 | A |
| LYS | O | 118 | 187.4 | 145.2 | 13.1 | 31 | A |
| LEU | N | 119 | 185.4 | 145.0 | 12.2 | 30 | A |
| LEU | CA | 119 | 184.7 | 145.1 | 13.5 | 29 | A |
| LEU | CB | 119 | 183.2 | 145.4 | 13.3 | 28 | A |
| LEU | CG | 119 | 182.3 | 145.2 | 14.6 | 27 | A |
| LEU | CD1 | 119 | 182.6 | 146.4 | 15.5 | 27 | A |
| LEU | CD2 | 119 | 180.9 | 145.2 | 14.2 | 27 | A |
| LEU | C | 119 | 184.9 | 143.8 | 14.3 | 30 | A |
| LEU | O | 119 | 185.0 | 143.9 | 15.6 | 30 | A |
| THR | N | 120 | 184.9 | 142.7 | 13.7 | 30 | A |
| THR | CA | 120 | 185.1 | 141.4 | 14.4 | 29 | A |
| THR | CB | 120 | 185.2 | 140.2 | 13.5 | 29 | A |
| THR | OG1 | 120 | 186.2 | 140.4 | 12.6 | 28 | A |
| THR | CG2 | 120 | 183.9 | 140.0 | 12.8 | 29 | A |
| THR | C | 120 | 186.4 | 141.5 | 15.2 | 29 | A |
| THR | O | 120 | 186.5 | 141.0 | 16.3 | 30 | A |
| ARG | N | 121 | 187.4 | 142.1 | 14.6 | 29 | A |
| ARG | CA | 121 | 188.7 | 142.2 | 15.3 | 31 | A |
| ARG | CB | 121 | 189.7 | 142.9 | 14.5 | 31 | A |
| ARG | CG | 121 | 191.0 | 143.1 | 15.2 | 34 | A |
| ARG | CD | 121 | 191.8 | 144.2 | 14.7 | 37 | A |
| ARG | NE | 121 | 192.6 | 143.7 | 13.7 | 40 | A |
| ARG | CZ | 121 | 193.9 | 144.0 | 13.6 | 42 | A |
| ARG | NH1 | 121 | 194.7 | 143.5 | 12.6 | 44 | A |
| ARG | NH2 | 121 | 194.4 | 144.8 | 14.5 | 43 | A |
| ARG | C | 121 | 188.6 | 142.9 | 16.6 | 32 | A |
| ARG | O | 121 | 189.2 | 142.5 | 17.6 | 33 | A |
| ASP | N | 122 | 187.7 | 143.9 | 16.7 | 32 | A |
| ASP | CA | 122 | 187.5 | 144.7 | 17.9 | 31 | A |
| ASP | CB | 122 | 186.8 | 146.0 | 17.6 | 31 | A |
| ASP | CG | 122 | 187.8 | 147.1 | 17.1 | 31 | A |
| ASP | OD1 | 122 | 189.0 | 146.9 | 17.3 | 32 | A |
| ASP | OD2 | 122 | 187.3 | 148.1 | 16.6 | 32 | A |
| ASP | C | 122 | 186.6 | 143.9 | 18.9 | 31 | A |
| ASP | O | 122 | 186.8 | 143.9 | 20.1 | 30 | A |
| ALA | N | 123 | 185.7 | 143.1 | 18.4 | 30 | A |
| ALA | CA | 123 | 184.8 | 142.3 | 19.1 | 30 | A |
| ALA | CB | 123 | 183.7 | 141.7 | 18.3 | 30 | A |
| ALA | C | 123 | 185.6 | 141.1 | 19.7 | 30 | A |
| ALA | O | 123 | 185.4 | 140.7 | 20.9 | 32 | A |
| ILE | N | 124 | 186.6 | 140.7 | 19.0 | 30 | A |
| ILE | CA | 124 | 187.5 | 139.6 | 19.4 | 28 | A |
| ILE | CB | 124 | 188.3 | 139.1 | 18.3 | 27 | A |
| ILE | CG2 | 124 | 189.6 | 138.4 | 18.8 | 27 | A |
| ILE | CG1 | 124 | 187.5 | 138.1 | 17.4 | 26 | A |
| ILE | CD1 | 124 | 188.2 | 137.7 | 16.1 | 26 | A |
| ILE | C | 124 | 188.4 | 140.1 | 20.5 | 28 | A |
| ILE | O | 124 | 188.6 | 139.5 | 21.5 | 28 | A |
| GLU | N | 125 | 188.9 | 141.3 | 20.3 | 29 | A |
| GLU | CA | 125 | 189.8 | 141.9 | 21.3 | 31 | A |
| GLU | CB | 125 | 190.3 | 143.3 | 20.9 | 35 | A |
| GLU | CG | 125 | 191.8 | 143.4 | 20.5 | 41 | A |
| GLU | CD | 125 | 192.2 | 144.8 | 20.1 | 45 | A |
| GLU | OE1 | 125 | 192.9 | 145.5 | 20.9 | 47 | A |
| GLU | OE2 | 125 | 191.9 | 145.3 | 19.0 | 46 | A |
| GLU | C | 125 | 189.0 | 142.1 | 22.6 | 30 | A |
| GLU | O | 125 | 189.6 | 141.9 | 23.7 | 30 | A |

TABLE 5-continued

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| LEU | N | 126 | 187.7 | 142.5 | 22.5 | 29 | A |
| LEU | CA | 126 | 186.9 | 142.7 | 23.7 | 26 | A |
| LEU | CB | 126 | 185.6 | 143.5 | 23.3 | 25 | A |
| LEU | CG | 126 | 185.8 | 144.9 | 22.9 | 24 | A |
| LEU | CD1 | 126 | 184.5 | 145.5 | 22.4 | 24 | A |
| LEU | CD2 | 126 | 186.3 | 145.8 | 24.1 | 23 | A |
| LEU | C | 126 | 186.6 | 141.4 | 24.4 | 25 | A |
| LEU | O | 126 | 186.4 | 141.4 | 25.6 | 25 | A |
| ASN | N | 127 | 186.5 | 140.3 | 23.7 | 24 | A |
| ASN | CA | 127 | 186.2 | 139.0 | 24.3 | 23 | A |
| ASN | CB | 127 | 184.7 | 138.9 | 24.6 | 22 | A |
| ASN | CG | 127 | 184.5 | 137.6 | 25.2 | 23 | A |
| ASN | OD1 | 127 | 185.4 | 136.9 | 25.8 | 24 | A |
| ASN | ND2 | 127 | 183.2 | 137.1 | 25.2 | 24 | A |
| ASN | C | 127 | 186.7 | 137.9 | 23.4 | 24 | A |
| ASN | O | 127 | 185.9 | 137.4 | 22.6 | 25 | A |
| ALA | N | 128 | 188.0 | 137.7 | 23.5 | 23 | A |
| ALA | CA | 128 | 188.6 | 136.7 | 22.6 | 23 | A |
| ALA | CB | 128 | 190.1 | 136.6 | 22.9 | 22 | A |
| ALA | C | 128 | 188.0 | 135.3 | 22.7 | 23 | A |
| ALA | O | 128 | 188.4 | 134.4 | 21.9 | 24 | A |
| ALA | N | 129 | 187.2 | 135.0 | 23.6 | 22 | A |
| ALA | CA | 129 | 186.6 | 133.7 | 23.8 | 21 | A |
| ALA | CB | 129 | 186.5 | 133.4 | 25.2 | 21 | A |
| ALA | C | 129 | 185.2 | 133.6 | 23.2 | 21 | A |
| ALA | O | 129 | 184.5 | 132.6 | 23.3 | 21 | A |
| ASN | N | 130 | 184.8 | 134.7 | 22.5 | 21 | A |
| ASN | CA | 130 | 183.5 | 134.7 | 21.8 | 20 | A |
| ASN | CB | 130 | 183.0 | 136.1 | 21.6 | 22 | A |
| ASN | CG | 130 | 181.6 | 136.1 | 21.2 | 24 | A |
| ASN | OD1 | 130 | 181.1 | 135.3 | 20.5 | 26 | A |
| ASN | ND2 | 130 | 180.9 | 137.1 | 21.8 | 24 | A |
| ASN | C | 130 | 183.7 | 133.9 | 20.5 | 20 | A |
| ASN | O | 130 | 184.1 | 134.4 | 19.5 | 20 | A |
| TYR | N | 131 | 183.4 | 132.6 | 20.6 | 20 | A |
| TYR | CA | 131 | 183.5 | 131.7 | 19.5 | 20 | A |
| TYR | CB | 131 | 183.2 | 130.2 | 19.9 | 18 | A |
| TYR | CG | 131 | 181.9 | 130.0 | 20.5 | 18 | A |
| TYR | CD1 | 131 | 180.8 | 129.6 | 19.8 | 18 | A |
| TYR | CE1 | 131 | 179.5 | 129.5 | 20.3 | 17 | A |
| TYR | CD2 | 131 | 181.7 | 130.3 | 21.9 | 17 | A |
| TYR | CE2 | 131 | 180.4 | 130.2 | 22.4 | 17 | A |
| TYR | CZ | 131 | 179.3 | 129.8 | 21.7 | 18 | A |
| TYR | OH | 131 | 178.1 | 129.8 | 22.3 | 19 | A |
| TYR | C | 131 | 182.5 | 132.0 | 18.3 | 20 | A |
| TYR | O | 131 | 182.7 | 131.5 | 17.2 | 22 | A |
| THR | N | 132 | 181.5 | 132.8 | 18.5 | 21 | A |
| THR | CA | 132 | 180.6 | 133.2 | 17.5 | 20 | A |
| THR | CB | 132 | 179.2 | 133.8 | 18.0 | 21 | A |
| THR | OG1 | 132 | 178.5 | 132.8 | 18.8 | 20 | A |
| THR | CG2 | 132 | 178.4 | 134.2 | 16.9 | 21 | A |
| THR | C | 132 | 181.2 | 134.2 | 16.6 | 21 | A |
| THR | O | 132 | 181.1 | 134.1 | 15.4 | 23 | A |
| VAL | N | 133 | 181.9 | 135.1 | 17.2 | 22 | A |
| VAL | CA | 133 | 182.6 | 136.2 | 16.4 | 23 | A |
| VAL | CB | 133 | 183.2 | 137.3 | 17.3 | 24 | A |
| VAL | CG1 | 133 | 183.9 | 138.3 | 16.4 | 23 | A |
| VAL | CG2 | 133 | 182.1 | 138.0 | 18.1 | 23 | A |
| VAL | C | 133 | 183.7 | 135.5 | 15.6 | 24 | A |
| VAL | O | 133 | 183.8 | 135.7 | 14.4 | 27 | A |
| TRP | N | 134 | 184.4 | 134.6 | 16.2 | 24 | A |
| TRP | CA | 134 | 185.5 | 133.8 | 15.5 | 24 | A |
| TRP | CB | 134 | 186.2 | 132.9 | 16.5 | 21 | A |
| TRP | CG | 134 | 187.2 | 133.5 | 17.4 | 20 | A |
| TRP | CD2 | 134 | 188.5 | 134.0 | 17.0 | 19 | A |
| TRP | CE2 | 134 | 189.2 | 134.5 | 18.1 | 18 | A |
| TRP | CE3 | 134 | 189.2 | 134.1 | 15.7 | 19 | A |
| TRP | CD1 | 134 | 187.2 | 133.7 | 18.7 | 19 | A |
| TRP | NE1 | 134 | 188.3 | 134.4 | 19.2 | 18 | A |
| TRP | CZ2 | 134 | 190.4 | 135.1 | 18.1 | 18 | A |
| TRP | CZ3 | 134 | 190.4 | 134.6 | 15.7 | 19 | A |
| TRP | CH2 | 134 | 191.0 | 135.1 | 16.8 | 19 | A |

TABLE 5-continued

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| TRP | C | 134 | 185.0 | 133.1 | 14.3 | 26 | A |
| TRP | O | 134 | 185.6 | 133.0 | 13.3 | 26 | A |
| HIS | N | 135 | 183.8 | 132.5 | 14.4 | 29 | A |
| HIS | CA | 135 | 183.1 | 131.8 | 13.3 | 31 | A |
| HIS | CB | 135 | 181.9 | 131.1 | 13.8 | 33 | A |
| HIS | CG | 135 | 181.1 | 130.5 | 12.7 | 34 | A |
| HIS | CD2 | 135 | 180.2 | 131.0 | 11.8 | 34 | A |
| HIS | ND1 | 135 | 181.2 | 129.1 | 12.4 | 34 | A |
| HIS | CE1 | 135 | 180.5 | 128.8 | 11.3 | 35 | A |
| HIS | NE2 | 135 | 179.9 | 130.0 | 11.0 | 35 | A |
| HIS | C | 135 | 182.8 | 132.8 | 12.2 | 31 | A |
| HIS | O | 135 | 183.3 | 132.5 | 11.1 | 31 | A |
| PHE | N | 136 | 182.1 | 133.8 | 12.5 | 31 | A |
| PHE | CA | 136 | 181.7 | 134.8 | 11.5 | 30 | A |
| PHE | CB | 136 | 180.9 | 136.0 | 12.1 | 32 | A |
| PHE | CG | 136 | 180.3 | 136.9 | 11.1 | 35 | A |
| PHE | CD1 | 136 | 179.4 | 136.5 | 10.1 | 35 | A |
| PHE | CD2 | 136 | 180.8 | 138.3 | 11.0 | 35 | A |
| PHE | CE1 | 136 | 178.9 | 137.3 | 9.1 | 34 | A |
| PHE | CE2 | 136 | 180.2 | 139.1 | 10.0 | 35 | A |
| PHE | CZ | 136 | 179.3 | 138.6 | 9.1 | 35 | A |
| PHE | C | 136 | 183.0 | 135.4 | 10.8 | 30 | A |
| PHE | O | 136 | 183.1 | 135.5 | 9.6 | 31 | A |
| ARG | N | 137 | 184.1 | 135.6 | 11.6 | 28 | A |
| ARG | CA | 137 | 185.3 | 136.1 | 11.0 | 25 | A |
| ARG | CB | 137 | 186.4 | 136.3 | 12.1 | 24 | A |
| ARG | CG | 137 | 187.7 | 136.9 | 11.5 | 21 | A |
| ARG | CD | 137 | 188.6 | 137.3 | 12.6 | 20 | A |
| ARG | NE | 137 | 189.9 | 137.8 | 12.0 | 19 | A |
| ARG | CZ | 137 | 190.2 | 139.1 | 11.9 | 20 | A |
| ARG | NH1 | 137 | 189.3 | 140.0 | 12.3 | 18 | A |
| ARG | NH2 | 137 | 191.4 | 139.4 | 11.4 | 20 | A |
| ARG | C | 137 | 185.9 | 135.0 | 10.0 | 26 | A |
| ARG | O | 137 | 186.3 | 135.4 | 8.9 | 27 | A |
| ARG | N | 138 | 185.9 | 133.8 | 10.3 | 26 | A |
| ARG | CA | 138 | 186.4 | 132.8 | 9.3 | 25 | A |
| ARG | CB | 138 | 186.4 | 131.4 | 9.9 | 24 | A |
| ARG | CG | 138 | 187.7 | 130.7 | 9.9 | 22 | A |
| ARG | CD | 138 | 188.2 | 130.5 | 11.3 | 21 | A |
| ARG | NE | 138 | 187.3 | 129.7 | 12.1 | 21 | A |
| ARG | CZ | 138 | 187.2 | 129.6 | 13.4 | 20 | A |
| ARG | NH1 | 138 | 188.0 | 130.4 | 14.1 | 21 | A |
| ARG | NH2 | 138 | 186.4 | 128.8 | 14.0 | 19 | A |
| ARG | C | 138 | 185.5 | 132.8 | 8.1 | 25 | A |
| ARG | O | 138 | 186.0 | 132.7 | 7.0 | 27 | A |
| VAL | N | 139 | 184.2 | 133.1 | 8.3 | 26 | A |
| VAL | CA | 139 | 183.2 | 133.2 | 7.2 | 26 | A |
| VAL | CB | 139 | 181.8 | 133.5 | 7.7 | 26 | A |
| VAL | CG1 | 139 | 180.9 | 133.9 | 6.5 | 26 | A |
| VAL | CG2 | 139 | 181.3 | 132.3 | 8.5 | 26 | A |
| VAL | C | 139 | 183.7 | 134.4 | 6.3 | 26 | A |
| VAL | O | 139 | 183.9 | 134.2 | 5.1 | 25 | A |
| LEU | N | 140 | 183.9 | 135.6 | 6.9 | 24 | A |
| LEU | CA | 140 | 184.3 | 136.7 | 6.1 | 25 | A |
| LEU | CB | 140 | 184.4 | 137.9 | 7.0 | 24 | A |
| LEU | CG | 140 | 183.0 | 138.3 | 7.6 | 25 | A |
| LEU | CD1 | 140 | 183.1 | 139.4 | 8.5 | 26 | A |
| LEU | CD2 | 140 | 182.1 | 138.5 | 6.5 | 25 | A |
| LEU | C | 140 | 185.6 | 136.5 | 5.4 | 27 | A |
| LEU | O | 140 | 185.9 | 137.0 | 4.3 | 28 | A |
| LEU | N | 141 | 186.5 | 135.7 | 6.1 | 29 | A |
| LEU | CA | 141 | 187.8 | 135.3 | 5.5 | 30 | A |
| LEU | CB | 141 | 188.6 | 134.5 | 6.5 | 28 | A |
| LEU | CG | 141 | 189.4 | 135.1 | 7.7 | 27 | A |
| LEU | CD1 | 141 | 190.1 | 134.0 | 8.4 | 26 | A |
| LEU | CD2 | 141 | 190.5 | 136.0 | 7.1 | 25 | A |
| LEU | C | 141 | 187.6 | 134.6 | 4.2 | 33 | A |
| LEU | O | 141 | 188.4 | 134.8 | 3.3 | 34 | A |
| ARG | N | 142 | 186.6 | 133.8 | 4.2 | 37 | A |
| ARG | CA | 142 | 186.2 | 133.0 | 3.0 | 41 | A |
| ARG | CB | 142 | 185.2 | 131.9 | 3.3 | 46 | A |
| ARG | CG | 142 | 185.6 | 131.0 | 4.5 | 51 | A |

TABLE 5-continued

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| ARG | CD | 142 | 184.4 | 130.2 | 5.1 | 55 | A |
| ARG | NE | 142 | 184.5 | 130.0 | 6.5 | 59 | A |
| ARG | CZ | 142 | 183.9 | 129.0 | 7.3 | 60 | A |
| ARG | NH1 | 142 | 183.3 | 128.0 | 6.7 | 61 | A |
| ARG | NH2 | 142 | 184.0 | 129.1 | 8.6 | 61 | A |
| ARG | C | 142 | 185.7 | 133.9 | 1.9 | 41 | A |
| ARG | O | 142 | 186.2 | 134.0 | 0.8 | 41 | A |
| SER | N | 143 | 184.6 | 134.6 | 2.2 | 40 | A |
| SER | CA | 143 | 184.0 | 135.5 | 1.3 | 39 | A |
| SER | CB | 143 | 182.8 | 136.2 | 1.9 | 39 | A |
| SER | OG | 143 | 182.0 | 135.2 | 2.5 | 41 | A |
| SER | C | 143 | 184.8 | 136.6 | 0.7 | 39 | A |
| SER | O | 143 | 184.9 | 136.8 | −0.5 | 40 | A |
| LEU | N | 144 | 185.4 | 137.5 | 1.6 | 38 | A |
| LEU | CA | 144 | 186.3 | 138.6 | 1.1 | 37 | A |
| LEU | CB | 144 | 186.5 | 139.6 | 2.2 | 37 | A |
| LEU | CG | 144 | 185.4 | 139.9 | 3.3 | 36 | A |
| LEU | CD1 | 144 | 185.9 | 140.9 | 4.2 | 37 | A |
| LEU | CD2 | 144 | 184.1 | 140.3 | 2.7 | 36 | A |
| LEU | C | 144 | 187.6 | 138.1 | 0.5 | 38 | A |
| LEU | O | 144 | 188.4 | 138.9 | 0.1 | 38 | A |
| GLN | N | 145 | 187.8 | 136.8 | 0.6 | 38 | A |
| GLN | CA | 145 | 189.1 | 136.2 | 0.1 | 39 | A |
| GLN | CB | 145 | 189.1 | 136.1 | −1.4 | 42 | A |
| GLN | CG | 145 | 188.2 | 134.9 | −1.9 | 47 | A |
| GLN | CD | 145 | 188.3 | 134.7 | −3.4 | 51 | A |
| GLN | OE1 | 145 | 188.1 | 135.7 | −4.2 | 52 | A |
| GLN | NE2 | 145 | 188.7 | 133.5 | −3.8 | 53 | A |
| GLN | C | 145 | 190.2 | 137.0 | 0.6 | 36 | A |
| GLN | O | 145 | 191.0 | 137.6 | −0.2 | 35 | A |
| LYS | N | 146 | 190.4 | 137.0 | 1.9 | 34 | A |
| LYS | CA | 146 | 191.4 | 137.7 | 2.6 | 33 | A |
| LYS | CB | 146 | 191.1 | 137.9 | 4.1 | 33 | A |
| LYS | CG | 146 | 189.8 | 138.7 | 4.3 | 33 | A |
| LYS | CD | 146 | 189.8 | 140.1 | 3.7 | 32 | A |
| LYS | CE | 146 | 190.9 | 140.9 | 4.3 | 33 | A |
| LYS | NZ | 146 | 190.7 | 142.3 | 3.9 | 33 | A |
| LYS | C | 146 | 192.7 | 137.0 | 2.5 | 32 | A |
| LYS | O | 146 | 192.7 | 135.8 | 2.3 | 31 | A |
| ASP | N | 147 | 193.8 | 137.8 | 2.5 | 32 | A |
| ASP | CA | 147 | 195.1 | 137.2 | 2.5 | 32 | A |
| ASP | CB | 147 | 196.2 | 138.2 | 2.3 | 32 | A |
| ASP | CG | 147 | 197.6 | 137.7 | 2.2 | 33 | A |
| ASP | OD1 | 147 | 198.0 | 136.9 | 3.0 | 34 | A |
| ASP | OD2 | 147 | 198.3 | 138.0 | 1.2 | 35 | A |
| ASP | C | 147 | 195.3 | 136.4 | 3.8 | 33 | A |
| ASP | O | 147 | 195.4 | 137.0 | 4.9 | 33 | A |
| LEU | N | 148 | 195.3 | 135.1 | 3.7 | 33 | A |
| LEU | CA | 148 | 195.5 | 134.3 | 4.9 | 32 | A |
| LEU | CB | 148 | 195.1 | 132.8 | 4.6 | 30 | A |
| LEU | CG | 148 | 193.6 | 132.6 | 4.2 | 29 | A |
| LEU | CD1 | 148 | 193.4 | 131.1 | 4.0 | 28 | A |
| LEU | CD2 | 148 | 192.7 | 133.1 | 5.2 | 28 | A |
| LEU | C | 148 | 196.9 | 134.3 | 5.6 | 32 | A |
| LEU | O | 148 | 197.0 | 134.0 | 6.7 | 34 | A |
| GLN | N | 149 | 197.9 | 134.7 | 4.8 | 33 | A |
| GLN | CA | 149 | 199.2 | 134.8 | 5.4 | 33 | A |
| GLN | CB | 149 | 200.3 | 134.9 | 4.4 | 34 | A |
| GLN | CG | 149 | 201.6 | 134.3 | 4.9 | 36 | A |
| GLN | CD | 149 | 201.3 | 133.0 | 5.6 | 37 | A |
| GLN | OE1 | 149 | 201.1 | 131.9 | 4.9 | 35 | A |
| GLN | NE2 | 149 | 201.3 | 133.0 | 6.9 | 38 | A |
| GLN | C | 149 | 199.2 | 136.1 | 6.3 | 34 | A |
| GLN | O | 149 | 199.9 | 136.1 | 7.3 | 36 | A |
| GLU | N | 150 | 198.4 | 137.1 | 5.9 | 35 | A |
| GLU | CA | 150 | 198.4 | 138.3 | 6.7 | 36 | A |
| GLU | CB | 150 | 197.7 | 139.4 | 5.9 | 40 | A |
| GLU | CG | 150 | 198.7 | 140.5 | 5.4 | 45 | A |
| GLU | CD | 150 | 199.9 | 140.0 | 4.6 | 47 | A |
| GLU | OE1 | 150 | 201.0 | 140.4 | 4.9 | 48 | A |
| GLU | OE2 | 150 | 199.6 | 139.3 | 3.6 | 48 | A |
| GLU | C | 150 | 197.5 | 138.0 | 7.9 | 35 | A |

TABLE 5-continued

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| GLU | O | 150 | 197.8 | 138.5 | 9.0 | 36 | A |
| GLU | N | 151 | 196.6 | 137.1 | 7.8 | 33 | A |
| GLU | CA | 151 | 195.8 | 136.6 | 8.9 | 31 | A |
| GLU | CB | 151 | 194.5 | 135.8 | 8.4 | 30 | A |
| GLU | CG | 151 | 193.6 | 135.3 | 9.5 | 28 | A |
| GLU | CD | 151 | 192.8 | 136.4 | 10.3 | 29 | A |
| GLU | OE1 | 151 | 192.9 | 137.6 | 10.0 | 28 | A |
| GLU | OE2 | 151 | 192.0 | 136.0 | 11.2 | 29 | A |
| GLU | C | 151 | 196.6 | 135.8 | 9.9 | 31 | A |
| GLU | O | 151 | 196.4 | 135.8 | 11.1 | 32 | A |
| MET | N | 152 | 197.6 | 135.1 | 9.4 | 30 | A |
| MET | CA | 152 | 198.5 | 134.3 | 10.2 | 29 | A |
| MET | CB | 152 | 199.5 | 133.5 | 9.4 | 29 | A |
| MET | CG | 152 | 199.0 | 132.2 | 8.9 | 30 | A |
| MET | SD | 152 | 199.0 | 131.0 | 10.2 | 31 | A |
| MET | CE | 152 | 200.6 | 130.3 | 9.9 | 32 | A |
| MET | C | 152 | 199.2 | 135.3 | 11.1 | 28 | A |
| MET | O | 152 | 199.4 | 135.1 | 12.3 | 28 | A |
| ASN | N | 153 | 199.6 | 136.4 | 10.5 | 28 | A |
| ASN | CA | 153 | 200.3 | 137.5 | 11.3 | 28 | A |
| ASN | CB | 153 | 200.6 | 138.6 | 10.3 | 29 | A |
| ASN | CG | 153 | 201.6 | 138.2 | 9.2 | 29 | A |
| ASN | OD1 | 153 | 202.1 | 137.1 | 9.2 | 28 | A |
| ASN | ND2 | 153 | 201.9 | 139.1 | 8.3 | 30 | A |
| ASN | C | 153 | 199.4 | 138.0 | 12.4 | 28 | A |
| ASN | O | 153 | 199.9 | 138.2 | 13.5 | 27 | A |
| TYR | N | 154 | 198.1 | 138.1 | 12.1 | 27 | A |
| TYR | CA | 154 | 197.2 | 138.6 | 13.1 | 26 | A |
| TYR | CB | 154 | 195.8 | 138.7 | 12.5 | 25 | A |
| TYR | CG | 154 | 194.6 | 138.9 | 13.4 | 25 | A |
| TYR | CD1 | 154 | 194.5 | 140.2 | 14.1 | 25 | A |
| TYR | CE1 | 154 | 193.5 | 140.4 | 15.0 | 25 | A |
| TYR | CD2 | 154 | 193.7 | 137.9 | 13.7 | 26 | A |
| TYR | CE2 | 154 | 192.7 | 138.2 | 14.6 | 26 | A |
| TYR | CZ | 154 | 192.6 | 139.4 | 15.3 | 26 | A |
| TYR | OH | 154 | 191.6 | 139.6 | 16.2 | 27 | A |
| TYR | C | 154 | 197.1 | 137.5 | 14.2 | 25 | A |
| TYR | O | 154 | 197.4 | 137.8 | 15.4 | 26 | A |
| ILE | N | 155 | 196.7 | 136.3 | 13.9 | 23 | A |
| ILE | CA | 155 | 196.6 | 135.3 | 14.9 | 21 | A |
| ILE | CB | 155 | 196.0 | 134.0 | 14.3 | 20 | A |
| ILE | CG2 | 155 | 197.0 | 133.2 | 13.6 | 19 | A |
| ILE | CG1 | 155 | 195.3 | 133.2 | 15.4 | 19 | A |
| ILE | CD1 | 155 | 194.0 | 133.9 | 16.0 | 16 | A |
| ILE | C | 155 | 197.8 | 135.0 | 15.7 | 21 | A |
| ILE | O | 155 | 197.8 | 134.6 | 16.8 | 21 | A |
| THR | N | 156 | 199.0 | 135.4 | 15.1 | 21 | A |
| THR | CA | 156 | 200.2 | 135.2 | 15.8 | 21 | A |
| THR | CB | 156 | 201.4 | 135.4 | 14.9 | 21 | A |
| THR | OG1 | 156 | 201.5 | 134.4 | 13.9 | 22 | A |
| THR | CG2 | 156 | 202.8 | 135.5 | 15.6 | 21 | A |
| THR | C | 156 | 200.3 | 136.2 | 17.0 | 22 | A |
| THR | O | 156 | 200.6 | 135.9 | 18.1 | 23 | A |
| ALA | N | 157 | 200.0 | 137.5 | 16.6 | 22 | A |
| ALA | CA | 157 | 200.0 | 138.6 | 17.6 | 21 | A |
| ALA | CB | 157 | 199.6 | 139.8 | 16.9 | 19 | A |
| ALA | C | 157 | 199.0 | 138.3 | 18.8 | 21 | A |
| ALA | O | 157 | 199.4 | 138.3 | 19.9 | 22 | A |
| ILE | N | 158 | 197.8 | 138.0 | 18.4 | 21 | A |
| ILE | CA | 158 | 196.7 | 137.7 | 19.4 | 22 | A |
| ILE | CB | 158 | 195.4 | 137.4 | 18.7 | 21 | A |
| ILE | CG2 | 158 | 194.3 | 137.0 | 19.7 | 22 | A |
| ILE | CG1 | 158 | 194.9 | 138.7 | 18.0 | 23 | A |
| ILE | CD1 | 158 | 194.7 | 139.8 | 19.0 | 25 | A |
| ILE | C | 158 | 197.0 | 136.5 | 20.3 | 22 | A |
| ILE | O | 158 | 196.7 | 136.6 | 21.5 | 23 | A |
| ILE | N | 159 | 197.6 | 135.5 | 19.8 | 22 | A |
| ILE | CA | 159 | 197.9 | 134.3 | 20.6 | 21 | A |
| ILE | CB | 159 | 198.4 | 133.1 | 19.8 | 19 | A |
| ILE | CG2 | 159 | 198.9 | 132.0 | 20.8 | 18 | A |
| ILE | CG1 | 159 | 197.3 | 132.5 | 19.0 | 18 | A |
| ILE | CD1 | 159 | 197.9 | 131.6 | 17.9 | 18 | A |

TABLE 5-continued

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| ILE | C | 159 | 199.1 | 134.8 | 21.6 | 23 | A |
| ILE | O | 159 | 199.0 | 134.4 | 22.8 | 24 | A |
| GLU | N | 160 | 200.0 | 135.5 | 21.1 | 24 | A |
| GLU | CA | 160 | 201.1 | 136.0 | 21.9 | 25 | A |
| GLU | CB | 160 | 202.1 | 136.8 | 21.2 | 24 | A |
| GLU | CG | 160 | 202.9 | 136.1 | 20.1 | 23 | A |
| GLU | CD | 160 | 204.1 | 135.4 | 20.5 | 23 | A |
| GLU | OE1 | 160 | 204.5 | 135.4 | 21.7 | 23 | A |
| GLU | OE2 | 160 | 204.7 | 134.7 | 19.7 | 23 | A |
| GLU | C | 160 | 200.5 | 136.7 | 23.1 | 27 | A |
| GLU | O | 160 | 201.0 | 136.6 | 24.2 | 28 | A |
| GLU | N | 161 | 199.5 | 137.6 | 22.9 | 28 | A |
| GLU | CA | 161 | 199.0 | 138.3 | 24.0 | 31 | A |
| GLU | CB | 161 | 198.4 | 139.6 | 23.6 | 32 | A |
| GLU | CG | 161 | 197.2 | 139.5 | 22.7 | 37 | A |
| GLU | CD | 161 | 197.1 | 140.7 | 21.8 | 39 | A |
| GLU | OE1 | 161 | 198.2 | 141.1 | 21.2 | 41 | A |
| GLU | OE2 | 161 | 196.0 | 141.3 | 21.6 | 41 | A |
| GLU | C | 161 | 198.0 | 137.5 | 24.9 | 31 | A |
| GLU | O | 161 | 197.9 | 137.7 | 26.1 | 33 | A |
| GLN | N | 162 | 197.4 | 136.4 | 24.4 | 30 | A |
| GLN | CA | 162 | 196.5 | 135.5 | 25.1 | 28 | A |
| GLN | CB | 162 | 195.1 | 136.1 | 25.2 | 32 | A |
| GLN | CG | 162 | 194.5 | 136.7 | 23.9 | 35 | A |
| GLN | CD | 162 | 193.3 | 137.6 | 24.3 | 39 | A |
| GLN | OE1 | 162 | 192.5 | 137.2 | 25.1 | 39 | A |
| GLN | NE2 | 162 | 193.2 | 138.7 | 23.6 | 40 | A |
| GLN | C | 162 | 196.6 | 134.1 | 24.6 | 26 | A |
| GLN | O | 162 | 195.6 | 133.6 | 24.0 | 25 | A |
| PRO | N | 163 | 197.6 | 133.4 | 25.0 | 23 | A |
| PRO | CD | 163 | 198.7 | 133.8 | 25.9 | 21 | A |
| PRO | CA | 163 | 197.9 | 132.0 | 24.5 | 22 | A |
| PRO | CB | 163 | 199.4 | 131.8 | 24.8 | 20 | A |
| PRO | CG | 163 | 199.6 | 132.5 | 26.0 | 20 | A |
| PRO | C | 163 | 197.1 | 130.9 | 25.3 | 22 | A |
| PRO | O | 163 | 197.3 | 129.7 | 25.1 | 23 | A |
| LYS | N | 164 | 196.2 | 131.4 | 26.2 | 22 | A |
| LYS | CA | 164 | 195.4 | 130.5 | 27.0 | 21 | A |
| LYS | CB | 164 | 195.6 | 130.6 | 28.5 | 20 | A |
| LYS | CG | 164 | 196.9 | 130.0 | 29.0 | 21 | A |
| LYS | CD | 164 | 197.0 | 129.9 | 30.4 | 19 | A |
| LYS | CE | 164 | 198.3 | 129.5 | 30.8 | 20 | A |
| LYS | NZ | 164 | 198.4 | 129.3 | 32.3 | 21 | A |
| LYS | C | 164 | 194.0 | 130.8 | 26.6 | 21 | A |
| LYS | O | 164 | 193.3 | 131.4 | 27.4 | 22 | A |
| ASN | N | 165 | 193.6 | 130.4 | 25.4 | 21 | A |
| ASN | CA | 165 | 192.3 | 130.6 | 24.9 | 20 | A |
| ASN | CB | 165 | 192.2 | 132.0 | 24.2 | 21 | A |
| ASN | CG | 165 | 191.0 | 132.1 | 23.3 | 21 | A |
| ASN | OD1 | 165 | 190.8 | 131.4 | 22.4 | 23 | A |
| ASN | ND2 | 165 | 190.1 | 133.1 | 23.6 | 22 | A |
| ASN | C | 165 | 192.2 | 129.5 | 23.8 | 19 | A |
| ASN | O | 165 | 193.1 | 129.1 | 23.2 | 20 | A |
| TYR | N | 166 | 191.0 | 128.9 | 23.8 | 19 | A |
| TYR | CA | 166 | 190.7 | 127.8 | 22.9 | 18 | A |
| TYR | CB | 166 | 189.5 | 127.0 | 23.3 | 19 | A |
| TYR | CG | 166 | 189.8 | 126.0 | 24.4 | 20 | A |
| TYR | CD1 | 166 | 189.4 | 126.4 | 25.7 | 21 | A |
| TYR | CE1 | 166 | 189.5 | 125.5 | 26.8 | 22 | A |
| TYR | CD2 | 166 | 190.3 | 124.8 | 24.2 | 22 | A |
| TYR | CE2 | 166 | 190.5 | 123.9 | 25.3 | 22 | A |
| TYR | CZ | 166 | 190.1 | 124.2 | 26.6 | 22 | A |
| TYR | OH | 166 | 190.3 | 123.4 | 27.6 | 23 | A |
| TYR | C | 166 | 190.5 | 128.2 | 21.4 | 18 | A |
| TYR | O | 166 | 190.9 | 127.5 | 20.5 | 18 | A |
| GLN | N | 167 | 189.8 | 129.4 | 21.2 | 17 | A |
| GLN | CA | 167 | 189.5 | 129.9 | 19.9 | 17 | A |
| GLN | CB | 167 | 188.5 | 131.0 | 20.0 | 17 | A |
| GLN | CG | 167 | 187.1 | 130.6 | 20.4 | 18 | A |
| GLN | CD | 167 | 187.1 | 130.1 | 21.8 | 20 | A |
| GLN | OE1 | 167 | 187.8 | 130.7 | 22.7 | 22 | A |
| GLN | NE2 | 167 | 186.3 | 129.1 | 22.1 | 22 | A |

TABLE 5-continued

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| GLN | C | 167 | 190.7 | 130.4 | 19.1 | 16 | A |
| GLN | O | 167 | 190.8 | 130.1 | 17.9 | 18 | A |
| VAL | N | 168 | 191.7 | 131.0 | 19.7 | 16 | A |
| VAL | CA | 168 | 192.8 | 131.5 | 19.0 | 15 | A |
| VAL | CB | 168 | 193.7 | 132.5 | 19.9 | 14 | A |
| VAL | CG1 | 168 | 192.9 | 133.7 | 20.4 | 14 | A |
| VAL | CG2 | 168 | 194.3 | 131.8 | 21.1 | 14 | A |
| VAL | C | 168 | 193.6 | 130.4 | 18.4 | 17 | A |
| VAL | O | 168 | 193.8 | 130.4 | 17.2 | 19 | A |
| TRP | N | 169 | 194.0 | 129.4 | 19.2 | 17 | A |
| TRP | CA | 169 | 194.7 | 128.3 | 18.7 | 16 | A |
| TRP | CB | 169 | 195.1 | 127.3 | 19.8 | 14 | A |
| TRP | CG | 169 | 196.2 | 127.9 | 20.7 | 14 | A |
| TRP | CD2 | 169 | 197.6 | 127.9 | 20.4 | 13 | A |
| TRP | CE2 | 169 | 198.2 | 128.5 | 21.5 | 13 | A |
| TRP | CE3 | 169 | 198.3 | 127.4 | 19.3 | 12 | A |
| TRP | CD1 | 169 | 196.0 | 128.5 | 21.9 | 13 | A |
| TRP | NE1 | 169 | 197.2 | 128.9 | 22.4 | 14 | A |
| TRP | CZ2 | 169 | 199.6 | 128.6 | 21.6 | 13 | A |
| TRP | CZ3 | 169 | 199.7 | 127.5 | 19.4 | 13 | A |
| TRP | CH2 | 169 | 200.4 | 128.1 | 20.5 | 13 | A |
| TRP | C | 169 | 194.0 | 127.5 | 17.6 | 17 | A |
| TRP | O | 169 | 194.5 | 127.2 | 16.6 | 17 | A |
| HIS | N | 170 | 192.7 | 127.3 | 17.8 | 19 | A |
| HIS | CA | 170 | 191.9 | 126.6 | 16.8 | 20 | A |
| HIS | CB | 170 | 190.5 | 126.3 | 17.3 | 22 | A |
| HIS | CG | 170 | 189.6 | 125.6 | 16.3 | 24 | A |
| HIS | CD2 | 170 | 188.6 | 126.0 | 15.5 | 26 | A |
| HIS | ND1 | 170 | 189.9 | 124.3 | 15.9 | 25 | A |
| HIS | CE1 | 170 | 189.1 | 123.9 | 15.0 | 26 | A |
| HIS | NE2 | 170 | 188.3 | 124.9 | 14.7 | 26 | A |
| HIS | C | 170 | 191.8 | 127.4 | 15.5 | 20 | A |
| HIS | O | 170 | 191.7 | 126.8 | 14.4 | 22 | A |
| HIS | N | 171 | 191.7 | 128.7 | 15.6 | 20 | A |
| HIS | CA | 171 | 191.7 | 129.5 | 14.5 | 18 | A |
| HIS | CB | 171 | 191.4 | 131.0 | 14.9 | 18 | A |
| HIS | CG | 171 | 191.3 | 131.9 | 13.7 | 17 | A |
| HIS | CD2 | 171 | 192.2 | 132.7 | 13.1 | 17 | A |
| HIS | ND1 | 171 | 190.1 | 132.2 | 13.1 | 16 | A |
| HIS | CE1 | 171 | 190.3 | 133.1 | 12.2 | 16 | A |
| HIS | NE2 | 171 | 191.5 | 133.4 | 12.2 | 17 | A |
| HIS | C | 171 | 193.0 | 129.4 | 13.8 | 18 | A |
| HIS | O | 171 | 193.1 | 129.3 | 12.5 | 19 | A |
| ARG | N | 172 | 194.1 | 129.3 | 14.5 | 18 | A |
| ARG | CA | 172 | 195.4 | 129.1 | 13.9 | 18 | A |
| ARG | CB | 172 | 196.5 | 129.2 | 14.9 | 17 | A |
| ARG | CG | 172 | 197.9 | 129.3 | 14.2 | 17 | A |
| ARG | CD | 172 | 199.0 | 129.4 | 15.2 | 17 | A |
| ARG | NE | 172 | 200.3 | 129.4 | 14.5 | 18 | A |
| ARG | CZ | 172 | 200.9 | 130.5 | 14.2 | 19 | A |
| ARG | NH1 | 172 | 200.5 | 131.7 | 14.5 | 18 | A |
| ARG | NH2 | 172 | 202.1 | 130.4 | 13.6 | 19 | A |
| ARG | C | 172 | 195.5 | 127.9 | 13.1 | 20 | A |
| ARG | O | 172 | 196.1 | 127.8 | 12.1 | 22 | A |
| ARG | N | 173 | 194.9 | 126.8 | 13.6 | 21 | A |
| ARG | CA | 173 | 194.9 | 125.5 | 13.0 | 21 | A |
| ARG | CB | 173 | 194.3 | 124.5 | 14.0 | 21 | A |
| ARG | CG | 173 | 194.1 | 123.1 | 13.4 | 23 | A |
| ARG | CD | 173 | 193.4 | 122.2 | 14.3 | 26 | A |
| ARG | NE | 173 | 192.9 | 121.0 | 13.7 | 29 | A |
| ARG | CZ | 173 | 192.9 | 119.8 | 14.1 | 31 | A |
| ARG | NH1 | 173 | 193.5 | 119.5 | 15.3 | 32 | A |
| ARG | NH2 | 173 | 192.4 | 118.8 | 13.4 | 32 | A |
| ARG | C | 173 | 194.1 | 125.5 | 11.8 | 22 | A |
| ARG | O | 173 | 194.4 | 124.8 | 10.8 | 23 | A |
| VAL | N | 174 | 192.9 | 126.2 | 11.8 | 24 | A |
| VAL | CA | 174 | 192.1 | 126.3 | 10.6 | 25 | A |
| VAL | CB | 174 | 190.8 | 127.0 | 10.9 | 25 | A |
| VAL | CG1 | 174 | 190.1 | 127.2 | 9.6 | 25 | A |
| VAL | CG2 | 174 | 190.0 | 126.2 | 11.8 | 24 | A |
| VAL | C | 174 | 192.9 | 126.9 | 9.4 | 27 | A |
| VAL | O | 174 | 192.8 | 126.4 | 8.3 | 29 | A |

TABLE 5-continued

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| LEU | N | 175 | 193.6 | 128.0 | 9.7 | 27 | A |
| LEU | CA | 175 | 194.4 | 128.7 | 8.7 | 27 | A |
| LEU | CB | 175 | 195.1 | 129.9 | 9.3 | 26 | A |
| LEU | CG | 175 | 194.2 | 131.0 | 9.9 | 27 | A |
| LEU | CD1 | 175 | 195.1 | 132.2 | 10.4 | 26 | A |
| LEU | CD2 | 175 | 193.2 | 131.5 | 8.8 | 26 | A |
| LEU | C | 175 | 195.5 | 127.8 | 8.1 | 28 | A |
| LEU | O | 175 | 195.7 | 127.7 | 6.9 | 30 | A |
| VAL | N | 176 | 196.2 | 127.1 | 9.0 | 29 | A |
| VAL | CA | 176 | 197.3 | 126.2 | 8.6 | 28 | A |
| VAL | CB | 176 | 198.1 | 125.6 | 9.8 | 28 | A |
| VAL | CG1 | 176 | 199.1 | 124.5 | 9.3 | 27 | A |
| VAL | CG2 | 176 | 198.8 | 126.7 | 10.5 | 28 | A |
| VAL | C | 176 | 196.7 | 125.0 | 7.7 | 28 | A |
| VAL | O | 176 | 197.4 | 124.5 | 6.8 | 28 | A |
| GLU | N | 177 | 195.4 | 124.7 | 8.0 | 28 | A |
| GLU | CA | 177 | 194.8 | 123.7 | 7.2 | 29 | A |
| GLU | CB | 177 | 193.5 | 123.2 | 7.9 | 30 | A |
| GLU | CG | 177 | 193.8 | 122.3 | 9.1 | 32 | A |
| GLU | CD | 177 | 192.6 | 121.8 | 9.8 | 34 | A |
| GLU | OE1 | 177 | 192.6 | 120.7 | 10.4 | 34 | A |
| GLU | OE2 | 177 | 191.6 | 122.5 | 9.7 | 35 | A |
| GLU | C | 177 | 194.5 | 124.2 | 5.8 | 29 | A |
| GLU | O | 177 | 194.8 | 123.6 | 4.8 | 29 | A |
| TRP | N | 178 | 193.8 | 125.4 | 5.8 | 28 | A |
| TRP | CA | 178 | 193.4 | 126.0 | 4.5 | 26 | A |
| TRP | CB | 178 | 192.9 | 127.4 | 4.8 | 24 | A |
| TRP | CG | 178 | 191.4 | 127.4 | 5.2 | 22 | A |
| TRP | CD2 | 178 | 190.6 | 128.5 | 5.6 | 21 | A |
| TRP | CE2 | 178 | 189.3 | 128.0 | 6.0 | 20 | A |
| TRP | CE3 | 178 | 190.9 | 129.8 | 6.1 | 22 | A |
| TRP | CD1 | 178 | 190.5 | 126.3 | 5.1 | 22 | A |
| TRP | NE1 | 178 | 189.3 | 126.7 | 5.6 | 21 | A |
| TRP | CZ2 | 178 | 188.3 | 128.8 | 6.5 | 20 | A |
| TRP | CZ3 | 178 | 189.9 | 130.6 | 6.7 | 21 | A |
| TRP | CH2 | 178 | 188.6 | 130.1 | 6.8 | 20 | A |
| TRP | C | 178 | 194.7 | 126.2 | 3.7 | 28 | A |
| TRP | O | 178 | 194.7 | 125.9 | 2.5 | 29 | A |
| LEU | N | 179 | 195.7 | 126.7 | 4.3 | 28 | A |
| LEU | CA | 179 | 197.0 | 127.0 | 3.6 | 30 | A |
| LEU | CB | 179 | 197.8 | 128.0 | 4.4 | 30 | A |
| LEU | CG | 179 | 197.4 | 129.5 | 4.6 | 30 | A |
| LEU | CD1 | 179 | 198.4 | 130.2 | 5.4 | 30 | A |
| LEU | CD2 | 179 | 197.3 | 130.1 | 3.2 | 30 | A |
| LEU | C | 179 | 197.9 | 125.8 | 3.4 | 32 | A |
| LEU | O | 179 | 198.8 | 125.8 | 2.7 | 32 | A |
| LYS | N | 180 | 197.6 | 124.7 | 4.2 | 34 | A |
| LYS | CA | 180 | 198.5 | 123.5 | 4.1 | 35 | A |
| LYS | CB | 180 | 198.3 | 122.9 | 2.7 | 36 | A |
| LYS | CG | 180 | 196.8 | 122.6 | 2.5 | 39 | A |
| LYS | CD | 180 | 196.5 | 122.6 | 1.0 | 42 | A |
| LYS | CE | 180 | 195.1 | 122.1 | 0.8 | 44 | A |
| LYS | NZ | 180 | 194.8 | 120.7 | 1.4 | 44 | A |
| LYS | C | 180 | 199.9 | 124.0 | 4.3 | 35 | A |
| LYS | O | 180 | 200.8 | 123.4 | 3.7 | 36 | A |
| ASP | N | 181 | 200.1 | 125.0 | 5.1 | 34 | A |
| ASP | CA | 181 | 201.5 | 125.5 | 5.4 | 33 | A |
| ASP | CB | 181 | 201.5 | 127.0 | 4.9 | 32 | A |
| ASP | CG | 181 | 202.9 | 127.5 | 4.8 | 32 | A |
| ASP | OD1 | 181 | 203.9 | 126.8 | 5.2 | 31 | A |
| ASP | OD2 | 181 | 203.1 | 128.7 | 4.5 | 33 | A |
| ASP | C | 181 | 201.9 | 125.5 | 6.9 | 34 | A |
| ASP | O | 181 | 201.4 | 126.3 | 7.7 | 34 | A |
| PRO | N | 182 | 202.7 | 124.5 | 7.2 | 33 | A |
| PRO | CD | 182 | 203.0 | 123.2 | 6.5 | 32 | A |
| PRO | CA | 182 | 203.2 | 124.3 | 8.6 | 32 | A |
| PRO | CB | 182 | 203.3 | 122.8 | 8.8 | 32 | A |
| PRO | CG | 182 | 203.8 | 122.4 | 7.4 | 31 | A |
| PRO | C | 182 | 204.6 | 124.9 | 8.8 | 32 | A |
| PRO | O | 182 | 205.1 | 124.8 | 9.9 | 33 | A |
| SER | N | 183 | 205.2 | 125.5 | 7.8 | 32 | A |
| SER | CA | 183 | 206.5 | 126.1 | 7.9 | 33 | A |

TABLE 5-continued

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| SER | CB | 183 | 206.9 | 126.8 | 6.6 | 34 | A |
| SER | OG | 183 | 206.1 | 127.9 | 6.5 | 37 | A |
| SER | C | 183 | 206.8 | 127.0 | 9.1 | 33 | A |
| SER | O | 183 | 207.9 | 126.9 | 9.7 | 35 | A |
| GLN | N | 184 | 205.8 | 127.8 | 9.5 | 32 | A |
| GLN | CA | 184 | 206.1 | 128.7 | 10.7 | 32 | A |
| GLN | CB | 184 | 205.6 | 130.1 | 10.4 | 33 | A |
| GLN | CG | 184 | 204.4 | 130.2 | 9.5 | 34 | A |
| GLN | CD | 184 | 204.0 | 131.7 | 9.3 | 34 | A |
| GLN | OE1 | 184 | 204.2 | 132.5 | 10.2 | 34 | A |
| GLN | NE2 | 184 | 203.3 | 131.9 | 8.2 | 35 | A |
| GLN | C | 184 | 205.7 | 128.2 | 12.1 | 30 | A |
| GLN | O | 184 | 206.0 | 128.8 | 13.1 | 29 | A |
| GLU | N | 185 | 205.1 | 127.0 | 12.1 | 27 | A |
| GLU | CA | 185 | 204.6 | 126.5 | 13.4 | 25 | A |
| GLU | CB | 185 | 203.6 | 125.3 | 13.1 | 25 | A |
| GLU | CG | 185 | 202.4 | 125.6 | 12.2 | 25 | A |
| GLU | CD | 185 | 201.7 | 126.9 | 12.5 | 25 | A |
| GLU | OE1 | 185 | 200.8 | 126.9 | 13.3 | 25 | A |
| GLU | OE2 | 185 | 202.1 | 127.9 | 11.9 | 27 | A |
| GLU | C | 185 | 205.5 | 126.1 | 14.5 | 24 | A |
| GLU | O | 185 | 205.4 | 126.6 | 15.6 | 24 | A |
| LEU | N | 186 | 206.4 | 125.1 | 14.2 | 23 | A |
| LEU | CA | 186 | 207.3 | 124.7 | 15.3 | 23 | A |
| LEU | CB | 186 | 208.3 | 123.6 | 14.8 | 21 | A |
| LEU | CG | 186 | 207.6 | 122.3 | 14.4 | 20 | A |
| LEU | CD1 | 186 | 208.6 | 121.2 | 14.2 | 20 | A |
| LEU | CD2 | 186 | 206.6 | 121.9 | 15.4 | 18 | A |
| LEU | C | 186 | 208.1 | 125.9 | 15.9 | 24 | A |
| LEU | O | 186 | 208.4 | 125.9 | 17.1 | 26 | A |
| GLU | N | 187 | 208.3 | 126.9 | 15.1 | 26 | A |
| GLU | CA | 187 | 209.0 | 128.1 | 15.6 | 28 | A |
| GLU | CB | 187 | 209.6 | 128.9 | 14.4 | 31 | A |
| GLU | CG | 187 | 210.5 | 130.0 | 14.8 | 35 | A |
| GLU | CD | 187 | 211.0 | 130.8 | 13.6 | 37 | A |
| GLU | OE1 | 187 | 211.2 | 130.1 | 12.5 | 38 | A |
| GLU | OE2 | 187 | 211.2 | 132.0 | 13.7 | 39 | A |
| GLU | C | 187 | 208.1 | 129.1 | 16.4 | 27 | A |
| GLU | O | 187 | 208.6 | 129.6 | 17.4 | 27 | A |
| PHE | N | 188 | 206.9 | 129.3 | 16.0 | 25 | A |
| PHE | CA | 188 | 205.9 | 130.1 | 16.7 | 23 | A |
| PHE | CB | 188 | 204.7 | 130.3 | 15.9 | 23 | A |
| PHE | CG | 188 | 203.5 | 130.8 | 16.7 | 23 | A |
| PHE | CD1 | 188 | 203.5 | 132.0 | 17.2 | 23 | A |
| PHE | CD2 | 188 | 202.5 | 129.9 | 17.0 | 23 | A |
| PHE | CE1 | 188 | 202.5 | 132.5 | 18.0 | 23 | A |
| PHE | CE2 | 188 | 201.4 | 130.4 | 17.8 | 24 | A |
| PHE | CZ | 188 | 201.4 | 131.7 | 18.3 | 23 | A |
| PHE | C | 188 | 205.6 | 129.5 | 18.0 | 23 | A |
| PHE | O | 188 | 205.6 | 130.1 | 19.1 | 23 | A |
| ILE | N | 189 | 205.3 | 128.2 | 18.0 | 23 | A |
| ILE | CA | 189 | 205.0 | 127.4 | 19.2 | 24 | A |
| ILE | CB | 189 | 204.7 | 125.9 | 18.9 | 22 | A |
| ILE | CG2 | 189 | 204.3 | 125.1 | 20.1 | 22 | A |
| ILE | CG1 | 189 | 203.6 | 125.8 | 17.8 | 21 | A |
| ILE | CD1 | 189 | 203.3 | 124.5 | 17.3 | 20 | A |
| ILE | C | 189 | 206.2 | 127.5 | 20.2 | 24 | A |
| ILE | O | 189 | 205.9 | 127.7 | 21.4 | 24 | A |
| ALA | N | 190 | 207.4 | 127.3 | 19.7 | 25 | A |
| ALA | CA | 190 | 208.6 | 127.4 | 20.6 | 24 | A |
| ALA | CB | 190 | 209.8 | 127.0 | 19.8 | 23 | A |
| ALA | C | 190 | 208.7 | 128.8 | 21.2 | 25 | A |
| ALA | O | 190 | 209.4 | 128.9 | 22.3 | 26 | A |
| ASP | N | 191 | 208.2 | 129.8 | 20.6 | 26 | A |
| ASP | CA | 191 | 208.3 | 131.1 | 21.2 | 26 | A |
| ASP | CB | 191 | 208.0 | 132.2 | 20.2 | 28 | A |
| ASP | CG | 191 | 208.1 | 133.6 | 20.8 | 30 | A |
| ASP | OD1 | 191 | 209.2 | 133.9 | 21.4 | 31 | A |
| ASP | OD2 | 191 | 207.1 | 134.4 | 20.8 | 31 | A |
| ASP | C | 191 | 207.2 | 131.2 | 22.3 | 25 | A |
| ASP | O | 191 | 207.5 | 131.9 | 23.3 | 27 | A |
| ILE | N | 192 | 206.0 | 130.7 | 22.1 | 23 | A |

TABLE 5-continued

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| ILE | CA | 192 | 205.0 | 130.7 | 23.2 | 21 | A |
| ILE | CB | 192 | 203.7 | 130.1 | 22.7 | 20 | A |
| ILE | CG2 | 192 | 202.7 | 130.0 | 23.8 | 19 | A |
| ILE | CG1 | 192 | 203.2 | 130.9 | 21.5 | 18 | A |
| ILE | CD1 | 192 | 202.8 | 132.2 | 21.9 | 17 | A |
| ILE | C | 192 | 205.5 | 129.8 | 24.4 | 22 | A |
| ILE | O | 192 | 205.4 | 130.3 | 25.5 | 22 | A |
| LEU | N | 193 | 206.1 | 128.7 | 24.1 | 23 | A |
| LEU | CA | 193 | 206.7 | 127.8 | 25.1 | 23 | A |
| LEU | CB | 193 | 207.1 | 126.4 | 24.6 | 21 | A |
| LEU | CG | 193 | 205.9 | 125.6 | 24.0 | 21 | A |
| LEU | CD1 | 193 | 206.5 | 124.3 | 23.5 | 21 | A |
| LEU | CD2 | 193 | 204.9 | 125.3 | 25.1 | 20 | A |
| LEU | C | 193 | 207.9 | 128.4 | 25.8 | 25 | A |
| LEU | O | 193 | 208.4 | 127.9 | 26.8 | 26 | A |
| ASN | N | 194 | 208.4 | 129.4 | 25.2 | 25 | A |
| ASN | CA | 194 | 209.5 | 130.0 | 25.8 | 26 | A |
| ASN | CB | 194 | 210.4 | 130.7 | 24.7 | 29 | A |
| ASN | CG | 194 | 211.5 | 131.5 | 25.3 | 30 | A |
| ASN | OD1 | 194 | 211.5 | 132.7 | 25.3 | 33 | A |
| ASN | ND2 | 194 | 212.5 | 130.8 | 25.9 | 30 | A |
| ASN | C | 194 | 209.0 | 131.0 | 26.8 | 27 | A |
| ASN | O | 194 | 209.7 | 131.4 | 27.8 | 29 | A |
| GLN | N | 195 | 207.7 | 131.3 | 26.7 | 26 | A |
| GLN | CA | 195 | 207.1 | 132.3 | 27.6 | 25 | A |
| GLN | CB | 195 | 206.1 | 133.1 | 26.9 | 26 | A |
| GLN | CG | 195 | 206.8 | 134.1 | 25.9 | 27 | A |
| GLN | CD | 195 | 205.9 | 134.6 | 24.7 | 27 | A |
| GLN | OE1 | 195 | 205.0 | 135.3 | 24.9 | 28 | A |
| GLN | NE2 | 195 | 206.3 | 134.2 | 23.5 | 27 | A |
| GLN | C | 195 | 206.4 | 131.5 | 28.8 | 24 | A |
| GLN | O | 195 | 206.6 | 131.8 | 29.9 | 25 | A |
| ASP | N | 196 | 205.7 | 130.4 | 28.4 | 22 | A |
| ASP | CA | 196 | 205.0 | 129.5 | 29.4 | 19 | A |
| ASP | CB | 196 | 203.6 | 129.8 | 29.4 | 18 | A |
| ASP | CG | 196 | 202.8 | 128.8 | 30.3 | 17 | A |
| ASP | OD1 | 196 | 203.4 | 127.8 | 30.8 | 17 | A |
| ASP | OD2 | 196 | 201.6 | 129.0 | 30.5 | 17 | A |
| ASP | C | 196 | 205.3 | 128.1 | 28.8 | 19 | A |
| ASP | O | 196 | 204.6 | 127.6 | 27.9 | 21 | A |
| ALA | N | 197 | 206.3 | 127.5 | 29.4 | 18 | A |
| ALA | CA | 197 | 206.7 | 126.1 | 28.9 | 17 | A |
| ALA | CB | 197 | 208.0 | 125.8 | 29.5 | 17 | A |
| ALA | C | 197 | 205.8 | 125.0 | 29.1 | 18 | A |
| ALA | O | 197 | 206.0 | 123.9 | 28.7 | 19 | A |
| LYS | N | 198 | 204.6 | 125.3 | 29.6 | 18 | A |
| LYS | CA | 198 | 203.6 | 124.2 | 29.9 | 18 | A |
| LYS | CB | 198 | 203.6 | 123.9 | 31.4 | 19 | A |
| LYS | CG | 198 | 204.9 | 123.7 | 32.0 | 19 | A |
| LYS | CD | 198 | 204.8 | 123.1 | 33.4 | 20 | A |
| LYS | CE | 198 | 206.1 | 122.9 | 34.1 | 20 | A |
| LYS | NZ | 198 | 206.0 | 122.4 | 35.5 | 20 | A |
| LYS | C | 198 | 202.3 | 124.5 | 29.3 | 18 | A |
| LYS | O | 198 | 201.3 | 123.9 | 29.7 | 20 | A |
| ASN | N | 199 | 202.2 | 125.5 | 28.5 | 18 | A |
| ASN | CA | 199 | 200.9 | 125.9 | 27.9 | 17 | A |
| ASN | CB | 199 | 201.1 | 127.0 | 26.8 | 17 | A |
| ASN | CG | 199 | 199.8 | 127.6 | 26.4 | 18 | A |
| ASN | OD1 | 199 | 199.1 | 127.1 | 25.6 | 20 | A |
| ASN | ND2 | 199 | 199.6 | 128.9 | 26.9 | 18 | A |
| ASN | C | 199 | 200.3 | 124.7 | 27.3 | 18 | A |
| ASN | O | 199 | 200.9 | 124.1 | 26.4 | 20 | A |
| TYR | N | 200 | 199.2 | 124.3 | 27.8 | 18 | A |
| TYR | CA | 200 | 198.5 | 123.0 | 27.3 | 16 | A |
| TYR | CB | 200 | 197.3 | 122.7 | 28.1 | 17 | A |
| TYR | CG | 200 | 196.9 | 121.3 | 28.1 | 18 | A |
| TYR | CD1 | 200 | 197.4 | 120.3 | 29.0 | 18 | A |
| TYR | CE1 | 200 | 197.0 | 119.0 | 28.9 | 18 | A |
| TYR | CD2 | 200 | 196.0 | 120.8 | 27.1 | 17 | A |
| TYR | CE2 | 200 | 195.7 | 119.5 | 27.0 | 18 | A |
| TYR | CZ | 200 | 196.2 | 118.6 | 27.8 | 17 | A |
| TYR | OH | 200 | 195.8 | 117.3 | 27.7 | 16 | A |
| TYR | C | 200 | 198.2 | 123.1 | 25.8 | 16 | A |
| TYR | O | 200 | 198.4 | 122.2 | 25.0 | 16 | A |
| HIS | N | 201 | 197.6 | 124.3 | 25.3 | 16 | A |
| HIS | CA | 201 | 197.2 | 124.5 | 24.0 | 16 | A |
| HIS | CB | 201 | 196.6 | 125.8 | 23.8 | 16 | A |
| HIS | CG | 201 | 195.5 | 126.1 | 24.9 | 16 | A |
| HIS | CD2 | 201 | 195.6 | 126.6 | 26.1 | 15 | A |
| HIS | ND1 | 201 | 194.2 | 125.6 | 24.7 | 15 | A |
| HIS | CE1 | 201 | 193.5 | 125.9 | 25.8 | 15 | A |
| HIS | NE2 | 201 | 194.3 | 126.5 | 26.7 | 15 | A |
| HIS | C | 201 | 198.4 | 124.4 | 23.0 | 17 | A |
| HIS | O | 201 | 198.4 | 123.8 | 21.9 | 17 | A |
| ALA | N | 202 | 199.5 | 125.1 | 23.4 | 18 | A |
| ALA | CA | 202 | 200.7 | 125.1 | 22.6 | 18 | A |
| ALA | CB | 202 | 201.8 | 126.0 | 23.4 | 18 | A |
| ALA | C | 202 | 201.3 | 123.8 | 22.4 | 19 | A |
| ALA | O | 202 | 201.8 | 123.5 | 21.3 | 22 | A |
| TRP | N | 203 | 201.4 | 122.9 | 23.4 | 18 | A |
| TRP | CA | 203 | 201.9 | 121.6 | 23.2 | 18 | A |
| TRP | CB | 203 | 202.1 | 120.9 | 24.6 | 18 | A |
| TRP | CG | 203 | 203.3 | 121.4 | 25.3 | 15 | A |
| TRP | CD2 | 203 | 204.6 | 121.1 | 25.0 | 15 | A |
| TRP | CE2 | 203 | 205.5 | 121.7 | 25.9 | 14 | A |
| TRP | CE3 | 203 | 205.2 | 120.4 | 23.9 | 15 | A |
| TRP | CD1 | 203 | 203.3 | 122.2 | 26.4 | 15 | A |
| TRP | NE1 | 203 | 204.6 | 122.4 | 26.8 | 14 | A |
| TRP | CZ2 | 203 | 206.8 | 121.7 | 25.9 | 14 | A |
| TRP | CZ3 | 203 | 206.6 | 120.3 | 23.9 | 14 | A |
| TRP | CH2 | 203 | 207.4 | 120.9 | 24.8 | 14 | A |
| TRP | C | 203 | 200.9 | 120.8 | 22.4 | 19 | A |
| TRP | O | 203 | 201.3 | 119.9 | 21.6 | 20 | A |
| GLN | N | 204 | 199.6 | 121.0 | 22.6 | 19 | A |
| GLN | CA | 204 | 198.6 | 120.3 | 21.8 | 19 | A |
| GLN | CB | 204 | 197.2 | 120.6 | 22.3 | 20 | A |
| GLN | CG | 204 | 196.2 | 119.5 | 21.9 | 23 | A |
| GLN | CD | 204 | 194.8 | 119.8 | 22.3 | 23 | A |
| GLN | OE1 | 204 | 193.9 | 119.7 | 21.5 | 25 | A |
| GLN | NE2 | 204 | 194.6 | 120.1 | 23.6 | 24 | A |
| GLN | C | 204 | 198.7 | 120.6 | 20.3 | 20 | A |
| GLN | O | 204 | 198.4 | 119.8 | 19.5 | 19 | A |
| HIS | N | 205 | 198.9 | 121.9 | 20.1 | 20 | A |
| HIS | CA | 205 | 199.0 | 122.4 | 18.7 | 19 | A |
| HIS | CB | 205 | 199.1 | 123.9 | 18.7 | 18 | A |
| HIS | CG | 205 | 199.0 | 124.5 | 17.3 | 18 | A |
| HIS | CD2 | 205 | 199.8 | 125.2 | 16.5 | 18 | A |
| HIS | ND1 | 205 | 197.8 | 124.4 | 16.5 | 18 | A |
| HIS | CE1 | 205 | 198.0 | 125.0 | 15.4 | 17 | A |
| HIS | NE2 | 205 | 199.2 | 125.5 | 15.3 | 17 | A |
| HIS | C | 205 | 200.3 | 121.8 | 18.1 | 19 | A |
| HIS | O | 205 | 200.3 | 121.3 | 17.0 | 22 | A |
| ARG | N | 206 | 201.3 | 121.8 | 18.9 | 20 | A |
| ARG | CA | 206 | 202.6 | 121.3 | 18.5 | 18 | A |
| ARG | CB | 206 | 203.6 | 121.4 | 19.6 | 18 | A |
| ARG | CG | 206 | 205.0 | 121.3 | 19.1 | 18 | A |
| ARG | CD | 206 | 206.1 | 121.7 | 20.2 | 17 | A |
| ARG | NE | 206 | 207.4 | 121.7 | 19.6 | 18 | A |
| ARG | CZ | 206 | 208.0 | 122.7 | 19.1 | 19 | A |
| ARG | NH1 | 206 | 207.4 | 123.9 | 19.0 | 20 | A |
| ARG | NH2 | 206 | 209.2 | 122.6 | 18.5 | 20 | A |
| ARG | C | 206 | 202.4 | 119.8 | 18.1 | 20 | A |
| ARG | O | 206 | 202.9 | 119.5 | 17.0 | 22 | A |
| GLN | N | 207 | 201.8 | 119.0 | 18.9 | 19 | A |
| GLN | CA | 207 | 201.7 | 117.6 | 18.6 | 19 | A |
| GLN | CB | 207 | 201.0 | 116.8 | 19.7 | 19 | A |
| GLN | CG | 207 | 201.7 | 116.8 | 21.0 | 20 | A |
| GLN | CD | 207 | 201.2 | 1157 | 22.0 | 21 | A |
| GLN | OE1 | 207 | 200.1 | 115.3 | 21.9 | 20 | A |
| GLN | NE2 | 207 | 202.1 | 115.3 | 22.8 | 19 | A |
| GLN | C | 207 | 200.9 | 117.3 | 17.3 | 21 | A |
| GLN | O | 207 | 201.1 | 116.4 | 16.5 | 22 | A |
| TRP | N | 208 | 199.9 | 118.2 | 17.0 | 21 | A |
| TRP | CA | 208 | 199.1 | 118.1 | 15.8 | 22 | A |

TABLE 5-continued

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| TRP | CB | 208 | 197.8 | 119.0 | 16.0 | 20 | A |
| TRP | CG | 208 | 197.0 | 119.1 | 14.7 | 19 | A |
| TRP | CD2 | 208 | 197.1 | 120.2 | 13.7 | 20 | A |
| TRP | CE2 | 208 | 196.3 | 119.9 | 12.7 | 19 | A |
| TRP | CE3 | 208 | 197.9 | 121.4 | 13.7 | 20 | A |
| TRP | CD1 | 208 | 196.2 | 118.2 | 14.2 | 19 | A |
| TRP | NE1 | 208 | 195.7 | 118.7 | 12.9 | 19 | A |
| TRP | CZ2 | 208 | 196.2 | 120.7 | 11.6 | 18 | A |
| TRP | CZ3 | 208 | 197.7 | 122.2 | 12.6 | 19 | A |
| TRP | CH2 | 208 | 196.9 | 121.8 | 11.5 | 19 | A |
| TRP | C | 208 | 199.8 | 118.4 | 14.5 | 24 | A |
| TRP | O | 208 | 199.5 | 117.8 | 13.5 | 26 | A |
| VAL | N | 209 | 200.6 | 119.5 | 14.5 | 25 | A |
| VAL | CA | 209 | 201.4 | 119.9 | 13.4 | 25 | A |
| VAL | CB | 209 | 202.1 | 121.2 | 13.6 | 24 | A |
| VAL | CG1 | 209 | 202.8 | 121.7 | 12.3 | 24 | A |
| VAL | CG2 | 209 | 201.1 | 122.3 | 14.0 | 24 | A |
| VAL | C | 209 | 202.4 | 118.8 | 13.1 | 26 | A |
| VAL | O | 209 | 202.6 | 118.5 | 11.9 | 28 | A |
| ILE | N | 210 | 203.1 | 118.3 | 14.1 | 26 | A |
| ILE | CA | 210 | 204.1 | 117.3 | 13.9 | 26 | A |
| ILE | CB | 210 | 204.8 | 116.9 | 15.3 | 25 | A |
| ILE | CG2 | 210 | 205.6 | 115.7 | 15.1 | 24 | A |
| ILE | CG1 | 210 | 205.6 | 118.1 | 15.8 | 23 | A |
| ILE | CD1 | 210 | 206.4 | 117.7 | 16.9 | 24 | A |
| ILE | C | 210 | 203.5 | 116.0 | 13.4 | 27 | A |
| ILE | O | 210 | 203.9 | 115.5 | 12.4 | 28 | A |
| GLN | N | 211 | 202.4 | 115.6 | 14.0 | 30 | A |
| GLN | CA | 211 | 201.7 | 114.4 | 13.5 | 32 | A |
| GLN | CB | 211 | 200.6 | 114.0 | 14.5 | 35 | A |
| GLN | CG | 211 | 200.0 | 112.7 | 14.2 | 39 | A |
| GLN | CD | 211 | 199.6 | 111.9 | 15.5 | 40 | A |
| GLN | OE1 | 211 | 199.1 | 112.5 | 16.5 | 42 | A |
| GLN | NE2 | 211 | 199.8 | 110.6 | 15.5 | 41 | A |
| GLN | C | 211 | 201.1 | 114.6 | 12.1 | 33 | A |
| GLN | O | 211 | 201.2 | 113.7 | 11.3 | 33 | A |
| GLU | N | 212 | 200.4 | 115.7 | 11.9 | 34 | A |
| GLU | CA | 212 | 199.8 | 115.9 | 10.6 | 35 | A |
| GLU | CB | 212 | 198.9 | 117.2 | 10.6 | 37 | A |
| GLU | CG | 212 | 197.6 | 117.0 | 11.2 | 42 | A |
| GLU | CD | 212 | 196.8 | 115.8 | 10.6 | 45 | A |
| GLU | OE1 | 212 | 196.2 | 116.0 | 9.5 | 48 | A |
| GLU | OE2 | 212 | 196.8 | 114.7 | 11.2 | 46 | A |
| GLU | C | 212 | 200.7 | 116.1 | 9.4 | 34 | A |
| GLU | O | 212 | 200.4 | 115.5 | 8.3 | 35 | A |
| PHE | N | 213 | 201.8 | 116.8 | 9.6 | 33 | A |
| PHE | CA | 213 | 202.7 | 117.1 | 8.5 | 32 | A |
| PHE | CB | 213 | 203.1 | 118.6 | 8.5 | 30 | A |
| PHE | CG | 213 | 201.9 | 119.4 | 8.3 | 29 | A |
| PHE | CD1 | 213 | 201.0 | 119.7 | 9.4 | 29 | A |
| PHE | CD2 | 213 | 201.5 | 119.9 | 7.0 | 29 | A |
| PHE | CE1 | 213 | 199.9 | 120.5 | 9.2 | 29 | A |
| PHE | CE2 | 213 | 200.4 | 120.6 | 6.8 | 29 | A |
| PHE | CZ | 213 | 199.6 | 120.9 | 7.9 | 29 | A |
| PHE | C | 213 | 204.0 | 116.3 | 8.6 | 33 | A |
| PHE | O | 213 | 205.0 | 116.6 | 8.0 | 35 | A |
| ARG | N | 214 | 204.0 | 115.2 | 9.5 | 35 | A |
| ARG | CA | 214 | 205.1 | 114.4 | 9.7 | 36 | A |
| ARG | CB | 214 | 205.2 | 113.4 | 8.5 | 39 | A |
| ARG | CG | 214 | 204.3 | 112.3 | 8.5 | 43 | A |
| ARG | CD | 214 | 203.6 | 112.1 | 7.1 | 46 | A |
| ARG | NE | 214 | 202.2 | 112.5 | 7.2 | 51 | A |
| ARG | CZ | 214 | 201.2 | 111.7 | 7.6 | 53 | A |
| ARG | NH1 | 214 | 200.0 | 112.2 | 7.7 | 53 | A |
| ARG | NH2 | 214 | 201.4 | 110.5 | 8.0 | 54 | A |
| ARG | C | 214 | 206.4 | 115.1 | 9.9 | 36 | A |
| ARG | O | 214 | 207.4 | 114.7 | 9.4 | 37 | A |
| LEU | N | 215 | 206.4 | 116.1 | 10.8 | 35 | A |
| LEU | CA | 215 | 207.6 | 116.9 | 11.2 | 34 | A |
| LEU | CB | 215 | 207.2 | 118.3 | 11.4 | 34 | A |
| LEU | CG | 215 | 206.5 | 119.1 | 10.3 | 33 | A |
| LEU | CD1 | 215 | 206.3 | 120.6 | 10.7 | 34 | A |

TABLE 5-continued

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| LEU | CD2 | 215 | 207.3 | 119.1 | 9.0 | 33 | A |
| LEU | C | 215 | 208.3 | 116.3 | 12.4 | 34 | A |
| LEU | O | 215 | 208.6 | 117.1 | 13.3 | 35 | A |
| TRP | N | 216 | 208.5 | 115.0 | 12.4 | 35 | A |
| TRP | CA | 216 | 209.2 | 114.3 | 13.6 | 34 | A |
| TRP | CB | 216 | 208.9 | 112.8 | 13.5 | 32 | A |
| TRP | CG | 216 | 207.5 | 112.5 | 13.4 | 30 | A |
| TRP | CD2 | 216 | 206.6 | 112.4 | 14.5 | 29 | A |
| TRP | CE2 | 216 | 205.3 | 112.0 | 14.0 | 29 | A |
| TRP | CE3 | 216 | 206.7 | 112.6 | 15.9 | 28 | A |
| TRP | CD1 | 216 | 206.8 | 112.1 | 12.3 | 30 | A |
| TRP | NE1 | 216 | 205.5 | 111.9 | 12.6 | 29 | A |
| TRP | CZ2 | 216 | 204.2 | 111.9 | 14.8 | 29 | A |
| TRP | CZ3 | 216 | 205.6 | 112.4 | 16.7 | 28 | A |
| TRP | CH2 | 216 | 204.3 | 112.1 | 16.1 | 28 | A |
| TRP | C | 216 | 210.7 | 114.5 | 13.8 | 36 | A |
| TRP | O | 216 | 211.1 | 114.5 | 15.0 | 38 | A |
| ASP | N | 217 | 211.4 | 114.8 | 12.7 | 38 | A |
| ASP | CA | 217 | 212.9 | 114.8 | 12.9 | 39 | A |
| ASP | CB | 217 | 213.4 | 115.0 | 11.5 | 40 | A |
| ASP | CG | 217 | 213.0 | 113.9 | 10.5 | 42 | A |
| ASP | OD1 | 217 | 213.1 | 114.1 | 9.3 | 43 | A |
| ASP | OD2 | 217 | 212.6 | 112.8 | 11.0 | 43 | A |
| ASP | C | 217 | 213.6 | 115.6 | 13.9 | 39 | A |
| ASP | O | 217 | 214.6 | 115.1 | 14.5 | 39 | A |
| ASN | N | 218 | 213.2 | 116.8 | 14.3 | 39 | A |
| ASN | CA | 218 | 213.9 | 117.6 | 15.3 | 38 | A |
| ASN | CB | 218 | 214.3 | 118.9 | 14.7 | 39 | A |
| ASN | CG | 218 | 214.9 | 118.8 | 13.3 | 40 | A |
| ASN | OD1 | 218 | 214.2 | 119.2 | 12.4 | 41 | A |
| ASN | ND2 | 218 | 216.1 | 118.3 | 13.1 | 40 | A |
| ASN | C | 218 | 213.2 | 117.7 | 16.6 | 37 | A |
| ASN | O | 218 | 213.6 | 118.5 | 17.4 | 38 | A |
| GLU | N | 219 | 212.1 | 117.0 | 16.8 | 35 | A |
| GLU | CA | 219 | 211.4 | 117.1 | 18.1 | 34 | A |
| GLU | CB | 219 | 210.0 | 116.7 | 17.9 | 34 | A |
| GLU | CG | 219 | 209.1 | 117.1 | 19.1 | 33 | A |
| GLU | CD | 219 | 209.0 | 118.6 | 19.2 | 33 | A |
| GLU | OE1 | 219 | 209.7 | 119.4 | 18.5 | 33 | A |
| GLU | OE2 | 219 | 208.1 | 119.0 | 20.0 | 34 | A |
| GLU | C | 219 | 212.1 | 116.5 | 19.3 | 35 | A |
| GLU | O | 219 | 212.0 | 117.1 | 20.4 | 34 | A |
| LEU | N | 220 | 212.7 | 115.3 | 19.2 | 35 | A |
| LEU | CA | 220 | 213.3 | 114.7 | 20.3 | 35 | A |
| LEU | CB | 220 | 213.8 | 113.3 | 20.1 | 35 | A |
| LEU | CG | 220 | 214.2 | 112.4 | 21.3 | 35 | A |
| LEU | CD1 | 220 | 213.3 | 112.5 | 22.5 | 35 | A |
| LEU | CD2 | 220 | 214.4 | 111.0 | 20.9 | 34 | A |
| LEU | C | 220 | 214.5 | 115.6 | 20.8 | 36 | A |
| LEU | O | 220 | 214.8 | 115.6 | 22.0 | 38 | A |
| GLN | N | 221 | 215.1 | 116.3 | 19.9 | 37 | A |
| GLN | CA | 221 | 216.2 | 117.2 | 20.2 | 37 | A |
| GLN | CB | 221 | 216.9 | 117.6 | 18.9 | 40 | A |
| GLN | CG | 221 | 217.9 | 118.6 | 19.1 | 45 | A |
| GLN | CD | 221 | 218.7 | 118.9 | 17.8 | 48 | A |
| GLN | OE1 | 221 | 219.3 | 118.0 | 17.2 | 50 | A |
| GLN | NE2 | 221 | 218.6 | 120.1 | 17.2 | 49 | A |
| GLN | C | 221 | 215.7 | 118.4 | 20.9 | 36 | A |
| GLN | O | 221 | 216.4 | 118.9 | 21.8 | 36 | A |
| TYR | N | 222 | 214.6 | 118.9 | 20.6 | 34 | A |
| TYR | CA | 222 | 213.9 | 120.0 | 21.2 | 32 | A |
| TYR | CB | 222 | 212.7 | 120.4 | 20.4 | 30 | A |
| TYR | CG | 222 | 211.9 | 121.6 | 21.0 | 29 | A |
| TYR | CD1 | 222 | 212.4 | 122.8 | 21.0 | 28 | A |
| TYR | CE1 | 222 | 211.7 | 123.9 | 21.5 | 28 | A |
| TYR | CD2 | 222 | 210.6 | 121.4 | 21.5 | 28 | A |
| TYR | CE2 | 222 | 209.9 | 122.4 | 22.0 | 28 | A |
| TYR | CZ | 222 | 210.4 | 123.7 | 22.0 | 27 | A |
| TYR | OH | 222 | 209.7 | 124.7 | 22.5 | 27 | A |
| TYR | C | 222 | 213.5 | 119.6 | 22.6 | 33 | A |
| TYR | O | 222 | 213.7 | 120.4 | 23.6 | 33 | A |
| VAL | N | 223 | 213.0 | 118.4 | 22.7 | 33 | A |

TABLE 5-continued

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| VAL | CA | 223 | 212.6 | 117.8 | 24.0 | 32 | A |
| VAL | CB | 223 | 212.0 | 116.4 | 23.8 | 31 | A |
| VAL | CG1 | 223 | 212.2 | 115.6 | 25.1 | 31 | A |
| VAL | CG2 | 223 | 210.5 | 116.6 | 23.5 | 30 | A |
| VAL | C | 223 | 213.9 | 117.8 | 24.9 | 33 | A |
| VAL | O | 223 | 213.8 | 118.1 | 26.1 | 33 | A |
| ASP | N | 224 | 215.0 | 117.4 | 24.4 | 33 | A |
| ASP | CA | 224 | 216.2 | 117.3 | 25.2 | 33 | A |
| ASP | CB | 224 | 217.4 | 116.7 | 24.4 | 33 | A |
| ASP | CG | 224 | 217.2 | 115.2 | 24.2 | 33 | A |
| ASP | OD1 | 224 | 216.5 | 114.6 | 25.0 | 33 | A |
| ASP | OD2 | 224 | 217.7 | 114.7 | 23.2 | 34 | A |
| ASP | C | 224 | 216.6 | 118.7 | 25.7 | 34 | A |
| ASP | O | 224 | 217.2 | 118.9 | 26.7 | 34 | A |
| GLN | N | 225 | 216.3 | 119.7 | 24.8 | 34 | A |
| GLN | CA | 225 | 216.6 | 121.1 | 25.2 | 36 | A |
| GLN | CB | 225 | 216.3 | 122.0 | 24.0 | 38 | A |
| GLN | CG | 225 | 216.4 | 123.5 | 24.3 | 41 | A |
| GLN | CD | 225 | 215.8 | 124.4 | 23.3 | 43 | A |
| GLN | OE1 | 225 | 215.8 | 124.1 | 22.1 | 44 | A |
| GLN | NE2 | 225 | 215.3 | 125.6 | 23.8 | 43 | A |
| GLN | C | 225 | 215.7 | 121.5 | 26.4 | 35 | A |
| GLN | O | 225 | 216.2 | 122.0 | 27.4 | 35 | A |
| LEU | N | 226 | 214.4 | 121.3 | 26.3 | 35 | A |
| LEU | CA | 226 | 213.5 | 121.8 | 27.4 | 34 | A |
| LEU | CB | 226 | 212.1 | 121.7 | 26.9 | 32 | A |
| LEU | CG | 226 | 211.8 | 122.6 | 25.7 | 32 | A |
| LEU | CD1 | 226 | 210.3 | 122.9 | 25.8 | 31 | A |
| LEU | CD2 | 226 | 212.5 | 123.9 | 25.8 | 31 | A |
| LEU | C | 226 | 213.8 | 121.0 | 28.7 | 34 | A |
| LEU | O | 226 | 213.7 | 121.6 | 29.7 | 34 | A |
| LEU | N | 227 | 214.1 | 119.7 | 28.6 | 36 | A |
| LEU | CA | 227 | 214.3 | 118.9 | 29.8 | 36 | A |
| LEU | CB | 227 | 214.4 | 117.4 | 29.5 | 35 | A |
| LEU | CG | 227 | 213.1 | 116.7 | 29.3 | 34 | A |
| LEU | CD1 | 227 | 213.3 | 115.3 | 28.8 | 33 | A |
| LEU | CD2 | 227 | 212.4 | 116.7 | 30.7 | 33 | A |
| LEU | C | 227 | 215.6 | 119.4 | 30.5 | 37 | A |
| LEU | O | 227 | 215.7 | 119.4 | 31.7 | 38 | A |
| LYS | N | 228 | 216.5 | 119.9 | 29.7 | 38 | A |
| LYS | CA | 228 | 217.8 | 120.4 | 30.2 | 39 | A |
| LYS | CB | 228 | 218.7 | 120.7 | 29.0 | 42 | A |
| LYS | CG | 228 | 220.1 | 120.8 | 29.4 | 46 | A |
| LYS | CD | 228 | 221.0 | 120.6 | 28.1 | 49 | A |
| LYS | CE | 228 | 222.5 | 120.9 | 28.4 | 51 | A |
| LYS | NZ | 228 | 223.3 | 120.9 | 27.1 | 52 | A |
| LYS | C | 228 | 217.4 | 121.7 | 30.9 | 39 | A |
| LYS | O | 228 | 218.0 | 122.0 | 32.0 | 39 | A |
| GLU | N | 229 | 216.5 | 122.5 | 30.4 | 37 | A |
| GLU | CA | 229 | 216.1 | 123.8 | 31.0 | 34 | A |
| GLU | CB | 229 | 215.3 | 124.6 | 30.1 | 34 | A |
| GLU | CG | 229 | 216.1 | 125.0 | 28.8 | 34 | A |
| GLU | CD | 229 | 215.3 | 125.9 | 27.9 | 34 | A |
| GLU | OE1 | 229 | 214.1 | 126.1 | 28.2 | 34 | A |
| GLU | OE2 | 229 | 215.8 | 126.3 | 26.9 | 35 | A |
| GLU | C | 229 | 215.3 | 123.5 | 32.3 | 33 | A |
| GLU | O | 229 | 215.3 | 124.2 | 33.3 | 33 | A |
| ASP | N | 230 | 214.5 | 122.4 | 32.3 | 32 | A |
| ASP | CA | 230 | 213.7 | 122.0 | 33.4 | 30 | A |
| ASP | CB | 230 | 212.5 | 123.0 | 33.5 | 30 | A |
| ASP | CG | 230 | 211.7 | 122.8 | 34.8 | 30 | A |
| ASP | OD1 | 230 | 212.1 | 122.0 | 35.7 | 30 | A |
| ASP | OD2 | 230 | 210.8 | 123.6 | 35.0 | 30 | A |
| ASP | C | 230 | 213.3 | 120.6 | 33.4 | 30 | A |
| ASP | O | 230 | 212.2 | 120.3 | 32.9 | 29 | A |
| VAL | N | 231 | 214.1 | 119.7 | 33.9 | 29 | A |
| VAL | CA | 231 | 213.8 | 118.3 | 34.0 | 29 | A |
| VAL | CB | 231 | 215.0 | 117.5 | 34.7 | 30 | A |
| VAL | CG1 | 231 | 215.0 | 117.9 | 36.2 | 30 | A |
| VAL | CG2 | 231 | 214.9 | 116.0 | 34.4 | 30 | A |
| VAL | C | 231 | 212.5 | 118.0 | 34.6 | 28 | A |
| VAL | O | 231 | 212.0 | 116.9 | 34.5 | 28 | A |

TABLE 5-continued

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| ARG | N | 232 | 211.9 | 118.9 | 35.3 | 28 | A |
| ARG | CA | 232 | 210.6 | 118.7 | 36.0 | 28 | A |
| ARG | CB | 232 | 210.5 | 119.5 | 37.3 | 29 | A |
| ARG | CG | 232 | 211.6 | 119.2 | 38.3 | 30 | A |
| ARG | CD | 232 | 211.3 | 120.0 | 39.5 | 31 | A |
| ARG | NE | 232 | 212.2 | 119.7 | 40.7 | 32 | A |
| ARG | CZ | 232 | 213.3 | 120.3 | 41.0 | 32 | A |
| ARG | NH1 | 232 | 213.8 | 121.3 | 40.2 | 32 | A |
| ARG | NH2 | 232 | 214.0 | 119.9 | 42.0 | 33 | A |
| ARG | C | 232 | 209.4 | 119.1 | 35.0 | 27 | A |
| ARG | O | 232 | 208.3 | 119.1 | 35.5 | 27 | A |
| ASN | N | 233 | 209.7 | 119.4 | 33.8 | 26 | A |
| ASN | CA | 233 | 208.6 | 119.8 | 32.9 | 25 | A |
| ASN | CB | 233 | 209.1 | 120.6 | 31.7 | 25 | A |
| ASN | CG | 233 | 207.9 | 121.3 | 31.0 | 25 | A |
| ASN | OD1 | 233 | 206.8 | 120.9 | 31.0 | 26 | A |
| ASN | ND2 | 233 | 208.2 | 122.5 | 30.4 | 24 | A |
| ASN | C | 233 | 207.9 | 118.6 | 32.5 | 25 | A |
| ASN | O | 233 | 208.3 | 117.9 | 31.5 | 27 | A |
| ASN | N | 234 | 206.7 | 118.3 | 33.1 | 25 | A |
| ASN | CA | 234 | 206.0 | 117.1 | 32.7 | 25 | A |
| ASN | CB | 234 | 204.8 | 116.9 | 33.6 | 25 | A |
| ASN | CG | 234 | 204.3 | 115.5 | 33.7 | 25 | A |
| ASN | OD1 | 234 | 205.1 | 114.6 | 34.1 | 25 | A |
| ASN | ND2 | 234 | 203.1 | 115.2 | 33.4 | 25 | A |
| ASN | C | 234 | 205.6 | 117.1 | 31.3 | 24 | A |
| ASN | O | 234 | 205.6 | 116.1 | 30.6 | 24 | A |
| SER | N | 235 | 205.2 | 118.3 | 30.8 | 23 | A |
| SER | CA | 235 | 204.8 | 118.5 | 29.4 | 21 | A |
| SER | CB | 235 | 204.5 | 120.0 | 29.2 | 21 | A |
| SER | OG | 235 | 203.4 | 120.4 | 30.0 | 21 | A |
| SER | C | 235 | 205.9 | 118.0 | 28.4 | 21 | A |
| SER | O | 235 | 205.6 | 117.5 | 27.3 | 21 | A |
| VAL | N | 236 | 207.2 | 118.2 | 28.8 | 22 | A |
| VAL | CA | 236 | 208.3 | 117.8 | 27.9 | 22 | A |
| VAL | CB | 236 | 209.5 | 118.5 | 28.3 | 21 | A |
| VAL | CG1 | 236 | 210.6 | 118.2 | 27.3 | 21 | A |
| VAL | CG2 | 236 | 209.3 | 120.0 | 28.3 | 21 | A |
| VAL | C | 236 | 208.4 | 116.3 | 28.1 | 23 | A |
| VAL | O | 236 | 208.8 | 115.6 | 27.1 | 25 | A |
| TRP | N | 237 | 208.2 | 115.8 | 29.2 | 24 | A |
| TRP | CA | 237 | 208.3 | 114.3 | 29.4 | 25 | A |
| TRP | CB | 237 | 208.2 | 113.9 | 30.8 | 24 | A |
| TRP | CG | 237 | 209.5 | 114.0 | 31.6 | 23 | A |
| TRP | CD2 | 237 | 210.6 | 113.1 | 31.6 | 23 | A |
| TRP | CE2 | 237 | 211.6 | 113.6 | 32.4 | 23 | A |
| TRP | CE3 | 237 | 210.8 | 111.9 | 31.0 | 22 | A |
| TRP | CD1 | 237 | 209.8 | 115.0 | 32.4 | 23 | A |
| TRP | NE1 | 237 | 211.1 | 114.8 | 32.9 | 23 | A |
| TRP | CZ2 | 237 | 212.8 | 113.0 | 32.7 | 21 | A |
| TRP | CZ3 | 237 | 212.0 | 111.2 | 31.2 | 21 | A |
| TRP | CH2 | 237 | 213.0 | 111.8 | 32.0 | 21 | A |
| TRP | C | 237 | 207.2 | 113.7 | 28.5 | 25 | A |
| TRP | O | 237 | 207.4 | 112.7 | 27.8 | 25 | A |
| ASN | N | 238 | 206.0 | 114.3 | 28.6 | 24 | A |
| ASN | CA | 238 | 205.0 | 113.7 | 27.7 | 24 | A |
| ASN | CB | 238 | 203.7 | 114.5 | 28.0 | 26 | A |
| ASN | CG | 238 | 202.6 | 113.9 | 27.1 | 28 | A |
| ASN | OD1 | 238 | 202.1 | 112.8 | 27.3 | 29 | A |
| ASN | ND2 | 238 | 202.1 | 114.8 | 26.2 | 27 | A |
| ASN | C | 238 | 205.3 | 113.8 | 26.3 | 23 | A |
| ASN | O | 238 | 205.2 | 112.9 | 25.6 | 23 | A |
| GLN | N | 239 | 205.9 | 114.9 | 25.9 | 24 | A |
| GLN | CA | 239 | 206.3 | 115.1 | 24.5 | 25 | A |
| GLN | CB | 239 | 206.9 | 116.5 | 24.2 | 25 | A |
| GLN | CG | 239 | 207.1 | 116.8 | 22.7 | 25 | A |
| GLN | CD | 239 | 205.8 | 117.0 | 21.9 | 25 | A |
| GLN | OE1 | 239 | 204.7 | 116.6 | 22.4 | 25 | A |
| GLN | NE2 | 239 | 205.9 | 117.6 | 20.8 | 24 | A |
| GLN | C | 239 | 207.4 | 114.0 | 24.0 | 25 | A |
| GLN | O | 239 | 207.3 | 113.6 | 22.9 | 25 | A |
| ARG | N | 240 | 208.2 | 113.7 | 25.0 | 26 | A |

TABLE 5-continued

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| ARG | CA | 240 | 209.3 | 112.7 | 24.7 | 26 | A |
| ARG | CB | 240 | 210.2 | 112.6 | 25.9 | 27 | A |
| ARG | CG | 240 | 211.4 | 111.7 | 25.7 | 27 | A |
| ARG | CD | 240 | 212.2 | 111.5 | 27.0 | 27 | A |
| ARG | NE | 240 | 213.5 | 111.0 | 26.6 | 28 | A |
| ARG | CZ | 240 | 214.4 | 111.7 | 26.0 | 29 | A |
| ARG | NH1 | 240 | 214.2 | 113.0 | 25.8 | 30 | A |
| ARG | NH2 | 240 | 215.5 | 111.2 | 25.5 | 29 | A |
| ARG | C | 240 | 208.7 | 111.4 | 24.4 | 27 | A |
| ARG | O | 240 | 209.2 | 110.7 | 23.5 | 30 | A |
| HIS | N | 241 | 207.6 | 111.0 | 25.1 | 27 | A |
| HIS | CA | 241 | 207.0 | 109.8 | 24.9 | 24 | A |
| HIS | CB | 241 | 206.1 | 109.4 | 26.1 | 25 | A |
| HIS | CG | 241 | 205.5 | 108.1 | 26.0 | 25 | A |
| HIS | CD2 | 241 | 205.8 | 106.9 | 26.7 | 25 | A |
| HIS | ND1 | 241 | 204.4 | 107.7 | 25.2 | 24 | A |
| HIS | CE1 | 241 | 204.1 | 106.5 | 25.4 | 25 | A |
| HIS | NE2 | 241 | 204.9 | 106.0 | 26.3 | 25 | A |
| HIS | C | 241 | 206.1 | 109.8 | 23.6 | 25 | A |
| HIS | O | 241 | 206.0 | 108.8 | 23.0 | 25 | A |
| PHE | N | 242 | 205.6 | 111.0 | 23.3 | 24 | A |
| PHE | CA | 242 | 204.7 | 111.1 | 22.1 | 23 | A |
| PHE | CB | 242 | 204.2 | 112.5 | 22.0 | 23 | A |
| PHE | CG | 242 | 203.5 | 112.9 | 20.7 | 22 | A |
| PHE | CD1 | 242 | 202.2 | 112.3 | 20.4 | 22 | A |
| PHE | CD2 | 242 | 204.0 | 113.8 | 19.8 | 22 | A |
| PHE | CE1 | 242 | 201.5 | 112.7 | 19.3 | 21 | A |
| PHE | CE2 | 242 | 203.3 | 114.1 | 18.7 | 22 | A |
| PHE | CZ | 242 | 202.1 | 113.6 | 18.4 | 22 | A |
| PHE | C | 242 | 205.6 | 110.9 | 20.9 | 24 | A |
| PHE | O | 242 | 205.3 | 110.1 | 20.0 | 25 | A |
| VAL | N | 243 | 206.8 | 111.5 | 20.9 | 25 | A |
| VAL | CA | 243 | 207.8 | 111.4 | 19.8 | 26 | A |
| VAL | CB | 243 | 209.0 | 112.4 | 20.1 | 26 | A |
| VAL | CG1 | 243 | 210.1 | 112.2 | 19.1 | 26 | A |
| VAL | CG2 | 243 | 208.4 | 113.8 | 20.0 | 26 | A |
| VAL | C | 243 | 208.3 | 110.0 | 19.6 | 26 | A |
| VAL | O | 243 | 208.3 | 109.5 | 18.5 | 27 | A |
| ILE | N | 244 | 208.9 | 109.4 | 20.7 | 26 | A |
| ILE | CA | 244 | 209.4 | 108.1 | 20.6 | 25 | A |
| ILE | CB | 244 | 210.1 | 107.7 | 21.9 | 24 | A |
| ILE | CG2 | 244 | 210.7 | 106.2 | 21.8 | 24 | A |
| ILE | CG1 | 244 | 211.2 | 108.7 | 22.2 | 21 | A |
| ILE | CD1 | 244 | 211.9 | 108.4 | 23.5 | 20 | A |
| ILE | C | 244 | 208.3 | 107.1 | 20.2 | 25 | A |
| ILE | O | 244 | 208.5 | 106.3 | 19.3 | 25 | A |
| SER | N | 245 | 207.2 | 107.2 | 20.9 | 27 | A |
| SER | CA | 245 | 206.1 | 106.3 | 20.5 | 29 | A |
| SER | CB | 245 | 204.8 | 106.8 | 21.2 | 29 | A |
| SER | OG | 245 | 204.8 | 106.3 | 22.6 | 33 | A |
| SER | C | 245 | 205.7 | 106.3 | 19.1 | 31 | A |
| SER | O | 245 | 205.5 | 105.3 | 18.5 | 32 | A |
| ASN | N | 246 | 205.6 | 107.5 | 18.5 | 33 | A |
| ASN | CA | 246 | 205.2 | 107.6 | 17.1 | 33 | A |
| ASN | CB | 246 | 204.4 | 108.9 | 16.8 | 33 | A |
| ASN | CG | 246 | 203.1 | 108.9 | 17.6 | 33 | A |
| ASN | OD1 | 246 | 203.1 | 109.5 | 18.7 | 33 | A |
| ASN | ND2 | 246 | 202.1 | 108.3 | 17.1 | 33 | A |
| ASN | C | 246 | 206.3 | 107.4 | 16.1 | 34 | A |
| ASN | O | 246 | 206.1 | 107.4 | 14.9 | 34 | A |
| THR | N | 247 | 207.6 | 107.3 | 16.5 | 35 | A |
| THR | CA | 247 | 208.7 | 107.1 | 15.6 | 36 | A |
| THR | CB | 247 | 209.8 | 108.2 | 15.8 | 35 | A |
| THR | OG1 | 247 | 210.2 | 108.3 | 17.2 | 35 | A |
| THR | CG2 | 247 | 209.2 | 109.6 | 15.4 | 35 | A |
| THR | C | 247 | 209.2 | 105.7 | 15.7 | 37 | A |
| THR | O | 247 | 208.8 | 104.8 | 15.0 | 37 | A |
| THR | N | 248 | 210.1 | 105.5 | 16.7 | 37 | A |
| THR | CA | 248 | 210.8 | 104.1 | 16.8 | 37 | A |
| THR | CB | 248 | 212.2 | 104.3 | 17.4 | 37 | A |
| THR | OG1 | 248 | 212.1 | 104.7 | 18.8 | 38 | A |
| THR | CG2 | 248 | 213.0 | 105.3 | 16.7 | 38 | A |
| THR | C | 248 | 210.0 | 103.2 | 17.8 | 38 | A |
| THR | O | 248 | 210.0 | 102.0 | 17.6 | 41 | A |
| GLY | N | 249 | 209.3 | 103.8 | 18.8 | 39 | A |
| GLY | CA | 249 | 208.6 | 103.0 | 19.7 | 38 | A |
| GLY | C | 249 | 209.5 | 102.6 | 20.8 | 39 | A |
| GLY | O | 249 | 210.7 | 102.9 | 20.7 | 38 | A |
| TYR | N | 250 | 209.0 | 101.8 | 21.8 | 40 | A |
| TYR | CA | 250 | 209.9 | 101.3 | 22.9 | 42 | A |
| TYR | CB | 250 | 209.2 | 101.7 | 24.2 | 41 | A |
| TYR | CG | 250 | 209.2 | 103.2 | 24.5 | 41 | A |
| TYR | CD1 | 250 | 208.2 | 103.9 | 23.9 | 40 | A |
| TYR | CE1 | 250 | 208.0 | 105.3 | 24.2 | 41 | A |
| TYR | CD2 | 250 | 210.1 | 103.8 | 25.4 | 41 | A |
| TYR | CE2 | 250 | 210.0 | 105.1 | 25.7 | 41 | A |
| TYR | CZ | 250 | 208.9 | 105.9 | 25.1 | 41 | A |
| TYR | OH | 250 | 208.8 | 107.2 | 25.4 | 41 | A |
| TYR | C | 250 | 210.2 | 99.8 | 22.8 | 43 | A |
| TYR | O | 250 | 210.8 | 99.3 | 23.7 | 43 | A |
| SER | N | 251 | 209.7 | 99.2 | 21.7 | 45 | A |
| SER | CA | 251 | 209.9 | 97.7 | 21.6 | 47 | A |
| SER | CB | 251 | 209.2 | 97.2 | 20.4 | 47 | A |
| SER | OG | 251 | 207.8 | 97.4 | 20.6 | 48 | A |
| SER | C | 251 | 211.4 | 97.6 | 21.3 | 48 | A |
| SER | O | 251 | 212.0 | 96.6 | 21.9 | 49 | A |
| ASP | N | 252 | 212.0 | 98.5 | 20.5 | 49 | A |
| ASP | CA | 252 | 213.4 | 98.5 | 20.2 | 50 | A |
| ASP | CB | 252 | 213.7 | 99.7 | 19.4 | 52 | A |
| ASP | CG | 252 | 215.2 | 99.8 | 18.9 | 53 | A |
| ASP | OD1 | 252 | 216.0 | 98.8 | 19.2 | 55 | A |
| ASP | OD2 | 252 | 215.6 | 100.8 | 18.3 | 54 | A |
| ASP | C | 252 | 214.2 | 98.5 | 21.5 | 50 | A |
| ASP | O | 252 | 214.3 | 99.6 | 22.2 | 49 | A |
| ARG | N | 253 | 214.8 | 97.4 | 21.9 | 49 | A |
| ARG | CA | 253 | 215.6 | 97.2 | 23.1 | 49 | A |
| ARG | CB | 253 | 216.3 | 95.9 | 23.1 | 52 | A |
| ARG | CG | 253 | 215.4 | 94.7 | 23.2 | 55 | A |
| ARG | CD | 253 | 216.2 | 93.4 | 23.1 | 58 | A |
| ARG | NE | 253 | 215.4 | 92.2 | 23.2 | 60 | A |
| ARG | CZ | 253 | 215.7 | 91.0 | 22.6 | 60 | A |
| ARG | NH1 | 253 | 216.7 | 90.9 | 21.7 | 60 | A |
| ARG | NH2 | 253 | 214.9 | 90.0 | 22.8 | 61 | A |
| ARG | C | 253 | 216.6 | 98.3 | 23.3 | 47 | A |
| ARG | O | 253 | 217.0 | 98.6 | 24.4 | 46 | A |
| ALA | N | 254 | 217.2 | 98.8 | 22.2 | 44 | A |
| ALA | CA | 254 | 218.2 | 99.8 | 22.3 | 42 | A |
| ALA | CB | 254 | 219.0 | 99.9 | 21.0 | 42 | A |
| ALA | C | 254 | 217.6 | 101.1 | 22.7 | 41 | A |
| ALA | O | 254 | 218.2 | 101.9 | 23.4 | 41 | A |
| VAL | N | 255 | 216.4 | 101.4 | 22.2 | 41 | A |
| VAL | CA | 255 | 215.7 | 102.6 | 22.5 | 41 | A |
| VAL | CB | 255 | 214.5 | 102.9 | 21.7 | 41 | A |
| VAL | CG1 | 255 | 213.8 | 104.2 | 22.2 | 41 | A |
| VAL | CG2 | 255 | 214.9 | 103.1 | 20.2 | 41 | A |
| VAL | C | 255 | 215.3 | 102.5 | 24.0 | 40 | A |
| VAL | O | 255 | 215.6 | 103.4 | 24.8 | 42 | A |
| LEU | N | 256 | 214.7 | 101.4 | 24.3 | 40 | A |
| LEU | CA | 256 | 214.2 | 101.1 | 25.7 | 39 | A |
| LEU | CB | 256 | 213.7 | 99.7 | 25.7 | 37 | A |
| LEU | CG | 256 | 213.1 | 99.2 | 27.0 | 37 | A |
| LEU | CD1 | 256 | 212.0 | 100.1 | 27.6 | 37 | A |
| LEU | CD2 | 256 | 212.5 | 97.8 | 26.6 | 37 | A |
| LEU | C | 256 | 215.4 | 101.3 | 26.7 | 40 | A |
| LEU | O | 256 | 215.3 | 102.1 | 27.6 | 41 | A |
| GLU | N | 257 | 216.5 | 100.7 | 26.4 | 42 | A |
| GLU | CA | 257 | 217.7 | 100.7 | 27.3 | 42 | A |
| GLU | CB | 257 | 218.8 | 99.8 | 26.7 | 45 | A |
| GLU | CG | 257 | 220.2 | 100.1 | 27.1 | 48 | A |
| GLU | CD | 257 | 220.6 | 99.3 | 28.4 | 51 | A |
| GLU | OE1 | 257 | 220.0 | 99.6 | 29.5 | 52 | A |
| GLU | OE2 | 257 | 221.5 | 98.5 | 28.3 | 52 | A |
| GLU | C | 257 | 218.2 | 102.2 | 27.4 | 42 | A |
| GLU | O | 257 | 218.5 | 102.7 | 28.5 | 42 | A |

TABLE 5-continued

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| ARG | N | 258 | 218.3 | 102.9 | 26.3 | 42 | A |
| ARG | CA | 258 | 218.7 | 104.3 | 26.2 | 41 | A |
| ARG | CB | 258 | 218.7 | 104.8 | 24.8 | 40 | A |
| ARG | CG | 258 | 219.1 | 106.3 | 24.6 | 40 | A |
| ARG | CD | 258 | 218.6 | 106.9 | 23.3 | 40 | A |
| ARG | NE | 258 | 217.2 | 107.2 | 23.3 | 40 | A |
| ARG | CZ | 258 | 216.4 | 107.2 | 22.2 | 40 | A |
| ARG | NH1 | 258 | 216.9 | 106.8 | 21.0 | 41 | A |
| ARG | NH2 | 258 | 215.2 | 107.4 | 22.3 | 40 | A |
| ARG | C | 258 | 217.8 | 105.2 | 27.1 | 41 | A |
| ARG | O | 258 | 218.3 | 106.0 | 27.8 | 42 | A |
| GLU | N | 259 | 216.5 | 104.9 | 27.0 | 41 | A |
| GLU | CA | 259 | 215.5 | 105.7 | 27.7 | 40 | A |
| GLU | CB | 259 | 214.1 | 105.5 | 27.2 | 40 | A |
| GLU | CG | 259 | 213.9 | 106.1 | 25.8 | 40 | A |
| GLU | CD | 259 | 214.0 | 107.6 | 25.8 | 40 | A |
| GLU | OE1 | 259 | 213.4 | 108.3 | 26.7 | 40 | A |
| GLU | OE2 | 259 | 214.8 | 108.2 | 25.0 | 39 | A |
| GLU | C | 259 | 215.5 | 105.3 | 29.2 | 40 | A |
| GLU | O | 259 | 215.4 | 106.2 | 30.0 | 40 | A |
| VAL | N | 260 | 215.7 | 104.1 | 29.5 | 41 | A |
| VAL | CA | 260 | 215.7 | 103.6 | 30.9 | 42 | A |
| VAL | CB | 260 | 215.6 | 102.1 | 31.1 | 41 | A |
| VAL | CG1 | 260 | 215.8 | 101.7 | 32.5 | 41 | A |
| VAL | CG2 | 260 | 214.2 | 101.7 | 30.6 | 41 | A |
| VAL | C | 260 | 217.0 | 104.1 | 31.6 | 44 | A |
| VAL | O | 260 | 216.9 | 104.6 | 32.7 | 44 | A |
| GLN | N | 261 | 218.1 | 104.1 | 30.8 | 45 | A |
| GLN | CA | 261 | 219.3 | 104.6 | 31.4 | 46 | A |
| GLN | CB | 261 | 220.5 | 104.2 | 30.4 | 49 | A |
| GLN | CG | 261 | 221.8 | 104.0 | 31.1 | 52 | A |
| GLN | CD | 261 | 221.9 | 102.7 | 31.8 | 53 | A |
| GLN | OE1 | 261 | 221.9 | 101.6 | 31.2 | 54 | A |
| GLN | NE2 | 261 | 222.0 | 102.8 | 33.2 | 54 | A |
| GLN | C | 261 | 219.2 | 106.1 | 31.6 | 45 | A |
| GLN | O | 261 | 219.5 | 106.6 | 32.7 | 46 | A |
| TYR | N | 262 | 218.9 | 106.8 | 30.5 | 44 | A |
| TYR | CA | 262 | 218.7 | 108.3 | 30.6 | 41 | A |
| TYR | CB | 262 | 218.0 | 108.8 | 29.4 | 41 | A |
| TYR | CG | 262 | 217.5 | 110.2 | 29.6 | 41 | A |
| TYR | CD1 | 262 | 218.4 | 111.3 | 29.6 | 41 | A |
| TYR | CE1 | 262 | 217.9 | 112.6 | 29.8 | 40 | A |
| TYR | CD2 | 262 | 216.1 | 110.5 | 29.7 | 41 | A |
| TYR | CE2 | 262 | 215.7 | 111.8 | 29.9 | 40 | A |
| TYR | CZ | 262 | 216.6 | 112.8 | 30.0 | 40 | A |
| TYR | OH | 262 | 216.2 | 114.1 | 30.1 | 40 | A |
| TYR | C | 262 | 217.9 | 108.7 | 31.8 | 41 | A |
| TYR | O | 262 | 218.2 | 109.6 | 32.5 | 41 | A |
| THR | N | 263 | 216.7 | 108.1 | 31.9 | 41 | A |
| THR | CA | 263 | 215.7 | 108.4 | 32.9 | 41 | A |
| THR | CB | 263 | 214.4 | 107.6 | 32.7 | 40 | A |
| THR | OG1 | 263 | 213.9 | 107.8 | 31.4 | 40 | A |
| THR | CG2 | 263 | 213.4 | 108.0 | 33.7 | 40 | A |
| THR | C | 263 | 216.3 | 108.1 | 34.3 | 41 | A |
| THR | O | 263 | 216.2 | 108.9 | 35.2 | 41 | A |
| LEU | N | 264 | 217.0 | 106.9 | 34.5 | 42 | A |
| LEU | CA | 264 | 217.6 | 106.6 | 35.8 | 43 | A |
| LEU | CB | 264 | 218.2 | 105.2 | 35.7 | 43 | A |
| LEU | CG | 264 | 217.3 | 104.0 | 35.8 | 42 | A |
| LEU | CD1 | 264 | 218.2 | 102.7 | 35.7 | 42 | A |
| LEU | CD2 | 264 | 216.5 | 104.0 | 37.1 | 42 | A |
| LEU | C | 264 | 218.7 | 107.7 | 36.1 | 44 | A |
| LEU | O | 264 | 218.7 | 108.1 | 37.3 | 43 | A |
| GLU | N | 265 | 219.4 | 108.1 | 35.2 | 46 | A |
| GLU | CA | 265 | 220.4 | 109.2 | 35.4 | 48 | A |
| GLU | CB | 265 | 221.3 | 109.4 | 34.2 | 50 | A |
| GLU | CG | 265 | 221.6 | 108.2 | 33.3 | 54 | A |
| GLU | CD | 265 | 222.3 | 107.1 | 34.1 | 57 | A |
| GLU | OE1 | 265 | 221.7 | 106.0 | 34.4 | 58 | A |
| GLU | OE2 | 265 | 223.5 | 107.2 | 34.3 | 58 | A |
| GLU | C | 265 | 219.7 | 110.4 | 35.9 | 48 | A |
| GLU | O | 265 | 220.2 | 111.1 | 36.8 | 49 | A |

TABLE 5-continued

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| MET | N | 266 | 218.6 | 110.7 | 35.3 | 47 | A |
| MET | CA | 266 | 217.8 | 111.9 | 35.7 | 46 | A |
| MET | CB | 266 | 216.6 | 112.1 | 34.8 | 46 | A |
| MET | CG | 266 | 217.0 | 112.4 | 33.3 | 45 | A |
| MET | SD | 266 | 218.4 | 113.5 | 33.4 | 44 | A |
| MET | CE | 266 | 217.7 | 115.0 | 32.8 | 46 | A |
| MET | C | 266 | 217.3 | 111.7 | 37.1 | 47 | A |
| MET | O | 266 | 217.2 | 112.7 | 37.9 | 47 | A |
| ILE | N | 267 | 216.9 | 110.5 | 37.4 | 47 | A |
| ILE | CA | 267 | 216.4 | 110.2 | 38.8 | 48 | A |
| ILE | CB | 267 | 215.9 | 108.7 | 38.9 | 47 | A |
| ILE | CG2 | 267 | 215.4 | 108.4 | 40.3 | 46 | A |
| ILE | CG1 | 267 | 214.7 | 108.5 | 37.9 | 46 | A |
| ILE | CD1 | 267 | 214.2 | 107.1 | 37.9 | 46 | A |
| ILE | C | 267 | 217.5 | 110.5 | 39.8 | 49 | A |
| ILE | O | 267 | 217.3 | 111.2 | 40.7 | 50 | A |
| LYS | N | 268 | 218.7 | 109.9 | 39.5 | 50 | A |
| LYS | CA | 268 | 219.8 | 110.2 | 40.3 | 51 | A |
| LYS | CB | 268 | 221.1 | 109.5 | 39.7 | 52 | A |
| LYS | CG | 268 | 221.0 | 108.0 | 39.8 | 54 | A |
| LYS | CD | 268 | 222.1 | 107.4 | 38.9 | 56 | A |
| LYS | CE | 268 | 221.6 | 105.9 | 38.5 | 57 | A |
| LYS | NZ | 268 | 222.5 | 105.3 | 37.5 | 58 | A |
| LYS | C | 268 | 220.0 | 111.6 | 40.6 | 51 | A |
| LYS | O | 268 | 220.0 | 112.0 | 41.8 | 52 | A |
| LEU | N | 269 | 220.1 | 112.5 | 39.6 | 50 | A |
| LEU | CA | 269 | 220.3 | 113.9 | 39.8 | 49 | A |
| LEU | CB | 269 | 220.3 | 114.7 | 38.5 | 48 | A |
| LEU | CG | 269 | 221.2 | 114.3 | 37.3 | 48 | A |
| LEU | CD1 | 269 | 221.2 | 115.5 | 36.4 | 49 | A |
| LEU | CD2 | 269 | 222.6 | 113.9 | 37.7 | 48 | A |
| LEU | C | 269 | 219.1 | 114.6 | 40.6 | 48 | A |
| LEU | O | 269 | 219.4 | 115.4 | 41.5 | 49 | A |
| VAL | N | 270 | 217.9 | 114.2 | 40.3 | 46 | A |
| VAL | CA | 270 | 216.8 | 114.8 | 41.0 | 44 | A |
| VAL | CB | 270 | 216.1 | 115.9 | 40.1 | 42 | A |
| VAL | CG1 | 270 | 215.2 | 116.8 | 40.9 | 42 | A |
| VAL | CG2 | 270 | 217.1 | 116.8 | 39.5 | 41 | A |
| VAL | C | 270 | 215.8 | 113.8 | 41.5 | 44 | A |
| VAL | O | 270 | 214.7 | 113.7 | 41.0 | 44 | A |
| PRO | N | 271 | 216.2 | 113.0 | 42.5 | 44 | A |
| PRO | CD | 271 | 217.4 | 113.2 | 43.2 | 43 | A |
| PRO | CA | 271 | 215.4 | 111.9 | 43.1 | 43 | A |
| PRO | CB | 271 | 216.3 | 111.6 | 44.4 | 43 | A |
| PRO | CG | 271 | 217.6 | 111.8 | 43.9 | 43 | A |
| PRO | C | 271 | 214.0 | 112.1 | 43.5 | 44 | A |
| PRO | O | 271 | 213.2 | 111.2 | 43.6 | 44 | A |
| HIS | N | 272 | 213.7 | 113.4 | 43.8 | 44 | A |
| HIS | CA | 272 | 212.3 | 113.7 | 44.2 | 44 | A |
| HIS | CB | 272 | 212.4 | 114.6 | 45.4 | 46 | A |
| HIS | CG | 272 | 212.8 | 113.9 | 46.7 | 47 | A |
| HIS | CD2 | 272 | 213.9 | 113.8 | 47.3 | 47 | A |
| HIS | ND1 | 272 | 211.8 | 113.2 | 47.5 | 48 | A |
| HIS | CE1 | 272 | 212.4 | 112.7 | 48.5 | 48 | A |
| HIS | NE2 | 272 | 213.7 | 113.0 | 48.5 | 48 | A |
| HIS | C | 272 | 211.5 | 114.4 | 43.1 | 43 | A |
| HIS | O | 272 | 210.5 | 115.1 | 43.4 | 43 | A |
| ASN | N | 273 | 211.9 | 114.1 | 41.8 | 41 | A |
| ASN | CA | 273 | 211.2 | 114.6 | 40.7 | 39 | A |
| ASN | CB | 273 | 212.2 | 115.0 | 39.5 | 38 | A |
| ASN | CG | 273 | 211.5 | 115.4 | 38.2 | 36 | A |
| ASN | OD1 | 273 | 210.3 | 115.7 | 38.2 | 35 | A |
| ASN | ND2 | 273 | 212.2 | 115.4 | 37.1 | 36 | A |
| ASN | C | 273 | 210.4 | 113.5 | 40.2 | 37 | A |
| ASN | O | 273 | 210.8 | 112.5 | 39.7 | 37 | A |
| GLU | N | 274 | 209.1 | 113.7 | 40.4 | 36 | A |
| GLU | CA | 274 | 208.1 | 112.7 | 40.0 | 35 | A |
| GLU | CB | 274 | 206.8 | 113.1 | 40.5 | 35 | A |
| GLU | CG | 274 | 205.7 | 112.1 | 40.5 | 36 | A |
| GLU | CD | 274 | 204.4 | 112.6 | 41.0 | 38 | A |
| GLU | OE1 | 274 | 203.4 | 112.2 | 40.5 | 39 | A |
| GLU | OE2 | 274 | 204.4 | 113.4 | 42.0 | 39 | A |

TABLE 5-continued

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| GLU | C | 274 | 207.9 | 112.4 | 38.5 | 34 | A |
| GLU | O | 274 | 207.5 | 111.3 | 38.2 | 36 | A |
| SER | N | 275 | 208.3 | 113.4 | 37.7 | 34 | A |
| SER | CA | 275 | 208.1 | 113.2 | 36.2 | 33 | A |
| SER | CB | 275 | 208.3 | 114.5 | 35.5 | 33 | A |
| SER | OG | 275 | 207.3 | 115.4 | 35.9 | 32 | A |
| SER | C | 275 | 209.0 | 112.1 | 35.7 | 33 | A |
| SER | O | 275 | 208.6 | 111.2 | 34.9 | 33 | A |
| ALA | N | 276 | 210.3 | 112.1 | 36.1 | 33 | A |
| ALA | CA | 276 | 211.2 | 111.1 | 35.6 | 33 | A |
| ALA | CB | 276 | 212.6 | 111.4 | 36.1 | 33 | A |
| ALA | C | 276 | 210.8 | 109.7 | 36.2 | 33 | A |
| ALA | O | 276 | 211.0 | 108.7 | 35.5 | 32 | A |
| TRP | N | 277 | 210.1 | 109.7 | 37.3 | 34 | A |
| TRP | CA | 277 | 209.6 | 108.5 | 37.9 | 33 | A |
| TRP | CB | 277 | 209.2 | 108.8 | 39.4 | 34 | A |
| TRP | CG | 277 | 210.4 | 108.7 | 40.2 | 35 | A |
| TRP | CD2 | 277 | 211.1 | 107.5 | 40.6 | 36 | A |
| TRP | CE2 | 277 | 212.1 | 107.8 | 41.5 | 36 | A |
| TRP | CE3 | 277 | 211.0 | 106.2 | 40.2 | 36 | A |
| TRP | CD1 | 277 | 211.0 | 109.7 | 40.9 | 36 | A |
| TRP | NE1 | 277 | 212.0 | 109.2 | 41.7 | 37 | A |
| TRP | CZ2 | 277 | 213.0 | 106.9 | 42.0 | 36 | A |
| TRP | CZ3 | 277 | 211.8 | 105.2 | 40.7 | 35 | A |
| TRP | CH2 | 277 | 212.8 | 105.6 | 41.6 | 36 | A |
| TRP | C | 277 | 208.3 | 108.0 | 37.2 | 33 | A |
| TRP | O | 277 | 208.3 | 106.8 | 37.0 | 34 | A |
| ASN | N | 278 | 207.4 | 108.8 | 36.9 | 32 | A |
| ASN | CA | 278 | 206.2 | 108.4 | 36.2 | 32 | A |
| ASN | CB | 278 | 205.2 | 109.6 | 36.1 | 33 | A |
| ASN | CG | 278 | 204.8 | 110.0 | 37.5 | 33 | A |
| ASN | OD1 | 278 | 205.0 | 109.3 | 38.5 | 33 | A |
| ASN | ND2 | 278 | 204.1 | 111.1 | 37.6 | 34 | A |
| ASN | C | 278 | 206.6 | 108.0 | 34.8 | 32 | A |
| ASN | O | 278 | 205.9 | 107.2 | 34.2 | 32 | A |
| TYR | N | 279 | 207.6 | 108.5 | 34.3 | 30 | A |
| TYR | CA | 279 | 208.1 | 108.2 | 32.9 | 31 | A |
| TYR | CB | 279 | 209.1 | 109.1 | 32.4 | 30 | A |
| TYR | CG | 279 | 209.6 | 108.9 | 31.0 | 30 | A |
| TYR | CD1 | 279 | 208.7 | 109.2 | 30.0 | 31 | A |
| TYR | CE1 | 279 | 209.1 | 109.0 | 28.7 | 31 | A |
| TYR | CD2 | 279 | 210.8 | 108.4 | 30.7 | 31 | A |
| TYR | CE2 | 279 | 211.2 | .08.2 | 29.4 | 31 | A |
| TYR | CZ | 279 | 210.4 | 108.5 | 28.4 | 31 | A |
| TYR | OH | 279 | 210.8 | 108.3 | 27.1 | 32 | A |
| TYR | C | 279 | 208.7 | 106.8 | 33.0 | 31 | A |
| TYR | O | 279 | 208.3 | 105.9 | 32.1 | 33 | A |
| LEU | N | 280 | 209.5 | 106.5 | 33.9 | 32 | A |
| LEU | CA | 280 | 210.2 | 105.2 | 34.1 | 33 | A |
| LEU | CB | 280 | 211.0 | 105.2 | 35.3 | 32 | A |
| LEU | CG | 280 | 211.9 | 103.9 | 35.6 | 32 | A |
| LEU | CD1 | 280 | 212.8 | 103.6 | 34.4 | 30 | A |
| LEU | CD2 | 280 | 212.6 | 104.0 | 36.9 | 30 | A |
| LEU | C | 280 | 209.1 | 104.1 | 34.2 | 35 | A |
| LEU | O | 280 | 209.2 | 103.1 | 33.5 | 35 | A |
| LYS | N | 281 | 208.1 | 104.4 | 35.0 | 37 | A |
| LYS | CA | 281 | 207.0 | 103.4 | 35.2 | 38 | A |
| LYS | CB | 281 | 206.1 | 103.9 | 36.3 | 38 | A |
| LYS | CG | 281 | 205.2 | 102.8 | 36.8 | 38 | A |
| LYS | CD | 281 | 204.6 | 103.3 | 38.2 | 39 | A |
| LYS | CE | 281 | 203.8 | 104.5 | 38.0 | 40 | A |
| LYS | NZ | 281 | 203.5 | 105.2 | 39.3 | 41 | A |
| LYS | C | 281 | 206.3 | 103.3 | 33.9 | 40 | A |
| LYS | O | 281 | 206.0 | 102.2 | 33.4 | 41 | A |
| GLY | N | 282 | 206.0 | 104.4 | 33.2 | 40 | A |
| GLY | CA | 282 | 205.3 | 104.4 | 32.0 | 40 | A |
| GLY | C | 282 | 205.9 | 103.6 | 30.8 | 41 | A |
| GLY | O | 282 | 205.1 | 103.0 | 30.1 | 42 | A |
| ILE | N | 283 | 207.2 | 103.6 | 30.7 | 42 | A |
| ILE | CA | 283 | 207.8 | 102.9 | 29.6 | 43 | A |
| ILE | CB | 283 | 209.1 | 103.6 | 29.1 | 42 | A |
| ILE | CG2 | 283 | 208.8 | 105.0 | 28.7 | 42 | A |

TABLE 5-continued

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| ILE | CG1 | 283 | 210.2 | 103.6 | 30.2 | 41 | A |
| ILE | CD1 | 283 | 211.5 | 104.2 | 29.7 | 39 | A |
| ILE | C | 283 | 208.1 | 101.4 | 29.8 | 46 | A |
| ILE | O | 283 | 208.2 | 100.6 | 28.9 | 47 | A |
| LEU | N | 284 | 208.2 | 101.0 | 31.1 | 48 | A |
| LEU | CA | 284 | 208.4 | 99.6 | 31.4 | 49 | A |
| LEU | CB | 284 | 209.4 | 99.5 | 32.6 | 49 | A |
| LEU | CG | 284 | 210.8 | 100.0 | 32.3 | 48 | A |
| LEU | CD1 | 284 | 211.7 | 99.8 | 33.5 | 49 | A |
| LEU | CD2 | 284 | 211.4 | 99.4 | 31.1 | 48 | A |
| LEU | C | 284 | 207.1 | 98.9 | 31.9 | 50 | A |
| LEU | O | 284 | 207.0 | 97.7 | 31.7 | 49 | A |
| GLN | N | 285 | 206.2 | 99.6 | 32.4 | 53 | A |
| GLN | CA | 285 | 204.9 | 99.1 | 32.9 | 56 | A |
| GLN | CB | 285 | 204.0 | 100.1 | 33.6 | 58 | A |
| GLN | CG | 285 | 203.4 | 101.1 | 32.5 | 60 | A |
| GLN | CD | 285 | 202.2 | 101.8 | 33.0 | 62 | A |
| GLN | OE1 | 285 | 201.3 | 102.1 | 32.2 | 62 | A |
| GLN | NE2 | 285 | 202.2 | 102.2 | 34.3 | 62 | A |
| GLN | C | 285 | 204.1 | 98.4 | 31.8 | 58 | A |
| GLN | O | 285 | 203.1 | 97.7 | 32.1 | 59 | A |
| ASP | N | 286 | 204.4 | 98.8 | 30.5 | 60 | A |
| ASP | CA | 286 | 203.7 | 98.2 | 29.5 | 62 | A |
| ASP | CB | 286 | 203.3 | 99.2 | 28.4 | 64 | A |
| ASP | CG | 286 | 201.8 | 99.6 | 28.4 | 66 | A |
| ASP | OD1 | 286 | 201.2 | 99.8 | 27.3 | 67 | A |
| ASP | OD2 | 286 | 201.2 | 99.7 | 29.5 | 67 | A |
| ASP | C | 286 | 204.3 | 96.9 | 28.9 | 61 | A |
| ASP | O | 286 | 204.5 | 96.9 | 27.6 | 62 | A |
| ARG | N | 287 | 204.7 | 96.0 | 29.7 | 60 | A |
| ARG | CA | 287 | 205.3 | 94.7 | 29.4 | 59 | A |
| ARG | CB | 287 | 206.7 | 94.8 | 28.8 | 60 | A |
| ARG | CG | 287 | 207.3 | 93.5 | 28.5 | 61 | A |
| ARG | CD | 287 | 208.8 | 93.5 | 28.2 | 63 | A |
| ARG | NE | 287 | 209.4 | 92.2 | 28.4 | 64 | A |
| ARG | CZ | 287 | 210.3 | 91.6 | 27.6 | 65 | A |
| ARG | NH1 | 287 | 210.6 | 92.2 | 26.4 | 65 | A |
| ARG | NH2 | 287 | 210.7 | 90.4 | 27.8 | 65 | A |
| ARG | C | 287 | 205.4 | 94.0 | 30.7 | 57 | A |
| ARG | O | 287 | 205.2 | 92.7 | 30.8 | 58 | A |
| GLY | N | 288 | 205.6 | 94.7 | 31.8 | 55 | A |
| GLY | CA | 288 | 205.7 | 94.1 | 33.1 | 53 | A |
| GLY | C | 288 | 207.0 | 94.5 | 33.8 | 52 | A |
| GLY | O | 288 | 208.1 | 94.2 | 33.3 | 52 | A |
| LEU | N | 289 | 206.8 | 95.2 | 34.9 | 51 | A |
| LEU | CA | 289 | 208.0 | 95.6 | 35.7 | 50 | A |
| LEU | CB | 289 | 207.6 | 96.4 | 36.9 | 49 | A |
| LEU | CG | 289 | 207.8 | 97.9 | 36.9 | 47 | A |
| LEU | CD1 | 289 | 207.6 | 98.5 | 35.5 | 47 | A |
| LEU | CD2 | 289 | 206.7 | 98.5 | 37.8 | 47 | A |
| LEU | C | 289 | 208.8 | 94.4 | 36.1 | 50 | A |
| LEU | O | 289 | 210.0 | 94.4 | 36.3 | 51 | A |
| SER | N | 290 | 208.1 | 93.2 | 36.3 | 50 | A |
| SER | CA | 290 | 208.7 | 92.0 | 36.7 | 51 | A |
| SER | CB | 290 | 207.7 | 91.0 | 37.3 | 51 | A |
| SER | OG | 290 | 206.7 | 90.7 | 36.3 | 52 | A |
| SER | C | 290 | 209.6 | 91.3 | 35.7 | 51 | A |
| SER | O | 290 | 210.3 | 90.4 | 36.0 | 51 | A |
| ARG | N | 291 | 209.5 | 91.8 | 34.4 | 51 | A |
| ARG | CA | 291 | 210.3 | 91.2 | 33.3 | 51 | A |
| ARG | CB | 291 | 209.5 | 91.3 | 32.0 | 53 | A |
| ARG | CG | 291 | 208.6 | 90.2 | 31.7 | 56 | A |
| ARG | CD | 291 | 207.9 | 90.3 | 30.4 | 60 | A |
| ARG | NE | 291 | 207.6 | 89.0 | 29.8 | 64 | A |
| ARG | CZ | 291 | 207.6 | 88.8 | 28.5 | 66 | A |
| ARG | NH1 | 291 | 207.3 | 87.6 | 28.0 | 67 | A |
| ARG | NH2 | 291 | 207.8 | 89.8 | 27.6 | 66 | A |
| ARG | C | 291 | 211.6 | 91.8 | 33.2 | 49 | A |
| ARG | O | 291 | 212.4 | 91.6 | 32.3 | 48 | A |
| TYR | N | 292 | 212.0 | 92.7 | 34.2 | 48 | A |
| TYR | CA | 292 | 213.3 | 93.3 | 34.3 | 46 | A |
| TYR | CB | 292 | 213.1 | 94.8 | 34.1 | 44 | A |

TABLE 5-continued

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| TYR | CG | 292 | 212.4 | 95.1 | 32.8 | 42 | A |
| TYR | CD1 | 292 | 211.0 | 95.5 | 32.7 | 42 | A |
| TYR | CE1 | 292 | 210.4 | 95.7 | 31.5 | 41 | A |
| TYR | CD2 | 292 | 213.1 | 94.9 | 31.6 | 42 | A |
| TYR | CE2 | 292 | 212.4 | 95.0 | 30.4 | 41 | A |
| TYR | CZ | 292 | 211.1 | 95.4 | 30.3 | 41 | A |
| TYR | OH | 292 | 210.5 | 95.6 | 29.1 | 40 | A |
| TYR | C | 292 | 213.8 | 93.0 | 35.7 | 47 | A |
| TYR | O | 292 | 213.7 | 93.8 | 36.7 | 47 | A |
| PRO | N | 293 | 214.5 | 91.9 | 35.9 | 47 | A |
| PRO | CD | 293 | 214.8 | 90.9 | 34.8 | 47 | A |
| PRO | CA | 293 | 215.0 | 91.4 | 37.1 | 48 | A |
| PRO | CB | 293 | 215.6 | 90.0 | 36.7 | 47 | A |
| PRO | CG | 293 | 215.9 | 90.2 | 35.3 | 46 | A |
| PRO | C | 293 | 216.1 | 92.3 | 37.7 | 49 | A |
| PRO | O | 293 | 216.2 | 92.4 | 38.9 | 50 | A |
| ASN | N | 294 | 217.0 | 92.9 | 36.9 | 50 | A |
| ASN | CA | 294 | 218.0 | 93.8 | 37.4 | 51 | A |
| ASN | CB | 294 | 219.0 | 94.2 | 36.2 | 50 | A |
| ASN | CG | 294 | 219.6 | 93.0 | 35.5 | 50 | A |
| ASN | OD1 | 294 | 219.4 | 92.8 | 34.3 | 51 | A |
| ASN | ND2 | 294 | 220.3 | 92.2 | 36.3 | 50 | A |
| ASN | C | 294 | 217.5 | 95.1 | 38.0 | 52 | A |
| ASN | O | 294 | 218.0 | 95.5 | 39.0 | 52 | A |
| LEU | N | 295 | 216.4 | 95.6 | 37.4 | 54 | A |
| LEU | CA | 295 | 215.8 | 96.8 | 37.8 | 54 | A |
| LEU | CB | 295 | 214.5 | 97.0 | 37.1 | 54 | A |
| LEU | CG | 295 | 213.7 | 98.3 | 37.2 | 54 | A |
| LEU | CD1 | 295 | 214.5 | 99.5 | 36.7 | 54 | A |
| LEU | CD2 | 295 | 212.4 | 98.2 | 36.5 | 54 | A |
| LEU | C | 295 | 215.6 | 97.0 | 39.3 | 55 | A |
| LEU | O | 295 | 216.0 | 98.0 | 39.9 | 55 | A |
| LEU | N | 296 | 215.0 | 95.9 | 39.9 | 55 | A |
| LEU | CA | 296 | 214.8 | 96.0 | 41.3 | 56 | A |
| LEU | CB | 296 | 214.2 | 94.6 | 41.8 | 55 | A |
| LEU | CG | 296 | 214.0 | 94.5 | 43.3 | 54 | A |
| LEU | CD1 | 296 | 213.1 | 95.6 | 43.8 | 54 | A |
| LEU | CD2 | 296 | 213.3 | 93.2 | 43.6 | 54 | A |
| LEU | C | 296 | 216.1 | 96.2 | 42.1 | 58 | A |
| LEU | O | 296 | 216.1 | 97.1 | 43.0 | 57 | A |
| ASN | N | 297 | 217.2 | 95.6 | 41.7 | 61 | A |
| ASN | CA | 297 | 218.5 | 95.7 | 42.3 | 64 | A |
| ASN | CB | 297 | 219.6 | 94.9 | 41.6 | 66 | A |
| ASN | CG | 297 | 219.3 | 93.5 | 41.4 | 67 | A |
| ASN | OD1 | 297 | 218.1 | 93.0 | 41.5 | 68 | A |
| ASN | ND2 | 297 | 220.3 | 92.7 | 41.0 | 68 | A |
| ASN | C | 297 | 218.9 | 97.2 | 42.3 | 64 | A |
| ASN | O | 297 | 218.8 | 97.9 | 43.3 | 63 | A |
| GLN | N | 298 | 219.2 | 97.7 | 41.1 | 65 | A |
| GLN | CA | 298 | 219.6 | 99.0 | 40.9 | 66 | A |
| GLN | CB | 298 | 219.5 | 99.4 | 39.4 | 66 | A |
| GLN | CG | 298 | 219.0 | 98.3 | 38.4 | 67 | A |
| GLN | CD | 298 | 220.2 | 97.4 | 38.0 | 67 | A |
| GLN | OE1 | 298 | 220.6 | 96.6 | 38.8 | 68 | A |
| GLN | NE2 | 298 | 220.6 | 97.5 | 36.7 | 66 | A |
| GLN | C | 298 | 218.8 | 100.0 | 41.7 | 67 | A |
| GLN | O | 298 | 219.4 | 101.0 | 42.2 | 68 | A |
| LEU | N | 299 | 217.5 | 99.8 | 41.9 | 68 | A |
| LEU | CA | 299 | 216.7 | 100.7 | 42.7 | 69 | A |
| LEU | CB | 299 | 215.2 | 100.5 | 42.4 | 69 | A |
| LEU | CG | 299 | 214.5 | 101.0 | 41.1 | 68 | A |
| LEU | CD1 | 299 | 213.0 | 100.9 | 41.3 | 68 | A |
| LEU | CD2 | 299 | 214.8 | 102.5 | 40.9 | 68 | A |
| LEU | C | 299 | 216.9 | 100.6 | 44.2 | 71 | A |
| LEU | O | 299 | 217.1 | 101.5 | 44.9 | 70 | A |
| LEU | N | 300 | 216.9 | 99.3 | 44.6 | 73 | A |
| LEU | CA | 300 | 217.1 | 99.0 | 46.0 | 74 | A |
| LEU | CB | 300 | 217.2 | 97.4 | 46.1 | 74 | A |
| LEU | CG | 300 | 216.1 | 96.7 | 46.8 | 75 | A |
| LEU | CD1 | 300 | 214.7 | 97.3 | 46.3 | 75 | A |
| LEU | CD2 | 300 | 216.1 | 95.2 | 46.4 | 75 | A |
| LEU | C | 300 | 218.4 | 99.6 | 46.5 | 75 | A |
| LEU | O | 300 | 218.5 | 100.1 | 47.6 | 76 | A |
| ASP | N | 301 | 219.4 | 99.6 | 45.6 | 76 | A |
| ASP | CA | 301 | 220.7 | 100.2 | 45.9 | 78 | A |
| ASP | CB | 301 | 221.7 | 99.9 | 44.8 | 78 | A |
| ASP | CG | 301 | 221.9 | 98.4 | 44.5 | 79 | A |
| ASP | OD1 | 301 | 221.4 | 97.6 | 45.3 | 79 | A |
| ASP | OD2 | 301 | 222.6 | 98.1 | 43.5 | 78 | A |
| ASP | C | 301 | 220.6 | 101.7 | 46.2 | 78 | A |
| ASP | O | 301 | 221.2 | 102.2 | 47.2 | 79 | A |
| LEU | N | 302 | 219.8 | 102.4 | 45.4 | 78 | A |
| LEU | CA | 302 | 219.6 | 103.9 | 45.6 | 79 | A |
| LEU | CB | 302 | 219.0 | 104.5 | 44.4 | 79 | A |
| LEU | CG | 302 | 219.9 | 104.6 | 43.2 | 80 | A |
| LEU | CD1 | 302 | 219.2 | 105.5 | 42.1 | 80 | A |
| LEU | CD2 | 302 | 221.2 | 105.3 | 43.5 | 80 | A |
| LEU | C | 302 | 218.9 | 104.2 | 46.9 | 79 | A |
| LEU | O | 302 | 218.8 | 105.4 | 47.3 | 78 | A |
| GLN | N | 303 | 218.3 | 103.2 | 47.5 | 79 | A |
| GLN | CA | 303 | 217.5 | 103.3 | 48.8 | 80 | A |
| GLN | CB | 303 | 217.4 | 102.0 | 49.5 | 80 | A |
| GLN | CG | 303 | 216.1 | 101.2 | 49.1 | 80 | A |
| GLN | CD | 303 | 214.9 | 101.8 | 49.8 | 80 | A |
| GLN | OE1 | 303 | 214.7 | 103.0 | 49.9 | 80 | A |
| GLN | NE2 | 303 | 214.1 | 100.9 | 50.4 | 80 | A |
| GLN | C | 303 | 218.1 | 104.4 | 49.8 | 81 | A |
| GLN | O | 303 | 217.4 | 105.2 | 50.3 | 81 | A |
| PRO | N | 304 | 219.4 | 104.3 | 50.1 | 81 | A |
| PRO | CD | 304 | 220.4 | 103.2 | 49.9 | 81 | A |
| PRO | CA | 304 | 219.9 | 105.3 | 51.0 | 81 | A |
| PRO | CB | 304 | 221.0 | 104.5 | 51.8 | 81 | A |
| PRO | CG | 304 | 221.6 | 103.6 | 50.6 | 81 | A |
| PRO | C | 304 | 220.5 | 106.5 | 50.4 | 81 | A |
| PRO | O | 304 | 220.4 | 107.6 | 51.0 | 82 | A |
| SER | N | 305 | 221.2 | 106.4 | 49.2 | 81 | A |
| SER | CA | 305 | 221.8 | 107.6 | 48.6 | 81 | A |
| SER | CB | 305 | 223.0 | 107.2 | 47.8 | 81 | A |
| SER | OG | 305 | 222.7 | 106.3 | 46.7 | 81 | A |
| SER | C | 305 | 220.9 | 108.5 | 47.7 | 80 | A |
| SER | O | 305 | 221.1 | 109.7 | 47.6 | 80 | A |
| HIS | N | 306 | 219.8 | 107.9 | 47.1 | 79 | A |
| HIS | CA | 306 | 218.9 | 108.7 | 46.3 | 78 | A |
| HIS | CB | 306 | 219.2 | 108.4 | 44.8 | 79 | A |
| HIS | CG | 306 | 220.5 | 108.8 | 44.4 | 80 | A |
| HIS | CD2 | 306 | 221.3 | 108.4 | 43.3 | 81 | A |
| HIS | ND1 | 306 | 221.3 | 109.7 | 45.0 | 81 | A |
| HIS | CE1 | 306 | 222.5 | 109.9 | 44.4 | 81 | A |
| HIS | NE2 | 306 | 222.5 | 109.1 | 43.4 | 81 | A |
| HIS | C | 306 | 217.5 | 108.3 | 46.6 | 77 | A |
| HIS | O | 306 | 216.7 | 108.0 | 45.7 | 78 | A |
| SER | N | 307 | 217.1 | 108.3 | 47.9 | 76 | A |
| SER | CA | 307 | 215.8 | 108.0 | 48.3 | 74 | A |
| SER | CB | 307 | 215.8 | 107.6 | 49.8 | 74 | A |
| SER | OG | 307 | 214.6 | 106.8 | 50.2 | 74 | A |
| SER | C | 307 | 214.7 | 109.1 | 48.1 | 72 | A |
| SER | O | 307 | 215.0 | 110.3 | 48.0 | 72 | A |
| SER | N | 308 | 213.4 | 108.7 | 48.0 | 69 | A |
| SER | CA | 308 | 212.3 | 109.5 | 47.8 | 66 | A |
| SER | CB | 308 | 212.3 | 110.2 | 46.4 | 66 | A |
| SER | OG | 308 | 212.2 | 109.2 | 45.4 | 66 | A |
| SER | C | 308 | 211.1 | 108.6 | 47.9 | 64 | A |
| SER | O | 308 | 211.2 | 107.4 | 47.5 | 65 | A |
| PRO | N | 309 | 210.0 | 109.1 | 48.4 | 62 | A |
| PRO | CD | 309 | 209.6 | 110.4 | 48.9 | 62 | A |
| PRO | CA | 309 | 208.8 | 108.1 | 48.5 | 60 | A |
| PRO | CB | 309 | 207.7 | 109.0 | 49.1 | 61 | A |
| PRO | CG | 309 | 208.1 | 110.4 | 48.7 | 61 | A |
| PRO | C | 309 | 208.4 | 107.6 | 47.1 | 59 | A |
| PRO | O | 309 | 207.6 | 106.7 | 47.1 | 60 | A |
| TYR | N | 310 | 209.1 | 108.0 | 46.1 | 57 | A |
| TYR | CA | 310 | 208.8 | 107.6 | 44.7 | 54 | A |
| TYR | CB | 310 | 209.3 | 108.6 | 43.7 | 55 | A |
| TYR | CG | 310 | 208.8 | 110.0 | 44.0 | 54 | A |

TABLE 5-continued

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| TYR | CD1 | 310 | 209.7 | 111.0 | 44.4 | 55 | A |
| TYR | CE1 | 310 | 209.2 | 112.3 | 44.7 | 55 | A |
| TYR | CD2 | 310 | 207.4 | 110.3 | 43.9 | 54 | A |
| TYR | CE2 | 310 | 207.0 | 111.6 | 44.3 | 55 | A |
| TYR | CZ | 310 | 207.9 | 112.5 | 44.7 | 56 | A |
| TYR | OH | 310 | 207.4 | 113.8 | 45.1 | 57 | A |
| TYR | C | 310 | 209.5 | 106.2 | 44.5 | 53 | A |
| TYR | O | 310 | 209.0 | 105.3 | 43.9 | 53 | A |
| LEU | N | 311 | 210.7 | 106.1 | 45.1 | 50 | A |
| LEU | CA | 311 | 211.5 | 104.9 | 45.0 | 48 | A |
| LEu | CB | 311 | 212.8 | 105.1 | 45.7 | 48 | A |
| LEU | CG | 311 | 213.8 | 103.9 | 45.8 | 48 | A |
| LEU | CD1 | 311 | 214.1 | 103.3 | 44.5 | 48 | A |
| LEU | CD2 | 311 | 215.1 | 104.4 | 46.4 | 48 | A |
| LEU | C | 311 | 210.7 | 103.8 | 45.8 | 48 | A |
| LEU | O | 311 | 210.5 | 102.7 | 45.3 | 46 | A |
| ILE | N | 312 | 210.2 | 104.2 | 46.9 | 47 | A |
| ILE | CA | 312 | 209.4 | 103.3 | 47.8 | 47 | A |
| ILE | CB | 312 | 208.9 | 103.9 | 49.1 | 48 | A |
| ILE | CG2 | 312 | 208.2 | 102.9 | 50.0 | 48 | A |
| ILE | CG1 | 312 | 210.1 | 104.4 | 49.9 | 48 | A |
| ILE | CD1 | 312 | 211.1 | 103.3 | 50.3 | 48 | A |
| ILE | C | 312 | 208.2 | 102.8 | 47.0 | 47 | A |
| ILE | O | 312 | 207.9 | 101.6 | 46.9 | 49 | A |
| ALA | N | 313 | 207.4 | 103.7 | 46.4 | 47 | A |
| ALA | CA | 313 | 206.2 | 103.3 | 45.6 | 45 | A |
| ALA | CB | 313 | 205.4 | 104.5 | 45.2 | 45 | A |
| ALA | C | 313 | 206.6 | 102.5 | 44.4 | 43 | A |
| ALA | O | 313 | 205.8 | 101.7 | 43.9 | 43 | A |
| PHE | N | 314 | 207.8 | 102.7 | 43.8 | 42 | A |
| PHE | CA | 314 | 208.2 | 101.9 | 42.6 | 42 | A |
| PHE | CB | 314 | 209.4 | 102.5 | 42.0 | 42 | A |
| PHE | CG | 314 | 209.5 | 102.3 | 40.5 | 42 | A |
| PHE | CD1 | 314 | 209.2 | 103.3 | 39.6 | 42 | A |
| PHE | CD2 | 314 | 209.8 | 101.0 | 40.0 | 42 | A |
| PHE | CE1 | 314 | 209.2 | 103.1 | 38.2 | 42 | A |
| PHE | CE2 | 314 | 209.9 | 100.8 | 38.6 | 42 | A |
| PHE | CZ | 314 | 209.6 | 101.8 | 37.7 | 42 | A |
| PHE | C | 314 | 208.4 | 100.4 | 43.0 | 41 | A |
| PHE | O | 314 | 208.0 | 99.5 | 42.3 | 42 | A |
| LEU | N | 315 | 209.1 | 100.2 | 44.1 | 41 | A |
| LEU | CA | 315 | 209.4 | 98.8 | 44.6 | 39 | A |
| LEU | CB | 315 | 210.2 | 98.8 | 45.9 | 39 | A |
| LEU | CG | 315 | 211.4 | 99.7 | 45.9 | 40 | A |
| LEU | CD1 | 315 | 211.9 | 99.8 | 47.3 | 40 | A |
| LEU | CD2 | 315 | 212.4 | 99.2 | 44.9 | 40 | A |
| LEU | C | 315 | 208.1 | 98.1 | 44.8 | 38 | A |
| LEU | O | 315 | 207.9 | 96.9 | 44.5 | 39 | A |
| VAL | N | 316 | 207.1 | 98.8 | 45.4 | 38 | A |
| VAL | CA | 316 | 205.8 | 98.1 | 45.6 | 39 | A |
| VAL | CB | 316 | 204.7 | 99.0 | 46.3 | 39 | A |
| VAL | CG1 | 316 | 203.5 | 98.3 | 46.5 | 39 | A |
| VAL | CG2 | 316 | 205.3 | 99.5 | 47.7 | 39 | A |
| VAL | C | 316 | 205.2 | 97.8 | 44.3 | 41 | A |
| VAL | O | 316 | 204.5 | 96.8 | 44.1 | 41 | A |
| ASP | N | 317 | 205.4 | 98.7 | 43.3 | 43 | A |
| ASP | CA | 317 | 204.9 | 98.5 | 41.9 | 44 | A |
| ASP | CB | 317 | 205.1 | 99.8 | 41.0 | 45 | A |
| ASP | CG | 317 | 204.2 | 100.9 | 41.4 | 46 | A |
| ASP | OD1 | 317 | 203.0 | 100.6 | 41.9 | 46 | A |
| ASP | OD2 | 317 | 204.6 | 102.1 | 41.3 | 46 | A |
| ASP | C | 317 | 205.6 | 97.3 | 41.2 | 44 | A |
| ASP | O | 317 | 205.0 | 96.7 | 40.3 | 45 | A |
| ILE | N | 318 | 206.8 | 97.0 | 41.6 | 44 | A |
| ILE | CA | 318 | 207.5 | 95.9 | 41.0 | 45 | A |
| ILE | CB | 318 | 209.0 | 95.9 | 41.3 | 44 | A |
| ILE | CG2 | 318 | 209.7 | 94.7 | 40.8 | 45 | A |
| ILE | CG1 | 318 | 209.6 | 97.1 | 40.6 | 44 | A |
| ILE | CD1 | 318 | 211.1 | 97.2 | 40.7 | 44 | A |
| ILE | C | 318 | 206.9 | 94.6 | 41.7 | 47 | A |
| ILE | O | 318 | 206.5 | 93.7 | 41.0 | 47 | A |
| TYR | N | 319 | 206.8 | 94.7 | 43.0 | 49 | A |

TABLE 5-continued

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| TYR | CA | 319 | 206.3 | 93.5 | 43.7 | 51 | A |
| TYR | CB | 319 | 206.3 | 93.8 | 45.2 | 52 | A |
| TYR | CG | 319 | 207.7 | 94.0 | 45.8 | 52 | A |
| TYR | CD1 | 319 | 207.9 | 94.7 | 47.0 | 53 | A |
| TYR | CE1 | 319 | 209.2 | 94.8 | 47.5 | 53 | A |
| TYR | CD2 | 319 | 208.8 | 93.4 | 45.1 | 52 | A |
| TYR | CE2 | 319 | 210.1 | 93.5 | 45.6 | 52 | A |
| TYR | CZ | 319 | 210.3 | 94.2 | 46.8 | 53 | A |
| TYR | OH | 319 | 211.6 | 94.3 | 47.2 | 54 | A |
| TYR | C | 319 | 204.9 | 93.1 | 43.3 | 53 | A |
| TYR | O | 319 | 204.7 | 92.0 | 43.1 | 54 | A |
| GLU | N | 320 | 204.0 | 94.1 | 43.1 | 55 | A |
| GLU | CA | 320 | 202.7 | 93.8 | 42.6 | 56 | A |
| GLU | CB | 320 | 201.9 | 95.1 | 42.4 | 59 | A |
| GLU | CG | 320 | 201.6 | 95.9 | 43.6 | 62 | A |
| GLU | CD | 320 | 201.4 | 97.4 | 43.3 | 64 | A |
| GLU | OE1 | 320 | 200.4 | 98.0 | 43.9 | 66 | A |
| GLU | OE2 | 320 | 202.1 | 98.0 | 42.5 | 65 | A |
| GLU | C | 320 | 202.7 | 93.0 | 41.4 | 56 | A |
| GLU | O | 320 | 202.0 | 92.0 | 41.2 | 55 | A |
| ASP | N | 321 | 203.6 | 93.3 | 40.5 | 56 | A |
| ASP | CA | 321 | 203.7 | 92.6 | 39.2 | 57 | A |
| ASP | CB | 321 | 204.4 | 93.4 | 38.1 | 56 | A |
| ASP | CG | 321 | 204.2 | 92.9 | 36.8 | 56 | A |
| ASP | OD1 | 321 | 203.0 | 92.6 | 36.4 | 56 | A |
| ASP | OD2 | 321 | 205.1 | 92.7 | 36.0 | 55 | A |
| ASP | C | 321 | 204.4 | 91.3 | 39.3 | 58 | A |
| ASP | O | 321 | 204.1 | 90.4 | 38.6 | 58 | A |
| MET | N | 322 | 205.4 | 91.2 | 40.2 | 59 | A |
| MET | CA | 322 | 206.1 | 89.9 | 40.3 | 61 | A |
| MET | CB | 322 | 207.3 | 90.0 | 41.3 | 60 | A |
| MET | CG | 322 | 208.5 | 90.8 | 40.7 | 60 | A |
| MET | SD | 322 | 210.1 | 90.5 | 41.5 | 60 | A |
| MET | CE | 322 | 209.8 | 91.2 | 43.0 | 59 | A |
| MET | C | 322 | 205.1 | 88.8 | 40.9 | 63 | A |
| MET | O | 322 | 205.2 | 87.7 | 40.4 | 63 | A |
| LEU | N | 323 | 204.3 | 89.2 | 41.8 | 66 | A |
| LEU | CA | 323 | 203.3 | 88.3 | 42.4 | 69 | A |
| LEU | CB | 323 | 202.5 | 89.0 | 43.5 | 68 | A |
| LEU | CG | 323 | 203.0 | 88.9 | 45.0 | 68 | A |
| LEU | CD1 | 323 | 204.4 | 88.4 | 45.1 | 67 | A |
| LEU | CD2 | 323 | 202.8 | 90.2 | 45.7 | 67 | A |
| LEU | C | 323 | 202.3 | 87.9 | 41.3 | 71 | A |
| LEU | O | 323 | 202.2 | 86.7 | 41.0 | 72 | A |
| GLU | N | 324 | 201.8 | 88.9 | 40.6 | 75 | A |
| GLU | CA | 324 | 200.9 | 88.7 | 39.5 | 78 | A |
| GLU | CB | 324 | 200.5 | 90.0 | 38.8 | 79 | A |
| GLU | CG | 324 | 199.6 | 91.0 | 39.5 | 81 | A |
| GLU | CD | 324 | 199.6 | 92.4 | 39.0 | 82 | A |
| GLU | OE1 | 324 | 199.8 | 92.7 | 37.8 | 82 | A |
| GLU | OE2 | 324 | 199.3 | 93.3 | 39.8 | 82 | A |
| GLU | C | 324 | 201.5 | 87.7 | 38.4 | 79 | A |
| GLU | O | 324 | 200.8 | 86.8 | 37.9 | 80 | A |
| ASN | N | 325 | 202.8 | 87.8 | 38.2 | 80 | A |
| ASN | CA | 325 | 203.5 | 86.9 | 37.2 | 81 | A |
| ASN | CB | 325 | 204.4 | 87.7 | 36.4 | 81 | A |
| ASN | CG | 325 | 203.7 | 88.8 | 35.6 | 82 | A |
| ASN | OD1 | 325 | 204.1 | 90.0 | 35.6 | 82 | A |
| ASN | ND2 | 325 | 202.7 | 88.4 | 34.9 | 82 | A |
| ASN | C | 325 | 204.1 | 85.7 | 37.9 | 82 | A |
| ASN | O | 325 | 205.2 | 85.3 | 37.4 | 82 | A |
| GLN | N | 326 | 203.5 | 85.2 | 38.9 | 84 | A |
| GLN | CA | 326 | 203.9 | 84.0 | 39.6 | 86 | A |
| GLN | CB | 326 | 203.5 | 82.8 | 38.8 | 86 | A |
| GLN | CG | 326 | 202.0 | 82.8 | 38.3 | 87 | A |
| GLN | CD | 326 | 201.9 | 83.1 | 36.8 | 87 | A |
| GLN | OE1 | 326 | 202.4 | 82.4 | 35.9 | 88 | A |
| GLN | NE2 | 326 | 201.1 | 84.1 | 36.5 | 88 | A |
| GLN | C | 326 | 205.4 | 84.0 | 40.0 | 86 | A |
| GLN | O | 326 | 206.1 | 83.0 | 39.6 | 86 | A |
| CYS | N | 327 | 205.9 | 85.0 | 40.7 | 87 | A |
| CYS | CA | 327 | 207.3 | 85.0 | 41.1 | 88 | A |

TABLE 5-continued

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| CYS | CB | 327 | 207.7 | 86.4 | 41.6 | 87 | A |
| CYS | SG | 327 | 207.1 | 86.8 | 43.3 | 87 | A |
| CYS | C | 327 | 207.5 | 84.0 | 42.3 | 90 | A |
| CYS | O | 327 | 206.5 | 83.8 | 43.0 | 90 | A |
| ASP | N | 328 | 208.7 | 83.5 | 42.4 | 91 | A |
| ASP | CA | 328 | 209.0 | 82.6 | 43.5 | 92 | A |
| ASP | CB | 328 | 210.1 | 81.6 | 43.2 | 93 | A |
| ASP | CG | 328 | 209.7 | 80.1 | 43.4 | 94 | A |
| ASP | OD1 | 328 | 209.3 | 79.4 | 42.5 | 94 | A |
| ASP | OD2 | 328 | 209.7 | 79.7 | 44.6 | 94 | A |
| ASP | C | 328 | 209.4 | 83.4 | 44.7 | 92 | A |
| ASP | O | 328 | 210.1 | 84.4 | 44.6 | 92 | A |
| ASN | N | 329 | 208.9 | 83.0 | 45.9 | 92 | A |
| ASN | CA | 329 | 209.0 | 83.7 | 47.2 | 91 | A |
| ASN | CB | 329 | 210.2 | 84.7 | 47.2 | 91 | A |
| ASN | CG | 329 | 211.6 | 83.9 | 47.1 | 91 | A |
| ASN | OD1 | 329 | 211.8 | 83.2 | 46.2 | 92 | A |
| ASN | ND2 | 329 | 212.4 | 84.2 | 48.2 | 92 | A |
| ASN | C | 329 | 207.8 | 84.5 | 47.4 | 91 | A |
| ASN | O | 329 | 207.8 | 85.5 | 48.2 | 91 | A |
| LYS | N | 330 | 206.7 | 84.1 | 46.8 | 91 | A |
| LYS | CA | 330 | 205.4 | 84.8 | 47.0 | 90 | A |
| LYS | CB | 330 | 204.2 | 83.9 | 46.5 | 91 | A |
| LYS | CG | 330 | 203.3 | 84.6 | 45.5 | 92 | A |
| LYS | CD | 330 | 202.2 | 83.7 | 45.0 | 92 | A |
| LYS | CE | 330 | 201.3 | 84.3 | 43.9 | 92 | A |
| LYS | NZ | 330 | 202.1 | 84.6 | 42.7 | 91 | A |
| LYS | C | 330 | 205.1 | 85.3 | 48.4 | 90 | A |
| LYS | O | 330 | 204.6 | 86.4 | 48.6 | 89 | A |
| GLU | N | 331 | 205.4 | 84.5 | 49.4 | 89 | A |
| GLU | CA | 331 | 205.2 | 84.8 | 50.8 | 88 | A |
| GLU | CB | 331 | 205.6 | 83.6 | 51.7 | 90 | A |
| GLU | CG | 331 | 204.8 | 82.3 | 51.4 | 92 | A |
| GLU | CD | 331 | 203.4 | 82.2 | 52.1 | 92 | A |
| GLU | OE1 | 331 | 202.6 | 81.3 | 51.7 | 93 | A |
| GLU | OE2 | 331 | 203.2 | 83.1 | 53.0 | 93 | A |
| GLU | C | 331 | 206.1 | 86.0 | 51.2 | 87 | A |
| GLU | O | 331 | 205.6 | 86.9 | 51.8 | 86 | A |
| ASP | N | 332 | 207.4 | 85.8 | 50.9 | 85 | A |
| ASP | CA | 332 | 208.4 | 86.8 | 51.2 | 83 | A |
| ASP | CB | 332 | 209.8 | 86.2 | 50.8 | 84 | A |
| ASP | CG | 332 | 210.9 | 87.2 | 50.8 | 85 | A |
| ASP | OD1 | 332 | 211.7 | 87.2 | 49.8 | 85 | A |
| ASP | OD2 | 332 | 211.1 | 88.0 | 51.7 | 86 | A |
| ASP | C | 332 | 208.2 | 88.2 | 50.5 | 82 | A |
| ASP | O | 332 | 208.1 | 89.2 | 51.1 | 81 | A |
| ILE | N | 333 | 208.2 | 88.2 | 49.1 | 79 | A |
| ILE | CA | 333 | 208.0 | 89.4 | 48.4 | 76 | A |
| ILE | CB | 333 | 208.0 | 89.1 | 46.8 | 76 | A |
| ILE | CG2 | 333 | 207.3 | 90.1 | 46.0 | 75 | A |
| ILE | CG1 | 333 | 209.5 | 88.9 | 46.4 | 75 | A |
| ILE | CD1 | 333 | 209.6 | 88.3 | 45.0 | 75 | A |
| ILE | C | 333 | 206.7 | 90.1 | 48.8 | 75 | A |
| ILE | O | 333 | 206.7 | 91.3 | 49.0 | 75 | A |
| LEU | N | 334 | 205.7 | 89.4 | 49.0 | 74 | A |
| LEU | CA | 334 | 204.4 | 89.9 | 49.5 | 74 | A |
| LEU | CB | 334 | 203.4 | 88.9 | 49.7 | 73 | A |
| LEU | CG | 334 | 202.0 | 89.3 | 50.4 | 73 | A |
| LEU | CD1 | 334 | 201.4 | 90.4 | 49.6 | 73 | A |
| LEU | CD2 | 334 | 201.1 | 88.1 | 50.4 | 73 | A |
| LEU | C | 334 | 204.6 | 90.8 | 50.8 | 74 | A |
| LEU | O | 334 | 204.1 | 91.9 | 50.8 | 75 | A |
| ASN | N | 335 | 205.2 | 90.2 | 51.8 | 74 | A |
| ASN | CA | 335 | 205.4 | 90.9 | 53.0 | 74 | A |
| ASN | CB | 335 | 206.2 | 90.1 | 54.0 | 75 | A |
| ASN | CG | 335 | 205.4 | 88.9 | 54.6 | 76 | A |
| ASN | OD1 | 335 | 204.2 | 89.1 | 55.1 | 76 | A |
| ASN | ND2 | 335 | 205.9 | 87.7 | 54.6 | 76 | A |
| ASN | C | 335 | 206.1 | 92.3 | 52.8 | 73 | A |
| ASN | O | 335 | 205.7 | 93.3 | 53.5 | 73 | A |
| LYS | N | 336 | 207.1 | 92.3 | 52.0 | 72 | A |
| LYS | CA | 336 | 207.9 | 93.5 | 51.7 | 71 | A |

TABLE 5-continued

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| LYS | CB | 336 | 209.0 | 93.2 | 50.7 | 72 | A |
| LYS | CG | 336 | 210.4 | 93.2 | 51.4 | 72 | A |
| LYS | CD | 336 | 211.4 | 92.4 | 50.5 | 73 | A |
| LYS | CE | 336 | 210.9 | 91.0 | 50.3 | 73 | A |
| LYS | NZ | 336 | 211.8 | 90.3 | 49.4 | 75 | A |
| LYS | C | 336 | 206.9 | 94.5 | 51.1 | 70 | A |
| LYS | O | 336 | 206.8 | 95.6 | 51.6 | 70 | A |
| ALA | N | 337 | 206.2 | 94.1 | 50.1 | 68 | A |
| ALA | CA | 337 | 205.2 | 94.9 | 49.4 | 66 | A |
| ALA | CB | 337 | 204.4 | 94.1 | 48.4 | 65 | A |
| ALA | C | 337 | 204.2 | 95.5 | 50.5 | 65 | A |
| ALA | O | 337 | 204.0 | 96.7 | 50.5 | 64 | A |
| LEU | N | 338 | 203.6 | 94.6 | 51.3 | 64 | A |
| LEU | CA | 338 | 202.6 | 95.0 | 52.3 | 62 | A |
| LEU | CB | 338 | 202.0 | 93.8 | 53.0 | 62 | A |
| LEU | CG | 338 | 201.1 | 92.9 | 52.1 | 61 | A |
| LEU | CD1 | 338 | 200.7 | 91.7 | 52.9 | 61 | A |
| LEU | CD2 | 338 | 199.8 | 93.7 | 51.8 | 61 | A |
| LEU | C | 338 | 203.2 | 95.9 | 53.4 | 62 | A |
| LEU | O | 338 | 202.6 | 96.8 | 53.9 | 61 | A |
| GLU | N | 339 | 204.5 | 95.8 | 53.7 | 62 | A |
| GLU | CA | 339 | 205.2 | 96.6 | 54.7 | 62 | A |
| GLU | CB | 339 | 206.6 | 96.0 | 55.0 | 65 | A |
| GLU | CG | 339 | 207.4 | 96.9 | 55.9 | 68 | A |
| GLU | CD | 339 | 208.9 | 96.5 | 56.0 | 70 | A |
| GLU | OE1 | 339 | 209.2 | 95.3 | 56.2 | 71 | A |
| GLU | OE2 | 339 | 209.7 | 97.4 | 55.7 | 71 | A |
| GLU | C | 339 | 205.4 | 98.0 | 54.1 | 60 | A |
| GLU | O | 339 | 205.1 | 99.0 | 54.8 | 60 | A |
| LEU | N | 340 | 205.9 | 98.1 | 52.9 | 58 | A |
| LEU | CA | 340 | 206.2 | 99.3 | 52.3 | 55 | A |
| LEU | CB | 340 | 206.8 | 99.1 | 50.9 | 54 | A |
| LEU | CG | 340 | 208.1 | 98.3 | 50.7 | 54 | A |
| LEU | CD1 | 340 | 208.7 | 98.5 | 49.4 | 53 | A |
| LEU | CD2 | 340 | 209.0 | 98.5 | 51.8 | 54 | A |
| LEU | C | 340 | 204.8 | 100.1 | 52.2 | 55 | A |
| LEU | O | 340 | 204.8 | 101.3 | 52.5 | 55 | A |
| CYS | N | 341 | 203.8 | 99.4 | 51.8 | 55 | A |
| CYS | CA | 341 | 202.4 | 100.0 | 51.8 | 55 | A |
| CYS | CB | 341 | 201.4 | 99.0 | 51.4 | 55 | A |
| CYS | SG | 341 | 201.5 | 98.4 | 49.7 | 55 | A |
| CYS | C | 341 | 202.0 | 100.6 | 53.1 | 55 | A |
| CYS | O | 341 | 201.2 | 101.6 | 53.1 | 55 | A |
| GLU | N | 342 | 202.5 | 100.0 | 54.2 | 55 | A |
| GLU | CA | 342 | 202.2 | 100.5 | 55.5 | 54 | A |
| GLU | CB | 342 | 202.2 | 99.4 | 56.6 | 55 | A |
| GLU | CG | 342 | 201.4 | 99.8 | 57.8 | 56 | A |
| GLU | CD | 342 | 199.9 | 100.3 | 57.5 | 57 | A |
| GLU | OE1 | 342 | 199.5 | 101.3 | 58.0 | 57 | A |
| GLU | OE2 | 342 | 199.2 | 99.6 | 56.8 | 58 | A |
| GLU | C | 342 | 203.1 | 101.7 | 55.9 | 54 | A |
| GLU | O | 342 | 202.7 | 102.7 | 56.5 | 54 | A |
| ILE | N | 343 | 204.4 | 101.5 | 55.5 | 54 | A |
| ILE | CA | 343 | 205.4 | 102.5 | 55.8 | 53 | A |
| ILE | CB | 343 | 206.8 | 102.2 | 55.2 | 53 | A |
| ILE | CG2 | 343 | 207.7 | 103.4 | 55.3 | 53 | A |
| ILE | CG1 | 343 | 207.4 | 101.0 | 55.9 | 54 | A |
| ILE | CD1 | 343 | 208.9 | 100.7 | 55.5 | 54 | A |
| ILE | C | 343 | 205.0 | 103.8 | 55.1 | 53 | A |
| ILE | O | 343 | 205.0 | 104.9 | 55.7 | 53 | A |
| LEU | N | 344 | 204.6 | 103.7 | 53.9 | 52 | A |
| LEU | CA | 344 | 204.1 | 104.8 | 53.1 | 51 | A |
| LEU | CB | 344 | 203.8 | 104.3 | 51.7 | 50 | A |
| LEU | CG | 344 | 205.0 | 104.0 | 50.8 | 49 | A |
| LEU | CD1 | 344 | 204.6 | 103.6 | 49.4 | 48 | A |
| LEU | CD2 | 344 | 205.9 | 105.2 | 50.7 | 49 | A |
| LEU | C | 344 | 202.8 | 105.3 | 53.8 | 52 | A |
| LEU | O | 344 | 202.7 | 106.5 | 54.2 | 53 | A |
| ALA | N | 345 | 201.8 | 104.5 | 53.9 | 53 | A |
| ALA | CA | 345 | 200.5 | 104.9 | 54.5 | 55 | A |
| ALA | CB | 345 | 199.5 | 103.7 | 54.5 | 54 | A |
| ALA | C | 345 | 200.6 | 105.5 | 55.9 | 56 | A |

TABLE 5-continued

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| ALA | O | 345 | 199.6 | 106.5 | 56.2 | 56 | A |
| LYS | N | 346 | 201.5 | 105.0 | 56.8 | 58 | A |
| LYS | CA | 346 | 201.6 | 105.5 | 58.1 | 59 | A |
| LYS | CB | 346 | 202.0 | 104.4 | 59.1 | 61 | A |
| LYS | CG | 346 | 200.9 | 103.6 | 59.8 | 63 | A |
| LYS | CD | 346 | 201.5 | 102.5 | 60.7 | 66 | A |
| LYS | CE | 346 | 200.5 | 101.5 | 61.3 | 67 | A |
| LYS | NZ | 346 | 201.1 | 100.5 | 62.2 | 67 | A |
| LYS | C | 346 | 202.7 | 106.6 | 58.3 | 59 | A |
| LYS | O | 346 | 202.6 | 107.5 | 59.1 | 58 | A |
| GLU | N | 347 | 203.7 | 106.5 | 57.5 | 59 | A |
| GLU | CA | 347 | 204.9 | 107.4 | 57.6 | 59 | A |
| GLU | CB | 347 | 206.0 | 106.6 | 58.1 | 61 | A |
| GLU | CG | 347 | 207.3 | 107.4 | 58.2 | 63 | A |
| GLU | CD | 347 | 208.6 | 106.5 | 58.4 | 65 | A |
| GLU | OE1 | 347 | 209.7 | 107.0 | 58.6 | 66 | A |
| GLU | OE2 | 347 | 208.4 | 105.2 | 58.4 | 66 | A |
| GLU | C | 347 | 205.3 | 108.2 | 56.3 | 57 | A |
| GLU | O | 347 | 205.1 | 109.4 | 56.3 | 57 | A |
| LYS | N | 348 | 205.9 | 107.6 | 55.3 | 56 | A |
| LYS | CA | 348 | 206.4 | 108.2 | 54.1 | 55 | A |
| LYS | CB | 348 | 207.3 | 107.2 | 53.3 | 56 | A |
| LYS | CG | 348 | 208.2 | 106.4 | 54.2 | 56 | A |
| LYS | CD | 348 | 209.3 | 107.3 | 54.8 | 56 | A |
| LYS | CE | 348 | 210.4 | 106.4 | 55.5 | 57 | A |
| LYS | NZ | 348 | 211.0 | 105.4 | 54.6 | 57 | A |
| LYS | C | 348 | 205.5 | 108.9 | 53.2 | 53 | A |
| LYS | O | 348 | 205.8 | 109.9 | 52.6 | 53 | A |
| ASP | N | 349 | 204.2 | 108.5 | 53.0 | 52 | A |
| ASP | CA | 349 | 203.3 | 109.1 | 52.1 | 51 | A |
| ASP | CB | 349 | 203.4 | 108.4 | 50.7 | 51 | A |
| ASP | CG | 349 | 202.9 | 109.2 | 49.6 | 51 | A |
| ASP | OD1 | 349 | 202.8 | 110.5 | 49.7 | 51 | A |
| ASP | OD2 | 349 | 202.6 | 108.7 | 48.6 | 52 | A |
| ASP | C | 349 | 201.9 | 109.1 | 52.6 | 49 | A |
| ASP | O | 349 | 201.0 | 108.7 | 51.9 | 49 | A |
| THR | N | 350 | 201.7 | 109.6 | 53.8 | 48 | A |
| THR | CA | 350 | 200.4 | 109.7 | 54.4 | 48 | A |
| THR | CB | 350 | 200.5 | 110.4 | 55.8 | 49 | A |
| THR | OG1 | 350 | 200.9 | 111.8 | 55.6 | 50 | A |
| THR | CG2 | 350 | 201.6 | 109.7 | 56.6 | 49 | A |
| THR | C | 350 | 199.2 | 110.3 | 53.7 | 47 | A |
| THR | O | 350 | 198.1 | 109.9 | 53.9 | 46 | A |
| ILE | N | 351 | 199.5 | 111.3 | 52.9 | 46 | A |
| ILE | CA | 351 | 198.4 | 112.0 | 52.2 | 44 | A |
| ILE | CB | 351 | 199.0 | 113.2 | 51.3 | 43 | A |
| ILE | CG2 | 351 | 199.7 | 112.6 | 50.1 | 43 | A |
| ILE | CG1 | 351 | 197.8 | 114.1 | 50.9 | 43 | A |
| ILE | CD1 | 351 | 197.4 | 115.0 | 52.1 | 42 | A |
| ILE | C | 351 | 197.5 | 111.0 | 51.4 | 43 | A |
| ILE | O | 351 | 196.3 | 111.2 | 51.3 | 42 | A |
| ARG | N | 352 | 198.1 | 109.9 | 51.0 | 43 | A |
| ARG | CA | 352 | 197.3 | 108.9 | 50.3 | 44 | A |
| ARG | CB | 352 | 197.7 | 108.7 | 48.9 | 43 | A |
| ARG | CG | 352 | 199.1 | 108.8 | 48.5 | 42 | A |
| ARG | CD | 352 | 199.3 | 109.4 | 47.2 | 41 | A |
| ARG | NE | 352 | 200.6 | 110.2 | 47.1 | 42 | A |
| ARG | CZ | 352 | 200.7 | 111.5 | 47.0 | 43 | A |
| ARG | NH1 | 352 | 199.6 | 112.3 | 47.0 | 42 | A |
| ARG | NH2 | 352 | 201.9 | 112.1 | 47.1 | 43 | A |
| ARG | C | 352 | 197.4 | 107.6 | 51.1 | 45 | A |
| ARG | O | 352 | 197.5 | 106.5 | 50.5 | 45 | A |
| LYS | N | 353 | 197.2 | 107.7 | 52.4 | 46 | A |
| LYS | CA | 353 | 197.2 | 106.5 | 53.3 | 46 | A |
| LYS | CB | 353 | 197.0 | 106.9 | 54.8 | 45 | A |
| LYS | CG | 353 | 195.6 | 107.5 | 55.0 | 45 | A |
| LYS | CD | 353 | 195.5 | 108.4 | 56.3 | 45 | A |
| LYS | CE | 353 | 194.1 | 109.0 | 56.5 | 45 | A |
| LYS | NZ | 353 | 194.0 | 110.0 | 57.5 | 45 | A |
| LYS | C | 353 | 196.0 | 105.6 | 52.8 | 46 | A |
| LYS | O | 353 | 196.1 | 104.4 | 52.8 | 46 | A |
| GLU | N | 354 | 194.9 | 106.2 | 52.4 | 47 | A |

TABLE 5-continued

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| GLU | CA | 354 | 193.8 | 105.5 | 51.9 | 48 | A |
| GLU | CB | 354 | 192.6 | 106.5 | 51.6 | 50 | A |
| GLU | CG | 354 | 192.0 | 107.2 | 52.8 | 53 | A |
| GLU | CD | 354 | 191.2 | 106.2 | 53.7 | 55 | A |
| GLU | OE1 | 354 | 191.4 | 106.2 | 54.9 | 56 | A |
| GLU | OE2 | 354 | 190.3 | 105.5 | 53.1 | 56 | A |
| GLU | C | 354 | 194.1 | 104.7 | 50.6 | 48 | A |
| GLU | O | 354 | 193.4 | 103.7 | 50.4 | 48 | A |
| TYR | N | 355 | 195.0 | 105.1 | 49.9 | 47 | A |
| TYR | CA | 355 | 195.4 | 104.4 | 48.6 | 46 | A |
| TYR | CB | 355 | 196.0 | 105.4 | 47.6 | 44 | A |
| TYR | CG | 355 | 196.7 | 104.7 | 46.4 | 41 | A |
| TYR | CD1 | 355 | 195.9 | 104.2 | 45.4 | 40 | A |
| TYR | CE1 | 355 | 196.4 | 103.4 | 44.4 | 39 | A |
| TYR | CD2 | 355 | 198.0 | 104.6 | 46.4 | 40 | A |
| TYR | CE2 | 355 | 198.6 | 103.8 | 45.3 | 40 | A |
| TYR | CZ | 355 | 197.8 | 103.3 | 44.4 | 39 | A |
| TYR | OH | 355 | 198.4 | 102.5 | 43.4 | 39 | A |
| TYR | C | 355 | 196.3 | 103.3 | 49.0 | 47 | A |
| TYR | O | 355 | 196.1 | 102.1 | 48.6 | 47 | A |
| TRP | N | 356 | 197.4 | 103.6 | 49.6 | 49 | A |
| TRP | CA | 356 | 198.4 | 102.7 | 50.0 | 51 | A |
| TRP | CB | 356 | 199.6 | 103.4 | 50.7 | 52 | A |
| TRP | CG | 356 | 200.3 | 104.2 | 49.7 | 52 | A |
| TRP | CD2 | 356 | 201.1 | 103.6 | 48.6 | 53 | A |
| TRP | CE2 | 356 | 201.6 | 104.7 | 47.9 | 52 | A |
| TRP | CE3 | 356 | 201.3 | 102.3 | 48.1 | 53 | A |
| TRP | CD1 | 356 | 200.5 | 105.5 | 49.6 | 52 | A |
| TRP | NE1 | 356 | 201.3 | 105.9 | 48.6 | 52 | A |
| TRP | CZ2 | 356 | 202.4 | 104.6 | 46.7 | 52 | A |
| TRP | CZ3 | 356 | 202.0 | 102.2 | 47.0 | 53 | A |
| TRP | CH2 | 356 | 202.6 | 103.3 | 46.3 | 53 | A |
| TRP | C | 356 | 197.9 | 101.5 | 50.9 | 52 | A |
| TRP | O | 356 | 198.4 | 100.4 | 50.8 | 52 | A |
| ARG | N | 357 | 196.9 | 101.8 | 51.6 | 52 | A |
| ARG | CA | 357 | 196.3 | 100.7 | 52.5 | 53 | A |
| ARG | CB | 357 | 195.5 | 101.3 | 53.6 | 55 | A |
| ARG | CG | 357 | 196.3 | 101.3 | 54.9 | 57 | A |
| ARG | CD | 357 | 196.3 | 102.6 | 55.6 | 58 | A |
| ARG | NE | 357 | 194.9 | 103.0 | 55.9 | 59 | A |
| ARG | CZ | 357 | 194.6 | 104.0 | 56.7 | 60 | A |
| ARG | NH1 | 357 | 193.3 | 104.2 | 57.0 | 61 | A |
| ARG | NH2 | 357 | 195.6 | 104.7 | 57.3 | 59 | A |
| ARG | C | 357 | 195.4 | 99.8 | 51.6 | 52 | A |
| ARG | O | 357 | 195.4 | 98.6 | 51.8 | 52 | A |
| TYR | N | 358 | 194.8 | 100.4 | 50.6 | 51 | A |
| TYR | CA | 358 | 193.9 | 99.7 | 49.6 | 49 | A |
| TYR | CB | 358 | 193.2 | 100.6 | 48.7 | 49 | A |
| TYR | CG | 358 | 192.8 | 99.9 | 47.4 | 48 | A |
| TYR | CD1 | 358 | 191.6 | 99.2 | 47.4 | 48 | A |
| TYR | CE1 | 358 | 191.2 | 98.5 | 46.3 | 47 | A |
| TYR | CD2 | 358 | 193.4 | 100.1 | 46.2 | 47 | A |
| TYR | CE2 | 358 | 193.0 | 99.4 | 45.0 | 46 | A |
| TYR | CZ | 358 | 191.9 | 98.7 | 45.1 | 47 | A |
| TYR | OH | 358 | 191.5 | 98.0 | 44.0 | 46 | A |
| TYR | C | 358 | 194.9 | 98.7 | 48.9 | 49 | A |
| TYR | O | 358 | 194.5 | 97.6 | 48.5 | 49 | A |
| ILE | N | 359 | 196.1 | 99.2 | 48.6 | 49 | A |
| ILE | CA | 359 | 197.1 | 98.4 | 47.9 | 49 | A |
| ILE | CB | 359 | 198.4 | 99.2 | 47.6 | 48 | A |
| ILE | CG2 | 359 | 199.5 | 98.3 | 47.1 | 47 | A |
| ILE | CG1 | 359 | 198.1 | 100.2 | 46.5 | 48 | A |
| ILE | CD1 | 359 | 197.5 | 99.6 | 45.3 | 47 | A |
| ILE | C | 359 | 197.4 | 97.2 | 48.8 | 51 | A |
| ILE | O | 359 | 197.6 | 96.1 | 48.3 | 50 | A |
| GLY | N | 360 | 197.5 | 97.4 | 50.1 | 52 | A |
| GLY | CA | 360 | 197.8 | 96.4 | 51.0 | 54 | A |
| GLY | C | 360 | 196.7 | 95.4 | 51.0 | 55 | A |
| GLY | O | 360 | 196.9 | 94.2 | 50.8 | 56 | A |
| ARG | N | 361 | 195.4 | 95.9 | 51.2 | 56 | A |
| ARG | CA | 361 | 194.2 | 95.1 | 51.2 | 57 | A |
| ARG | CB | 361 | 193.0 | 96.0 | 51.4 | 58 | A |

TABLE 5-continued

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| ARG | CG | 361 | 192.4 | 95.8 | 52.8 | 59 | A |
| ARG | CD | 361 | 192.0 | 97.1 | 53.4 | 59 | A |
| ARG | NE | 361 | 191.1 | 97.9 | 52.6 | 60 | A |
| ARG | CZ | 361 | 191.3 | 99.2 | 52.3 | 61 | A |
| ARG | NH1 | 361 | 190.4 | 99.8 | 51.5 | 62 | A |
| ARG | NH2 | 361 | 192.3 | 99.9 | 52.8 | 62 | A |
| ARG | C | 361 | 194.1 | 94.2 | 49.9 | 58 | A |
| ARG | O | 361 | 193.7 | 93.1 | 50.0 | 59 | A |
| SER | N | 362 | 194.3 | 94.8 | 48.7 | 59 | A |
| SER | CA | 362 | 194.2 | 94.1 | 47.5 | 58 | A |
| SER | CB | 362 | 194.2 | 95.0 | 46.3 | 58 | A |
| SER | OG | 362 | 192.9 | 95.6 | 46.1 | 59 | A |
| SER | C | 362 | 195.3 | 93.1 | 47.4 | 58 | A |
| ER | O | 362 | 195.1 | 91.9 | 47.2 | 57 | A |
| LEU | N | 363 | 196.5 | 93.5 | 47.6 | 58 | A |
| LEU | CA | 363 | 197.7 | 92.6 | 47.6 | 59 | A |
| LEU | CB | 363 | 198.9 | 93.4 | 48.1 | 58 | A |
| LEU | CG | 363 | 200.0 | 93.6 | 47.1 | 58 | A |
| LEU | CD1 | 363 | 199.5 | 94.4 | 45.9 | 59 | A |
| LEU | CD2 | 363 | 201.2 | 94.3 | 47.7 | 58 | A |
| LEU | C | 363 | 197.4 | 91.5 | 48.6 | 59 | A |
| LEU | O | 363 | 197.9 | 90.3 | 48.4 | 59 | A |
| GLN | N | 364 | 196.7 | 91.7 | 49.6 | 61 | A |
| GLN | CA | 364 | 196.3 | 90.8 | 50.6 | 62 | A |
| GLN | CB | 364 | 195.5 | 91.4 | 51.7 | 63 | A |
| GLN | CG | 364 | 195.5 | 90.7 | 53.0 | 64 | A |
| GLN | CD | 364 | 196.8 | 90.9 | 53.7 | 65 | A |
| GLN | OE1 | 364 | 196.9 | 91.7 | 54.7 | 66 | A |
| GLN | NE2 | 364 | 197.9 | 90.3 | 53.2 | 65 | A |
| GLN | C | 364 | 195.5 | 89.6 | 50.0 | 63 | A |
| GLN | O | 364 | 195.8 | 88.5 | 50.2 | 64 | A |
| SER | N | 365 | 194.5 | 89.9 | 49.2 | 65 | A |
| SER | CA | 365 | 193.8 | 88.8 | 48.5 | 67 | A |
| SER | CB | 365 | 192.3 | 89.2 | 48.4 | 66 | A |
| SER | OG | 365 | 192.0 | 90.3 | 47.6 | 67 | A |
| SER | C | 365 | 194.3 | 88.4 | 47.2 | 69 | A |
| SER | O | 365 | 193.5 | 88.0 | 46.3 | 69 | A |
| LYS | N | 366 | 195.6 | 88.4 | 47.0 | 71 | A |
| LYS | CA | 366 | 196.2 | 87.9 | 45.7 | 73 | A |
| LYS | CB | 366 | 195.7 | 88.7 | 44.5 | 74 | A |
| LYS | CG | 366 | 196.1 | 90.1 | 44.3 | 75 | A |
| LYS | CD | 366 | 194.9 | 91.0 | 44.7 | 77 | A |
| LYS | CE | 366 | 193.6 | 90.7 | 43.9 | 78 | A |
| LYS | NZ | 366 | 192.5 | 91.6 | 44.4 | 79 | A |
| LYS | C | 366 | 197.8 | 87.8 | 45.7 | 73 | A |
| LYS | OT1 | 366 | 198.3 | 87.2 | 46.7 | 73 | A |
| LYS | OT2 | 366 | 198.5 | 88.4 | 44.8 | 73 | A |
| LEU | CB | 523 | 194.0 | 121.4 | 61.8 | 44 | B |
| LEU | CG | 523 | 192.7 | 122.2 | 62.1 | 45 | B |
| LEU | CD1 | 523 | 193.0 | 123.6 | 61.8 | 45 | B |
| LEU | CD2 | 523 | 191.6 | 121.6 | 61.3 | 45 | B |
| LEU | C | 523 | 195.1 | 119.1 | 61.5 | 45 | B |
| LEU | O | 523 | 196.2 | 119.4 | 62.0 | 44 | B |
| LEU | N | 523 | 193.6 | 119.5 | 63.4 | 45 | B |
| LEU | CA | 523 | 193.8 | 119.8 | 62.0 | 44 | B |
| TYR | N | 524 | 194.9 | 118.3 | 60.5 | 44 | B |
| TYR | CA | 524 | 196.0 | 117.5 | 59.9 | 44 | B |
| TYR | CB | 524 | 195.4 | 116.6 | 58.8 | 43 | B |
| TYR | CG | 524 | 196.4 | 115.9 | 58.0 | 43 | B |
| TYR | CD1 | 524 | 197.1 | 114.8 | 58.5 | 42 | B |
| TYR | CE1 | 524 | 198.1 | 114.1 | 57.7 | 43 | B |
| TYR | CD2 | 524 | 196.7 | 116.3 | 56.7 | 43 | B |
| TYR | CE2 | 524 | 197.7 | 115.7 | 55.9 | 43 | B |
| TYR | CZ | 524 | 198.3 | 114.6 | 56.4 | 43 | B |
| TYR | OH | 524 | 199.2 | 113.9 | 55.6 | 41 | B |
| TYR | C | 524 | 197.1 | 118.4 | 59.4 | 45 | B |
| TYR | O | 524 | 198.3 | 118.1 | 59.6 | 44 | B |
| SER | N | 525 | 196.8 | 119.4 | 58.6 | 46 | B |
| SER | CA | 525 | 197.8 | 120.2 | 58.0 | 48 | B |
| SER | CB | 525 | 197.2 | 121.1 | 56.9 | 48 | B |
| SER | OG | 525 | 195.9 | 121.5 | 57.3 | 48 | B |
| SER | C | 525 | 198.6 | 121.0 | 59.1 | 50 | B |
| SER | O | 525 | 199.8 | 121.2 | 58.9 | 50 | B |
| LEU | N | 526 | 197.9 | 121.3 | 60.2 | 52 | B |
| LEU | CA | 526 | 198.6 | 122.1 | 61.2 | 53 | B |
| LEU | CB | 526 | 197.6 | 122.8 | 62.1 | 52 | B |
| LEU | CG | 526 | 197.5 | 124.3 | 61.9 | 52 | B |
| LEU | CD1 | 526 | 198.6 | 124.8 | 61.0 | 53 | B |
| LEU | CD2 | 526 | 196.2 | 124.7 | 61.3 | 52 | B |
| LEU | C | 526 | 199.4 | 121.1 | 62.1 | 54 | B |
| LEU | O | 526 | 200.0 | 121.6 | 63.1 | 54 | B |
| ARG | N | 527 | 199.4 | 119.8 | 61.8 | 55 | B |
| ARG | CA | 527 | 200.2 | 118.9 | 62.6 | 57 | B |
| ARG | CB | 527 | 199.8 | 117.5 | 62.1 | 58 | B |
| ARG | CG | 527 | 200.1 | 116.4 | 63.1 | 58 | B |
| ARG | CD | 527 | 199.2 | 115.2 | 62.9 | 58 | B |
| ARG | NE | 527 | 197.7 | 115.6 | 63.1 | 57 | B |
| ARG | CZ | 527 | 196.7 | 114.8 | 62.7 | 57 | B |
| ARG | NH1 | 527 | 196.9 | 113.7 | 62.0 | 57 | B |
| ARG | NH2 | 527 | 195.5 | 115.2 | 62.9 | 57 | B |
| ARG | C | 527 | 201.6 | 119.2 | 62.4 | 59 | B |
| ARG | O | 527 | 202.1 | 119.6 | 61.3 | 59 | B |
| PRO | N | 528 | 202.4 | 119.0 | 63.5 | 60 | B |
| PRO | CD | 528 | 202.0 | 118.7 | 64.8 | 61 | B |
| PRO | CA | 528 | 203.9 | 119.3 | 63.5 | 60 | B |
| PRO | CB | 528 | 204.3 | 119.0 | 64.9 | 60 | B |
| PRO | CG | 528 | 203.1 | 119.3 | 65.7 | 61 | B |
| PRO | C | 528 | 204.7 | 118.5 | 62.5 | 60 | B |
| PRO | O | 528 | 205.7 | 119.0 | 61.9 | 60 | B |
| GLU | N | 529 | 204.4 | 117.2 | 62.4 | 61 | B |
| GLU | CA | 529 | 205.1 | 116.3 | 61.5 | 62 | B |
| GLU | CB | 529 | 204.7 | 114.9 | 61.8 | 63 | B |
| GLU | CG | 529 | 203.2 | 114.6 | 62.0 | 65 | B |
| GLU | CD | 529 | 202.9 | 114.6 | 63.5 | 66 | B |
| GLU | OE1 | 529 | 201.9 | 113.9 | 63.9 | 66 | B |
| GLU | OE2 | 529 | 203.5 | 115.4 | 64.3 | 67 | B |
| GLU | C | 529 | 204.8 | 116.7 | 60.0 | 62 | B |
| GLU | O | 529 | 205.6 | 116.4 | 59.1 | 63 | B |
| HIS | N | 530 | 203.7 | 117.3 | 59.8 | 62 | B |
| HIS | CA | 530 | 203.3 | 117.7 | 58.4 | 62 | B |
| HIS | CB | 530 | 201.8 | 118.3 | 58.5 | 62 | B |
| HIS | CG | 530 | 201.3 | 118.9 | 57.2 | 63 | B |
| HIS | CD2 | 530 | 200.5 | 118.4 | 56.2 | 62 | B |
| HIS | ND1 | 530 | 201.7 | 120.2 | 56.8 | 63 | B |
| HIS | CE1 | 530 | 201.1 | 120.4 | 55.7 | 63 | B |
| HIS | NE2 | 530 | 200.4 | 119.4 | 55.3 | 62 | B |
| HIS | C | 530 | 204.2 | 118.7 | 57.7 | 60 | B |
| HIS | O | 530 | 204.1 | 118.9 | 56.5 | 60 | B |
| ALA | N | 531 | 205.1 | 119.4 | 58.5 | 59 | B |
| ALA | CA | 531 | 206.0 | 120.3 | 57.9 | 59 | B |
| ALA | CB | 531 | 206.6 | 121.2 | 59.0 | 59 | B |
| ALA | C | 531 | 207.1 | 119.6 | 57.2 | 58 | B |
| ALA | O | 531 | 207.9 | 120.1 | 56.4 | 57 | B |
| ARG | N1 | 532 | 207.2 | 118.3 | 57.5 | 57 | B |
| ARG | CA | 532 | 208.2 | 117.4 | 56.8 | 57 | B |
| ARG | CB | 532 | 208.4 | 116.1 | 57.5 | 59 | B |
| ARG | CG | 532 | 209.4 | 116.1 | 58.7 | 63 | B |
| ARG | CD | 532 | 208.7 | 115.8 | 60.0 | 66 | B |
| ARG | NE | 532 | 208.4 | 114.4 | 60.2 | 69 | B |
| ARG | CZ | 532 | 208.0 | 113.9 | 61.4 | 70 | B |
| ARG | NH1 | 532 | 207.9 | 114.6 | 62.5 | 71 | B |
| ARG | NH2 | 532 | 207.8 | 112.6 | 61.5 | 71 | B |
| ARG | C | 532 | 207.8 | 117.2 | 55.4 | 56 | B |
| ARG | O | 532 | 208.7 | 116.9 | 54.5 | 56 | B |
| GLU | N | 533 | 206.5 | 117.3 | 55.1 | 54 | B |
| GLU | CA | 533 | 206.0 | 117.2 | 53.8 | 53 | B |
| GLU | CB | 533 | 204.5 | 117.0 | 53.9 | 52 | B |
| GLU | CG | 533 | 204.1 | 115.6 | 54.5 | 51 | B |
| GLU | CD | 533 | 204.6 | 114.4 | 53.8 | 51 | B |
| GLU | OE1 | 533 | 203.8 | 113.8 | 53.1 | 51 | B |
| GLU | OE2 | 533 | 205.8 | 114.1 | 53.9 | 51 | B |
| GLU | C | 533 | 206.2 | 118.4 | 52.9 | 53 | B |
| GLU | O | 533 | 205.5 | 118.6 | 51.9 | 53 | B |
| ARG | N | 534 | 207.3 | 119.2 | 53.2 | 52 | B |

TABLE 5-continued

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| ARG | CA | 534 | 207.6 | 120.3 | 52.4 | 50 | B |
| ARG | CB | 534 | 208.4 | 121.3 | 53.3 | 51 | B |
| ARG | CG | 534 | 208.2 | 122.7 | 53.0 | 52 | B |
| ARG | CD | 534 | 206.9 | 123.2 | 53.4 | 53 | B |
| ARG | NE | 534 | 206.6 | 124.6 | 53.0 | 55 | B |
| ARG | CZ | 534 | 207.4 | 125.6 | 53.4 | 57 | B |
| ARG | NH1 | 534 | 208.4 | 125.5 | 54.1 | 58 | B |
| ARG | NH2 | 534 | 207.0 | 126.8 | 52.9 | 58 | B |
| ARG | C | 534 | 208.4 | 119.8 | 51.3 | 49 | B |
| ARG | O | 534 | 209.1 | 118.8 | 51.4 | 48 | B |
| LEU | N | 535 | 208.4 | 120.6 | 50.2 | 49 | B |
| LEU | CA | 535 | 209.1 | 120.2 | 49.0 | 49 | B |
| LEU | CB | 535 | 208.9 | 121.3 | 47.9 | 47 | B |
| LEU | CG | 535 | 209.7 | 121.1 | 46.6 | 46 | B |
| LEU | CD1 | 535 | 209.2 | 119.9 | 45.8 | 46 | B |
| LEU | CD2 | 535 | 209.7 | 122.4 | 45.7 | 45 | B |
| LEU | C | 535 | 210.6 | 120.0 | 49.2 | 49 | B |
| LEU | O | 535 | 211.2 | 120.7 | 50.0 | 50 | B |
| GLN | N | 536 | 211.2 | 119.1 | 48.4 | 49 | B |
| GLN | CA | 536 | 212.6 | 118.8 | 48.5 | 50 | B |
| GLN | CB | 536 | 212.8 | 117.4 | 49.0 | 51 | B |
| GLN | CG | 536 | 211.9 | 117.0 | 50.1 | 52 | B |
| GLN | CD | 536 | 212.5 | 115.9 | 51.0 | 52 | B |
| GLN | OE1 | 536 | 211.7 | 115.2 | 51.6 | 54 | B |
| GLN | NE2 | 536 | 213.8 | 115.8 | 50.9 | 52 | B |
| GLN | C | 536 | 213.1 | 119.0 | 47.1 | 51 | B |
| GLN | O | 536 | 213.0 | 118.1 | 46.3 | 52 | B |
| ASP | N | 537 | 213.8 | 120.1 | 46.9 | 52 | B |
| ASP | CA | 537 | 214.3 | 120.4 | 45.6 | 52 | B |
| ASP | CB | 537 | 214.4 | 122.0 | 45.4 | 53 | B |
| ASP | CG | 537 | 215.7 | 122.5 | 45.8 | 53 | B |
| ASP | OD1 | 537 | 216.4 | 122.0 | 46.7 | 54 | B |
| ASP | OD2 | 537 | 216.1 | 123.6 | 45.3 | 54 | B |
| ASP | C | 537 | 215.6 | 119.8 | 45.1 | 52 | B |
| ASP | O | 537 | 216.1 | 120.1 | 44.1 | 52 | B |
| ASP | N | 538 | 216.1 | 118.8 | 45.9 | 52 | B |
| ASP | CA | 538 | 217.4 | 118.1 | 45.6 | 52 | B |
| ASP | CB | 538 | 217.2 | 117.2 | 44.4 | 53 | B |
| ASP | CG | 538 | 216.1 | 116.2 | 44.6 | 54 | B |
| ASP | OD1 | 538 | 216.2 | 115.4 | 45.6 | 56 | B |
| ASP | OD2 | 538 | 215.2 | 116.1 | 43.8 | 55 | B |
| ASP | C | 538 | 218.5 | 119.1 | 45.4 | 52 | B |
| ASP | O | 538 | 219.6 | 118.7 | 44.9 | 51 | B |
| SER | N | 539 | 218.3 | 120.3 | 45.7 | 53 | B |
| SER | CA | 539 | 219.3 | 121.4 | 45.5 | 54 | B |
| SER | CB | 539 | 220.6 | 121.1 | 46.2 | 56 | B |
| SER | OG | 539 | 220.3 | 120.9 | 47.6 | 58 | B |
| SER | C | 539 | 219.6 | 121.6 | 44.0 | 53 | B |
| SER | O | 539 | 220.6 | 122.1 | 43.6 | 54 | B |
| VAL | N | 540 | 218.6 | 121.3 | 43.2 | 51 | B |
| VAL | CA | 540 | 218.6 | 121.5 | 41.8 | 49 | B |
| VAL | CB | 540 | 218.5 | 120.1 | 41.0 | 48 | B |
| VAL | CG1 | 540 | 218.4 | 120.4 | 39.5 | 47 | B |
| VAL | CG2 | 540 | 219.7 | 119.2 | 41.3 | 47 | B |
| VAL | C | 540 | 217.3 | 122.3 | 41.5 | 48 | B |
| VAL | O | 540 | 216.2 | 121.8 | 41.4 | 48 | B |
| GLU | N | 541 | 217.5 | 123.6 | 41.4 | 47 | B |
| GLU | CA | 541 | 216.4 | 124.5 | 41.1 | 46 | B |
| GLU | CB | 541 | 216.6 | 125.9 | 41.6 | 48 | B |
| GLU | CG | 541 | 217.5 | 126.0 | 42.8 | 51 | B |
| GLU | CD | 541 | 217.3 | 127.3 | 43.4 | 52 | B |
| GLU | OE1 | 541 | 217.8 | 128.3 | 42.8 | 53 | B |
| GLU | OE2 | 541 | 216.7 | 127.4 | 44.5 | 54 | B |
| GLU | C | 541 | 216.0 | 124.6 | 39.7 | 44 | B |
| GLU | O | 541 | 216.8 | 124.7 | 38.8 | 45 | B |
| THR | N | 542 | 214.7 | 124.7 | 39.5 | 42 | B |
| THR | CA | 542 | 214.1 | 124.9 | 38.1 | 40 | B |
| THR | CB | 542 | 213.8 | 123.6 | 37.5 | 39 | B |
| THR | OG1 | 542 | 212.9 | 122.9 | 38.2 | 40 | B |
| THR | CG2 | 542 | 215.1 | 122.8 | 37.3 | 39 | B |
| THR | C | 542 | 212.9 | 125.8 | 38.3 | 38 | B |
| THR | O | 542 | 212.4 | 126.1 | 39.4 | 38 | B |

TABLE 5-continued

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| VAL | N | 543 | 212.3 | 126.3 | 37.2 | 36 | B |
| VAL | CA | 543 | 211.2 | 127.1 | 37.3 | 35 | B |
| VAL | CB | 543 | 210.6 | 127.4 | 35.9 | 35 | B |
| VAL | CG1 | 543 | 209.4 | 128.4 | 36.0 | 34 | B |
| VAL | CG2 | 543 | 211.6 | 128.0 | 35.0 | 35 | B |
| VAL | C | 543 | 210.1 | 126.4 | 38.1 | 34 | B |
| VAL | O | 543 | 209.4 | 127.1 | 38.9 | 35 | B |
| THR | N | 544 | 210.0 | 125.1 | 38.0 | 34 | B |
| THR | CA | 544 | 209.0 | 124.3 | 38.7 | 33 | B |
| THR | CB | 544 | 209.0 | 122.8 | 38.1 | 33 | B |
| THR | OG1 | 544 | 208.9 | 122.9 | 36.7 | 33 | B |
| THR | CG2 | 544 | 207.9 | 122.1 | 38.8 | 33 | B |
| THR | C | 544 | 209.1 | 124.2 | 40.2 | 33 | B |
| THR | O | 544 | 208.1 | 124.4 | 40.9 | 34 | B |
| SER | N | 545 | 210.3 | 124.0 | 40.7 | 33 | B |
| SER | CA | 545 | 210.5 | 123.9 | 42.2 | 33 | B |
| SER | CB | 545 | 211.8 | 123.2 | 42.5 | 33 | B |
| SER | OG | 545 | 212.9 | 123.9 | 41.9 | 33 | B |
| SER | C | 545 | 210.4 | 125.3 | 42.7 | 33 | B |
| SER | O | 545 | 209.7 | 125.5 | 43.7 | 34 | B |
| ILE | N | 546 | 211.0 | 126.3 | 42.0 | 33 | B |
| ILE | CA | 546 | 210.9 | 127.7 | 42.4 | 32 | B |
| ILE | CB | 546 | 211.6 | 128.5 | 41.4 | 32 | B |
| ILE | CG2 | 546 | 211.3 | 130.0 | 41.6 | 31 | B |
| ILE | CG1 | 546 | 213.1 | 128.2 | 41.4 | 32 | B |
| ILE | CD1 | 546 | 213.9 | 128.8 | 40.2 | 34 | B |
| ILE | C | 546 | 209.5 | 128.1 | 42.6 | 32 | B |
| ILE | O | 546 | 209.1 | 128.7 | 43.6 | 33 | B |
| GLU | N | 547 | 208.6 | 127.8 | 41.7 | 32 | B |
| GLU | CA | 547 | 207.2 | 128.2 | 41.7 | 31 | B |
| GLU | CB | 547 | 206.5 | 128.0 | 40.4 | 31 | B |
| GLU | CG | 547 | 207.0 | 129.0 | 39.4 | 30 | B |
| GLU | CD | 547 | 207.0 | 130.5 | 39.9 | 31 | B |
| GLU | OE1 | 547 | 205.9 | 130.9 | 40.3 | 30 | B |
| GLU | OE2 | 547 | 208.0 | 131.1 | 39.9 | 32 | B |
| GLU | C | 547 | 206.4 | 127.4 | 42.8 | 31 | B |
| GLU | O | 547 | 205.5 | 127.9 | 43.4 | 30 | B |
| GLN | N | 548 | 206.7 | 126.1 | 42.8 | 32 | B |
| GLN | CA | 548 | 206.0 | 125.2 | 43.8 | 33 | B |
| GLN | CB | 548 | 206.5 | 123.7 | 43.6 | 30 | B |
| GLN | CG | 548 | 205.9 | 122.7 | 44.6 | 29 | B |
| GLN | CD | 548 | 204.4 | 122.8 | 44.7 | 29 | B |
| GLN | OE1 | 548 | 203.9 | 122.6 | 45.8 | 30 | B |
| GLN | NE2 | 548 | 203.8 | 123.1 | 43.6 | 29 | B |
| GLN | C | 548 | 206.4 | 125.7 | 45.2 | 35 | B |
| GLN | O | 548 | 205.5 | 125.8 | 46.1 | 36 | B |
| ALA | N | 549 | 207.6 | 126.1 | 45.4 | 36 | B |
| ALA | CA | 549 | 208.1 | 126.6 | 46.7 | 37 | B |
| ALA | CB | 549 | 209.6 | 126.9 | 46.6 | 35 | B |
| ALA | C | 549 | 207.4 | 127.9 | 47.1 | 37 | B |
| ALA | O | 549 | 207.0 | 128.1 | 48.2 | 38 | B |
| LYS | N | 550 | 207.2 | 128.8 | 46.1 | 39 | B |
| LYS | CA | 550 | 206.5 | 130.0 | 46.4 | 40 | B |
| LYS | CB | 550 | 206.4 | 130.9 | 45.2 | 41 | B |
| LYS | CG | 550 | 207.7 | 131.3 | 44.6 | 43 | B |
| LYS | CD | 550 | 207.5 | 132.4 | 43.5 | 45 | B |
| LYS | CE | 550 | 208.7 | 132.6 | 42.7 | 46 | B |
| LYS | NZ | 550 | 208.5 | 133.5 | 41.5 | 47 | B |
| LYS | C | 550 | 205.1 | 129.8 | 46.9 | 40 | B |
| LYS | O | 550 | 204.6 | 130.4 | 47.8 | 40 | B |
| VAL | N | 551 | 204.5 | 128.8 | 46.3 | 41 | B |
| VAL | CA | 551 | 203.1 | 128.4 | 46.7 | 41 | B |
| VAL | CB | 551 | 202.5 | 127.4 | 45.8 | 41 | B |
| VAL | CG1 | 551 | 201.3 | 126.7 | 46.3 | 41 | B |
| VAL | CG2 | 551 | 202.1 | 128.1 | 44.5 | 42 | B |
| VAL | C | 551 | 203.1 | 127.9 | 48.1 | 42 | B |
| VAL | O | 551 | 202.4 | 128.4 | 49.0 | 42 | B |
| GLU | N | 552 | 203.9 | 126.8 | 48.4 | 43 | B |
| GLU | CA | 552 | 204.0 | 126.2 | 49.7 | 43 | B |
| GLU | CB | 552 | 205.1 | 125.2 | 49.8 | 42 | B |
| GLU | CG | 552 | 204.8 | 123.9 | 49.0 | 39 | B |
| GLU | CD | 552 | 205.8 | 122.9 | 49.1 | 39 | B |

TABLE 5-continued

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| GLU | OE1 | 552 | 206.9 | 123.1 | 49.6 | 38 | B |
| GLU | OE2 | 552 | 205.5 | 121.7 | 48.7 | 39 | B |
| GLU | C | 552 | 204.2 | 127.3 | 50.8 | 45 | B |
| GLU | O | 552 | 203.4 | 127.3 | 51.8 | 46 | B |
| GLU | N | 553 | 205.1 | 128.2 | 50.6 | 48 | B |
| GLU | CA | 553 | 205.4 | 129.3 | 51.5 | 49 | B |
| GLU | CB | 553 | 206.4 | 130.2 | 51.0 | 52 | B |
| GLU | CG | 553 | 206.8 | 131.3 | 51.9 | 56 | B |
| GLU | CD | 553 | 208.3 | 131.2 | 52.3 | 59 | B |
| GLU | OE1 | 553 | 208.6 | 130.3 | 53.1 | 60 | B |
| GLU | OE2 | 553 | 209.1 | 132.1 | 51.8 | 60 | B |
| GLU | C | 553 | 204.2 | 130.0 | 51.9 | 49 | B |
| GLU | O | 553 | 203.9 | 130.2 | 53.1 | 49 | B |
| LYS | N | 554 | 203.4 | 130.5 | 51.0 | 49 | B |
| LYS | CA | 554 | 202.2 | 131.2 | 51.3 | 51 | B |
| LYS | CB | 554 | 201.5 | 131.7 | 50.0 | 53 | B |
| LYS | CG | 554 | 202.4 | 132.4 | 49.0 | 57 | B |
| LYS | CD | 554 | 201.6 | 132.8 | 47.8 | 61 | B |
| LYS | CE | 554 | 202.4 | 133.7 | 46.9 | 63 | B |
| LYS | NZ | 554 | 201.5 | 134.5 | 46.0 | 65 | B |
| LYS | C | 554 | 201.2 | 130.4 | 52.1 | 51 | B |
| LYS | O | 554 | 200.6 | 130.8 | 53.0 | 51 | B |
| ILE | N | 555 | 201.2 | 129.1 | 51.7 | 50 | B |
| ILE | CA | 555 | 200.3 | 128.1 | 52.4 | 49 | B |
| ILE | CB | 555 | 200.3 | 126.8 | 51.7 | 49 | B |
| ILE | CG2 | 555 | 199.3 | 125.8 | 52.4 | 48 | B |
| ILE | CG1 | 555 | 199.8 | 126.9 | 50.2 | 49 | B |
| ILE | CD1 | 555 | 198.4 | 127.5 | 50.1 | 48 | B |
| ILE | C | 555 | 200.8 | 128.0 | 53.8 | 50 | B |
| ILE | O | 555 | 200.0 | 128.0 | 54.8 | 49 | B |
| GLN | N | 556 | 202.1 | 127.8 | 54.0 | 50 | B |
| GLN | CA | 556 | 202.7 | 127.7 | 55.3 | 51 | B |
| GLN | CB | 556 | 204.3 | 127.7 | 55.1 | 51 | B |
| GLN | CG | 556 | 205.0 | 127.5 | 56.4 | 52 | B |
| GLN | CD | 556 | 204.7 | 126.2 | 57.1 | 53 | B |
| GLN | OE1 | 556 | 205.6 | 125.3 | 57.1 | 53 | B |
| GLN | NE2 | 556 | 203.6 | 126.1 | 57.8 | 52 | B |
| GLN | C | 556 | 202.3 | 128.8 | 56.1 | 52 | B |
| GLN | O | 556 | 201.9 | 128.7 | 57.3 | 54 | B |
| GLU | N | 557 | 202.4 | 130.0 | 55.6 | 53 | B |
| GLU | CA | 557 | 202.0 | 131.2 | 56.3 | 54 | B |
| GLU | CB | 557 | 202.4 | 132.5 | 55.5 | 57 | B |
| GLU | CG | 557 | 203.9 | 132.5 | 55.1 | 60 | B |
| GLU | CD | 557 | 204.4 | 133.8 | 54.3 | 62 | B |
| GLU | OE1 | 557 | 203.5 | 134.6 | 53.9 | 63 | B |
| GLU | OE2 | 557 | 205.6 | 133.9 | 54.0 | 62 | B |
| GLU | C | 557 | 200.6 | 131.3 | 56.7 | 53 | B |
| GLU | O | 557 | 200.2 | 132.0 | 57.6 | 54 | B |
| VAL | N | 558 | 199.7 | 130.5 | 56.0 | 53 | B |
| VAL | CA | 558 | 198.3 | 130.5 | 56.2 | 52 | B |
| VAL | CB | 558 | 197.5 | 130.0 | 55.0 | 52 | B |
| VAL | CG1 | 558 | 196.0 | 129.7 | 55.4 | 51 | B |
| VAL | CG2 | 558 | 197.5 | 131.0 | 53.9 | 52 | B |
| VAL | C | 558 | 198.0 | 129.5 | 57.4 | 52 | B |
| VAL | O | 558 | 197.3 | 129.8 | 58.3 | 52 | B |
| PHE | N | 559 | 198.6 | 128.3 | 57.3 | 52 | B |
| PHE | CA | 559 | 198.5 | 127.3 | 58.3 | 51 | B |
| PHE | CB | 559 | 199.3 | 126.1 | 57.9 | 49 | B |
| PHE | CG | 559 | 198.7 | 125.4 | 56.8 | 47 | B |
| PHE | CD1 | 559 | 199.4 | 124.4 | 56.1 | 47 | B |
| PHE | CD2 | 559 | 197.4 | 125.6 | 56.4 | 47 | B |
| PHE | CE1 | 559 | 198.8 | 123.7 | 55.0 | 46 | B |
| PHE | CE2 | 559 | 196.8 | 124.9 | 55.3 | 46 | B |
| PHE | CZ | 559 | 197.5 | 123.9 | 54.7 | 46 | B |
| PHE | C | 559 | 196.9 | 127.9 | 59.7 | 52 | B |
| PHE | O | 559 | 198.1 | 127.8 | 60.7 | 52 | B |
| SER | N | 560 | 200.1 | 128.4 | 59.8 | 54 | B |
| SER | CA | 560 | 200.6 | 129.0 | 61.0 | 56 | B |
| SER | CB | 560 | 202.1 | 129.3 | 60.8 | 55 | B |
| SER | OG | 560 | 202.8 | 128.1 | 60.5 | 55 | B |
| SER | C | 560 | 199.9 | 130.3 | 61.5 | 59 | B |
| SER | O | 560 | 200.2 | 130.8 | 62.5 | 59 | B |

TABLE 5-continued

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| SER | N | 561 | 199.0 | 130.8 | 60.7 | 62 | B |
| SER | CA | 561 | 198.3 | 132.0 | 61.1 | 65 | B |
| SER | CB | 561 | 197.3 | 132.5 | 60.1 | 65 | B |
| SER | OG | 561 | 196.3 | 131.6 | 59.9 | 65 | B |
| SER | C | 561 | 197.6 | 131.7 | 62.4 | 68 | B |
| SER | O | 561 | 197.5 | 132.6 | 63.3 | 68 | B |
| TYR | N | 562 | 197.1 | 130.5 | 62.5 | 71 | B |
| TYR | CA | 562 | 196.4 | 130.1 | 63.7 | 74 | B |
| TYR | CB | 562 | 195.7 | 128.7 | 63.5 | 74 | B |
| TYR | CG | 562 | 194.6 | 128.8 | 62.4 | 74 | B |
| TYR | CD1 | 562 | 194.9 | 128.3 | 61.1 | 74 | B |
| TYR | CE1 | 562 | 193.9 | 128.4 | 60.1 | 75 | B |
| TYR | CD2 | 562 | 193.4 | 129.5 | 62.7 | 75 | B |
| TYR | CE2 | 562 | 192.5 | 129.6 | 61.7 | 75 | B |
| TYR | CZ | 562 | 192.7 | 129.1 | 60.4 | 75 | B |
| TYR | OH | 562 | 191.7 | 129.3 | 59.5 | 76 | B |
| TYR | C | 562 | 197.3 | 130.0 | 64.9 | 76 | B |
| TYR | O | 562 | 197.1 | 130.6 | 66.0 | 75 | B |
| LYS | N | 563 | 198.4 | 129.2 | 64.7 | 78 | B |
| LYS | CA | 563 | 199.4 | 129.0 | 65.7 | 81 | B |
| LYS | CB | 563 | 200.3 | 127.8 | 65.3 | 81 | B |
| LYS | CG | 563 | 199.6 | 126.6 | 64.8 | 82 | B |
| LYS | CD | 563 | 200.4 | 125.4 | 64.4 | 83 | B |
| LYS | CE | 563 | 202.0 | 125.7 | 64.3 | 83 | B |
| LYS | NZ | 563 | 202.8 | 124.5 | 64.4 | 83 | B |
| LYS | C | 563 | 200.2 | 130.3 | 65.9 | 82 | B |
| LYS | O | 563 | 201.5 | 130.2 | 65.9 | 82 | B |
| PHE | N | 564 | 199.5 | 131.4 | 66.1 | 84 | B |
| PHE | CA | 564 | 200.2 | 132.7 | 66.2 | 87 | B |
| PHE | CB | 564 | 199.8 | 133.5 | 64.9 | 90 | B |
| PHE | CG | 564 | 200.2 | 134.9 | 65.0 | 93 | B |
| PHE | CD1 | 564 | 201.5 | 135.3 | 65.1 | 94 | B |
| PHE | CD2 | 564 | 199.2 | 135.9 | 64.9 | 93 | B |
| PHE | CE1 | 564 | 201.9 | 136.7 | 65.1 | 95 | B |
| PHE | CE2 | 564 | 199.5 | 137.3 | 64.9 | 94 | B |
| PHE | CZ | 564 | 200.9 | 137.7 | 65.0 | 95 | B |
| PHE | C | 564 | 199.8 | 133.4 | 67.5 | 87 | B |
| PHE | O | 564 | 199.0 | 134.4 | 67.4 | 88 | B |
| ASN | N | 565 | 200.3 | 132.9 | 68.6 | 87 | B |
| ASN | CA | 565 | 200.0 | 133.5 | 69.9 | 86 | B |
| ASN | CB | 565 | 200.9 | 134.7 | 70.2 | 88 | B |
| ASN | CG | 565 | 202.3 | 134.3 | 70.8 | 90 | B |
| ASN | OD1 | 565 | 202.6 | 133.2 | 70.9 | 91 | B |
| ASN | ND2 | 565 | 203.0 | 135.4 | 71.1 | 91 | B |
| ASN | C | 565 | 198.6 | 134.0 | 70.0 | 85 | B |
| ASN | O | 565 | 198.4 | 135.0 | 70.7 | 84 | B |
| HIS | N | 566 | 197.7 | 133.4 | 69.4 | 84 | B |
| HIS | CA | 566 | 196.3 | 133.9 | 69.4 | 83 | B |
| HIS | CB | 566 | 196.0 | 134.4 | 67.9 | 85 | B |
| HIS | CG | 566 | 196.0 | 135.9 | 67.8 | 88 | B |
| HIS | CD2 | 566 | 195.0 | 136.8 | 68.0 | 88 | B |
| HIS | ND1 | 566 | 197.2 | 136.6 | 67.6 | 89 | B |
| HIS | CE1 | 566 | 196.9 | 137.9 | 67.6 | 89 | B |
| HIS | NE2 | 566 | 195.6 | 138.1 | 67.8 | 89 | B |
| HIS | C | 566 | 195.2 | 133.1 | 69.8 | 80 | B |
| HIS | O | 566 | 194.9 | 133.0 | 71.0 | 79 | B |
| LEU | N | 567 | 194.5 | 132.5 | 68.9 | 79 | B |
| LEU | CA | 567 | 193.3 | 131.7 | 69.2 | 78 | B |
| LEU | CB | 567 | 192.1 | 132.3 | 68.5 | 77 | B |
| LEU | CG | 567 | 192.2 | 133.5 | 67.6 | 77 | B |
| LEU | CD1 | 567 | 192.6 | 134.8 | 68.4 | 76 | B |
| LEU | CD2 | 567 | 193.2 | 133.3 | 66.4 | 76 | B |
| LEU | C | 567 | 193.5 | 130.2 | 68.7 | 77 | B |
| LEU | O | 567 | 194.6 | 129.8 | 68.4 | 77 | B |
| VAL | N | 568 | 192.4 | 129.5 | 68.7 | 76 | B |
| VAL | CA | 568 | 192.4 | 128.1 | 68.3 | 75 | B |
| VAL | CB | 568 | 191.4 | 127.3 | 69.2 | 75 | B |
| VAL | CG1 | 568 | 191.8 | 125.8 | 69.1 | 76 | B |
| VAL | CG2 | 568 | 191.5 | 127.7 | 70.6 | 75 | B |
| VAL | C | 568 | 191.8 | 128.1 | 66.8 | 74 | B |
| VAL | O | 568 | 190.9 | 128.9 | 66.5 | 75 | B |
| PRO | N | 569 | 192.4 | 127.2 | 65.9 | 73 | B |

TABLE 5-continued

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| PRO | CD | 569 | 193.5 | 126.3 | 66.0 | 73 | B |
| PRO | CA | 569 | 191.8 | 127.3 | 64.6 | 72 | B |
| PRO | CB | 569 | 192.7 | 126.2 | 63.8 | 72 | B |
| PRO | CG | 569 | 193.2 | 125.3 | 64.9 | 72 | B |
| PRO | C | 569 | 190.3 | 126.9 | 64.6 | 71 | B |
| PRO | O | 569 | 189.9 | 125.9 | 65.2 | 71 | B |
| ARG | N | 570 | 189.5 | 127.8 | 64.0 | 71 | B |
| ARG | CA | 570 | 188.1 | 127.7 | 63.9 | 70 | B |
| ARG | CB | 570 | 187.4 | 128.9 | 64.4 | 72 | B |
| ARG | CG | 570 | 187.3 | 129.0 | 65.9 | 75 | B |
| ARG | CD | 570 | 186.1 | 128.3 | 66.5 | 78 | B |
| ARG | NE | 570 | 186.1 | 126.9 | 66.3 | 80 | B |
| ARG | CZ | 570 | 185.2 | 126.1 | 66.9 | 81 | B |
| ARG | NH1 | 570 | 184.3 | 126.6 | 67.8 | 81 | B |
| ARG | NH2 | 570 | 185.2 | 124.8 | 66.6 | 81 | B |
| ARG | C | 570 | 187.8 | 127.5 | 62.5 | 68 | B |
| ARG | O | 570 | 187.5 | 128.4 | 61.7 | 67 | B |
| LEU | N | 571 | 187.8 | 126.2 | 62.0 | 64 | B |
| LEU | CA | 571 | 187.5 | 126.0 | 60.6 | 60 | B |
| LEU | CB | 571 | 187.9 | 124.6 | 60.1 | 60 | B |
| LEU | CG | 571 | 189.2 | 124.6 | 59.3 | 59 | B |
| LEU | CD1 | 571 | 190.4 | 125.0 | 60.1 | 59 | B |
| LEU | CD2 | 571 | 189.4 | 123.2 | 58.6 | 59 | B |
| LEU | C | 571 | 186.0 | 126.2 | 60.4 | 59 | B |
| LEU | O | 571 | 185.1 | 125.6 | 61.1 | 59 | B |
| VAL | N | 572 | 185.6 | 127.2 | 59.6 | 57 | B |
| VAL | CA | 572 | 184.2 | 127.6 | 59.4 | 55 | B |
| VAL | CB | 572 | 183.9 | 128.9 | 60.1 | 56 | B |
| VAL | CG1 | 572 | 182.5 | 129.4 | 59.8 | 55 | B |
| VAL | CG2 | 572 | 184.0 | 128.7 | 61.6 | 56 | B |
| VAL | C | 572 | 184.1 | 127.9 | 57.9 | 55 | B |
| VAL | O | 572 | 185.1 | 128.2 | 57.2 | 56 | B |
| LEU | N | 573 | 182.9 | 127.7 | 57.4 | 52 | B |
| LEU | CA | 573 | 182.6 | 128.0 | 56.0 | 50 | B |
| LEU | CB | 573 | 181.9 | 126.8 | 55.3 | 48 | B |
| LEU | CG | 573 | 181.3 | 127.1 | 53.9 | 47 | B |
| LEU | CD1 | 573 | 182.5 | 127.1 | 53.0 | 47 | B |
| LEU | CD2 | 573 | 180.3 | 126.1 | 53.6 | 47 | B |
| LEU | C | 573 | 181.7 | 129.2 | 56.0 | 50 | B |
| LEU | O | 573 | 180.5 | 129.2 | 56.4 | 49 | B |
| GLN | N | 574 | 182.2 | 130.4 | 55.5 | 49 | B |
| GLN | CA | 574 | 181.5 | 131.6 | 55.5 | 49 | B |
| GLN | CB | 574 | 182.4 | 132.7 | 54.9 | 50 | B |
| GLN | CG | 574 | 183.8 | 132.7 | 55.5 | 51 | B |
| GLN | CD | 574 | 183.8 | 132.7 | 57.1 | 52 | B |
| GLN | OE1 | 574 | 184.7 | 132.1 | 57.7 | 53 | B |
| GLN | NE2 | 574 | 182.8 | 133.4 | 57.7 | 52 | B |
| GLN | C | 574 | 180.2 | 131.6 | 54.6 | 49 | B |
| GLN | O | 574 | 180.0 | 132.5 | 53.8 | 50 | B |
| ARG | N | 575 | 179.3 | 130.8 | 55.0 | 49 | B |
| ARG | CA | 575 | 178.0 | 130.6 | 54.2 | 50 | B |
| ARG | CB | 575 | 177.0 | 129.8 | 55.1 | 50 | B |
| ARG | CG | 575 | 177.4 | 128.4 | 55.3 | 51 | B |
| ARG | CD | 575 | 176.3 | 127.6 | 56.0 | 51 | B |
| ARG | NE | 575 | 176.5 | 126.2 | 55.9 | 51 | B |
| ARG | CZ | 575 | 175.9 | 125.4 | 55.0 | 51 | B |
| ARG | NH1 | 575 | 175.0 | 126.0 | 54.2 | 51 | B |
| ARG | NH2 | 575 | 176.1 | 124.1 | 55.0 | 51 | B |
| ARG | C | 575 | 177.3 | 131.9 | 53.8 | 51 | B |
| ARG | O | 575 | 176.9 | 132.0 | 52.7 | 50 | B |
| GLU | N | 576 | 177.0 | 132.7 | 54.8 | 51 | B |
| GLU | CA | 576 | 176.3 | 134.0 | 54.6 | 52 | B |
| GLU | CB | 576 | 176.0 | 134.7 | 55.9 | 54 | B |
| GLU | CG | 576 | 175.7 | 133.8 | 57.1 | 56 | B |
| GLU | CD | 576 | 174.5 | 132.8 | 56.7 | 58 | B |
| GLU | OE1 | 576 | 173.4 | 133.2 | 56.3 | 59 | B |
| GLU | OE2 | 576 | 174.7 | 131.5 | 57.0 | 59 | B |
| GLU | C | 576 | 177.1 | 134.9 | 53.6 | 50 | B |
| GLU | O | 576 | 176.5 | 135.4 | 52.7 | 49 | B |
| LYS | N | 577 | 178.4 | 135.0 | 53.8 | 48 | B |
| LYS | CA | 577 | 179.2 | 135.8 | 53.0 | 47 | B |
| LYS | CB | 577 | 180.6 | 135.8 | 53.5 | 48 | B |
| LYS | CG | 577 | 181.1 | 137.2 | 53.8 | 49 | B |
| LYS | CD | 577 | 180.3 | 137.9 | 54.9 | 51 | B |
| LYS | CE | 577 | 180.1 | 139.4 | 54.6 | 53 | B |
| LYS | NZ | 577 | 179.0 | 139.7 | 53.5 | 53 | B |
| LYS | C | 577 | 179.1 | 135.2 | 51.5 | 45 | B |
| LYS | O | 577 | 178.7 | 136.0 | 50.6 | 45 | B |
| HIS | N | 578 | 179.3 | 133.9 | 51.3 | 42 | B |
| HIS | CA | 578 | 179.3 | 133.3 | 50.0 | 39 | B |
| HIS | CB | 578 | 179.5 | 131.8 | 50.1 | 35 | B |
| HIS | CG | 578 | 180.8 | 131.4 | 50.7 | 31 | B |
| HIS | CD2 | 578 | 181.3 | 130.2 | 51.2 | 31 | B |
| HIS | ND1 | 578 | 181.9 | 132.3 | 50.8 | 31 | B |
| HIS | CE1 | 578 | 182.9 | 131.7 | 51.4 | 30 | B |
| HIS | NE2 | 578 | 182.6 | 130.4 | 51.6 | 30 | B |
| HIS | C | 578 | 177.8 | 133.5 | 49.5 | 40 | B |
| HIS | O | 578 | 177.7 | 133.6 | 48.3 | 40 | B |
| PHE | N | 579 | 176.8 | 133.4 | 50.3 | 40 | B |
| PHE | CA | 579 | 175.5 | 133.5 | 49.9 | 41 | B |
| PHE | CB | 579 | 174.5 | 133.3 | 51.1 | 40 | B |
| PHE | CG | 579 | 173.1 | 133.5 | 50.7 | 41 | B |
| PHE | CD1 | 579 | 172.4 | 132.6 | 50.0 | 41 | B |
| PHE | CD2 | 579 | 172.5 | 134.8 | 51.0 | 42 | B |
| PHE | CE1 | 579 | 171.1 | 132.8 | 49.6 | 41 | B |
| PHE | CE2 | 579 | 171.2 | 135.0 | 50.6 | 42 | B |
| PHE | CZ | 579 | 170.5 | 134.1 | 49.9 | 42 | B |
| PHE | C | 579 | 175.1 | 134.9 | 49.3 | 43 | B |
| PHE | O | 579 | 174.4 | 134.9 | 48.2 | 43 | B |
| HIS | N | 580 | 175.5 | 135.9 | 49.9 | 46 | B |
| HIS | CA | 580 | 175.2 | 137.3 | 49.4 | 48 | B |
| HIS | CB | 580 | 175.7 | 138.3 | 50.4 | 52 | B |
| HIS | CG | 580 | 175.2 | 138.0 | 51.8 | 56 | B |
| HIS | CD2 | 580 | 174.0 | 137.7 | 52.3 | 57 | B |
| HIS | ND1 | 580 | 176.1 | 138.0 | 52.9 | 58 | B |
| HIS | CE1 | 580 | 175.5 | 137.7 | 54.0 | 58 | B |
| HIS | NE2 | 580 | 174.2 | 137.5 | 53.7 | 58 | B |
| HIS | C | 580 | 176.0 | 137.5 | 48.1 | 47 | B |
| HIS | O | 580 | 175.6 | 138.3 | 47.3 | 47 | B |
| TYR | N | 581 | 177.2 | 136.9 | 48.0 | 46 | B |
| TYR | CA | 581 | 178.0 | 137.0 | 46.8 | 45 | B |
| TYR | CB | 581 | 179.4 | 136.3 | 47.1 | 45 | B |
| TYR | CG | 581 | 180.3 | 136.3 | 45.9 | 46 | B |
| TYR | CD1 | 581 | 180.5 | 137.3 | 45.1 | 47 | B |
| TYR | CE1 | 581 | 181.4 | 137.3 | 44.0 | 47 | B |
| TYR | CD2 | 581 | 181.0 | 135.1 | 45.7 | 47 | B |
| TYR | CE2 | 581 | 181.8 | 135.0 | 44.6 | 46 | B |
| TYR | CZ | 581 | 182.0 | 136.0 | 43.7 | 47 | B |
| TYR | OH | 581 | 182.9 | 135.9 | 42.7 | 47 | B |
| TYR | C | 581 | 177.3 | 136.4 | 45.6 | 45 | B |
| TYR | O | 581 | 177.1 | 137.0 | 44.6 | 44 | B |
| LEU | N | 582 | 176.8 | 135.1 | 45.9 | 44 | B |
| LEU | CA | 582 | 176.2 | 134.3 | 44.9 | 43 | B |
| LEU | CB | 582 | 175.9 | 132.9 | 45.4 | 41 | B |
| LEU | CG | 582 | 177.2 | 132.1 | 45.6 | 40 | B |
| LEU | CD1 | 582 | 177.0 | 131.1 | 46.7 | 40 | B |
| LEU | CD2 | 582 | 177.6 | 131.5 | 44.3 | 40 | B |
| LEU | C | 582 | 174.8 | 135.0 | 44.5 | 45 | B |
| LEU | O | 582 | 174.5 | 135.0 | 43.3 | 45 | B |
| LYS | N | 583 | 174.2 | 135.5 | 45.5 | 48 | B |
| LYS | CA | 583 | 172.9 | 136.2 | 45.4 | 51 | B |
| LYS | CB | 583 | 172.4 | 136.5 | 46.8 | 53 | B |
| LYS | CG | 583 | 171.2 | 137.4 | 46.9 | 56 | B |
| LYS | CD | 583 | 171.1 | 138.1 | 48.3 | 58 | B |
| LYS | CE | 583 | 170.0 | 139.2 | 48.3 | 59 | B |
| LYS | NZ | 583 | 168.6 | 138.7 | 48.3 | 60 | B |
| LYS | C | 583 | 172.9 | 137.4 | 44.5 | 51 | B |
| LYS | O | 583 | 171.8 | 137.7 | 43.8 | 51 | B |
| ARG | N | 584 | 173.9 | 138.2 | 44.4 | 52 | B |
| ARG | CA | 584 | 173.9 | 139.5 | 43.6 | 53 | B |
| ARG | CB | 584 | 174.7 | 140.6 | 44.2 | SS | B |
| ARG | CG | 584 | 174.0 | 142.0 | 43.9 | 59 | B |
| ARG | CD | 584 | 174.9 | 143.2 | 43.9 | 62 | B |
| ARG | NE | 584 | 175.5 | 143.4 | 42.6 | 66 | B |

TABLE 5-continued

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| ARG | CZ | 584 | 176.6 | 144.2 | 42.4 | 67 | B |
| ARG | NH1 | 584 | 177.2 | 144.8 | 43.5 | 68 | B |
| ARG | NH2 | 584 | 177.2 | 144.3 | 41.2 | 67 | B |
| ARG | C | 584 | 174.5 | 139.1 | 42.2 | 51 | B |
| ARG | O | 584 | 174.1 | 139.7 | 41.2 | 50 | B |
| GLY | N | 585 | 175.5 | 138.3 | 42.2 | 50 | B |
| GLY | CA | 585 | 176.1 | 137.9 | 40.9 | 49 | B |
| GLY | C | 585 | 175.1 | 137.1 | 40.1 | 47 | B |
| GLY | O | 585 | 175.3 | 137.0 | 38.8 | 47 | B |
| LEU | N | 586 | 174.1 | 136.5 | 40.7 | 46 | B |
| LEU | CA | 586 | 173.1 | 135.8 | 39.9 | 45 | B |
| LEU | CB | 586 | 172.3 | 134.9 | 40.8 | 45 | B |
| LEU | CG | 586 | 171.2 | 134.0 | 40.2 | 45 | B |
| LEU | CD1 | 586 | 171.8 | 133.0 | 39.2 | 44 | B |
| LEU | CD2 | 586 | 170.5 | 133.2 | 41.3 | 44 | B |
| LEU | C | 586 | 172.2 | 136.9 | 39.2 | 44 | B |
| LEU | O | 586 | 171.5 | 136.5 | 38.2 | 45 | B |
| ARG | N | 587 | 172.3 | 138.1 | 39.6 | 44 | B |
| ARG | CA | 587 | 171.5 | 139.2 | 39.0 | 43 | B |
| ARG | CB | 587 | 170.7 | 140.0 | 40.0 | 44 | B |
| ARG | CG | 587 | 169.2 | 139.8 | 40.0 | 46 | B |
| ARG | CD | 587 | 168.8 | 138.3 | 40.3 | 48 | B |
| ARG | NE | 587 | 167.4 | 138.1 | 40.6 | 51 | B |
| ARG | CZ | 587 | 166.4 | 138.2 | 39.8 | 51 | B |
| ARG | NH1 | 587 | 166.6 | 138.4 | 38.5 | 51 | B |
| ARG | NH2 | 587 | 165.2 | 137.9 | 40.2 | 52 | B |
| ARG | C | 587 | 172.3 | 140.1 | 38.1 | 42 | B |
| ARG | O | 587 | 171.8 | 140.4 | 37.0 | 41 | B |
| GLN | N | 588 | 173.5 | 140.4 | 38.5 | 41 | B |
| GLN | CA | 588 | 174.3 | 141.3 | 37.8 | 41 | B |
| GLN | CB | 588 | 173.9 | 142.7 | 37.8 | 43 | B |
| GLN | CG | 588 | 174.0 | 143.3 | 39.2 | 47 | B |
| GLN | CD | 588 | 173.7 | 144.7 | 39.3 | 49 | B |
| GLN | OE1 | 588 | 173.1 | 145.3 | 38.3 | 49 | B |
| GLN | NE2 | 588 | 174.1 | 145.4 | 40.3 | 50 | B |
| GLN | C | 588 | 175.8 | 141.2 | 38.2 | 39 | B |
| GLN | O | 588 | 176.1 | 140.9 | 39.3 | 39 | B |
| LEU | N | 589 | 176.7 | 141.4 | 37.2 | 37 | B |
| LEU | CA | 589 | 178.1 | 141.3 | 37.4 | 35 | B |
| LEU | CB | 589 | 178.7 | 140.1 | 36.7 | 34 | B |
| LEU | CG | 589 | 178.0 | 138.7 | 37.0 | 32 | B |
| LEU | CD1 | 589 | 177.9 | 137.9 | 35.7 | 32 | B |
| LEU | CD2 | 589 | 178.7 | 138.0 | 38.1 | 31 | B |
| LEU | C | 589 | 178.8 | 142.5 | 36.8 | 34 | B |
| LEU | O | 589 | 178.2 | 143.1 | 35.8 | 33 | B |
| THR | N | 590 | 179.9 | 142.9 | 37.3 | 34 | B |
| THR | CA | 590 | 180.6 | 144.1 | 36.8 | 34 | B |
| THR | CB | 590 | 181.7 | 144.5 | 37.8 | 35 | B |
| THR | OG1 | 590 | 182.8 | 143.6 | 37.8 | 36 | B |
| THR | CG2 | 590 | 181.2 | 144.7 | 39.1 | 36 | B |
| THR | C | 590 | 181.3 | 143.7 | 35.5 | 35 | B |
| THR | O | 590 | 181.3 | 142.5 | 35.1 | 35 | B |
| ASP | N | 591 | 181.8 | 144.6 | 34.7 | 34 | B |
| ASP | CA | 591 | 182.4 | 144.4 | 33.4 | 34 | B |
| ASP | CB | 591 | 182.6 | 145.6 | 32.7 | 34 | B |
| ASP | CG | 591 | 183.5 | 146.6 | 33.4 | 36 | B |
| ASP | OD1 | 591 | 183.7 | 147.7 | 32.8 | 36 | B |
| ASP | OD2 | 591 | 184.0 | 146.3 | 34.5 | 36 | B |
| ASP | C | 591 | 183.7 | 143.5 | 33.5 | 35 | B |
| ASP | O | 591 | 184.2 | 143.2 | 32.5 | 37 | B |
| ALA | N | 592 | 184.1 | 143.2 | 34.7 | 34 | B |
| ALA | CA | 592 | 185.3 | 142.3 | 34.8 | 33 | B |
| ALA | CB | 592 | 185.7 | 142.2 | 36.2 | 33 | B |
| ALA | C | 592 | 184.9 | 141.0 | 34.2 | 33 | B |
| ALA | O | 592 | 185.8 | 140.2 | 33.8 | 33 | B |
| TYR | N | 593 | 183.6 | 140.7 | 34.1 | 32 | B |
| TYR | CA | 593 | 183.1 | 139.5 | 33.5 | 31 | B |
| TYR | CB | 593 | 181.8 | 139.1 | 34.3 | 31 | B |
| TYR | CG | 593 | 182.1 | 138.4 | 35.5 | 31 | B |
| TYR | CD1 | 593 | 182.2 | 139.0 | 36.8 | 32 | B |
| TYR | CE1 | 593 | 182.6 | 138.3 | 37.9 | 32 | B |
| TYR | CD2 | 593 | 182.4 | 137.0 | 35.5 | 31 | B |
| TYR | CE2 | 593 | 182.9 | 136.3 | 36.6 | 31 | B |
| TYR | CZ | 593 | 183.0 | 137.0 | 37.8 | 32 | B |
| TYR | OH | 593 | 183.4 | 136.4 | 38.9 | 32 | B |
| TYR | C | 593 | 182.8 | 139.6 | 32.0 | 32 | B |
| TYR | O | 593 | 182.2 | 138.7 | 31.5 | 32 | B |
| GLU | N | 594 | 183.2 | 140.7 | 31.4 | 31 | B |
| GLU | CA | 594 | 183.0 | 140.8 | 29.9 | 29 | B |
| GLU | CB | 594 | 183.6 | 142.1 | 29.4 | 30 | B |
| GLU | CG | 594 | 182.8 | 143.3 | 29.8 | 31 | B |
| GLU | CD | 594 | 183.5 | 144.6 | 29.3 | 33 | B |
| GLU | OE1 | 594 | 182.7 | 145.5 | 29.1 | 33 | B |
| GLU | OE2 | 594 | 184.7 | 144.6 | 29.2 | 34 | B |
| GLU | C | 594 | 183.7 | 139.6 | 29.3 | 27 | B |
| GLU | O | 594 | 183.1 | 139.0 | 28.4 | 27 | B |
| CYS | N | 595 | 184.8 | 139.1 | 29.8 | 25 | B |
| CYS | CA | 595 | 185.5 | 138.0 | 29.3 | 23 | B |
| CYS | CB | 595 | 186.9 | 137.8 | 30.0 | 22 | B |
| CYS | SG | 595 | 186.8 | 137.3 | 31.8 | 22 | B |
| CYS | C | 595 | 184.7 | 136.7 | 29.4 | 23 | B |
| CYS | O | 595 | 185.1 | 135.7 | 28.7 | 22 | B |
| LEU | N | 596 | 183.6 | 136.7 | 30.1 | 22 | B |
| LEU | CA | 596 | 182.8 | 135.5 | 30.3 | 21 | B |
| LEU | CB | 596 | 182.6 | 135.1 | 31.8 | 21 | B |
| LEU | CG | 596 | 183.8 | 134.2 | 32.3 | 21 | B |
| LEU | CD1 | 596 | 183.8 | 134.2 | 33.8 | 20 | B |
| LEU | CD2 | 596 | 183.7 | 132.8 | 31.9 | 20 | B |
| LEU | C | 596 | 181.4 | 135.9 | 29.7 | 22 | B |
| LEU | O | 596 | 180.4 | 135.2 | 29.9 | 22 | B |
| ASP | N | 597 | 181.4 | 136.8 | 28.7 | 24 | B |
| ASP | CA | 597 | 180.1 | 137.2 | 28.1 | 25 | B |
| ASP | CB | 597 | 180.4 | 138.4 | 27.2 | 24 | B |
| ASP | CG | 597 | 179.1 | 138.9 | 26.5 | 24 | B |
| ASP | OD1 | 597 | 178.0 | 138.9 | 27.1 | 24 | B |
| ASP | OD2 | 597 | 179.2 | 139.3 | 25.3 | 25 | B |
| ASP | C | 597 | 179.6 | 136.1 | 27.1 | 27 | B |
| ASP | O | 597 | 178.5 | 136.2 | 26.6 | 29 | B |
| ALA | N | 598 | 180.4 | 135.0 | 26.9 | 28 | B |
| ALA | CA | 598 | 180.0 | 133.9 | 26.1 | 28 | B |
| ALA | CB | 598 | 181.0 | 133.7 | 24.9 | 28 | B |
| ALA | C | 598 | 179.9 | 132.6 | 26.9 | 29 | B |
| ALA | O | 598 | 179.8 | 131.5 | 26.3 | 29 | B |
| SER | N | 599 | 179.8 | 132.7 | 28.2 | 30 | B |
| SER | CA | 599 | 179.7 | 131.6 | 29.1 | 29 | B |
| SER | CB | 599 | 181.0 | 131.3 | 29.8 | 28 | B |
| SER | OG | 599 | 182.1 | 131.3 | 28.8 | 28 | B |
| SER | C | 599 | 178.6 | 131.9 | 30.1 | 29 | B |
| SER | O | 599 | 178.7 | 131.6 | 31.3 | 30 | B |
| ARG | N | 600 | 177.6 | 132.6 | 29.7 | 29 | B |
| ARG | CA | 600 | 176.5 | 133.0 | 30.7 | 30 | B |
| ARG | CB | 600 | 175.7 | 134.2 | 30.2 | 30 | B |
| ARG | CG | 600 | 176.5 | 135.4 | 30.0 | 30 | B |
| ARG | CD | 600 | 175.7 | 136.6 | 29.4 | 31 | B |
| ARG | NE | 600 | 174.8 | 137.1 | 30.4 | 32 | B |
| ARG | CZ | 600 | 173.8 | 137.8 | 30.1 | 32 | B |
| ARG | NH1 | 600 | 173.5 | 138.2 | 28.8 | 33 | B |
| ARG | NH2 | 600 | 172.9 | 138.2 | 31.0 | 34 | B |
| ARG | C | 600 | 175.8 | 131.9 | 31.3 | 31 | B |
| ARG | O | 600 | 175.4 | 131.9 | 32.4 | 33 | B |
| PRO | N | 601 | 175.6 | 130.8 | 30.5 | 30 | B |
| PRO | CD | 601 | 175.5 | 130.6 | 29.1 | 30 | B |
| PRO | CA | 601 | 174.8 | 129.7 | 31.2 | 28 | B |
| PRO | CB | 601 | 174.5 | 128.7 | 30.1 | 28 | B |
| PRO | CG | 601 | 174.3 | 129.6 | 28.9 | 29 | B |
| PRO | C | 601 | 175.8 | 129.1 | 32.2 | 28 | B |
| PRO | O | 601 | 175.4 | 128.6 | 33.2 | 30 | B |
| TRP | N | 602 | 177.1 | 129.2 | 32.0 | 27 | B |
| TRP | CA | 602 | 178.0 | 128.7 | 33.0 | 26 | B |
| TRP | CB | 602 | 179.5 | 128.8 | 32.6 | 25 | B |
| TRP | CG | 602 | 179.9 | 127.8 | 31.7 | 26 | B |
| TRP | CD2 | 602 | 180.2 | 126.4 | 32.0 | 26 | B |
| TRP | CE2 | 602 | 180.6 | 125.8 | 30.9 | 26 | B |
| TRP | CE3 | 602 | 180.1 | 125.7 | 33.2 | 26 | B |

TABLE 5-continued

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| TRP | CD1 | 602 | 180.2 | 127.9 | 30.4 | 25 | B |
| TRP | NE1 | 602 | 180.6 | 126.7 | 29.9 | 26 | B |
| TRP | CZ2 | 602 | 181.0 | 124.4 | 30.8 | 26 | B |
| TRP | CZ3 | 602 | 180.5 | 124.3 | 33.2 | 26 | B |
| TRP | CH2 | 602 | 180.9 | 123.7 | 32.0 | 26 | B |
| TRP | C | 602 | 177.8 | 129.5 | 34.3 | 27 | B |
| TRP | O | 602 | 177.8 | 128.9 | 35.4 | 28 | B |
| LEU | N | 603 | 177.6 | 130.8 | 34.1 | 28 | B |
| LEU | CA | 603 | 177.4 | 131.6 | 35.3 | 28 | B |
| LEU | CB | 603 | 177.4 | 133.1 | 35.0 | 29 | B |
| LEU | CG | 603 | 178.9 | 133.5 | 34.7 | 30 | B |
| LEU | CD1 | 603 | 178.9 | 134.9 | 34.0 | 30 | B |
| LEU | CD2 | 603 | 179.7 | 133.5 | 36.0 | 29 | B |
| LEU | C | 603 | 176.1 | 131.2 | 36.1 | 29 | B |
| LEU | O | 603 | 176.1 | 131.3 | 37.3 | 30 | B |
| CYS | N | 604 | 175.1 | 130.8 | 35.3 | 28 | B |
| CYS | CA | 604 | 173.8 | 130.4 | 36.0 | 28 | B |
| CYS | CB | 604 | 172.7 | 130.2 | 35.0 | 28 | B |
| CYS | SG | 604 | 172.2 | 131.6 | 34.0 | 31 | B |
| CYS | C | 604 | 174.2 | 129.1 | 36.7 | 28 | B |
| CYS | O | 604 | 174.0 | 129.1 | 37.9 | 29 | B |
| TYR | N | 605 | 174.7 | 128.1 | 36.0 | 26 | B |
| TYR | CA | 605 | 175.1 | 126.9 | 36.7 | 24 | B |
| TYR | CB | 605 | 175.7 | 125.9 | 35.7 | 23 | B |
| TYR | CG | 605 | 176.3 | 124.7 | 36.4 | 23 | B |
| TYR | CD1 | 605 | 175.5 | 123.7 | 37.0 | 23 | B |
| TYR | CE1 | 605 | 176.1 | 122.7 | 37.7 | 22 | B |
| TYR | CD2 | 605 | 177.7 | 124.5 | 36.3 | 22 | B |
| TYR | CE2 | 605 | 178.3 | 123.5 | 37.0 | 22 | B |
| TYR | CZ | 605 | 177.5 | 122.5 | 37.6 | 22 | B |
| TYR | OH | 605 | 178.2 | 121.5 | 38.2 | 24 | B |
| TYR | C | 605 | 176.0 | 127.0 | 37.9 | 25 | B |
| TYR | O | 605 | 175.7 | 126.5 | 39.0 | 25 | B |
| TRP | N | 606 | 177.1 | 127.7 | 37.7 | 27 | B |
| TRP | CA | 606 | 178.1 | 127.9 | 38.8 | 27 | B |
| TRP | CB | 606 | 179.2 | 128.8 | 38.3 | 27 | B |
| TRP | CG | 606 | 180.2 | 128.3 | 37.2 | 27 | B |
| TRP | CD2 | 606 | 180.9 | 129.1 | 36.3 | 28 | B |
| TRP | CE2 | 606 | 181.7 | 128.2 | 35.5 | 28 | B |
| TRP | CE3 | 606 | 181.0 | 130.5 | 36.0 | 29 | B |
| TRP | CD1 | 606 | 180.5 | 127.0 | 37.0 | 27 | B |
| TRP | NE1 | 606 | 181.4 | 127.0 | 35.9 | 27 | B |
| TRP | CZ2 | 606 | 182.5 | 128.7 | 34.4 | 28 | B |
| TRP | CZ3 | 606 | 181.8 | 131.0 | 35.0 | 29 | B |
| TRP | CH2 | 606 | 182.6 | 130.1 | 34.2 | 28 | B |
| TRP | C | 606 | 177.4 | 128.4 | 40.0 | 28 | B |
| TRP | O | 606 | 177.5 | 127.9 | 41.1 | 28 | B |
| ILE | N | 607 | 176.6 | 129.5 | 39.8 | 30 | B |
| ILE | CA | 607 | 175.9 | 130.1 | 40.9 | 30 | B |
| ILE | CB | 607 | 175.4 | 131.6 | 40.6 | 29 | B |
| ILE | CG2 | 607 | 174.5 | 132.1 | 41.7 | 29 | B |
| ILE | CG1 | 607 | 176.6 | 132.4 | 40.3 | 28 | B |
| ILE | CD1 | 607 | 176.3 | 133.6 | 39.4 | 28 | B |
| ILE | C | 607 | 174.7 | 129.3 | 41.5 | 31 | B |
| ILE | O | 607 | 174.7 | 129.0 | 42.7 | 33 | B |
| LEU | N | 608 | 173.8 | 128.9 | 40.7 | 31 | B |
| LEU | CA | 608 | 172.6 | 128.0 | 41.1 | 29 | B |
| LEU | CB | 608 | 171.7 | 127.7 | 39.9 | 28 | B |
| LEU | CG | 608 | 170.4 | 128.4 | 39.9 | 28 | B |
| LEU | CD1 | 608 | 170.4 | 129.8 | 40.5 | 28 | B |
| LEU | CD2 | 608 | 169.9 | 128.5 | 38.4 | 29 | B |
| LEU | C | 608 | 173.1 | 126.8 | 41.7 | 30 | B |
| LEU | O | 608 | 172.4 | 126.2 | 42.5 | 33 | B |
| HIS | N | 609 | 174.3 | 126.3 | 41.3 | 30 | B |
| HIS | CA | 609 | 174.8 | 125.0 | 41.9 | 29 | B |
| HIS | CB | 609 | 175.7 | 124.3 | 41.0 | 27 | B |
| HIS | CG | 609 | 176.3 | 123.1 | 41.6 | 26 | B |
| HIS | CD2 | 609 | 177.6 | 122.7 | 41.8 | 26 | B |
| HIS | ND1 | 609 | 175.6 | 122.1 | 42.2 | 25 | B |
| HIS | CE1 | 609 | 176.4 | 121.1 | 42.7 | 26 | B |
| HIS | NE2 | 609 | 177.6 | 121.5 | 42.5 | 26 | B |
| HIS | C | 609 | 175.4 | 125.3 | 43.3 | 30 | B |

TABLE 5-continued

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| HIS | O | 609 | 175.4 | 124.5 | 44.2 | 32 | B |
| SER | N | 610 | 176.1 | 126.4 | 43.4 | 32 | B |
| SER | CA | 610 | 176.8 | 126.8 | 44.7 | 34 | B |
| SER | CB | 610 | 177.6 | 128.0 | 44.5 | 34 | B |
| SER | OG | 610 | 178.6 | 127.8 | 43.5 | 35 | B |
| SER | C | 610 | 175.7 | 127.0 | 45.8 | 34 | B |
| SER | O | 610 | 175.8 | 126.6 | 46.9 | 35 | B |
| LEU | N | 611 | 174.6 | 127.7 | 45.4 | 35 | B |
| LEU | CA | 611 | 173.5 | 127.9 | 46.3 | 36 | B |
| LEU | CB | 611 | 172.4 | 128.7 | 45.6 | 34 | B |
| LEU | CG | 611 | 172.8 | 130.1 | 45.2 | 33 | B |
| LEU | CD1 | 611 | 171.6 | 130.8 | 44.4 | 34 | B |
| LEU | CD2 | 611 | 173.1 | 130.9 | 46.4 | 33 | B |
| LEU | C | 611 | 173.0 | 126.6 | 46.7 | 38 | B |
| LEU | O | 611 | 172.8 | 126.3 | 47.9 | 40 | B |
| GLU | N | 612 | 172.8 | 125.7 | 45.7 | 39 | B |
| GLU | CA | 612 | 172.3 | 124.3 | 46.0 | 40 | B |
| GLU | CB | 612 | 172.3 | 123.5 | 44.7 | 42 | B |
| GLU | CG | 612 | 171.9 | 122.1 | 44.8 | 44 | B |
| GLU | CD | 612 | 172.6 | 121.2 | 43.8 | 45 | B |
| GLU | OE1 | 612 | 173.3 | 120.3 | 44.3 | 44 | B |
| GLU | OE2 | 612 | 172.4 | 121.4 | 42.6 | 45 | B |
| GLU | C | 612 | 173.1 | 123.6 | 47.0 | 41 | B |
| GLU | O | 612 | 172.6 | 123.0 | 48.0 | 42 | B |
| LEU | N | 613 | 174.5 | 123.7 | 46.9 | 41 | B |
| LEU | CA | 613 | 175.3 | 123.1 | 47.8 | 41 | B |
| LEU | CB | 613 | 176.8 | 123.2 | 47.4 | 40 | B |
| LEU | CG | 613 | 177.1 | 122.3 | 46.1 | 40 | B |
| LEU | CD1 | 613 | 178.4 | 122.9 | 45.5 | 40 | B |
| LEU | CD2 | 613 | 177.4 | 120.9 | 46.6 | 39 | B |
| LEU | C | 613 | 175.2 | 123.7 | 49.2 | 43 | B |
| LEU | O | 613 | 175.1 | 123.0 | 50.2 | 43 | B |
| LEU | N | 614 | 175.1 | 125.1 | 49.2 | 45 | B |
| LEU | CA | 614 | 174.9 | 125.8 | 50.4 | 47 | B |
| LEU | CB | 614 | 175.2 | 127.3 | 50.2 | 45 | B |
| LEU | CG | 614 | 176.6 | 127.7 | 49.7 | 45 | B |
| LEU | CD1 | 614 | 176.6 | 129.1 | 49.3 | 45 | B |
| LEU | CD2 | 614 | 177.7 | 127.5 | 50.7 | 44 | B |
| LEU | C | 614 | 173.5 | 125.8 | 51.0 | 49 | B |
| LEU | O | 614 | 173.1 | 126.5 | 51.8 | 48 | B |
| ASP | N | 615 | 172.7 | 124.9 | 50.4 | 52 | B |
| ASP | CA | 615 | 171.3 | 124.7 | 50.8 | 54 | B |
| ASP | CB | 615 | 171.2 | 124.1 | 52.2 | 55 | B |
| ASP | CG | 615 | 169.9 | 123.3 | 52.4 | 55 | B |
| ASP | OD1 | 615 | 169.0 | 123.4 | 51.6 | 55 | B |
| ASP | OD2 | 615 | 169.8 | 122.8 | 53.5 | 56 | B |
| ASP | C | 615 | 170.5 | 126.0 | 50.7 | 56 | B |
| ASP | O | 615 | 169.4 | 126.1 | 51.3 | 58 | B |
| GLU | N | 616 | 171.0 | 127.0 | 50.0 | 57 | B |
| GLU | CA | 616 | 170.2 | 128.2 | 49.9 | 59 | B |
| GLU | CB | 616 | 171.2 | 129.4 | 49.6 | 61 | B |
| GLU | CG | 616 | 172.4 | 129.4 | 50.6 | 64 | B |
| GLU | CD | 616 | 172.1 | 130.0 | 51.9 | 65 | B |
| GLU | OE1 | 616 | 171.0 | 130.4 | 52.2 | 67 | B |
| GLU | OE2 | 616 | 173.1 | 130.1 | 52.7 | 66 | B |
| GLU | C | 616 | 169.2 | 128.0 | 48.7 | 60 | B |
| GLU | O | 616 | 169.5 | 127.3 | 47.8 | 60 | B |
| PRO | N | 617 | 168.0 | 128.5 | 48.8 | 61 | B |
| PRO | CD | 617 | 167.7 | 129.5 | 49.9 | 62 | B |
| PRO | CA | 617 | 166.9 | 128.4 | 47.9 | 62 | B |
| PRO | CB | 617 | 165.7 | 128.9 | 48.7 | 62 | B |
| PRO | CG | 617 | 166.3 | 130.1 | 49.4 | 63 | B |
| PRO | C | 617 | 167.0 | 129.2 | 46.6 | 62 | B |
| PRO | O | 617 | 167.6 | 130.3 | 46.5 | 62 | B |
| ILE | N | 618 | 166.2 | 128.7 | 45.6 | 62 | B |
| ILE | CA | 618 | 166.1 | 129.3 | 44.3 | 62 | B |
| ILE | CB | 618 | 166.5 | 128.3 | 43.1 | 62 | B |
| ILE | CG2 | 618 | 166.1 | 128.9 | 41.7 | 62 | B |
| ILE | CG1 | 618 | 168.0 | 127.9 | 43.2 | 62 | B |
| ILE | CD1 | 618 | 168.4 | 127.0 | 44.3 | 62 | B |
| ILE | C | 618 | 164.6 | 129.8 | 44.0 | 61 | B |
| ILE | O | 618 | 163.8 | 129.1 | 43.5 | 61 | B |

TABLE 5-continued

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| PRO | N | 619 | 164.3 | 131.0 | 44.5 | 60 | B |
| PRO | CD | 619 | 165.2 | 131.9 | 45.2 | 60 | B |
| PRO | CA | 619 | 162.9 | 131.6 | 44.4 | 59 | B |
| PRO | CB | 619 | 163.2 | 133.0 | 44.7 | 59 | B |
| PRO | CG | 619 | 164.2 | 133.0 | 45.7 | 59 | B |
| PRO | C | 619 | 162.3 | 131.3 | 43.1 | 59 | B |
| PRO | O | 619 | 162.9 | 131.6 | 42.1 | 59 | B |
| GLN | N | 620 | 161.0 | 131.0 | 43.2 | 59 | B |
| GLN | CA | 620 | 160.2 | 130.7 | 42.0 | 60 | B |
| GLN | CB | 620 | 158.8 | 130.4 | 42.5 | 62 | B |
| GLN | CG | 620 | 158.7 | 129.5 | 43.8 | 64 | B |
| GLN | CD | 620 | 157.4 | 128.7 | 43.9 | 65 | B |
| GLN | OE1 | 620 | 156.4 | 128.9 | 43.2 | 66 | B |
| GLN | NE2 | 620 | 157.4 | 127.9 | 44.9 | 65 | B |
| GLN | C | 620 | 160.3 | 131.7 | 40.9 | 59 | B |
| GLN | O | 620 | 160.3 | 131.4 | 39.7 | 59 | B |
| ILE | N | 621 | 160.6 | 133.0 | 41.4 | 57 | B |
| ILE | CA | 621 | 160.7 | 134.1 | 40.4 | 56 | B |
| ILE | CB | 621 | 160.4 | 135.5 | 41.2 | 57 | B |
| ILE | CG2 | 621 | 160.4 | 136.6 | 40.1 | 57 | B |
| ILE | CG1 | 621 | 159.1 | 135.4 | 42.0 | 58 | B |
| ILE | CD1 | 621 | 159.2 | 134.7 | 43.4 | 58 | B |
| ILE | C | 621 | 162.1 | 134.2 | 39.7 | 54 | B |
| ILE | O | 621 | 162.2 | 134.5 | 38.6 | 52 | B |
| VAL | N | 622 | 163.1 | 134.0 | 40.5 | 53 | B |
| VAL | CA | 622 | 164.4 | 134.1 | 39.9 | 52 | B |
| VAL | CB | 622 | 165.6 | 134.1 | 41.0 | 52 | B |
| VAL | CG1 | 622 | 165.8 | 132.7 | 41.6 | 52 | B |
| VAL | CG2 | 622 | 166.8 | 134.6 | 40.3 | 53 | B |
| VAL | C | 622 | 164.6 | 132.9 | 39.0 | 52 | B |
| VAL | O | 622 | 165.2 | 133.0 | 37.9 | 52 | B |
| ALA | N | 623 | 164.0 | 131.7 | 39.4 | 51 | B |
| ALA | CA | 623 | 164.0 | 130.5 | 38.6 | 50 | B |
| ALA | CB | 623 | 163.3 | 129.4 | 39.3 | 49 | B |
| ALA | C | 623 | 163.4 | 130.8 | 37.2 | 50 | B |
| ALA | O | 623 | 164.0 | 130.4 | 36.2 | 51 | B |
| THR | N | 624 | 162.2 | 131.3 | 37.2 | 49 | B |
| THR | CA | 624 | 161.6 | 131.6 | 35.9 | 47 | B |
| THR | CB | 624 | 160.2 | 132.4 | 36.1 | 46 | B |
| THR | OG1 | 624 | 159.4 | 131.5 | 36.9 | 47 | B |
| THR | CG2 | 624 | 159.6 | 132.6 | 34.8 | 46 | B |
| THR | C | 624 | 162.5 | 132.5 | 35.0 | 47 | B |
| THR | O | 624 | 162.6 | 132.2 | 33.8 | 48 | B |
| ASP | N | 625 | 163.1 | 133.5 | 35.7 | 47 | B |
| ASP | CA | 625 | 164.0 | 134.4 | 34.9 | 46 | B |
| ASP | CB | 625 | 164.5 | 135.5 | 35.9 | 49 | B |
| ASP | CG | 625 | 163.5 | 136.4 | 36.5 | 50 | B |
| ASP | OD1 | 625 | 162.5 | 136.8 | 35.8 | 49 | B |
| ASP | OD2 | 625 | 163.6 | 136.9 | 37.7 | 50 | B |
| ASP | C | 625 | 165.1 | 133.6 | 34.3 | 44 | B |
| ASP | O | 625 | 165.4 | 133.7 | 33.1 | 43 | B |
| VAL | N | 626 | 165.7 | 132.8 | 35.2 | 41 | B |
| VAL | CA | 626 | 166.8 | 131.9 | 34.7 | 40 | B |
| VAL | CB | 626 | 167.2 | 130.9 | 35.7 | 40 | B |
| VAL | CG1 | 626 | 168.2 | 130.0 | 35.1 | 40 | B |
| VAL | CG2 | 626 | 167.9 | 131.6 | 36.9 | 40 | B |
| VAL | C | 626 | 166.2 | 131.1 | 33.5 | 41 | B |
| VAL | O | 626 | 166.9 | 131.1 | 32.4 | 43 | B |
| CYS | N | 627 | 165.0 | 130.6 | 33.6 | 40 | B |
| CYS | CA | 627 | 164.4 | 129.8 | 32.6 | 39 | B |
| CYS | CB | 627 | 163.1 | 129.1 | 33.1 | 38 | B |
| CYS | SG | 627 | 163.3 | 127.7 | 34.2 | 39 | B |
| CYS | C | 627 | 164.2 | 130.5 | 31.3 | 40 | B |
| CYS | O | 627 | 164.5 | 130.0 | 30.2 | 40 | B |
| GLN | N | 628 | 163.7 | 131.7 | 31.4 | 40 | B |
| GLN | CA | 628 | 163.4 | 132.5 | 30.3 | 40 | B |
| GLN | CB | 628 | 162.5 | 133.7 | 30.6 | 42 | B |
| GLN | CG | 628 | 161.1 | 133.4 | 31.1 | 44 | B |
| GLN | CD | 628 | 160.3 | 134.6 | 31.5 | 45 | B |
| GLN | OE1 | 628 | 160.5 | 135.7 | 31.0 | 44 | B |
| GLN | NE2 | 628 | 159.3 | 134.4 | 32.4 | 45 | B |
| GLN | C | 628 | 164.7 | 133.0 | 29.6 | 40 | B |

TABLE 5-continued

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| GLN | O | 628 | 164.7 | 133.2 | 28.4 | 40 | B |
| PHE | N | 629 | 165.7 | 133.2 | 30.4 | 39 | B |
| PHE | CA | 629 | 167.0 | 133.6 | 29.9 | 37 | B |
| PHE | CB | 629 | 168.0 | 134.1 | 31.0 | 37 | B |
| PHE | CG | 629 | 169.3 | 134.4 | 30.6 | 37 | B |
| PHE | CD1 | 629 | 169.5 | 135.4 | 29.6 | 37 | B |
| PHE | CD2 | 629 | 170.4 | 133.7 | 31.0 | 36 | B |
| PHE | CE1 | 629 | 170.8 | 135.7 | 29.1 | 37 | B |
| PHE | CE2 | 629 | 171.7 | 133.9 | 30.5 | 36 | B |
| PHE | CZ | 629 | 171.9 | 134.9 | 29.5 | 37 | B |
| PHE | C | 629 | 167.7 | 132.5 | 29.1 | 37 | B |
| PHE | O | 629 | 168.2 | 132.8 | 28.0 | 36 | B |
| LEU | N | 630 | 167.7 | 131.3 | 29.6 | 36 | B |
| LEU | CA | 630 | 168.2 | 130.1 | 29.0 | 35 | B |
| LEU | CB | 630 | 168.3 | 128.9 | 29.9 | 33 | B |
| LEU | CG | 630 | 169.3 | 129.2 | 31.1 | 31 | B |
| LEU | CD1 | 630 | 169.3 | 128.0 | 32.0 | 30 | B |
| LEU | CD2 | 630 | 170.7 | 129.5 | 30.6 | 31 | B |
| LEU | C | 630 | 167.5 | 129.8 | 27.7 | 36 | B |
| LEU | O | 630 | 168.1 | 129.2 | 26.7 | 38 | B |
| GLU | N | 631 | 166.3 | 130.3 | 27.5 | 37 | B |
| GLU | CA | 631 | 165.5 | 130.1 | 26.3 | 39 | B |
| GLU | CB | 631 | 164.1 | 130.4 | 26.5 | 43 | B |
| GLU | CG | 631 | 163.4 | 129.6 | 27.6 | 47 | B |
| GLU | CD | 631 | 161.9 | 129.8 | 27.5 | 51 | B |
| GLU | OE1 | 631 | 161.3 | 130.5 | 28.3 | 52 | B |
| GLU | OE2 | 631 | 161.2 | 129.1 | 26.6 | 53 | B |
| GLU | C | 631 | 166.0 | 131.0 | 25.2 | 38 | B |
| GLU | O | 631 | 165.9 | 130.7 | 24.0 | 37 | B |
| LEU | N | 632 | 166.6 | 132.2 | 25.6 | 37 | B |
| LEU | CA | 632 | 167.1 | 133.1 | 24.7 | 36 | B |
| LEU | CB | 632 | 167.2 | 134.5 | 25.4 | 35 | B |
| LEU | CG | 632 | 165.9 | 135.2 | 25.8 | 35 | B |
| LEU | CD1 | 632 | 166.3 | 136.5 | 26.5 | 35 | B |
| LEU | CD2 | 632 | 165.0 | 135.5 | 24.7 | 35 | B |
| LEU | C | 632 | 168.5 | 132.6 | 24.2 | 36 | B |
| LEU | O | 632 | 168.9 | 132.9 | 23.1 | 36 | B |
| CYS | N | 633 | 169.2 | 131.9 | 25.1 | 36 | B |
| CYS | CA | 633 | 170.5 | 131.4 | 24.8 | 35 | B |
| CYS | CB | 633 | 171.2 | 130.9 | 26.1 | 35 | B |
| CYS | SG | 633 | 171.5 | 132.2 | 27.2 | 36 | B |
| CYS | C | 633 | 170.3 | 130.2 | 23.8 | 35 | B |
| CYS | O | 633 | 171.1 | 130.0 | 22.9 | 36 | B |
| GLN | N | 634 | 169.2 | 129.4 | 24.1 | 36 | B |
| GLN | CA | 634 | 168.9 | 128.2 | 23.3 | 35 | B |
| GLN | CB | 634 | 167.6 | 127.6 | 23.7 | 34 | B |
| GLN | CG | 634 | 167.2 | 126.3 | 23.0 | 34 | B |
| GLN | CD | 634 | 166.3 | 125.4 | 23.7 | 34 | B |
| GLN | OE1 | 634 | 165.2 | 125.8 | 24.1 | 35 | B |
| GLN | NE2 | 634 | 166.7 | 124.2 | 24.0 | 33 | B |
| GLN | C | 634 | 168.8 | 128.5 | 21.8 | 35 | B |
| GLN | O | 634 | 168.3 | 129.6 | 21.4 | 36 | B |
| SER | N | 635 | 169.3 | 127.6 | 21.0 | 36 | B |
| SER | CA | 635 | 169.4 | 127.8 | 19.5 | 36 | B |
| SER | CB | 635 | 170.7 | 127.4 | 19.0 | 34 | B |
| SER | OG | 635 | 170.7 | 127.2 | 17.6 | 34 | B |
| SER | C | 635 | 168.3 | 127.1 | 18.8 | 37 | B |
| SER | O | 635 | 167.8 | 126.1 | 19.2 | 37 | B |
| PRO | N | 636 | 167.8 | 127.6 | 17.6 | 38 | B |
| PRO | CD | 636 | 168.2 | 129.0 | 17.1 | 39 | B |
| PRO | CA | 636 | 166.8 | 127.0 | 16.8 | 39 | B |
| PRO | CB | 636 | 166.5 | 128.1 | 15.8 | 40 | B |
| PRO | CG | 636 | 167.8 | 128.9 | 15.7 | 40 | B |
| PRO | C | 636 | 167.4 | 125.8 | 16.1 | 40 | B |
| PRO | O | 636 | 166.8 | 125.3 | 15.1 | 40 | B |
| ASP | N | 637 | 168.6 | 125.4 | 16.4 | 41 | B |
| ASP | CA | 637 | 169.2 | 124.3 | 15.8 | 40 | B |
| ASP | CB | 637 | 170.4 | 124.8 | 15.0 | 43 | B |
| ASP | CG | 637 | 170.1 | 125.7 | 13.9 | 45 | B |
| ASP | OD1 | 637 | 168.9 | 125.6 | 13.3 | 47 | B |
| ASP | OD2 | 637 | 170.9 | 126.6 | 13.5 | 46 | B |
| ASP | C | 637 | 169.7 | 123.4 | 16.9 | 39 | B |

TABLE 5-continued

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| ASP | O | 637 | 170.5 | 122.5 | 16.8 | 40 | B |
| GLY | N | 638 | 169.0 | 123.6 | 18.1 | 38 | B |
| GLY | CA | 638 | 169.3 | 122.8 | 19.3 | 35 | B |
| GLY | C | 638 | 170.6 | 123.3 | 20.0 | 34 | B |
| GLY | O | 638 | 171.4 | 124.0 | 19.4 | 36 | B |
| GLY | N | 639 | 170.7 | 123.0 | 21.3 | 32 | B |
| GLY | CA | 639 | 171.9 | 123.4 | 22.0 | 30 | B |
| GLY | C | 639 | 171.7 | 124.9 | 22.4 | 30 | B |
| GLY | O | 639 | 170.8 | 125.6 | 22.0 | 28 | B |
| PHE | N | 640 | 172.6 | 125.3 | 23.3 | 29 | B |
| PHE | CA | 640 | 172.5 | 126.7 | 23.8 | 29 | B |
| PHE | CB | 640 | 172.3 | 126.7 | 25.4 | 29 | B |
| PHE | CG | 640 | 171.1 | 125.9 | 25.8 | 29 | B |
| PHE | CD1 | 640 | 171.1 | 124.5 | 25.9 | 29 | B |
| PHE | CD2 | 640 | 170.0 | 126.6 | 26.2 | 29 | B |
| PHE | CE1 | 640 | 170.0 | 123.8 | 26.3 | 29 | B |
| PHE | CE2 | 640 | 168.8 | 125.9 | 26.6 | 29 | B |
| PHE | CZ | 640 | 168.9 | 124.5 | 26.6 | 29 | B |
| PHE | C | 640 | 173.8 | 127.4 | 23.5 | 29 | B |
| PHE | O | 640 | 174.9 | 126.8 | 23.4 | 30 | B |
| GLY | N | 641 | 173.6 | 128.7 | 23.3 | 27 | B |
| GLY | CA | 641 | 174.8 | 129.6 | 23.0 | 27 | B |
| GLY | C | 641 | 175.3 | 130.1 | 24.3 | 27 | B |
| GLY | O | 641 | 174.8 | 129.8 | 25.4 | 28 | B |
| GLY | N | 642 | 176.4 | 130.8 | 24.3 | 28 | B |
| GLY | CA | 642 | 177.0 | 131.3 | 25.5 | 27 | B |
| GLY | C | 642 | 176.3 | 132.6 | 26.0 | 28 | B |
| GLY | O | 642 | 176.7 | 133.2 | 27.1 | 28 | B |
| GLY | N | 643 | 175.2 | 133.0 | 25.4 | 27 | B |
| GLY | CA | 643 | 174.5 | 134.2 | 25.7 | 27 | B |
| GLY | C | 643 | 173.4 | 134.3 | 24.7 | 29 | B |
| GLY | O | 643 | 173.5 | 133.7 | 23.6 | 29 | B |
| PRO | N | 644 | 172.4 | 135.2 | 24.9 | 29 | B |
| PRO | CD | 644 | 172.2 | 136.1 | 26.0 | 29 | B |
| PRO | CA | 644 | 171.3 | 135.3 | 23.9 | 29 | B |
| PRO | CB | 644 | 170.5 | 136.5 | 24.4 | 28 | B |
| PRO | CG | 644 | 170.7 | 136.5 | 25.9 | 29 | B |
| PRO | C | 644 | 171.8 | 135.6 | 22.5 | 31 | B |
| PRO | O | 644 | 172.6 | 136.6 | 22.3 | 33 | B |
| GLY | N | 645 | 171.5 | 134.8 | 21.6 | 33 | B |
| GLY | CA | 645 | 171.9 | 135.0 | 20.2 | 33 | B |
| GLY | C | 645 | 173.2 | 134.4 | 19.7 | 34 | B |
| GLY | O | 645 | 173.6 | 134.5 | 18.5 | 35 | B |
| GLN | N | 646 | 173.9 | 133.7 | 20.6 | 33 | B |
| GLN | CA | 646 | 175.1 | 133.0 | 20.2 | 32 | B |
| GLN | CB | 646 | 176.1 | 133.0 | 21.4 | 32 | B |
| GLN | CG | 646 | 176.5 | 134.4 | 21.8 | 31 | B |
| GLN | CD | 646 | 177.2 | 134.5 | 23.1 | 31 | B |
| GLN | OE1 | 646 | 176.9 | 135.4 | 23.9 | 31 | B |
| GLN | NE2 | 646 | 178.1 | 133.5 | 23.4 | 30 | B |
| GLN | C | 646 | 174.9 | 131.6 | 19.7 | 32 | B |
| GLN | O | 646 | 173.9 | 131.0 | 20.0 | 32 | B |
| TYR | N | 647 | 175.7 | 131.2 | 18.7 | 31 | B |
| TYR | CA | 647 | 175.6 | 129.9 | 18.1 | 30 | B |
| TYR | CB | 647 | 176.8 | 129.7 | 17.1 | 30 | B |
| TYR | CG | 647 | 176.8 | 130.7 | 16.0 | 30 | B |
| TYR | CD1 | 647 | 177.9 | 130.8 | 15.2 | 31 | B |
| TYR | CE1 | 647 | 177.9 | 131.6 | 14.0 | 31 | B |
| TYR | CD2 | 647 | 175.7 | 131.4 | 15.6 | 30 | B |
| TYR | CE2 | 647 | 175.7 | 132.2 | 14.5 | 30 | B |
| TYR | CZ | 647 | 176.8 | 132.3 | 13.7 | 31 | B |
| TYR | OH | 647 | 176.8 | 133.0 | 12.6 | 33 | B |
| TYR | C | 647 | 175.8 | 128.9 | 19.2 | 30 | B |
| TYR | O | 647 | 176.5 | 129.1 | 20.2 | 31 | B |
| PRO | N | 648 | 175.1 | 127.8 | 19.1 | 30 | B |
| PRO | CD | 648 | 174.2 | 127.3 | 18.0 | 31 | B |
| PRO | CA | 648 | 175.2 | 126.7 | 20.1 | 29 | B |
| PRO | CB | 648 | 174.1 | 125.7 | 19.7 | 30 | B |
| PRO | CG | 648 | 174.2 | 125.8 | 18.2 | 31 | B |
| PRO | C | 648 | 176.6 | 126.2 | 20.3 | 28 | B |
| PRO | O | 648 | 177.3 | 126.0 | 19.4 | 29 | B |
| HIS | N | 649 | 176.9 | 125.8 | 21.5 | 25 | B |

TABLE 5-continued

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| HIS | CA | 649 | 178.2 | 125.3 | 21.8 | 23 | B |
| HIS | CB | 649 | 179.1 | 126.5 | 22.2 | 22 | B |
| HIS | CG | 649 | 180.5 | 126.1 | 22.6 | 20 | B |
| HIS | CD2 | 649 | 181.7 | 126.4 | 21.9 | 19 | B |
| HIS | ND1 | 649 | 180.9 | 125.5 | 23.7 | 19 | B |
| HIS | CE1 | 649 | 182.2 | 125.4 | 23.8 | 19 | B |
| HIS | NE2 | 649 | 182.7 | 125.9 | 22.7 | 19 | B |
| HIS | C | 649 | 178.0 | 124.3 | 23.0 | 25 | B |
| HIS | O | 649 | 177.1 | 124.6 | 23.8 | 26 | B |
| LEU | N | 650 | 178.7 | 123.2 | 23.0 | 24 | B |
| LEU | CA | 650 | 178.5 | 122.2 | 24.0 | 24 | B |
| LEU | CB | 650 | 179.2 | 120.9 | 23.7 | 23 | B |
| LEU | CG | 650 | 178.6 | 119.9 | 22.7 | 22 | B |
| LEU | CD1 | 650 | 179.6 | 118.8 | 22.4 | 22 | B |
| LEU | CD2 | 650 | 177.3 | 119.3 | 23.3 | 21 | B |
| LEU | C | 650 | 178.8 | 122.6 | 25.5 | 25 | B |
| LEU | O | 650 | 178.1 | 122.1 | 26.4 | 26 | B |
| ALA | N | 651 | 179.7 | 123.5 | 25.7 | 24 | B |
| ALA | CA | 651 | 180.0 | 123.9 | 27.1 | 24 | B |
| ALA | CB | 651 | 181.3 | 124.7 | 27.2 | 24 | B |
| ALA | C | 651 | 178.8 | 124.7 | 27.7 | 25 | B |
| ALA | O | 651 | 178.3 | 124.4 | 28.8 | 25 | B |
| PRO | N | 652 | 178.3 | 125.7 | 26.9 | 25 | B |
| PRO | CD | 652 | 178.9 | 126.4 | 25.8 | 24 | B |
| PRO | CA | 652 | 177.1 | 126.4 | 27.4 | 25 | B |
| PRO | CB | 652 | 176.9 | 127.5 | 26.4 | 25 | B |
| PRO | CG | 652 | 178.3 | 127.8 | 25.9 | 24 | B |
| PRO | C | 652 | 175.9 | 125.4 | 27.5 | 26 | B |
| PRO | O | 652 | 175.0 | 125.6 | 28.3 | 28 | B |
| THR | N | 653 | 175.8 | 124.5 | 26.5 | 26 | B |
| THR | CA | 653 | 174.7 | 123.5 | 26.5 | 26 | B |
| THR | CB | 653 | 174.8 | 122.6 | 25.3 | 26 | B |
| THR | OG1 | 653 | 174.7 | 123.4 | 24.1 | 27 | B |
| THR | CG2 | 653 | 173.7 | 121.7 | 25.2 | 26 | B |
| THR | C | 653 | 174.7 | 122.6 | 27.7 | 26 | B |
| THR | O | 653 | 173.7 | 122.3 | 28.3 | 27 | B |
| TYR | N | 654 | 175.9 | 122.2 | 28.2 | 25 | B |
| TYR | CA | 654 | 175.9 | 121.3 | 29.4 | 24 | B |
| TYR | CB | 654 | 177.4 | 120.8 | 29.5 | 24 | B |
| TYR | CG | 654 | 177.7 | 120.4 | 30.9 | 24 | B |
| TYR | CD1 | 654 | 177.4 | 119.1 | 31.4 | 23 | B |
| TYR | CE1 | 654 | 177.8 | 118.6 | 32.6 | 24 | B |
| TYR | CD2 | 654 | 178.4 | 121.2 | 31.8 | 24 | B |
| TYR | CE2 | 654 | 178.8 | 120.8 | 33.1 | 24 | B |
| TYR | CZ | 654 | 178.5 | 119.5 | 33.5 | 24 | B |
| TYR | OH | 654 | 178.9 | 119.0 | 34.7 | 25 | B |
| TYR | C | 654 | 175.5 | 122.2 | 30.6 | 25 | B |
| TYR | O | 654 | 174.8 | 121.7 | 31.4 | 26 | B |
| ALA | N | 655 | 176.0 | 123.4 | 30.6 | 26 | B |
| ALA | CA | 655 | 175.7 | 124.3 | 31.7 | 26 | B |
| ALA | CB | 655 | 176.5 | 125.6 | 31.5 | 25 | B |
| ALA | C | 655 | 174.2 | 124.7 | 31.7 | 26 | B |
| ALA | O | 655 | 173.6 | 124.7 | 32.8 | 26 | B |
| ALA | N | 656 | 173.6 | 125.0 | 30.6 | 27 | B |
| ALA | CA | 656 | 172.2 | 125.3 | 30.5 | 29 | B |
| ALA | CB | 656 | 171.8 | 125.7 | 29.2 | 28 | B |
| ALA | C | 656 | 171.4 | 124.1 | 31.0 | 31 | B |
| ALA | O | 656 | 170.6 | 124.3 | 31.9 | 33 | B |
| VAL | N | 657 | 171.6 | 123.0 | 30.4 | 32 | B |
| VAL | CA | 657 | 170.9 | 121.8 | 30.8 | 32 | B |
| VAL | CB | 657 | 171.2 | 120.6 | 30.0 | 32 | B |
| VAL | CG1 | 657 | 170.5 | 119.4 | 30.4 | 32 | B |
| VAL | CG2 | 657 | 170.9 | 120.8 | 28.5 | 30 | B |
| VAL | C | 657 | 171.0 | 121.6 | 32.3 | 32 | B |
| VAL | O | 657 | 170.0 | 121.4 | 33.0 | 34 | B |
| ASN | N | 658 | 172.3 | 121.6 | 32.9 | 32 | B |
| ASN | CA | 658 | 172.5 | 121.4 | 34.3 | 31 | B |
| ASN | CB | 658 | 174.0 | 121.4 | 34.7 | 31 | B |
| ASN | CG | 658 | 174.6 | 120.1 | 34.8 | 31 | B |
| ASN | OD1 | 658 | 174.1 | 119.1 | 34.3 | 33 | B |
| ASN | ND2 | 658 | 175.7 | 120.0 | 35.6 | 32 | B |
| ASN | C | 658 | 171.7 | 122.4 | 35.1 | 31 | B |

TABLE 5-continued

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| ASN | O | 658 | 171.1 | 122.0 | 36.1 | 31 | B |
| ALA | N | 659 | 171.8 | 123.6 | 34.7 | 31 | B |
| ALA | CA | 659 | 171.1 | 124.7 | 35.4 | 31 | B |
| ALA | CB | 659 | 171.3 | 126.1 | 34.8 | 30 | B |
| ALA | C | 659 | 169.6 | 124.3 | 35.5 | 31 | B |
| ALA | O | 659 | 169.0 | 124.2 | 36.6 | 31 | B |
| LEU | N | 660 | 169.0 | 124.2 | 34.3 | 31 | B |
| LEU | CA | 660 | 167.6 | 123.8 | 34.2 | 31 | B |
| LEU | CB | 660 | 167.3 | 123.5 | 32.7 | 30 | B |
| LEU | CG | 660 | 167.3 | 124.8 | 31.8 | 29 | B |
| LEU | CD1 | 660 | 167.1 | 124.4 | 30.4 | 29 | B |
| LEU | CD2 | 660 | 166.2 | 125.7 | 32.3 | 29 | B |
| LEU | C | 660 | 167.2 | 122.7 | 35.0 | 33 | B |
| LEU | O | 660 | 166.1 | 122.6 | 35.6 | 35 | B |
| CYS | N | 661 | 168.1 | 121.7 | 35.3 | 35 | B |
| CYS | CA | 661 | 167.8 | 120.5 | 36.1 | 36 | B |
| CYS | CB | 661 | 168.7 | 119.4 | 35.7 | 35 | B |
| CYS | SG | 661 | 168.3 | 118.6 | 34.2 | 34 | B |
| CYS | C | 661 | 167.9 | 120.8 | 37.6 | 37 | B |
| CYS | O | 661 | 167.2 | 120.2 | 38.4 | 37 | B |
| ILE | N | 662 | 168.7 | 121.8 | 38.0 | 38 | B |
| ILE | CA | 662 | 168.9 | 122.2 | 39.4 | 39 | B |
| ILE | CB | 662 | 170.1 | 123.1 | 39.6 | 38 | B |
| ILE | CG2 | 662 | 170.2 | 123.4 | 41.1 | 39 | B |
| ILE | CG1 | 662 | 171.4 | 122.4 | 39.2 | 38 | B |
| ILE | CD1 | 662 | 172.6 | 123.2 | 39.5 | 37 | B |
| ILE | C | 662 | 167.5 | 122.8 | 39.8 | 39 | B |
| ILE | O | 662 | 167.0 | 122.6 | 40.9 | 40 | B |
| ILE | N | 663 | 167.0 | 123.6 | 38.9 | 39 | B |
| ILE | CA | 663 | 165.7 | 124.3 | 39.1 | 39 | B |
| ILE | CB | 663 | 165.5 | 125.3 | 38.0 | 37 | B |
| ILE | CG2 | 663 | 164.1 | 125.9 | 38.0 | 37 | B |
| ILE | CG1 | 663 | 166.5 | 126.5 | 38.2 | 36 | B |
| ILE | CD1 | 663 | 166.6 | 127.4 | 37.0 | 34 | B |
| ILE | C | 663 | 164.6 | 123.2 | 39.0 | 41 | B |
| ILE | O | 663 | 163.6 | 123.3 | 39.7 | 42 | B |
| GLY | N | 664 | 164.9 | 122.1 | 38.3 | 41 | B |
| GLY | CA | 664 | 163.9 | 121.0 | 36.2 | 42 | B |
| GLY | C | 664 | 162.4 | 121.2 | 38.2 | 42 | B |
| GLY | O | 664 | 161.7 | 120.4 | 38.8 | 44 | B |
| THR | N | 665 | 161.9 | 122.2 | 37.5 | 42 | B |
| THR | CA | 665 | 160.5 | 122.4 | 37.4 | 42 | B |
| THR | CB | 665 | 160.1 | 123.9 | 37.6 | 41 | B |
| THR | OG1 | 665 | 160.3 | 124.6 | 36.4 | 41 | B |
| THR | CG2 | 665 | 160.9 | 124.5 | 38.7 | 41 | B |
| THR | C | 665 | 160.0 | 122.0 | 36.1 | 43 | B |
| THR | O | 665 | 160.8 | 121.8 | 35.1 | 43 | B |
| GLU | N | 666 | 158.7 | 121.8 | 35.9 | 45 | B |
| GLU | CA | 666 | 158.2 | 121.4 | 34.6 | 47 | B |
| GLU | CB | 666 | 156.7 | 120.9 | 34.7 | 49 | B |
| GLU | CG | 666 | 156.6 | 119.3 | 35.0 | 51 | B |
| GLU | CD | 666 | 157.4 | 118.9 | 36.3 | 53 | B |
| GLU | OE1 | 666 | 157.5 | 119.6 | 37.3 | 54 | B |
| GLU | OE2 | 666 | 157.9 | 117.7 | 36.3 | 53 | B |
| GLU | C | 666 | 158.3 | 122.5 | 33.7 | 47 | B |
| GLU | O | 666 | 158.1 | 122.3 | 32.5 | 48 | B |
| GLU | N | 667 | 158.7 | 123.7 | 34.2 | 46 | B |
| GLU | CA | 667 | 158.9 | 124.8 | 33.3 | 46 | B |
| GLU | CB | 667 | 158.7 | 126.1 | 34.1 | 48 | B |
| GLU | CG | 667 | 158.8 | 127.4 | 33.3 | 49 | B |
| GLU | CD | 667 | 159.2 | 128.6 | 34.1 | 50 | B |
| GLU | OE1 | 667 | 159.2 | 128.5 | 35.3 | 49 | B |
| GLU | OE2 | 667 | 159.5 | 129.6 | 33.4 | 51 | B |
| GLU | C | 667 | 160.4 | 124.8 | 32.8 | 45 | B |
| GLU | O | 667 | 160.6 | 125.1 | 31.7 | 45 | B |
| ALA | N | 668 | 161.3 | 124.5 | 33.7 | 42 | B |
| ALA | CA | 668 | 162.7 | 124.4 | 33.4 | 40 | B |
| ALA | CB | 668 | 163.5 | 124.1 | 34.6 | 40 | B |
| ALA | C | 668 | 162.8 | 123.3 | 32.3 | 39 | B |
| ALA | O | 668 | 163.2 | 123.5 | 31.2 | 38 | B |
| TYR | N | 669 | 162.4 | 122.1 | 32.7 | 38 | B |
| TYR | CA | 669 | 162.5 | 120.9 | 31.8 | 36 | B |
| TYR | CB | 669 | 161.7 | 119.7 | 32.4 | 34 | B |
| TYR | CG | 669 | 162.2 | 119.2 | 33.7 | 32 | B |
| TYR | CD1 | 669 | 161.3 | 118.8 | 34.7 | 32 | B |
| TYR | CE1 | 669 | 161.8 | 118.2 | 35.9 | 30 | B |
| TYR | CD2 | 669 | 163.6 | 119.1 | 34.0 | 31 | B |
| TYR | CE2 | 669 | 164.0 | 118.6 | 35.3 | 30 | B |
| TYR | CZ | 669 | 163.1 | 118.2 | 36.2 | 29 | B |
| TYR | OH | 669 | 163.5 | 117.7 | 37.4 | 28 | B |
| TYR | C | 669 | 161.9 | 121.2 | 30.5 | 37 | B |
| TYR | O | 669 | 162.5 | 120.9 | 29.4 | 38 | B |
| ASN | N | 670 | 160.8 | 121.9 | 30.5 | 37 | B |
| ASN | CA | 670 | 160.2 | 122.3 | 29.2 | 38 | B |
| ASN | CB | 670 | 158.7 | 122.7 | 29.4 | 39 | B |
| ASN | CG | 670 | 157.8 | 121.5 | 29.6 | 39 | B |
| ASN | OD1 | 670 | 158.0 | 120.6 | 30.4 | 39 | B |
| ASN | ND2 | 670 | 156.7 | 121.5 | 28.8 | 40 | B |
| ASN | C | 670 | 160.9 | 123.2 | 28.3 | 38 | B |
| ASN | O | 670 | 160.5 | 123.5 | 27.2 | 39 | B |
| VAL | N | 671 | 161.9 | 123.8 | 28.8 | 37 | B |
| VAL | CA | 671 | 162.7 | 124.8 | 28.0 | 37 | B |
| VAL | CB | 671 | 163.8 | 125.5 | 28.9 | 37 | B |
| VAL | CG1 | 671 | 164.7 | 126.3 | 28.0 | 37 | B |
| VAL | CG2 | 671 | 163.1 | 126.4 | 29.9 | 37 | B |
| VAL | C | 671 | 163.5 | 124.0 | 26.9 | 37 | B |
| VAL | O | 671 | 163.4 | 124.4 | 25.7 | 37 | B |
| ILE | N | 672 | 164.1 | 122.9 | 27.3 | 37 | B |
| ILE | CA | 672 | 164.9 | 122.1 | 26.4 | 36 | B |
| ILE | CB | 672 | 165.6 | 121.0 | 27.2 | 34 | B |
| ILE | CG2 | 672 | 166.7 | 120.3 | 26.3 | 34 | B |
| ILE | CG1 | 672 | 166.3 | 121.5 | 28.5 | 34 | B |
| ILE | CD1 | 672 | 166.8 | 120.5 | 29.4 | 33 | B |
| ILE | C | 672 | 164.2 | 121.5 | 25.3 | 37 | B |
| ILE | O | 672 | 163.3 | 120.7 | 25.5 | 38 | B |
| ASN | N | 673 | 164.6 | 121.8 | 24.0 | 38 | B |
| ASN | CA | 673 | 164.0 | 121.2 | 22.8 | 39 | B |
| ASN | CB | 673 | 164.1 | 122.2 | 21.7 | 40 | B |
| ASN | CG | 673 | 163.6 | 121.7 | 20.4 | 42 | B |
| ASN | OD1 | 673 | 163.8 | 120.5 | 20.0 | 43 | B |
| ASN | ND2 | 673 | 162.8 | 122.5 | 19.6 | 42 | B |
| ASN | C | 673 | 164.8 | 119.9 | 22.5 | 40 | B |
| ASN | O | 673 | 165.8 | 120.0 | 21.8 | 40 | B |
| ARG | N | 674 | 164.3 | 118.8 | 23.0 | 40 | B |
| ARG | CA | 674 | 165.0 | 117.5 | 22.8 | 39 | B |
| ARG | CB | 674 | 164.3 | 116.5 | 23.7 | 38 | B |
| ARG | CG | 674 | 164.2 | 116.9 | 25.1 | 38 | B |
| ARG | CD | 674 | 163.2 | 116.0 | 25.9 | 40 | B |
| ARG | NE | 674 | 163.6 | 114.5 | 25.8 | 41 | B |
| ARG | CZ | 674 | 163.1 | 113.6 | 25.0 | 41 | B |
| ARG | NH1 | 674 | 162.1 | 113.9 | 24.1 | 41 | B |
| ARG | NH2 | 674 | 163.5 | 112.4 | 25.0 | 42 | B |
| ARG | C | 674 | 165.2 | 117.0 | 21.4 | 40 | B |
| ARG | O | 674 | 166.1 | 116.4 | 21.1 | 40 | B |
| GLU | N | 675 | 164.2 | 117.3 | 20.5 | 41 | B |
| GLU | CA | 675 | 164.4 | 116.7 | 19.1 | 43 | B |
| GLU | CB | 675 | 163.1 | 116.9 | 18.3 | 46 | B |
| GLU | CG | 675 | 162.1 | 117.9 | 18.9 | 51 | B |
| GLU | CD | 675 | 161.3 | 117.5 | 20.2 | 53 | B |
| GLU | OE1 | 675 | 161.5 | 118.2 | 21.2 | 53 | B |
| GLU | OE2 | 675 | 160.6 | 116.5 | 20.2 | 54 | B |
| GLU | C | 675 | 165.5 | 117.5 | 18.4 | 42 | B |
| GLU | O | 675 | 166.3 | 116.9 | 17.7 | 41 | B |
| LYS | N | 676 | 165.6 | 118.8 | 18.7 | 41 | B |
| LYS | CA | 676 | 166.6 | 119.6 | 18.1 | 40 | B |
| LYS | CB | 676 | 166.2 | 121.0 | 17.9 | 41 | B |
| LYS | CG | 676 | 165.7 | 121.2 | 16.5 | 43 | B |
| LYS | CD | 676 | 165.6 | 122.7 | 16.2 | 46 | B |
| LYS | CE | 676 | 164.6 | 123.4 | 17.0 | 48 | B |
| LYS | NZ | 676 | 164.3 | 124.9 | 16.6 | 49 | B |
| LYS | C | 676 | 167.9 | 119.5 | 18.9 | 37 | B |
| LYS | O | 676 | 169.0 | 119.6 | 18.3 | 37 | B |
| LEU | N | 677 | 167.9 | 119.2 | 20.2 | 36 | B |
| LEU | CA | 677 | 169.1 | 119.0 | 20.9 | 34 | B |

TABLE 5-continued

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| LEU | CB | 677 | 168.8 | 118.7 | 22.4 | 33 | B |
| LEU | CG | 677 | 170.0 | 118.4 | 23.3 | 32 | B |
| LEU | CD1 | 677 | 171.1 | 119.4 | 23.1 | 32 | B |
| LEU | CD2 | 677 | 169.6 | 118.3 | 24.7 | 31 | B |
| LEU | C | 677 | 169.9 | 117.8 | 20.3 | 35 | B |
| LEU | O | 677 | 171.1 | 117.9 | 20.1 | 36 | B |
| LEU | N | 678 | 169.2 | 116.7 | 20.0 | 36 | B |
| LEU | CA | 678 | 169.7 | 115.5 | 19.4 | 37 | B |
| LEU | CB | 678 | 168.6 | 114.5 | 19.2 | 37 | B |
| LEU | CG | 678 | 168.9 | 113.0 | 19.2 | 38 | B |
| LEU | CD1 | 678 | 167.9 | 112.3 | 18.3 | 37 | B |
| LEU | CD2 | 678 | 170.3 | 112.7 | 18.8 | 38 | B |
| LEU | C | 678 | 170.3 | 115.9 | 18.1 | 37 | B |
| LEU | O | 678 | 171.4 | 115.5 | 17.7 | 37 | B |
| GLN | N | 679 | 169.5 | 116.6 | 17.3 | 37 | B |
| GLN | CA | 679 | 169.9 | 117.0 | 16.0 | 38 | B |
| GLN | CB | 679 | 168.9 | 118.0 | 15.4 | 41 | B |
| GLN | CG | 679 | 169.1 | 118.5 | 14.0 | 44 | B |
| GLN | CD | 679 | 167.9 | 119.2 | 13.4 | 46 | B |
| GLN | OE1 | 679 | 167.9 | 120.4 | 13.2 | 48 | B |
| GLN | NE2 | 679 | 166.8 | 118.4 | 13.3 | 47 | B |
| GLN | C | 679 | 171.3 | 117.6 | 16.0 | 37 | B |
| GLN | O | 679 | 172.2 | 117.3 | 15.3 | 37 | B |
| TYR | N | 680 | 171.4 | 118.5 | 17.0 | 34 | B |
| TYR | CA | 680 | 172.7 | 119.3 | 17.3 | 31 | B |
| TYR | CB | 680 | 172.5 | 120.3 | 18.4 | 31 | B |
| TYR | CG | 680 | 173.7 | 121.1 | 18.7 | 29 | B |
| TYR | CD1 | 680 | 174.3 | 121.9 | 17.8 | 29 | B |
| TYR | CE1 | 680 | 175.4 | 122.6 | 18.1 | 28 | B |
| TYR | CD2 | 680 | 174.3 | 121.1 | 20.0 | 28 | B |
| TYR | CE2 | 680 | 175.4 | 121.8 | 20.3 | 27 | B |
| TYR | CZ | 680 | 175.9 | 122.6 | 19.3 | 27 | B |
| TYR | OH | 680 | 177.0 | 123.3 | 19.7 | 28 | B |
| TYR | C | 680 | 173.8 | 118.3 | 17.6 | 30 | B |
| TYR | O | 680 | 174.8 | 118.2 | 17.0 | 29 | B |
| LEU | N | 681 | 173.6 | 117.4 | 18.6 | 28 | B |
| LEU | CA | 681 | 174.6 | 116.5 | 19.0 | 29 | B |
| LEU | CB | 681 | 174.1 | 115.6 | 20.2 | 28 | B |
| LEU | CG | 681 | 173.7 | 116.2 | 21.5 | 27 | B |
| LEU | CD1 | 681 | 173.3 | 115.2 | 22.5 | 26 | B |
| LEU | CD2 | 681 | 174.9 | 117.0 | 22.0 | 27 | B |
| LEU | C | 681 | 175.1 | 115.6 | 17.8 | 29 | B |
| LEU | O | 681 | 176.2 | 115.3 | 17.7 | 29 | B |
| TYR | N | 682 | 174.1 | 115.4 | 16.9 | 30 | B |
| TYR | CA | 682 | 174.5 | 114.6 | 15.7 | 31 | B |
| TYR | CB | 682 | 173.2 | 114.1 | 15.0 | 32 | B |
| TYR | CG | 682 | 172.8 | 112.7 | 15.3 | 32 | B |
| TYR | CD1 | 682 | 171.5 | 112.4 | 15.6 | 32 | B |
| TYR | CE1 | 682 | 171.1 | 111.1 | 15.9 | 32 | B |
| TYR | CD2 | 682 | 173.8 | 111.7 | 15.3 | 33 | B |
| TYR | CE2 | 682 | 173.4 | 110.4 | 15.6 | 33 | B |
| TYR | CZ | 682 | 172.1 | 110.1 | 15.9 | 33 | B |
| TYR | OH | 682 | 171.7 | 108.8 | 16.2 | 33 | B |
| TYR | C | 682 | 175.3 | 115.5 | 14.8 | 32 | B |
| TYR | O | 682 | 176.2 | 115.0 | 14.1 | 32 | B |
| SER | N | 683 | 175.1 | 116.8 | 14.8 | 32 | F |
| SER | CA | 683 | 175.9 | 117.7 | 14.0 | 31 | B |
| SER | CB | 683 | 175.2 | 119.1 | 13.9 | 30 | B |
| SER | OG | 683 | 175.4 | 119.8 | 15.2 | 28 | B |
| SER | C | 683 | 177.3 | 117.8 | 14.4 | 32 | B |
| SER | O | 683 | 178.2 | 118.3 | 13.7 | 33 | B |
| LEU | N | 684 | 177.6 | 117.3 | 15.6 | 30 | B |
| LEU | CA | 684 | 179.0 | 117.4 | 16.1 | 29 | B |
| LEU | CB | 684 | 178.9 | 118.0 | 17.5 | 27 | B |
| LEU | CG | 684 | 178.2 | 119.3 | 17.7 | 25 | B |
| LEU | CD1 | 684 | 178.1 | 119.7 | 19.1 | 24 | B |
| LEU | CD2 | 684 | 178.8 | 120.4 | 16.8 | 25 | B |
| LEU | C | 684 | 179.8 | 116.1 | 16.1 | 29 | B |
| LEU | O | 684 | 181.0 | 116.1 | 16.0 | 30 | B |
| LYS | N | 685 | 179.0 | 115.0 | 16.1 | 28 | B |
| LYS | CA | 685 | 179.7 | 113.7 | 16.1 | 27 | B |
| LYS | CB | 685 | 178.6 | 112.6 | 15.9 | 27 | B |
| LYS | CG | 685 | 178.7 | 111.4 | 16.8 | 27 | B |
| LYS | CD | 685 | 180.1 | 110.8 | 16.9 | 27 | B |
| LYS | CE | 685 | 180.1 | 109.6 | 17.7 | 27 | B |
| LYS | NZ | 685 | 179.3 | 108.4 | 17.1 | 27 | B |
| LYS | C | 685 | 180.7 | 113.6 | 15.0 | 27 | B |
| LYS | O | 685 | 180.5 | 114.2 | 13.9 | 26 | B |
| GLN | N | 686 | 181.8 | 112.9 | 15.2 | 27 | B |
| GLN | CA | 686 | 182.8 | 112.7 | 14.2 | 27 | B |
| GLN | CB | 686 | 184.1 | 113.3 | 14.8 | 27 | B |
| GLN | CG | 686 | 184.1 | 114.7 | 15.0 | 28 | B |
| GLN | CD | 686 | 183.9 | 115.5 | 13.8 | 29 | B |
| GLN | OE1 | 686 | 184.7 | 115.6 | 12.9 | 31 | B |
| GLN | NE2 | 686 | 182.7 | 116.1 | 13.7 | 30 | B |
| GLN | C | 686 | 183.0 | 111.2 | 14.0 | 28 | B |
| GLN | O | 686 | 182.5 | 110.4 | 14.8 | 29 | B |
| PRO | N | 687 | 183.5 | 110.8 | 12.9 | 29 | B |
| PRO | CD | 687 | 183.9 | 111.7 | 11.7 | 30 | B |
| PRO | CA | 687 | 183.7 | 109.4 | 12.6 | 29 | B |
| PRO | CB | 687 | 184.4 | 109.5 | 11.2 | 29 | B |
| PRO | CG | 687 | 183.8 | 110.6 | 10.6 | 30 | B |
| PRO | C | 687 | 184.6 | 108.7 | 13.6 | 30 | B |
| PRO | O | 687 | 184.4 | 107.5 | 13.8 | 31 | B |
| ASP | N | 688 | 185.6 | 109.4 | 14.2 | 29 | B |
| ASP | CA | 688 | 186.4 | 108.7 | 15.1 | 28 | B |
| ASP | CB | 688 | 187.8 | 109.3 | 15.2 | 28 | B |
| ASP | CG | 688 | 187.9 | 110.7 | 15.7 | 29 | B |
| ASP | OD1 | 688 | 186.8 | 111.3 | 15.9 | 30 | B |
| ASP | OD2 | 688 | 189.0 | 111.2 | 15.9 | 30 | B |
| ASP | C | 688 | 185.8 | 108.6 | 16.5 | 27 | B |
| ASP | O | 688 | 186.4 | 108.1 | 17.4 | 29 | B |
| GLY | N | 689 | 184.5 | 109.1 | 16.6 | 25 | B |
| GLY | CA | 689 | 183.9 | 109.0 | 17.9 | 24 | B |
| GLY | C | 689 | 183.8 | 110.3 | 18.7 | 24 | B |
| GLY | O | 689 | 183.0 | 110.4 | 19.6 | 25 | B |
| SER | N | 690 | 184.6 | 111.2 | 18.3 | 22 | B |
| SER | CA | 690 | 184.7 | 112.5 | 19.0 | 21 | B |
| SER | CB | 690 | 186.0 | 113.2 | 18.8 | 20 | B |
| SER | OG | 690 | 186.2 | 113.3 | 17.4 | 20 | B |
| SER | C | 690 | 183.s | 113.4 | 18.6 | 21 | B |
| SER | O | 690 | 182.7 | 113.0 | 17.7 | 23 | B |
| PHE | N | 691 | 183.4 | 114.5 | 19.2 | 21 | B |
| PHE | CA | 691 | 182.4 | 115.5 | 18.9 | 20 | B |
| PHE | CB | 691 | 181.4 | 115.6 | 20.0 | 19 | B |
| PHE | CG | 691 | 180.5 | 114.5 | 20.2 | 19 | B |
| PHE | CD1 | 691 | 180.8 | 113.4 | 20.9 | 18 | B |
| PHE | CD2 | 691 | 179.2 | 114.5 | 19.6 | 19 | B |
| PHE | CE1 | 691 | 180.0 | 112.3 | 21.1 | 18 | B |
| PHE | CE2 | 691 | 178.3 | 113.4 | 19.8 | 19 | B |
| PHE | CZ | 691 | 178.7 | 112.3 | 20.5 | 18 | B |
| PHE | C | 691 | 183.1 | 116.9 | 18.8 | 21 | B |
| PHE | O | 691 | 184.1 | 117.1 | 19.5 | 20 | B |
| LEU | N | 692 | 182.6 | 117.8 | 18.0 | 21 | B |
| LEU | CA | 692 | 183.2 | 119.1 | 18.0 | 22 | B |
| LEU | CB | 692 | 182.8 | 119.9 | 16.7 | 21 | B |
| LEU | CG | 692 | 183.0 | 119.2 | 15.4 | 21 | B |
| LEU | CD1 | 692 | 182.3 | 120.0 | 14.4 | 20 | B |
| LEU | CD2 | 692 | 184.5 | 119.0 | 15.1 | 19 | B |
| LEU | C | 692 | 182.6 | 119.8 | 19.2 | 23 | B |
| LEU | O | 692 | 181.6 | 119.4 | 19.7 | 24 | B |
| MET | N | 693 | 183.2 | 120.9 | 19.7 | 24 | B |
| MET | CA | 693 | 182.6 | 121.7 | 20.8 | 22 | B |
| MET | CB | 693 | 183.7 | 122.5 | 21.5 | 21 | B |
| MET | CG | 693 | 184.7 | 121.8 | 22.3 | 21 | B |
| MET | SD | 693 | 184.0 | 120.8 | 23.7 | 23 | B |
| MET | CE | 693 | 183.2 | 122.1 | 24.7 | 21 | B |
| MET | C | 693 | 181.5 | 122.5 | 20.2 | 21 | B |
| MET | O | 693 | 180.5 | 122.9 | 20.9 | 22 | B |
| HIS | N | 694 | 181.6 | 122.8 | 19.0 | 22 | B |
| HIS | CA | 694 | 180.6 | 123.6 | 18.2 | 23 | B |
| HIS | CB | 694 | 180.5 | 125.0 | 18.7 | 23 | B |
| HIS | CG | 694 | 181.8 | 125.8 | 18.5 | 23 | B |
| HIS | CD2 | 694 | 183.0 | 125.7 | 19.1 | 23 | B |

TABLE 5-continued

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| HIS | ND1 | 694 | 181.9 | 126.8 | 17.5 | 23 | B |
| HIS | CE1 | 694 | 183.1 | 127.3 | 17.6 | 23 | B |
| HIS | NE2 | 694 | 183.8 | 126.7 | 18.5 | 23 | B |
| HIS | C | 694 | 181.0 | 123.5 | 16.7 | 25 | B |
| HIS | O | 694 | 182.0 | 122.9 | 16.3 | 26 | B |
| VAL | N | 695 | 180.1 | 123.9 | 15.8 | 25 | B |
| VAL | CA | 695 | 180.3 | 123.8 | 14.4 | 25 | B |
| VAL | CB | 695 | 179.0 | 124.3 | 13.7 | 26 | B |
| VAL | CG1 | 695 | 179.3 | 124.5 | 12.2 | 27 | B |
| VAL | CG2 | 695 | 177.9 | 123.2 | 13.8 | 25 | B |
| VAL | C | 695 | 181.5 | 124.7 | 14.0 | 26 | B |
| VAL | O | 695 | 181.5 | 125.9 | 14.3 | 28 | B |
| GLY | N | 696 | 182.4 | 124.1 | 13.4 | 25 | B |
| GLY | CA | 696 | 183.6 | 124.9 | 13.0 | 25 | B |
| GLY | C | 696 | 184.6 | 125.0 | 14.2 | 25 | B |
| GLY | O | 696 | 185.6 | 125.6 | 14.0 | 25 | B |
| GLY | N | 697 | 184.2 | 124.3 | 15.3 | 24 | B |
| GLY | CA | 697 | 185.1 | 124.4 | 16.5 | 23 | B |
| GLY | C | 697 | 186.1 | 123.3 | 16.7 | 23 | B |
| GLY | O | 697 | 186.2 | 122.3 | 15.9 | 23 | B |
| GLU | N | 698 | 186.7 | 123.4 | 17.8 | 22 | B |
| GLU | CA | 698 | 187.7 | 122.4 | 18.3 | 22 | B |
| GLU | CB | 698 | 188.6 | 123.1 | 19.3 | 21 | B |
| GLU | CG | 698 | 188.1 | 123.3 | 20.7 | 22 | B |
| GLU | CD | 698 | 187.2 | 124.5 | 20.9 | 23 | B |
| GLU | OE1 | 698 | 186.9 | 125.2 | 19.9 | 23 | B |
| GLU | OE2 | 698 | 186.8 | 124.7 | 22.1 | 24 | B |
| GLU | C | 698 | 187.1 | 121.1 | 18.8 | 21 | B |
| GLU | O | 698 | 186.0 | 121.0 | 19.2 | 22 | B |
| VAL | N | 699 | 188.0 | 120.1 | 18.9 | 21 | B |
| VAL | CA | 699 | 187.6 | 118.8 | 19.5 | 20 | B |
| VAL | CB | 699 | 187.7 | 117.6 | 18.4 | 20 | B |
| VAL | CG1 | 699 | 187.7 | 116.3 | 19.1 | 20 | B |
| VAL | CG2 | 699 | 186.7 | 117.7 | 17.4 | 21 | B |
| VAL | C | 699 | 188.5 | 118.3 | 20.6 | 21 | B |
| VAL | O | 699 | 189.7 | 118.3 | 20.5 | 22 | B |
| ASP | N | 700 | 187.9 | 118.0 | 21.8 | 21 | B |
| ASP | CA | 700 | 188.7 | 117.5 | 22.9 | 22 | B |
| ASP | CB | 700 | 189.6 | 118.6 | 23.6 | 24 | B |
| ASP | CG | 700 | 188.8 | 119.7 | 24.2 | 27 | B |
| ASP | OD1 | 700 | 187.9 | 119.4 | 25.0 | 27 | B |
| ASP | OD2 | 700 | 189.1 | 120.9 | 23.9 | 28 | B |
| ASP | C | 700 | 187.7 | 116.8 | 23.8 | 22 | B |
| ASP | O | 700 | 186.5 | 116.9 | 23.6 | 22 | B |
| VAL | N | 701 | 188.1 | 116.1 | 24.9 | 22 | B |
| VAL | CA | 701 | 187.2 | 115.4 | 25.8 | 21 | B |
| VAL | CB | 701 | 187.9 | 114.6 | 26.9 | 20 | B |
| VAL | CG1 | 701 | 187.6 | 113.1 | 26.8 | 20 | B |
| VAL | CG2 | 701 | 189.3 | 114.9 | 27.0 | 22 | B |
| VAL | C | 701 | 186.0 | 116.1 | 26.4 | 22 | B |
| VAL | O | 701 | 185.0 | 115.5 | 26.7 | 23 | B |
| ARG | N | 702 | 186.1 | 117.4 | 26.5 | 22 | B |
| ARG | CA | 702 | 185.0 | 118.1 | 27.1 | 23 | B |
| ARG | CB | 702 | 185.3 | 119.6 | 27.2 | 23 | B |
| ARG | CG | 702 | 186.5 | 120.1 | 28.0 | 22 | B |
| ARG | CD | 702 | 186.8 | 121.5 | 27.7 | 23 | B |
| ARG | NE | 702 | 187.2 | 121.8 | 26.3 | 24 | B |
| ARG | CZ | 702 | 186.9 | 122.8 | 25.6 | 24 | B |
| ARG | NH1 | 702 | 187.3 | 122.9 | 24.3 | 24 | B |
| ARG | NH2 | 702 | 186.3 | 123.8 | 26.2 | 25 | B |
| ARG | C | 702 | 183.7 | 117.8 | 26.4 | 25 | B |
| ARG | O | 702 | 182.7 | 117.5 | 27.0 | 26 | B |
| SER | N | 703 | 183.8 | 117.7 | 25.1 | 26 | B |
| SER | CA | 703 | 182.6 | 117.5 | 24.2 | 26 | B |
| SER | CB | 703 | 183.0 | 117.6 | 22.7 | 26 | B |
| SER | OG | 703 | 183.9 | 116.7 | 22.3 | 27 | B |
| SER | C | 703 | 182.0 | 116.1 | 24.4 | 27 | B |
| SER | O | 703 | 180.7 | 116.0 | 24.4 | 28 | B |
| ALA | N | 704 | 182.8 | 115.1 | 24.7 | 27 | B |
| ALA | CA | 704 | 182.3 | 113.7 | 24.9 | 27 | B |
| ALA | CB | 704 | 183.5 | 112.8 | 25.1 | 27 | B |
| ALA | C | 704 | 181.5 | 113.7 | 26.2 | 27 | B |
| ALA | O | 704 | 180.5 | 113.0 | 26.3 | 28 | B |
| TYR | N | 705 | 181.9 | 114.5 | 27.2 | 28 | B |
| TYR | CA | 705 | 181.2 | 114.6 | 28.5 | 27 | B |
| TYR | CB | 705 | 182.2 | 115.1 | 29.6 | 27 | B |
| TYR | CG | 705 | 181.6 | 115.5 | 30.9 | 27 | B |
| TYR | CD1 | 705 | 180.9 | 114.5 | 31.6 | 27 | B |
| TYR | CE1 | 705 | 180.4 | 114.8 | 32.9 | 27 | B |
| TYR | CD2 | 705 | 181.6 | 116.8 | 31.4 | 26 | B |
| TYR | CE2 | 705 | 181.1 | 117.1 | 32.6 | 27 | B |
| TYR | CZ | 705 | 180.4 | 116.1 | 33.3 | 26 | B |
| TYR | OH | 705 | 179.9 | 116.4 | 34.5 | 27 | B |
| TYR | C | 705 | 180.0 | 115.5 | 28.4 | 26 | B |
| TYR | O | 705 | 178.9 | 115.2 | 29.0 | 25 | B |
| CYS | N | 706 | 180.2 | 116.7 | 27.8 | 25 | B |
| CYS | CA | 706 | 179.1 | 117.6 | 27.7 | 25 | B |
| CYS | CB | 706 | 179.5 | 118.8 | 26.9 | 25 | B |
| CYS | SG | 706 | 180.7 | 119.8 | 27.9 | 24 | B |
| CYS | C | 706 | 177.9 | 116.9 | 27.0 | 26 | B |
| CYS | O | 706 | 176.8 | 116.9 | 27.4 | 27 | B |
| ALA | N | 707 | 178.2 | 116.2 | 25.9 | 26 | B |
| ALA | CA | 707 | 177.2 | 115.4 | 25.1 | 24 | B |
| ALA | CB | 707 | 177.9 | 114.9 | 23.8 | 24 | B |
| ALA | C | 707 | 176.6 | 114.3 | 25.9 | 24 | B |
| ALA | O | 707 | 175.4 | 114.2 | 25.9 | 24 | B |
| ALA | N | 708 | 177.4 | 113.5 | 26.5 | 25 | B |
| ALA | CA | 708 | 176.9 | 112.3 | 27.3 | 25 | B |
| ALA | CB | 708 | 178.0 | 111.4 | 27.7 | 24 | B |
| ALA | C | 708 | 176.0 | 112.8 | 28.5 | 27 | B |
| ALA | O | 708 | 175.2 | 112.0 | 28.9 | 28 | B |
| SER | N | 709 | 176.3 | 113.9 | 29.0 | 28 | B |
| SER | CA | 709 | 175.6 | 114.5 | 30.2 | 29 | B |
| SER | CB | 709 | 176.4 | 115.6 | 30.9 | 29 | B |
| SER | OG | 709 | 175.7 | 116.0 | 32.1 | 30 | B |
| SER | C | 709 | 174.2 | 115.0 | 29.8 | 29 | B |
| SER | O | 709 | 173.2 | 114.7 | 30.4 | 30 | B |
| VAL | N | 710 | 174.1 | 115.8 | 28.7 | 30 | B |
| VAL | CA | 710 | 172.9 | 116.3 | 28.2 | 30 | B |
| VAL | CB | 710 | 173.1 | 117.5 | 27.3 | 31 | B |
| VAL | CG1 | 710 | 174.0 | 118.5 | 28.0 | 31 | B |
| VAL | CG2 | 710 | 173.6 | 117.1 | 25.9 | 31 | B |
| VAL | C | 710 | 172.0 | 115.2 | 27.6 | 30 | B |
| VAL | O | 710 | 170.8 | 115.1 | 27.9 | 30 | B |
| ALA | N | 711 | 172.6 | 114.4 | 26.7 | 30 | B |
| ALA | CA | 711 | 171.8 | 113.4 | 26.0 | 30 | B |
| ALA | CB | 711 | 172.7 | 112.6 | 25.0 | 28 | B |
| ALA | C | 711 | 171.2 | 112.4 | 27.0 | 30 | B |
| ALA | O | 711 | 170.1 | 111.9 | 26.8 | 30 | B |
| SER | N | 712 | 172.0 | 112.0 | 28.0 | 31 | B |
| SER | CA | 712 | 171.5 | 111.1 | 29.0 | 31 | B |
| SER | CB | 712 | 172.6 | 110.5 | 29.8 | 31 | B |
| SER | OG | 712 | 173.3 | 111.4 | 30.7 | 31 | B |
| SER | C | 712 | 170.4 | 111.7 | 29.9 | 31 | B |
| SER | O | 712 | 169.3 | 111.1 | 30.0 | 31 | B |
| LEU | N | 713 | 170.7 | 112.8 | 30.6 | 30 | B |
| LEU | CA | 713 | 169.7 | 113.4 | 31.4 | 30 | B |
| LEU | CB | 713 | 170.2 | 114.8 | 32.0 | 29 | B |
| LEU | CG | 713 | 171.2 | 114.8 | 33.1 | 29 | B |
| LEU | CD1 | 713 | 171.7 | 116.3 | 33.3 | 28 | B |
| LEU | CD2 | 713 | 170.7 | 114.3 | 34.4 | 28 | B |
| LEU | C | 713 | 168.4 | 113.7 | 30.7 | 32 | B |
| LEU | O | 713 | 167.3 | 113.5 | 31.3 | 32 | B |
| THR | N | 714 | 168.4 | 114.0 | 29.4 | 33 | B |
| THR | CA | 714 | 167.2 | 114.3 | 28.7 | 33 | B |
| THR | CB | 714 | 167.4 | 115.5 | 27.7 | 34 | B |
| THR | OG1 | 714 | 168.6 | 115.2 | 26.8 | 34 | B |
| THR | CG2 | 714 | 167.7 | 116.8 | 28.4 | 33 | B |
| THR | C | 714 | 166.7 | 113.1 | 27.9 | 34 | B |
| THR | O | 714 | 165.6 | 113.2 | 27.3 | 35 | B |
| ASN | N | 715 | 167.3 | 111.9 | 28.0 | 34 | B |
| ASN | CA | 715 | 166.9 | 110.7 | 27.4 | 33 | B |
| ASN | CB | 715 | 165.5 | 110.3 | 28.0 | 34 | B |
| ASN | CG | 715 | 164.8 | 109.1 | 27.4 | 35 | B |

TABLE 5-continued

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| ASN | OD1 | 715 | 165.5 | 108.1 | 27.0 | 36 | B |
| ASN | ND2 | 715 | 163.5 | 109.1 | 27.3 | 36 | B |
| ASN | C | 715 | 166.8 | 110.8 | 25.9 | 32 | B |
| ASN | O | 715 | 165.7 | 110.6 | 25.3 | 34 | B |
| ILE | N | 716 | 167.9 | 111.2 | 25.2 | 31 | B |
| ILE | CA | 716 | 167.8 | 111.3 | 23.7 | 30 | B |
| ILE | CB | 716 | 168.1 | 112.7 | 23.2 | 30 | B |
| ILE | CG2 | 716 | 166.9 | 113.6 | 23.6 | 30 | B |
| ILE | CG1 | 716 | 169.4 | 113.3 | 23.8 | 31 | B |
| ILE | CD1 | 716 | 169.8 | 114.6 | 23.3 | 30 | B |
| ILE | C | 716 | 168.9 | 110.5 | 23.2 | 30 | B |
| ILE | O | 716 | 169.3 | 110.7 | 22.0 | 30 | B |
| ILE | N | 717 | 169.4 | 109.5 | 24.0 | 30 | B |
| ILE | CA | 717 | 170.4 | 108.6 | 23.5 | 32 | B |
| ILE | CB | 717 | 171.2 | 108.0 | 24.7 | 32 | B |
| ILE | CG2 | 717 | 172.2 | 107.0 | 24.2 | 31 | B |
| ILE | CG1 | 717 | 171.8 | 109.0 | 25.6 | 31 | B |
| ILE | CD1 | 717 | 172.8 | 108.5 | 26.6 | 31 | B |
| ILE | C | 717 | 169.9 | 107.6 | 22.5 | 33 | B |
| ILE | O | 717 | 169.2 | 106.6 | 22.9 | 34 | B |
| THR | N | 718 | 170.1 | 107.8 | 21.2 | 34 | B |
| THR | CA | 718 | 169.8 | 106.9 | 20.2 | 35 | B |
| THR | CB | 718 | 169.8 | 107.6 | 18.8 | 35 | B |
| THR | OG1 | 718 | 171.1 | 107.9 | 18.5 | 35 | B |
| THR | CG2 | 718 | 169.0 | 108.8 | 18.8 | 35 | B |
| THR | C | 718 | 170.8 | 105.8 | 20.3 | 37 | B |
| THR | O | 718 | 171.7 | 105.8 | 21.0 | 38 | B |
| PRO | N | 719 | 170.6 | 104.7 | 19.4 | 39 | B |
| PRO | CD | 719 | 169.5 | 104.5 | 18.6 | 39 | B |
| PRO | CA | 719 | 171.6 | 103.6 | 19.4 | 39 | B |
| PRO | CB | 719 | 170.9 | 102.7 | 18.4 | 40 | B |
| PRO | CG | 719 | 169.4 | 103.0 | 18.5 | 40 | B |
| PRO | C | 719 | 173.0 | 103.8 | 18.9 | 38 | B |
| PRO | O | 719 | 173.9 | 103.2 | 19.4 | 37 | B |
| ASP | N | 720 | 173.1 | 104.7 | 17.9 | 38 | B |
| ASP | CA | 720 | 174.5 | 105.0 | 17.4 | 39 | B |
| ASP | CB | 720 | 174.4 | 104.9 | 15.9 | 40 | B |
| ASP | CG | 720 | 173.5 | 105.9 | 15.2 | 41 | B |
| ASP | OD1 | 720 | 173.9 | 106.3 | 14.1 | 42 | B |
| ASP | OD2 | 720 | 172.5 | 106.3 | 15.9 | 42 | B |
| ASP | C | 720 | 175.0 | 106.4 | 17.7 | 38 | B |
| ASP | O | 720 | 176.0 | 106.8 | 17.2 | 38 | B |
| LEU | N | 721 | 174.3 | 107.2 | 18.6 | 37 | B |
| LEU | CA | 721 | 174.8 | 108.5 | 18.9 | 36 | B |
| LEU | CB | 721 | 173.9 | 109.1 | 20.0 | 35 | B |
| LEU | CG | 721 | 174.3 | 110.5 | 20.4 | 34 | B |
| LEU | CD1 | 721 | 174.6 | 111.4 | 19.2 | 33 | B |
| LEU | CD2 | 721 | 173.3 | 111.1 | 21.3 | 33 | B |
| LEU | C | 721 | 176.2 | 108.5 | 19.4 | 36 | B |
| LEU | O | 721 | 177.1 | 109.2 | 18.9 | 37 | B |
| PHE | N | 722 | 176.5 | 107.6 | 20.4 | 36 | B |
| PHE | CA | 722 | 177.8 | 107.6 | 21.0 | 36 | B |
| PHE | CB | 722 | 177.6 | 107.5 | 22.6 | 36 | B |
| PHE | CG | 722 | 177.0 | 108.8 | 23.1 | 36 | B |
| PHE | CD1 | 722 | 175.7 | 108.8 | 23.6 | 35 | B |
| PHE | CD2 | 722 | 177.7 | 110.0 | 23.0 | 35 | B |
| PHE | CE1 | 722 | 175.2 | 109.9 | 24.1 | 35 | B |
| PHE | CE2 | 722 | 177.1 | 111.1 | 23.5 | 35 | B |
| PHE | CZ | 722 | 175.8 | 111.1 | 24.0 | 35 | B |
| PHE | C | 722 | 178.6 | 106.4 | 20.6 | 37 | B |
| PHE | O | 722 | 179.4 | 105.8 | 21.3 | 38 | B |
| GLU | N | 723 | 178.4 | 106.1 | 19.3 | 38 | B |
| GLU | CA | 723 | 179.2 | 105.0 | 18.7 | 37 | B |
| GLU | CB | 723 | 178.7 | 104.7 | 17.3 | 41 | B |
| GLU | CG | 723 | 178.8 | 103.2 | 17.0 | 45 | B |
| GLU | CD | 723 | 178.1 | 102.4 | 18.0 | 47 | B |
| GLU | OE1 | 723 | 176.8 | 102.4 | 18.0 | 49 | B |
| GLU | OE2 | 723 | 178.8 | 101.9 | 18.9 | 48 | B |
| GLU | C | 723 | 180.6 | 105.4 | 18.6 | 34 | B |
| GLU | O | 723 | 181.0 | 106.4 | 18.0 | 33 | B |
| GLY | N | 724 | 181.5 | 104.5 | 19.2 | 32 | B |
| GLY | CA | 724 | 182.9 | 104.8 | 19.2 | 31 | B |
| GLY | C | 724 | 183.4 | 105.9 | 20.1 | 30 | B |
| GLY | O | 724 | 184.6 | 106.0 | 20.2 | 30 | B |
| THR | N | 725 | 182.6 | 106.6 | 20.8 | 29 | B |
| THR | CA | 725 | 183.1 | 107.6 | 21.7 | 29 | B |
| THR | CB | 725 | 182.1 | 108.8 | 21.9 | 28 | B |
| THR | OG1 | 725 | 181.9 | 109.0 | 23.3 | 30 | B |
| THR | CG2 | 725 | 180.9 | 108.7 | 21.1 | 26 | B |
| THR | C | 725 | 183.8 | 107.1 | 22.9 | 28 | B |
| THR | O | 725 | 184.7 | 107.6 | 23.4 | 28 | B |
| ALA | N | 726 | 183.4 | 105.9 | 23.3 | 27 | B |
| ALA | CA | 726 | 184.0 | 105.3 | 24.5 | 26 | B |
| ALA | CB | 726 | 183.2 | 104.1 | 24.9 | 26 | B |
| ALA | C | 726 | 185.4 | 104.9 | 24.1 | 27 | B |
| ALA | O | 726 | 186.4 | 105.0 | 24.8 | 28 | B |
| GLU | N | 727 | 185.5 | 104.5 | 22.8 | 27 | B |
| GLU | CA | 727 | 186.8 | 104.0 | 22.2 | 27 | B |
| GLU | CB | 727 | 186.6 | 103.3 | 20.9 | 28 | B |
| GLU | CG | 727 | 186.1 | 101.8 | 21.1 | 28 | B |
| GLU | CD | 727 | 184.6 | 101.6 | 21.4 | 29 | B |
| GLU | OE1 | 727 | 184.3 | 100.5 | 21.8 | 31 | B |
| GLU | OE2 | 727 | 183.8 | 102.6 | 21.2 | 30 | B |
| GLU | C | 727 | 187.8 | 105.2 | 22.1 | 26 | B |
| GLU | O | 727 | 189.0 | 105.1 | 22.4 | 26 | B |
| TRP | N | 728 | 187.2 | 106.3 | 21.5 | 24 | B |
| TRP | CA | 728 | 188.1 | 107.5 | 21.3 | 23 | B |
| TRP | CB | 728 | 187.3 | 108.6 | 20.6 | 22 | B |
| TRP | CG | 728 | 188.1 | 109.8 | 20.3 | 20 | B |
| TRP | CD2 | 728 | 188.2 | 110.9 | 21.1 | 20 | B |
| TRP | CE2 | 728 | 189.1 | 111.8 | 20.4 | 20 | B |
| TRP | CE3 | 728 | 187.7 | 111.3 | 22.3 | 20 | B |
| TRP | CD1 | 728 | 188.9 | 109.9 | 19.2 | 20 | B |
| TRP | NE1 | 728 | 189.5 | 111.2 | 19.3 | 20 | B |
| TRP | C22 | 728 | 189.5 | 113.0 | 20.9 | 20 | B |
| TRP | CZ3 | 728 | 188.0 | 112.6 | 22.8 | 19 | B |
| TRP | CH2 | 728 | 188.9 | 113.4 | 22.1 | 20 | B |
| TRP | C | 728 | 188.6 | 108.0 | 22.7 | 24 | B |
| TRP | O | 728 | 189.8 | 108.2 | 22.8 | 25 | B |
| ILE | N | 729 | 187.7 | 108.1 | 23.7 | 24 | B |
| ILE | CA | 729 | 188.0 | 108.6 | 25.0 | 23 | B |
| ILE | CB | 729 | 186.8 | 108.6 | 25.9 | 23 | B |
| ILE | CG2 | 729 | 187.3 | 108.9 | 27.4 | 23 | B |
| ILE | CG1 | 729 | 185.8 | 109.6 | 25.5 | 23 | B |
| ILE | CD1 | 729 | 184.4 | 109.5 | 26.1 | 22 | B |
| ILE | C | 729 | 189.1 | 107.7 | 25.6 | 24 | B |
| ILE | O | 729 | 190.1 | 108.2 | 26.1 | 24 | B |
| ALA | N | 730 | 189.0 | 106.4 | 25.4 | 23 | B |
| ALA | CA | 730 | 190.0 | 105.5 | 25.9 | 23 | B |
| ALA | CB | 730 | 189.5 | 104.0 | 25.6 | 23 | B |
| ALA | C | 730 | 191.4 | 105.8 | 25.3 | 24 | B |
| ALA | O | 730 | 192.4 | 105.4 | 25.8 | 25 | B |
| ARG | N | 731 | 191.4 | 106.5 | 24.2 | 25 | B |
| ARG | CA | 731 | 192.7 | 106.8 | 23.5 | 25 | B |
| ARG | CB | 731 | 192.4 | 107.1 | 22.0 | 26 | B |
| ARG | CG | 731 | 192.0 | 105.8 | 21.2 | 27 | B |
| ARG | CD | 731 | 192.5 | 105.9 | 19.8 | 27 | B |
| ARG | NE | 731 | 191.8 | 106.8 | 19.0 | 28 | B |
| ARG | CZ | 731 | 192.3 | 107.8 | 18.3 | 30 | B |
| ARG | NH1 | 731 | 193.6 | 107.9 | 18.2 | 28 | B |
| ARG | NH2 | 731 | 191.5 | 108.6 | 17.5 | 30 | B |
| ARG | C | 731 | 193.3 | 108.0 | 24.1 | 26 | B |
| ARG | O | 731 | 194.5 | 108.3 | 23.8 | 26 | B |
| CYS | N | 732 | 192.6 | 108.8 | 24.9 | 26 | B |
| CYS | CA | 732 | 193.1 | 110.0 | 25.5 | 24 | B |
| CYS | CB | 732 | 191.9 | 110.9 | 25.9 | 24 | B |
| CYS | SG | 732 | 191.1 | 111.4 | 24.4 | 24 | B |
| CYS | C | 732 | 193.9 | 109.6 | 26.8 | 24 | B |
| CYS | O | 732 | 194.6 | 110.4 | 27.3 | 24 | B |
| GLN | N | 733 | 193.7 | 108.3 | 27.2 | 24 | B |
| GLN | CA | 733 | 194.5 | 107.9 | 28.4 | 24 | B |
| GLN | CB | 733 | 193.9 | 106.6 | 29.0 | 23 | B |
| GLN | CG | 733 | 194.6 | 106.1 | 30.3 | 23 | B |
| GLN | CD | 733 | 193.9 | 104.9 | 31.0 | 22 | B |

TABLE 5-continued

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| GLN | OE1 | 733 | 193.2 | 104.1 | 30.3 | 23 | B |
| GLN | NE2 | 733 | 194.1 | 104.8 | 32.3 | 22 | B |
| GLN | C | 733 | 196.0 | 107.6 | 28.0 | 24 | B |
| GLN | O | 733 | 196.2 | 106.8 | 27.0 | 24 | B |
| ASN | N | 734 | 196.9 | 108.2 | 28.6 | 24 | B |
| ASN | CA | 734 | 198.3 | 108.1 | 28.3 | 23 | B |
| ASN | CB | 734 | 198.9 | 109.5 | 28.1 | 23 | B |
| ASN | CG | 734 | 199.2 | 110.2 | 29.4 | 22 | B |
| ASN | OD1 | 734 | 198.9 | 109.7 | 30.5 | 21 | B |
| ASN | ND2 | 734 | 200.0 | 111.3 | 29.4 | 21 | B |
| ASN | C | 734 | 199.2 | 107.3 | 29.2 | 22 | B |
| ASN | O | 734 | 198.7 | 106.7 | 30.2 | 23 | B |
| TRP | N | 735 | 200.5 | 107.3 | 29.0 | 22 | B |
| TRP | CA | 735 | 201.5 | 106.6 | 29.8 | 23 | B |
| TRP | CB | 735 | 202.8 | 106.9 | 29.3 | 21 | B |
| TRP | CG | 735 | 203.2 | 108.4 | 29.3 | 21 | B |
| TRP | CD2 | 735 | 203.9 | 109.1 | 30.2 | 21 | B |
| TRP | CE2 | 735 | 204.0 | 110.4 | 29.8 | 22 | B |
| TRP | CE3 | 735 | 204.5 | 108.8 | 31.5 | 21 | B |
| TRP | CD1 | 735 | 202.8 | 109.2 | 28.3 | 22 | B |
| TRP | NE1 | 735 | 203.3 | 110.5 | 28.6 | 22 | B |
| TRP | CZ2 | 735 | 204.6 | 111.5 | 30.5 | 21 | B |
| TRP | CZ3 | 735 | 205.1 | 109.8 | 32.2 | 21 | B |
| TRP | CH2 | 735 | 205.2 | 111.1 | 31.7 | 21 | B |
| TRP | C | 735 | 201.4 | 107.0 | 31.3 | 25 | B |
| TRP | O | 735 | 201.9 | 106.2 | 32.2 | 26 | B |
| GLU | N | 736 | 200.8 | 108.1 | 31.7 | 25 | B |
| GLU | CA | 736 | 200.7 | 108.6 | 33.0 | 24 | B |
| GLU | CB | 736 | 200.5 | 110.1 | 33.1 | 23 | B |
| GLU | CG | 736 | 201.5 | 111.0 | 32.4 | 23 | B |
| GLU | CD | 736 | 201.2 | 112.5 | 32.5 | 24 | B |
| GLU | OE1 | 736 | 200.9 | 113.1 | 31.5 | 23 | B |
| GLU | OE2 | 736 | 201.3 | 113.0 | 33.7 | 23 | B |
| GLU | C | 736 | 199.6 | 108.0 | 33.9 | 24 | B |
| GLU | O | 736 | 199.6 | 108.1 | 35.1 | 27 | B |
| GLY | N | 737 | 196.6 | 107.5 | 33.2 | 22 | B |
| GLY | CA | 737 | 197.5 | 106.9 | 33.9 | 18 | B |
| GLY | C | 737 | 196.3 | 107.9 | 33.8 | 18 | B |
| GLY | O | 737 | 195.2 | 107.5 | 33.9 | 18 | B |
| GLY | N | 738 | 196.7 | 109.1 | 33.5 | 17 | B |
| GLY | CA | 738 | 195.6 | 110.1 | 33.4 | 17 | B |
| GLY | C | 738 | 195.0 | 110.2 | 32.0 | 17 | B |
| GLY | O | 738 | 195.3 | 109.3 | 31.1 | 17 | B |
| ILE | N | 739 | 194.2 | 111.2 | 31.7 | 16 | B |
| ILE | CA | 739 | 193.6 | 111.3 | 30.4 | 15 | B |
| ILE | CB | 739 | 192.1 | 111.1 | 30.5 | 14 | B |
| ILE | CG2 | 739 | 191.4 | 111.6 | 29.3 | 13 | B |
| ILE | CG1 | 739 | 191.8 | 109.6 | 30.8 | 14 | B |
| ILE | CD1 | 739 | 190.3 | 109.3 | 30.9 | 13 | B |
| ILE | C | 739 | 193.9 | 112.7 | 29.9 | 16 | B |
| ILE | O | 739 | 193.8 | 113.7 | 30.6 | 17 | B |
| GLY | N | 740 | 194.3 | 112.8 | 28.6 | 16 | B |
| GLY | CA | 740 | 194.6 | 114.1 | 28.0 | 15 | B |
| GLY | C | 740 | 193.4 | 114.7 | 27.3 | 14 | B |
| GLY | O | 740 | 192.3 | 114.1 | 27.3 | 14 | B |
| GLY | N | 741 | 193.5 | 115.9 | 26.8 | 16 | B |
| GLY | CA | 741 | 192.4 | 116.5 | 26.0 | 18 | B |
| GLY | C | 741 | 192.1 | 115.8 | 24.7 | 18 | B |
| GLY | O | 741 | 190.9 | 115.8 | 24.3 | 20 | B |
| VAL | N | 742 | 193.1 | 115.3 | 24.1 | 19 | B |
| VAL | CA | 742 | 193.0 | 114.5 | 22.8 | 18 | B |
| VAL | CB | 742 | 193.3 | 115.4 | 21.6 | 17 | B |
| VAL | CG1 | 742 | 192.2 | 116.4 | 21.4 | 16 | B |
| VAL | CG2 | 742 | 194.7 | 116.0 | 21.7 | 17 | B |
| VAL | C | 742 | 194.2 | 113.5 | 23.0 | 19 | B |
| VAL | O | 742 | 195.1 | 113.7 | 23.8 | 20 | B |
| PRO | N | 743 | 194.1 | 112.4 | 22.2 | 20 | B |
| PRO | CD | 743 | 193.1 | 111.9 | 21.3 | 19 | B |
| PRO | CA | 743 | 195.2 | 111.4 | 22.2 | 19 | B |
| PRO | CB | 743 | 194.9 | 110.4 | 21.1 | 18 | B |
| PRO | CG | 743 | 193.4 | 110.4 | 21.2 | 18 | B |
| PRO | C | 743 | 196.6 | 111.9 | 22.1 | 20 | B |
| PRO | O | 743 | 196.9 | 112.8 | 21.3 | 21 | B |
| GLY | N | 744 | 197.5 | 111.5 | 23.0 | 20 | B |
| GLY | CA | 744 | 198.9 | 112.0 | 22.9 | 20 | B |
| GLY | C | 744 | 199.2 | 113.1 | 23.9 | 21 | B |
| GLY | O | 744 | 200.4 | 113.3 | 24.1 | 20 | B |
| MET | N | 745 | 198.2 | 113.8 | 24.4 | 21 | B |
| MET | CA | 745 | 198.3 | 114.9 | 25.3 | 21 | B |
| MET | CB | 745 | 197.2 | 115.9 | 25.1 | 20 | B |
| MET | CG | 745 | 197.5 | 117.0 | 24.1 | 20 | B |
| MET | SD | 745 | 199.1 | 117.6 | 24.3 | 20 | B |
| MET | CE | 745 | 198.8 | 118.9 | 25.3 | 21 | B |
| MET | C | 745 | 198.6 | 114.6 | 26.8 | 21 | B |
| MET | O | 745 | 198.2 | 113.5 | 27.2 | 22 | B |
| GLU | N | 746 | 199.2 | 115.5 | 27.4 | 22 | B |
| GLU | CA | 746 | 199.5 | 115.3 | 28.8 | 23 | B |
| GLU | CB | 746 | 200.3 | 116.5 | 29.4 | 23 | B |
| GLU | CG | 746 | 200.7 | 116.4 | 30.8 | 25 | B |
| GLU | CD | 746 | 201.3 | 117.7 | 31.3 | 27 | B |
| GLU | OE1 | 746 | 201.1 | 118.7 | 30.7 | 28 | B |
| GLU | OE2 | 746 | 201.9 | 117.6 | 32.4 | 27 | B |
| GLU | C | 746 | 198.3 | 115.1 | 29.7 | 24 | B |
| GLU | O | 746 | 197.3 | 115.8 | 29.4 | 25 | B |
| ALA | N | 747 | 198.3 | 114.1 | 30.6 | 23 | B |
| ALA | CA | 747 | 197.2 | 113.9 | 31.5 | 23 | B |
| ALA | CB | 747 | 197.4 | 112.7 | 32.4 | 23 | B |
| ALA | C | 747 | 196.8 | 115.1 | 32.3 | 23 | B |
| ALA | O | 747 | 197.7 | 115.6 | 32.9 | 23 | B |
| HIS | N | 748 | 195.5 | 115.4 | 32.3 | 22 | B |
| HIS | CA | 748 | 195.1 | 116.6 | 33.1 | 22 | B |
| HIS | CB | 748 | 194.9 | 117.8 | 32.1 | 21 | B |
| HIS | CG | 748 | 194.8 | 119.1 | 32.7 | 21 | B |
| HIS | CD2 | 748 | 195.7 | 120.0 | 32.9 | 20 | B |
| HIS | ND1 | 748 | 193.7 | 119.6 | 33.4 | 21 | B |
| HIS | CE1 | 748 | 193.9 | 120.7 | 33.9 | 20 | B |
| HIS | NE2 | 748 | 195.2 | 121.0 | 33.7 | 20 | B |
| HIS | C | 748 | 193.8 | 116.3 | 33.9 | 23 | B |
| HIS | O | 748 | 193.0 | 115.4 | 33.5 | 24 | B |
| GLY | N | 749 | 193.6 | 117.0 | 35.0 | 23 | B |
| GLY | CA | 749 | 192.4 | 116.8 | 35.8 | 21 | B |
| GLY | C | 749 | 191.0 | 117.1 | 35.2 | 21 | B |
| GLY | O | 749 | 190.1 | 116.3 | 35.4 | 23 | B |
| GLY | N | 750 | 190.9 | 118.3 | 34.6 | 21 | B |
| GLY | CA | 750 | 189.6 | 118.6 | 34.0 | 20 | B |
| GLY | C | 750 | 189.2 | 117.6 | 32.9 | 20 | B |
| GLY | O | 750 | 188.0 | 117.3 | 32.8 | 21 | B |
| TYR | N | 751 | 190.2 | 117.2 | 32.2 | 20 | B |
| TYR | CA | 751 | 190.0 | 116.2 | 31.1 | 19 | B |
| TYR | CB | 751 | 191.1 | 116.2 | 30.1 | 18 | B |
| TYR | CG | 751 | 191.2 | 117.5 | 29.3 | 16 | B |
| TYR | CD1 | 751 | 192.4 | 118.2 | 29.3 | 16 | B |
| TYR | CE1 | 751 | 192.6 | 119.4 | 28.6 | 16 | B |
| TYR | CD2 | 751 | 190.1 | 118.0 | 28.6 | 16 | B |
| TYR | CE2 | 751 | 190.2 | 119.2 | 27.9 | 16 | B |
| TYR | CZ | 751 | 191.4 | 119.9 | 27.9 | 17 | B |
| TYR | OH | 751 | 191.6 | 121.1 | 27.2 | 18 | B |
| TYR | C | 751 | 189.7 | 114.8 | 31.6 | 20 | B |
| TYR | O | 751 | 188.9 | 114.1 | 31.1 | 20 | B |
| THR | N | 752 | 190.5 | 114.4 | 32.6 | 20 | B |
| THR | CA | 752 | 190.4 | 113.1 | 33.2 | 20 | B |
| THR | CB | 752 | 191.5 | 112.9 | 34.2 | 20 | B |
| THR | OG1 | 752 | 192.7 | 113.1 | 33.6 | 21 | B |
| THR | CG2 | 752 | 191.4 | 111.4 | 34.7 | 20 | B |
| THR | C | 752 | 189.0 | 113.0 | 33.9 | 22 | B |
| THR | O | 752 | 188.4 | 111.9 | 33.9 | 24 | B |
| PHE | N | 753 | 188.4 | 114.0 | 34.4 | 22 | B |
| PHE | CA | 753 | 187.1 | 114.0 | 35.0 | 21 | B |
| PHE | CB | 753 | 186.7 | 115.2 | 35.8 | 19 | B |
| PHE | CG | 753 | 185.3 | 115.2 | 36.2 | 18 | B |
| PHE | CD1 | 753 | 184.9 | 114.4 | 37.2 | 17 | B |
| PHE | CD2 | 753 | 184.4 | 115.9 | 35.5 | 18 | B |
| PHE | CE1 | 753 | 183.5 | 114.3 | 37.5 | 18 | B |
| PHE | CE2 | 753 | 183.0 | 115.8 | 35.7 | 19 | B |

TABLE 5-continued

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| PHE | CZ | 753 | 182.6 | 115.0 | 36.8 | 19 | B |
| PHE | C | 753 | 186.1 | 113.8 | 33.8 | 21 | B |
| PHE | O | 753 | 185.3 | 112.9 | 33.8 | 23 | B |
| CYS | N | 754 | 186.3 | 114.6 | 32.7 | 22 | B |
| CYS | CA | 754 | 185.4 | 114.5 | 31.5 | 22 | B |
| CYS | CB | 754 | 185.8 | 115.5 | 30.5 | 23 | B |
| CYS | SG | 754 | 185.4 | 117.2 | 31.0 | 23 | B |
| CYS | C | 754 | 185.5 | 113.1 | 30.9 | 22 | B |
| CYS | O | 754 | 184.4 | 112.5 | 30.6 | 23 | B |
| GLY | N | 755 | 186.7 | 112.5 | 30.8 | 22 | B |
| GLY | CA | 755 | 186.9 | 111.2 | 30.2 | 22 | B |
| GLY | C | 755 | 186.2 | 110.2 | 31.0 | 24 | B |
| GLY | O | 755 | 185.3 | 109.5 | 30.5 | 24 | B |
| LEU | N | 756 | 186.6 | 110.0 | 32.3 | 24 | B |
| LEU | CA | 756 | 186.0 | 109.0 | 33.2 | 25 | B |
| LEU | CB | 756 | 186.6 | 109.0 | 34.5 | 25 | B |
| LEU | CG | 756 | 186.2 | 107.9 | 35.5 | 24 | B |
| LEU | CD1 | 756 | 186.5 | 106.5 | 35.0 | 24 | B |
| LEU | CD2 | 756 | 186.9 | 108.1 | 36.8 | 24 | B |
| LEU | C | 756 | 184.4 | 109.2 | 33.3 | 26 | B |
| LEU | O | 756 | 183.7 | 108.2 | 33.1 | 26 | B |
| ALA | N | 757 | 184.0 | 110.3 | 33.7 | 25 | B |
| ALA | CA | 757 | 182.5 | 110.6 | 33.9 | 23 | B |
| ALA | CB | 757 | 182.3 | 112.0 | 34.2 | 22 | B |
| ALA | C | 757 | 181.7 | 110.2 | 32.6 | 23 | B |
| ALA | O | 757 | 180.7 | 109.6 | 32.8 | 24 | B |
| ALA | N | 758 | 182.2 | 110.5 | 31.5 | 23 | B |
| ALA | CA | 758 | 181.5 | 110.2 | 30.2 | 24 | B |
| ALA | CB | 758 | 182.2 | 110.8 | 29.0 | 24 | B |
| ALA | C | 758 | 181.4 | 108.7 | 30.0 | 24 | B |
| ALA | O | 758 | 180.4 | 108.2 | 29.6 | 24 | B |
| LEU | N | 759 | 182.5 | 108.0 | 30.4 | 24 | B |
| LEU | CA | 759 | 182.6 | 106.5 | 30.2 | 24 | B |
| LEU | CB | 759 | 184.0 | 106.0 | 30.5 | 22 | B |
| LEU | CG | 759 | 184.9 | 106.2 | 29.2 | 21 | B |
| LEU | CD1 | 759 | 186.2 | 105.6 | 29.5 | 20 | B |
| LEU | CD2 | 759 | 184.2 | 105.6 | 28.0 | 20 | B |
| LEU | C | 759 | 181.6 | 105.9 | 31.2 | 26 | B |
| LEU | O | 759 | 180.8 | 105.0 | 30.9 | 26 | B |
| VAL | N | 760 | 181.6 | 106.5 | 32.4 | 27 | B |
| VAL | CA | 760 | 180.6 | 106.0 | 33.5 | 26 | B |
| VAL | CB | 760 | 180.8 | 106.8 | 34.7 | 27 | B |
| VAL | CG1 | 760 | 179.7 | 106.5 | 35.7 | 27 | B |
| VAL | CG2 | 760 | 182.2 | 106.5 | 35.4 | 26 | B |
| VAL | C | 760 | 179.2 | 106.2 | 32.9 | 27 | B |
| VAL | O | 760 | 178.4 | 105.3 | 33.0 | 29 | B |
| ILE | N | 761 | 178.9 | 107.3 | 32.3 | 27 | B |
| ILE | CA | 761 | 177.6 | 107.5 | 31.7 | 28 | B |
| ILE | CB | 761 | 177.5 | 109.0 | 31.1 | 28 | B |
| ILE | CG2 | 761 | 176.0 | 109.2 | 30.6 | 27 | B |
| ILE | CG1 | 761 | 177.7 | 110.0 | 32.2 | 27 | B |
| ILE | CD1 | 761 | 177.7 | 111.4 | 31.7 | 27 | B |
| ILE | C | 761 | 177.4 | 106.5 | 30.6 | 30 | B |
| ILE | O | 761 | 176.2 | 106.0 | 30.4 | 31 | B |
| LEU | N | 762 | 178.4 | 106.2 | 29.8 | 32 | B |
| LEU | CA | 762 | 178.3 | 105.2 | 28.7 | 32 | B |
| LEU | CB | 762 | 179.4 | 105.5 | 27.7 | 30 | B |
| LEU | CG | 762 | 179.4 | 106.8 | 26.8 | 29 | B |
| LEU | CD1 | 762 | 180.4 | 106.7 | 25.8 | 28 | B |
| LEU | CD2 | 762 | 178.0 | 107.0 | 26.2 | 27 | B |
| LEU | C | 762 | 178.4 | 103.8 | 29.2 | 34 | B |
| LEU | O | 762 | 178.4 | 102.8 | 28.5 | 34 | B |
| LYS | N | 763 | 178.6 | 103.7 | 30.6 | 36 | B |
| LYS | CA | 763 | 178.8 | 102.3 | 31.2 | 38 | B |
| LYS | CB | 763 | 177.5 | 101.5 | 31.0 | 39 | B |
| LYS | CG | 763 | 176.3 | 102.1 | 31.6 | 42 | B |
| LYS | CD | 763 | 175.0 | 101.6 | 30.9 | 44 | B |
| LYS | CE | 763 | 173.8 | 102.3 | 31.3 | 45 | B |
| LYS | NZ | 763 | 172.7 | 101.9 | 30.4 | 46 | B |
| LYS | C | 763 | 179.9 | 101.6 | 30.5 | 38 | B |
| LYS | O | 763 | 179.9 | 100.4 | 30.4 | 39 | B |
| LYS | N | 764 | 181.0 | 102.4 | 30.2 | 37 | B |

TABLE 5-continued

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| LYS | CA | 764 | 182.2 | 101.8 | 29.6 | 37 | B |
| LYS | CB | 764 | 182.4 | 102.4 | 28.2 | 37 | B |
| LYS | CG | 764 | 181.3 | 102.0 | 27.3 | 38 | B |
| LYS | CD | 764 | 181.2 | 100.6 | 27.1 | 39 | B |
| LYS | CE | 764 | 180.2 | 100.3 | 26.0 | 39 | B |
| LYS | NZ | 764 | 179.2 | 101.3 | 26.0 | 41 | B |
| LYS | C | 764 | 183.5 | 102.0 | 30.3 | 38 | B |
| LYS | O | 764 | 184.5 | 101.9 | 29.7 | 37 | B |
| GLU | N | 765 | 183.4 | 102.4 | 31.6 | 39 | B |
| GLU | CA | 765 | 184.7 | 102.7 | 32.4 | 41 | B |
| GLU | CB | 765 | 184.4 | 102.8 | 33.9 | 42 | B |
| GLU | CG | 765 | 183.1 | 103.4 | 34.3 | 43 | B |
| GLU | CD | 765 | 182.0 | 102.3 | 34.4 | 44 | B |
| GLU | OE1 | 765 | 182.0 | 101.6 | 35.4 | 45 | B |
| GLU | OE2 | 765 | 181.2 | 102.2 | 33.4 | 44 | B |
| GLU | C | 765 | 185.7 | 101.6 | 32.2 | 42 | B |
| GLU | O | 765 | 186.9 | 101.9 | 32.2 | 43 | B |
| ARG | N | 766 | 185.3 | 100.4 | 32.0 | 43 | B |
| ARG | CA | 766 | 186.3 | 99.3 | 31.8 | 45 | B |
| ARG | CB | 766 | 185.5 | 97.9 | 31.6 | 48 | B |
| ARG | CG | 766 | 185.1 | 97.3 | 33.0 | 52 | B |
| ARG | CD | 766 | 183.8 | 97.8 | 33.4 | 55 | B |
| ARG | NE | 766 | 183.8 | 98.2 | 34.8 | 57 | B |
| ARG | CZ | 766 | 182.7 | 98.7 | 35.5 | 58 | B |
| ARG | NH1 | 766 | 182.9 | 99.1 | 36.8 | 58 | B |
| ARG | NH2 | 766 | 181.5 | 98.8 | 34.9 | 59 | B |
| ARG | C | 766 | 187.2 | 99.5 | 30.6 | 44 | B |
| ARG | O | 766 | 188.2 | 98.8 | 30.6 | 43 | B |
| SER | N | 767 | 186.8 | 100.4 | 29.7 | 43 | B |
| SER | CA | 767 | 187.7 | 100.7 | 28.6 | 43 | B |
| SER | CB | 767 | 186.9 | 101.6 | 27.6 | 43 | B |
| SER | OG | 767 | 185.8 | 100.9 | 27.1 | 45 | B |
| SER | C | 767 | 189.0 | 101.5 | 28.9 | 42 | B |
| SER | O | 767 | 189.8 | 101.7 | 28.0 | 43 | B |
| LEU | N | 768 | 189.1 | 101.8 | 30.2 | 41 | B |
| LEU | CA | 768 | 190.4 | 102.5 | 30.7 | 40 | B |
| LEU | CB | 768 | 190.0 | 103.7 | 31.5 | 39 | B |
| LEU | CG | 768 | 189.2 | 104.9 | 30.8 | 39 | B |
| LEU | CD1 | 768 | 188.8 | 105.9 | 31.9 | 39 | B |
| LEU | CD2 | 768 | 190.0 | 105.5 | 29.7 | 39 | B |
| LEU | C | 768 | 191.1 | 101.6 | 31.6 | 39 | B |
| LEU | O | 768 | 190.5 | 100.6 | 32.1 | 39 | B |
| ASN | N | 769 | 192.4 | 101.8 | 31.8 | 37 | B |
| ASN | CA | 769 | 193.2 | 101.0 | 32.8 | 35 | B |
| ASN | CB | 769 | 194.6 | 101.1 | 32.5 | 35 | B |
| ASN | CG | 769 | 195.5 | 100.3 | 33.5 | 36 | B |
| ASN | OD1 | 769 | 195.0 | 100.1 | 34.6 | 36 | B |
| ASN | ND2 | 769 | 196.7 | 100.0 | 33.1 | 37 | B |
| ASN | C | 769 | 192.8 | 101.7 | 34.1 | 35 | B |
| ASN | O | 769 | 193.5 | 102.6 | 34.5 | 36 | B |
| LEU | N | 770 | 191.8 | 101.3 | 34.8 | 33 | B |
| LEU | CA | 770 | 191.4 | 101.9 | 36.0 | 31 | B |
| LEU | CB | 770 | 190.0 | 101.3 | 36.5 | 29 | B |
| LEU | CG | 770 | 188.9 | 101.5 | 35.5 | 27 | B |
| LEU | CD1 | 770 | 187.6 | 101.0 | 36.1 | 27 | B |
| LEU | CD2 | 770 | 188.7 | 103.0 | 35.1 | 27 | B |
| LEU | C | 770 | 192.4 | 101.8 | 37.1 | 32 | B |
| LEU | O | 770 | 192.4 | 102.7 | 38.0 | 33 | B |
| LYS | N | 771 | 193.4 | 101.0 | 37.0 | 34 | B |
| LYS | CA | 771 | 194.4 | 100.9 | 38.0 | 36 | B |
| LYS | CB | 771 | 195.1 | 99.6 | 38.1 | 39 | B |
| LYS | CG | 771 | 194.4 | 98.6 | 39.0 | 42 | B |
| LYS | CD | 771 | 194.0 | 99.3 | 40.4 | 45 | B |
| LYS | CE | 771 | 193.2 | 98.4 | 41.3 | 46 | B |
| LYS | NZ | 771 | 191.8 | 98.0 | 40.8 | 47 | B |
| LYS | C | 771 | 195.5 | 102.0 | 37.9 | 37 | B |
| LYS | O | 771 | 195.8 | 102.7 | 38.9 | 38 | B |
| SER | N | 772 | 196.0 | 102.3 | 36.7 | 37 | B |
| SER | CA | 772 | 196.9 | 103.3 | 36.4 | 37 | B |
| SER | CB | 772 | 197.5 | 103.2 | 35.0 | 37 | B |
| SER | OG | 772 | 196.5 | 103.3 | 34.0 | 39 | B |
| SER | C | 772 | 196.3 | 104.6 | 36.6 | 36 | B |

TABLE 5-continued

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| SER | O | 772 | 196.9 | 105.6 | 37.0 | 37 | B |
| LEU | N | 773 | 195.0 | 104.7 | 36.3 | 36 | B |
| LEU | CA | 773 | 194.2 | 105.9 | 36.5 | 36 | B |
| LEU | CB | 773 | 192.9 | 105.8 | 35.8 | 35 | B |
| LEU | CG | 773 | 191.8 | 106.8 | 36.1 | 35 | B |
| LEU | CD1 | 773 | 192.3 | 108.3 | 36.1 | 34 | B |
| LEU | CD2 | 773 | 190.7 | 106.7 | 35.0 | 35 | B |
| LEU | C | 773 | 194.1 | 106.2 | 38.0 | 37 | B |
| LEU | O | 773 | 194.5 | 107.2 | 38.5 | 38 | B |
| LEU | N | 774 | 193.7 | 105.1 | 38.7 | 36 | B |
| LEU | CA | 774 | 193.6 | 105.3 | 40.2 | 34 | B |
| LEU | CB | 774 | 193.2 | 104.0 | 40.9 | 34 | B |
| LEU | CG | 774 | 193.3 | 104.1 | 42.5 | 34 | B |
| LEU | CD1 | 774 | 192.3 | 105.1 | 42.9 | 33 | B |
| LEU | CD2 | 774 | 193.1 | 102.8 | 43.2 | 34 | B |
| LEU | C | 774 | 194.9 | 105.8 | 40.8 | 34 | B |
| LEU | O | 774 | 194.9 | 106.8 | 41.5 | 35 | B |
| GLN | N | 775 | 196.0 | 105.2 | 40.3 | 34 | B |
| GLN | CA | 775 | 197.3 | 105.6 | 40.8 | 34 | B |
| GLN | CB | 775 | 198.3 | 104.7 | 40.3 | 35 | B |
| GLN | CG | 775 | 199.7 | 105.0 | 40.9 | 39 | B |
| GLN | CD | 775 | 200.7 | 103.9 | 40.6 | 43 | B |
| GLN | OE1 | 775 | 201.5 | 103.5 | 41.5 | 45 | B |
| GLN | NE2 | 775 | 200.7 | 103.4 | 39.3 | 44 | B |
| GLN | C | 775 | 197.7 | 107.1 | 40.5 | 33 | B |
| GLN | O | 775 | 198.2 | 107.8 | 41.3 | 34 | B |
| TRP | N | 776 | 197.4 | 107.5 | 39.2 | 30 | B |
| TRP | CA | 776 | 197.7 | 108.9 | 38.8 | 27 | B |
| TRP | CB | 776 | 197.6 | 109.0 | 37.3 | 25 | B |
| TRP | CG | 776 | 197.7 | 110.4 | 36.8 | 23 | B |
| TRP | CD2 | 776 | 196.6 | 111.3 | 36.6 | 21 | B |
| TRP | CE2 | 776 | 197.1 | 112.5 | 36.1 | 21 | B |
| TRP | CE3 | 776 | 195.2 | 111.3 | 36.8 | 22 | B |
| TRP | CD1 | 776 | 198.8 | 111.1 | 36.4 | 22 | B |
| TRP | NE1 | 776 | 198.5 | 112.3 | 35.9 | 21 | B |
| TRP | CZ2 | 776 | 196.4 | 113.6 | 35.8 | 22 | B |
| TRP | CZ3 | 776 | 194.4 | 112.4 | 36.5 | 22 | B |
| TRP | CH2 | 776 | 195.0 | 113.5 | 36.0 | 23 | B |
| TRP | C | 776 | 196.9 | 109.9 | 39.6 | 26 | B |
| TRP | O | 776 | 197.5 | 110.8 | 40.2 | 26 | B |
| VAL | N | 777 | 195.6 | 109.8 | 39.7 | 25 | B |
| VAL | CA | 777 | 194.7 | 110.8 | 40.4 | 24 | B |
| VAL | CB | 777 | 193.2 | 110.4 | 40.3 | 24 | B |
| VAL | CG1 | 777 | 192.9 | 109.1 | 41.0 | 23 | B |
| VAL | CG2 | 777 | 192.4 | 111.5 | 40.8 | 24 | B |
| VAL | C | 777 | 195.1 | 110.9 | 41.8 | 26 | B |
| VAL | O | 777 | 195.2 | 112.1 | 42.3 | 26 | B |
| THR | N | 778 | 195.4 | 109.8 | 42.5 | 27 | B |
| THR | CA | 778 | 195.8 | 109.9 | 43.9 | 28 | B |
| THR | CB | 778 | 195.9 | 108.5 | 44.6 | 27 | B |
| THR | OG1 | 778 | 196.9 | 107.7 | 44.0 | 26 | B |
| THR | CG2 | 778 | 194.5 | 107.7 | 44.4 | 26 | B |
| THR | C | 778 | 197.1 | 110.6 | 44.1 | 29 | B |
| THR | O | 778 | 197.4 | 111.2 | 45.1 | 30 | B |
| SER | N | 779 | 198.0 | 110.4 | 43.0 | 29 | B |
| SER | CA | 779 | 199.3 | 111.1 | 43.1 | 29 | B |
| SER | CB | 779 | 200.1 | 110.6 | 41.9 | 30 | B |
| SER | OG | 779 | 200.4 | 109.2 | 42.1 | 32 | B |
| SER | C | 779 | 199.1 | 112.6 | 42.9 | 30 | B |
| SER | O | 779 | 200.1 | 113.4 | 43.1 | 31 | B |
| ARG | N | 780 | 197.9 | 113.1 | 42.5 | 29 | B |
| ARG | CA | 780 | 197.7 | 114.5 | 42.3 | 28 | B |
| ARG | CB | 780 | 196.5 | 114.7 | 41.3 | 28 | B |
| ARG | CG | 780 | 196.8 | 114.1 | 39.9 | 27 | B |
| ARG | CD | 780 | 197.7 | 114.9 | 39.0 | 24 | B |
| ARG | NE | 780 | 199.1 | 114.9 | 39.5 | 23 | B |
| ARG | CZ | 780 | 199.9 | 113.8 | 39.4 | 22 | B |
| ARG | NH1 | 780 | 199.4 | 112.6 | 39.0 | 22 | B |
| ARG | NH2 | 780 | 201.1 | 113.9 | 39.8 | 21 | B |
| ARG | C | 780 | 197.4 | 115.3 | 43.6 | 29 | B |
| ARG | O | 780 | 197.3 | 116.5 | 43.5 | 28 | B |
| GLN | N | 781 | 197.2 | 114.7 | 44.7 | 30 | B |
| GLN | CA | 781 | 196.9 | 115.4 | 45.9 | 31 | B |
| GLN | CB | 781 | 196.2 | 114.5 | 47.0 | 32 | B |
| GLN | CG | 781 | 195.6 | 115.4 | 48.1 | 32 | B |
| GLN | CD | 781 | 194.6 | 114.6 | 48.9 | 33 | B |
| GLN | OE1 | 781 | 194.5 | 113.4 | 48.9 | 34 | B |
| GLN | NE2 | 781 | 193.7 | 115.4 | 49.6 | 33 | B |
| GLN | C | 781 | 198.2 | 115.9 | 46.5 | 52 | B |
| GLN | O | 781 | 199.2 | 115.1 | 46.5 | 33 | B |
| MET | N | 782 | 198.3 | 117.2 | 4.7 | 31 | B |
| MET | CA | 782 | 199.5 | 117.8 | 47.2 | 31 | B |
| MET | CB | 782 | 199.5 | 119.3 | 47.0 | 30 | B |
| MET | CG | 782 | 199.3 | 119.7 | 45.6 | 29 | B |
| MET | SD | 782 | 200.5 | 118.9 | 44.5 | 28 | B |
| MET | CE | 782 | 201.8 | 120.1 | 44.5 | 28 | B |
| MET | C | 782 | 199.7 | 117.4 | 48.7 | 33 | B |
| MET | O | 782 | 198.9 | 117.8 | 49.5 | 33 | B |
| ARG | N | 783 | 200.8 | 116.7 | 48.9 | 35 | B |
| ARG | CA | 783 | 201.2 | 116.3 | 50.3 | 36 | B |
| ARG | CB | 783 | 202.4 | 115.4 | 50.3 | 37 | B |
| ARG | CG | 783 | 203.6 | 116.2 | 49.8 | 39 | B |
| ARG | CD | 783 | 204.7 | 115.4 | 49.1 | 41 | B |
| ARG | NE | 783 | 205.1 | 114.3 | 50.0 | 43 | B |
| ARG | CZ | 783 | 205.3 | 113.1 | 49.6 | 45 | B |
| ARG | NH1 | 783 | 205.1 | 112.7 | 48.4 | 45 | B |
| ARG | NH2 | 783 | 205.6 | 112.2 | 50.6 | 46 | B |
| ARG | C | 783 | 201.3 | 117.4 | 51.4 | 36 | B |
| ARG | O | 783 | 201.2 | 117.1 | 52.6 | 38 | B |
| PHE | N | 784 | 201.6 | 118.6 | 50.9 | 35 | B |
| PHE | CA | 784 | 201.7 | 119.7 | 51.8 | 34 | B |
| PHE | CB | 784 | 202.9 | 120.6 | 51.5 | 34 | B |
| PHE | CG | 784 | 203.2 | 121.6 | 52.5 | 34 | B |
| PHE | CD1 | 784 | 204.0 | 121.3 | 53.6 | 34 | B |
| PHE | CD2 | 784 | 202.6 | 122.9 | 52.4 | 34 | B |
| PHE | CE1 | 784 | 204.2 | 122.2 | 54.6 | 34 | B |
| PHE | CE2 | 784 | 202.8 | 123.8 | 53.4 | 34 | B |
| PHE | CZ | 784 | 203.6 | 123.5 | 54.5 | 34 | B |
| PHE | C | 784 | 200.5 | 120.6 | 51.8 | 33 | B |
| PHE | O | 784 | 199.9 | 120.8 | 52.9 | 35 | B |
| GLU | N | 785 | 200.1 | 121.1 | 50.7 | 31 | B |
| GLU | CA | 785 | 198.9 | 122.0 | 50.6 | 29 | B |
| GLU | CB | 785 | 198.9 | 122.7 | 49.3 | 30 | B |
| GLU | CG | 785 | 200.2 | 123.4 | 48.9 | 30 | B |
| GLU | CD | 785 | 201.2 | 122.6 | 48.1 | 32 | B |
| GLU | OE1 | 785 | 201.1 | 122.6 | 46.9 | 34 | B |
| GLU | OE2 | 785 | 202.0 | 121.9 | 48.8 | 33 | B |
| GLU | C | 785 | 197.6 | 121.2 | 50.8 | 29 | B |
| GLU | O | 785 | 196.6 | 121.8 | 51.2 | 28 | B |
| GLY | N | 786 | 197.7 | 119.9 | 50.6 | 28 | B |
| GLY | CA | 786 | 196.5 | 119.0 | 50.8 | 27 | B |
| GLY | C | 786 | 195.5 | 119.1 | 49.6 | 27 | B |
| GLY | O | 786 | 194.7 | 118.2 | 49.5 | 28 | B |
| GLY | N | 787 | 195.5 | 120.2 | 48.9 | 26 | B |
| GLY | CA | 787 | 194.6 | 120.4 | 47.8 | 24 | B |
| GLY | C | 787 | 195.2 | 119.6 | 46.6 | 23 | B |
| GLY | O | 787 | 196.3 | 119.0 | 46.7 | 22 | B |
| PHE | N | 788 | 194.4 | 119.6 | 45.5 | 23 | B |
| PHE | CA | 788 | 194.9 | 118.9 | 44.2 | 23 | B |
| PHE | CB | 788 | 193.7 | 118.1 | 43.6 | 22 | B |
| PHE | CG | 788 | 193.4 | 116.7 | 44.2 | 22 | B |
| PHE | CD1 | 788 | 192.5 | 116.6 | 45.2 | 22 | B |
| PHE | CD2 | 788 | 194.1 | 115.6 | 43.8 | 22 | B |
| PHE | CE1 | 788 | 192.2 | 115.3 | 45.8 | 21 | B |
| PHE | CE2 | 788 | 193.9 | 114.4 | 44.4 | 21 | B |
| PHE | CZ | 788 | 192.9 | 114.2 | 45.4 | 21 | B |
| PHE | C | 788 | 195.5 | 119.7 | 43.2 | 22 | B |
| PHE | O | 788 | 195.2 | 120.9 | 43.0 | 23 | B |
| GLN | N | 789 | 196.4 | 119.2 | 42.4 | 23 | B |
| GLN | CA | 789 | 197.1 | 119.9 | 41.3 | 24 | B |
| GLN | CB | 789 | 198.6 | 119.6 | 41.3 | 23 | B |
| GLN | CG | 789 | 198.9 | 118.1 | 41.0 | 23 | B |
| GLN | CD | 789 | 200.4 | 117.9 | 41.0 | 24 | B |
| GLN | OE1 | 789 | 200.9 | 116.7 | 40.8 | 24 | B |

TABLE 5-continued

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| GLN | NE2 | 789 | 201.2 | 118.9 | 41.3 | 25 | B |
| GLN | C | 789 | 196.4 | 119.4 | 40.0 | 24 | B |
| GLN | O | 789 | 195.9 | 118.2 | 40.0 | 25 | B |
| GLY | N | 790 | 196.5 | 120.2 | 39.0 | 23 | B |
| GLY | CA | 790 | 195.9 | 119.8 | 37.7 | 20 | B |
| GLY | C | 790 | 196.6 | 118.7 | 36.9 | 19 | B |
| GLY | O | 790 | 196.0 | 117.9 | 36.3 | 18 | B |
| ARG | N | 791 | 198.0 | 118.8 | 37.0 | 18 | B |
| ARG | CA | 791 | 198.8 | 117.8 | 36.2 | 19 | B |
| ARG | CB | 791 | 198.9 | 118.2 | 34.7 | 19 | B |
| ARG | CG | 791 | 198.8 | 119.8 | 34.5 | 19 | B |
| ARG | CD | 791 | 199.0 | 120.2 | 33.0 | 20 | B |
| ARG | NE | 791 | 198.9 | 121.6 | 32.8 | 19 | B |
| ARG | CZ | 791 | 199.6 | 122.3 | 31.8 | 19 | B |
| ARG | NH1 | 791 | 200.3 | 121.7 | 30.9 | 19 | B |
| ARG | NH2 | 791 | 199.5 | 123.6 | 31.7 | 17 | B |
| ARG | C | 791 | 200.1 | 117.8 | 37.0 | 20 | B |
| ARG | O | 791 | 200.5 | 118.7 | 37.6 | 20 | B |
| CYS | N | 792 | 200.8 | 116.6 | 36.8 | 22 | B |
| CYS | CA | 792 | 202.1 | 116.4 | 37.5 | 23 | B |
| CYS | CB | 792 | 202.7 | 115.2 | 37.0 | 24 | B |
| CYS | SG | 792 | 204.1 | 114.7 | 37.9 | 26 | B |
| CYS | C | 792 | 203.0 | 117.6 | 37.4 | 25 | B |
| CYS | O | 792 | 203.1 | 118.2 | 36.3 | 26 | B |
| ASN | N | 793 | 203.7 | 117.9 | 38.5 | 27 | B |
| ASN | CA | 793 | 204.7 | 119.0 | 38.5 | 27 | B |
| ASN | CB | 793 | 205.9 | 118.7 | 37.6 | 28 | B |
| ASN | CG | 793 | 207.0 | 118.0 | 38.3 | 29 | B |
| ASN | OD1 | 793 | 207.1 | 118.1 | 39.6 | 29 | B |
| ASN | ND2 | 793 | 207.9 | 117.3 | 37.6 | 28 | B |
| ASN | C | 793 | 204.1 | 120.4 | 38.2 | 27 | B |
| ASN | O | 793 | 204.8 | 121.4 | 37.7 | 27 | B |
| LYS | N | 794 | 202.8 | 120.6 | 38.5 | 27 | B |
| LYS | CA | 794 | 202.1 | 121.8 | 38.4 | 26 | B |
| LYS | CB | 794 | 200.9 | 121.5 | 37.5 | 28 | B |
| LYS | CG | 794 | 200.7 | 122.6 | 36.5 | 28 | B |
| LYS | CD | 794 | 201.8 | 122.6 | 35.5 | 27 | B |
| LYS | CE | 794 | 201.5 | 123.5 | 34.4 | 28 | B |
| LYS | NZ | 794 | 200.9 | 124.9 | 34.8 | 26 | B |
| LYS | C | 794 | 201.7 | 122.2 | 39.8 | 26 | B |
| LYS | O | 794 | 202.0 | 121.6 | 40.8 | 26 | B |
| LEU | N | 795 | 200.9 | 123.3 | 39.9 | 26 | B |
| LEU | CA | 795 | 200.5 | 123.9 | 41.2 | 25 | B |
| LEU | CB | 795 | 200.6 | 125.4 | 41.2 | 24 | B |
| LEU | CG | 795 | 202.0 | 126.0 | 40.8 | 22 | B |
| LEU | CD1 | 795 | 201.9 | 127.5 | 41.1 | 22 | B |
| LEU | CD2 | 795 | 203.1 | 125.3 | 41.5 | 23 | B |
| LEU | C | 795 | 199.1 | 123.5 | 41.6 | 25 | B |
| LEU | O | 795 | 198.3 | 123.2 | 40.8 | 25 | B |
| VAL | N | 796 | 198.9 | 123.6 | 42.9 | 25 | B |
| VAL | CA | 796 | 197.5 | 123.3 | 43.5 | 24 | B |
| VAL | CB | 796 | 197.5 | 123.5 | 45.0 | 25 | B |
| VAL | CG1 | 796 | 197.1 | 122.3 | 45.7 | 26 | B |
| VAL | CG2 | 796 | 198.8 | 124.1 | 45.5 | 26 | B |
| VAL | C | 796 | 196.6 | 124.3 | 43.0 | 23 | B |
| VAL | O | 796 | 196.9 | 125.5 | 42.7 | 25 | B |
| ASP | N | 797 | 195.3 | 124.0 | 43.0 | 23 | B |
| ASP | CA | 797 | 194.3 | 125.0 | 42.6 | 22 | B |
| ASP | CB | 797 | 194.3 | 125.0 | 41.1 | 21 | B |
| ASP | CG | 797 | 193.1 | 125.9 | 40.5 | 21 | B |
| ASP | OD1 | 797 | 192.1 | 126.1 | 41.1 | 22 | B |
| ASP | OD2 | 797 | 193.3 | 126.4 | 39.4 | 22 | B |
| ASP | C | 797 | 193.0 | 124.4 | 43.1 | 22 | B |
| ASP | O | 797 | 192.6 | 123.3 | 42.9 | 23 | B |
| GLY | N | 798 | 192.2 | 125.2 | 43.8 | 23 | B |
| GLY | CA | 798 | 191.0 | 124.8 | 44.4 | 24 | B |
| GLY | C | 798 | 189.9 | 124.2 | 43.5 | 25 | B |
| GLY | O | 798 | 189.2 | 123.3 | 44.1 | 27 | B |
| CYS | N | 799 | 189.8 | 124.5 | 42.3 | 25 | B |
| CYS | CA | 799 | 188.7 | 123.9 | 41.4 | 25 | B |
| CYS | CB | 799 | 188.5 | 124.5 | 40.1 | 26 | B |
| CYS | SG | 799 | 190.0 | 124.7 | 39.0 | 27 | B |

TABLE 5-continued

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| CYS | C | 799 | 189.0 | 122.4 | 41.2 | 26 | B |
| CYS | O | 799 | 188.1 | 121.6 | 41.0 | 26 | B |
| TYR | N | 800 | 190.3 | 122.0 | 41.3 | 25 | B |
| TYR | CA | 800 | 190.7 | 120.6 | 41.1 | 27 | B |
| TYR | CB | 800 | 192.2 | 120.5 | 40.9 | 26 | B |
| TYR | CG | 800 | 192.7 | 121.1 | 39.6 | 26 | B |
| TYR | CD1 | 800 | 193.7 | 122.0 | 39.6 | 26 | B |
| TYR | CE1 | 800 | 194.1 | 122.6 | 38.4 | 27 | B |
| TYR | CD2 | 800 | 192.0 | 120.8 | 38.4 | 26 | B |
| TYR | CE2 | 800 | 192.4 | 121.4 | 37.2 | 27 | B |
| TYR | CZ | 800 | 193.5 | 122.3 | 37.2 | 27 | B |
| TYR | OH | 800 | 193.9 | 123.0 | 36.1 | 27 | B |
| TYR | C | 800 | 190.3 | 119.8 | 42.3 | 29 | B |
| TYR | O | 800 | 190.5 | 118.6 | 42.3 | 30 | B |
| SER | N | 801 | 189.7 | 120.4 | 43.3 | 30 | B |
| SER | CA | 801 | 189.2 | 119.7 | 44.5 | 29 | B |
| SER | CB | 801 | 188.7 | 120.7 | 45.5 | 29 | B |
| SER | OG | 801 | 189.8 | 121.7 | 45.8 | 28 | B |
| SER | C | 801 | 188.1 | 118.9 | 44.0 | 30 | B |
| SER | O | 801 | 187.8 | 117.8 | 44.5 | 31 | B |
| PHE | N | 802 | 187.4 | 119.3 | 42.9 | 30 | B |
| PHE | CA | 802 | 186.3 | 118.6 | 42.2 | 29 | B |
| PHE | CB | 802 | 185.2 | 119.4 | 41.8 | 27 | B |
| PHE | CG | 802 | 184.1 | 118.6 | 41.1 | 27 | B |
| PHE | CD1 | 802 | 183.1 | 118.0 | 41.9 | 27 | B |
| PHE | CD2 | 802 | 184.1 | 118.5 | 39.8 | 26 | B |
| PHE | CE1 | 802 | 182.1 | 117.2 | 41.2 | 27 | B |
| PHE | CE2 | 802 | 183.2 | 117.7 | 39.1 | 27 | B |
| PHE | CZ | 802 | 182.2 | 117.0 | 39.9 | 27 | B |
| PHE | C | 802 | 186.7 | 117.8 | 41.0 | 29 | B |
| PHE | O | 802 | 186.3 | 116.6 | 40.8 | 32 | B |
| TRP | N | 803 | 187.4 | 118.4 | 40.1 | 26 | B |
| TRP | CA | 803 | 187.6 | 117.7 | 38.8 | 22 | B |
| TRP | CB | 803 | 188.6 | 118.7 | 37.9 | 20 | B |
| TRP | CG | 803 | 187.8 | 119.9 | 37.5 | 17 | B |
| TRP | CD2 | 803 | 186.6 | 119.9 | 36.8 | 16 | B |
| TRP | CE2 | 803 | 186.3 | 121.3 | 36.6 | 16 | B |
| TRP | CE3 | 803 | 185.7 | 118.9 | 36.4 | 17 | B |
| TRP | CD1 | 803 | 188.2 | 121.2 | 37.6 | 17 | B |
| TRP | NE1 | 803 | 187.3 | 122.0 | 37.1 | 17 | B |
| TRP | CZ2 | 803 | 185.1 | 121.7 | 35.9 | 17 | B |
| TRP | CZ3 | 803 | 184.5 | 119.3 | 35.8 | 17 | B |
| TRP | CH2 | 803 | 184.2 | 120.7 | 35.5 | 17 | B |
| TRP | C | 803 | 188.7 | 116.5 | 39.1 | 23 | B |
| TRP | O | 803 | 188.5 | 115.5 | 38.5 | 24 | B |
| GLN | N | 804 | 189.6 | 116.6 | 40.1 | 24 | B |
| GLN | CA | 804 | 190.5 | 115.5 | 40.5 | 24 | B |
| GLN | CB | 804 | 191.8 | 116.0 | 41.0 | 23 | B |
| GLN | CG | 804 | 192.6 | 116.8 | 40.0 | 24 | B |
| GLN | CD | 804 | 193.4 | 115.9 | 39.1 | 24 | B |
| GLN | OE1 | 804 | 192.9 | 114.8 | 38.7 | 25 | B |
| GLN | NE2 | 804 | 194.6 | 116.3 | 38.7 | 24 | B |
| GLN | C | 804 | 189.9 | 114.6 | 41.6 | 26 | B |
| GLN | O | 804 | 189.7 | 113.4 | 41.4 | 27 | B |
| ALA | N | 805 | 189.6 | 115.2 | 42.8 | 25 | B |
| ALA | CA | 805 | 189.0 | 114.4 | 43.9 | 24 | B |
| ALA | CB | 805 | 188.8 | 115.3 | 45.1 | 23 | B |
| ALA | C | 805 | 187.7 | 1.3.8 | 43.5 | 24 | B |
| ALA | O | 805 | 187.3 | 112.8 | 44.0 | 25 | B |
| GLY | N | 806 | 187.0 | 114.4 | 42.5 | 24 | B |
| GLY | CA | 806 | 185.7 | 113.9 | 42.0 | 24 | B |
| GLY | C | 806 | 185.9 | 112.6 | 41.4 | 25 | B |
| GLY | O | 806 | 185.0 | 111.8 | 41.4 | 26 | B |
| LEU | N | 807 | 187.1 | 112.3 | 40.9 | 26 | B |
| LEU | CA | 807 | 187.4 | 111.0 | 40.2 | 28 | B |
| LEU | CB | 807 | 188.8 | 111.0 | 39.6 | 28 | B |
| LEU | CG | 807 | 189.0 | 111.8 | 38.3 | 28 | B |
| LEU | CD1 | 807 | 190.5 | 112.1 | 38.1 | 28 | B |
| LEU | CD2 | 807 | 188.5 | 111.1 | 37.1 | 27 | B |
| LEU | C | 807 | 187.2 | 109.8 | 41.1 | 30 | B |
| LEU | O | 807 | 186.9 | 108.7 | 40.7 | 31 | B |
| LEU | N | 808 | 187.5 | 110.0 | 42.4 | 30 | B |

TABLE 5-continued

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| LEU | CA | 808 | 187.5 | 108.9 | 43.4 | 30 | B |
| LEU | CB | 808 | 188.2 | 109.3 | 44.6 | 30 | B |
| LEU | CG | 808 | 189.7 | 109.4 | 44.1 | 31 | B |
| LEU | CD1 | 808 | 190.4 | 110.6 | 44.6 | 31 | B |
| LEU | CD2 | 808 | 190.5 | 108.1 | 44.3 | 29 | B |
| LEU | C | 808 | 186.1 | 108.3 | 43.6 | 31 | B |
| LEU | O | 808 | 185.9 | 107.1 | 43.8 | 32 | B |
| PRO | N | 809 | 185.0 | 109.1 | 43.7 | 30 | B |
| PRO | CD | 809 | 185.0 | 110.6 | 44.0 | 30 | B |
| PRO | CA | 809 | 183.7 | 108.6 | 43.8 | 29 | B |
| PRO | CB | 809 | 182.8 | 109.8 | 43.9 | 29 | B |
| PRO | CG | 809 | 183.7 | 110.7 | 44.7 | 30 | B |
| PRO | C | 809 | 183.4 | 107.8 | 42.6 | 30 | B |
| PRO | O | 809 | 182.8 | 106.7 | 42.6 | 31 | B |
| LEU | N | 810 | 183.8 | 108.3 | 41.4 | 30 | B |
| LEU | CA | 810 | 183.5 | 107.6 | 40.1 | 29 | B |
| LEU | CB | 810 | 184.0 | 108.5 | 39.0 | 28 | B |
| LEU | CG | 810 | 183.1 | 109.7 | 38.7 | 27 | B |
| LEU | CD1 | 810 | 183.6 | 110.5 | 37.5 | 27 | B |
| LEU | CD2 | 810 | 181.7 | 109.3 | 38.6 | 27 | B |
| LEU | C | 810 | 184.3 | 106.3 | 40.1 | 30 | B |
| LEU | O | 810 | 183.7 | 105.3 | 39.6 | 29 | B |
| LEU | N | 811 | 185.5 | 106.3 | 40.5 | 32 | B |
| LEU | CA | 811 | 186.3 | 105.1 | 40.5 | 35 | B |
| LEU | CB | 811 | 187.8 | 105.4 | 40.8 | 33 | B |
| LEU | CG | 811 | 188.7 | 105.8 | 39.6 | 32 | B |
| LEU | CD1 | 811 | 189.9 | 106.5 | 40.2 | 31 | B |
| LEU | CD2 | 811 | 189.0 | 104.6 | 38.8 | 30 | B |
| LEU | C | 811 | 185.8 | 104.1 | 41.5 | 39 | B |
| LEU | O | 811 | 186.1 | 102.9 | 41.4 | 41 | B |
| HIS | N | 812 | 185.1 | 104.5 | 42.5 | 43 | B |
| HIS | CA | 812 | 184.5 | 103.6 | 43.5 | 46 | B |
| HIS | CB | 812 | 183.9 | 104.4 | 44.7 | 49 | B |
| HIS | CG | 812 | 184.2 | 103.7 | 46.1 | 51 | B |
| HIS | CD2 | 812 | 183.5 | 102.8 | 46.7 | 51 | B |
| HIS | ND1 | 812 | 185.3 | 104.0 | 46.8 | 52 | B |
| HIS | CE1 | 812 | 185.3 | 103.3 | 47.9 | 51 | B |
| HIS | NE2 | 812 | 184.2 | 102.5 | 47.9 | 51 | B |
| HIS | C | 812 | 183.5 | 102.7 | 42.8 | 47 | B |
| HIS | O | 812 | 183.6 | 101.5 | 42.9 | 46 | B |
| ARG | N | 813 | 182.5 | 103.4 | 42.2 | 48 | B |
| ARG | CA | 813 | 181.5 | 102.7 | 41.5 | 49 | B |
| ARG | CB | 813 | 180.7 | 103.6 | 40.5 | 52 | B |
| ARG | CG | 813 | 179.8 | 104.6 | 41.2 | 56 | B |
| ARG | CD | 813 | 179.3 | 105.7 | 40.2 | 59 | B |
| ARG | NE | 813 | 178.2 | 106.5 | 40.7 | 62 | B |
| ARG | CZ | 813 | 178.2 | 107.3 | 41.8 | 63 | B |
| ARG | NH1 | 813 | 179.3 | 107.4 | 42.6 | 63 | B |
| ARG | NH2 | 813 | 177.0 | 107.9 | 42.2 | 64 | B |
| ARG | C | 813 | 182.1 | 101.6 | 40.6 | 48 | B |
| ARG | O | 813 | 181.8 | 100.5 | 40.6 | 49 | B |
| ALA | N | 814 | 183.0 | 102.1 | 39.7 | 47 | B |
| ALA | CA | 814 | 183.7 | 101.2 | 38.8 | 46 | B |
| ALA | CB | 814 | 184.7 | 102.0 | 38.0 | 46 | B |
| ALA | C | 814 | 184.4 | 100.0 | 39.4 | 46 | B |
| ALA | O | 814 | 184.1 | 98.9 | 39.1 | 46 | B |
| LEU | N | 815 | 185.4 | 100.3 | 40.3 | 47 | B |
| LEU | CA | 815 | 186.1 | 99.2 | 41.0 | 48 | B |
| LEU | CB | 815 | 187.1 | 99.8 | 41.9 | 47 | B |
| LEU | CG | 815 | 188.3 | 100.6 | 41.4 | 48 | B |
| LEU | CD1 | 815 | 189.0 | 101.3 | 42.4 | 48 | B |
| LEU | CD2 | 815 | 189.2 | 99.7 | 40.6 | 48 | B |
| LEU | C | 815 | 185.2 | 98.3 | 41.7 | 49 | B |
| LEU | O | 815 | 185.2 | 97.0 | 41.5 | 50 | B |
| HIS | N | 816 | 184.3 | 98.8 | 42.4 | 51 | B |
| HIS | CA | 816 | 183.3 | 98.0 | 43.2 | 53 | B |
| HIS | CB | 816 | 182.5 | 98.9 | 44.1 | 55 | B |
| HIS | CG | 816 | 181.4 | 98.2 | 44.7 | 57 | B |
| HIS | CD2 | 816 | 181.3 | 97.4 | 45.8 | 58 | B |
| HIS | ND1 | 816 | 180.1 | 98.4 | 44.3 | 58 | B |
| HIS | CE1 | 816 | 179.3 | 97.7 | 45.0 | 59 | B |
| HIS | NE2 | 816 | 180.0 | 97.1 | 46.0 | 59 | B |

TABLE 5-continued

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| HIS | C | 816 | 182.4 | 97.3 | 42.3 | 54 | B |
| HIS | O | 816 | 181.8 | 96.2 | 42.7 | 54 | B |
| ALA | N | 817 | 182.1 | 97.8 | 41.1 | 54 | B |
| ALA | CA | 817 | 181.2 | 97.1 | 40.1 | 54 | B |
| ALA | CB | 817 | 180.9 | 98.0 | 39.0 | 54 | B |
| ALA | C | 817 | 181.9 | 95.9 | 39.6 | 55 | B |
| ALA | O | 817 | 181.2 | 95.1 | 38.9 | 55 | B |
| GLN | N | 818 | 183.1 | 95.7 | 39.9 | 56 | B |
| GLN | CA | 818 | 183.9 | 94.5 | 39.5 | 56 | B |
| GLN | CB | 818 | 185.2 | 94.9 | 38.9 | 56 | B |
| GLN | CG | 818 | 184.9 | 95.7 | 37.6 | 57 | B |
| GLN | CD | 818 | 186.1 | 96.5 | 37.2 | 57 | B |
| GLN | OE1 | 818 | 187.3 | 96.1 | 37.3 | 58 | B |
| GLN | NE2 | 818 | 185.8 | 97.7 | 36.7 | 58 | B |
| GLN | C | 818 | 184.1 | 93.8 | 40.8 | 57 | B |
| GLN | O | 818 | 185.0 | 92.9 | 40.9 | 58 | B |
| GLY | N | 819 | 183.2 | 94.1 | 41.8 | 58 | B |
| GLY | CA | 819 | 183.3 | 93.5 | 43.1 | 59 | B |
| GLY | C | 819 | 184.7 | 93.5 | 43.7 | 60 | B |
| GLY | O | 819 | 185.2 | 92.5 | 44.2 | 61 | B |
| ASP | N | 820 | 185.3 | 94.7 | 43.7 | 60 | B |
| ASP | CA | 820 | 186.6 | 94.8 | 44.3 | 59 | B |
| ASP | CB | 820 | 187.2 | 96.2 | 44.0 | 59 | B |
| ASP | CG | 820 | 188.8 | 96.2 | 44.0 | 58 | B |
| ASP | OD1 | 820 | 189.3 | 96.1 | 42.9 | 59 | B |
| ASP | OD2 | 820 | 189.4 | 96.2 | 45.1 | 57 | B |
| ASP | C | 820 | 186.3 | 94.6 | 45.8 | 59 | B |
| ASP | O | 820 | 185.4 | 95.2 | 46.4 | 59 | B |
| PRO | N | 821 | 187.1 | 93.6 | 46.4 | 59 | B |
| PRO | CD | 821 | 187.8 | 92.6 | 45.7 | 59 | B |
| PRO | CA | 821 | 186.9 | 93.4 | 47.8 | 59 | B |
| PRO | CB | 821 | 187.5 | 92.0 | 48.0 | 59 | B |
| PRO | CG | 821 | 188.5 | 91.9 | 46.9 | 59 | B |
| PRO | C | 821 | 187.6 | 94.4 | 48.7 | 59 | B |
| PRO | O | 821 | 187.1 | 94.9 | 49.7 | 60 | B |
| ALA | N | 822 | 188.9 | 94.8 | 48.3 | 57 | B |
| ALA | CA | 822 | 189.7 | 95.8 | 49.1 | 55 | B |
| ALA | CB | 822 | 191.1 | 95.7 | 48.6 | 54 | B |
| ALA | C | 822 | 189.2 | 97.2 | 49.2 | 55 | B |
| ALA | O | 822 | 189.9 | 98.0 | 49.7 | 55 | B |
| LEU | N | 823 | 187.9 | 97.5 | 48.7 | 55 | B |
| LEU | CA | 823 | 187.4 | 98.8 | 48.7 | 55 | B |
| LEU | CB | 823 | 186.3 | 99.0 | 47.7 | 54 | B |
| LEU | CG | 823 | 186.7 | 99.1 | 46.2 | 53 | B |
| LEU | CD1 | 823 | 185.5 | 99.5 | 45.4 | 53 | B |
| LEU | CD2 | 823 | 187.8 | 100.1 | 46.1 | 53 | B |
| LEU | C | 823 | 186.7 | 99.2 | 50.1 | 57 | B |
| LEU | O | 823 | 185.7 | 98.6 | 50.5 | 57 | B |
| SER | N | 824 | 187.3 | 100.3 | 50.6 | 58 | B |
| SER | CA | 824 | 186.8 | 100.8 | 51.9 | 58 | B |
| SER | CB | 824 | 187.6 | 102.1 | 52.3 | 59 | B |
| SER | OG | 824 | 187.3 | 102.5 | 53.6 | 59 | B |
| SER | C | 824 | 185.3 | 101.0 | 52.0 | 59 | B |
| SER | O | 824 | 184.7 | 101.3 | 50.9 | 59 | B |
| MET | N | 825 | 184.7 | 100.9 | 53.1 | 60 | B |
| MET | CA | 825 | 183.3 | 101.1 | 53.3 | 60 | B |
| MET | CB | 825 | 182.7 | 100.0 | 54.0 | 63 | B |
| MET | CG | 825 | 182.7 | 98.6 | 53.3 | 66 | B |
| MET | SD | 825 | 181.8 | 98.6 | 51.7 | 70 | B |
| MET | CE | 825 | 183.0 | 97.5 | 50.6 | 69 | B |
| MET | C | 825 | 183.0 | 102.4 | 54.0 | 59 | B |
| MET | O | 825 | 181.8 | 102.6 | 54.4 | 59 | B |
| SER | N | 826 | 184.0 | 103.3 | 54.1 | 57 | B |
| SER | CA | 826 | 183.8 | 104.6 | 54.7 | 55 | B |
| SER | CB | 826 | 184.3 | 104.5 | 56.2 | 55 | B |
| SER | OG | 826 | 185.7 | 104.1 | 56.2 | 54 | B |
| SER | C | 826 | 184.4 | 105.8 | 54.1 | 53 | B |
| SER | O | 826 | 183.9 | 106.9 | 54.2 | 53 | B |
| HIS | N | 827 | 185.5 | 105.6 | 53.3 | 52 | B |
| HIS | CA | 827 | 186.2 | 106.7 | 52.7 | 49 | B |
| HIS | CB | 827 | 187.5 | 107.1 | 53.5 | 51 | B |
| HIS | CG | 827 | 187.2 | 107.4 | 55.0 | 52 | B |

TABLE 5-continued

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| HIS | CD2 | 827 | 187.7 | 106.8 | 56.1 | 52 | B |
| HIS | ND1 | 827 | 186.3 | 108.3 | 55.4 | 52 | B |
| HIS | CE1 | 827 | 186.3 | 108.4 | 56.7 | 53 | B |
| HIS | NE2 | 827 | 187.1 | 107.5 | 57.2 | 53 | B |
| HIS | C | 827 | 186.7 | 106.6 | 51.3 | 46 | B |
| HIS | O | 827 | 187.0 | 105.5 | 50.8 | 45 | B |
| TRP | N | 828 | 186.7 | 107.8 | 50.6 | 42 | B |
| TRP | CA | 828 | 187.2 | 107.8 | 49.2 | 36 | B |
| TRP | CB | 828 | 186.9 | 109.2 | 48.6 | 32 | B |
| TRP | CG | 828 | 185.4 | 109.5 | 48.6 | 29 | B |
| TRP | CD2 | 828 | 184.4 | 108.7 | 48.1 | 27 | B |
| TRP | CE2 | 828 | 183.2 | 109.4 | 48.2 | 26 | B |
| TRP | CE3 | 828 | 184.4 | 107.4 | 47.5 | 26 | B |
| TRP | CD1 | 828 | 184.9 | 110.7 | 49.0 | 28 | B |
| TRP | NE1 | 828 | 183.5 | 110.6 | 48.8 | 27 | B |
| TRP | CZ2 | 828 | 182.0 | 108.9 | 47.8 | 26 | B |
| TRP | CZ3 | 828 | 183.1 | 106.9 | 47.1 | 27 | B |
| TRP | CH2 | 828 | 182.0 | 107.7 | 47.3 | 26 | B |
| TRP | C | 828 | 188.7 | 107.7 | 49.3 | 36 | B |
| TRP | O | 828 | 189.3 | 108.0 | 50.3 | 35 | B |
| MET | N | 829 | 189.3 | 107.1 | 48.2 | 35 | B |
| MET | CA | 829 | 190.7 | 106.9 | 48.3 | 35 | B |
| MET | CB | 829 | 191.1 | 105.8 | 47.3 | 35 | B |
| MET | CG | 829 | 190.3 | 104.5 | 47.5 | 36 | B |
| MET | SD | 829 | 190.8 | 103.1 | 46.5 | 37 | B |
| MET | CE | 829 | 192.6 | 103.3 | 46.6 | 35 | B |
| MET | C | 829 | 191.6 | 108.1 | 48.1 | 35 | B |
| MET | O | 829 | 192.4 | 108.2 | 47.2 | 35 | B |
| PHE | N | 830 | 191.4 | 109.1 | 49.0 | 35 | B |
| PHE | CA | 830 | 192.2 | 110.3 | 49.0 | 34 | B |
| PHE | CB | 830 | 191.8 | 111.3 | 47.9 | 30 | B |
| PHE | CG | 830 | 190.5 | 112.1 | 48.1 | 26 | B |
| PHE | CD1 | 830 | 190.6 | 113.3 | 48.8 | 25 | B |
| PHE | CD2 | 830 | 189.3 | 111.7 | 47.6 | 25 | B |
| PHE | CE1 | 830 | 189.4 | 114.1 | 48.9 | 24 | B |
| PHE | CE2 | 830 | 188.2 | 112.4 | 47.8 | 24 | B |
| PHE | CZ | 830 | 188.2 | 113.6 | 48.4 | 24 | B |
| PHE | C | 830 | 192.0 | 111.0 | 50.4 | 36 | B |
| PHE | O | 830 | 190.9 | 110.7 | 51.0 | 37 | B |
| HIS | N | 831 | 192.9 | 111.7 | 50.8 | 38 | B |
| HIS | CA | 831 | 192.8 | 112.4 | 52.1 | 38 | B |
| HIS | CB | 831 | 194.1 | 113.0 | 52.5 | 39 | B |
| HIS | CG | 831 | 194.4 | 113.1 | 54.0 | 40 | B |
| HIS | CD2 | 831 | 193.7 | 113.7 | 55.0 | 39 | B |
| HIS | ND1 | 831 | 195.5 | 112.5 | 54.6 | 40 | B |
| HIS | CE1 | 831 | 195.4 | 112.7 | 55.9 | 40 | B |
| HIS | NE2 | 831 | 194.4 | 113.4 | 56.1 | 41 | B |
| HIS | C | 831 | 191.7 | 113.4 | 52.1 | 39 | B |
| HIS | O | 831 | 191.9 | 114.6 | 51.8 | 40 | B |
| GLN | N | 832 | 190.5 | 113.0 | 52.5 | 38 | B |
| GLN | CA | 832 | 189.3 | 113.9 | 52.6 | 39 | B |
| GLN | CB | 832 | 188.1 | 113.2 | 52.9 | 38 | B |
| GLN | CG | 832 | 187.8 | 112.0 | 52.0 | 36 | B |
| GLN | CD | 832 | 186.8 | 111.1 | 52.5 | 35 | B |
| GLN | OE1 | 832 | 185.7 | 111.5 | 53.0 | 36 | B |
| GLN | NE2 | 832 | 187.1 | 109.8 | 52.4 | 34 | B |
| GLN | C | 832 | 189.5 | 115.1 | 53.6 | 40 | B |
| GLN | O | 832 | 188.9 | 116.1 | 53.5 | 39 | B |
| GLN | N | 833 | 190.3 | 114.8 | 54.6 | 42 | B |
| GLN | CA | 833 | 190.6 | 115.7 | 55.7 | 43 | B |
| GLN | CB | 833 | 191.3 | 115.0 | 56.8 | 44 | B |
| GLN | CG | 833 | 191.2 | 115.7 | 58.2 | 45 | B |
| GLN | CD | 833 | 192.4 | 115.4 | 59.1 | 46 | B |
| GLN | OE1 | 833 | 193.1 | 114.5 | 59.0 | 46 | B |
| GLN | NE2 | 833 | 192.5 | 116.3 | 60.1 | 46 | B |
| GLN | C | 833 | 191.5 | 116.9 | 55.2 | 42 | B |
| GLN | O | 833 | 191.1 | 118.0 | 55.3 | 41 | B |
| ALA | N | 834 | 192.6 | 116.5 | 54.6 | 40 | B |
| ALA | CA | 834 | 193.5 | 117.5 | 54.1 | 38 | B |
| ALA | CB | 834 | 194.8 | 116.9 | 53.6 | 37 | B |
| ALA | C | 834 | 192.9 | 118.4 | 53.0 | 38 | B |
| ALA | O | 834 | 193.1 | 119.6 | 53.0 | 39 | B |

TABLE 5-continued

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| LEU | N | 835 | 192.1 | 117.7 | 52.2 | 38 | B |
| LEU | CA | 835 | 191.4 | 118.5 | 51.1 | 38 | B |
| LEU | CB | 835 | 190.7 | 117.6 | 50.1 | 38 | B |
| LEU | CG | 835 | 189.8 | 118.3 | 49.1 | 38 | B |
| LEU | CD1 | 835 | 190.6 | 119.3 | 48.3 | 38 | B |
| LEU | CD2 | 835 | 189.1 | 117.4 | 48.2 | 38 | B |
| LEU | C | 835 | 190.4 | 119.6 | 51.8 | 38 | B |
| LEU | O | 835 | 190.4 | 120.7 | 51.3 | 38 | B |
| GLN | N | 836 | 189.7 | 119.1 | 52.8 | 38 | B |
| GLN | CA | 836 | 188.7 | 120.0 | 53.4 | 38 | B |
| GLN | CB | 836 | 187.9 | 119.3 | 54.5 | 38 | B |
| GLN | CG | 836 | 186.6 | 118.7 | 53.9 | 38 | B |
| GLN | CD | 836 | 185.8 | 117.9 | 54.9 | 37 | B |
| GLN | OE1 | 836 | 185.1 | 118.4 | 55.8 | 36 | B |
| GLN | NE2 | 836 | 186.0 | 116.6 | 54.8 | 37 | B |
| GLN | C | 836 | 189.4 | 121.2 | 54.1 | 37 | B |
| GLN | O | 836 | 188.9 | 122.3 | 54.2 | 37 | B |
| GLU | N | 837 | 190.6 | 121.0 | 54.6 | 36 | B |
| GLU | CA | 837 | 191.4 | 122.0 | 55.3 | 37 | B |
| GLU | CB | 837 | 192.5 | 121.4 | 56.1 | 36 | B |
| GLU | CG | 837 | 191.9 | 120.7 | 57.4 | 36 | B |
| GLU | CD | 837 | 192.9 | 119.8 | 58.1 | 36 | B |
| GLU | OE1 | 837 | 194.1 | 120.0 | 58.0 | 36 | B |
| GLU | OE2 | 837 | 192.5 | 118.8 | 58.7 | 37 | B |
| GLU | C | 837 | 191.9 | 123.0 | 54.3 | 38 | B |
| GLU | O | 837 | 191.7 | 124.2 | 54.4 | 39 | B |
| TYR | N | 838 | 192.5 | 122.5 | 53.1 | 38 | B |
| TYR | CA | 838 | 193.0 | 123.4 | 52.1 | 35 | B |
| TYR | CB | 838 | 193.5 | 122.6 | 50.9 | 35 | B |
| TYR | CG | 838 | 193.9 | 123.5 | 49.7 | 35 | B |
| TYR | CD1 | 838 | 195.1 | 124.2 | 49.8 | 34 | B |
| TYR | CE1 | 838 | 195.4 | 125.2 | 48.8 | 34 | B |
| TYR | CD2 | 838 | 193.1 | 123.8 | 48.6 | 34 | B |
| TYR | CE2 | 838 | 193.4 | 124.7 | 47.7 | 33 | B |
| TYR | CZ | 838 | 194.6 | 125.4 | 47.7 | 33 | B |
| TYR | OH | 838 | 194.8 | 126.4 | 46.8 | 33 | B |
| TYR | C | 838 | 191.8 | 124.3 | 51.7 | 34 | B |
| TYR | O | 838 | 191.8 | 125.5 | 51.8 | 34 | B |
| ILE | N | 839 | 190.7 | 123.6 | 51.3 | 32 | B |
| ILE | CA | 839 | 189.5 | 124.4 | 50.9 | 31 | B |
| ILE | CB | 839 | 188.3 | 123.5 | 50.4 | 30 | B |
| ILE | CG2 | 839 | 187.3 | 124.4 | 49.9 | 29 | B |
| ILE | CG1 | 839 | 188.7 | 122.6 | 49.3 | 30 | B |
| ILE | CD1 | 839 | 187.5 | 121.8 | 48.8 | 29 | B |
| ILE | C | 839 | 189.0 | 125.4 | 51.9 | 32 | B |
| ILE | O | 839 | 188.6 | 126.5 | 51.6 | 35 | B |
| LEU | N | 840 | 189.0 | 125.0 | 53.2 | 32 | B |
| LEU | CA | 840 | 188.5 | 125.9 | 54.3 | 32 | B |
| LEU | CB | 840 | 188.1 | 125.1 | 55.5 | 30 | B |
| LEU | CG | 840 | 186.7 | 124.5 | 55.2 | 29 | B |
| LEU | CD1 | 840 | 186.5 | 123.4 | 56.3 | 30 | B |
| LEU | CD2 | 840 | 185.6 | 125.5 | 55.2 | 28 | B |
| LEU | C | 840 | 189.5 | 127.0 | 54.6 | 32 | B |
| LEU | O | 840 | 189.1 | 128.2 | 54.7 | 32 | B |
| MET | N | 841 | 190.7 | 126.6 | 54.9 | 32 | B |
| MET | CA | 841 | 191.8 | 127.5 | 55.3 | 33 | B |
| MET | CB | 841 | 192.9 | 126.8 | 55.9 | 33 | B |
| MET | CG | 841 | 192.6 | 126.0 | 57.2 | 34 | B |
| MET | SD | 841 | 193.9 | 125.8 | 58.3 | 35 | B |
| MET | CE | 841 | 194.3 | 124.1 | 58.0 | 34 | B |
| MET | C | 841 | 192.3 | 128.4 | 54.2 | 34 | B |
| MET | O | 841 | 192.3 | 129.6 | 54.3 | 35 | B |
| CYS | N | 842 | 192.7 | 127.8 | 53.1 | 35 | B |
| CYS | CA | 842 | 193.3 | 128.5 | 52.0 | 34 | B |
| CYS | CB | 842 | 194.4 | 127.7 | 51.4 | 34 | B |
| CYS | SG | 842 | 195.6 | 127.2 | 52.6 | 36 | B |
| CYS | C | 842 | 192.4 | 129.1 | 50.8 | 34 | B |
| CYS | O | 842 | 192.8 | 130.1 | 50.2 | 35 | B |
| CYS | N | 843 | 191.3 | 128.5 | 50.5 | 34 | B |
| CYS | CA | 843 | 190.5 | 128.9 | 49.4 | 34 | B |
| CYS | CB | 843 | 190.2 | 127.8 | 48.4 | 32 | B |
| CYS | SG | 843 | 191.7 | 126.8 | 48.1 | 31 | B |

TABLE 5-continued

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| CYS | C | 843 | 189.3 | 129.7 | 49.6 | 36 | B |
| CYS | O | 843 | 188.4 | 129.9 | 48.7 | 37 | B |
| GLN | N | 844 | 189.1 | 130.3 | 50.8 | 38 | B |
| GLN | CA | 844 | 187.9 | 131.1 | 51.1 | 39 | B |
| GLN | CB | 844 | 187.4 | 130.6 | 52.4 | 39 | B |
| GLN | CG | 844 | 186.0 | 130.8 | 52.6 | 39 | B |
| GLN | CD | 844 | 185.4 | 129.8 | 53.6 | 40 | B |
| GLN | OE1 | 844 | 184.2 | 129.6 | 53.6 | 40 | B |
| GLN | NE2 | 844 | 186.3 | 129.2 | 54.4 | 39 | B |
| GLN | C | 844 | 188.2 | 132.6 | 51.1 | 40 | B |
| GLN | O | 844 | 189.2 | 133.0 | 51.6 | 40 | B |
| CYS | N | 845 | 187.3 | 133.4 | 50.5 | 41 | B |
| CYS | CA | 845 | 187.5 | 134.8 | 50.5 | 43 | B |
| CYS | CB | 845 | 187.1 | 135.4 | 49.1 | 43 | B |
| CYS | SG | 845 | 186.9 | 137.2 | 49.0 | 44 | B |
| CYS | C | 845 | 186.6 | 135.4 | 51.5 | 45 | B |
| CYS | O | 845 | 185.4 | 135.1 | 51.6 | 46 | B |
| PRO | N | 846 | 187.1 | 136.2 | 52.4 | 45 | B |
| PRO | CD | 846 | 188.5 | 136.7 | 52.5 | 45 | B |
| PRO | CA | 846 | 186.4 | 136.9 | 53.5 | 45 | B |
| PRO | CB | 846 | 187.4 | 137.9 | 54.0 | 45 | B |
| PRO | CG | 846 | 188.7 | 137.3 | 53.9 | 45 | B |
| PRO | C | 846 | 185.1 | 137.5 | 53.0 | 44 | B |
| PRO | O | 846 | 184.0 | 137.2 | 53.6 | 46 | B |
| ALA | N | 847 | 185.2 | 138.3 | 52.0 | 42 | B |
| ALA | CA | 847 | 184.1 | 139.0 | 51.3 | 41 | B |
| ALA | CB | 847 | 184.6 | 140.0 | 50.4 | 41 | B |
| ALA | C | 847 | 183.1 | 138.1 | 50.7 | 40 | B |
| ALA | O | 847 | 182.0 | 138.6 | 50.2 | 40 | B |
| GLY | N | 848 | 183.4 | 136.8 | 50.5 | 39 | B |
| GLY | CA | 848 | 182.4 | 135.9 | 49.9 | 38 | B |
| GLY | C | 848 | 183.2 | 135.3 | 48.7 | 37 | B |
| GLY | O | 848 | 184.1 | 135.9 | 48.2 | 38 | B |
| GLY | N | 849 | 182.8 | 134.2 | 48.2 | 35 | B |
| GLY | CA | 849 | 183.5 | 133.5 | 47.1 | 32 | B |
| GLY | C | 849 | 184.7 | 132.7 | 47.6 | 30 | B |
| GLY | O | 849 | 185.3 | 133.0 | 48.6 | 29 | B |
| LEU | N | 850 | 184.9 | 131.6 | 46.8 | 29 | B |
| LEU | CA | B50 | 186.1 | 130.8 | 47.1 | 28 | B |
| LEU | CB | 850 | 185.7 | 129.3 | 47.1 | 28 | B |
| LEU | CG | 850 | 185.0 | 128.5 | 48.2 | 28 | B |
| LEU | CD1 | 850 | 185.9 | 128.2 | 49.4 | 26 | B |
| LEU | CD2 | 850 | 183.7 | 129.3 | 48.6 | 26 | B |
| LEU | C | 850 | 187.1 | 131.1 | 46.0 | 28 | B |
| LEU | O | 850 | 186.7 | 131.8 | 45.0 | 27 | B |
| LEU | N | 851 | 188.2 | 130.5 | 46.0 | 27 | B |
| LEU | CA | 851 | 189.2 | 130.8 | 45.0 | 28 | B |
| LEU | CB | 851 | 189.8 | 132.2 | 45.3 | 28 | B |
| LEU | CG | 851 | 190.3 | 132.4 | 46.8 | 28 | B |
| LEU | CD1 | 851 | 191.7 | 131.8 | 47.0 | 28 | B |
| LEU | CD2 | 851 | 190.2 | 133.8 | 47.2 | 27 | B |
| LEU | C | 851 | 190.3 | 129.8 | 44.7 | 30 | B |
| LEU | O | 851 | 190.3 | 128.7 | 45.3 | 31 | B |
| ASP | N | 852 | 191.1 | 130.1 | 43.7 | 29 | B |
| ASP | CA | 852 | 192.2 | 129.2 | 43.3 | 29 | B |
| ASP | CB | 852 | 193.0 | 129.9 | 42.2 | 29 | B |
| ASP | CG | 852 | 194.2 | 129.1 | 41.7 | 30 | B |
| ASP | OD1 | 852 | 194.6 | 128.1 | 42.3 | 31 | B |
| ASP | OD2 | 852 | 194.8 | 129.5 | 40.7 | 32 | B |
| ASP | C | 852 | 193.0 | 128.8 | 44.5 | 29 | B |
| ASP | O | 852 | 192.9 | 127.6 | 44.9 | 28 | B |
| LYS | N | 853 | 193.9 | 129.7 | 44.9 | 28 | B |
| LYS | CA | 853 | 194.8 | 129.4 | 46.0 | 27 | B |
| LYS | CB | 853 | 196.1 | 128.9 | 45.5 | 24 | B |
| LYS | CG | 853 | 196.9 | 129.9 | 44.6 | 23 | B |
| LYS | CD | 853 | 198.3 | 129.5 | 44.3 | 22 | B |
| LYS | CE | 853 | 198.3 | 128.1 | 43.7 | 22 | B |
| LYS | NZ | 853 | 197.5 | 128.0 | 42.4 | 22 | B |
| LYS | C | 853 | 194.9 | 130.8 | 46.5 | 29 | B |
| LYS | O | 853 | 194.5 | 131.8 | 45.9 | 27 | B |
| PRO | N | 854 | 195.6 | 131.0 | 47.7 | 32 | B |
| PRO | CD | 854 | 196.1 | 129.9 | 48.6 | 32 | B |
| PRO | CA | 854 | 195.8 | 132.3 | 48.3 | 33 | B |
| PRO | CB | 854 | 196.4 | 132.0 | 49.6 | 33 | B |
| PRO | CG | 854 | 197.1 | 130.7 | 49.4 | 32 | B |
| PRO | C | 854 | 196.6 | 133.2 | 47.4 | 34 | B |
| PRO | O | 854 | 197.6 | 132.9 | 46.8 | 35 | B |
| GLY | N | 855 | 196.0 | 134.4 | 47.2 | 35 | B |
| GLY | CA | 855 | 196.7 | 135.4 | 46.3 | 36 | B |
| GLY | C | 855 | 195.8 | 135.6 | 45.1 | 37 | B |
| GLY | O | 855 | 195.8 | 136.7 | 44.6 | 39 | B |
| LYS | N | 856 | 195.1 | 134.6 | 44.7 | 36 | B |
| LYS | CA | 856 | 194.2 | 134.6 | 43.6 | 34 | B |
| LYS | CB | 856 | 193.9 | 133.2 | 43.1 | 34 | B |
| LYS | CG | 856 | 195.1 | 132.5 | 42.7 | 33 | B |
| LYS | CD | 856 | 195.9 | 133.3 | 41.7 | 34 | B |
| LYS | CE | 856 | 197.2 | 132.7 | 41.3 | 35 | B |
| LYS | NZ | 856 | 197.1 | 131.8 | 40.2 | 36 | B |
| LYS | C | 856 | 192.9 | 135.3 | 44.0 | 35 | B |
| LYS | O | 856 | 192.6 | 135.6 | 45.1 | 36 | B |
| SER | N | 857 | 192.1 | 135.8 | 42.9 | 35 | B |
| SER | CA | 857 | 190.8 | 136.4 | 43.1 | 34 | B |
| SER | CB | 857 | 190.6 | 137.5 | 42.0 | 34 | B |
| SER | OG | 857 | 191.4 | 138.6 | 42.2 | 37 | B |
| SER | C | 857 | 189.7 | 135.4 | 43.1 | 34 | B |
| SER | O | 857 | 189.8 | 134.4 | 42.5 | 34 | B |
| ARG | N | 858 | 188.6 | 135.8 | 43.7 | 32 | B |
| ARG | CA | 858 | 187.4 | 135.0 | 43.8 | 31 | B |
| ARG | CB | 858 | 186.5 | 135.5 | 44.9 | 30 | B |
| ARG | CG | 858 | 186.0 | 136.9 | 44.7 | 30 | B |
| ARG | CD | 858 | 185.4 | 137.5 | 46.0 | 30 | B |
| ARG | NE | 858 | 184.5 | 138.6 | 45.7 | 30 | B |
| ARG | CZ | 858 | 183.6 | 139.1 | 46.5 | 30 | B |
| ARG | NH1 | 858 | 183.4 | 138.4 | 47.6 | 31 | B |
| ARG | NH2 | 858 | 182.8 | 140.0 | 46.1 | 30 | B |
| ARG | C | 858 | 186.6 | 135.1 | 42.5 | 30 | B |
| ARG | O | 858 | 186.8 | 136.0 | 41.7 | 30 | B |
| ASP | N | 859 | 185.8 | 134.0 | 42.2 | 29 | B |
| ASP | CA | 859 | 185.0 | 134.0 | 41.0 | 28 | B |
| ASP | CB | 859 | 185.8 | 133.9 | 39.7 | 29 | B |
| ASP | CG | 859 | 186.6 | 132.7 | 39.6 | 29 | B |
| ASP | OD1 | 859 | 186.1 | 131.6 | 39.5 | 30 | B |
| ASP | OD2 | 859 | 187.9 | 132.8 | 39.7 | 30 | B |
| ASP | C | 859 | 184.0 | 132.9 | 41.2 | 28 | B |
| ASP | O | 859 | 184.2 | 132.0 | 42.1 | 28 | B |
| PHE | N | 860 | 182.9 | 132.9 | 40.4 | 28 | B |
| PHE | CA | 860 | 181.9 | 131.9 | 40.5 | 28 | B |
| PHE | CB | 860 | 180.7 | 132.3 | 39.7 | 28 | B |
| PHE | CG | 860 | 180.3 | 133.7 | 40.1 | 28 | B |
| PHE | CD1 | 860 | 180.6 | 134.8 | 39.4 | 28 | B |
| PHE | CD2 | 860 | 179.6 | 133.9 | 41.3 | 28 | B |
| PHE | CE1 | 860 | 180.3 | 136.1 | 39.8 | 27 | B |
| PHE | CE2 | 860 | 179.3 | 135.2 | 41.8 | 27 | B |
| PHE | CZ | 860 | 179.6 | 136.3 | 41.0 | 27 | B |
| PHE | C | 860 | 182.3 | 130.5 | 40.1 | 29 | B |
| PHE | O | 860 | 181.8 | 129.5 | 40.6 | 31 | B |
| TYR | N | 861 | 183.3 | 130.4 | 39.2 | 28 | B |
| TYR | CA | 861 | 183.9 | 129.1 | 38.7 | 25 | B |
| TYR | CB | 861 | 184.9 | 129.3 | 37.6 | 22 | B |
| TYR | CG | 861 | 185.7 | 128.1 | 37.3 | 19 | B |
| TYR | CD1 | 861 | 185.1 | 126.9 | 36.9 | 17 | B |
| TYR | CE1 | 861 | 185.9 | 125.7 | 36.7 | 15 | B |
| TYR | CD2 | 861 | 187.1 | 128.1 | 37.5 | 16 | B |
| TYR | CE2 | 861 | 187.9 | 127.0 | 37.3 | 15 | B |
| TYR | CZ | 861 | 187.2 | 125.8 | 36.9 | 15 | B |
| TYR | OH | 861 | 188.0 | 124.7 | 36.8 | 14 | B |
| TYR | C | 861 | 184.5 | 128.3 | 39.9 | 26 | B |
| TYR | O | 861 | 184.2 | 127.2 | 40.2 | 26 | B |
| HIS | N | 862 | 185.4 | 129.0 | 40.6 | 27 | B |
| HIS | CA | 862 | 186.1 | 128.4 | 41.8 | 27 | B |
| HIS | CB | 862 | 187.3 | 129.2 | 42.2 | 25 | B |
| HIS | CG | 862 | 188.3 | 129.2 | 41.2 | 25 | B |
| HIS | CD2 | 862 | 189.4 | 128.4 | 41.0 | 25 | B |
| HIS | ND1 | 862 | 188.4 | 130.2 | 40.2 | 26 | B |

TABLE 5-continued

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| HIS | CE1 | 862 | 189.4 | 130.0 | 39.4 | 27 | B |
| HIS | NE2 | 862 | 190.1 | 128.9 | 39.9 | 25 | B |
| HIS | C | 862 | 185.1 | 128.3 | 43.0 | 28 | B |
| HIS | O | 862 | 185.3 | 127.4 | 43.9 | 29 | B |
| THR | N | 863 | 184.1 | 129.2 | 43.1 | 28 | B |
| THR | CA | 863 | 183.2 | 129.2 | 44.1 | 30 | B |
| THR | CB | 863 | 182.2 | 130.3 | 44.0 | 30 | B |
| THR | OG1 | 863 | 182.9 | 131.6 | 44.2 | 32 | B |
| THR | CG2 | 863 | 181.0 | 130.2 | 45.1 | 29 | B |
| THR | C | 863 | 182.4 | 127.8 | 44.0 | 30 | B |
| THR | O | 863 | 182.4 | 127.0 | 44.9 | 30 | B |
| CYS | N | 864 | 182.0 | 127.6 | 42.8 | 30 | B |
| CYS | CA | 864 | 181.3 | 126.4 | 42.4 | 29 | B |
| CYS | CB | 864 | 180.7 | 126.4 | 41.0 | 29 | B |
| CYS | SG | 864 | 180.2 | 124.8 | 40.4 | 30 | B |
| CYS | C | 864 | 182.1 | 125.1 | 42.6 | 29 | B |
| CYS | O | 864 | 181.7 | 124.2 | 43.2 | 29 | B |
| TYR | N | 865 | 183.3 | 125.2 | 42.1 | 28 | B |
| TYR | CA | 865 | 184.1 | 124.0 | 42.2 | 28 | B |
| TYR | CB | 865 | 185.1 | 123.8 | 41.0 | 28 | B |
| TYR | CG | 865 | 184.3 | 123.5 | 39.8 | 26 | B |
| TYR | CD1 | 865 | 183.8 | 124.5 | 38.9 | 26 | B |
| TYR | CE1 | 865 | 182.9 | 124.2 | 37.9 | 26 | B |
| TYR | CD2 | 865 | 183.9 | 122.2 | 39.5 | 26 | B |
| TYR | CE2 | 865 | 183.0 | 121.9 | 38.4 | 25 | B |
| TYR | CZ | 865 | 182.5 | 122.9 | 37.6 | 26 | B |
| TYR | OH | 865 | 181.7 | 122.6 | 36.6 | 26 | B |
| TYR | C | 865 | 184.7 | 123.7 | 43.6 | 29 | B |
| TYR | O | 865 | 184.9 | 122.5 | 44.0 | 30 | B |
| CYS | N | 866 | 185.1 | 124.7 | 44.3 | 30 | B |
| CYS | CA | 866 | 185.6 | 124.5 | 45.7 | 30 | B |
| CYS | CB | 866 | 186.1 | 125.9 | 46.3 | 30 | B |
| CYS | SG | 866 | 187.6 | 126.5 | 45.6 | 31 | B |
| CYS | C | 866 | 184.5 | 123.9 | 46.6 | 30 | B |
| CYS | O | 866 | 184.8 | 122.9 | 47.3 | 31 | B |
| LEU | N | 867 | 183.3 | 124.5 | 46.5 | 29 | B |
| LEU | CA | 867 | 182.2 | 124.0 | 47.3 | 29 | B |
| LEU | CB | 867 | 181.0 | 124.9 | 47.2 | 27 | B |
| LEU | CG | 867 | 181.3 | 126.3 | 47.8 | 26 | B |
| LEU | CD1 | 867 | 180.0 | 127.1 | 47.6 | 26 | B |
| LEU | CD2 | 867 | 181.7 | 126.1 | 49.2 | 25 | B |
| LEU | C | 867 | 181.9 | 122.6 | 46.8 | 30 | B |
| LEU | O | 867 | 181.7 | 121.7 | 47.6 | 31 | B |
| SER | N | 868 | 181.9 | 122.3 | 45.5 | 31 | B |
| SER | CA | 868 | 181.6 | 121.0 | 44.9 | 30 | B |
| SER | CB | 868 | 181.7 | 121.1 | 43.4 | 29 | B |
| SER | OG | 868 | 180.5 | 121.7 | 42.8 | 28 | B |
| SER | C | 868 | 182.5 | 120.0 | 45.5 | 30 | B |
| SER | O | 868 | 182.1 | 118.9 | 46.0 | 31 | B |
| GLY | N | 869 | 183.8 | 120.3 | 45.4 | 31 | B |
| GLY | CA | 869 | 184.9 | 119.4 | 45.9 | 32 | B |
| GLY | C | 869 | 184.8 | 119.2 | 47.4 | 34 | B |
| GLY | O | 869 | 185.4 | 118.2 | 47.9 | 35 | B |
| LEU | N | 870 | 184.2 | 120.1 | 48.2 | 35 | B |
| LEU | CA | 870 | 184.2 | 120.0 | 49.6 | 34 | B |
| LEU | CB | 870 | 183.7 | 121.3 | 50.2 | 33 | B |
| LEU | CG | 870 | 183.7 | 121.6 | 51.8 | 31 | B |
| LEU | CD1 | 870 | 185.1 | 121.4 | 52.3 | 30 | B |
| LEU | CD2 | 870 | 183.2 | 122.9 | 52.1 | 29 | B |
| LEU | C | 870 | 183.1 | 118.9 | 49.9 | 35 | B |
| LEU | O | 870 | 183.3 | 118.0 | 50.7 | 35 | B |
| SER | N | 871 | 181.9 | 119.1 | 49.3 | 35 | B |
| SER | CA | 871 | 180.8 | 118.2 | 49.4 | 35 | B |
| SER | CB | 871 | 179.7 | 118.6 | 48.4 | 36 | B |
| SER | OG | 871 | 178.6 | 117.8 | 48.6 | 36 | B |
| SER | C | 871 | 181.2 | 116.8 | 49.1 | 36 | B |
| SER | O | 871 | 180.8 | 115.9 | 49.9 | 37 | B |
| ILE | N | 872 | 182.0 | 116.6 | 48.1 | 36 | B |
| ILE | CA | 872 | 182.5 | 115.3 | 47.8 | 37 | B |
| ILE | CB | 872 | 183.2 | 115.2 | 46.3 | 35 | B |
| ILE | CG2 | 872 | 184.0 | 114.0 | 46.1 | 33 | B |
| ILE | CG1 | 872 | 182.1 | 115.3 | 45.3 | 35 | B |
| ILE | CD1 | 872 | 182.6 | 115.3 | 43.9 | 35 | B |
| ILE | C | 872 | 183.4 | 114.7 | 48.9 | 37 | B |
| ILE | O | 872 | 183.2 | 113.6 | 49.3 | 38 | B |
| ALA | N | 873 | 184.4 | 115.5 | 49.3 | 38 | B |
| ALA | CA | 873 | 185.3 | 115.1 | 50.4 | 39 | B |
| ALA | CB | 873 | 186.5 | 116.1 | 50.5 | 39 | B |
| ALA | C | 873 | 184.7 | 114.8 | 51.7 | 39 | B |
| ALA | O | 873 | 185.3 | 114.2 | 52.6 | 38 | B |
| GLN | N | 874 | 183.5 | 115.4 | 52.0 | 39 | B |
| GLN | CA | 874 | 182.9 | 115.2 | 53.2 | 40 | B |
| GLN | CB | 874 | 182.4 | 116.5 | 53.8 | 38 | B |
| GLN | CG | 874 | 181.3 | 117.2 | 53.1 | 36 | B |
| GLN | CD | 874 | 181.0 | 118.6 | 53.7 | 36 | B |
| GLN | OE1 | 874 | 179.9 | 119.1 | 53.4 | 36 | B |
| GLN | NE2 | 874 | 181.9 | 119.1 | 54.5 | 34 | B |
| GLN | C | 874 | 181.7 | 114.2 | 53.2 | 42 | B |
| GLN | O | 874 | 181.2 | 113.8 | 54.2 | 42 | B |
| HIS | N | 875 | 181.4 | 113.8 | 52.0 | 44 | B |
| HIS | CA | 875 | 180.3 | 112.9 | 51.8 | 46 | B |
| HIS | CB | 875 | 179.1 | 113.5 | 51.0 | 45 | B |
| HIS | CG | 875 | 178.4 | 114.6 | 51.7 | 45 | B |
| HIS | CD2 | 875 | 177.7 | 115.6 | 51.2 | 45 | B |
| HIS | ND1 | 875 | 178.4 | 114.7 | 53.0 | 45 | B |
| HIS | CE1 | 875 | 177.7 | 115.8 | 53.4 | 45 | B |
| HIS | NE2 | 875 | 177.2 | 116.3 | 52.3 | 45 | B |
| HIS | C | 875 | 180.7 | 111.5 | 51.1 | 48 | B |
| HIS | O | 875 | 181.0 | 111.5 | 49.9 | 48 | B |
| PHE | N | 876 | 180.7 | 110.5 | 51.9 | 51 | B |
| PHE | CA | 876 | 181.0 | 109.2 | 51.4 | 53 | B |
| PHE | CB | 876 | 182.0 | 108.4 | 52.2 | 51 | B |
| PHE | CG | 876 | 182.2 | 107.0 | 51.8 | 51 | B |
| PHE | CD1 | 876 | 183.2 | 106.7 | 50.8 | 51 | B |
| PHE | CD2 | 876 | 181.4 | 106.0 | 52.2 | 51 | B |
| PHE | CE1 | 876 | 183.4 | 105.4 | 50.3 | 51 | B |
| PHE | CE2 | 876 | 181.5 | 104.7 | 51.7 | 50 | B |
| PHE | CZ | 876 | 182.5 | 104.4 | 50.8 | 51 | B |
| PHE | C | 876 | 179.7 | 108.3 | 51.3 | 56 | B |
| PHE | O | 876 | 178.8 | 108.5 | 52.2 | 56 | B |
| GLY | N | 877 | 179.7 | 107.4 | 50.4 | 58 | B |
| GLY | CA | 877 | 178.5 | 106.5 | 50.2 | 62 | B |
| GLY | C | 877 | 178.9 | 105.3 | 49.3 | 64 | B |
| GLY | O | 877 | 179.6 | 105.5 | 48.3 | 64 | B |
| SER | N | 878 | 178.5 | 104.1 | 49.7 | 66 | B |
| SER | CA | 878 | 178.9 | 102.9 | 48.9 | 67 | B |
| SER | CB | 878 | 180.2 | 102.4 | 49.4 | 67 | B |
| SER | OG | 878 | 180.8 | 101.5 | 48.4 | 67 | B |
| SER | C | 878 | 177.7 | 101.9 | 49.1 | 69 | B |
| SER | O | 878 | 177.9 | 100.9 | 49.8 | 69 | B |
| GLY | N | 879 | 176.6 | 102.2 | 48.5 | 70 | B |
| GLY | CA | 879 | 175.4 | 101.3 | 48.6 | 71 | B |
| GLY | C | 879 | 174.7 | 101.7 | 49.8 | 72 | B |
| GLY | O | 879 | 174.1 | 102.8 | 49.9 | 72 | B |
| ALA | N | 880 | 174.7 | 100.8 | 50.8 | 72 | B |
| ALA | CA | 880 | 174.1 | 101.0 | 52.1 | 72 | B |
| ALA | CB | 880 | 173.8 | 99.7 | 52.8 | 72 | B |
| ALA | C | 880 | 174.9 | 102.0 | 52.9 | 72 | B |
| ALA | O | 880 | 174.4 | 102.6 | 53.9 | 73 | B |
| MET | N | 881 | 176.2 | 102.0 | 52.6 | 72 | B |
| MET | CA | 881 | 177.2 | 102.9 | 53.3 | 71 | B |
| MET | CB | 881 | 178.6 | 102.5 | 53.0 | 72 | B |
| MET | CG | 881 | 179.1 | 101.2 | 53.6 | 74 | B |
| MET | SD | 881 | 178.0 | 99.9 | 53.2 | 75 | B |
| MET | CE | 881 | 177.4 | 99.5 | 54.9 | 75 | B |
| MET | C | 881 | 177.0 | 104.3 | 53.1 | 69 | B |
| MET | O | 881 | 176.7 | 104.7 | 52.0 | 69 | B |
| LEU | N | 882 | 177.3 | 105.1 | 54.1 | 68 | B |
| LEU | CA | 882 | 177.2 | 106.6 | 54.1 | 66 | B |
| LEU | CB | 882 | 175.7 | 107.0 | 54.3 | 66 | B |
| LEU | CG | 882 | 174.8 | 107.2 | 53.1 | 67 | B |
| LEU | CD1 | 882 | 175.5 | 107.8 | 51.9 | 67 | B |
| LEU | CD2 | 882 | 174.1 | 105.8 | 52.7 | 67 | B |
| LEU | C | 882 | 178.0 | 107.1 | 55.3 | 64 | B |

TABLE 5-continued

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| LEU | O | 882 | 177.6 | 107.0 | 56.4 | 65 | B |
| HIS | N | 883 | 179.2 | 107.6 | 55.0 | 62 | B |
| HIS | CA | 883 | 180.0 | 108.2 | 56.0 | 60 | B |
| HIS | CB | 883 | 181.3 | 107.3 | 56.3 | 60 | B |
| HIS | CG | 883 | 182.2 | 107.8 | 57.4 | 60 | B |
| HIS | CD2 | 883 | 182.8 | 109.0 | 57.6 | 60 | B |
| HIS | ND1 | 883 | 182.6 | 107.0 | 58.4 | 61 | B |
| HIS | CE1 | 883 | 183.4 | 107.7 | 59.2 | 60 | B |
| HIS | NE2 | 883 | 183.5 | 108.9 | 58.8 | 60 | B |
| HIS | C | 883 | 180.5 | 109.6 | 55.7 | 58 | B |
| HIS | O | 883 | 181.0 | 109.9 | 54.6 | 58 | B |
| ASP | N | 884 | 180.1 | 110.5 | 56.5 | 56 | B |
| ASP | CA | 884 | 180.5 | 111.9 | 56.3 | 53 | B |
| ASP | CB | 884 | 179.3 | 112.8 | 56.7 | 52 | B |
| ASP | CG | 884 | 178.1 | 112.6 | 55.7 | 52 | B |
| ASP | OD1 | 884 | 177.2 | 113.5 | 55.7 | 51 | B |
| ASP | OD2 | 884 | 178.1 | 111.6 | 55.0 | 52 | B |
| ASP | C | 884 | 181.7 | 112.3 | 57.2 | 52 | B |
| ASP | O | 884 | 181.9 | 111.6 | 58.2 | 52 | B |
| VAL | N | 885 | 182.4 | 113.2 | 56.8 | 51 | B |
| VAL | CA | 885 | 183.6 | 113.7 | 57.5 | 48 | B |
| VAL | CB | 885 | 184.9 | 113.2 | 56.9 | 47 | B |
| VAL | CG1 | 885 | 186.1 | 113.9 | 57.6 | 46 | B |
| VAL | CG2 | 885 | 185.1 | 111.7 | 57.2 | 46 | B |
| VAL | C | 885 | 183.5 | 115.2 | 57.3 | 48 | B |
| VAL | O | 885 | 183.9 | 115.7 | 56.3 | 50 | B |
| VAL | N | 886 | 182.9 | 116.0 | 58.3 | 47 | B |
| VAL | CA | 886 | 182.8 | 117.4 | 58.2 | 48 | B |
| VAL | CB | 886 | 181.5 | 117.9 | 58.6 | 48 | B |
| VAL | CG1 | 886 | 181.4 | 119.4 | 58.3 | 47 | B |
| VAL | CG2 | 886 | 180.4 | 117.2 | 57.8 | 48 | B |
| VAL | C | 886 | 183.9 | 118.0 | 59.1 | 49 | B |
| VAL | O | 886 | 183.9 | 117.7 | 60.2 | 50 | B |
| MET | N | 887 | 184.8 | 118.8 | 58.5 | 50 | B |
| MET | CA | 887 | 185.8 | 119.5 | 59.2 | 49 | B |
| MET | CB | 887 | 187.0 | 119.8 | 58.4 | 49 | B |
| MET | CG | 887 | 187.7 | 118.5 | 57.9 | 49 | B |
| MET | SD | 887 | 188.1 | 117.5 | 59.3 | 49 | B |
| MET | CE | 887 | 189.6 | 118.2 | 59.8 | 48 | B |
| MET | C | 887 | 185.3 | 120.8 | 59.8 | 50 | B |
| MET | O | 887 | 184.5 | 121.5 | 59.1 | 50 | B |
| GLY | N | 888 | 185.8 | 121.2 | 60.9 | 52 | B |
| GLY | CA | 888 | 185.4 | 122.5 | 61.5 | 53 | B |
| GLY | C | 888 | 184.0 | 122.5 | 62.1 | 54 | B |
| GLY | O | 888 | 183.4 | 121.5 | 62.4 | 54 | B |
| VAL | N | 889 | 183.4 | 123.7 | 62.2 | 55 | B |
| VAL | CA | 889 | 182.0 | 123.8 | 62.7 | 56 | B |
| VAL | CB | 889 | 181.6 | 125.3 | 62.7 | 56 | B |
| VAL | CG1 | 889 | 180.7 | 125.6 | 61.5 | 56 | B |
| VAL | CG2 | 889 | 181.0 | 125.7 | 64.0 | 57 | B |
| VAL | C | 889 | 181.1 | 122.9 | 61.9 | 57 | B |
| VAL | O | 889 | 181.2 | 122.9 | 60.7 | 59 | B |
| PRO | N | 890 | 180.3 | 122.1 | 62.5 | 57 | B |
| PRO | CD | 890 | 180.0 | 122.0 | 64.0 | 58 | B |
| PRO | CA | 890 | 179.4 | 121.2 | 61.8 | 57 | B |
| PRO | CB | 890 | 178.7 | 120.4 | 62.9 | 58 | B |
| PRO | CG | 890 | 178.6 | 121.4 | 64.0 | 58 | B |
| PRO | C | 890 | 178.4 | 121.9 | 60.8 | 57 | B |
| PRO | O | 890 | 177.6 | 121.2 | 60.1 | 57 | B |
| GLU | N | 891 | 178.3 | 123.2 | 60.9 | 56 | B |
| GLU | CA | 891 | 177.4 | 124.0 | 60.0 | 56 | B |
| GLU | CB | 891 | 177.3 | 125.4 | 60.6 | 58 | B |
| GLU | CG | 891 | 176.3 | 125.5 | 61.8 | 60 | B |
| GLU | CD | 891 | 176.8 | 124.8 | 63.0 | 62 | B |
| GLU | OE1 | 891 | 178.1 | 124.7 | 63.2 | 62 | B |
| GLU | OE2 | 891 | 176.0 | 124.3 | 63.8 | 63 | B |
| GLU | C | 891 | 178.1 | 124.0 | 58.7 | 56 | B |
| GLU | O | 891 | 177.6 | 124.5 | 57.7 | 56 | B |
| ASN | N | 892 | 179.3 | 123.4 | 58.6 | 53 | B |
| ASN | CA | 892 | 180.1 | 123.4 | 57.4 | 51 | B |
| ASN | CB | 892 | 181.6 | 123.2 | 57.7 | 49 | B |
| ASN | CG | 892 | 182.2 | 124.5 | 58.4 | 47 | B |
| ASN | OD1 | 892 | 183.3 | 124.4 | 58.9 | 46 | B |
| ASN | ND2 | 892 | 181.5 | 125.6 | 58.4 | 45 | B |
| ASN | C | 892 | 179.7 | 122.2 | 56.5 | 50 | B |
| ASN | O | 892 | 180.4 | 121.9 | 55.5 | 52 | B |
| VAL | N | 893 | 178.6 | 121.6 | 56.7 | 49 | B |
| VAL | CA | 893 | 178.2 | 120.5 | 55.9 | 47 | B |
| VAL | CB | 893 | 177.6 | 119.3 | 56.6 | 47 | B |
| VAL | CG1 | 893 | 176.4 | 119.7 | 57.4 | 48 | B |
| VAL | CG2 | 893 | 177.3 | 118.2 | 55.7 | 48 | B |
| VAL | C | 893 | 177.3 | 121.0 | 54.8 | 46 | B |
| VAL | O | 893 | 176.2 | 121.6 | 55.1 | 46 | B |
| LEU | N | 894 | 177.7 | 120.7 | 53.5 | 45 | B |
| LEU | CA | 894 | 176.9 | 121.1 | 52.3 | 44 | B |
| LEU | CB | 894 | 177.9 | 121.5 | 51.2 | 43 | B |
| LEU | CG | 894 | 179.0 | 122.5 | 51.6 | 42 | B |
| LEU | CD1 | 894 | 180.2 | 122.4 | 50.6 | 41 | B |
| LEU | CD2 | 894 | 178.4 | 123.8 | 51.6 | 42 | B |
| LEU | C | 894 | 176.0 | 120.0 | 51.8 | 43 | B |
| LEU | O | 894 | 176.3 | 118.8 | 52.1 | 44 | B |
| GLN | N | 895 | 175.0 | 120.4 | 51.0 | 42 | B |
| GLN | CA | 895 | 174.2 | 119.4 | 50.4 | 42 | B |
| GLN | CB | 895 | 173.1 | 120.1 | 49.5 | 43 | B |
| GLN | CG | 895 | 172.1 | 120.7 | 50.4 | 45 | B |
| GLN | CD | 895 | 171.3 | 119.7 | 51.2 | 46 | B |
| GLN | OE1 | 895 | 170.5 | 119.0 | 50.7 | 46 | B |
| GLN | NE2 | 895 | 171.7 | 119.7 | 52.5 | 46 | B |
| GLN | C | 895 | 175.1 | 118.5 | 49.5 | 42 | B |
| GLN | O | 895 | 176.1 | 119.0 | 49.0 | 42 | B |
| PRO | N | 896 | 174.7 | 117.2 | 49.3 | 41 | B |
| PRO | CD | 896 | 173.5 | 116.5 | 49.8 | 40 | B |
| PRO | CA | 896 | 175.5 | 116.3 | 48.5 | 40 | B |
| PRO | CB | 896 | 174.9 | 115.0 | 48.9 | 39 | B |
| PRO | CG | 896 | 173.5 | 115.3 | 49.1 | 40 | B |
| PRO | C | 896 | 175.3 | 116.6 | 46.9 | 39 | B |
| PRO | O | 896 | 174.3 | 117.1 | 46.5 | 39 | B |
| THR | N | 897 | 176.4 | 116.3 | 46.2 | 38 | B |
| THR | CA | 897 | 176.5 | 116.5 | 44.8 | 36 | B |
| THR | CB | 897 | 177.6 | 117.6 | 44.4 | 36 | B |
| THR | OG1 | 897 | 177.5 | 117.9 | 43.0 | 37 | B |
| THR | CG2 | 897 | 179.0 | 117.1 | 44.7 | 35 | B |
| THR | C | 897 | 176.7 | 115.2 | 44.1 | 34 | B |
| THR | O | 897 | 177.4 | 114.3 | 44.6 | 35 | B |
| HIS | N | 898 | 176.1 | 115.0 | 42.9 | 33 | B |
| HIS | CA | 898 | 176.2 | 113.7 | 42.2 | 33 | B |
| HIS | CB | 898 | 175.1 | 113.7 | 41.1 | 32 | B |
| HIS | CG | 898 | 175.0 | 112.4 | 40.4 | 32 | B |
| HIS | CD2 | 898 | 173.9 | 111.6 | 40.0 | 32 | B |
| HIS | ND1 | 898 | 176.1 | 111.6 | 40.0 | 32 | B |
| HIS | CE1 | 898 | 175.7 | 110.5 | 39.3 | 31 | B |
| HIS | NE2 | 898 | 174.4 | 110.5 | 39.4 | 32 | B |
| HIS | C | 898 | 177.6 | 113.8 | 41.5 | 32 | B |
| HIS | O | 898 | 177.8 | 114.7 | 40.7 | 33 | B |
| PRO | N | 899 | 178.5 | 112.9 | 41.7 | 32 | B |
| PRO | CD | 899 | 178.4 | 111.8 | 42.6 | 32 | B |
| PRO | CA | 899 | 179.9 | 112.9 | 41.1 | 32 | B |
| PRO | CB | 899 | 180.6 | 111.8 | 41.9 | 32 | B |
| PRO | CG | 899 | 179.6 | 110.9 | 42.2 | 33 | B |
| PRO | C | 899 | 180.0 | 112.8 | 39.6 | 31 | B |
| PRO | O | 899 | 181.2 | 112.9 | 39.1 | 32 | B |
| VAL | N | 900 | 179.0 | 112.5 | 38.9 | 30 | B |
| VAL | CA | 900 | 179.1 | 112.4 | 37.4 | 29 | B |
| VAL | CB | 900 | 178.2 | 111.2 | 36.9 | 28 | B |
| VAL | CG1 | 900 | 178.2 | 111.2 | 35.4 | 26 | B |
| VAL | CG2 | 900 | 178.7 | 109.9 | 37.4 | 27 | B |
| VAL | C | 900 | 178.6 | 113.7 | 36.8 | 30 | B |
| VAL | O | 900 | 179.4 | 114.3 | 36.0 | 30 | B |
| TYR | N | 901 | 177.4 | 114.2 | 37.2 | 29 | B |
| TYR | CA | 901 | 176.8 | 115.4 | 36.7 | 29 | B |
| TYR | CB | 901 | 175.3 | 115.2 | 36.7 | 28 | B |
| TYR | CG | 901 | 174.8 | 114.1 | 35.8 | 28 | B |
| TYR | CD1 | 901 | 174.4 | 112.9 | 36.3 | 29 | B |
| TYR | CE1 | 901 | 174.0 | 1118 | 35.5 | 29 | B |

TABLE 5-continued

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| TYR | CD2 | 901 | 174.8 | 114.3 | 34.4 | 28 | B |
| TYR | CE2 | 901 | 174.5 | 113.2 | 33.6 | 29 | B |
| TYR | CZ | 901 | 174.1 | 112.0 | 34.1 | 29 | B |
| TYR | OH | 901 | 173.7 | 111.0 | 33.3 | 28 | B |
| TYR | C | 901 | 177.1 | 116.7 | 37.5 | 30 | B |
| TYR | O | 901 | 176.9 | 117.8 | 37.0 | 30 | B |
| ASN | N | 902 | 177.5 | 116.5 | 38.8 | 30 | B |
| ASN | CA | 902 | 177.8 | 117.6 | 39.7 | 30 | B |
| ASN | CB | 902 | 179.0 | 118.5 | 39.2 | 30 | B |
| ASN | CG | 902 | 179.6 | 119.3 | 40.4 | 29 | B |
| ASN | OD1 | 902 | 179.6 | 118.8 | 41.5 | 29 | B |
| ASN | ND2 | 902 | 180.1 | 120.4 | 40.1 | 29 | B |
| ASN | C | 902 | 176.6 | 118.5 | 39.9 | 29 | B |
| ASN | O | 902 | 176.6 | 119.7 | 39.7 | 29 | B |
| ILE | N | 903 | 175.5 | 117.9 | 40.3 | 30 | B |
| ILE | CA | 903 | 174.3 | 118.6 | 40.7 | 31 | B |
| ILE | CB | 903 | 173.3 | 118.8 | 39.5 | 30 | B |
| ILE | CG2 | 903 | 174.0 | 119.5 | 38.4 | 30 | B |
| ILE | CG1 | 903 | 172.7 | 117.5 | 39.0 | 30 | B |
| ILE | CD1 | 903 | 171.6 | 117.6 | 38.0 | 28 | B |
| ILE | C | 903 | 173.6 | 117.7 | 41.7 | 33 | B |
| ILE | O | 903 | 174.1 | 116.5 | 41.8 | 34 | B |
| GLY | N | 904 | 172.7 | 118.2 | 42.4 | 35 | B |
| GLY | CA | 904 | 172.0 | 117.4 | 43.4 | 36 | B |
| GLY | C | 904 | 171.6 | 116.0 | 42.9 | 37 | B |
| GLY | O | 904 | 171.0 | 115.9 | 41.9 | 37 | B |
| PRO | N | 905 | 171.9 | 115.0 | 43.7 | 38 | B |
| PRO | CD | 905 | 172.7 | 115.1 | 44.9 | 38 | B |
| PRO | CA | 905 | 171.6 | 113.6 | 43.4 | 39 | B |
| PRO | CB | 905 | 172.0 | 112.9 | 44.7 | 38 | B |
| PRO | CG | 905 | 173.2 | 113.7 | 45.2 | 38 | B |
| PRO | C | 905 | 170.2 | 113.4 | 43.1 | 40 | B |
| PRO | O | 905 | 169.8 | 112.6 | 42.3 | 41 | B |
| ASP | N | 906 | 169.4 | 114.2 | 43.8 | 42 | B |
| ASP | CA | 906 | 167.9 | 114.2 | 43.6 | 45 | B |
| ASP | CB | 906 | 167.3 | 114.9 | 44.8 | 47 | B |
| ASP | CG | 906 | 168.0 | 116.2 | 45.2 | 50 | B |
| ASP | OD1 | 906 | 169.0 | 116.2 | 45.9 | 51 | B |
| ASP | OD2 | 906 | 167.5 | 117.3 | 44.8 | 51 | B |
| ASP | C | 906 | 167.4 | 114.8 | 42.4 | 44 | B |
| ASP | O | 906 | 166.4 | 114.5 | 41.8 | 45 | B |
| LYS | N | 907 | 168.2 | 115.8 | 41.9 | 44 | B |
| LYS | CA | 907 | 168.0 | 116.5 | 40.6 | 43 | B |
| LYS | CB | 907 | 168.9 | 117.7 | 40.5 | 43 | B |
| LYS | CG | 907 | 168.7 | 11e.7 | 41.6 | 42 | B |
| LYS | CD | 907 | 167.3 | 119.2 | 41.5 | 42 | B |
| LYS | CE | 907 | 167.0 | 120.0 | 42.7 | 43 | B |
| LYS | NZ | 907 | 165.6 | 120.6 | 42.6 | 44 | B |
| LYS | C | 907 | 168.2 | 115.5 | 39.5 | 43 | B |
| LYS | O | 907 | 167.5 | 115.5 | 38.5 | 43 | B |
| VAL | N | 908 | 169.3 | 114.8 | 39.6 | 42 | B |
| VAL | CA | 908 | 169.7 | 113.8 | 38.6 | 42 | B |
| VAL | CB | 908 | 171.0 | 113.0 | 39.1 | 41 | B |
| VAL | CG1 | 908 | 171.2 | 111.9 | 38.1 | 41 | B |
| VAL | CG2 | 908 | 172.1 | 114.0 | 39.1 | 40 | B |
| VAL | C | 908 | 168.5 | 112.8 | 38.5 | 42 | B |
| VAL | O | 908 | 168.0 | 112.5 | 37.5 | 42 | B |
| ILE | N | 909 | 168.0 | 112.3 | 39.7 | 42 | B |
| ILE | CA | 909 | 166.9 | 111.4 | 39.7 | 42 | B |
| ILE | CB | 909 | 166.7 | 110.9 | 41.1 | 42 | B |
| ILE | CG2 | 909 | 165.4 | 110.0 | 41.1 | 42 | B |
| ILE | CG1 | 909 | 167.9 | 110.2 | 41.6 | 42 | B |
| ILE | CD1 | 909 | 167.9 | 109.8 | 43.1 | 42 | B |
| ILE | C | 909 | 165.7 | 112.1 | 39.2 | 43 | B |
| ILE | O | 909 | 165.0 | 111.6 | 38.2 | 43 | B |
| GLN | N | 910 | 165.3 | 113.2 | 39.7 | 43 | B |
| GLN | CA | 910 | 164.2 | 114.0 | 39.3 | 44 | B |
| GLN | CB | 910 | 164.1 | 115.3 | 40.0 | 45 | B |
| GLN | CG | 910 | 162.8 | 116.0 | 40.0 | 47 | B |
| GLN | CD | 910 | 162.8 | 117.4 | 40.7 | 48 | B |
| GLN | OE1 | 910 | 161.8 | 118.1 | 40.6 | 49 | B |
| GLN | NE2 | 910 | 163.9 | 117.7 | 41.5 | 49 | B |
| GLN | C | 910 | 164.1 | 114.2 | 37.7 | 44 | B |
| GLN | O | 910 | 163.1 | 113.9 | 37.1 | 44 | B |
| ALA | N | 911 | 165.2 | 114.7 | 37.2 | 44 | B |
| ALA | CA | 911 | 165.2 | 115.0 | 35.7 | 43 | B |
| ALA | CB | 911 | 166.4 | 115.8 | 35.4 | 44 | B |
| ALA | C | 911 | 165.2 | 113.8 | 34.8 | 43 | B |
| ALA | O | 911 | 164.5 | 113.8 | 33.9 | 42 | B |
| THR | N | 912 | 165.9 | 112.7 | 35.2 | 43 | B |
| THR | CA | 912 | 166.0 | 111.5 | 34.4 | 43 | B |
| THR | CB | 912 | 167.0 | 110.5 | 34.9 | 43 | B |
| THR | OG1 | 912 | 166.8 | 110.3 | 36.3 | 45 | B |
| THR | CG2 | 912 | 168.5 | 111.1 | 34.7 | 43 | B |
| THR | C | 912 | 164.7 | 110.8 | 34.3 | 43 | B |
| THR | O | 912 | 164.3 | 110.4 | 33.1 | 45 | B |
| THR | N | 913 | 163.9 | 110.7 | 35.4 | 43 | B |
| THR | CA | 913 | 162.6 | 110.0 | 35.3 | 42 | B |
| THR | CB | 913 | 162.2 | 109.5 | 36.7 | 42 | B |
| THR | OG1 | 913 | 161.3 | 110.4 | 37.3 | 43 | B |
| THR | CG2 | 913 | 163.4 | 109.3 | 37.6 | 42 | B |
| THR | C | 913 | 161.6 | 110.9 | 34.6 | 41 | B |
| THR | O | 913 | 160.6 | 110.4 | 34.0 | 42 | B |
| HIS | N | 914 | 161.7 | 112.2 | 34.7 | 40 | B |
| HIS | CA | 914 | 160.7 | 113.0 | 34.1 | 39 | B |
| HIS | CB | 914 | 160.8 | 114.5 | 34.5 | 38 | B |
| HIS | CG | 914 | 160.1 | 115.4 | 33.5 | 37 | B |
| HIS | CD2 | 914 | 158.8 | 115.9 | 33.5 | 37 | B |
| HIS | ND1 | 914 | 160.7 | 115.9 | 32.4 | 37 | B |
| HIS | CE1 | 914 | 159.8 | 116.6 | 31.7 | 36 | B |
| HIS | NE2 | 914 | 158.7 | 116.6 | 32.3 | 37 | B |
| HIS | C | 914 | 160.9 | 113.0 | 32.5 | 40 | B |
| HIS | O | 914 | 160.0 | 112.9 | 31.8 | 40 | B |
| PHE | N | 915 | 162.2 | 113.1 | 32.1 | 40 | B |
| PHE | CA | 915 | 162.5 | 113.0 | 30.7 | 40 | B |
| PHE | CB | 915 | 164.0 | 113.5 | 30.4 | 39 | B |
| PHE | CG | 915 | 164.1 | 115.0 | 30.5 | 37 | B |
| PHE | CD1 | 915 | 164.8 | 115.6 | 31.6 | 37 | B |
| PHE | CD2 | 915 | 163.5 | 115.8 | 29.6 | 37 | B |
| PHE | CE1 | 915 | 164.9 | 117.0 | 31.7 | 36 | B |
| PHE | CE2 | 915 | 163.6 | 117.2 | 29.7 | 36 | B |
| PHE | CZ | 915 | 164.3 | 117.8 | 30.7 | 36 | B |
| PHE | C | 915 | 162.2 | 111.6 | 30.1 | 41 | B |
| PHE | O | 915 | 162.0 | 111.4 | 28.9 | 41 | B |
| LEU | N | 916 | 162.2 | 110.7 | 31.0 | 42 | B |
| LEU | CA | 916 | 162.0 | 109.3 | 30.7 | 44 | B |
| LEU | CB | 916 | 162.3 | 108.4 | 31.9 | 43 | B |
| LEU | CG | 916 | 163.4 | 107.3 | 31.8 | 43 | B |
| LEU | CD1 | 916 | 164.4 | 107.7 | 30.7 | 44 | B |
| LEU | CD2 | 916 | 164.1 | 107.2 | 33.1 | 43 | B |
| LEU | C | 916 | 160.5 | 109.1 | 30.3 | 45 | B |
| LEU | O | 916 | 160.2 | 108.3 | 29.5 | 44 | B |
| GLN | N | 917 | 159.6 | 110.0 | 30.7 | 47 | B |
| GLN | CA | 917 | 158.2 | 110.0 | 30.4 | 48 | B |
| GLN | CB | 917 | 157.5 | 111.1 | 31.1 | 50 | B |
| GLN | CG | 917 | 157.6 | 111.1 | 32.6 | 51 | B |
| GLN | CD | 917 | 157.1 | 112.4 | 33.2 | 53 | B |
| GLN | OE1 | 917 | 157.8 | 113.0 | 34.1 | 54 | B |
| GLN | NE2 | 917 | 156.0 | 113.0 | 32.7 | 53 | B |
| GLN | C | 917 | 158.1 | 110.3 | 28.9 | 49 | B |
| GLN | O | 917 | 157.0 | 110.1 | 28.3 | 50 | B |
| LYS | N | 918 | 159.2 | 110.8 | 28.3 | 51 | B |
| LYS | CA | 918 | 159.2 | 111.1 | 26.9 | 52 | B |
| LYS | CB | 918 | 159.7 | 112.5 | 26.6 | 54 | B |
| LYS | CG | 918 | 159.0 | 113.6 | 27.3 | 55 | B |
| LYS | CD | 918 | 159.5 | 113.7 | 28.8 | 56 | B |
| LYS | CE | 918 | 158.5 | 114.5 | 29.6 | 57 | B |
| LYS | NZ | 918 | 158.2 | 115.9 | 29.1 | 58 | B |
| LYS | C | 918 | 160.0 | 110.1 | 26.1 | 53 | B |
| LYS | O | 918 | 160.8 | 109.4 | 26.7 | 54 | B |
| PRO | N | 919 | 159.7 | 109.9 | 24.8 | 55 | B |
| PRO | CD | 919 | 158.6 | 110.5 | 24.0 | 55 | B |
| PRO | CA | 919 | 160.5 | 108.9 | 24.1 | 55 | B |
| PRO | CB | 919 | 159.5 | 108.5 | 23.0 | 55 | B |

TABLE 5-continued

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| PRO | CG | 919 | 158.8 | 109.8 | 22.7 | 55 | B |
| PRO | C | 919 | 161.7 | 109.6 | 23.5 | 56 | B |
| PRO | O | 919 | 161.7 | 110.8 | 23.2 | 57 | B |
| VAL | N | 920 | 162.7 | 108.8 | 23.3 | 58 | B |
| VAL | CA | 920 | 164.0 | 109.2 | 22.7 | 59 | B |
| VAL | CB | 920 | 164.9 | 108.0 | 22.5 | 58 | B |
| VAL | CG1 | 920 | 166.1 | 108.5 | 21.6 | 58 | B |
| VAL | CG2 | 920 | 165.4 | 107.5 | 23.8 | 57 | B |
| VAL | C | 920 | 163.6 | 109.7 | 21.3 | 62 | B |
| VAL | O | 920 | 162.9 | 109.0 | 20.6 | 62 | B |
| PRO | N | 921 | 163.9 | 111.0 | 20.9 | 65 | B |
| PRO | CD | 921 | 164.6 | 112.0 | 21.7 | 65 | B |
| PRO | CA | 921 | 163.5 | 111.5 | 19.6 | 68 | 8 |
| PRO | CB | 921 | 164.3 | 112.8 | 19.5 | 67 | B |
| PRO | CG | 921 | 164.3 | 113.3 | 20.9 | 66 | B |
| PRO | C | 921 | 163.7 | 110.5 | 18.5 | 71 | B |
| PRO | O | 921 | 164.8 | 110.5 | 17.9 | 71 | B |
| GLY | N | 922 | 162.7 | 109.7 | 18.3 | 76 | B |
| GLY | CA | 922 | 162.8 | 108.6 | 17.3 | 81 | B |
| GLY | C | 922 | 162.7 | 109.0 | 15.8 | 85 | B |
| GLY | O | 922 | 162.6 | 110.2 | 15.5 | 86 | B |
| PHE | N | 923 | 162.9 | 108.1 | 14.9 | 88 | B |
| PHE | CA | 923 | 162.8 | 108.3 | 13.5 | 91 | B |
| PHE | CB | 923 | 164.3 | 108.2 | 12.9 | 92 | B |
| PHE | CG | 923 | 165.3 | 108.7 | 13.9 | 94 | B |
| PHE | CD1 | 923 | 165.8 | 110.0 | 13.8 | 94 | B |
| PHE | CD2 | 923 | 165.9 | 107.8 | 14.9 | 94 | B |
| PHE | CE1 | 923 | 166.7 | 110.5 | 14.8 | 94 | B |
| PHE | CE2 | 923 | 166.8 | 108.3 | 15.8 | 94 | B |
| PHE | CZ | 923 | 167.2 | 109.6 | 15.7 | 94 | B |
| PHE | C | 923 | 162.0 | 107.2 | 12.9 | 92 | B |
| PHE | O11 | 923 | 162.5 | 106.1 | 12.7 | 92 | B |
| PHE | O12 | 923 | 160.7 | 107.4 | 12.8 | 92 | B |
| ZIN | ZN | 1000 | 191.3 | 126.5 | 39.1 | 29 | Z |
| FPP | P | 2001 | 196.5 | 125.9 | 33.1 | 25 | F |
| FPP | O | 2001 | 196.4 | 127.5 | 33.0 | 26 | F |
| FPP | O1 | 2001 | 197.9 | 125.5 | 32.5 | 26 | F |
| FPP | O2 | 2001 | 196.3 | 125.5 | 34.6 | 27 | F |
| FPP | O3 | 2001 | 195.3 | 125.3 | 32.2 | 26 | F |
| FPP | C | 2001 | 195.4 | 124.0 | 31.7 | 25 | F |
| FPP | C1 | 2001 | 193.1 | 123.5 | 30.5 | 23 | F |
| FPP | C2 | 2001 | 193.9 | 123.4 | 31.5 | 25 | F |
| FPP | C3 | 2001 | 191.7 | 123.0 | 30.5 | 23 | F |
| FPP | C4 | 2001 | 193.6 | 124.1 | 29.1 | 24 | F |
| FPP | C5 | 2001 | 191.4 | 122.1 | 31.7 | 22 | F |
| FPP | C6 | 2001 | 188.9 | 121.7 | 32.5 | 18 | F |
| FPP | C7 | 2001 | 189.9 | 121.5 | 31.7 | 20 | F |
| FPP | C8 | 2001 | 188.9 | 122.8 | 33.6 | 17 | F |
| FPP | C9 | 2001 | 187.7 | 120.9 | 32.4 | 17 | F |
| FPP | C10 | 2001 | 186.4 | 121.6 | 31.9 | 16 | F |
| FPP | C11 | 2001 | 185.2 | 120.7 | 31.9 | 15 | F |
| FPP | C12 | 2001 | 184.0 | 121.0 | 31.4 | 16 | F |
| FPP | C13 | 2001 | 183.8 | 122.3 | 30.6 | 15 | F |
| FPP | C14 | 2001 | 182.8 | 120.0 | 31.5 | 16 | F |
| FPP | P1 | 2001 | 197.0 | 124.2 | 35.2 | 27 | F |
| FPP | O4 | 2001 | 196.2 | 123.9 | 36.6 | 27 | F |
| FPP | O5 | 2001 | 196.8 | 123.0 | 34.2 | 28 | F |
| FPP | O6 | 2001 | 198.5 | 124.5 | 35.5 | 27 | F |
| SCH | C | 2002 | 188.1 | 132.3 | 33.6 | 32 | I |
| SCH | C1 | 2002 | 187.5 | 129.8 | 33.0 | 32 | I |
| SCH | C2 | 2002 | 186.4 | 129.9 | 34.0 | 32 | I |
| SCH | C3 | 2002 | 186.9 | 130.8 | 35.2 | 33 | I |
| SCH | N | 2002 | 187.2 | 132.1 | 34.7 | 33 | I |
| SCH | C4 | 2002 | 187.9 | 131.2 | 32.5 | 32 | I |
| SCH | CL1 | 2002 | 183.7 | 124.3 | 33.8 | 31 | I |
| SCH | C5 | 2002 | 190.2 | 127.3 | 30.3 | 32 | I |
| SCH | C6 | 2002 | 184.7 | 125.6 | 33.2 | 33 | I |
| SCH | C7 | 2002 | 186.0 | 125.7 | 33.5 | 33 | I |
| SCH | C8 | 2002 | 188.2 | 126.9 | 33.5 | 33 | I |
| SCH | C9 | 2002 | 189.1 | 126.5 | 32.4 | 34 | I |
| SCH | C10 | 2002 | 184.8 | 127.7 | 32.0 | 39 | I |
| SCH | C11 | 2002 | 190.3 | 128.2 | 29.2 | 32 | I |
| SCH | C12 | 2002 | 189.4 | 129.2 | 29.0 | 31 | I |
| SCH | N1 | 2002 | 188.3 | 129.3 | 29.8 | 30 | I |
| SCH | C13 | 2002 | 187.0 | 128.9 | 31.8 | 33 | I |
| SCH | C14 | 2002 | 184.1 | 126.6 | 32.5 | 36 | I |
| SCH | BR1 | 2002 | 191.8 | 128.0 | 28.0 | 32 | I |
| SCH | BR2 | 2002 | 184.0 | 129.0 | 31.0 | 54 | I |
| SCH | C15 | 2002 | 188.2 | 128.5 | 30.9 | 32 | I |
| SCH | C16 | 2002 | 186.2 | 127.7 | 32.3 | 36 | I |
| SCH | C17 | 2002 | 189.2 | 127.5 | 31.2 | 33 | I |
| SCH | C18 | 2002 | 186.8 | 126.7 | 33.1 | 33 | I |
| SCH | C19 | 2002 | 186.3 | 137.0 | 35.1 | 32 | I |
| SCH | C20 | 2002 | 186.2 | 138.2 | 36.0 | 32 | I |
| SCH | C21 | 2002 | 186.5 | 135.7 | 35.8 | 32 | I |
| SCH | C22 | 2002 | 187.5 | 135.8 | 37.1 | 32 | I |
| SCH | N2 | 2002 | 187.4 | 138.3 | 36.9 | 32 | I |
| SCH | C23 | 2002 | 187.3 | 137.1 | 37.8 | 32 | I |
| SCH | C24 | 2002 | 187.0 | 134.6 | 34.9 | 33 | I |
| SCH | O | 2002 | 185.9 | 133.1 | 36.4 | 35 | I |
| SCH | C25 | 2002 | 186.7 | 133.2 | 35.4 | 33 | I |
| HOH | OH2 | 1002 | 187.9 | 129.7 | 16.9 | 16 | W |
| HOH | OH2 | 1003 | 201.5 | 124.1 | 44.5 | 15 | W |
| HOH | OH2 | 1004 | 203.3 | 117.4 | 25.9 | 18 | W |
| HOH | OH2 | 1005 | 198.0 | 115.2 | 20.3 | 16 | W |
| HOH | OH2 | 1007 | 199.8 | 114.9 | 34.8 | 16 | W |
| HOH | OH2 | 1009 | 191.9 | 123.0 | 17.7 | 21 | W |
| HOH | OH2 | 1011 | 196.8 | 117.6 | 19.2 | 8 | W |
| HOH | OH2 | 1012 | 204.8 | 119.9 | 34.9 | 16 | W |
| HOH | OH2 | 1016 | 202.7 | 109.1 | 23.5 | 34 | W |
| HOH | OH2 | 1019 | 194.1 | 118.5 | 18.8 | 24 | W |
| HOH | OH2 | 1020 | 179.4 | 133.1 | 21.3 | 26 | W |
| HOH | OH2 | 1021 | 203.2 | 120.1 | 32.8 | 14 | W |
| HOH | OH2 | 1022 | 206.9 | 126.2 | 33.3 | 26 | W |
| HOH | OH2 | 1023 | 204.5 | 127.0 | 36.5 | 27 | W |
| HOH | OH2 | 1024 | 181.2 | 104.2 | 22.9 | 33 | W |
| HOH | OH2 | 1026 | 177.7 | 137.8 | 20.1 | 25 | W |
| HOH | OH2 | 1032 | 205.1 | 124.6 | 37.1 | 18 | W |
| HOH | OH2 | 1033 | 197.7 | 103.4 | 28.1 | 34 | W |
| HOH | OH2 | 1034 | 203.3 | 119.7 | 48.3 | 29 | W |
| HOH | OH2 | 1038 | 190.3 | 120.7 | 16.9 | 27 | W |
| HOH | OH2 | 1039 | 209.4 | 125.2 | 32.9 | 21 | W |
| HOH | OH2 | 1042 | 192.4 | 121.3 | 45.2 | 23 | W |
| HOH | OH2 | 1044 | 193.8 | 139.7 | 8.4 | 21 | W |
| HOH | OH2 | 1045 | 191.5 | 118.1 | 18.3 | 27 | W |
| HOH | OH2 | 1046 | 201.7 | 115.0 | 46.8 | 43 | W |
| HOH | OH2 | 1050 | 179.8 | 127.6 | 15.8 | 32 | W |
| HOH | OH2 | 1051 | 189.8 | 139.0 | 25.5 | 31 | W |
| HOH | OH2 | 1052 | 206.2 | 133.4 | 14.1 | 33 | W |
| HOH | OH2 | 1054 | 191.0 | 115.7 | 17.4 | 41 | W |
| HOH | OH2 | 1055 | 193.7 | 139.2 | 5.6 | 17 | W |
| HOH | OH2 | 1061 | 175.6 | 137.8 | 26.3 | 29 | W |
| HOH | OH2 | 1063 | 202.3 | 139.1 | 14.3 | 36 | W |
| HOH | OH2 | 1064 | 195.2 | 113.3 | 18.7 | 37 | W |
| HOH | OH2 | 1065 | 207.2 | 124.5 | 11.5 | 22 | W |
| HOH | OH2 | 1066 | 178.6 | 139.0 | 43.6 | 38 | W |
| HOH | OH2 | 1067 | 185.2 | 129.7 | 16.4 | 35 | W |
| HOH | OH2 | 1068 | 185.9 | 125.9 | 10.0 | 33 | W |
| HOH | OH2 | 1070 | 185.2 | 114.3 | 22.0 | 34 | W |
| HOH | OH2 | 1071 | 206.4 | 108.4 | 11.4 | 46 | W |
| HOH | OH2 | 1073 | 201.6 | 111.0 | 25.1 | 23 | W |
| HOH | OH2 | 1074 | 200.2 | 107.5 | 25.7 | 36 | W |
| HOH | OH2 | 1075 | 211.4 | 126.6 | 32.0 | 20 | W |
| HOH | OH2 | 1076 | 207.2 | 134.3 | 16.9 | 47 | W |
| HOH | OH2 | 1077 | 203.8 | 112.5 | 35.2 | 18 | W |
| HOH | OH2 | 1078 | 207.5 | 128.7 | 32.0 | 24 | W |
| HOH | OH2 | 1080 | 187.0 | 111.5 | 12.5 | 43 | W |
| HOH | OH2 | 1081 | 203.3 | 111.3 | 11.6 | 21 | W |
| HOH | OH2 | 1082 | 177.7 | 125.8 | 16.7 | 43 | W |
| HOH | OH2 | 1084 | 174.6 | 122.2 | 14.4 | 34 | W |
| HOH | OH2 | 1085 | 203.1 | 127.6 | 9.2 | 23 | W |
| HOH | OH2 | 1087 | 207.9 | 136.9 | 21.9 | 37 | W |
| HOH | OH2 | 1089 | 211.4 | 129.9 | 29.4 | 33 | W |
| HOH | OH2 | 1090 | 179.0 | 102.9 | 34.6 | 41 | W |

TABLE 5-continued

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| HOH | OH2 | 1091 | 184.6 | 127.9 | 11.0 | 31 | W |
| HOH | OH2 | 1092 | 211.9 | 125.9 | 29.6 | 29 | W |
| HOH | OH2 | 1093 | 201.2 | 109.8 | 38.8 | 42 | W |
| HOH | OH2 | 1095 | 198.4 | 109.2 | 24.6 | 35 | W |
| HOH | OH2 | 1096 | 187.2 | 123.9 | 11.8 | 39 | W |
| HOH | OH2 | 1097 | 190.1 | 102.7 | 22.4 | 41 | W |
| HOH | OH2 | 1098 | 184.9 | 158.2 | 8.1 | 31 | W |
| HOH | OH2 | 1099 | 186.6 | 127.7 | 18.2 | 28 | W |
| HOH | OH2 | 1100 | 186.7 | 124.8 | 7.7 | 39 | W |
| HOH | OH2 | 1102 | 200.8 | 137.2 | 27.8 | 44 | W |
| HOH | OH2 | 1103 | 191.8 | 141.4 | 18.1 | 42 | W |
| HOH | OH2 | 1104 | 213.1 | 113.6 | 16.5 | 32 | W |
| HOH | OH2 | 1105 | 203.6 | 117.6 | 41.3 | 15 | W |
| HOH | OH2 | 1106 | 187.5 | 106.2 | 46.3 | 45 | W |
| HOH | OH2 | 1107 | 178.8 | 115.1 | 47.8 | 27 | W |
| HOH | OH2 | 1109 | 188.6 | 100.8 | 24.0 | 46 | W |
| HOH | OH2 | 1110 | 204.0 | 130.4 | 42.5 | 30 | W |
| HOH | OH2 | 1111 | 211.2 | 123.0 | 30.0 | 29 | W |
| HOH | OH2 | 1112 | 176.2 | 127.7 | 13.0 | 36 | W |
| HOH | OH2 | 1113 | 199.9 | 106.7 | 44.2 | 24 | W |
| HOH | OH2 | 1114 | 186.2 | 98.5 | 22.2 | 38 | W |
| HOH | OH2 | 1115 | 198.1 | 142.0 | 12.9 | 65 | W |
| HOH | OH2 | 1116 | 174.3 | 118.5 | 31.6 | 31 | W |
| HOH | OH2 | 1117 | 220.4 | 119.4 | 25.1 | 37 | W |
| HOH | OH2 | 1118 | 208.7 | 132.2 | 48.7 | 42 | W |
| HOH | OH2 | 1119 | 174.7 | 107.7 | 35.8 | 45 | W |
| HOH | OH2 | 1120 | 182.3 | 99.5 | 23.2 | 47 | W |
| HOH | OH2 | 1121 | 200.4 | 132.2 | 32.8 | 63 | W |
| HOH | OH2 | 1122 | 197.1 | 114.6 | 14.9 | 50 | W |
| HOH | OH2 | 1123 | 210.7 | 127.4 | 27.8 | 32 | W |
| HOH | OH2 | 1124 | 162.3 | 133.7 | 25.6 | 39 | W |
| HOH | OH2 | 1125 | 213.2 | 127.7 | 22.0 | 39 | W |
| HOH | OH2 | 1126 | 219.8 | 125.6 | 31.4 | 54 | W |
| HOH | OH2 | 1127 | 198.4 | 103.0 | 31.4 | 37 | W |
| HOH | OH2 | 1128 | 209.9 | 135.1 | 24.0 | 44 | W |
| HOH | OH2 | 1129 | 200.6 | 107.7 | 21.9 | 55 | W |
| HOH | OH2 | 1130 | 172.2 | 143.3 | 28.2 | 33 | W |
| HOH | OH2 | 1131 | 195.0 | 111.4 | 47.5 | 33 | W |
| HOH | OH2 | 1132 | 201.6 | 109.1 | 13.1 | 63 | W |
| HOH | OH2 | 1133 | 214.3 | 129.8 | 29.5 | 46 | W |
| HOH | OH2 | 1134 | 211.5 | 124.2 | 17.5 | 44 | W |
| HOH | OH2 | 1135 | 188.7 | 114.2 | 16.3 | 45 | W |
| HOH | OH2 | 1136 | 168.0 | 122.5 | 22.2 | 35 | W |
| HOH | OH2 | 1137 | 177.2 | 140.7 | 24.4 | 28 | W |
| HOH | OH2 | 1138 | 218.6 | 124.5 | 26.1 | 44 | W |
| HOH | OH2 | 1139 | 194.7 | 141.2 | 4.4 | 35 | W |
| HOH | OH2 | 1140 | 210.8 | 119.7 | 16.2 | 25 | W |
| HOH | OH2 | 1141 | 181.0 | 138.9 | 23.8 | 31 | W |
| HOH | OH2 | 1142 | 177.2 | 111.6 | 46.8 | 63 | W |
| HOH | OH2 | 1143 | 185.4 | 151.4 | 10.4 | 33 | W |
| HOH | OH2 | 1144 | 172.2 | 138.7 | 17.7 | 52 | W |
| HOH | OH2 | 1145 | 214.5 | 101.9 | 15.6 | 45 | W |
| HOH | OH2 | 1146 | 213.8 | 106.7 | 19.5 | 38 | W |
| HOH | OH2 | 1147 | 218.0 | 123.3 | 49.2 | 43 | W |
| HOH | OH2 | 1148 | 200.3 | 96.8 | 26.4 | 53 | W |
| HOH | OH2 | 1149 | 210.7 | 133.1 | 17.2 | 48 | W |
| HOH | OH2 | 1150 | 202.9 | 135.0 | 10.9 | 33 | W |
| HOH | OH2 | 1151 | 177.8 | 140.9 | 41.6 | 27 | W |
| HOH | OH2 | 1152 | 220.4 | 124.4 | 40.8 | 58 | W |
| HOH | OH2 | 1155 | 195.5 | 123.4 | 17.9 | 36 | W |
| HOH | OH2 | 1156 | 174.3 | 101.1 | 16.3 | 50 | W |
| HOH | OH2 | 1157 | 202.9 | 135.0 | 7.6 | 48 | W |
| HOH | OH2 | 1158 | 189.3 | 106.7 | 17.8 | 31 | W |
| HOH | OH2 | 1159 | 176.7 | 143.5 | 24.6 | 35 | W |
| HOH | OH2 | 1160 | 196.1 | 123.7 | 20.6 | 31 | W |
| HOH | OH2 | 1161 | 205.0 | 103.4 | 15.4 | 59 | W |
| HOH | OH2 | 1162 | 171.6 | 121.4 | 14.4 | 35 | W |
| HOH | OH2 | 1163 | 193.6 | 143.4 | 17.5 | 46 | W |
| HOH | OH2 | 1164 | 193.7 | 140.7 | 1.6 | 35 | W |
| HOH | OH2 | 1165 | 213.9 | 127.4 | 33.1 | 31 | W |
| HOH | OH2 | 1166 | 210.2 | 128.9 | 31.6 | 20 | W |
| HOH | OH2 | 1167 | 178.5 | 120.3 | 11.6 | 54 | W |

TABLE 5-continued

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| HOH | OH2 | 1168 | 204.5 | 122.0 | 41.6 | 33 | W |
| HOH | OH2 | 1169 | 169.5 | 142.2 | 37.6 | 40 | W |
| HOH | OH2 | 1170 | 205.0 | 117.8 | 45.9 | 57 | W |
| HOH | OH2 | 1171 | 201.9 | 120.8 | 2.8 | 60 | W |
| HOH | OH2 | 1172 | 216.1 | 115.2 | 17.4 | 32 | W |
| HOH | OH2 | 1173 | 208.4 | 116.8 | 41.5 | 29 | W |
| HOH | OH2 | 1174 | 218.5 | 125.0 | 46.5 | 63 | W |
| HOH | OH2 | 1175 | 156.5 | 125.2 | 36.4 | 43 | W |
| HOH | OH2 | 1176 | 206.0 | 130.7 | 32.9 | 36 | W |
| HOH | OH2 | 1177 | 206.0 | 118.8 | 48.3 | 43 | W |
| HOH | OH2 | 1178 | 204.0 | 132.3 | 13.1 | 34 | W |
| HOH | OH2 | 1179 | 190.8 | 100.7 | 25.6 | 54 | W |
| HOH | OH2 | 1181 | 172.0 | 129.8 | 16.6 | 32 | W |
| HOH | OH2 | 1182 | 159.5 | 126.2 | 29.6 | 52 | W |
| HOH | OH2 | 1183 | Z07.7 | 122.3 | 7.1 | 36 | W |
| HOH | OH2 | 1184 | 215.1 | 121.3 | 17.6 | 44 | W |
| HOH | OH2 | 1185 | 203.5 | 127.3 | 33.5 | 51 | W |
| HOH | OH2 | 1186 | 192.0 | 143.7 | 6.4 | 40 | W |
| HOH | OH2 | 1187 | 206.3 | 136.8 | 17.2 | 48 | W |
| HOH | OH2 | 1188 | 211.7 | 90.0 | 38.0 | 36 | W |
| HOH | OH2 | 1189 | 201.0 | 105.6 | 19.2 | 53 | W |
| HOH | OH2 | 1190 | 204.8 | 136.9 | 12.4 | 47 | W |
| HOH | OH2 | 1191 | 176.9 | 133.5 | 8.2 | 34 | W |
| HOH | OH2 | 1193 | 187.0 | 140.9 | 31.4 | 40 | W |
| HOH | OH2 | 1194 | 205.6 | 123.8 | 40.0 | 28 | W |
| HOH | OH2 | 1195 | 204.8 | 103.1 | 26.5 | 49 | W |
| HOH | OH2 | 1196 | 176.0 | 151.6 | 22.3 | 51 | W |
| HOH | OH2 | 1197 | 187.7 | 114.0 | 13.1 | 37 | W |
| HOH | OH2 | 1198 | 204.4 | 138.5 | 24.0 | 34 | W |
| HOH | OH2 | 1200 | 194.0 | 117.9 | 9.4 | 56 | W |
| HOH | OH2 | 1201 | 159.6 | 117.8 | 26.7 | 60 | W |
| HOH | OH2 | 1202 | 185.7 | 122.3 | 13.2 | 33 | W |
| HOH | OH2 | 1203 | 180.7 | 147.4 | 35.9 | 33 | W |
| HOH | OH2 | 1204 | 188.9 | 120.0 | 14.5 | 48 | W |
| HOH | OH2 | 1205 | 173.4 | 107.8 | 39.8 | 71 | W |
| HOH | OH2 | 1206 | 216.1 | 122.6 | 19.8 | 44 | W |
| HOH | OH2 | 1207 | 206.3 | 120.0 | 41.8 | 46 | W |
| HOH | OH2 | 1208 | 213.1 | 117.8 | 43.5 | 42 | W |
| HOH | OH2 | 1209 | 210.8 | 127.1 | 23.2 | 40 | W |
| HOH | OH2 | 1210 | 193.1 | 116.5 | 16.3 | 36 | W |
| HOH | OH2 | 1211 | 190.3 | 123.2 | 65.5 | 48 | W |
| HOH | OH2 | 1212 | 177.9 | 141.9 | 45.3 | 49 | W |
| HOH | OH2 | 1213 | 182.1 | 99.6 | 32.0 | 49 | W |
| HOH | OH2 | 1214 | 211.4 | 120.5 | 11.4 | 56 | W |
| HOH | OH2 | 1215 | 208.8 | 126.6 | 12.3 | 30 | W |
| HOH | OH2 | 1216 | 211.1 | 129.9 | 18.4 | 38 | W |
| HOH | OH2 | 1217 | 165.0 | 105.0 | 26.9 | 58 | W |
| HOH | OH2 | 1219 | 190.4 | 122.2 | 6.3 | 55 | W |
| HOH | OH2 | 1220 | 209.9 | 116.7 | 47.6 | 49 | W |
| HOH | OH2 | 1221 | 196.4 | 107.6 | 18.8 | 70 | W |
| HOH | OH2 | 1222 | 183.3 | 158.3 | 20.2 | 33 | W |
| HOH | OH2 | 1223 | 215.2 | 128.1 | 24.6 | 53 | W |
| HOH | OH2 | 1224 | 174.6 | 146.0 | 5.0 | 50 | W |
| HOH | OH2 | 1225 | 200.4 | 105.0 | 36.7 | 35 | W |
| HOH | OH2 | 1226 | 191.0 | 142.2 | 10.9 | 50 | W |
| HOH | OH2 | 1227 | 157.0 | 122.0 | 39.3 | 57 | W |
| HOH | OH2 | 1228 | 210.3 | 130.6 | 38.8 | 51 | W |
| HOH | OH2 | 1229 | 209.5 | 122.9 | 10.2 | 46 | W |
| HOH | OH2 | 1230 | 196.1 | 118.8 | 7.2 | 48 | W |
| HOH | OH2 | 1231 | 174.7 | 140.7 | 30.0 | 29 | W |
| HOH | OH2 | 1232 | 189.5 | 159.0 | 14.9 | 40 | W |
| HOH | OH2 | 1233 | 171.5 | 117.6 | 46.7 | 30 | W |
| HOH | OH2 | 1234 | 162.2 | 118.9 | 27.6 | 44 | W |
| HOH | OH2 | 1235 | 207.6 | 98.1 | 25.6 | 37 | W |
| HOH | OH2 | 1236 | 201.1 | 100.8 | 44.0 | 35 | W |
| HOH | OH2 | 1237 | 208.5 | 131.3 | 35.9 | 47 | W |
| HOH | OH2 | 1238 | 185.4 | 148.8 | 10.4 | 32 | W |
| HOH | OH2 | 1239 | 211.7 | 125.4 | 12.9 | 48 | W |
| HOH | OH2 | 1240 | 212.7 | 108.8 | 18.1 | 42 | W |
| HOH | OH2 | 1241 | 217.1 | 120.5 | 34.6 | 58 | W |
| HOH | OH2 | 1242 | 211.9 | 94.9 | 26.9 | 55 | W |
| HOH | OH2 | 1243 | 192.2 | 146.3 | 23.6 | 55 | W |

TABLE 5-continued

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| HOH | OH2 | 1244 | 189.4 | 144.7 | 26.3 | 60 | W |
| HOH | OH2 | 1245 | 168.5 | 107.9 | 26.2 | 37 | W |
| HOH | OH2 | 1246 | 170.2 | 147.1 | 12.0 | 49 | W |
| HOH | OH2 | 1247 | 194.8 | 108.7 | 48.0 | 36 | W |
| HOH | OH2 | 1248 | 210.9 | 118.6 | 13.9 | 33 | W |
| HOH | OH2 | 1249 | 201.1 | 114.6 | 53.7 | 38 | W |
| HOH | OH2 | 1250 | 186.8 | 149.3 | 5.7 | 46 | W |
| HOH | OH2 | 1251 | 216.5 | 128.1 | 31.1 | 56 | W |
| HOH | OH2 | 1252 | 179.2 | 126.9 | 57.9 | 31 | W |
| HOH | OH2 | 1253 | 202.5 | 102.9 | 28.7 | 42 | W |
| HOH | OH2 | 1254 | 213.1 | 122.9 | 13.3 | 44 | W |
| HOH | OH2 | 1255 | 195.9 | 115.9 | 17.0 | 53 | W |
| HOH | OH2 | 1256 | 196.3 | 142.9 | 17.1 | 53 | W |
| HOH | OH2 | 1257 | 213.3 | 126.6 | 19.3 | 50 | W |
| HOH | OH2 | 125B | 175.9 | 138.8 | 21.7 | 57 | W |
| HOH | OH2 | 1259 | 182.6 | 158.5 | 23.3 | 55 | W |
| HOH | OH2 | 1260 | 211.8 | 118.5 | 53.4 | 51 | W |
| HOH | OH2 | 1261 | 203.6 | 138.7 | 6.0 | 63 | W |
| HOH | OH2 | 1263 | 200.2 | 141.6 | 8.4 | 51 | W |
| HOH | OH2 | 1264 | 202.7 | 134.4 | 25.6 | 46 | W |
| HOH | OH2 | 1265 | 218.7 | 123.2 | 36.6 | 52 | W |
| HOH | OH2 | 1266 | 203.5 | 132.1 | 32.8 | 48 | W |
| HOH | OH2 | 1267 | 211.3 | 109.7 | 12.3 | 60 | W |
| HOH | OH2 | 1268 | 191.3 | 113.0 | 18.2 | 53 | W |
| HOH | OH2 | 1269 | 183.8 | 98.2 | 27.8 | 57 | W |
| HOH | OH2 | 1270 | 168.9 | 121.4 | 47.5 | 62 | W |
| HOH | OH2 | 1271 | 209.9 | 125.3 | 8.5 | 61 | W |
| HOH | OH2 | 1272 | 180.3 | 140.3 | 48.3 | 55 | W |
| HOH | OH2 | 1273 | 199.5 | 109.3 | 19.4 | 47 | W |
| HOH | OH2 | 1274 | 199.3 | 107.3 | 58.9 | 65 | W |
| HOH | OH2 | 1275 | 205.0 | 118.6 | 5.8 | 41 | W |
| HOH | OH2 | 1276 | 206.1 | 115.3 | 5.2 | 57 | W |
| HOH | OH2 | 1277 | 171.1 | 131.4 | 20.4 | 46 | W |
| HOH | OH2 | 1278 | 160.7 | 127.3 | 37.1 | 51 | W |
| HOH | OH2 | 1279 | 211.8 | 102.7 | 53.5 | 62 | W |
| HOH | OH2 | 1281 | 221.0 | 113.1 | 44.8 | 80 | W |
| HOH | OH2 | 1282 | 190.0 | 140.1 | 30.7 | 83 | W |
| HOH | OH2 | 1283 | 172.1 | 148.3 | 25.2 | 57 | W |
| HOH | OH2 | 1284 | 176.9 | 110.4 | 53.0 | 39 | W |
| HOH | OH2 | 1285 | 203.1 | 115.6 | 43.0 | 51 | W |
| HOH | OH2 | 1286 | 168.7 | 105.2 | 25.9 | 52 | W |
| HOH | OH2 | 1287 | 192.1 | 123.8 | 2.2 | 46 | W |
| HOH | OH2 | 1288 | 173.6 | 145.4 | 24.6 | 44 | W |
| HOH | OH2 | 1289 | 196.7 | 111.5 | 26.0 | 29 | W |
| HOH | OH2 | 1290 | 166.0 | 117.8 | 38.C | 30 | W |
| HOH | OH2 | 1291 | 180.8 | 140.9 | 39.6 | 36 | W |
| HOH | OH2 | 1292 | 212.1 | 128.0 | 25.6 | 51 | W |
| HOH | OH2 | 1293 | 190.8 | 133.8 | 1.7 | 35 | W |
| HOH | OH2 | 1295 | 189.7 | 110.1 | 53.4 | 63 | W |
| HOH | OH2 | 1296 | 178.9 | 131.5 | 58.4 | 63 | W |
| HOH | OH2 | 1297 | 203.7 | 96.2 | 34.8 | 69 | W |
| HOH | OH2 | 1298 | 210.8 | 120.2 | 56.4 | 71 | W |
| HOH | OH2 | 1299 | 205.6 | 129.3 | 3.4 | 68 | W |
| HOH | OH2 | 1300 | 193.9 | 142.0 | 9.6 | 55 | W |
| HOH | OH2 | 1301 | 194.9 | 112.9 | 60.3 | 46 | W |
| HOH | OH2 | 1302 | 180.0 | 112.3 | 47.5 | 48 | W |
| HOH | OH2 | 1303 | 208.7 | 113.9 | 47.9 | 65 | W |
| HOH | OH2 | 1304 | 164.7 | 126.1 | 19.9 | 54 | W |
| HOH | OH2 | 1305 | 219.4 | 118.6 | 21.8 | 53 | W |
| HOH | OH2 | 1306 | 178.8 | 132.9 | 10.4 | 48 | W |
| HOH | OH2 | 1307 | 202.2 | 108.5 | 36.5 | 37 | W |
| HOH | OH2 | 1308 | 161.6 | 127.4 | 42.1 | 69 | W |
| HOH | OH2 | 1309 | 203.4 | 106.7 | 34.9 | 29 | W |
| HOH | OH2 | 1310 | 198.1 | 118.7 | 53.9 | 39 | W |
| HOH | OH2 | 1311 | 216.9 | 104.4 | 16.0 | 71 | W |
| HOH | OH2 | 1312 | 160.1 | 112.5 | 21.4 | 52 | W |
| HOH | OH2 | 1313 | 219.1 | 104.3 | 19.5 | 55 | W |
| HOH | OH2 | 1314 | 213.2 | 110.9 | 15.8 | 46 | W |
| HOH | OH2 | 1315 | 186.7 | 133.3 | 55.5 | 43 | W |
| HOH | OH2 | 1316 | 200.6 | 104.9 | 26.6 | 68 | W |
| HOH | OH2 | 1317 | 206.1 | 105.8 | 39.1 | 47 | W |
| HOH | OH2 | 1318 | 191.0 | 111.8 | 55.0 | 45 | W |
| HOH | OH2 | 1319 | 190.5 | 131.0 | 53.0 | 62 | W |
| HOH | OH2 | 1320 | 187.9 | 150.2 | 14.9 | 50 | W |
| HOH | OH2 | 1321 | 180.9 | 107.7 | 14.6 | 51 | W |
| HOH | OH2 | 1322 | 194.7 | 147.1 | 18.0 | 81 | W |
| HOH | OH2 | 1323 | 198.3 | 99.2 | 54.4 | 51 | W |
| HOH | OH2 | 1324 | 188.5 | 151.6 | 27.6 | 62 | W |
| HOH | OH2 | 1325 | 163.5 | 120.3 | 41.0 | 54 | W |
| HOH | OH2 | 1326 | 205.8 | 131.2 | 36.0 | 50 | W |
| HOH | OH2 | 1327 | 183.3 | 147.4 | 37.3 | 72 | W |
| HOH | OH2 | 1328 | 203.0 | 139.0 | 17.0 | 62 | W |
| HOH | OH2 | 1329 | 186.9 | 149.0 | 12.6 | 57 | W |
| HOH | OH2 | 1330 | 189.4 | 122.2 | 11.7 | 60 | W |
| HOH | OH2 | 1331 | 206.7 | 105.9 | 41.8 | 51 | W |
| HOH | OH2 | 1332 | 199.4 | 98.5 | 31.9 | 73 | W |
| HOH | OH2 | 1333 | 201.2 | 140.6 | 20.4 | 41 | W |
| HOH | OH2 | 1334 | 186.7 | 124.1 | 5.1 | 71 | W |
| HOH | OH2 | 1335 | 184.3 | 137.8 | 41.1 | 35 | W |
| HOH | OH2 | 1336 | 189.3 | 157.5 | 22.7 | 37 | W |
| HOH | OH2 | 1337 | 185.9 | 147.2 | 27.7 | 55 | W |
| HOH | OH2 | 1338 | 202.4 | 140.2 | 23.6 | 65 | W |
| HOH | OH2 | 1339 | 169.8 | 139.3 | 22.0 | 55 | W |
| HOH | OH2 | 1340 | 159.0 | 121.2 | 41.4 | 58 | W |
| HOH | OH2 | 1341 | 186.8 | 105.5 | 18.7 | 48 | W |
| HOH | OH2 | 1342 | 173.7 | 127.7 | 14.0 | 59 | W |
| HOH | OH2 | 1343 | 172.9 | 134.6 | 9.0 | 52 | W |
| HOH | OH2 | 1344 | 183.7 | 120.7 | 56.4 | 26 | W |
| HOH | OH2 | 1345 | 189.8 | 147.5 | 14.3 | 28 | W |
| HOH | OH2 | 1346 | 193.7 | 121.1 | 4.5 | 60 | W |
| HOH | OH2 | 1347 | 176.9 | 130.9 | 9.6 | 53 | W |
| HOH | OH2 | 1348 | 173.5 | 117.7 | 54.3 | 55 | W |
| HOH | OH2 | 1349 | 201.4 | 131.2 | 43.4 | 68 | W |
| HOH | OH2 | 1350 | 175.1 | 137.5 | 18.7 | 44 | W |
| HOH | OH2 | 1351 | 179.6 | 138.3 | 50.6 | 42 | W |
| HOH | OH2 | 1352 | 194.7 | 114.4 | 13.2 | 74 | W |
| HOH | OH2 | 1353 | 197.7 | 103.3 | 58.0 | 48 | W |
| HOH | OH2 | 1354 | 186.7 | 143.6 | 30.9 | 50 | W |
| HOH | OH2 | 1355 | 174.0 | 123.5 | 53.0 | 43 | W |
| HOH | OH2 | 1356 | 183.6 | 148.1 | 3.5 | 61 | W |
| HOH | OH2 | 1357 | 170.1 | 144.3 | 27.5 | 39 | W |
| HOH | OH2 | 1358 | 166.6 | 142.0 | 19.9 | 61 | W |
| HOH | OH2 | 1359 | 161.6 | 125.4 | 23.7 | 60 | W |
| HOH | OH2 | 1360 | 175.1 | 135.3 | 10.2 | 49 | W |
| HOH | OH2 | 1361 | 192.9 | 115.8 | 62.8 | 78 | W |
| HOH | OH2 | 1362 | 176.9 | 109.0 | 14.8 | 82 | W |
| HOH | OH2 | 1363 | 202.2 | 130.1 | 6.7 | 55 | W |
| HOH | OH2 | 1364 | 196.1 | 106.8 | 22.2 | 59 | W |
| HOH | OH2 | 1365 | 156.5 | 125.4 | 30.5 | 72 | W |
| HOH | OH2 | 1366 | 203.2 | 96.4 | 38.6 | 69 | W |
| HOH | OH2 | 1367 | 193.3 | 130.3 | 57.4 | 56 | W |
| HOH | OH2 | 1368 | 180.2 | 149.2 | 33.9 | 71 | W |
| HOH | OH2 | 1369 | 218.9 | 125.7 | 34.7 | 59 | W |
| HOH | OH2 | 1370 | 187.1 | 144.0 | 27.9 | 55 | W |
| HOH | OH2 | 1371 | 183.3 | 150.7 | 20.8 | 51 | W |
| HOH | OH2 | 1372 | 176.0 | 148.4 | 29.7 | 56 | W |
| HOH | OH2 | 1373 | 191.4 | 141.9 | 0.8 | 54 | W |
| HOH | OH2 | 1374 | 213.7 | 125.2 | 44.1 | 40 | W |
| HOH | OH2 | 1375 | 176.4 | 104.1 | 21.0 | 48 | W |
| HOH | OH2 | 1376 | 216.4 | 112.2 | 14.3 | 52 | W |
| HOH | OH2 | 1377 | 197.5 | 152.8 | 17.5 | 64 | W |
| HOH | OH2 | 1378 | 184.1 | 144.9 | 0.9 | 50 | W |
| HOH | OH2 | 1379 | 208.9 | .20.2 | 41.9 | 54 | W |
| HOH | OH2 | 1380 | 183.8 | 109.8 | 54.8 | 32 | W |
| HOH | OH2 | 1381 | 214.4 | 113.8 | 37.6 | 46 | W |
| HOH | OH2 | 1382 | 212.4 | 121.8 | 16.5 | 45 | W |
| HOH | OH2 | 1383 | 187.9 | 142.5 | 0.9 | 66 | W |
| HOH | OH2 | 1384 | 206.5 | 100.5 | 21.0 | 63 | W |
| HOH | OH2 | 1385 | 158.0 | 131.5 | 31.9 | 65 | W |
| HOH | OH2 | 1386 | 173.8 | 146.6 | 28.2 | 60 | W |
| HOH | OH2 | 1388 | 172.8 | 135.5 | 54.3 | 56 | W |
| HOH | OH2 | 1389 | 217.8 | 116.5 | 28.5 | 71 | W |
| HOH | OH2 | 1390 | 216.5 | 97.0 | 26.3 | 55 | W |
| HOH | OH2 | 1391 | 175.2 | 124.9 | 15.1 | 69 | W |

TABLE 5-continued

Table 5 lists the atomic structure coordinates for FPT in complex with FPP and the inhibitor SCH69132 as derived by X-ray diffraction from crystals of that complex. The abbreviations are the same as those used in Table 2.

| RES | ATOM | # | X | Y | Z | B | C |
|---|---|---|---|---|---|---|---|
| HOH | OH2 | 1392 | 206.3 | 117.0 | 43.7 | 82 | W |
| HOH | OH2 | 1393 | 168.1 | 124.1 | 46.2 | 73 | W |
| HOH | OH2 | 1394 | 179.1 | 134.0 | 56.6 | 56 | W |
| HOH | OH2 | 1395 | 169.2 | 108.0 | 29.3 | 60 | W |
| HOH | OH2 | 1396 | 173.5 | 143.2 | 3.9 | 55 | W |
| HOH | OH2 | 1397 | 159.1 | 118.5 | 39.3 | 67 | W |
| HOH | OH2 | 1398 | 189.5 | 124.2 | 7.7 | 39 | W |
| HOH | OH2 | 1399 | 211.8 | 92.2 | 39.5 | 48 | W |
| HOH | OH2 | 1400 | 196.5 | 142.5 | 6.1 | 86 | W |
| HOH | OH2 | 1401 | 212.6 | 126.9 | 16.6 | 59 | W |
| HOH | OH2 | 1402 | 165.5 | 130.5 | 21.0 | 69 | W |
| HOH | OH2 | 1403 | 203.0 | 132.7 | 27.6 | 50 | W |
| HOH | OH2 | 1404 | 177.1 | 102.9 | 26.1 | 65 | W |
| HOH | OH2 | 1405 | 174.6 | 105.9 | 21.8 | 47 | W |
| HOH | OH2 | 1406 | 212.5 | 130.4 | 21.4 | 72 | W |
| HOH | OH2 | 1407 | 214.2 | 128.8 | 27.0 | 81 | W |
| HOH | OH2 | 1408 | 183.5 | 141.5 | 39.6 | 65 | W |
| HOH | OH2 | 1409 | 163.4 | 128.6 | 24.0 | 38 | W |
| HOH | OH2 | 1410 | 216.1 | 118.5 | 49.3 | 67 | W |
| HOH | OH2 | 1411 | 210.6 | 118.0 | 42.4 | 47 | W |
| HOH | OH2 | 1412 | 177.9 | 147.7 | 37.4 | 57 | W |
| HOH | OH2 | 1413 | 185.0 | 135.9 | 56.1 | 52 | W |
| HOH | OH2 | 1414 | 218.0 | 90.3 | 39.9 | 70 | W |
| HOH | OH2 | 1415 | 207.6 | 131.2 | 13.5 | 42 | W |
| HOH | OH2 | 1416 | 203.9 | 130.1 | 38.9 | 68 | W |
| HOH | OH2 | 1417 | 165.4 | 136.5 | 32.1 | 43 | W |
| HOH | OH2 | 1418 | 187.6 | 140.8 | 28.3 | 50 | W |
| HOH | OH2 | 1419 | 206.7 | 133.7 | 32.6 | 77 | W |
| HOH | OH2 | 1420 | 186.6 | 146.2 | 31.1 | 63 | W |
| HOH | OH2 | 1421 | 189.5 | 104.6 | 19.5 | 76 | W |
| HOH | OH2 | 1422 | 208.6 | 111.3 | 9.7 | 70 | W |
| HOH | OH2 | 1423 | 202.3 | 133.4 | 59.6 | 77 | W |
| HOH | OH2 | 1424 | 215.2 | 126.8 | 35.8 | 66 | W |
| HOH | OH2 | 1425 | 217.6 | 116.9 | 15.3 | 47 | W |
| HOH | OH2 | 1426 | 159.9 | 118.2 | 29.6 | 51 | W |
| HOH | OH2 | 1427 | 174.2 | 132.9 | 7.3 | 41 | W |
| HOH | OH2 | 1428 | 180.6 | 101.6 | 22.1 | 61 | W |
| HOH | OH2 | 1429 | 171.0 | 109.3 | 35.2 | 72 | W |
| HOH | OH2 | 1430 | 197.1 | 110.9 | 58.2 | 64 | W |
| HOH | OH2 | 1431 | 183.4 | 105.8 | 11.6 | 57 | W |
| HOH | OH2 | 1432 | 195.0 | 153.0 | 15.4 | 65 | W |
| HOH | OH2 | 1433 | 201.5 | 137.6 | 3.0 | 53 | W |
| HOH | OH2 | 1434 | 195.4 | 147.5 | 21.1 | 81 | W |
| HOH | OH2 | 1435 | 203.9 | 111.2 | 54.4 | 71 | W |
| HOH | OH2 | 1436 | 215.8 | 107.4 | 17.8 | 70 | W |
| HOH | OH2 | 1437 | 174.5 | 145.8 | 31.0 | 66 | W |
| HOH | OH2 | 1438 | 181.7 | 156.1 | 25.3 | 77 | W |
| HOH | OH2 | 3001 | 183.5 | 132.9 | 37.3 | 27 | W |
| HOH | OH2 | 3002 | 186.6 | 131.2 | 28.9 | 12 | W |
| HOH | OH2 | 3003 | 190.7 | 132.1 | 42.0 | 16 | W |
| HOH | OH2 | 3004 | 189.8 | 134.7 | 39.6 | 48 | W |
| HOH | OH2 | 3005 | 189.5 | 138.1 | 45.9 | 50 | W |
| HOH | OH2 | 3006 | 191.9 | 125.9 | 35.9 | 35 | W |
| HOH | OH2 | 3007 | 187.7 | 136.6 | 27.0 | 30 | W |
| HOH | OH2 | 3008 | 197.9 | 122.3 | 38.1 | 25 | W |
| HOH | OH2 | 3009 | 196.1 | 126.3 | 38.5 | 31 | W |
| HOH | OH2 | 3010 | 200.5 | 130.8 | 28.8 | 26 | W |
| HOH | OH2 | 3011 | 197.9 | 126.1 | 29.9 | 16 | W |
| HOH | OH2 | 3012 | 195.3 | 127.3 | 29.3 | 19 | W |
| HOH | OH2 | 3013 | 193.7 | 128.1 | 31.9 | 37 | W |
| HOH | OH2 | 3014 | 200.4 | 126.4 | 31.4 | 39 | W |
| HOH | OH2 | 3015 | 183.4 | 134.8 | 27.0 | 30 | W |
| HOH | OH2 | 3016 | 187.2 | 134.1 | 29.8 | 34 | W |

EXAMPLE 6

Phasing, Model Building and Refinement

The structure of the crystal form described in Examples 1–3 was solved by molecular replacement, as implemented in XPLOR [Yale University, ©1992, distributed by Molecular Simulations, Inc.; see, e.g., Blundell & Johnson, supra; *Meth. Enzymol.,* vol. 114 and 115, H. W. Wyckoff et al., eds., Academic Press (1985)], using a 2.2 Å resolution model of unliganded FPT as the search model (Beese et al., 1997, *Science* 275:1800–1804). The structure of the FPT:FPP-:SCH66381 complex was highly refined and used as the starting point for further structure determinations. After rigid body refinement using XPLOR, the refinement of each additional structure started from a model of FPT retaining the bound FPP, but with the inhibitor and its associated waters removed. The inhibitors or peptides were built using INSIGHT and QUANTA and fit into the initial omit electron density with CHAIN [J. Sack, *J. Molecular Graphics* 6:224–225]. The structure was refined by several cycles of model building and positional refinement using XPLOR. Positions of discrete water molecules were taken from positive (Fo-Fc),$\alpha_{calc}$ difference density peaks if a hydrogen bonding pattern to protein, peptide, inhibitors or solvent atoms could be established.

EXAMPLE 7

Structure Determination of FPT:αHFP: CVIM Co-crystals

Co-crystals of FPT:αHFP:CVIM were grown as described in Example 2. Data on these crystals was collected as described in Example 5 and the structure determined as described in Example 6. The structure clearly showed the position of αHFP and the CVIM peptide. Refinement statistics are shown in Table 1 and the coordinates are shown in Table 2.

EXAMPLE 8

Structure Determination of FPT:FPP:SCH66381 Co-crystals

Co-crystals of FPT:FPP:SCH66381 were grown as described in Example 3. Data on these crystals was collected as described in Example 5 and the structure determined as described in Example 6. The structure clearly showed the positions of FPP and SCH66381. Refinement statistics are shown in Table 1 and the coordinates are shown in Table 3.

EXAMPLE 9

Structure Determination of FPT:FPP:SCH66701 Co-crystals

Co-crystals of FPT:FPP:SCH66701 were grown as described in Example 3. Data on these crystals was collected as described in Example 5 and the structure determined as described in Example 6. The structure clearly showed the positions of FPP and SCH66701. Refinement statistics are shown in Table 1 and the coordinates are shown in Table 4.

EXAMPLE 10

Structure Determination of FPT:FPP:SCH69132 Co-crystals

Co-crystals of FPT:FPP:SCH69132 were grown as described in Example 3. Data on these crystals was collected as described in Example 5 and the structure determined as described in Example 6. The structure clearly showed the positions of FPP and SCH69132. Refinement statistics are shown in Table 1 and the coordinates are shown in Table 5.

We claim:

1. A crystalline complex comprising rat farnesyl protein transferase complexed with α-hydroxy phosphonic acid and a peptide whose amino acid sequence consists of AcCys-Val-Ile-Met(Se) (SEQ ID NO: 1).

2. The crystalline complex of claim 1 whose structural coordinates are set forth in Table 2.

3. A crystalline complex comprising rat farnesyl protein transferase complexed with farnesyl diphosphate and an FPT inhibitor selected from the group consisting of SCH66381, SCH66701 and SCH69132.

4. The crystalline complex of claim 3 whose structural coordinates are set forth in Table 3.

5. The crystalline complex of claim 3 whose structural coordinates are set forth in Table 4.

6. The crystalline complex of claim 3 whose structural coordinates are set forth in Table 5.

7. A crystalline complex comprising rat farnesyl protein transferase which transferase consists of an α-subunit encoded by the nucleotide sequence of SEQ ID NO: 5 and a β-subunit encoded by the nucleotide sequence of SEQ ID NO: 6, complexed with α-hydroxy phosphonic acid and a peptide whose amino acid sequence consists of AcCys-Val-Ile-Met(Se) (SEQ ID NO: 1).

8. The crystalline complex of claim 7 whose structural coordinates are set forth in Table 2.

9. A crystalline complex comprising rat farnesyl protein transferase which transferase consists of an α-subunit encoded by the nucleotide sequence of SEQ ID NO: 5 and a β-subunit encoded by the nucleotide sequence of SEQ ID NO: 6, complexed with farnesyl diphosphate and an FPT inhibitor selected from the group consisting of SCH66381, SCH66701 and SCH69132.

10. The crystalline complex of claim 9 whose structural coordinates are set forth in Table 3.

11. The crystalline complex of claim 9 whose structural coordinates are set forth in Table 4.

12. The crystalline complex of claim 9 whose structural coordinates are set forth in Table 5.

* * * * *